US012648353B2

(12) United States Patent
Toyoshima et al.

(10) Patent No.: US 12,648,353 B2
(45) Date of Patent: Jun. 2, 2026

(54) COMPOSITION, ORGANIC ELECTROLUMINESCENCE DEVICE, AND ELECTRONIC APPARATUS

(71) Applicant: IDEMITSU KOSAN CO., LTD., Tokyo (JP)

(72) Inventors: Hiroaki Toyoshima, Tokyo (JP); Masatoshi Saito, Tokyo (JP); Kei Yoshida, Tokyo (JP); Masato Mitani, Tokyo (JP); Sayaka Mizutani, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1014 days.

(21) Appl. No.: 17/742,162

(22) Filed: May 11, 2022

(65) Prior Publication Data

US 2022/0416178 A1 Dec. 29, 2022

(30) Foreign Application Priority Data

May 14, 2021 (JP) ................................ 2021-082820

(51) Int. Cl.
*H10K 85/60* (2023.01)
*C07D 307/91* (2006.01)
(Continued)

(52) U.S. Cl.
CPC ....... *H10K 85/6574* (2023.02); *C07D 307/91* (2013.01); *C07D 403/10* (2013.01);
(Continued)

(58) Field of Classification Search
CPC .. C07D 307/91; C07D 333/76; C07D 493/04; C07D 495/04; C07D 491/048;
(Continued)

(56) References Cited

U.S. PATENT DOCUMENTS

2014/0306207 A1* 10/2014 Nishimura ......... H10K 85/6574 252/500
2020/0388767 A1 12/2020 Masuda et al.

FOREIGN PATENT DOCUMENTS

WO WO-2019/163824 A1 8/2019

* cited by examiner

*Primary Examiner* — Vu A Nguyen
(74) *Attorney, Agent, or Firm* — Foley & Lardner LLP

(57) ABSTRACT

An organic electroluminescence device having a cathode; an anode; and an emitting layer disposed between the cathode, wherein a first layer in an electron-transporting zone disposed between the emitting layer and the cathode contains a first compound and a second compound, the electron mobility $\mu_1$ of the first compound is $1.0\times10^{-5}$ $cm^2/Vs$ or lower, and the second compound is one or more selected from the group consisting of compounds represented by each of the following formulas (11), (12), and (13), provided that the first compound and the second compound are different compounds.

(11)

(Continued)

-continued (12)

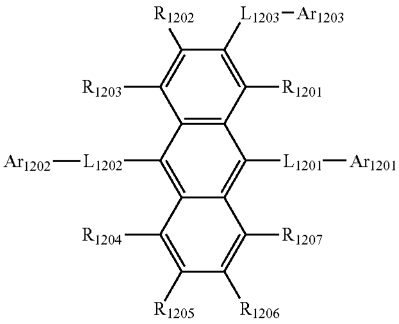

(13)

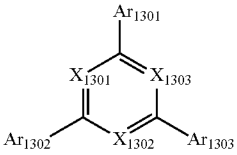

29 Claims, 1 Drawing Sheet

(51) Int. Cl.

| | |
|---|---|
| ***C07D 403/10*** | (2006.01) |
| ***C07D 405/10*** | (2006.01) |
| ***C07D 405/14*** | (2006.01) |
| ***C07D 491/048*** | (2006.01) |
| ***C07D 493/04*** | (2006.01) |
| ***C09K 11/06*** | (2006.01) |
| ***H10K 50/16*** | (2023.01) |

(52) U.S. Cl.

CPC ......... *C07D 405/10* (2013.01); *C07D 405/14* (2013.01); *C07D 491/048* (2013.01); *C07D 493/04* (2013.01); *C09K 11/06* (2013.01); *H10K 85/615* (2023.02); *H10K 85/654* (2023.02); *H10K 85/657* (2023.02); *H10K 85/6572* (2023.02); *C09K 2211/1018* (2013.01); *H10K 50/16* (2023.02)

(58) Field of Classification Search

CPC .. C07D 403/10; C07D 405/10; C07D 251/24; H10K 85/615; H10K 2101/90; H10K 50/16

See application file for complete search history.

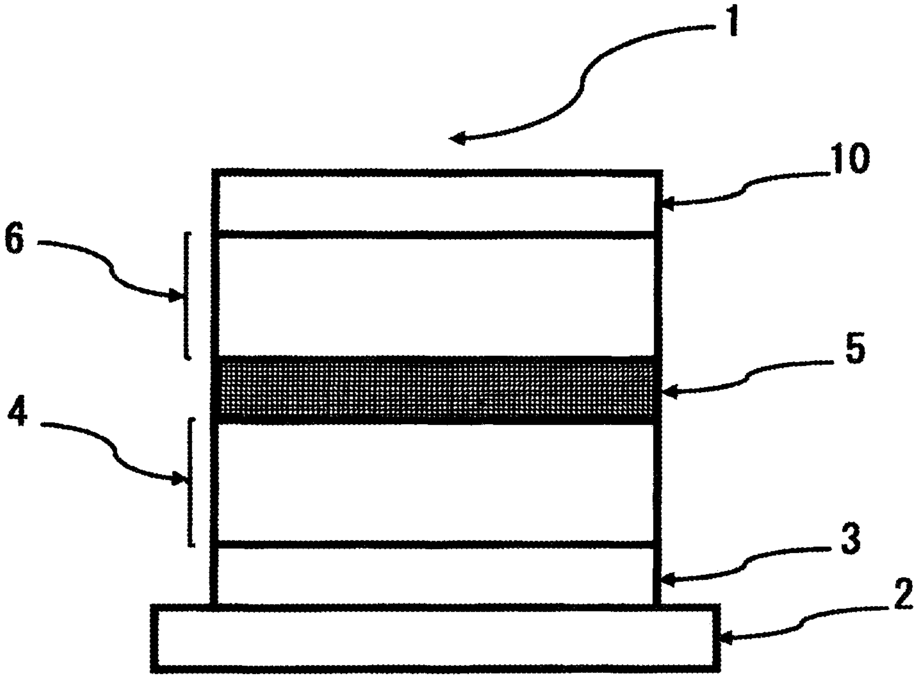
1
10
6
5
4
3
2

COMPOSITION, ORGANIC ELECTROLUMINESCENCE DEVICE, AND ELECTRONIC APPARATUS

TECHNICAL FIELD

Embodiments described herein generally relate to a composition, an organic electroluminescence device and an electronic apparatus.

BACKGROUND ART

When voltage is applied to an organic electroluminescence device (hereinafter, referred to as an organic EL device), holes and electrons are injected into an emitting layer from an anode and a cathode, respectively. Then, thus injected holes and electrons are recombined in the emitting layer, and excitons are formed therein.

Various studies have been made to increase the device performance, but the luminous efficiency and the device lifetime are in a so-called trade-off (approximately inversely proportional or inversely correlated) relationship, and by the conventional technologies, it has been difficult to increase one without decreasing the other (for example, Patent Document 1).

RELATED ART DOCUMENTS

Patent Documents

[Patent Document 1] WO 2019/163824 A1

SUMMARY OF THE INVENTION

It is an object of the invention to provide an organic EL device in which one of the luminous efficiency and the device lifetime is increased without decreasing the other, and to provide a composition applicable to the organic EL device.

As a result of intense studies by the inventors, it was considered that, in the conventional organic EL device, carriers (electrons) are likely to accumulate at the interface between the emitting layer and the electron-transporting zone, causing interaction between the carriers and excitons in the emitting layer, which makes it difficult to increase the device performance. The inventors found that carrier accumulation can be prevented by adding a compound having an insulating property to one layer in the electron-transporting zone so as to partially inhibit the flow of electrons, and as a result, higher device performance can be obtained, thereby completing the invention.

According to the invention, the following organic EL device and so on are provided.

An organic electroluminescence device comprising:

a cathode;

an anode; and an emitting layer disposed between the cathode and the anode, wherein a first layer in an electron-transporting zone disposed between the emitting layer and the cathode comprises a first compound and a second compound, the first compound has an electron mobility $\mu_1$ of the first compound of $1.0\times10^{-5}$ $cm^2/Vs$ or lower, the second compound is one or more selected from the group consisting of compounds represented by each of the following formulas (11), (12), and (13), provided that the first compound and the second compound are different compounds:

(11)

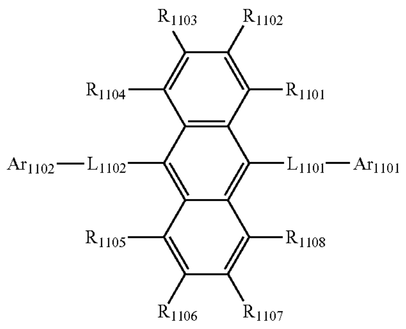

wherein in the formula (11), $R_{1101}$ to $R_{1108}$ are independently a hydrogen atom or a substituent R;

$L_{1101}$ and $L_{1102}$ are independently a single bond, a substituted or unsubstituted arylene group including 6 to 50 ring carbon atoms, or a substituted or unsubstituted divalent heterocyclic group including 5 to 50 ring atoms;

$Ar_{1101}$ is a substituted or unsubstituted monovalent nitrogen-containing heterocyclic group including 5 to 50 ring atoms;

$Ar_{1102}$ is a substituted or unsubstituted aryl group including 6 to 50 ring carbon atoms, or a substituted or unsubstituted monovalent heterocyclic group including 5 to 50 ring atoms;

the substituent R is selected form the group consisting of a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{900})(R_{902})(R_{903})$,

—O—$(R_{904})$,

—S—$(R_{905})$,

—$N(R_{906})(R_{907})$ (where $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; and when two or more of each of $R_{901}$ to $R_{907}$ are present, the two or more of each of $R_{901}$ to $R_{907}$ are the same as or different from each other), a halogen atom, a cyano group, a nitro group, a substituted or unsubstituted aryl group including 6 to 50 ring carbon atoms, and a substituted or unsubstituted monovalent heterocyclic group including 5 to 50 ring atoms;

when two or more substituent R's are present, the two or more substituent R's may be the same as or different from each other;

(12)

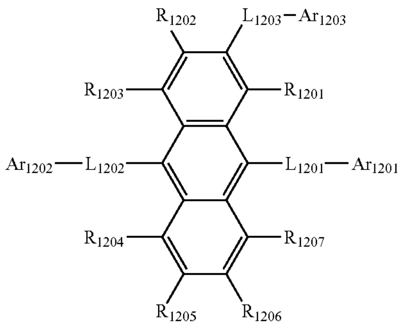

wherein in the formula (12), $R_{1201}$ to $R_{1207}$ are independently a hydrogen atom or a substituent R;

$L_{1201}$ to $L_{1203}$ are independently a single bond, a substituted or unsubstituted arylene group including 6 to 50 ring carbon atoms, or a substituted or unsubstituted divalent heterocyclic group including 5 to 50 ring atoms;

$Ar_{1201}$ and $Ar_{1202}$ are independently a substituted or unsubstituted aryl group including 6 to 50 ring carbon atoms, or a substituted or unsubstituted monovalent heterocyclic group including 5 to 50 ring atoms;

$Ar_{1203}$ is a substituted or unsubstituted monovalent nitrogen-containing heterocyclic group including 5 to 50 ring atoms; and the substituent R is as defined in the formula (11);

(13)

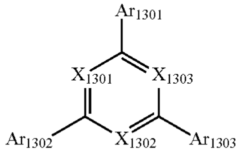

wherein in the formula (13), $X_{1301}$ to $X_{1303}$ are independently N or $CR_{1301}$, and at least two of $X_{1301}$ to $X_{1303}$ are N; $R_{1301}$ is a hydrogen atom or a substituent R;

$Ar_{1301}$ to $Ar_{1303}$ are independently a substituted or unsubstituted aryl group including 6 to 50 ring carbon atoms, or a group represented by the following formula (13A), and at least one of $Ar_{1301}$ to $Ar_{1303}$ is a group represented by the formula (13A); provided that none of $Ar_{1301}$ to $Ar_{1303}$ is a triphenylenyl group;

$$-(L_{13A})_{n13A}-Ar_{13A} \quad (13A)$$

wherein in the formula (13A), $L_{13A}$ is a single bond, a substituted or unsubstituted arylene group including 6 to 50 ring carbon atoms, or a substituted or unsubstituted divalent heterocyclic group including 5 to 50 ring atoms;

$Ar_{13A}$ is a substituted or unsubstituted monovalent heterocyclic group including 5 to 50 ring atoms; and n13A is an integer of 1 to 3; when two or more $L_{13A}$'s are present, the two or more $L_{13A}$'s may be the same as or different from each other;

when two or more groups represented by the formula (13A) are present, the two or more groups represented by the formula (13A) may be the same as or different from each other; and the substituent R is as defined in the formula (11).

According to the invention, it is possible to provide an organic EL device in which one of the luminous efficiency and the device lifetime is increased without decreasing the other, and a composition applicable to the organic EL device.

BRIEF DESCRIPTION OF THE DRAWINGS

The FIGURE is a diagram showing a schematic configuration of the organic EL device according to an aspect of the invention.

MODE FOR CARRYING OUT THE INVENTION

Definition

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms which do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group"is a" ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent"). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted aryl group (specific example group G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived by removing one hydrogen atom from the ring structures represented by each of the following general formulas (TEMP-1) to (TEMP-15).

(TEMP-1)

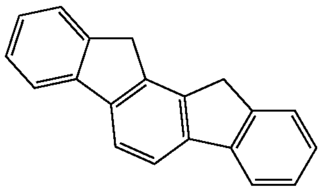

(TEMP-2)

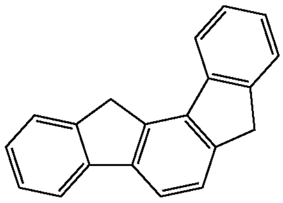

-continued (TEMP-3)

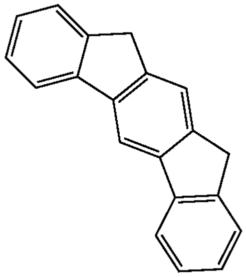

(TEMP-4)

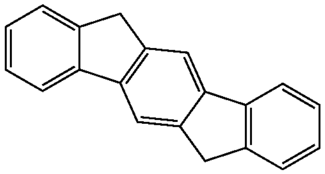

(TEMP-5)

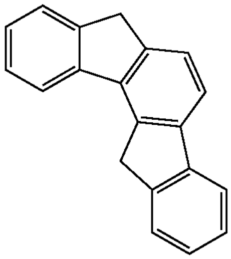

(TEMP-6)

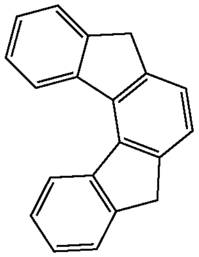

(TEMP-7)

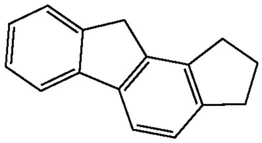

(TEMP-8)

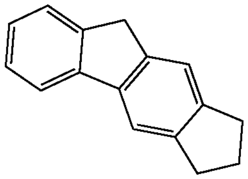

(TEMP-9)

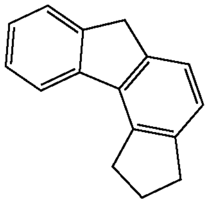

-continued (TEMP-10)

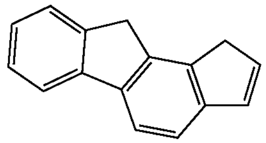

(TEMP-11)

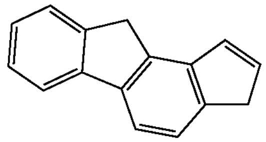

(TEMP-12)

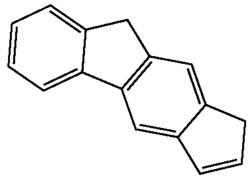

(TEMP-13)

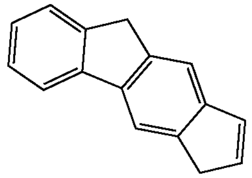

(TEMP-14)

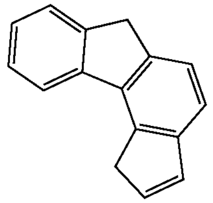

(TEMP-15)

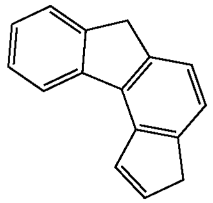

Substituted aryl group (specific example group G1B):
- an o-tolyl group,
- a m-tolyl group,
- a p-tolyl group,
- a p-xylyl group,
- a m-xylyl group,
- an o-xylyl group,
- a p-isopropylphenyl group,
- a m-isopropylphenyl group,
- an o-isopropylphenyl group,
- a p-t-butylphenyl group,
- a m-t-butylphenyl group,
- an o-t-butylphenyl group,
- a 3,4,5-trimethylphenyl group,
- a 9,9-dimethylfluorenyl group,
- a 9,9-diphenylfluorenyl group,
- a 9,9-bis(4-methylphenyl)fluorenyl group,
- a 9,9-bis(4-isopropylphenyl)fluorenyl group,
- a 9,9-bis(4-t-butylphenyl)fluorenyl group,
- a cyanophenyl group,
- a triphenylsilylphenyl group,
- a trimethylsilylphenyl group,
- a phenylnaphthyl group,
- a naphthylphenyl group, and
- a group in which one or more hydrogen atoms of a monovalent group derived from the ring structures represented by each of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group"is a" heterocyclic group substituted by a substituent"). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by each of the following general formulas (TEMP-16) to (TEMP-33) (specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by each of the following general formulas (TEMP-16) to (TEMP-33) are substituted by a substituent (specific example group G2B4).

Unsubstituted heterocyclic group containing a nitrogen atom (specific example group G2A1):
- a pyrrolyl group,
- an imidazolyl group,
- a pyrazolyl group,
- a triazolyl group,
- a tetrazolyl group,
- an oxazolyl group,
- an isoxazolyl group,
- an oxadiazolyl group,
- a thiazolyl group,
- an isothiazolyl group,
- a thiadiazolyl group,
- a pyridyl group,
- a pyridazinyl group,
- a pyrimidinyl group,
- a pyrazinyl group,
- a triazinyl group,
- an indolyl group,
- an isoindolyl group,
- an indolizinyl group,
- a quinolizinyl group,
- a quinolyl group,
- an isoquinolyl group,
- a cinnolyl group,
- a phthalazinyl group,
- a quinazolinyl group,
- a quinoxalinyl group,
- a benzimidazolyl group,
- an indazolyl group,
- a phenanthrolinyl group,
- a phenanthridinyl group,
- an acridinyl group,
- a phenazinyl group,
- a carbazolyl group,
- a benzocarbazolyl group,
- a morpholino group,
- a phenoxazinyl group,
- a phenothiazinyl group,
- an azacarbazolyl group, and
- a diazacarbazolyl group.

Unsubstituted heterocyclic group containing an oxygen atom (specific example group G2A2):
- a furyl group,
- an oxazolyl group,
- an isoxazolyl group,
- an oxadiazolyl group,
- a xanthenyl group,
- a benzofuranyl group,
- an isobenzofuranyl group,
- a dibenzofuranyl group,
- a naphthobenzofuranyl group,
- a benzoxazolyl group,
- a benzisoxazolyl group,
- a phenoxazinyl group,
- a morpholino group,
- a dinaphthofuranyl group,
- an azadibenzofuranyl group,
- a diazadibenzofuranyl group,
- an azanaphthobenzofuranyl group, and
- a diazanaphthobenzofuranyl group.

Unsubstituted heterocyclic group containing a sulfur atom (specific example group G2A3):
- a thienyl group,
- a thiazolyl group,
- an isothiazolyl group,
- a thiadiazolyl group,
- a benzothiophenyl group (benzothienyl group),
- an isobenzothiophenyl group (isobenzothienyl group),
- a dibenzothiophenyl group (dibenzothienyl group),
- a naphthobenzothiophenyl group (naphthobenzothienyl group),
- a benzothiazolyl group,
- a benzisothiazolyl group,
- a phenothiazinyl group,
- a dinaphthothiophenyl group (dinaphthothienyl group),
- an azadibenzothiophenyl group (azadibenzothienyl group),
- a diazadibenzothiophenyl group (diazadibenzothienyl group),
- an azanaphthobenzothiophenyl group (azanaphthobenzothienyl group), and
- a diazanaphthobenzothiophenyl group (diazanaphthobenzothienyl group).

Monovalent heterocyclic group derived by removing one hydrogen atom from the ring structures represented by each of the following general formulas (TEMP-16) to (TEMP-33) (specific example group G2A4):

(TEMP-16)

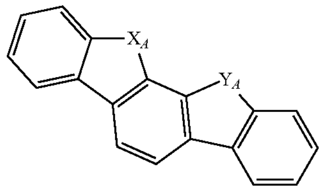

(TEMP-17)

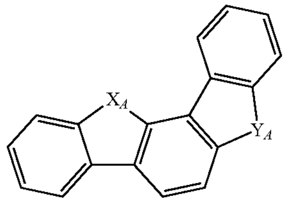

(TEMP-18)

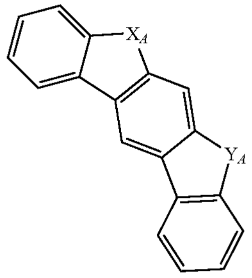

-continued (TEMP-19)

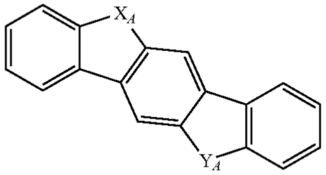

(TEMP-20)

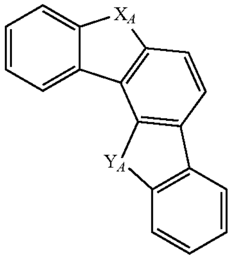

(TEMP-21)

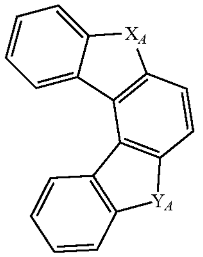

(TEMP-22)

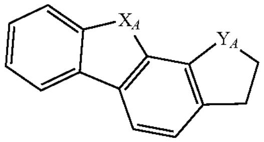

(TEMP-23)

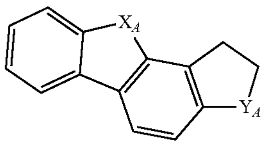

(TEMP-24)

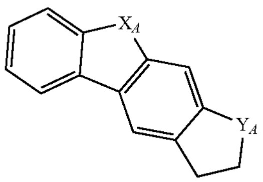

(TEMP-25)

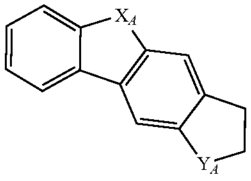

(TEMP-26)

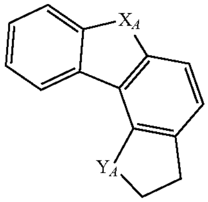

-continued (TEMP-27)

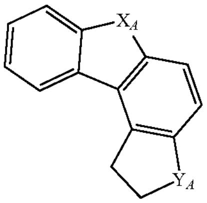

(TEMP-28)

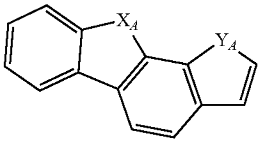

(TEMP-29)

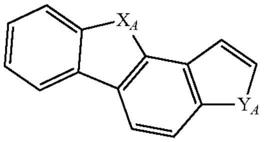

(TEMP-30)

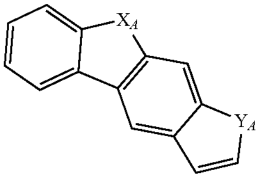

(TEMP-31)

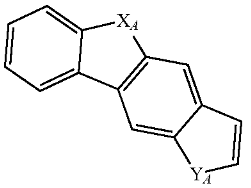

(TEMP-32)

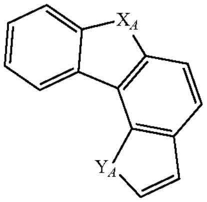

(TEMP-33)

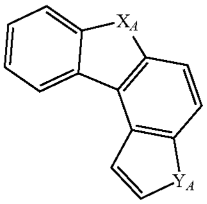

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic group derived from the ring structures represented by each of the general formulas (TEMP-16) to (TEMP-33) includes a monovalent group derived by removing one hydrogen atom from these NH or $CH_2$.

Substituted heterocyclic group containing a nitrogen atom (specific example group G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Substituted heterocyclic group containing an oxygen atom (specific example group G2B2):
a phenyldibenzofuranyl group,
a methyldibenzofuranyl group,
a t-butyldibenzofuranyl group, and
a monovalent residue of spiro[9H-xanthene-9,9'-[9H]fluorene].

Substituted heterocyclic group containing a sulfur atom (specific example group G2B3):
a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Group in which one or more hydrogen atoms of the monovalent heterocyclic group derived from the ring structures represented by each of the following general formulas (TEMP-16) to (TEMP-33) are substituted by a substituent (specific example group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent"). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted alkyl group (specific example group G3A):
a methyl group,
an ethyl group,
a n-propyl group,
an isopropyl group,
a n-butyl group,
an isobutyl group,
a s-butyl group, and
a t-butyl group.

Substituted alkyl group (specific example group G3B):
a heptafluoropropyl group (including isomers),
a pentafluoroethyl group,
a 2,2,2-trifluoroethyl group, and
a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group"is a" alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted alkenyl group (specific example group G4A):
a vinyl group,
an allyl group,
a 1-butenyl group,
a 2-butenyl group, and
a 3-butenyl group.

Substituted alkenyl group (specific example group G4B):
a 1,3-butanedienyl group,
a 1-methylvinyl group,
a 1-methylallyl group,
a 1,1-dimethylallyl group,
a 2-methylally group, and
a 1,2-dimethylallyl group.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent"). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted alkynyl group (specific example group G5A):

an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group"is a" cycloalkyl group substituted by a substituent"). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted cycloalkyl group (specific example group G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted cycloalkyl group (specific example group G6B):

a 4-methylcyclohexyl group.

"Group represented by —Si($R_{901}$)($R_{902}$)($R_{903}$)"

Specific examples of the group represented by —Si($R_{901}$)($R_{902}$)($R_{903}$) described in this specification (specific example group G7) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —Si(G1)(G1)(G1) are the same or different.

Plural G2's in —Si(G1)(G2)(G2) are the same or different.

Plural G1's in —Si(G1)(G1)(G2) are the same or different.

Plural G2's in —Si(G2)(G2)(G2) are be the same or different.

Plural G3's in —Si(G3)(G3)(G3) are the same or different.

Plural G6's in —Si(G6)(G6)(G6) are be the same or different.

"Group Represented by —O—($R_{904}$)"

Specific examples of the group represented by —O—($R_{904}$) in this specification (specific example group G8) include:

—O(G1),
—O(G2),
—O(G3), and
—O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{905}$) in this specification (specific example group G9) include:

—S(G1),
—S(G2),
—S(G3), and
—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —N($R_{906}$)($R_{907}$)"

Specific examples of the group represented by —N($R_{905}$)($R_{907}$) in this specification (specific example group G10) include:

—N(G1)(G1),
—N(G2)(G2),
—N(G1)(G2),
—N(G3)(G3), and
—N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —N(G1)(G1) are the same or different.

Plural G2's in —N(G2)(G2) are the same or different.

Plural G3's in —N(G3)(G3) are the same or different.

Plural G6's in —N(G6)(G6) are the same or different.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. Plural G3's in —Si(G3)(G3)(G3) are the same or different. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a pi-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically each of the following groups, unless otherwise specified in this specification.

(TEMP-Cz1)

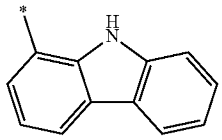

(TEMP-Cz2)

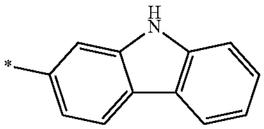

-continued (TEMP-Cz3)

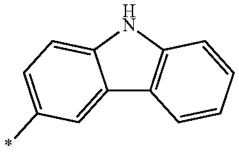

(TEMP-Cz4)

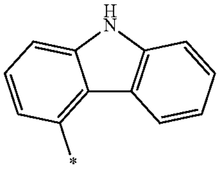

(TEMP-Cz5)

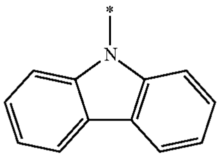

In this specification, the (9-phenyl)carbazolyl group is specifically any of the following groups, unless otherwise specified in this specification.

(TEMP-Cz6)

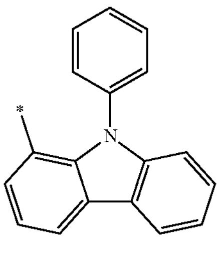

(TEMP-Cz7)

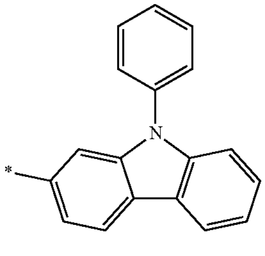

(TEMP-Cz8)

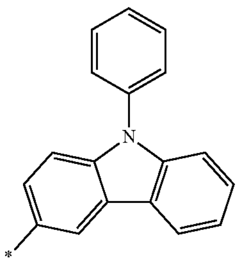

-continued (TEMP-Cz9)

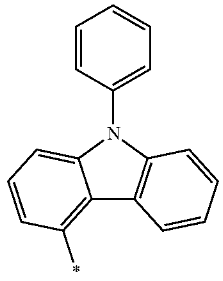

In the general formulas (TEMP-Cz1) to (TEMP-Cz9), * represents a bonding site.

In this specification, the dibenzofuranyl group and the dibenzothiophenyl group are specifically any of the following groups, unless otherwise specified in this specification.

(TEMP-34)

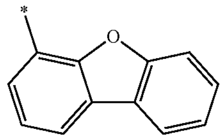

(TEMP-35)

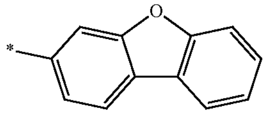

(TEMP-36)

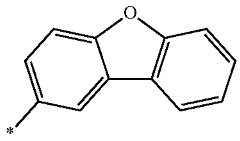

(TEMP-37)

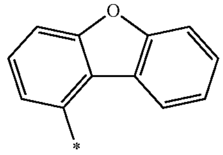

(TEMP-38)

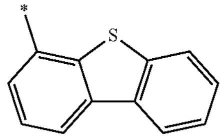

(TEMP-39)

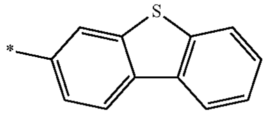

(TEMP-40)

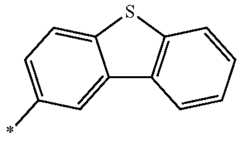

-continued (TEMP-41)

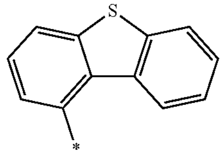

In the general formulas (TEMP-34) to (TEMP-41), * represents a bonding site.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocycle of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocycle of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

(TEMP-42)

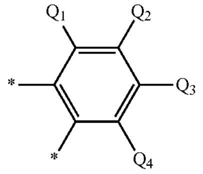

-continued
(TEMP-43)
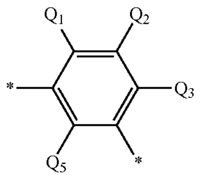
(TEMP-44)
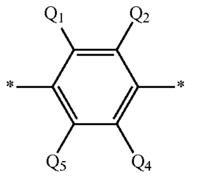
(TEMP-45)
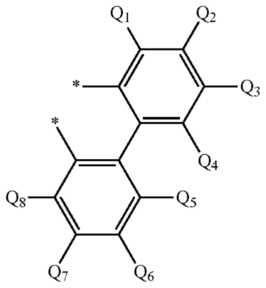
(TEMP-46)
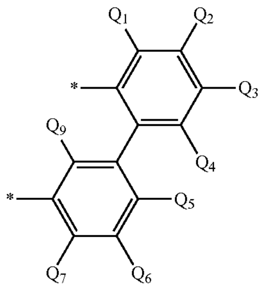
(TEMP-47)
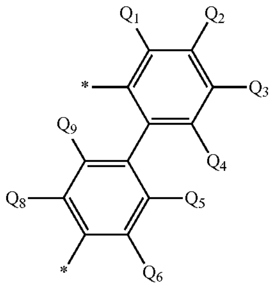
(TEMP-48)
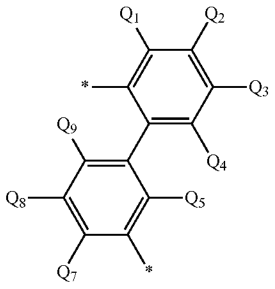
-continued
(TEMP-49)
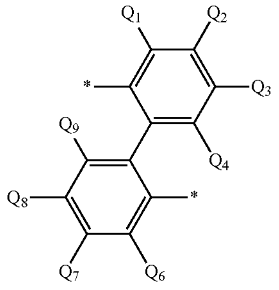
(TEMP-50)
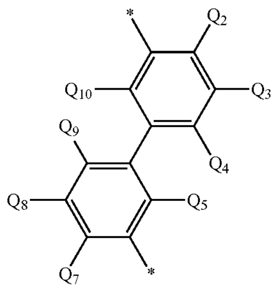
(TEMP-51)
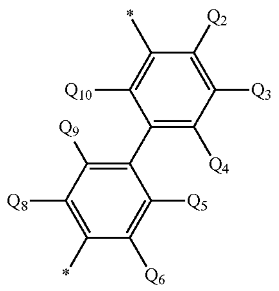
(TEMP-52)
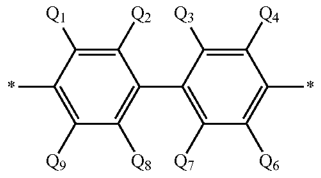
In the general formulas (TEMP-42) to (TEMP-52), $Q_1$ to $Q_{10}$ are independently a hydrogen atom or a substituent.
In the general formulas (TEMP-42) to (TEMP-52), * represents a bonding site.
(TEMP-53)
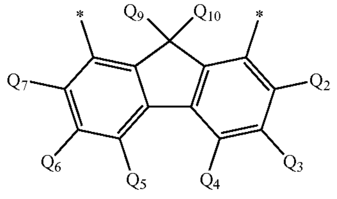

-continued
(TEMP-54)
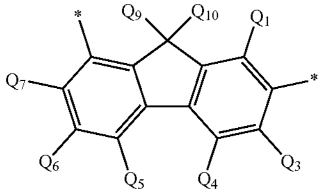
(TEMP-55)
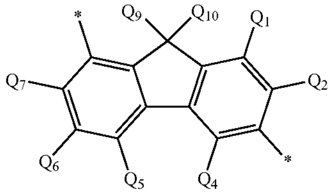
(TEMP-56)
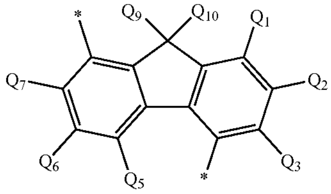
(TEMP-57)
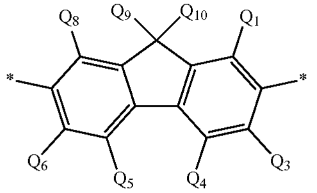
(TEMP-58)
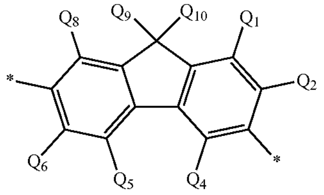
(TEMP-59)
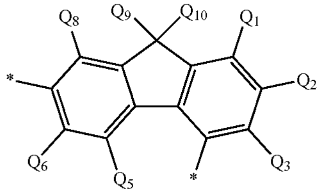
(TEMP-60)
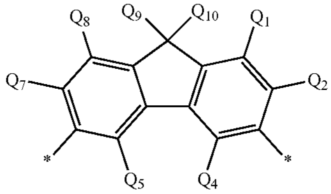
(TEMP-61)
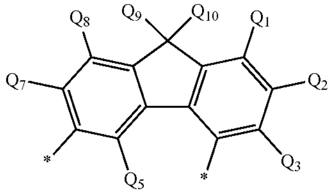
-continued
(TEMP-62)
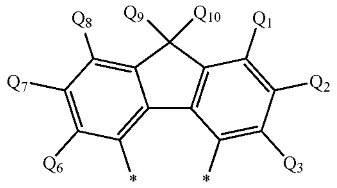
In the general formulas (TEMP-5) to (TEMP-62), $Q_1$ to $Q_{10}$ are independently a hydrogen atom or a substituent.
$Q_9$ and $Q_{10}$ may be bonded with each other via a single bond to form a ring.
In the general formulas (TEMP-53) to (TEMP-62), * represents a bonding site.
(TEMP-63)
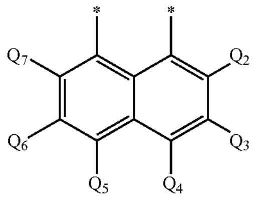
(TEMP-64)
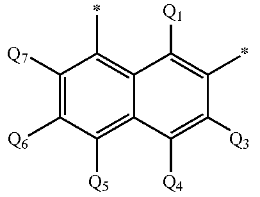
(TEMP-65)
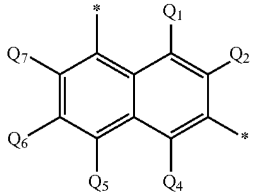
(TEMP-66)
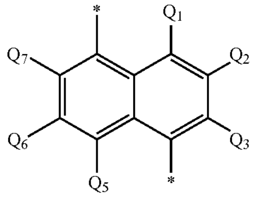
(TEMP-67)
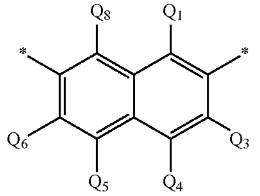

-continued (TEMP-68)

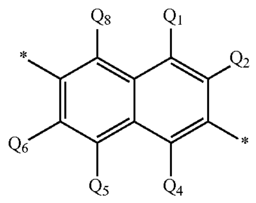

In the general formulas (TEMP-63) to (TEMP-68), $Q_1$ to $Q_8$ are independently a hydrogen atom or a substituent.

In the general formulas (TEMP-63) to (TEMP-68), * represents a bonding site.

The substituted or unsubstituted divalent heterocyclic group described in this specification is preferably any group of the following general formulas (TEMP-69) to (TEMP-102), unless otherwise specified in this specification.

(TEMP-69)

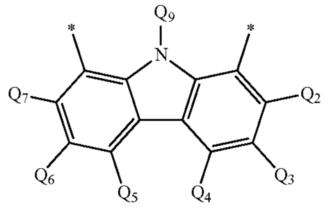

(TEMP-70)

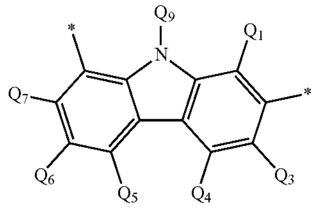

(TEMP-71)

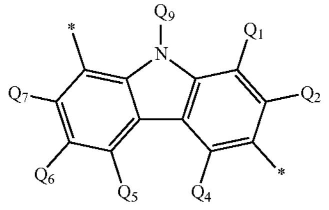

(TEMP-72)

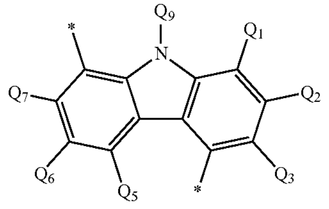

(TEMP-73)

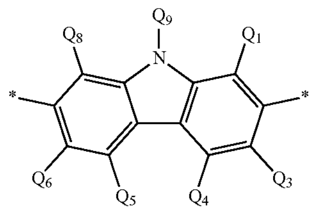

-continued (TEMP-74)

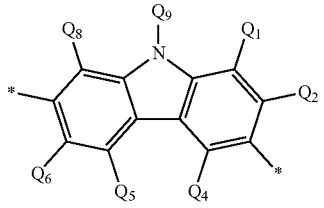

(TEMP-75)

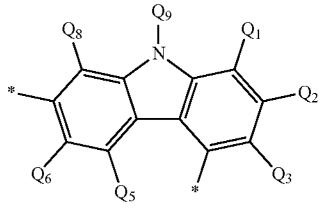

(TEMP-76)

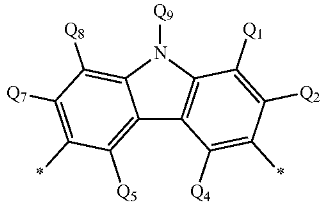

(TEMP-77)

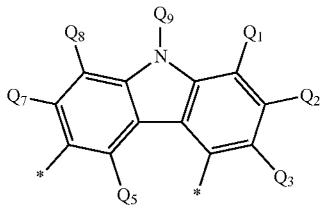

(TEMP-78)

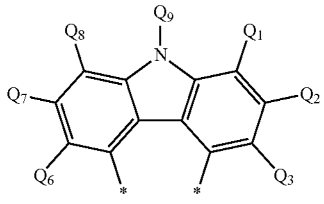

(TEMP-79)

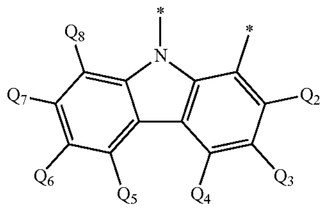

(TEMP-80)

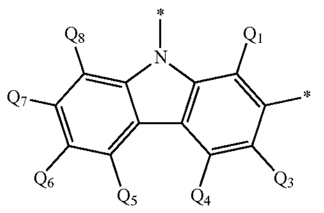

-continued
(TEMP-81)
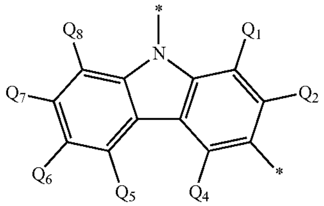
(TEMP-82)
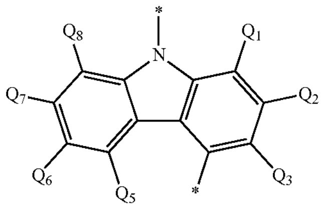
In the general formulas (TEMP-69) to (TEMP-82), $Q_1$ to $Q_9$ are independently a hydrogen atom or a substituent.
(TEMP-83)
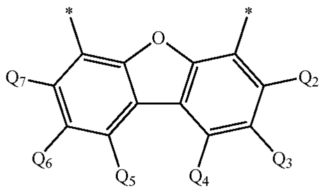
(TEMP-84)
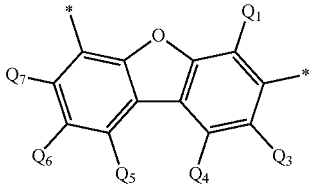
(TEMP-85)
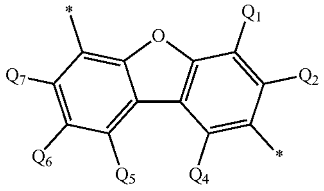
(TEMP-86)
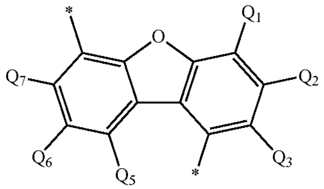
(TEMP-87)
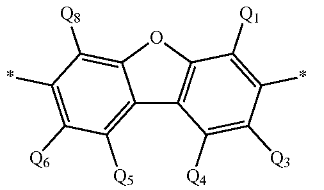
-continued
(TEMP-88)
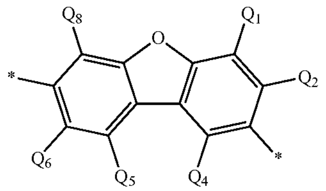
(TEMP-89)
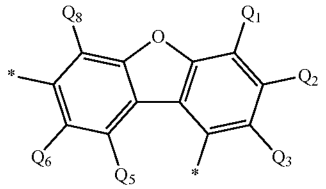
(TEMP-90)
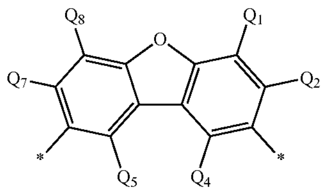
(TEMP-91)
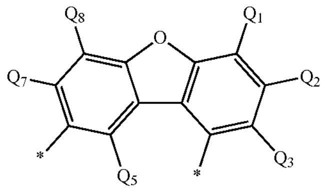
(TEMP-92)
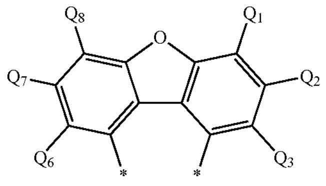
(TEMP-93)
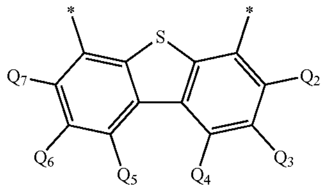
(TEMP-94)
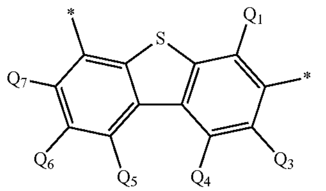
(TEMP-95)
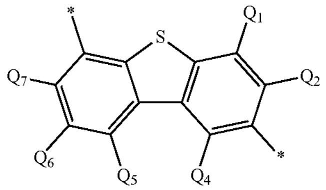

-continued (TEMP-96)

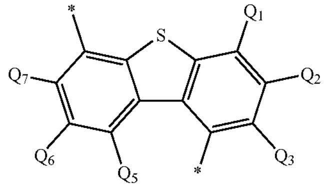

(TEMP-97)

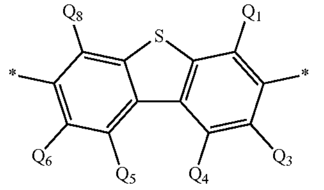

(TEMP-98)

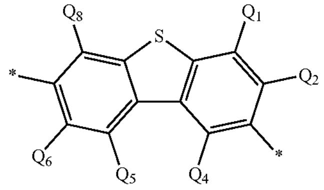

(TEMP-99)

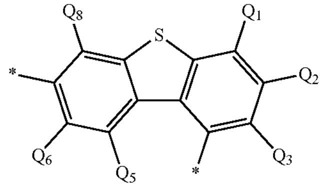

(TEMP-100)

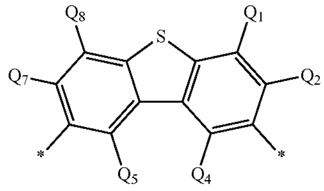

(TEMP-101)

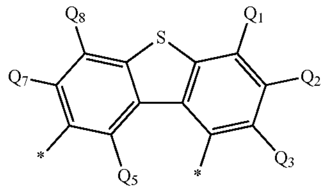

(TEMP-102)

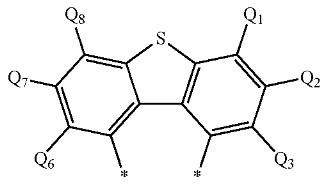

In the general formulas (TEMP-83) to (TEMP-102), $Q_1$ to $Q_8$ are independently a hydrogen atom or a substituent.

The above is the explanation of the "Substituent described in this specification."

"The Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

(TEMP-103)

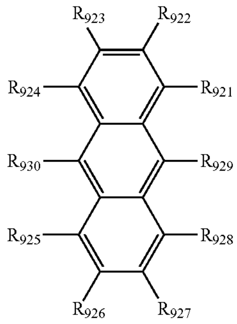

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

(TEMP-104)

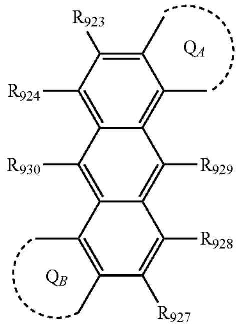

The case where the "set of adjacent two or more" form a ring includes not only the case where the set (pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and $R_{923}$ form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

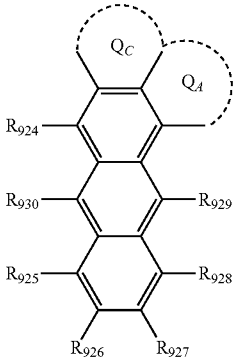

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may form a saturated ring or an unsaturated ring. For example, the ring $Q_A$ and the ring $Q_B$ formed in the general formula (TEMP-104) are independently a "monocycle" or a "fused ring." The ring $Q_A$ and the ring $Q_C$ formed in the general formula (TEMP-105) are "fused ring." The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" includes, in addition to an aromatic hydrocarbon ring and an aromatic heterocycle, an aliphatic hydrocarbon ring with an unsaturated bond, i.e., double and/or triple bonds in the ring structure (e.g., cyclohexene, cyclohexadiene, etc.), and a non-aromatic heterocycle with an unsaturated bond (e.g., dihydropyran, imidazoline, pyrazoline, quinolizine, indoline, isoindoline, etc.). The "saturated ring" includes an aliphatic hydrocarbon ring without an unsaturated bond and a non-aromatic heterocycle without ab unsaturated bond.

Specific examples of the aromatic hydrocarbon ring include a structure in which the group listed as a specific example in the specific example group G1 is terminated by a hydrogen atom.

Specific examples of the aromatic heterocycle include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with plural atoms of the mother skeleton, or with plural atoms of the mother skeleton and one or more arbitrary atoms in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary atoms. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary atom" is preferably at least one atom selected from the group consisting of a carbon atom, a nitrogen atom, an oxygen atom, and a sulfur atom, unless otherwise specified in this specification. In the arbitrary atom (for example, a carbon atom or a nitrogen atom), a bond which does not form a ring may be terminated with a hydrogen atom or the like, or may be substituted with "arbitrary substituent" described below. When an arbitrary atom other than a carbon atom is contained, the ring formed is a heterocycle.

The number of "one or more arbitrary atom(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from plural atoms of the mother skeleton and one or more and 15 or less atoms which is at least one kind selected from a carbon atom, a nitrogen atom, an oxygen atom, and a sulfur atom.

The substituent in the case where the above-mentioned "monocycle" or "fused ring" has a substituent is, for example, an "arbitrary substituent" described below. Specific examples of the substituent which the above-mentioned "monocycle" or "fused ring" has include the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has include the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the Case of "Substituted or Unsubstituted"

In one embodiment in this specification, the substituent (in this specification, sometimes referred to as an "arbitrary substituent") in the case of "substituted or unsubstituted" is, for example, a group selected from the group consisting of:

an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{900}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group including 6 to 50 ring carbon atoms, and
an unsubstituted heterocyclic group including 5 to 50 ring atoms, wherein, $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted heterocyclic group including 5 to 50 ring atoms.

When two or more $R_{901}$'s are present, the two or more $R_{901}$'s may be the same or different.

When two or more $R_{902}$'s are present, the two or more $R_{902}$'s may be the same or different.

When two or more $R_{903}$'s are present, the two or more $R_{903}$'s may be the same or different.

When two or more $R_{904}$'s are present, the two or more $R_{904}$'s may be the same or different.

When two or more $R_{905}$'s are present, the two or more $R_{905}$'s may be the same or different.

When two or more $R_{906}$'s are present, the two or more $R_{906}$'s may be the same or different.

When two or more $R_{907}$'s are present, the two or more $R_{907}$'s may be the same or different.

In one embodiment, the substituent in the case of "substituted or unsubstituted" is a group selected from the group consisting of:

an alkyl group including 1 to 50 carbon atoms,
an aryl group including 6 to 50 ring carbon atoms, and
a heterocyclic group including 5 to 50 ring atoms.

In one embodiment, the substituent in the case of "substituted or unsubstituted" is a group selected from the group consisting of:

an alkyl group including 1 to 18 carbon atoms,
an aryl group including 6 to 18 ring carbon atoms, and
a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Organic EL Device]

An organic EL device according to an aspect of the invention (first organic EL device) contains a cathode; an anode; and an emitting layer disposed between the cathode and the anode, wherein a first layer in an electron-transporting zone disposed between the emitting layer and the cathode contains a first compound and a second compound, wherein the first layer has an electron mobility $\mu_1$ of the first compound of $1.0\times10^{-5}$ $cm^2/Vs$ or lower, the second compound is one or more selected from the group consisting of compounds represented by each of the following formulas (11), (12), and (13), and provided that the first compound and the second compound are different compounds;

(11)

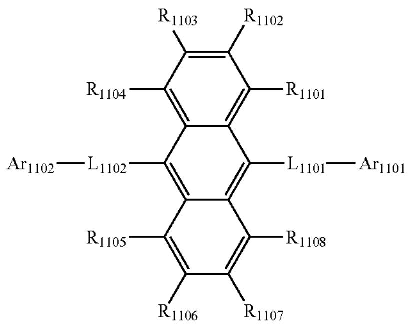

wherein in the formula (11), $R_{1101}$ to $R_{1108}$ are independently a hydrogen atom or a substituent R;

$L_{1101}$ and $L_{1102}$ are independently
a single bond,
a substituted or unsubstituted arylene group including 6 to 50 ring carbon atoms, or
a substituted or unsubstituted divalent heterocyclic group including 5 to 50 ring atoms;

$Ar_{1101}$ is
a substituted or unsubstituted monovalent nitrogen-containing heterocyclic group including 5 to 50 ring atoms;

$Ar_{1102}$ is
a substituted or unsubstituted aryl group including 6 to 50 ring carbon atoms, or
a substituted or unsubstituted monovalent heterocyclic group including 5 to 50 ring atoms;

the substituent R is selected form the group consisting of a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—$Si(R_{900})(R_{902})(R_{903})$,
—O—$(R_{904})$,
—S—$(R_{905})$,
—$N(R_{906})(R_{907})$
(where $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and when
two or more of each of $R_{901}$ to $R_{907}$ are present, the two or more of each of $R_{901}$ to $R_{907}$ are the same as or different from each other),
a halogen atom, a cyano group, a nitro group,
a substituted or unsubstituted aryl group including 6 to 50 ring carbon atoms, and
a substituted or unsubstituted monovalent heterocyclic group including 5 to 50 ring atoms, and
when two or more substituent R's are present, the two or more substituent R's may be the same as or different from each other;

(12)

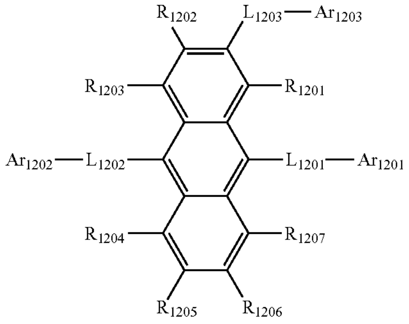

wherein in the formula (12),
$R_{1201}$ to $R_{1207}$ are independently a hydrogen atom or a substituent R;
$L_{1201}$ to $L_{1203}$ are independently
a single bond,
a substituted or unsubstituted arylene group including 6 to 50 ring carbon atoms, or
a substituted or unsubstituted divalent heterocyclic group including 5 to 50 ring atoms;
$Ar_{1201}$ and $Ar_{1202}$ are independently
a substituted or unsubstituted aryl group including 6 to 50 ring carbon atoms, or
a substituted or unsubstituted monovalent heterocyclic group including 5 to 50 ring atoms;
$Ar_{1203}$ is
a substituted or unsubstituted monovalent nitrogen-containing heterocyclic group including 5 to 50 ring atoms; and
the substituent R is as defined in the formula (11);

(13)

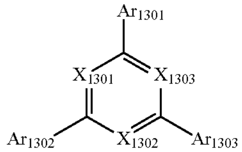

wherein in the formula (13),
$X_{1301}$ to $X_{1303}$ are independently N or $CR_{1301}$, and at least two of $X_{1301}$ to $X_{1303}$ are N; $R_{1301}$ is a hydrogen atom or a substituent R;
$Ar_{1301}$ to $Ar_{1303}$ are independently a substituted or unsubstituted aryl group including 6 to 50 ring carbon atoms, or a group represented by the following formula (13A), and at least one of $Ar_{1301}$ to $Ar_{1303}$ is the group represented by the formula (13A); provided that none of $Ar_{1301}$ to $Ar_{1303}$ is a triphenylenyl group;

$$-(L_{13A})_{n13A}-Ar_{13A} \quad (13A)$$

wherein in the formula (13A),
$L_{13A}$ is
a single bond,
a substituted or unsubstituted arylene group including 6 to 50 ring carbon atoms, or
a substituted or unsubstituted divalent heterocyclic group including 5 to 50 ring atoms;
$Ar_{13A}$ is
a substituted or unsubstituted monovalent heterocyclic group including 5 to 50 ring atoms;
n13A is an integer of 1 to 3; when two or more $L_{13A}$'s are present, the two or more $L_{13A}$'s may be the same as or different from each other;
when two or more groups represented by the formula (13A) are present, the two or more groups represented by the formula (13A) may be the same as or different from each other; and
the substituent R is as defined in the formula (11).

The organic EL device according to an aspect of the invention can attain higher device performance by using the first compound having an electron mobility $\mu_1$ of $1.0\times10^{-5}$ $cm^2/Vs$ or lower in the electron-transporting zone. Specifically, as compared with the conventional device, one of the luminous efficiency and the device lifetime can be increased without decreasing the other, and the limit value of the trade-off (product of the luminous efficiency and the device lifetime) which has been difficult to exceed can be pushed up to a higher level. Such an effect is considered to be due to the use of the first compound in the electron-transporting zone, which prevents carriers (electrons) from accumulating at the interface between the emitting layer and the electron-transporting zone, thereby suppressing unwanted interactions between the carriers and excitons of the emitting layer.

Hereinafter, each configuration of the organic EL device according to an aspect of the invention will be described.

(First Compound)

In the organic EL device according to an aspect of the invention, the above-described device performance can be increased by using the first compound having an insulating property in the electron-transporting zone.

In one embodiment, the first compound has an electron mobility $\mu_1$ of $1.0\times10^{-6}$ $cm^2/Vs$ or lower, preferably $1.0\times10^{-7}$ $cm^2/Vs$ lower, $1.0\times10^{-8}$ $cm^2/Vs$ or lower, or $1.0\times10^{-9}$ $cm^2/Vs$ or lower. The lower limit is not particularly limited, and is usually $1.0\times10^{-17}$ $cm^2/Vs$ or higher.

The electron mobility $\mu_1$ is measured by the methods described in Examples.

In one embodiment, the first compound has a hole mobility $\mu_2$ of $1.0\times10^{-5}$ $cm^2/Vs$ or lower, preferably $1.0\times10^{-7}$ $cm^2/Vs$ or lower, for example, $1.0\times10^{-8}$ $cm^2/Vs$ or lower, or $1.0\times10^{-9}$ $cm^2/Vs$ or lower. The lower limit is not particularly limited, and is usually $1.0\times10^{-17}$ $cm^2/Vs$ or higher.

The hole mobility $\mu_2$ is measured by the methods described in Examples.

In one embodiment, the first compound has an ionization potential (Ip) of 5.80 to 6.50 eV.

The ionization potential (Ip) is measured by the method described in Examples.

In one embodiment, the first compound has an electron affinity (Af) of 1.40 to 2.20 eV.

The electron affinity (Af) is measured by the method described in Examples.

In one embodiment, the first compound has a band gap (Eg) of 2.80 to 3.80 eV.

The band gap (Eg) is measured by the method described in Examples.

In one embodiment, the first compound has a triplet energy ($T_1$) of 2.50 to 3.10 eV.

The triplet energy ($T_1$) is measured by the method described in Examples.

In one embodiment, the first compound is one or more selected from the group consisting of compounds represented by each of the following formulas (1), (2), (3), and (4).

(1)

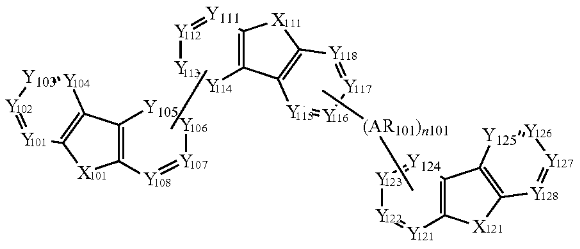

wherein in the formula (1), $X_{101}$, $X_{111}$, and $X_{121}$ are independently O or S;

$Ar_{101}$ is a substituted or unsubstituted arylene group including 6 to 30 ring carbon atoms, or a substituted or unsubstituted heteroarylene group including 5 to 30 ring atoms;

n101 is 0 or 1;

one of $Y_{105}$ to $Y_{108}$ and one of $Y_{111}$ to $Y_{114}$ are respectively $CR_{132}$, and these $R_{132}$'s are bonded with each other by a single bond;

when n101 is 0, one of $Y_{115}$ to $Y_{118}$ and one of $Y_{121}$ to $Y_{124}$ are respectively $CR_{132}$, and these $R_{132}$'s are bonded with each other by a single bond;

when n101 is 1, one of $Y_{115}$ to $Y_{118}$ and one of $Y_{121}$ to $Y_{124}$ are respectively $CR_{132}$, and these $R_{132}$'s are respectively bonded with $Ar_{101}$ by a single bond;

$Y_{101}$ to $Y_{104}$, $Y_{125}$ to $Y_{128}$, $Y_{105}$ to $Y_{108}$ which are not $CR_{132}$'s, $Y_{111}$ to $Y_{118}$ which are not $CR_{132}$, and $Y_{121}$ to $Y_{124}$ which are not $CR_{132}$ are independently N or $CR_{131}$;

$R_{131}$ is a hydrogen atom or a substituent R;

when two or more $R_{131}$'s are present, the two or more $R_{131}$'s may be the same as or different from each other;

the substituent R is selected form the group consisting of a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$ (where $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; and when two or more of each of $R_{901}$ to $R_{907}$ are present, the two or more of each of $R_{901}$ to $R_{907}$ are the same as or different from each other), a halogen atom, a cyano group, a nitro group, a substituted or unsubstituted aryl group including 6 to 50 ring carbon atoms, and a substituted or unsubstituted monovalent heterocyclic group including 5 to 50 ring atoms; and when two or more substituent R's are present, the two or more substituent R's may be the same as or different from each other;

(2)

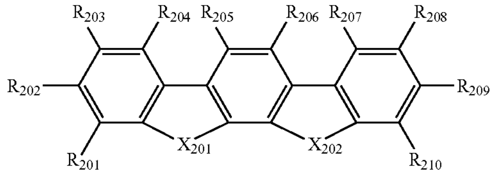

wherein in the formula (2), $X_{201}$ and $X_{202}$ are independently O or S;

at least one of $R_{201}$ to $R_{204}$ and $R_{207}$ to $R_{210}$ is a group represented by the following formula (2A);

$$-L_{201}-Ar_{201} \quad (2A)$$

wherein in the formula (2A), $L_{201}$ is a single bond, a substituted or unsubstituted arylene group including 6 to 50 ring carbon atoms, or a substituted or unsubstituted divalent heterocyclic group including 5 to 50 ring atoms;

$Ar_{201}$ is a substituted or unsubstituted aryl group including 6 to 50 ring carbon atoms, or a substituted or unsubstituted monovalent heterocyclic group including 5 to 50 ring atoms; and $R_{205}$ and $R_{206}$, and $R_{201}$ to $R_{204}$ and $R_{207}$ to $R_{210}$ which are not the group represented by the formulas (2A) are a hydrogen atom, a substituted or unsubstituted alkyl group including 1 to 50 carbon atoms, a substituted or unsubstituted aryl group including 6 to 50 ring carbon atoms, or a substituted or unsubstituted monovalent heterocyclic group including 5 to 50 ring atoms;

(3)

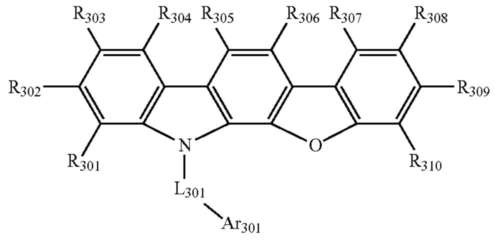

wherein in the formula (3), $R_{301}$ to $R_{310}$ are a hydrogen atom, a substituted or unsubstituted alkyl group including 1 to 50 carbon atoms, or a substituted or unsubstituted aryl group including 6 to 50 ring carbon atoms;

$L_{301}$ is a single bond, a substituted or unsubstituted arylene group including 6 to 50 ring carbon atoms, or a substituted or unsubstituted divalent heterocyclic group including 5 to 50 ring atoms; and $Ar_{301}$ is a substituted or unsubstituted monovalent heterocyclic group including 5 to 50 ring atoms;

(4)

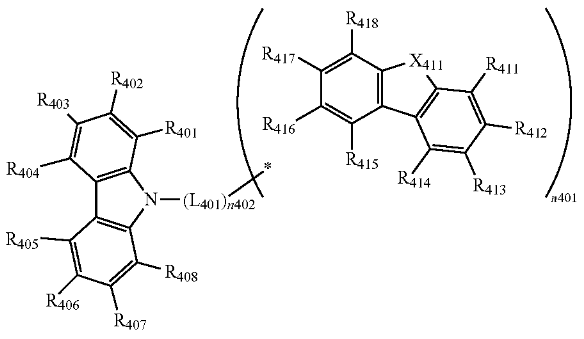

wherein in the formula (4), $R_{401}$ to $R_{408}$ are a hydrogen atom or a substituent R;

$L_{401}$ is a single bond, a substituted or unsubstituted aromatic hydrocarbon group including 6 to 50 ring carbon atoms, or a substituted or unsubstituted heterocyclic group including 5 to 50 ring atoms;

$X_{411}$ is O, S, or $NR_{419}$;

one of $R_{411}$ to $R_{418}$ is a single bond which bonds with $L_{401}$;

$R_{419}$, and $R_{411}$ to $R_{418}$ which are not a single bond which bonds with $L_{401}$ are independently a hydrogen atom or a substituent R;

n401 is an integer of 1 to 3;

when n401 is 2 or 3, the plurality of structures in parentheses may be the same as or different from each other;

n402 is an integer of 1 to 3;

when n402 is 2 or 3, the two or more $L_{401}$'s may be the same as or different from each other; and the substituent R is as defined in the formula (1).

The expression of "bonded with each other by a single bond" will be explained. Regarding the expression of "one of $Y_{105}$ to $Y_{108}$ and one of $Y_{111}$ to $Y_{114}$ are respectively $CR_{132}$ and these $R_{132}$'s are bonded with each other by a single bond," when $Y_{106}$ and $Y_{113}$ are respectively $CR_{132}$ and these $R_{132}$'s are bonded with each other by a single bond, C of $Y_{106}$ and C of $Y_{113}$ are bonded by a single bond, and the compound represented by the formula (1) has the following structure.

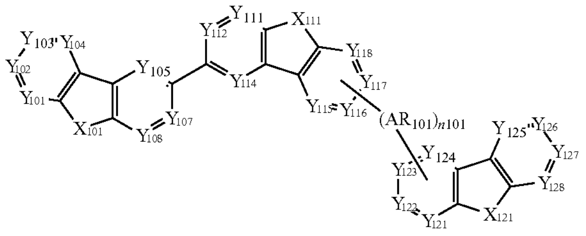

wherein in the structure, $X_{101}$, $X_{111}$, $X_{121}$, $Y_{101}$ to $Y_{105}$, $Y_{107}$ to $Y_{108}$, $Y_{111}$ to $Y_{112}$, $Y_{114}$ to $Y_{118}$, $Y_{121}$ to $Y_{128}$, $Ar_{101}$, and n101 are as defined in the formula (1).

The expression of "respectively bonded with $Ar_{101}$ by a single bond" will be explained. Regarding the expression of "when n101 is 1, one of $Y_{115}$ to $Y_{118}$ and one of $Y_{121}$ to $Y_{124}$ are respectively $CR_{132}$, and these $R_{132}$'s are respectively bonded with $Ar_{101}$ by a single bond," when $Y_{116}$ and $Y_{123}$ are respectively $CR_{132}$, and these $R_{132}$'s are respectively bonded with $Ar_{101}$ by a single bond, C of $Y_{116}$ and $Ar_{101}$ are bonded by a single bond, C of $Y_{123}$ and $Ar_{101}$ are bonded by a single bond, and the compound represented by the formula (1) has the following structure.

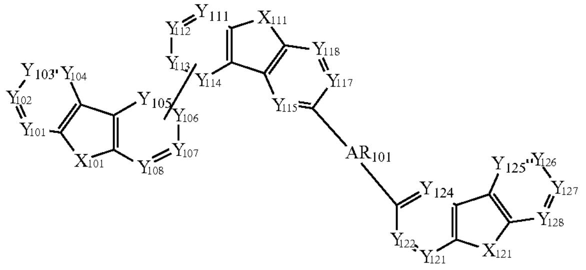

wherein in the structure, $X_{101}$, $X_{111}$, $X_{121}$, $Y_{101}$ to $Y_{108}$, $Y_{111}$ to $Y_{115}$, $Y_{117}$ to $Y_{118}$, $Y_{121}$ to $Y_{122}$, $Y_{124}$ to $Y_{128}$, and $Ar_{101}$ are as defined in the formula (1).

In one embodiment, the compound represented by the formula (1) is a compound represented by the following formula (1-1).

(1-1)

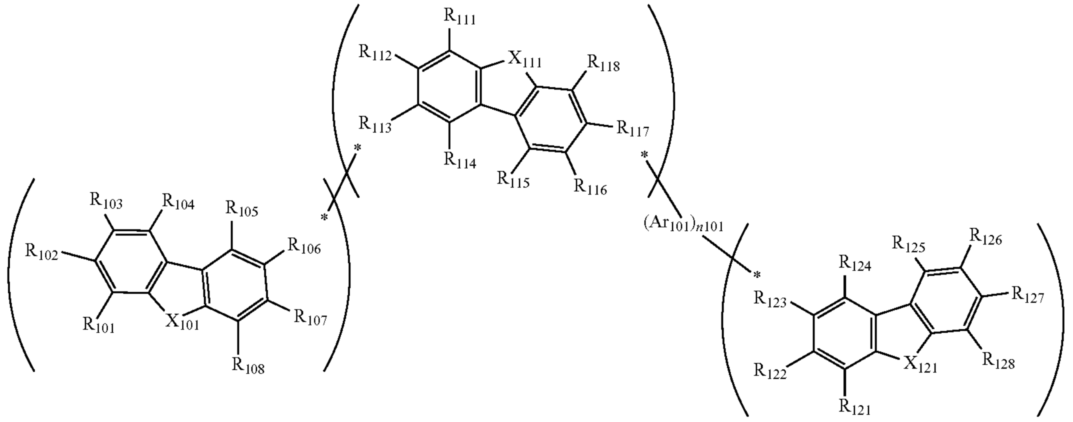

wherein in the formula (1-1), $X_{101}$, $X_{111}$, $X_{121}$, $Ar_{101}$, and n101 are as defined in the formula (1);

one of $R_{105}$ to $R_{108}$ and one of Rin to $R_{114}$ are bonded with each other by a single bond;

when n101 is 0, one of $R_{115}$ to $R_{118}$ and one of $R_{121}$ to $R_{124}$ are bonded with each other by a single bond;

when n101 is 1, one of $R_{115}$ to $R_{118}$ and one of $R_{121}$ to $R_{124}$ are respectively bonded with $Ar_{101}$ by a single bond;

$R_{101}$ to $R_{104}$, $R_{125}$ to $R_{128}$, $R_{105}$ to $R_{108}$ which do not form a single bond, Rin to $R_{118}$ which do not form a single bond, and $R_{121}$ to $R_{124}$ which do not form a single bond are independently a hydrogen atom or a substituent R;

and the substituent R is as defined in the formula (1).

In one embodiment, the compound represented by the formula (1) is a compound represented by the following formula (1-2).

(1-2)

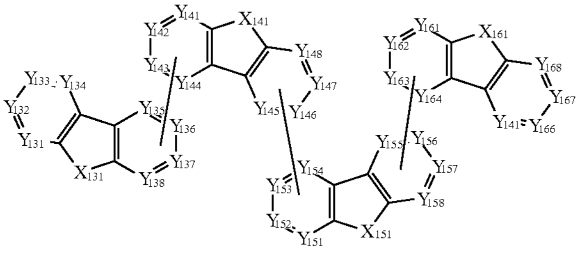

wherein in the formula (1-2), $X_{131}$, $X_{141}$, $X_{151}$, and $X_{161}$ are independently O or S;

one of $Y_{135}$ to $Y_{138}$ and one of $Y_{141}$ to $Y_{144}$ are respectively $CR_{132}$, and these $R_{132}$'s are bonded with each other by a single bond;

one of $Y_{145}$ to $Y_{148}$ and one of $Y_{151}$ to $Y_{154}$ are respectively $CR_{132}$, and these $R_{132's}$ are bonded with each other by a single bond;

one of $Y_{155}$ to $Y_{158}$ and one of $Y_{161}$ to $Y_{164}$ are respectively $CR_{132}$, and these $R_{132}$'s are bonded with each other by a single bond;

$Y_{131}$ to $Y_{134}$, $Y_{165}$ to $Y_{168}$, $Y_{135}$ to $Y_{138}$ which are not $CR_{132}$, $Y_{141}$ to $Y_{148}$ which are not $CR_{132}$, $Y_{151}$ to $Y_{158}$ which are not $CR_{132}$, and $Y_{161}$ to $Y_{164}$ which are not $CR_{132}$ are independently N or $CR_{131}$; $R_{131}$ is a hydrogen atom or a substituent R;

when two or more $R_{131}$'s are present, the two or more $R_{131}$'s may be the same as or different from each other; and the substituent R is as defined in the formula (1).

In one embodiment, the compound represented by the formula (1) is a compound represented by the following formula (1-11).

(1-11)

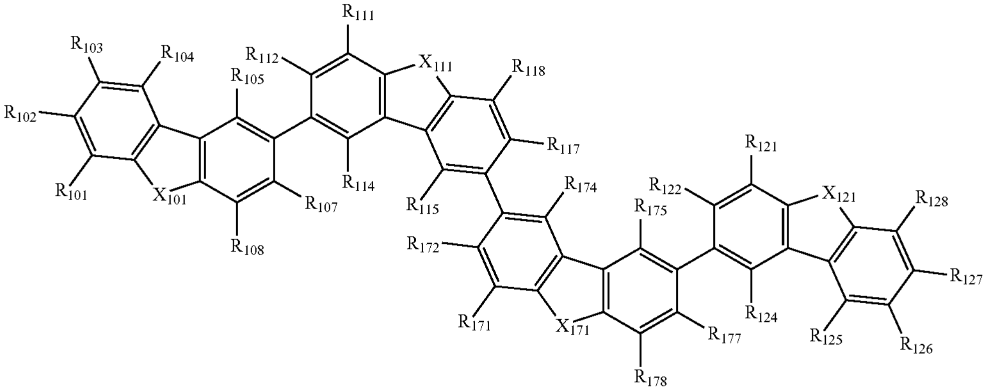

wherein in the formula (1-11), $X_{101}$, $X_{111}$, and $X_{121}$ are as defined in the formula (1);

$X_{171}$ is O or S;

$R_{101}$ to $R_{105}$, $R_{107}$ to $R_{108}$, $R_{111}$ to $R_{112}$, $R_{114}$ to $R_{115}$, $R_{117}$ to $R_{118}$, $R_{121}$ to $R_{122}$, $R_{124}$ to $R_{128}$, $R_{171}$ to $R_{172}$, $R_{174}$ to $R_{175}$, and $R_{177}$ to $R_{178}$ are independently a hydrogen atom or a substituents R; and the substituent R is as defined in the formula (1).

In one embodiment, at least one of $R_{201}$ to $R_{204}$ in the formula (2) is the group represented by the formula (2A), and at least one of $R_{207}$ to $R_{210}$ is the group represented by the formula (2A).

In one embodiment, one of $R_{201}$ to $R_{204}$ in the formula (2) is the group represented by the formula (2A), and one of $R_{207}$ to $R_{210}$ is the group represented by the formula (2A).

In one embodiment, $L_{201}$ in the formula (2A) is a single bond or a substituted or unsubstituted arylene group including 6 to 50 ring carbon atoms, and $Ar_{201}$ is a substituted or unsubstituted aryl group including 6 to 50 ring carbon atoms.

In one embodiment, the compound represented by the formula (2) is a compound represented by the following formula (2-1).

(2-1)

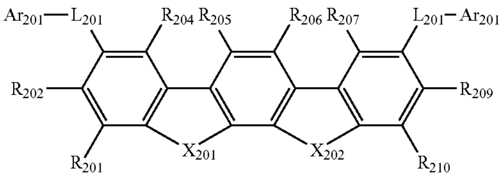

wherein in the formula (2-1), $X_{201}$, $X_{202}$, $L_{201}$, and $Ar_{201}$ are as defined in the formula (2); and $R_{201}$ to $R_{202}$, $R_{204}$ to $R_{207}$, and $R_{209}$ to $R_{210}$ are independently a hydrogen atoms, a substituted or unsubstituted alkyl group including 1 to 50 carbon atoms, or a substituted or unsubstituted aryl group including 6 to 50 ring carbon atoms.

In one embodiment, the compound represented by the formula (2) is a compound represented by the following formula (2-11).

(2-11)

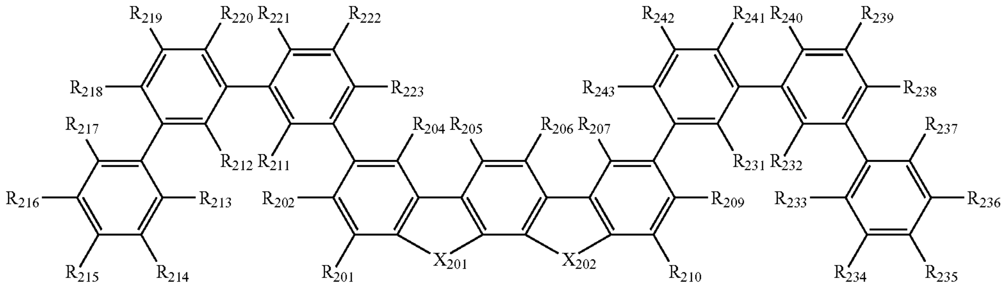

wherein in the formula (2-11), $X_{201}$ and $X_{202}$ are as defined in the formula (2); and $R_{201}$ to $R_{202}$, $R_{204}$ to $R_{207}$, $R_{209}$ to $R_{210}$, $R_{211}$ to $R_{223}$, and $R_{231}$ to $R_{243}$ are independently a hydrogen atom, a substituted or unsubstituted alkyl group including 1 to 50 carbon atoms, or a substituted or unsubstituted aryl group including 6 to 50 ring carbon atoms.

In one embodiment, $L_{301}$ in the formula (3) is a substituted or unsubstituted arylene group including 6 to 50 ring carbon atoms.

In one embodiment, the compound represented by the formula (3) is a compound represented by the following formula (3-1).

(3-1)

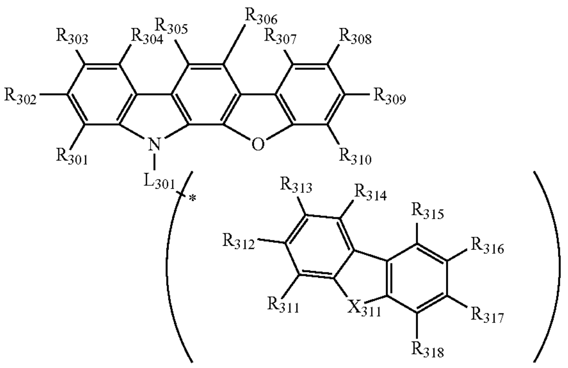

wherein in the formula (3-1), $R_{301}$ to $R_{310}$ and $L_{301}$ are as defined in the formula (3);

$X_{311}$ is O, S, or $NR_{319}$;

one of $R_{311}$ to $R_{319}$ is a single bond which bonds with $L_{301}$;

$R_{311}$ to $R_{319}$ which are not a single bond which bonds with $L_{301}$ are independently a hydrogen atom or a substituent R; and the substituent R is as defined in the formula (1).

In one embodiment, the compound represented by the formula (3) is a compound represented by the following formula (3-2).

(3-2)

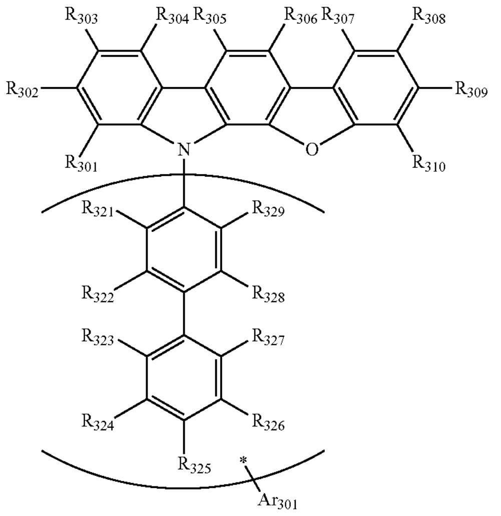

wherein in the formula (3-2), $R_{301}$ to $R_{310}$ and $Ar_{301}$ are as defined in the formula (3);

one of $R_{321}$ to $R_{329}$ is a single bond which bonds with $Ar_{301}$;

$R_{321}$ to $R_{329}$ which are not a single bond which bonds with $Ar_{301}$ are independently a hydrogen atom or a substituent R; and the substituent R is as defined in the formula (1).

In one embodiment, the compound represented by the formula (3) is a compound represented by the following formula (3-11).

(3-11)

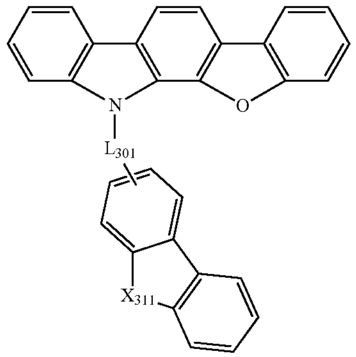

wherein in the formula (3-11), $L_{301}$ is as defined in the formula (3); $X_{311}$ is O, S, or $NR_{319}$; $R_{319}$ is a hydrogen atom or a substituent R; and the substituent R is as defined in the formula (1).

In one embodiment, $X_{411}$ in the formula (4) is O or S.

In one embodiment, n401 in the formula (4) is 1.

In one embodiment, $L_{401}$ in the formula (4) is a single bond or a substituted or unsubstituted arylene group including 6 to 50 ring carbon atoms.

In one embodiment, at least one of $R_{401}$ to $R_{408}$ in the formula (4) is a substituent R.

In one embodiment, at least one of $R_{401}$ to $R_{408}$ in the formula (4) is a substituted or unsubstituted monovalent heterocyclic group including 5 to 50 ring atoms.

In one embodiment, the compound represented by the formula (4) is a compound represented by the following formula (4-1).

(4-1)

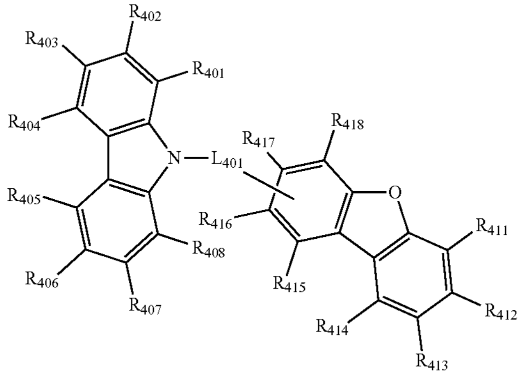

wherein in the formula (4-1), $R_{401}$ to $R_{408}$ and $L_{401}$ are as defined in the formula (4);

one of $R_{415}$ to $R_{418}$ is a single bond which bonds with $L_{401}$; $R_{411}$ to $R_{414}$, and $R_{415}$ to $R_{418}$ which are not a single bond which bonds with $L_{401}$ are independently a hydrogen atom or a substituent R; and the substituent R is as defined in the formula (1).

In one embodiment, the compound represented by the formula (4) is a compound represented by the following formula (4-11).

(4-11)

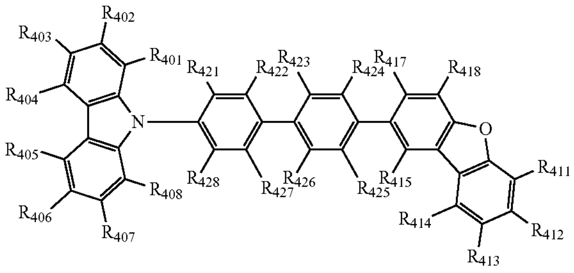

wherein in the formula (4-11), $R_{401}$ to $R_{408}$ is as defined in the formula (4);

$R_{411}$ to $R_{415}$, $R_{417}$ to $R_{418}$, and $R_{421}$ to $R_{428}$ are independently a hydrogen atom or a substituent R; and the substituent R is as defined in the formula (1).

The compounds represented by each of the formulas (1), (2), (3), and (4) can be synthesized by using known alternative reactions or raw materials tailored to the target product.

Specific examples of the first compound will be described below, but these are merely illustrative, and the first compound is not limited to the following specific examples.

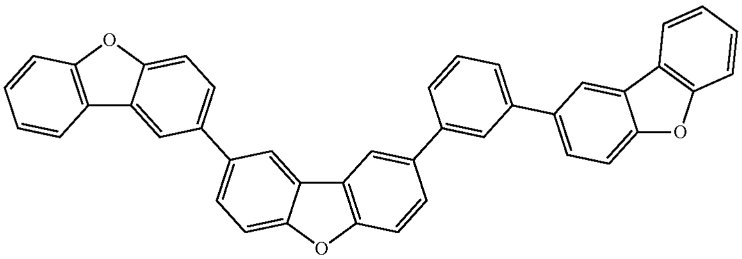

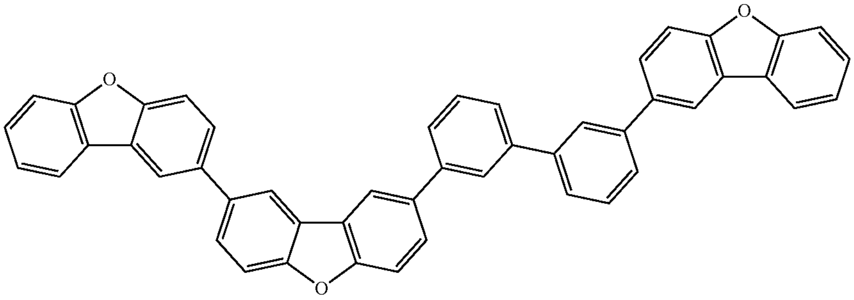

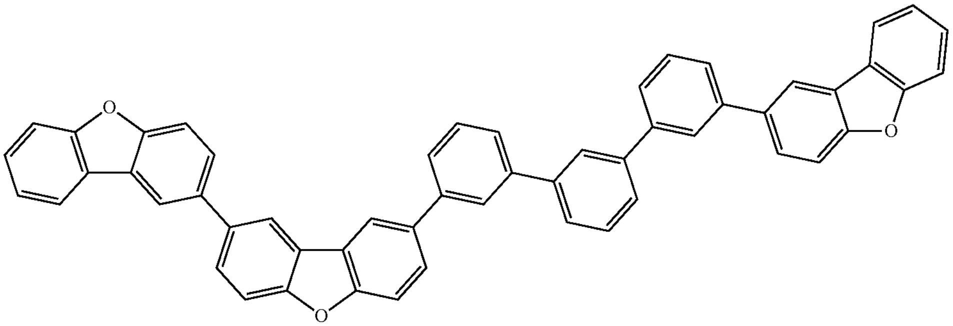

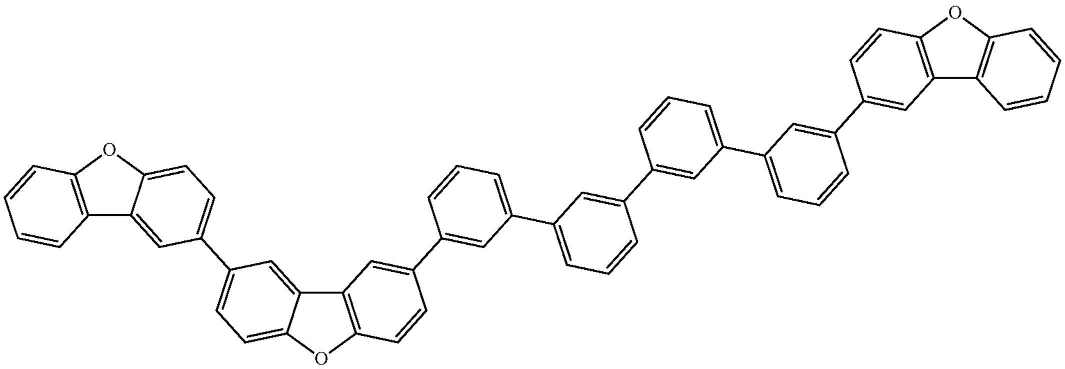

-continued
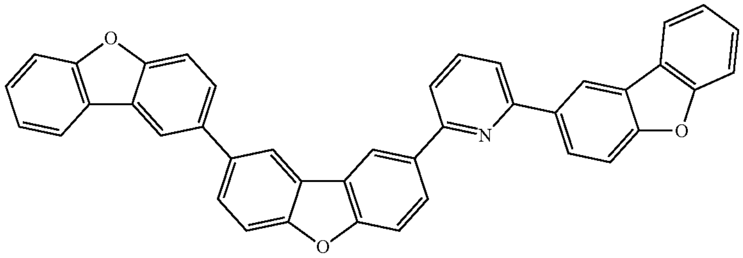
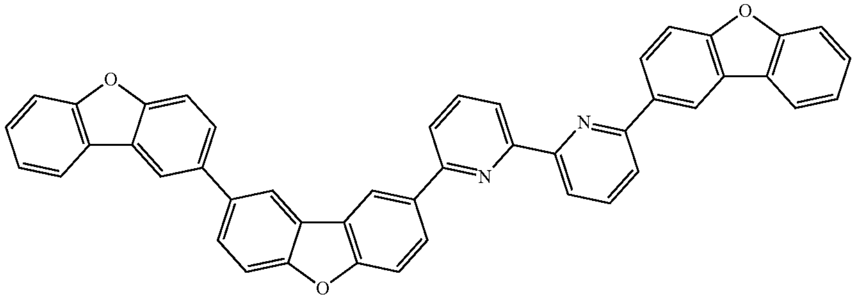
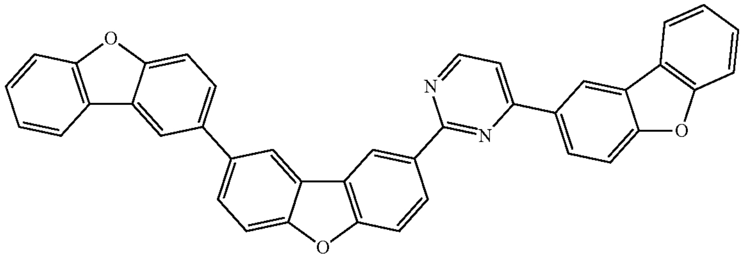
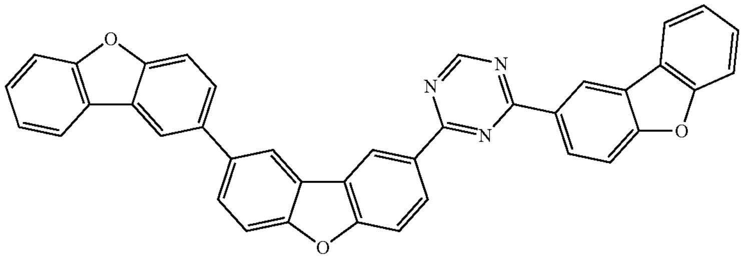
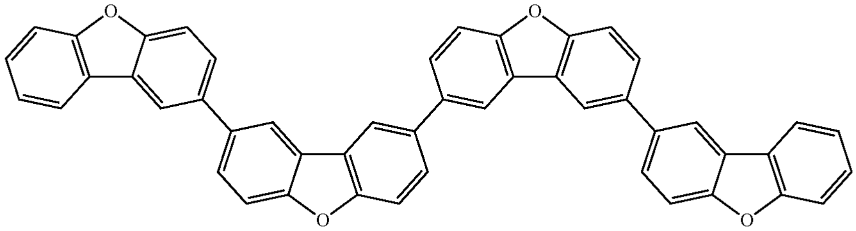
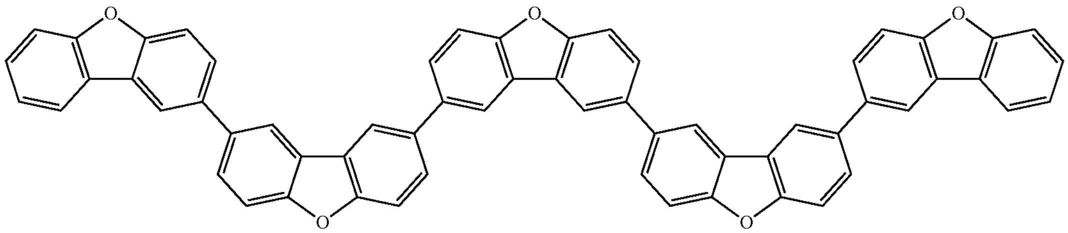

-continued
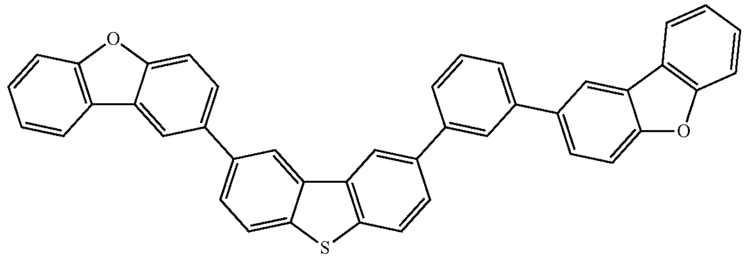
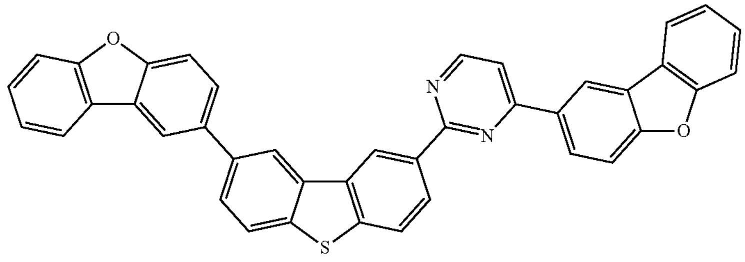
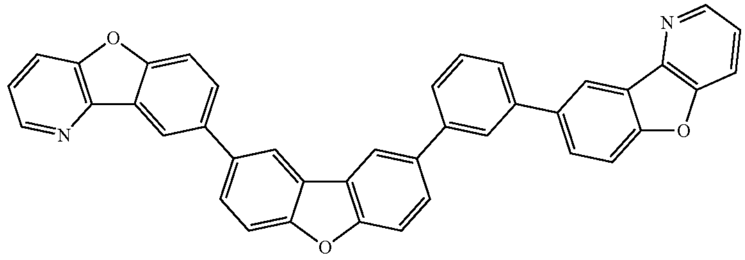
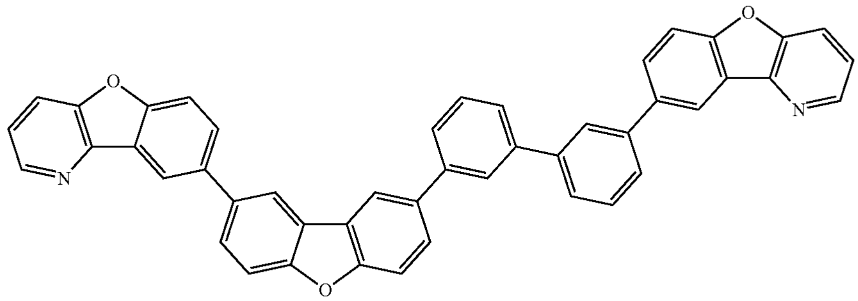
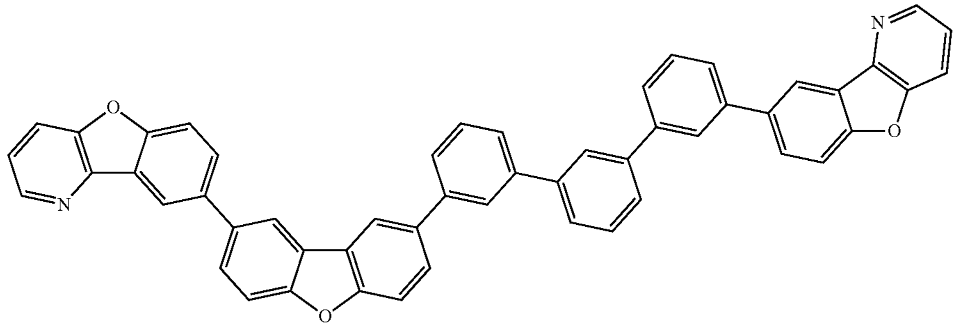

-continued
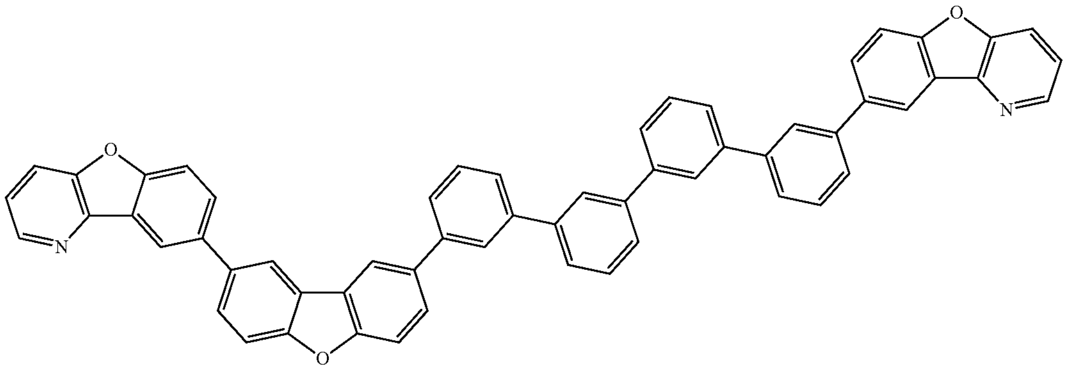
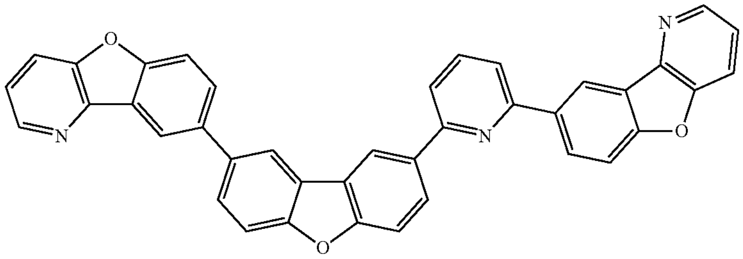
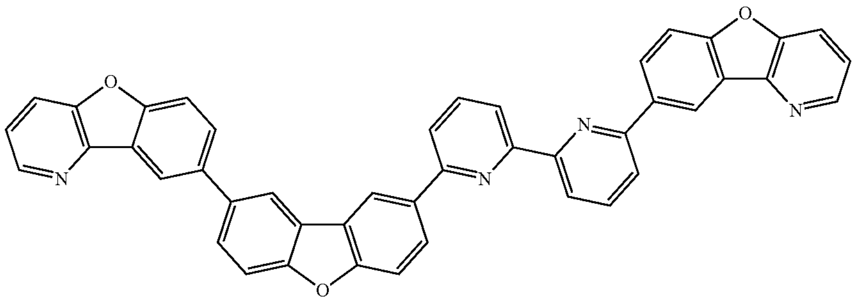
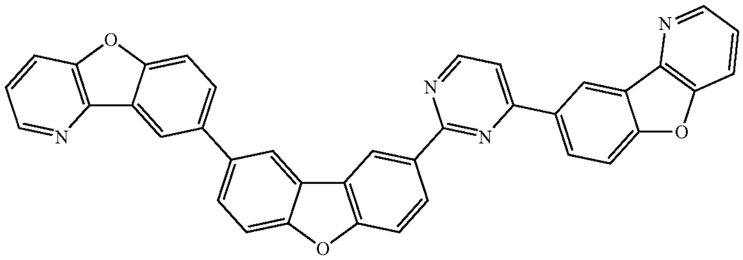
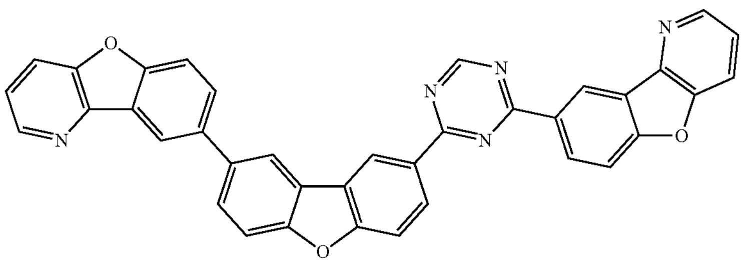
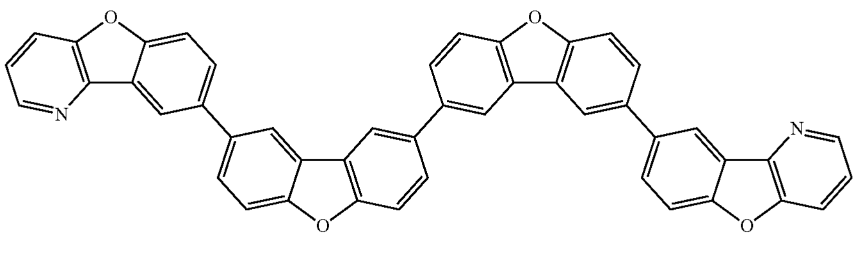

-continued
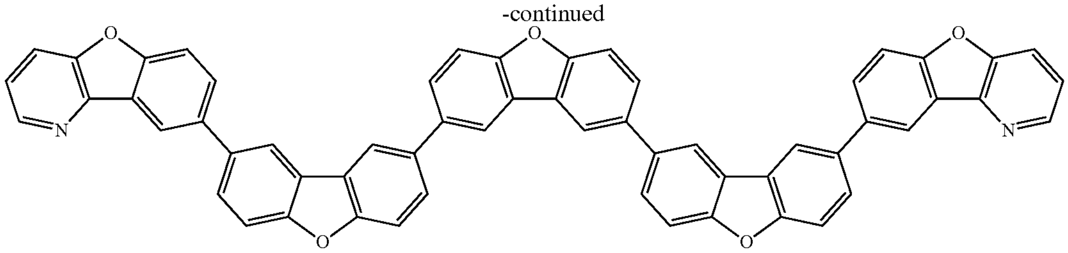
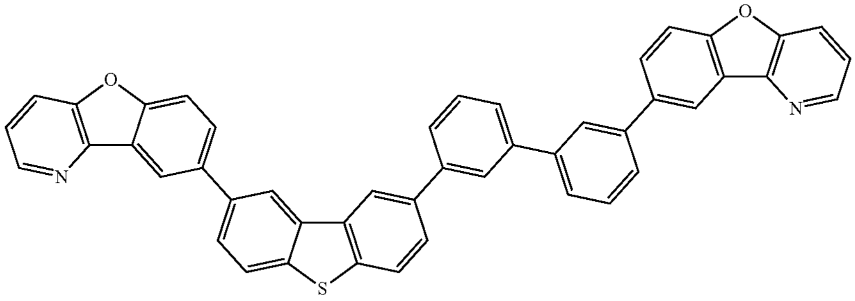
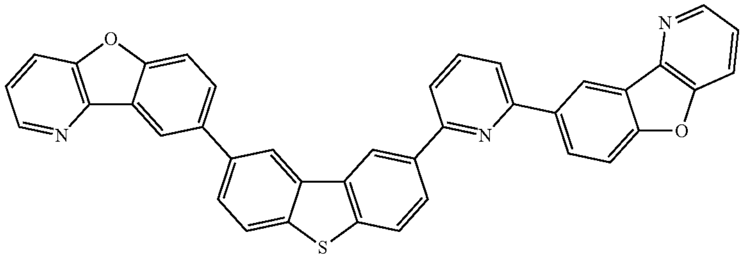
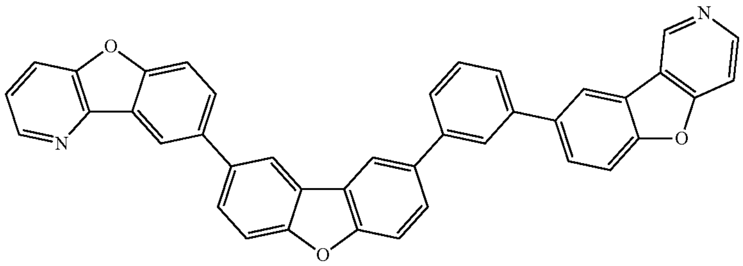
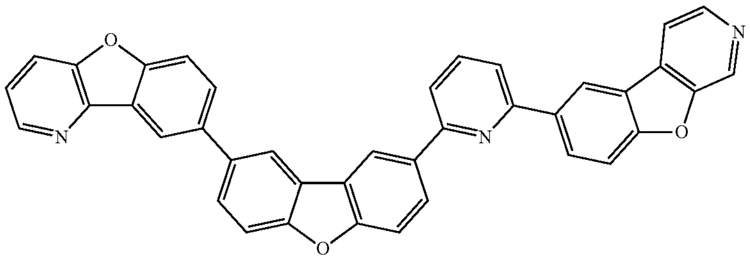
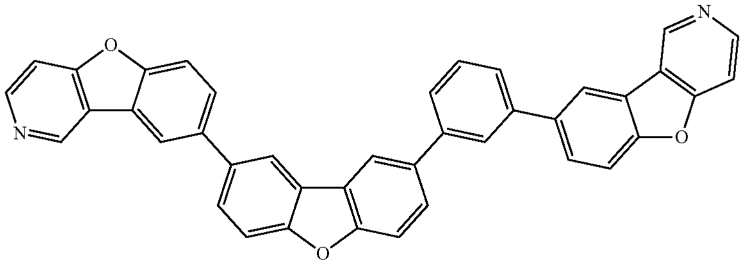

-continued
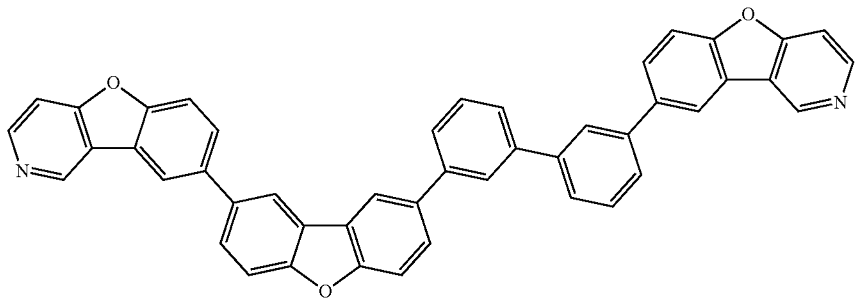
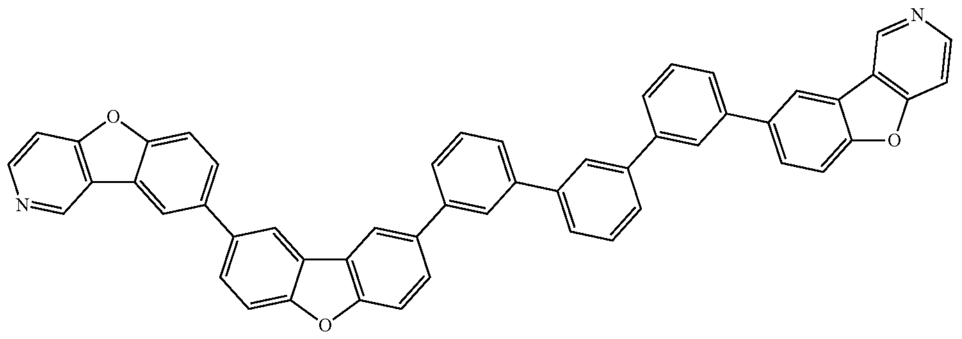
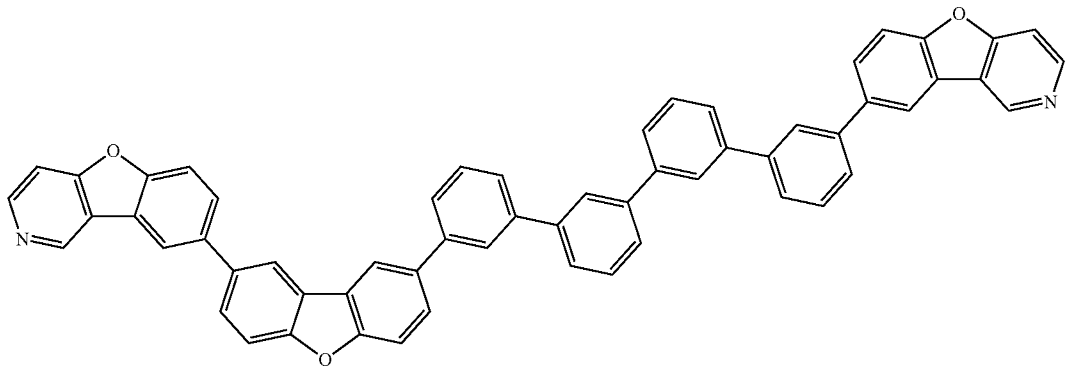
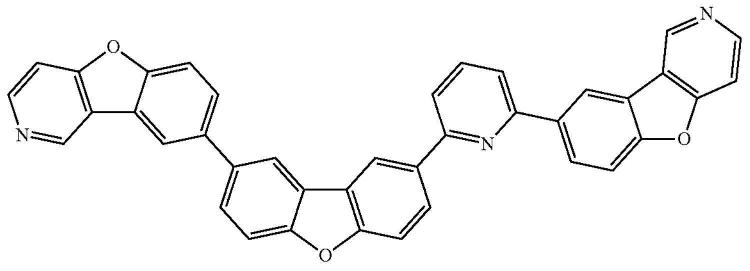
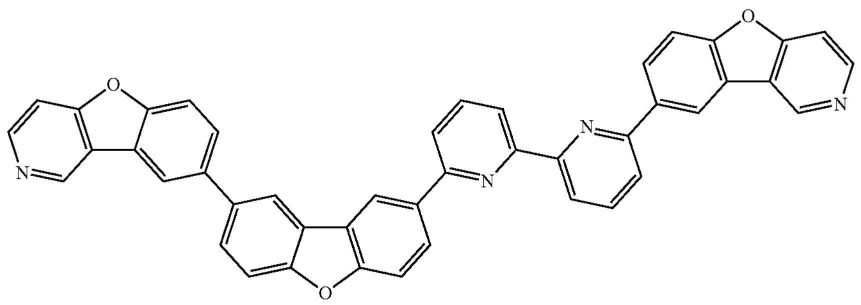

-continued
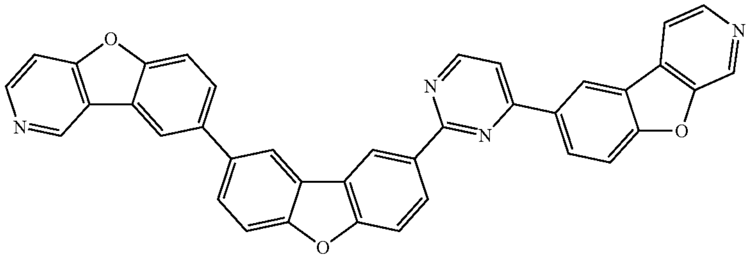
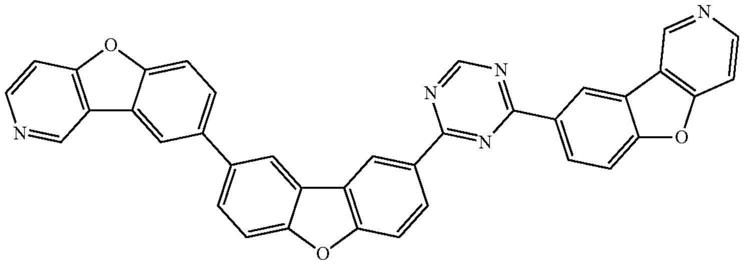
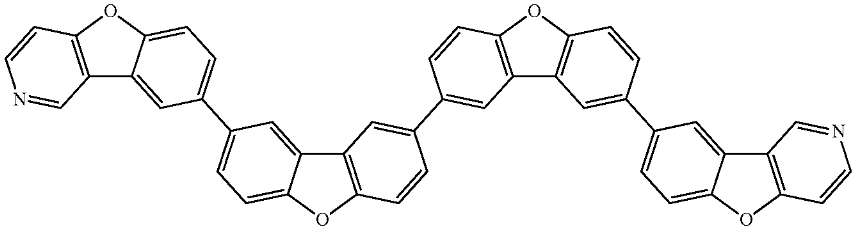
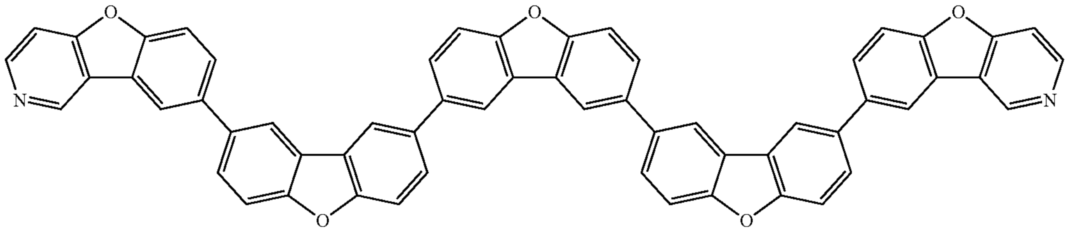
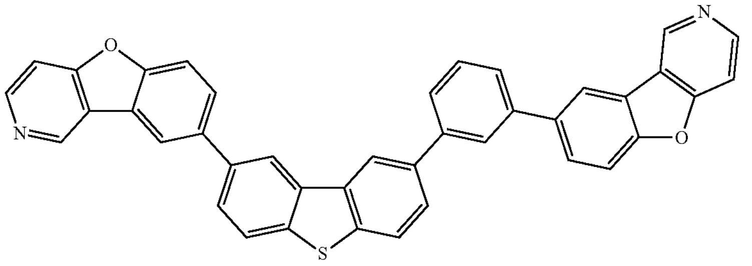
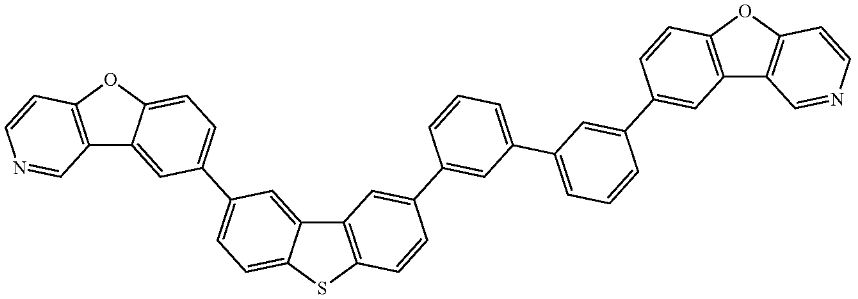

-continued
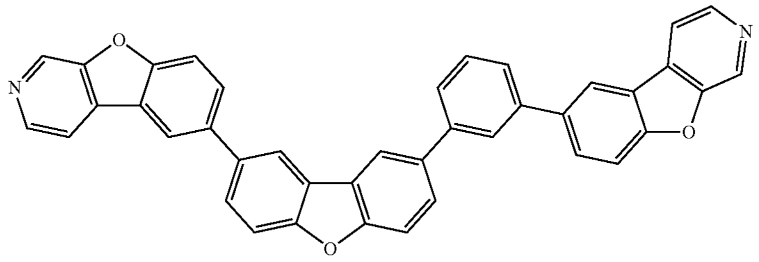
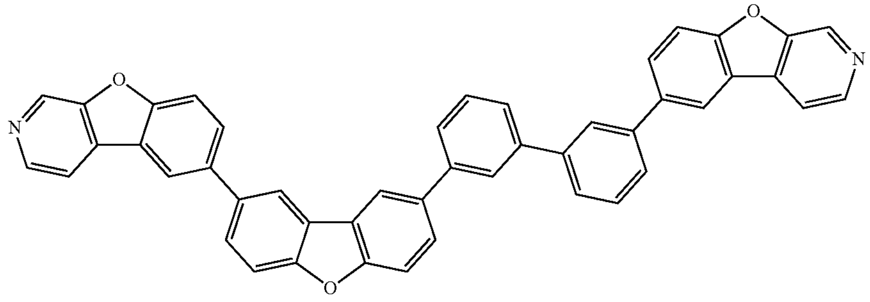
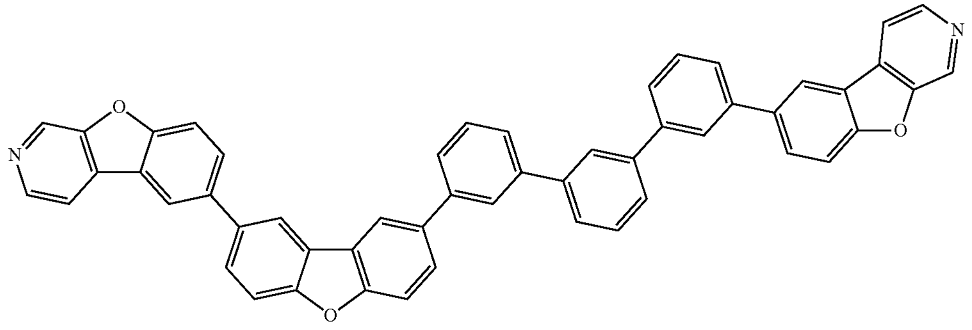
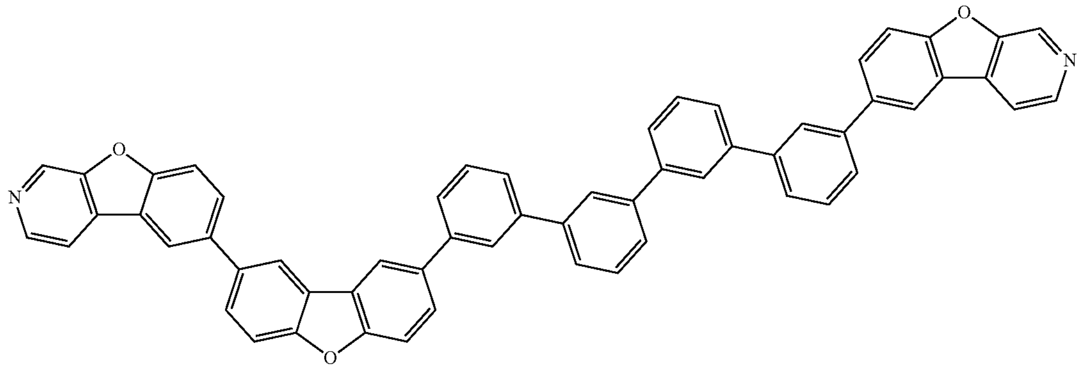
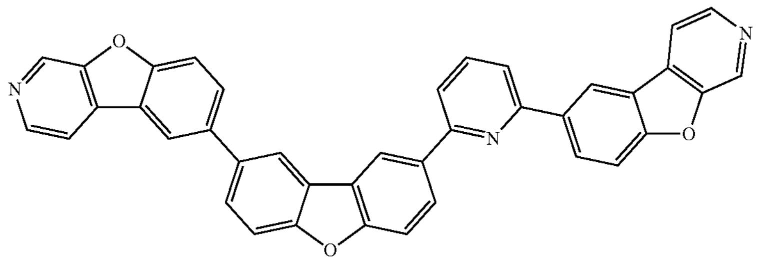

-continued
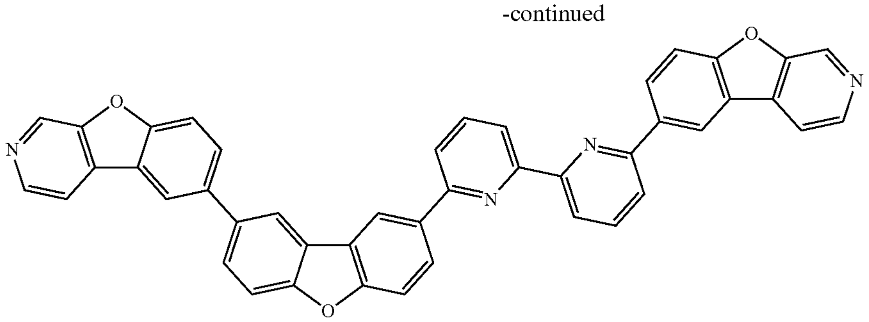
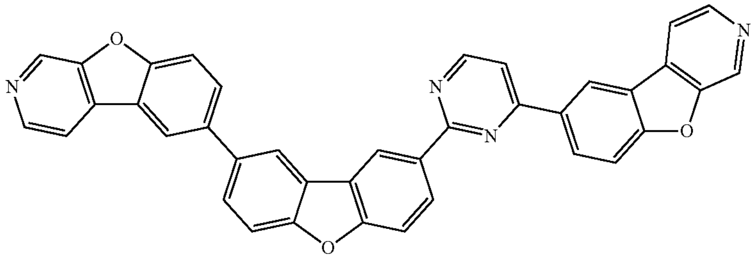
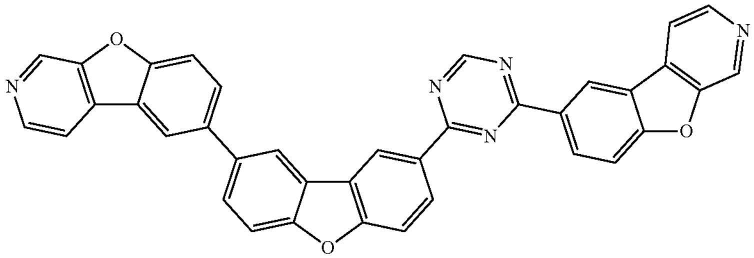
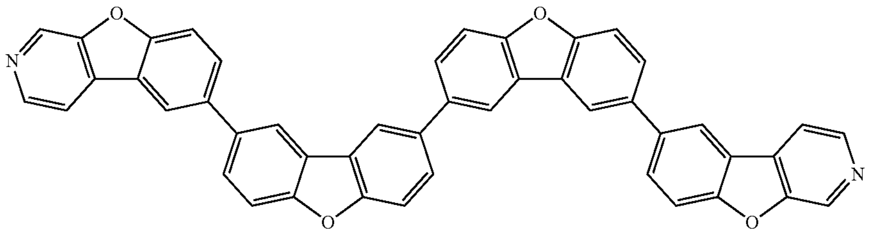
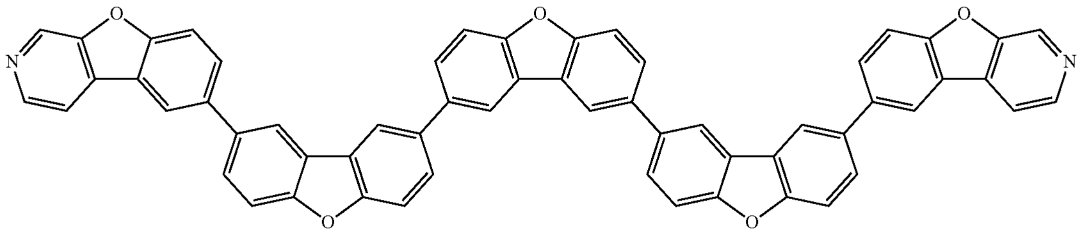
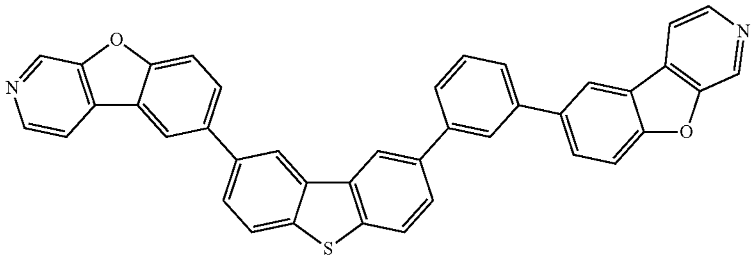

-continued
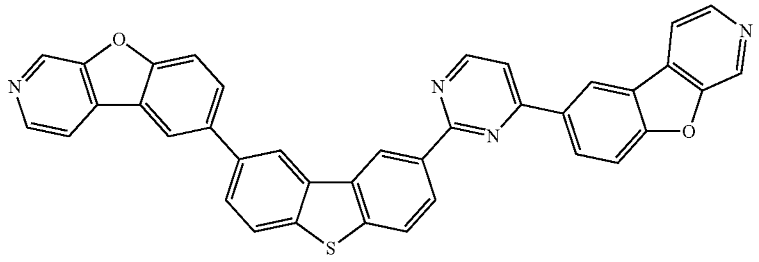
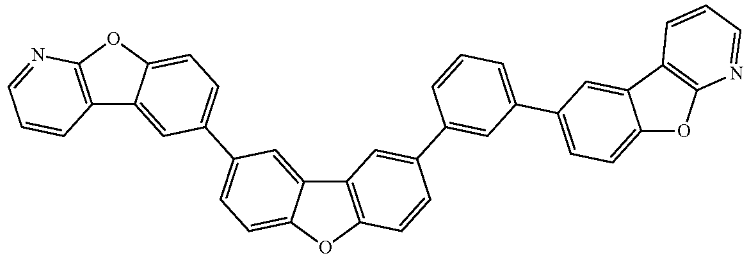
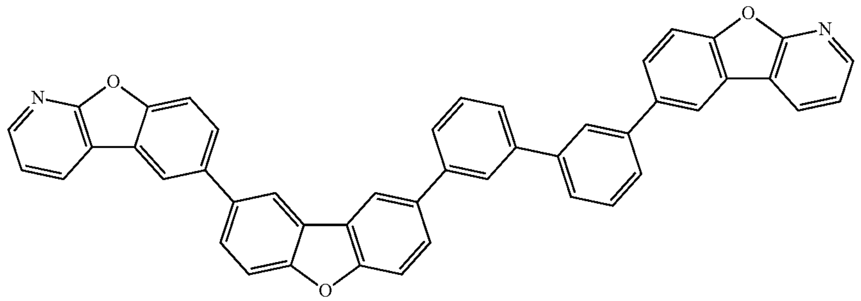
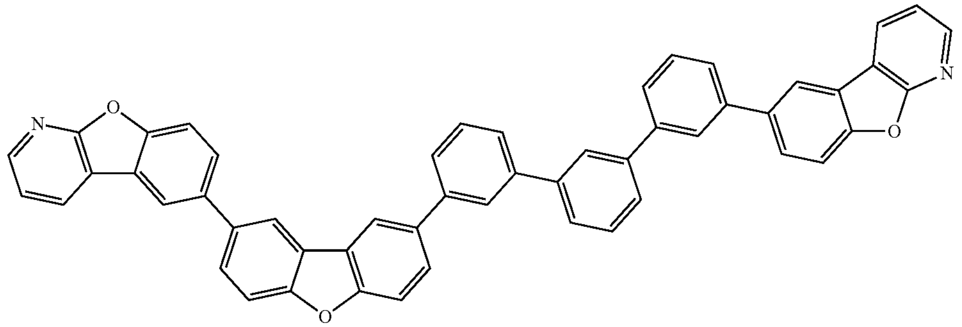
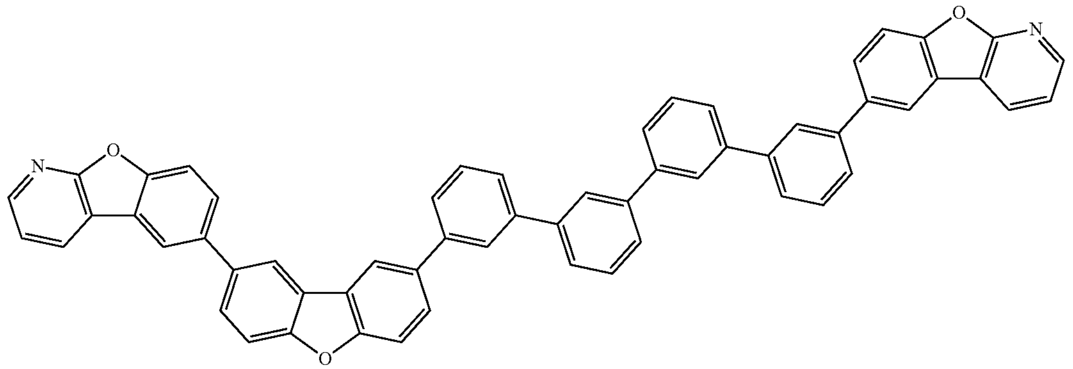

-continued
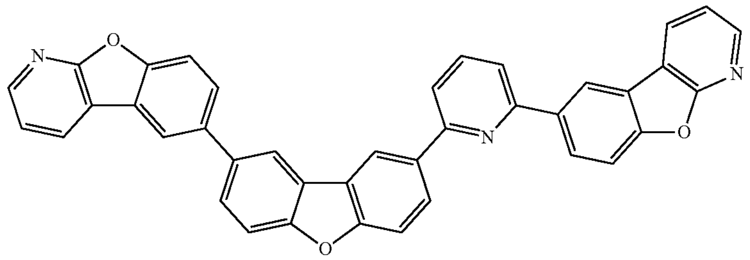
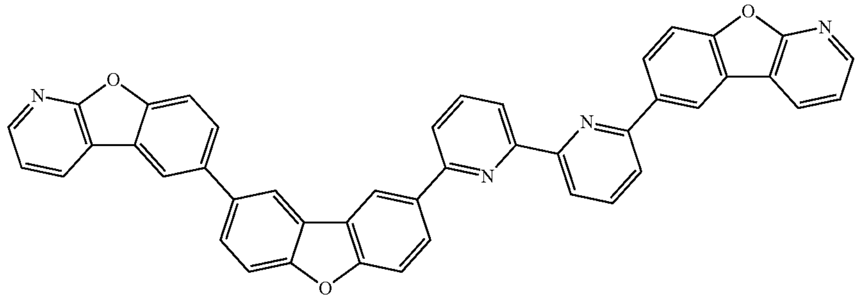
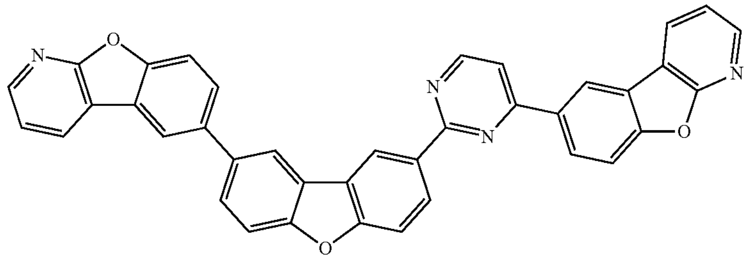
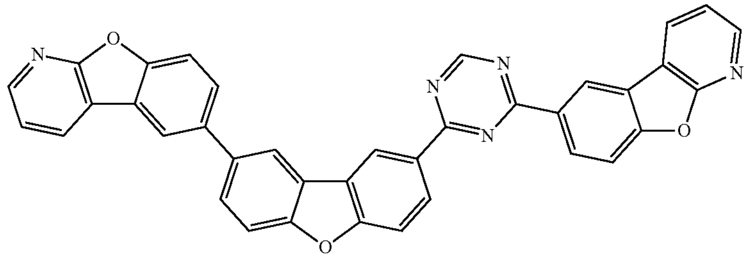
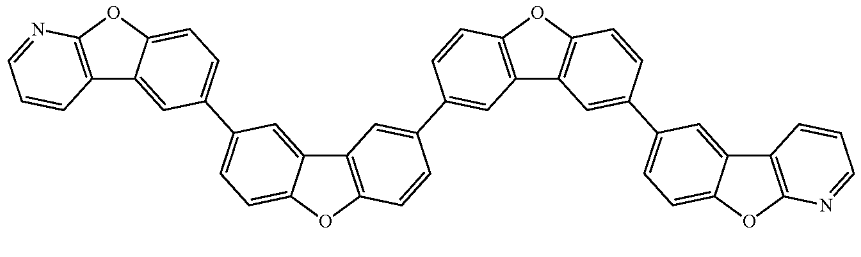
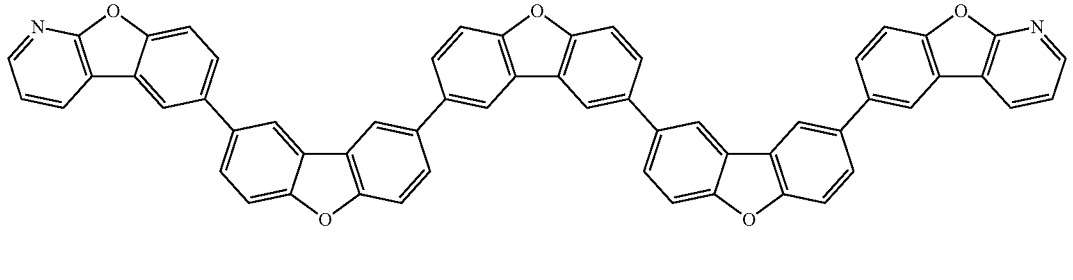

-continued
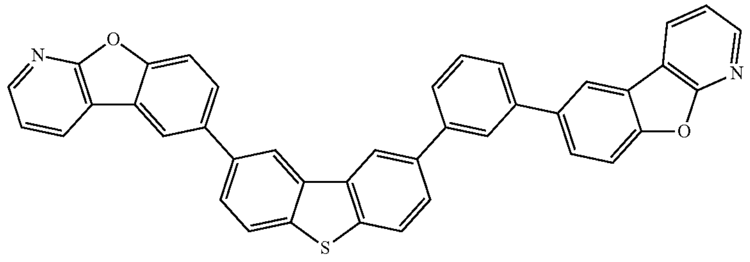
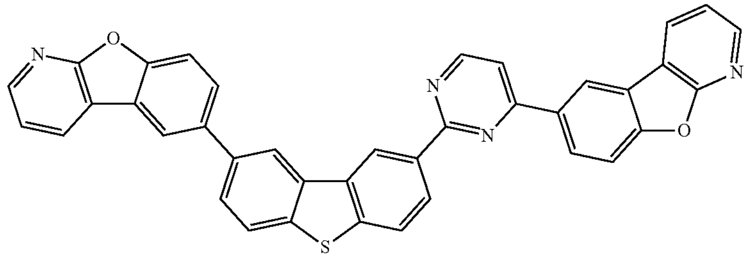
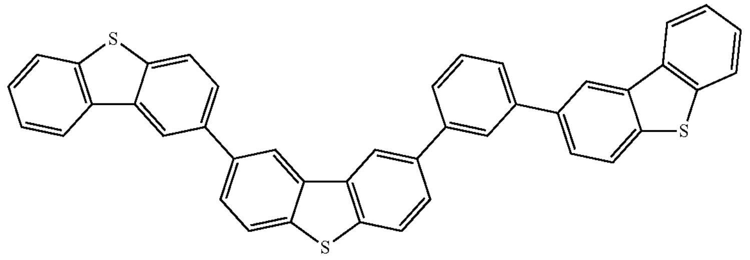
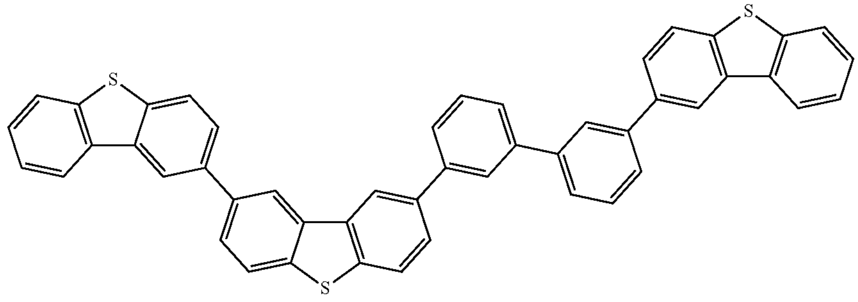
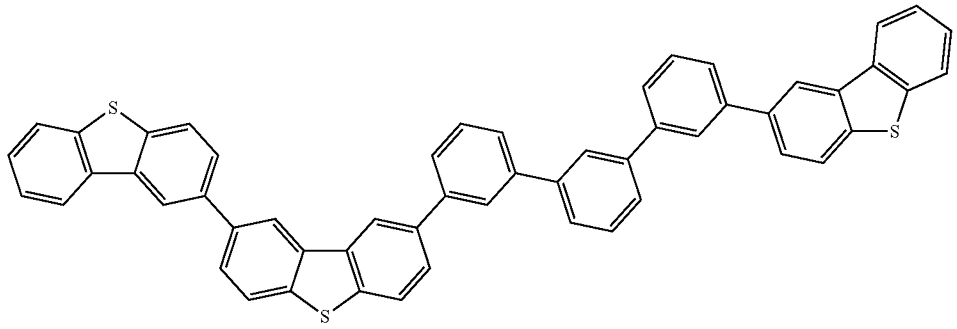

-continued
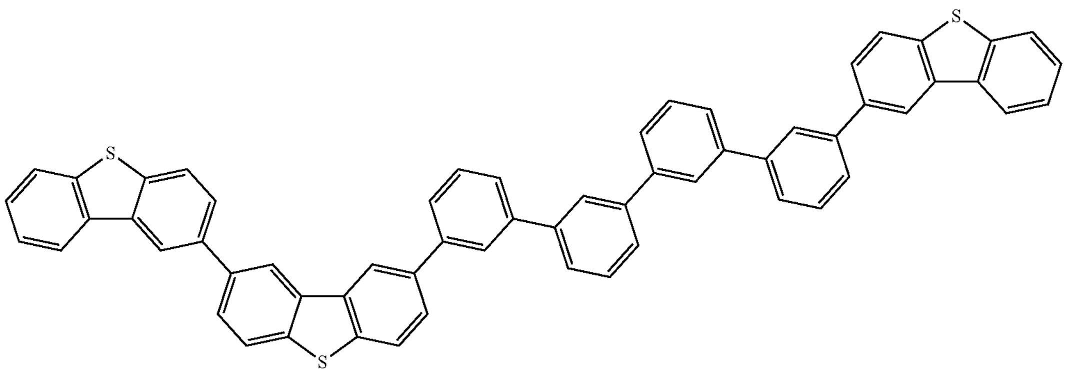
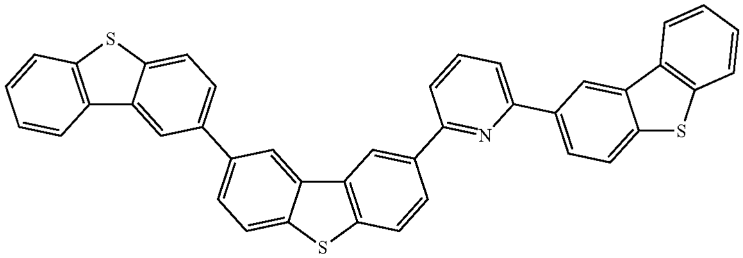
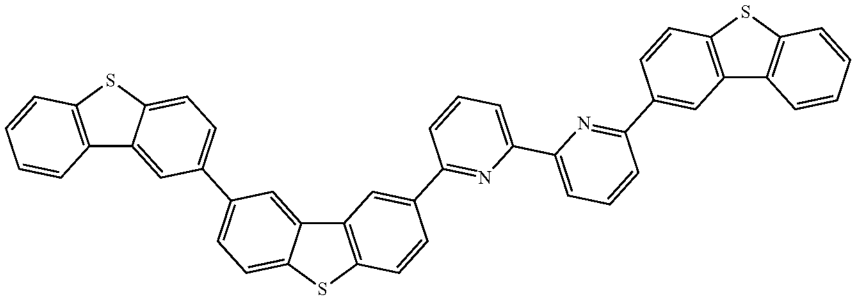
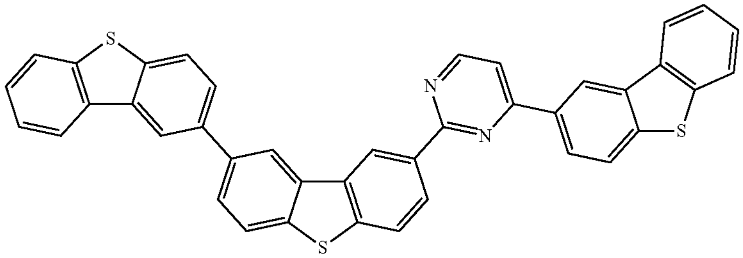
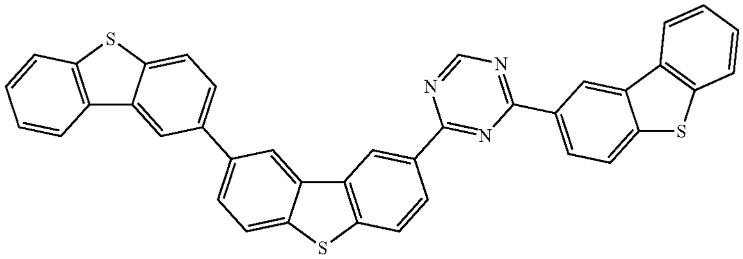
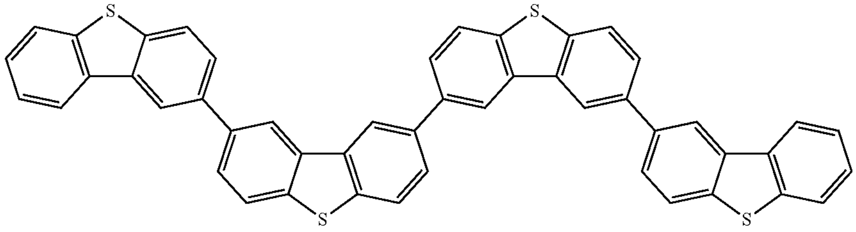

-continued
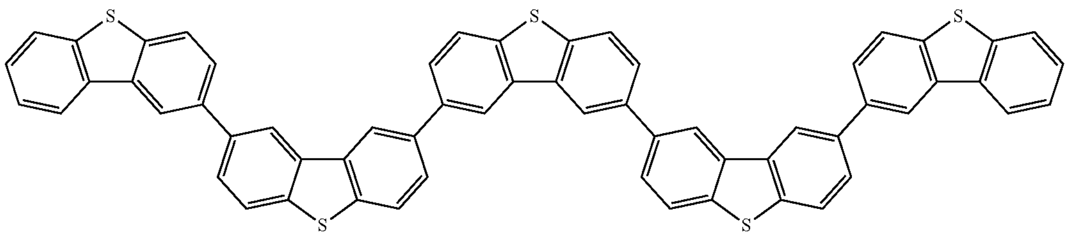
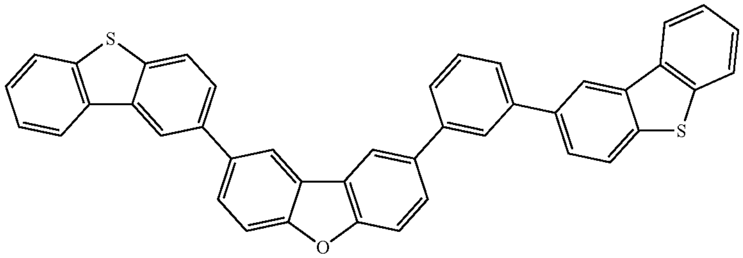
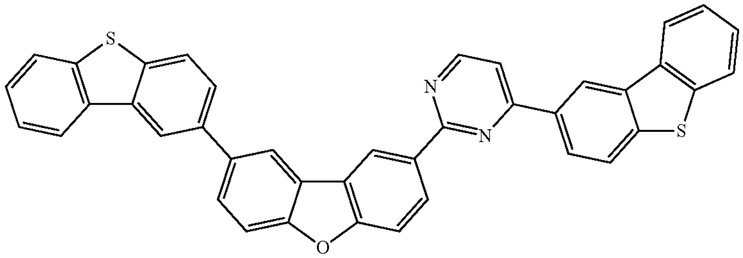
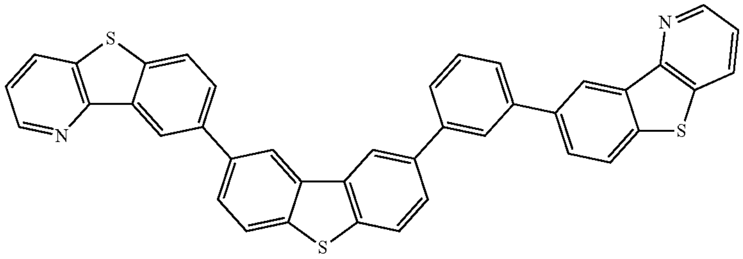
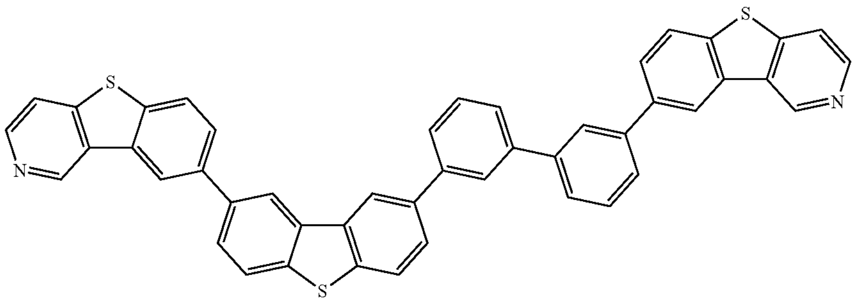
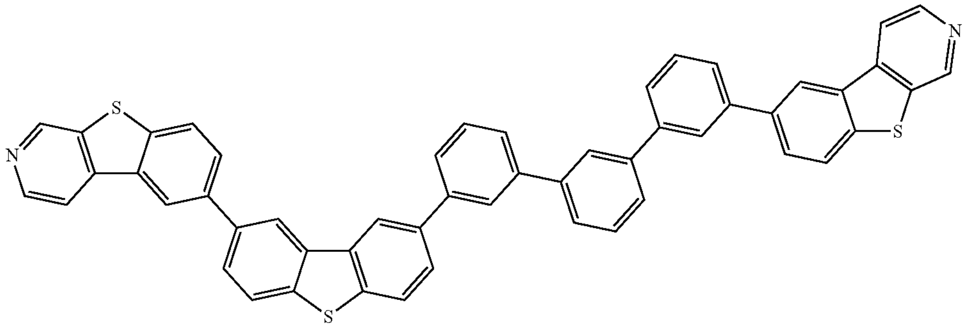

-continued
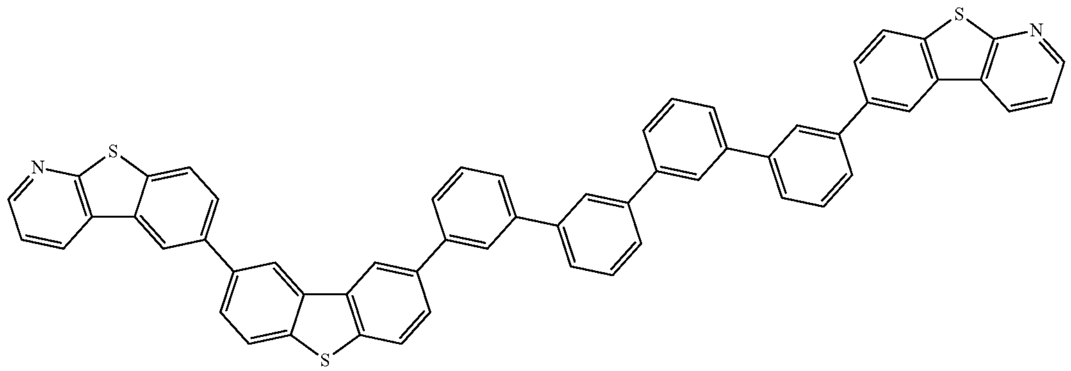
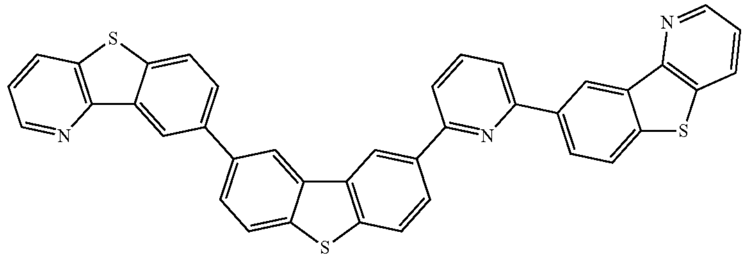
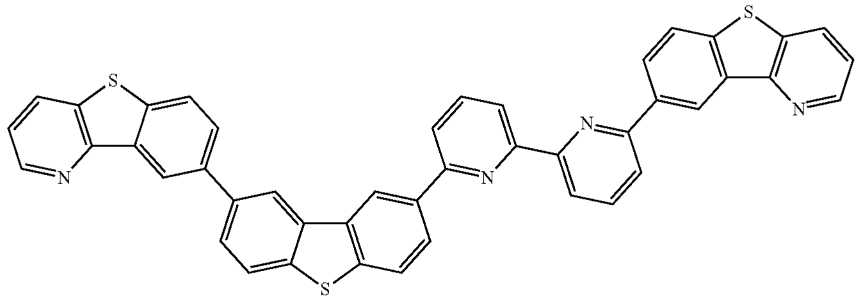
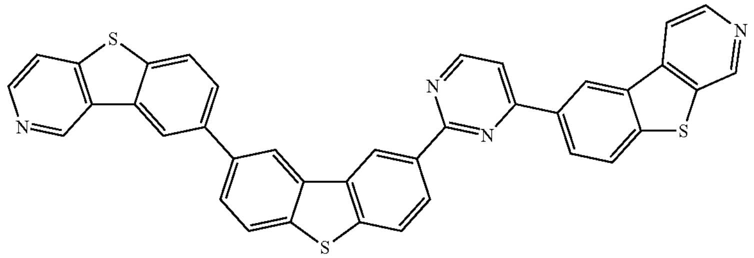
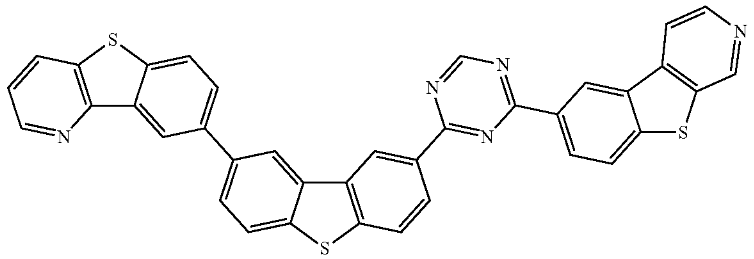
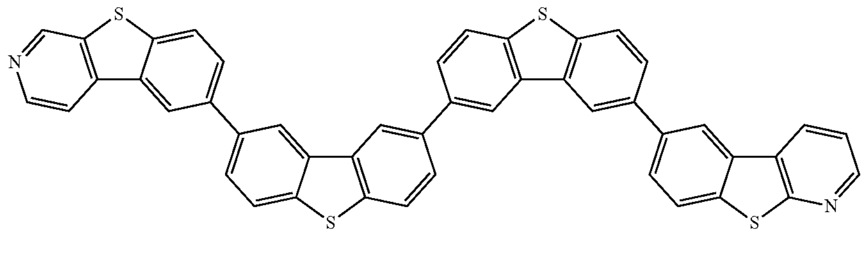

-continued
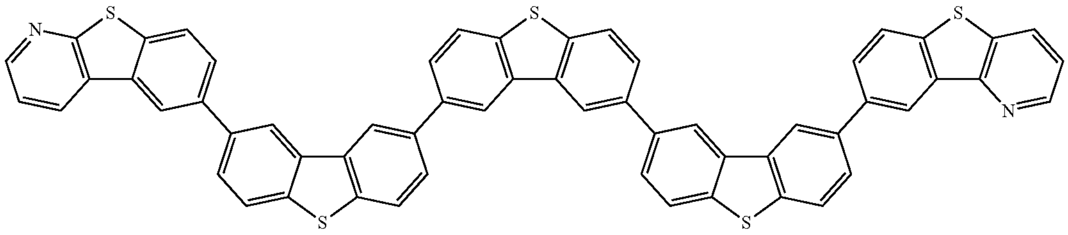
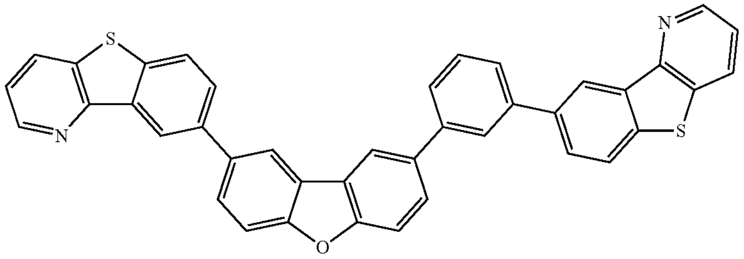
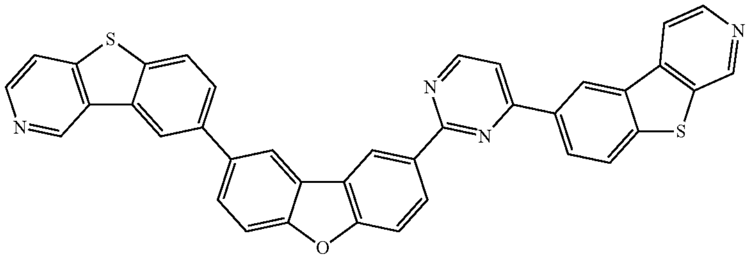
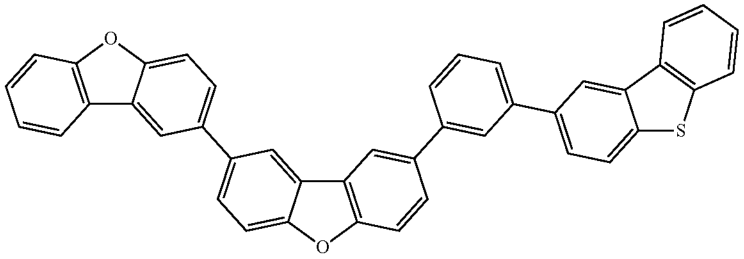
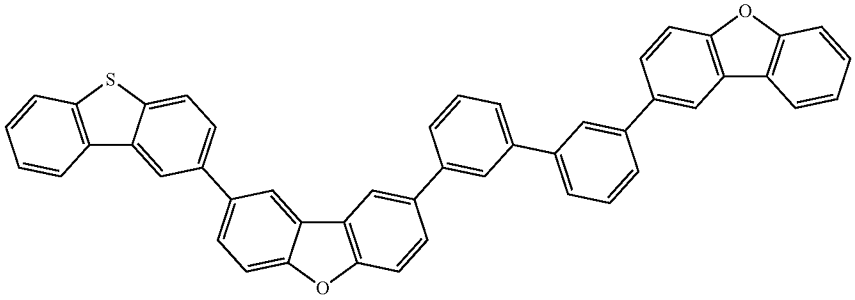
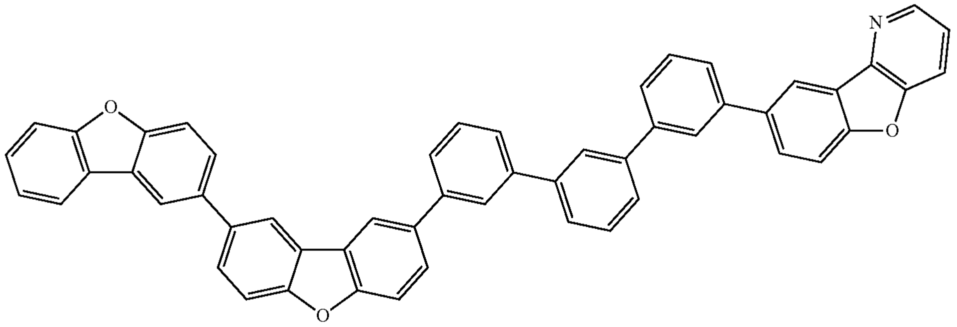

-continued
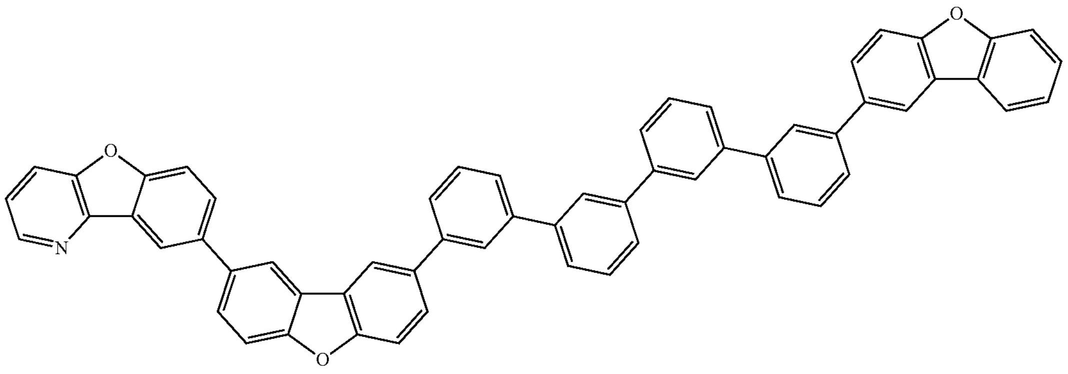
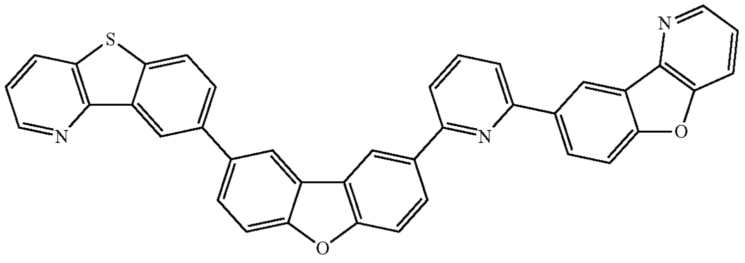
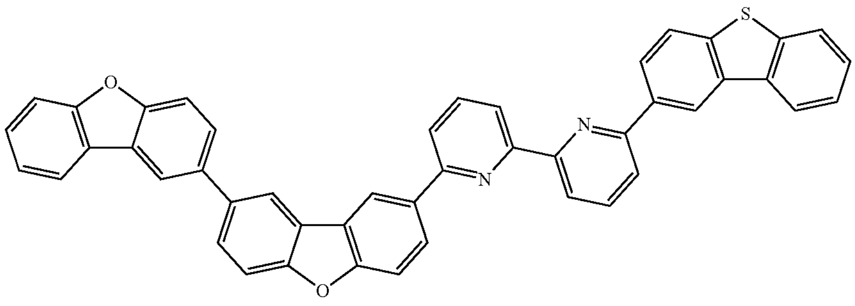
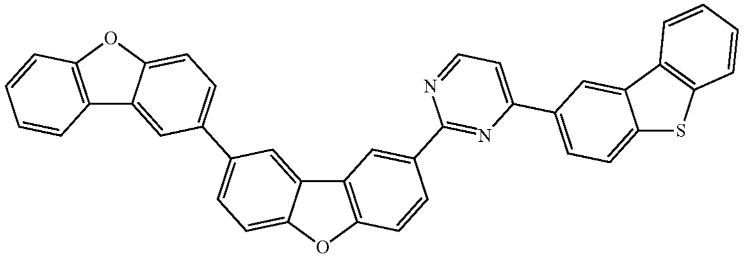
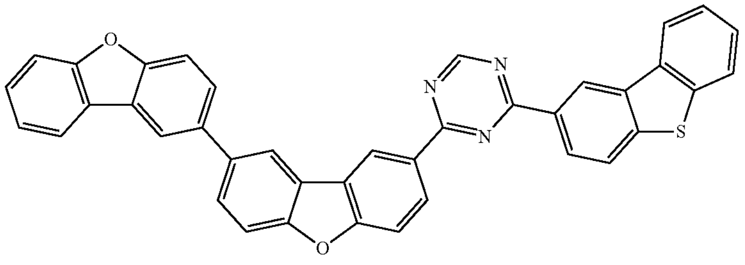
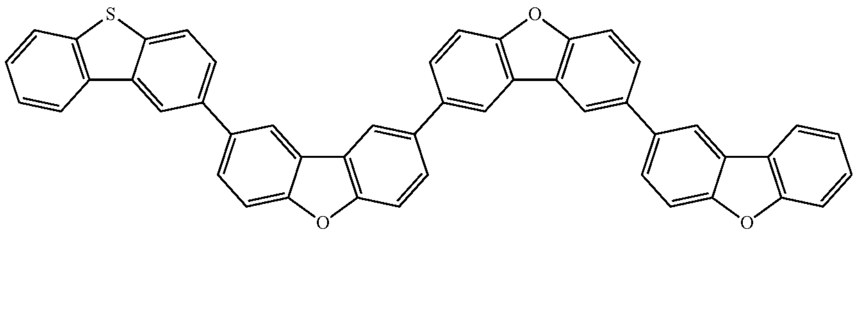

-continued
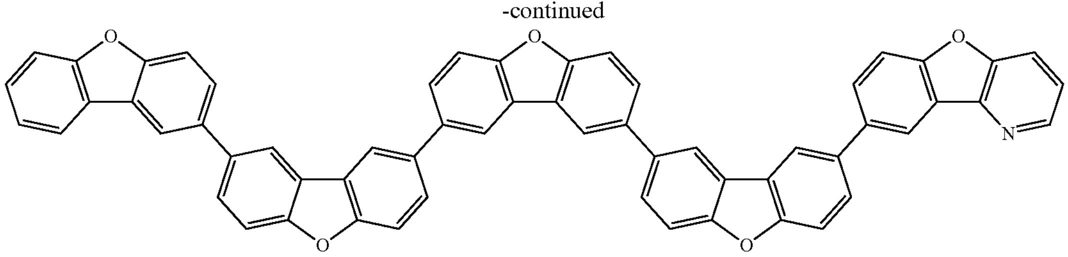
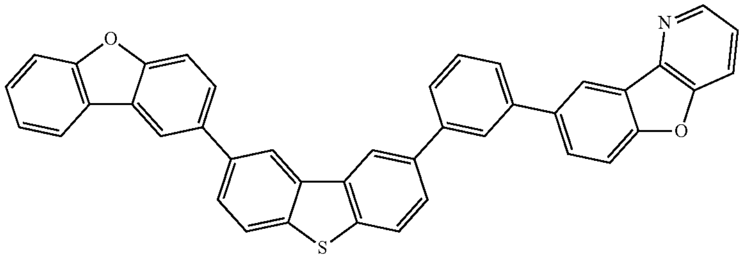
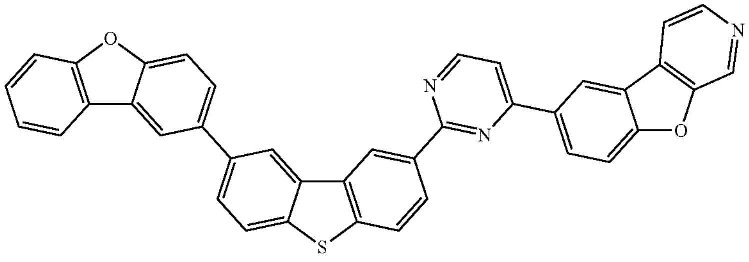
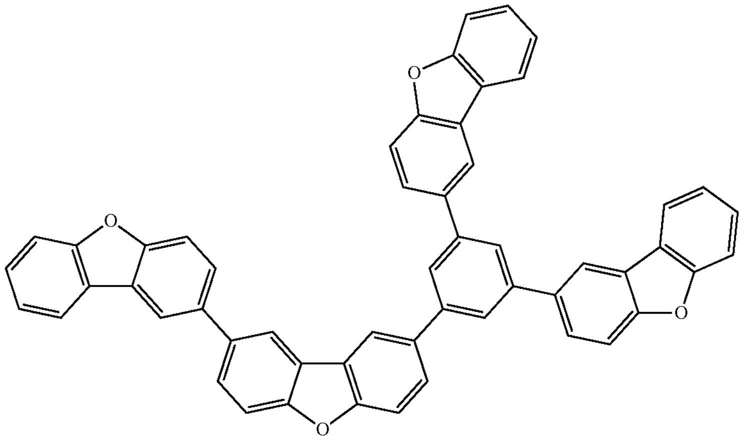
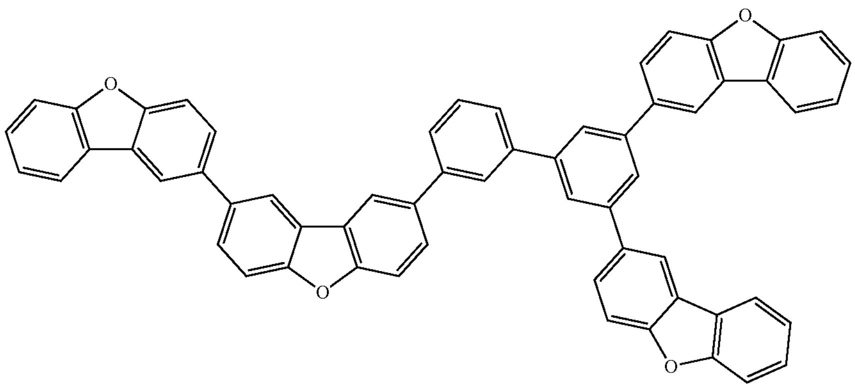

-continued
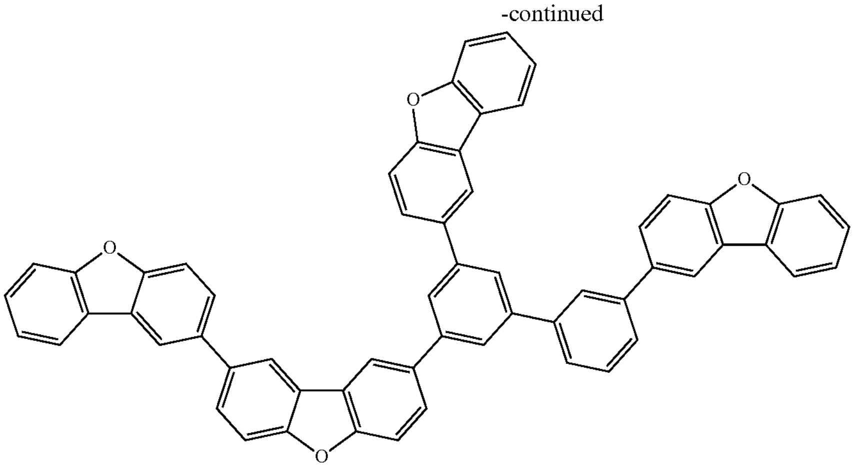
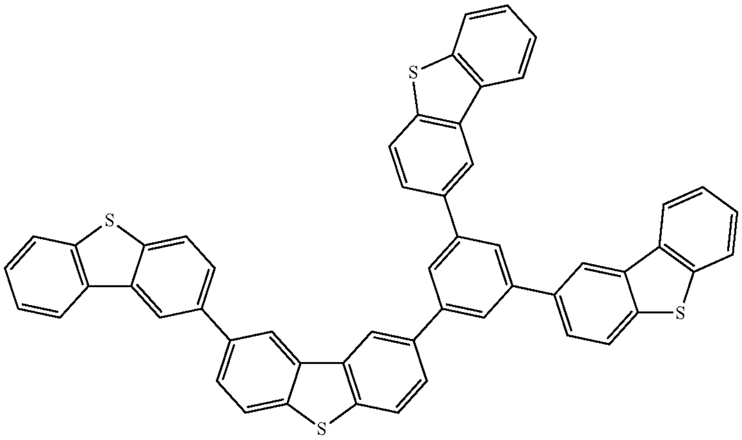
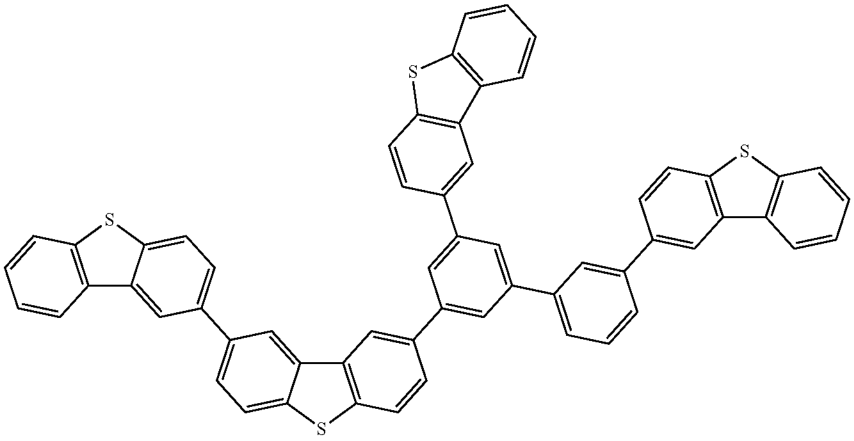
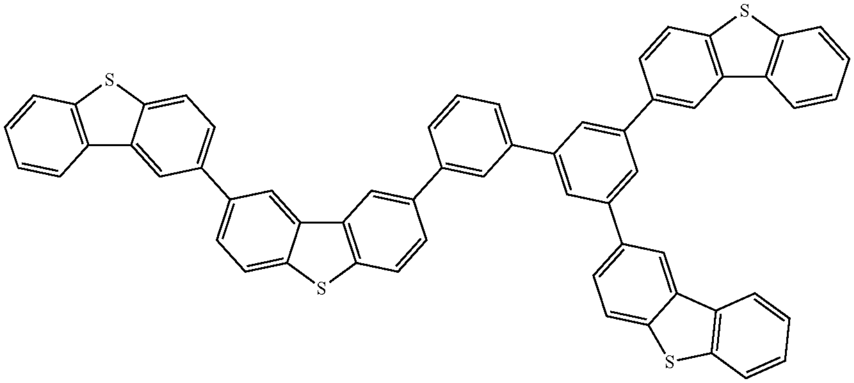

-continued
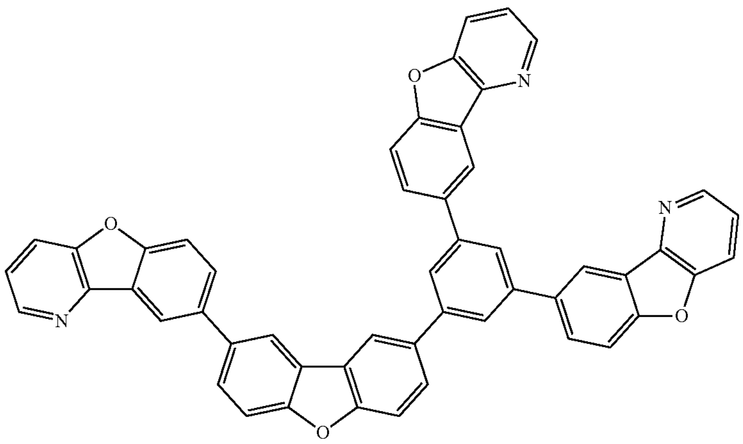
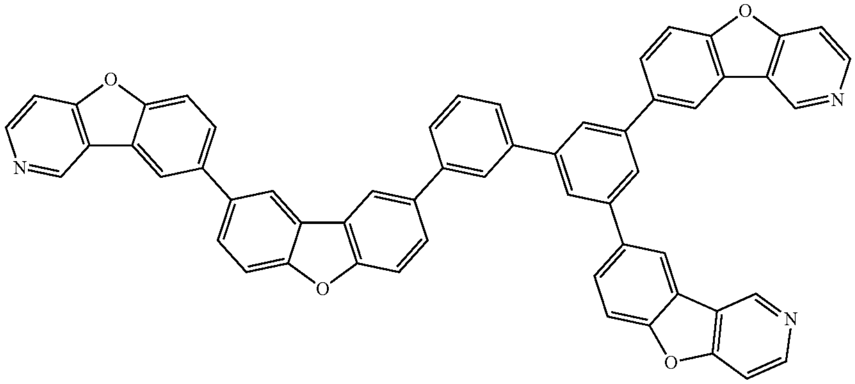
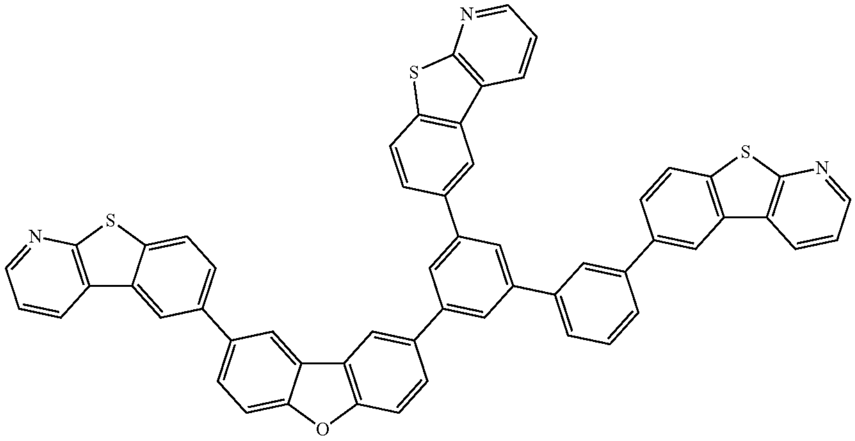
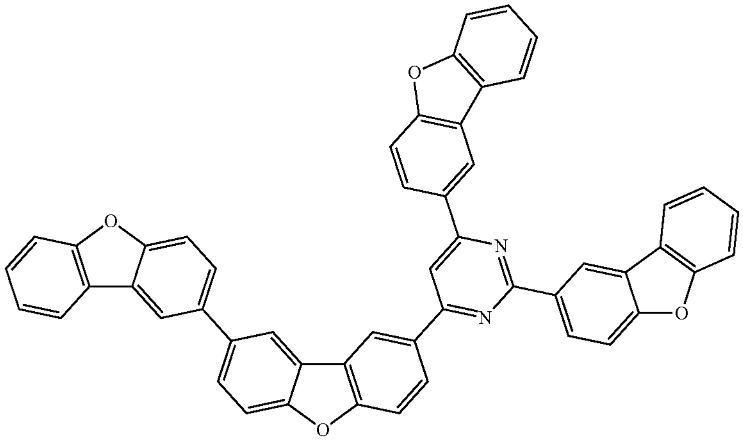

-continued
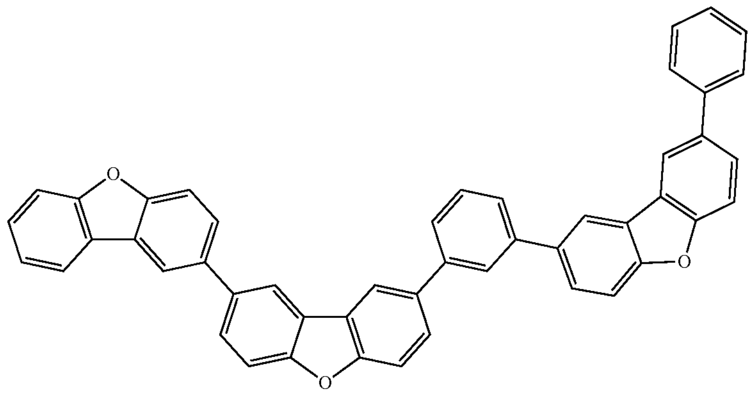
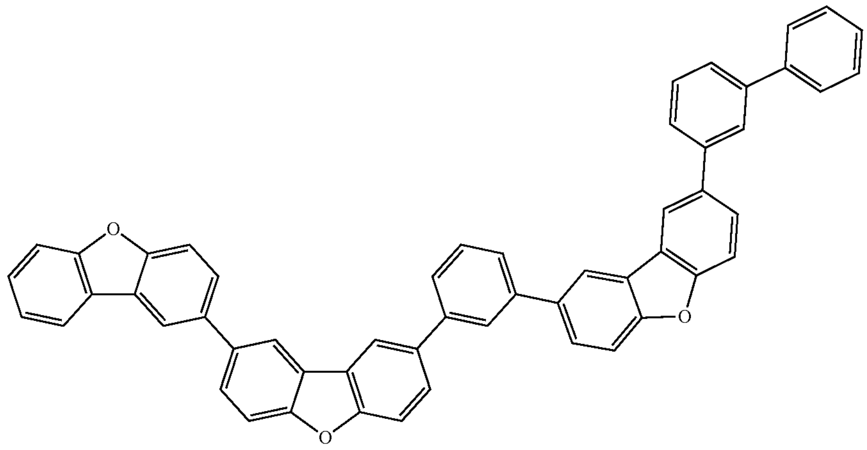
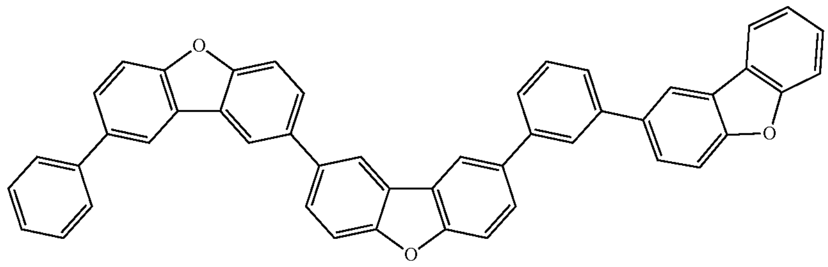
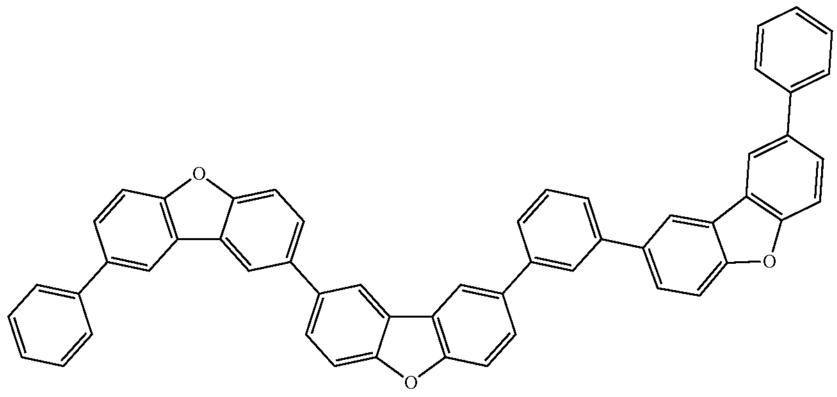

-continued
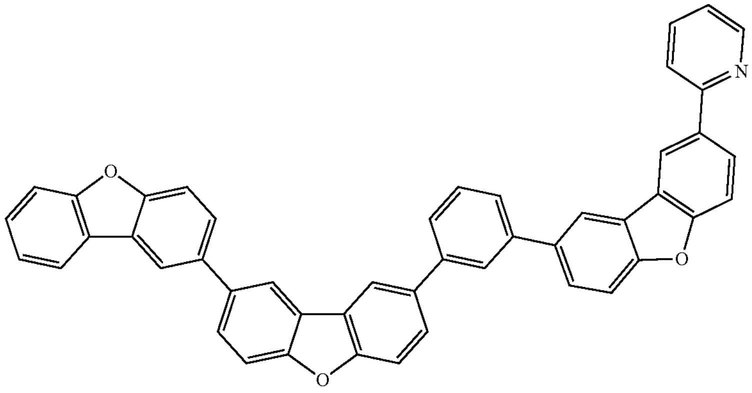
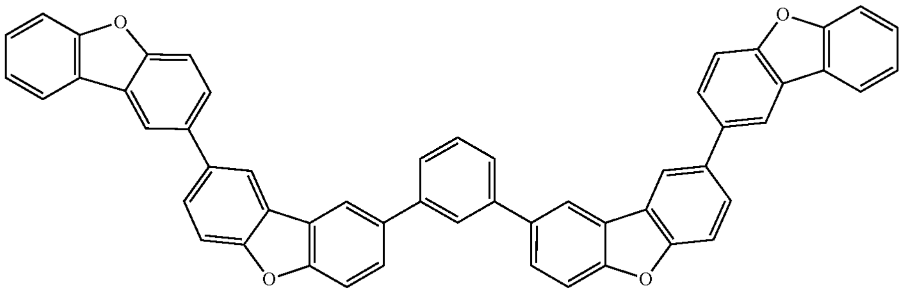
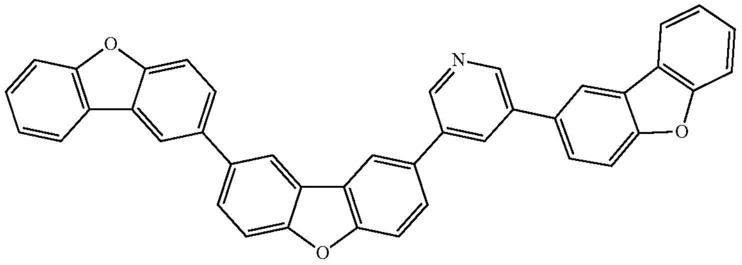
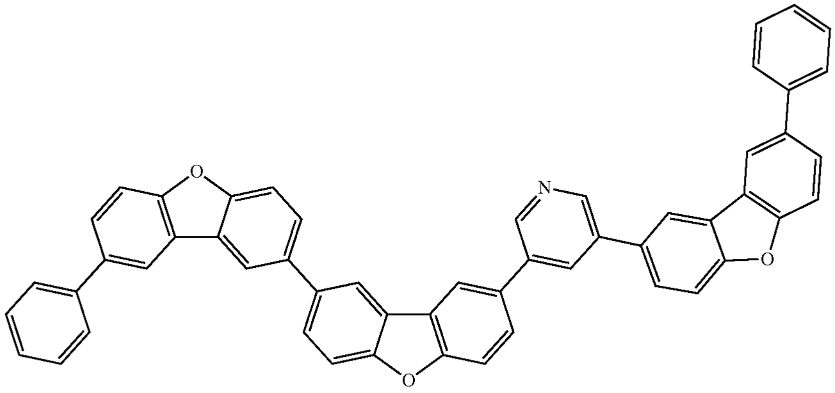
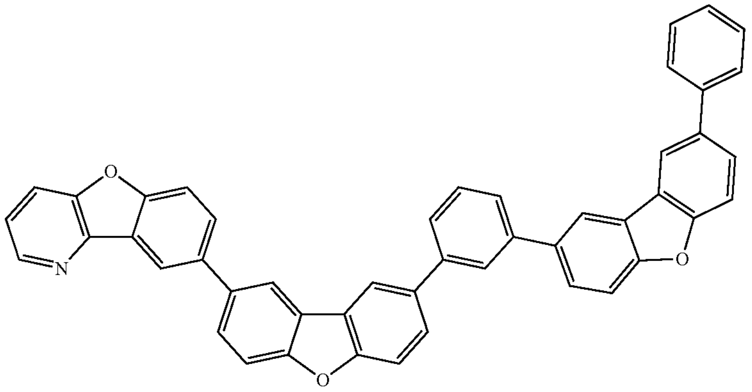

-continued
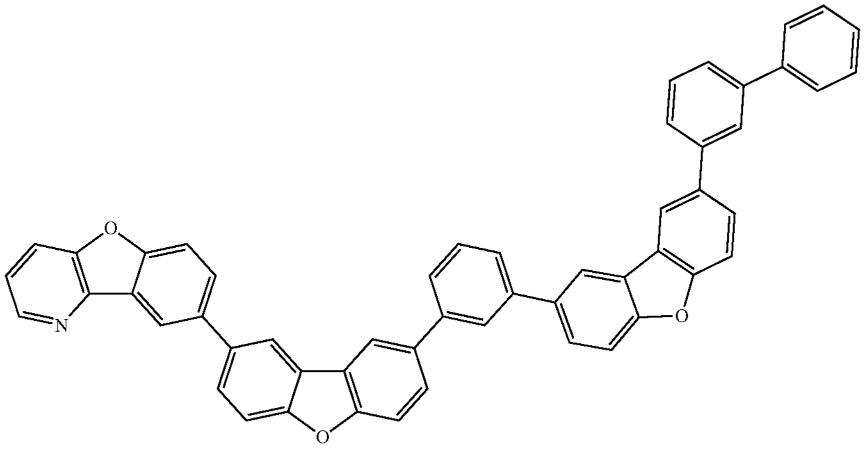
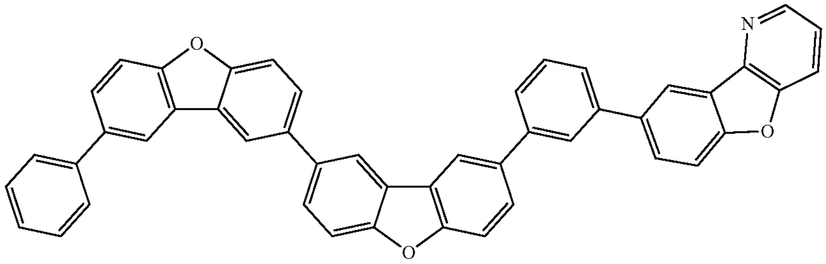
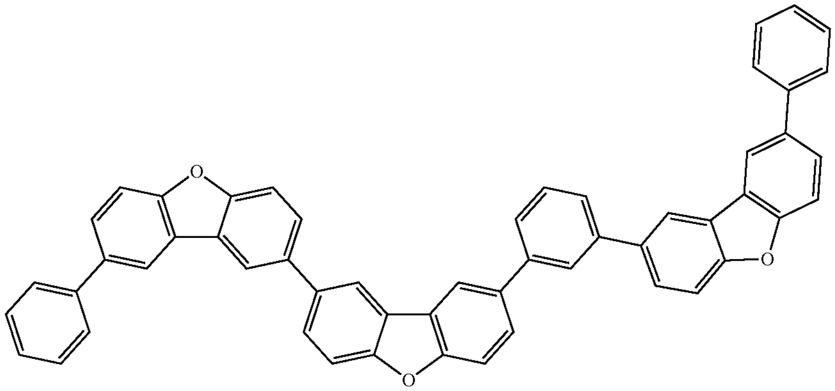
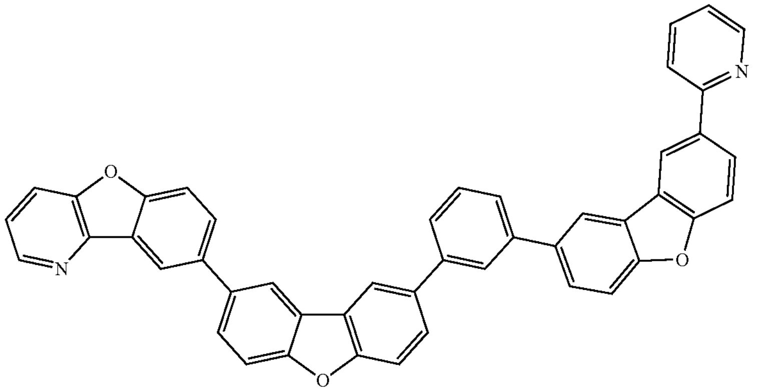

-continued
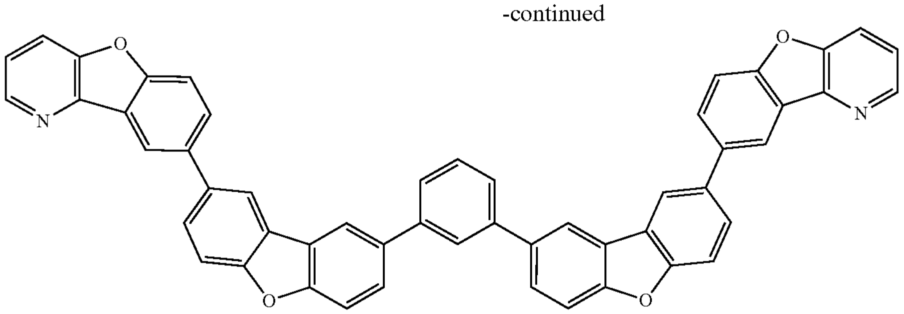
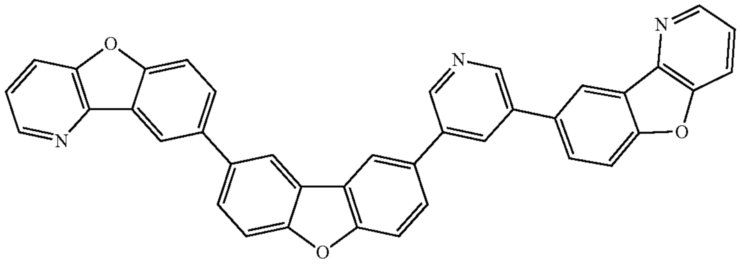
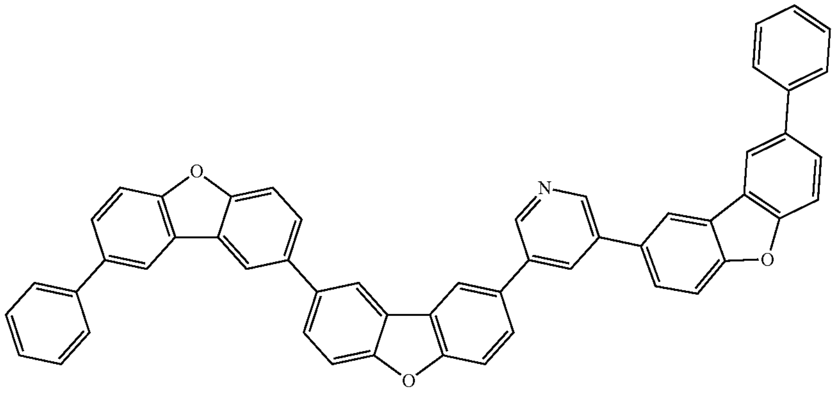
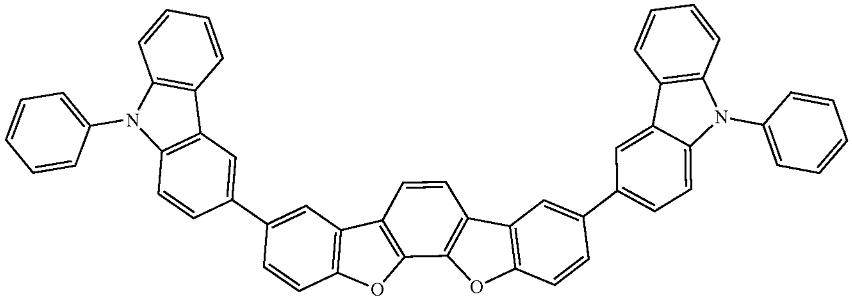
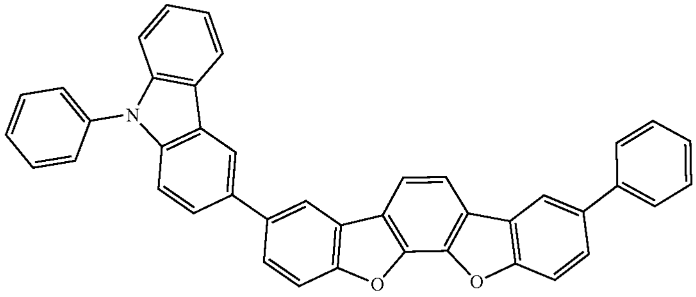

-continued
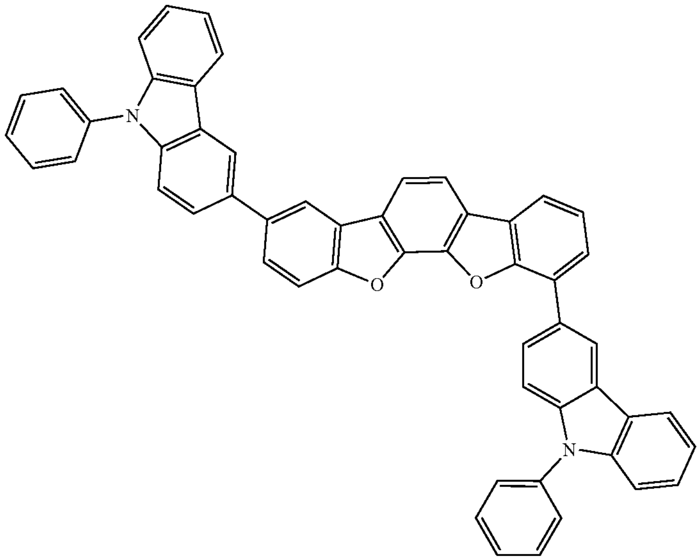
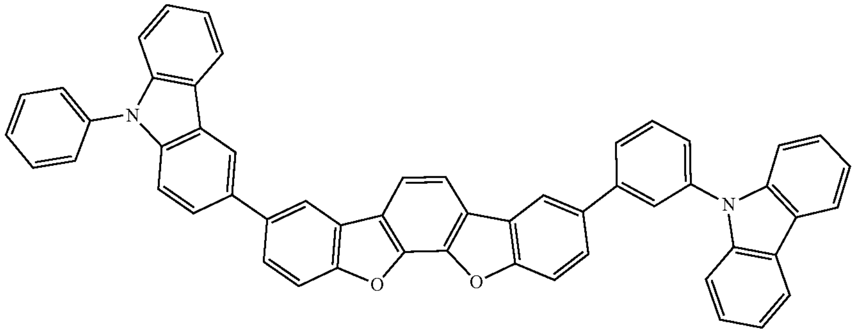
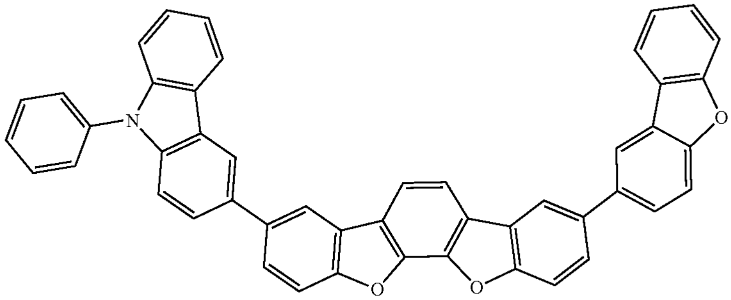
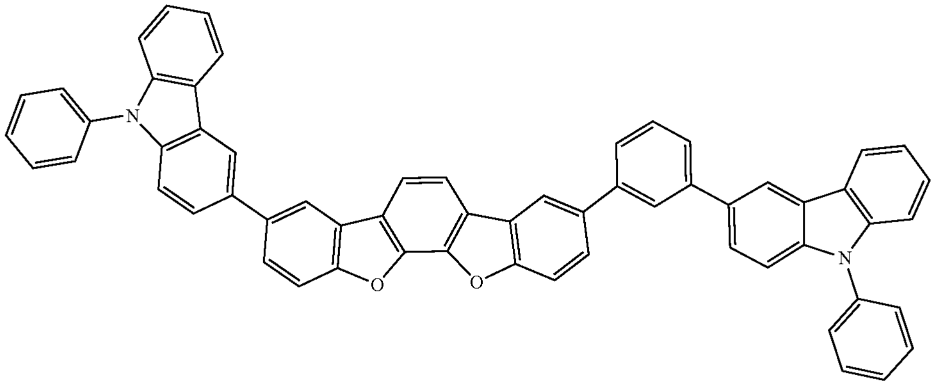

-continued
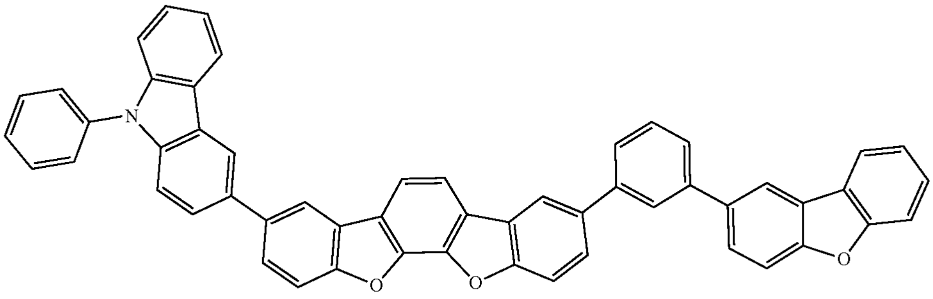
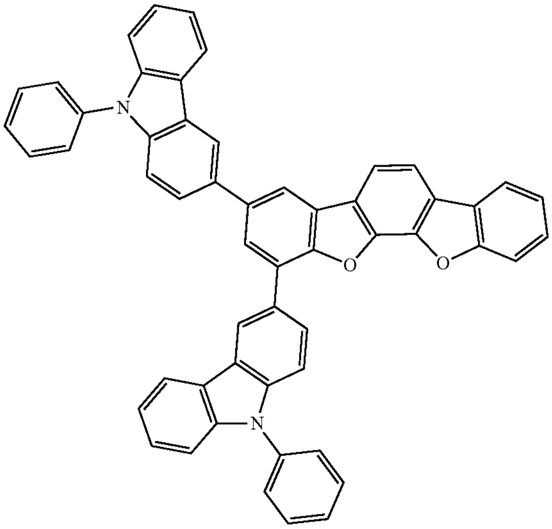
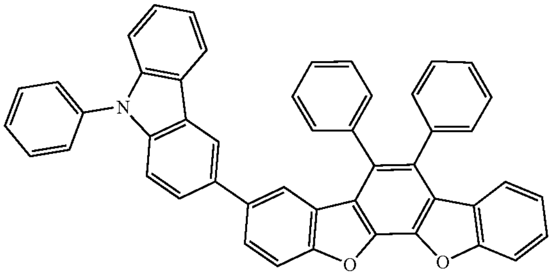
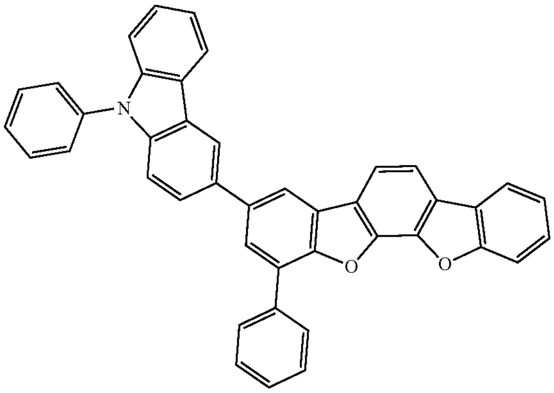
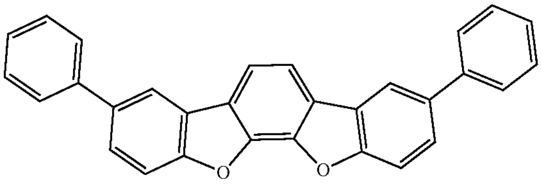
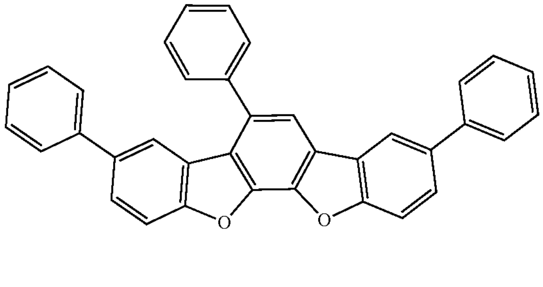
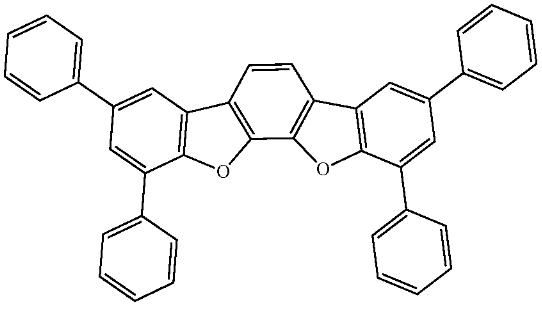

-continued
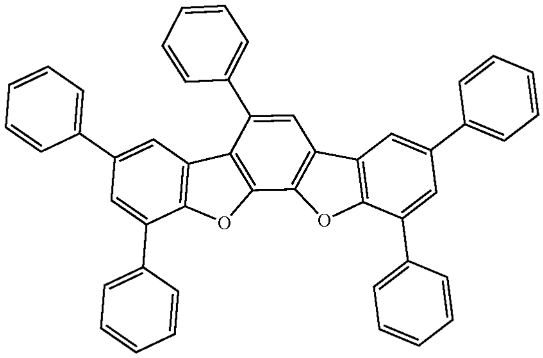
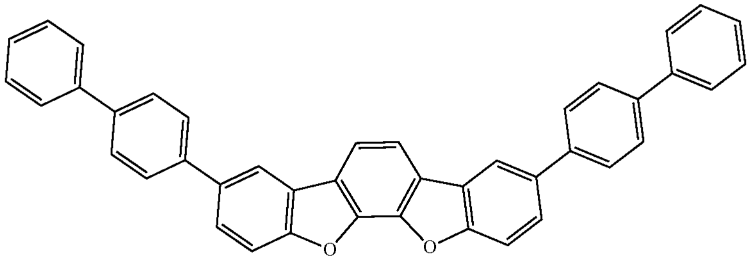
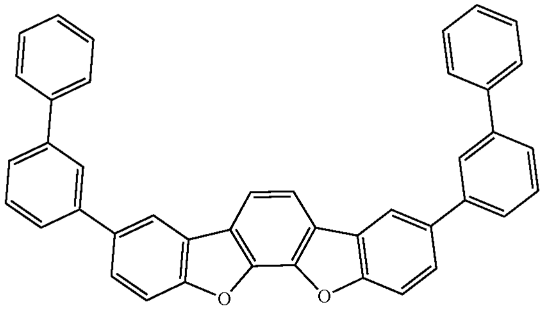
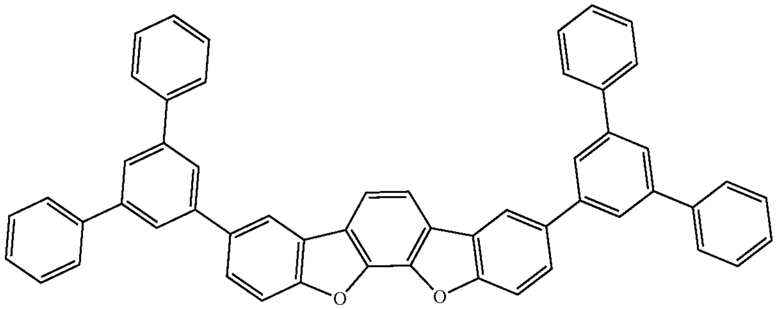
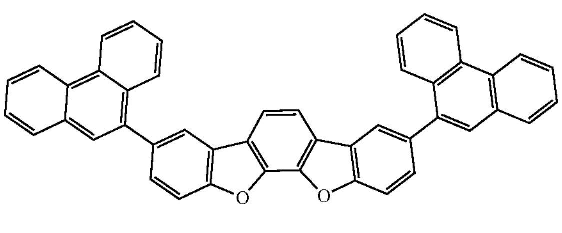
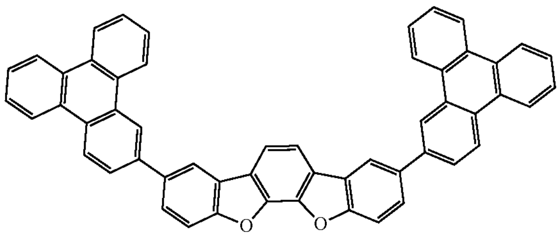

-continued
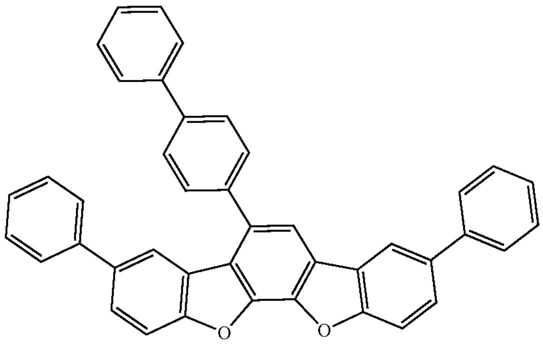
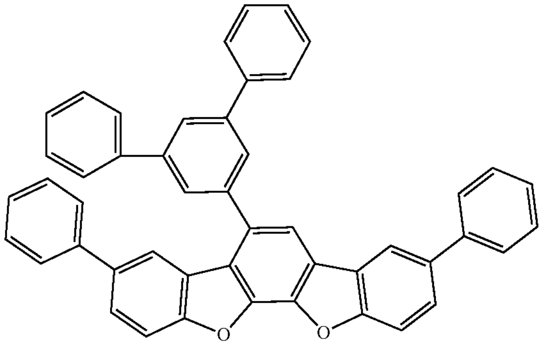
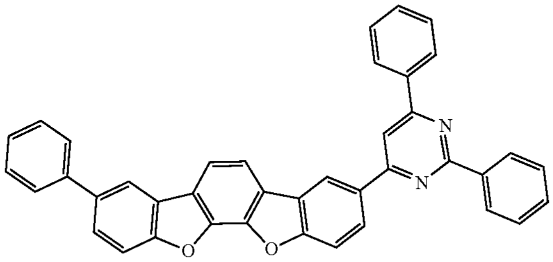
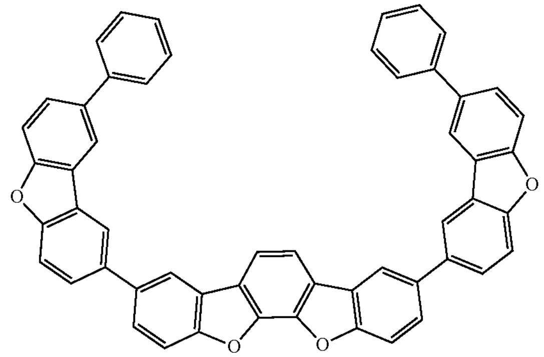
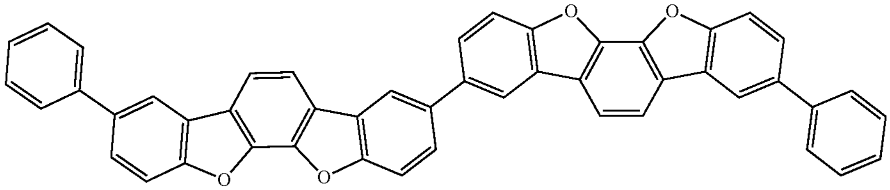
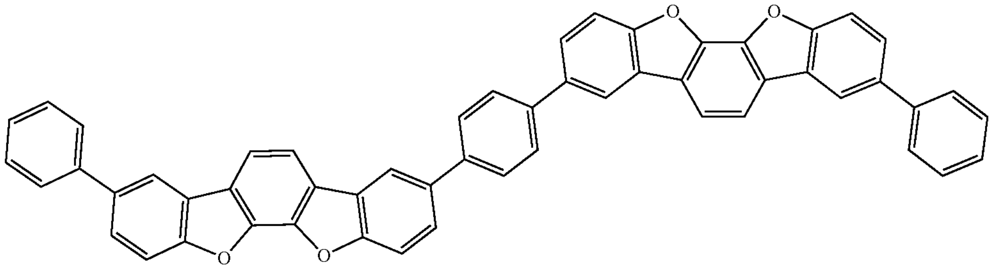
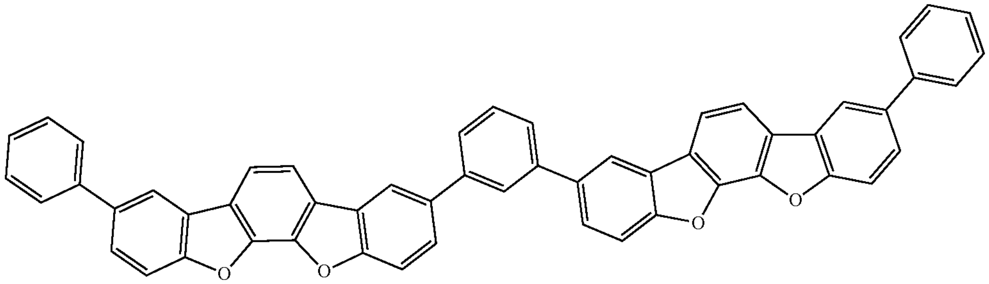
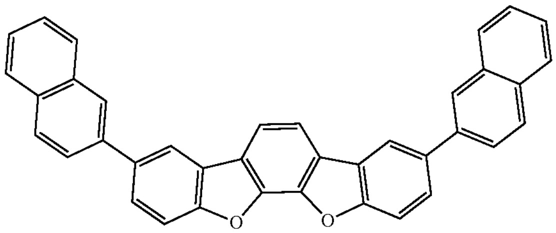
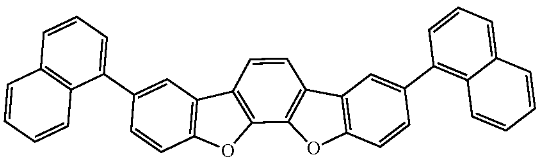

-continued
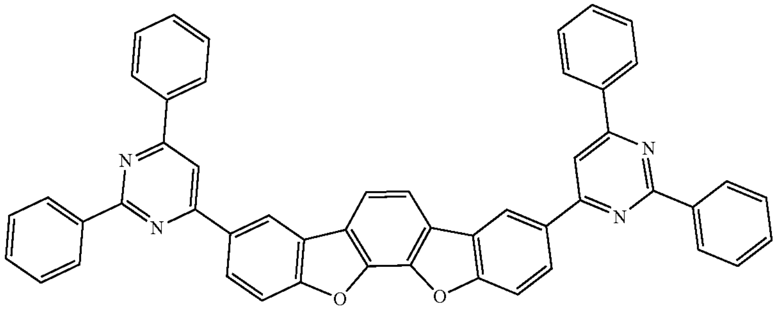
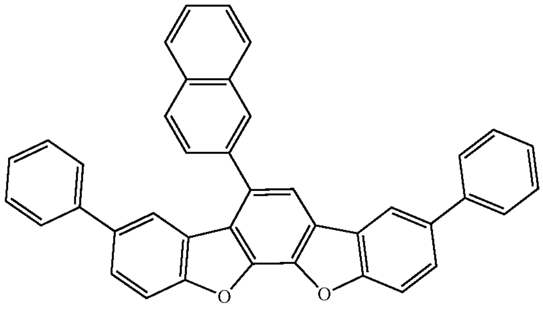
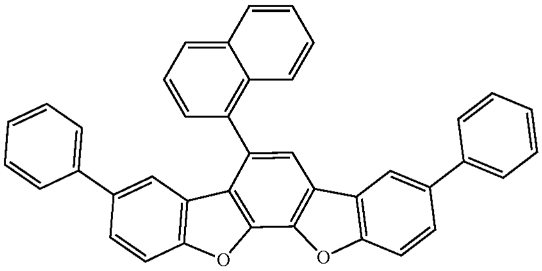
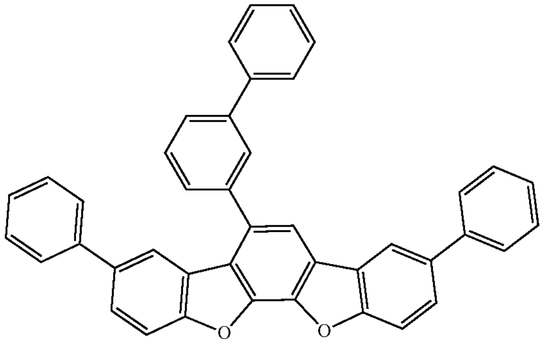
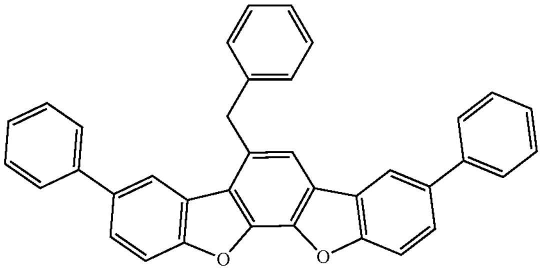
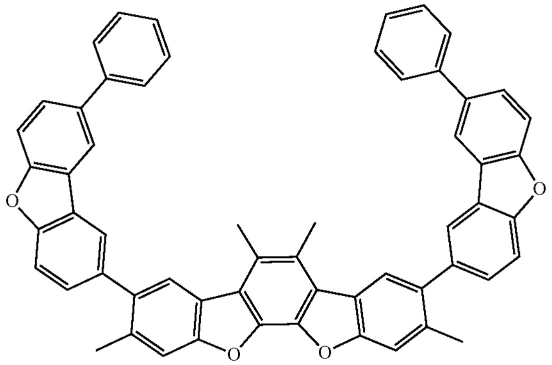
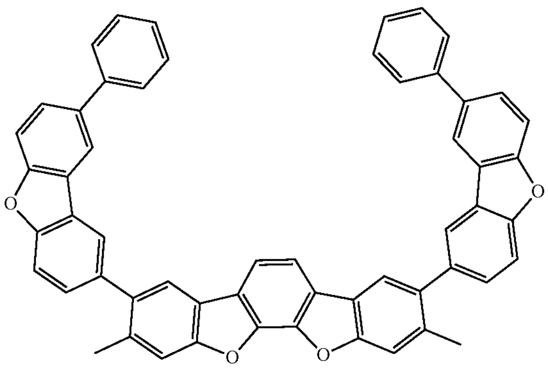

-continued
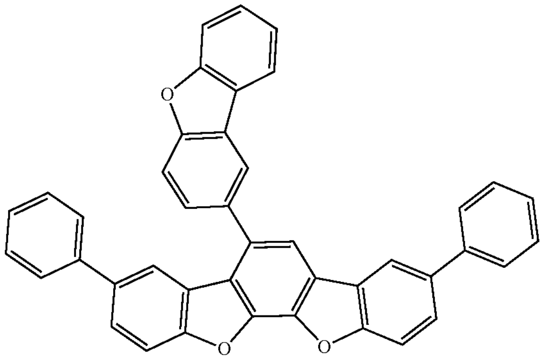
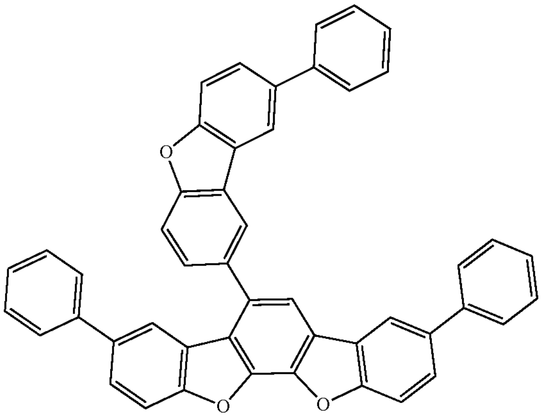
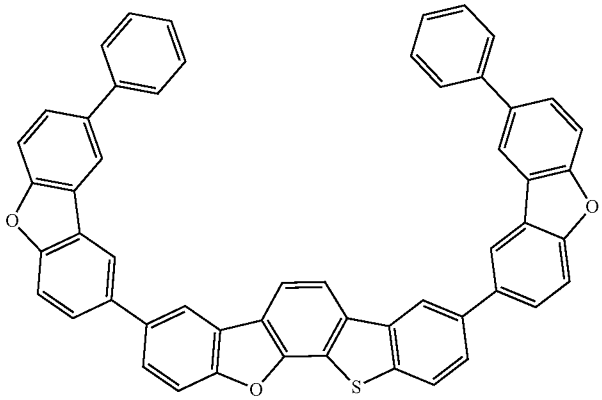
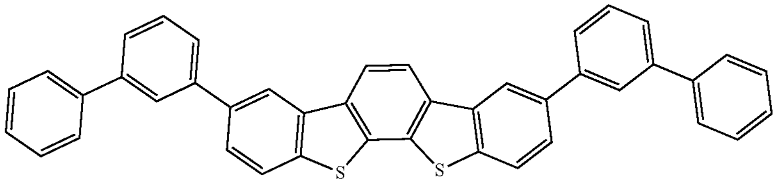
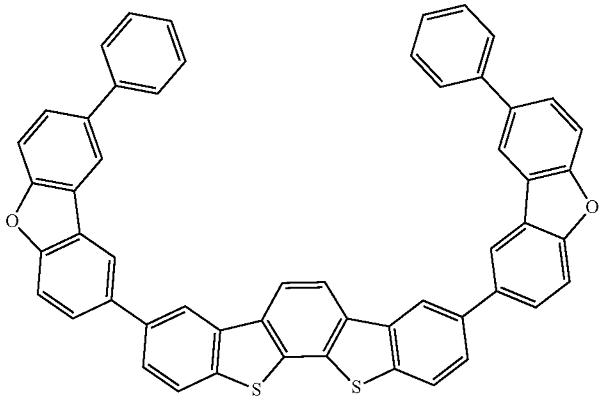
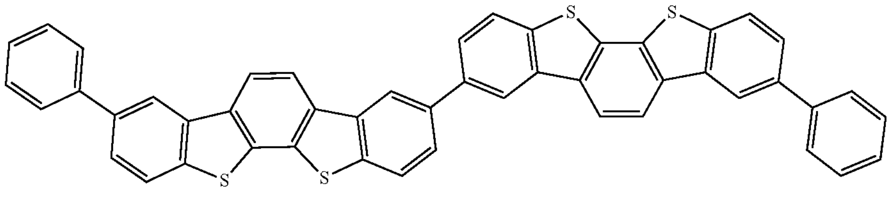

-continued
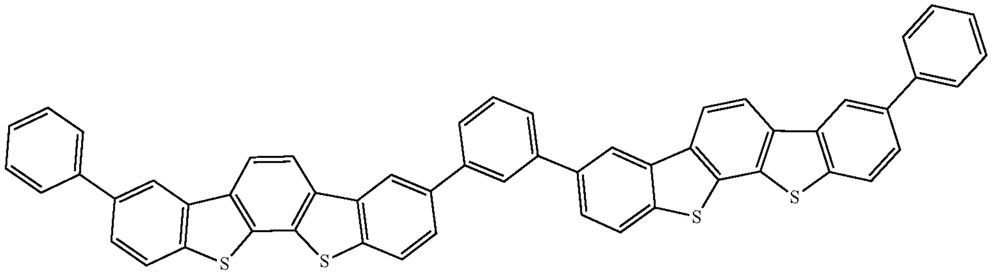
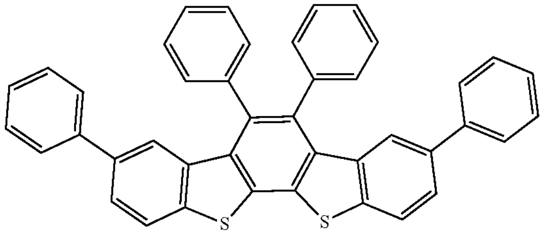
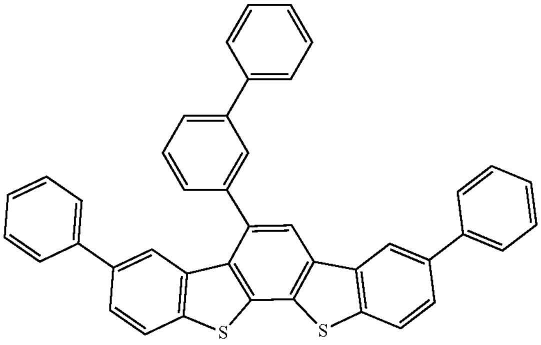
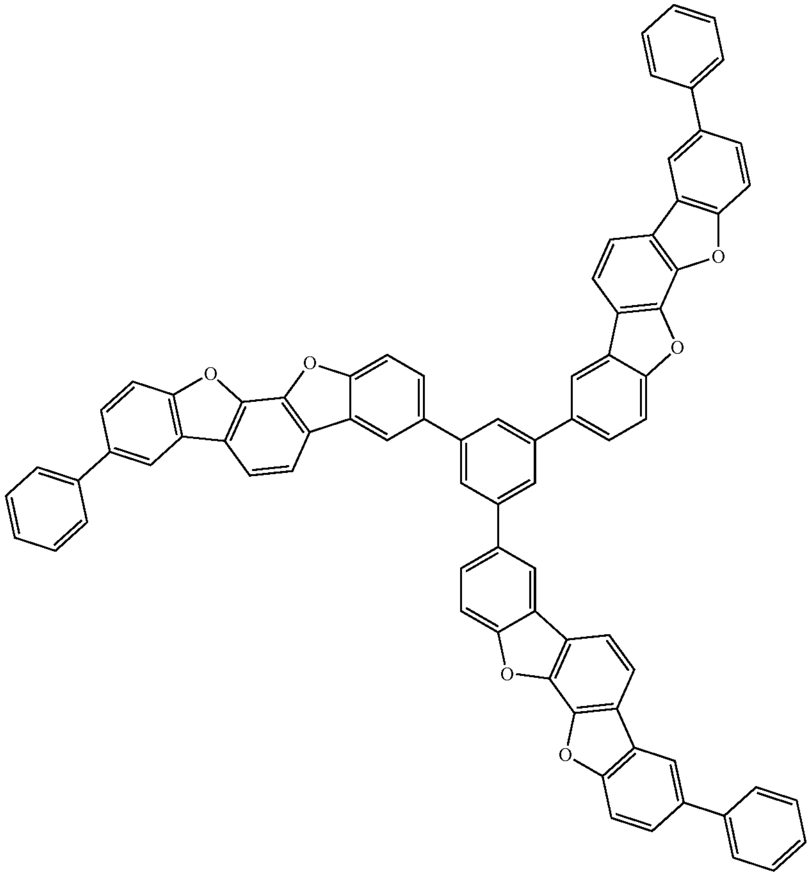
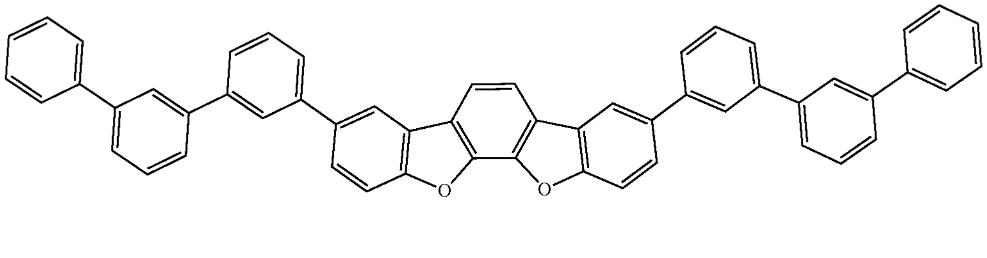

-continued
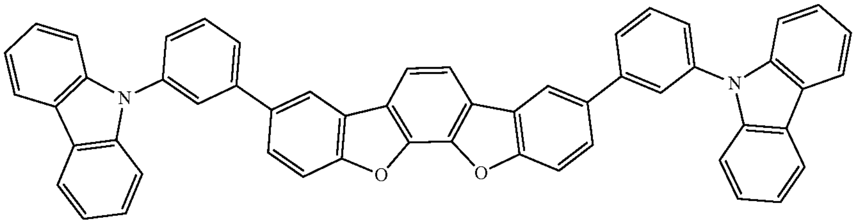
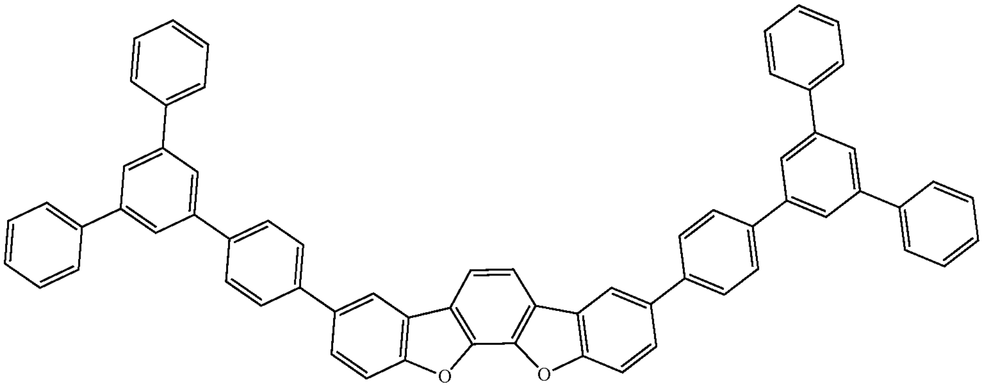
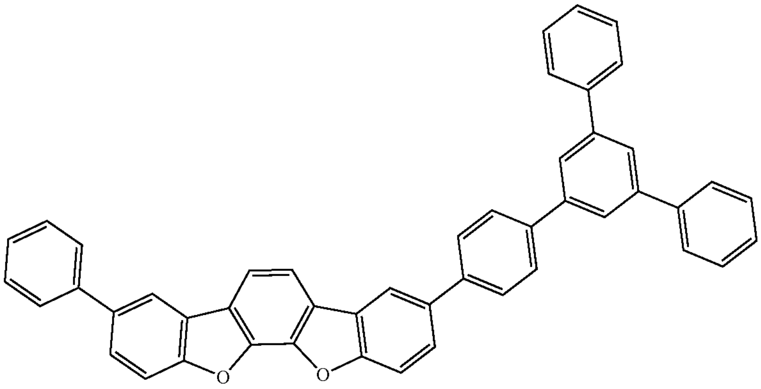
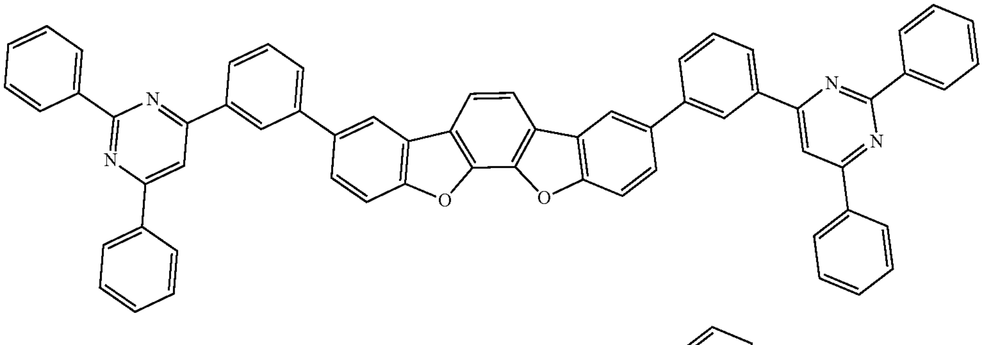
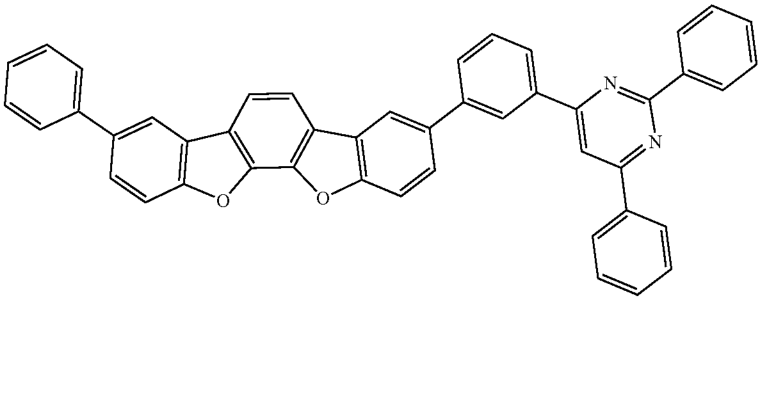

-continued
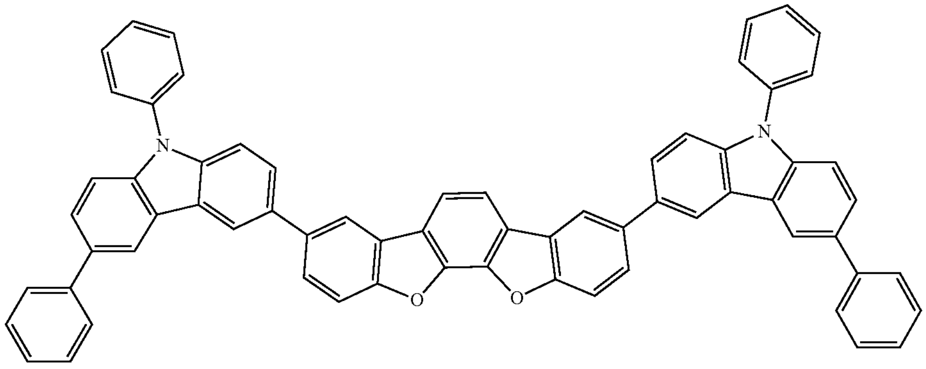
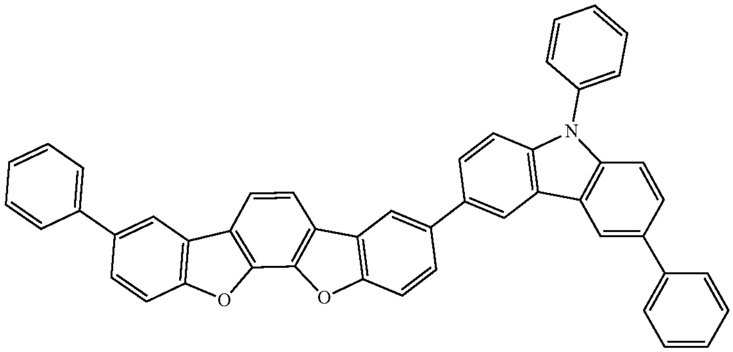
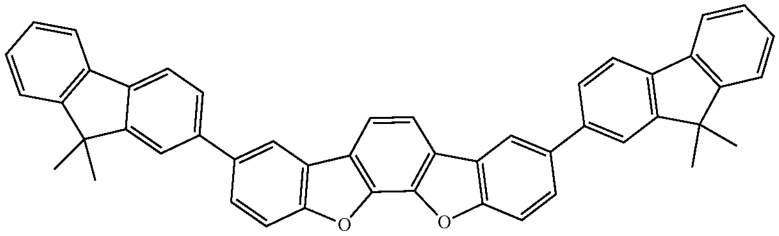
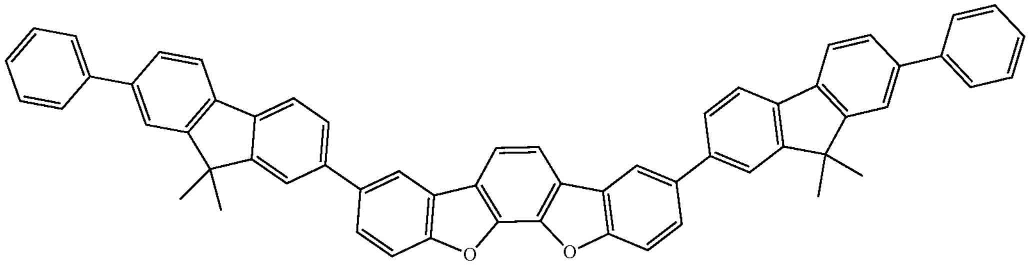
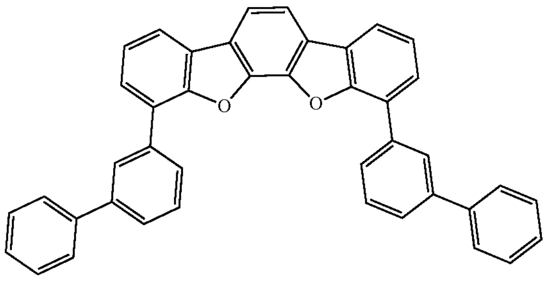
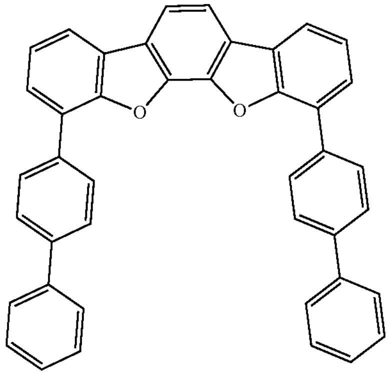

-continued
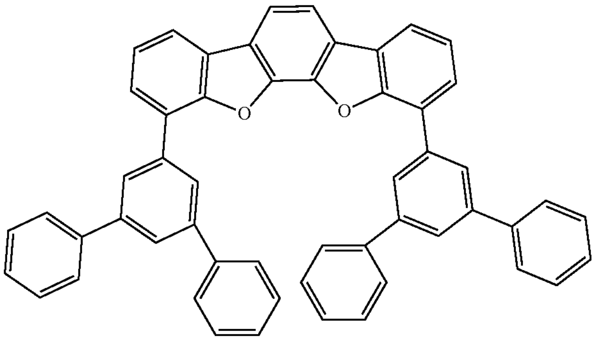
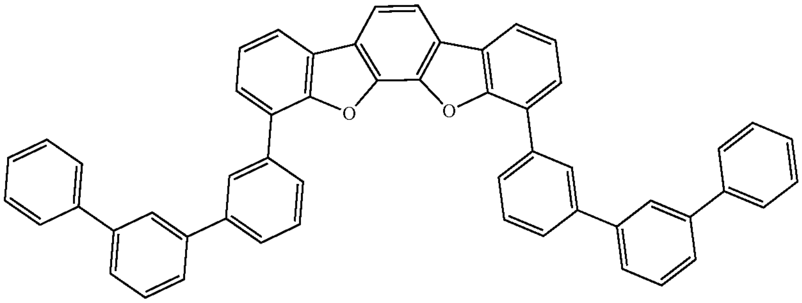
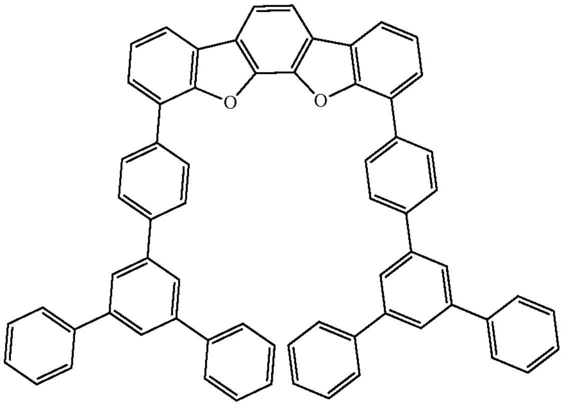
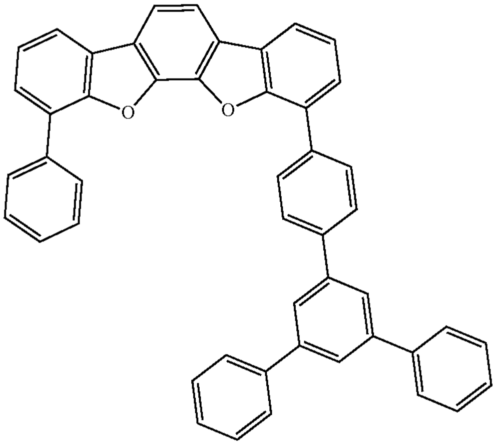
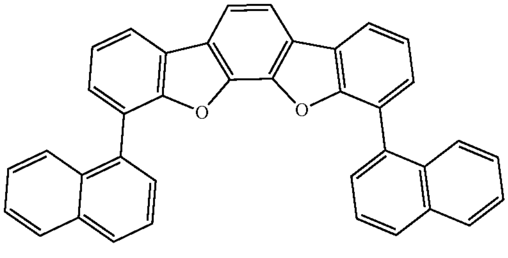
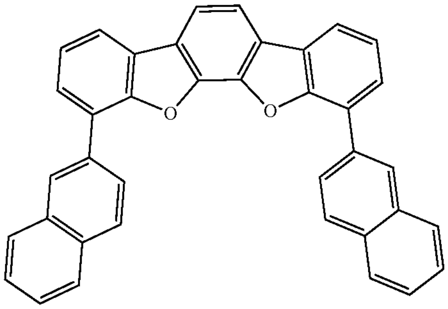

-continued
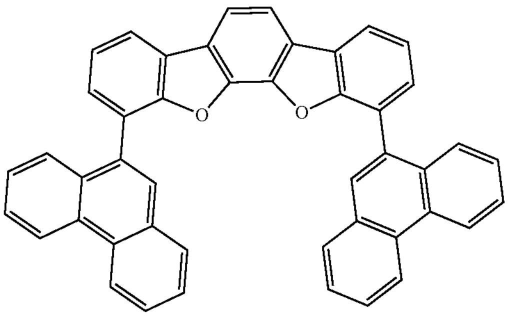
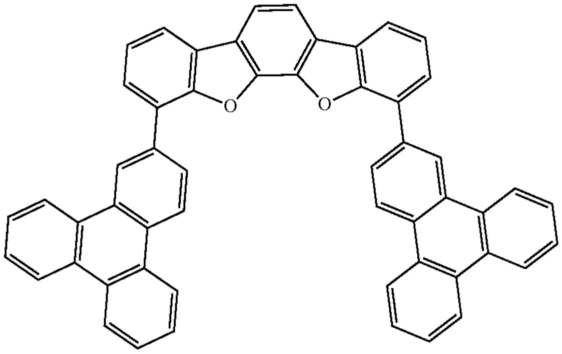
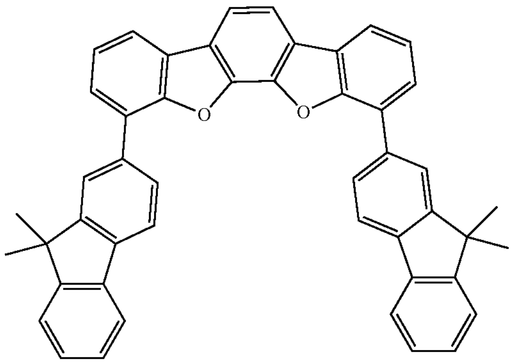
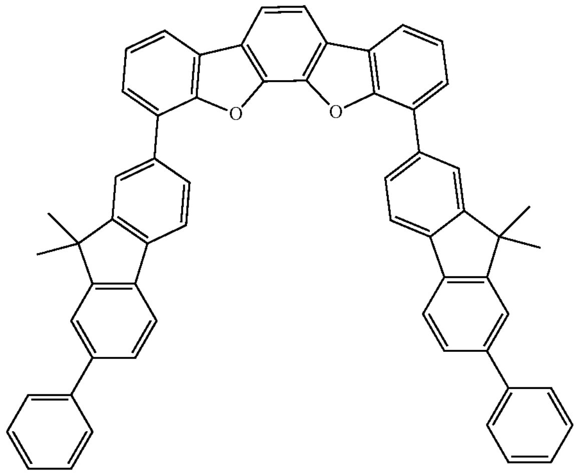
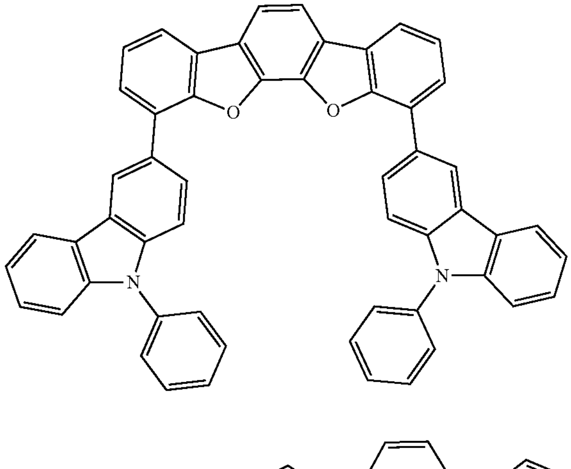
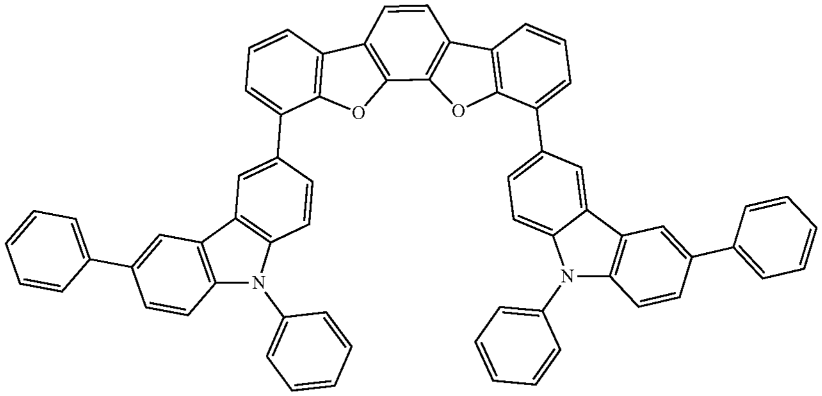

-continued
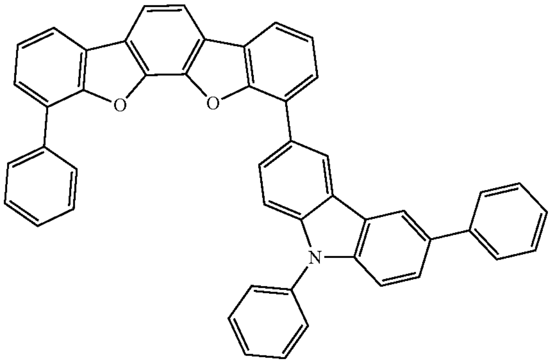
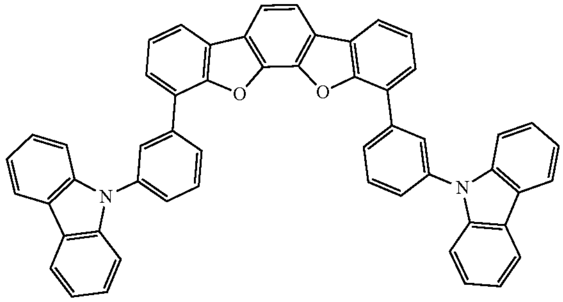
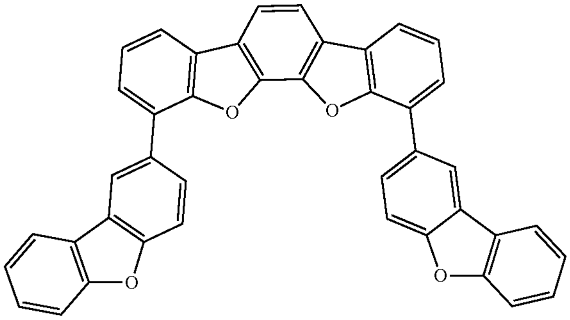
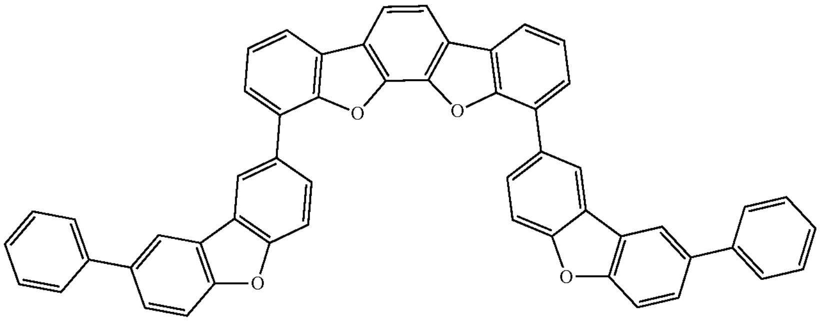
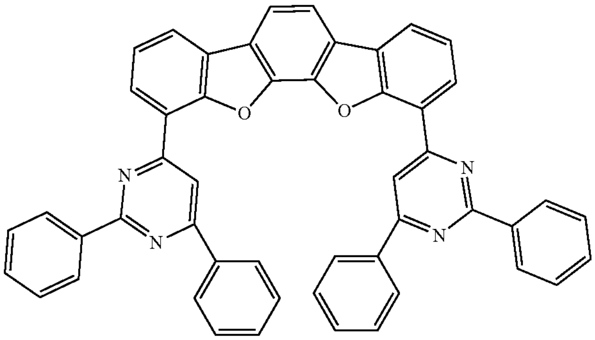

-continued
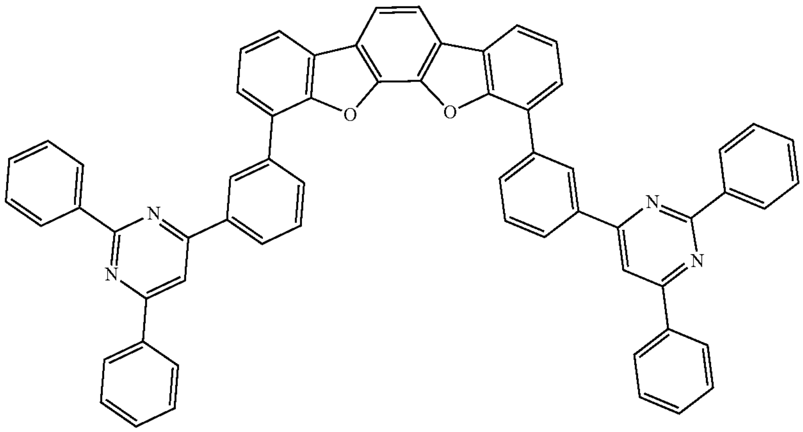
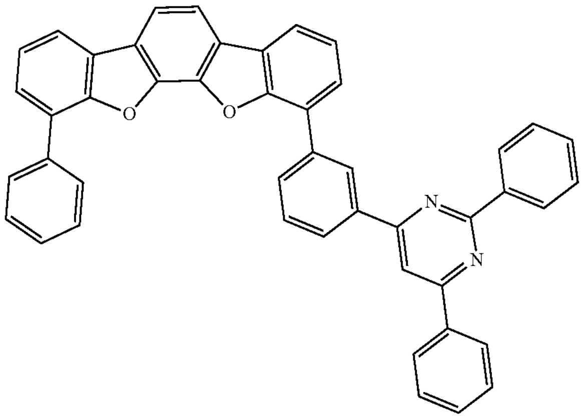
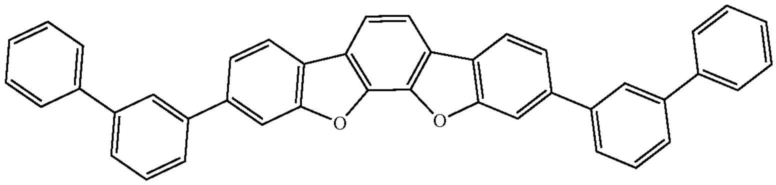
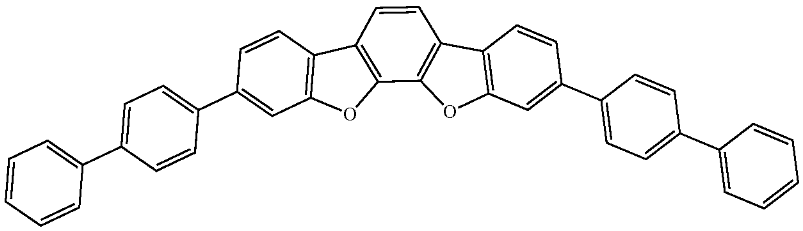
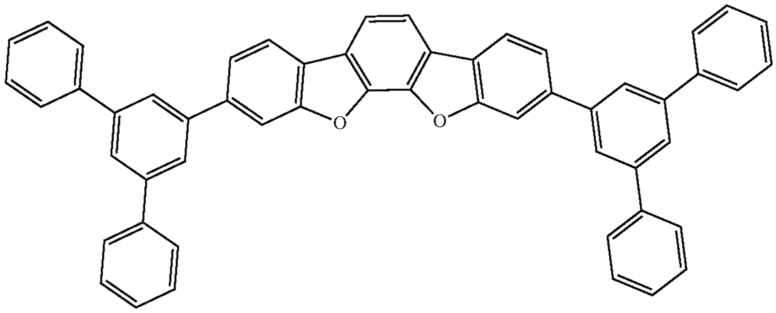

-continued
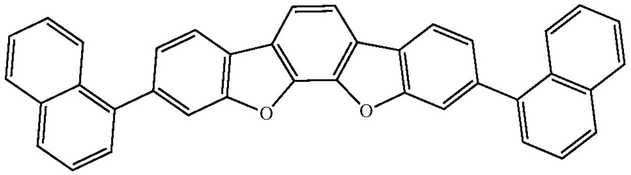
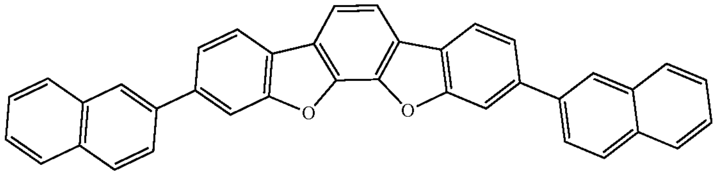
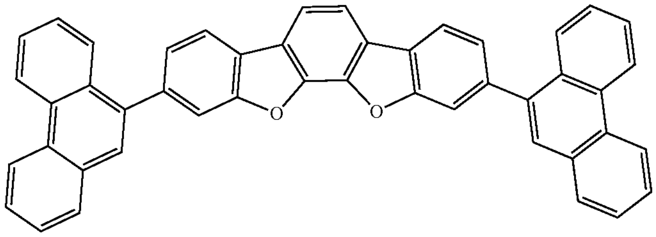
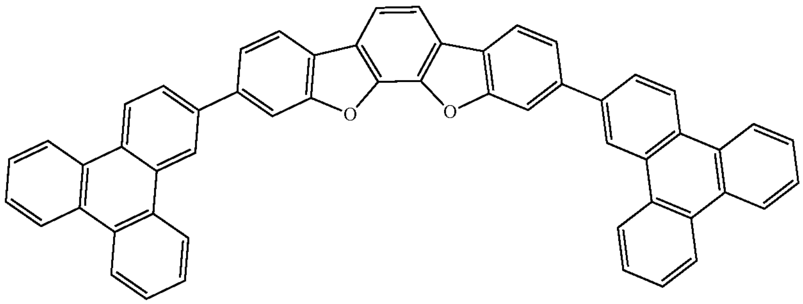
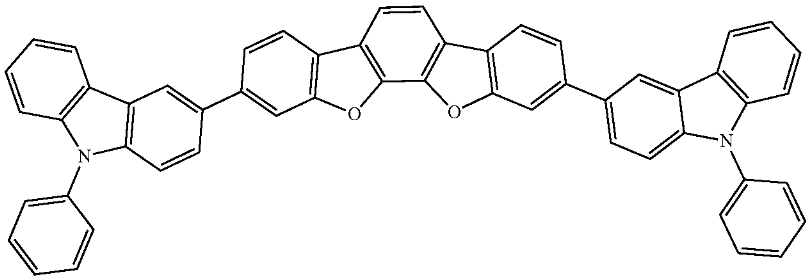
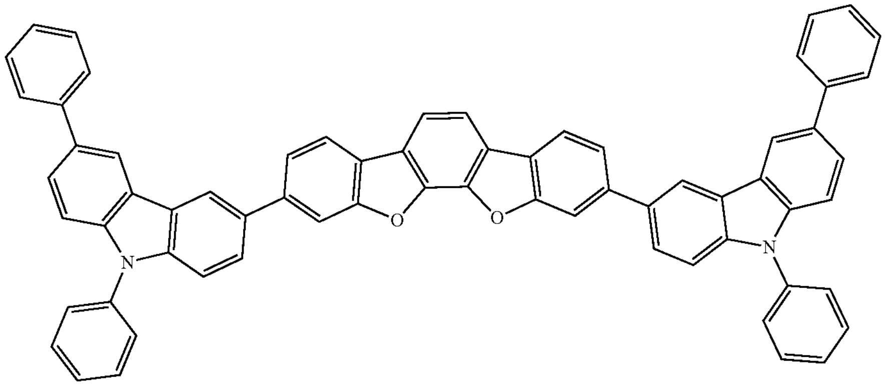

-continued
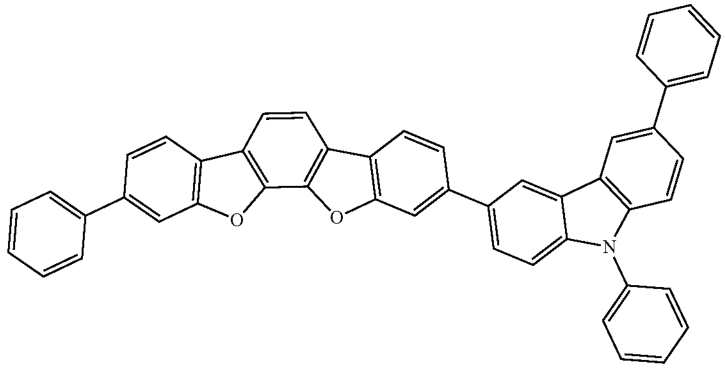
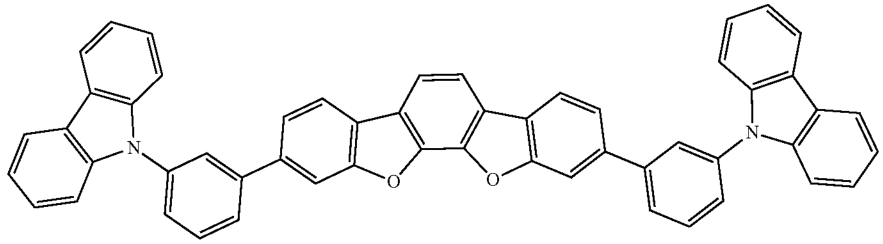
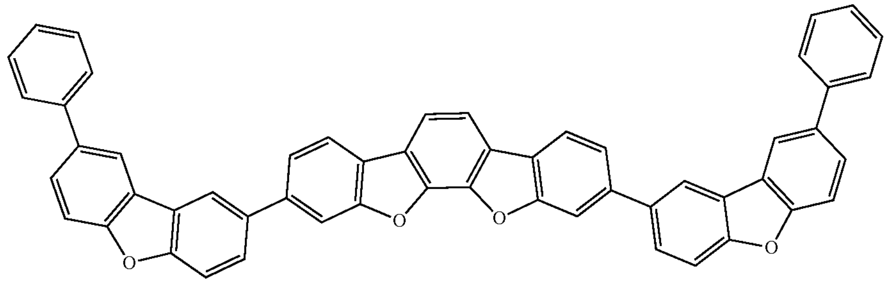
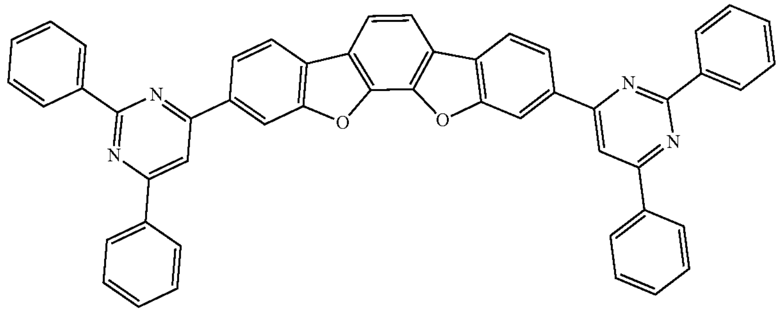
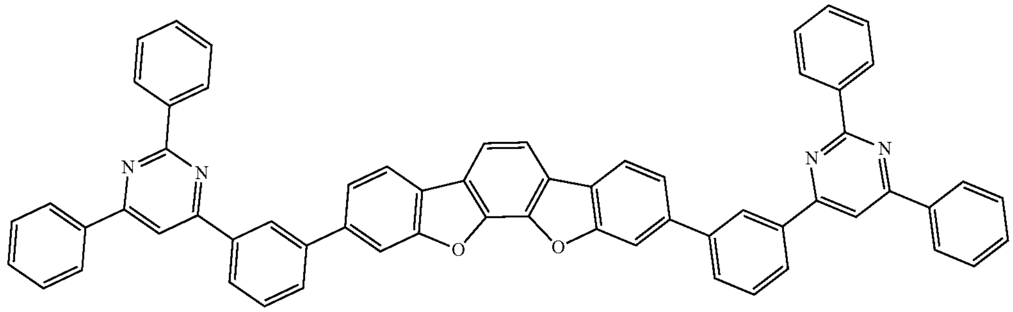

-continued
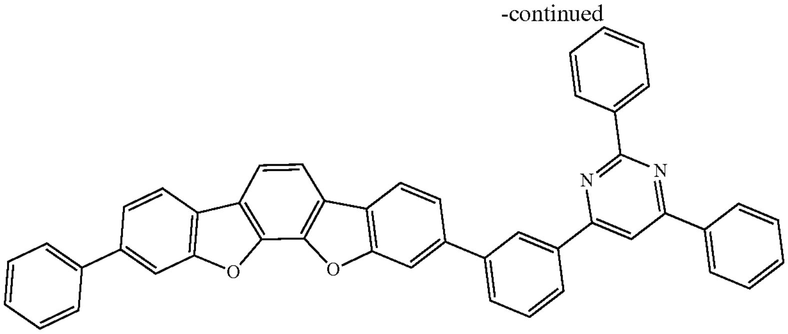
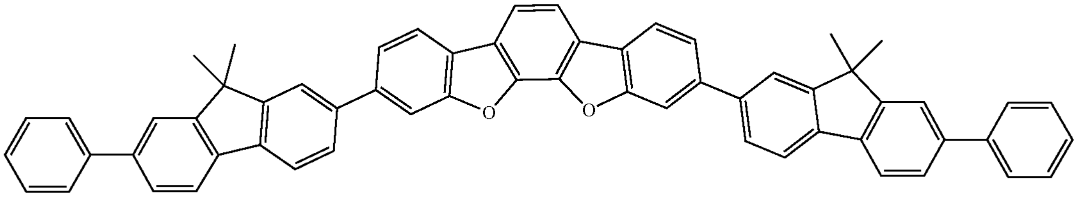
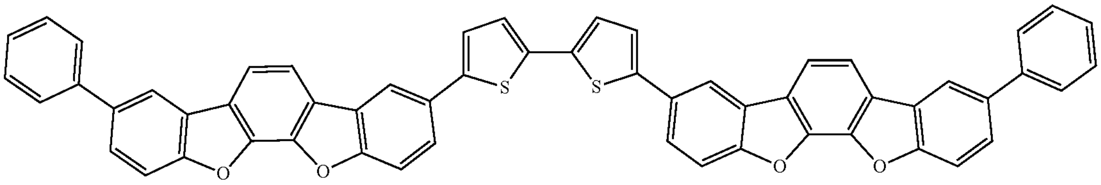
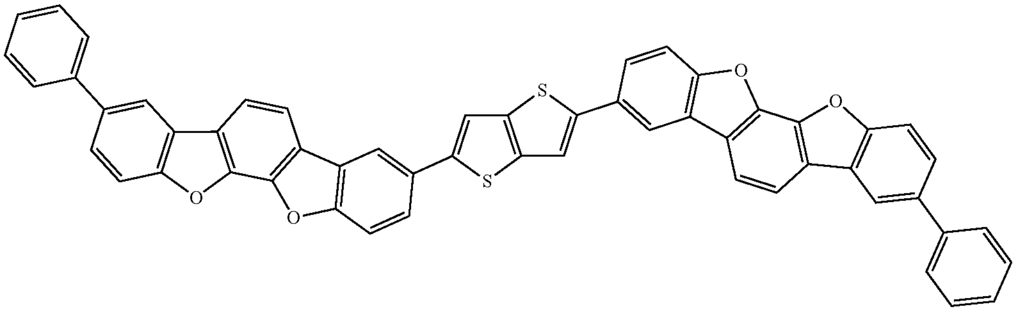
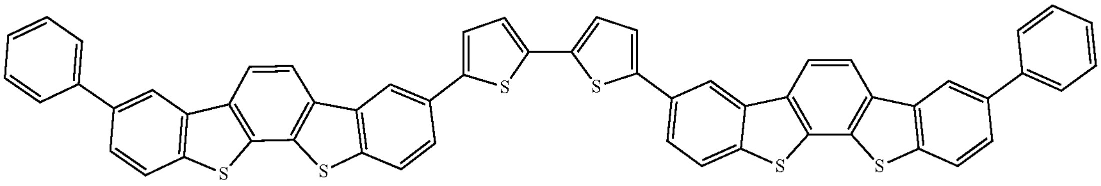
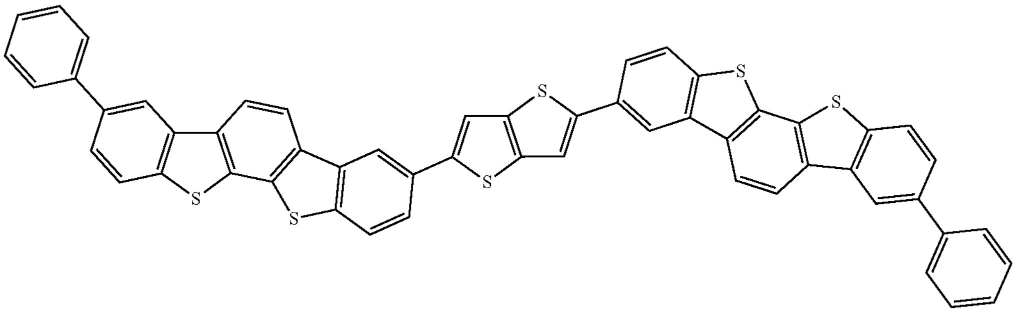

-continued
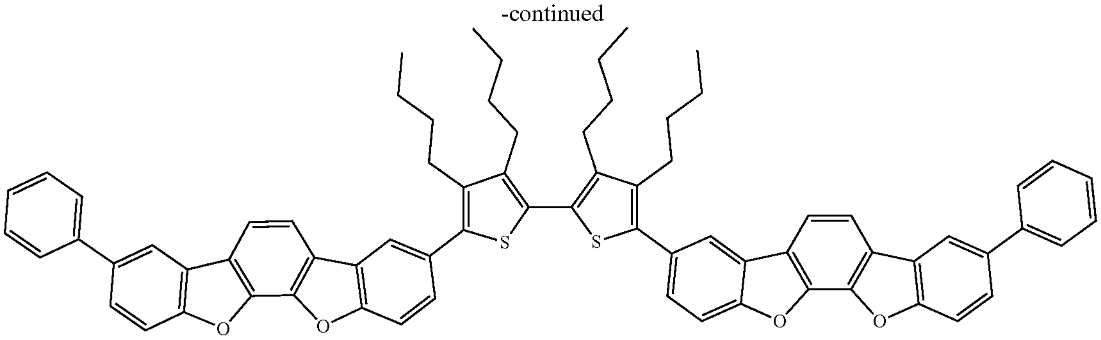
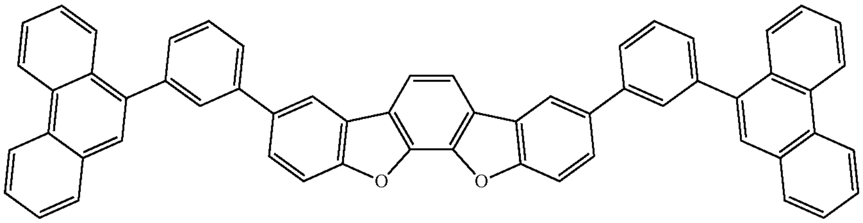
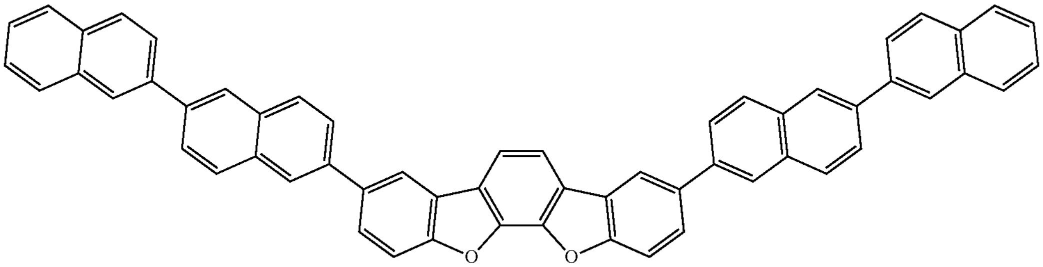
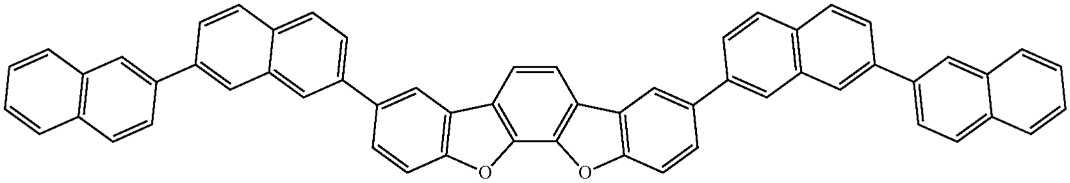
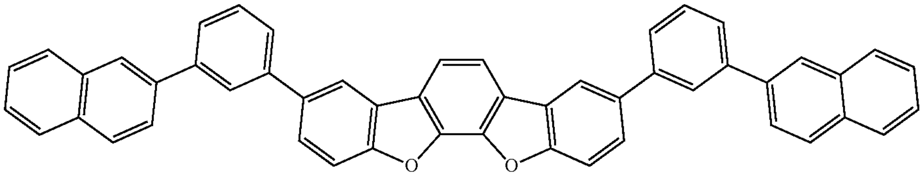
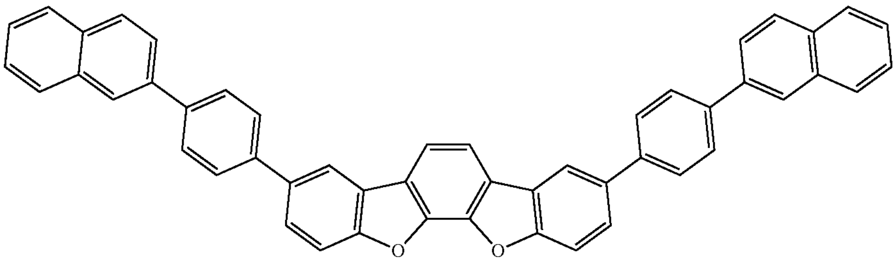

-continued
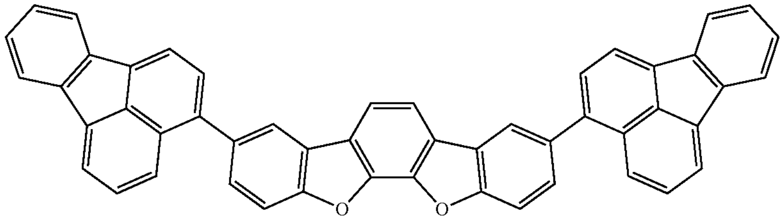
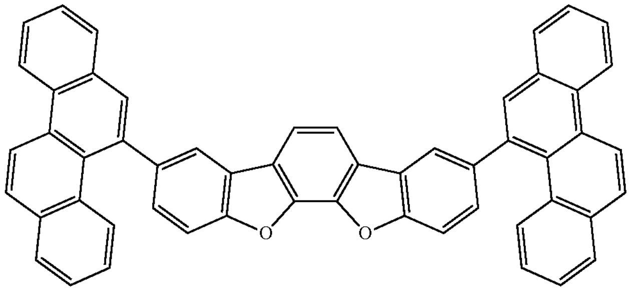
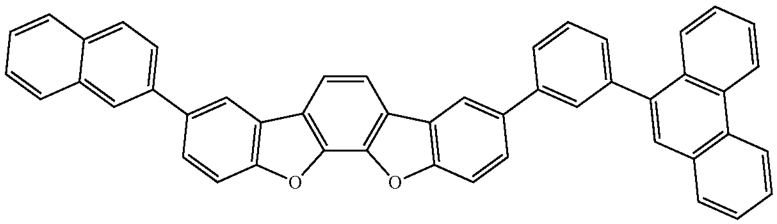
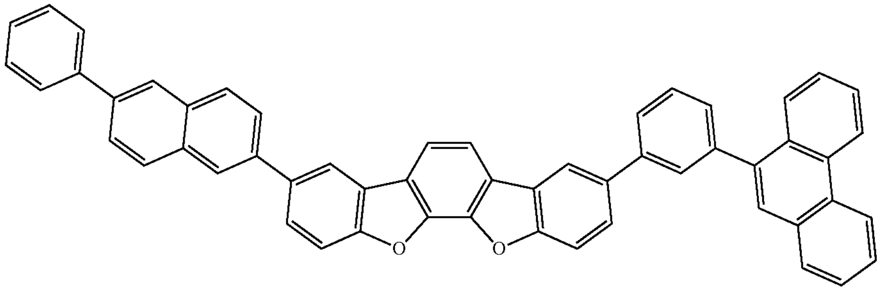
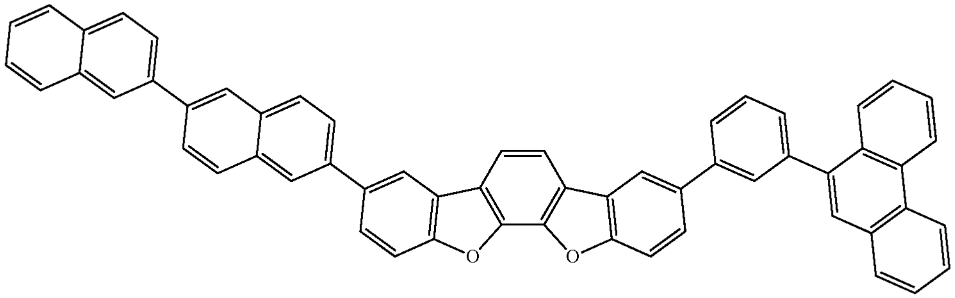
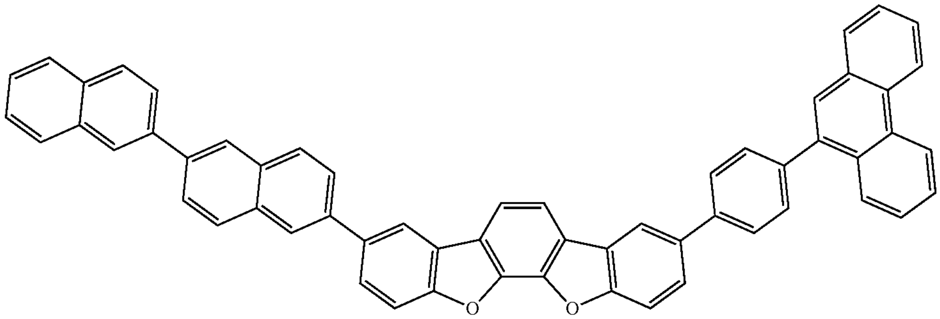

-continued
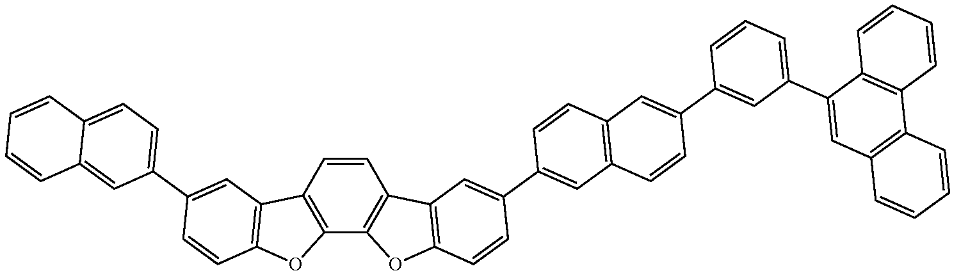
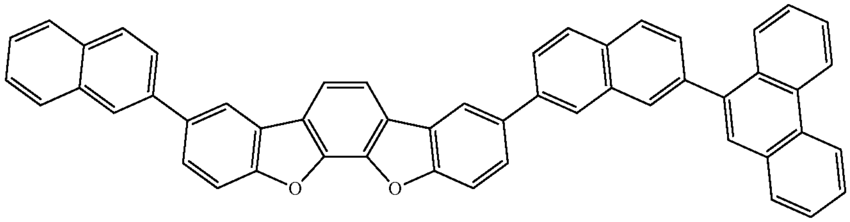
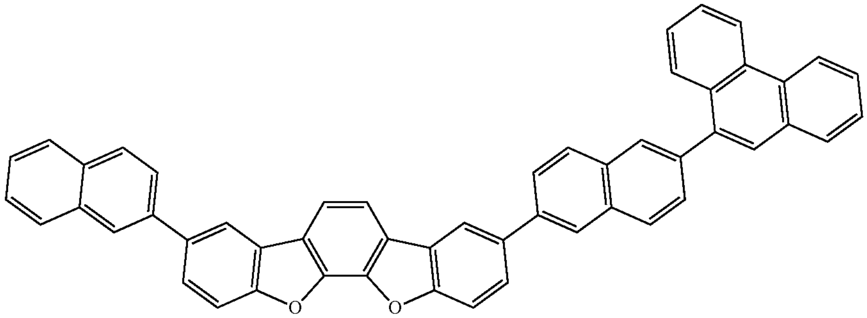
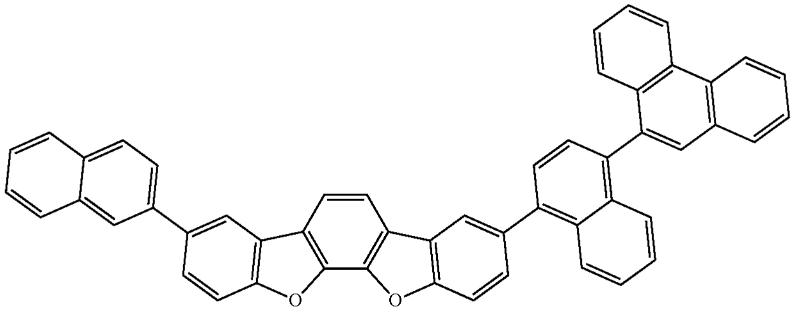
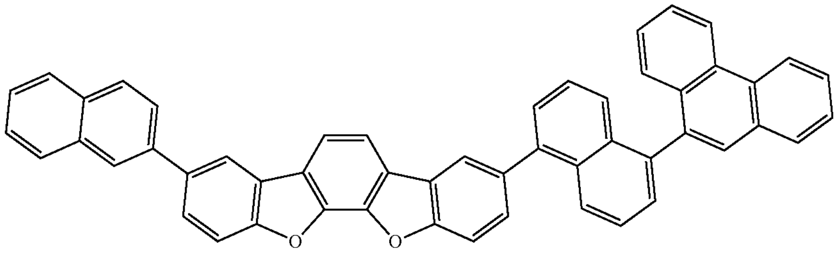
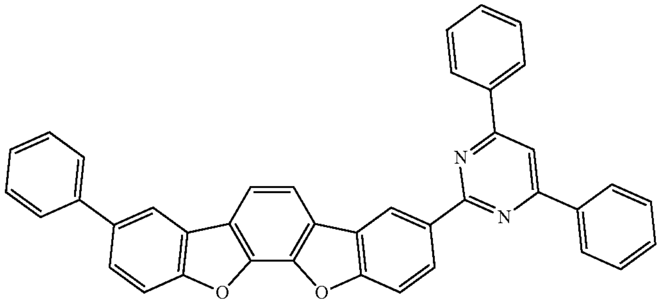

-continued
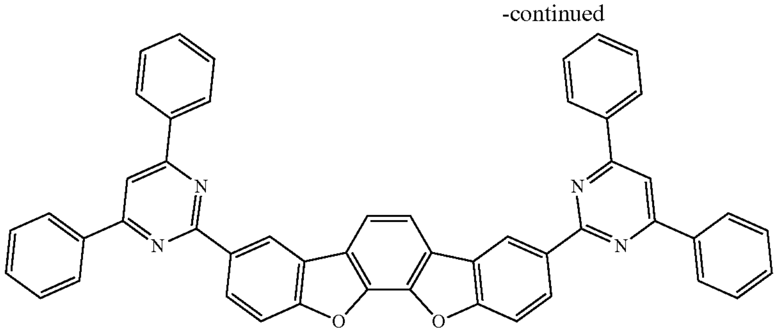
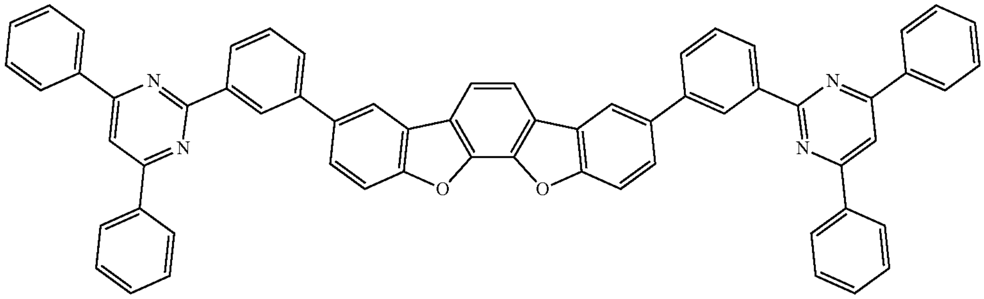
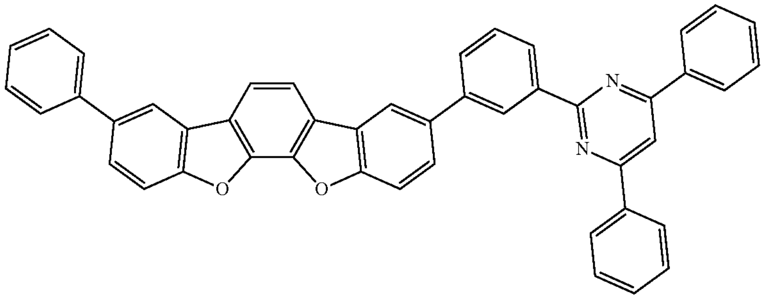
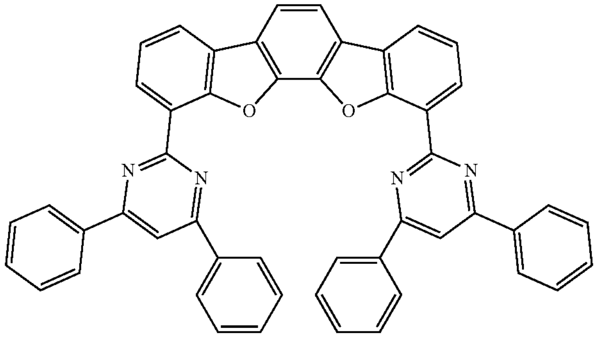
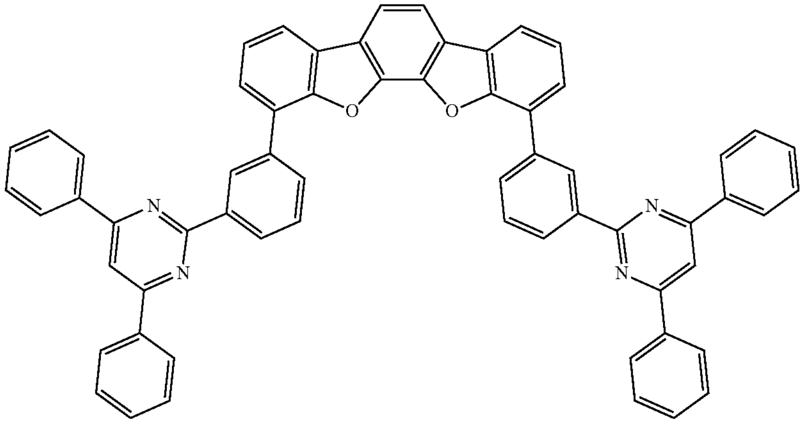

-continued
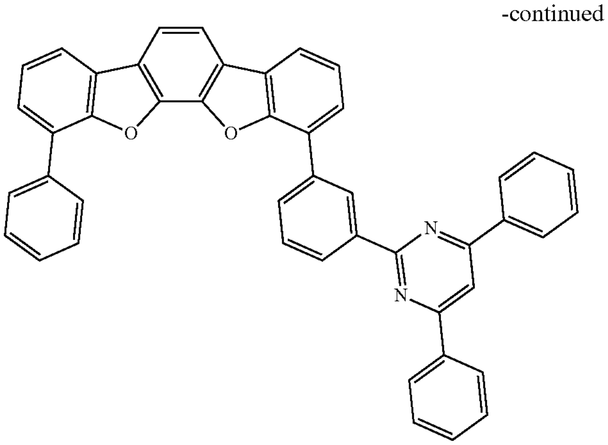
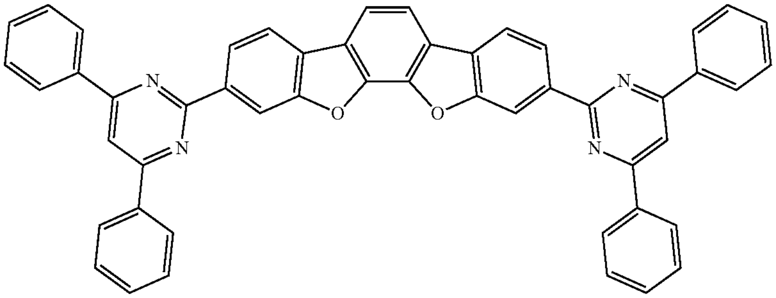
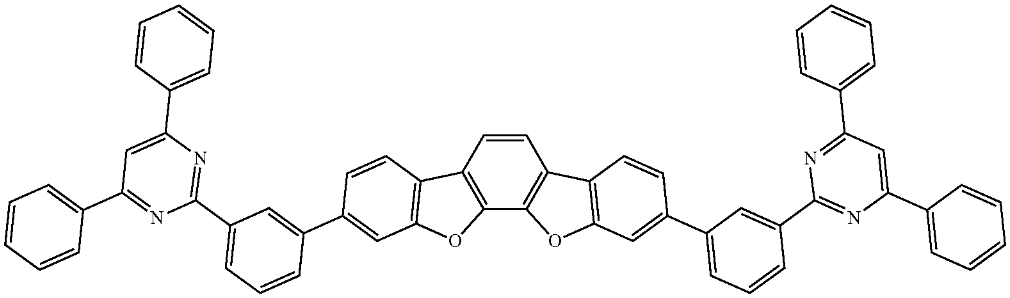
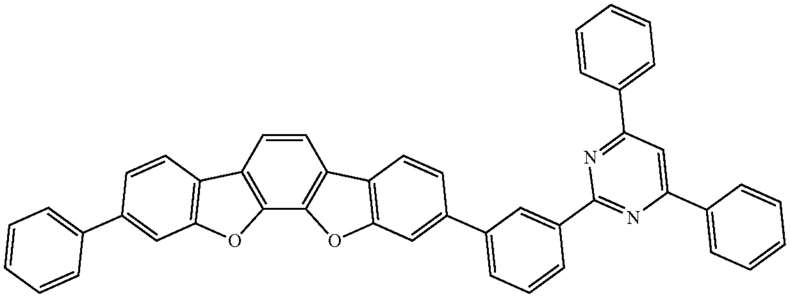
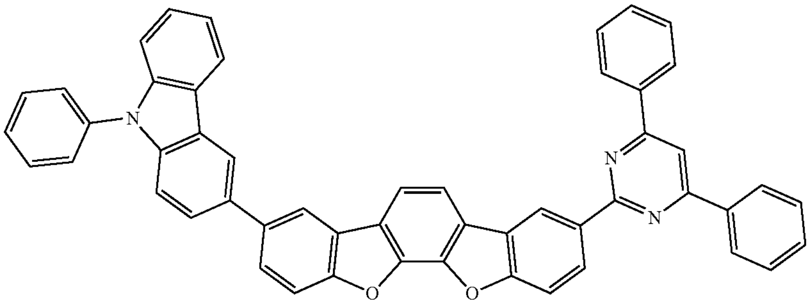

-continued
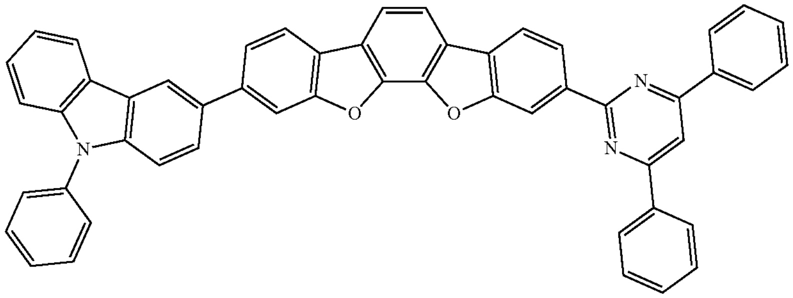
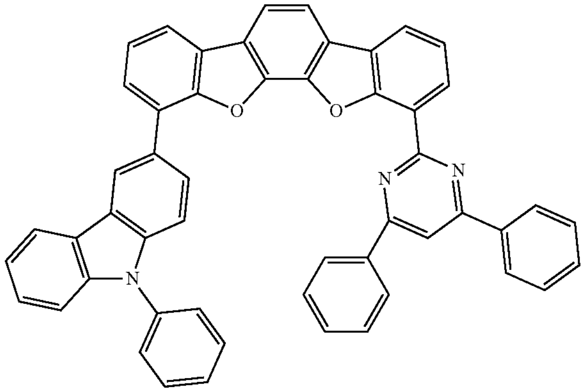
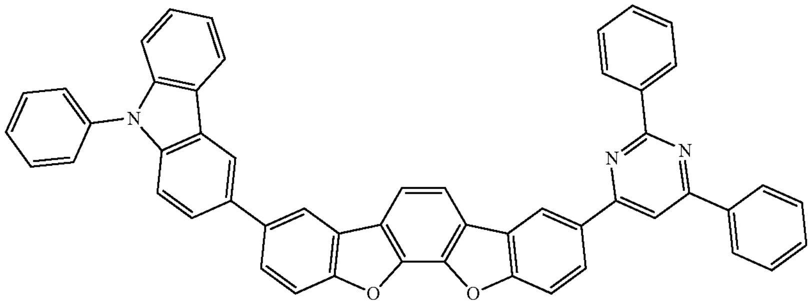
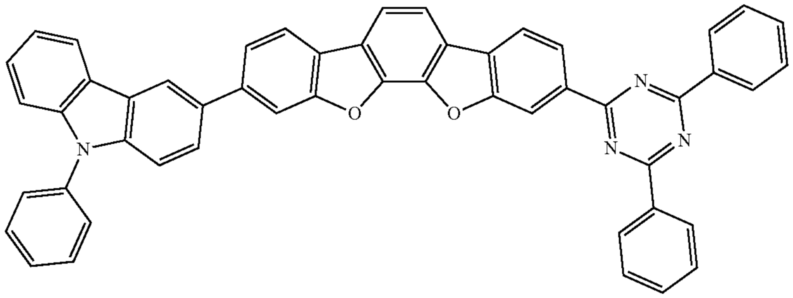
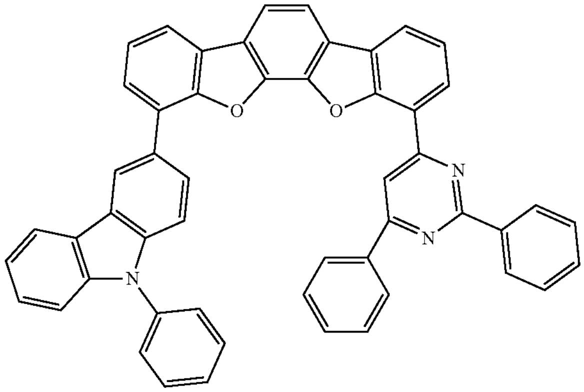

-continued
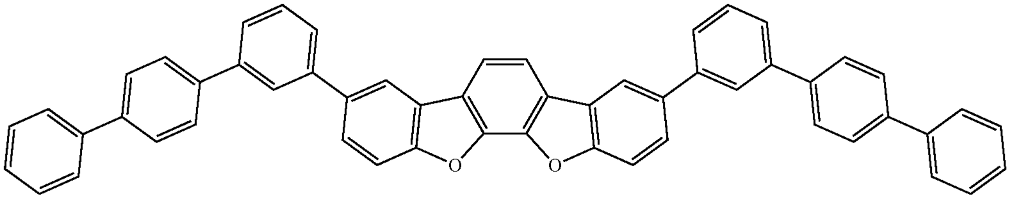
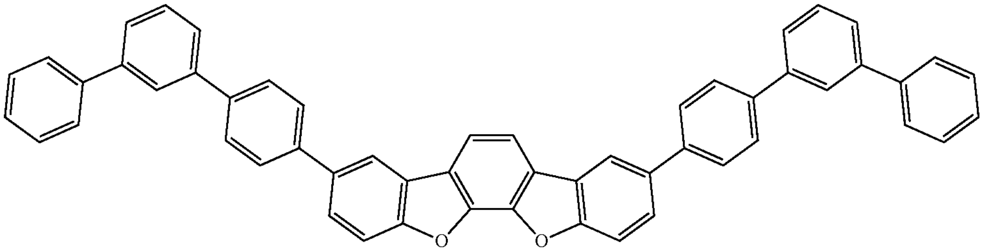
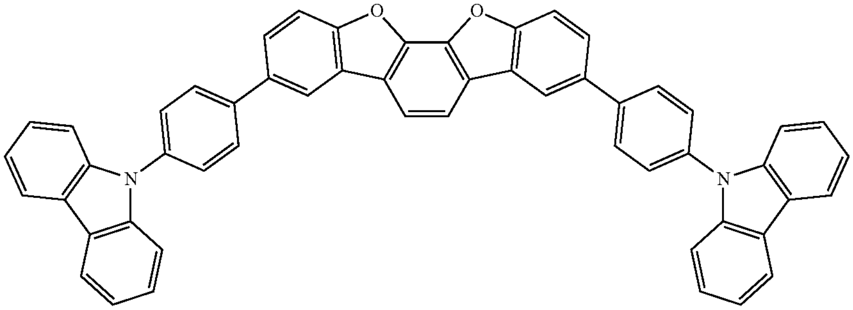
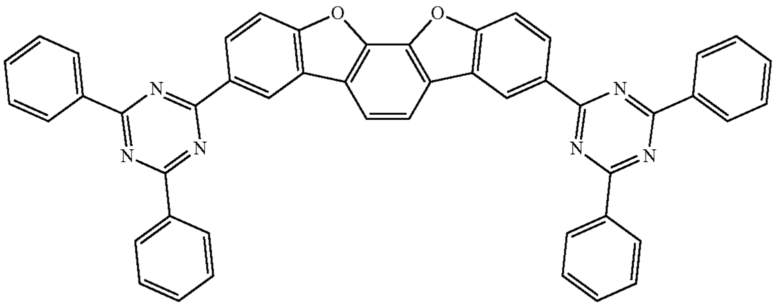
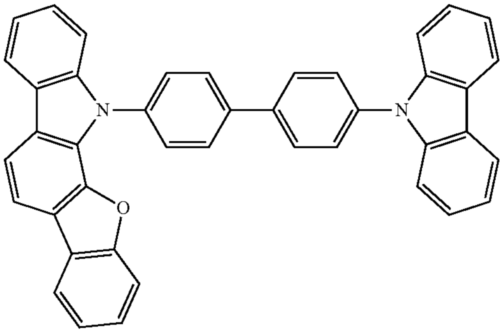
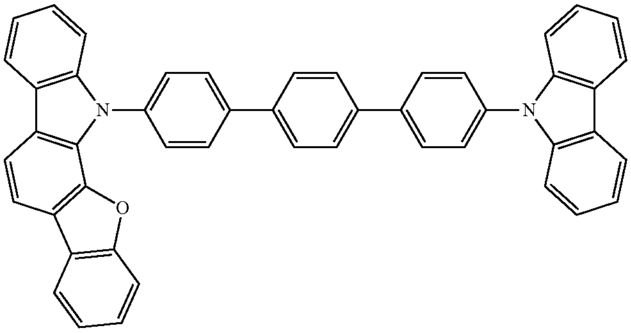
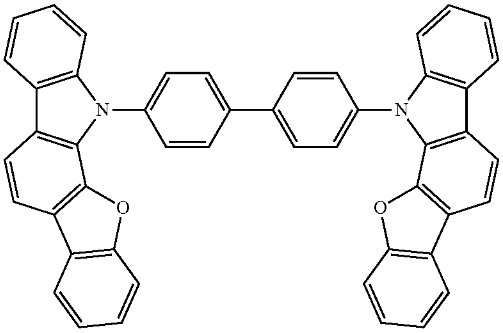
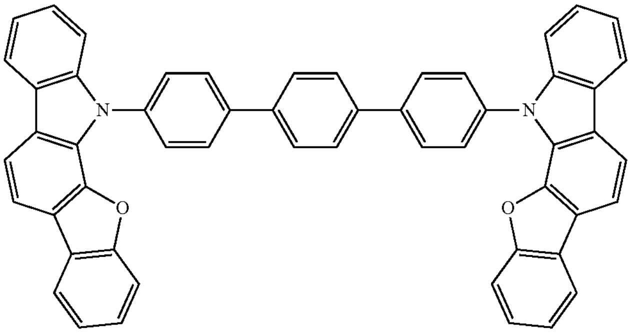

-continued
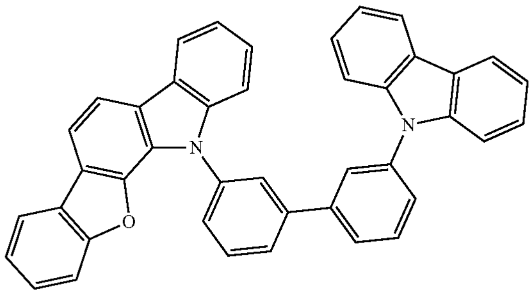
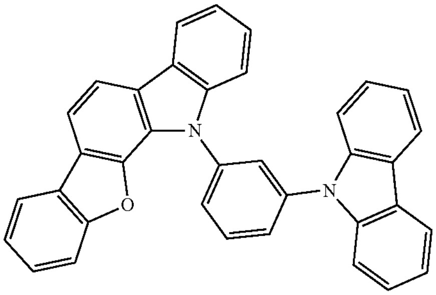
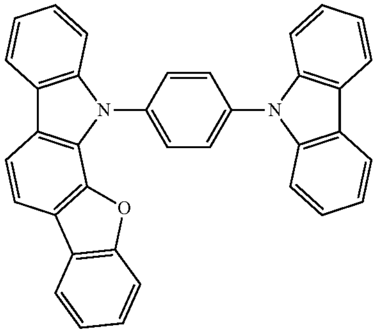
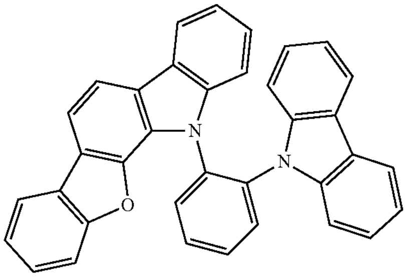
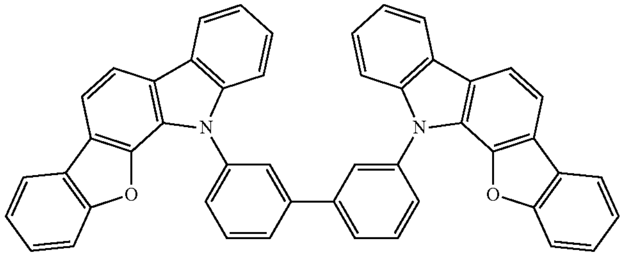
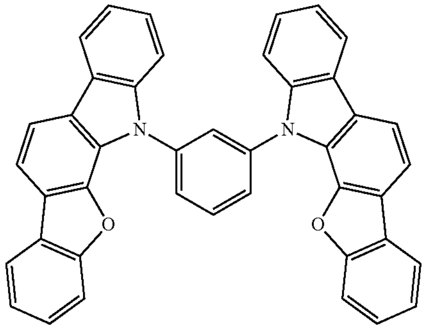
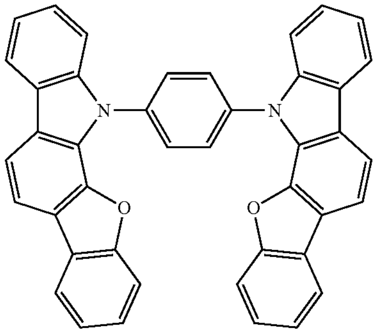
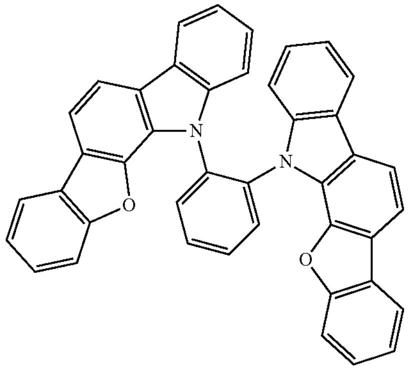

-continued
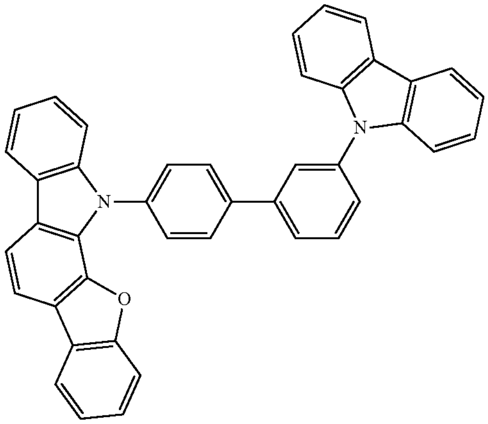
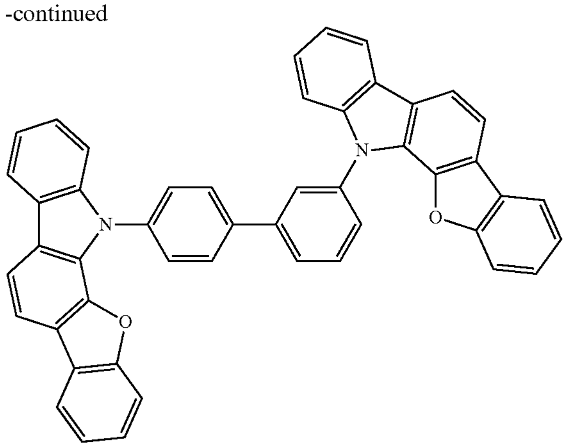
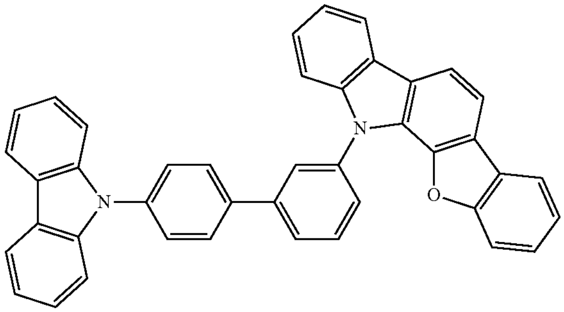
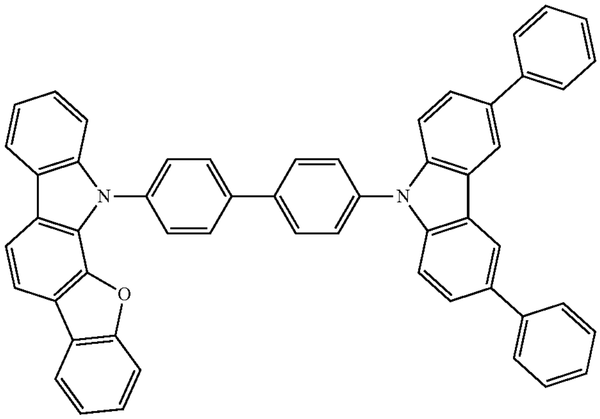
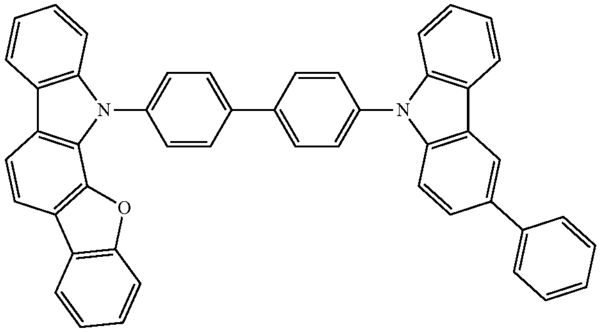
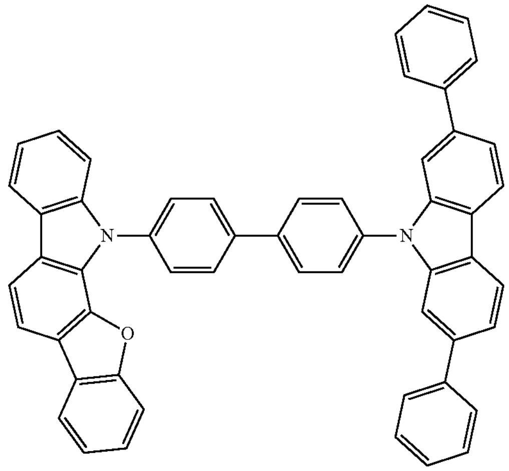

-continued
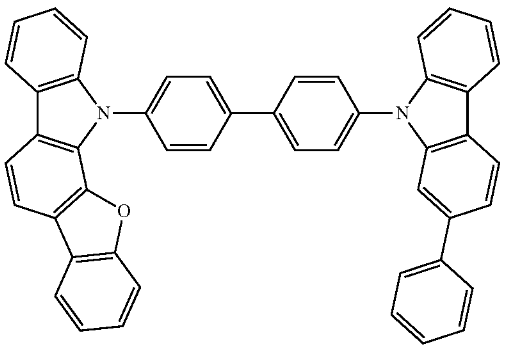
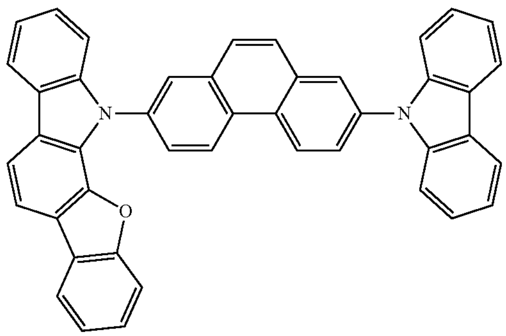
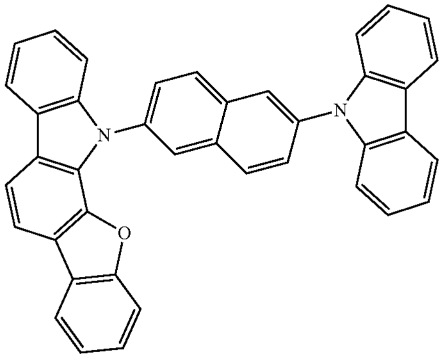
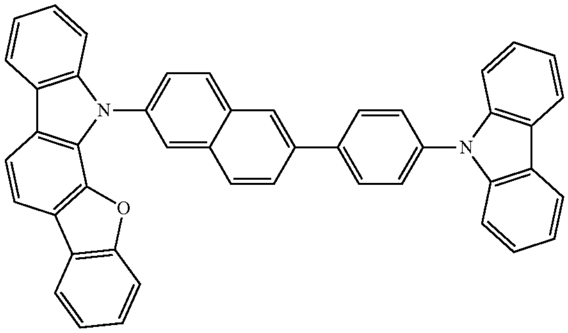
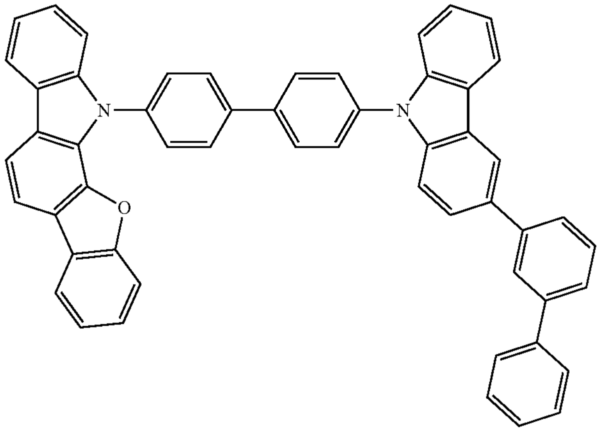
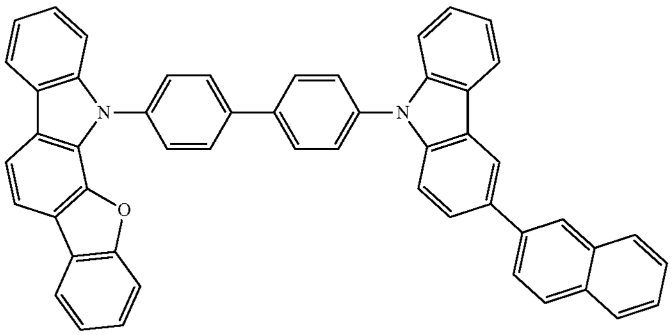

-continued
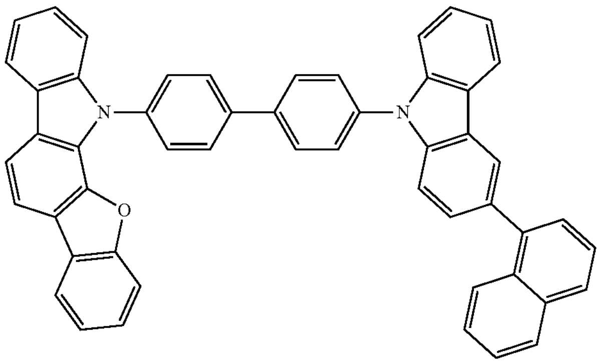
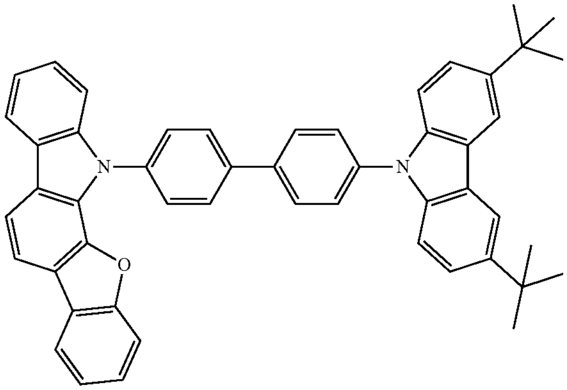
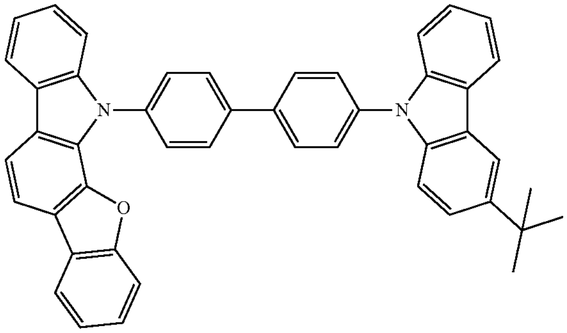
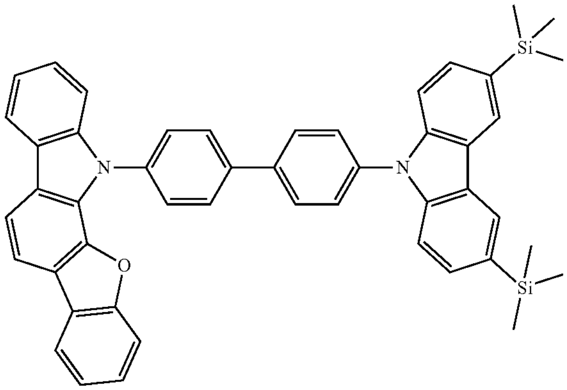
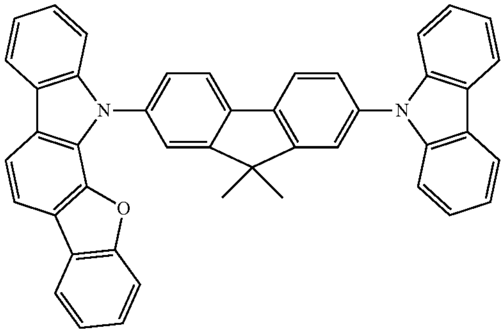
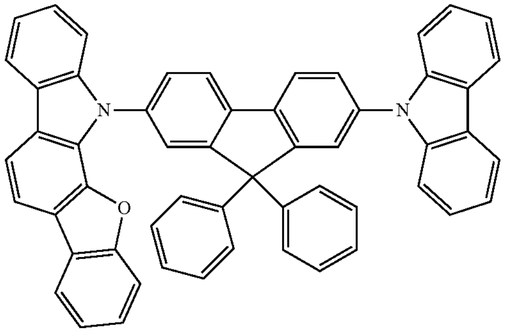
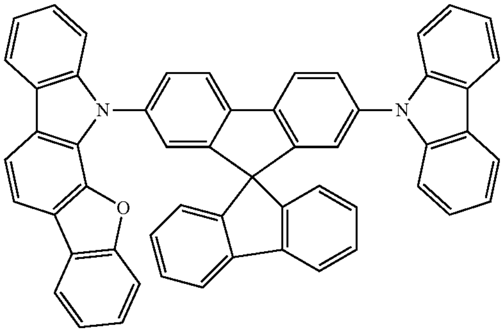

-continued
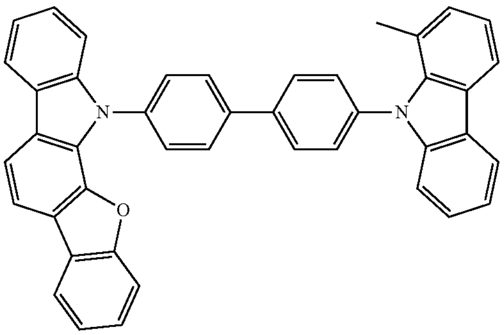
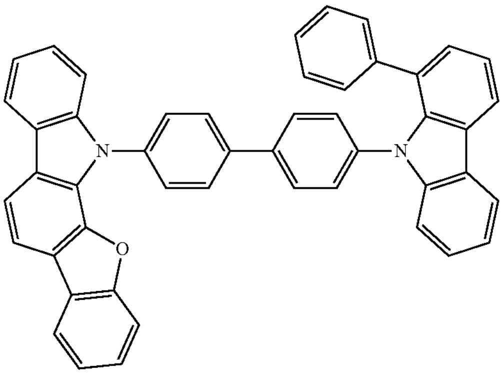
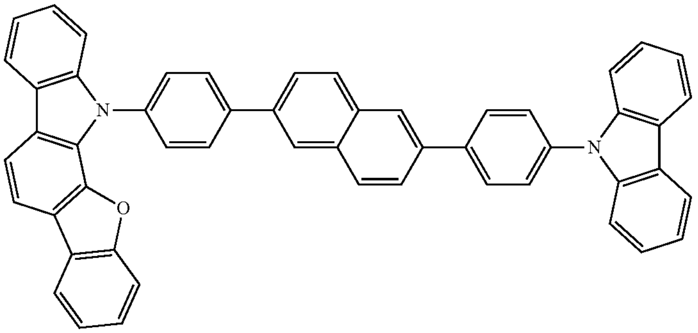
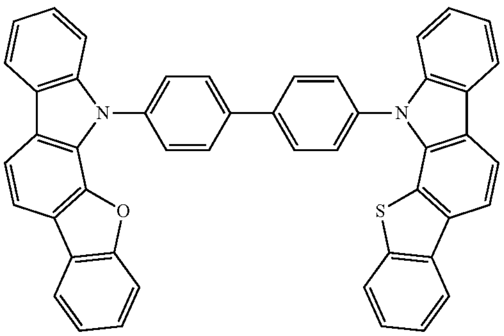
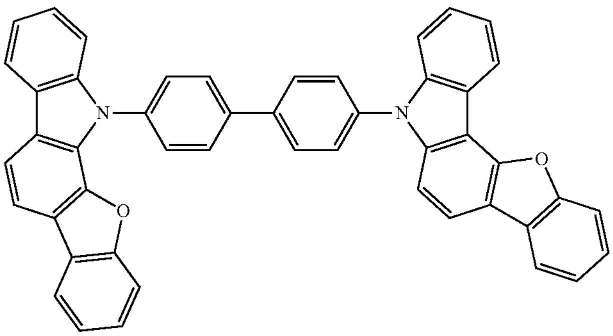
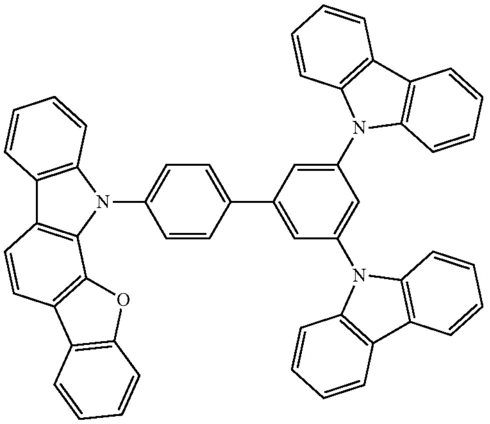
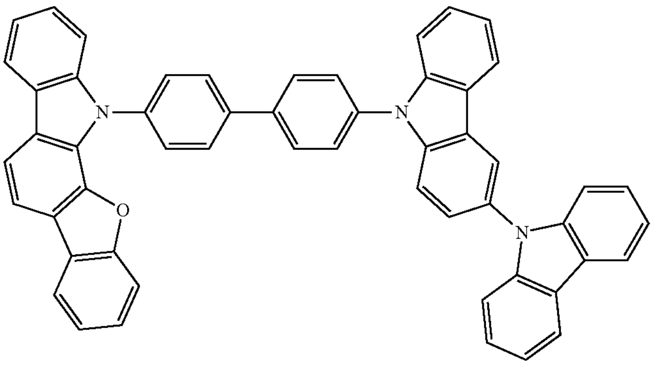

-continued
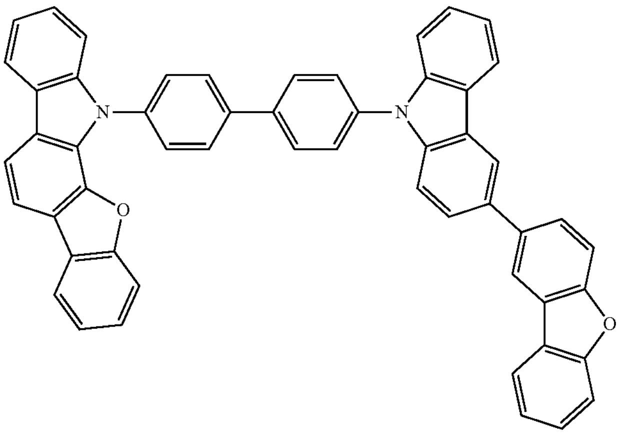
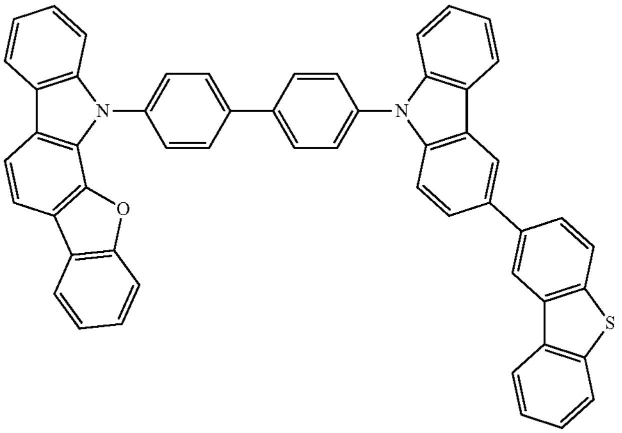
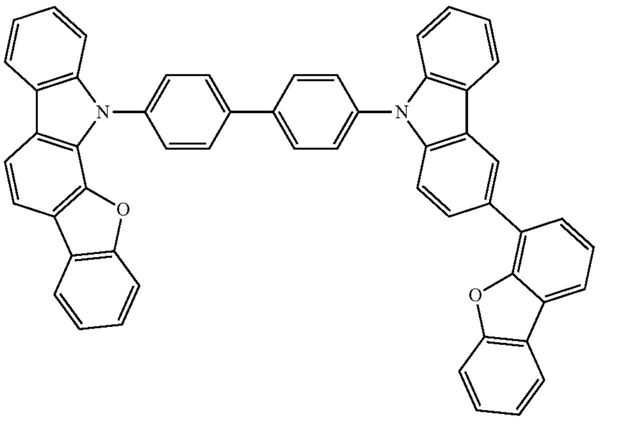
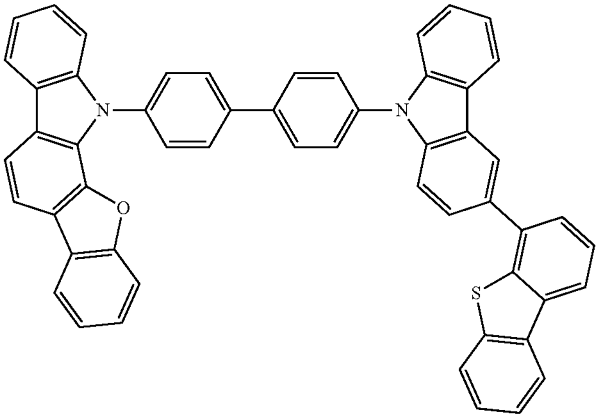
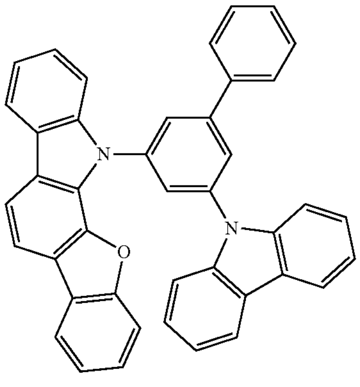

-continued
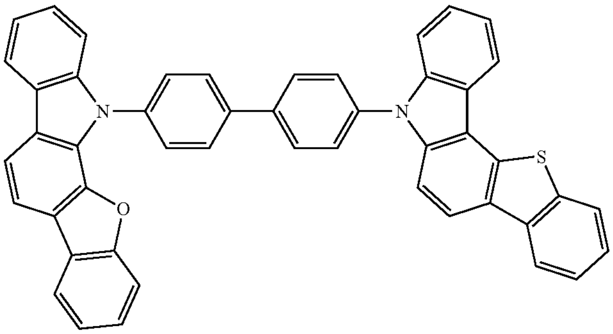
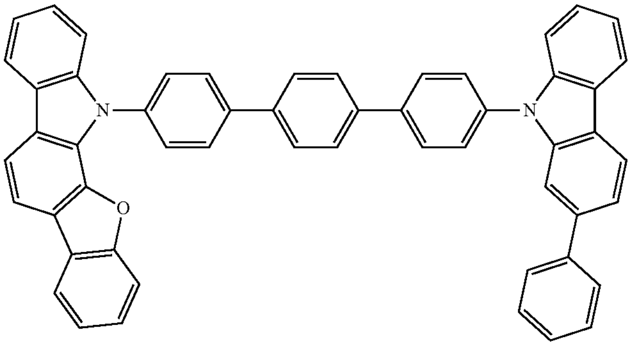
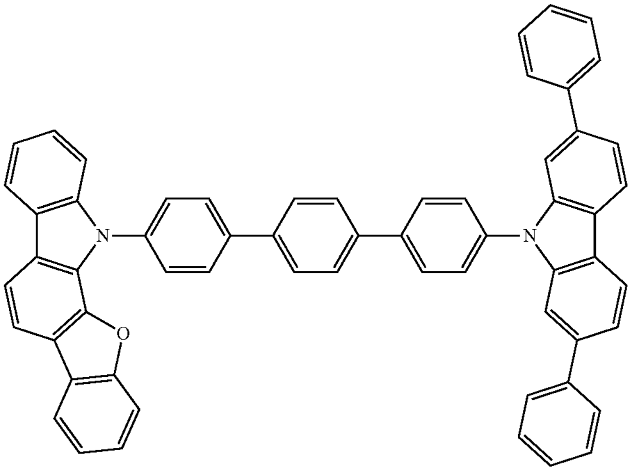
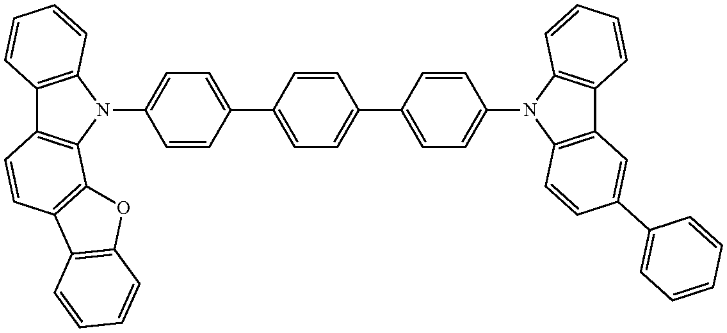

-continued
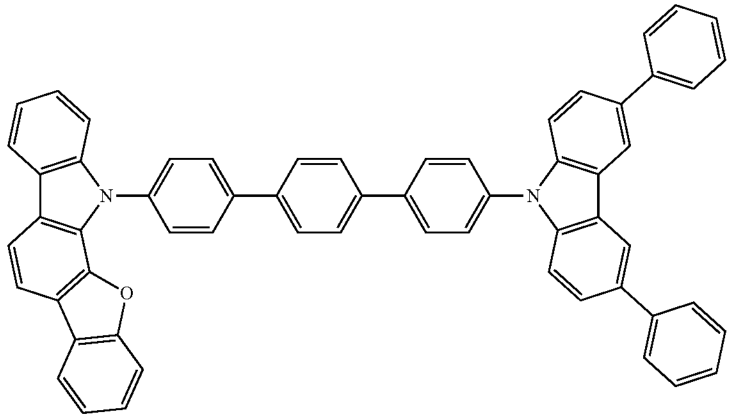
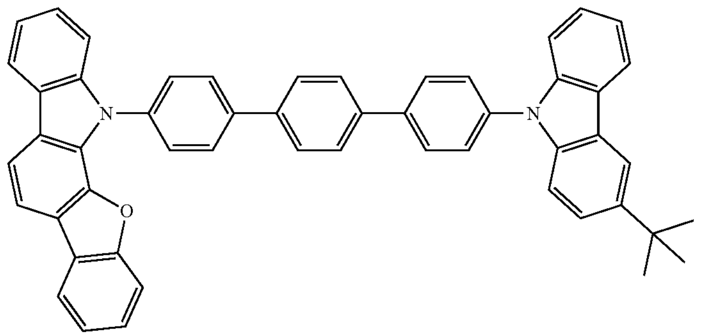
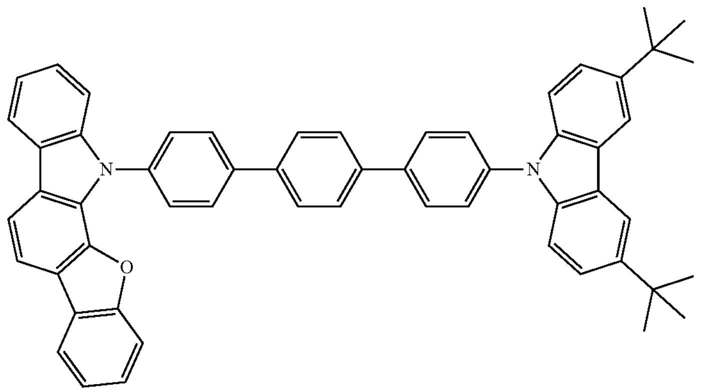
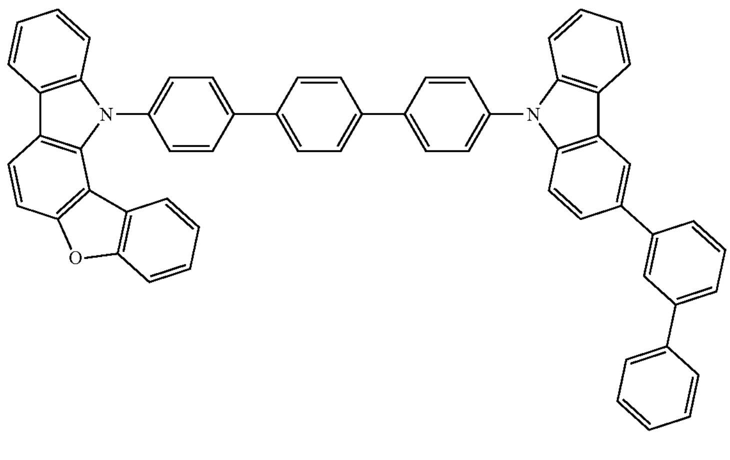

-continued
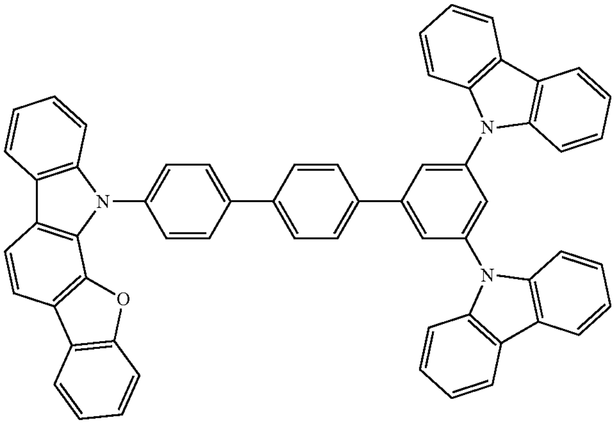
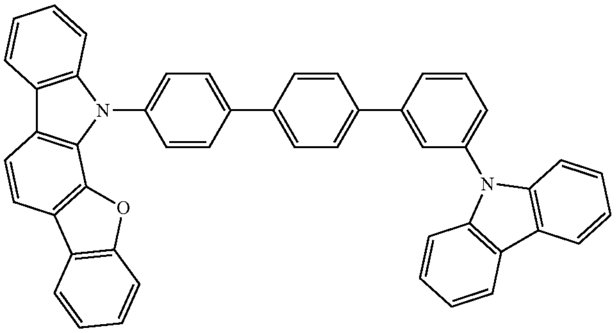
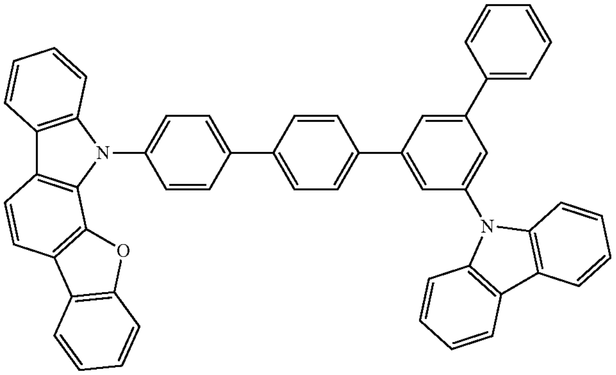
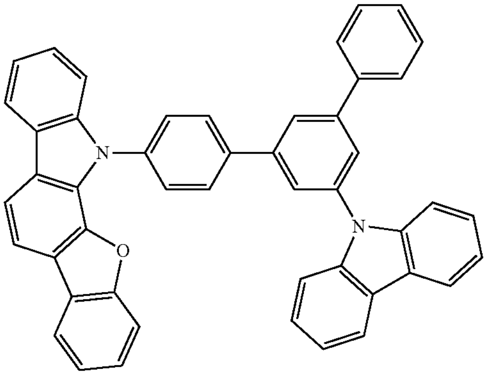
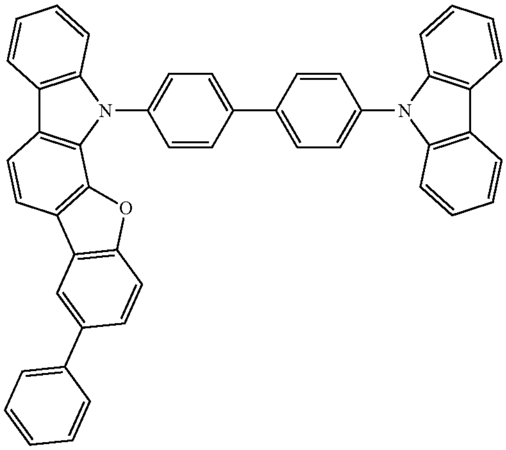
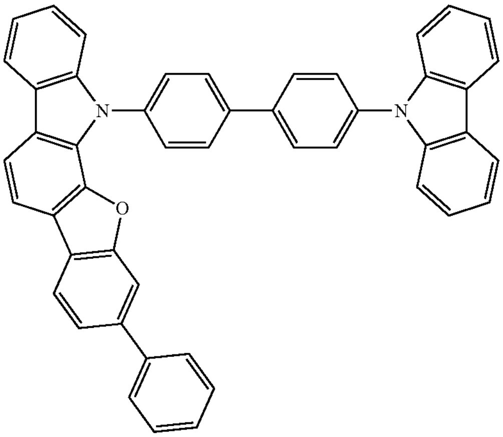

-continued
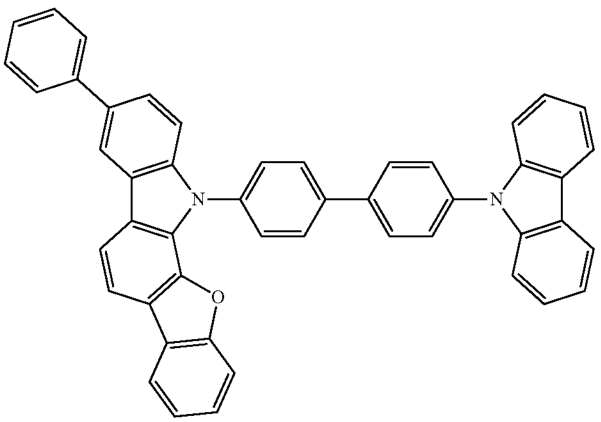
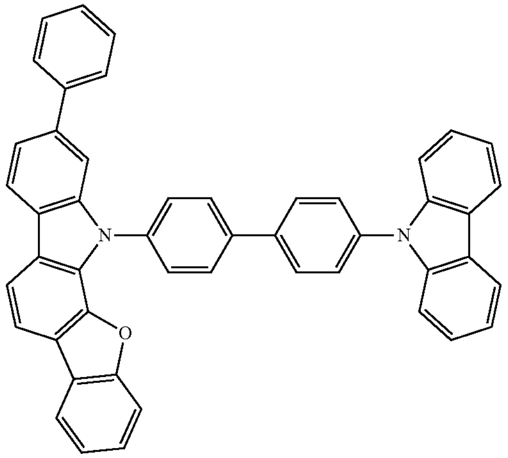
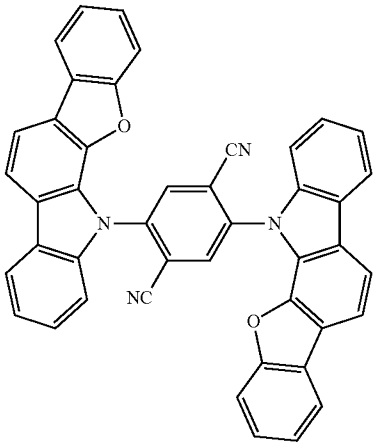
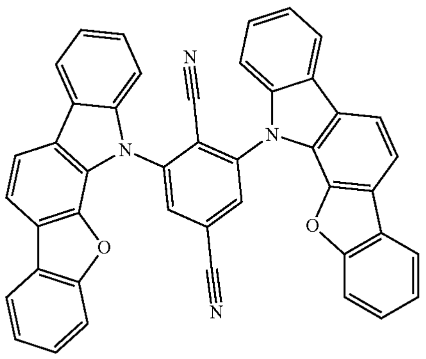
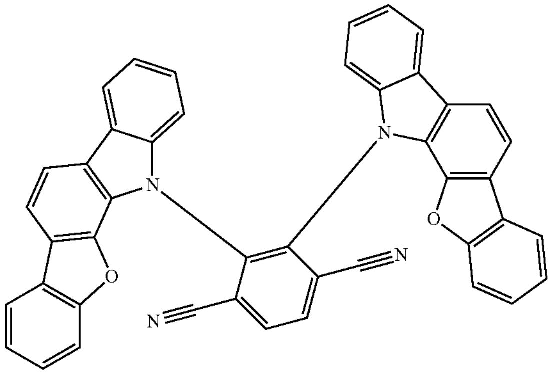
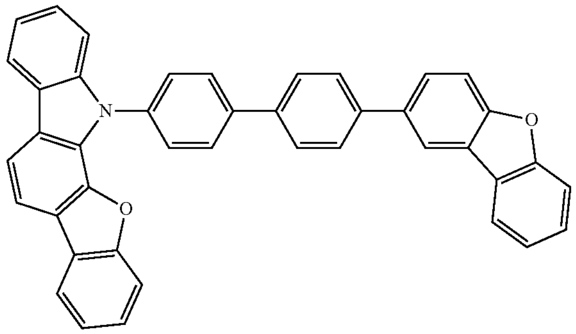
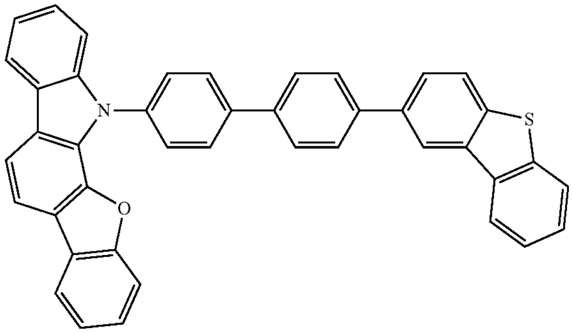
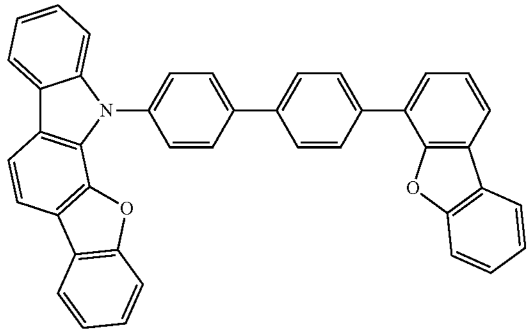

-continued
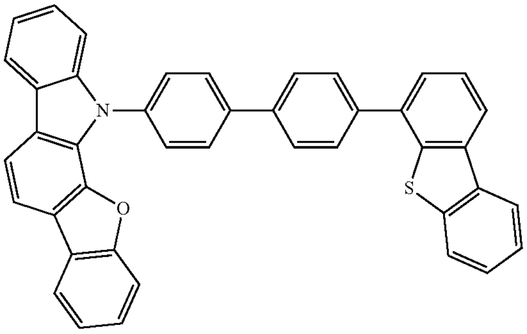
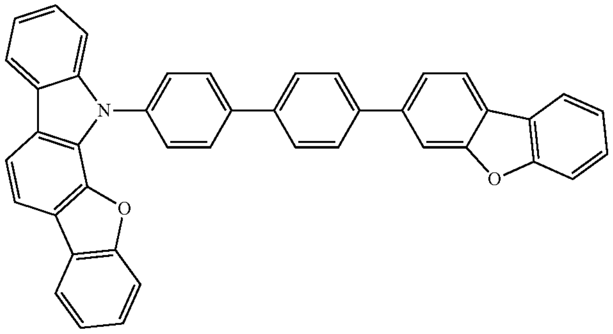
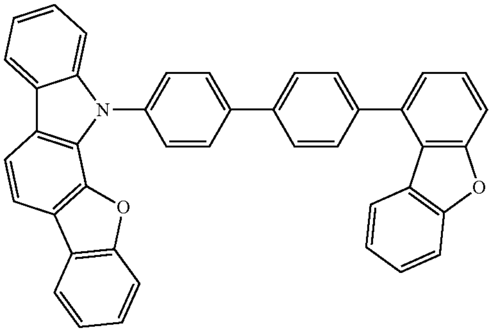
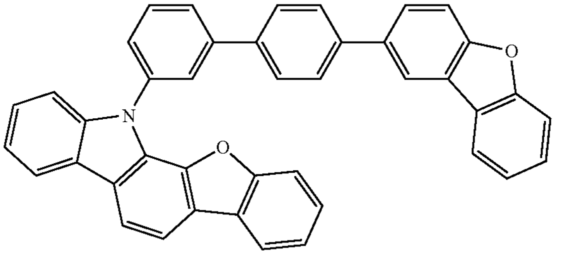
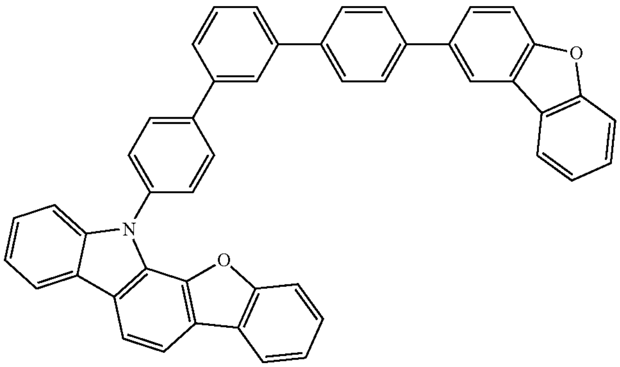
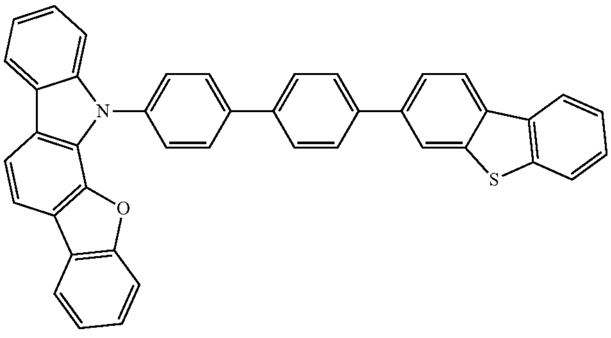
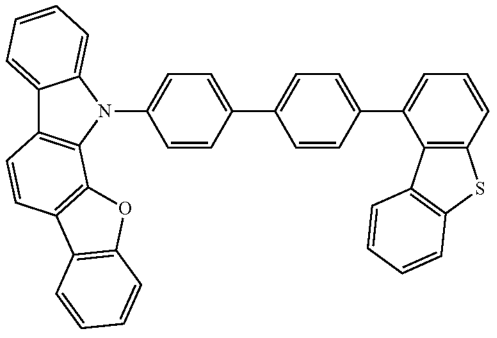
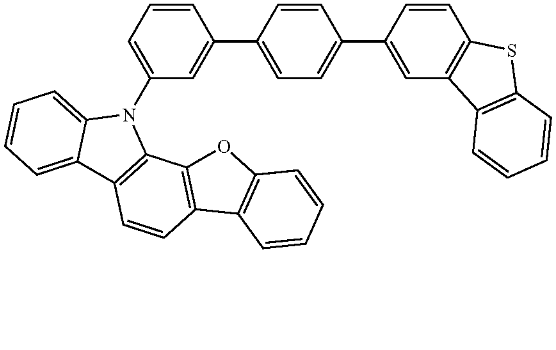

-continued
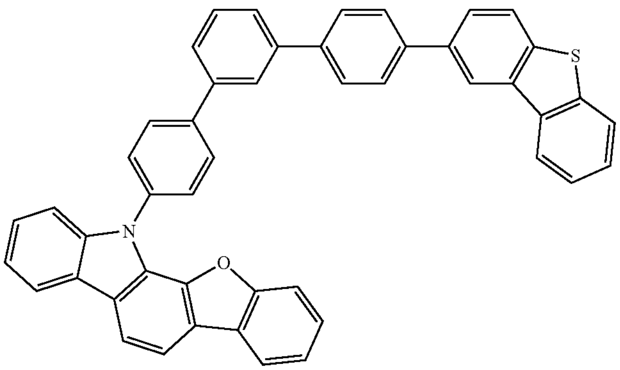
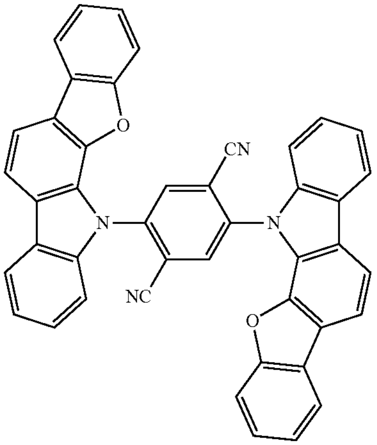
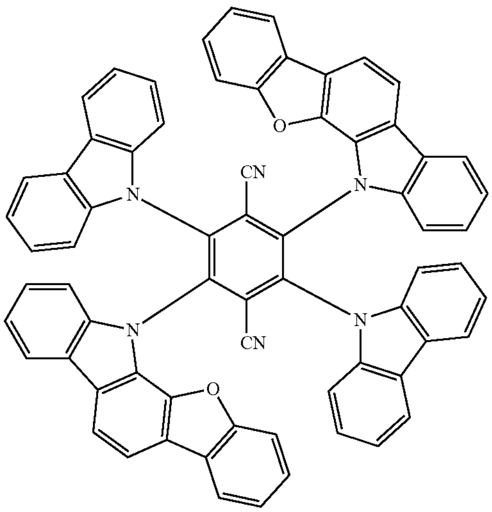
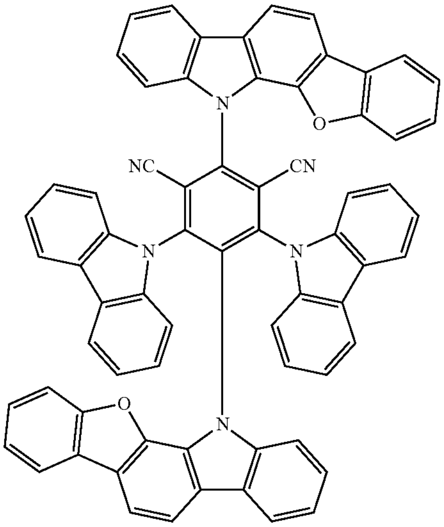
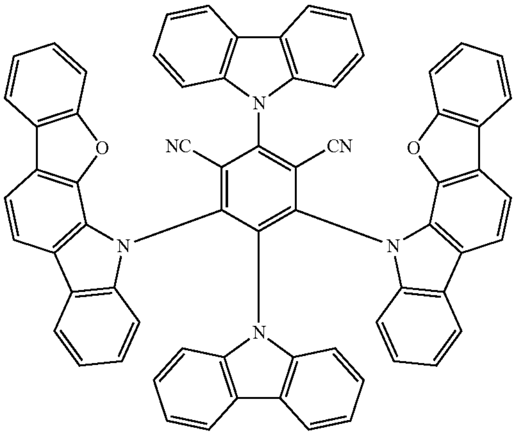
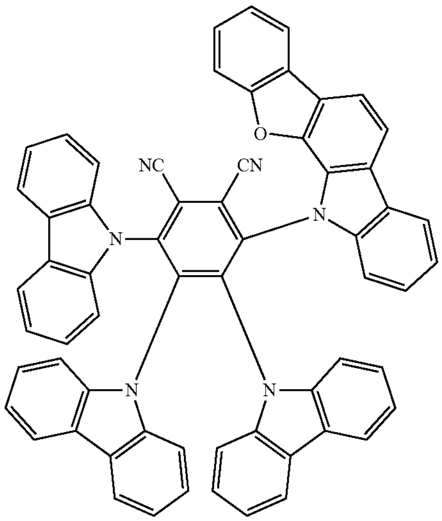

-continued
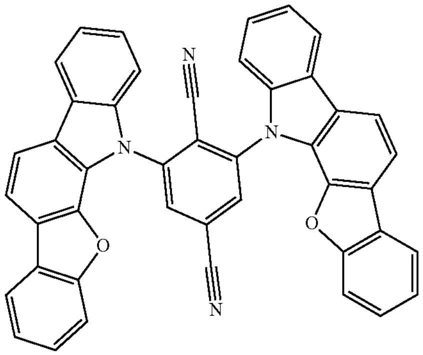
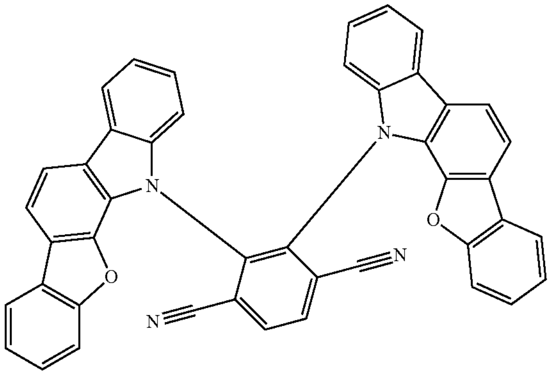
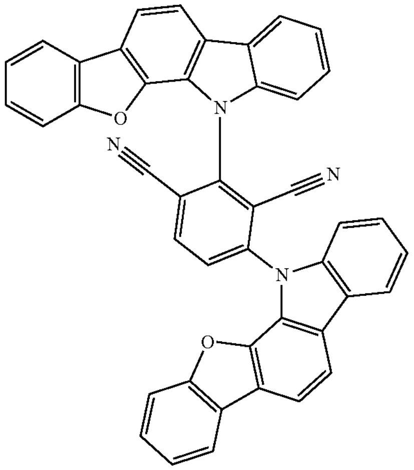
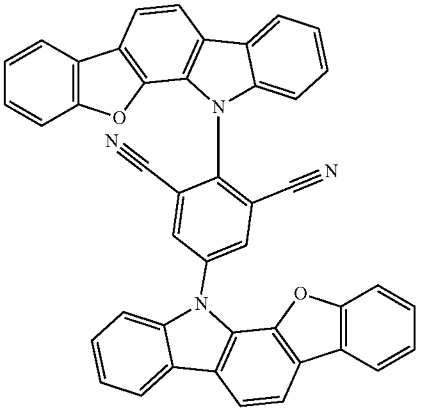
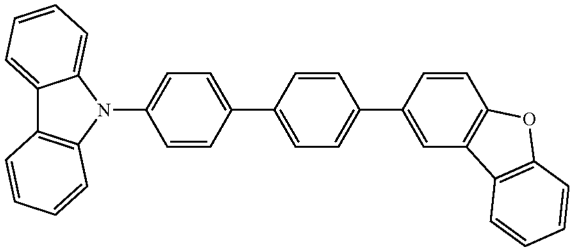
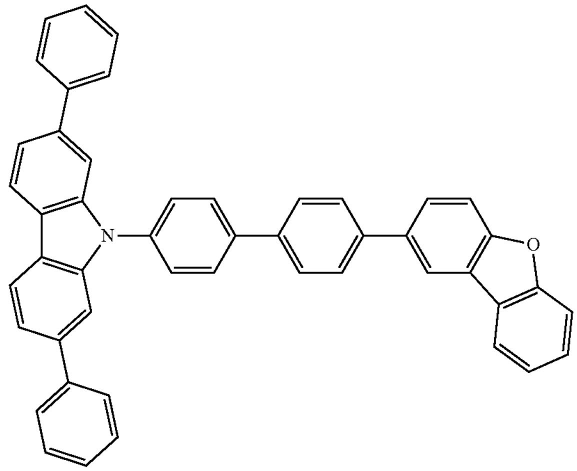
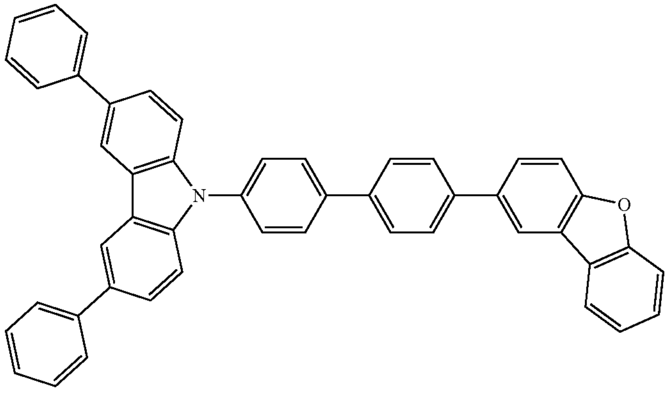

-continued
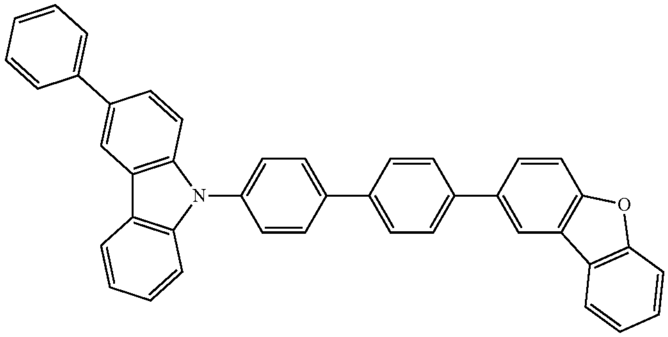
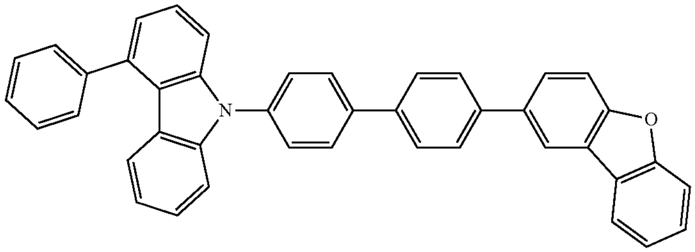
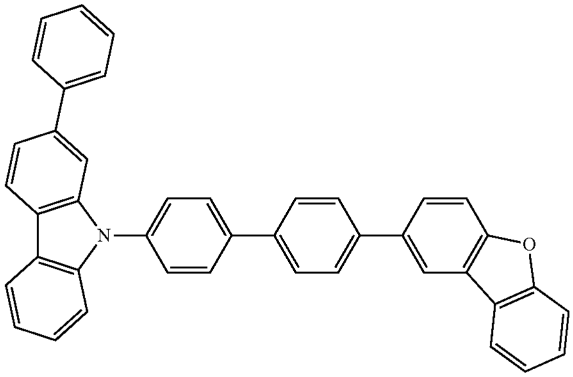
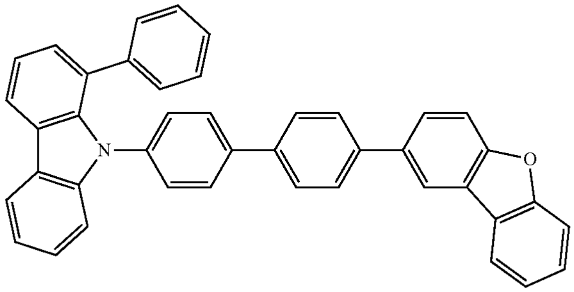
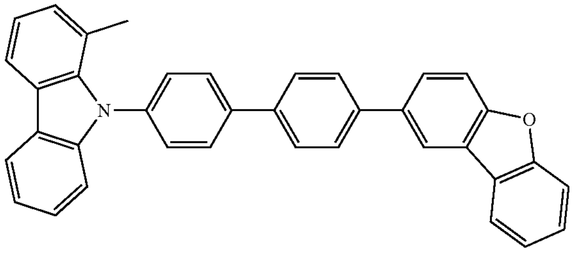
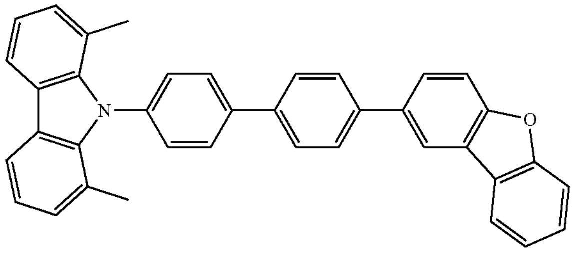
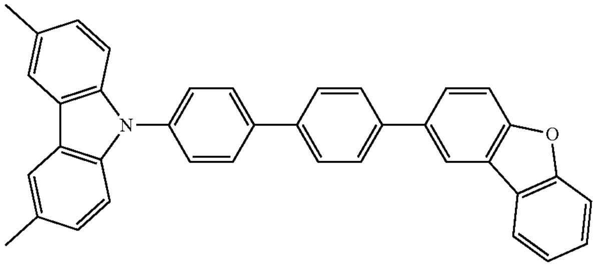

-continued
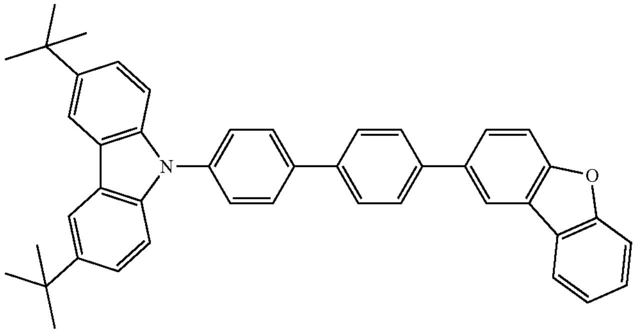
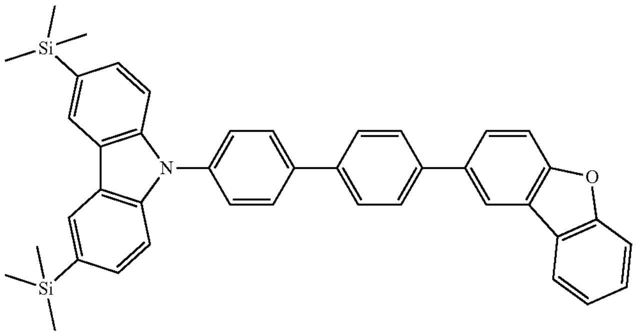
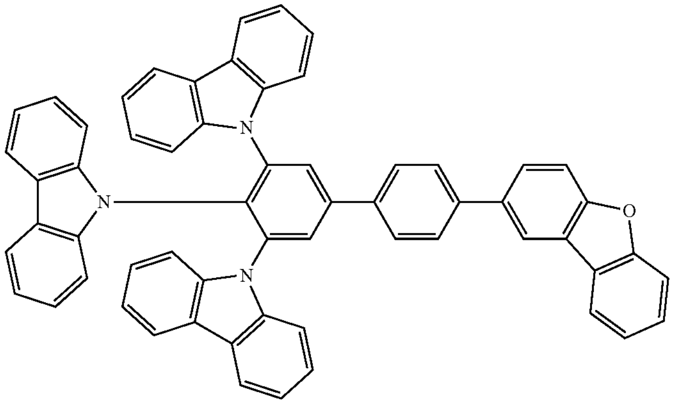
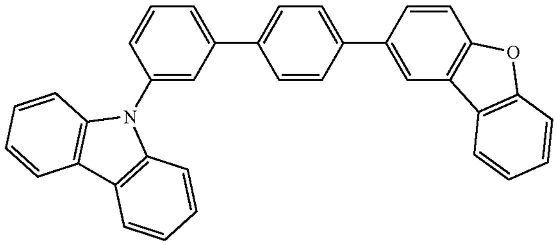
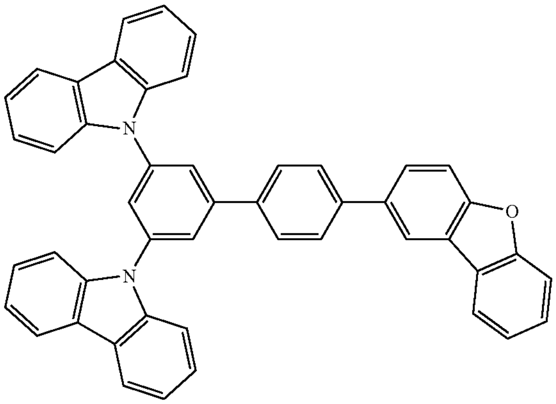
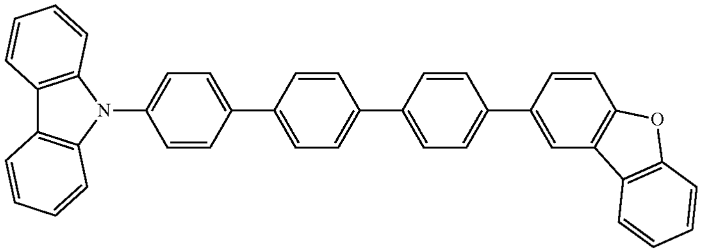

-continued
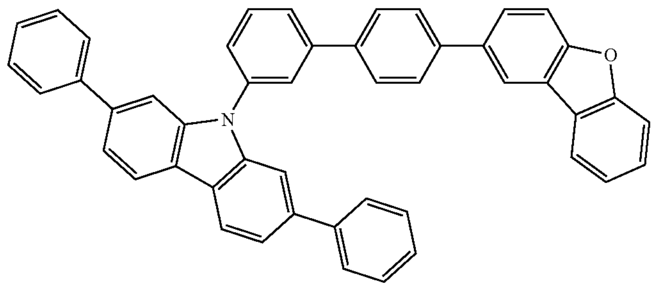
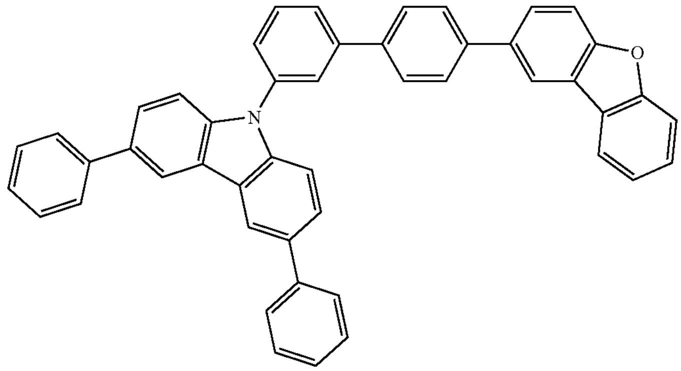
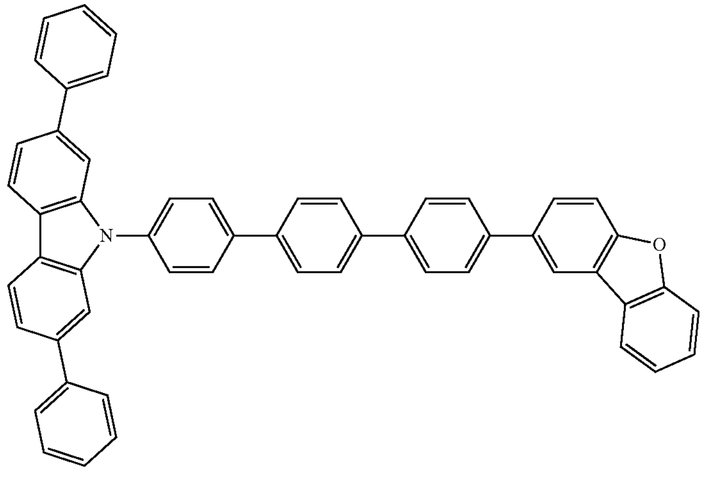
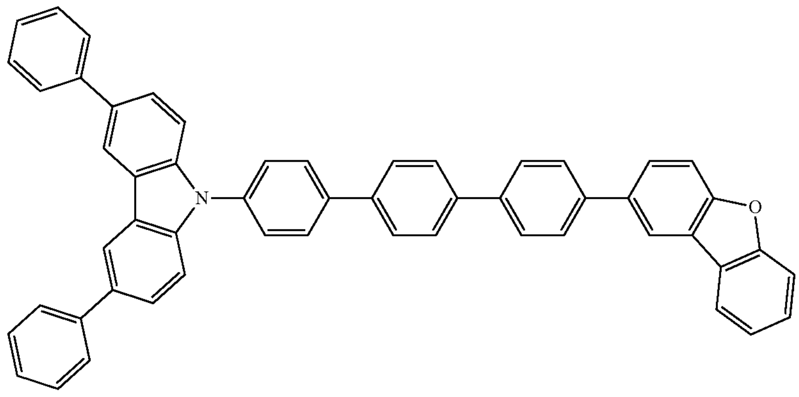

-continued
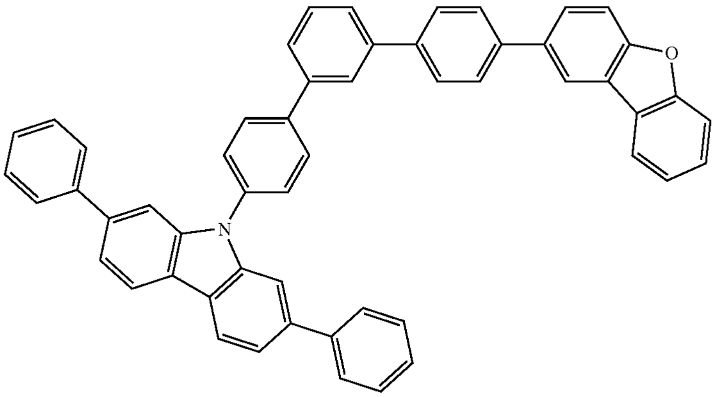
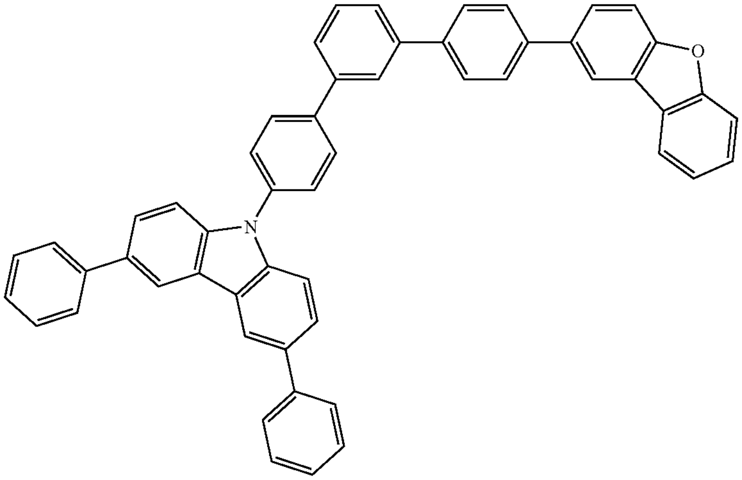
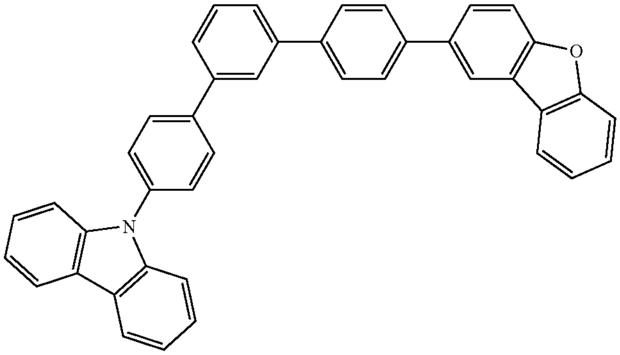
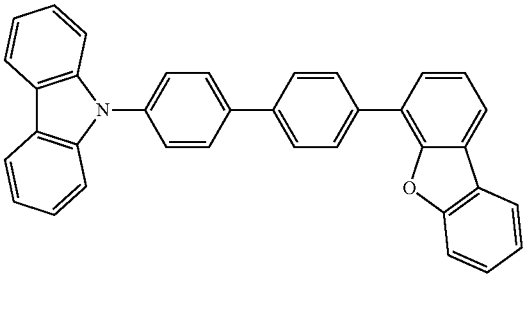
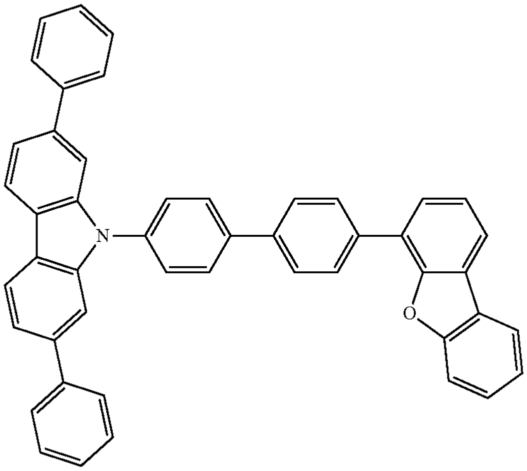

-continued
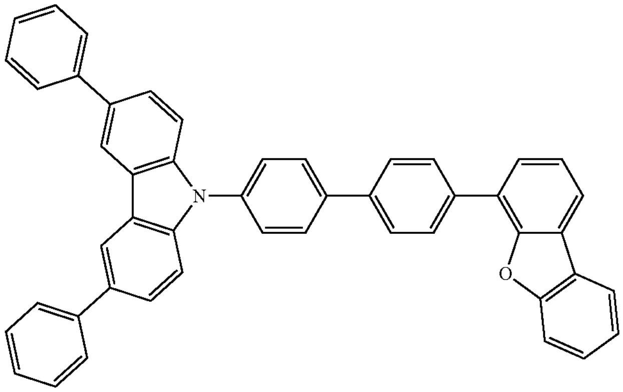
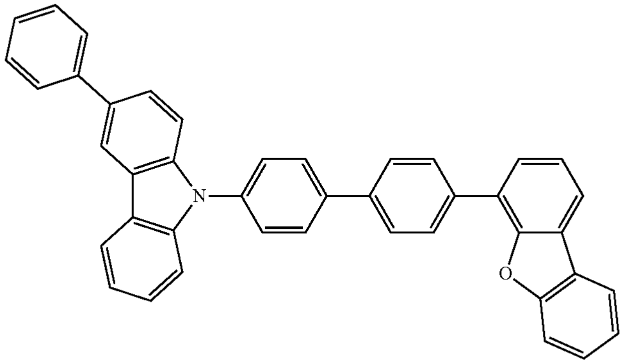
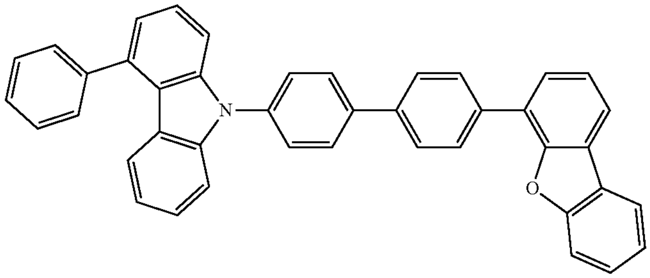
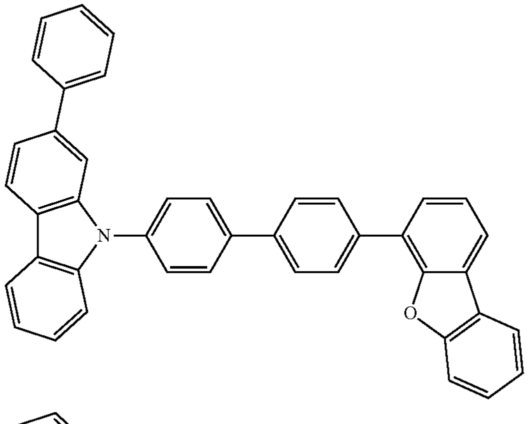
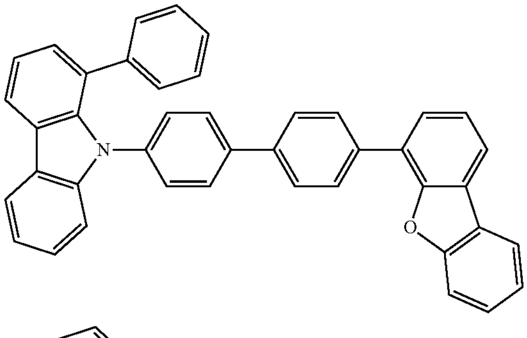
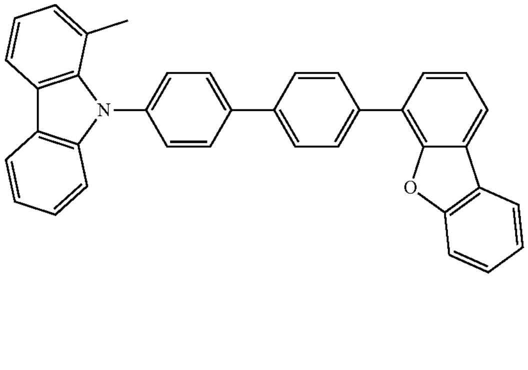
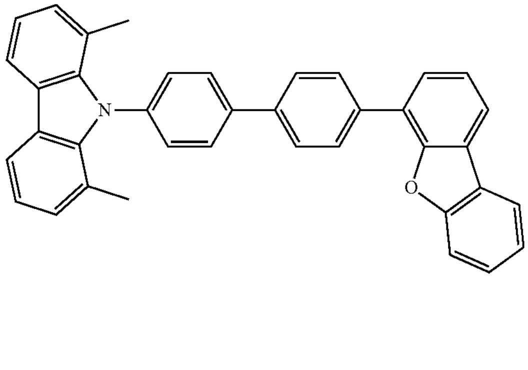

-continued
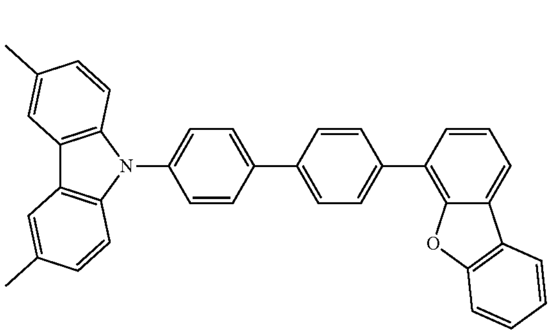
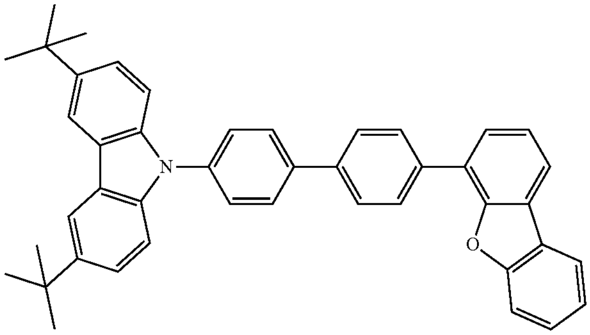
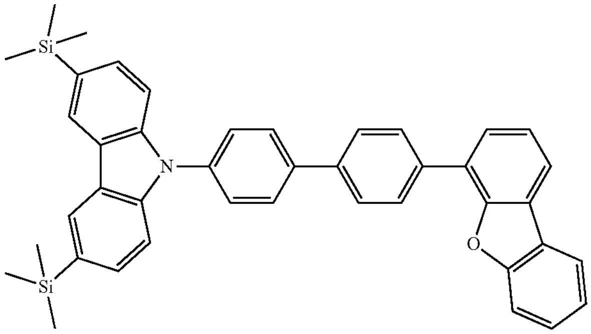
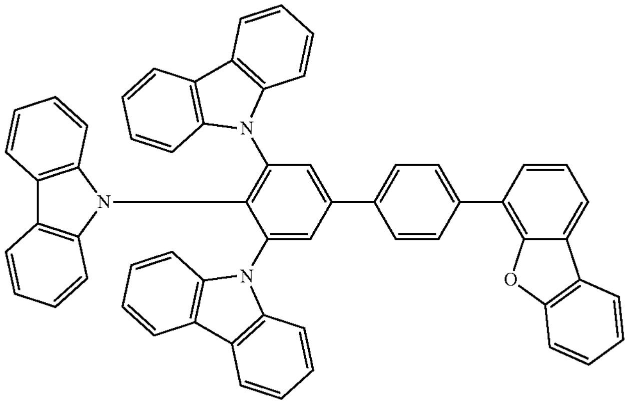
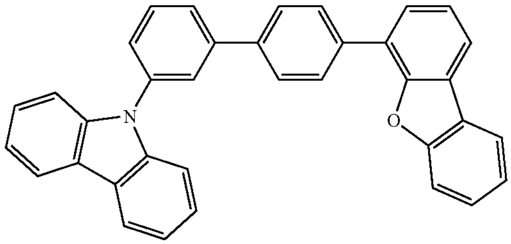
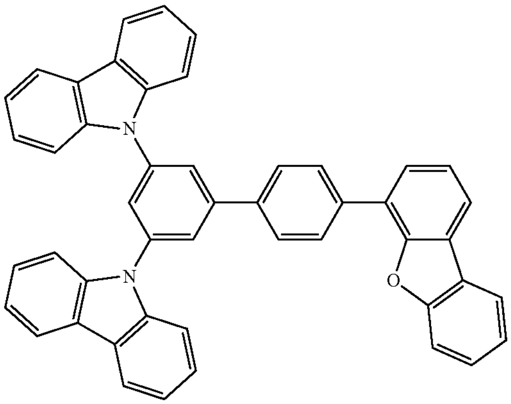

-continued
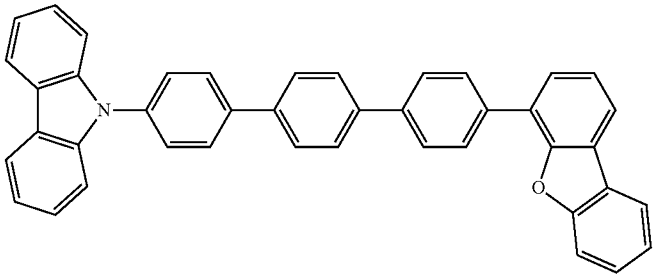
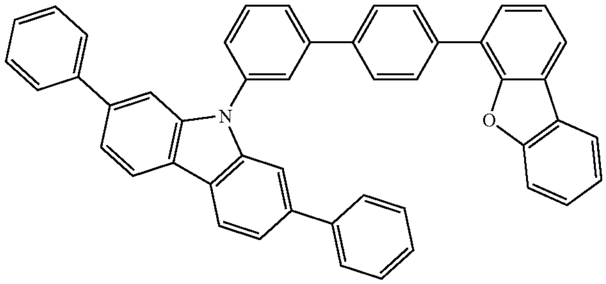
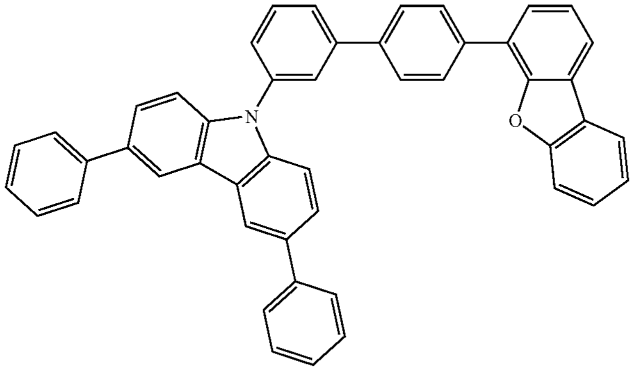
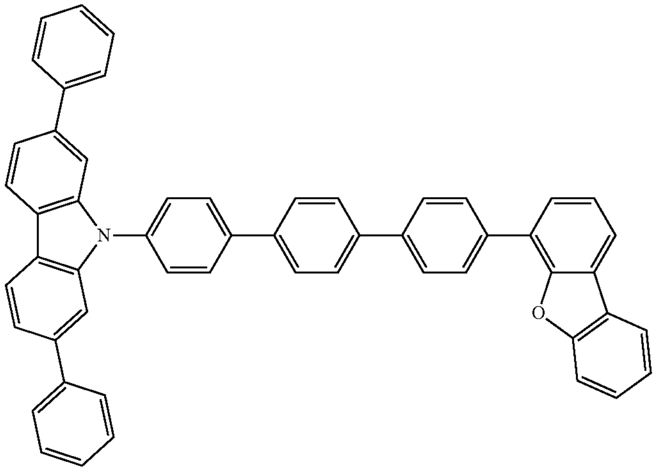

-continued
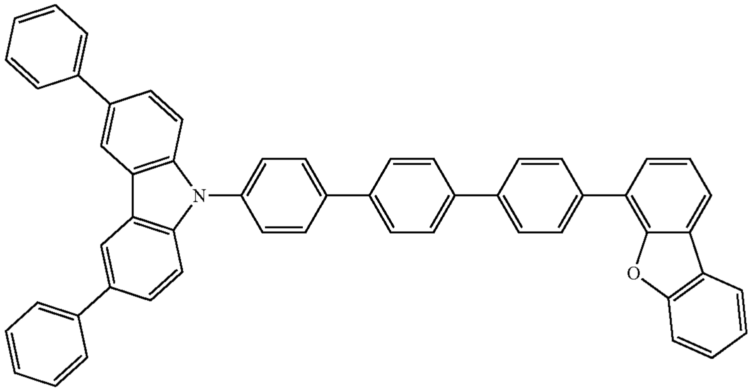
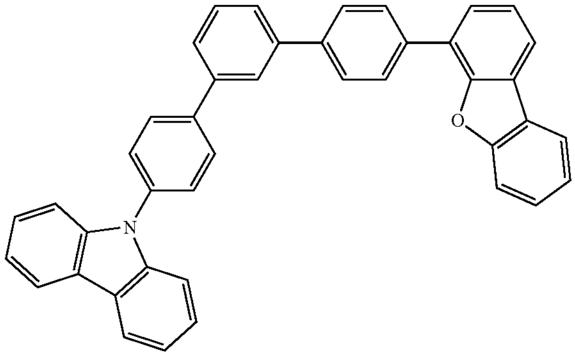
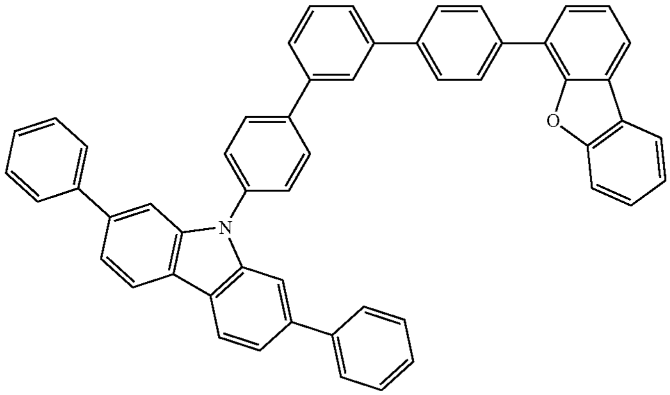
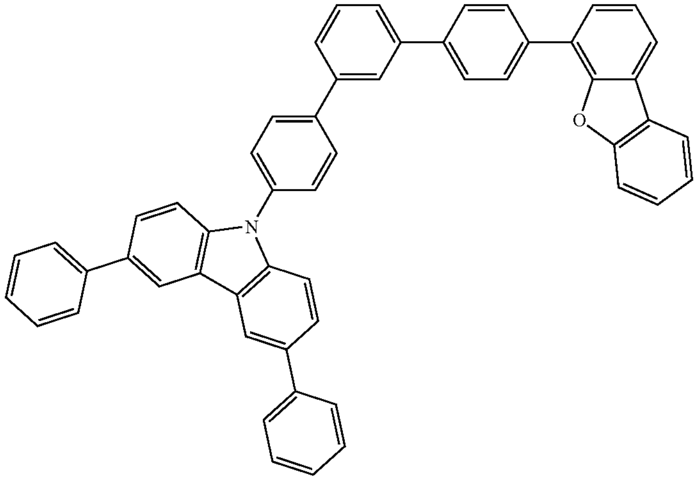

-continued
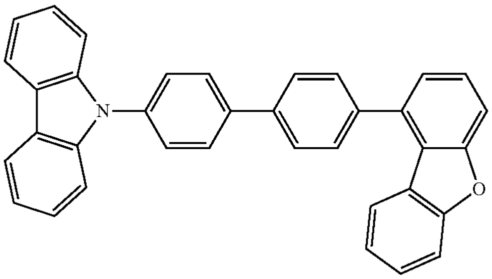
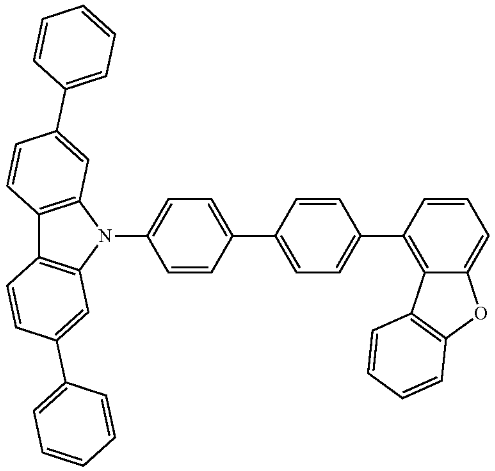
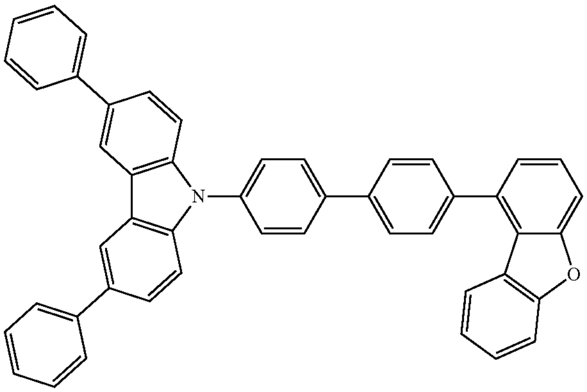
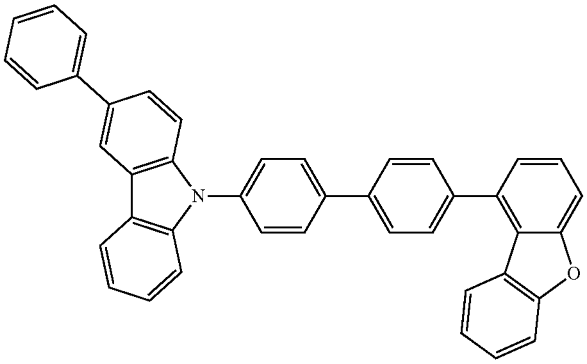
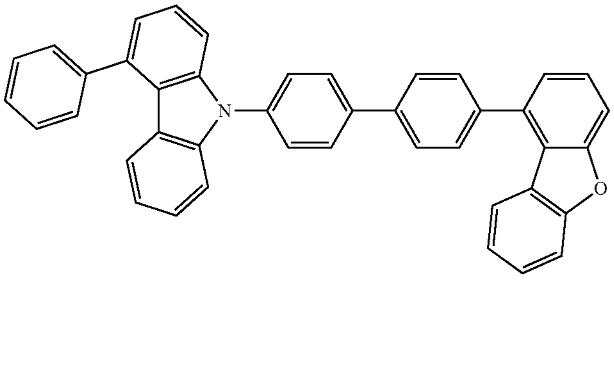
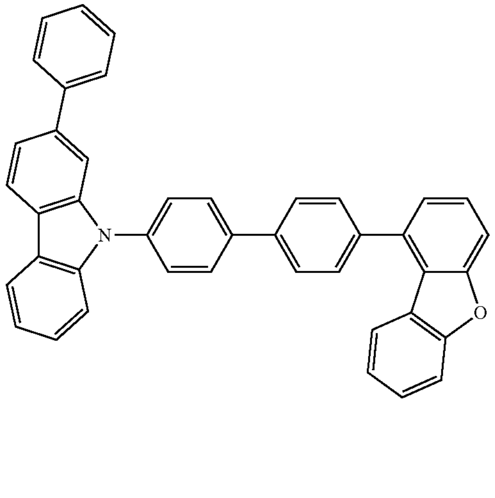

-continued
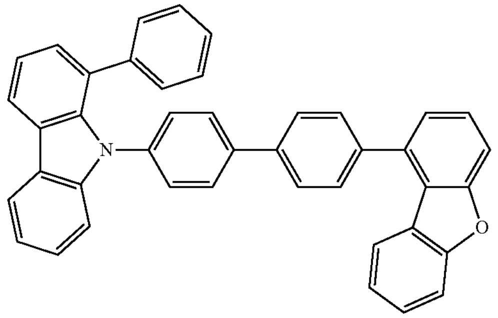
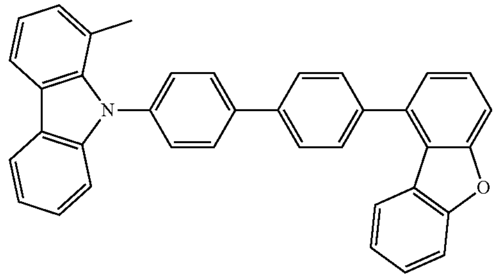
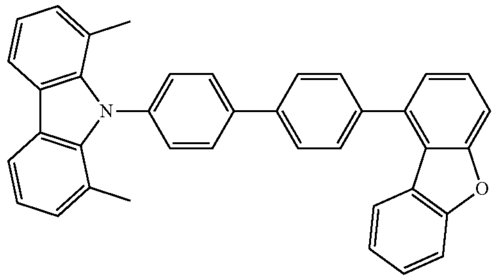
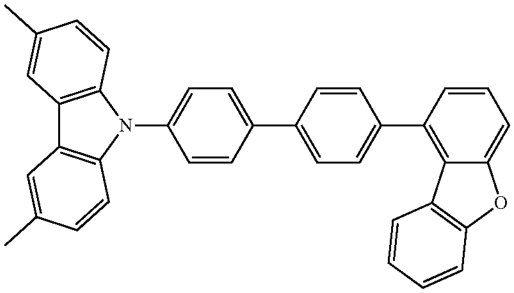
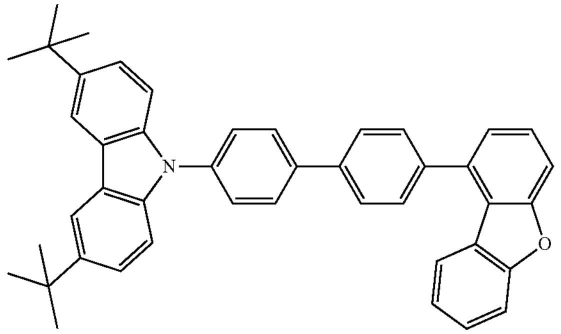
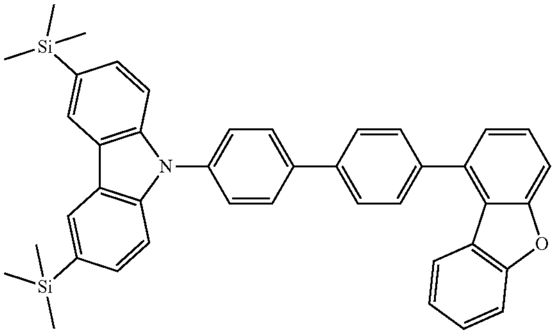
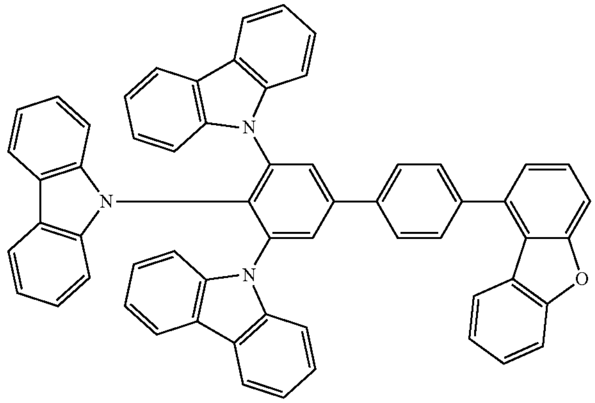
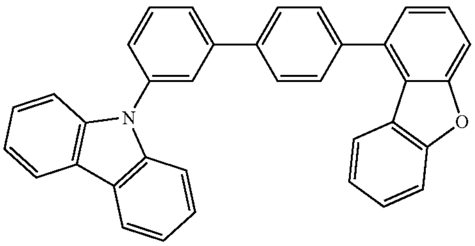

-continued
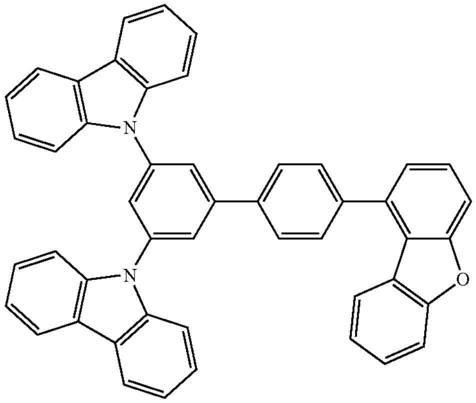
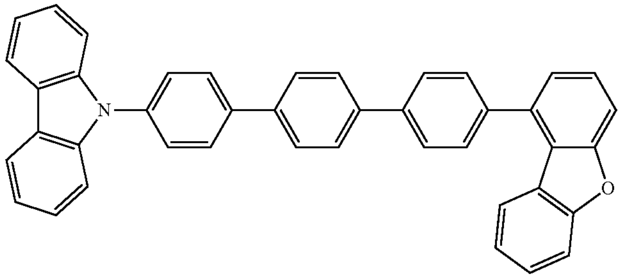
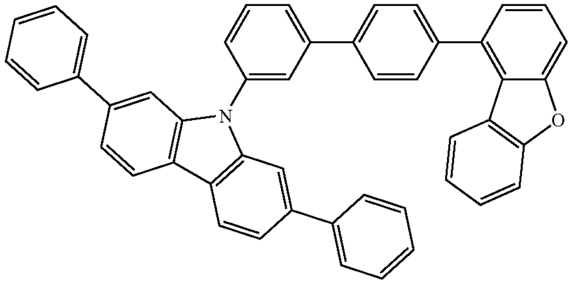
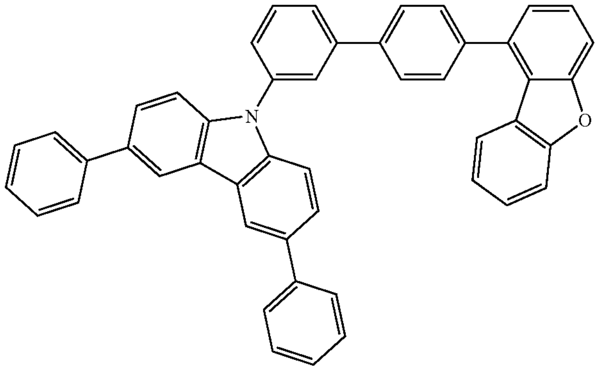
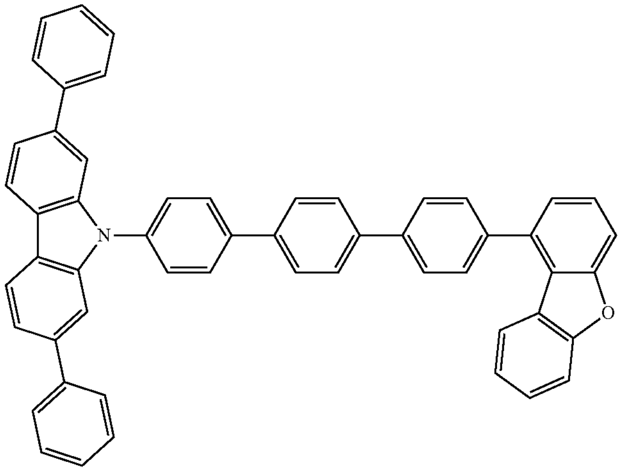

-continued
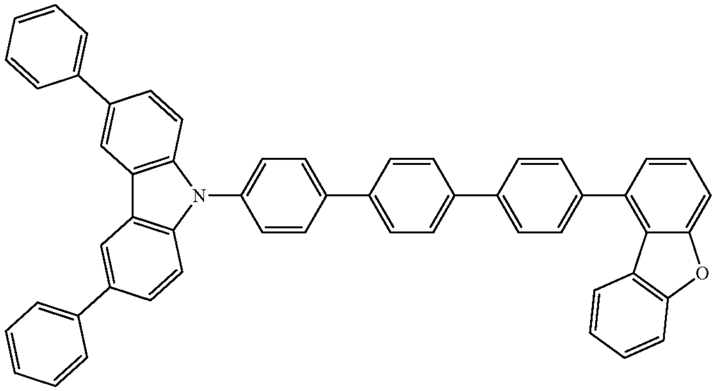
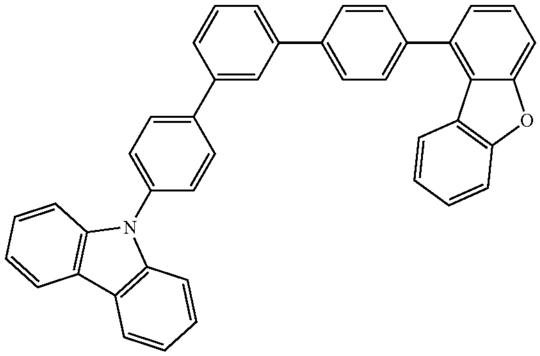
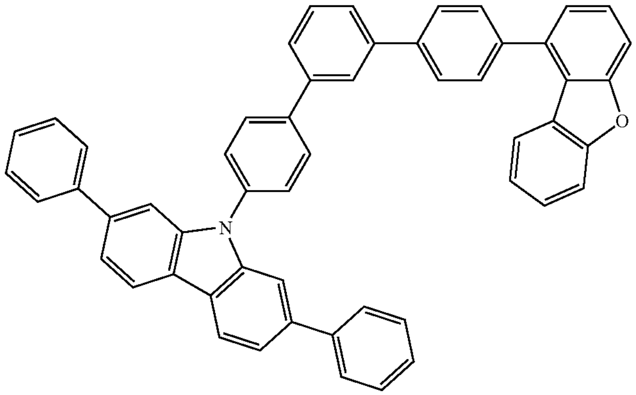
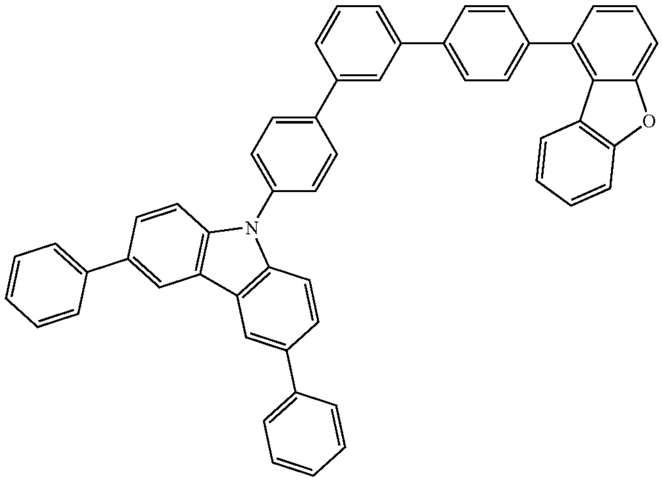

-continued
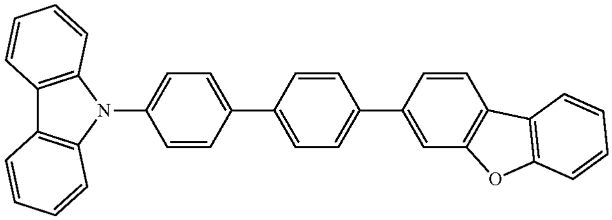
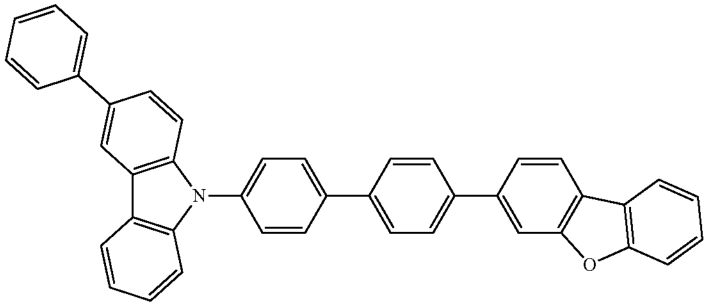
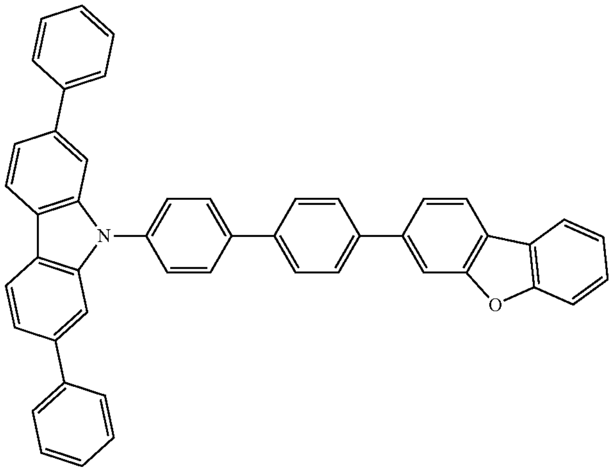
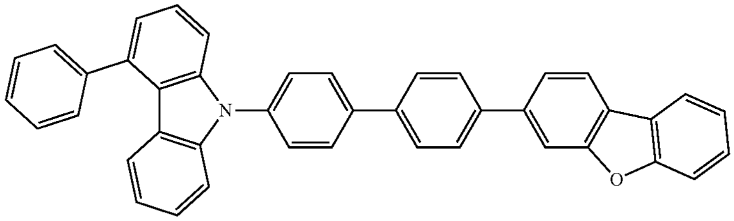
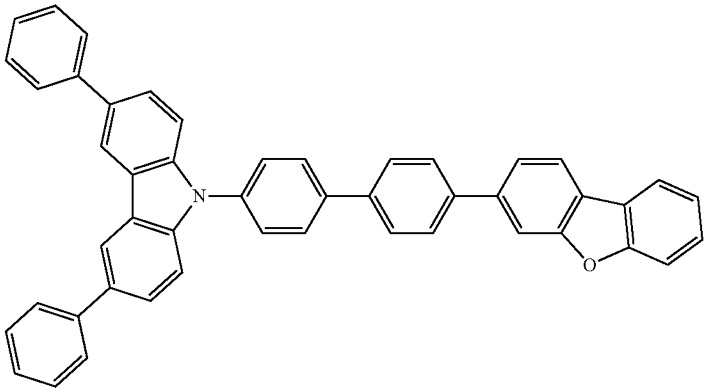

-continued
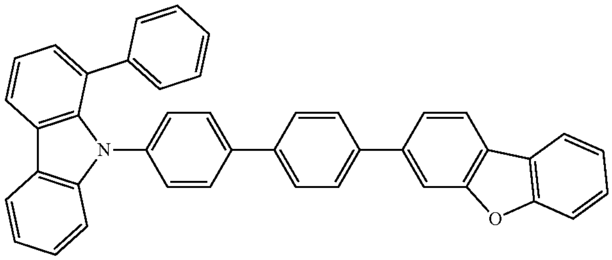
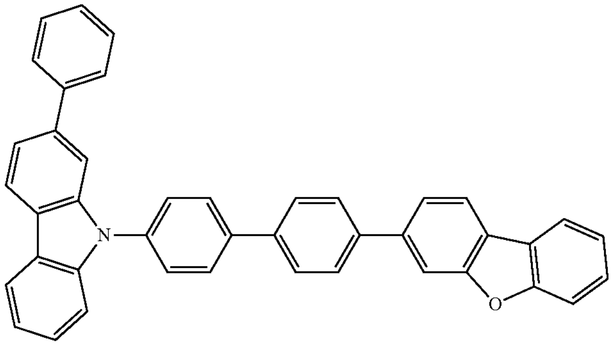
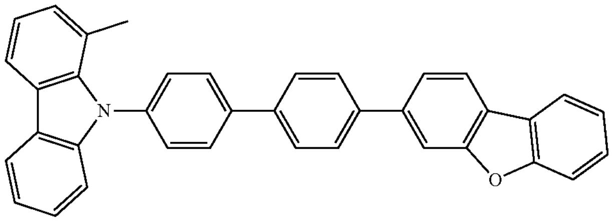
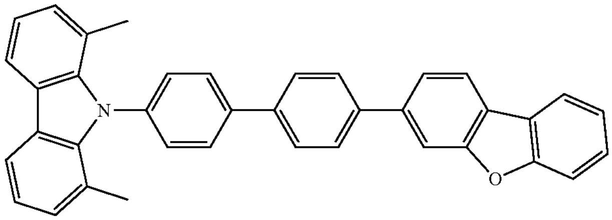
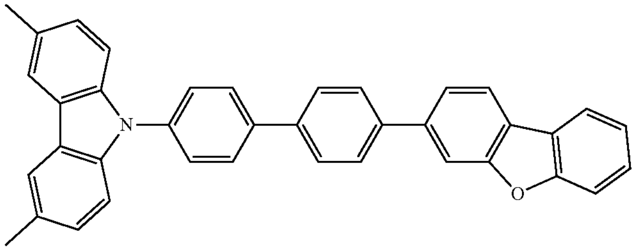
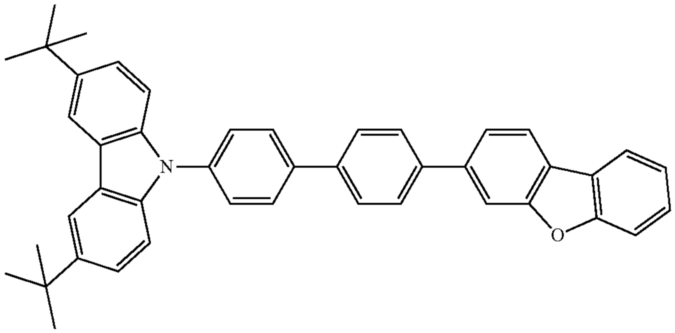

-continued
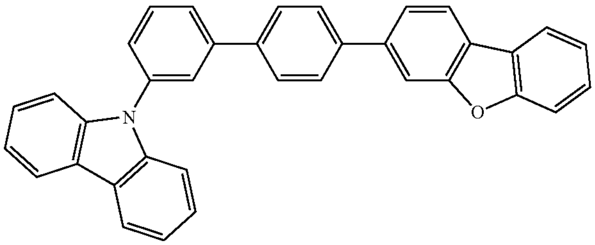
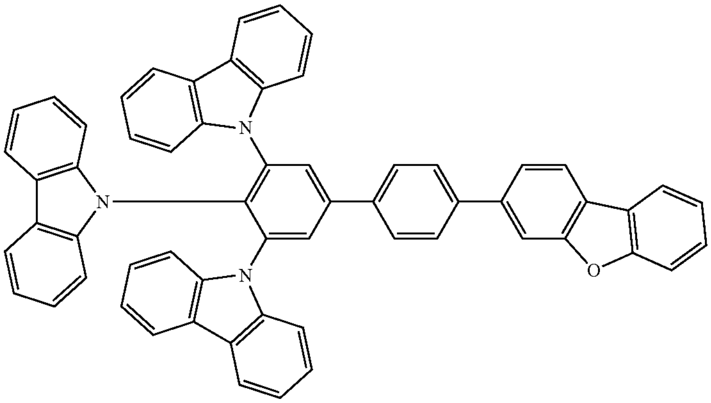
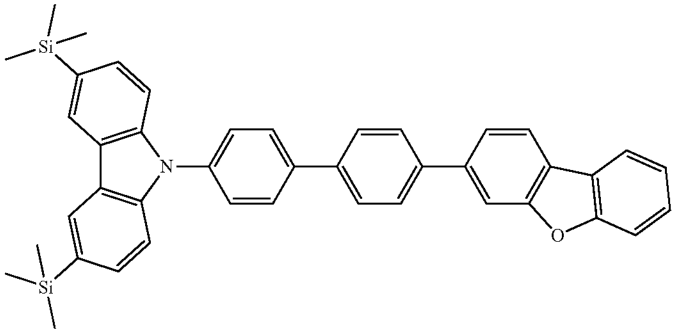
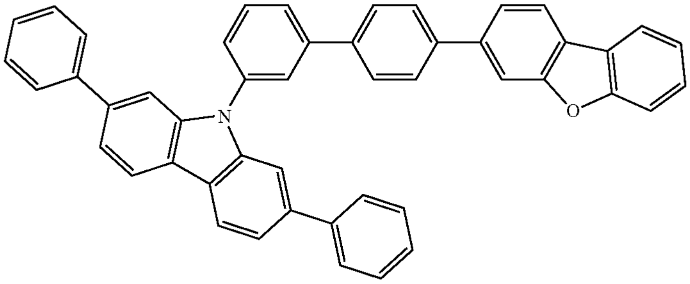
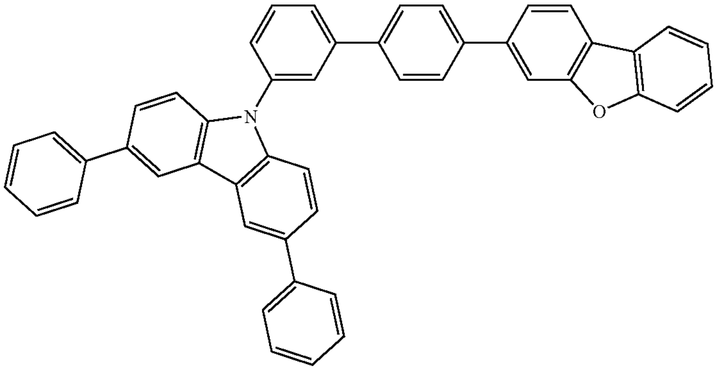

-continued
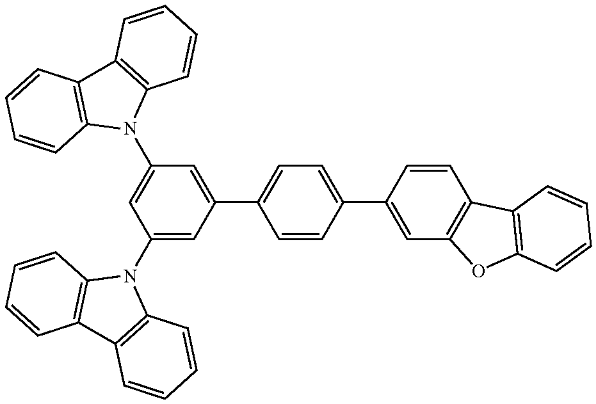
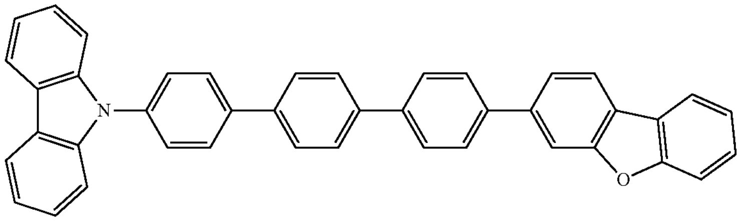
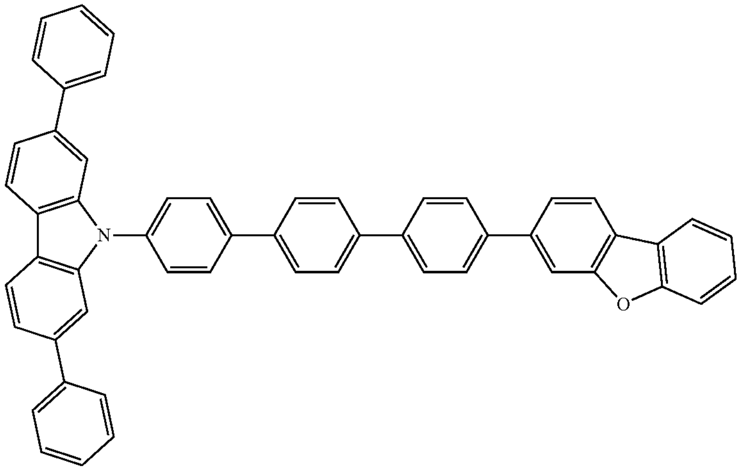
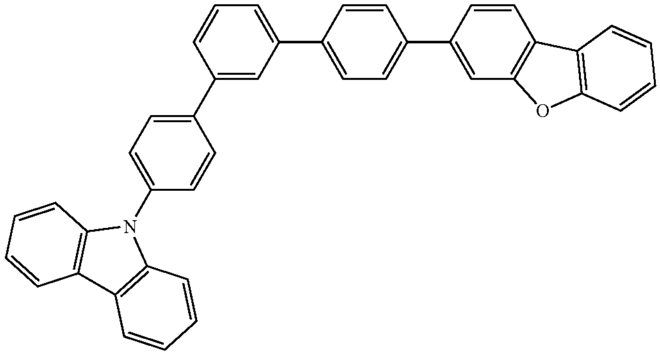

-continued
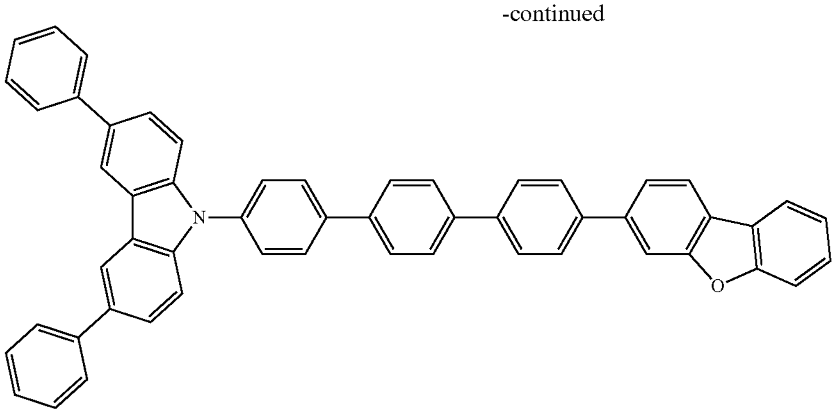
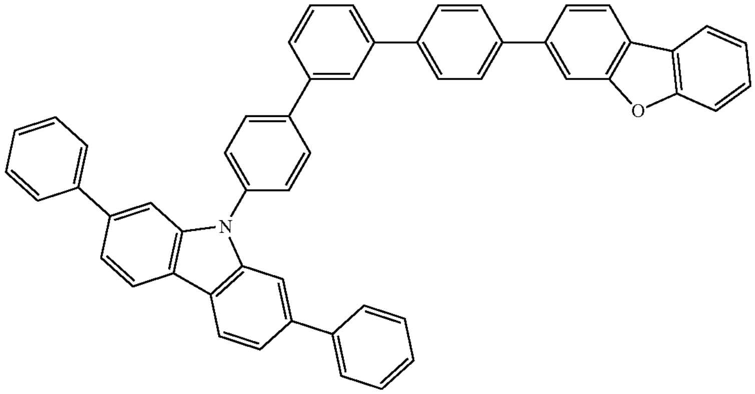
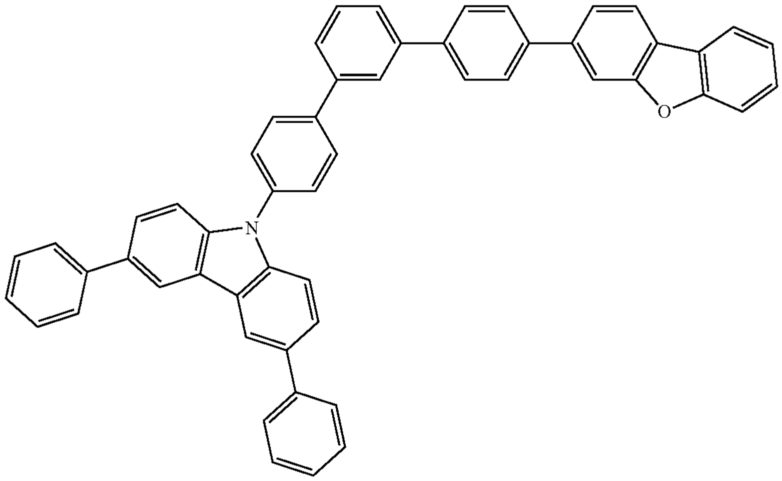

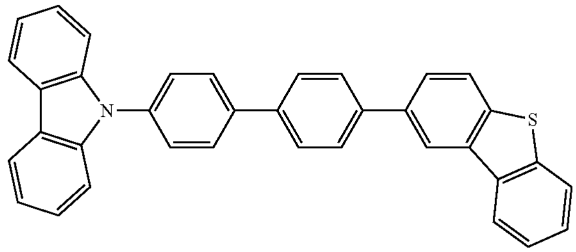
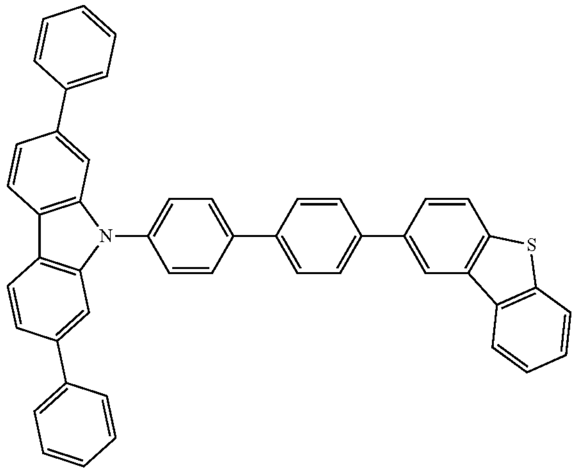
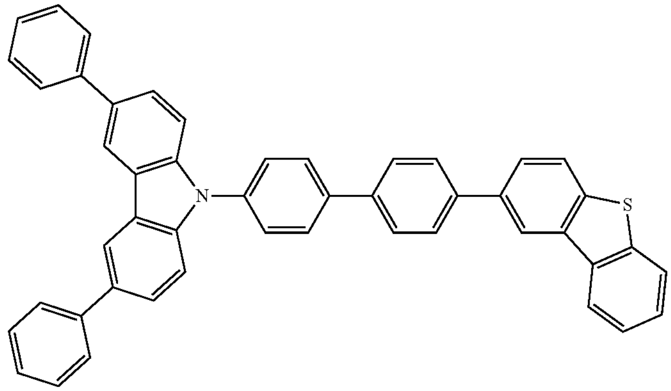
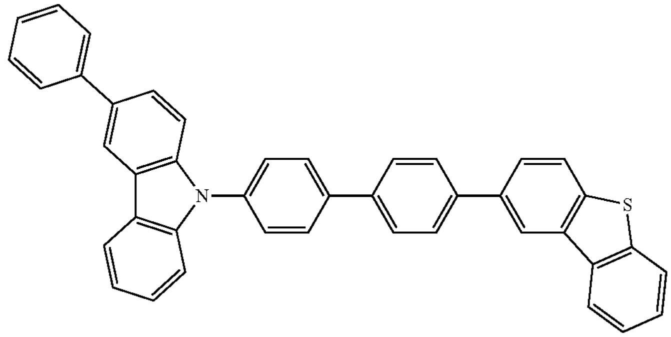
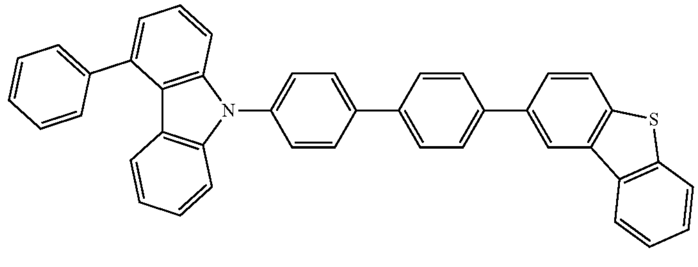

-continued
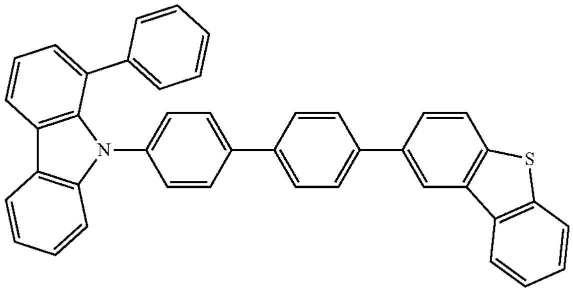
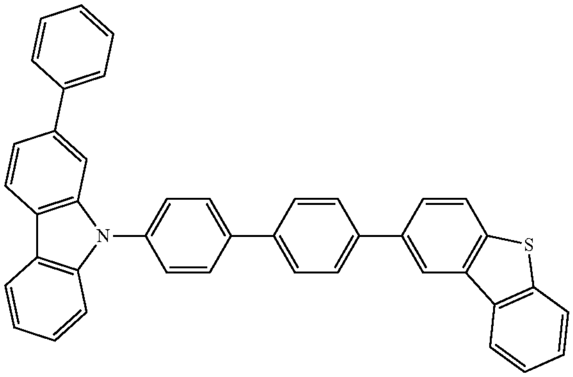
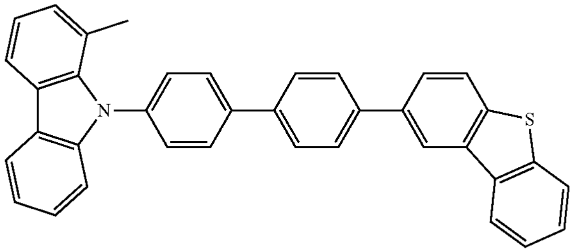
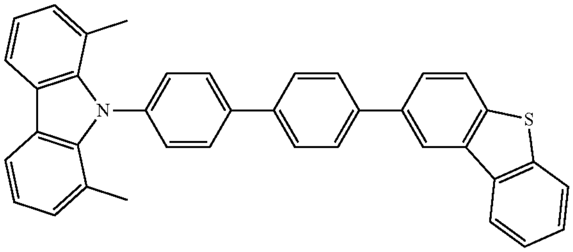
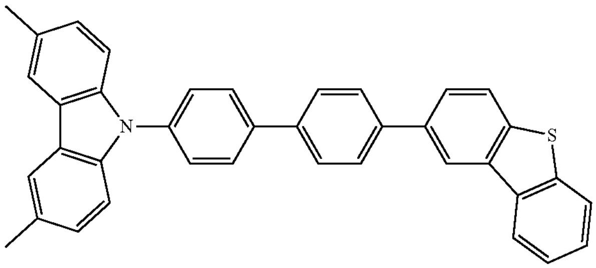
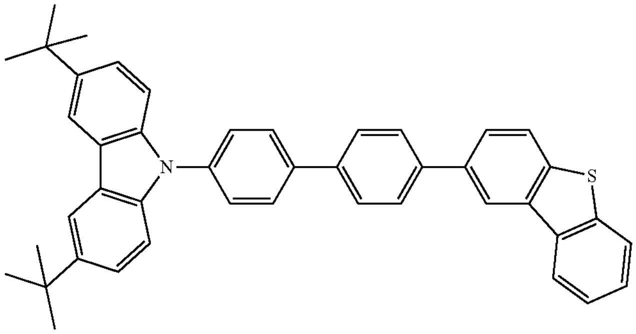
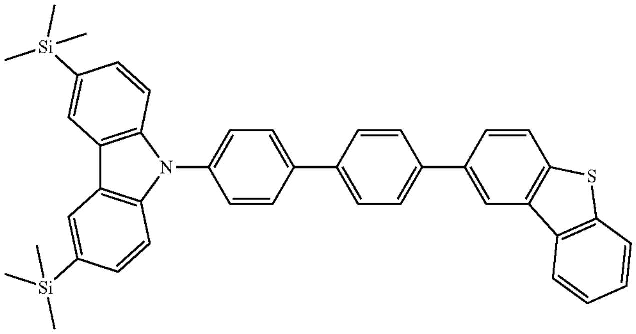

-continued
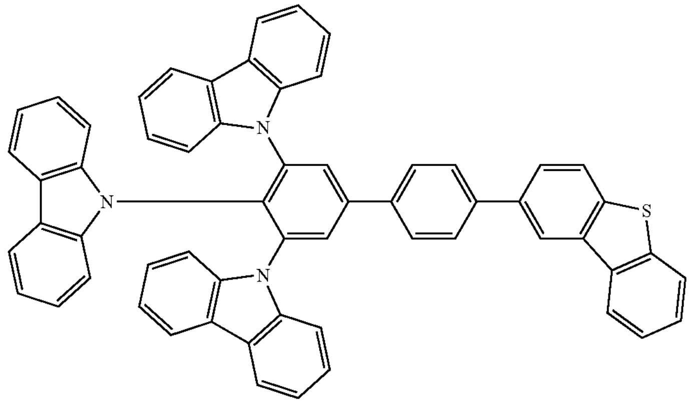
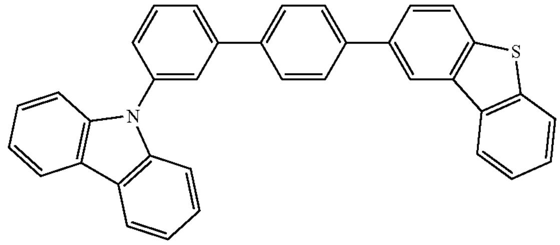
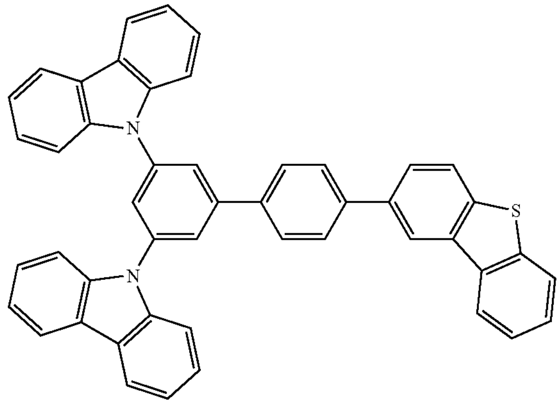
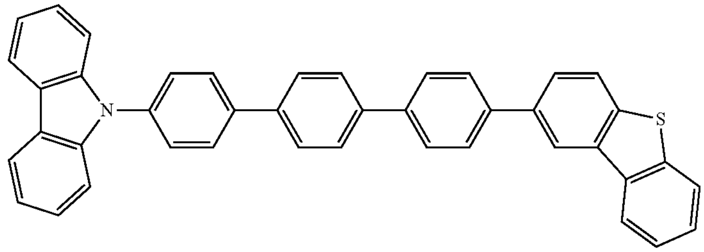
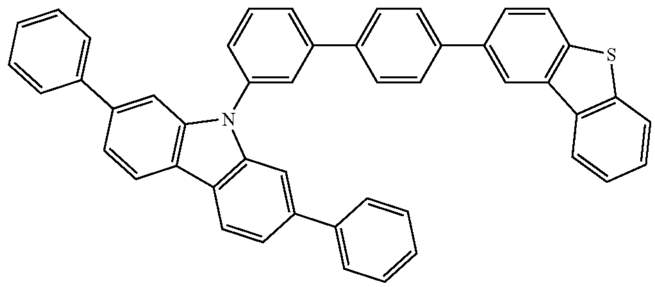

-continued
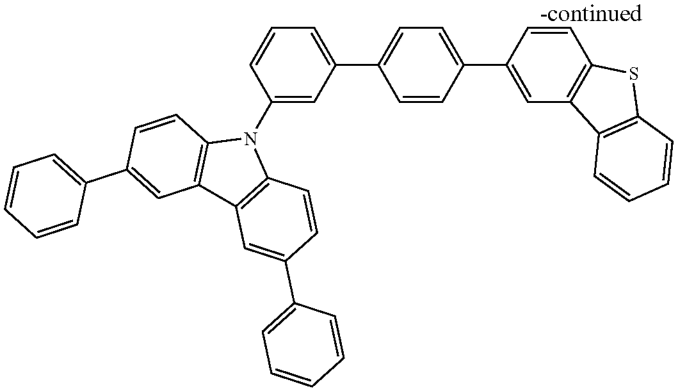
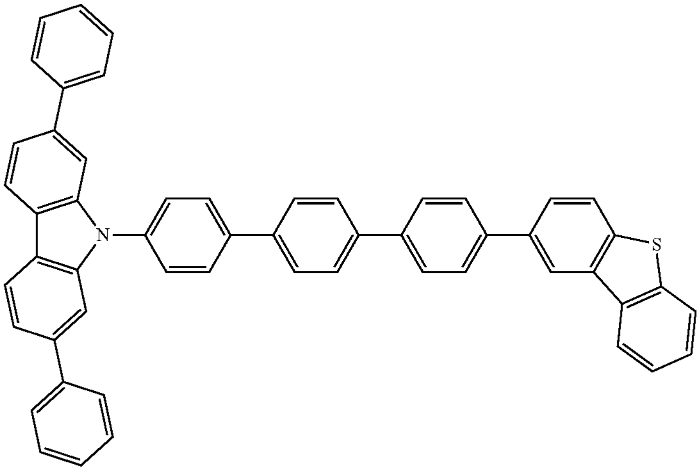
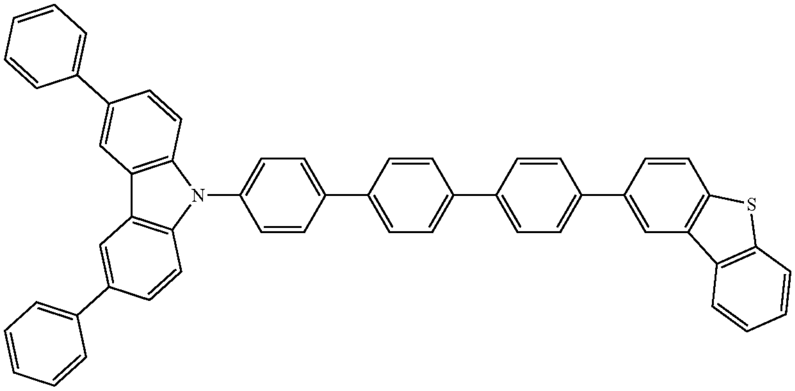
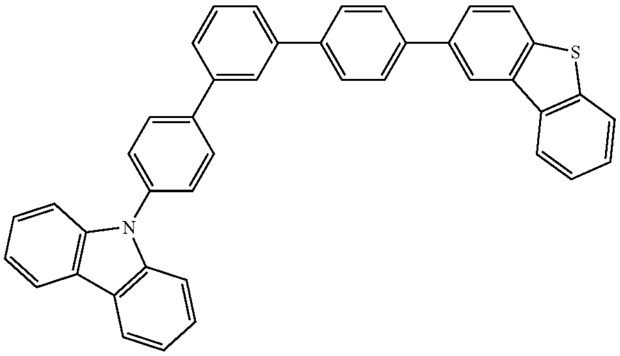

-continued
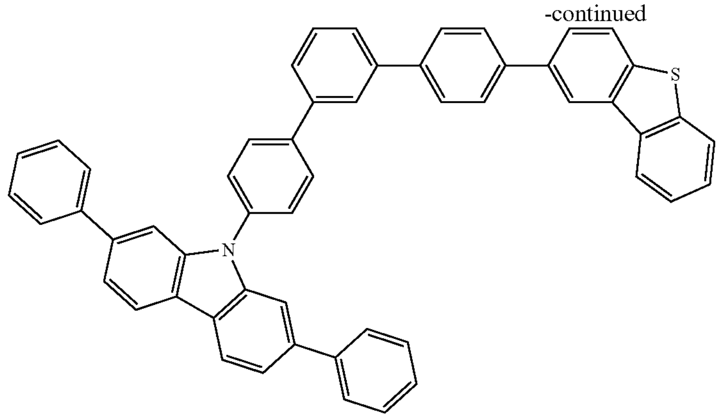
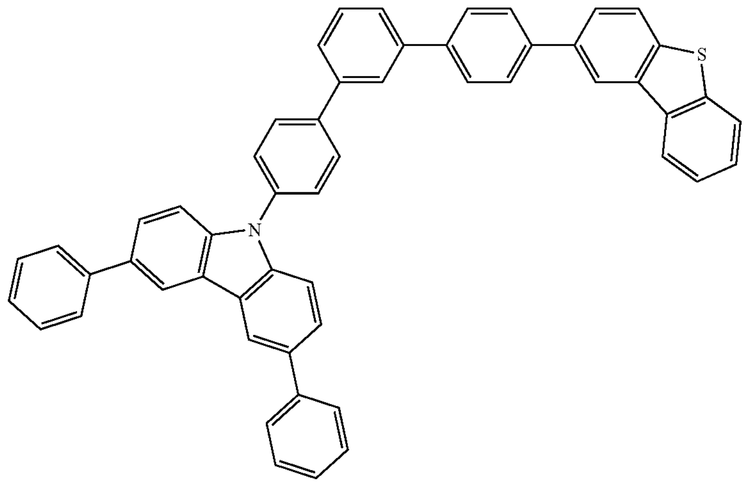
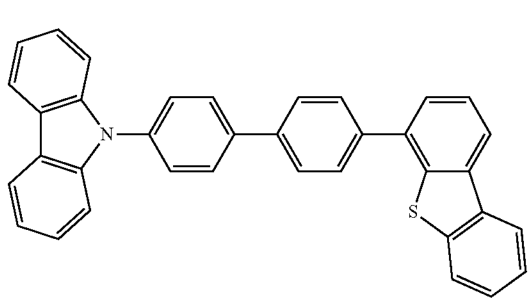
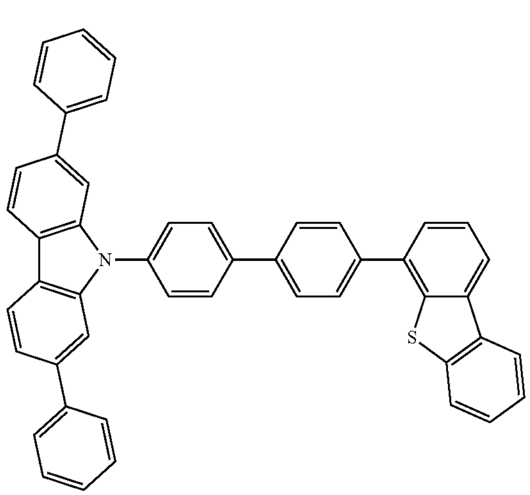

-continued
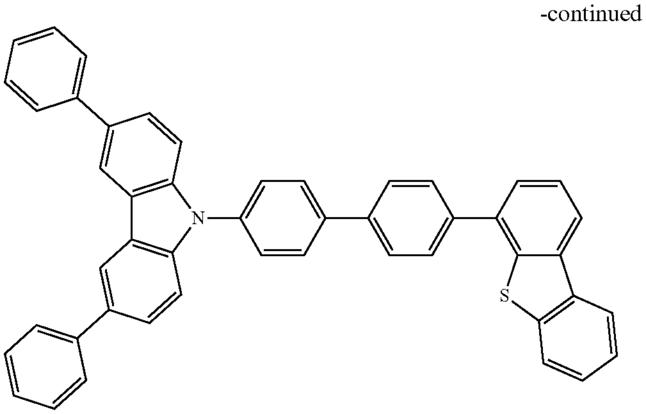
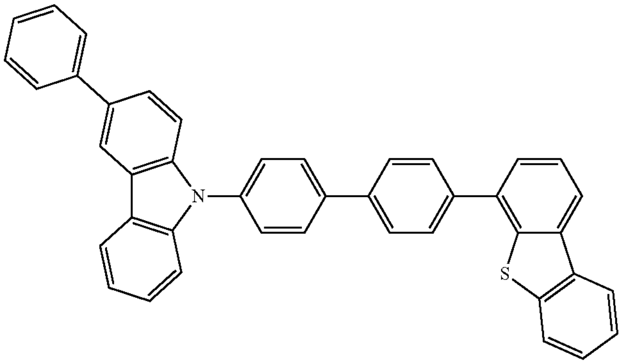
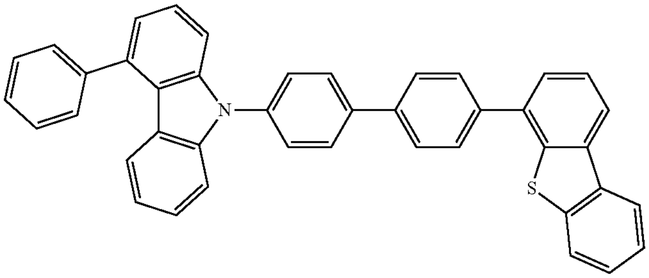
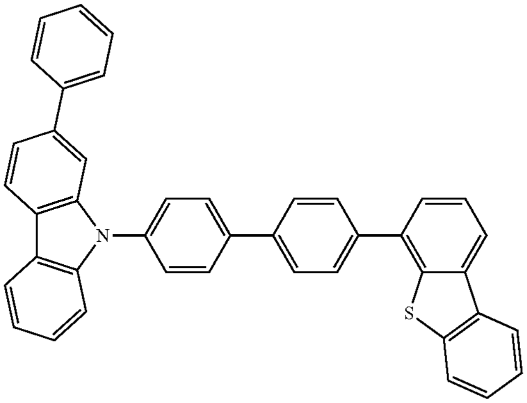
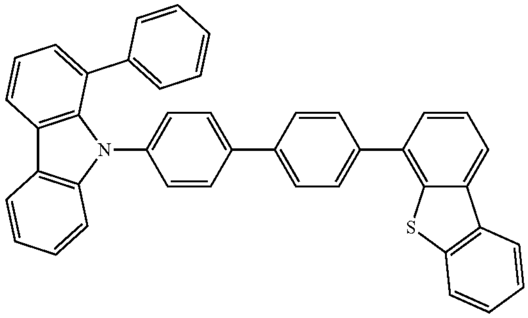
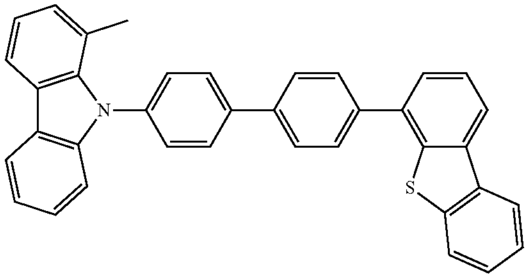
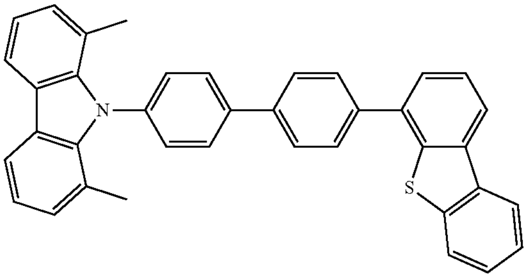

-continued
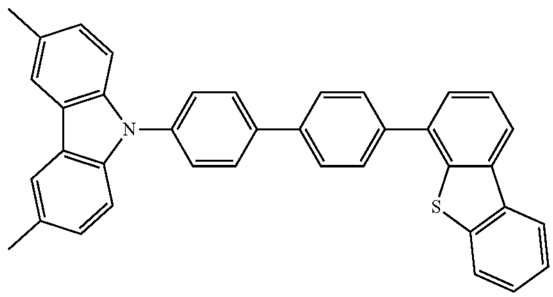
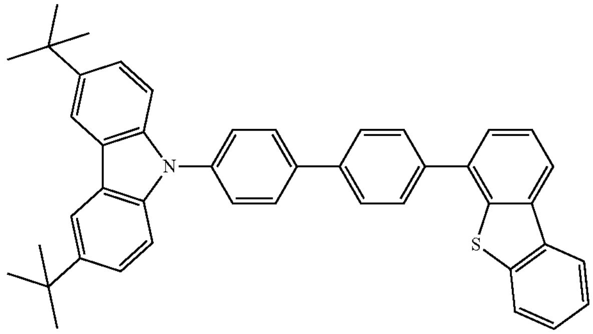
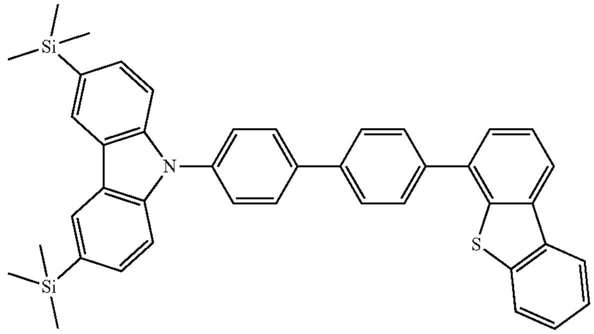
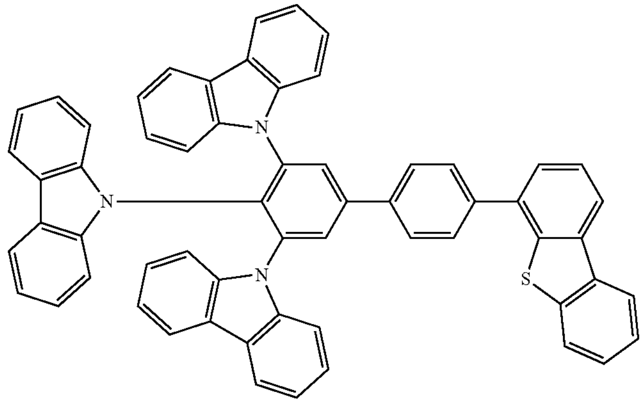
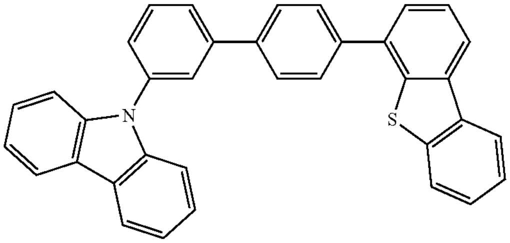
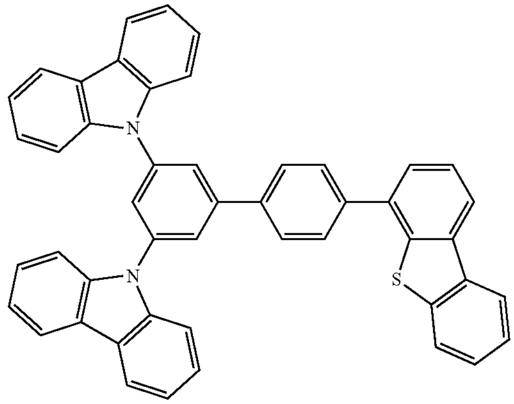

-continued
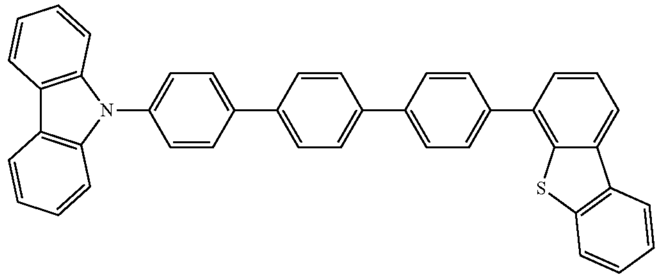
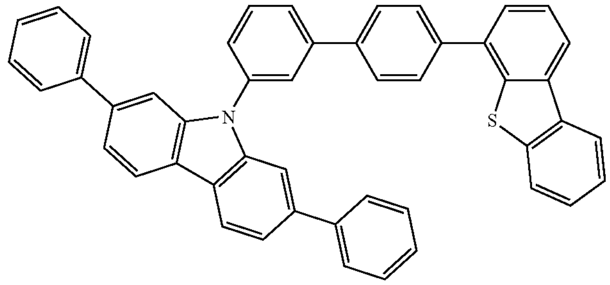
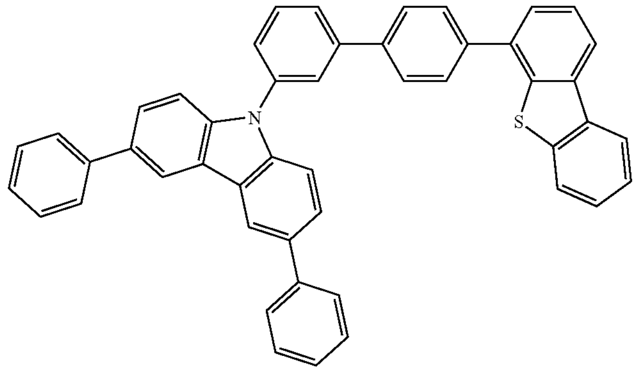
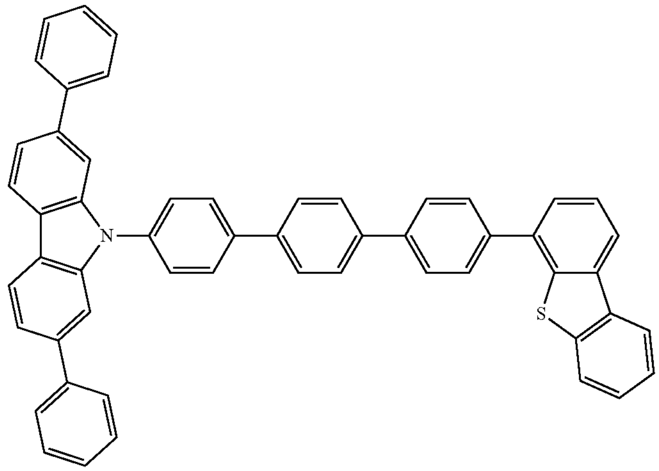

-continued
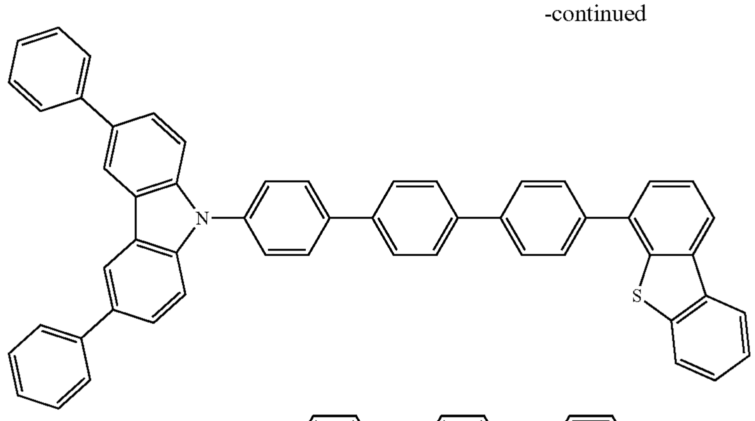
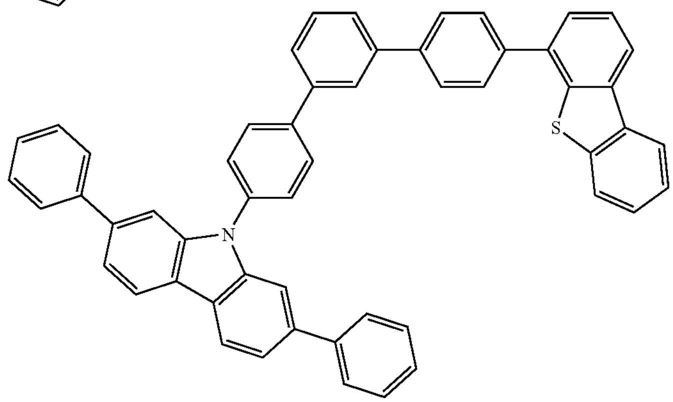
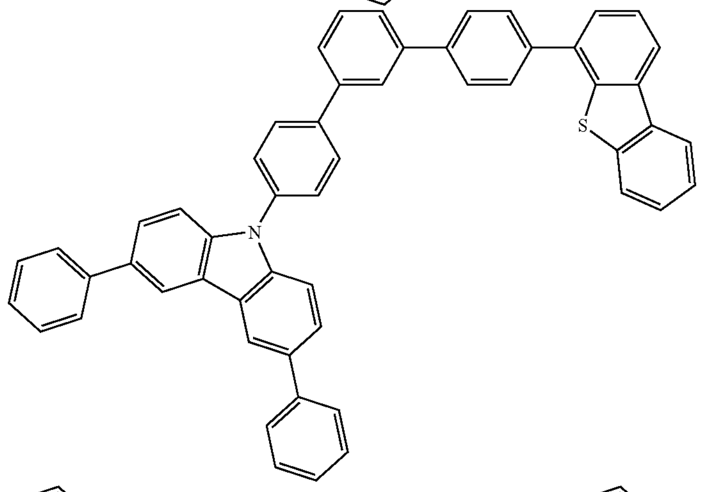
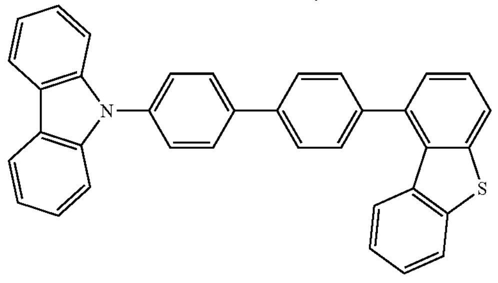
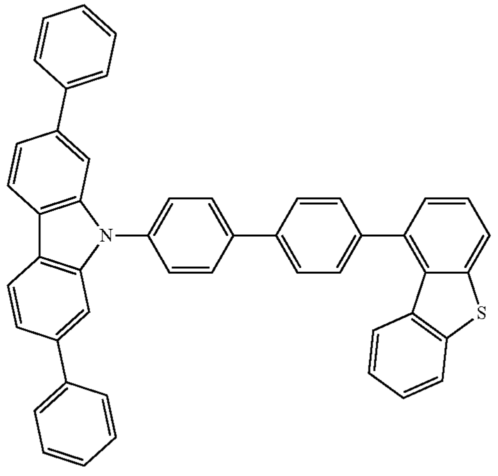

-continued
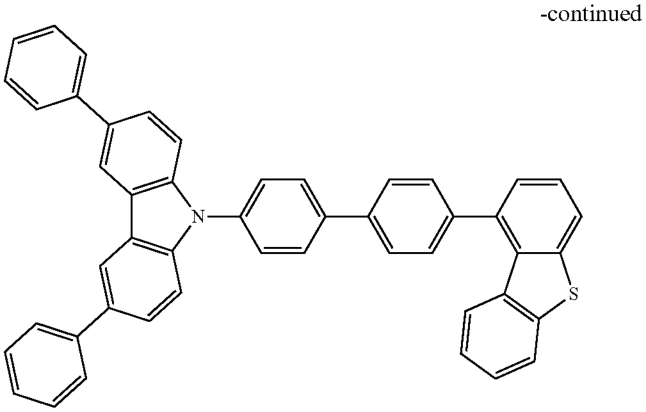
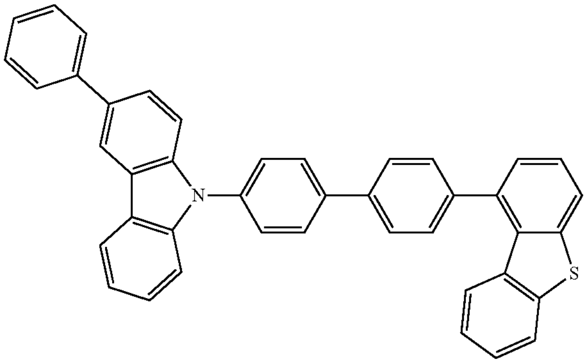
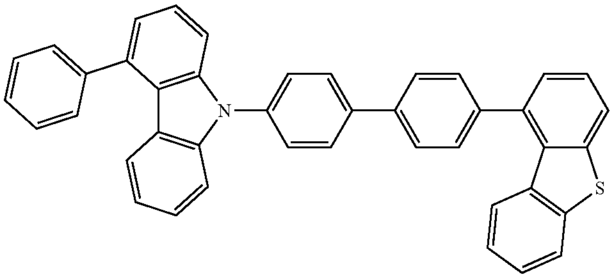
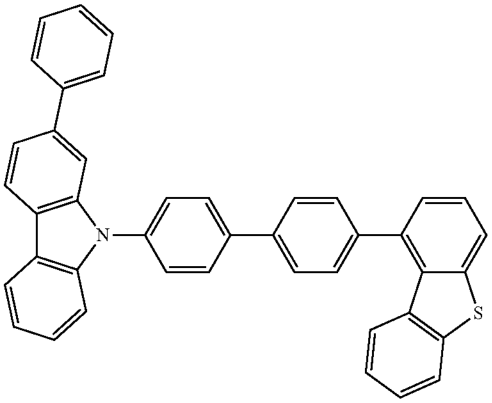
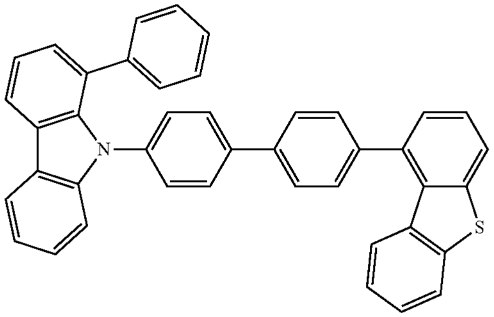
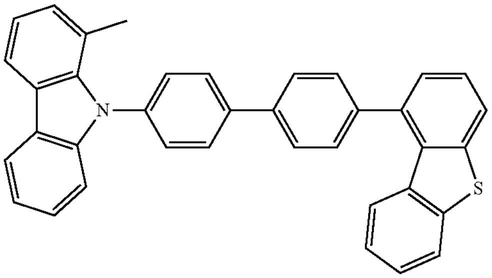
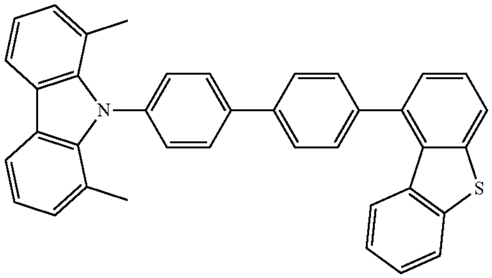

-continued
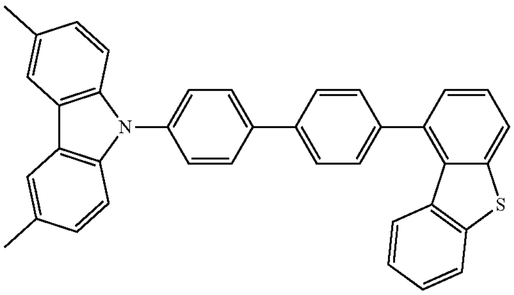
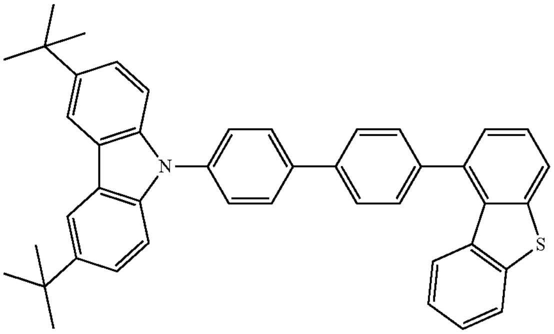
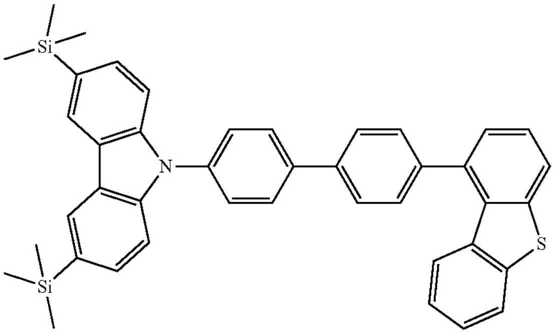
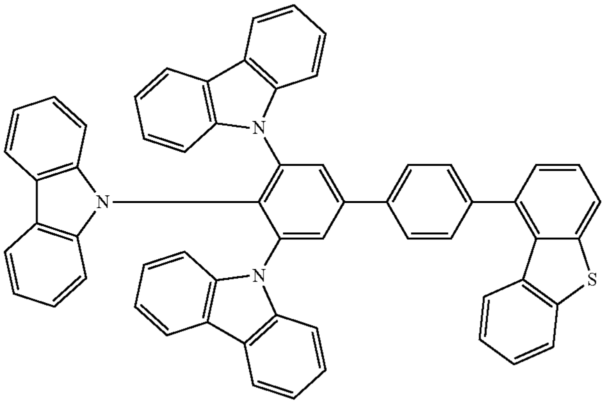
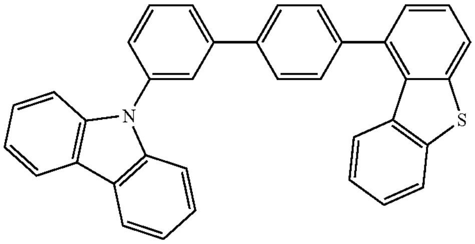
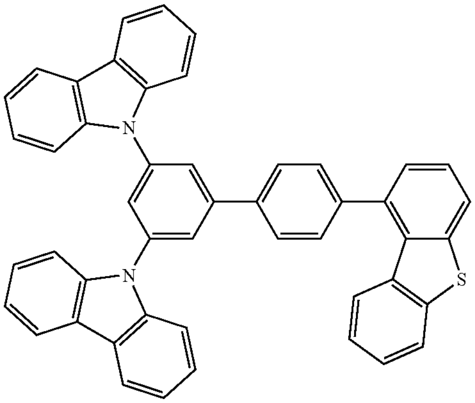

-continued
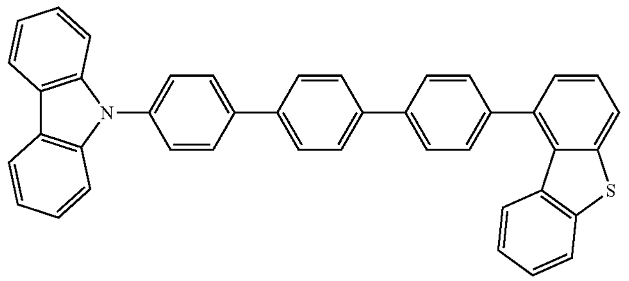
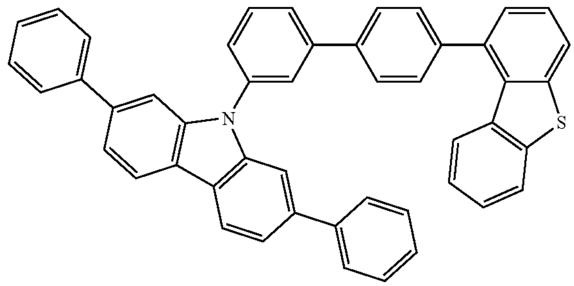
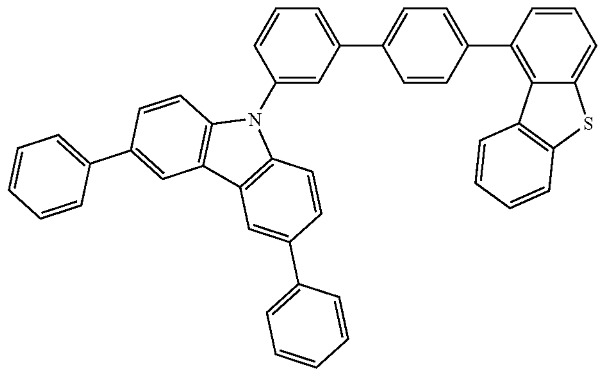
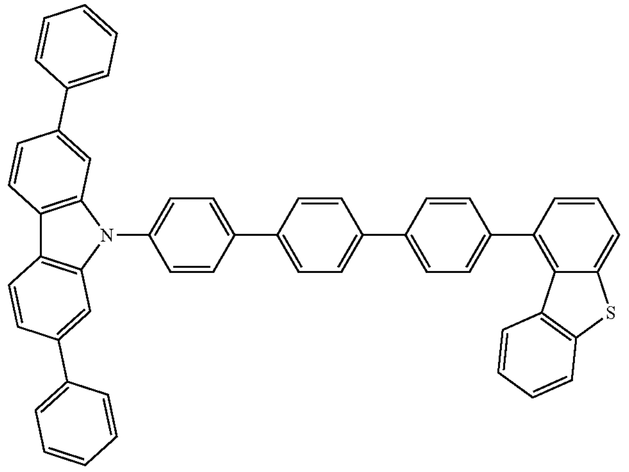

-continued
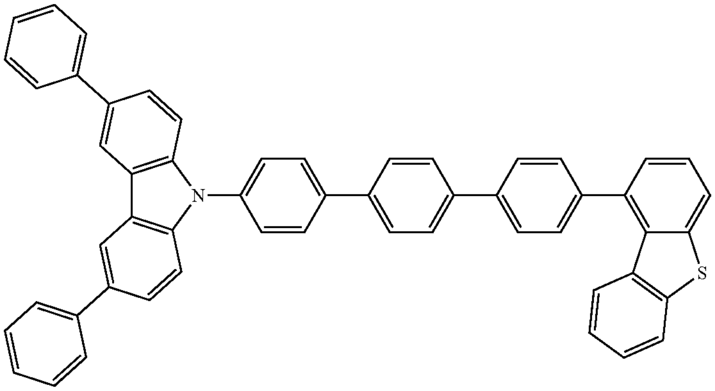
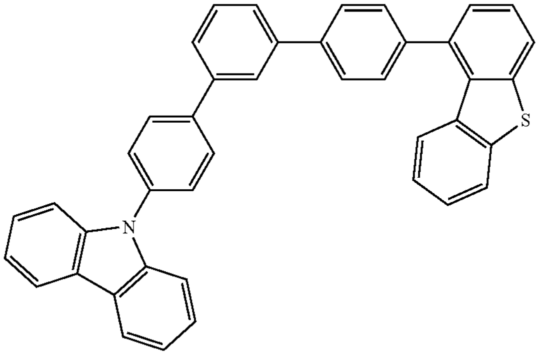
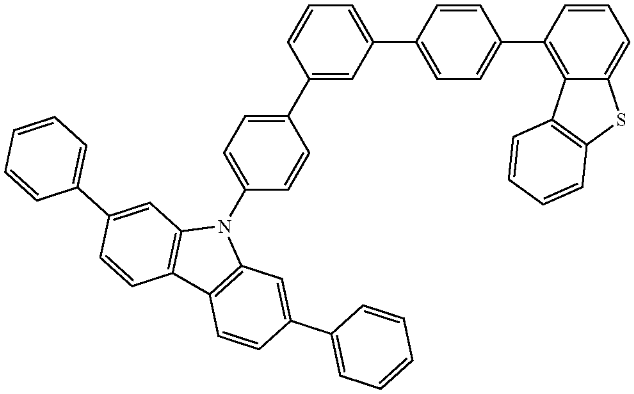
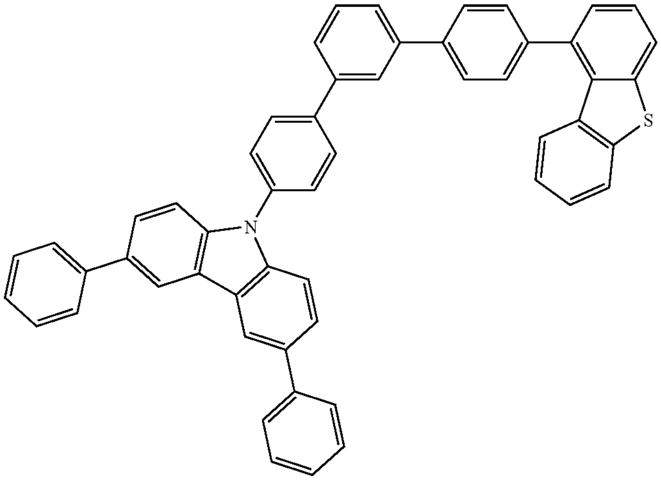

-continued
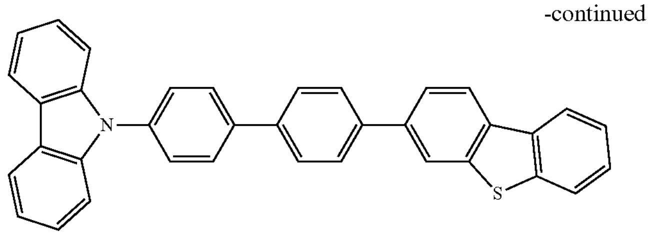
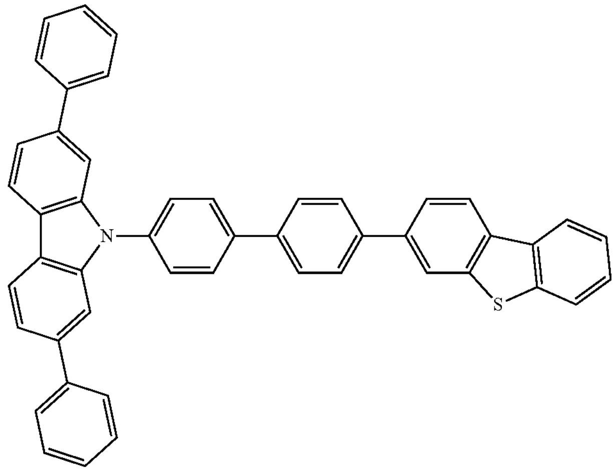
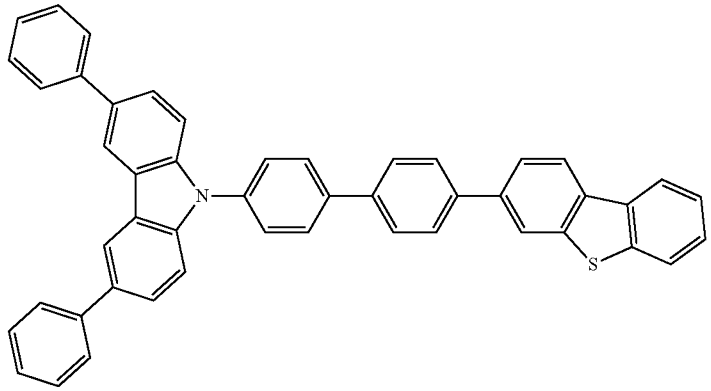
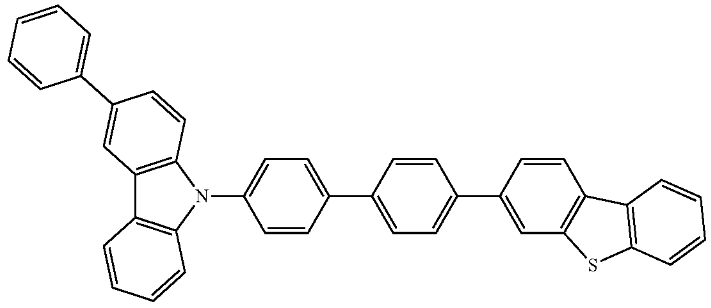
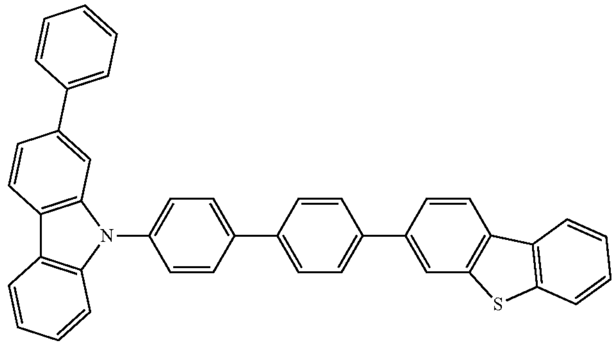

-continued
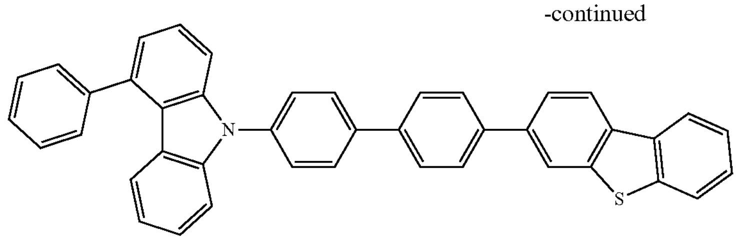
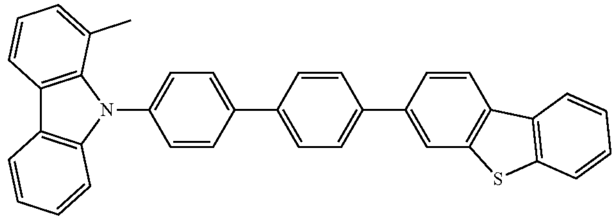
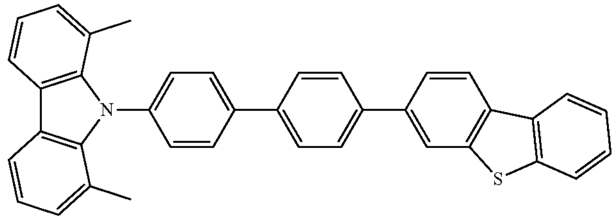
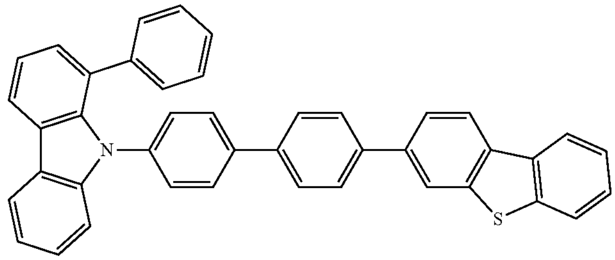
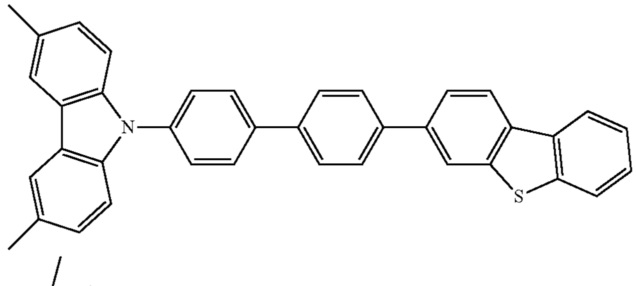
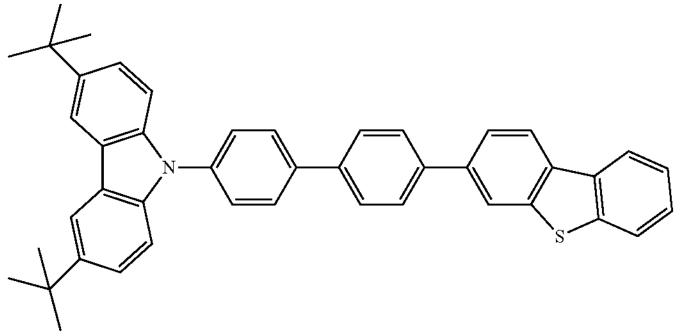

-continued
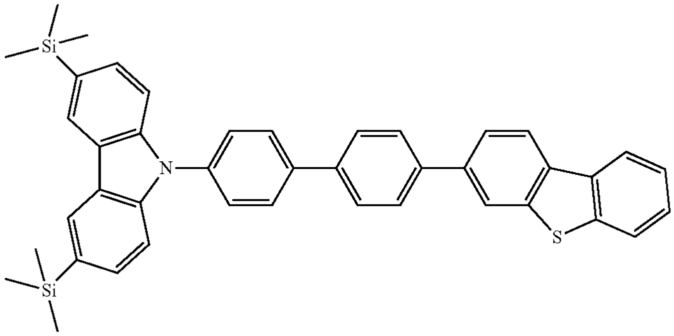
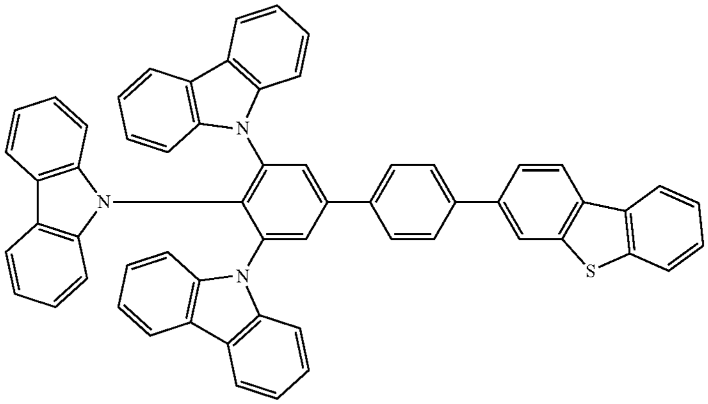
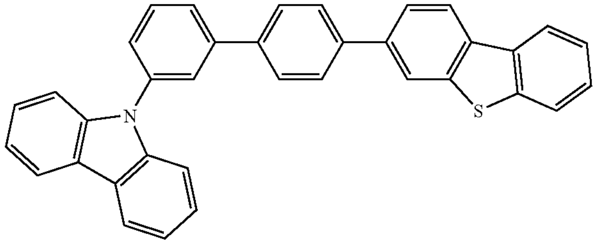
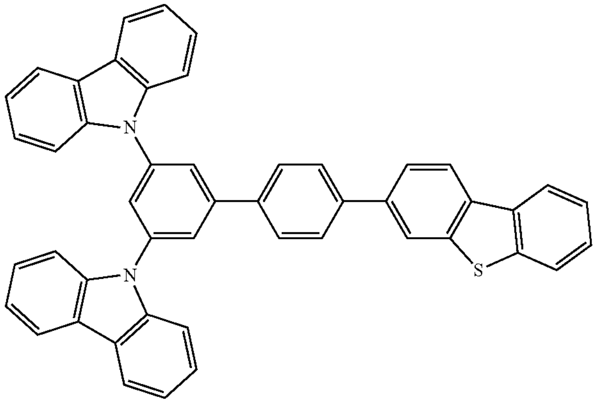
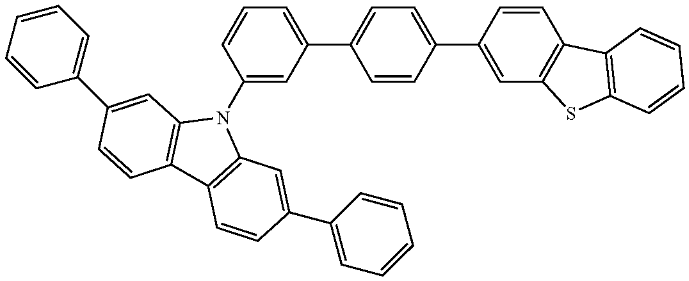

-continued
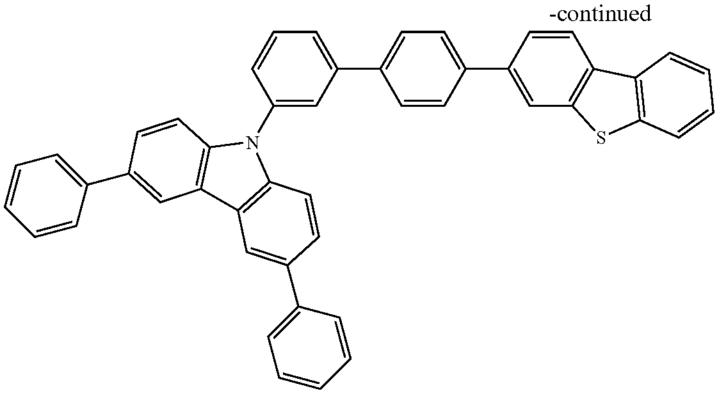
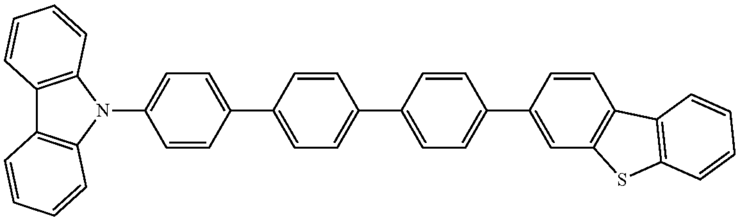
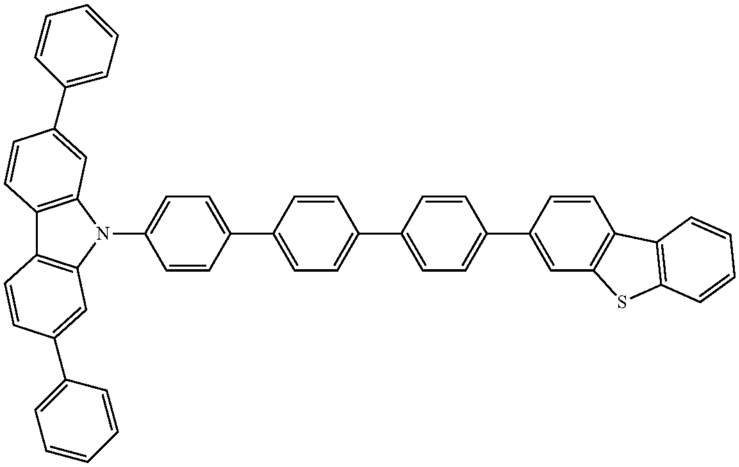
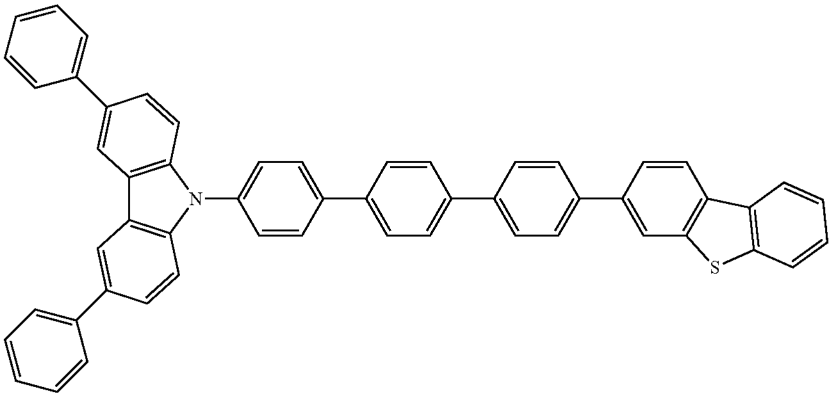

-continued
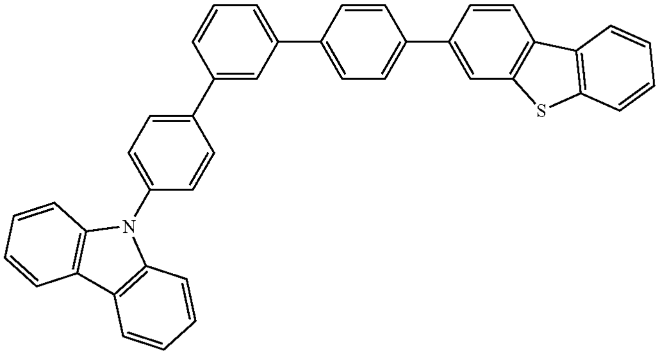
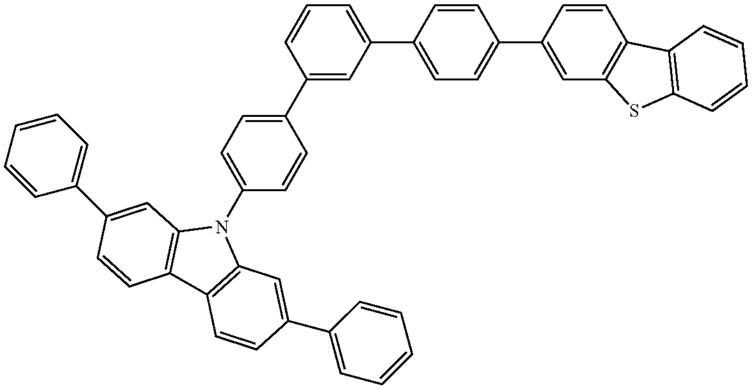
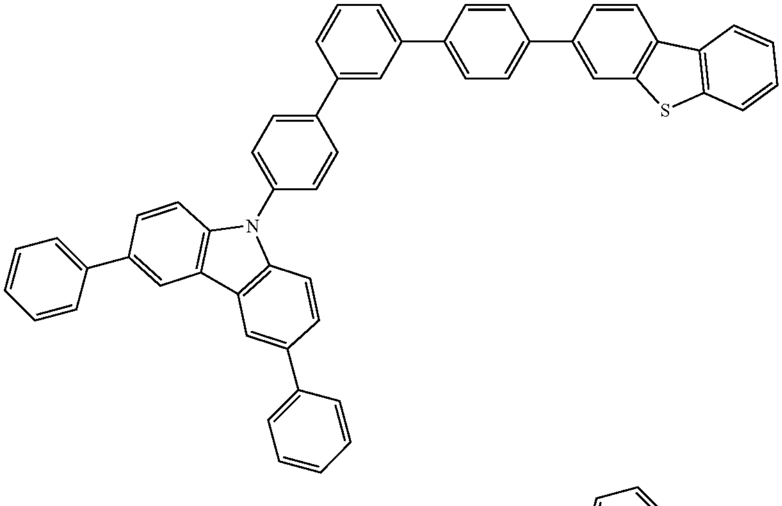
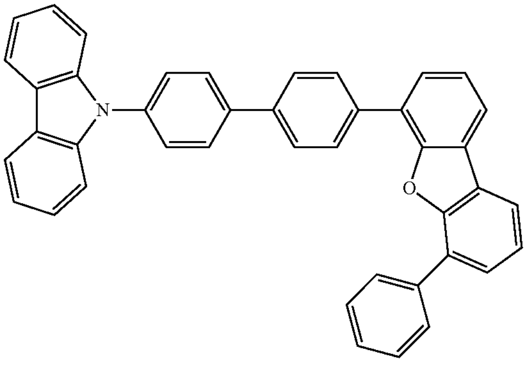
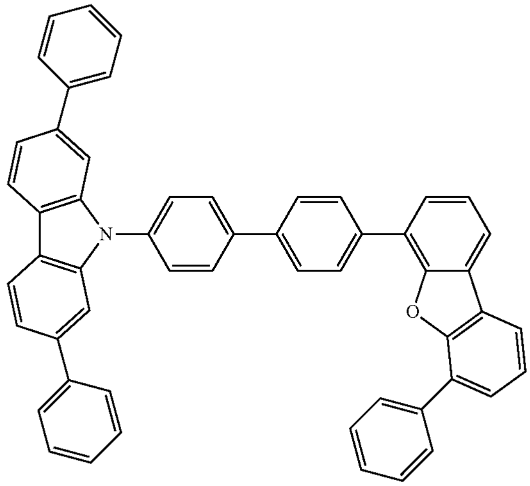

-continued
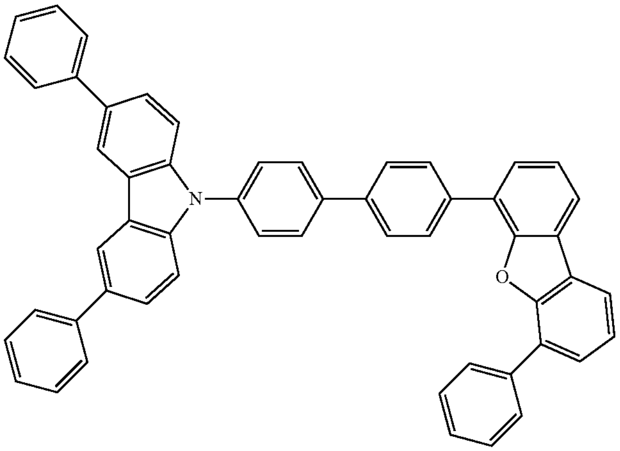
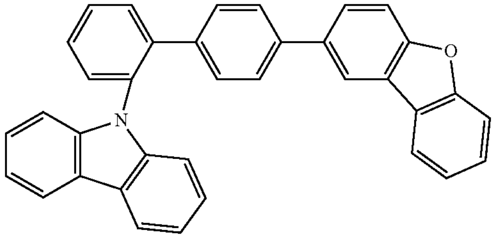
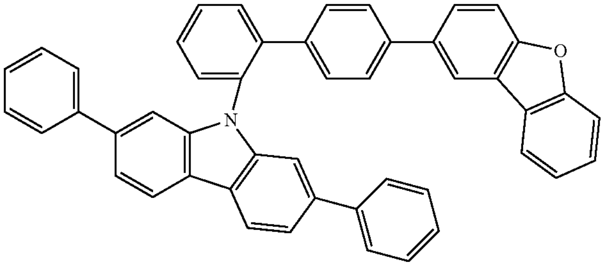
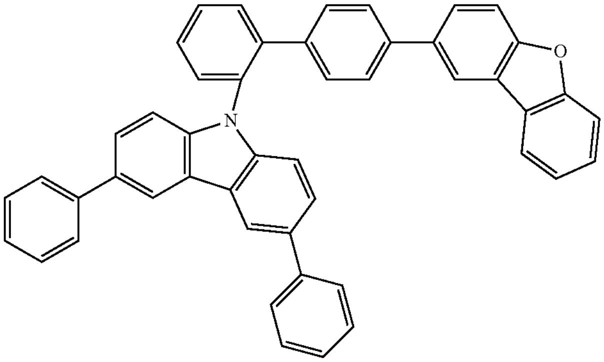
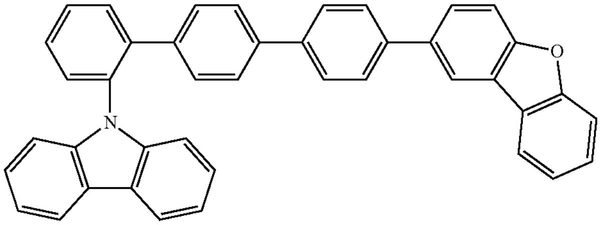
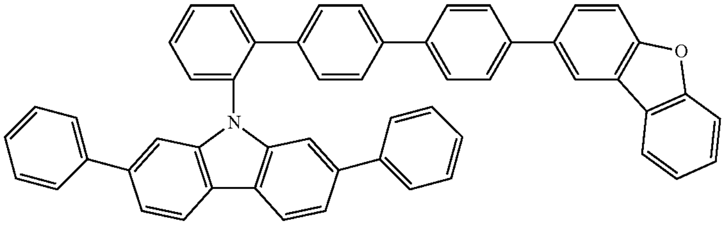

-continued
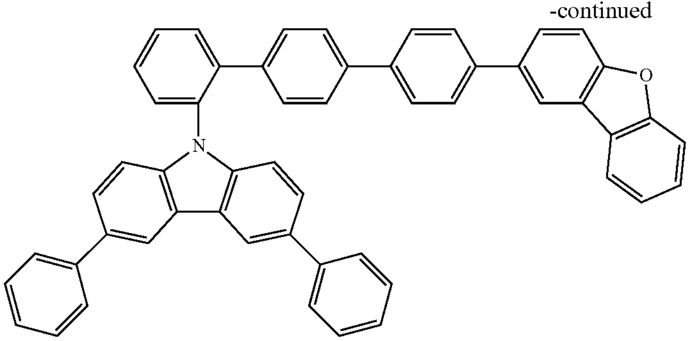
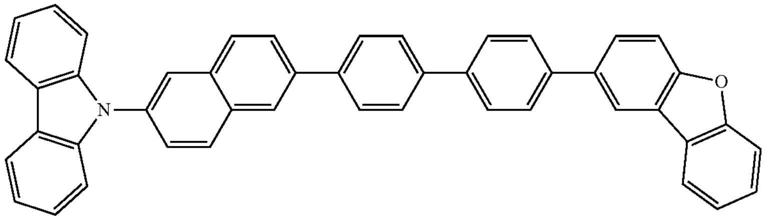
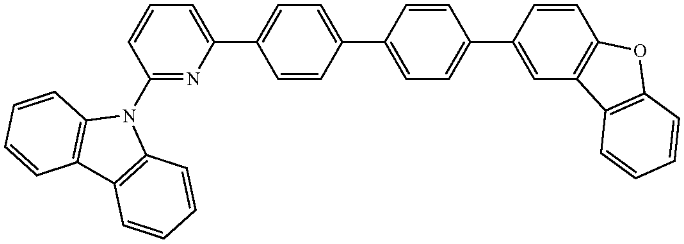
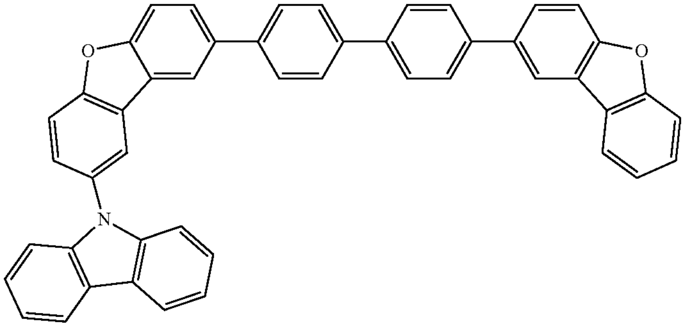
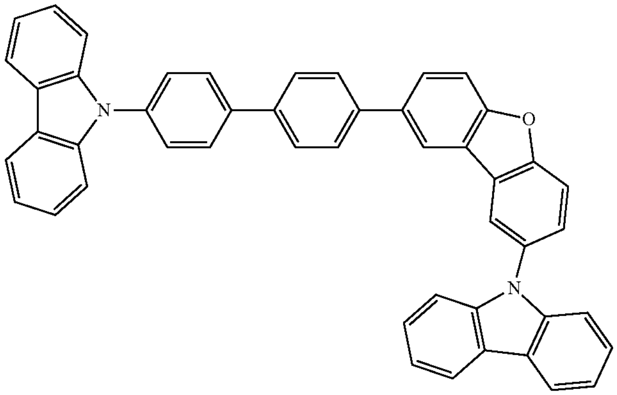

-continued
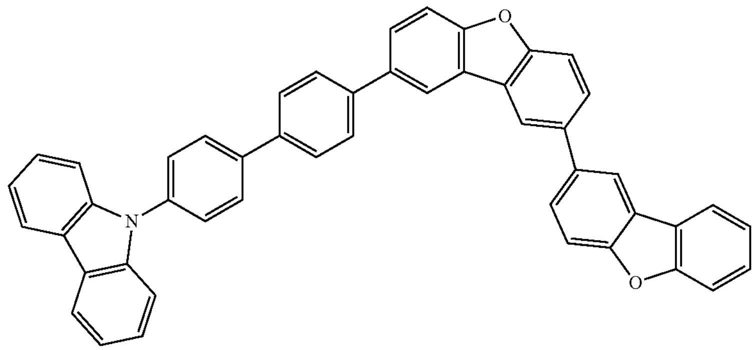
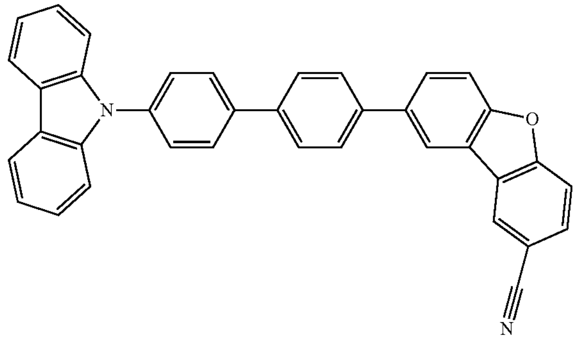
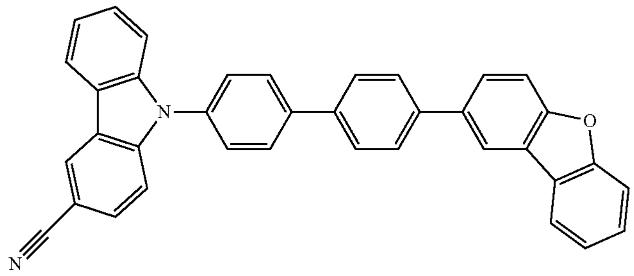
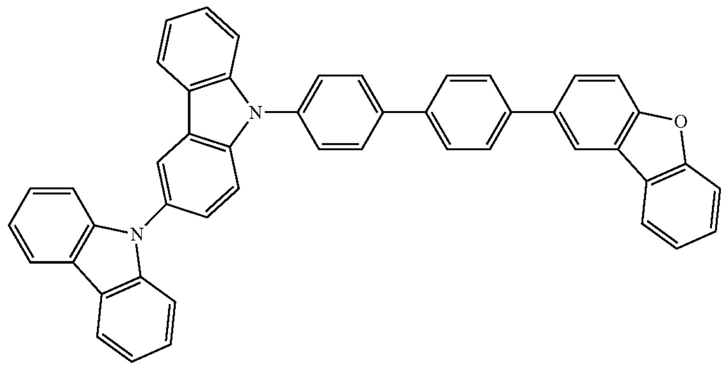

-continued
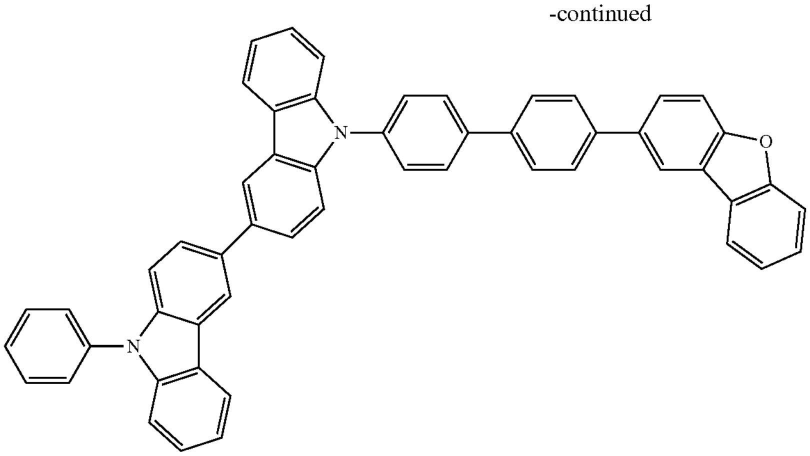
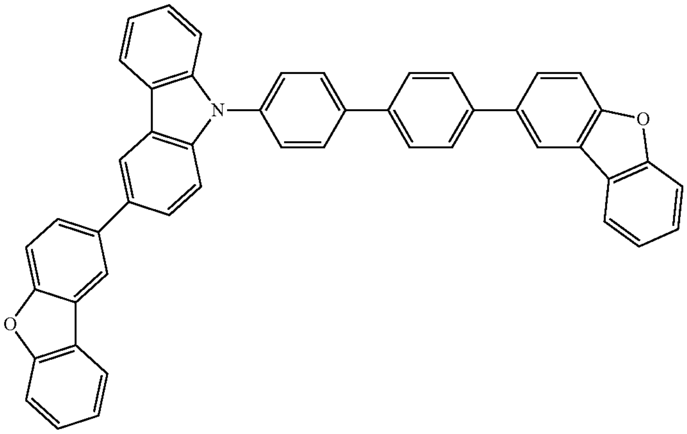
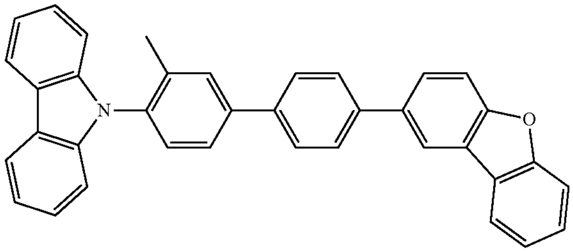
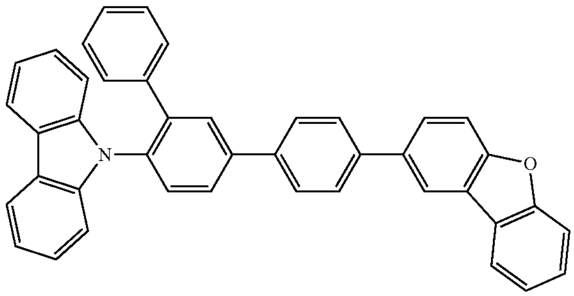
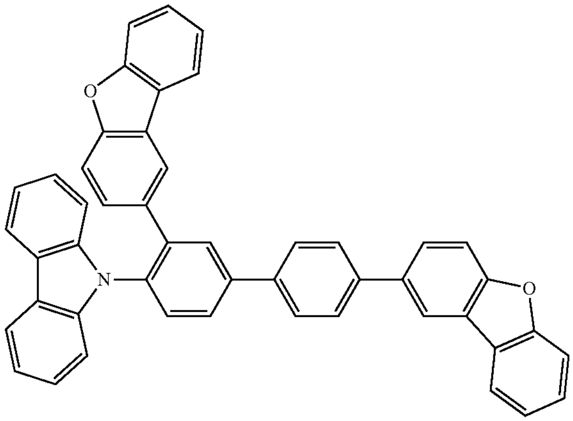

-continued
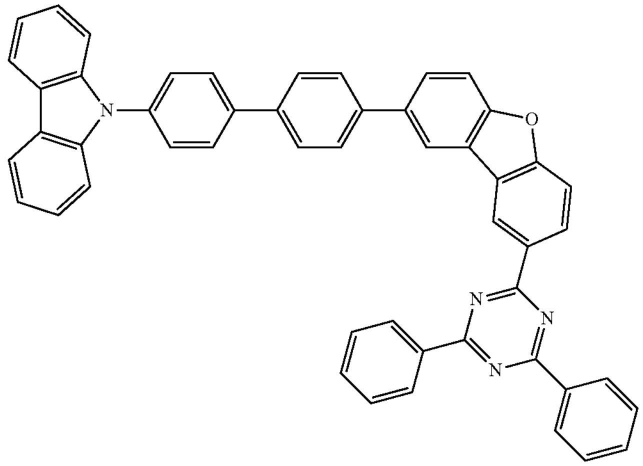
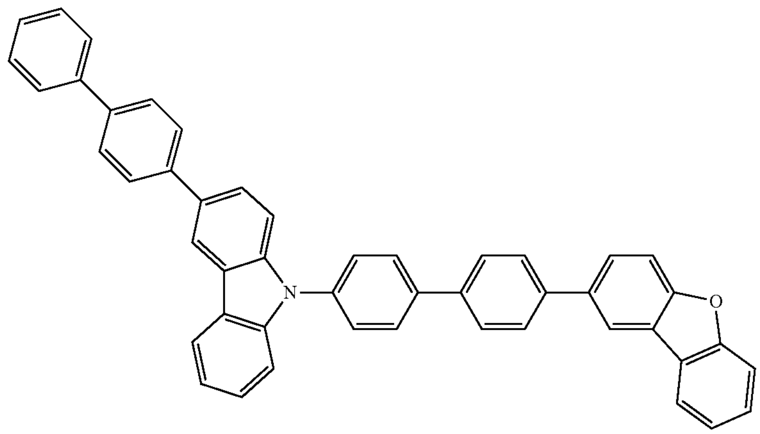
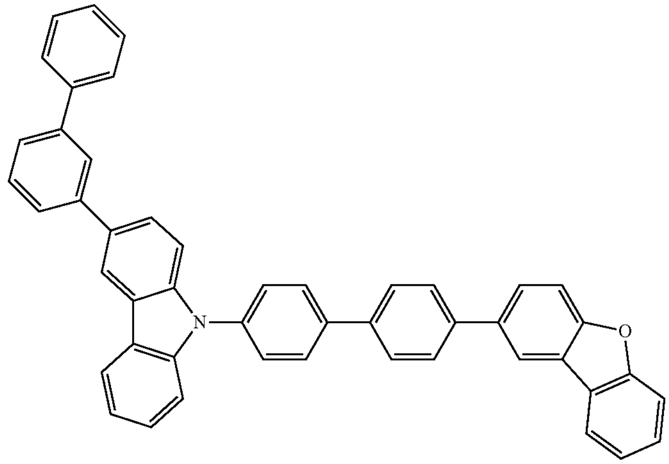

-continued
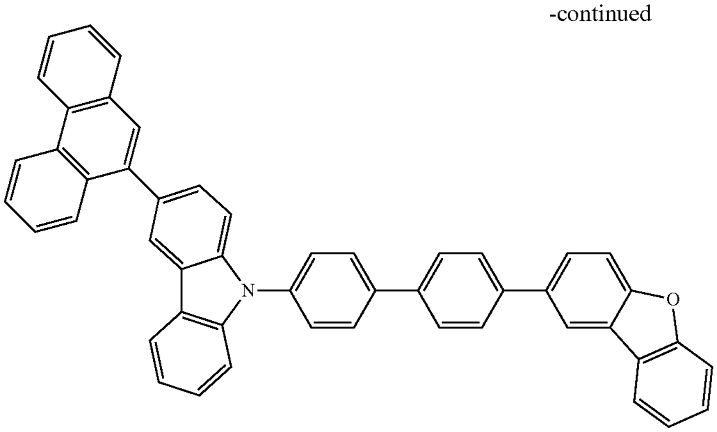
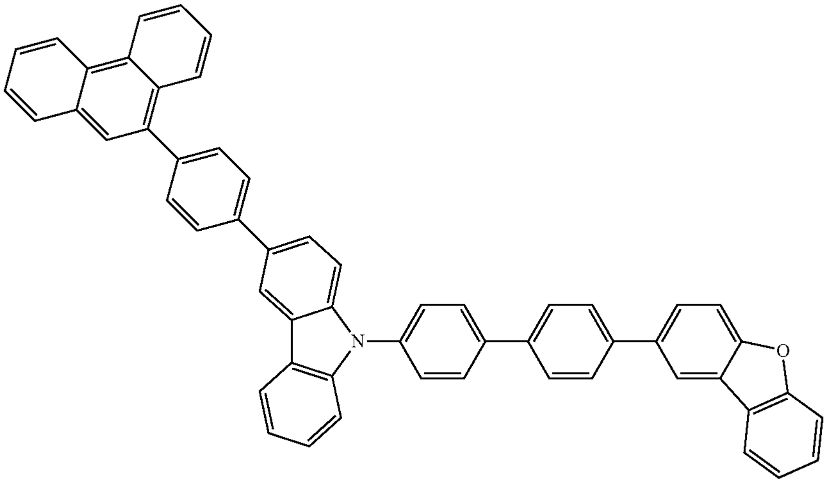
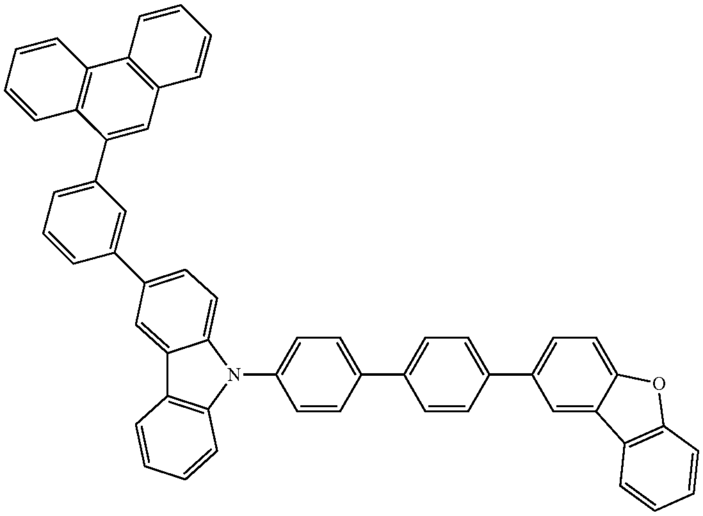

-continued
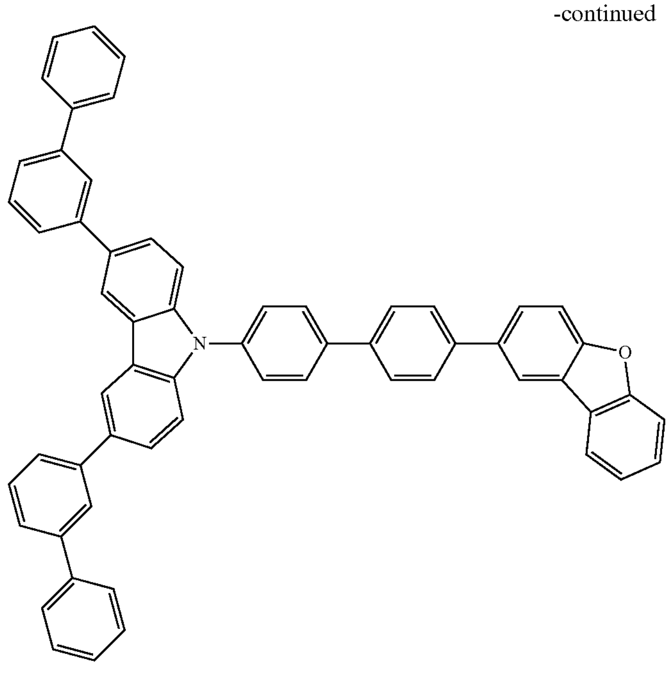
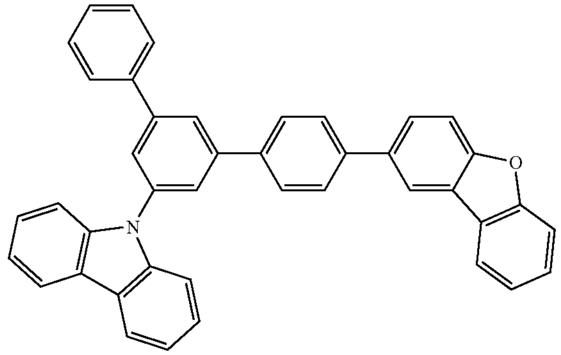
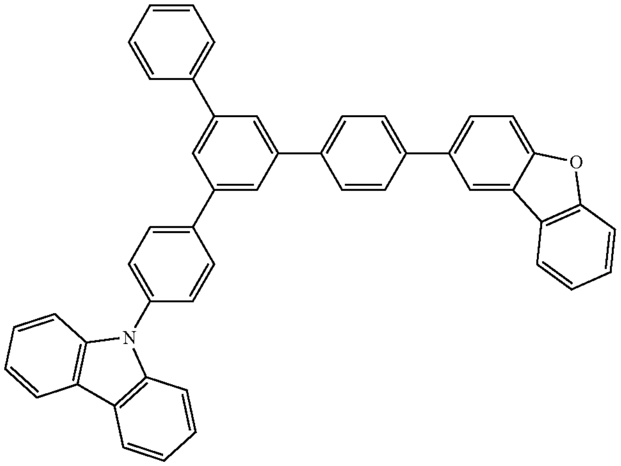
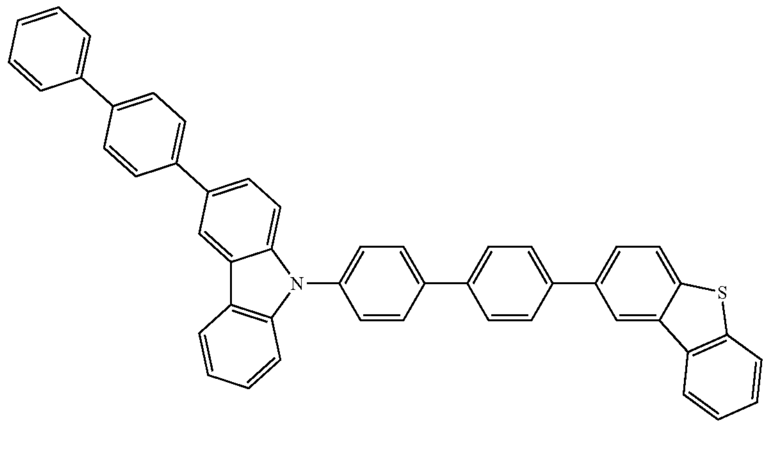

-continued
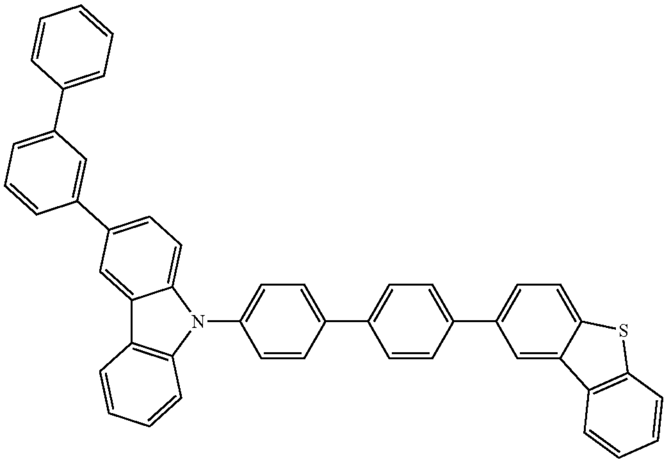
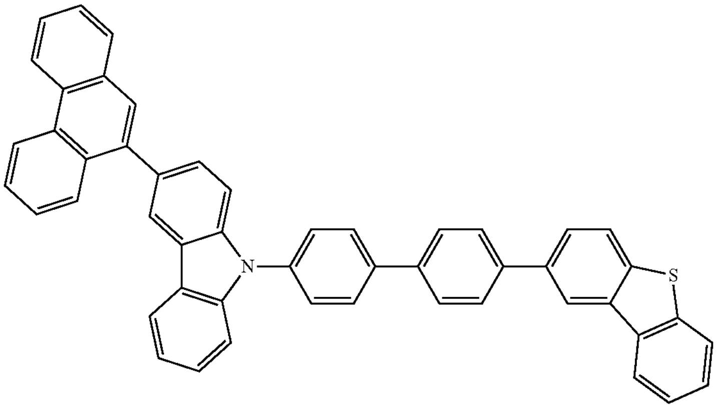
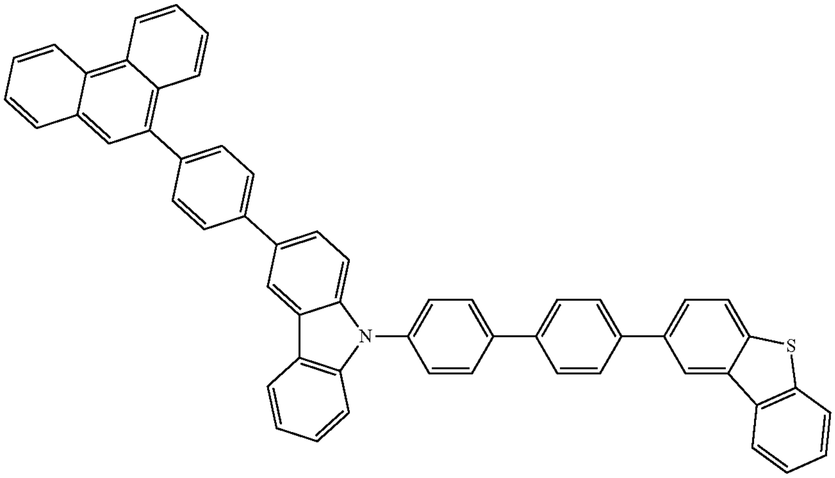

-continued
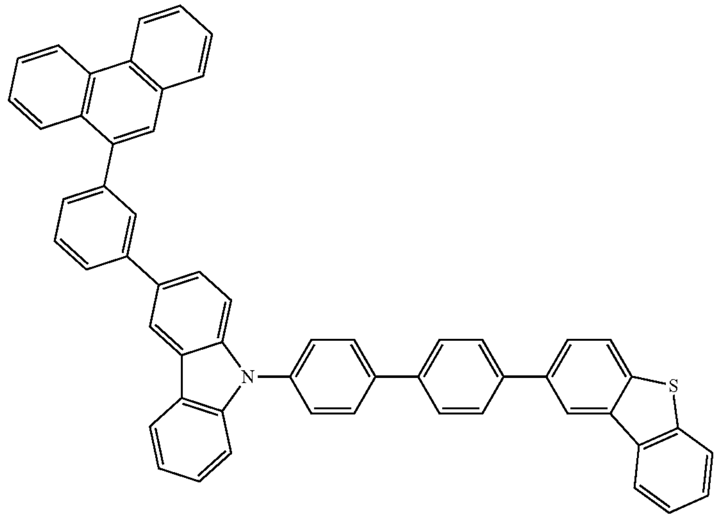
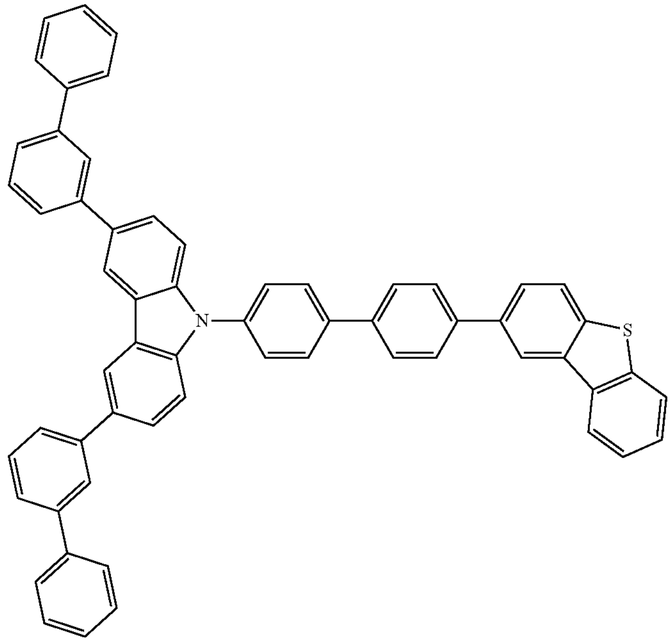
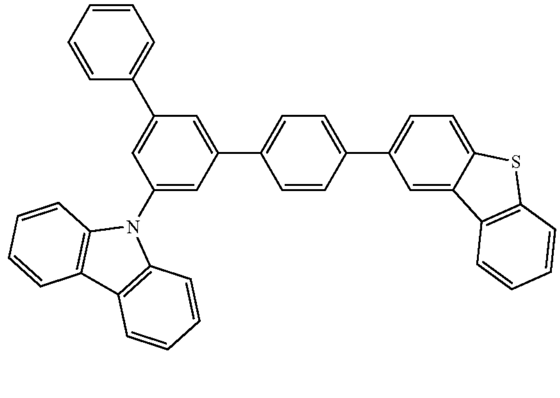
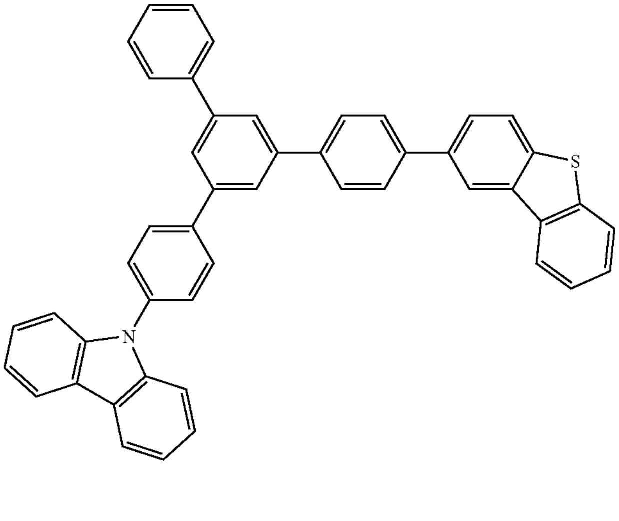

-continued
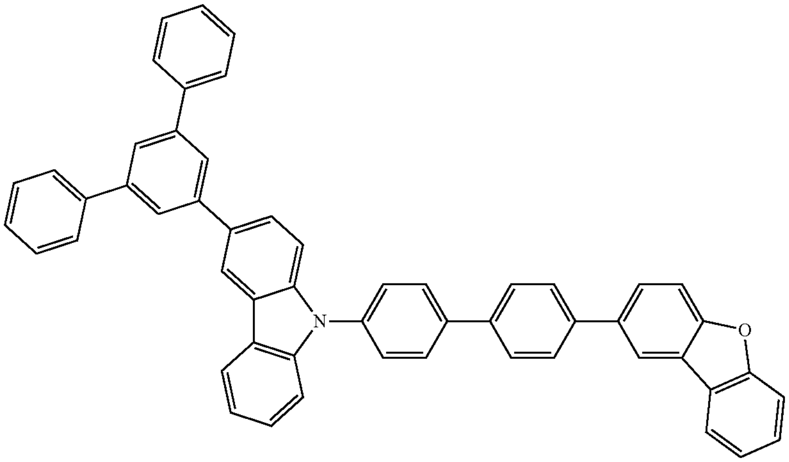
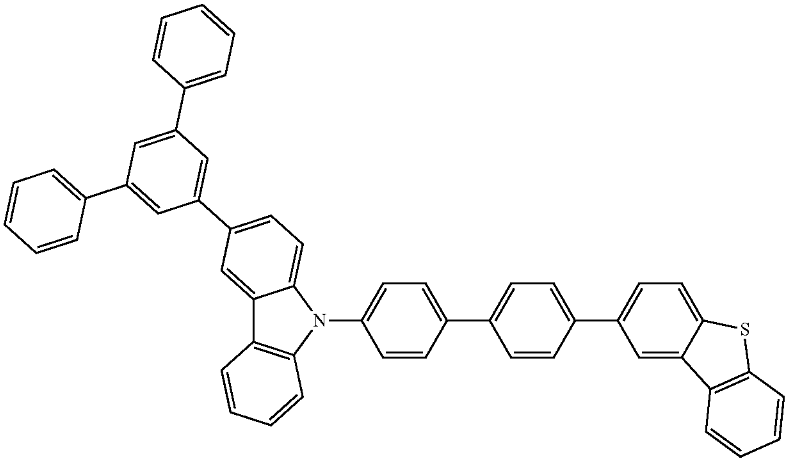
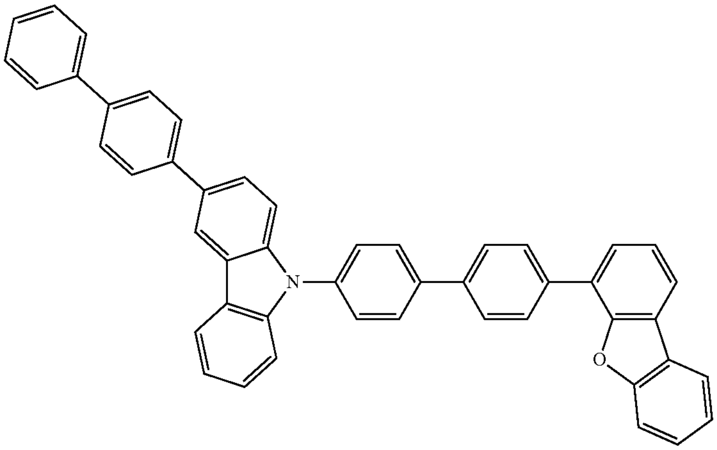

-continued
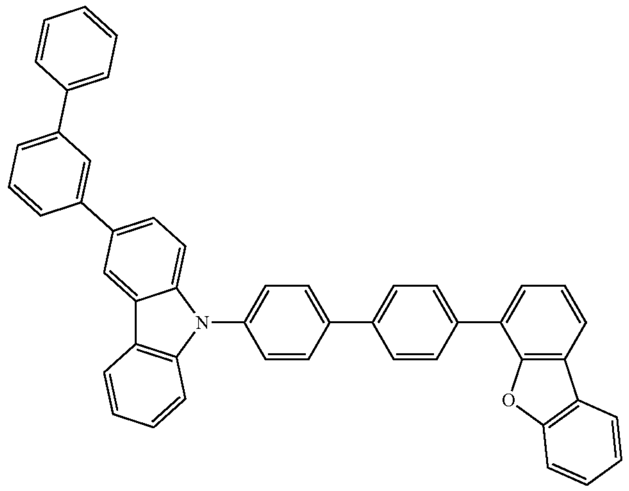
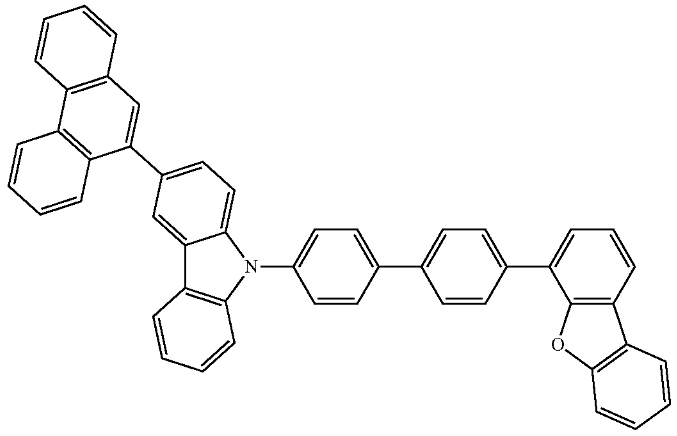
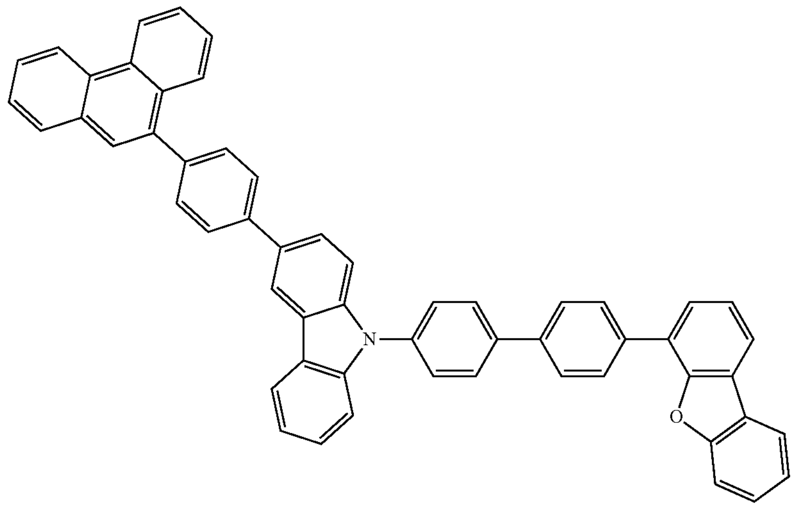

-continued
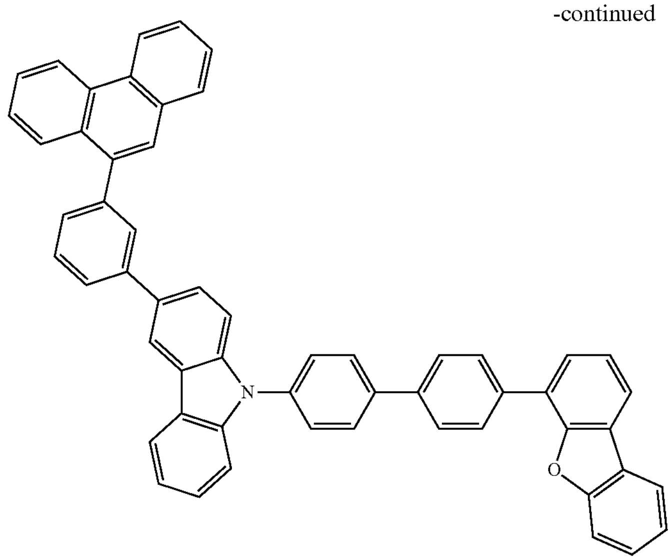
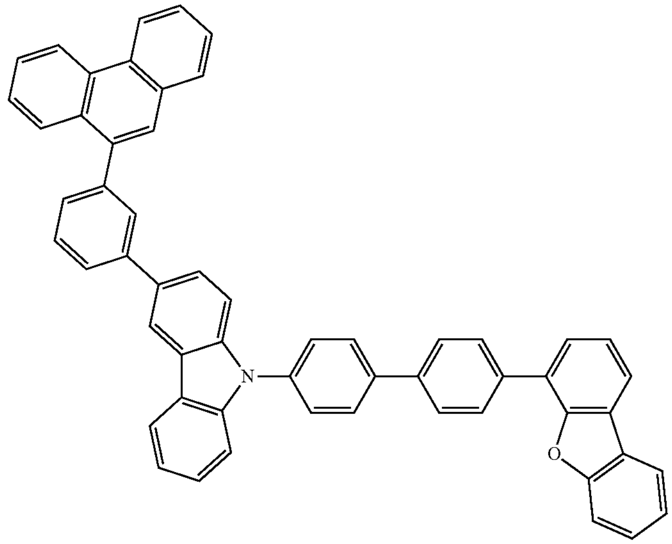
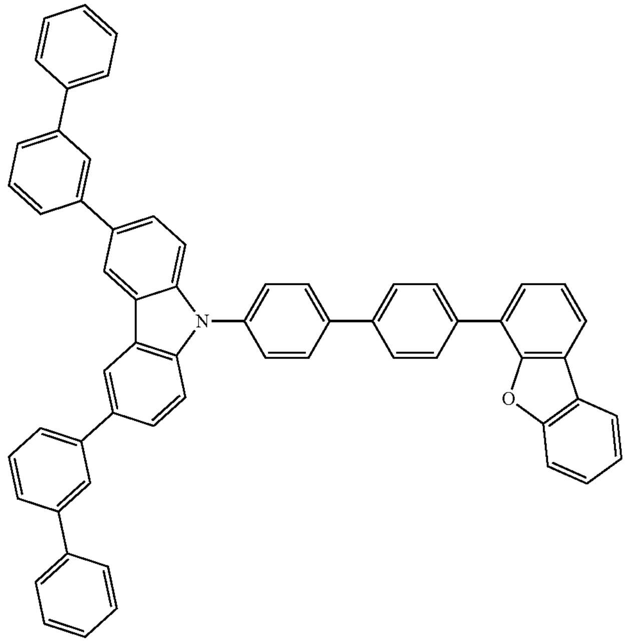

-continued
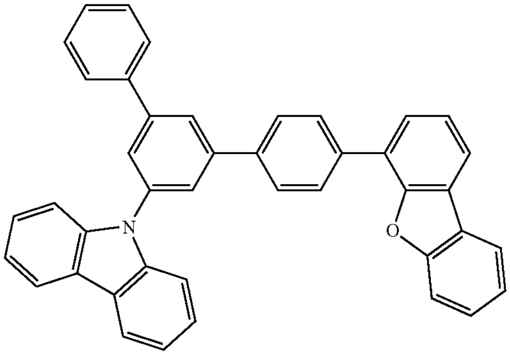
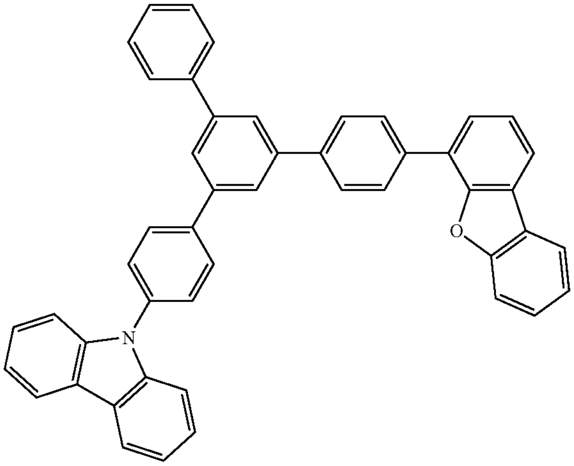
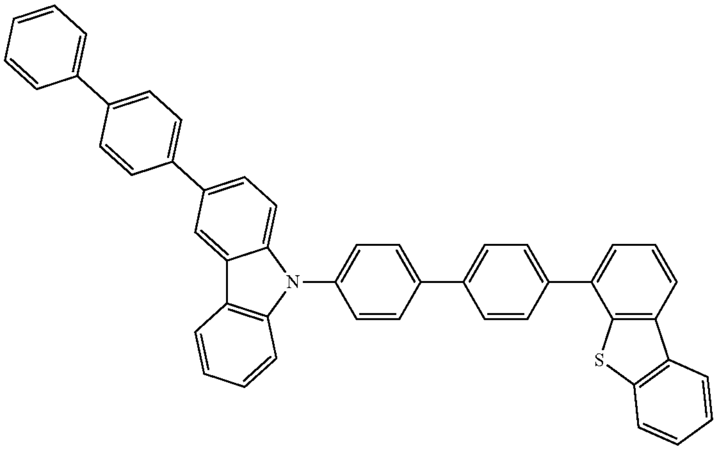
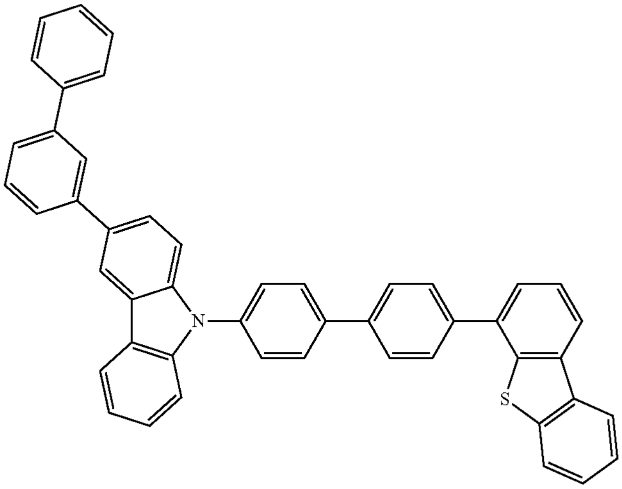

-continued
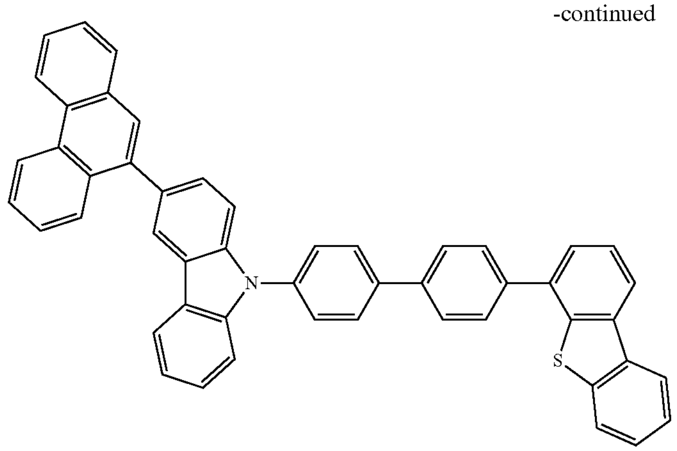
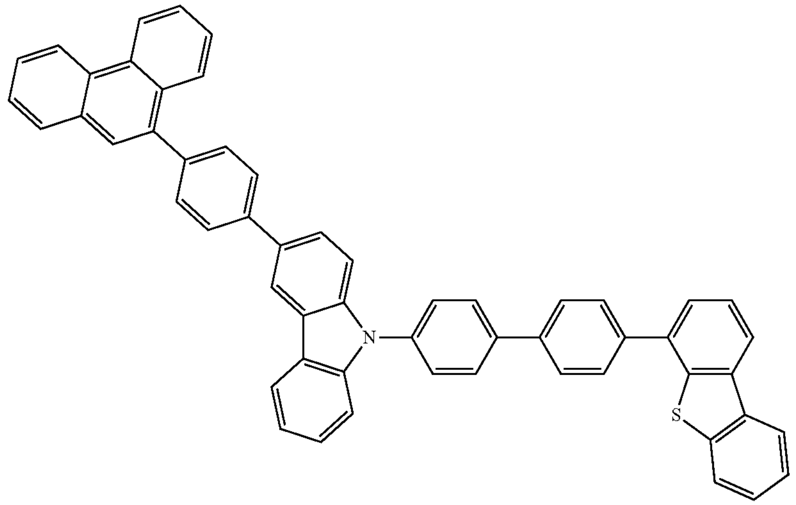
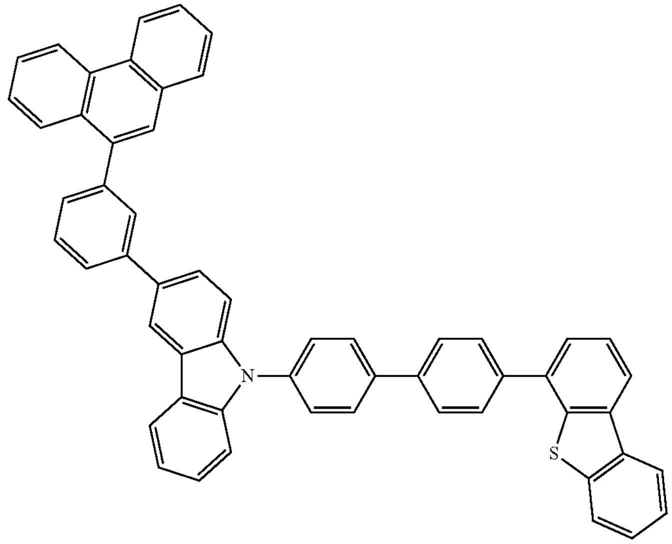

-continued
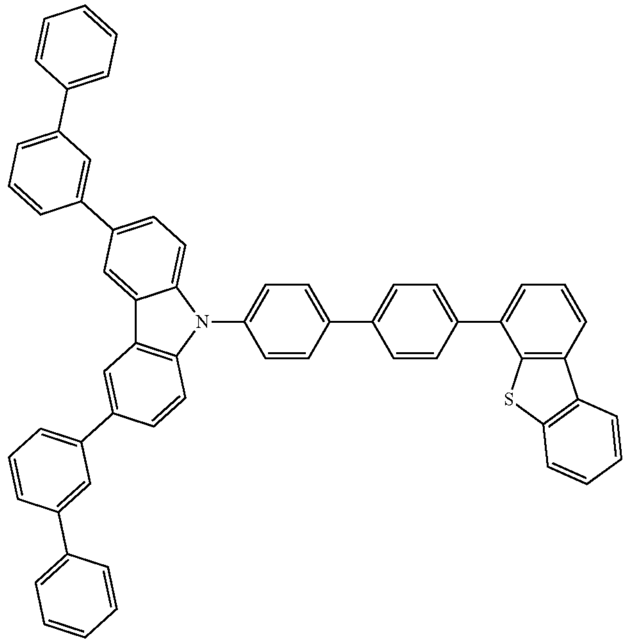
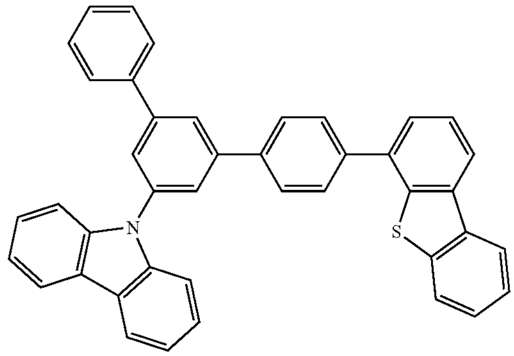
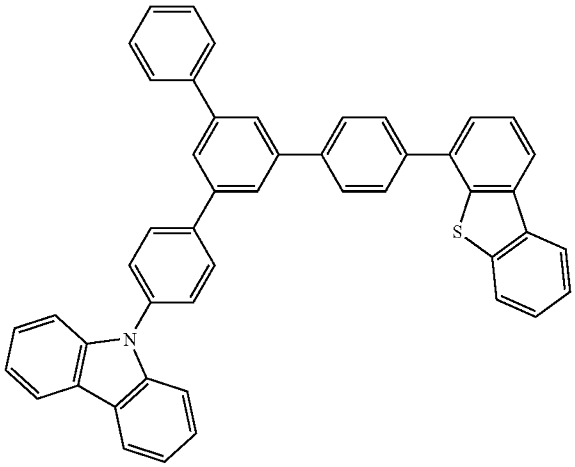
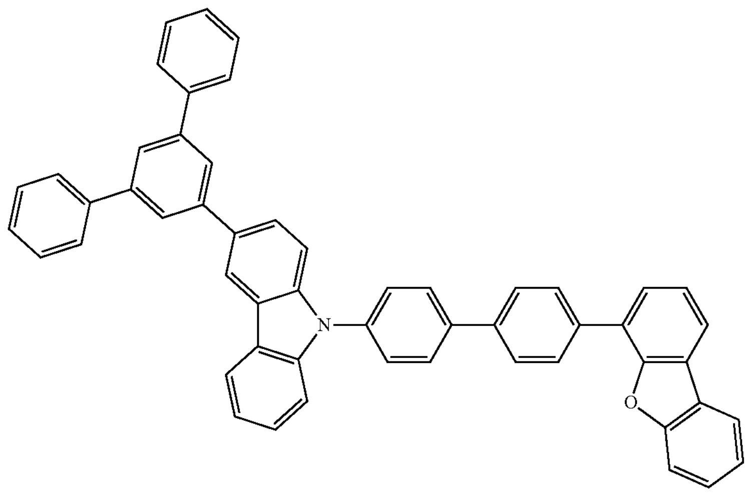

-continued
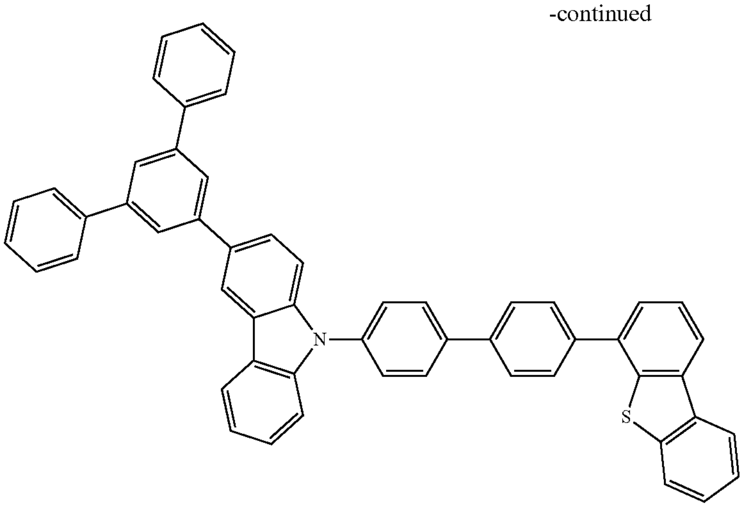
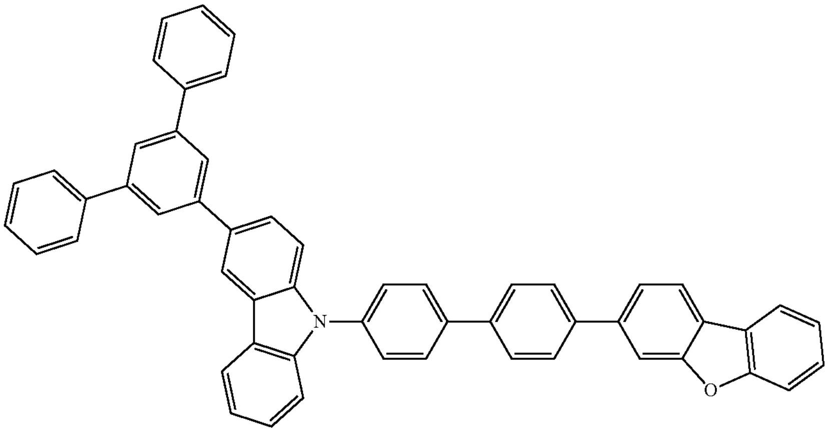
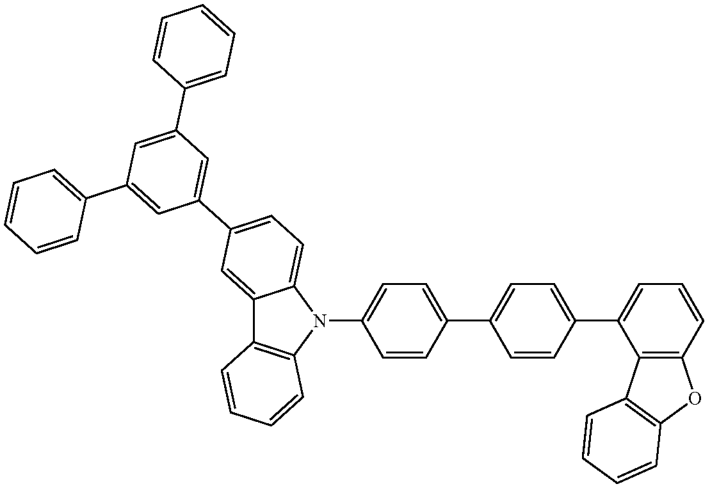
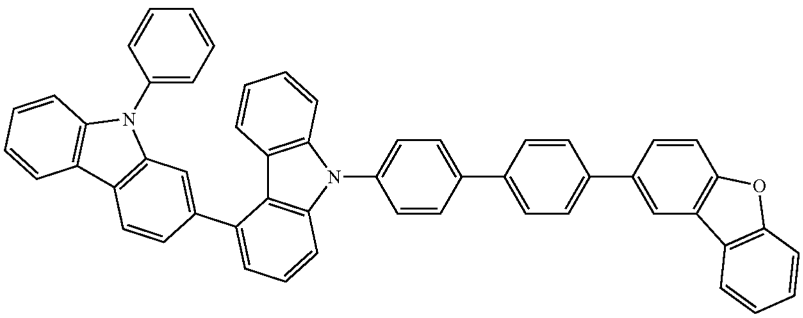

-continued
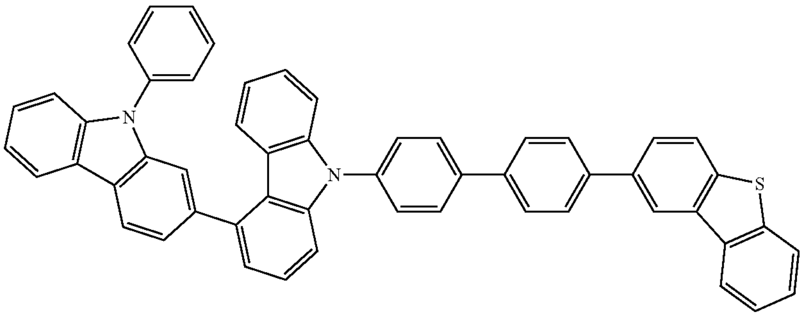
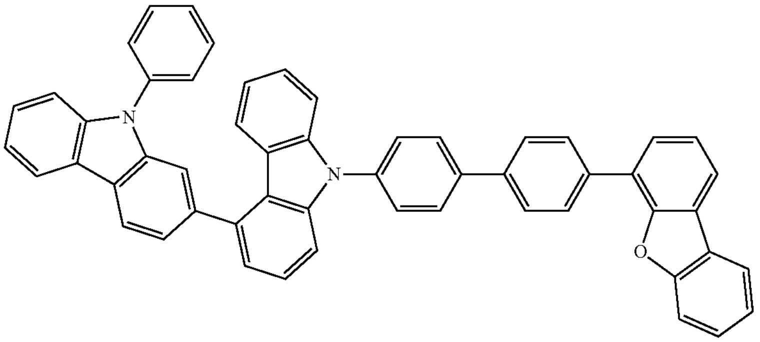
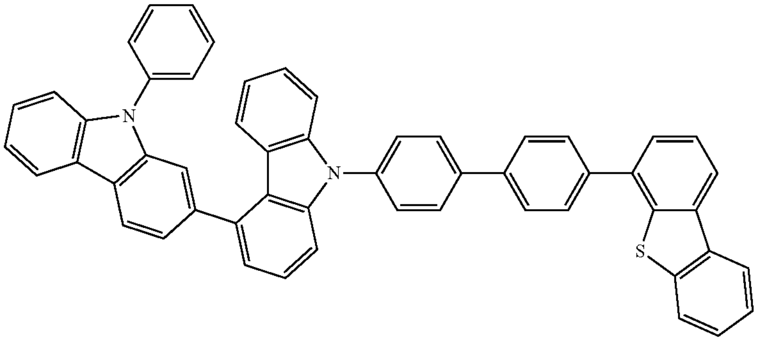
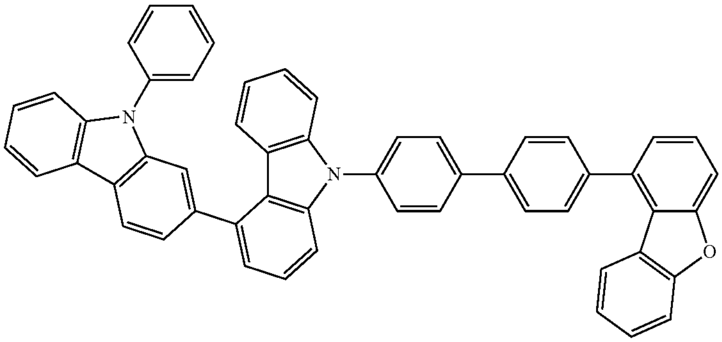

-continued
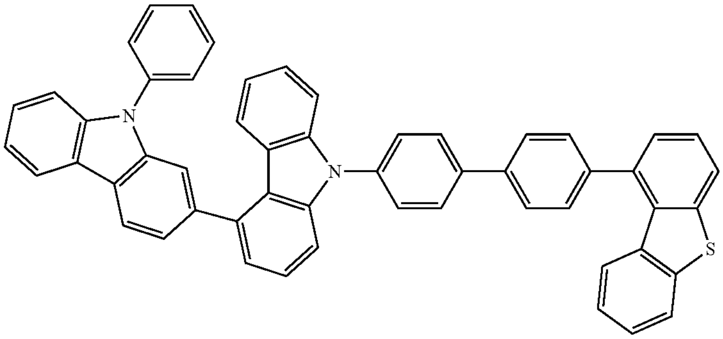
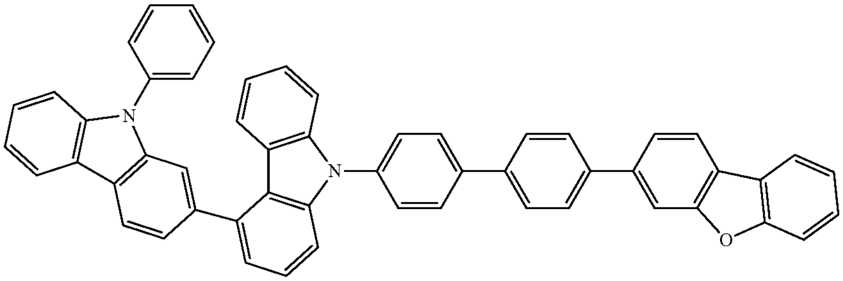
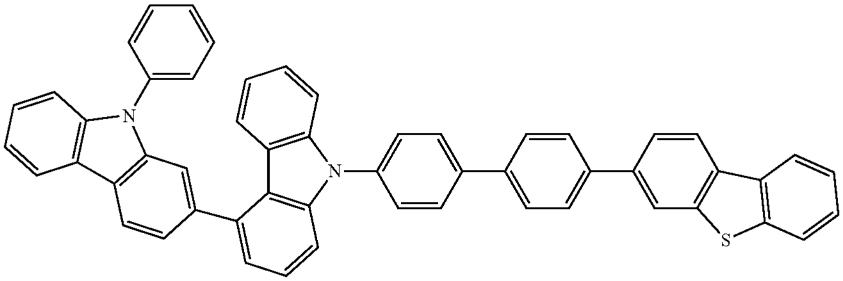
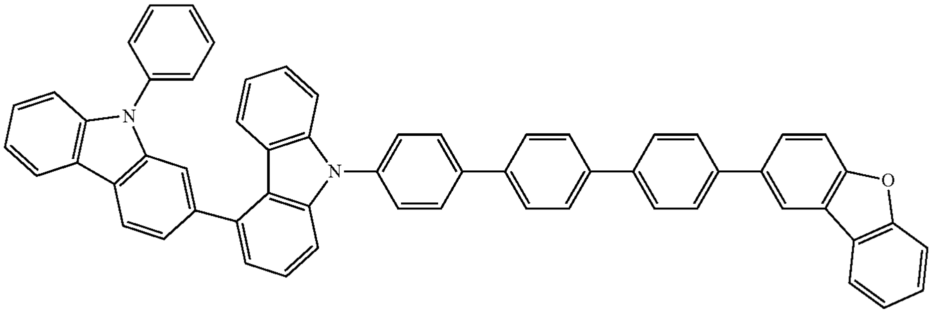
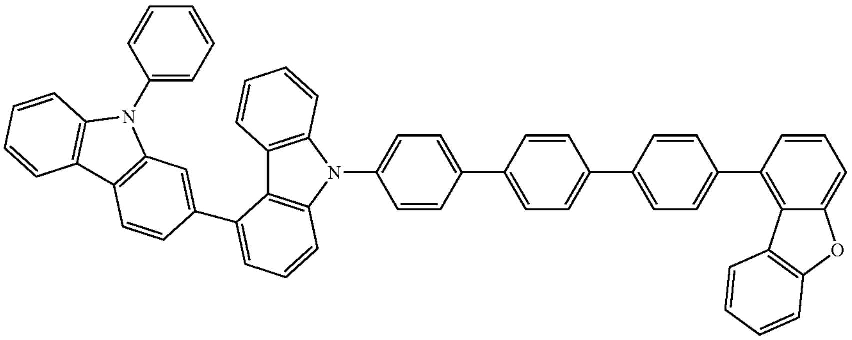

-continued
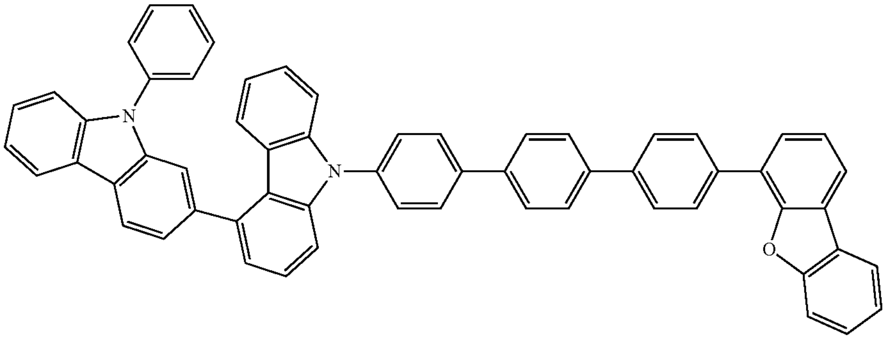
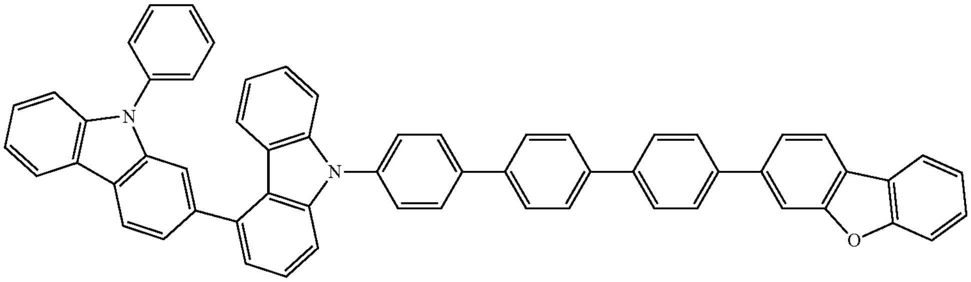
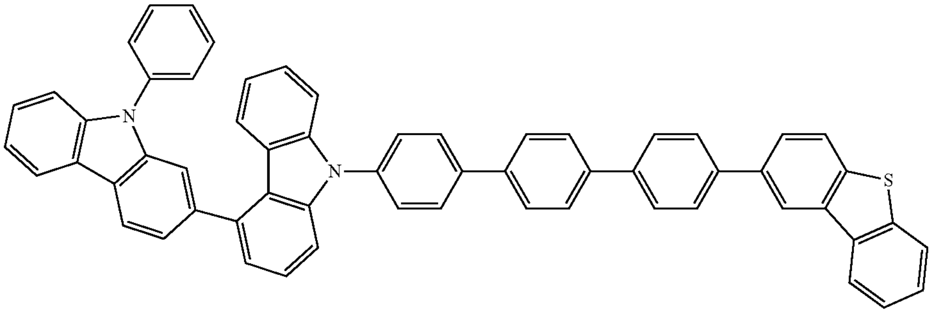
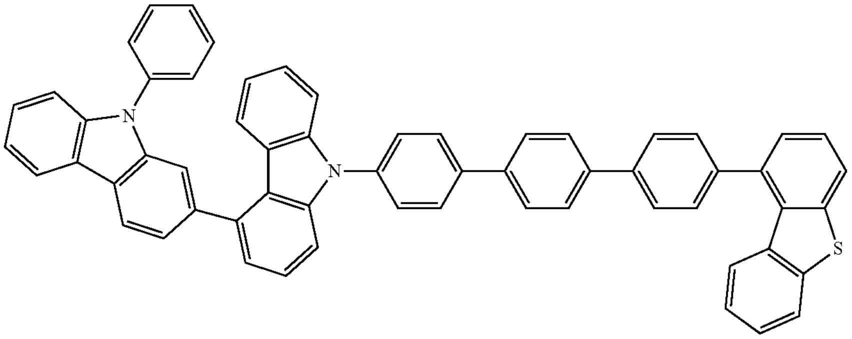
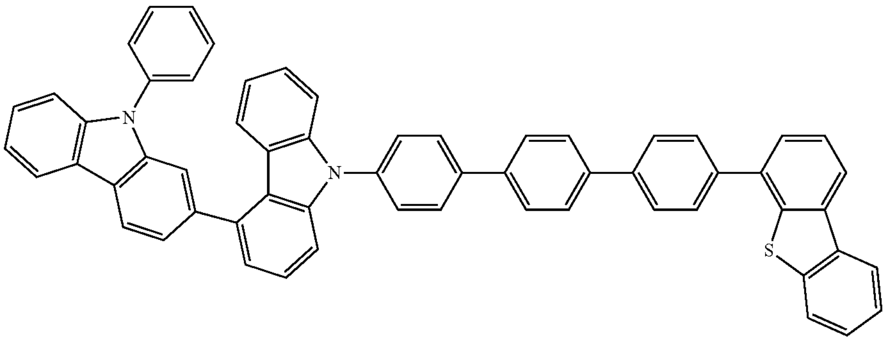

-continued
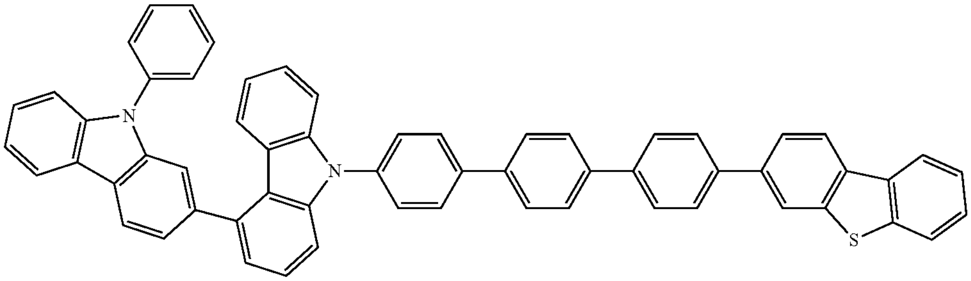
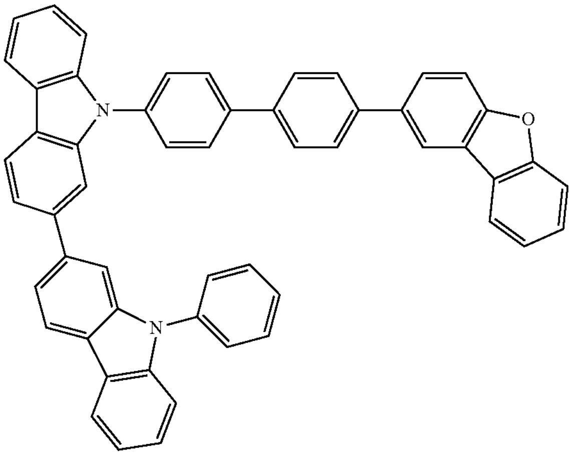
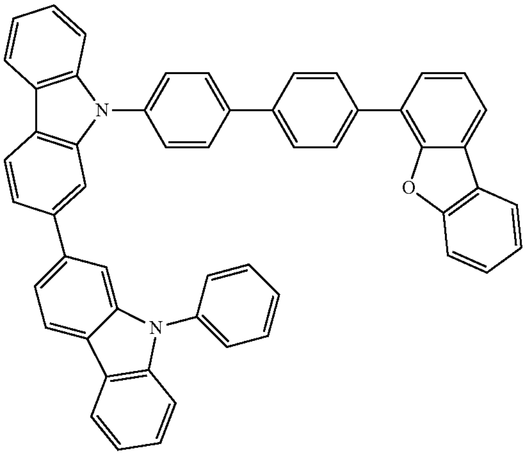
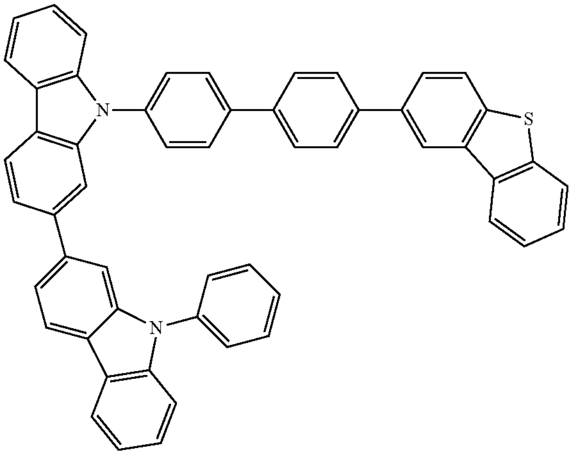
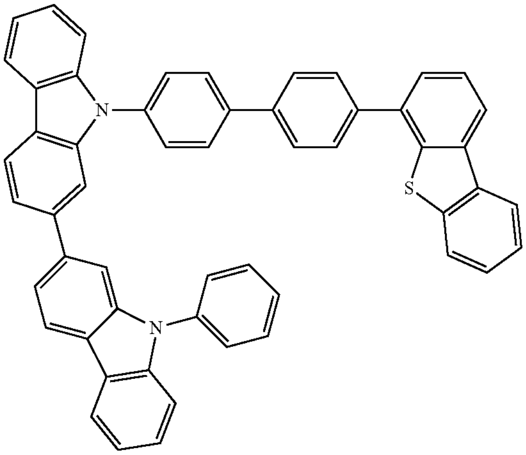
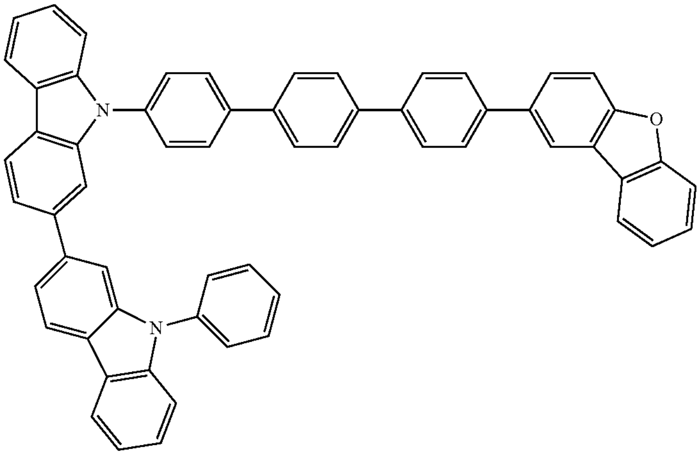

-continued
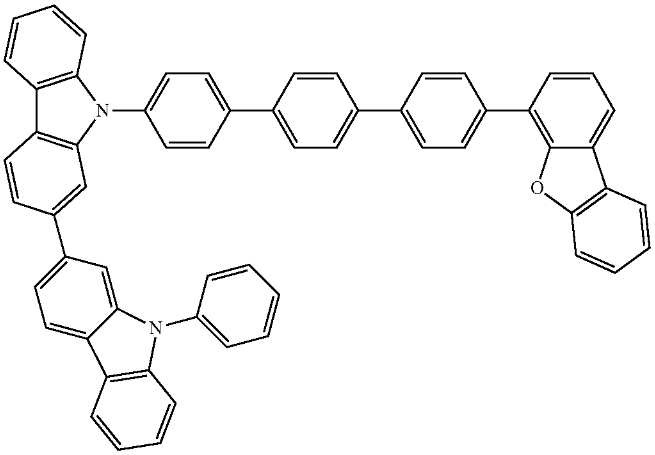
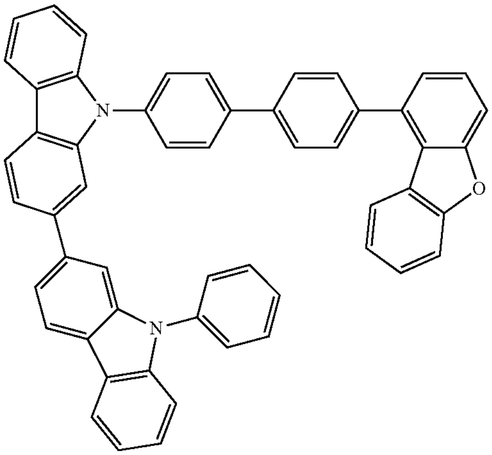
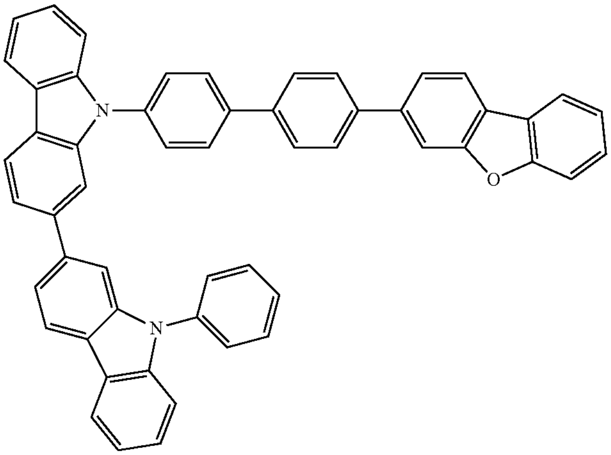
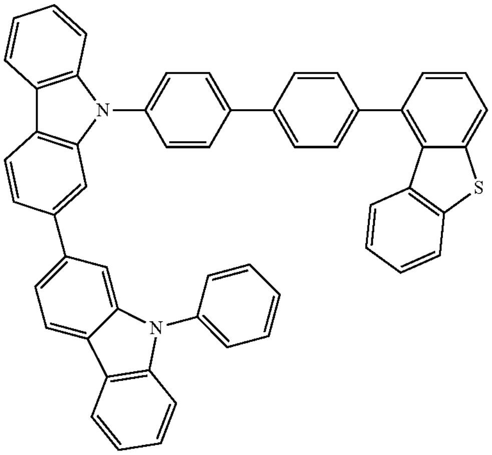
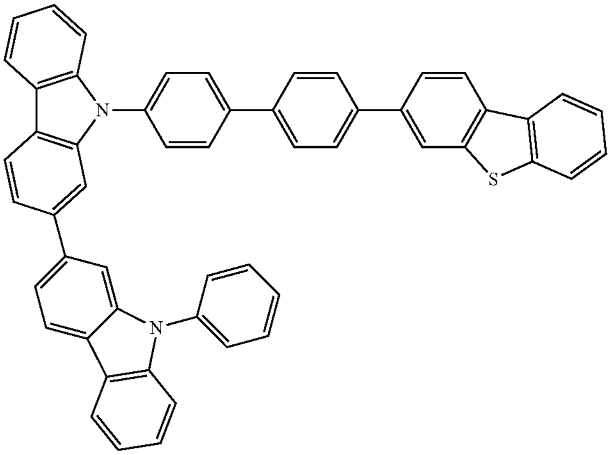

-continued
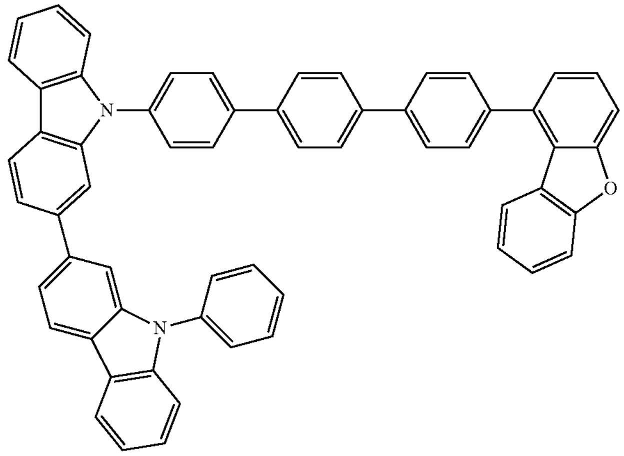
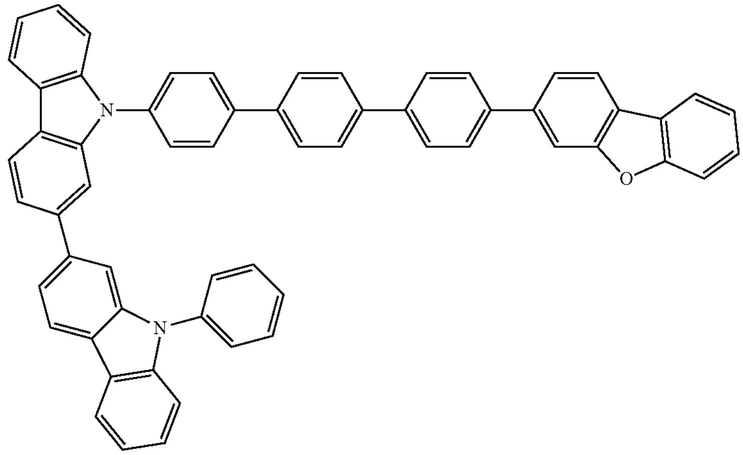
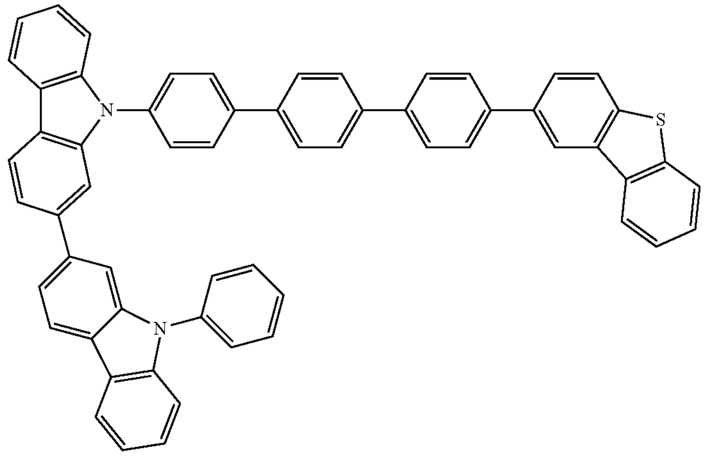

-continued
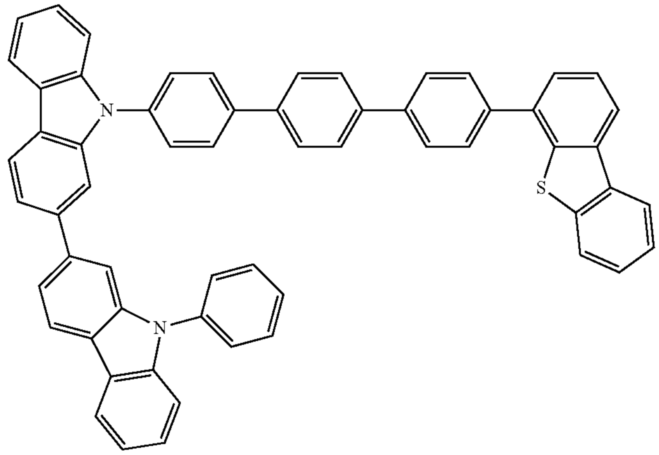
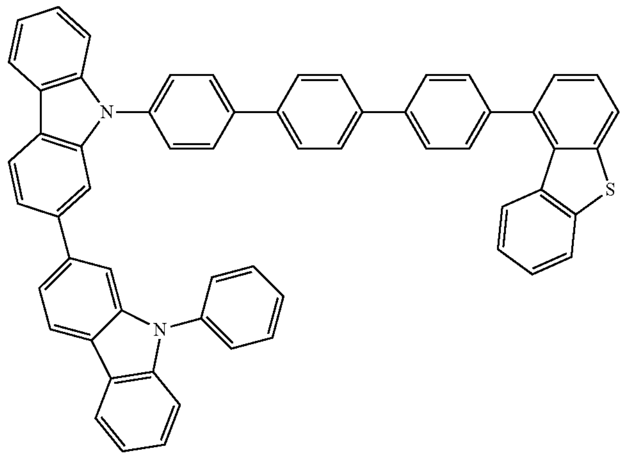
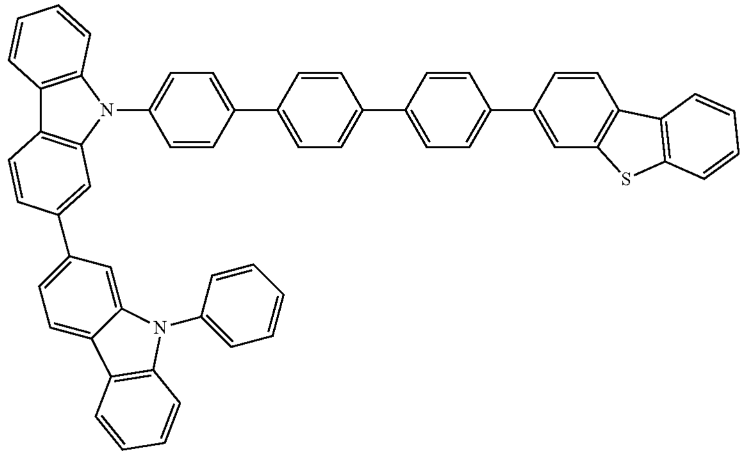

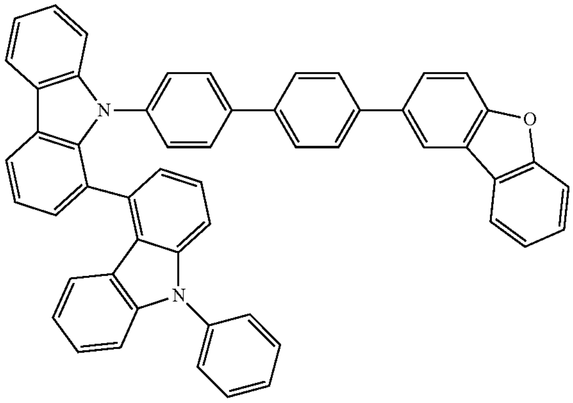
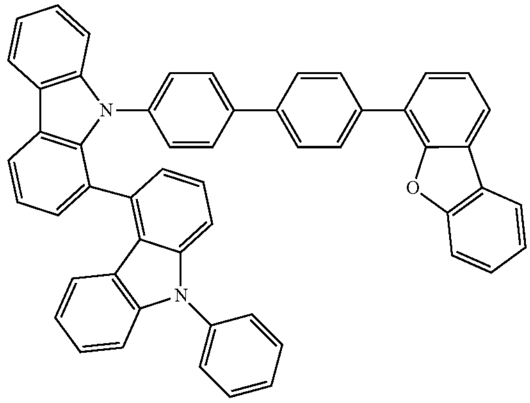
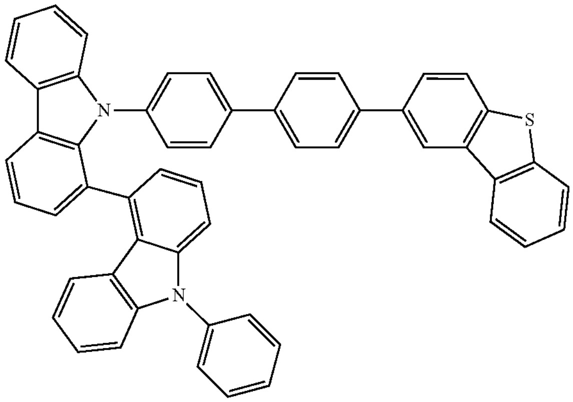
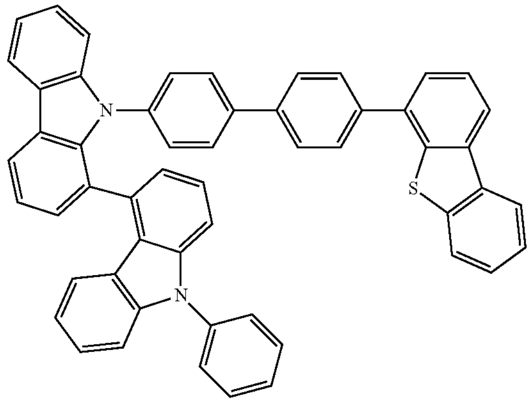
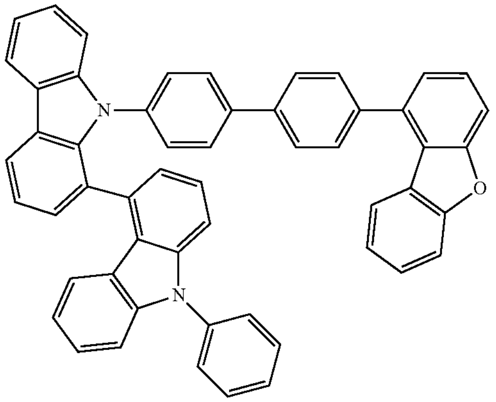
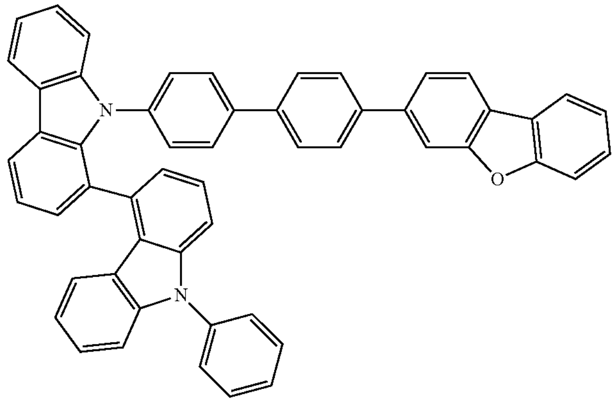
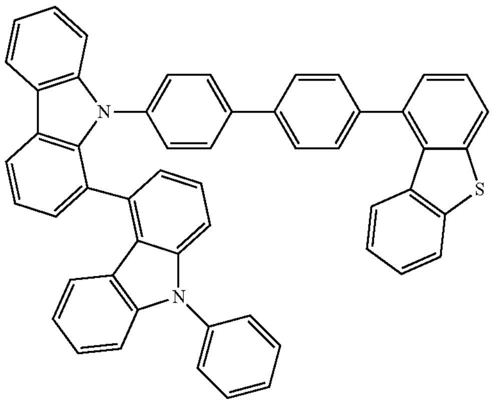
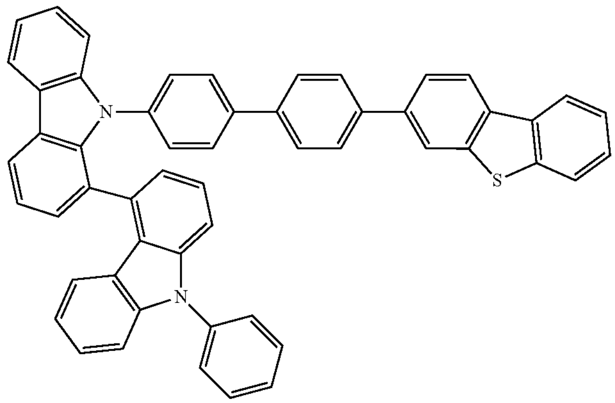

-continued
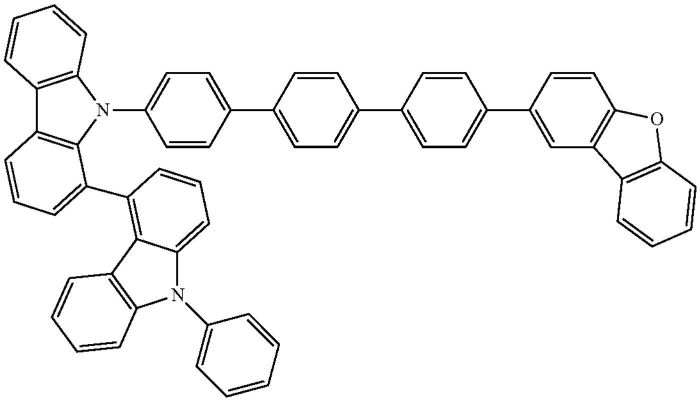
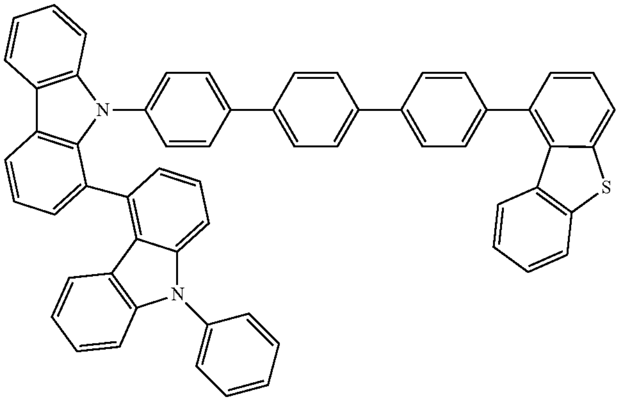
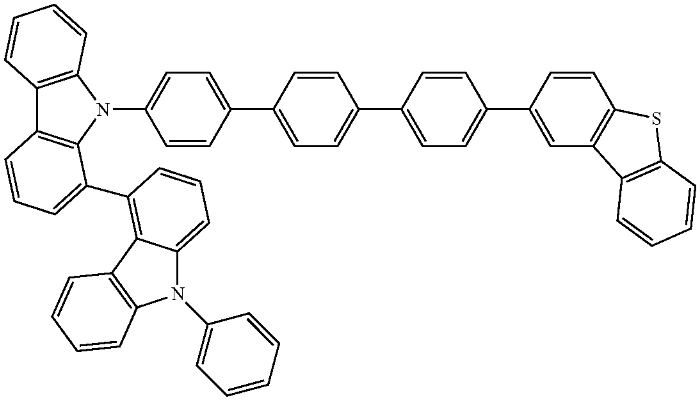
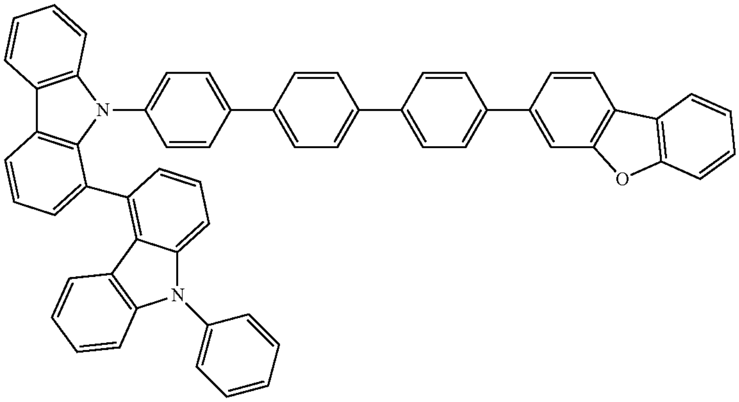

-continued
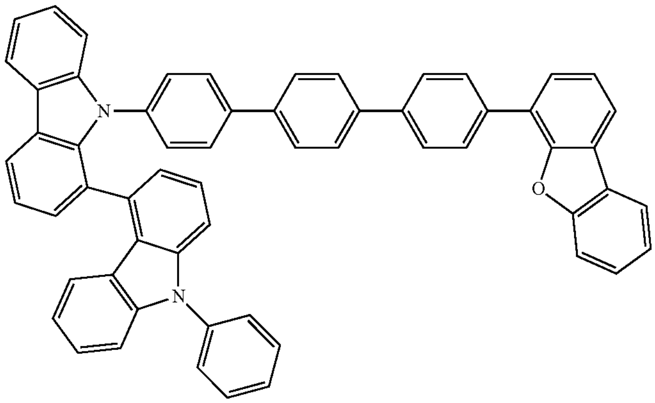
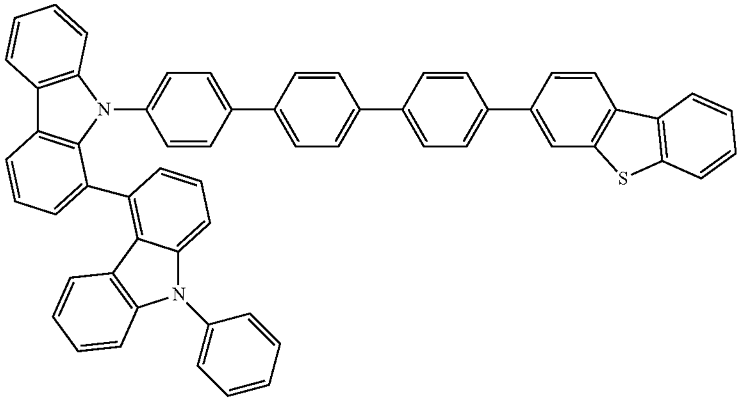
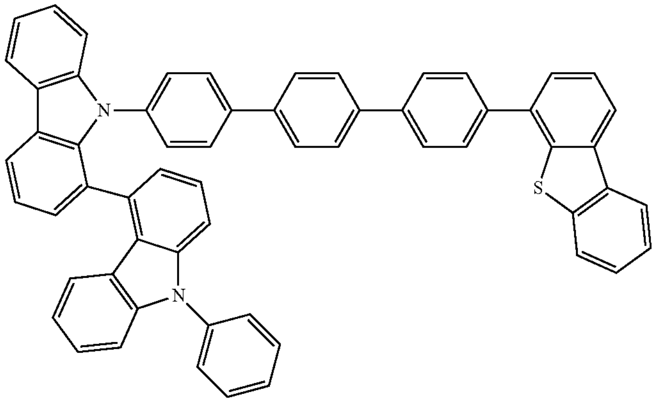
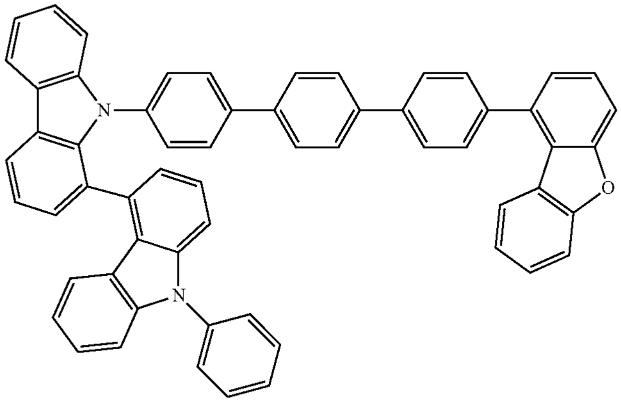

-continued
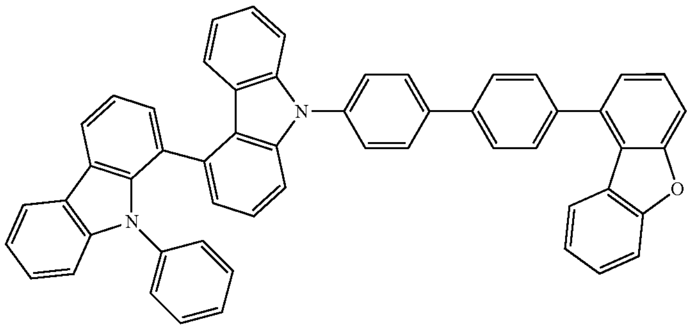
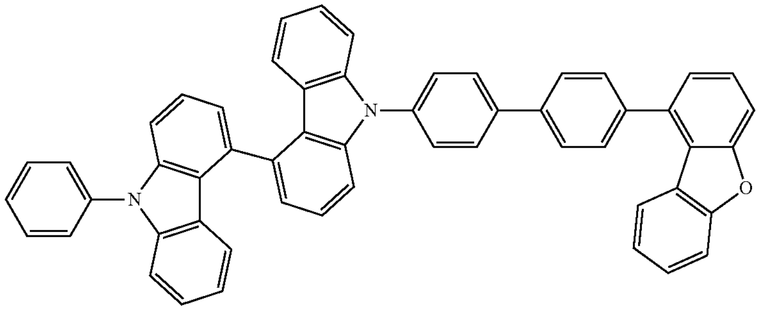
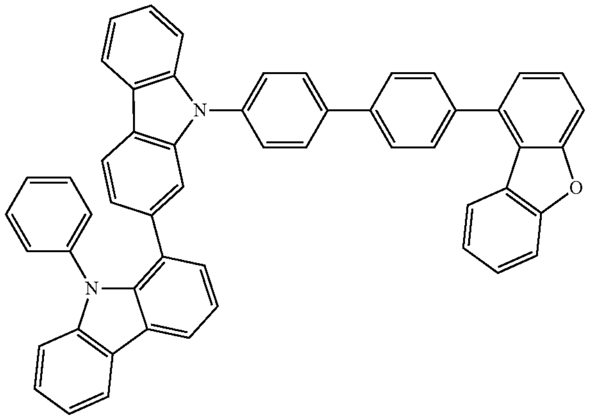
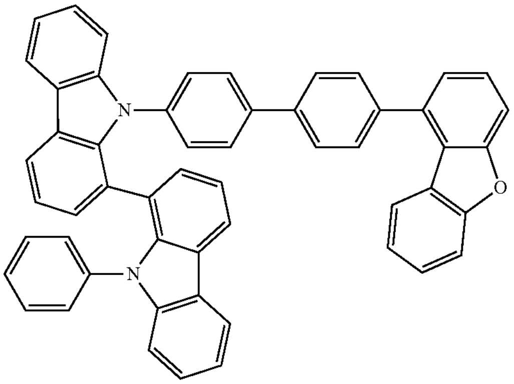
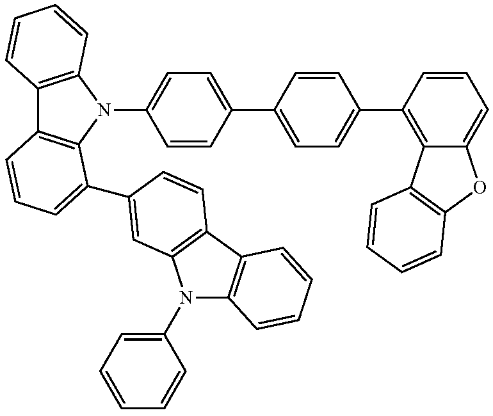
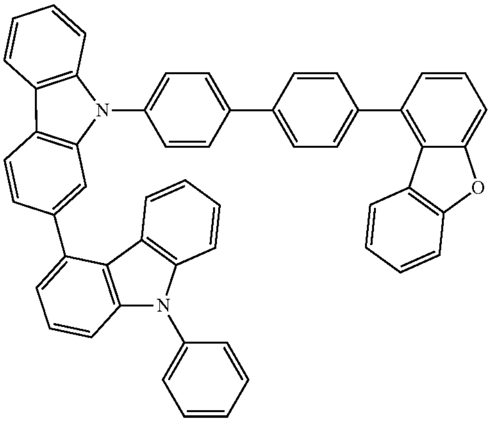

-continued
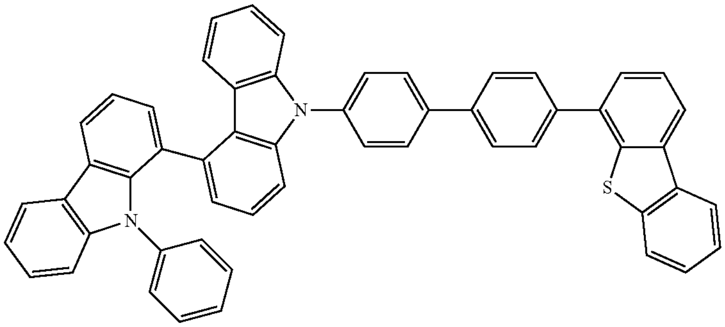
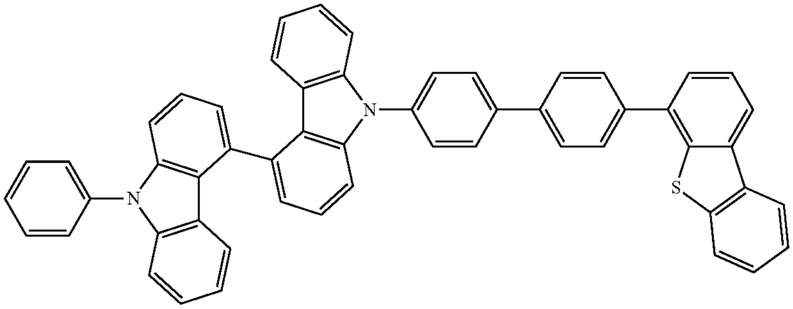
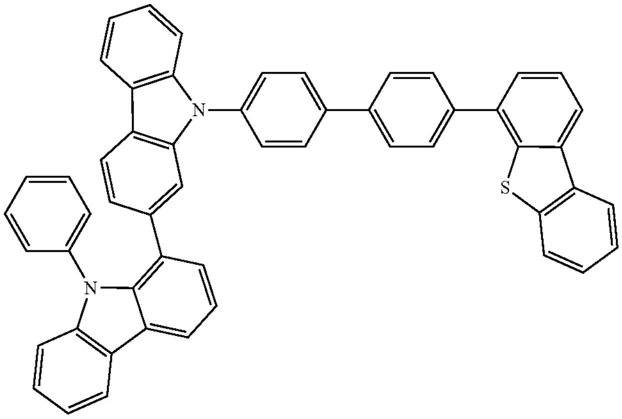
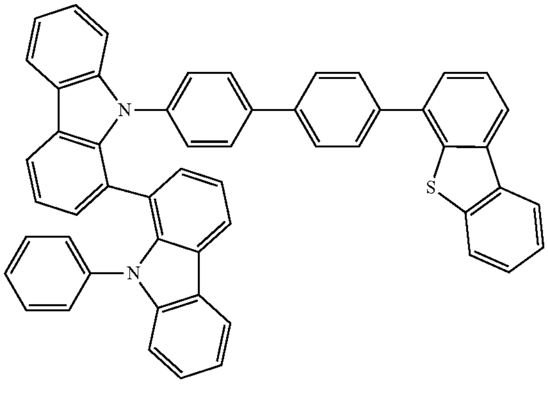
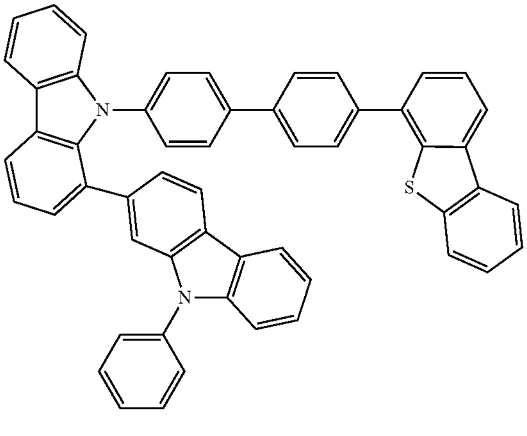

-continued
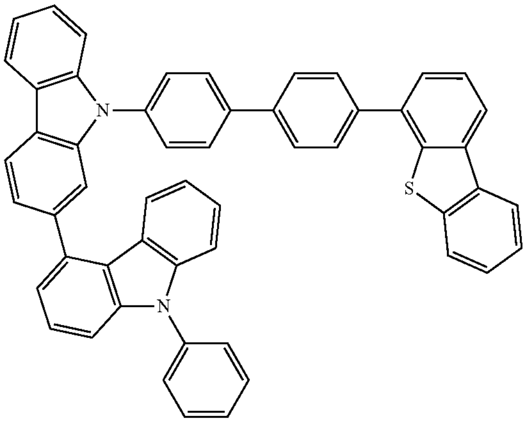
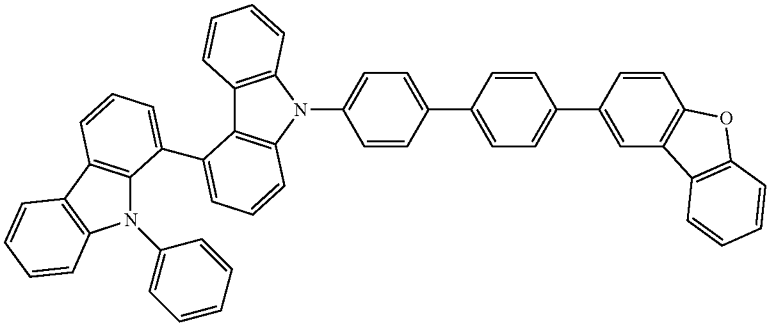
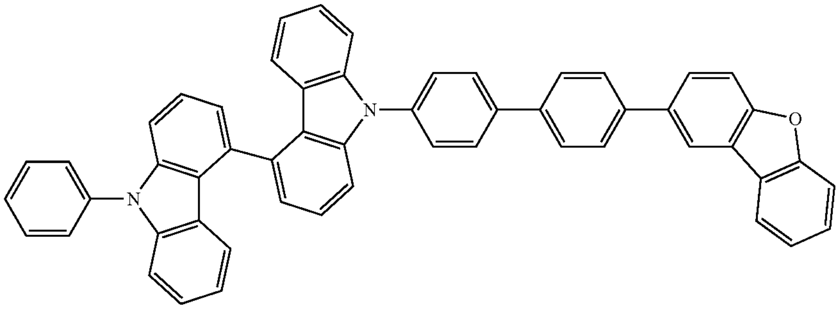
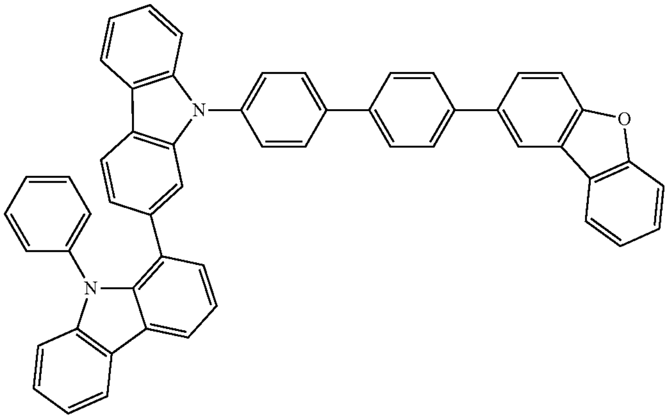

-continued
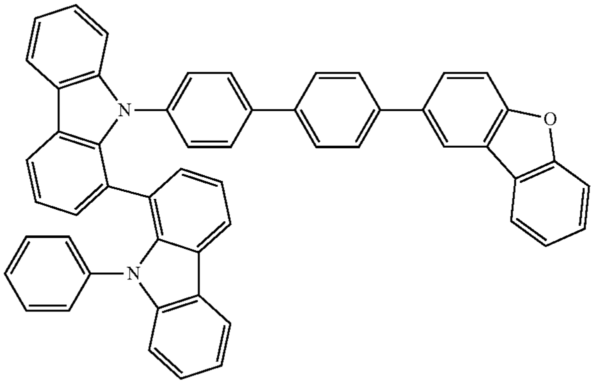
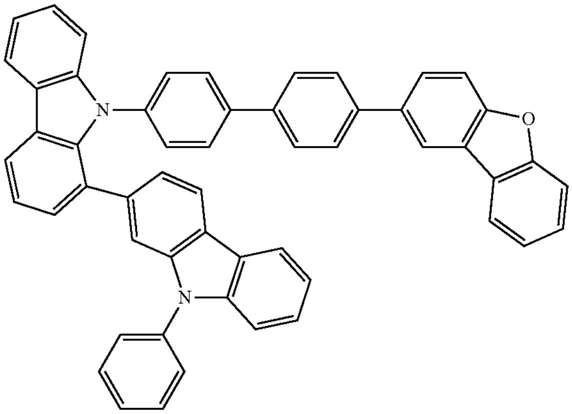
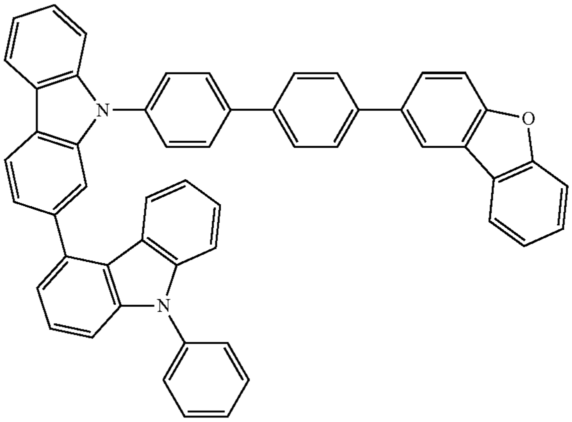
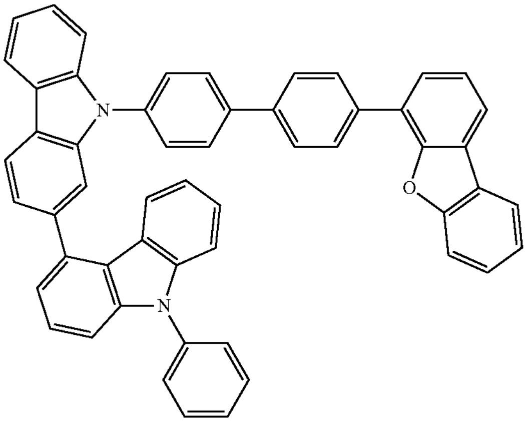
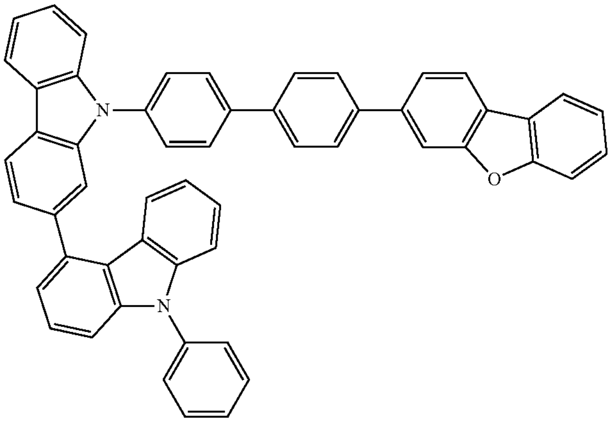

-continued
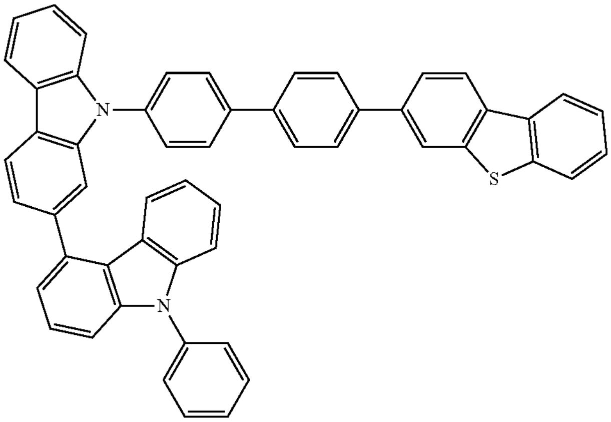
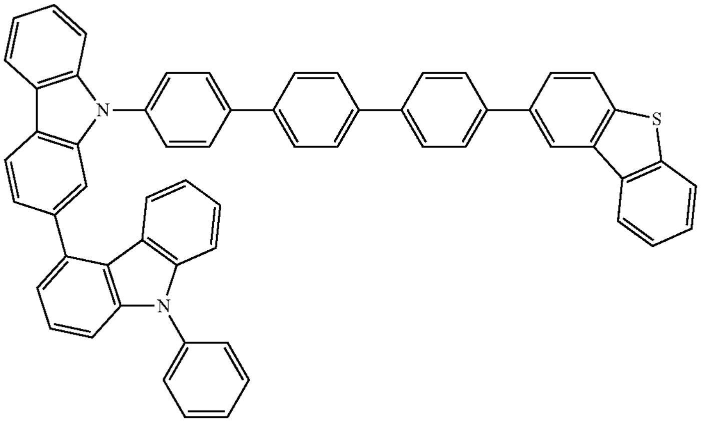
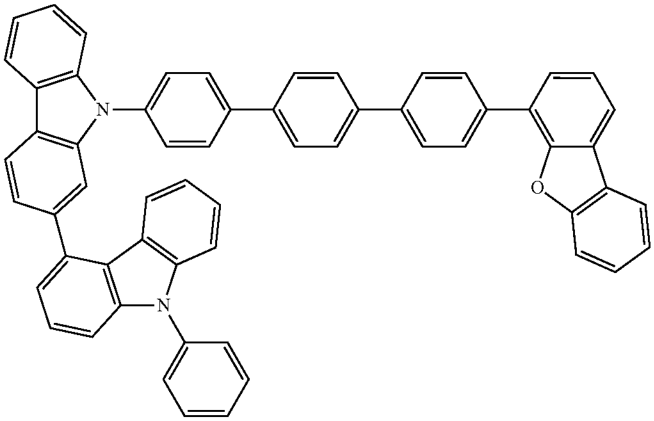
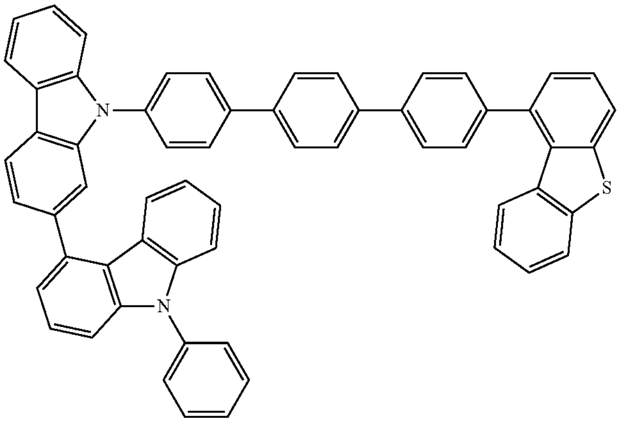

-continued
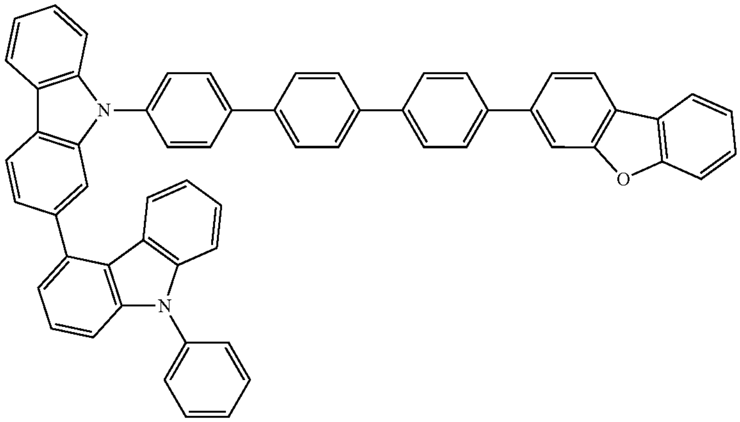
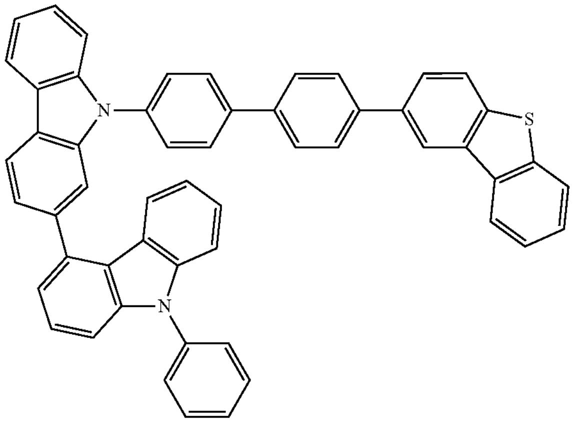
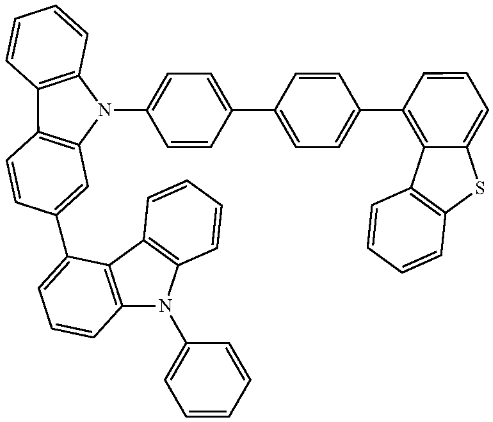
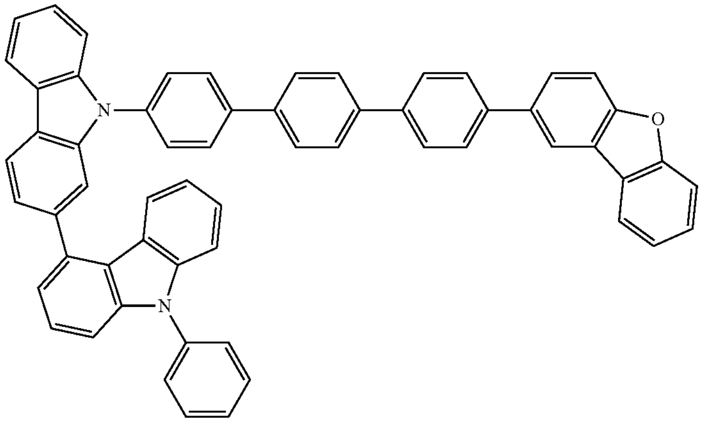
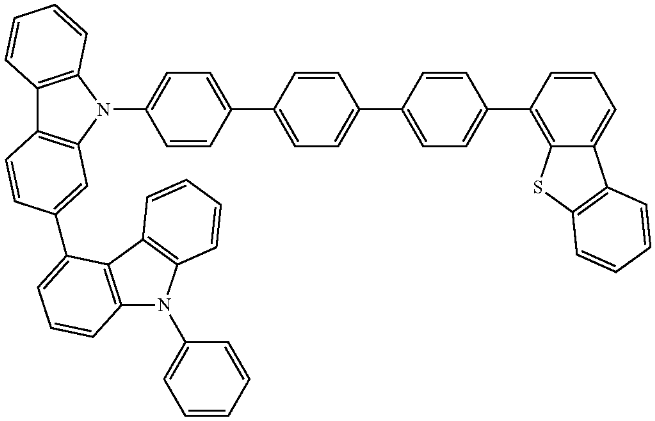

-continued
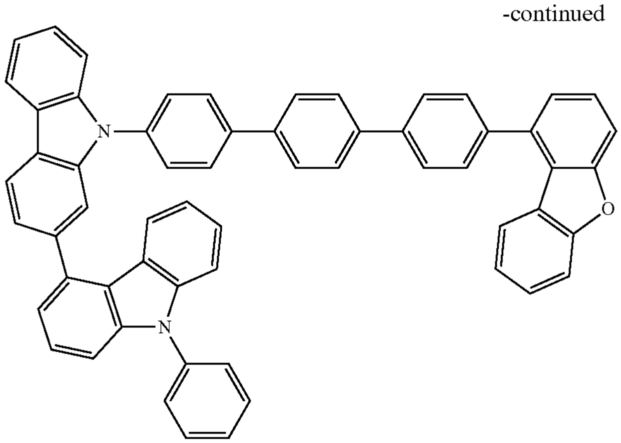
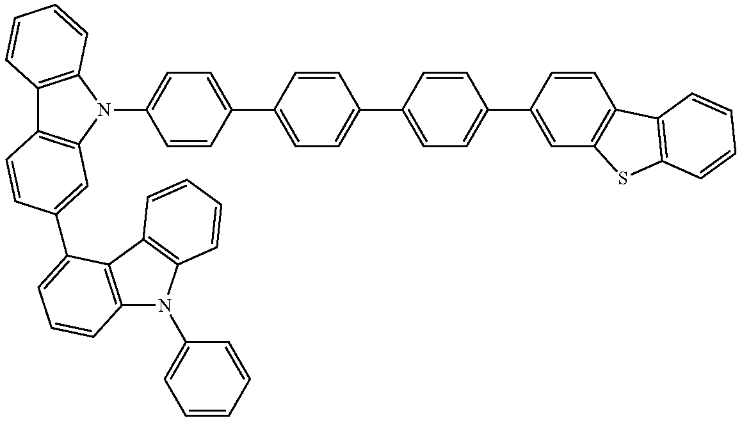
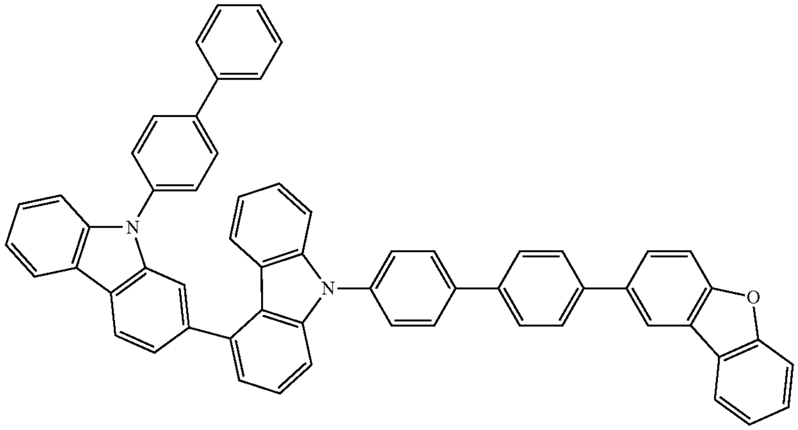
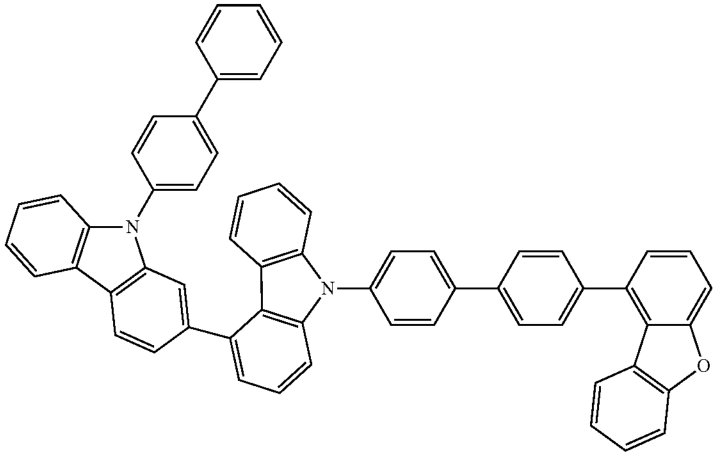

-continued
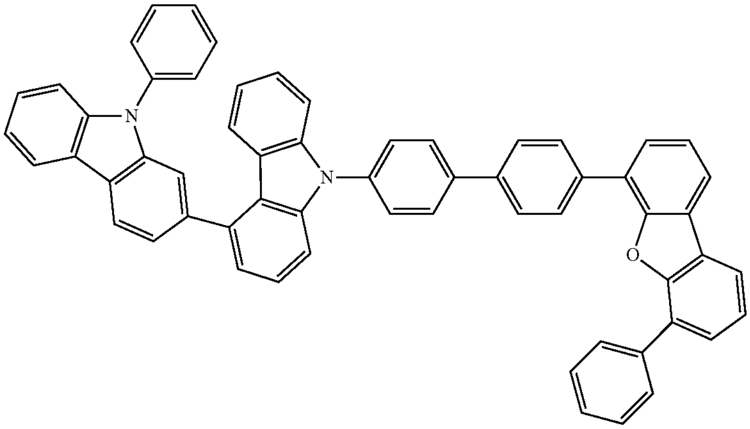
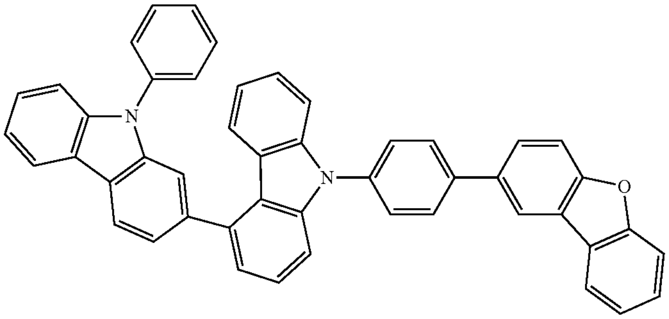
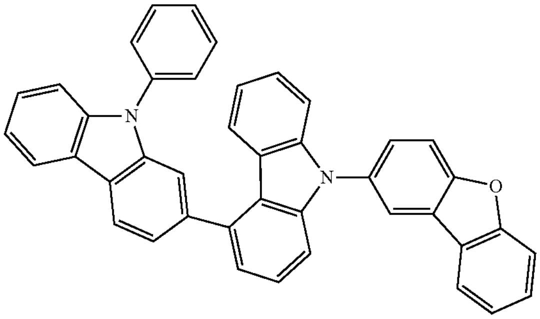
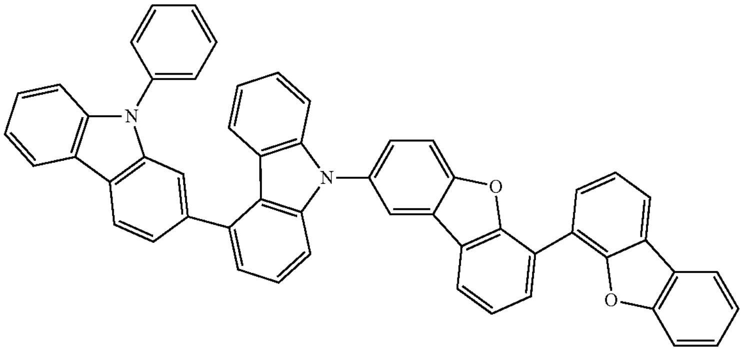
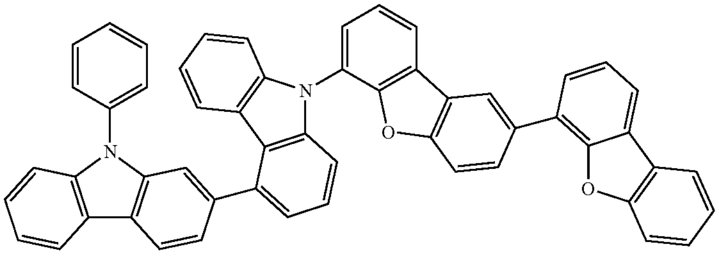

-continued
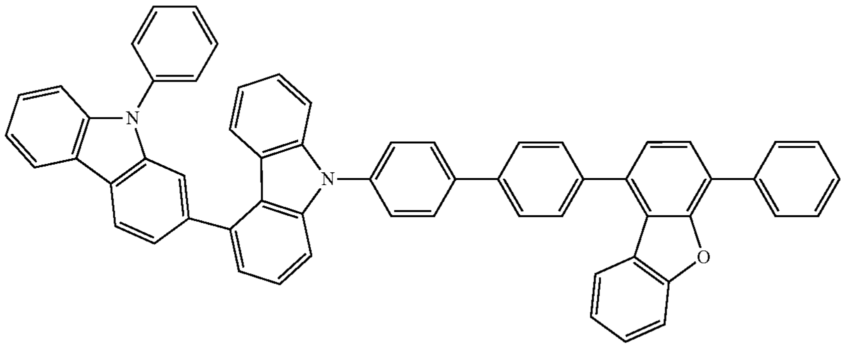
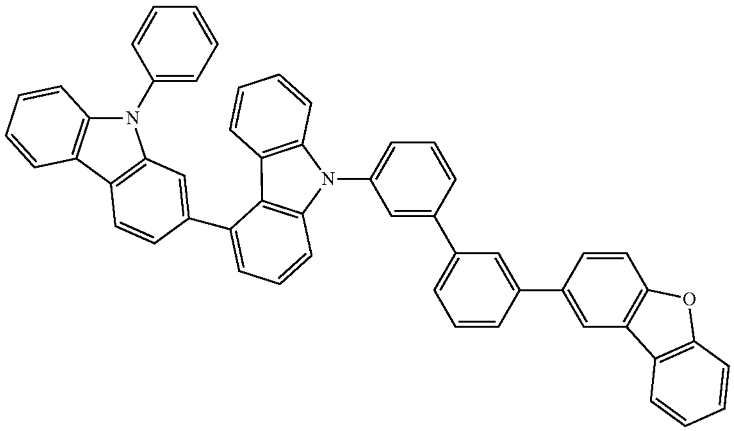
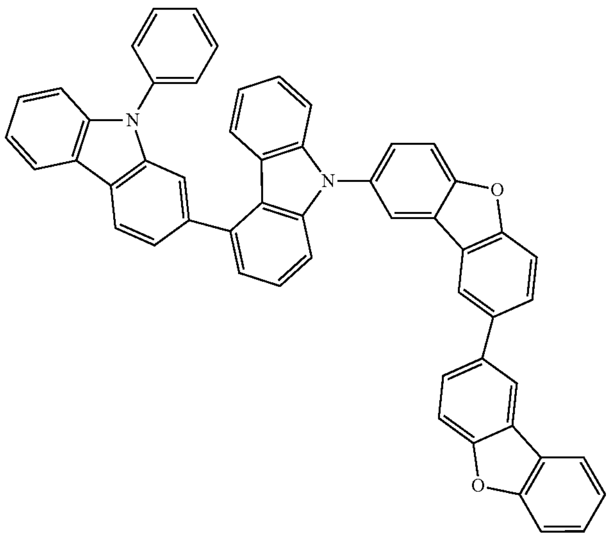

-continued
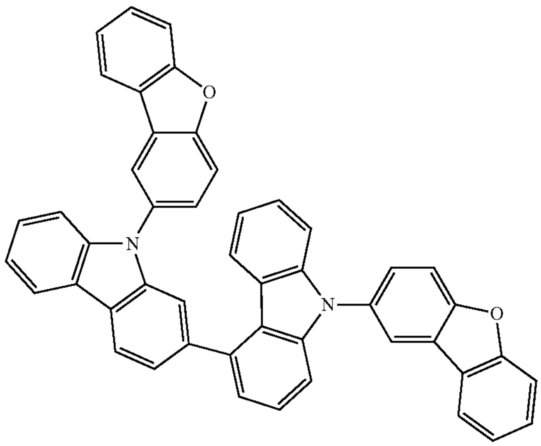
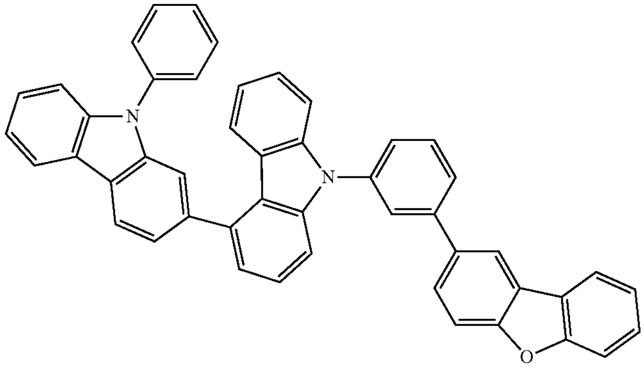
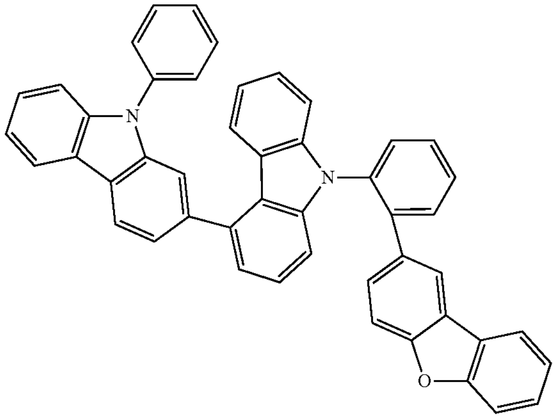
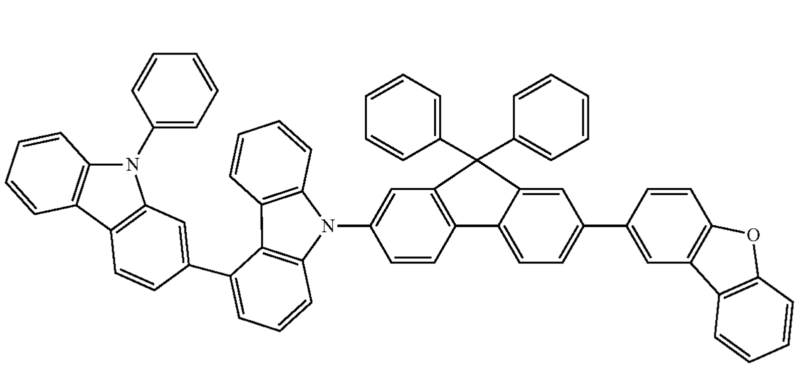

-continued
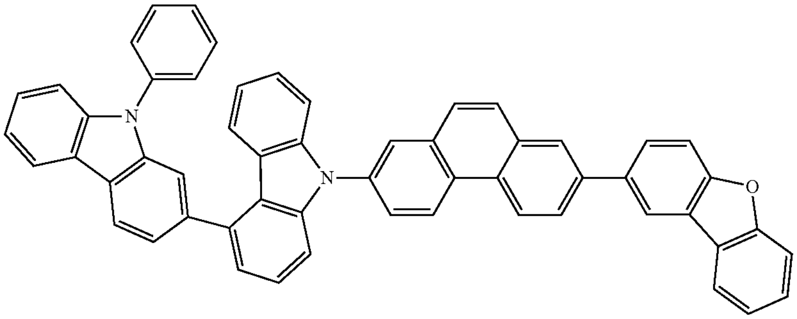
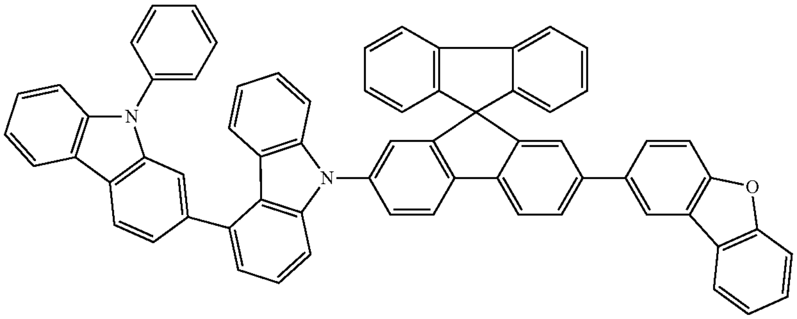
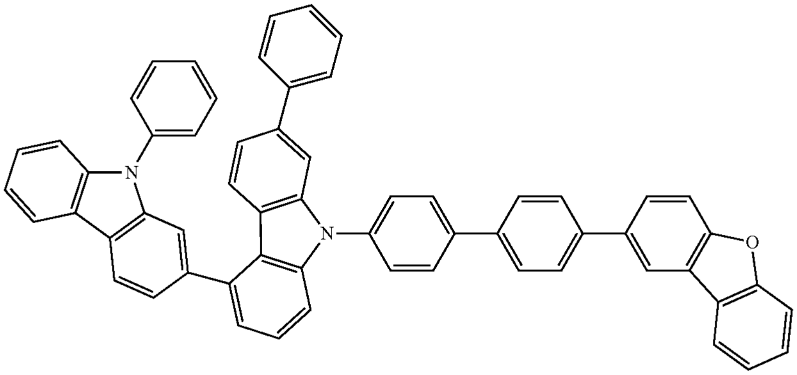
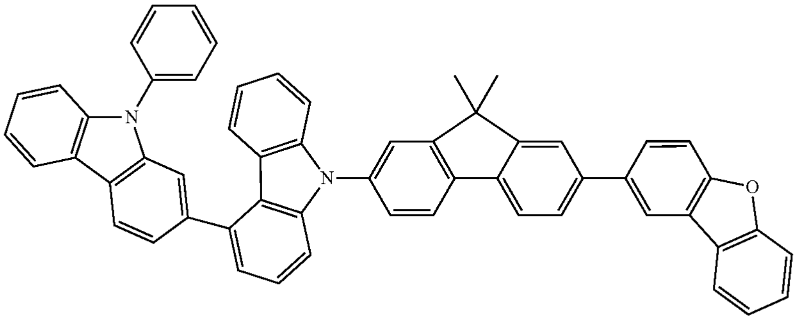
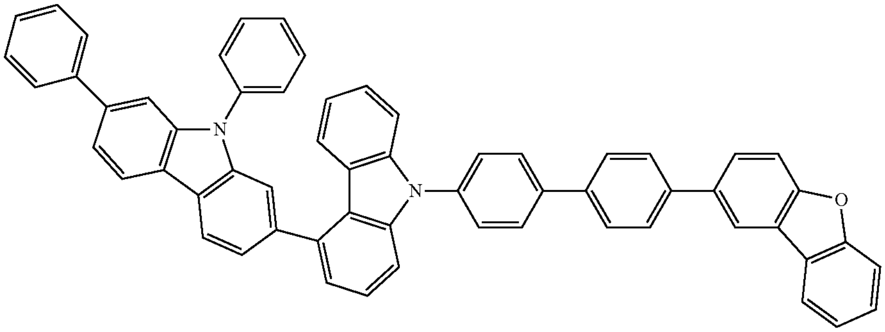

-continued
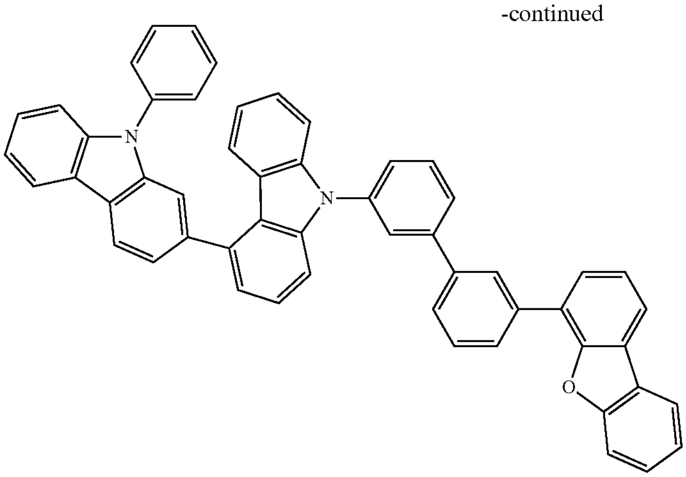
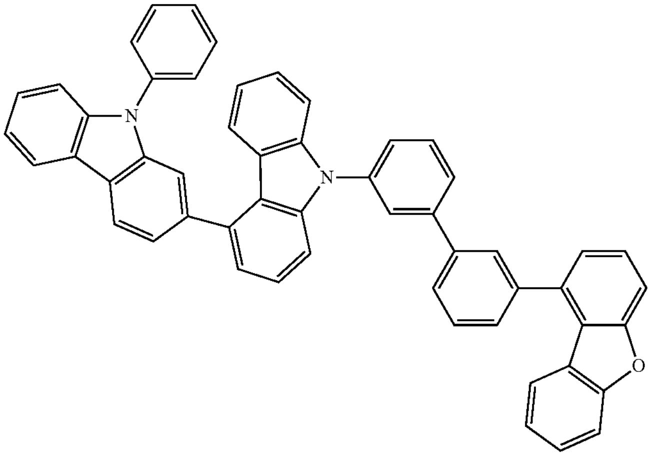
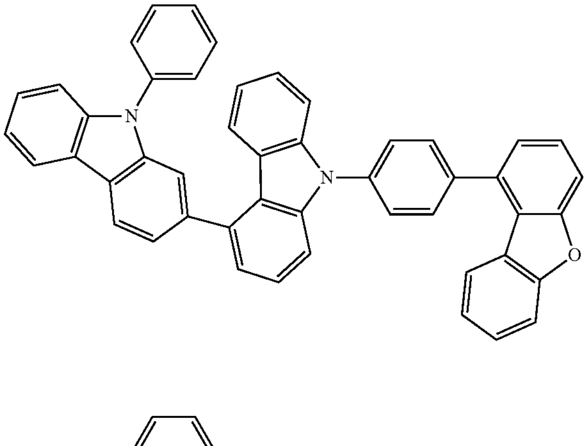
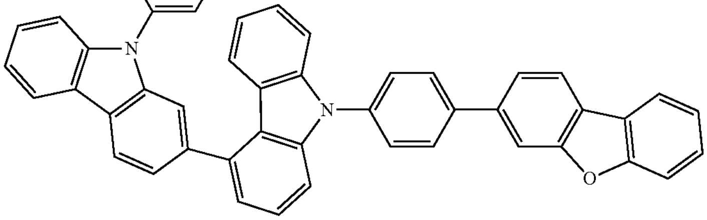

-continued
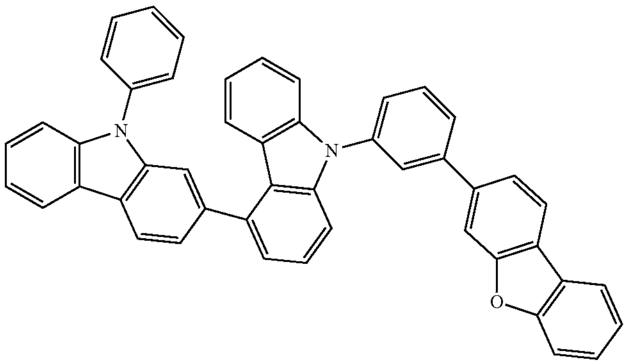
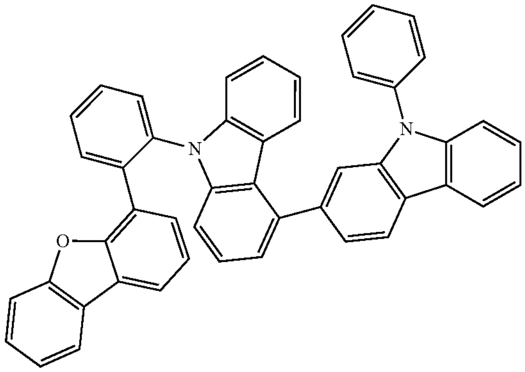
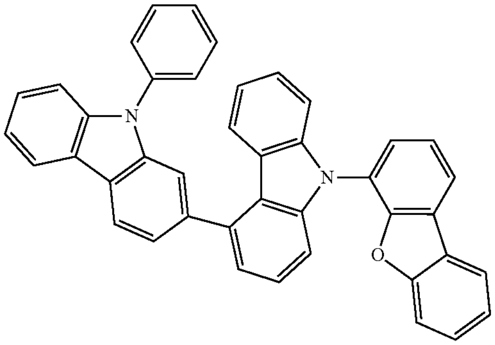
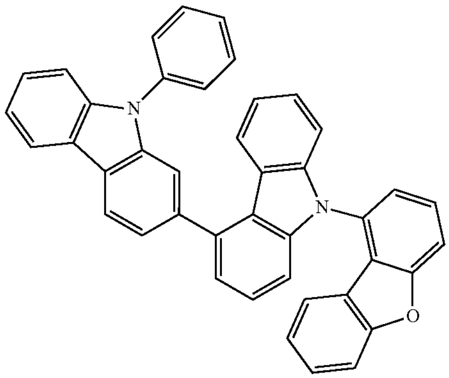
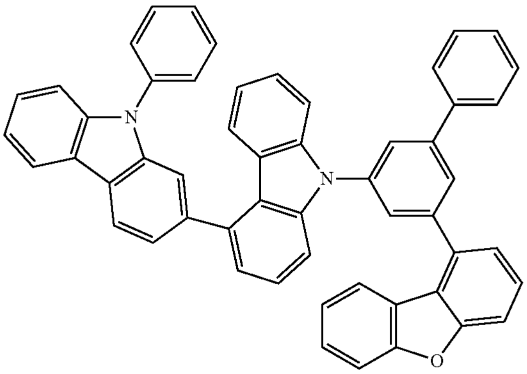
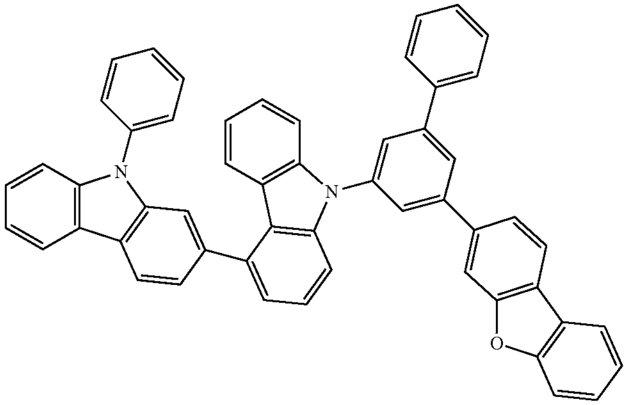

-continued
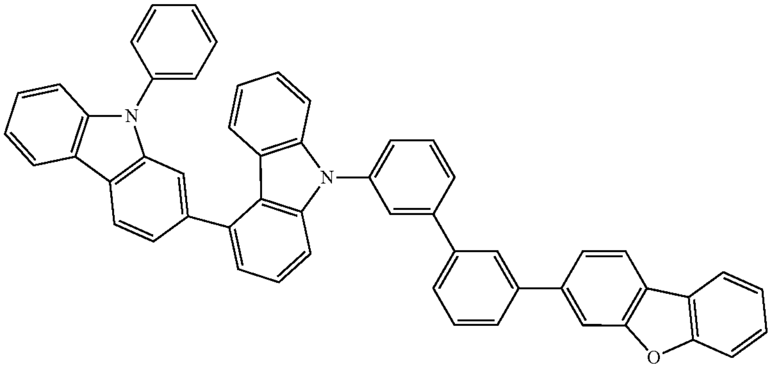
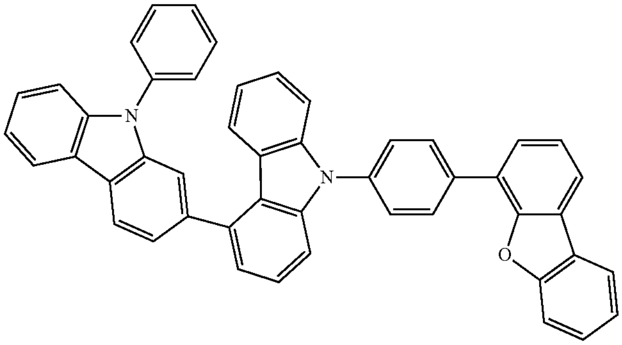
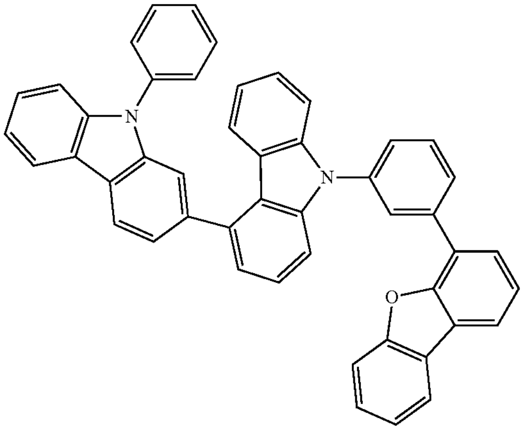
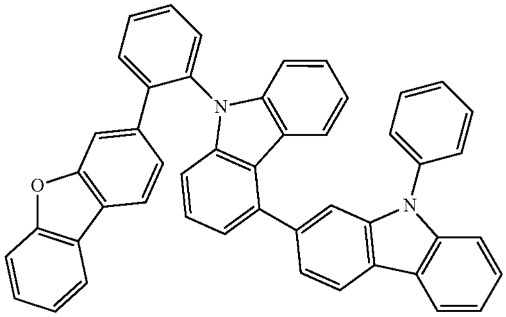
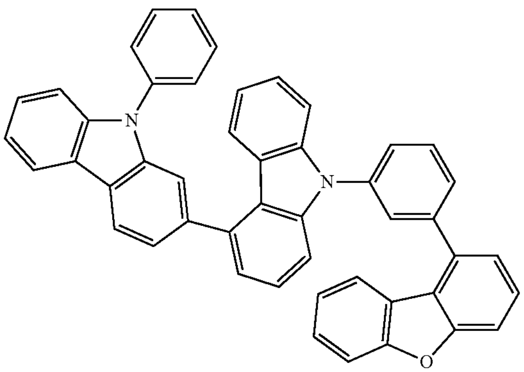
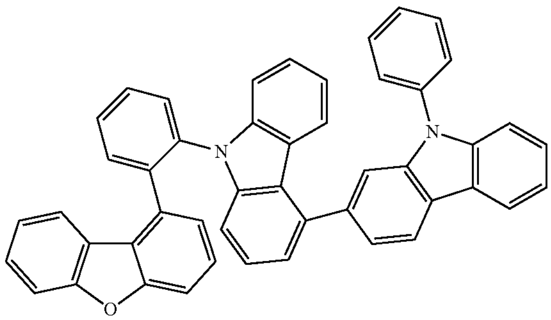

-continued
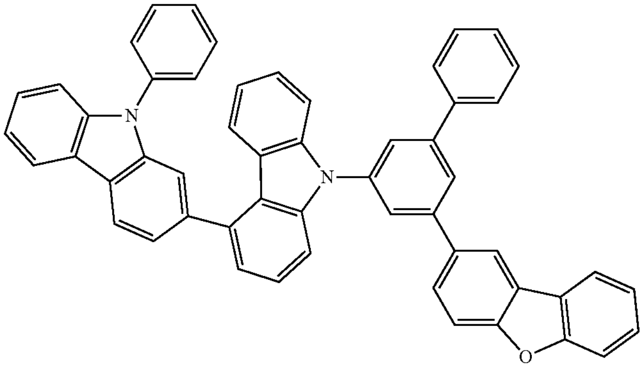
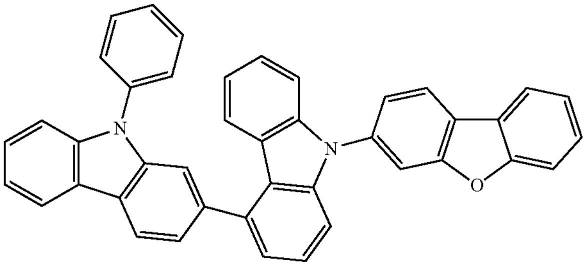
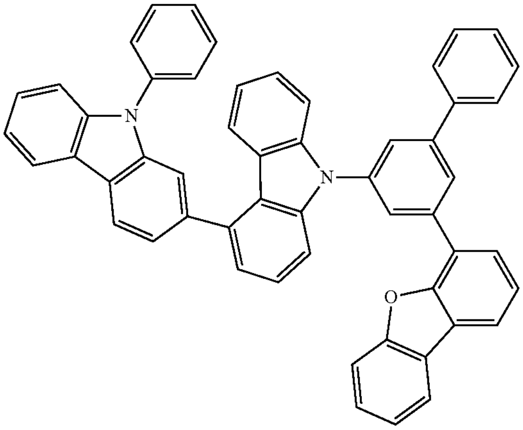
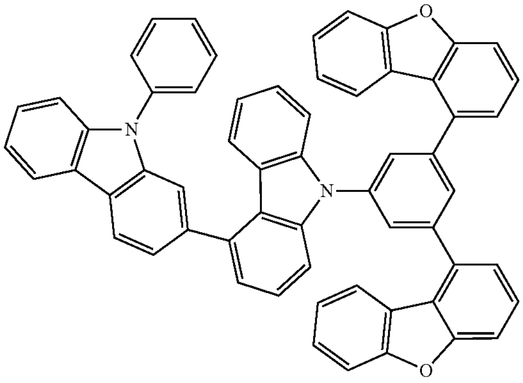
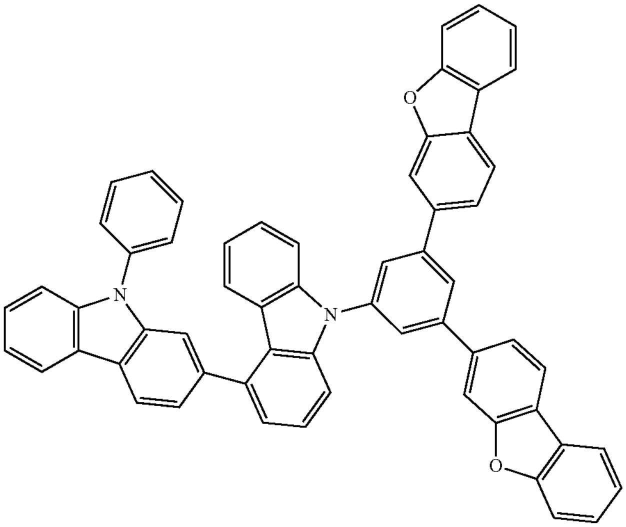

-continued
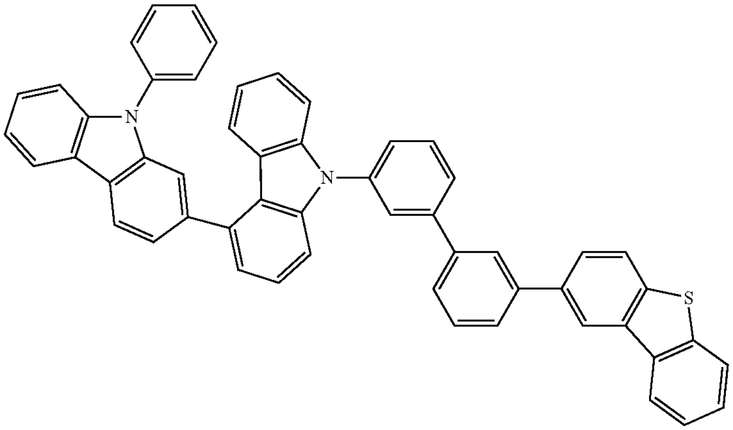
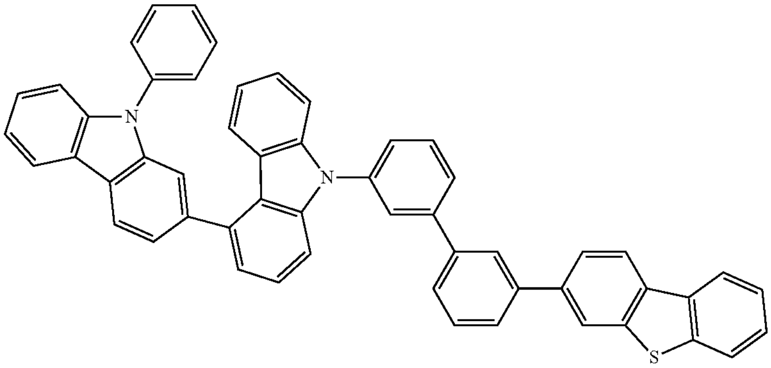
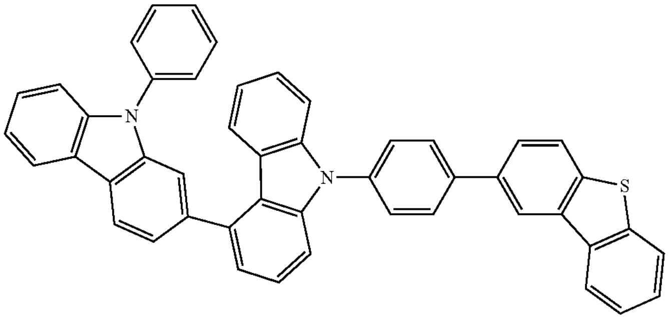
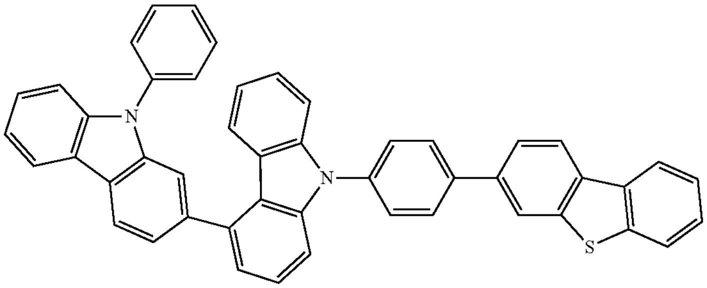

-continued
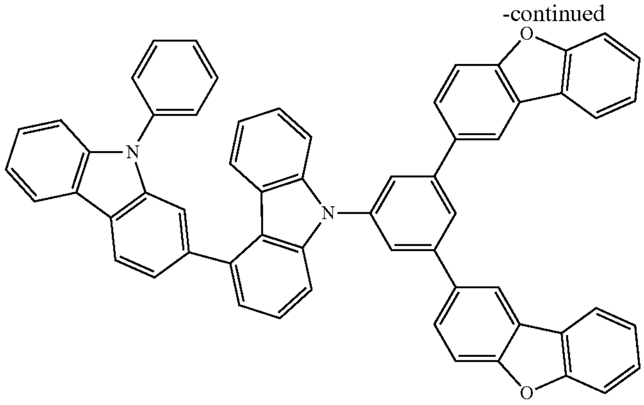
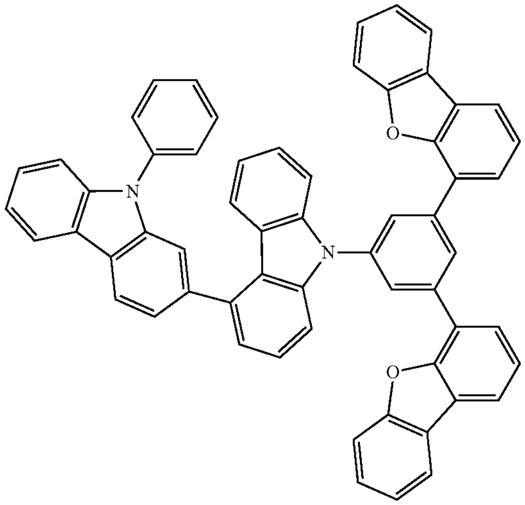
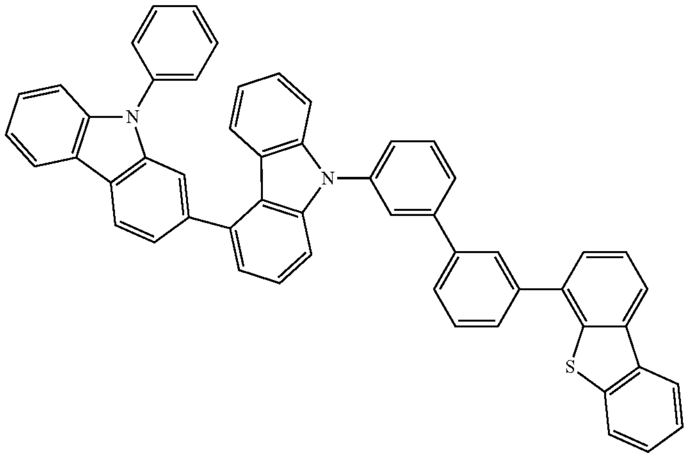

-continued
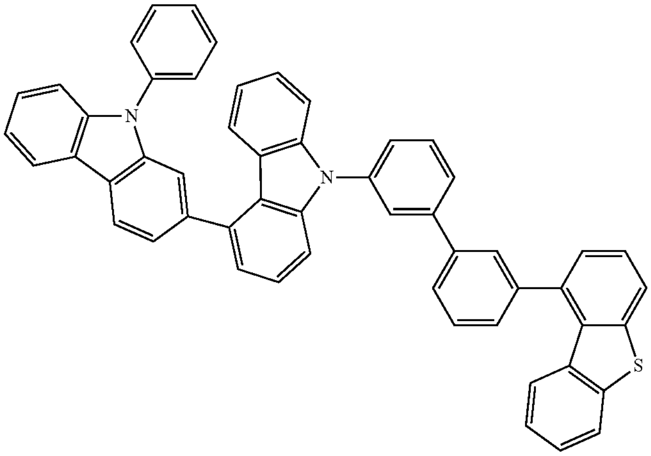
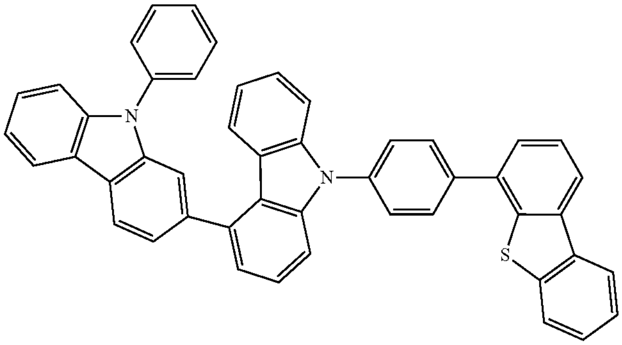
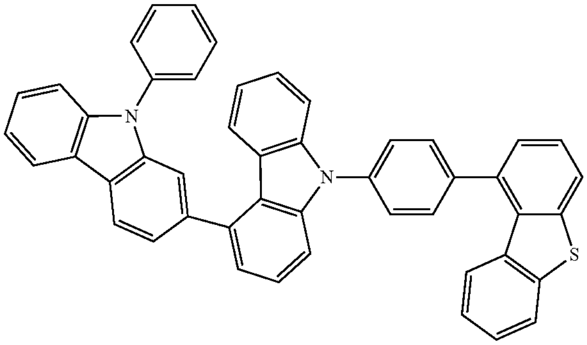
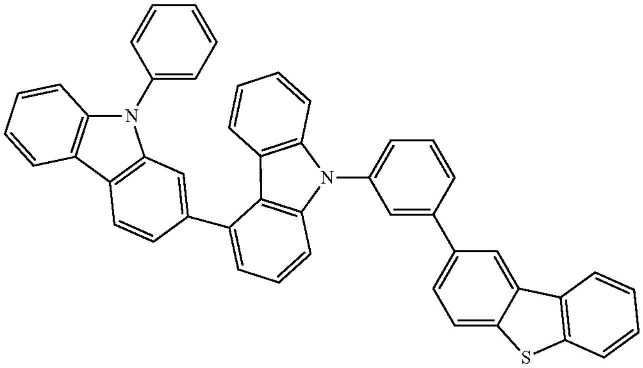

-continued
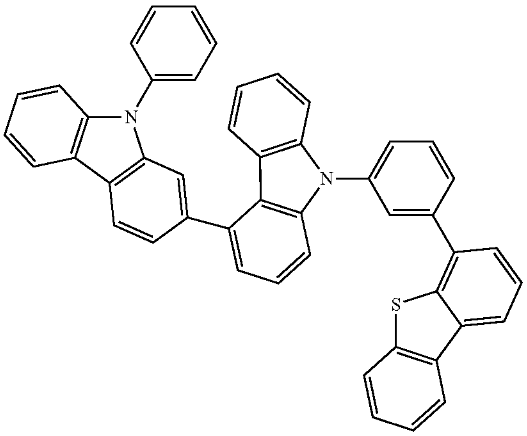
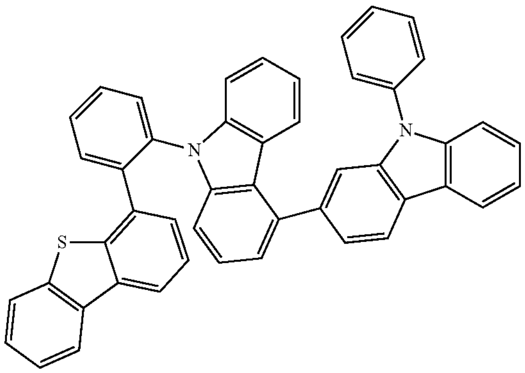
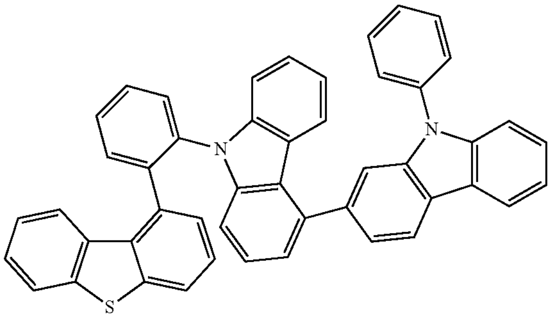
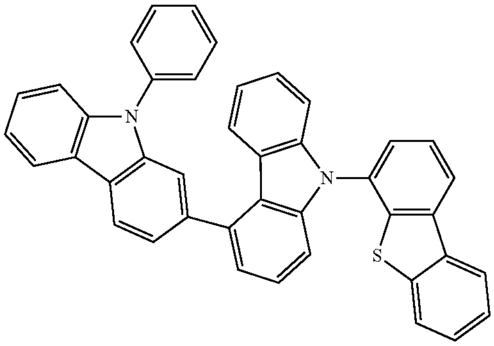
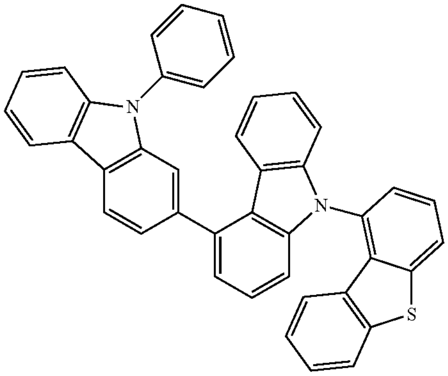
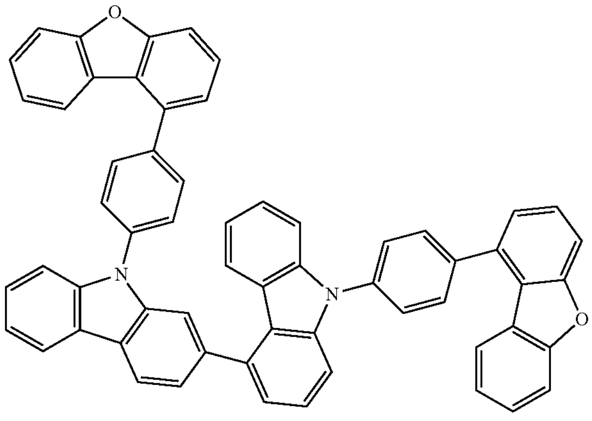
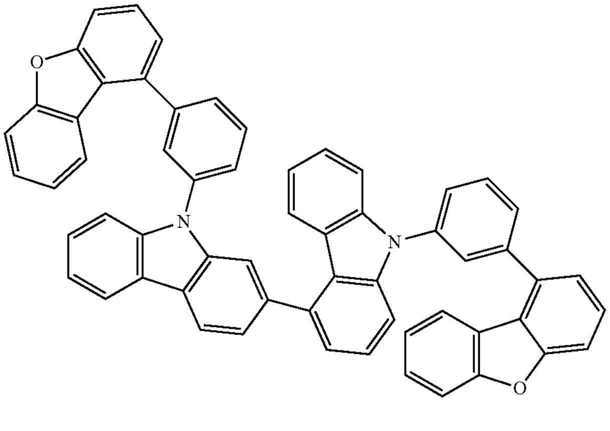
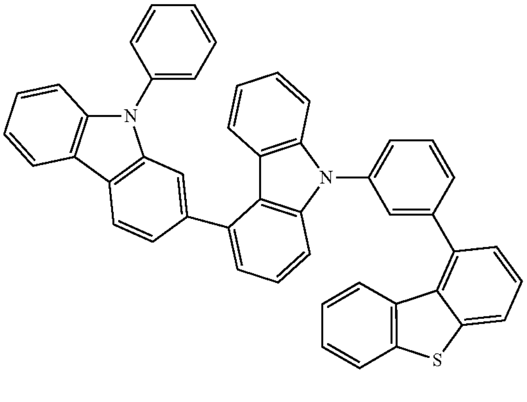

-continued
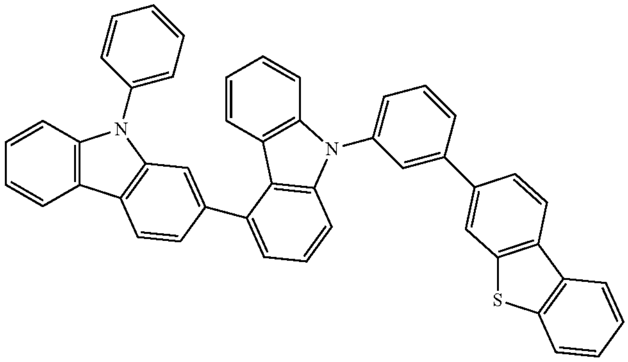
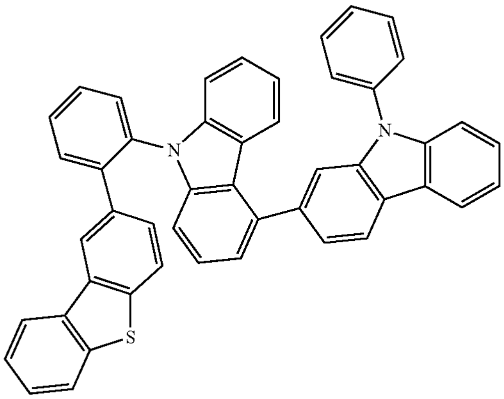
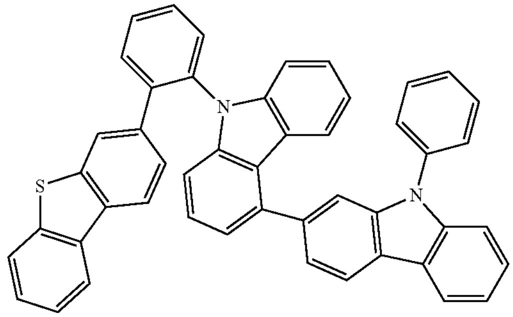
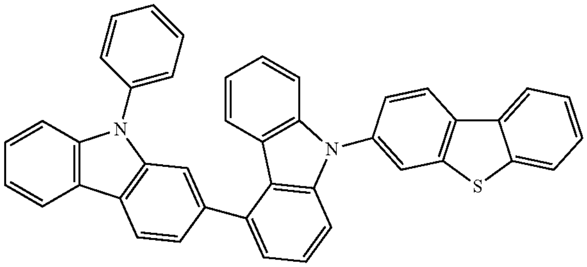
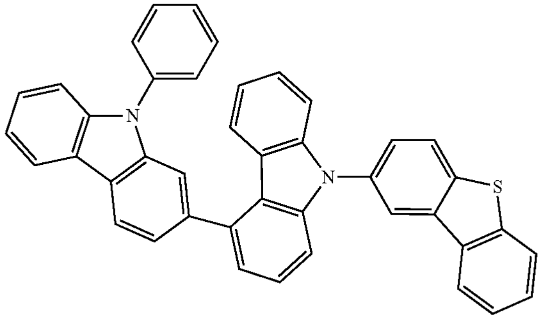
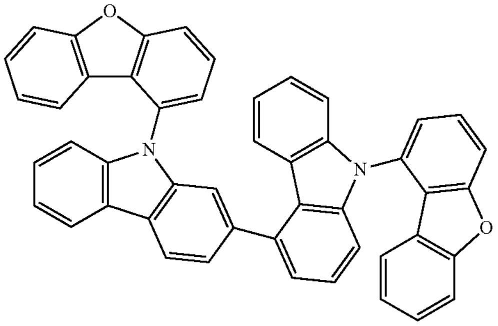
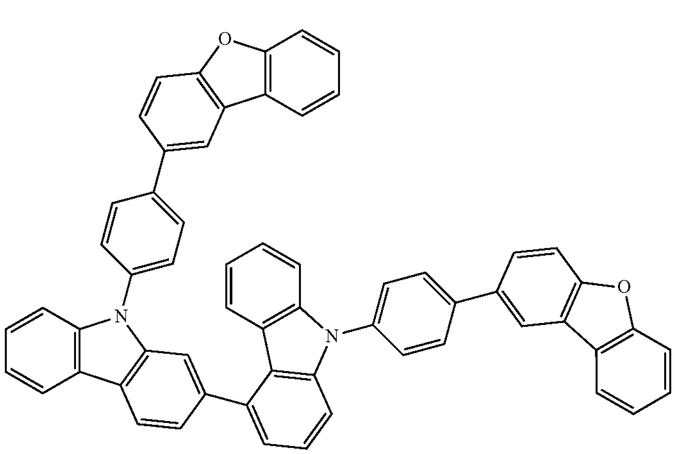

-continued
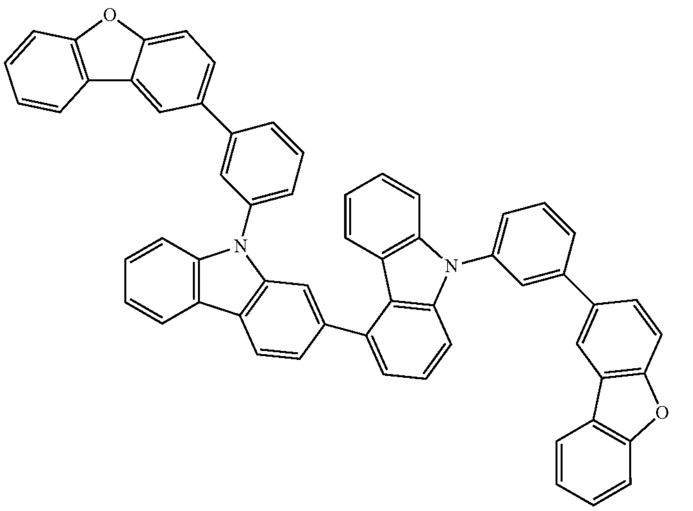
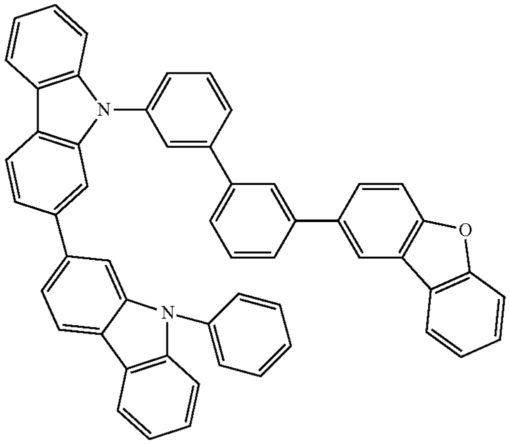
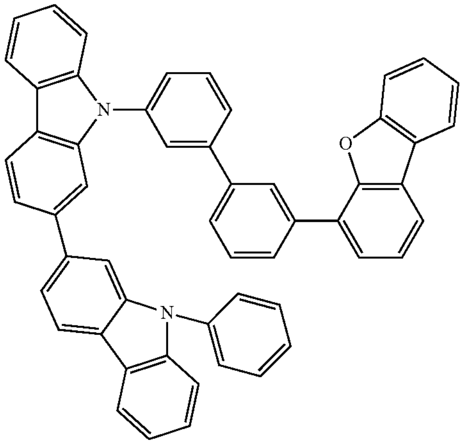
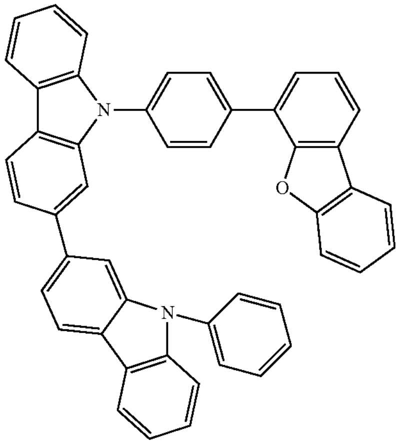
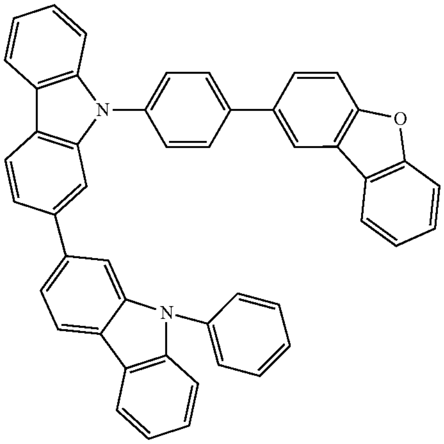

-continued
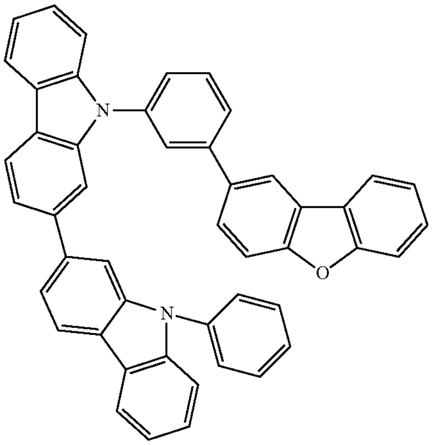
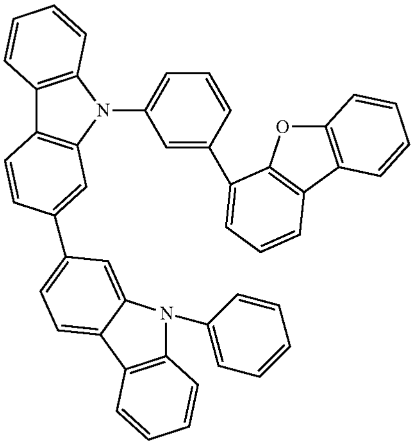
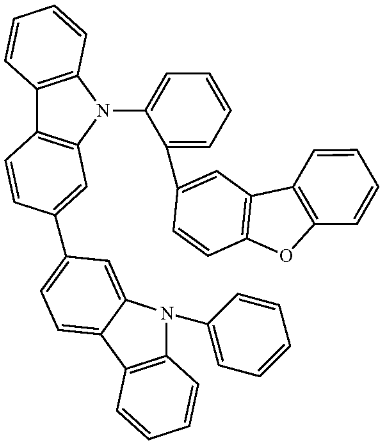
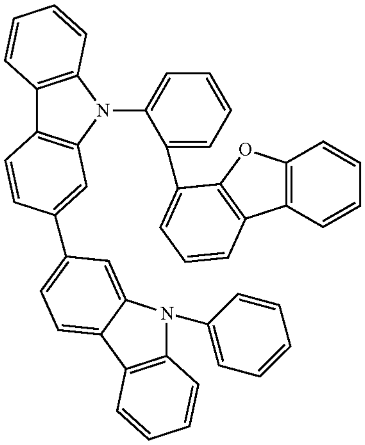
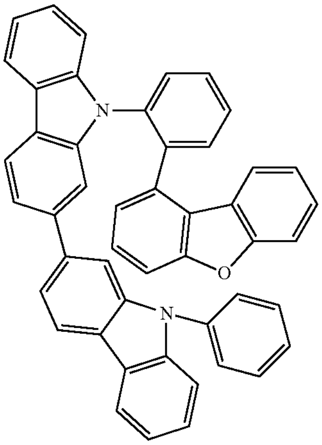
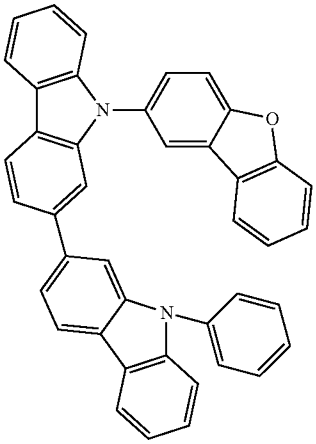
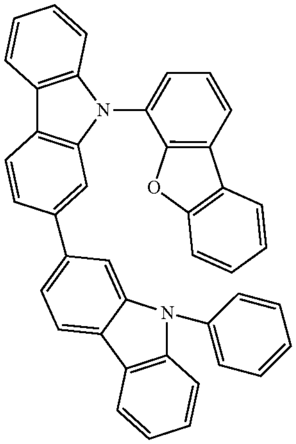
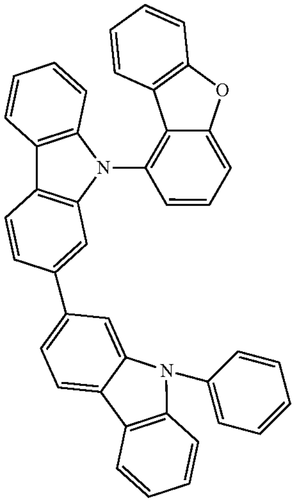

-continued
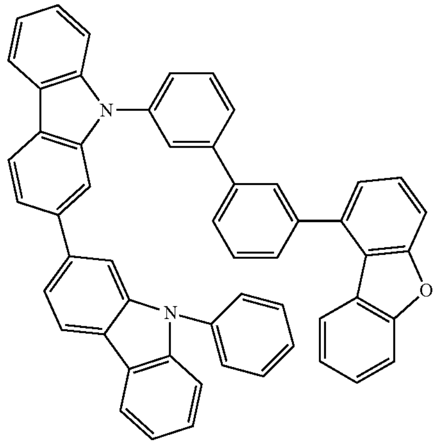
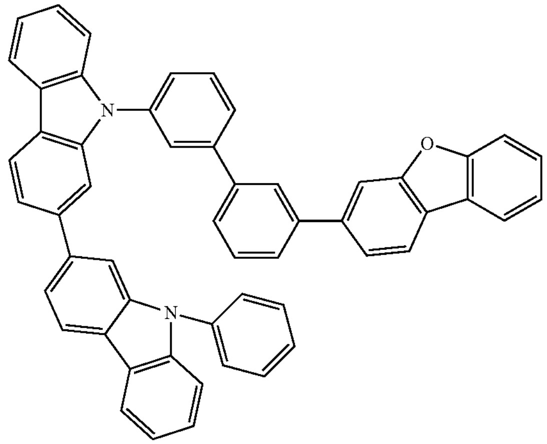
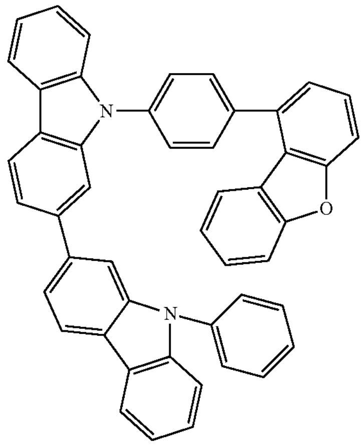
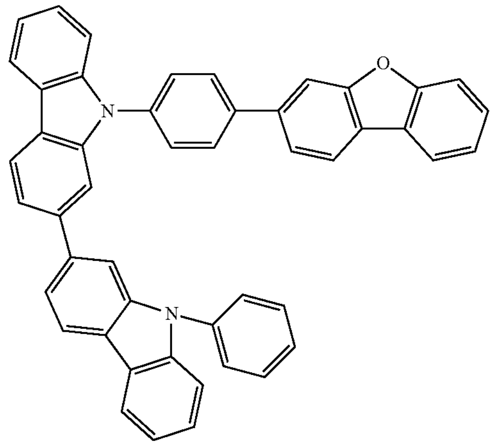
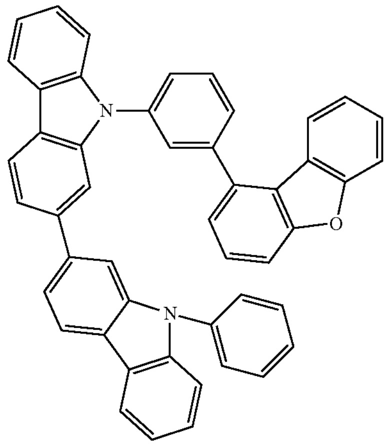
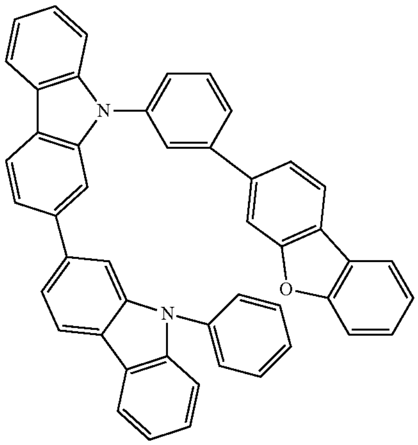

-continued
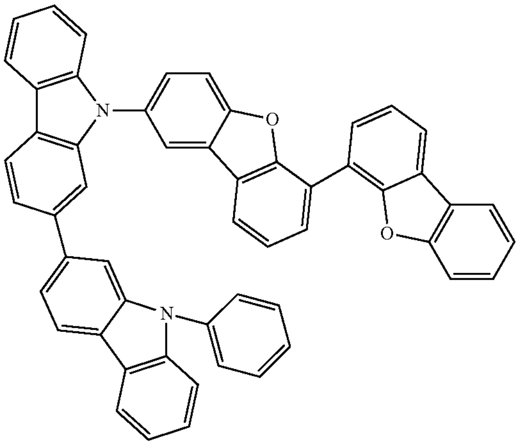
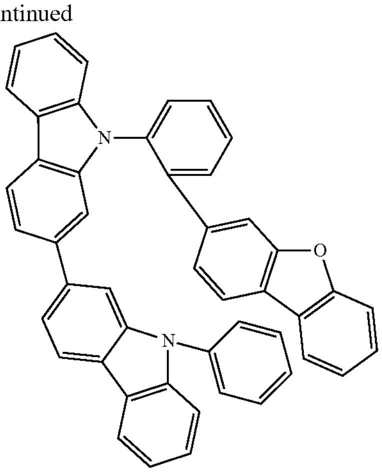
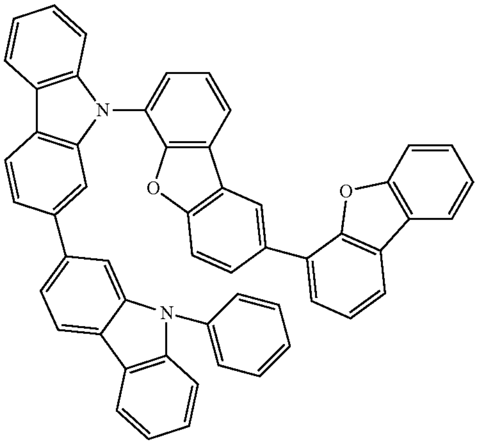
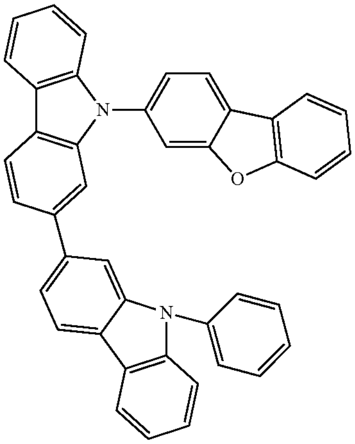
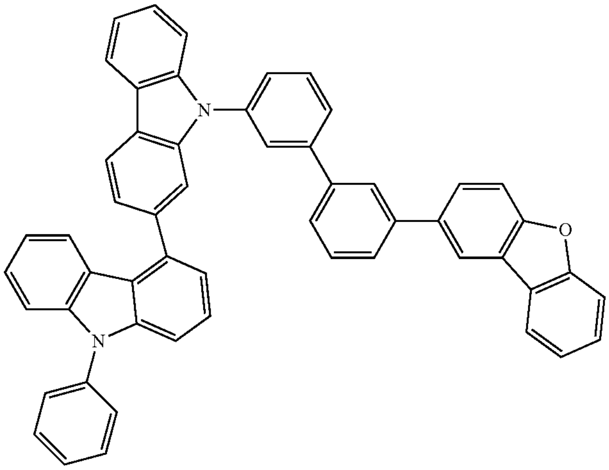

-continued
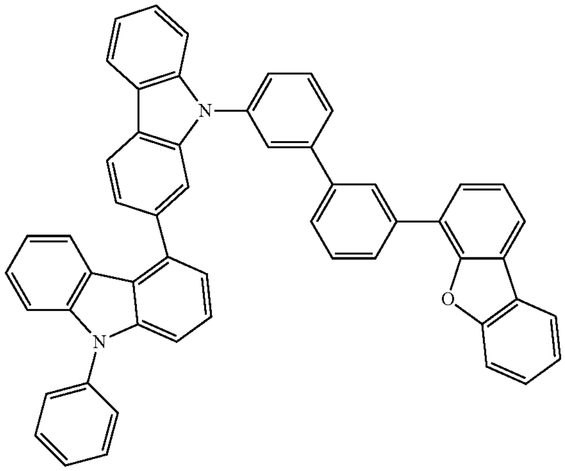
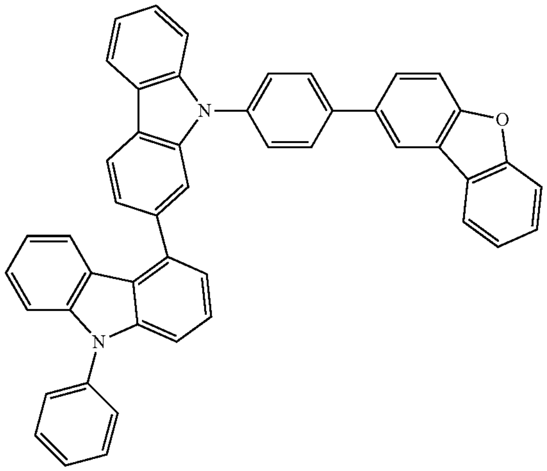
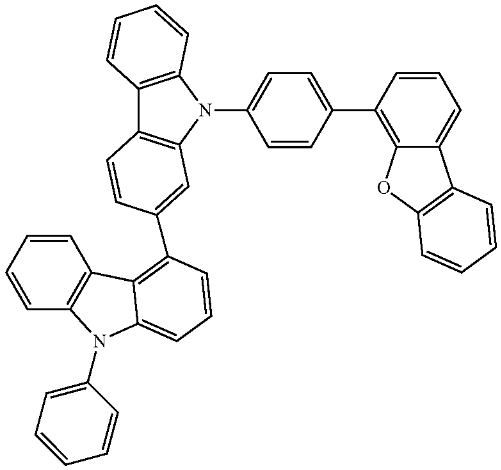
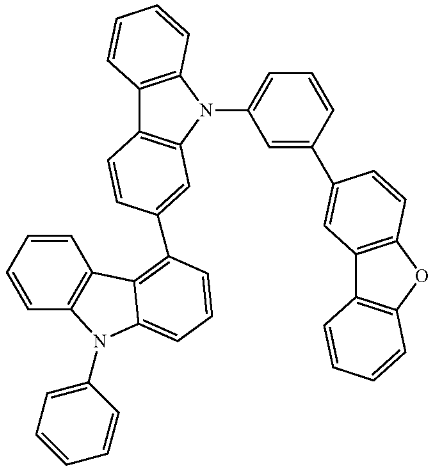
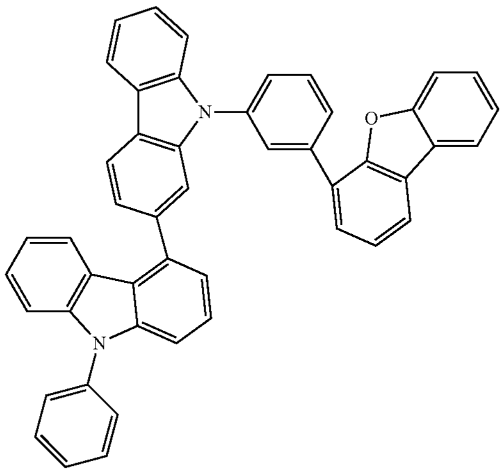
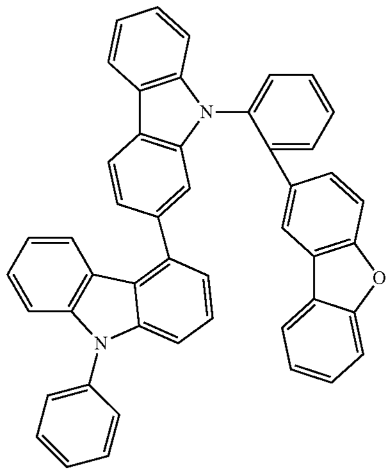

-continued
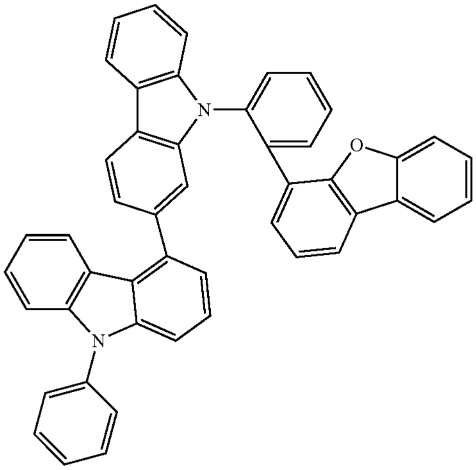
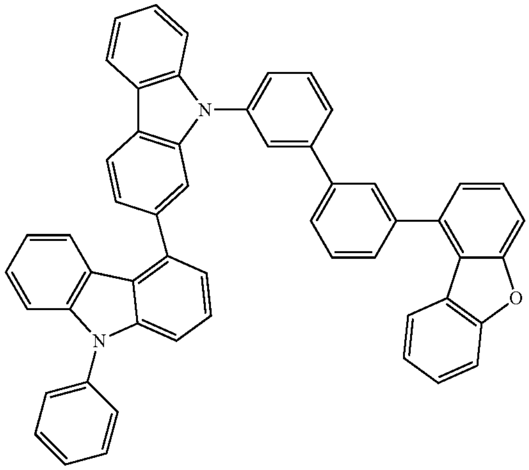
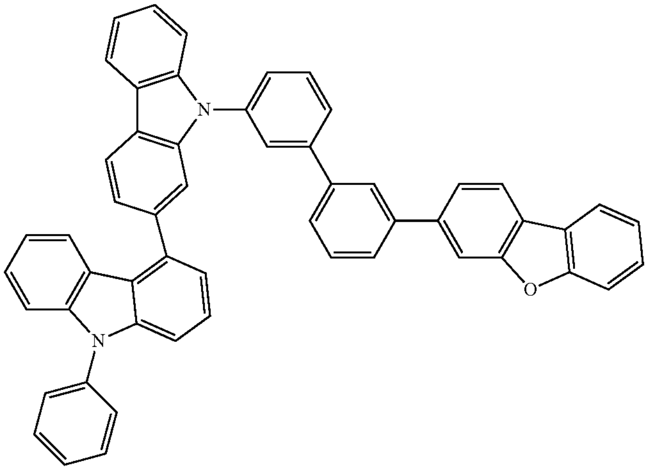
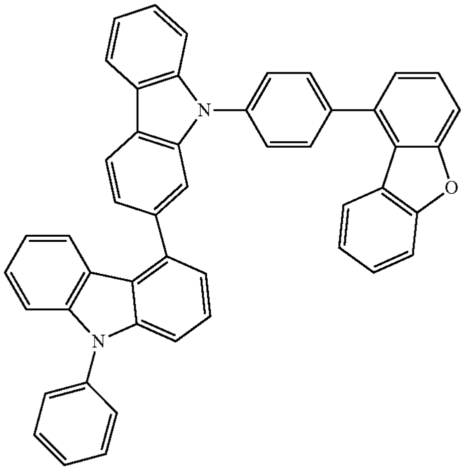
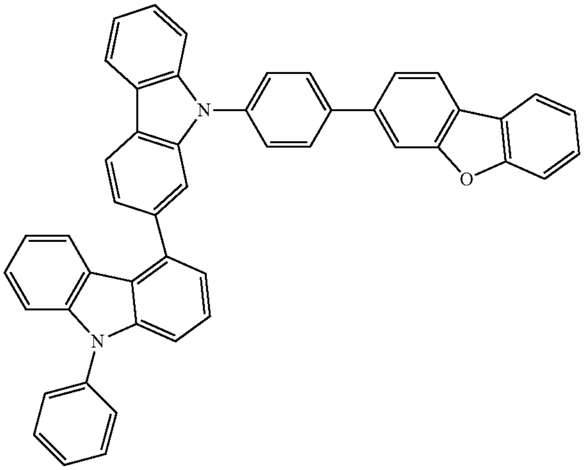

-continued
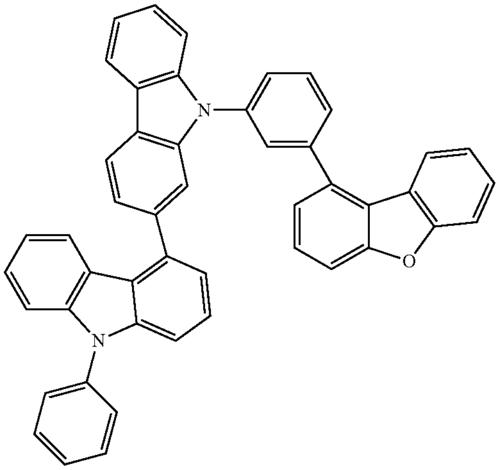
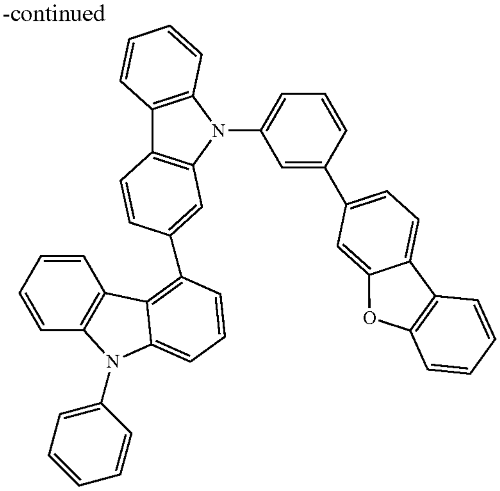
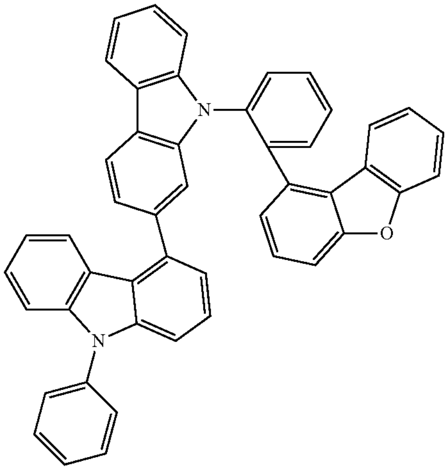
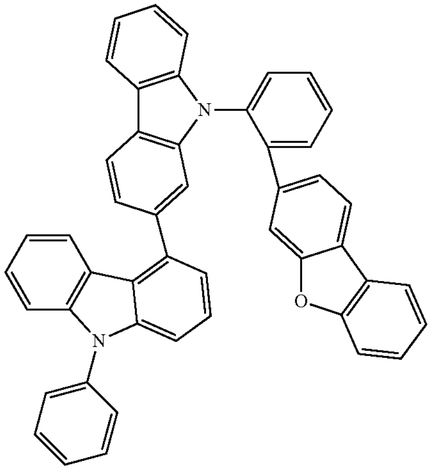
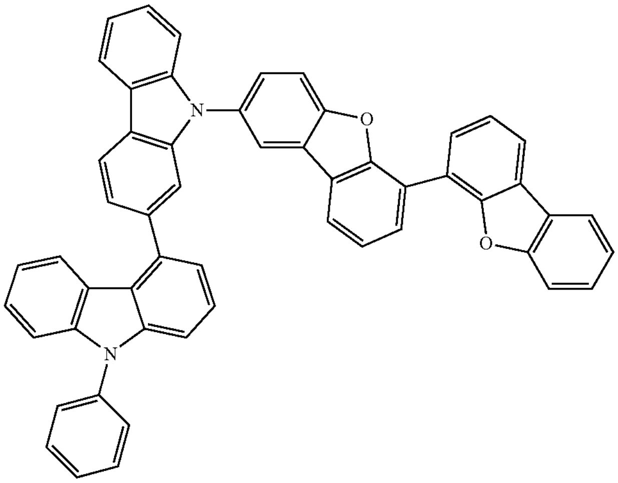
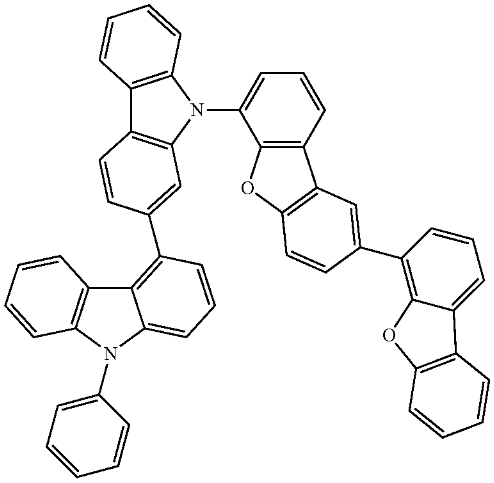

-continued
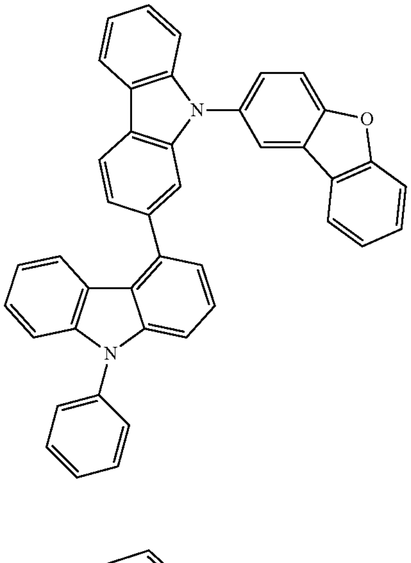
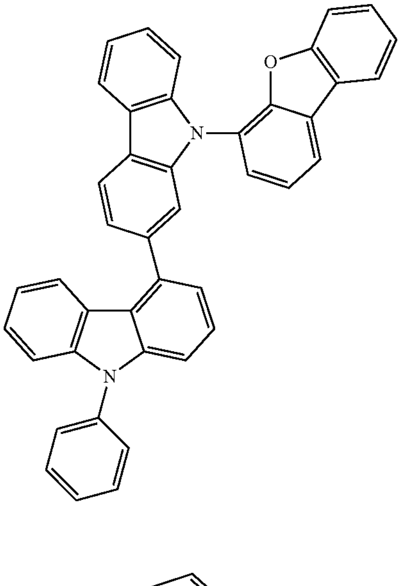
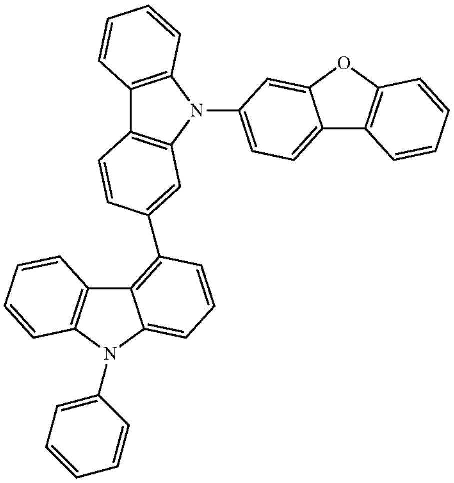
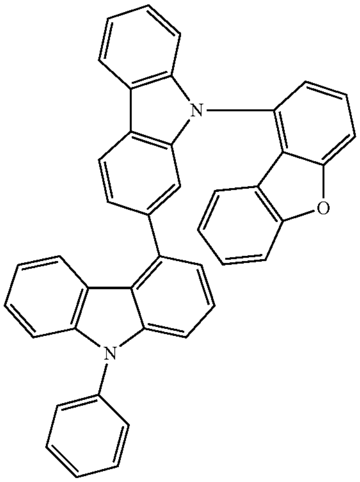
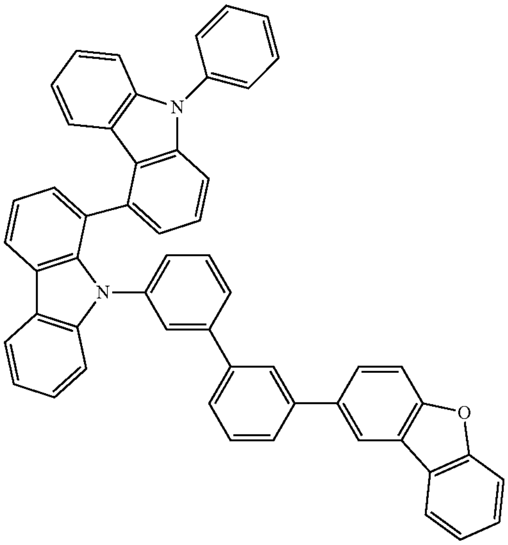
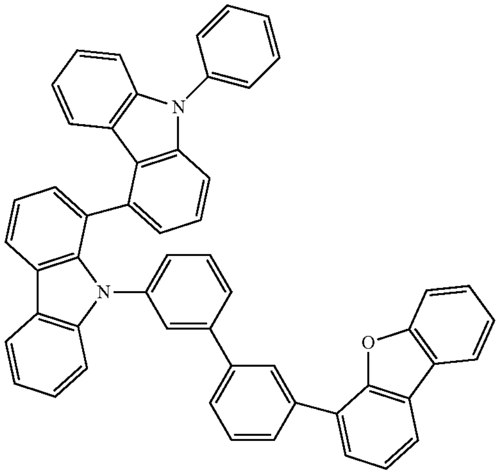

-continued
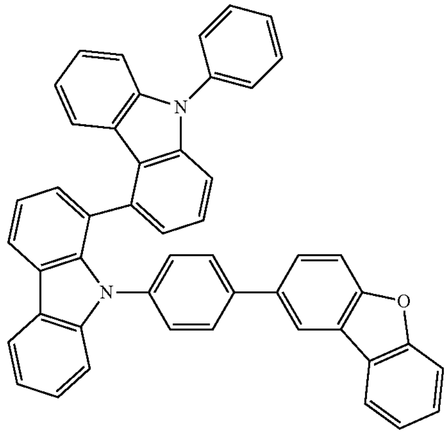
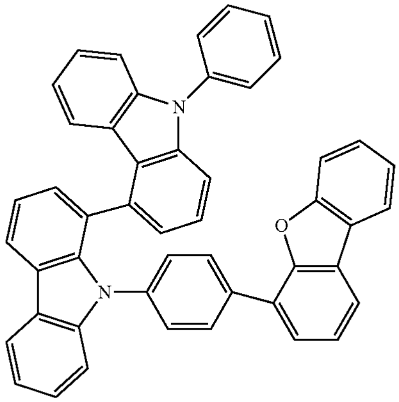
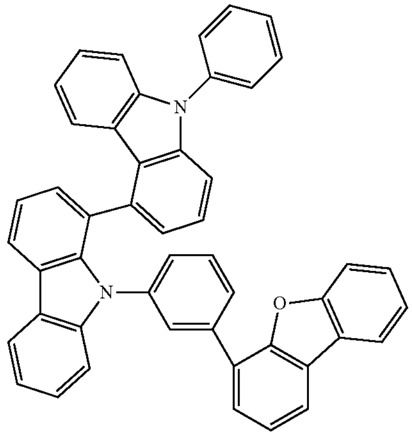
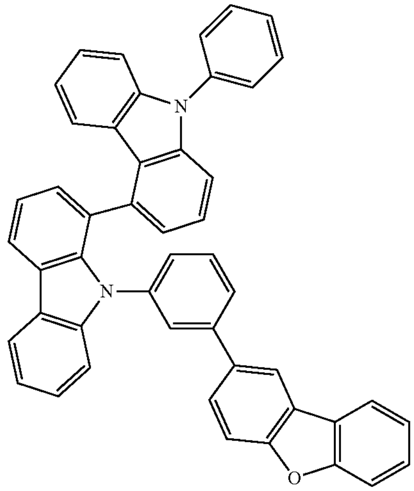
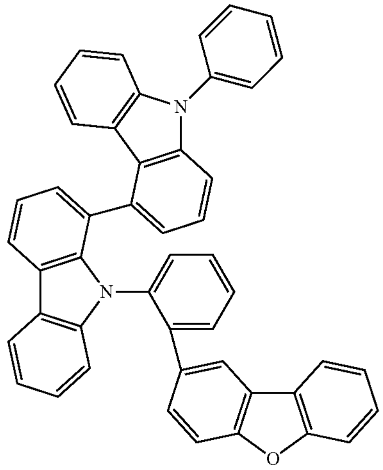
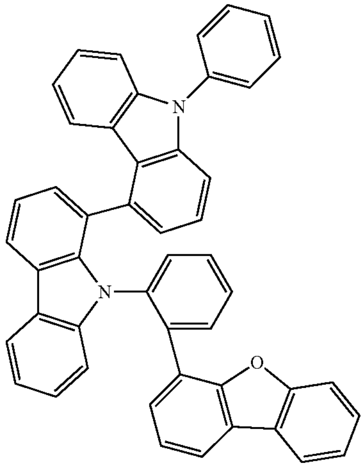

-continued
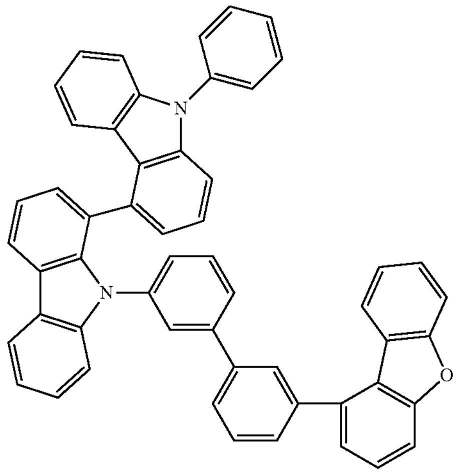
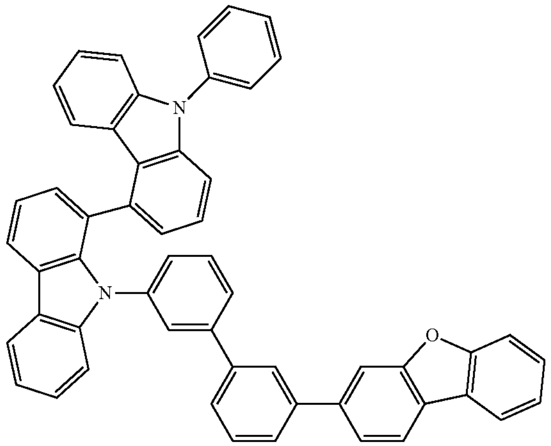
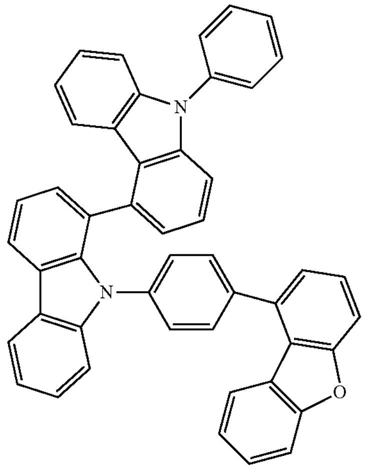
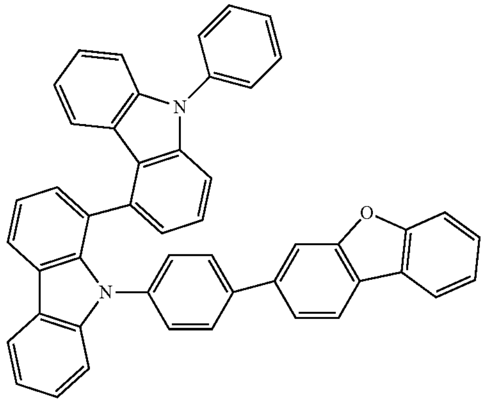
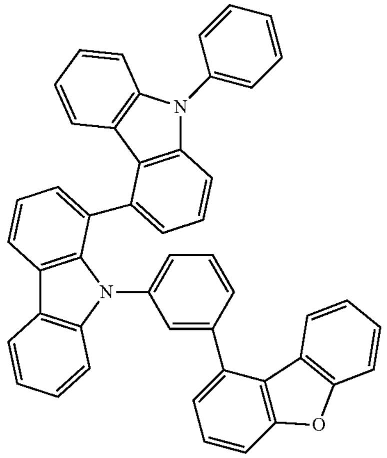
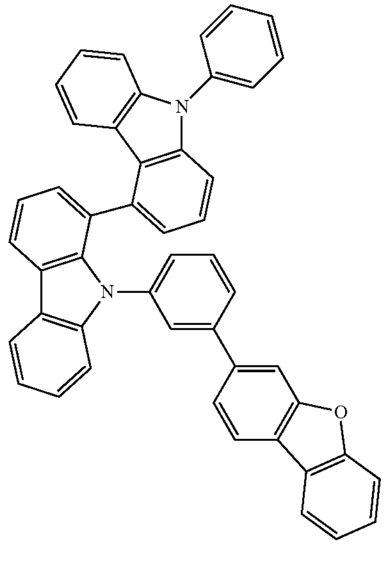
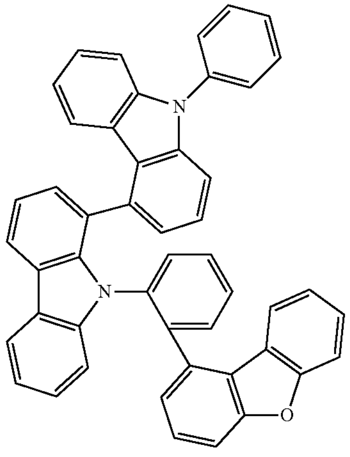

-continued
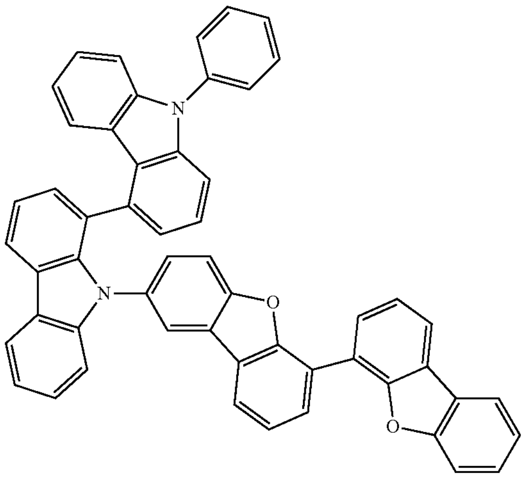
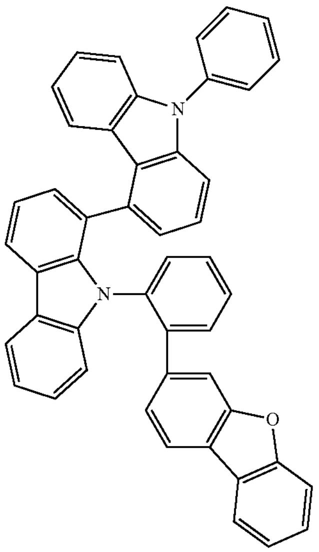
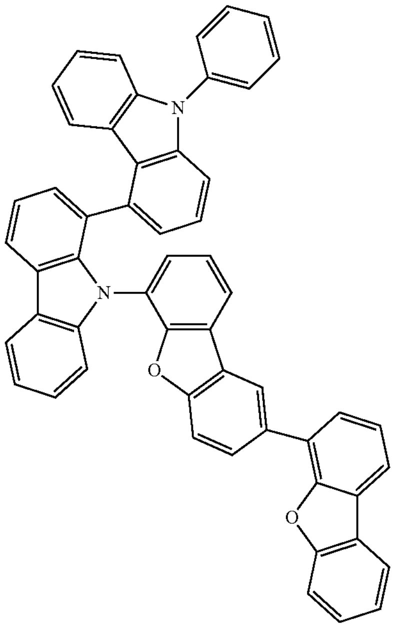
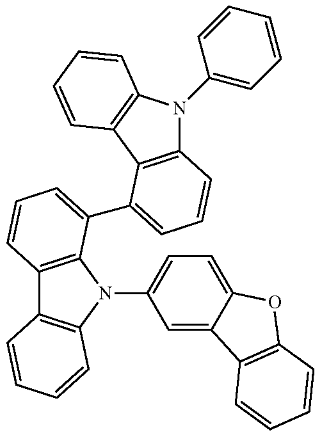
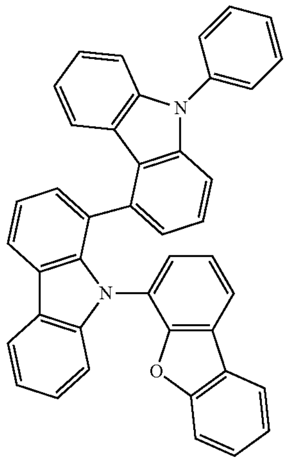
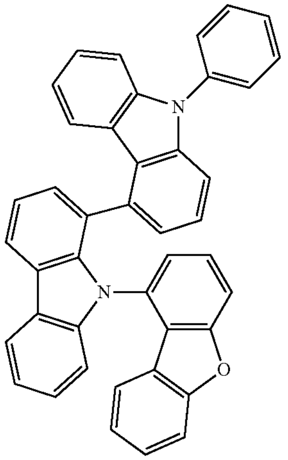
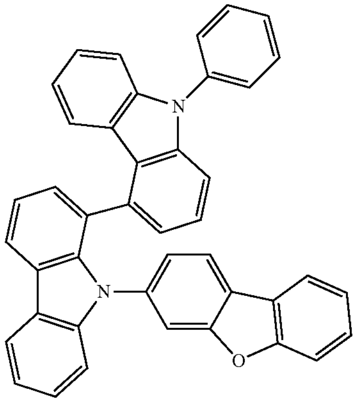

-continued
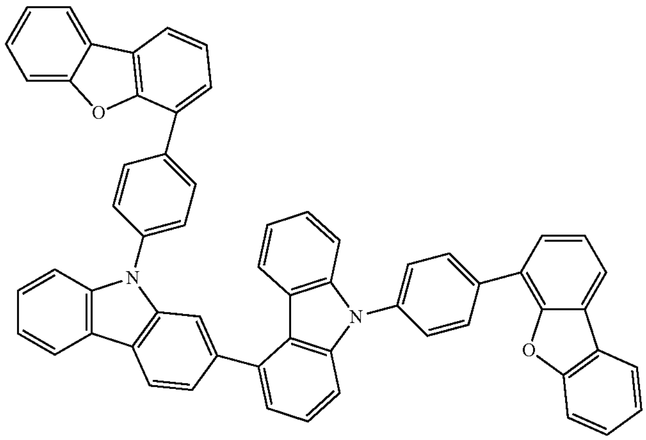
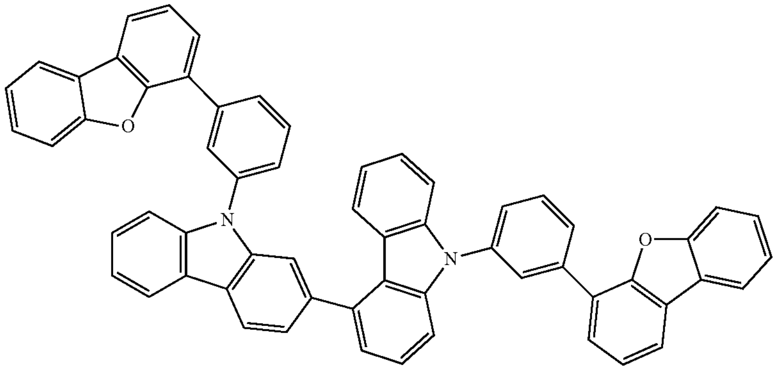
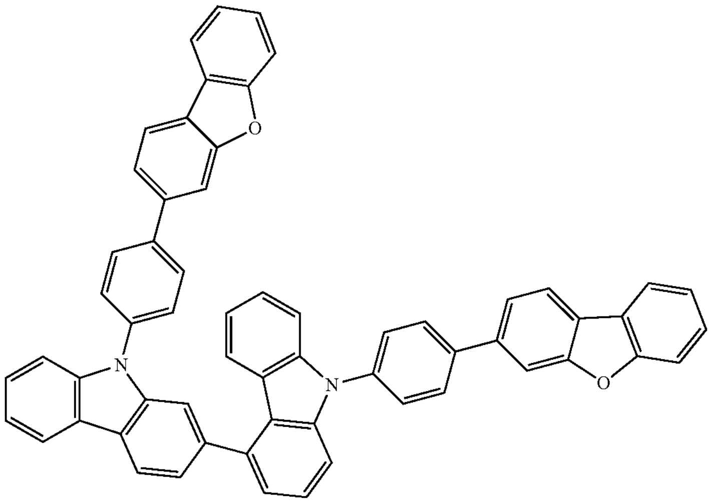

-continued
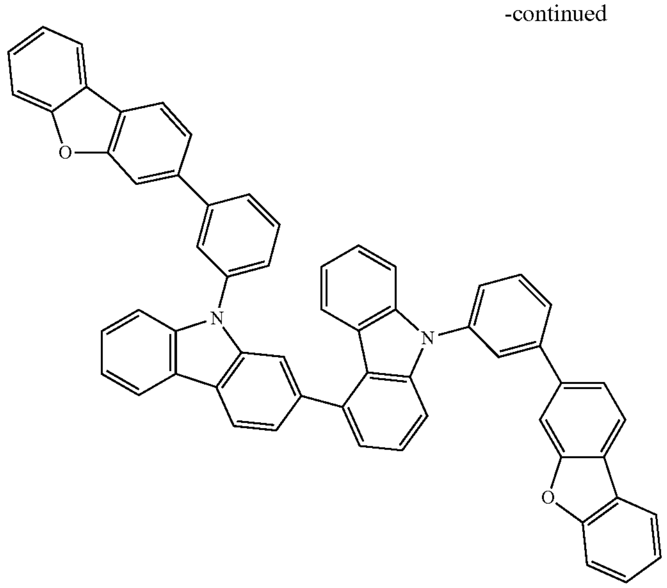
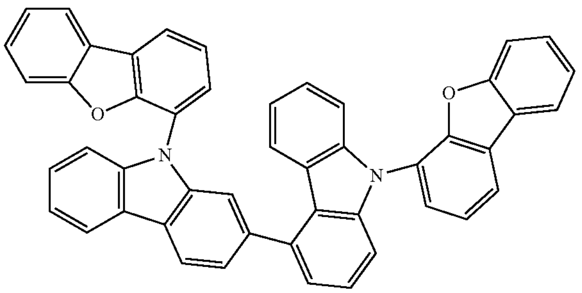
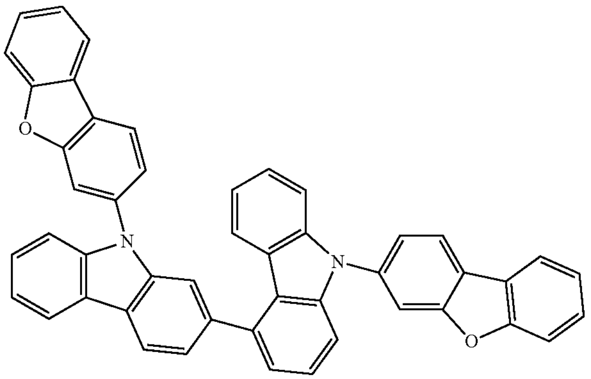
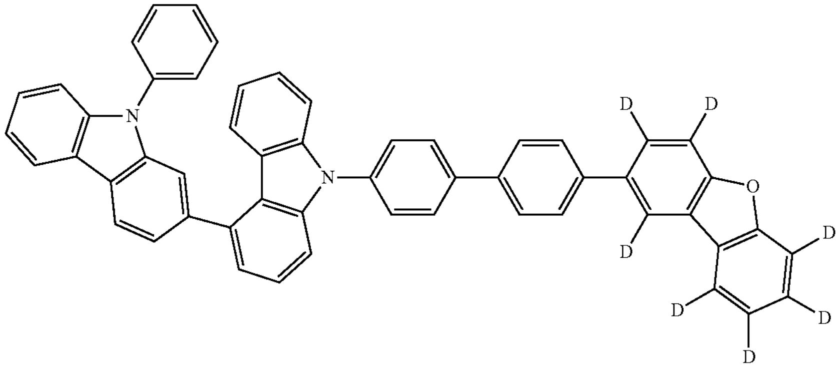

-continued
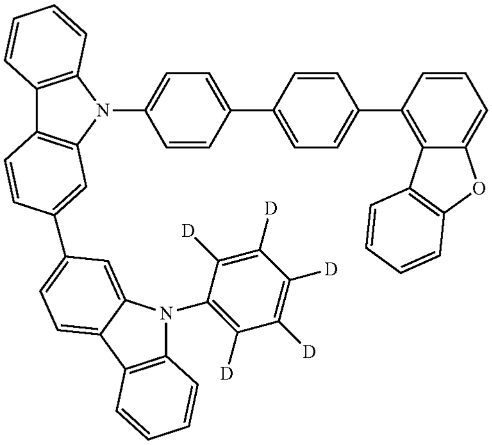
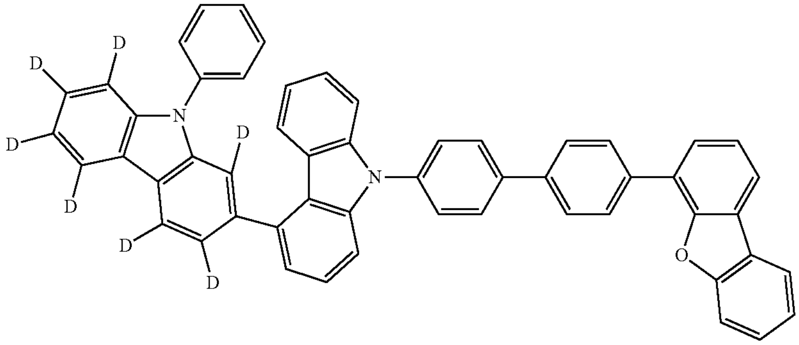
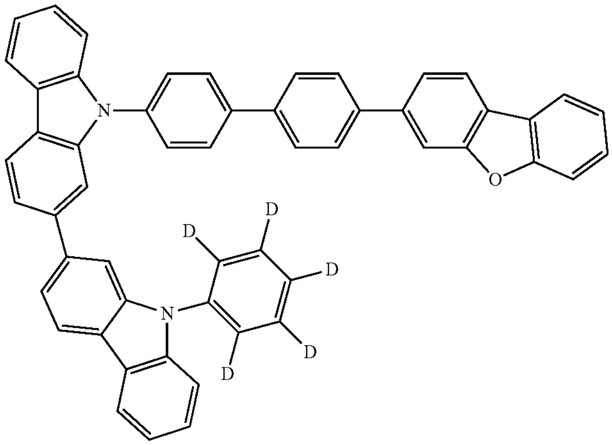
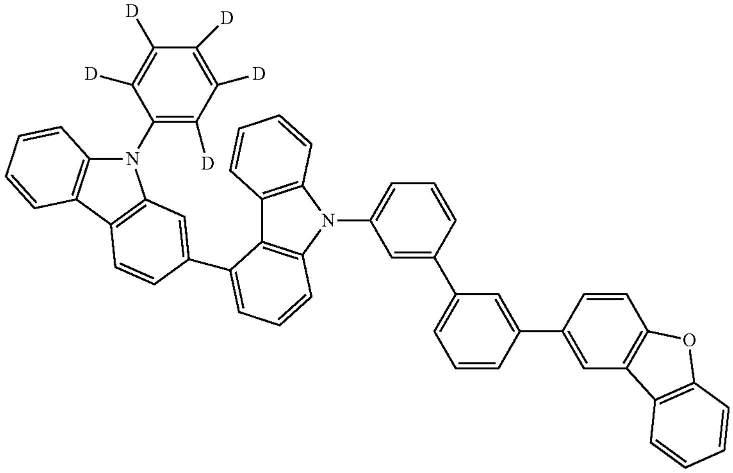

-continued
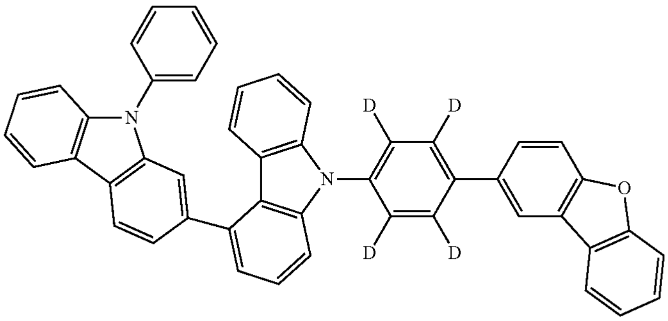
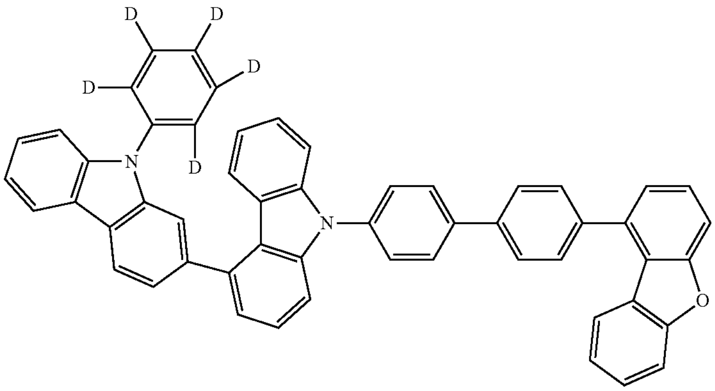
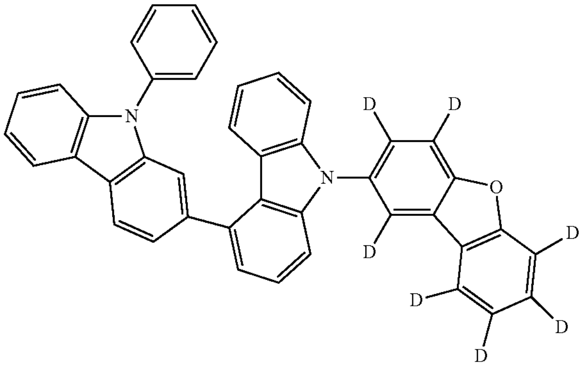
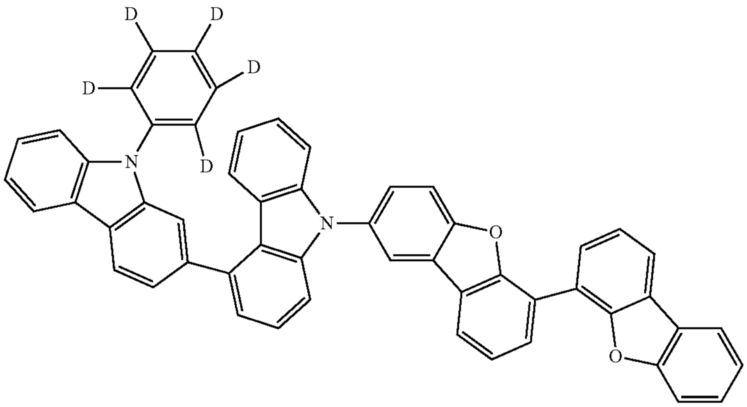

-continued
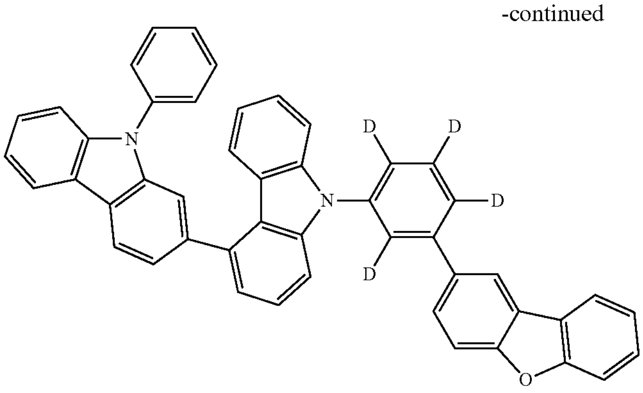
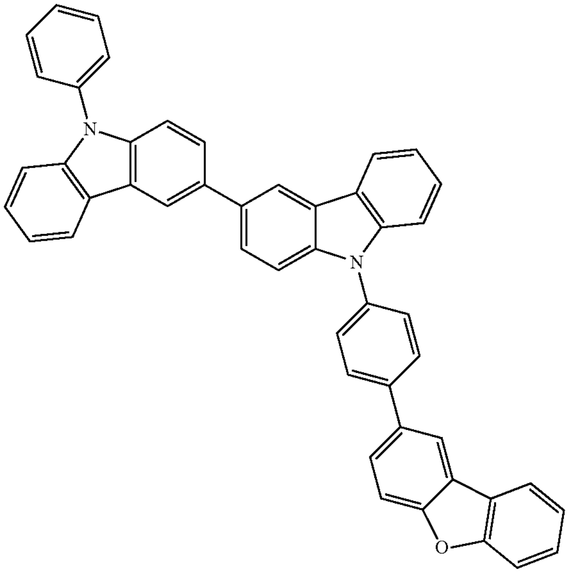
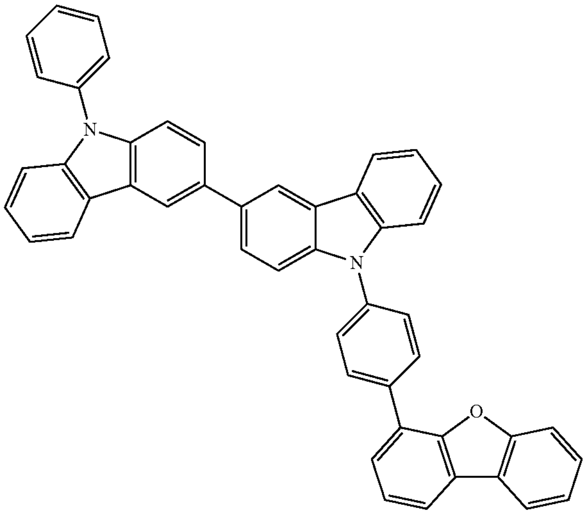
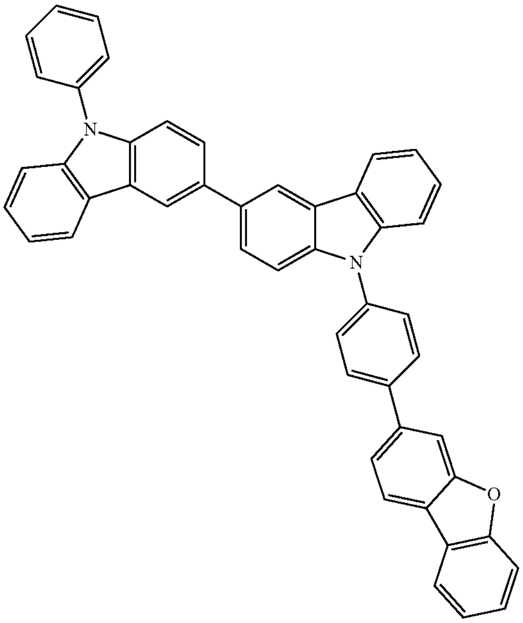

-continued
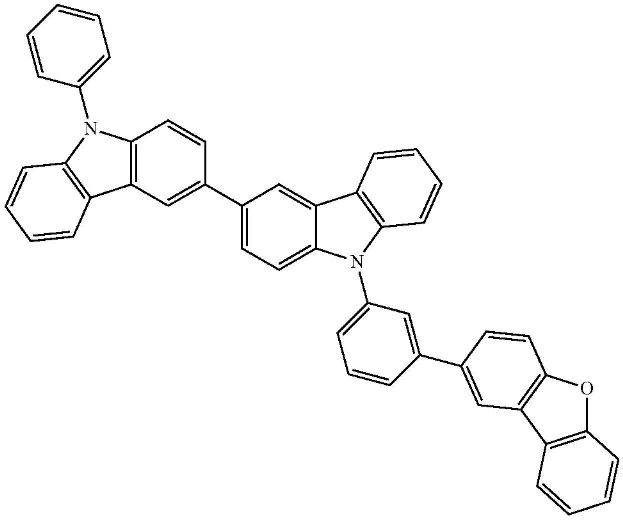
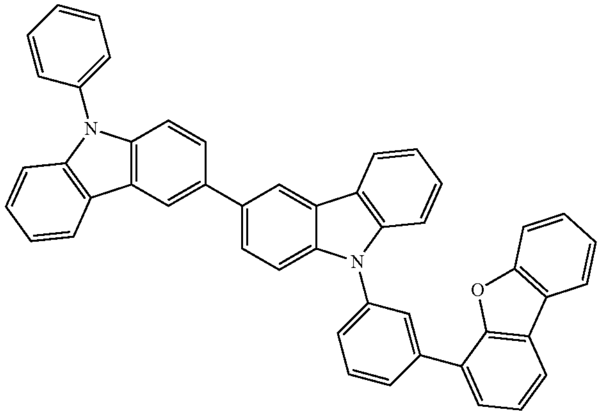
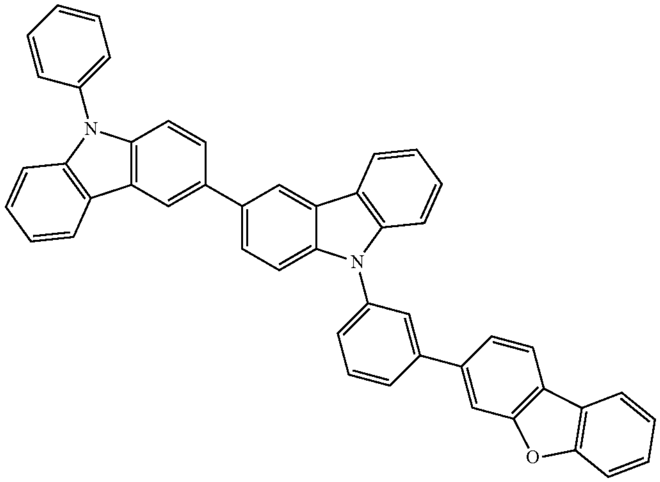

-continued
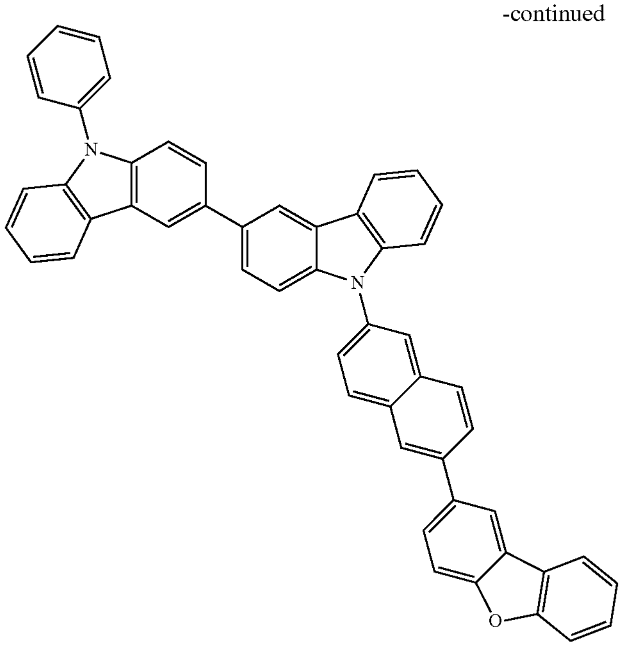
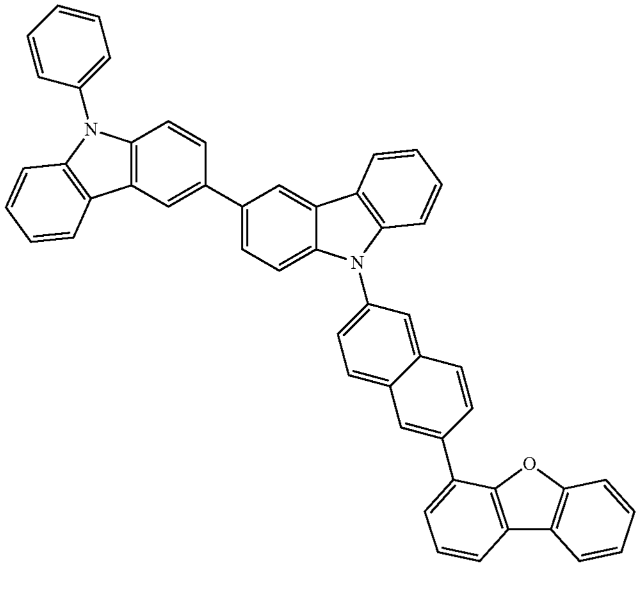

-continued
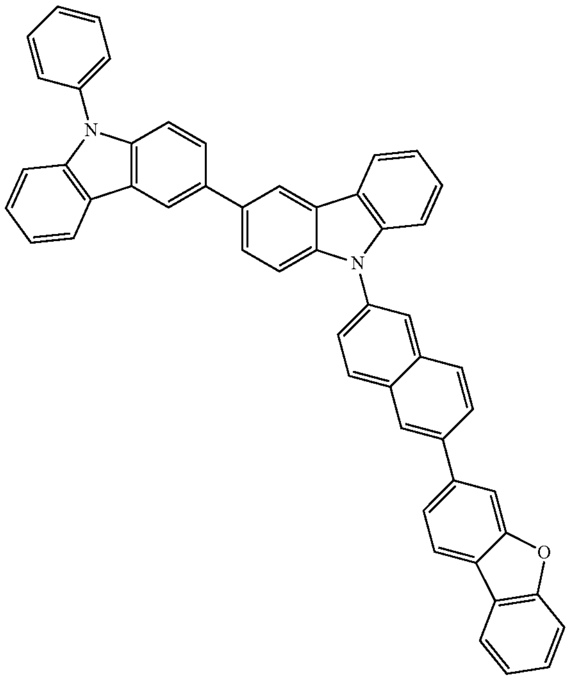
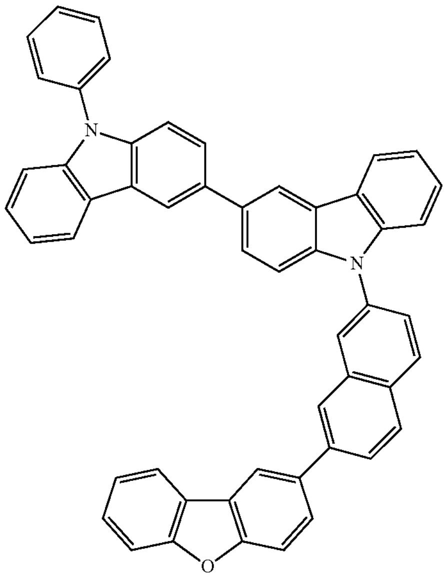
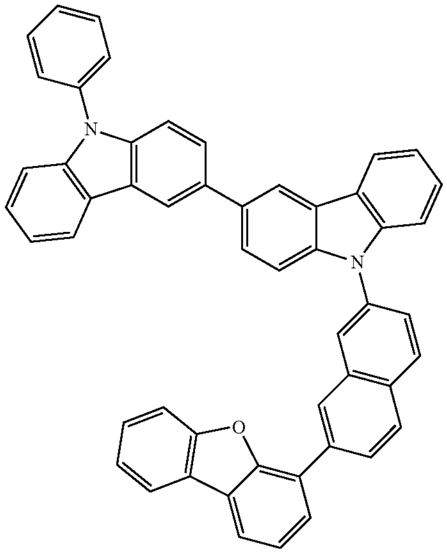
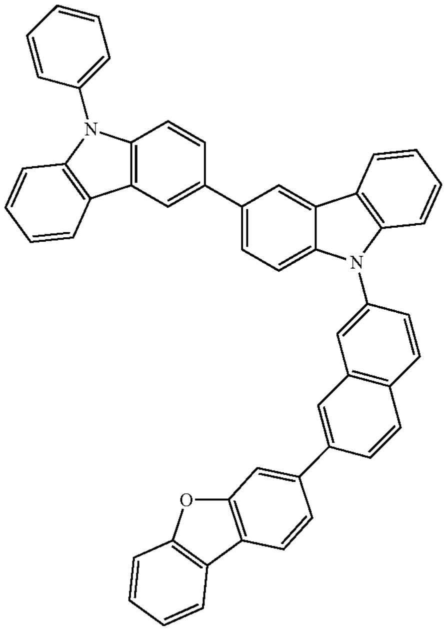
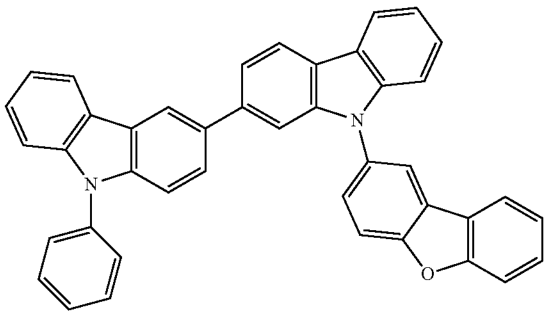
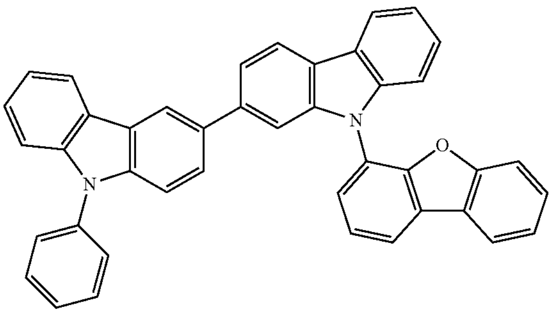

-continued
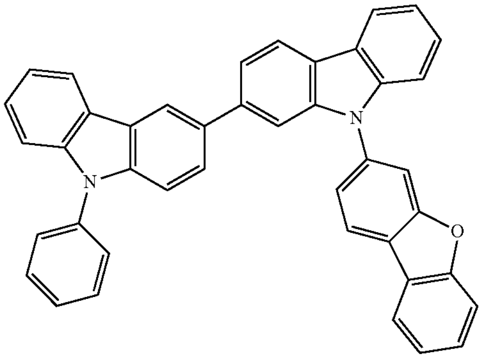
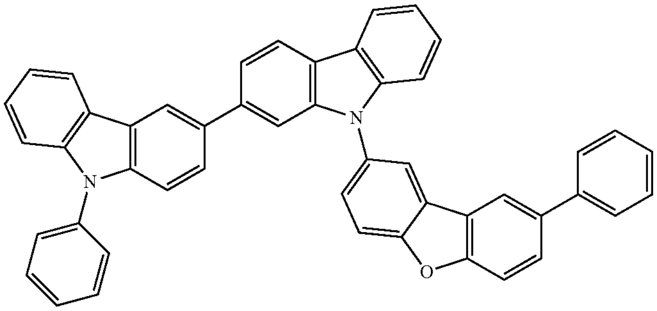
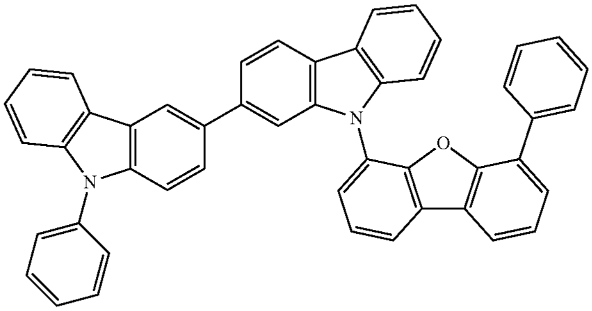
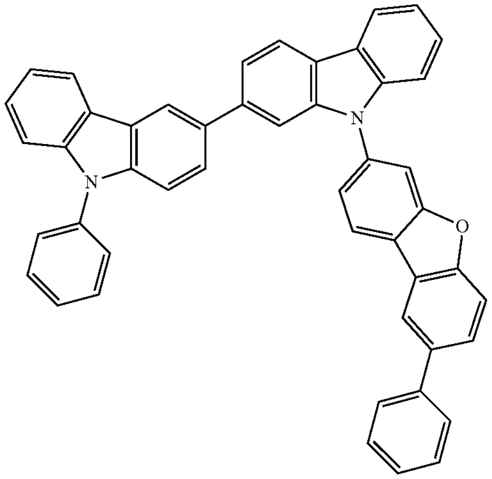
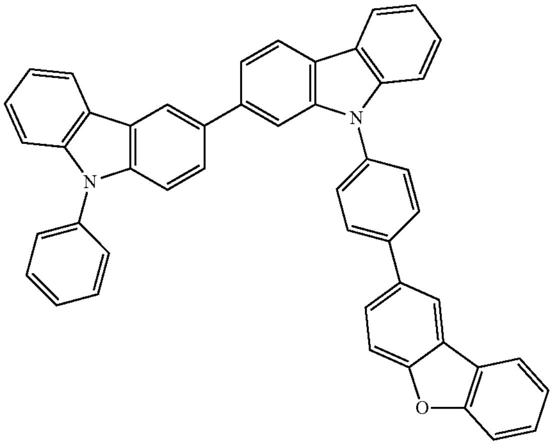
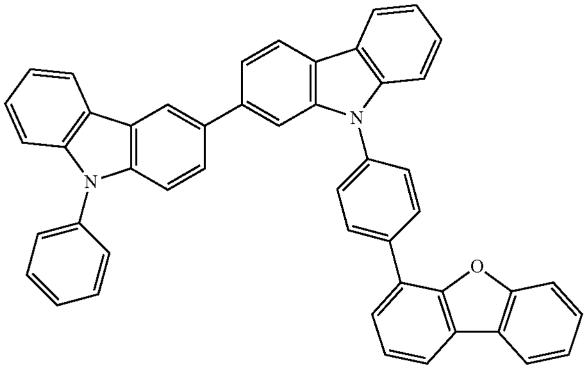

-continued
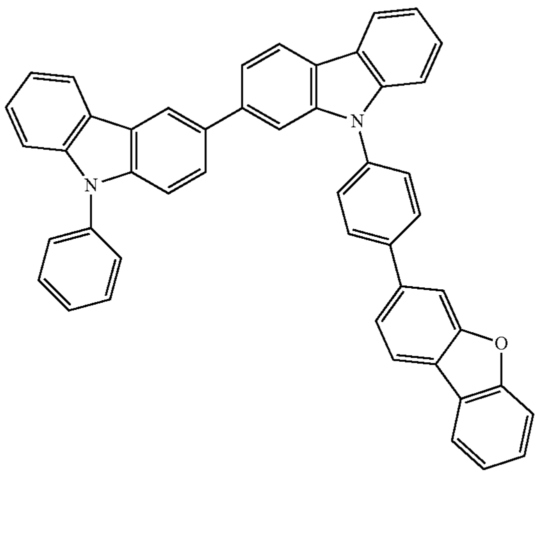
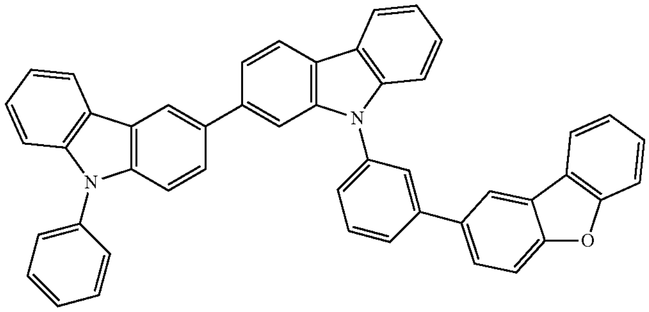
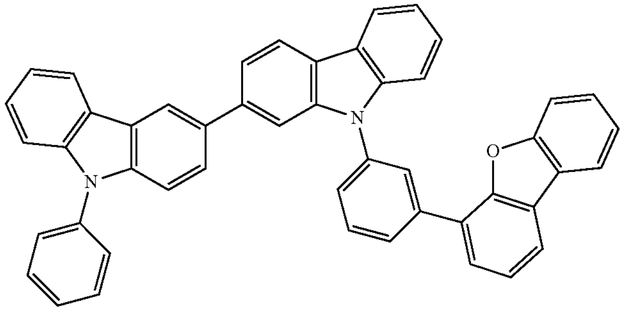
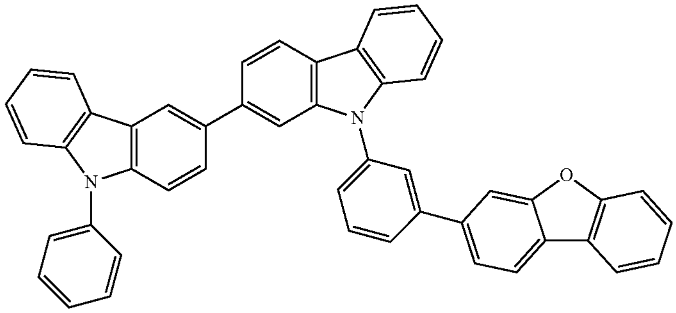

-continued
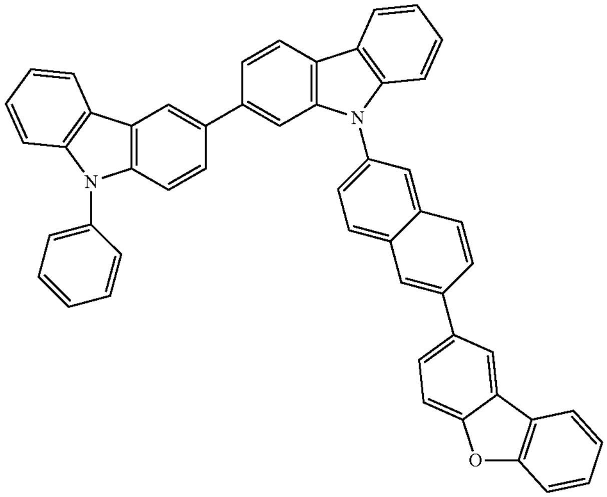
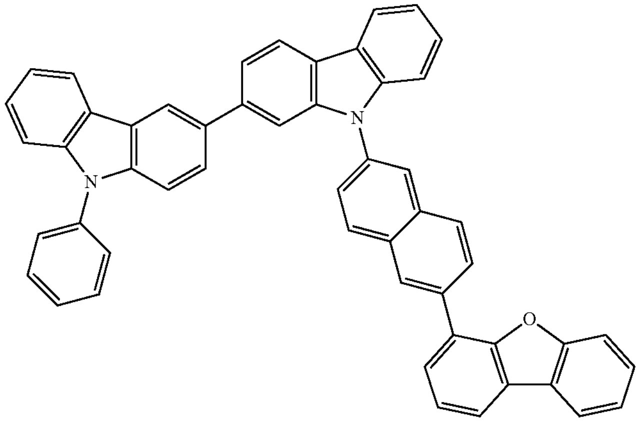
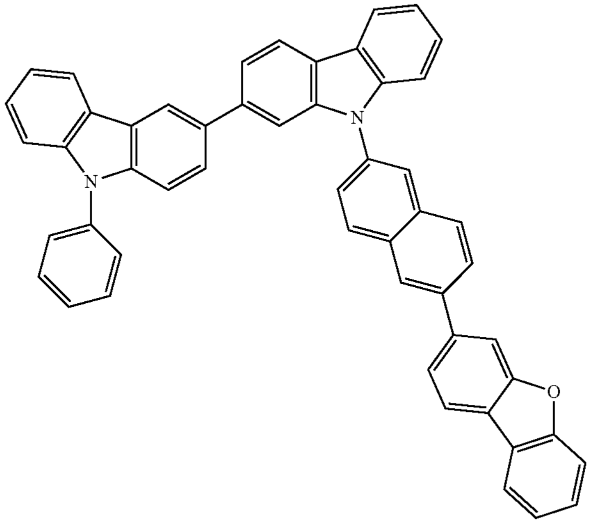
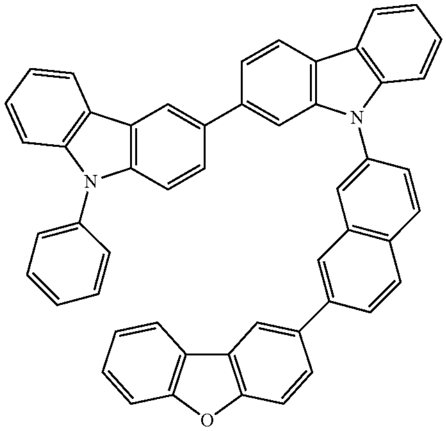

-continued
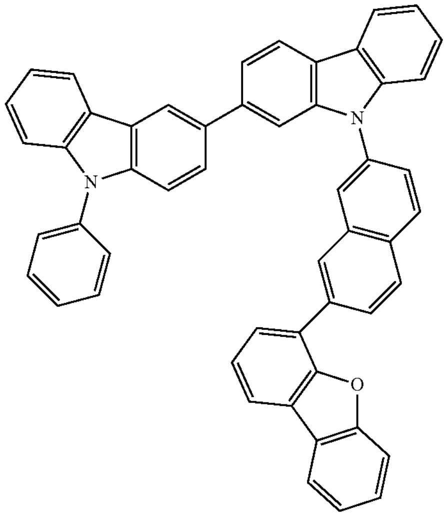
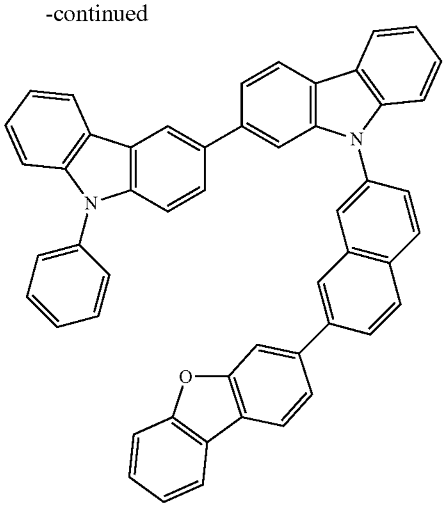
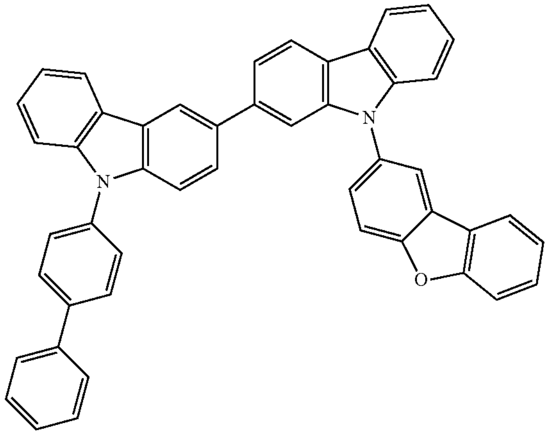
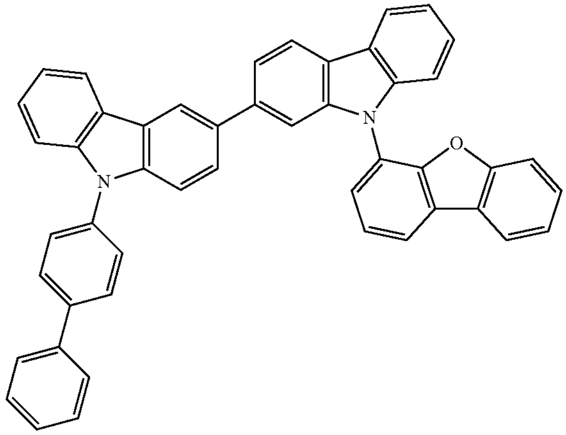
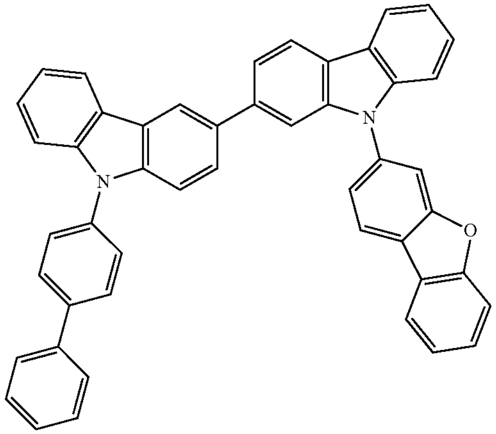
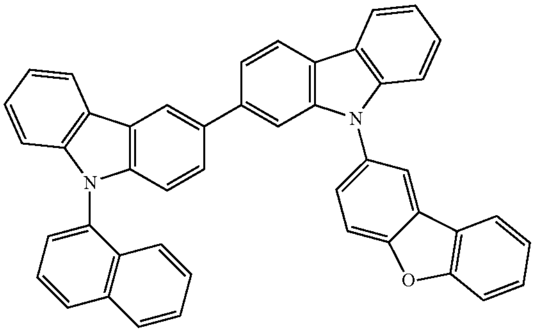

-continued
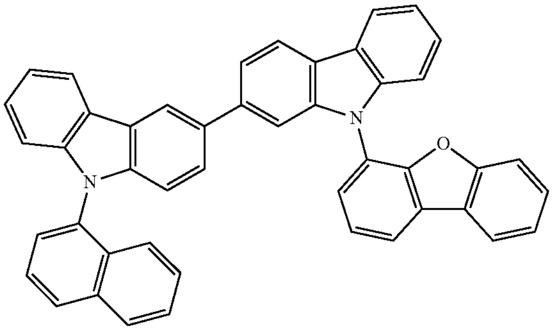
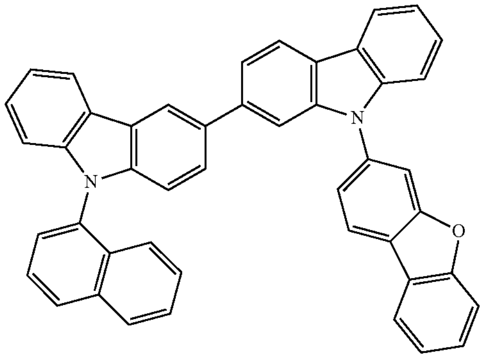
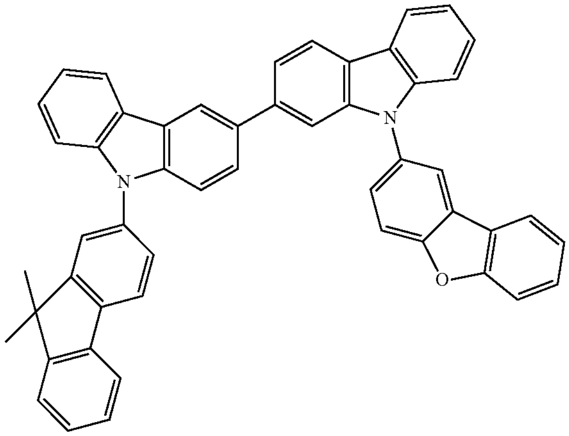
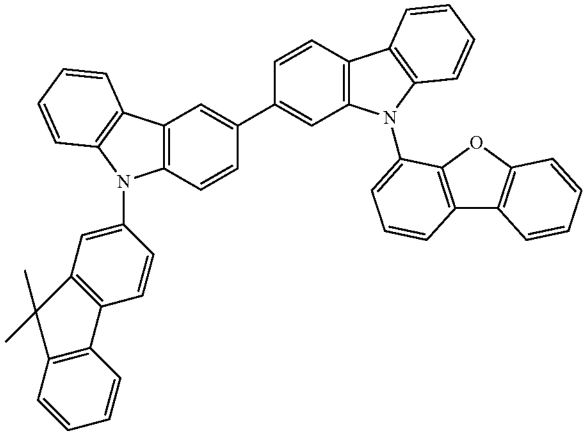
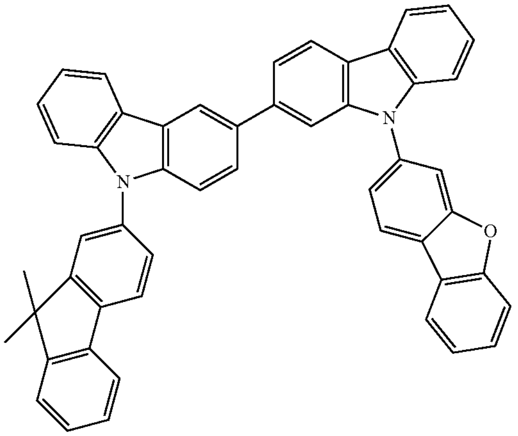
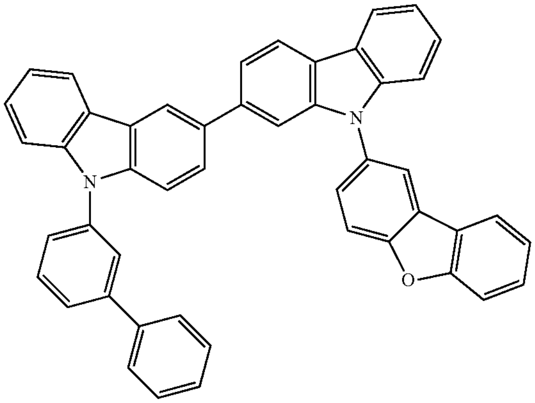
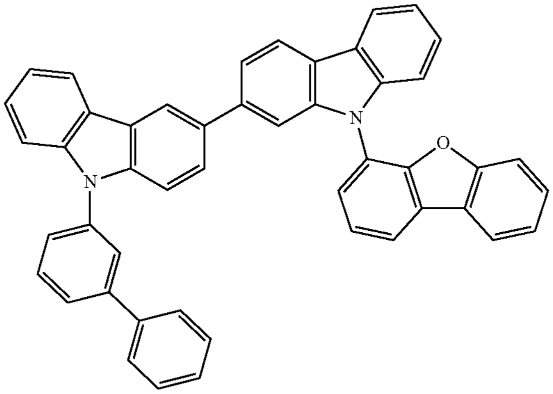

-continued
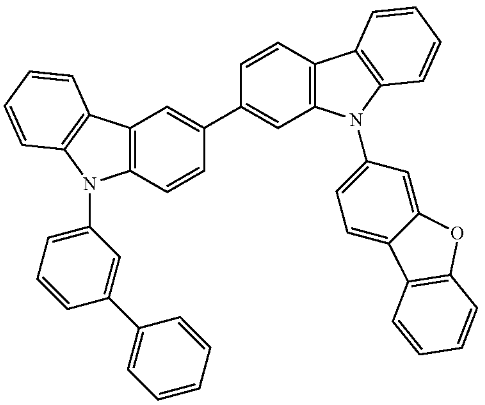
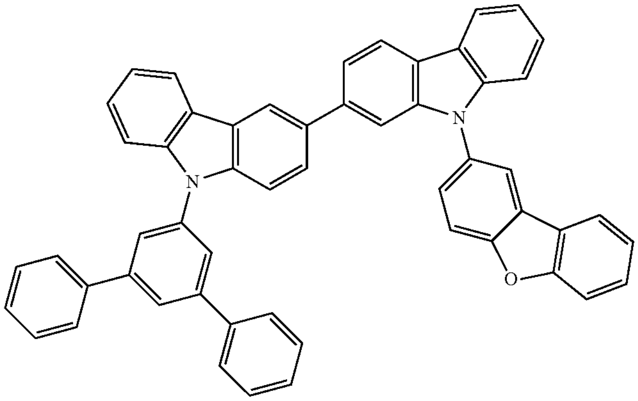
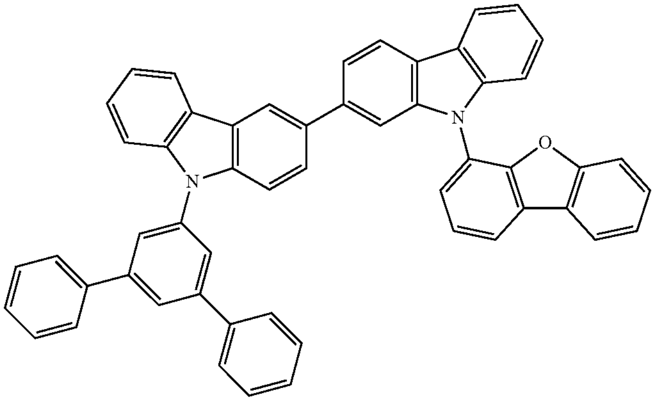
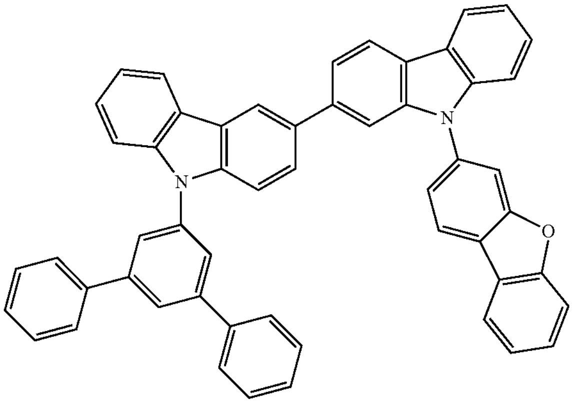
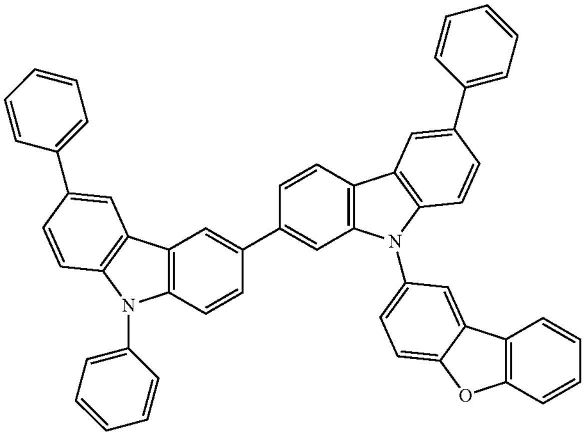

-continued
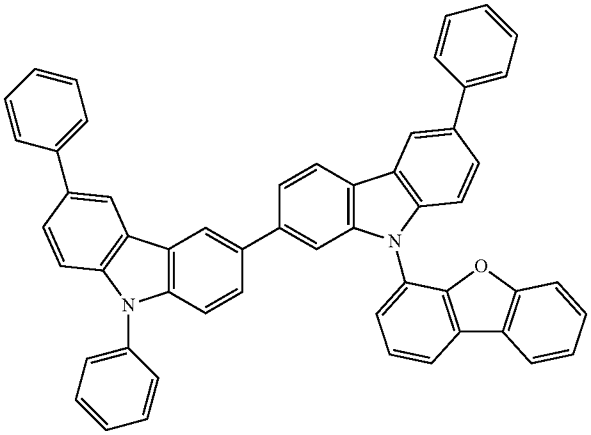
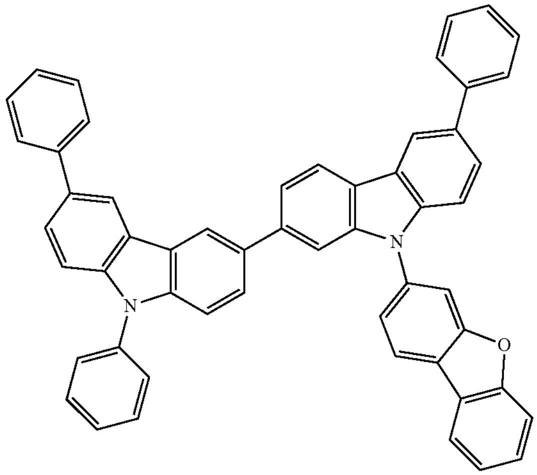
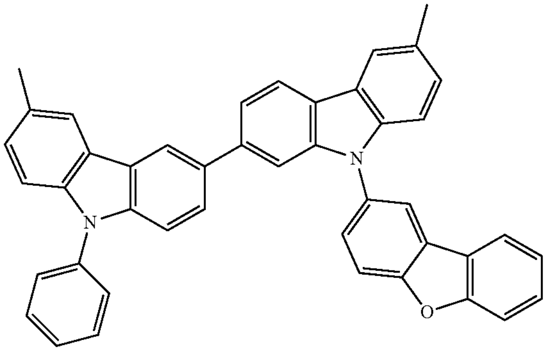
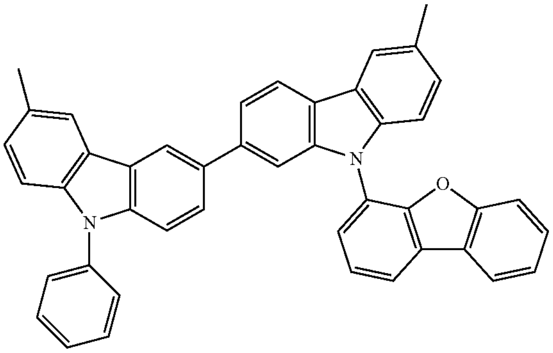
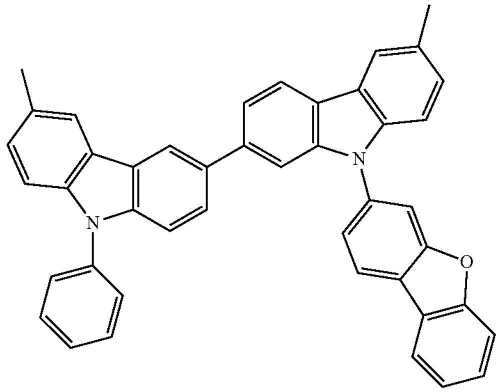
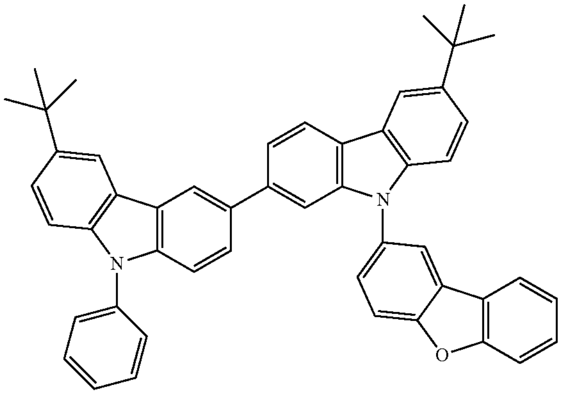
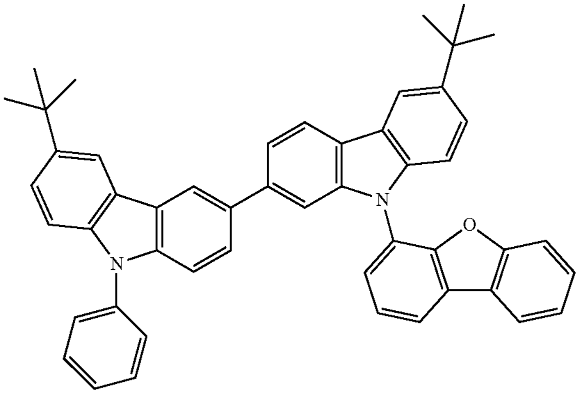
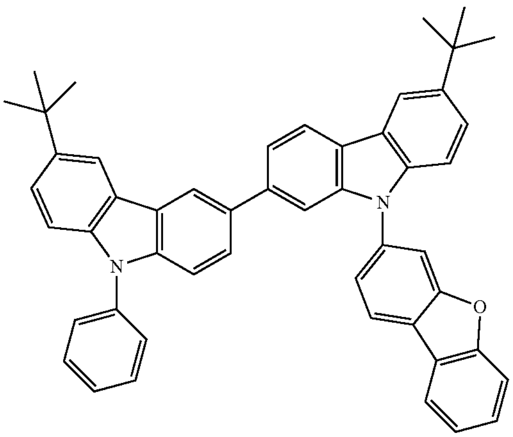

-continued
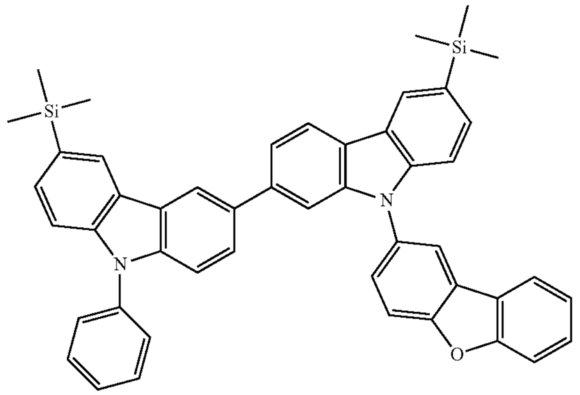
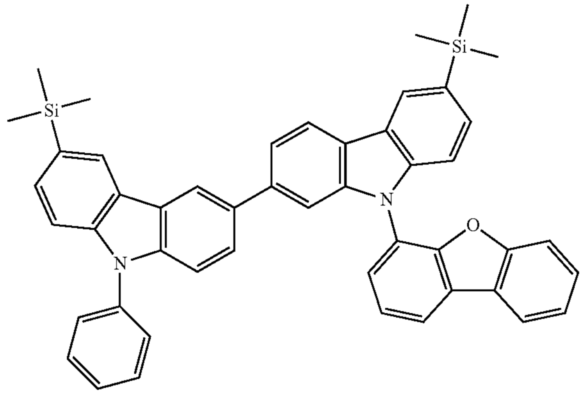
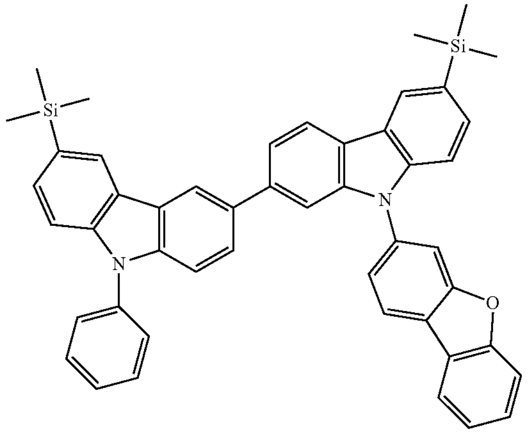
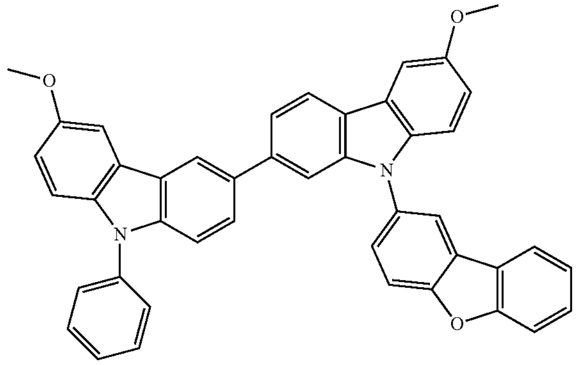
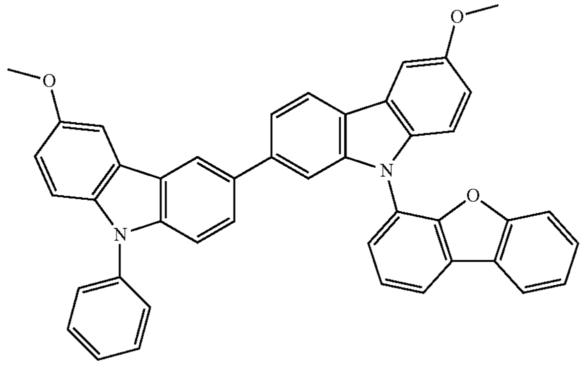
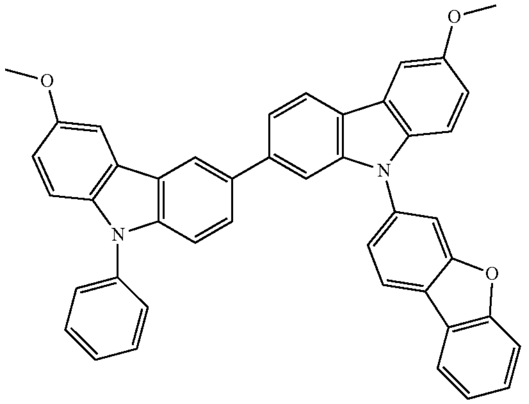

-continued
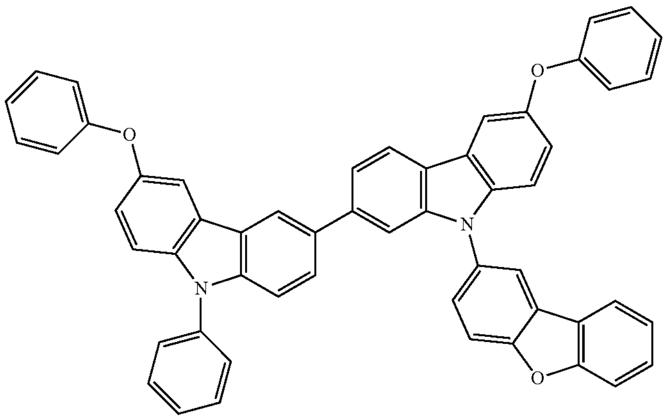
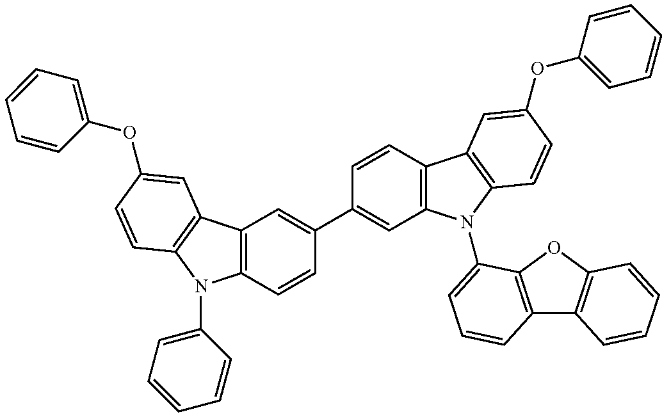
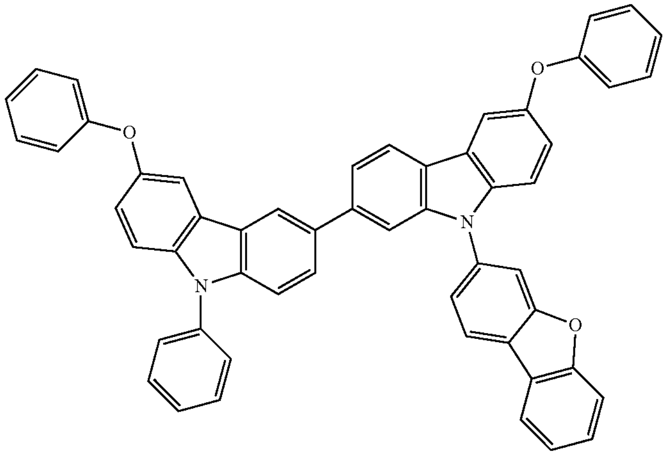
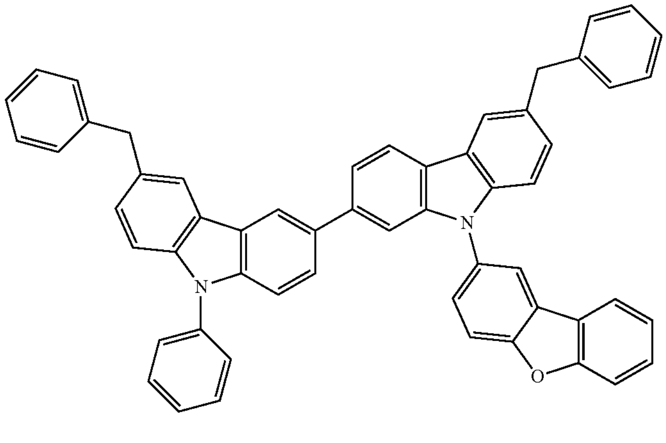

-continued
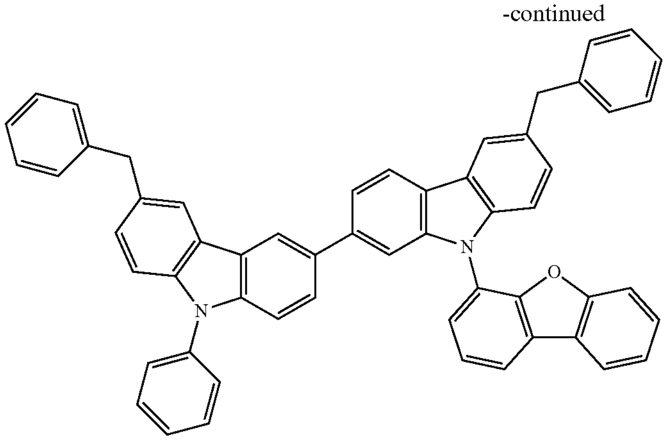
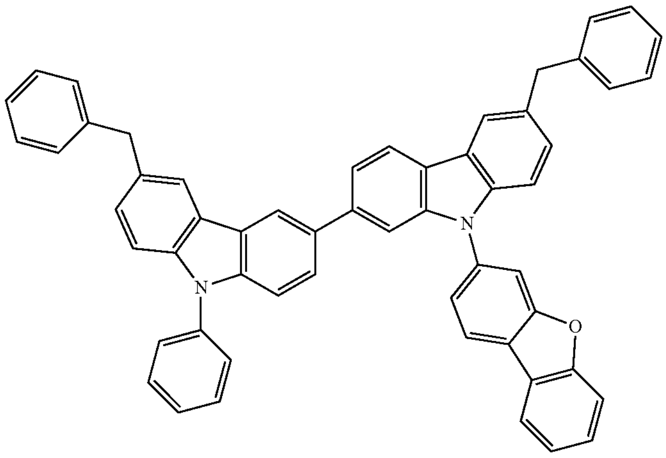
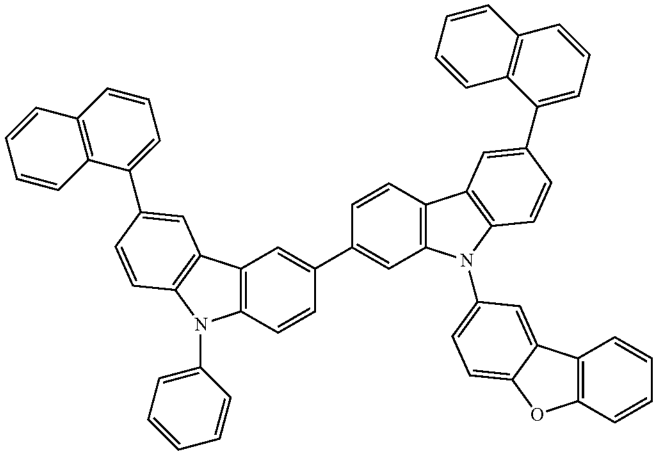

-continued
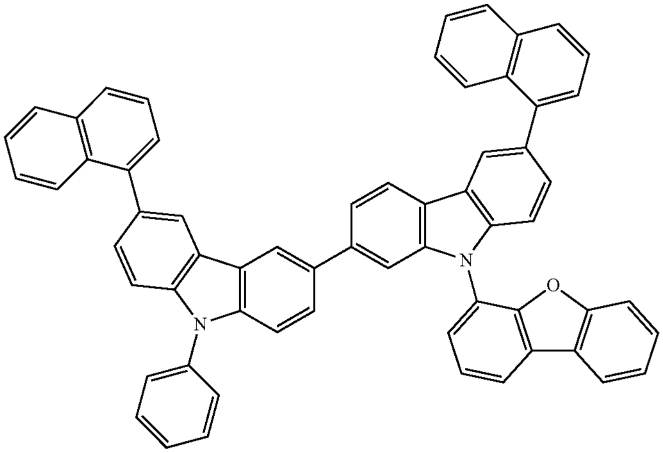
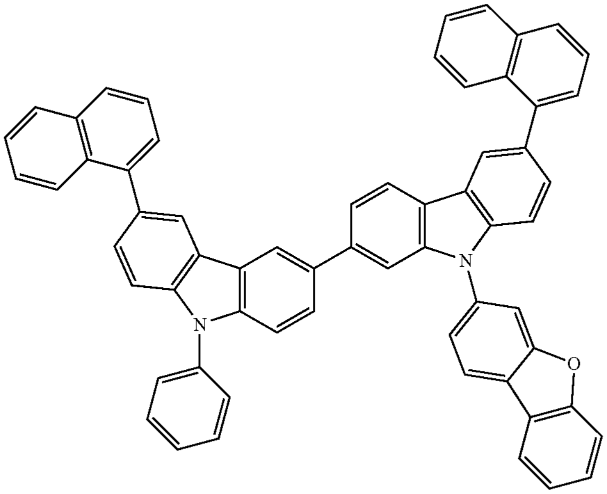
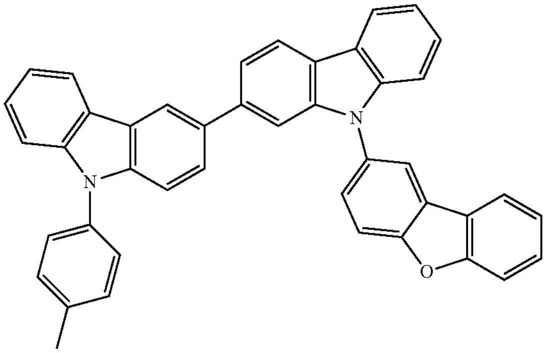
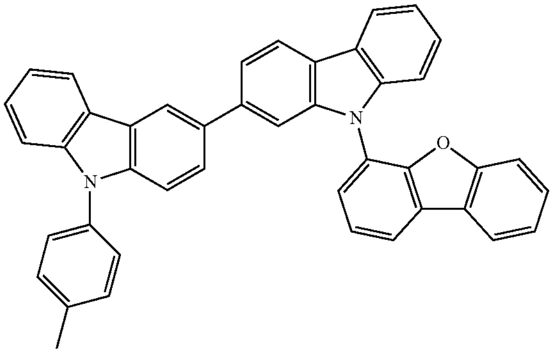
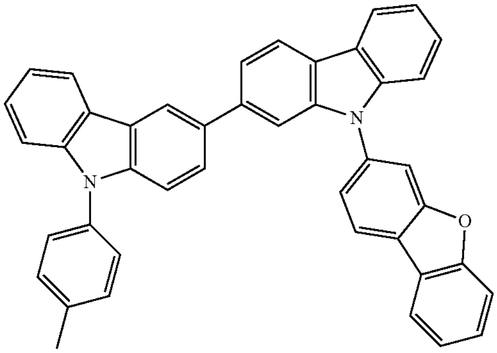

-continued
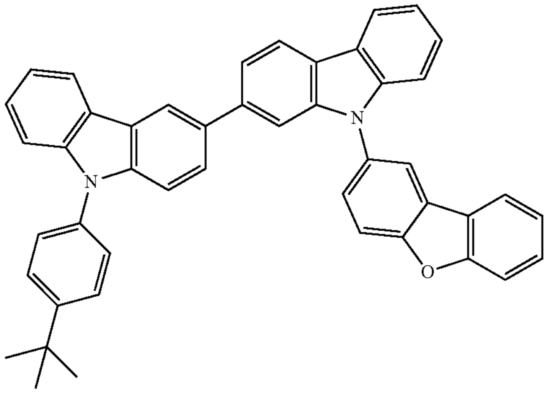
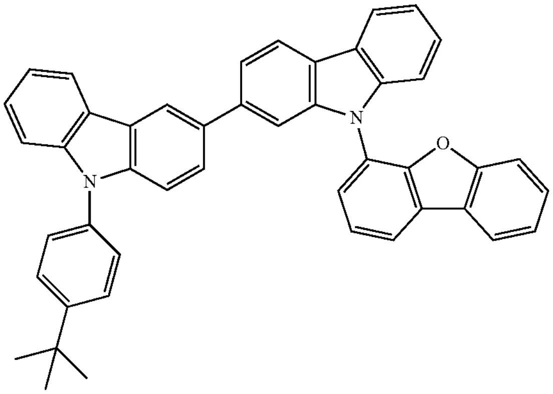
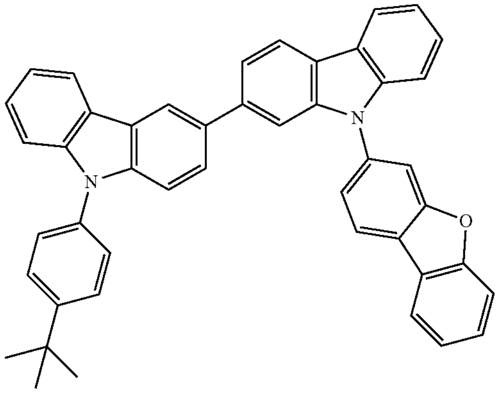
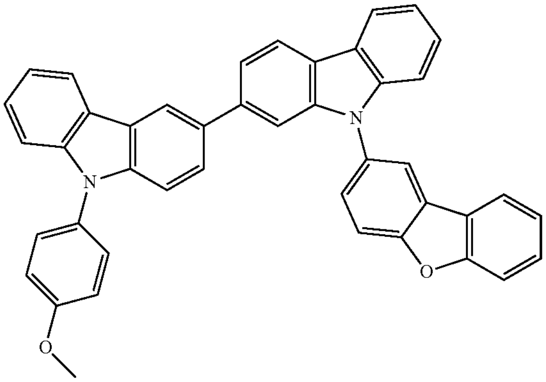
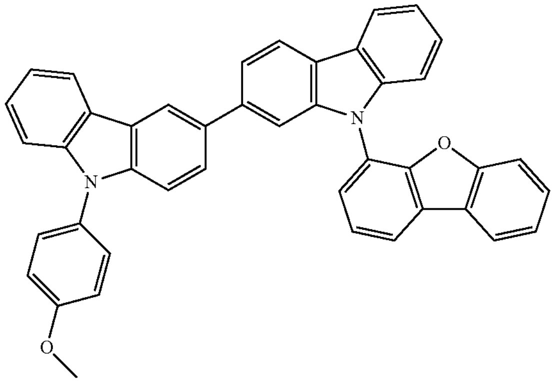
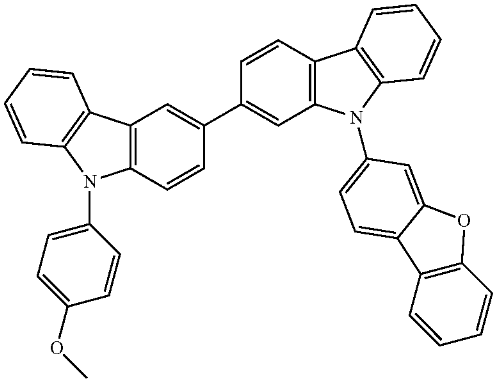
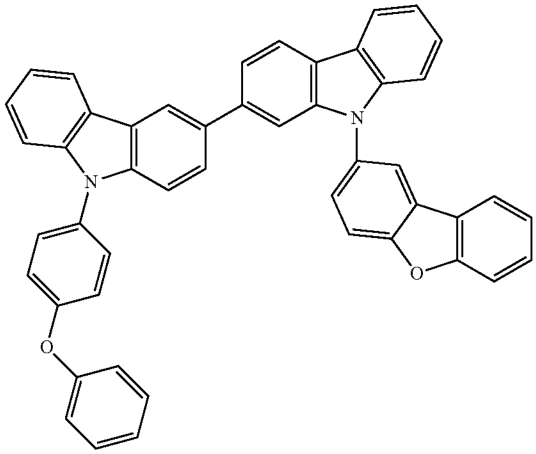

-continued
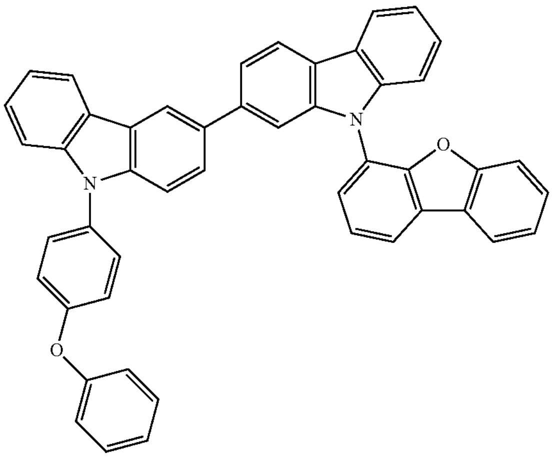
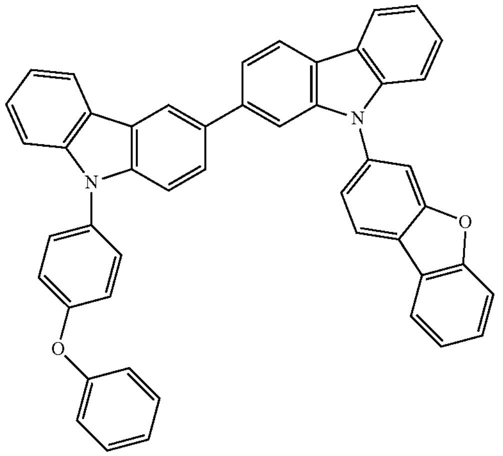
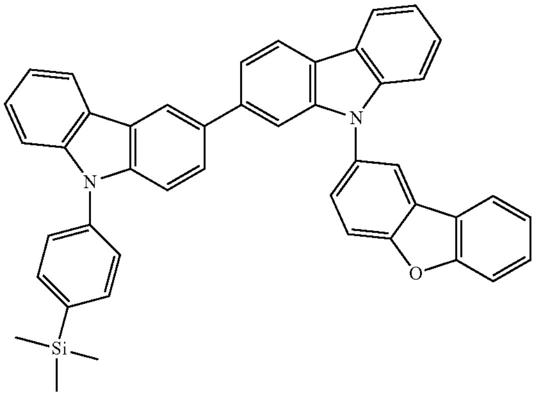
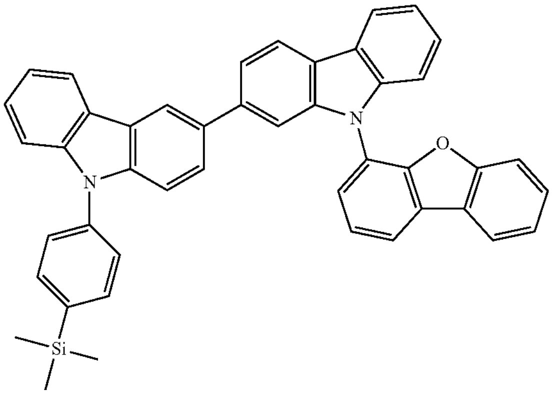
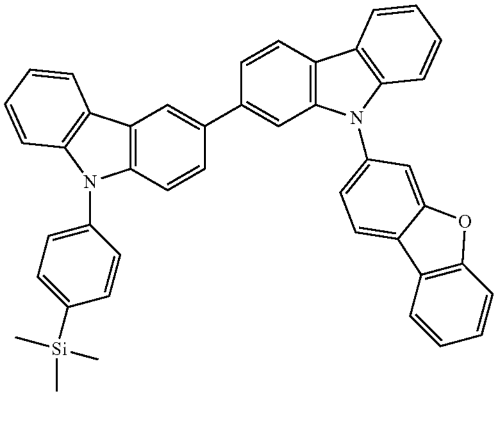
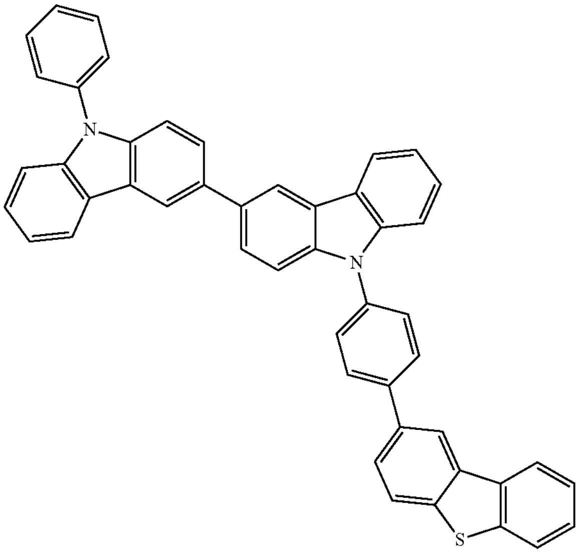

-continued
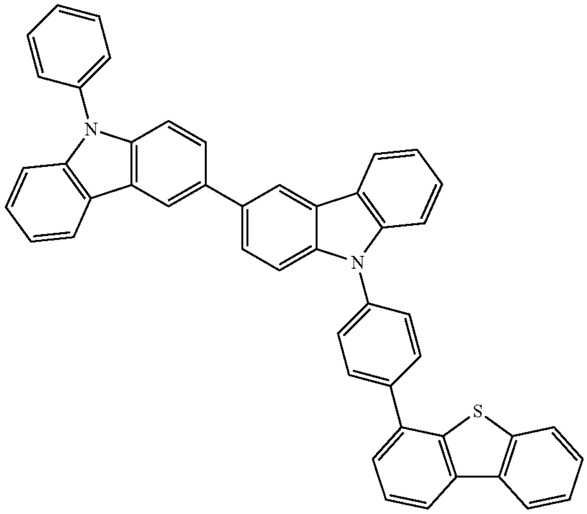
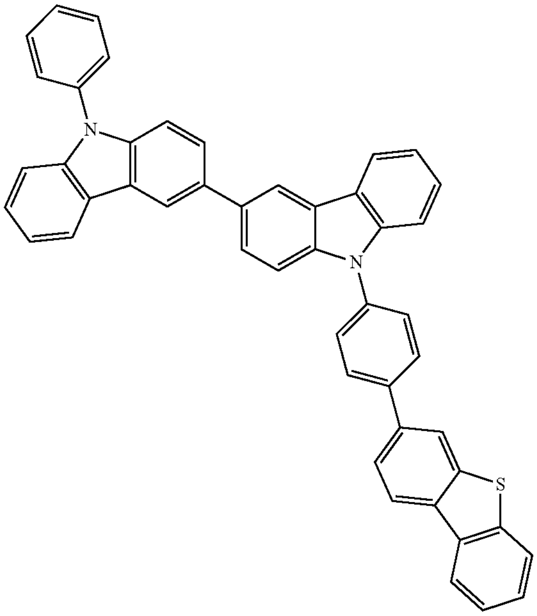
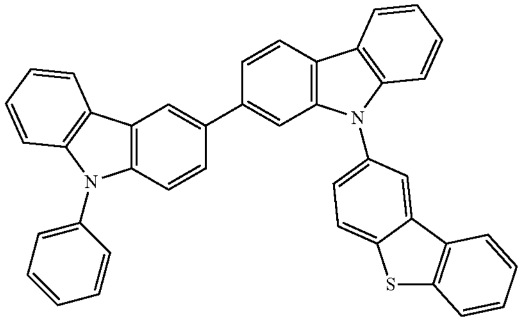
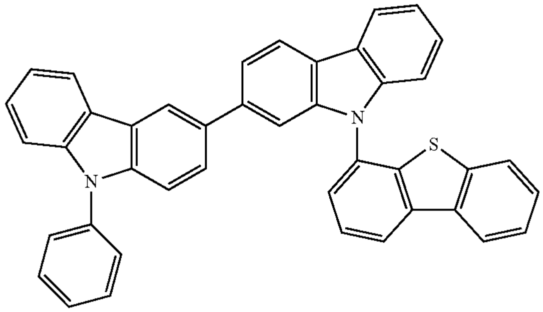
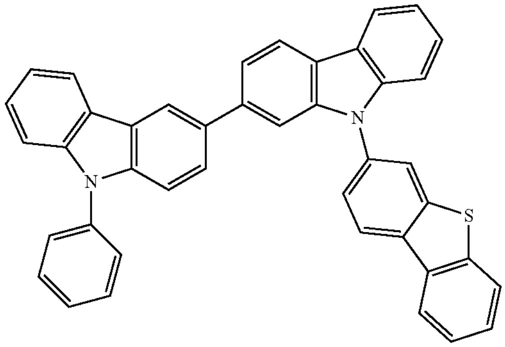
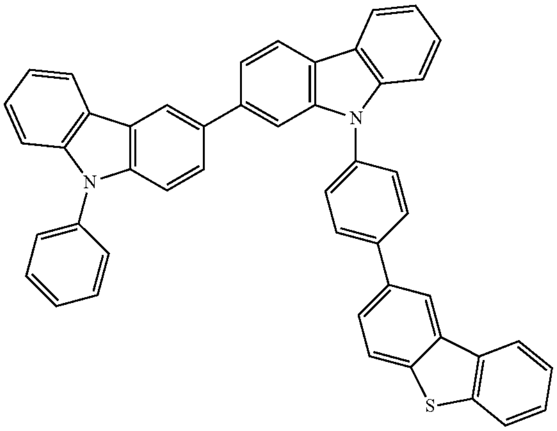

-continued
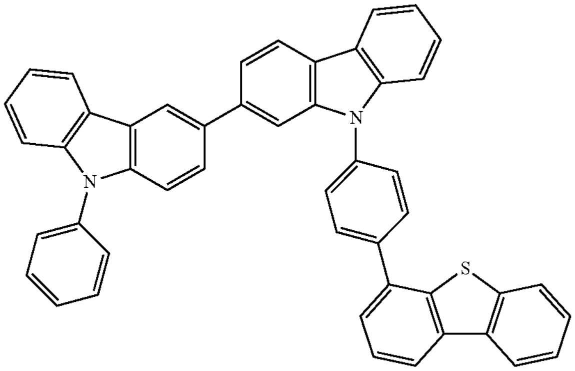
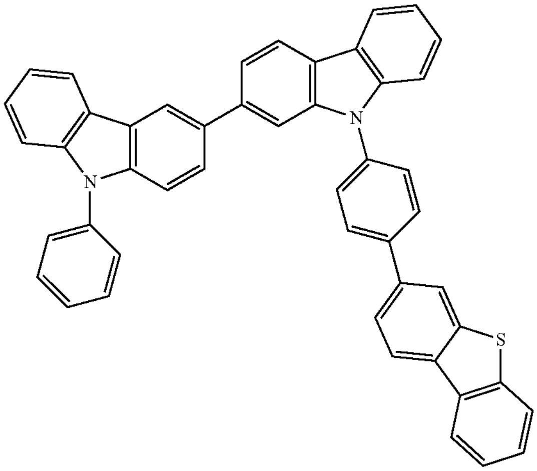
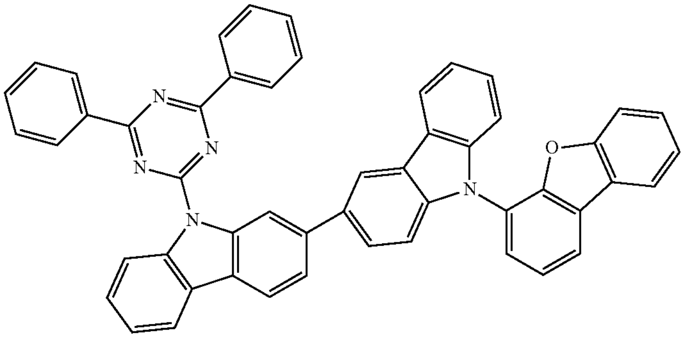
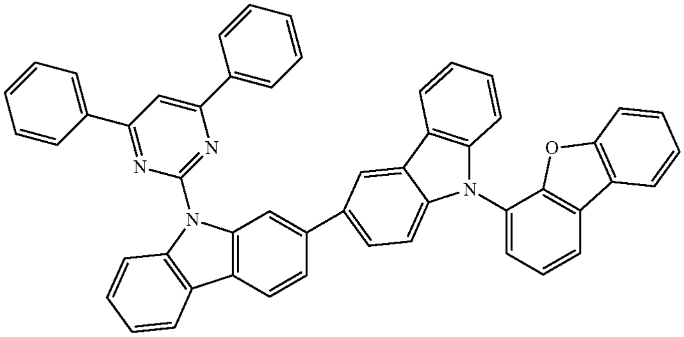
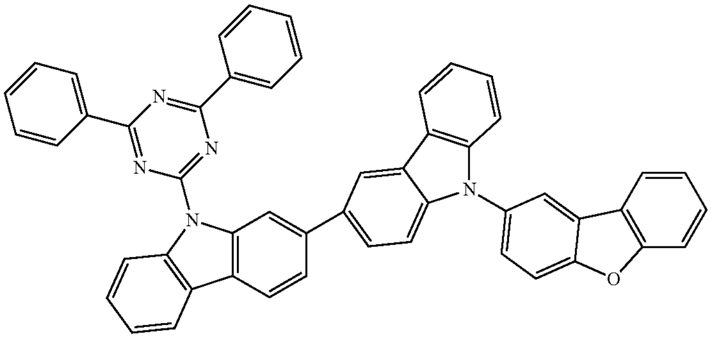

-continued
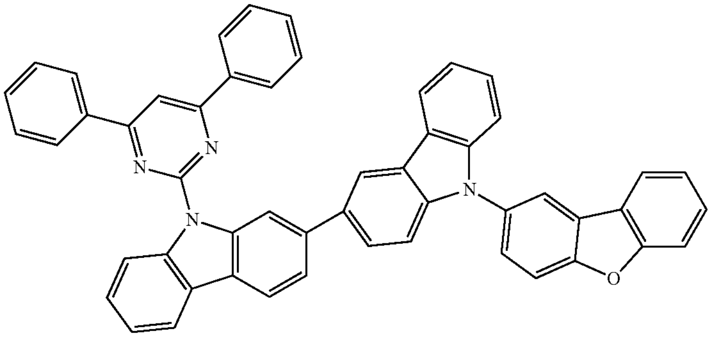
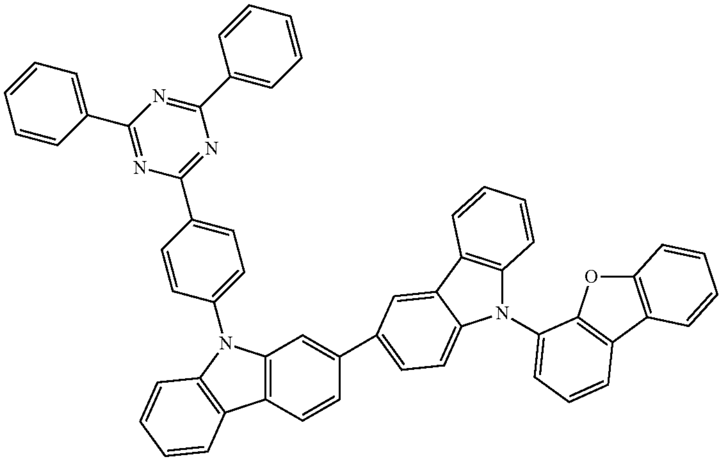
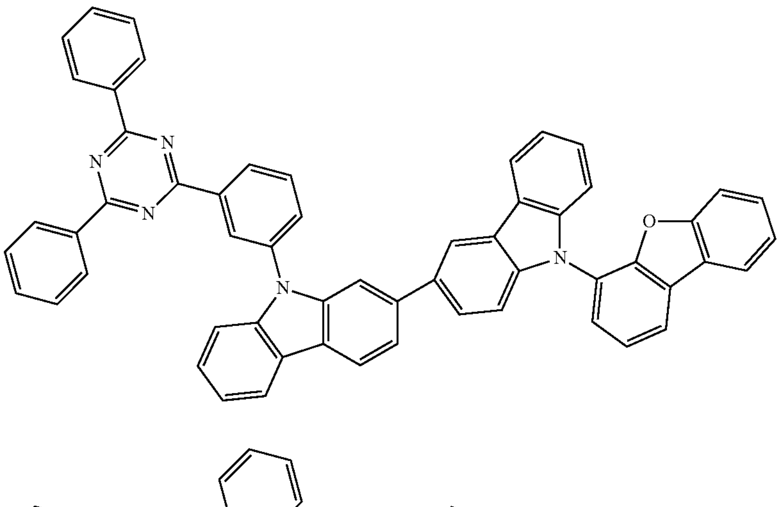
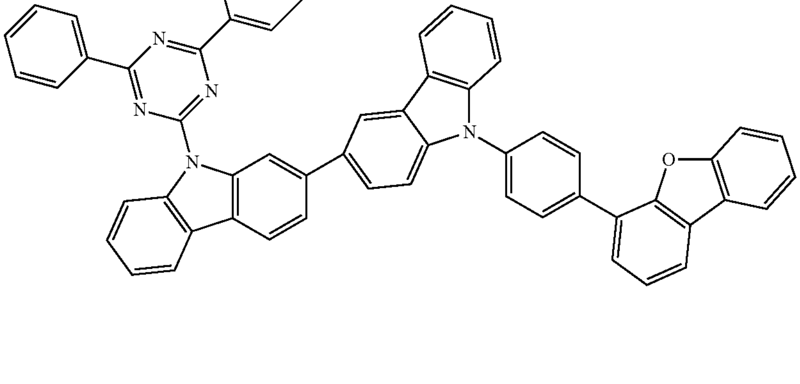

-continued
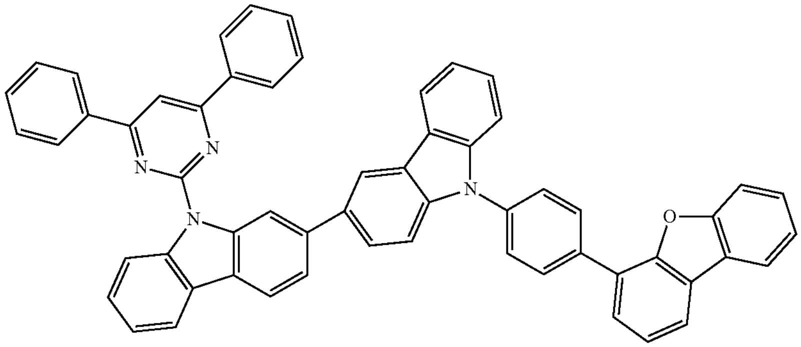
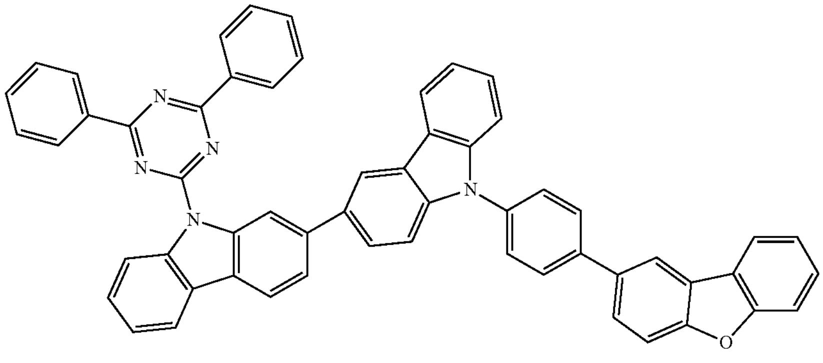
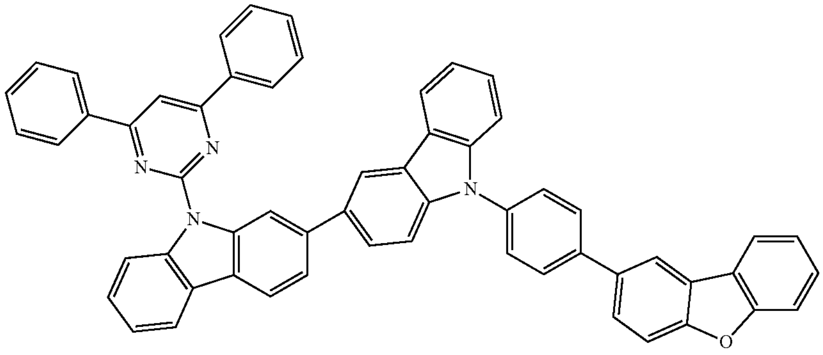
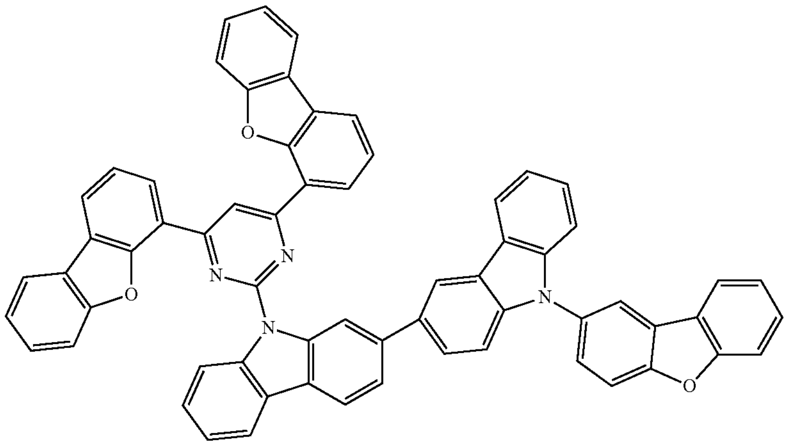

-continued
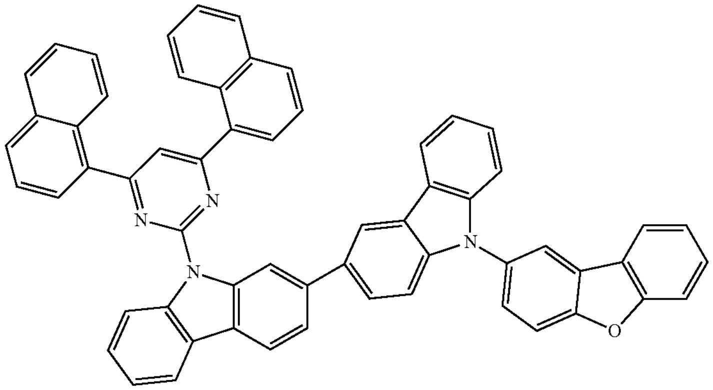
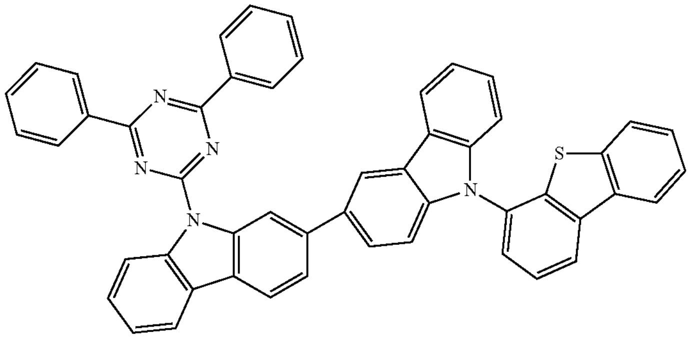
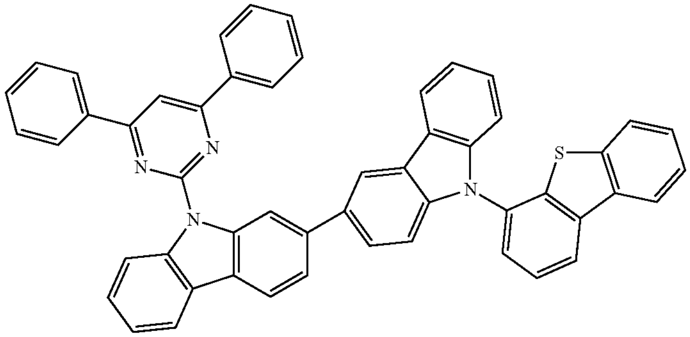
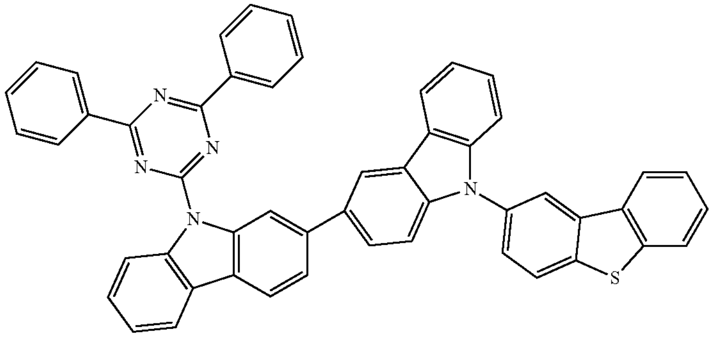

-continued
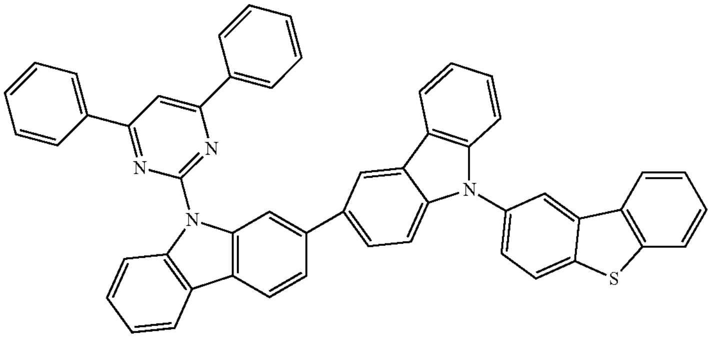
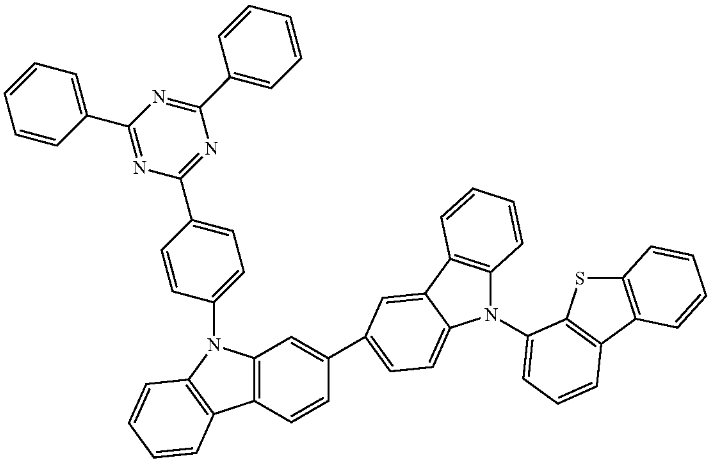
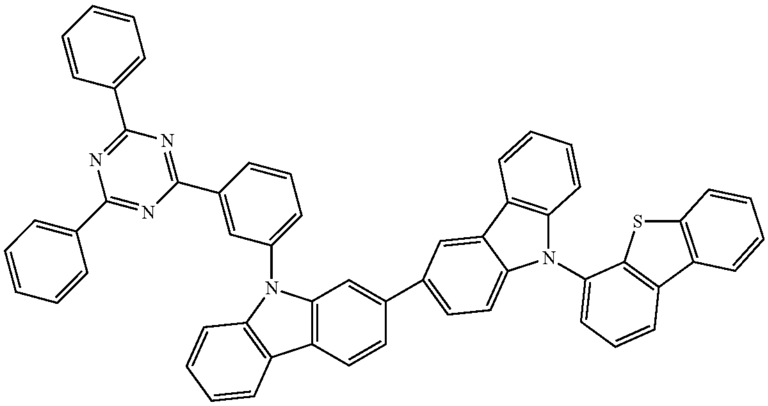
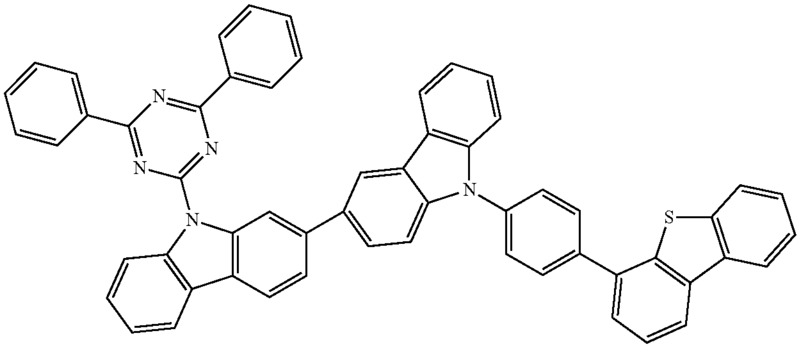

-continued
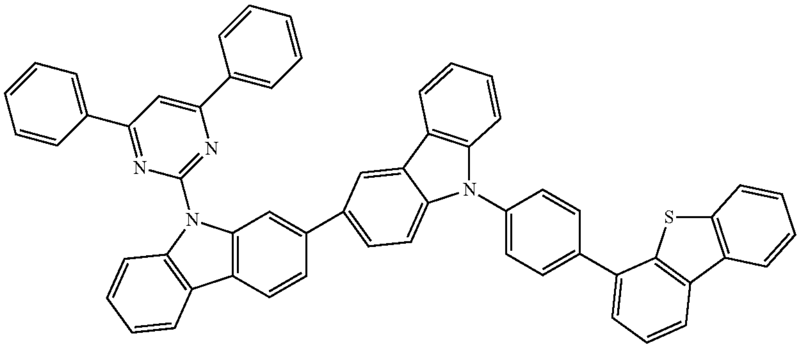
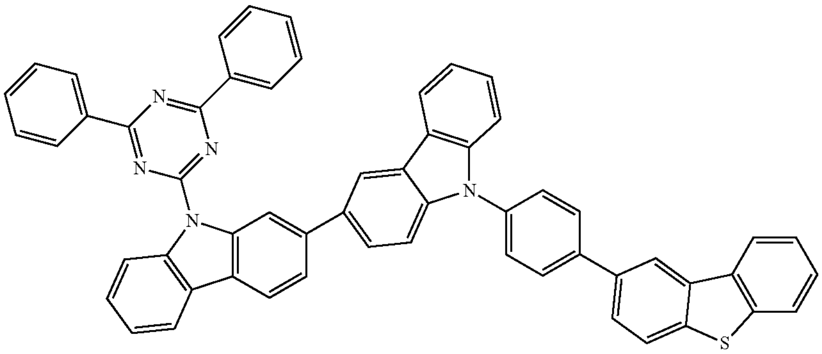
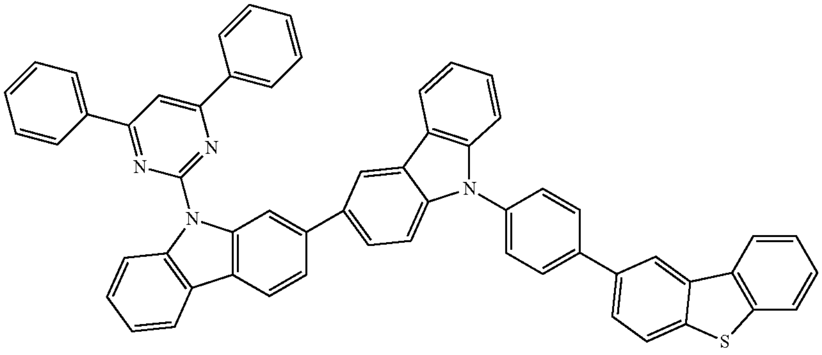
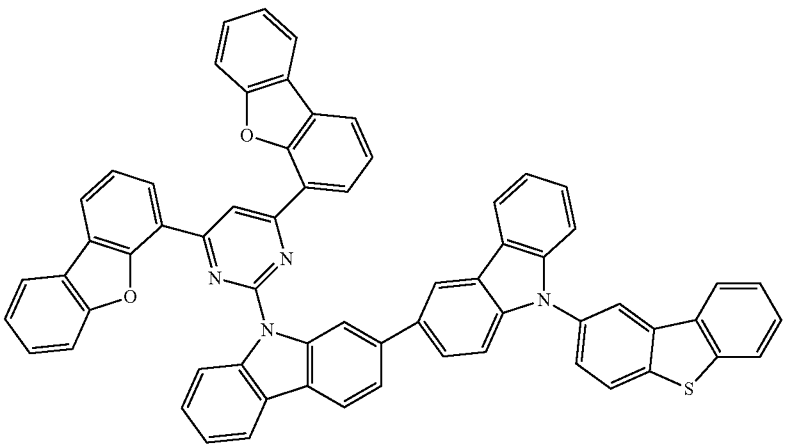

-continued
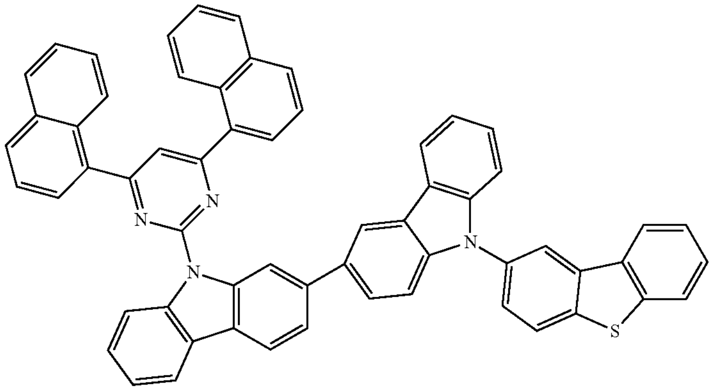
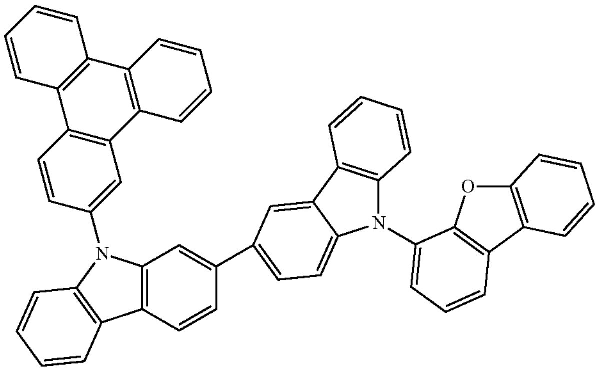
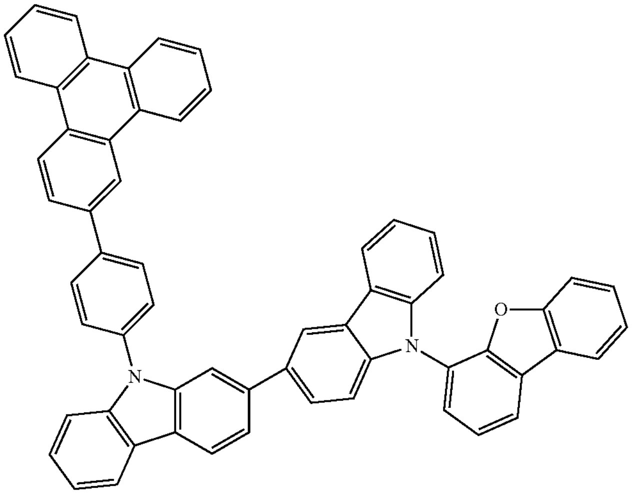
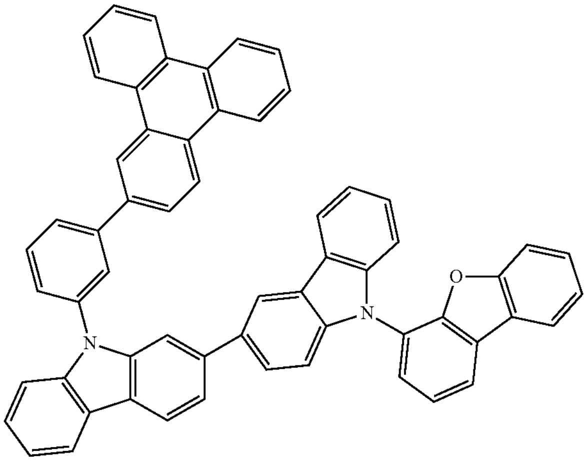

-continued
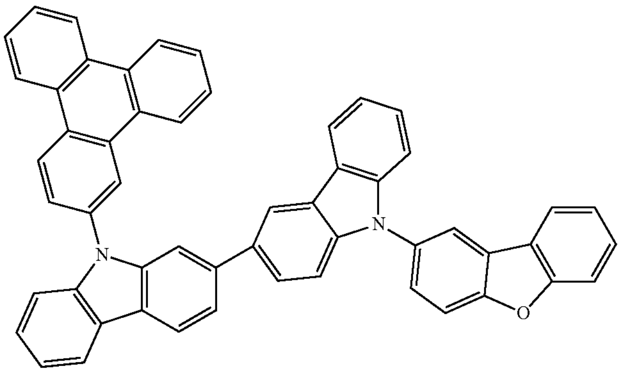
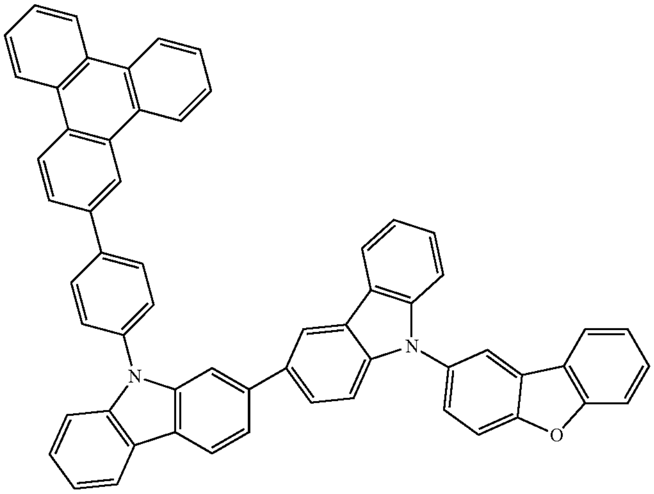
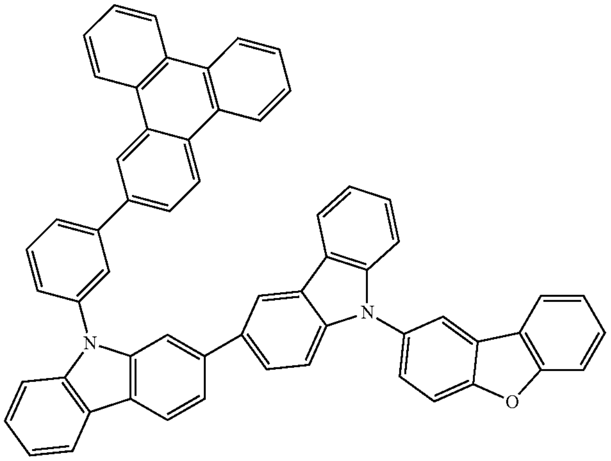
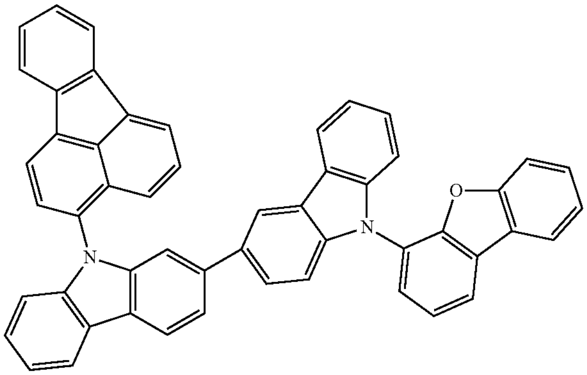

-continued
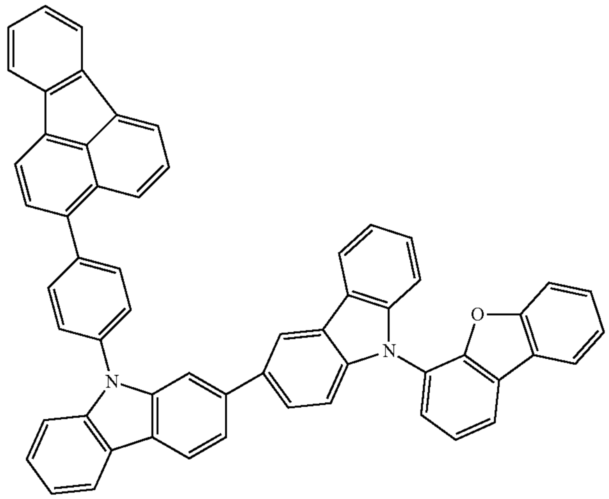
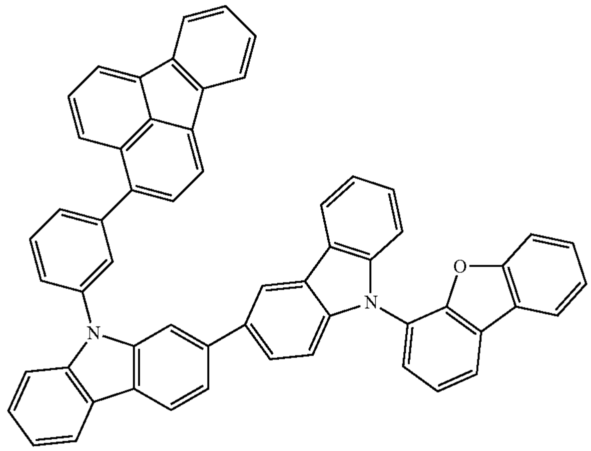
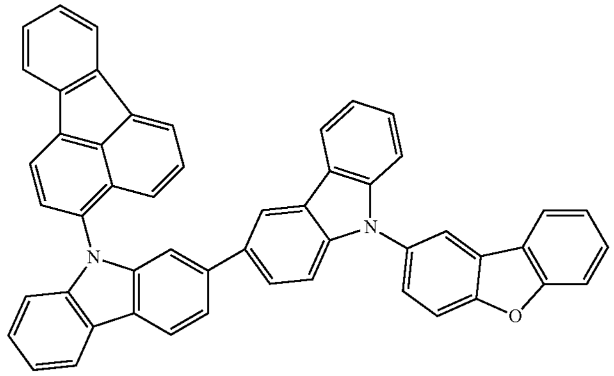

-continued
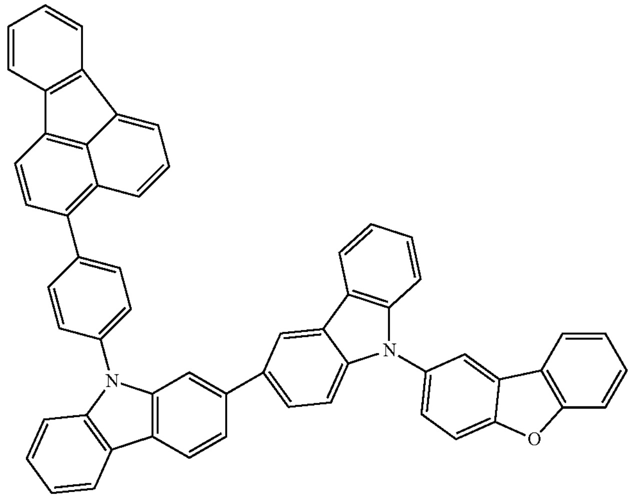
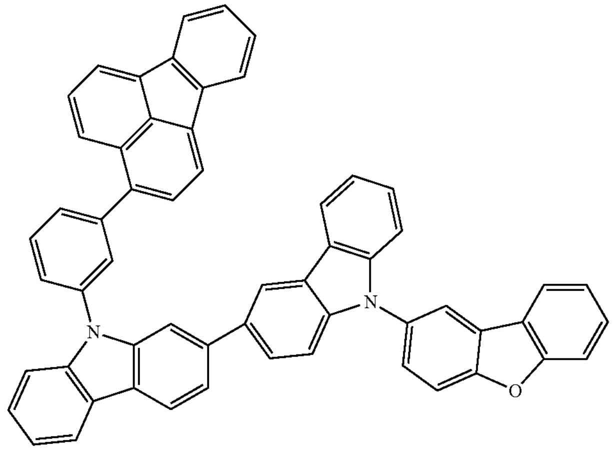
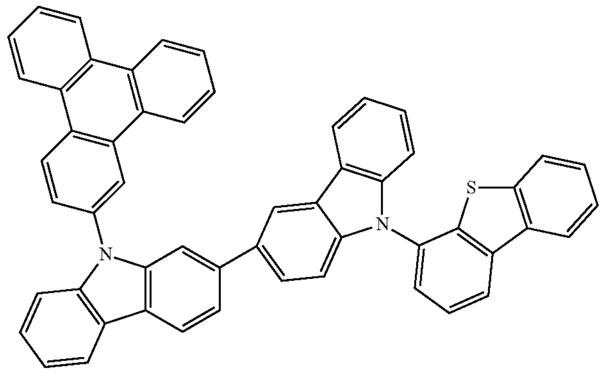

-continued
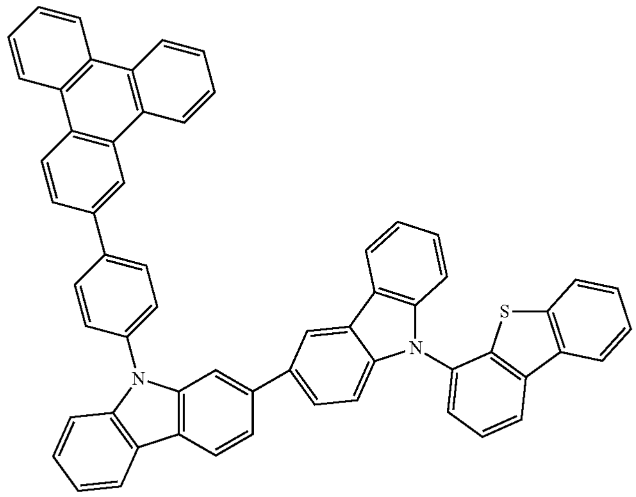
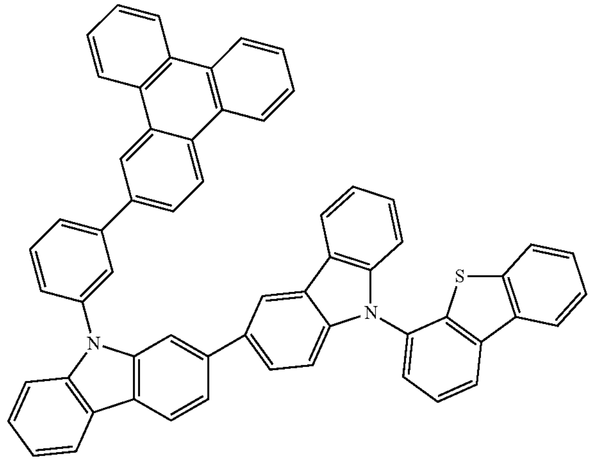
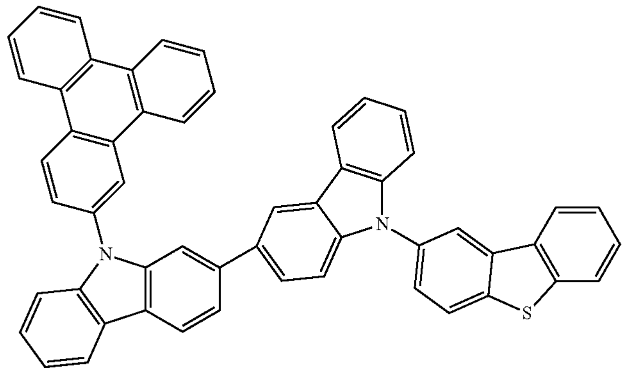

-continued
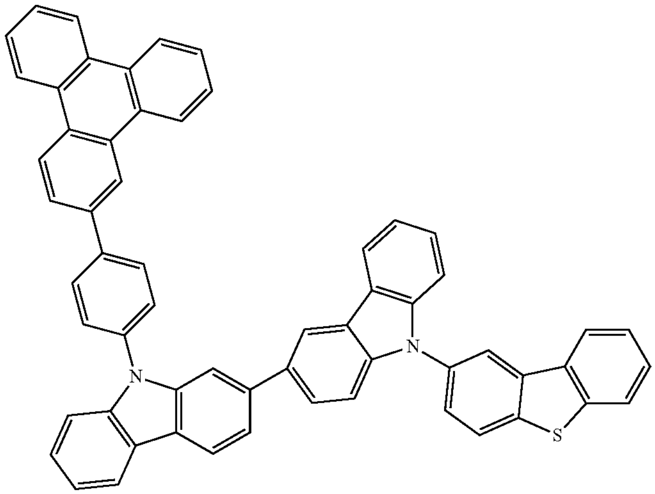
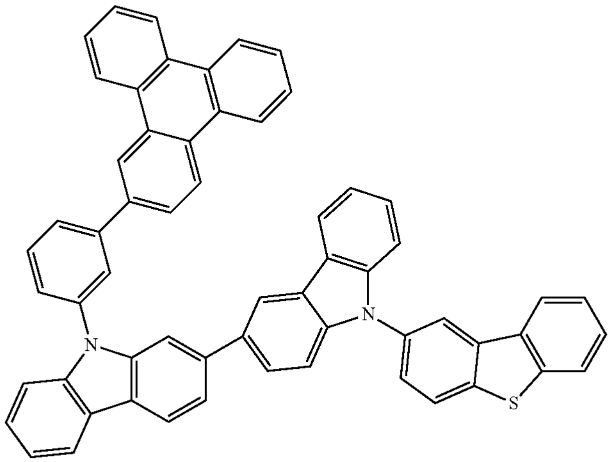
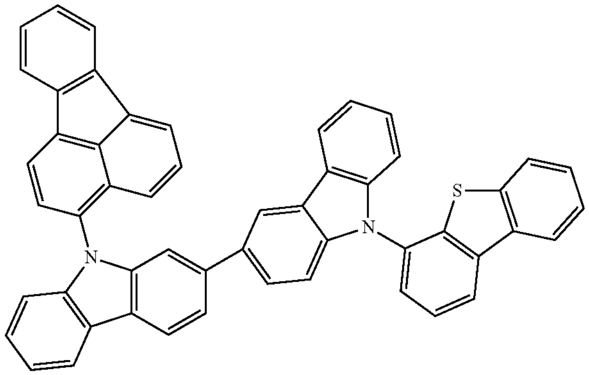

-continued
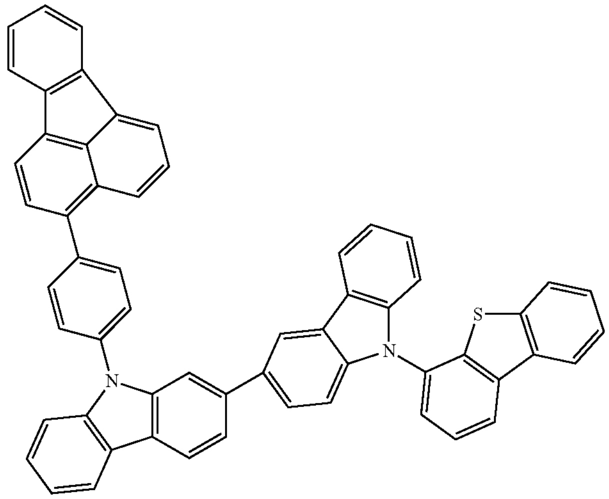
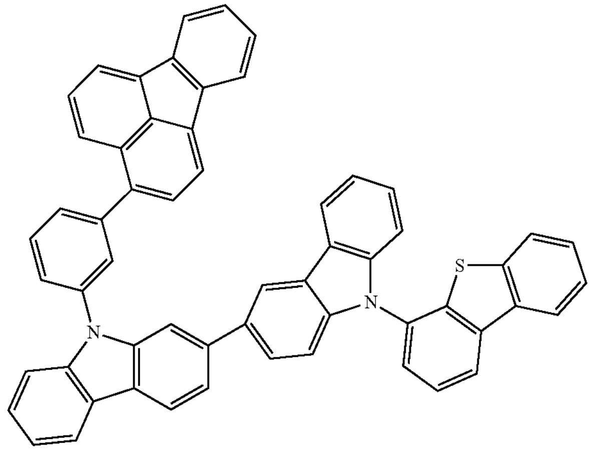
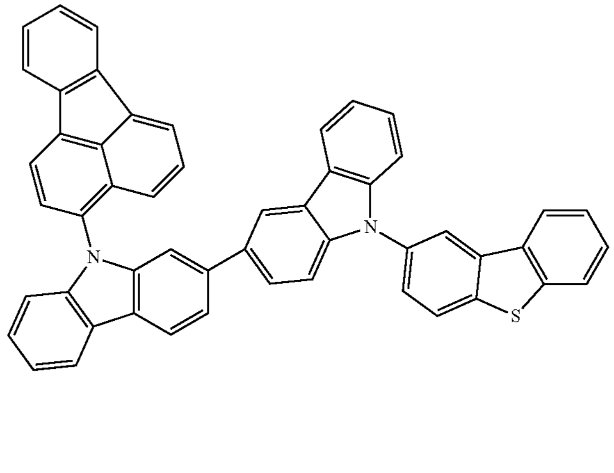

-continued
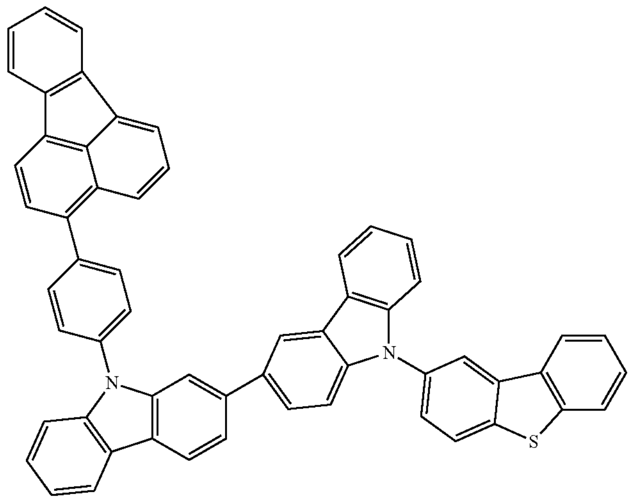
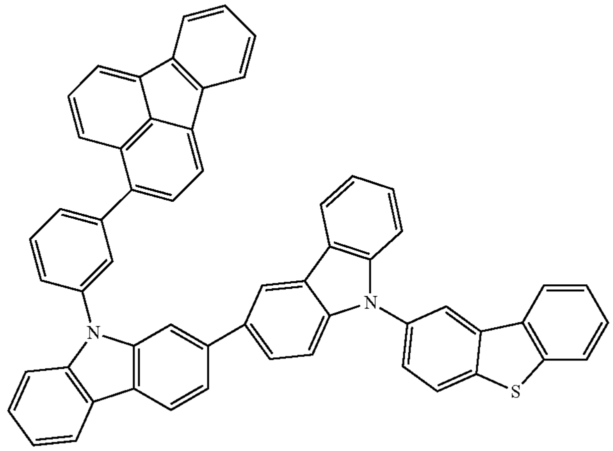
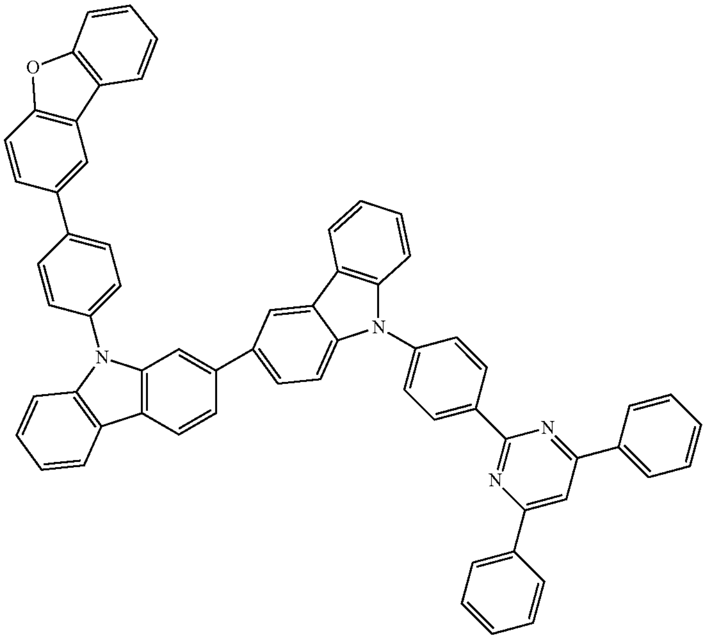

-continued
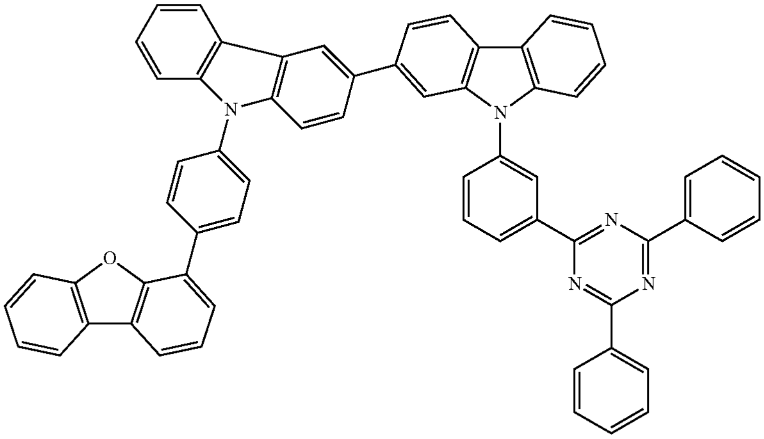
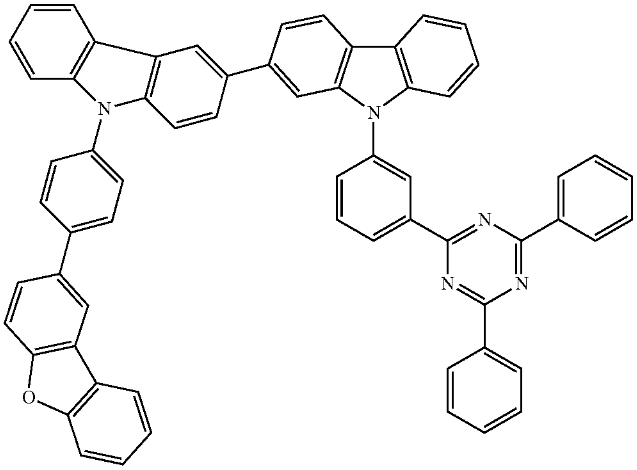
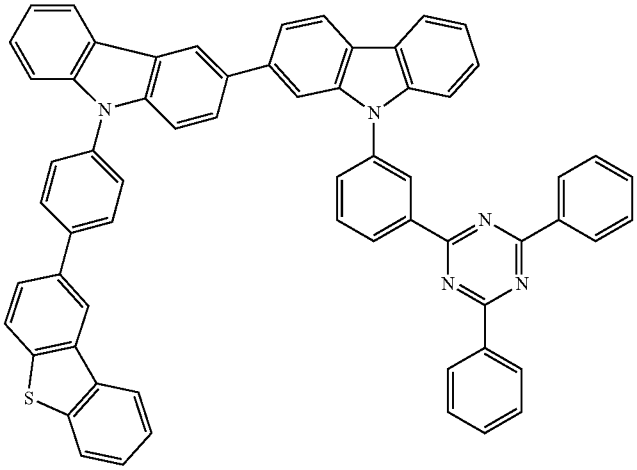

-continued
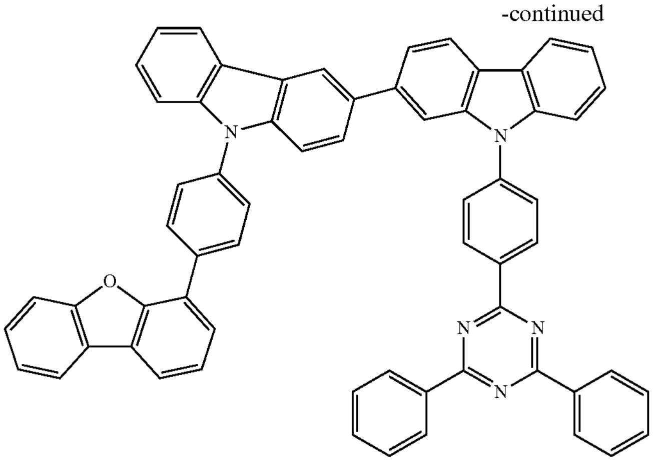
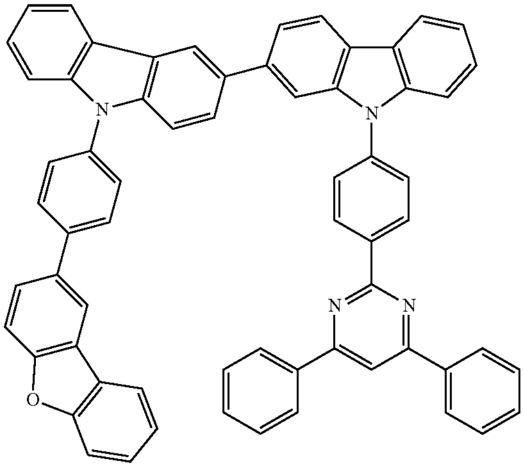
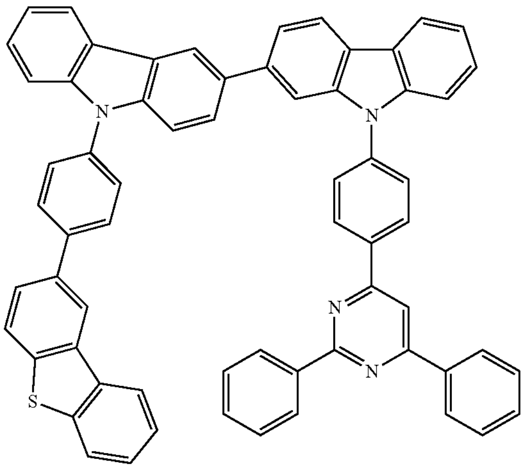 [SMILES: c1ccc(-c2cc(-c3ccc(-n4c5ccccc5c5ccc(-c6ccc7c(c6)c6ccccc6n7-c6ccc(-c7ccc8sc9ccccc9c8c7)cc6)cc54)cc3)nc(-c3ccccc3)n2)cc1]

-continued
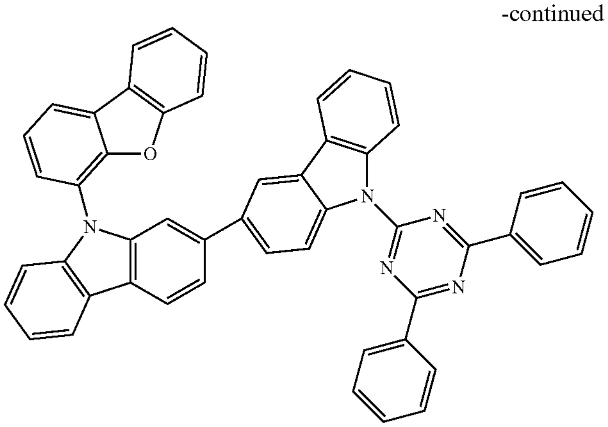
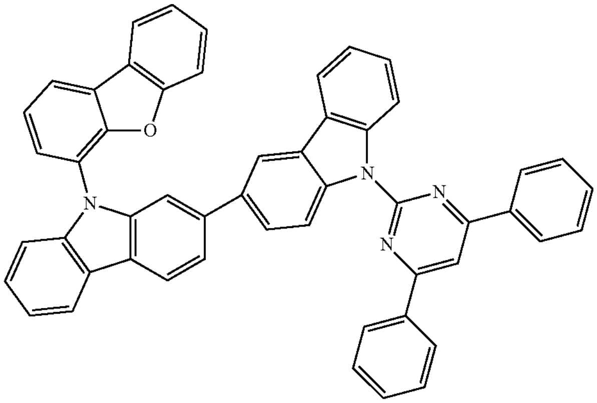
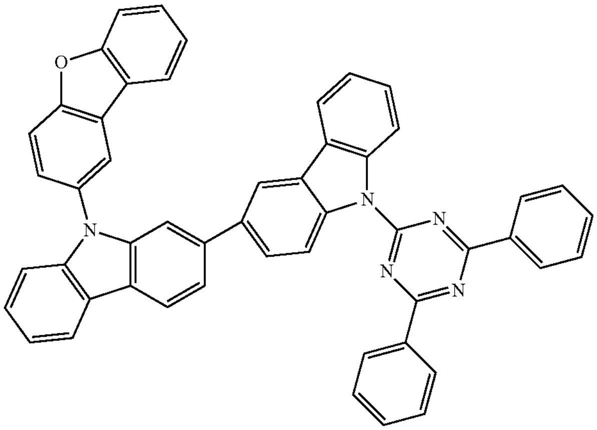
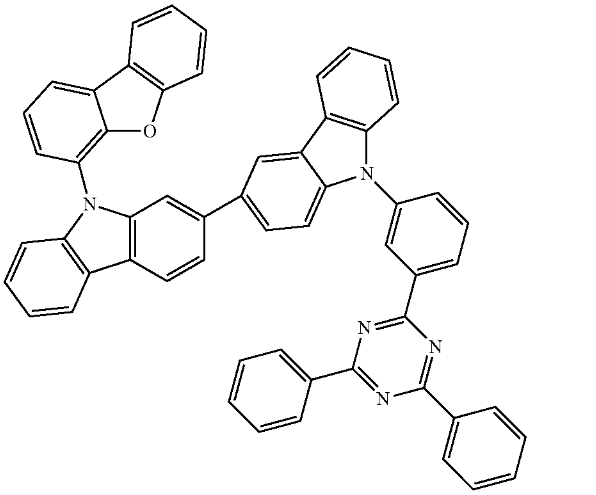

-continued
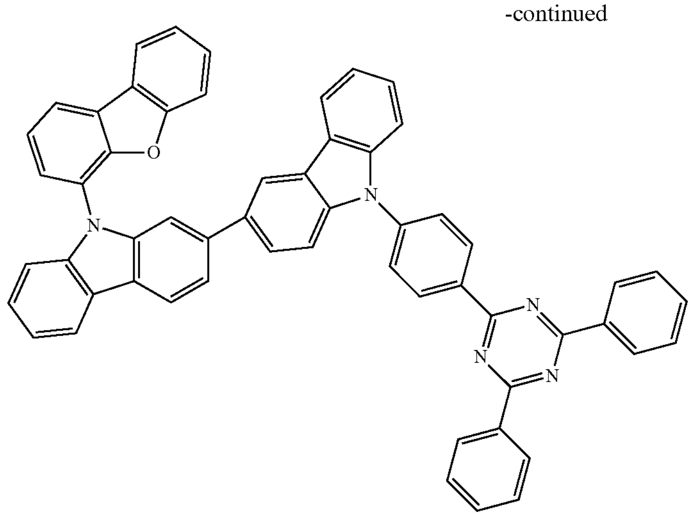
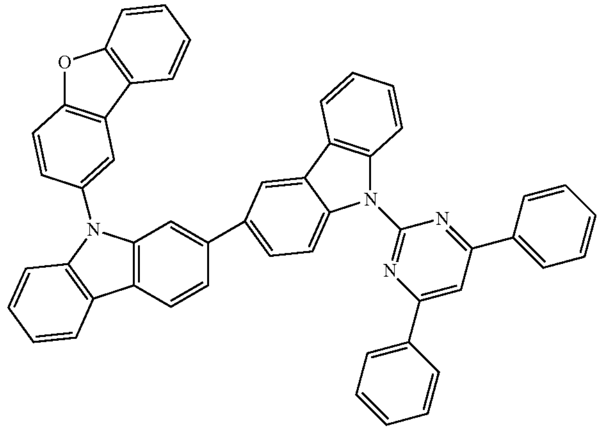
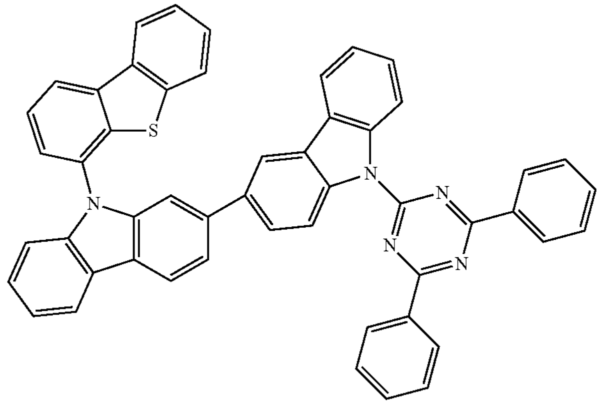
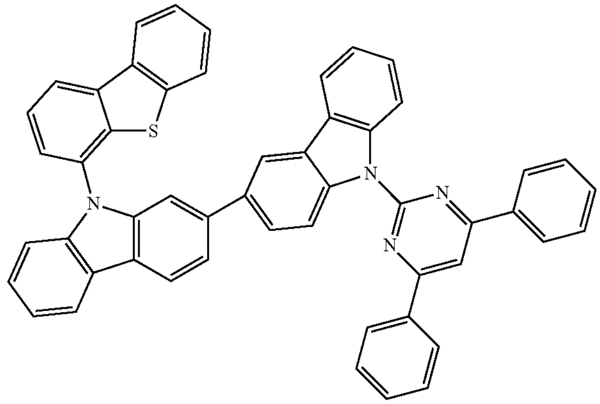

-continued
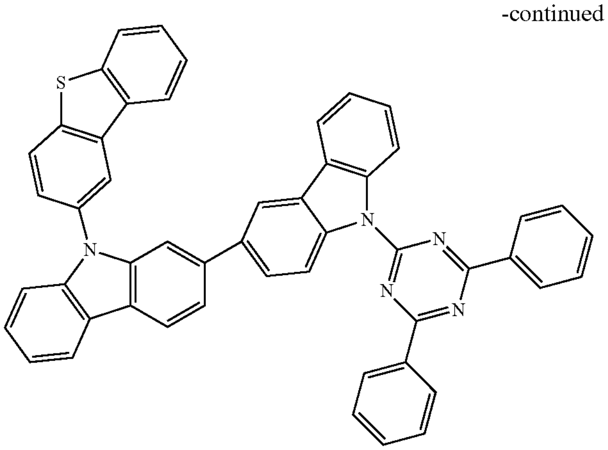
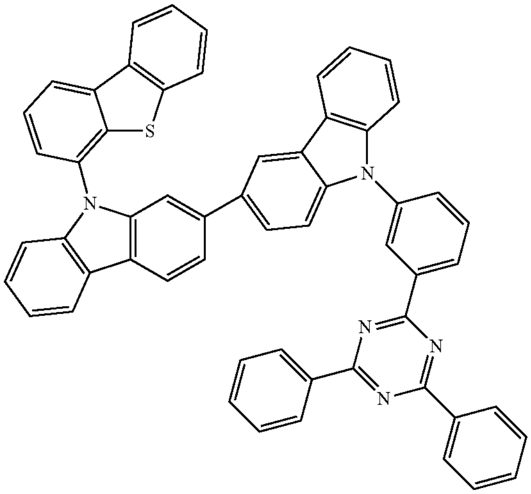
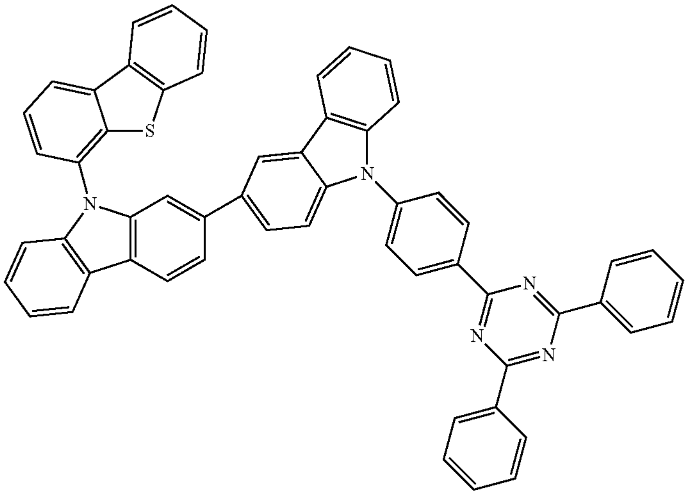

-continued
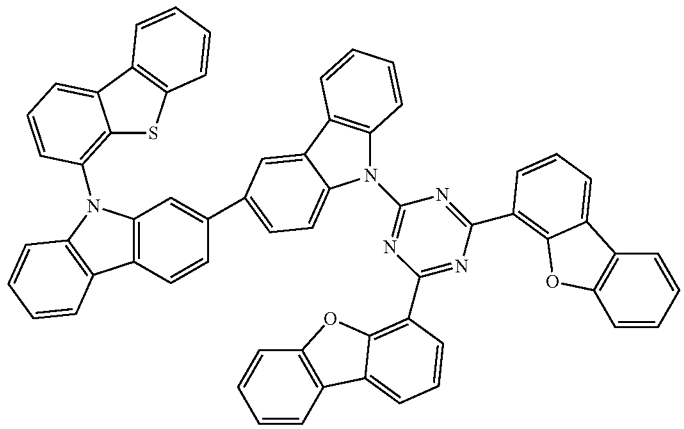
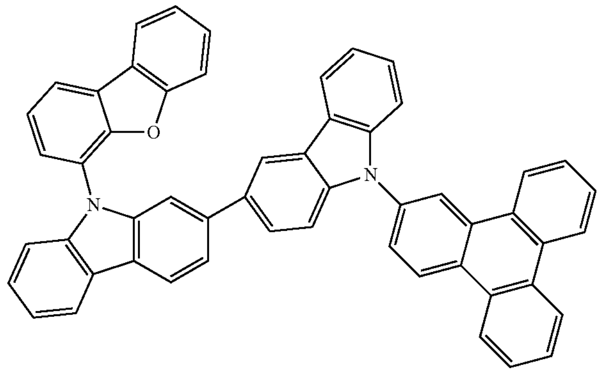
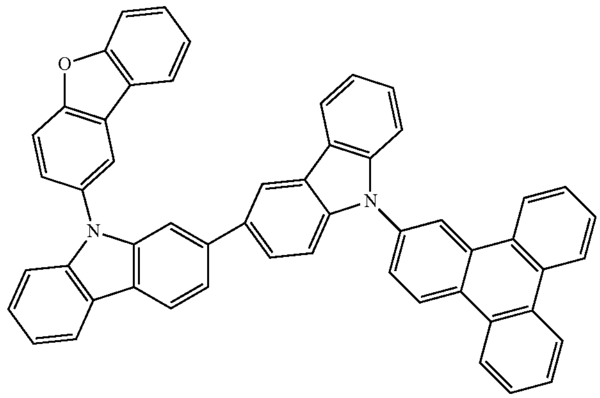
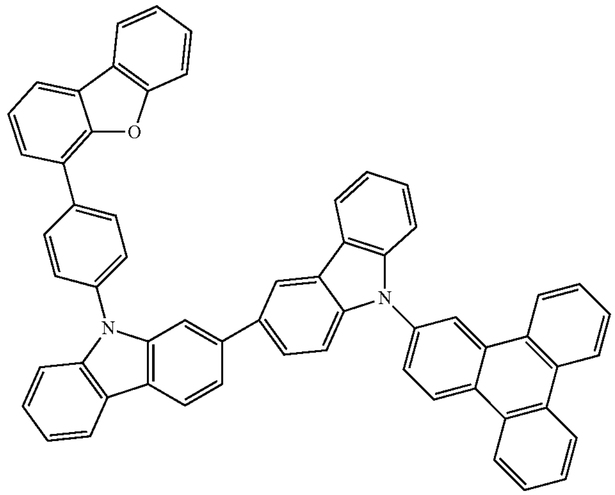

-continued
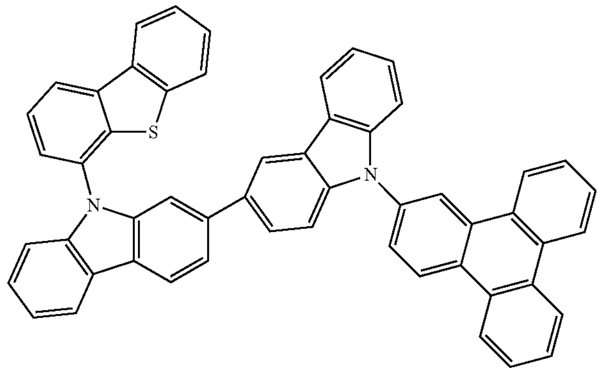
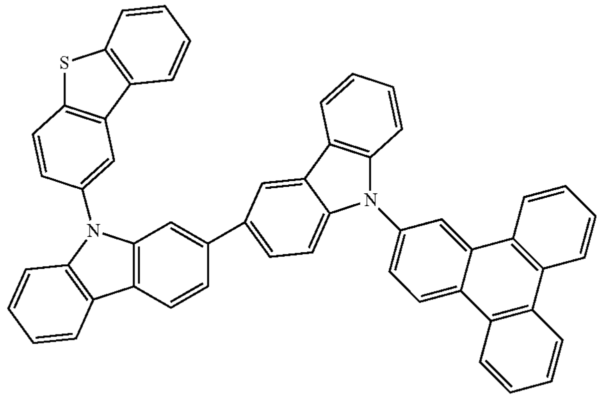
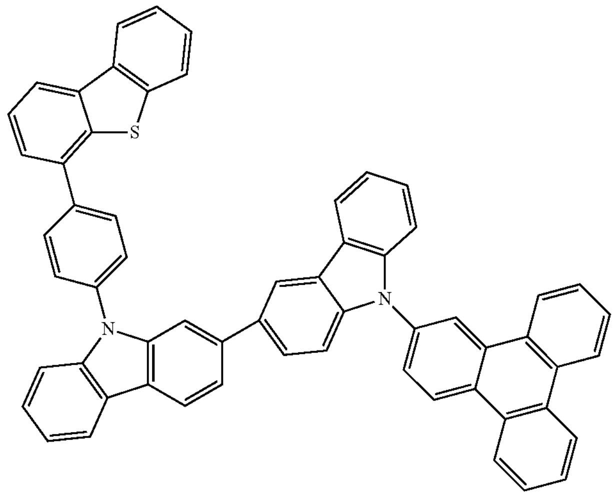

-continued
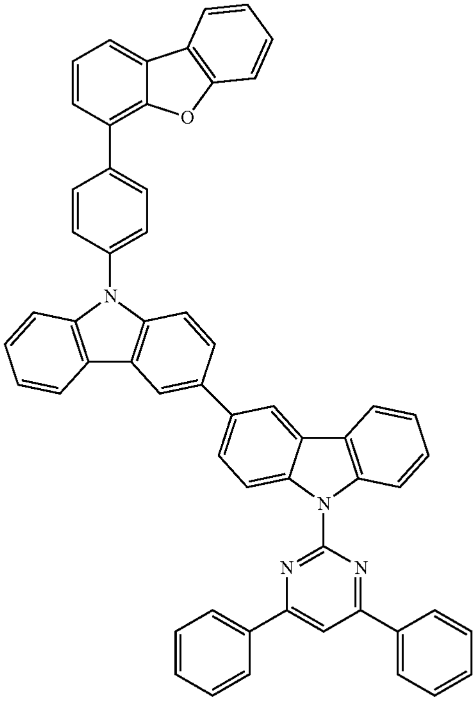
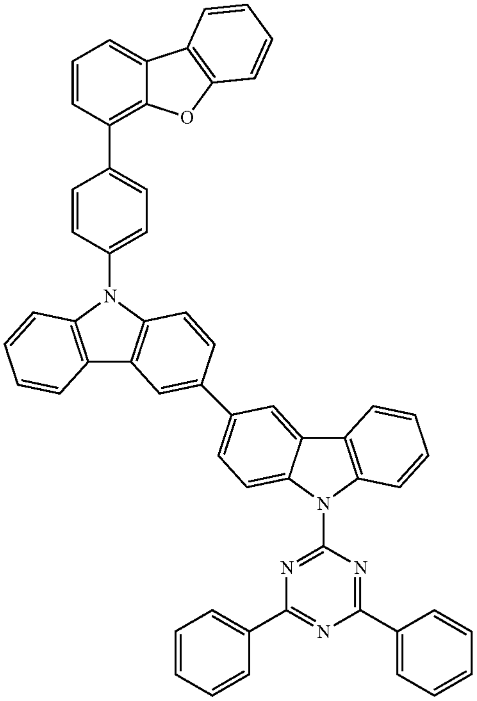
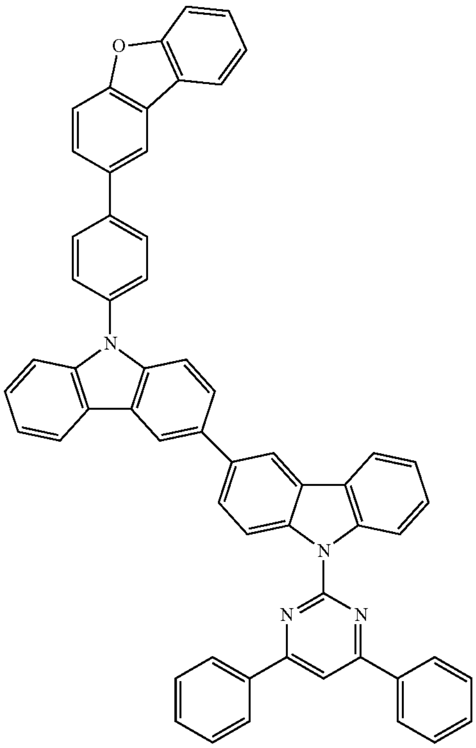
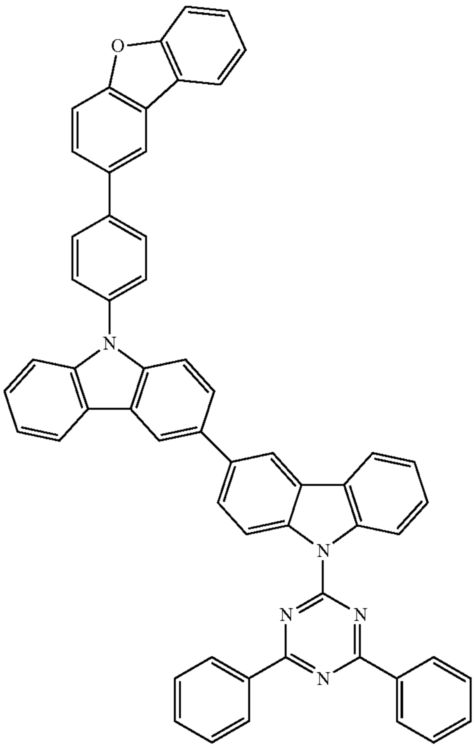

-continued
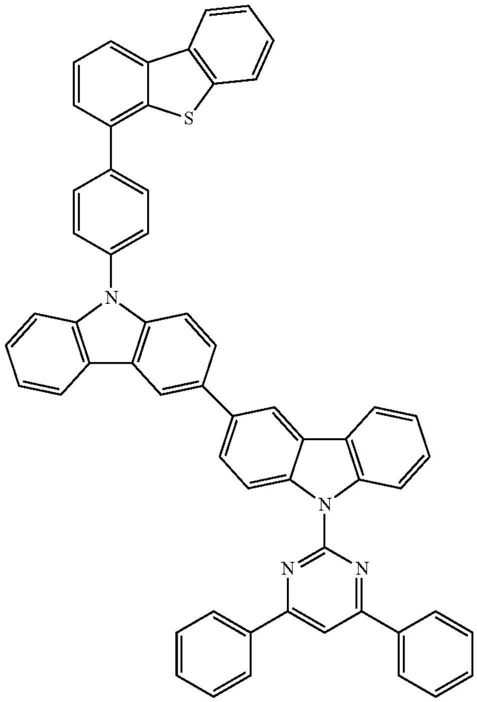
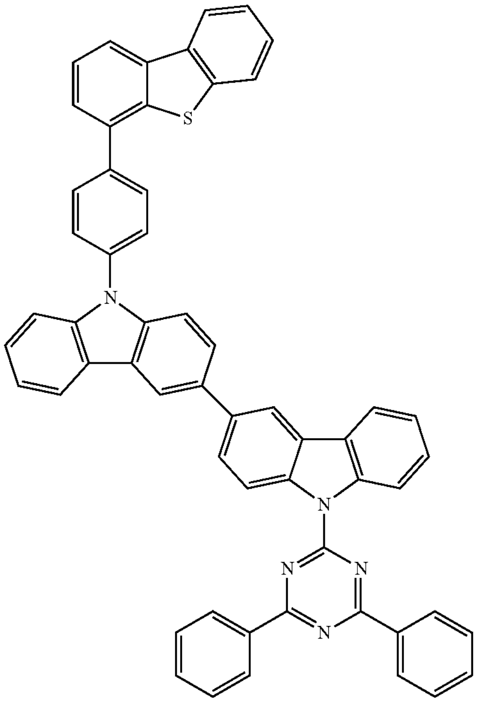
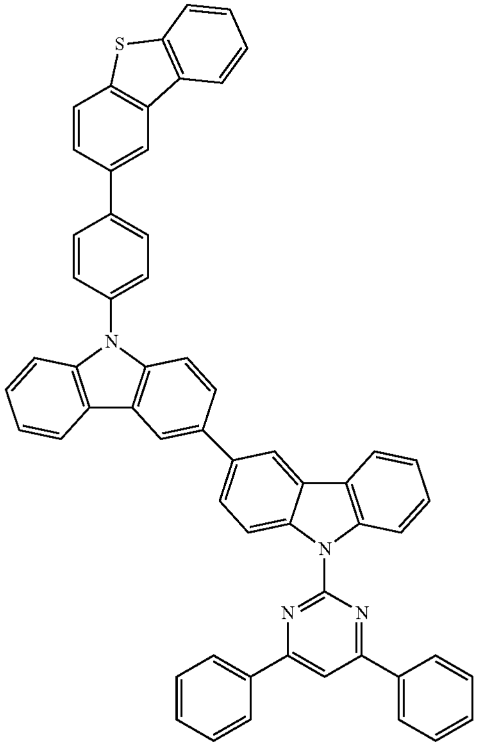
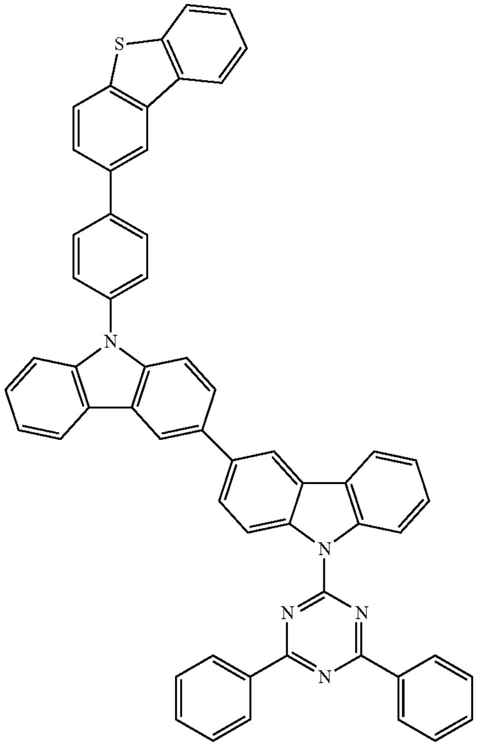

-continued
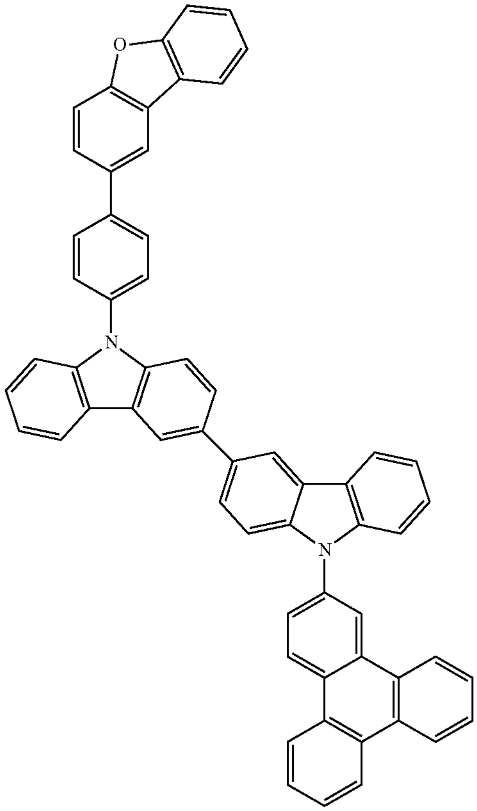
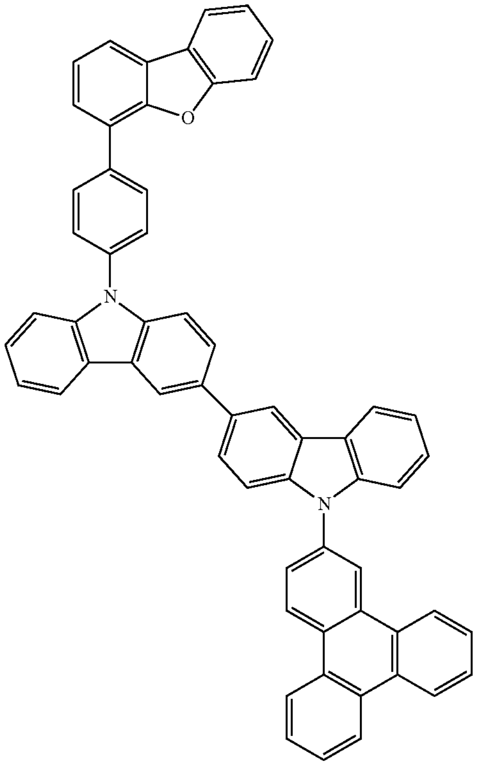
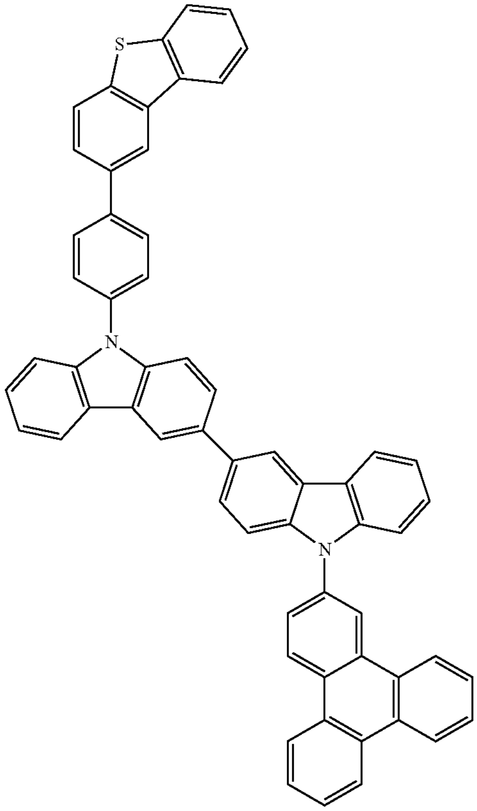
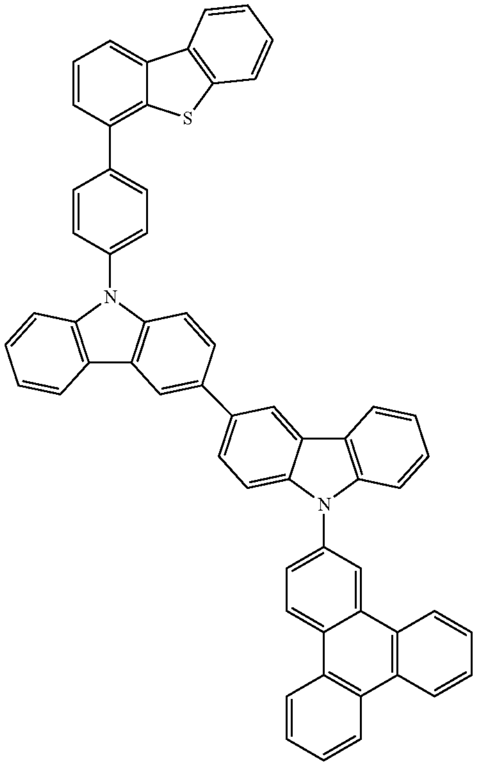

-continued
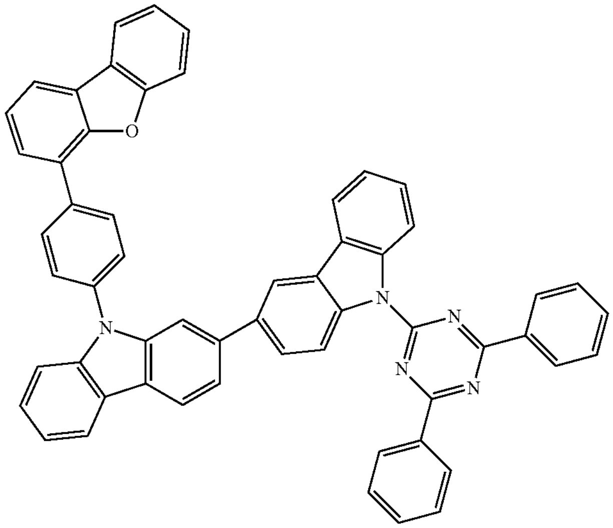
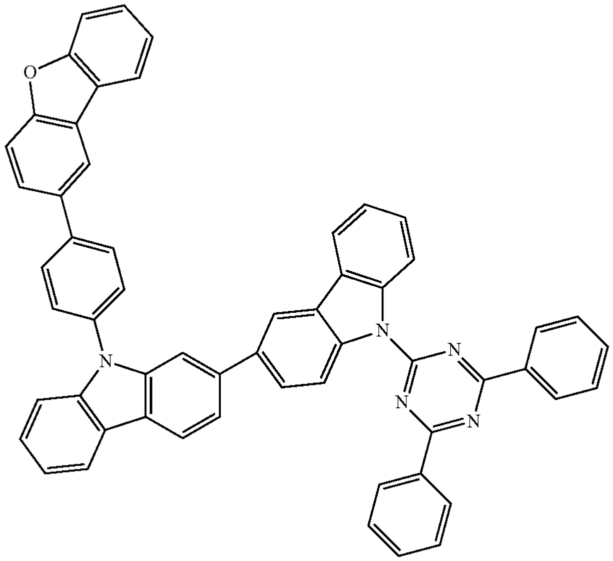
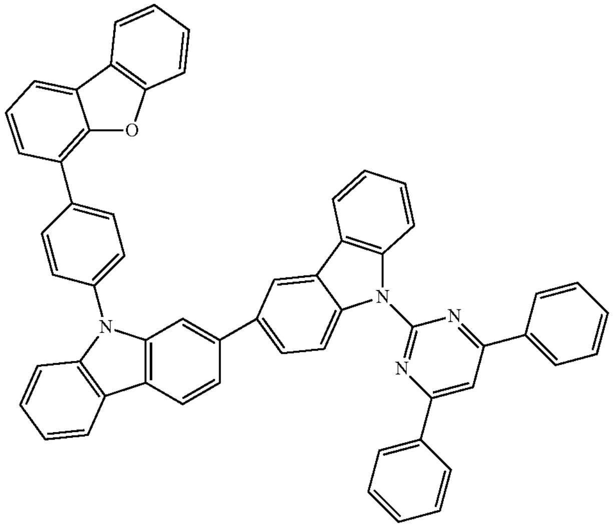

-continued
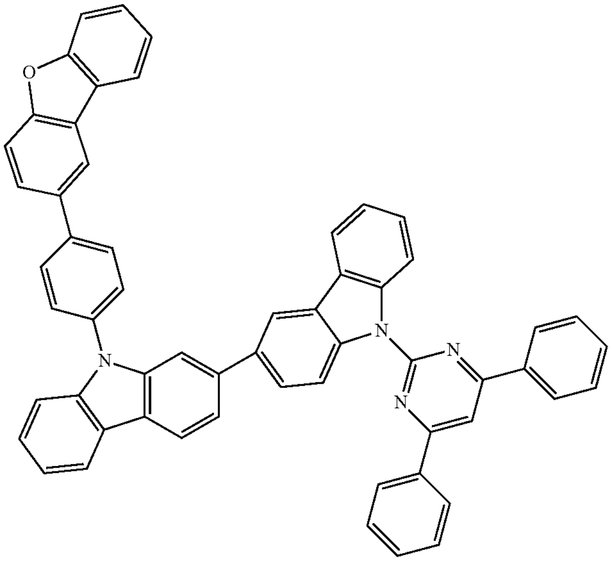
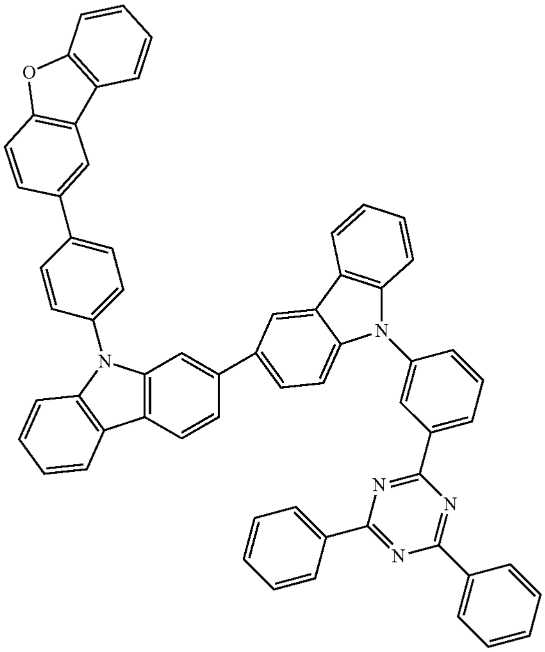
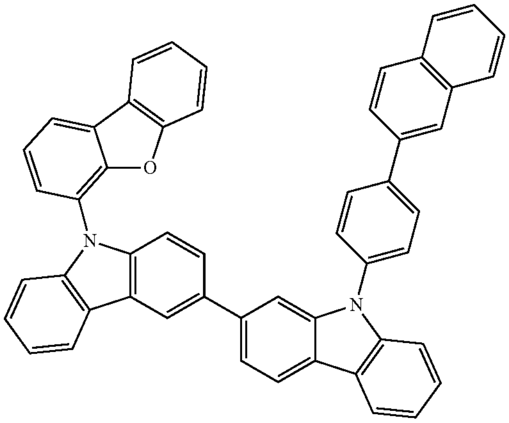
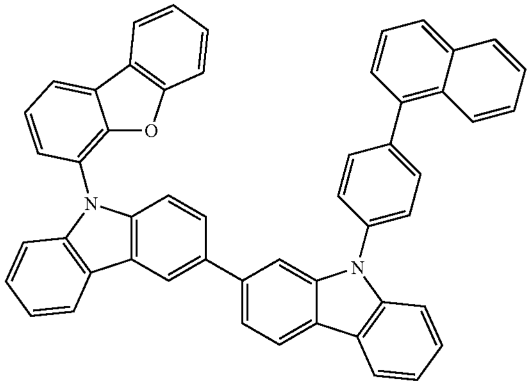
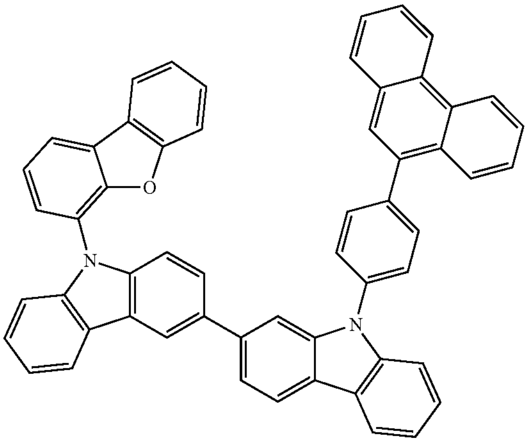

-continued
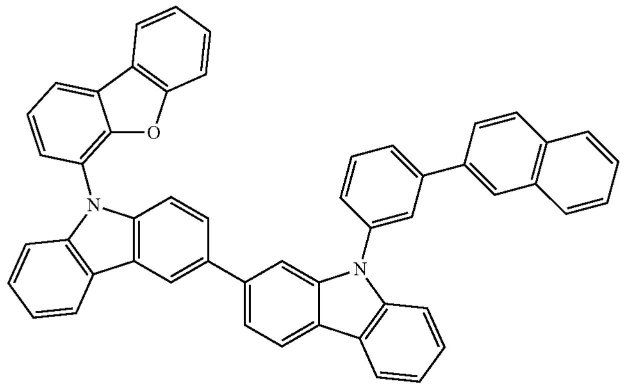
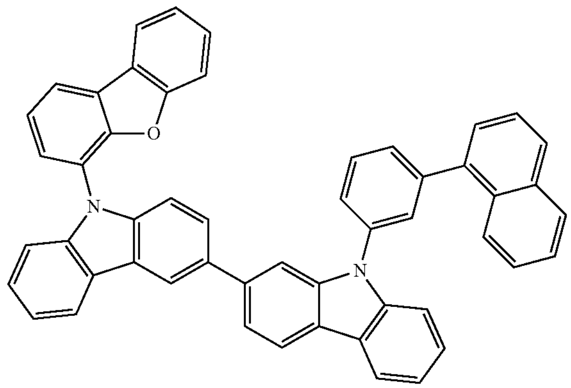
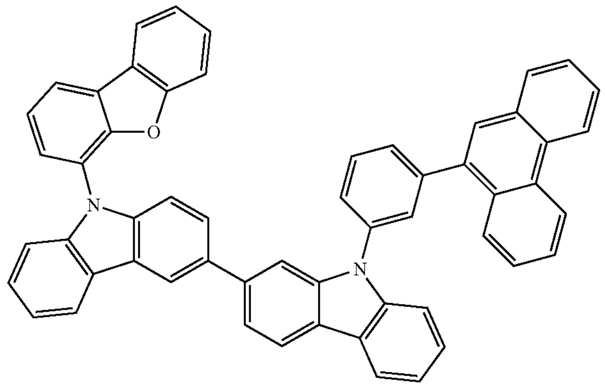
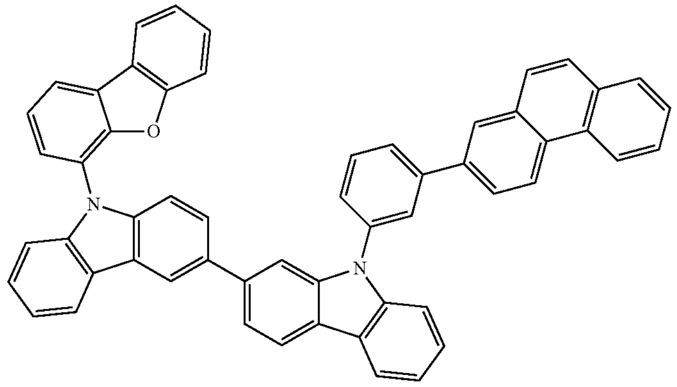

-continued
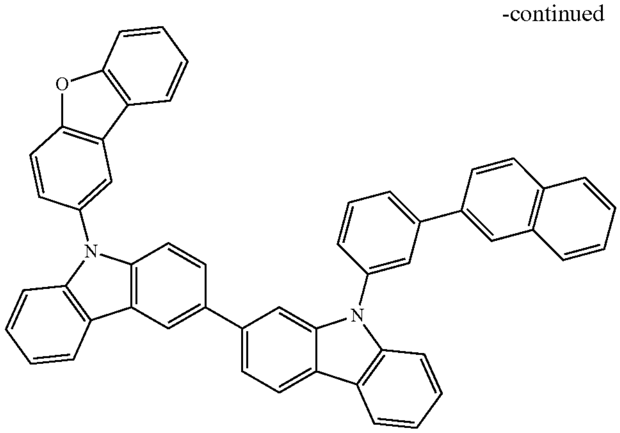
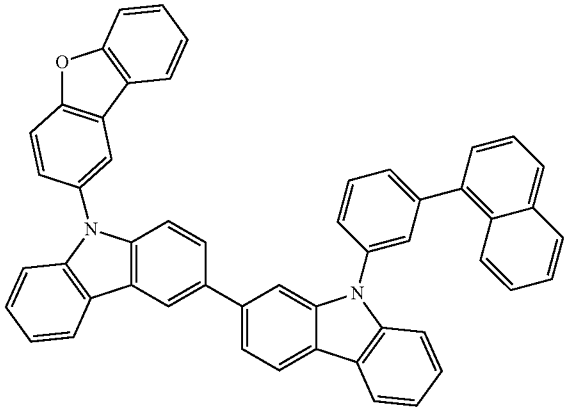
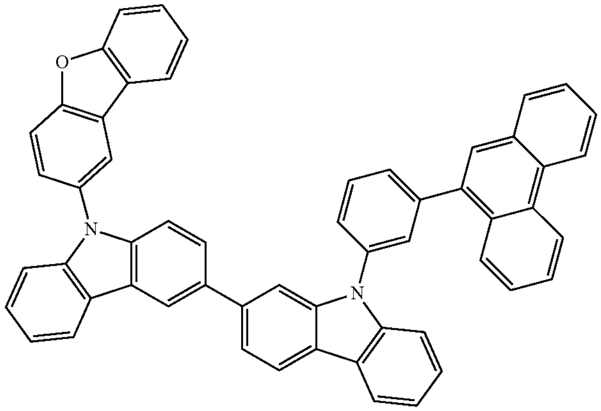
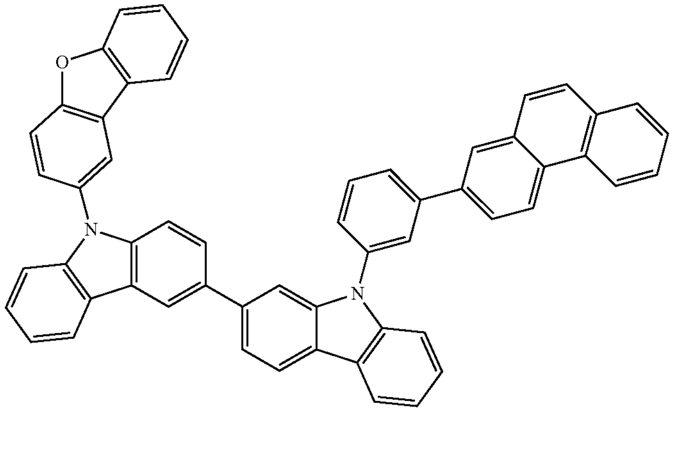

-continued
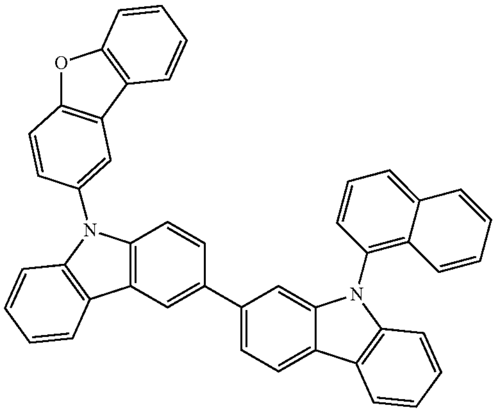
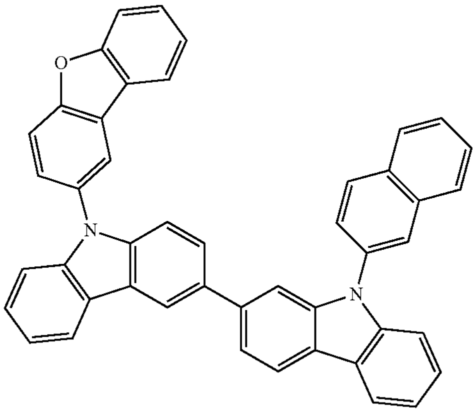
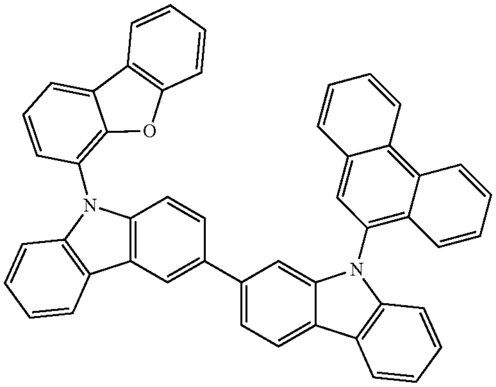
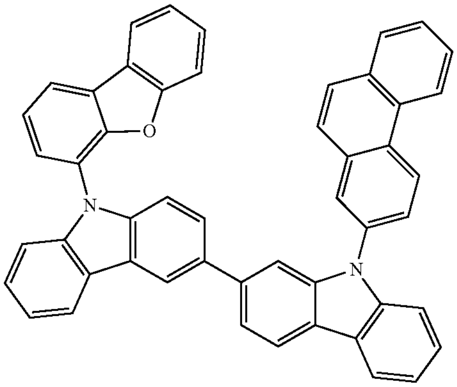
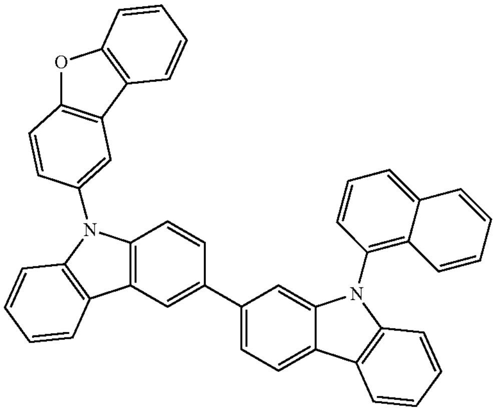
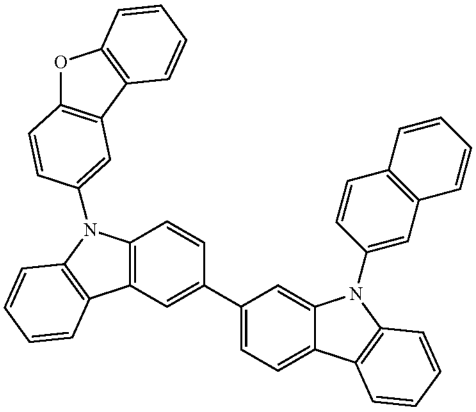
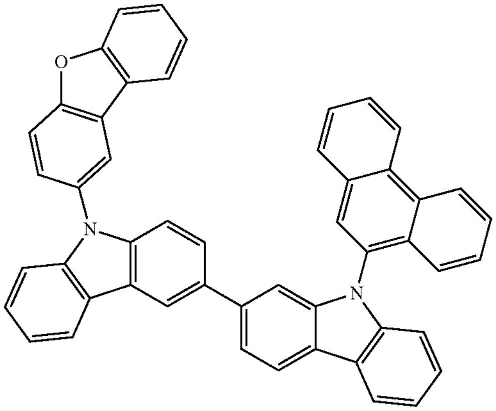
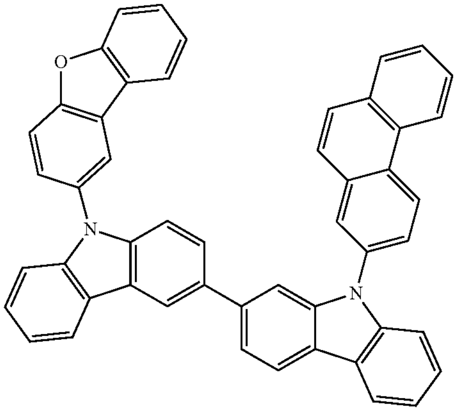

-continued
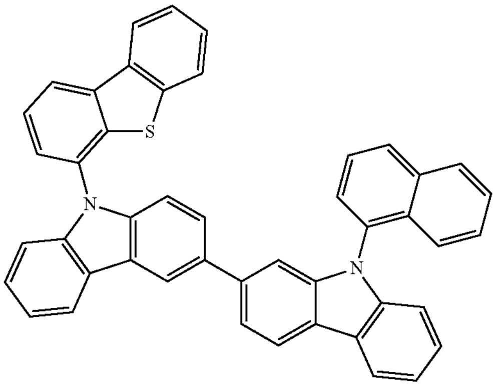
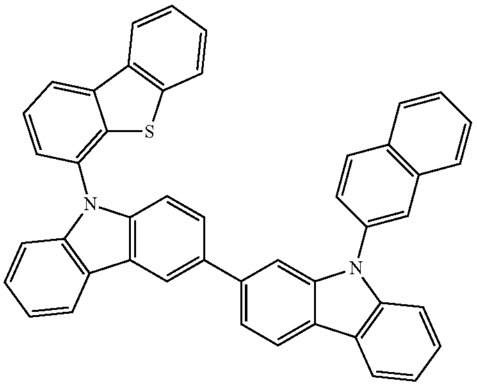
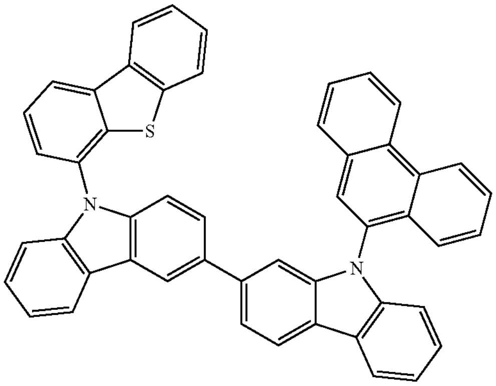
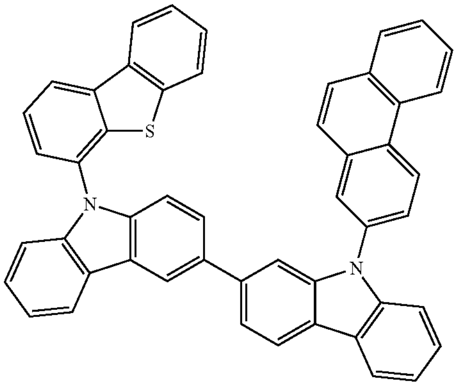
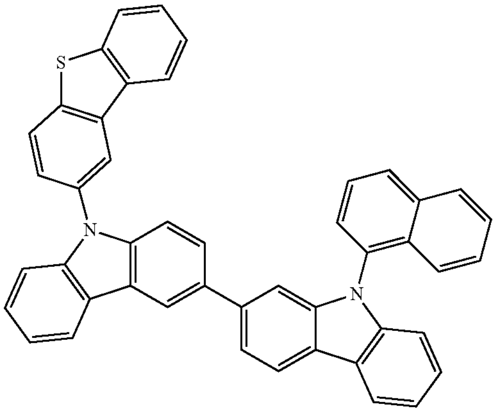
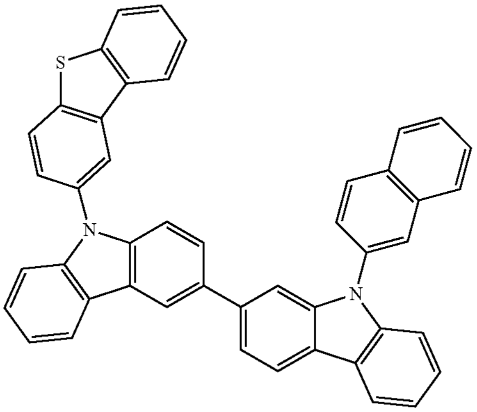
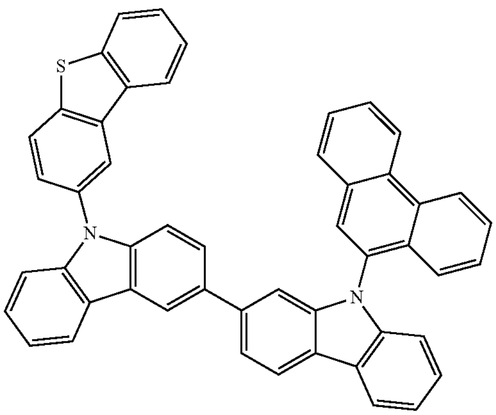
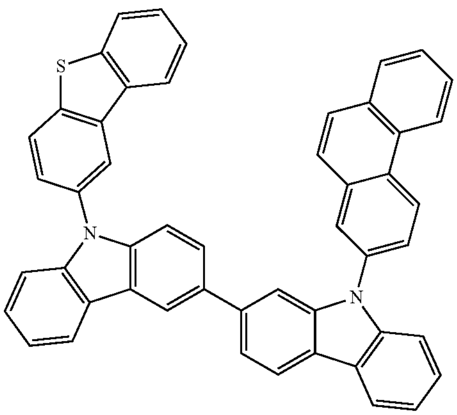

-continued
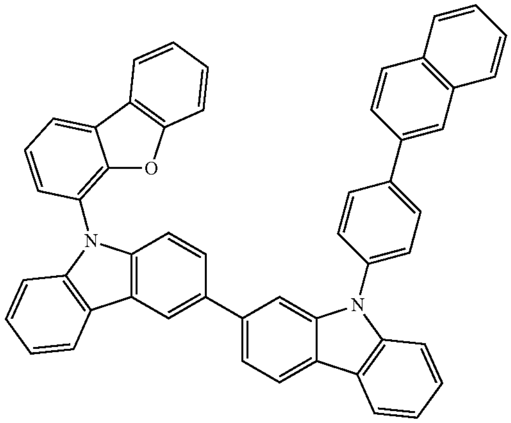
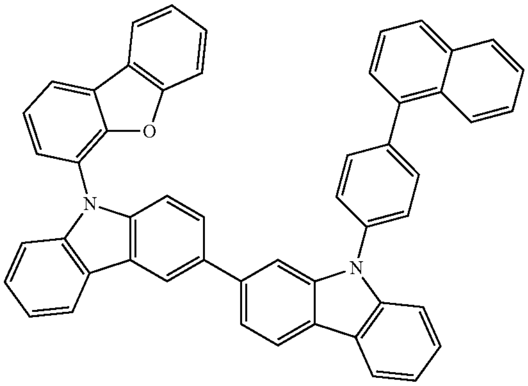
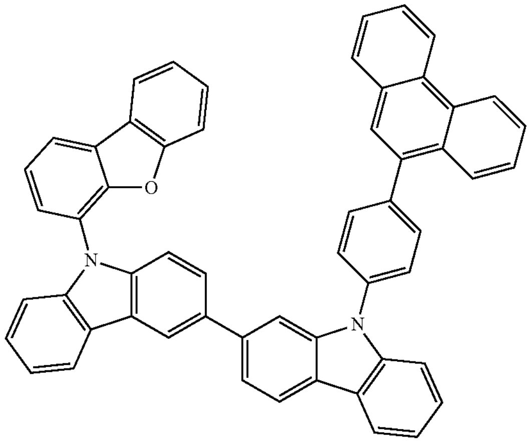
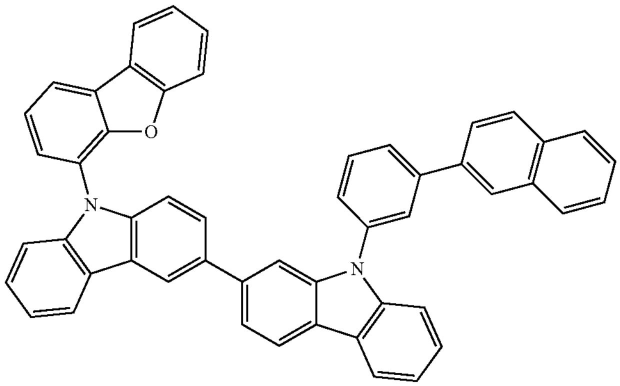
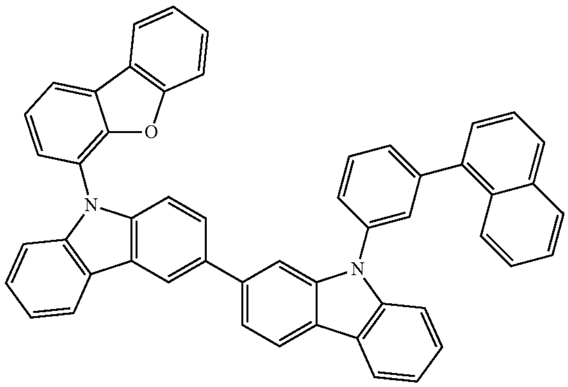

-continued
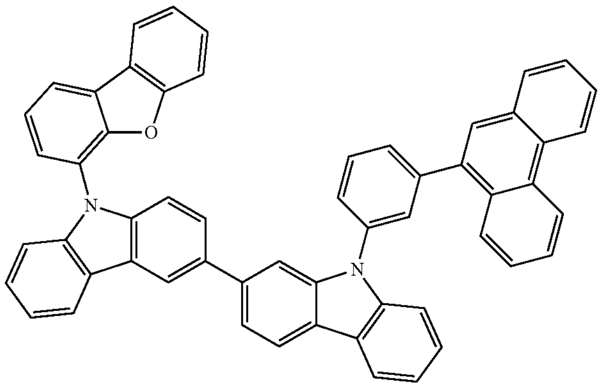
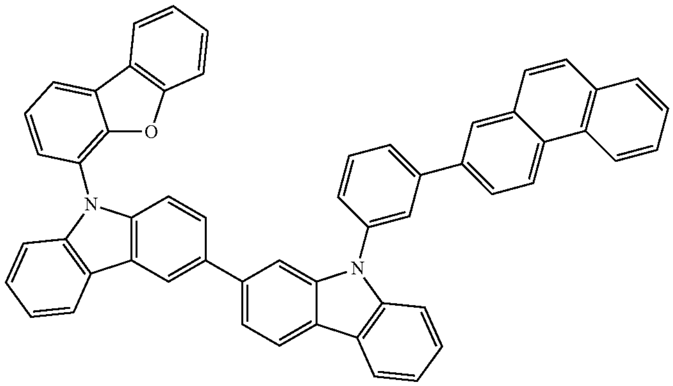
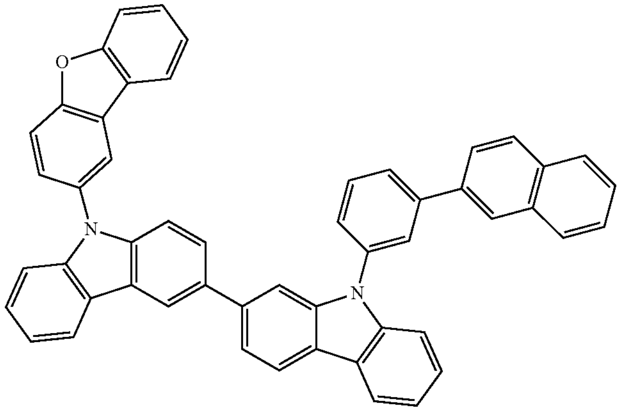
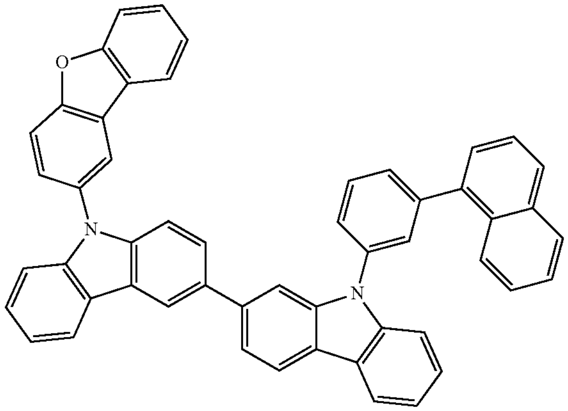

-continued

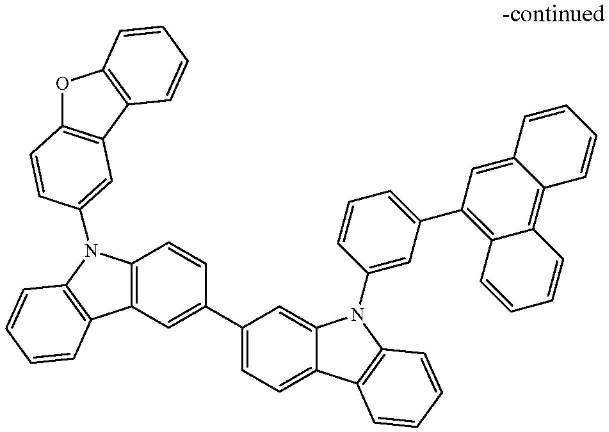

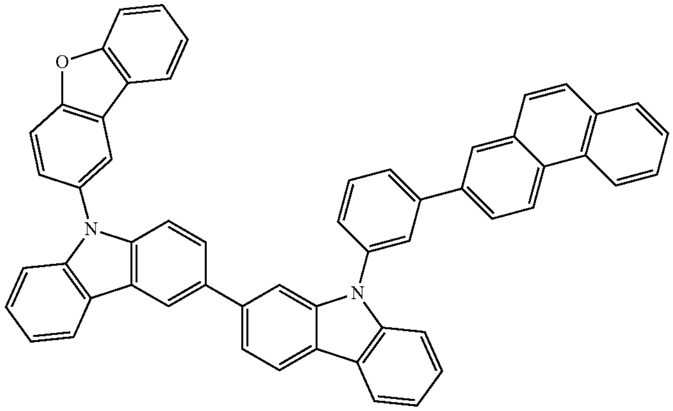

(Second Compound)

The second compound used in the organic EL device according to an aspect of the invention is one or more compounds selected from the group consisting of compounds represented by each of the formulas (11), (12), and (13).

In one embodiment, $L_{1101}$ and $L_{1102}$ in the formula (11) are independently a single bond or a substituted or unsubstituted arylene group including 6 to 50 ring carbon atoms.

In one embodiment, $Ar_{1102}$ in the formula (11) is a substituted or unsubstituted aryl group including 6 to 50 ring carbon atoms.

In one embodiment, $R_{1101}$ to $R_{1108}$ in the formula (11) are hydrogen atoms.

Note that, in this specification, the "nitrogen-containing heterocyclic group" is a heterocyclic group containing a nitrogen atom. Specific examples include the above-mentioned unsubstituted heterocyclic groups containing a nitrogen atom (specific example group G2A1), monovalent heterocyclic groups derived by removing one hydrogen atom from the above-mentioned ring structures represented by each of the formulas (TEMP-16) to (TEMP-33) (specific example group G2A4) in which at least one of $X_A$ and $Y_A$ is NH, the above-mentioned substituted heterocyclic groups containing a nitrogen atom (specific example group G2B1), and groups in which one or more hydrogen atoms of the above-mentioned monovalent heterocyclic groups derived from the ring structures represented by each of the formulas (TEMP-16) to (TEMP-33) are substituted by a substituent (specific example group G2B4) in which at least one of $X_A$ and $Y_A$ is NH.

In one embodiment, $L_{1201}$ to $L_{1203}$ in the formula (12) are independently a single bond or a substituted or unsubstituted arylene group including 6 to 50 ring carbon atoms.

In one embodiment, $Ar_{1201}$ and $Ar_{1202}$ in the formula (12) are independently a substituted or unsubstituted aryl group including 6 to 50 ring carbon atoms.

In one embodiment, $R_{1201}$ to $R_{1207}$ in the formula (12) are hydrogen atoms.

In one embodiment, one of $Ar_{1301}$ to $Ar_{1303}$ in the formula (13) is the group represented by the formula (13A).

In one embodiment, two of $Ar_{1301}$ to $Ar_{1303}$ in the formula (13) are groups represented by the formula (13A).

In one embodiment, two of $X_{1301}$ to $X_{1303}$ in the formula (13) are N's.

In one embodiment, $L_{13A}$ in the formula (13A) is a single bond or a substituted or unsubstituted arylene group including 6 to 50 ring carbon atoms.

In one embodiment, the compound represented by the formula (13) is a compound represented by the following formula (13-1).

(13-1)

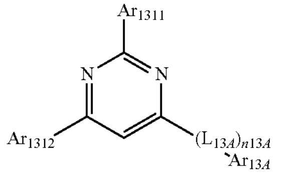

wherein in the formula (13-1), $L_{13A}$, $Ar_{13A}$, and n13A are as defined in the formula (13A); $Ar_{1311}$ and $Ar_{1312}$ are independently a substituted or unsubstituted aryl group including 6 to 50 ring carbon atoms, or the group represented by the formula (13A).

In one embodiment, $Ar_{1311}$ and $Ar_{1312}$ in the compound represented by the formula (13-1) are independently a substituted or unsubstituted aryl group including 6 to 50 ring carbon atoms.

In one embodiment, the compound represented by the formula (13) is a compound represented by the following formula (13-2).

(13-2)

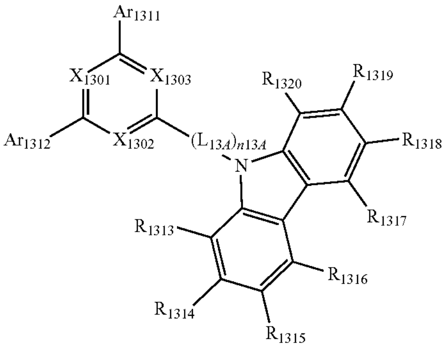

wherein in the formula (13-2), $X_{1301}$ to $X_{1303}$, $L_{13A}$, and n13A are as defined in the formula (13); $Ar_{1311}$ and $Ar_{1312}$ are independently a substituted or unsubstituted aryl group including 6 to 50 ring carbon atoms, or the group represented by the formula (13A); $R_{1313}$ to $R_{1320}$ are hydrogen atoms or substituent R's; and the substituent R is as defined in the formula (11).

In one embodiment, $Ar_{1311}$ and $Ar_{1312}$ in the compound represented by the formula (13-2) are independently a substituted or unsubstituted aryl group including 6 to 50 ring carbon atoms.

In one embodiment, the compound represented by the formula (13) is a compound represented by the following formula (13-11).

(13-11)

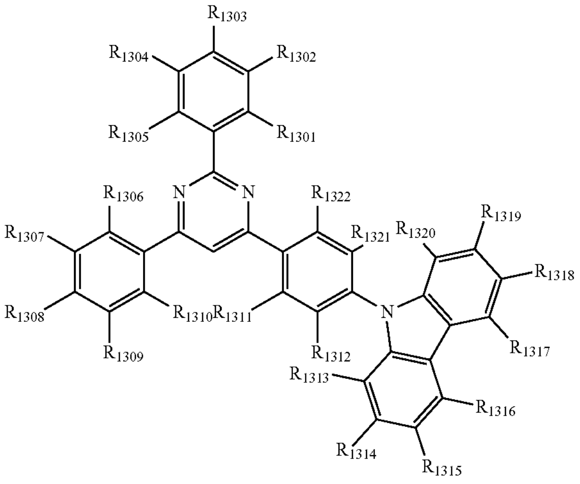

wherein in the formula (13-11), $R_{1301}$ to $R_{1322}$ are hydrogen atoms or substituent R's; and the substituent R is as defined in the formula (11).

In one embodiment, the compound represented by the formula (13) is a compound represented by the following formula (13-12).

(13-12)

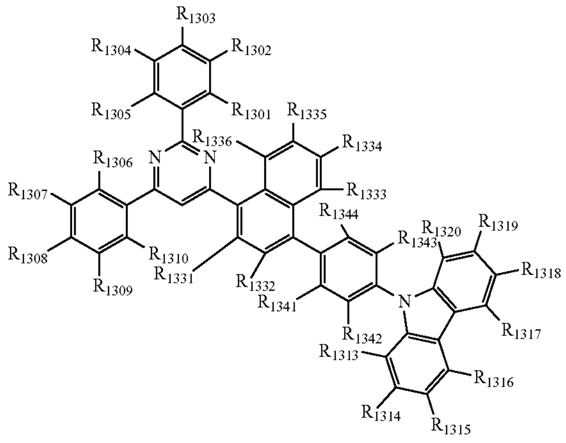

wherein in the formula (13-12), $R_{1301}$ to $R_{1310}$, $R_{1313}$ to $R_{1320}$, $R_{1331}$ to $R_{1336}$, and $R_{1341}$ to $R_{1344}$ are hydrogen atoms or substituent R's; and the substituent R is as defined in the formula (11).

The compounds represented by each of the above formulas (11), (12), and (13) can be synthesized by using known alternative reactions or raw materials tailored to the target product.

Specific examples of the second compound will be described below, but these are merely illustrative, and the second compound is not limited to the following specific examples.

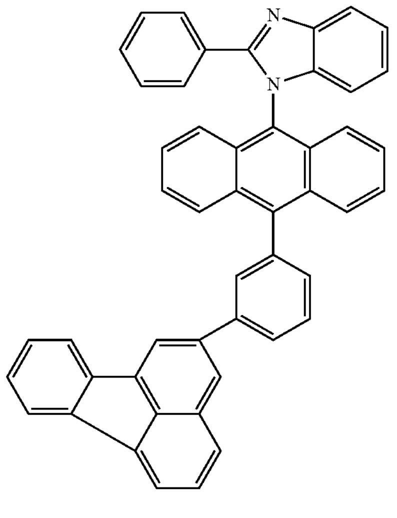

-continued
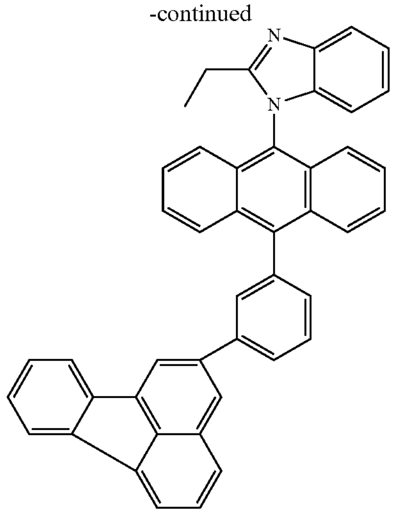
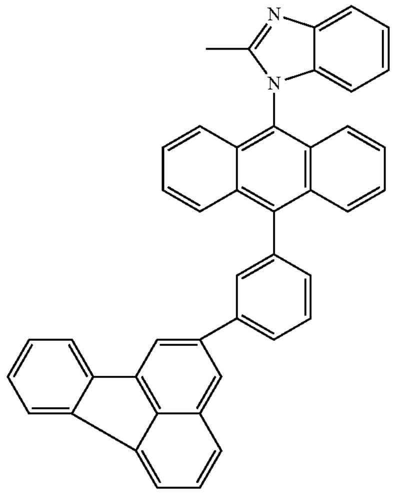
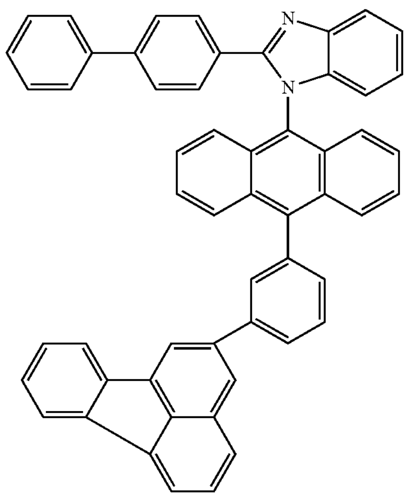
-continued
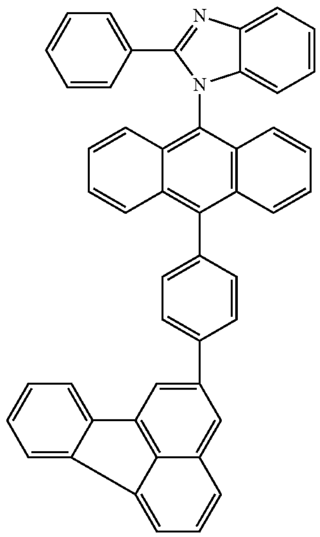
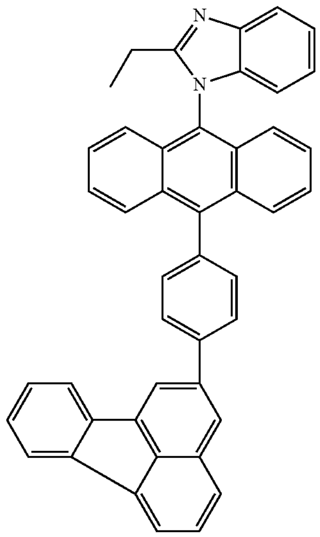
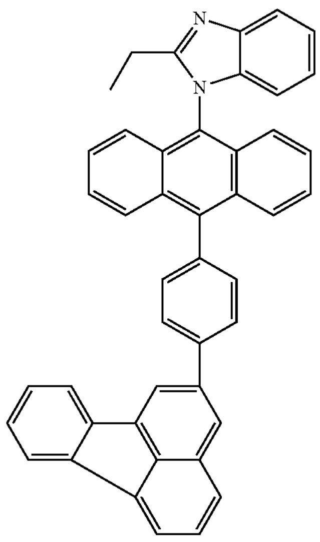

-continued
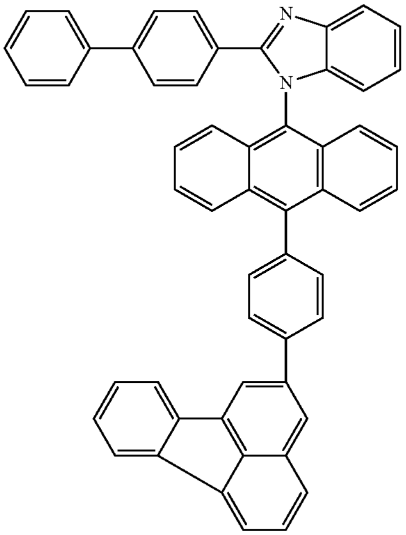
-continued
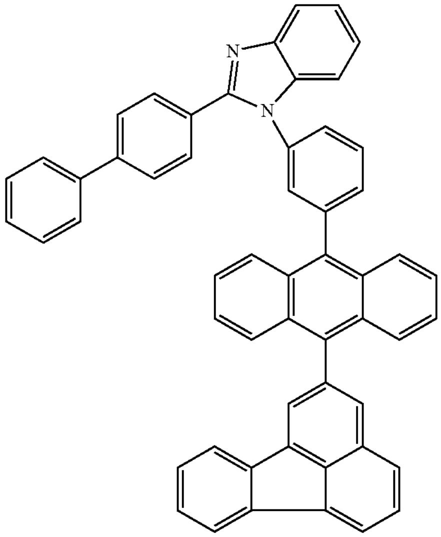
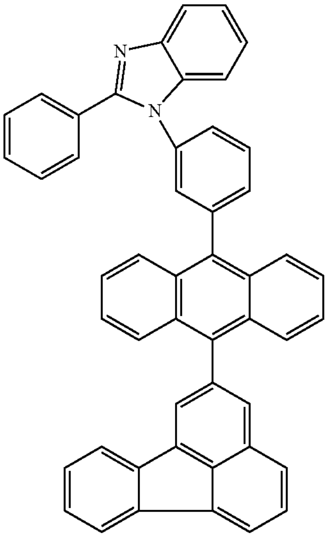
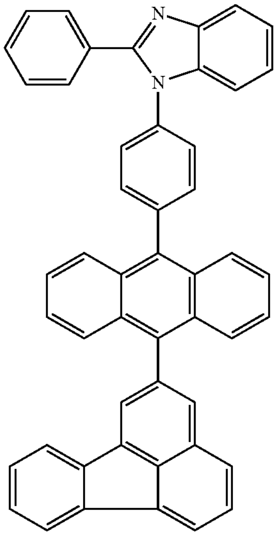
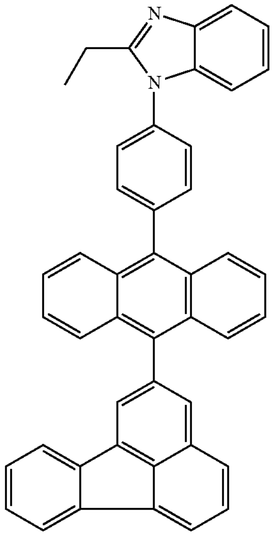
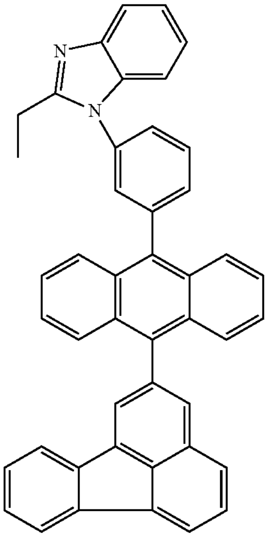
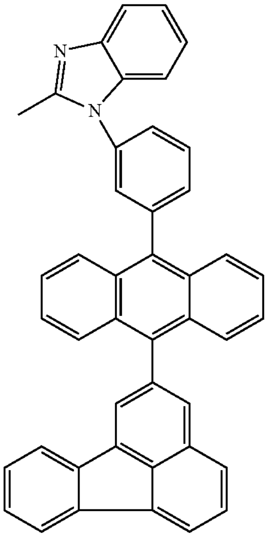
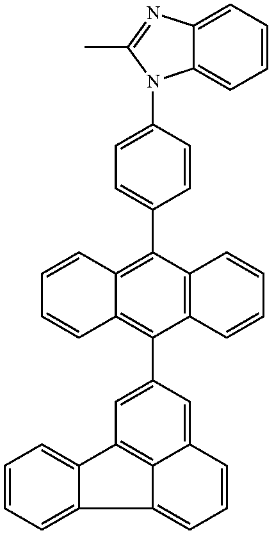

-continued
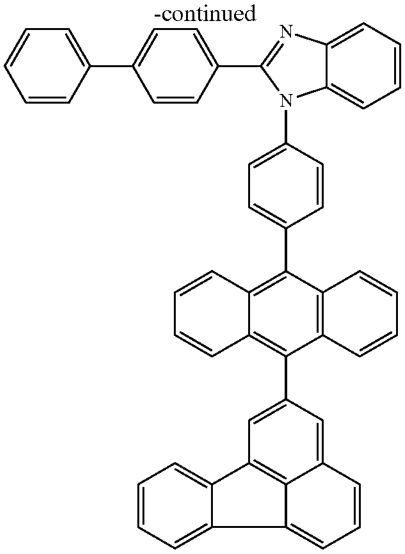
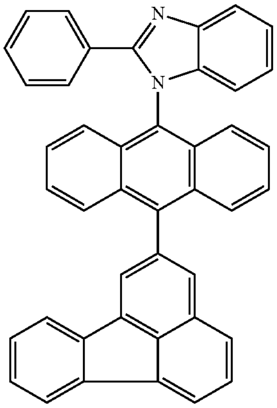
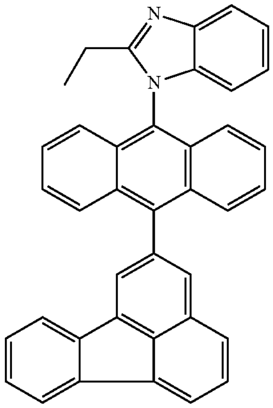
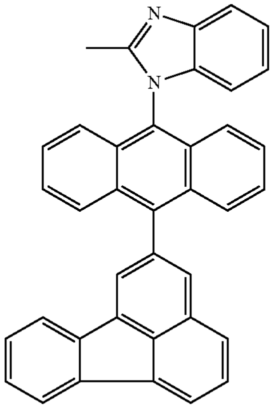
-continued
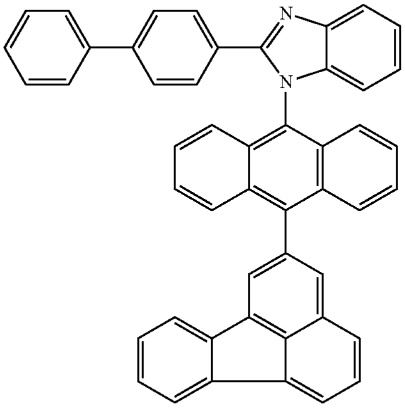
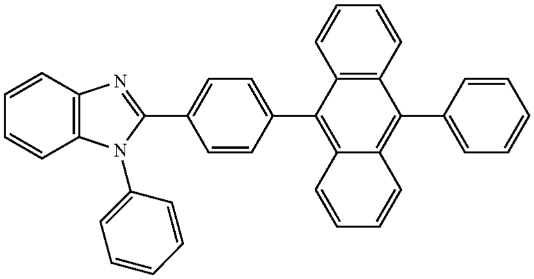
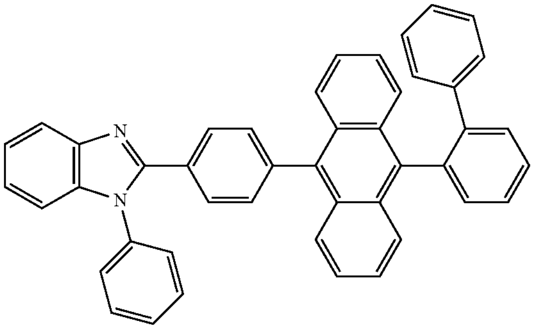
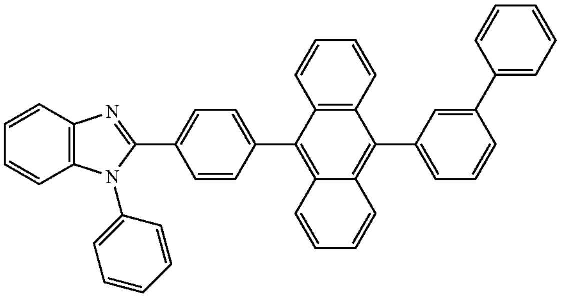
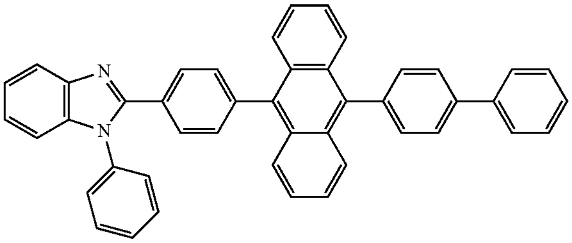

-continued
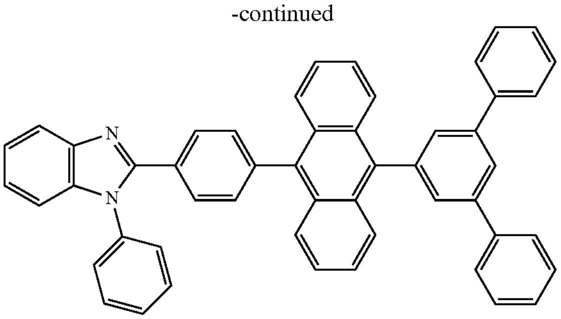
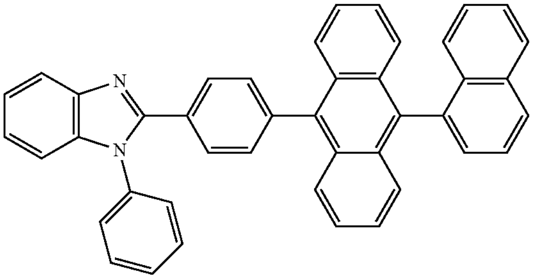
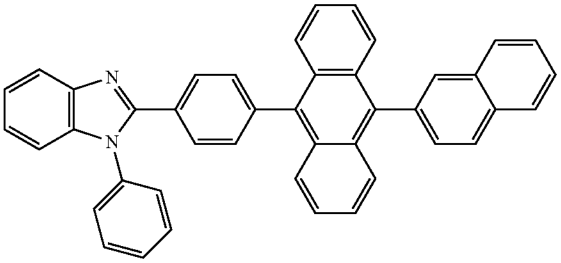
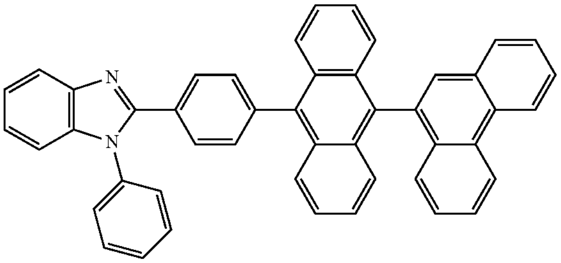
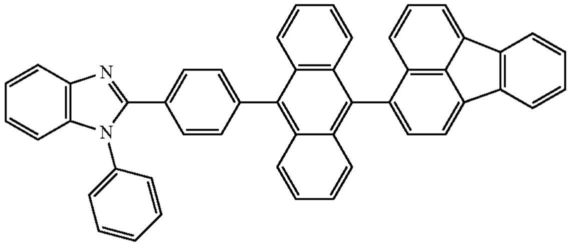
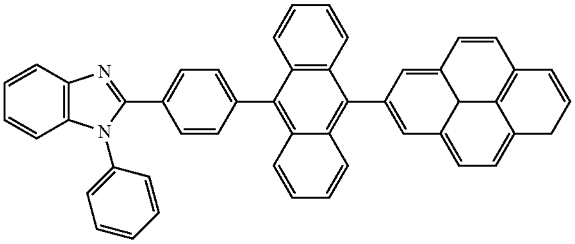
-continued
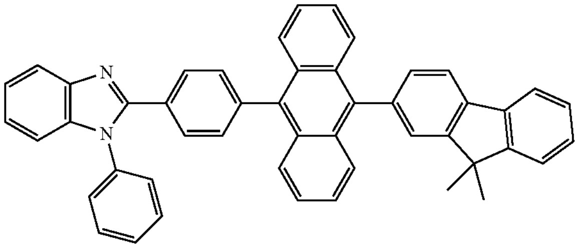
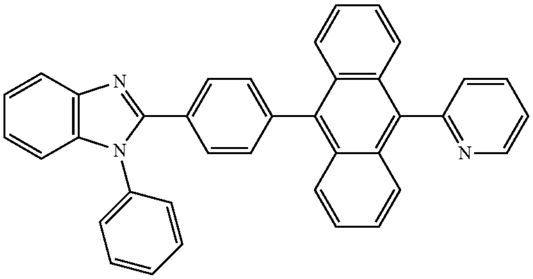
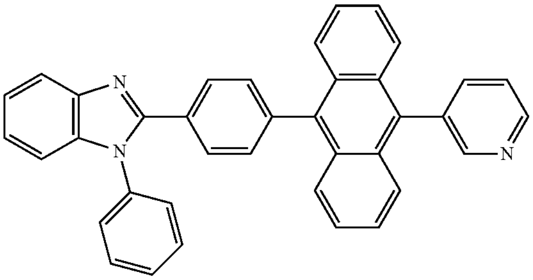
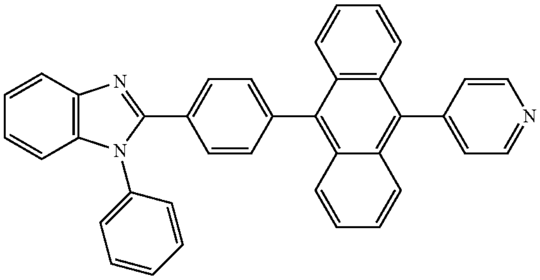
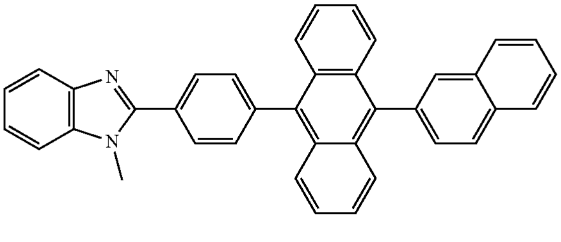
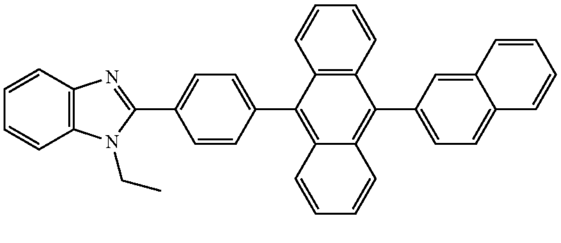

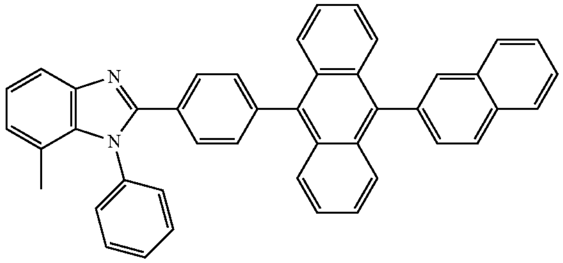
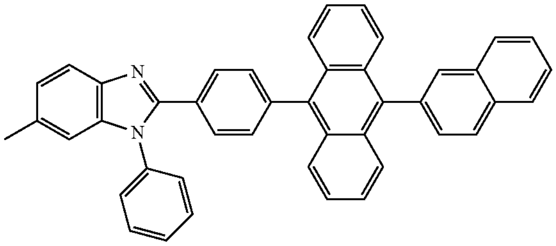
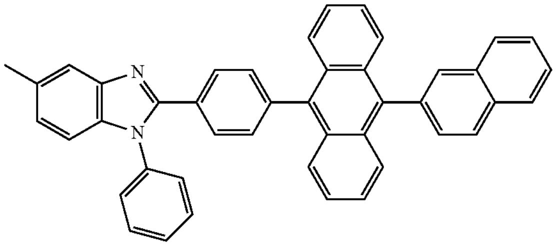
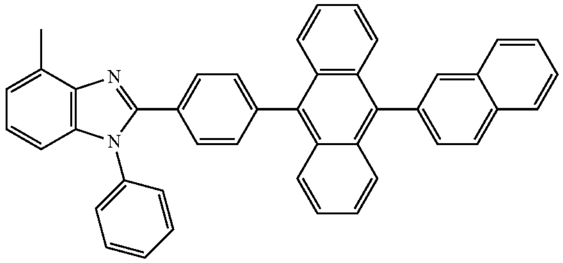
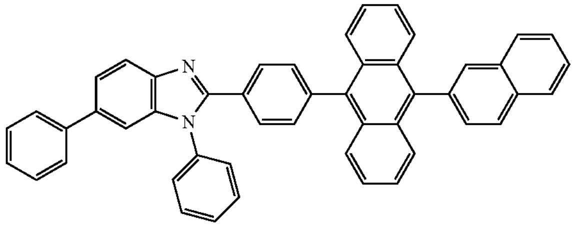
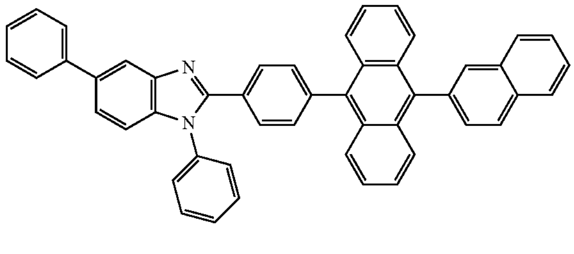
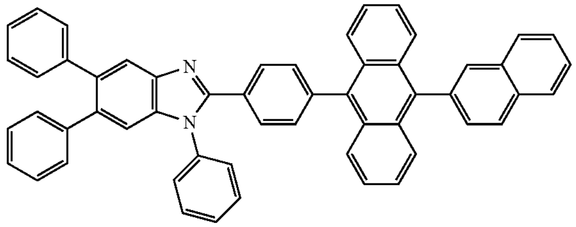
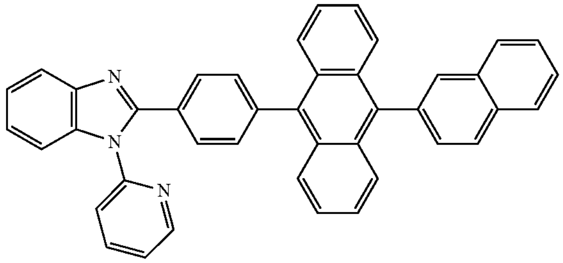
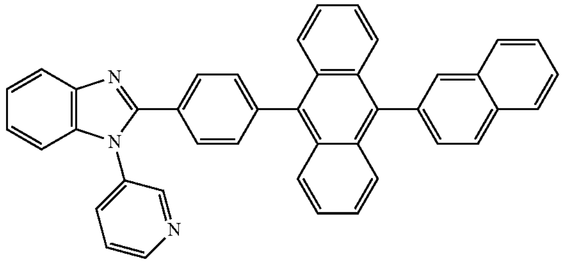
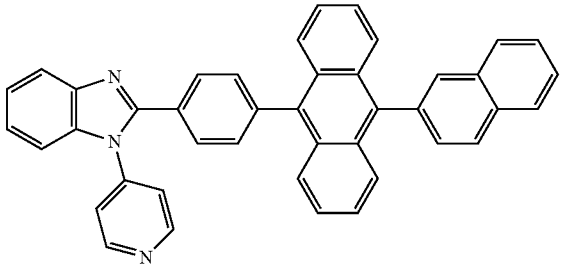
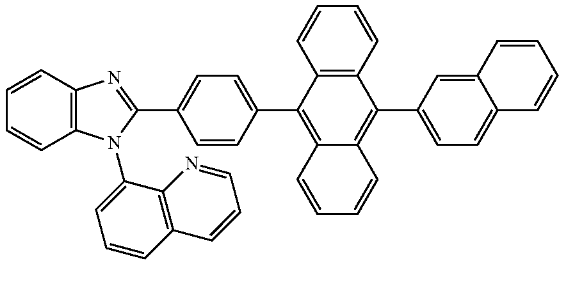

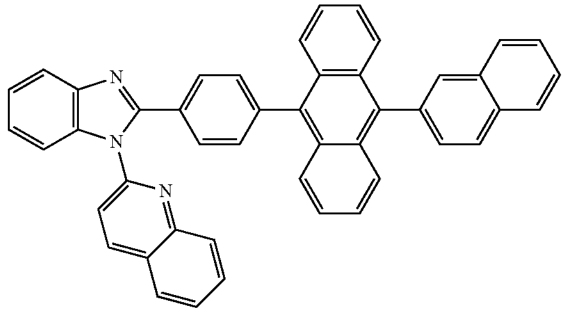
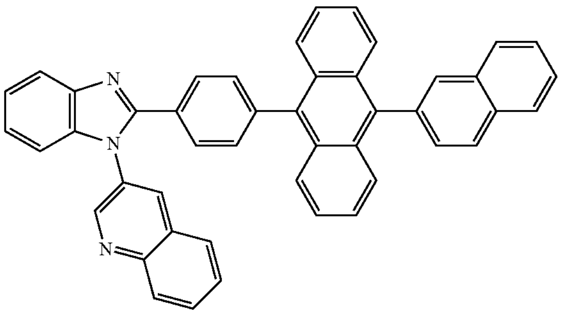
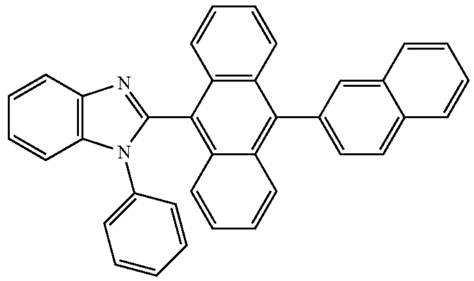
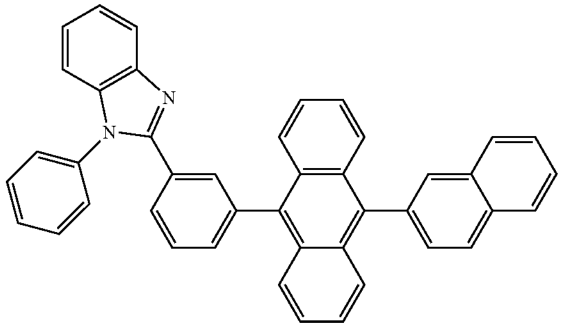
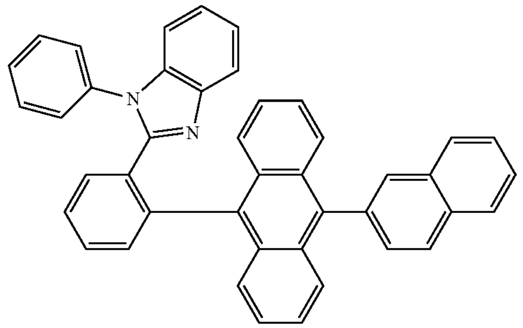
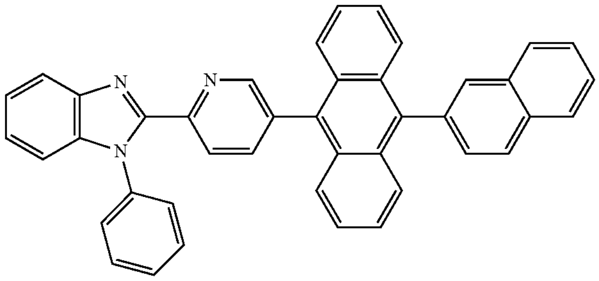
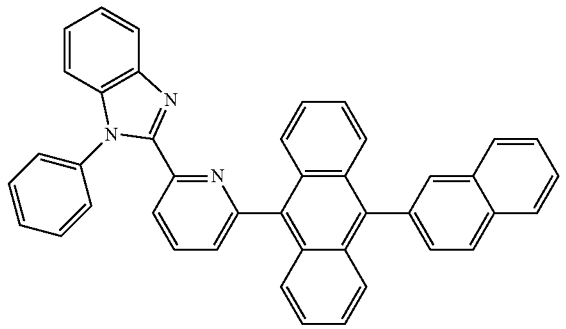
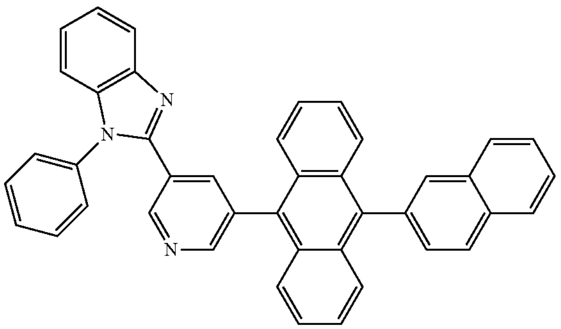
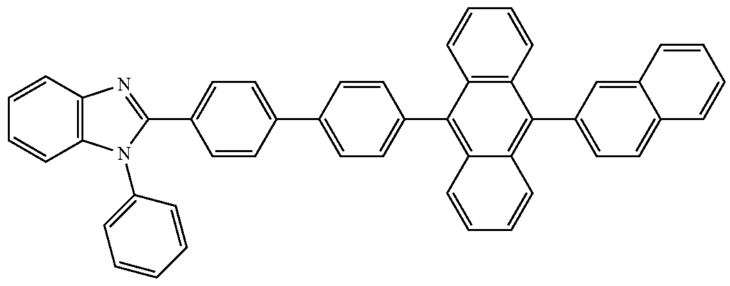

-continued
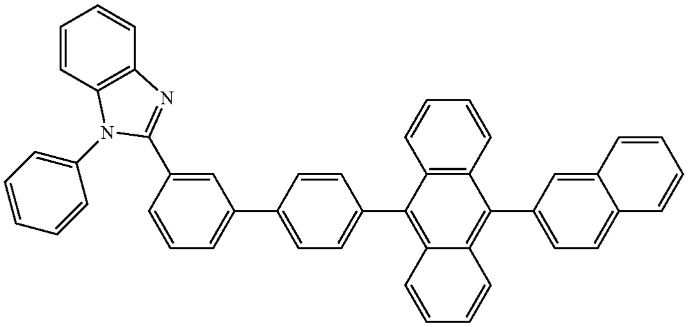
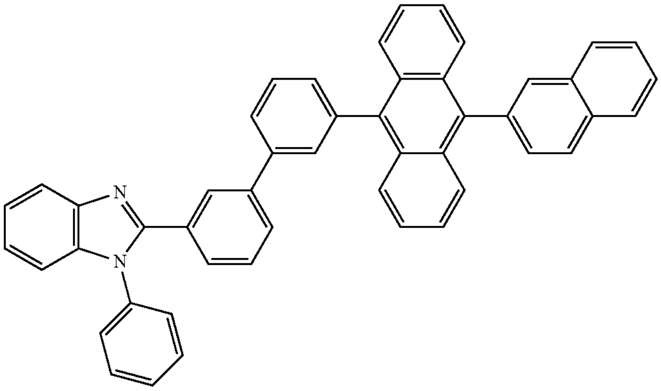
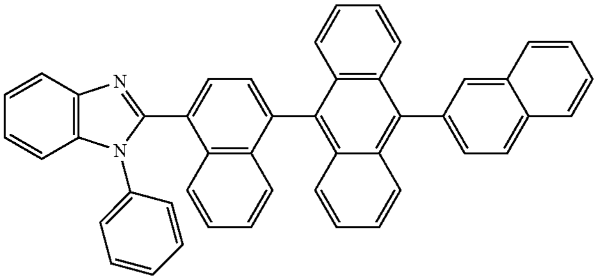
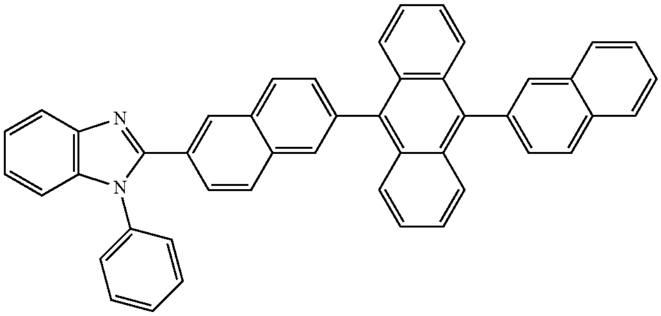
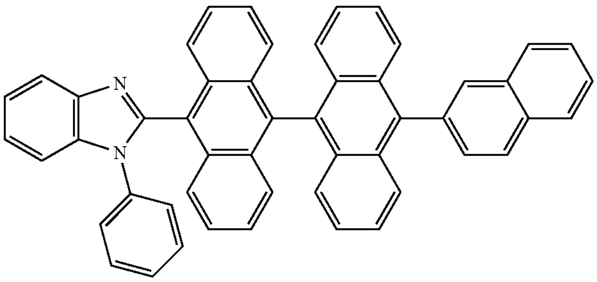
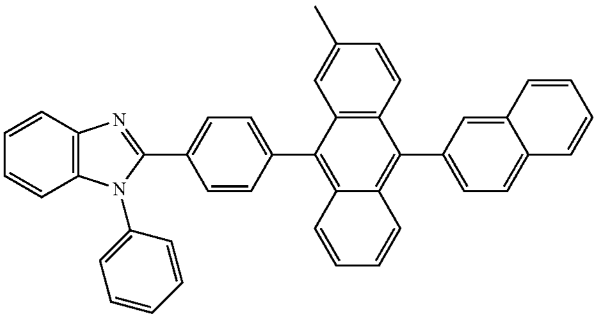

-continued
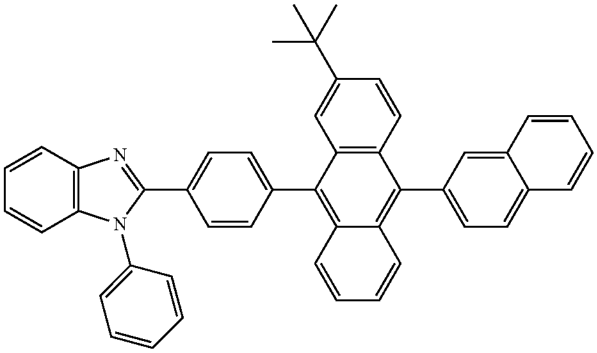
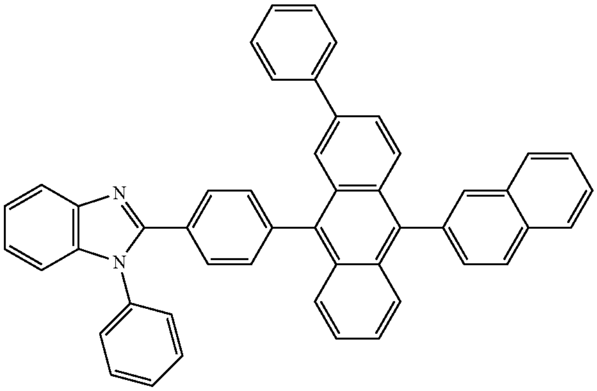
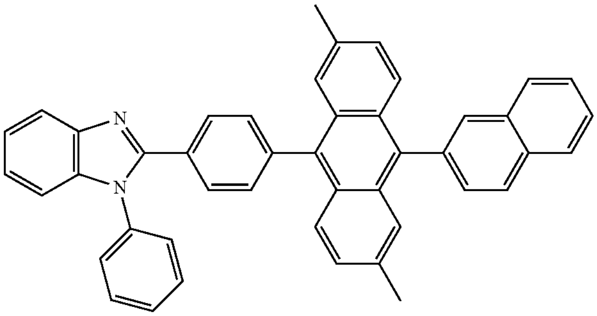
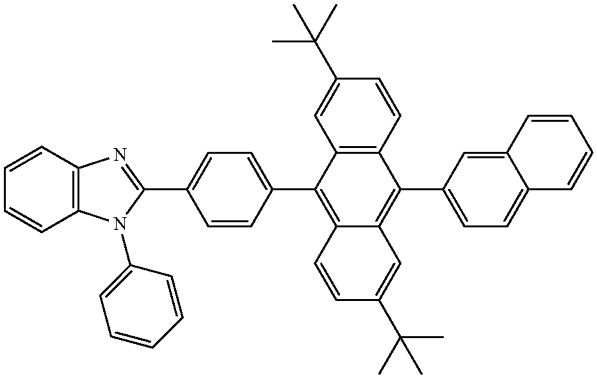
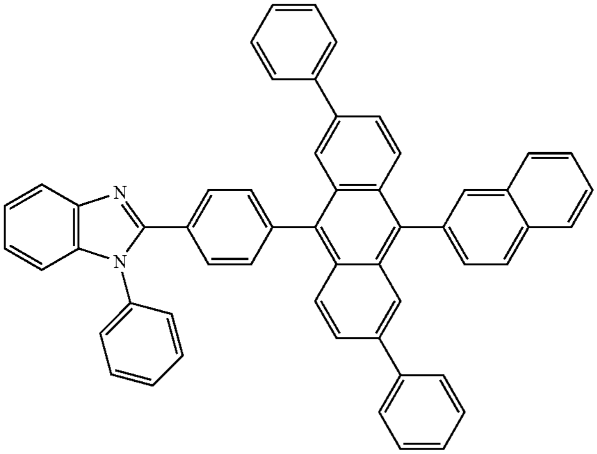
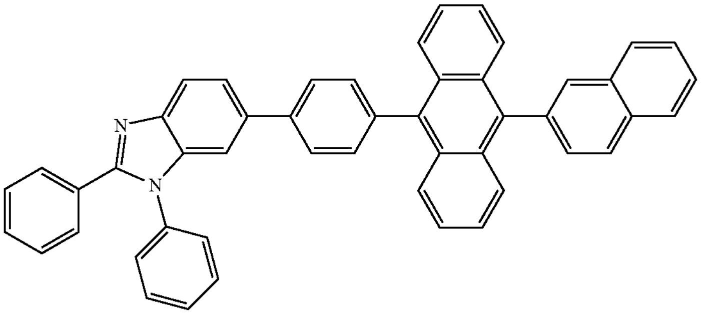

-continued
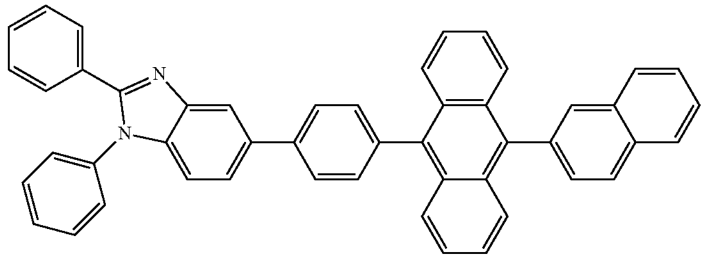
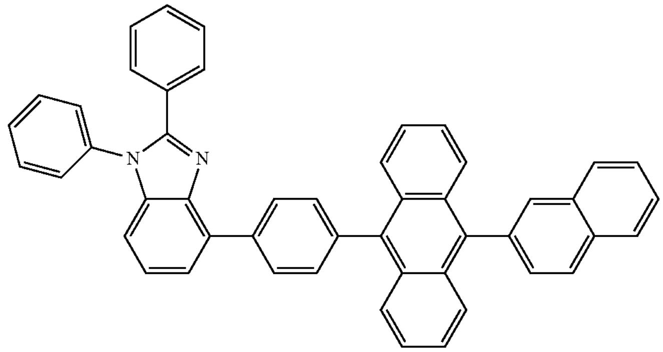
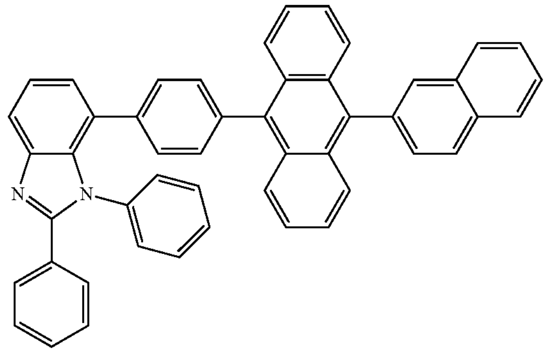
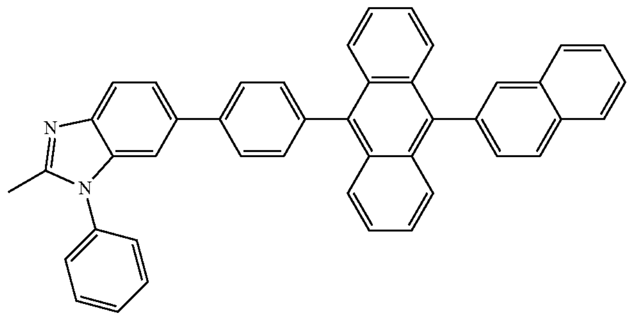
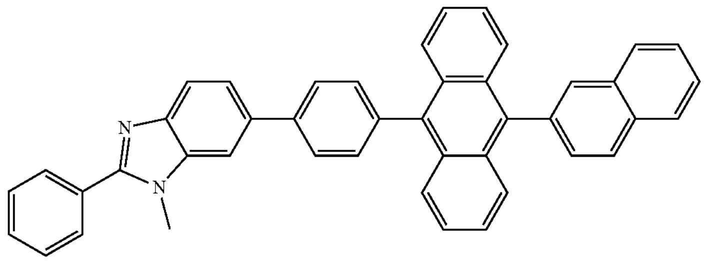

-continued
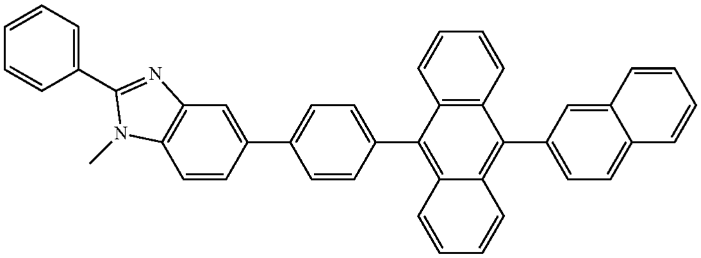
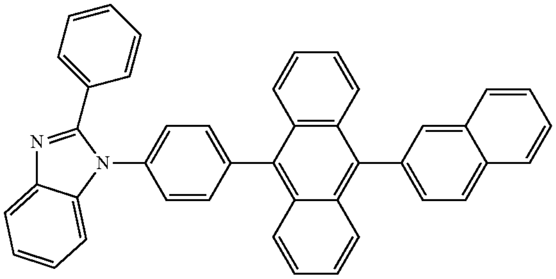
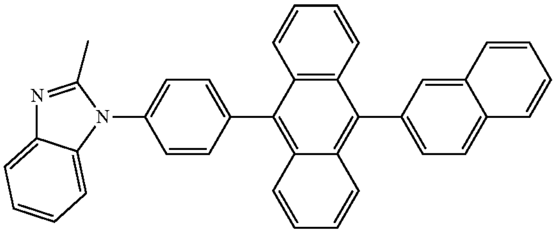
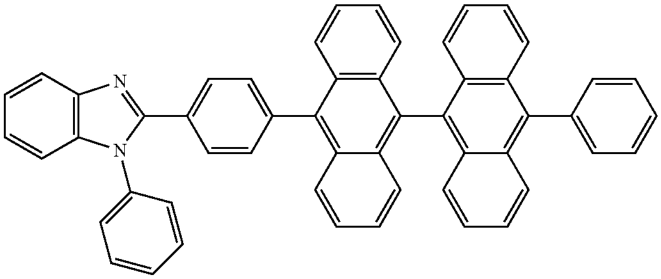
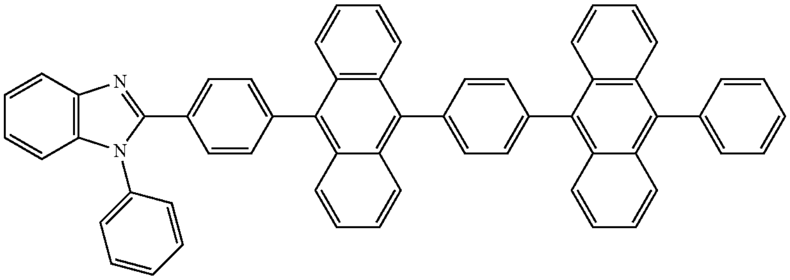
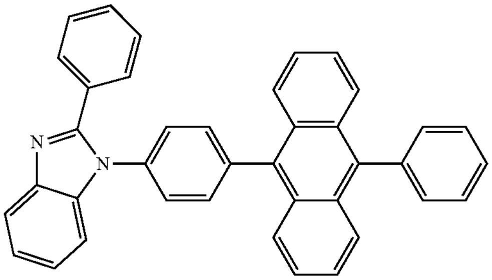
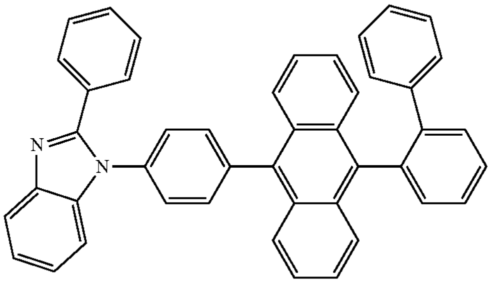
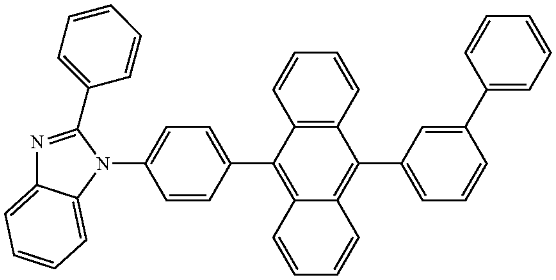

-continued
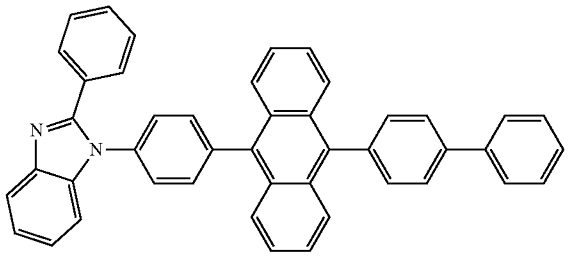
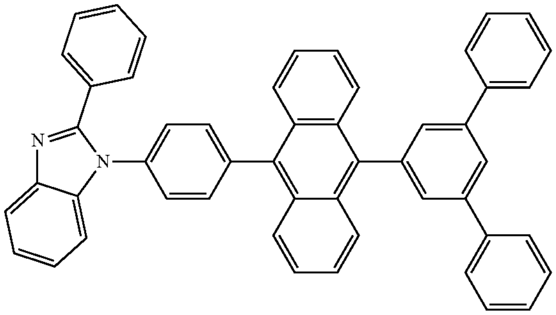
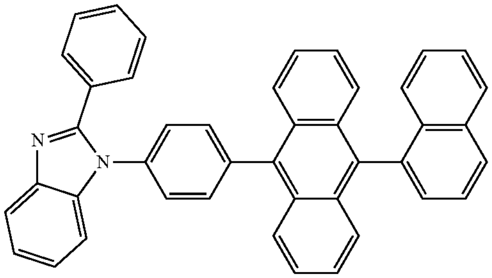
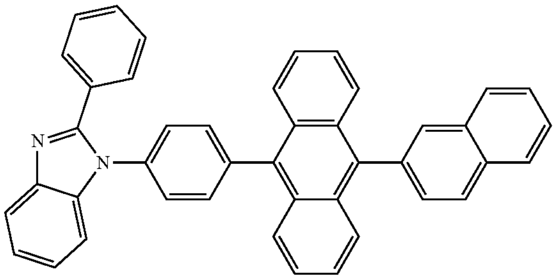
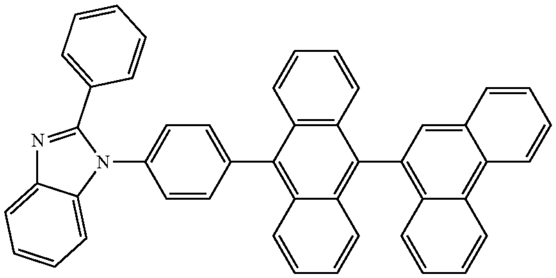
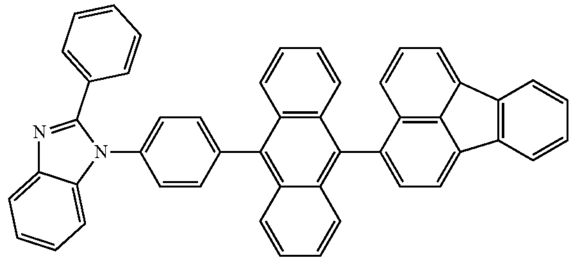
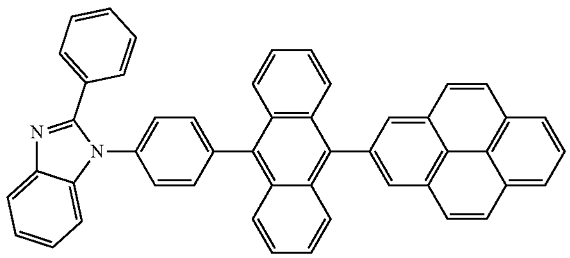
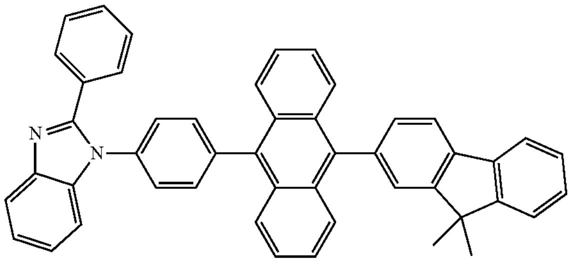
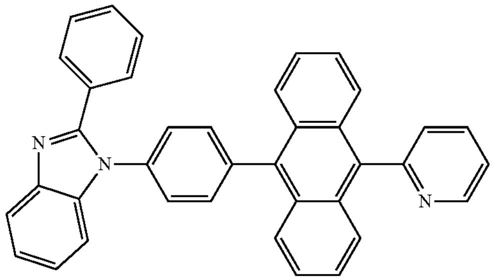
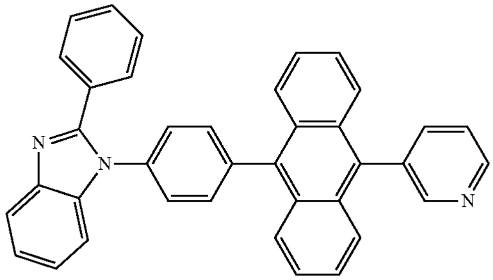
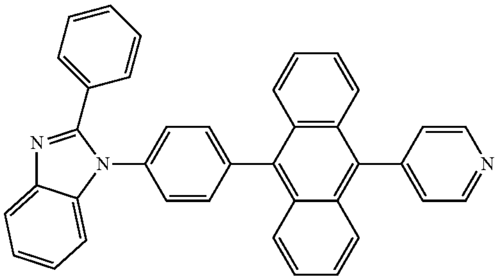
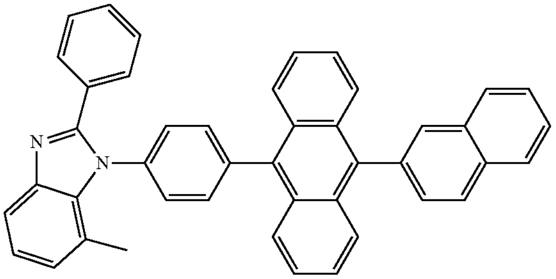

-continued
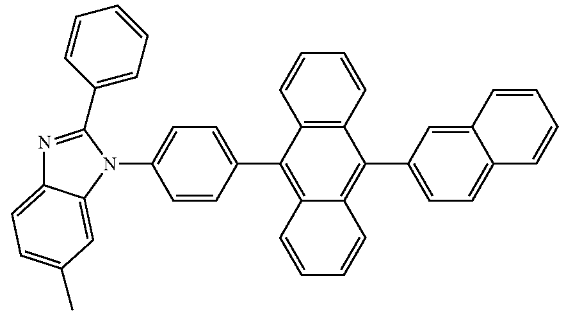
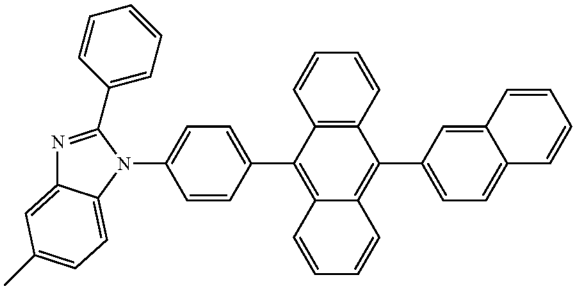
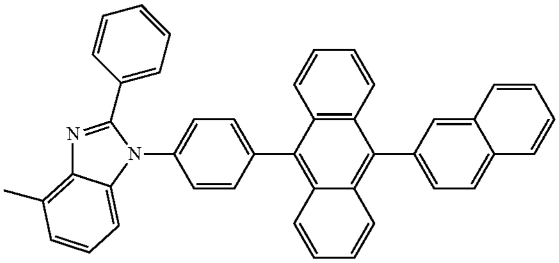
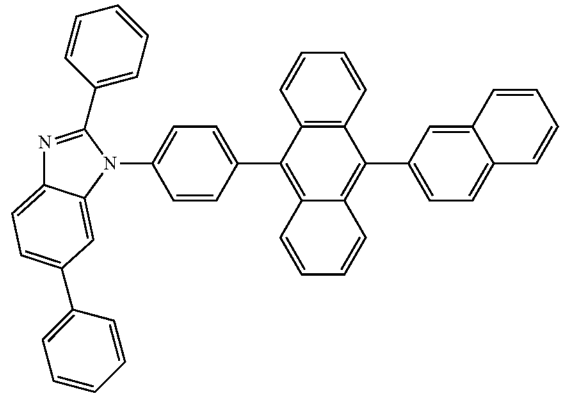
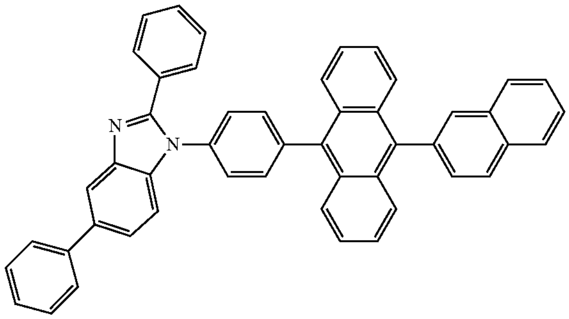
-continued
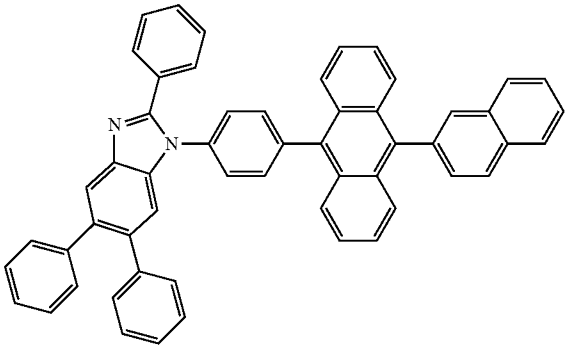
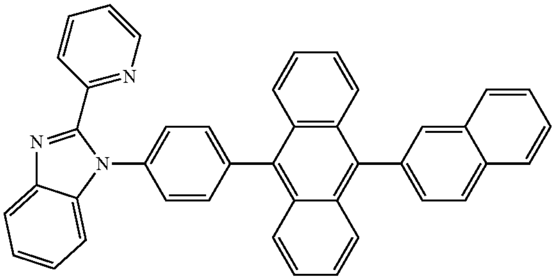
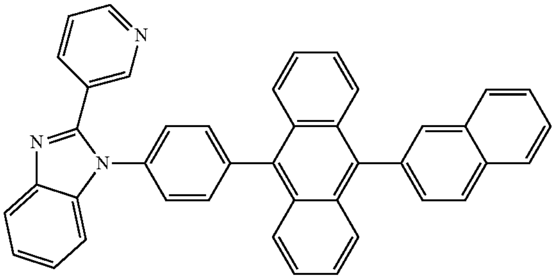
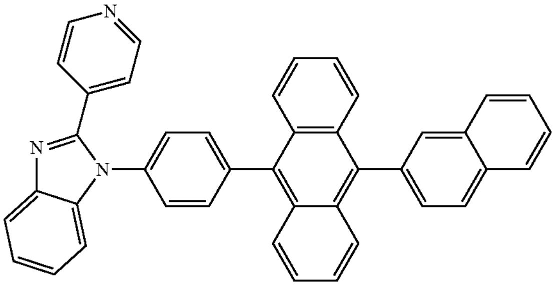
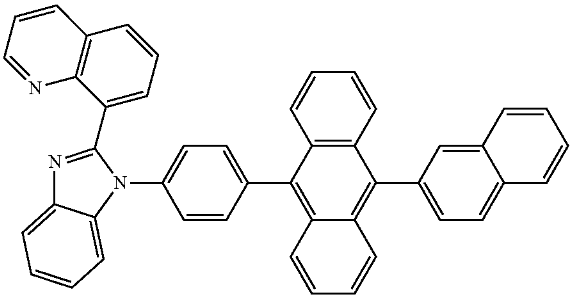

-continued
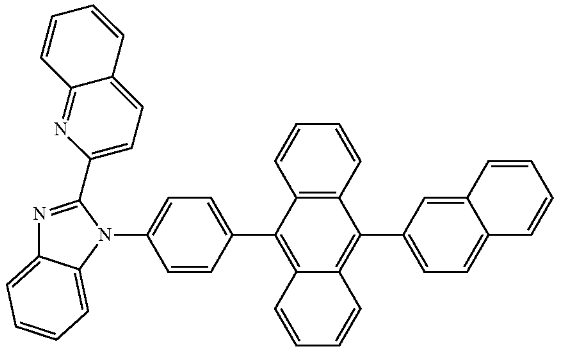
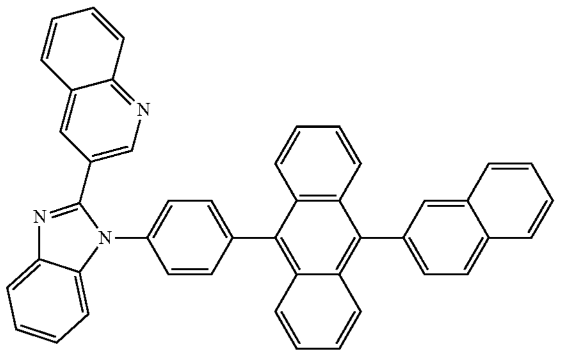
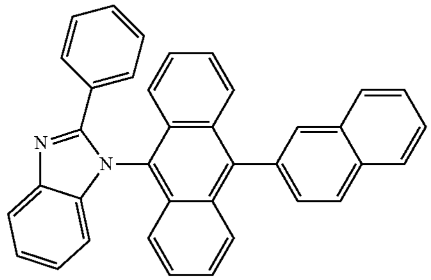
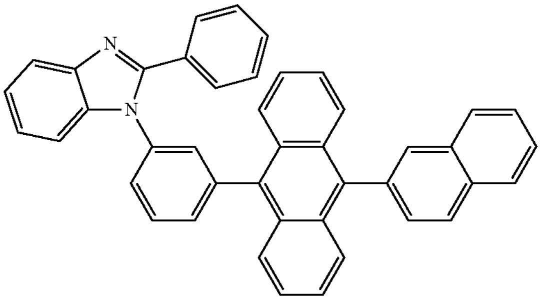
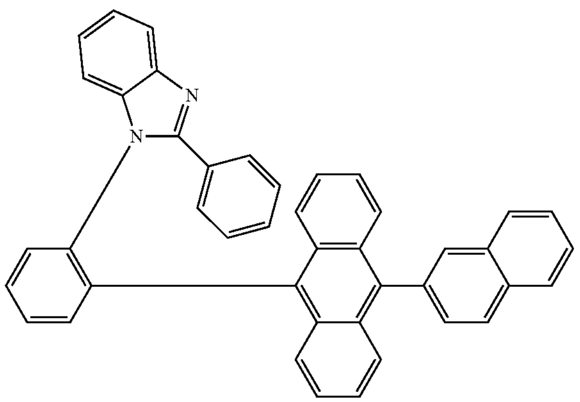
-continued
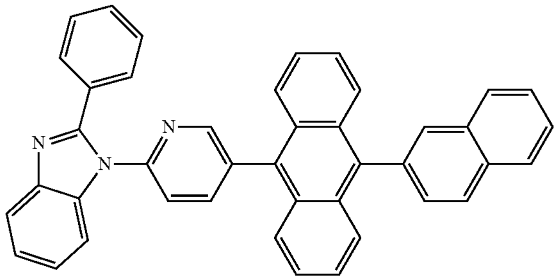
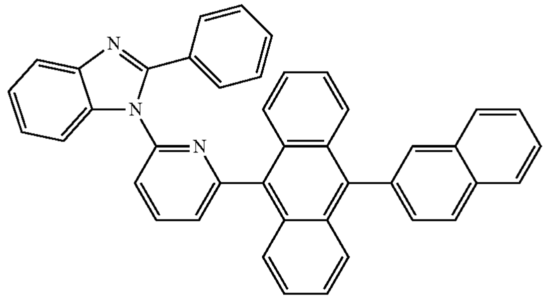
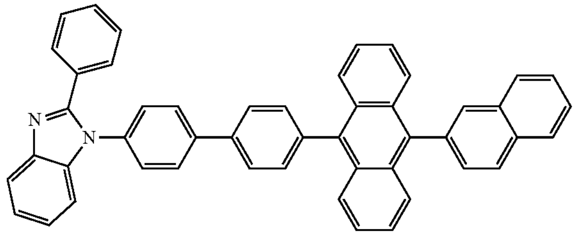
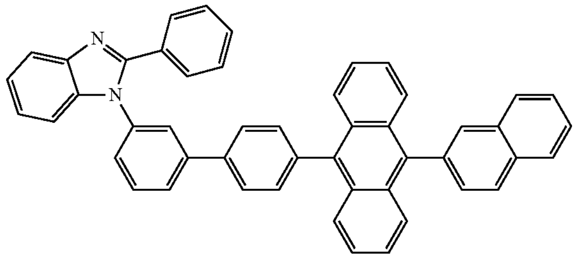
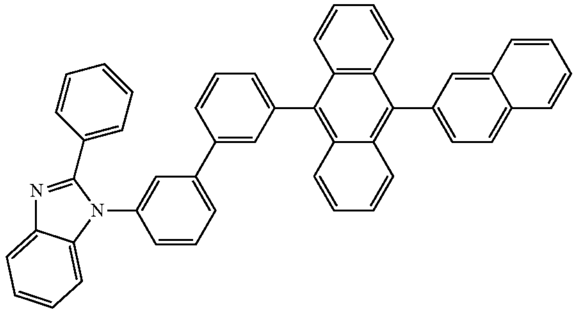
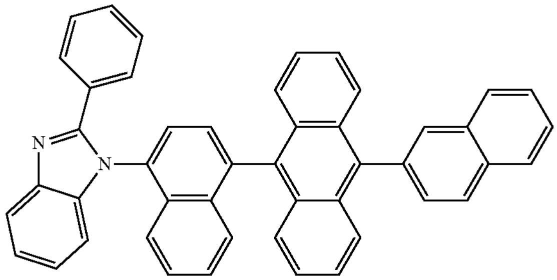

-continued
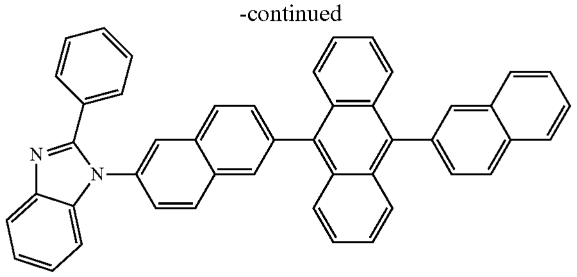
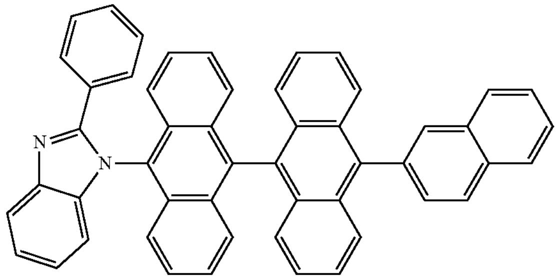
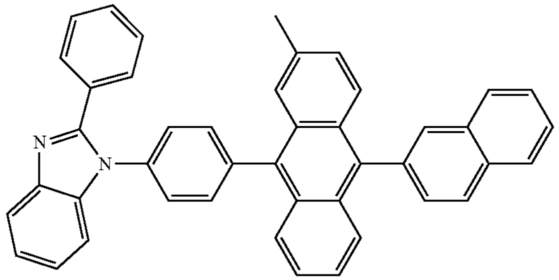
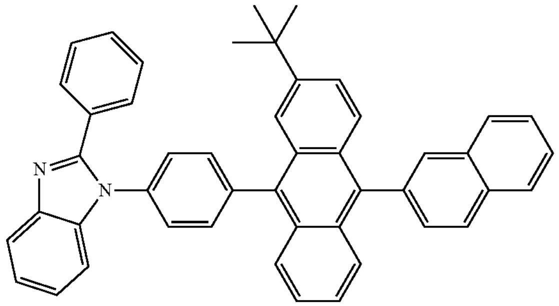
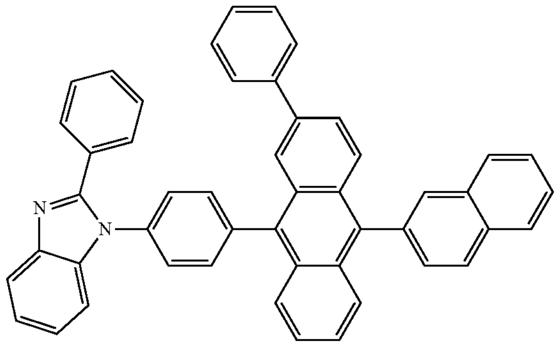
-continued
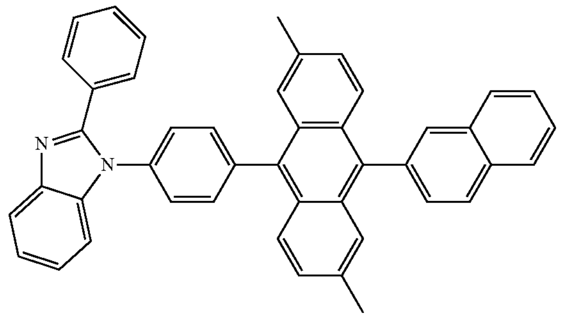
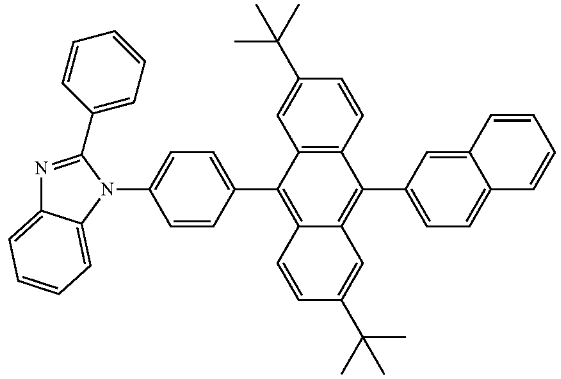
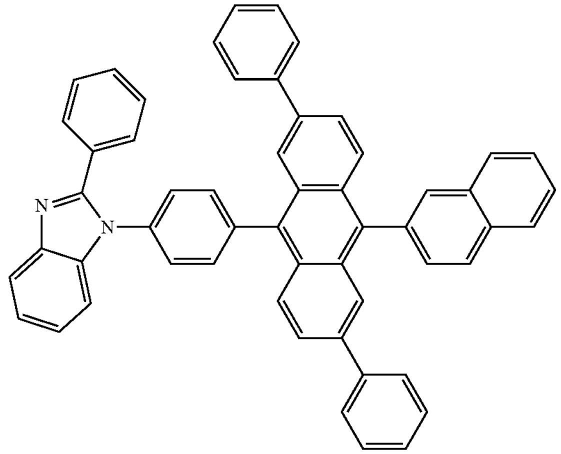
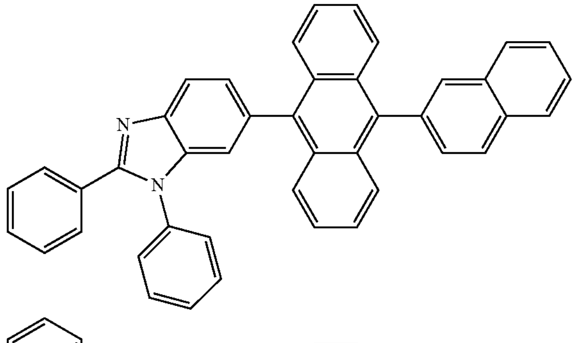
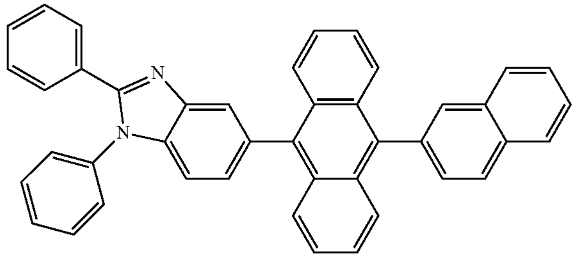

-continued
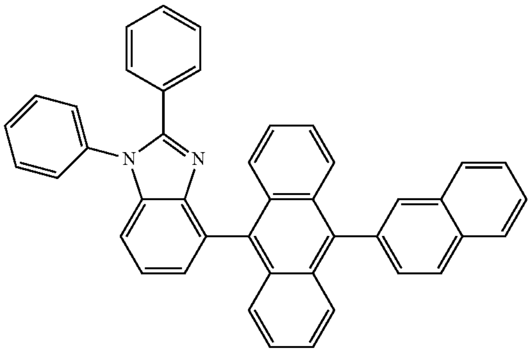
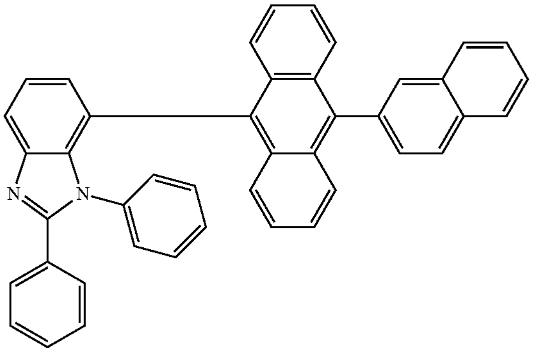
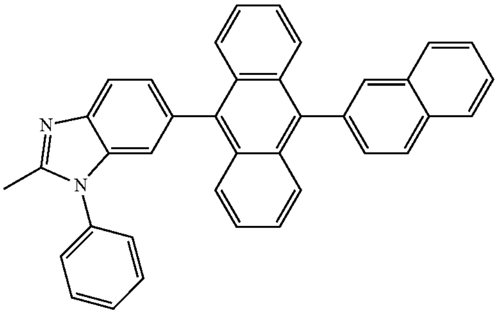
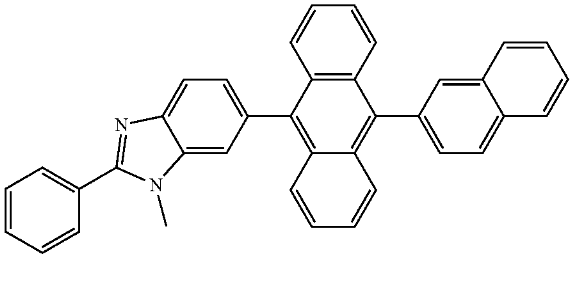
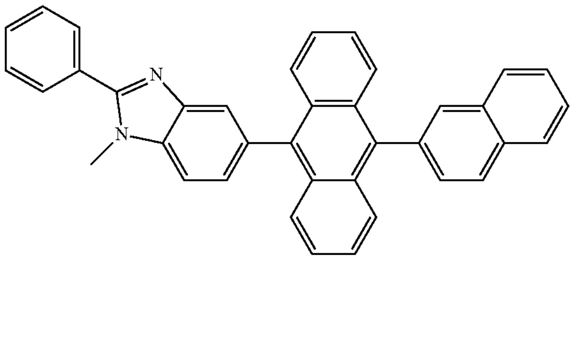
-continued
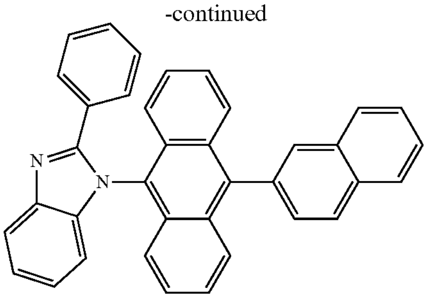
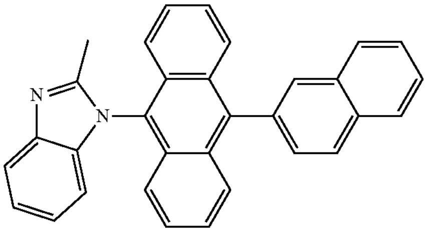
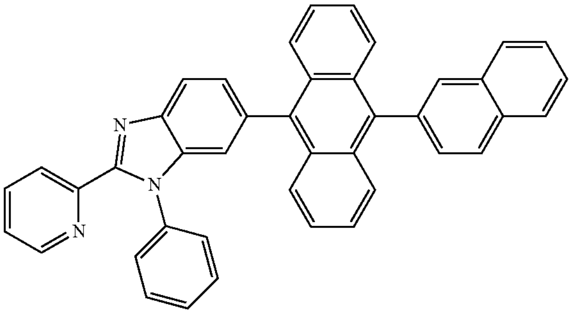
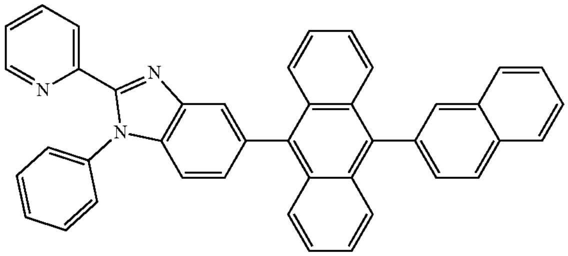
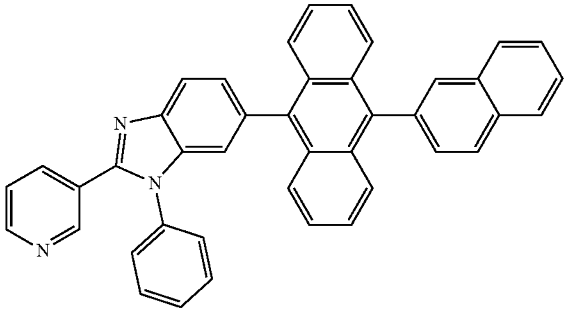
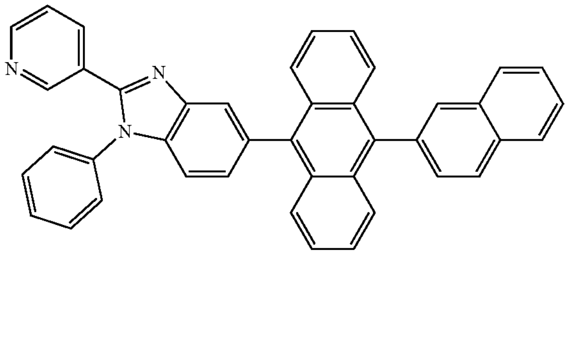

-continued
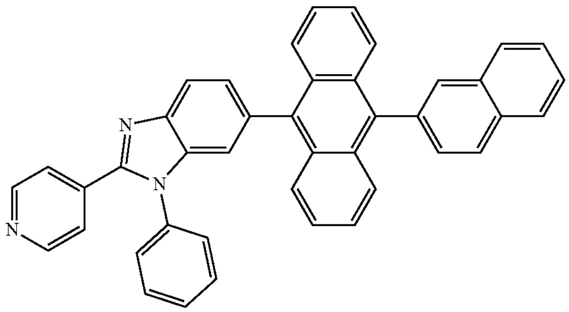
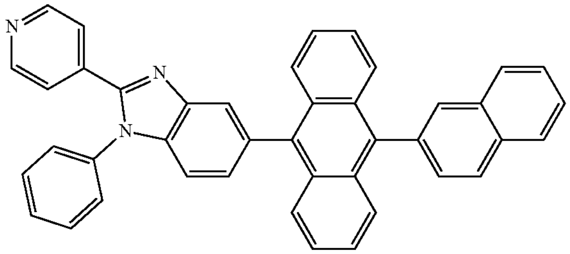
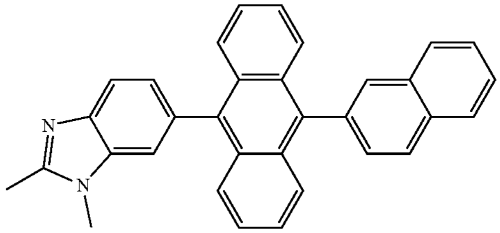
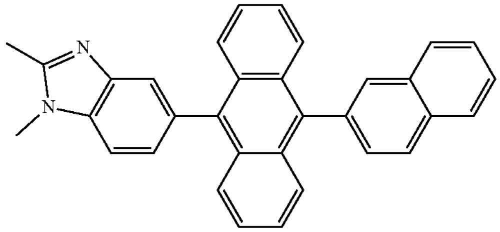
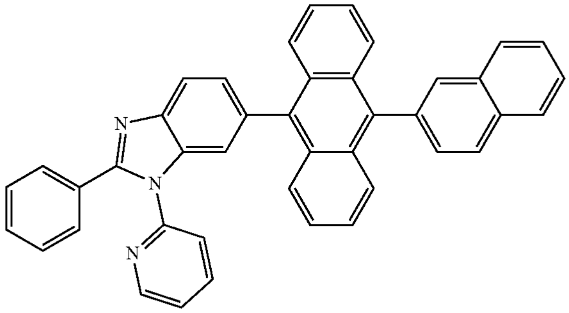
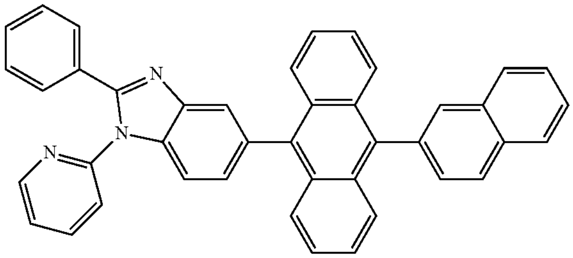
-continued
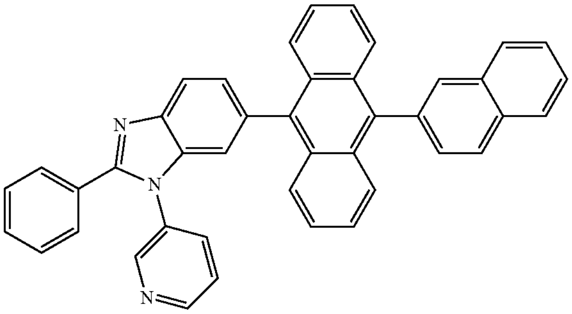
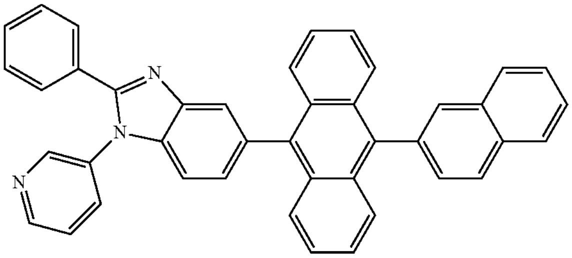
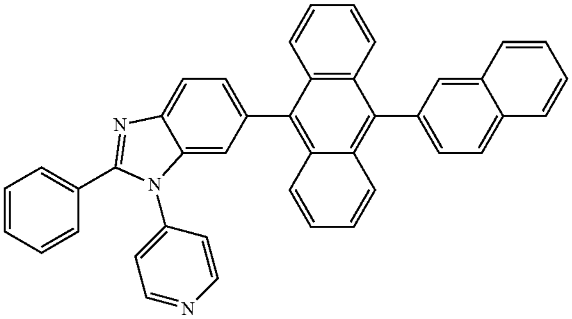
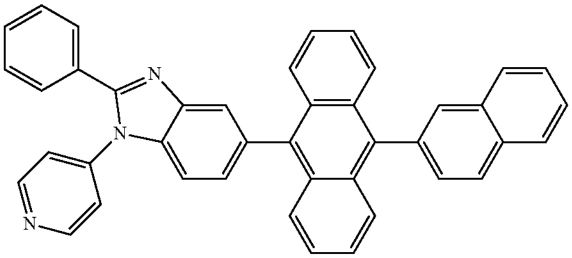
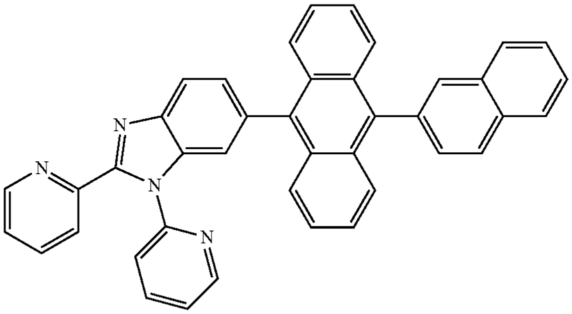
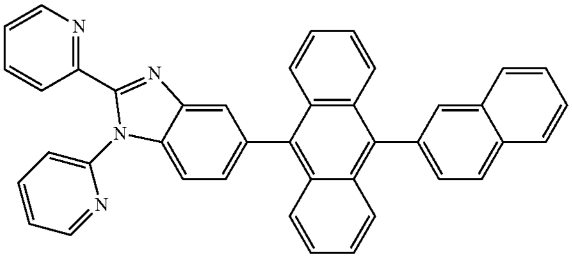

-continued
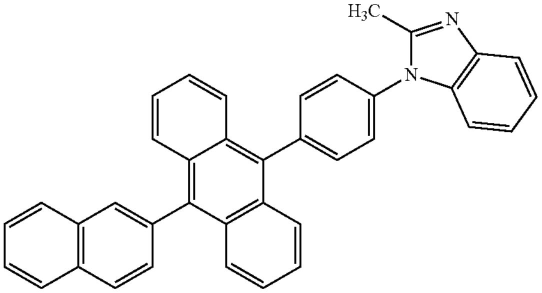
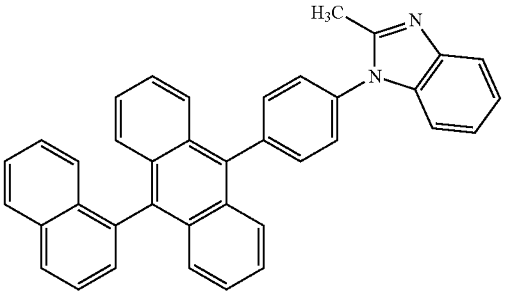
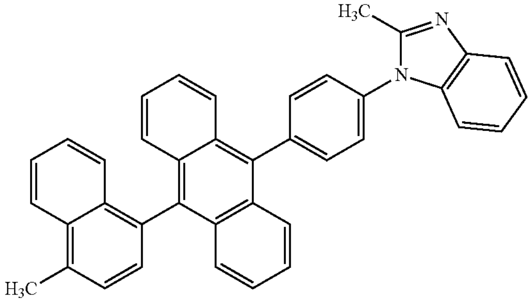
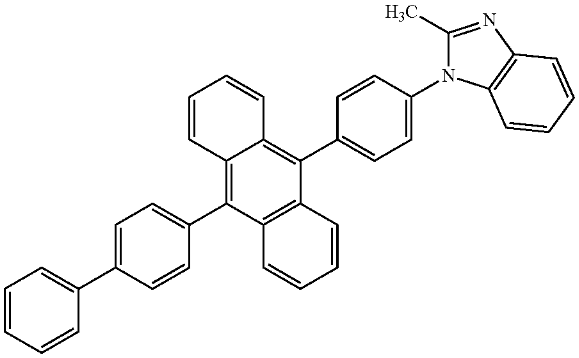
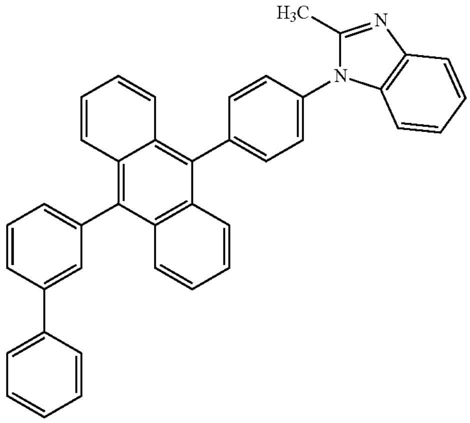
-continued
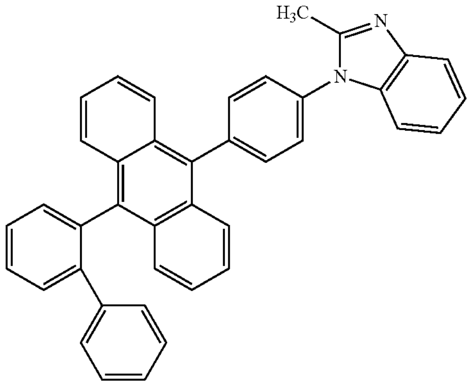
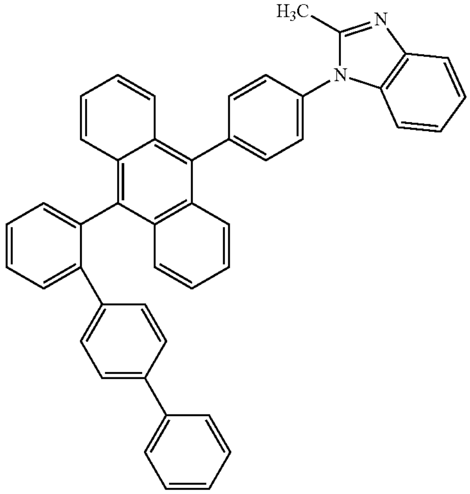
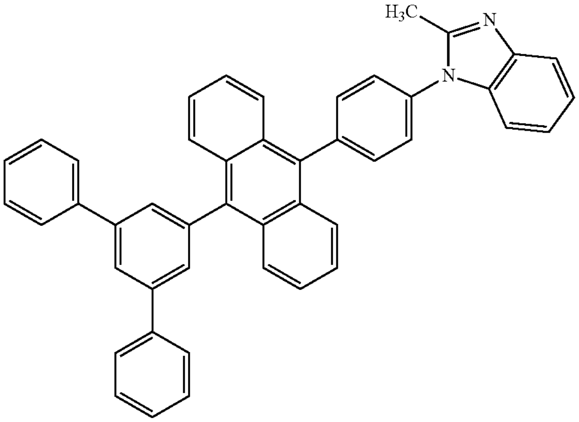
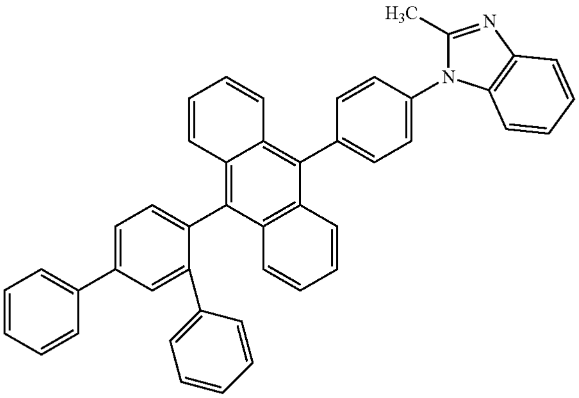

-continued
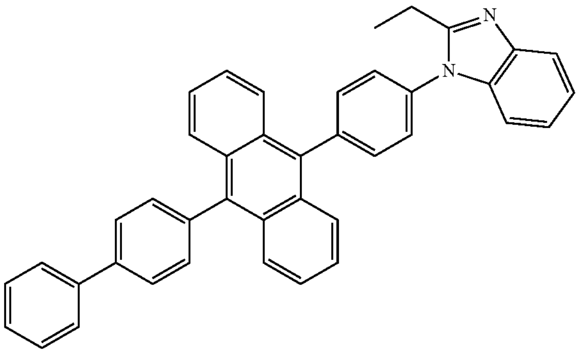
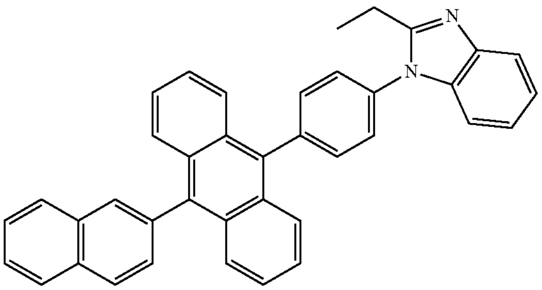
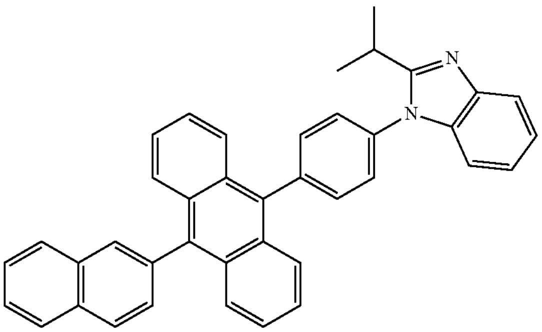
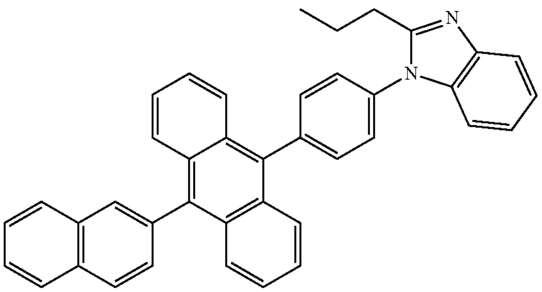
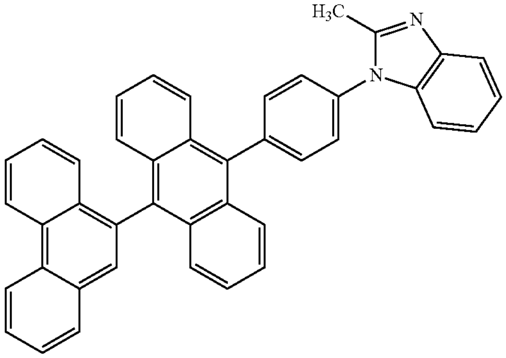
-continued
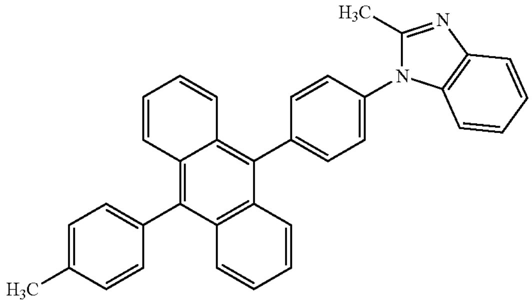
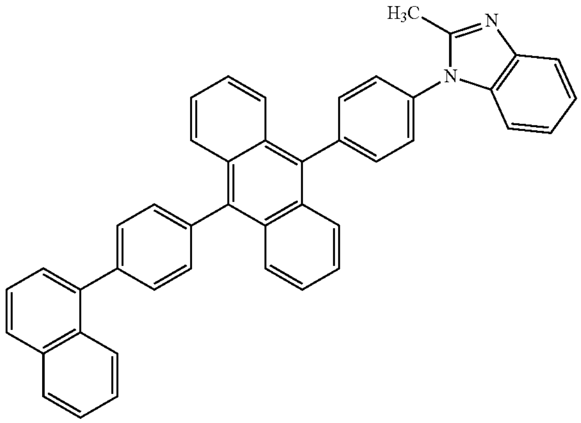
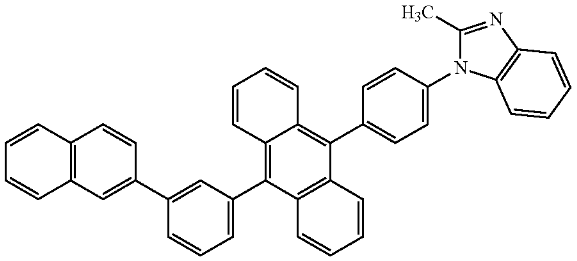
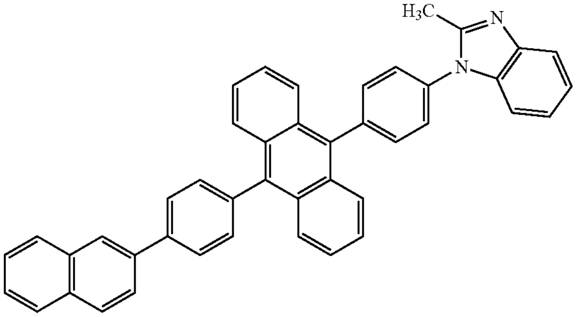

-continued
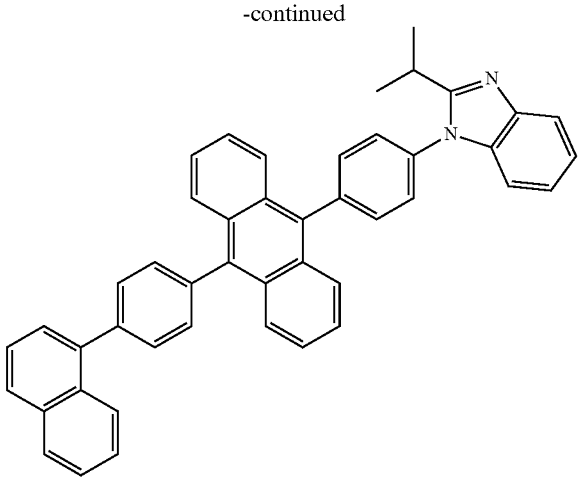
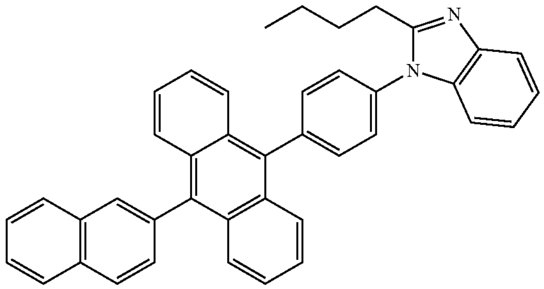
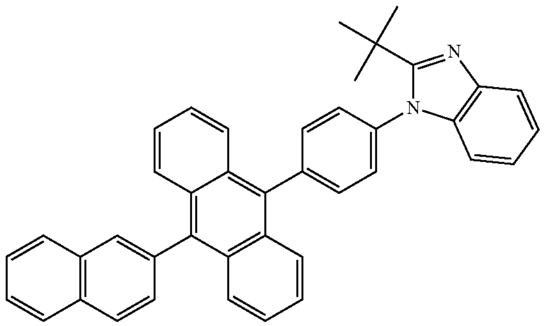
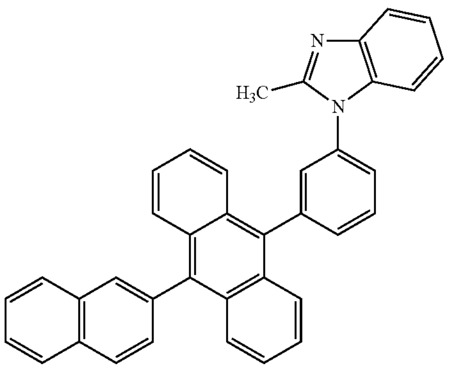
-continued
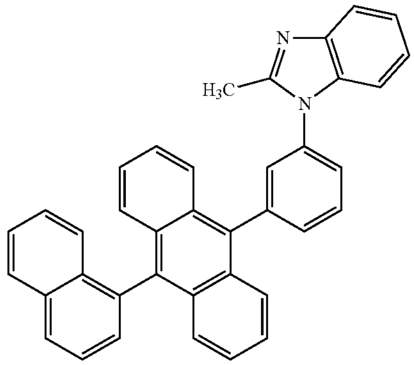
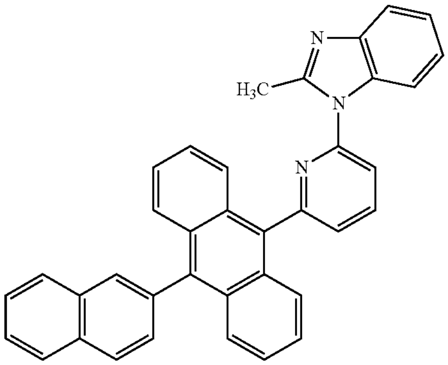
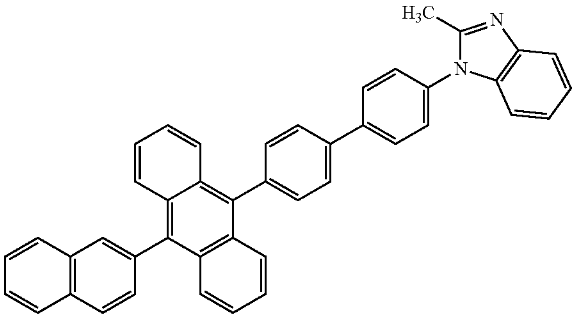
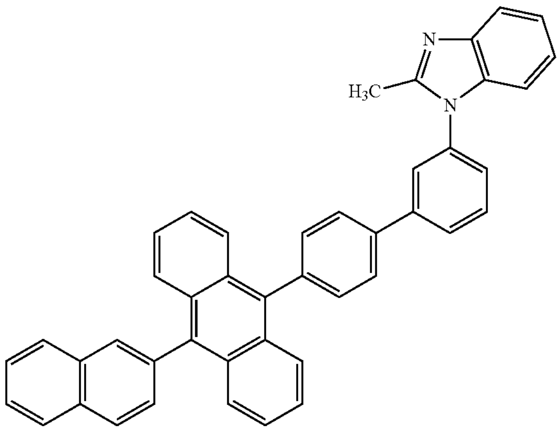

-continued
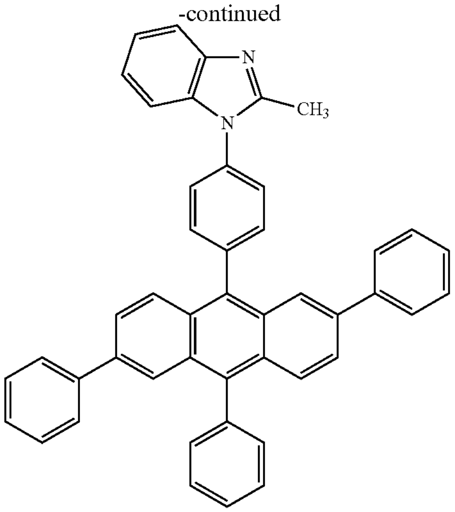
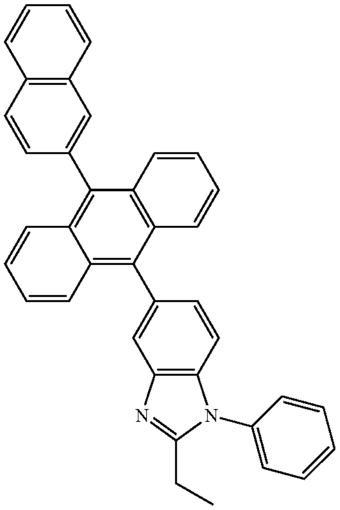
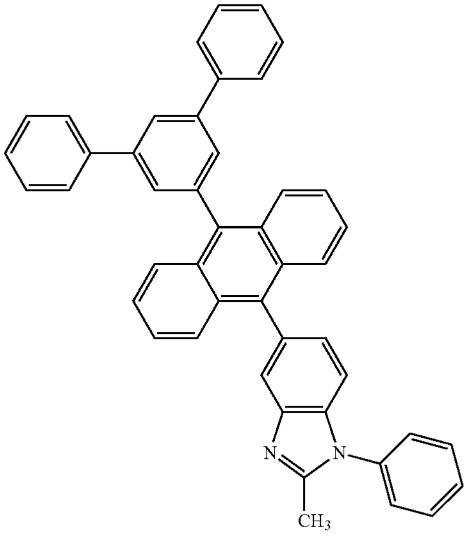
-continued
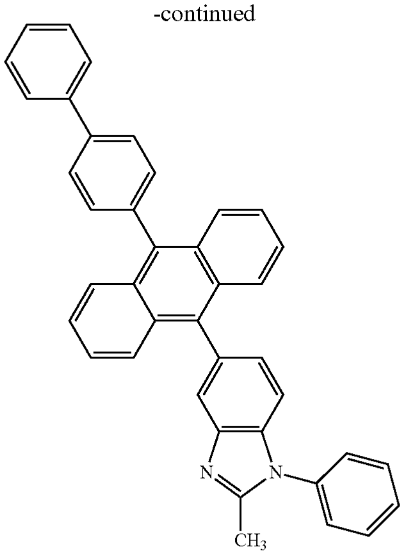
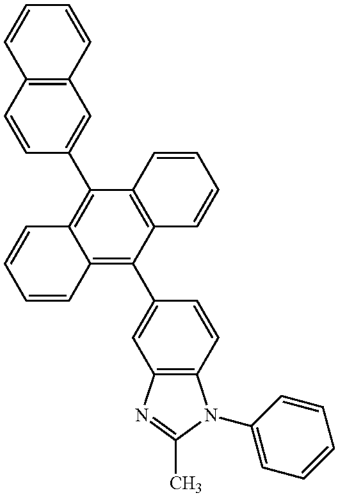
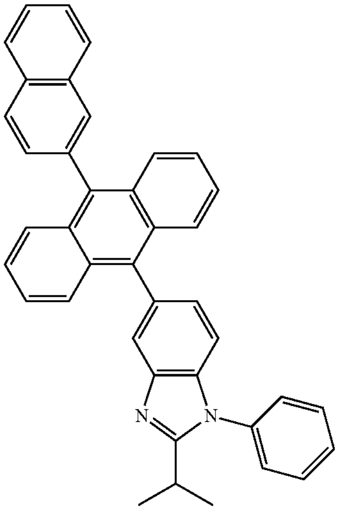

-continued
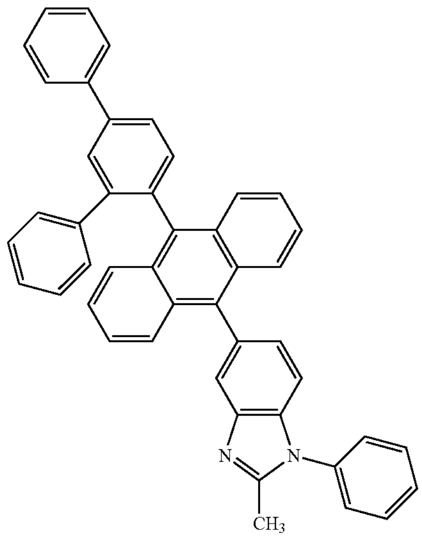
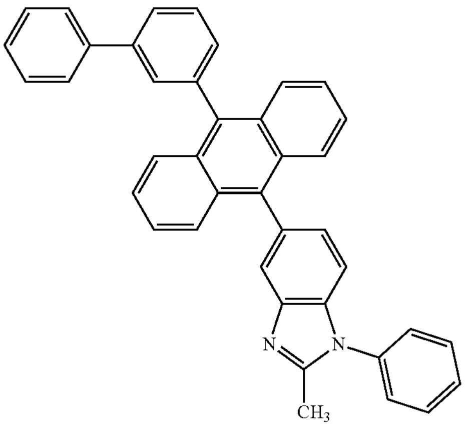
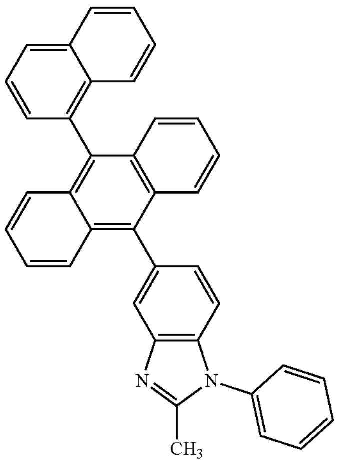
-continued
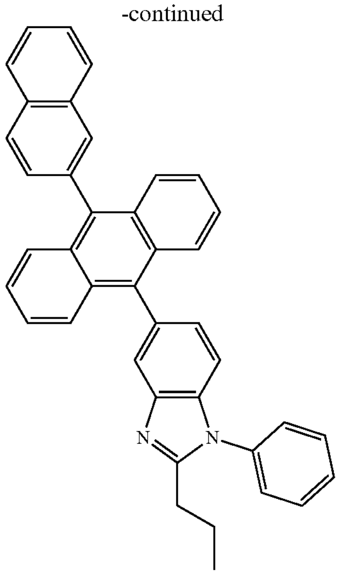
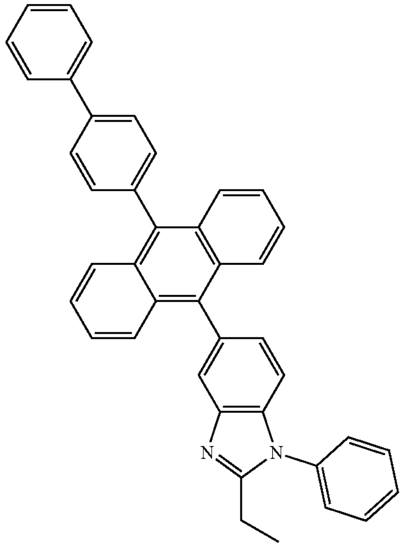
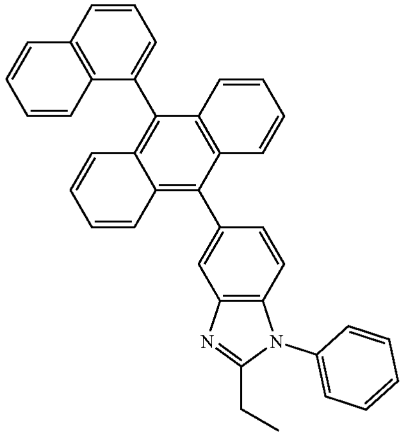

-continued
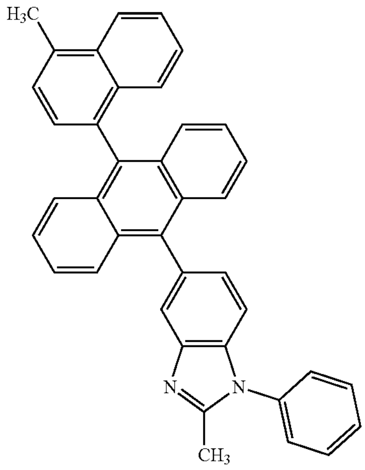
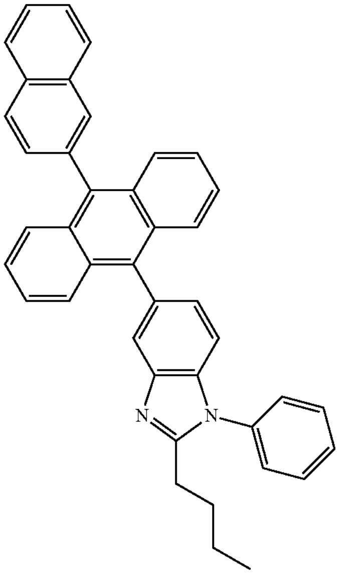
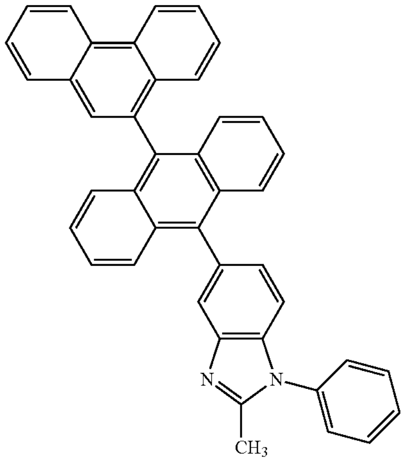
-continued
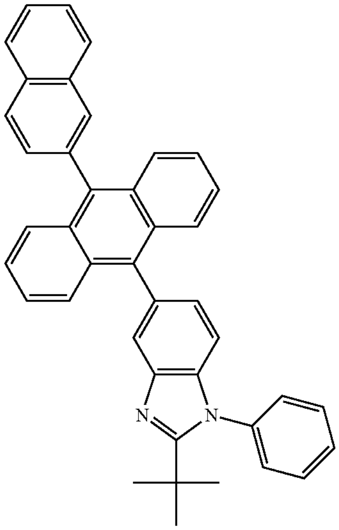
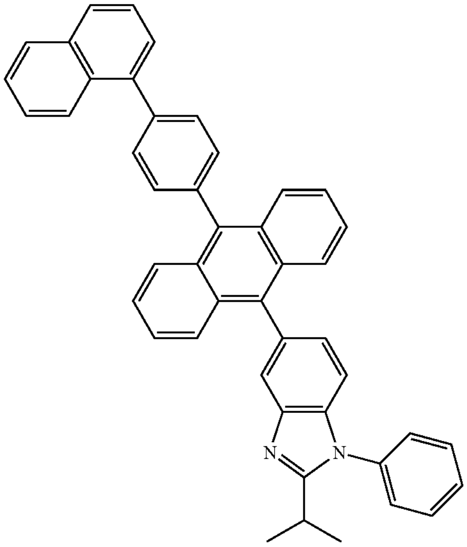
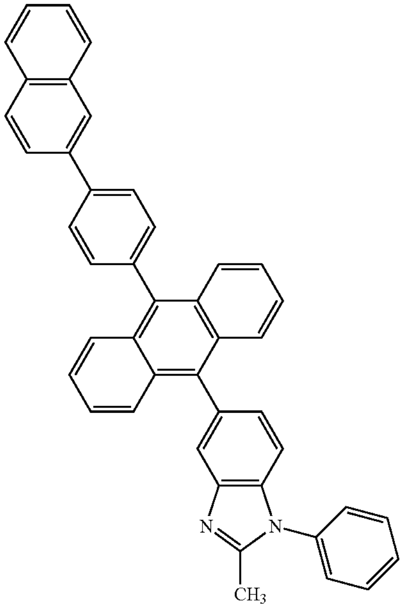

-continued
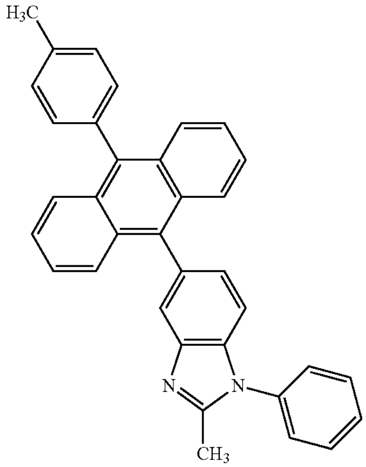
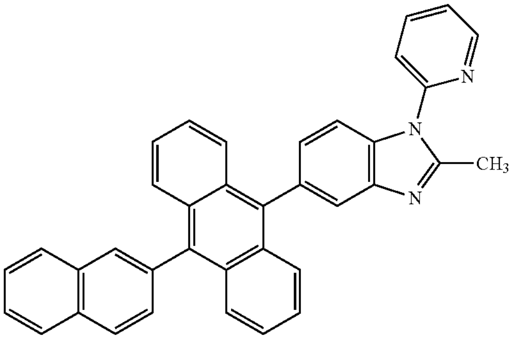
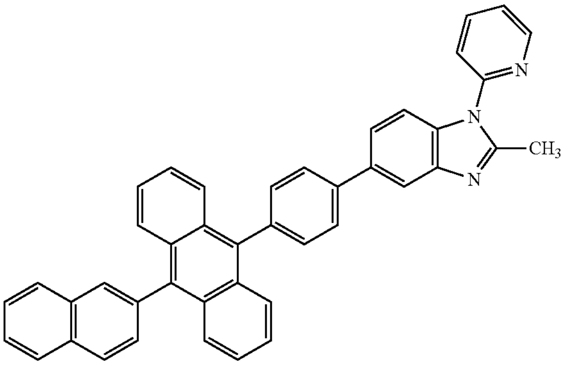
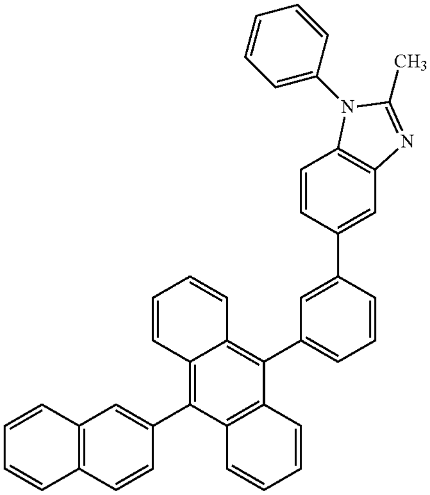
-continued
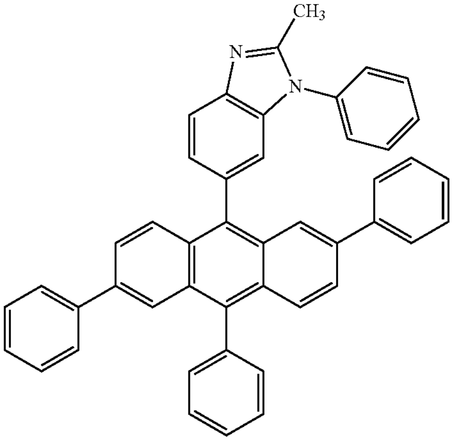
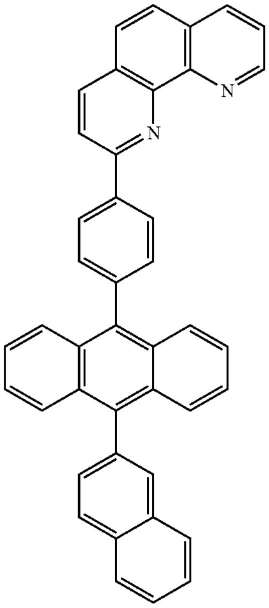
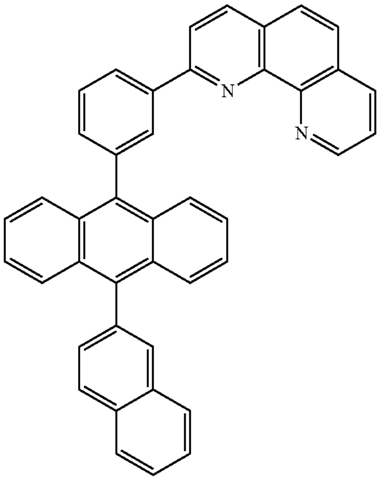

-continued
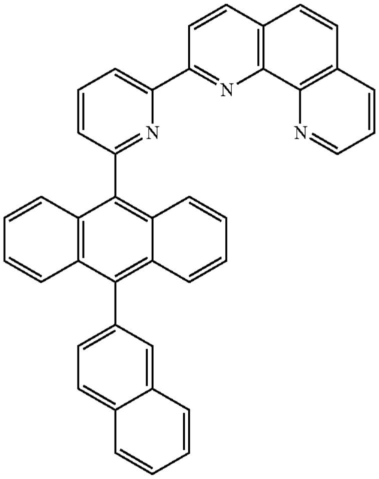
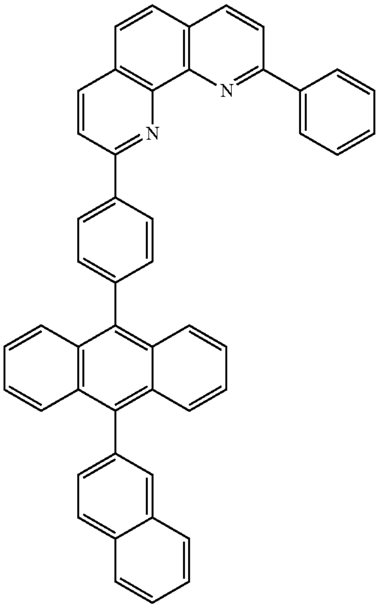
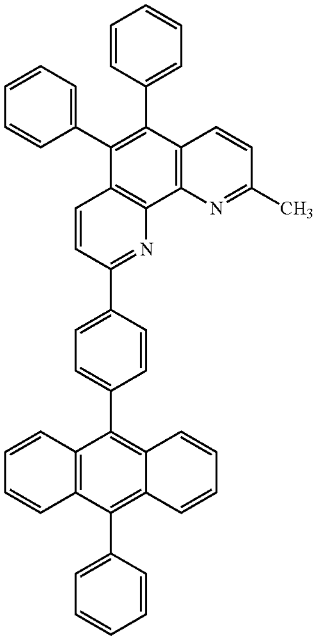
-continued
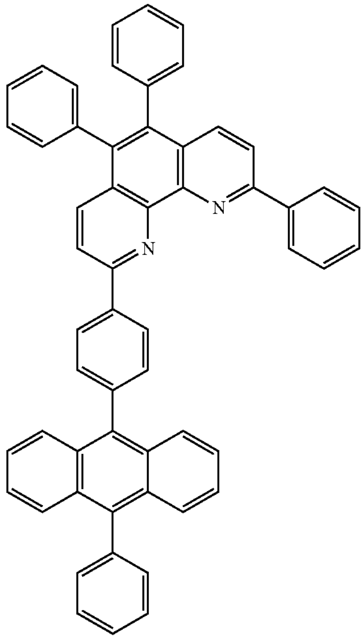
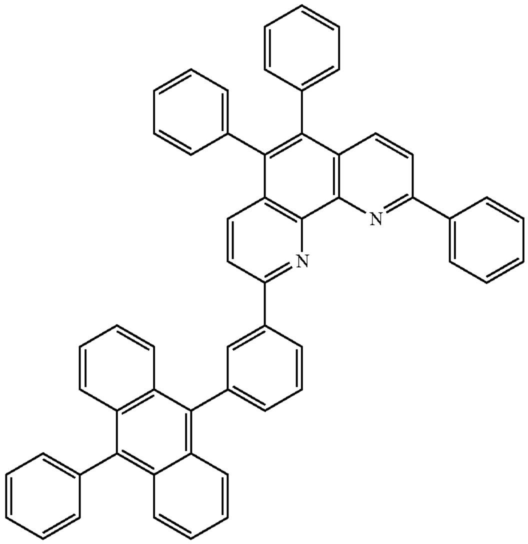
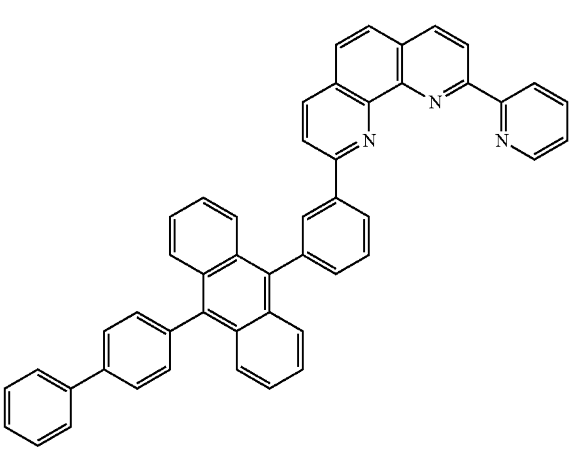

-continued
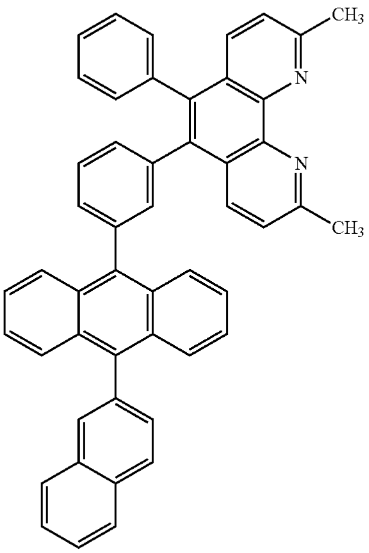
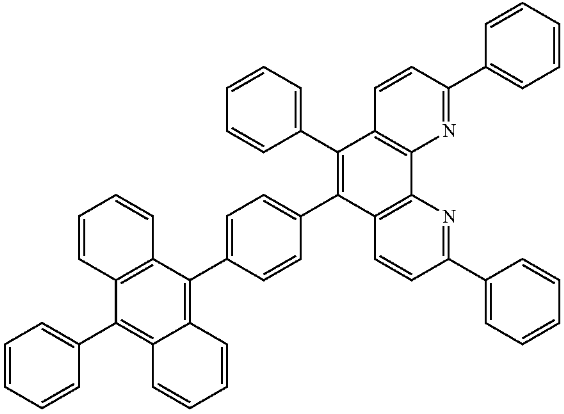
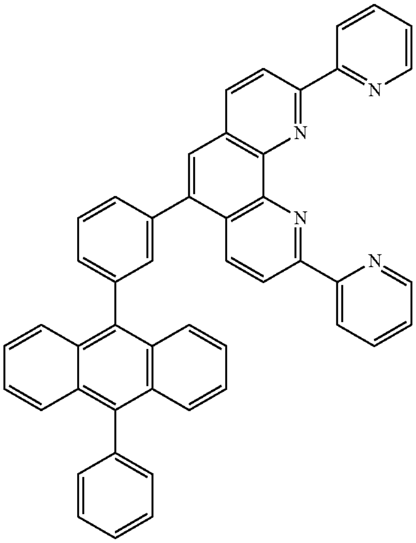
-continued
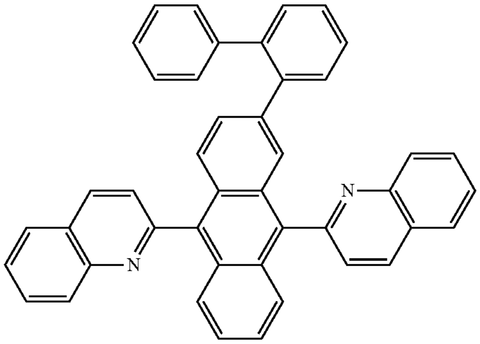
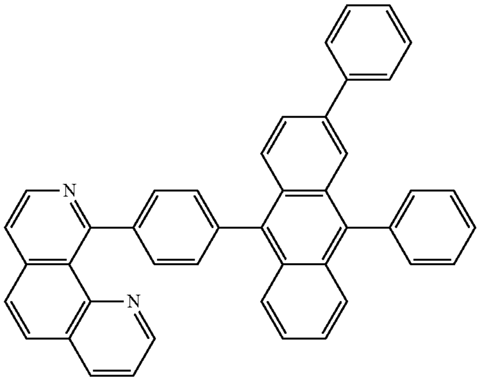
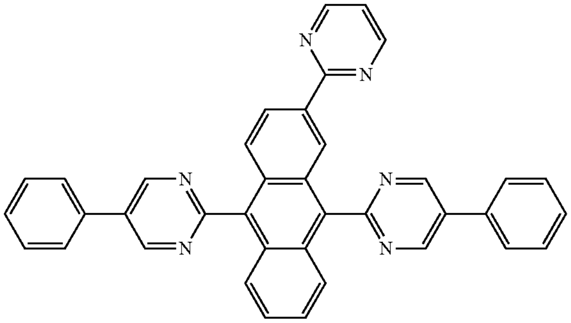
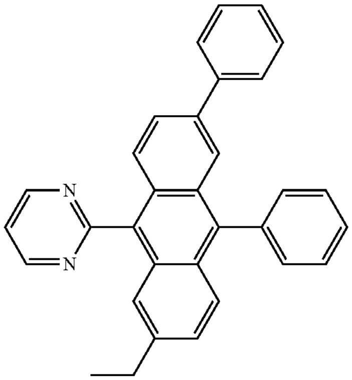

-continued
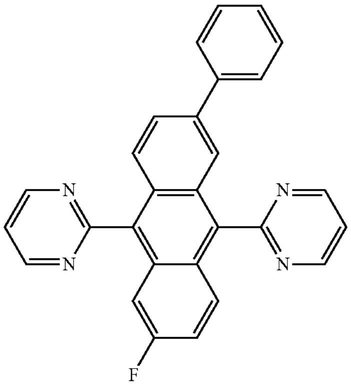
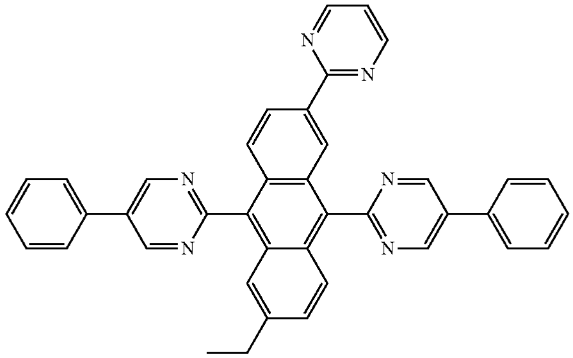
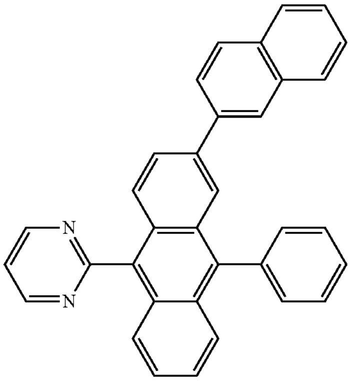
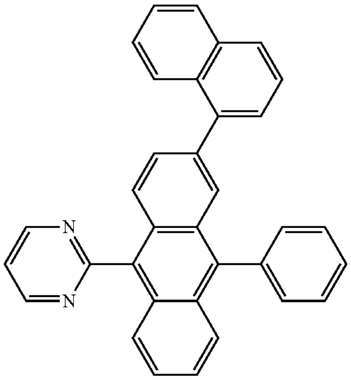
-continued
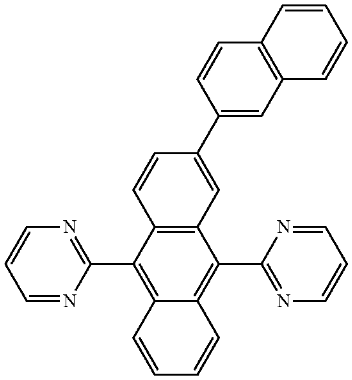
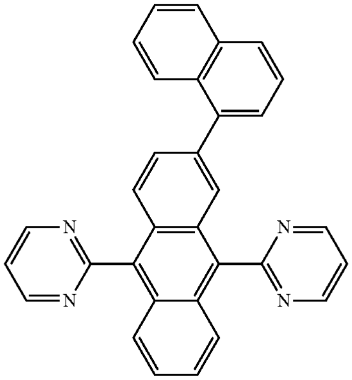
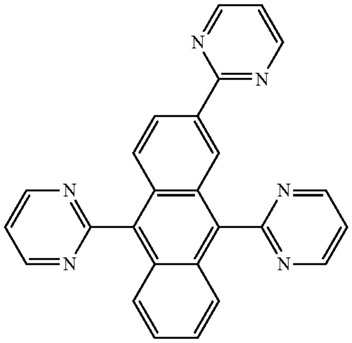
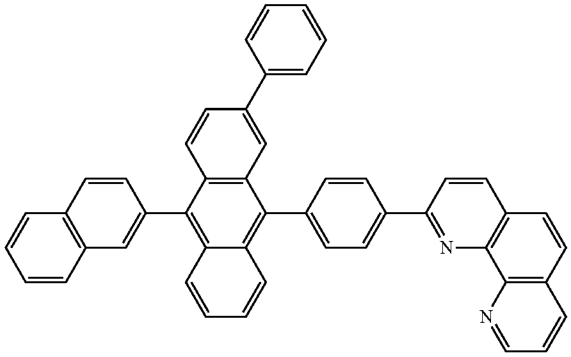

-continued
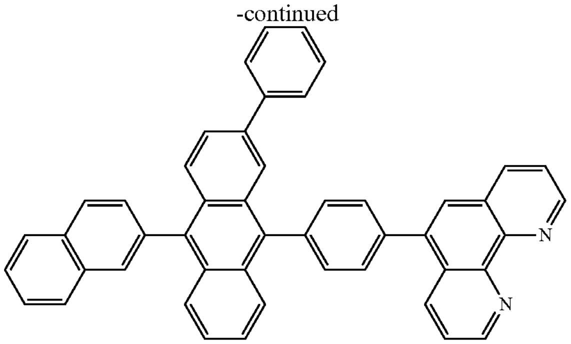
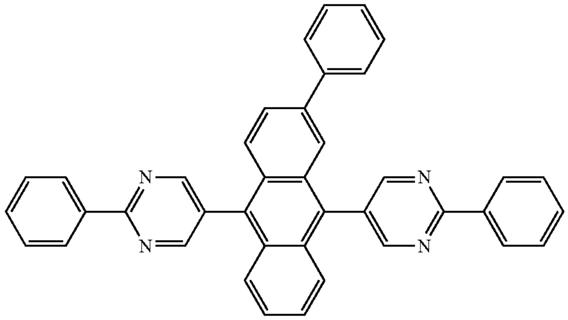
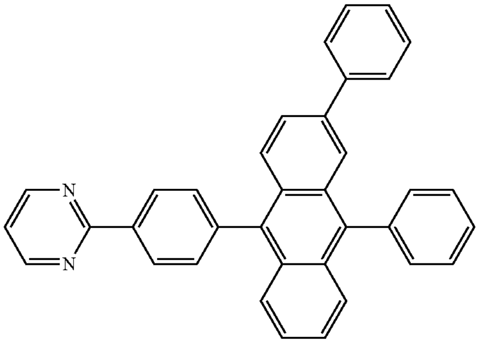
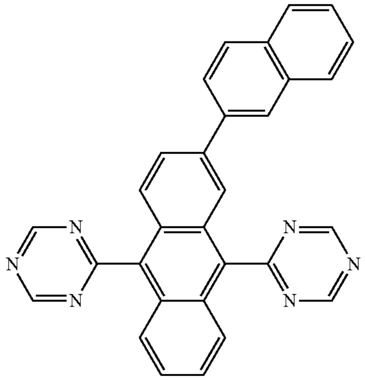
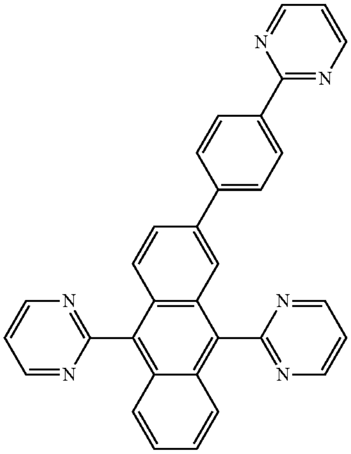
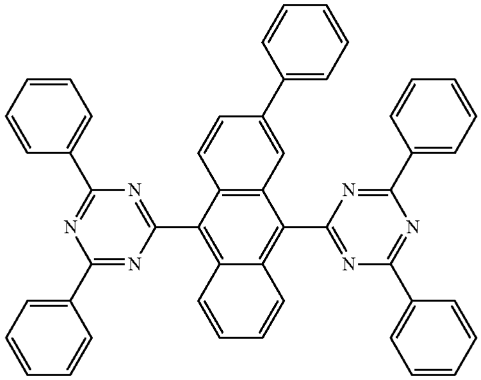
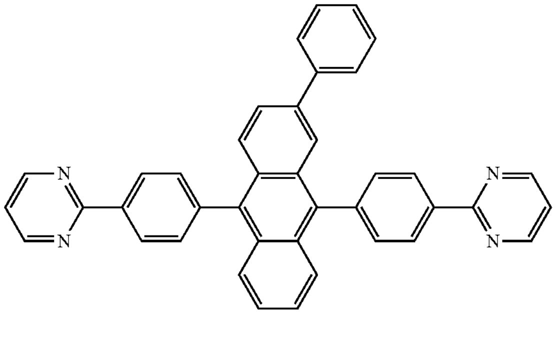
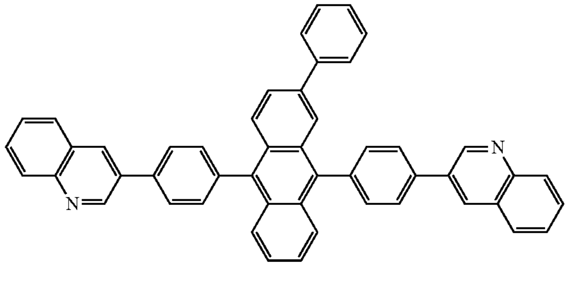

-continued
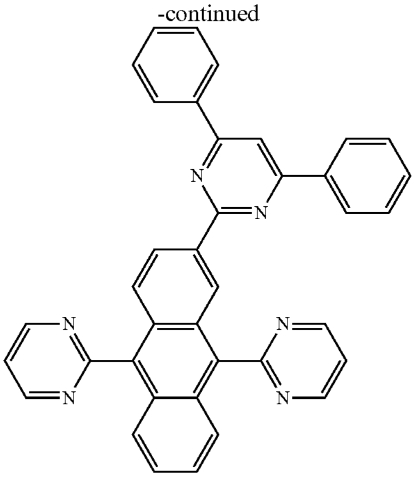
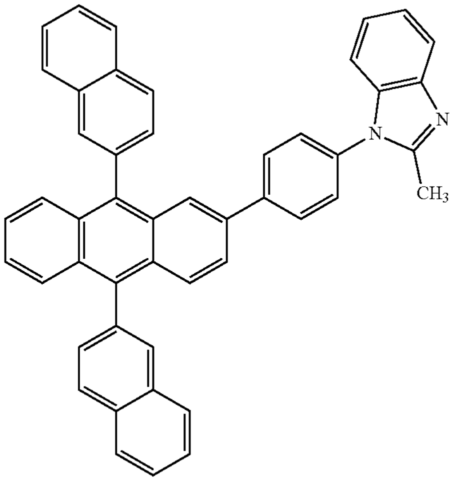
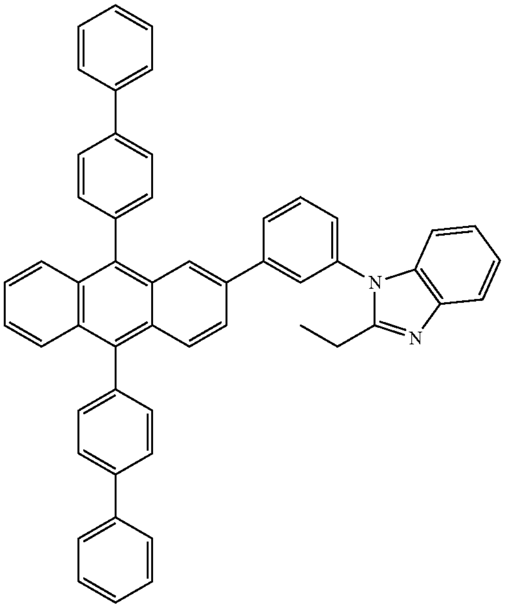
-continued
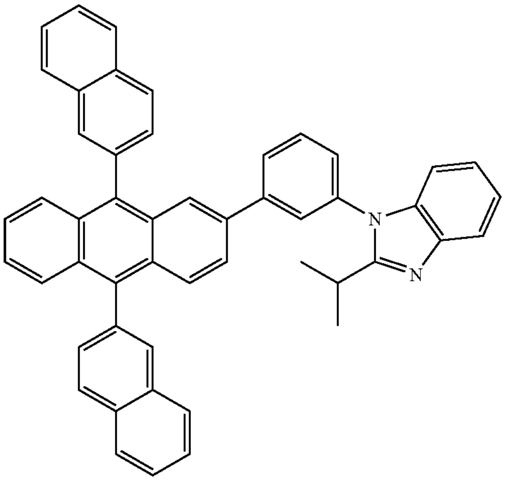
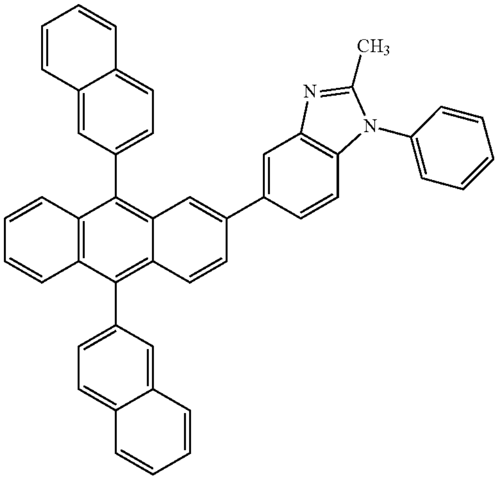
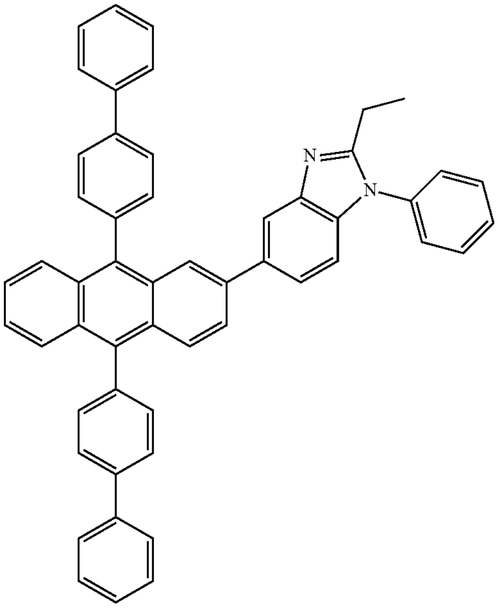

-continued
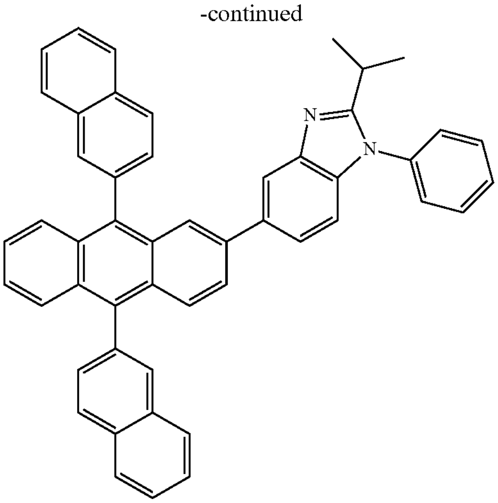
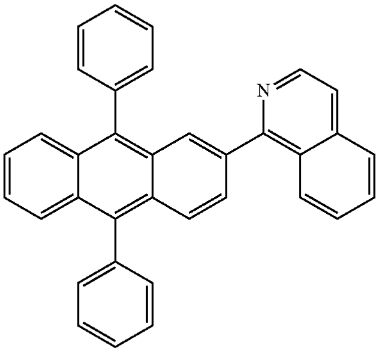
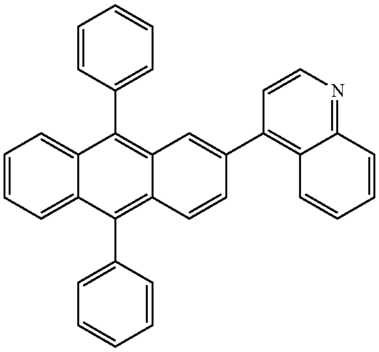
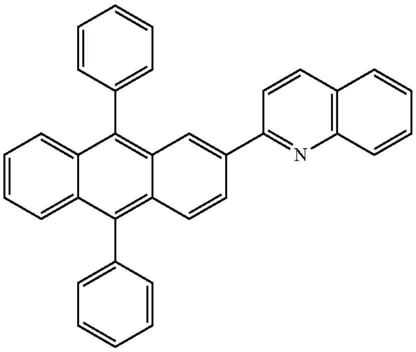
-continued
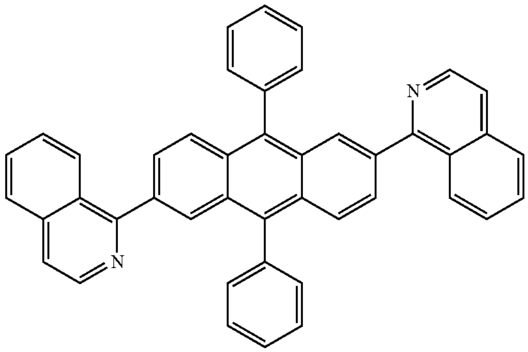
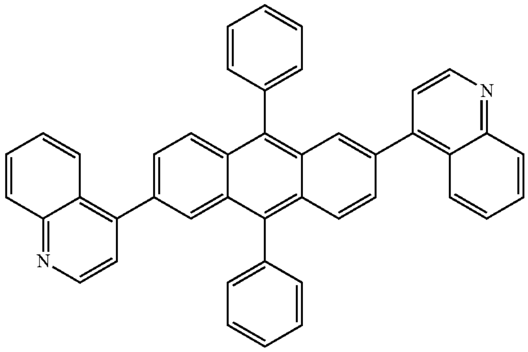
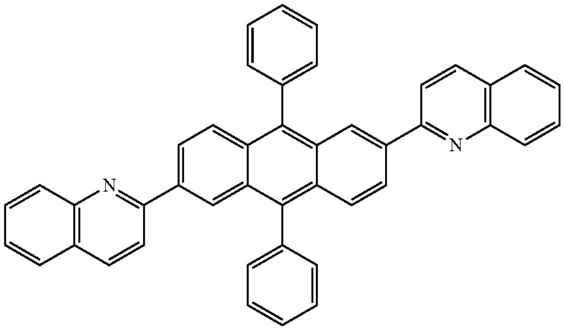
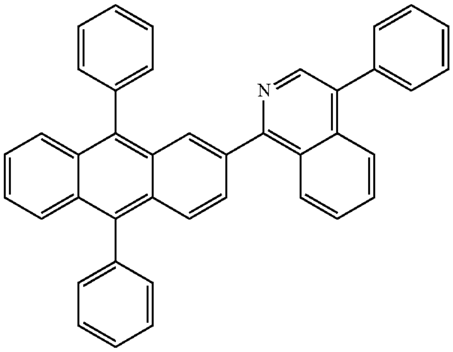
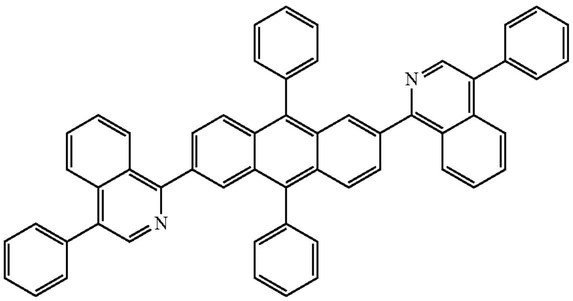

-continued
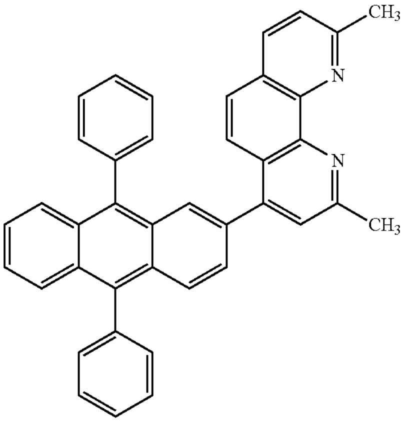
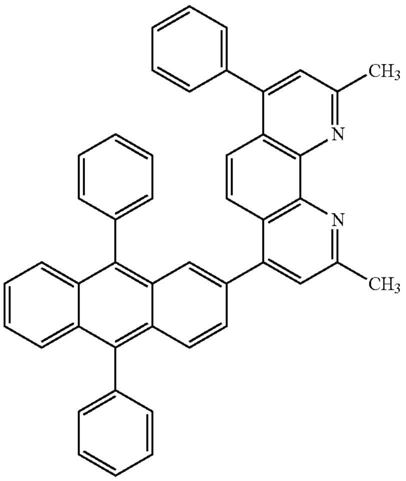
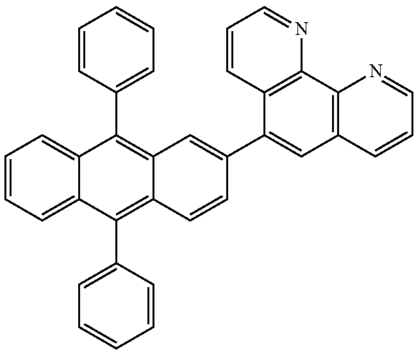
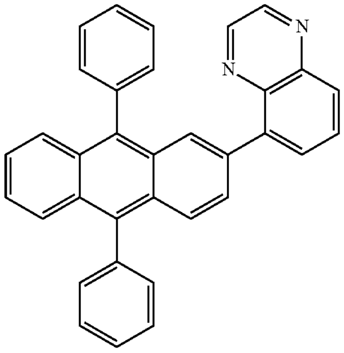
-continued
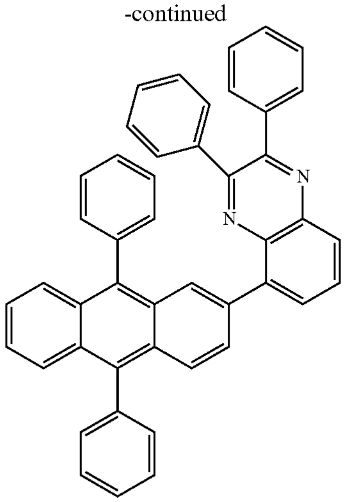
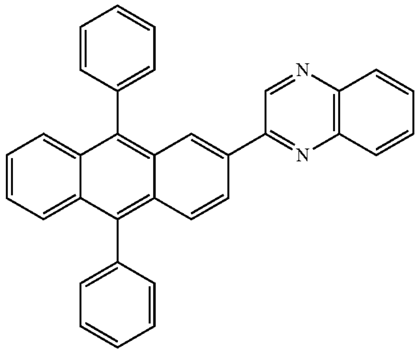
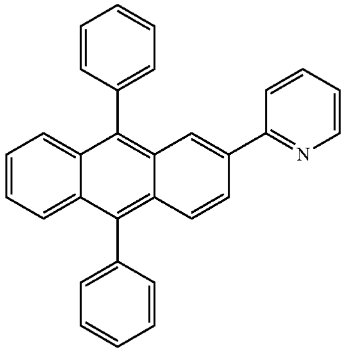
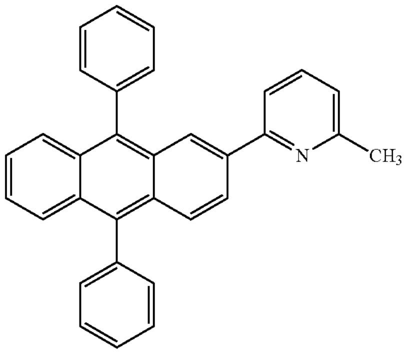

-continued
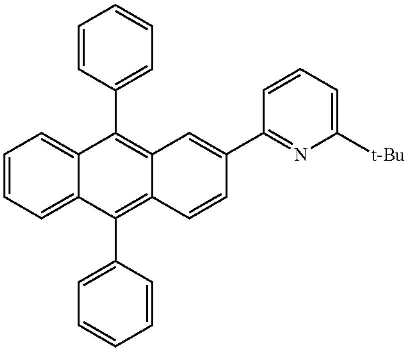
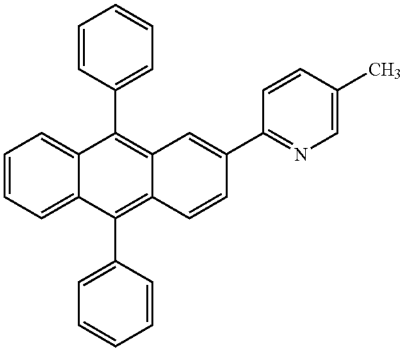
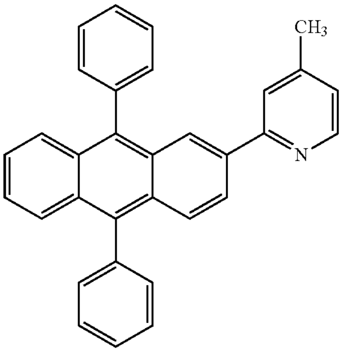
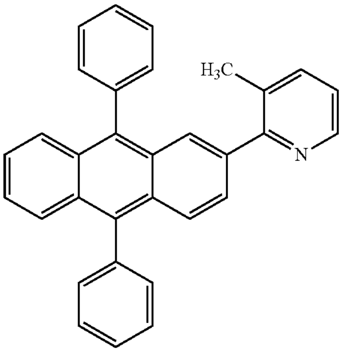
-continued
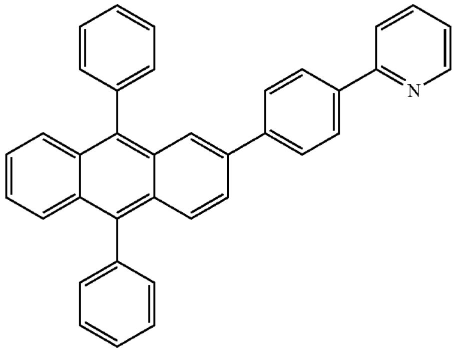
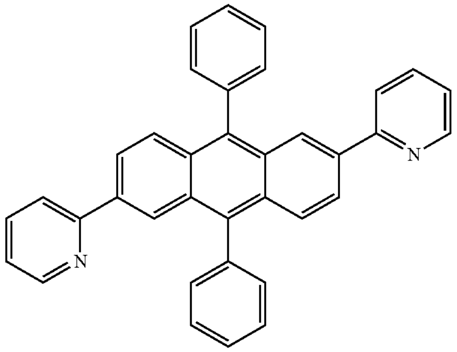
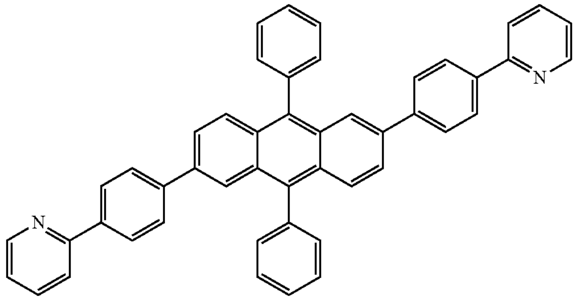
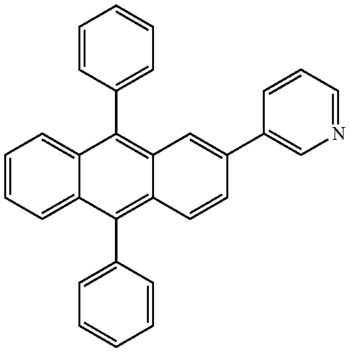
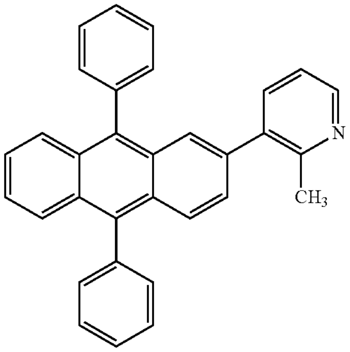

-continued
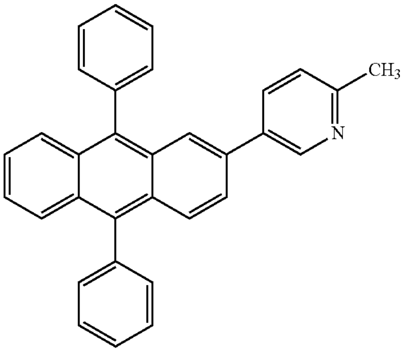
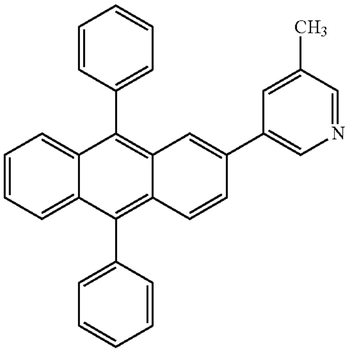
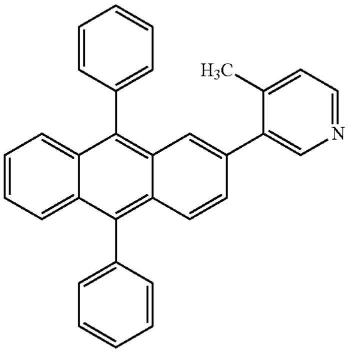
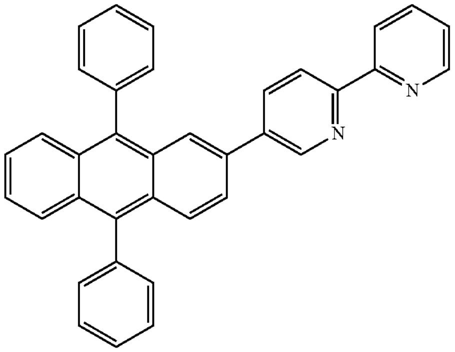
-continued
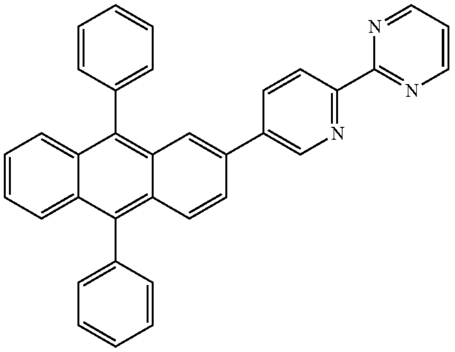
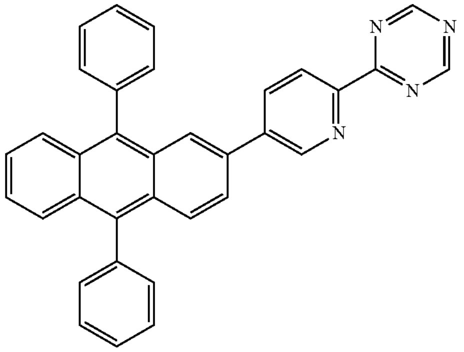
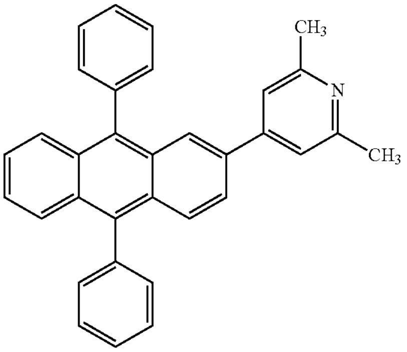
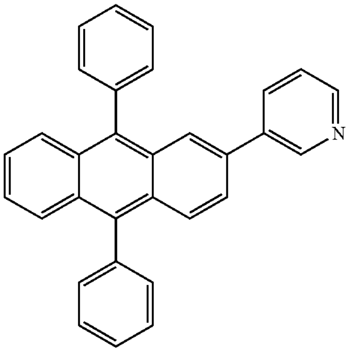

-continued
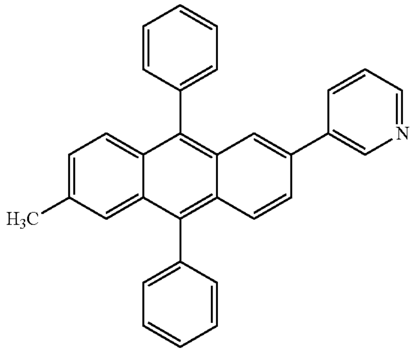
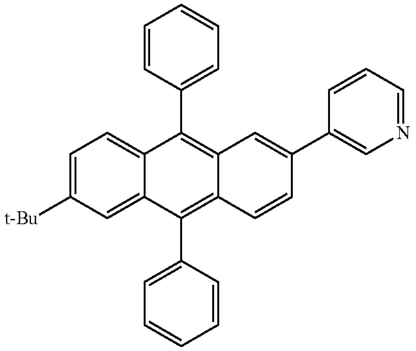
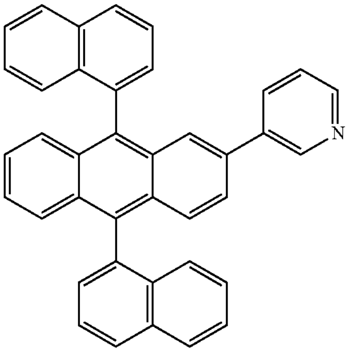
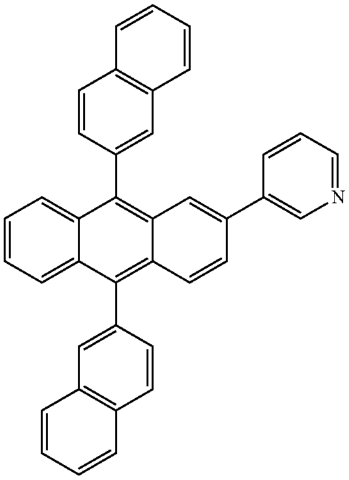
-continued
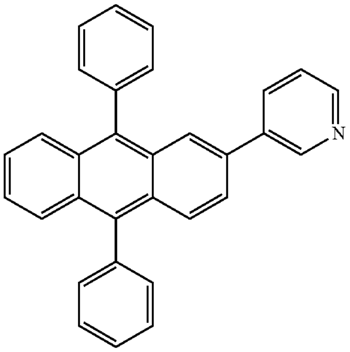
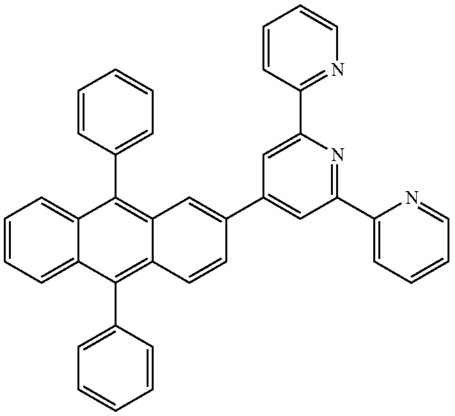
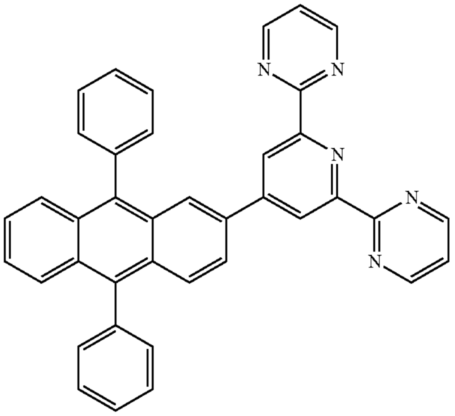
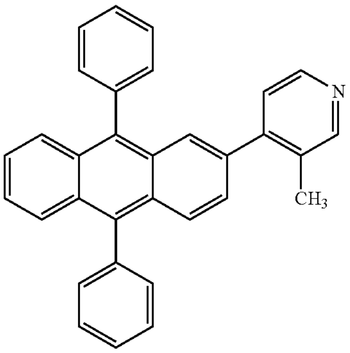

-continued
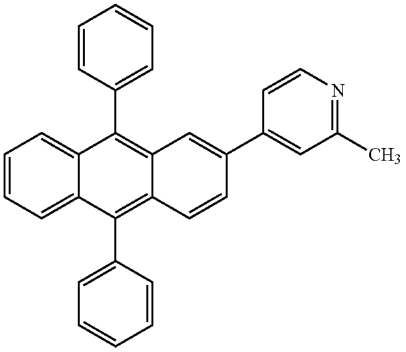
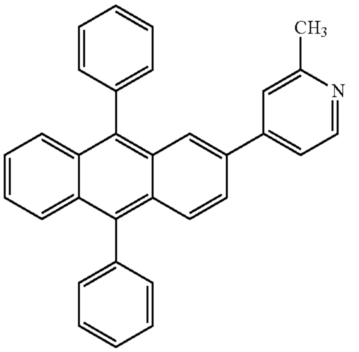
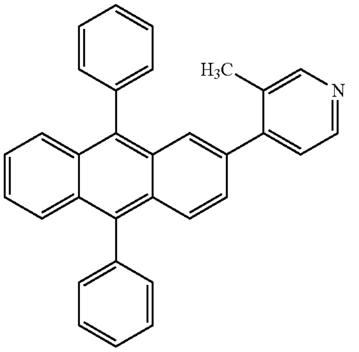
-continued
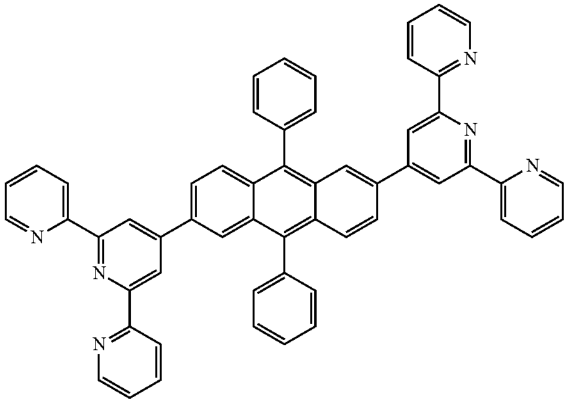
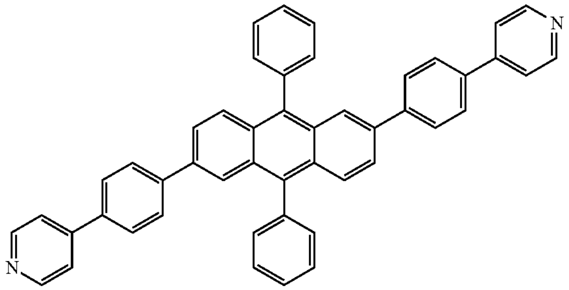
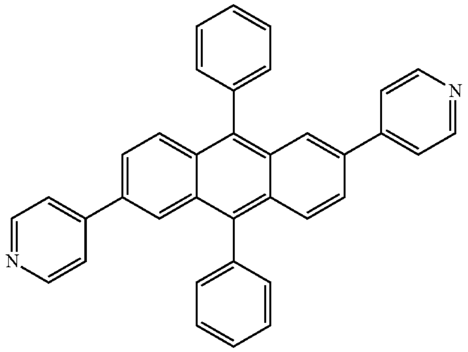

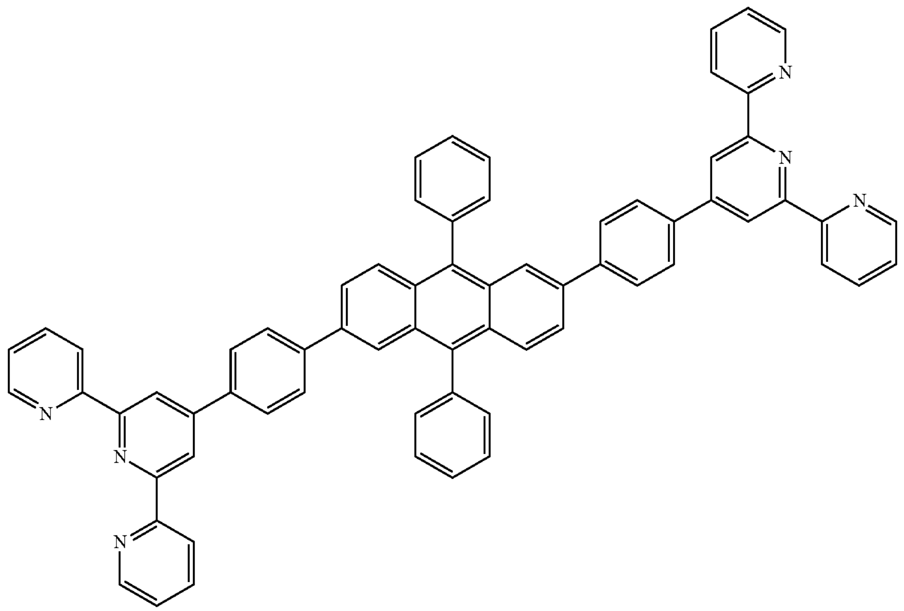
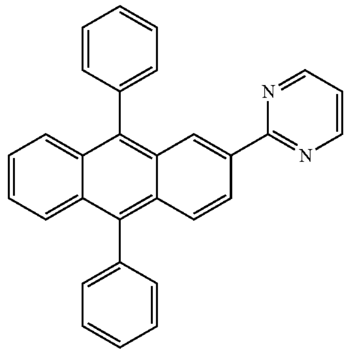
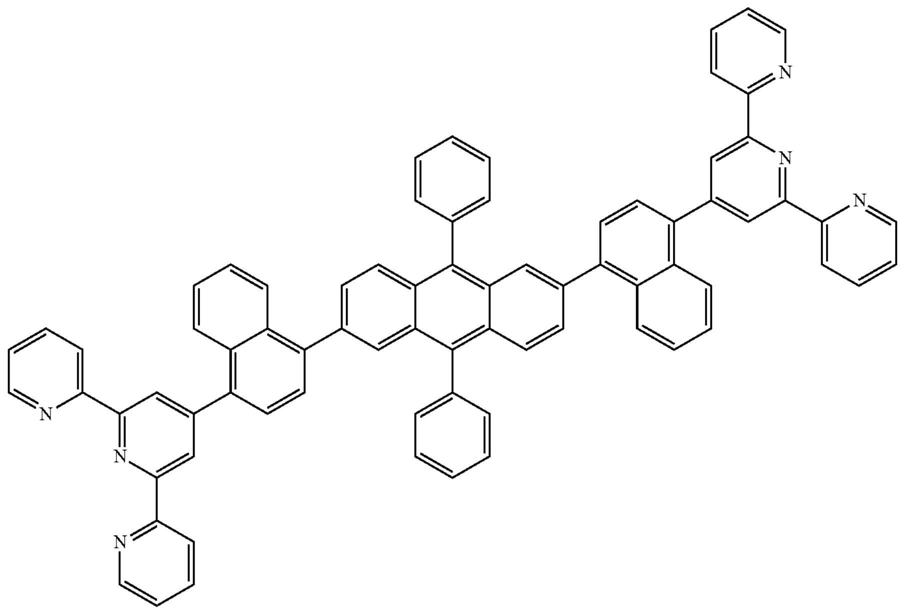

-continued
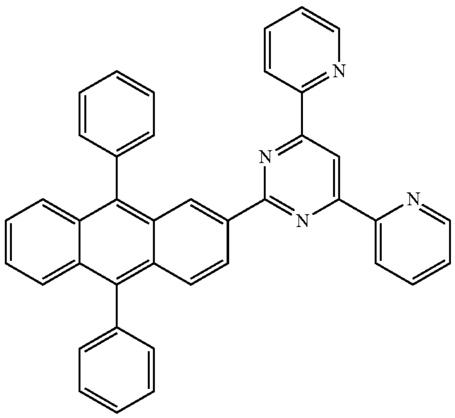
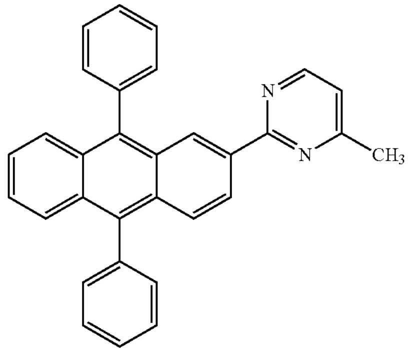
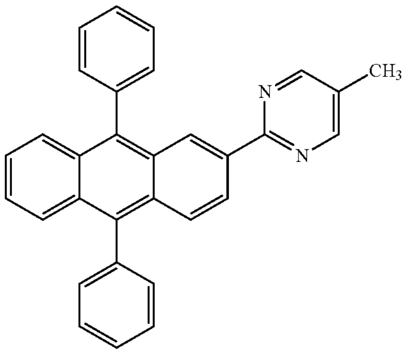
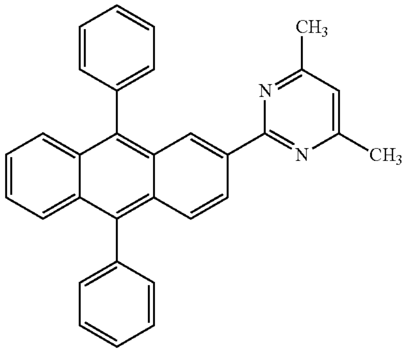
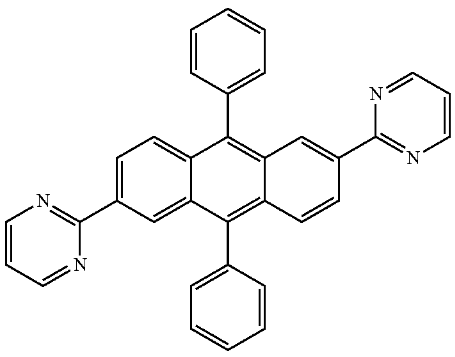
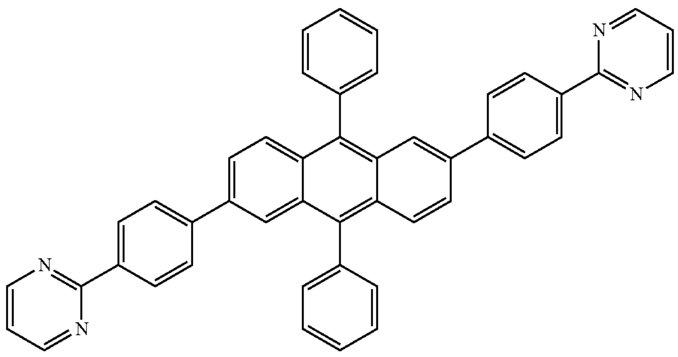
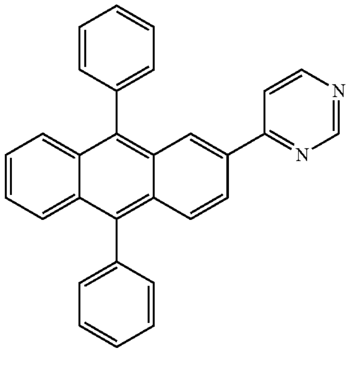
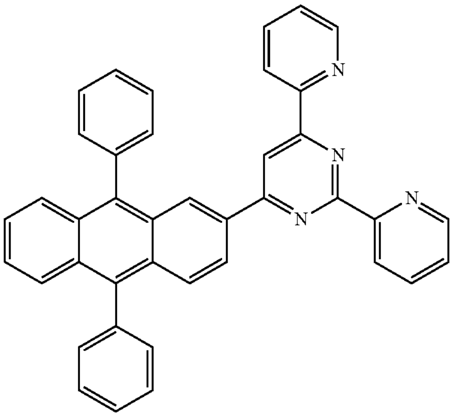

-continued
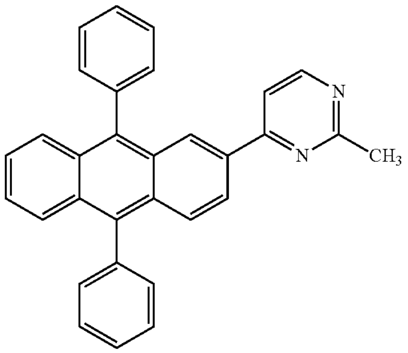
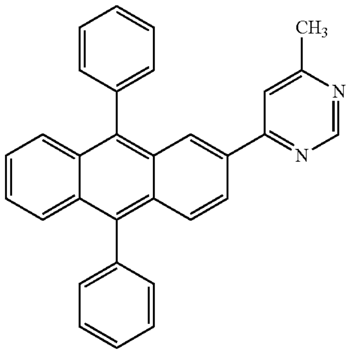
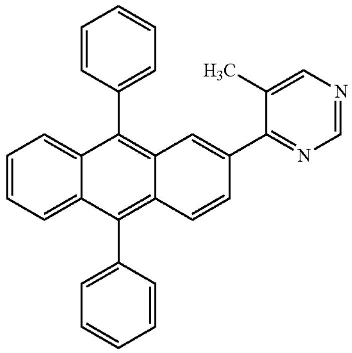
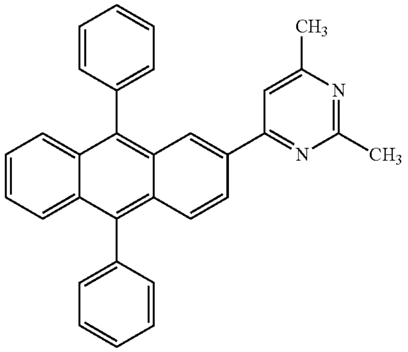
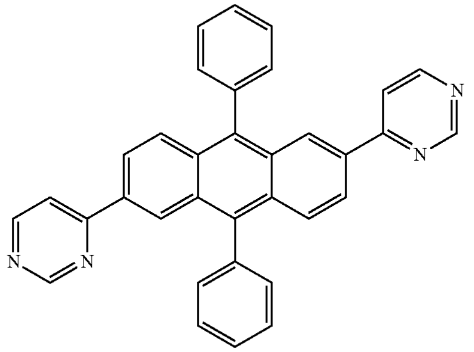
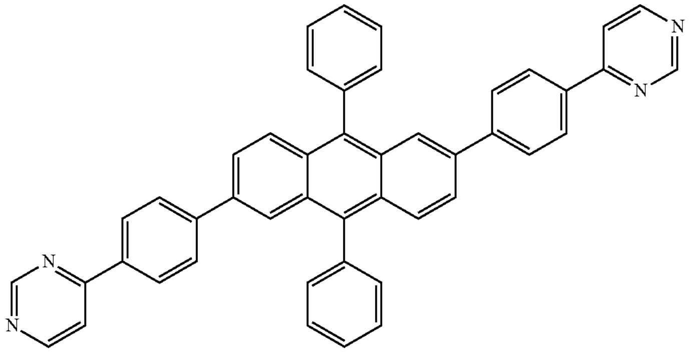
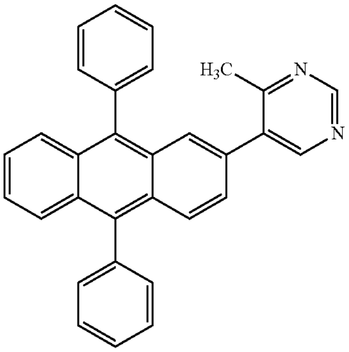
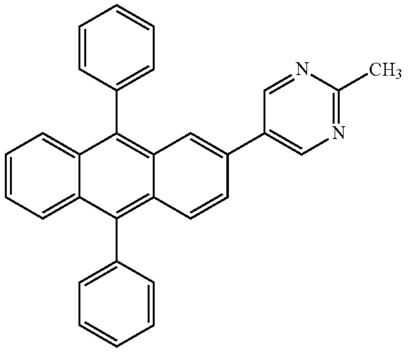
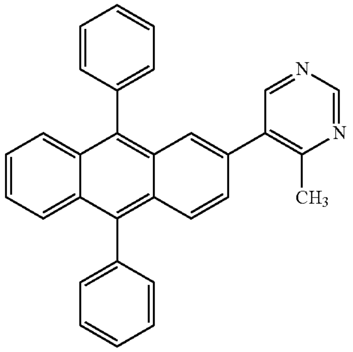
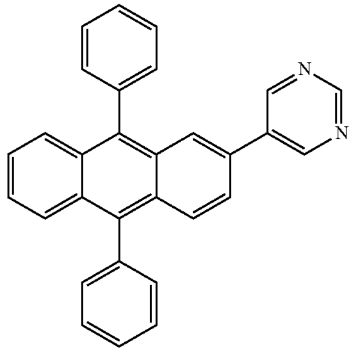

-continued
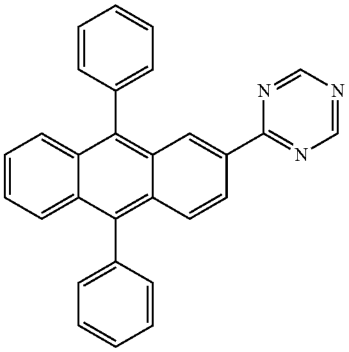
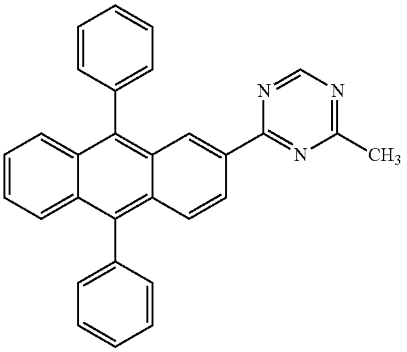
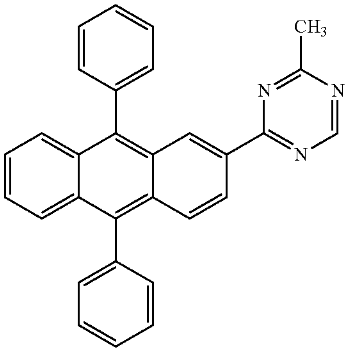
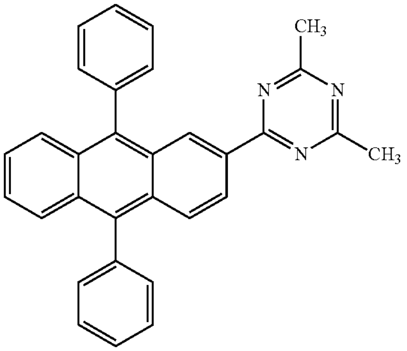
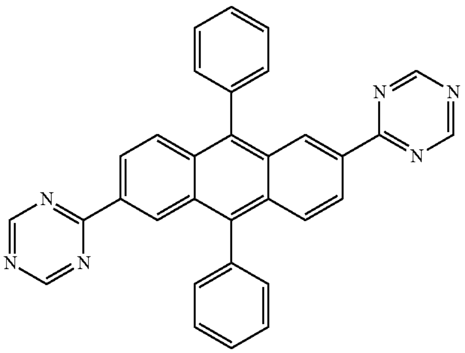
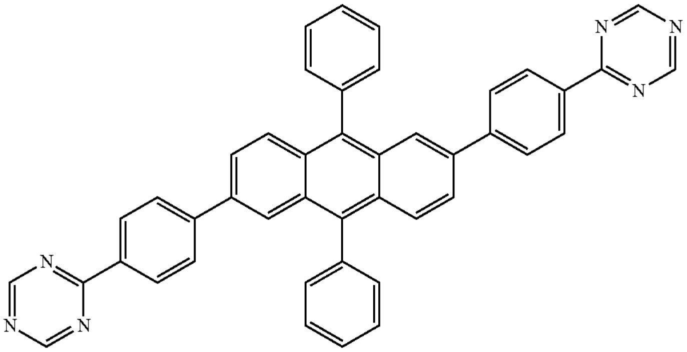
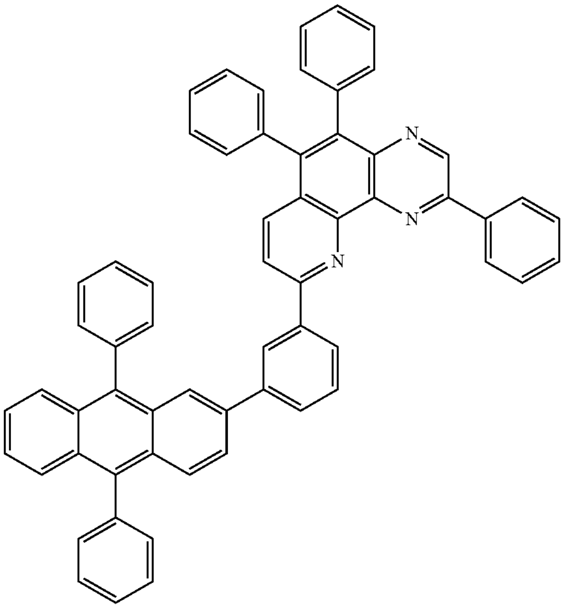

-continued
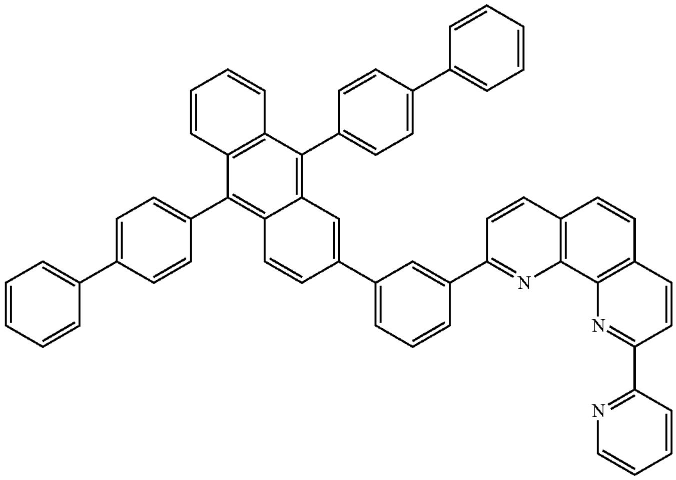
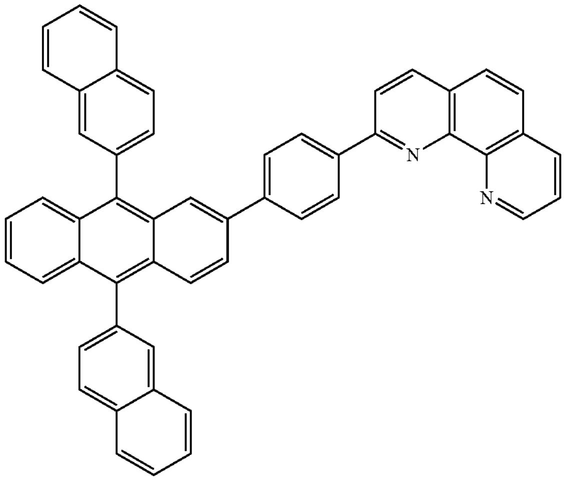
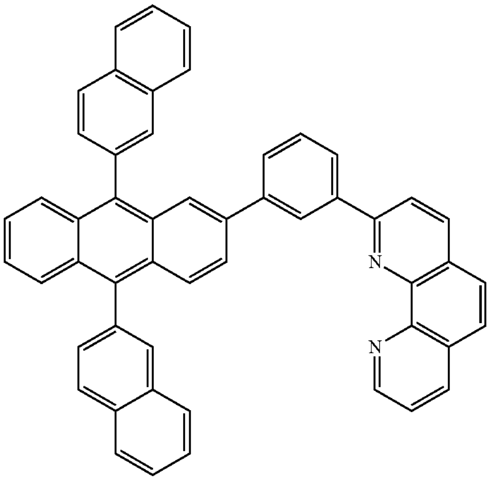
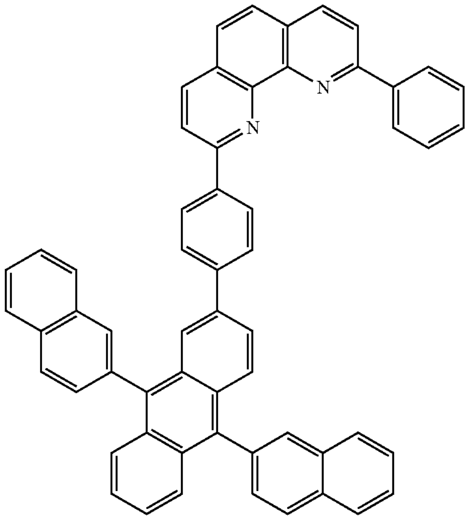
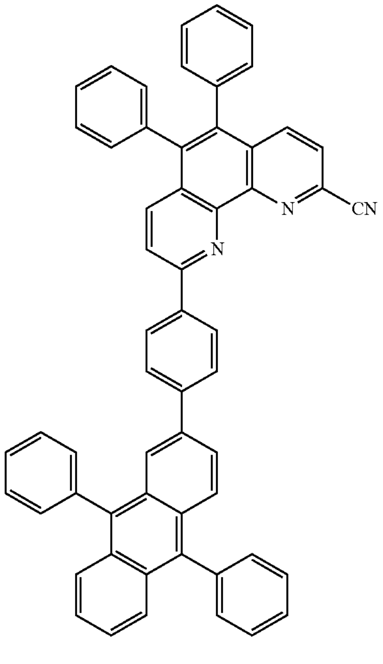

-continued
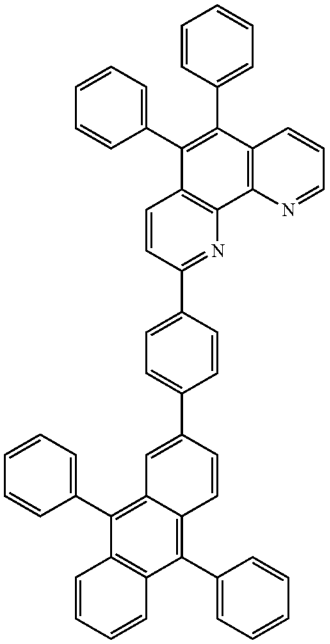
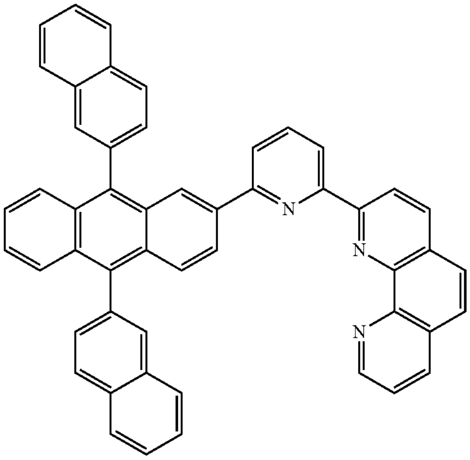
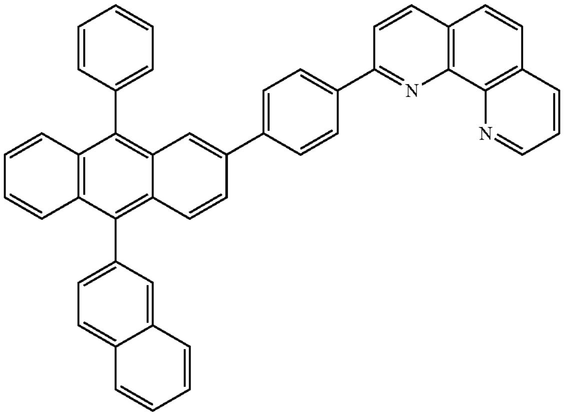
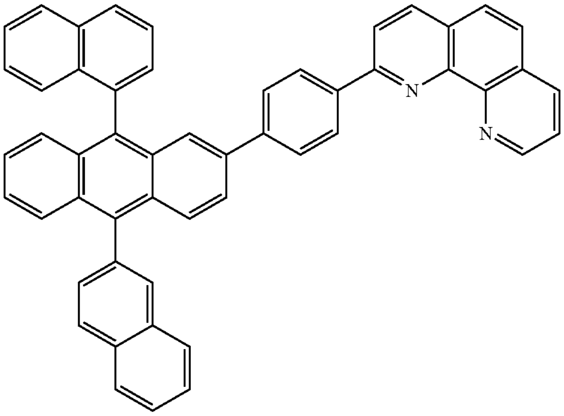
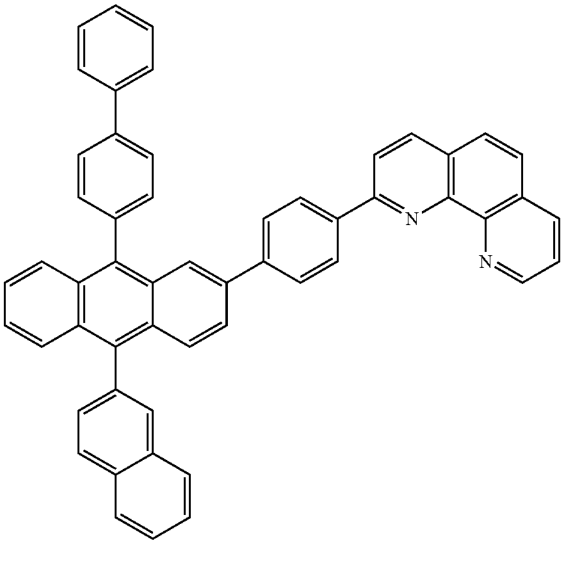

-continued
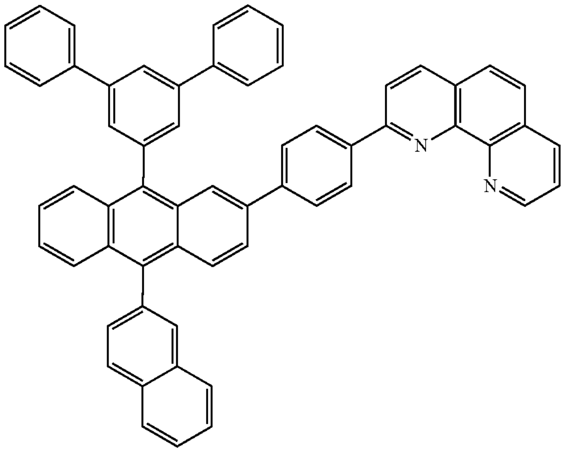
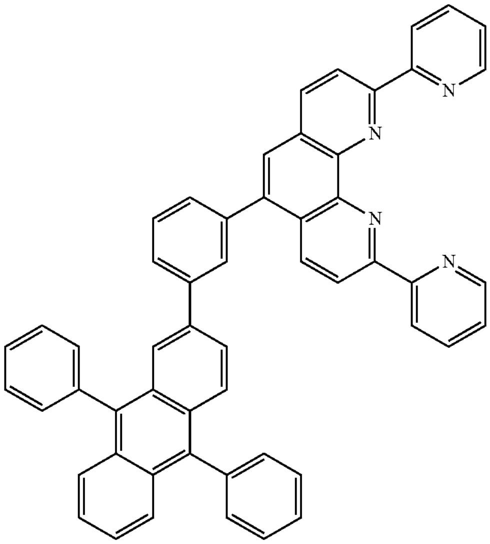
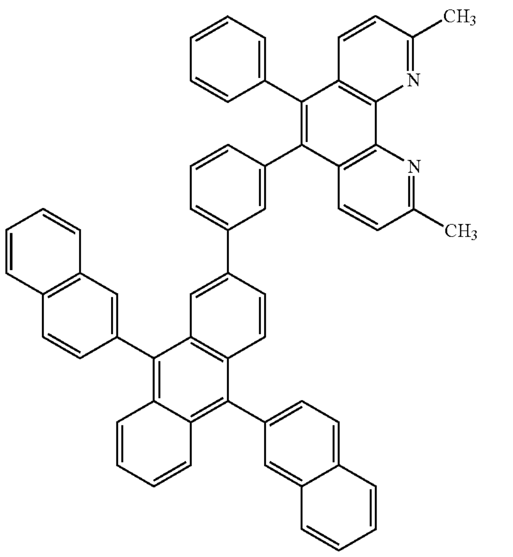
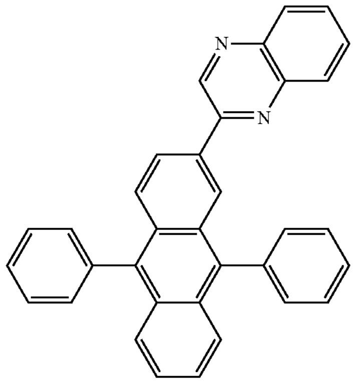
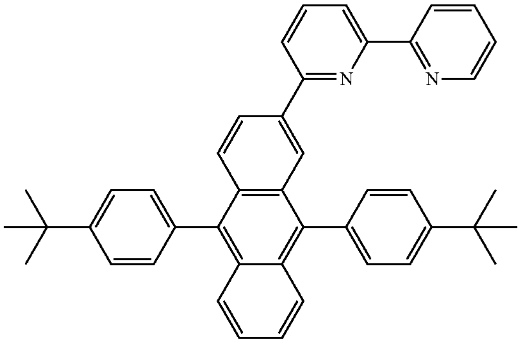
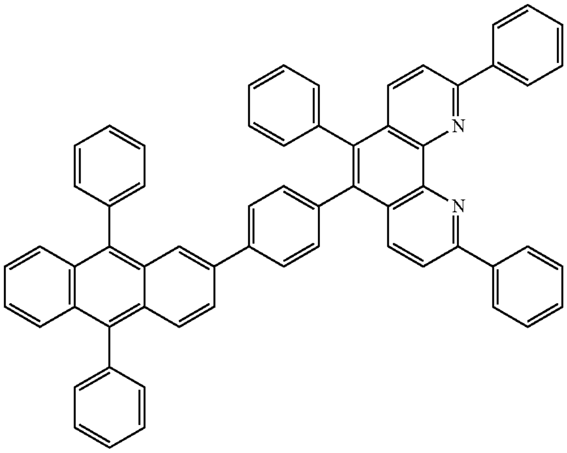
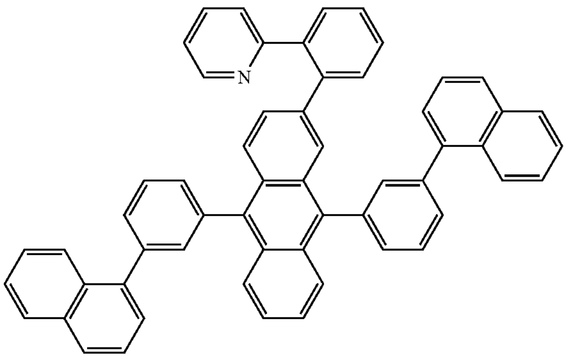

-continued
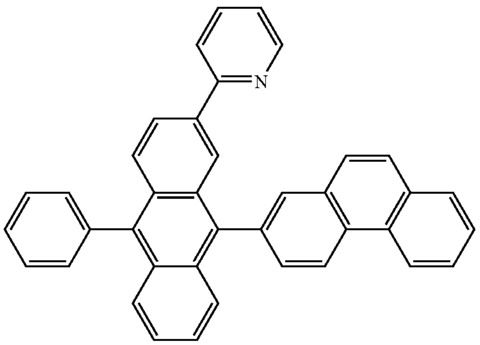
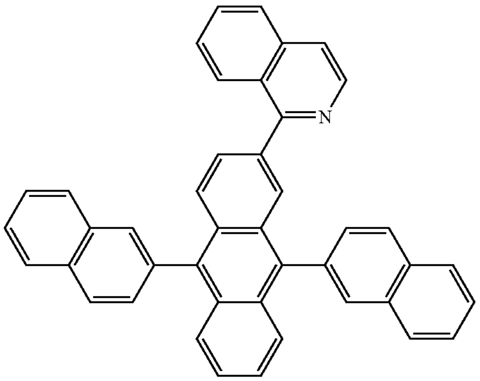
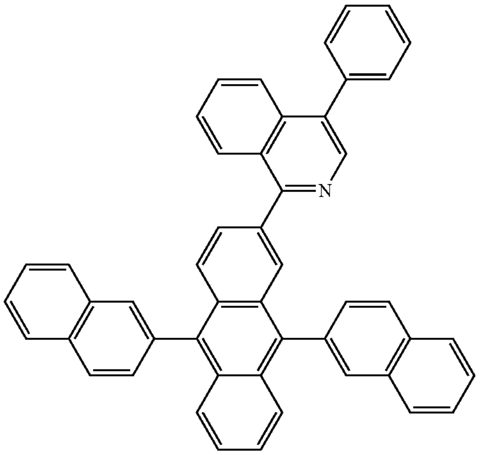
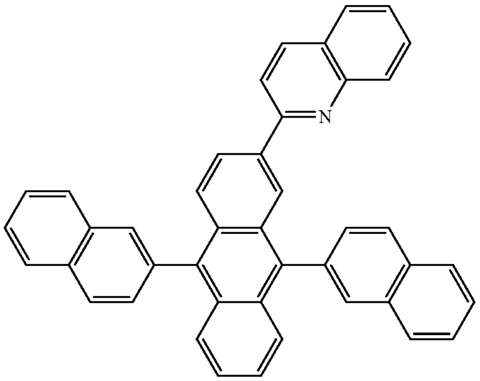
-continued
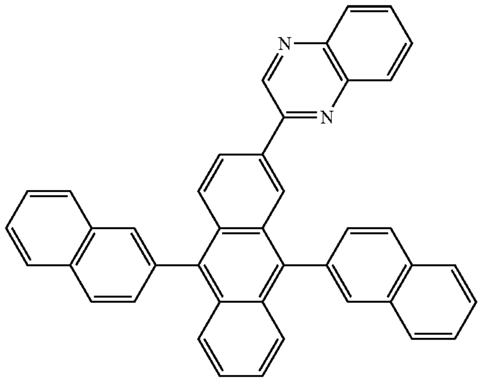
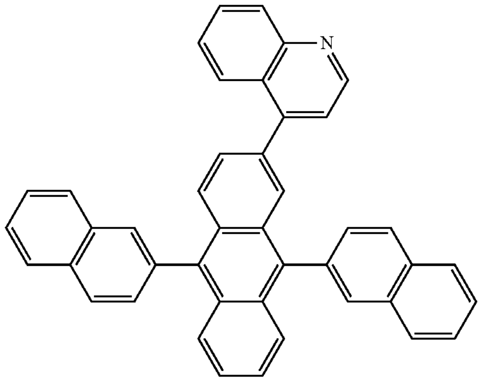
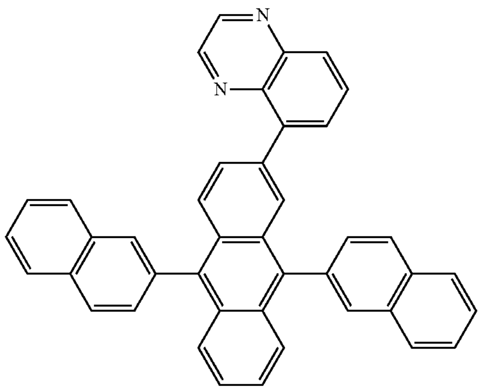
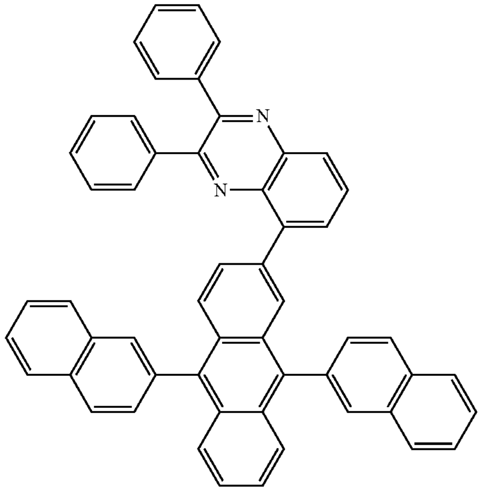

-continued
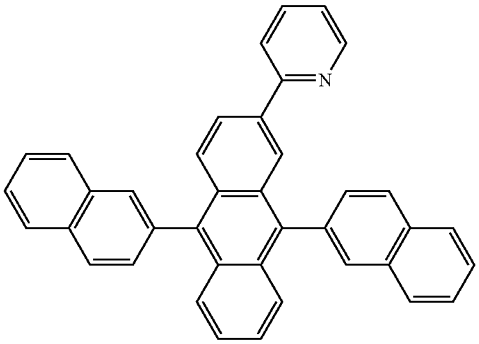
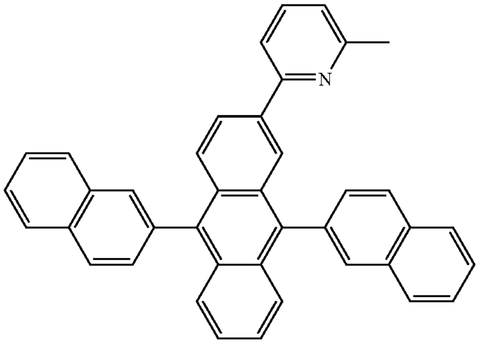
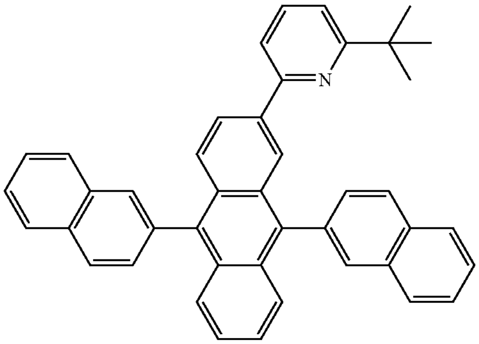
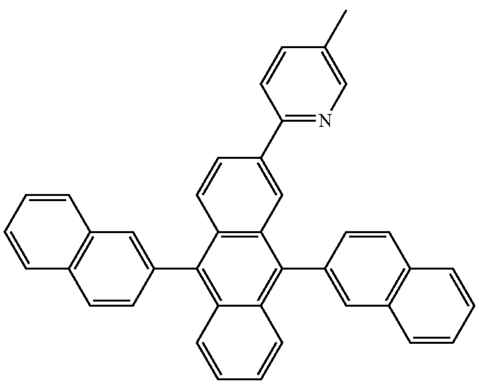
-continued
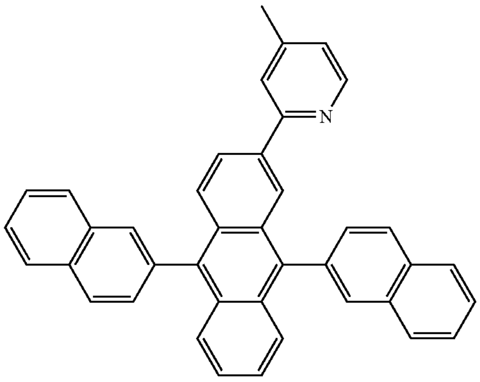
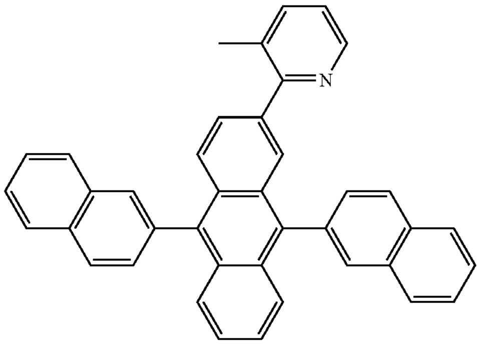
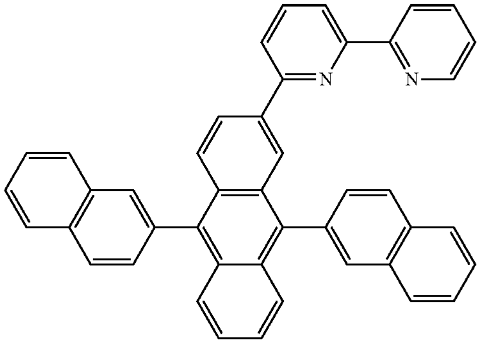
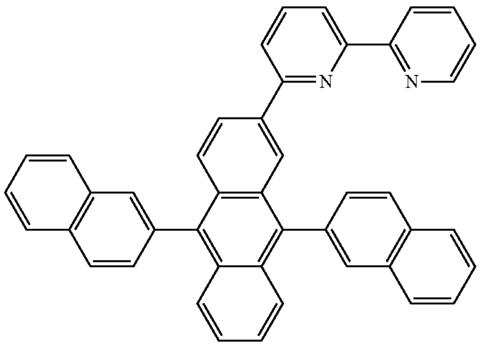

-continued
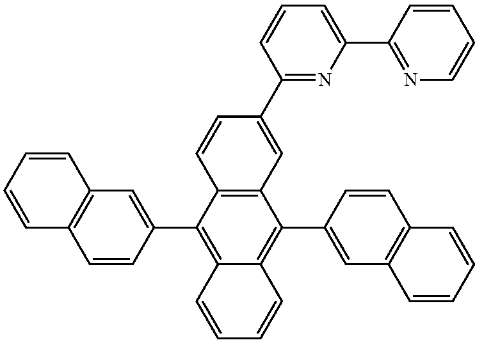
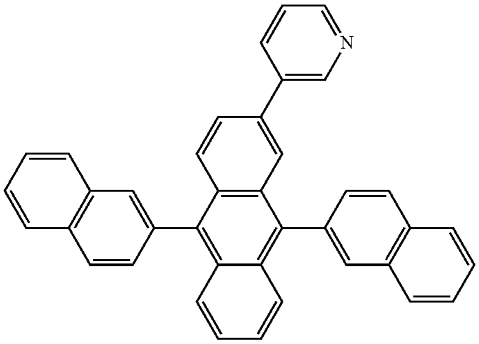
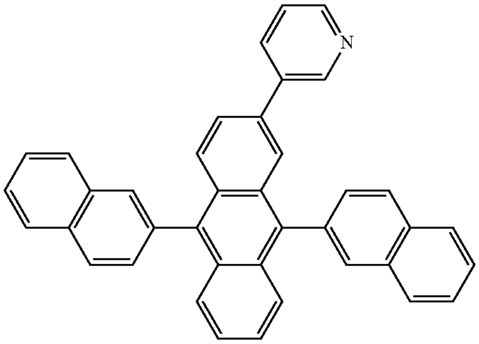
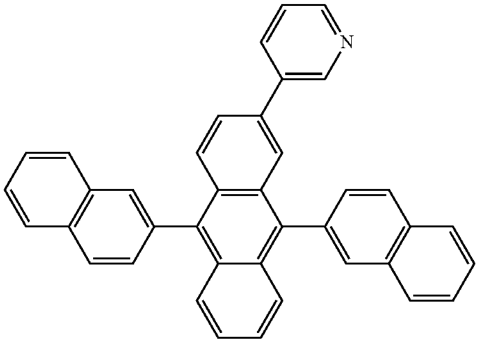
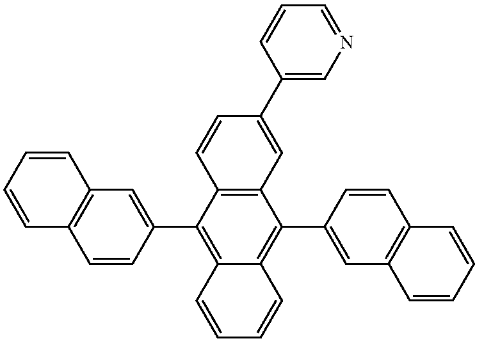
-continued
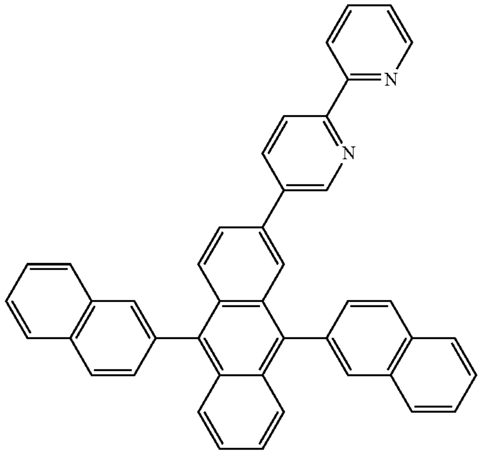
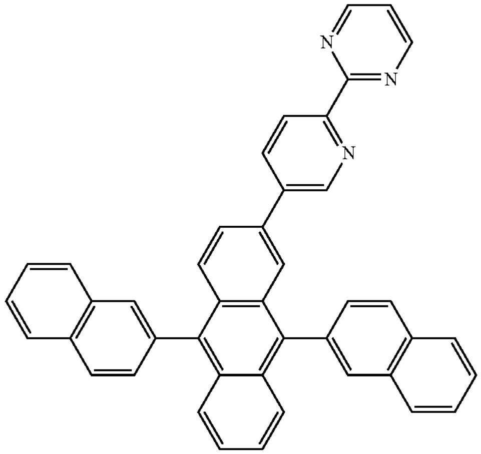
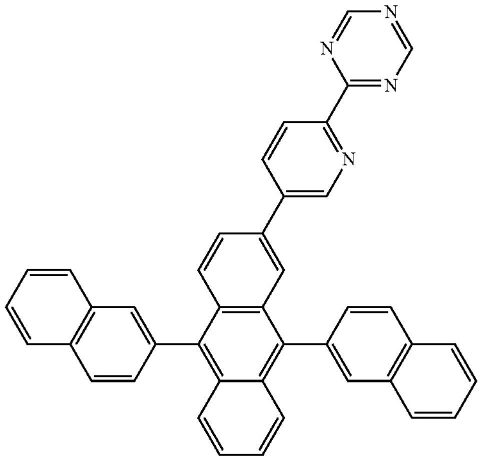

-continued
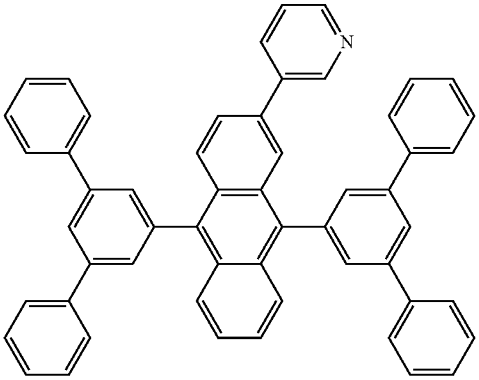
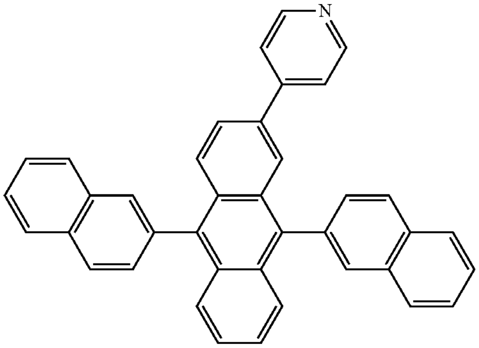
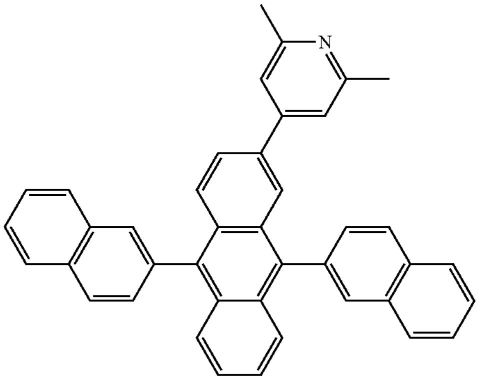
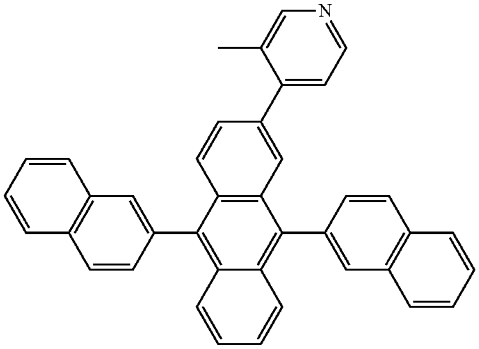
-continued
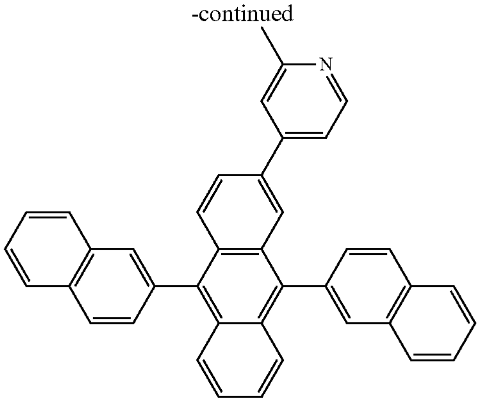
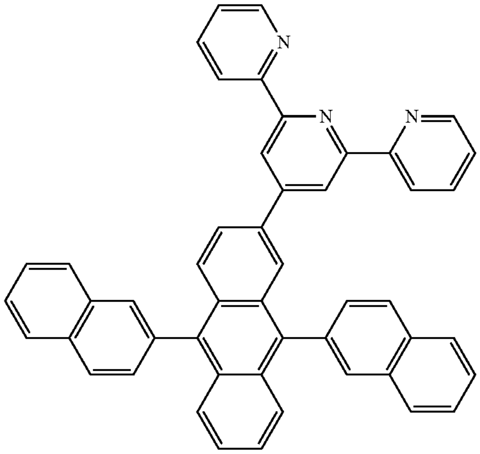
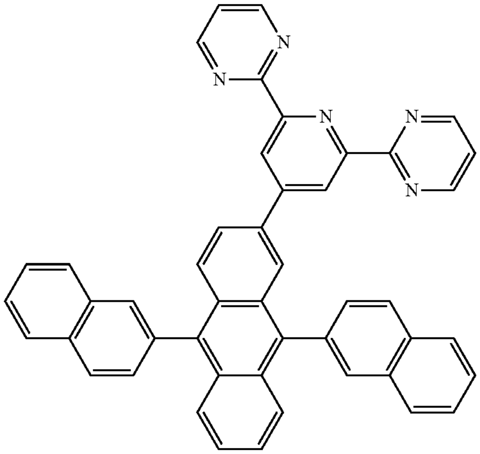
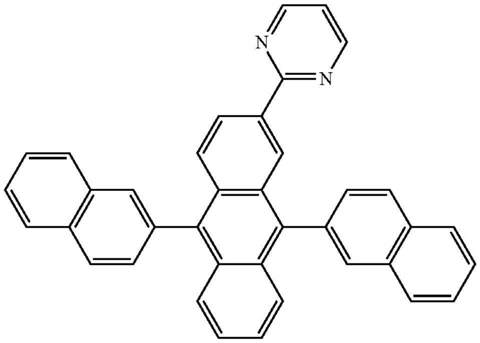

-continued
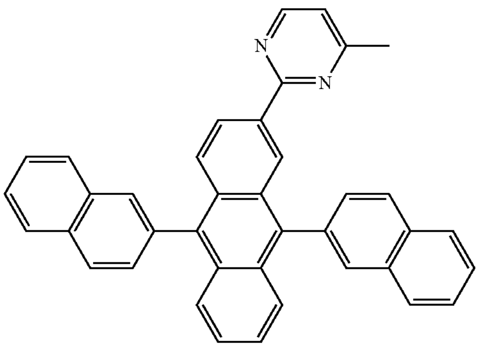
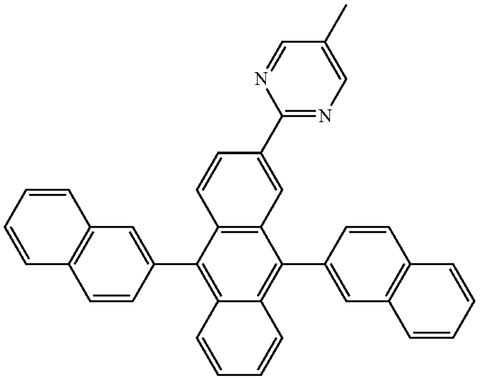
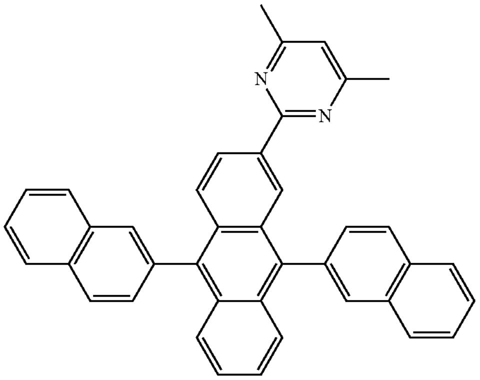
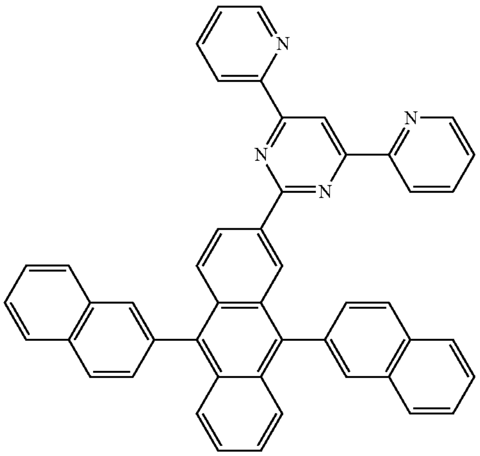
-continued
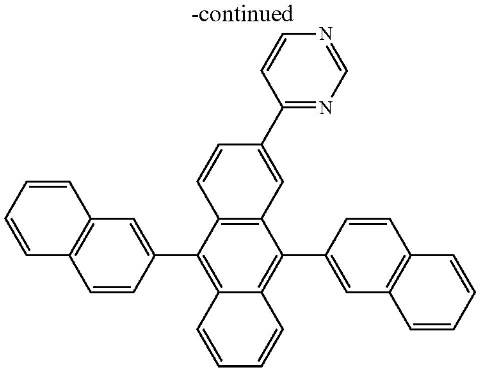
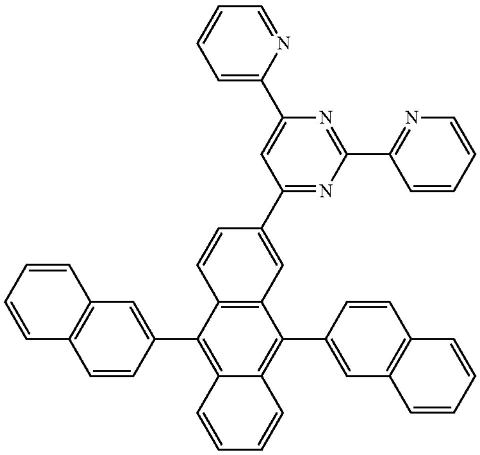
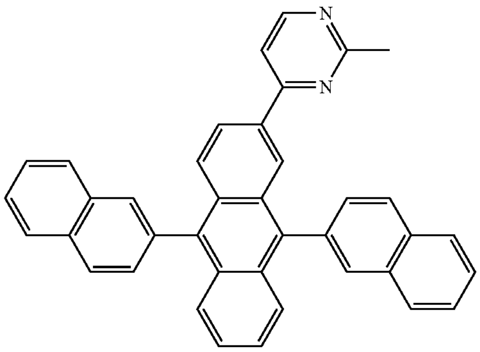
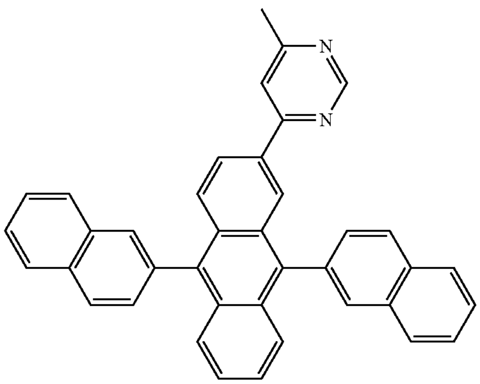

-continued
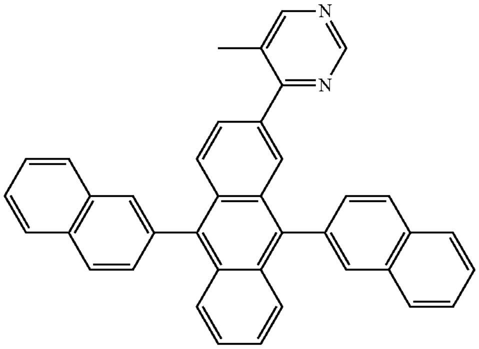
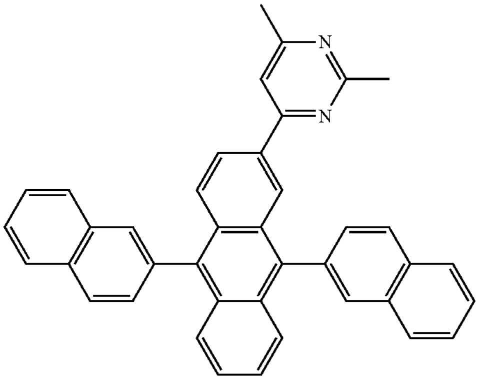
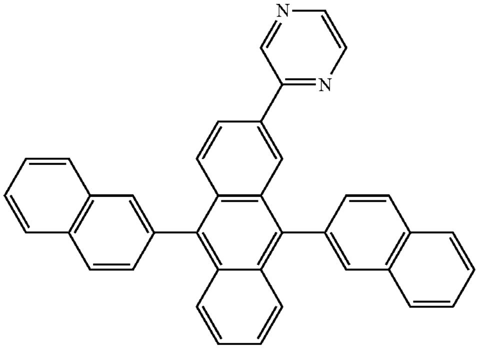
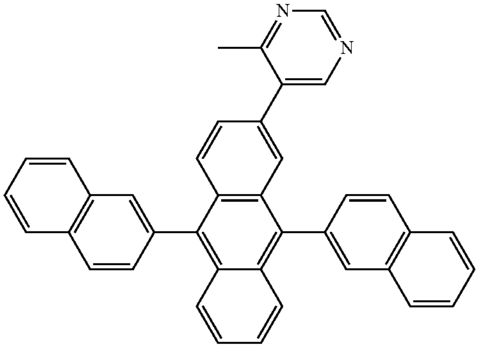
-continued
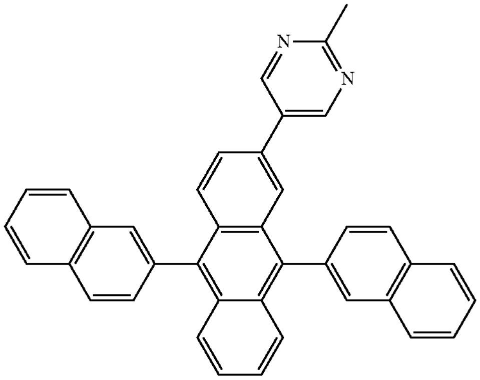
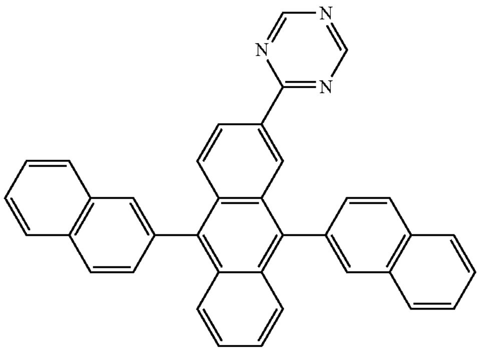
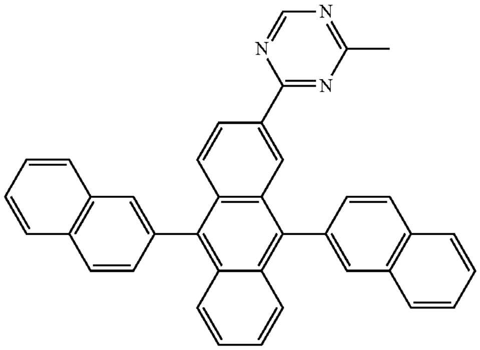
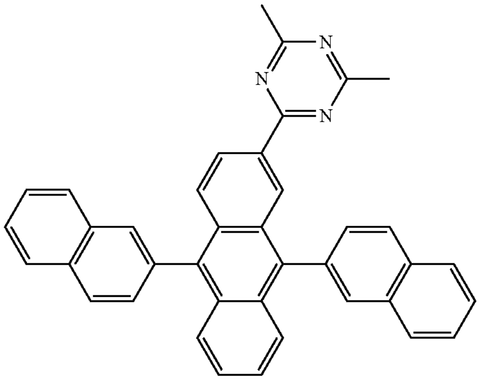

-continued
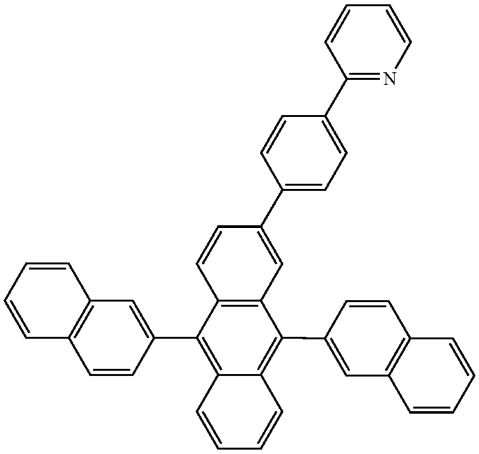
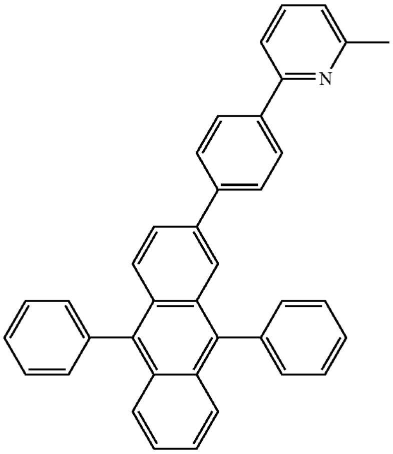
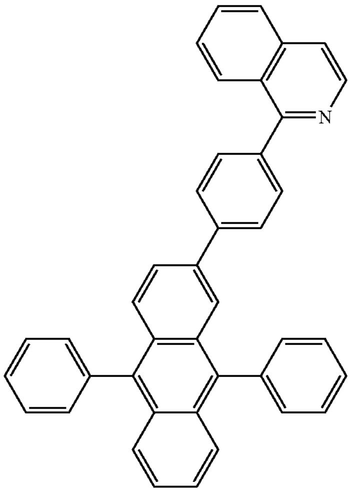
-continued
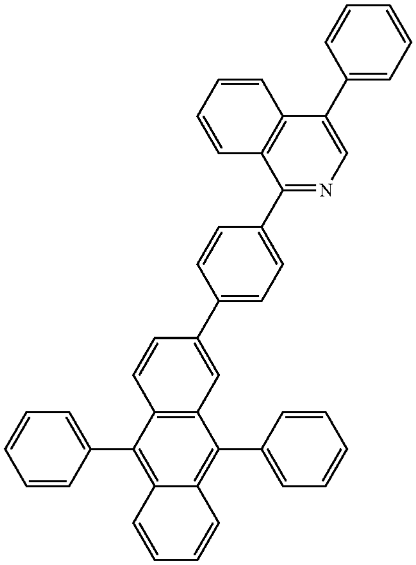
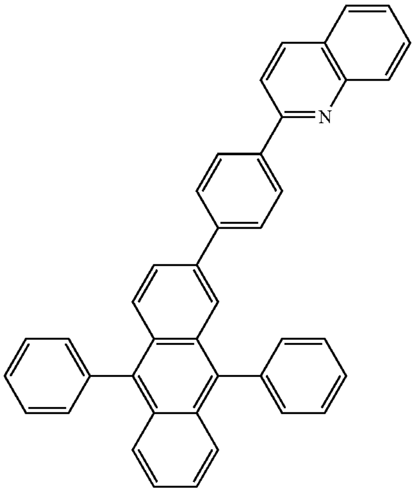
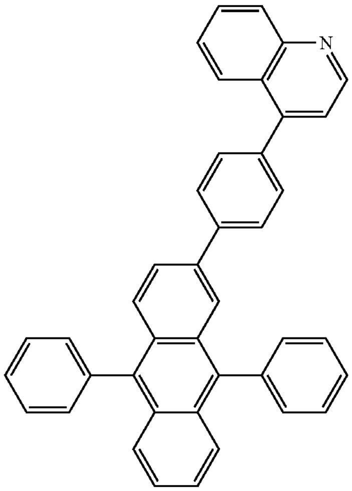

-continued
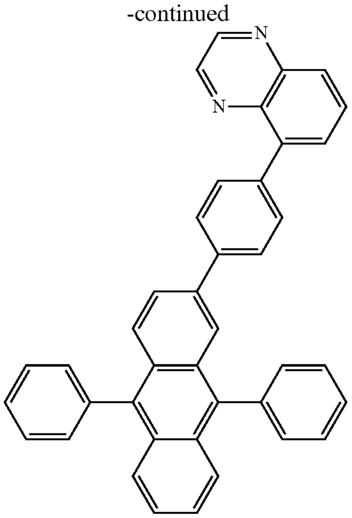
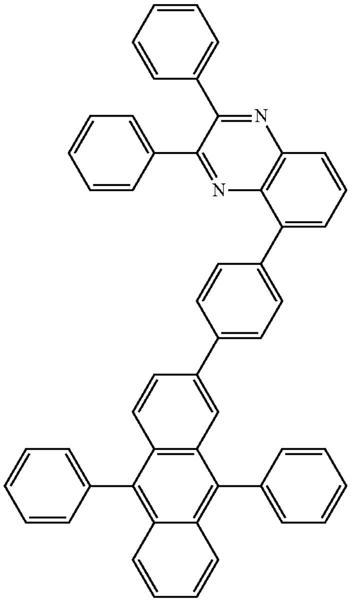
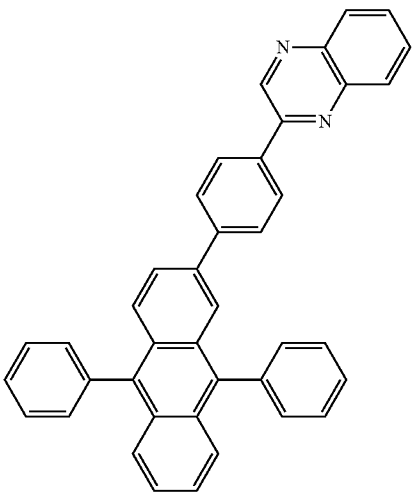
-continued
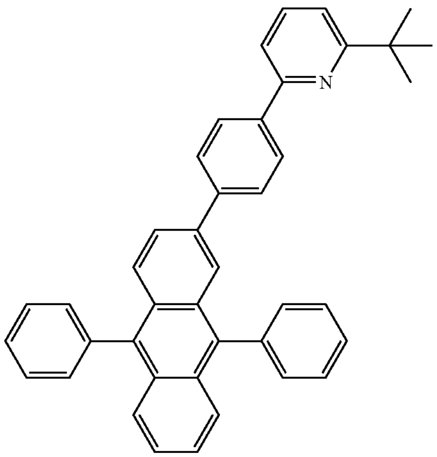
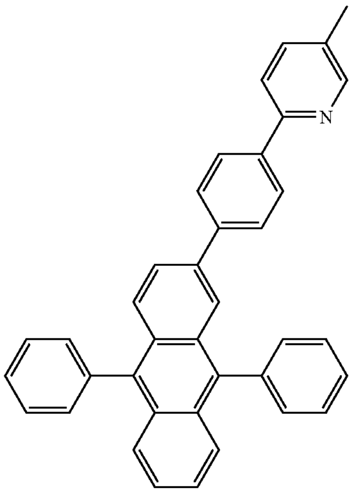
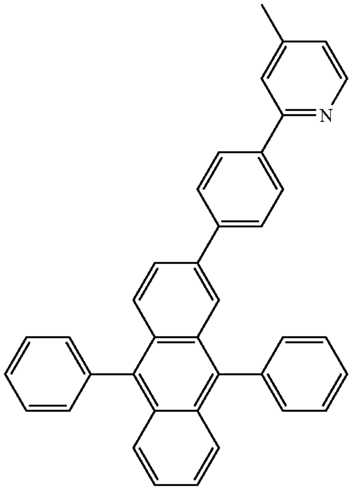

-continued
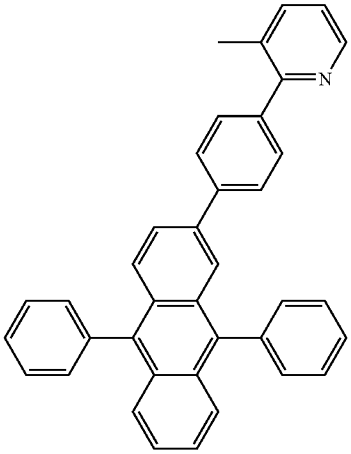
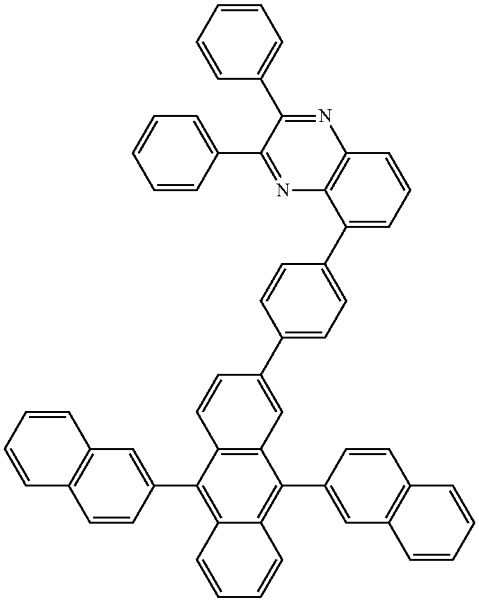
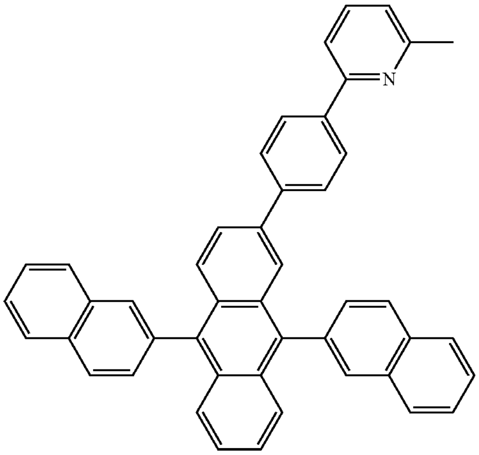
-continued
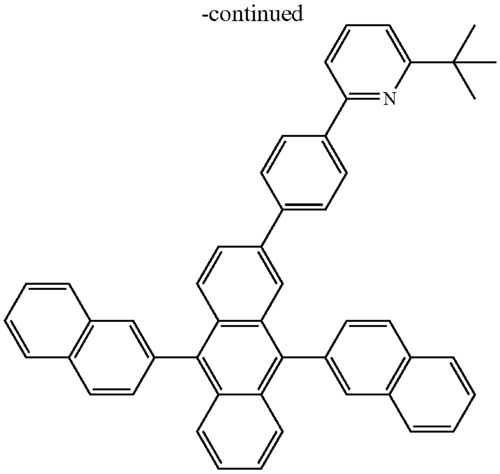
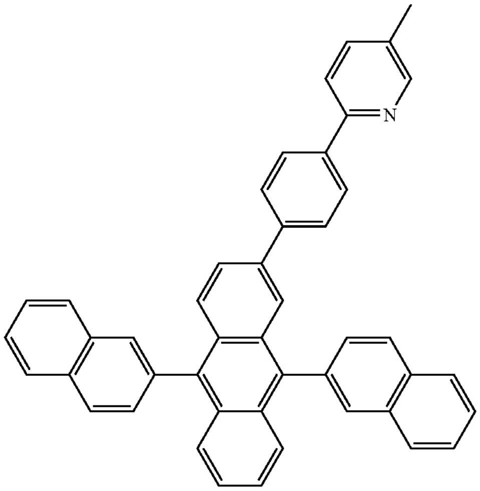
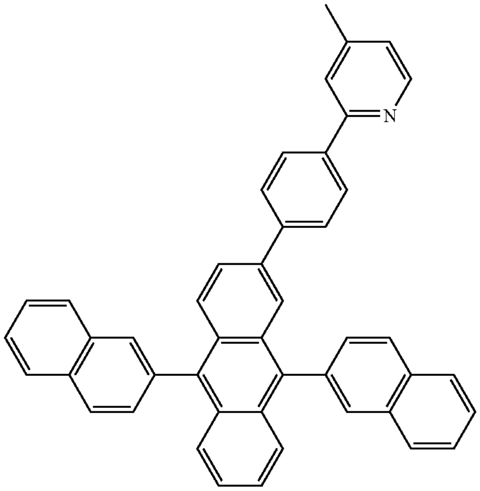

-continued
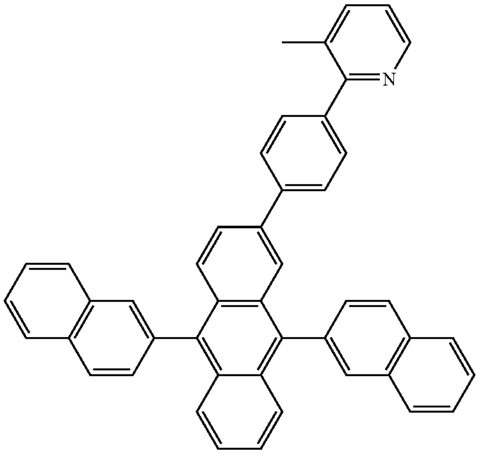
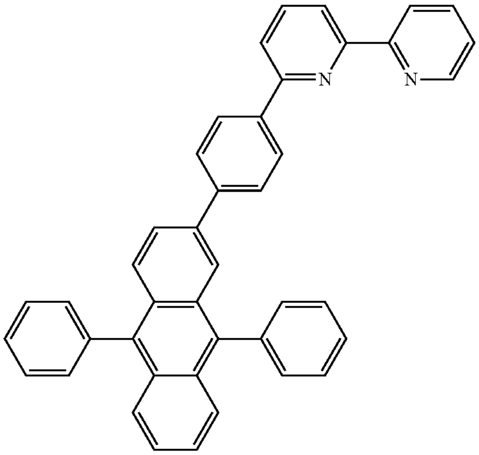
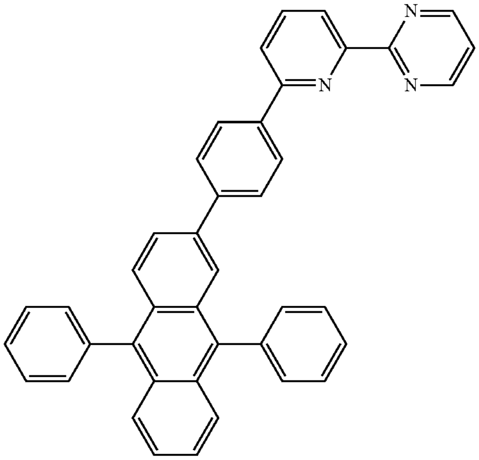
-continued
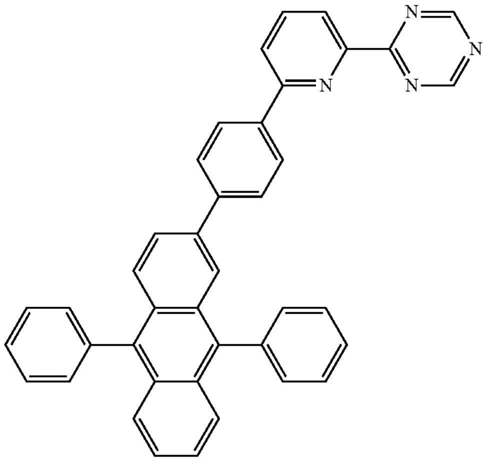
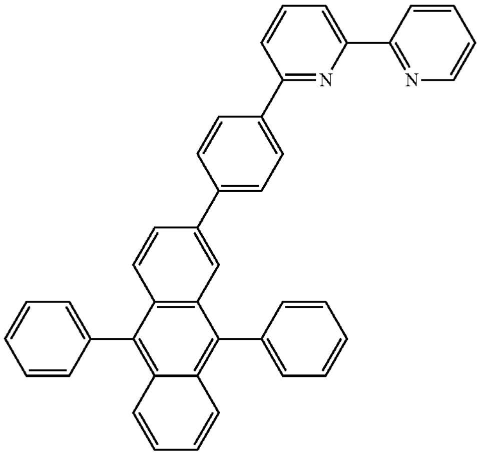
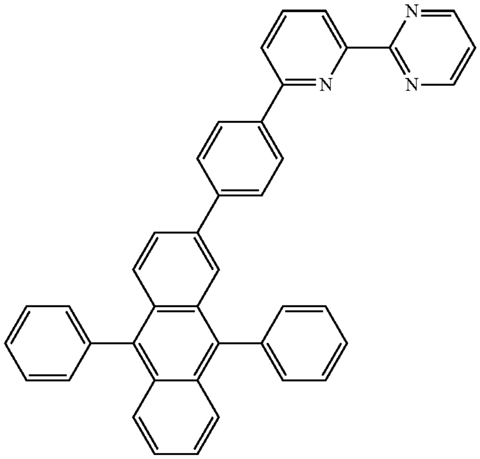

-continued
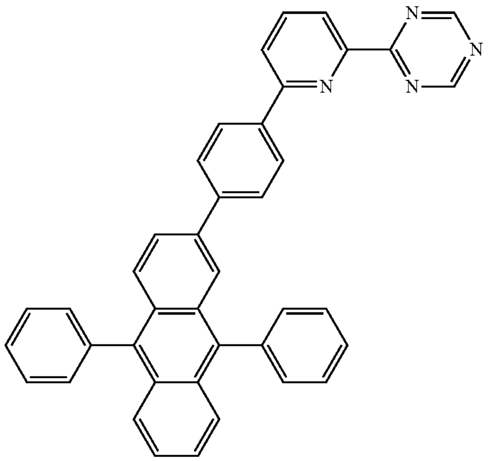
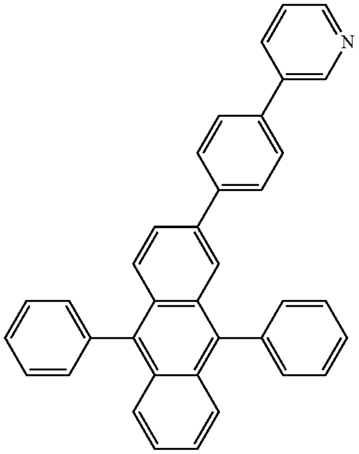
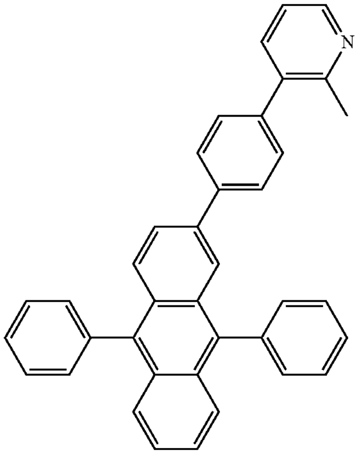
-continued
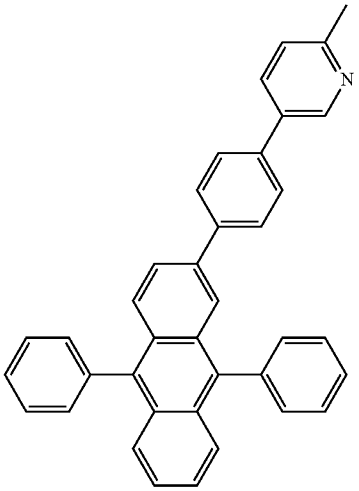
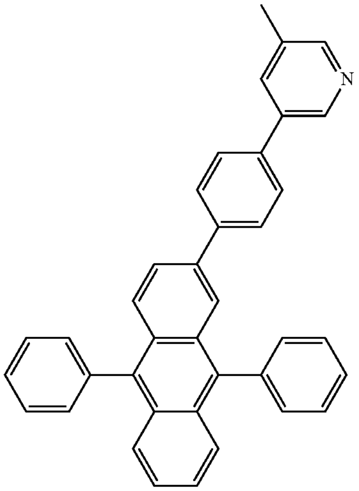
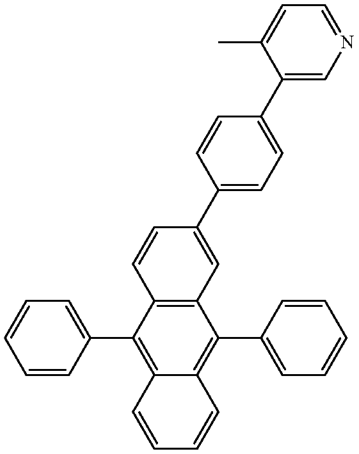

-continued
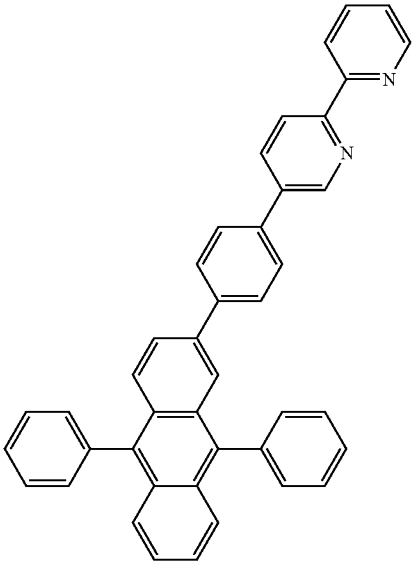
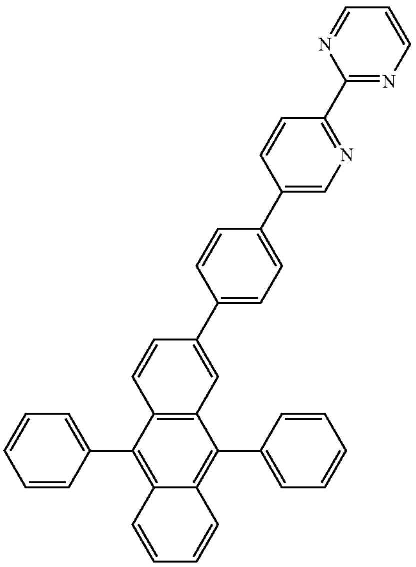
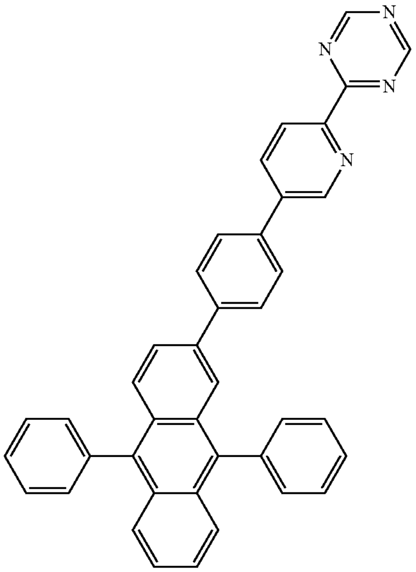
-continued
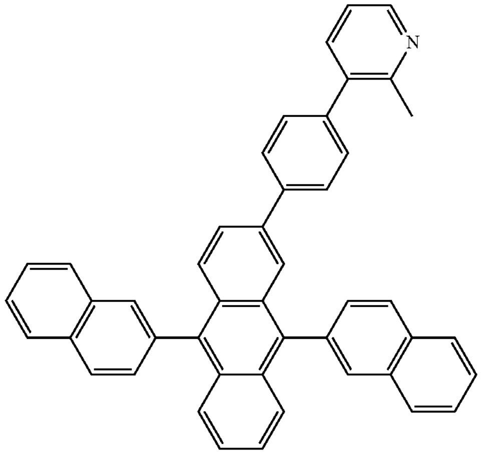
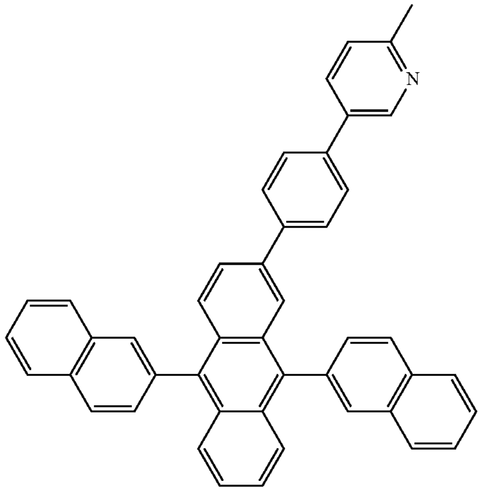
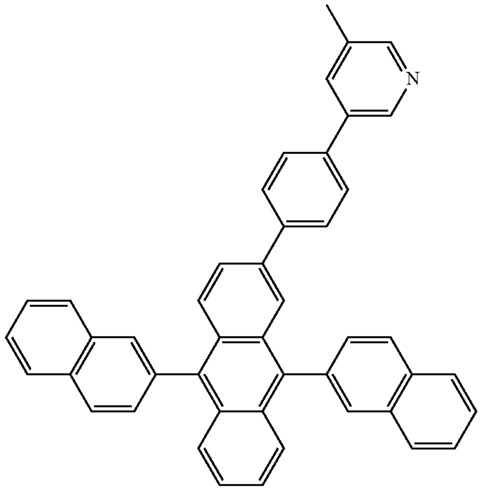

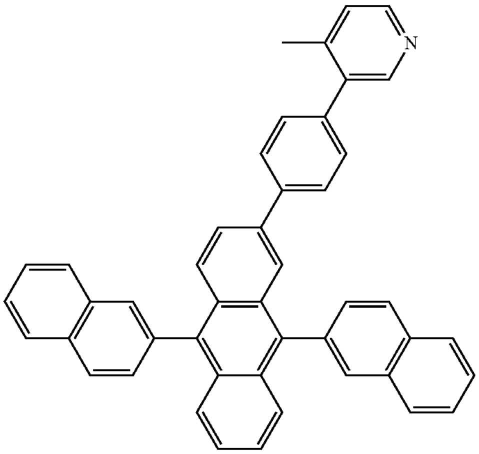
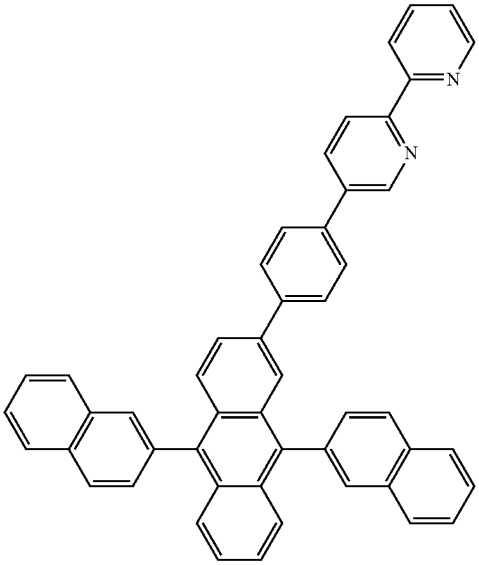
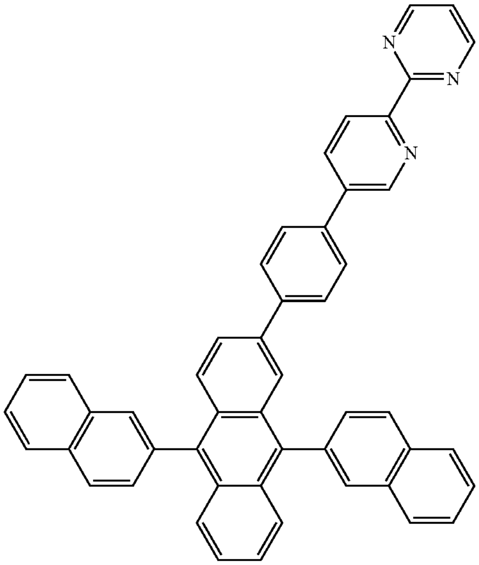
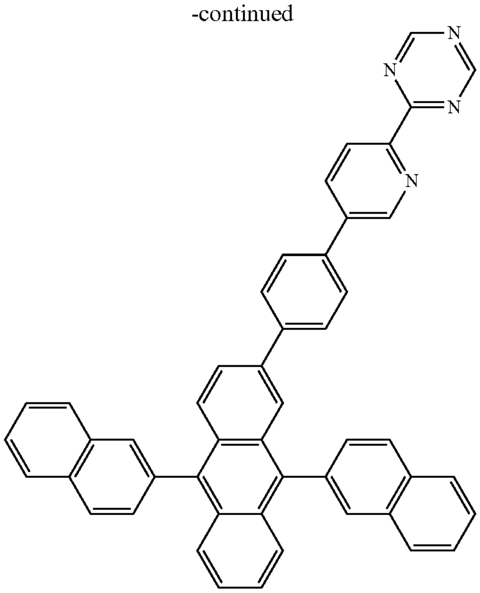
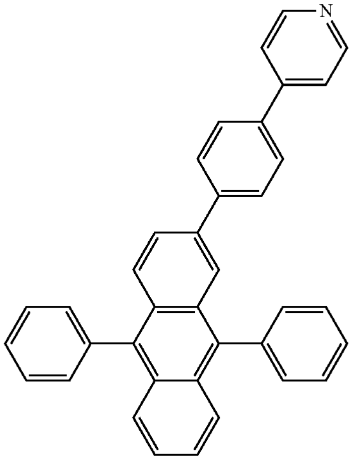
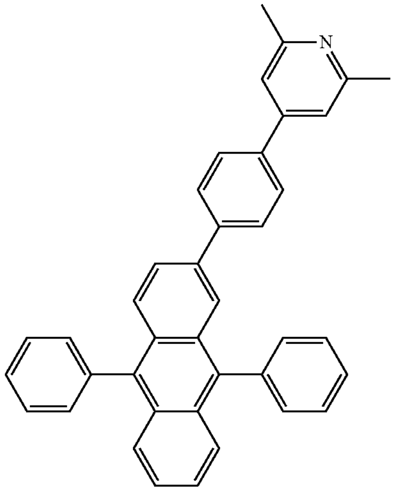

575
-continued
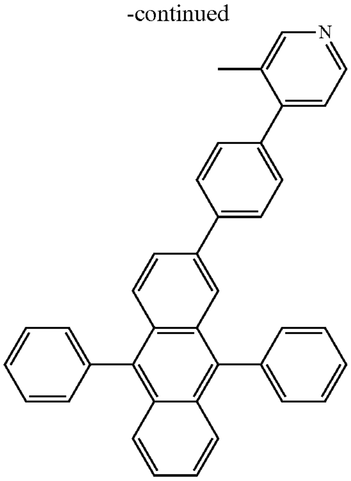
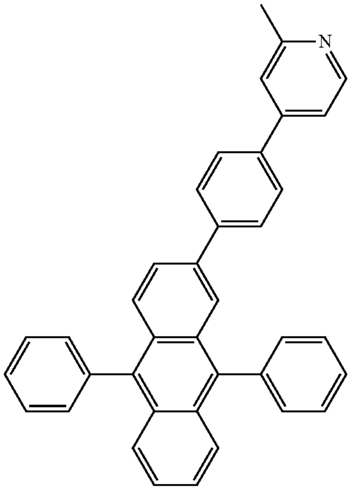
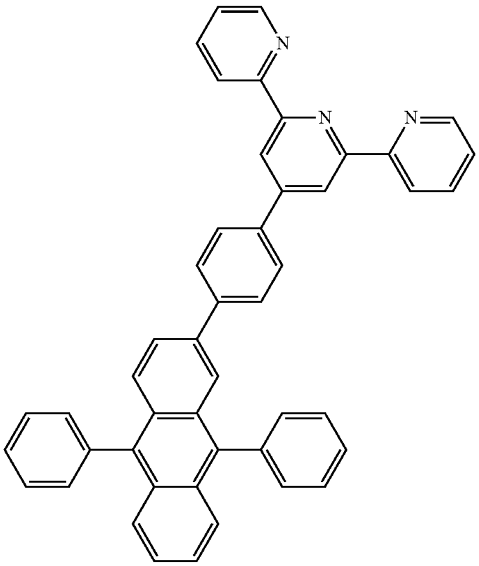
576
-continued
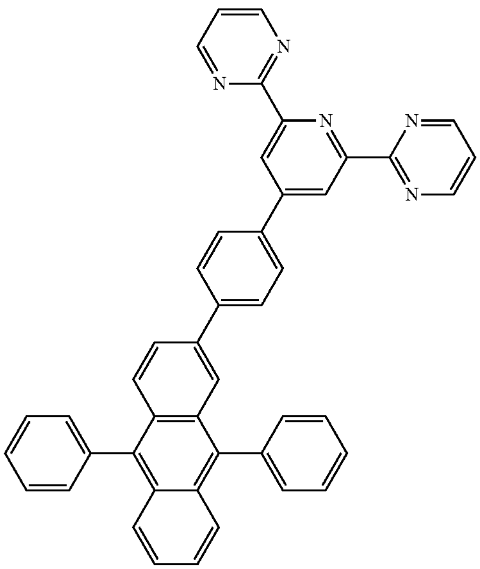
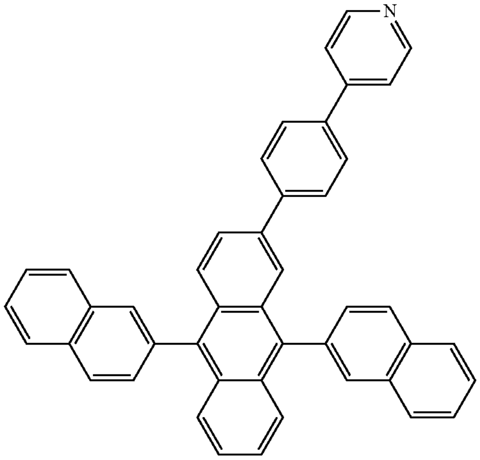
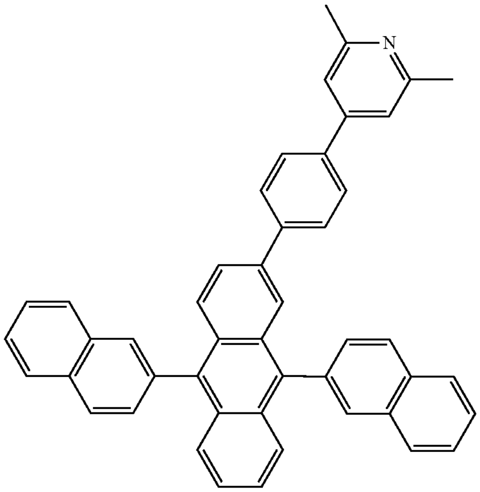

-continued
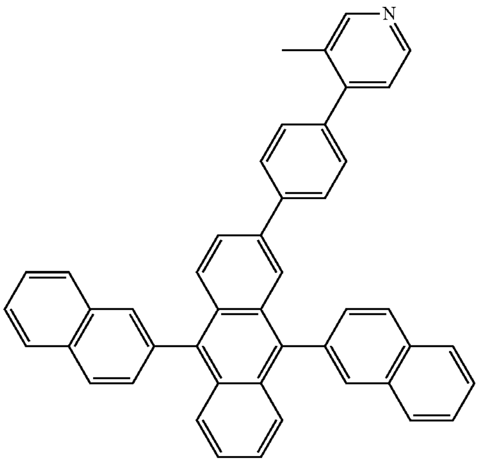
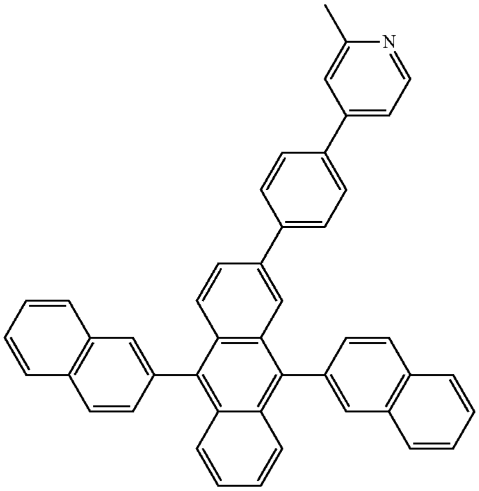
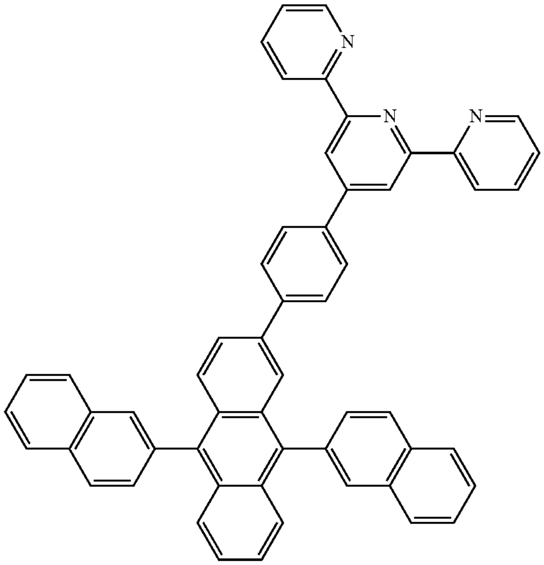
-continued
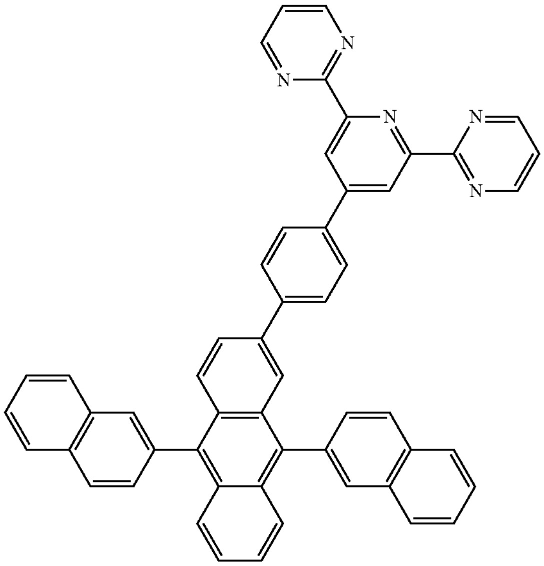
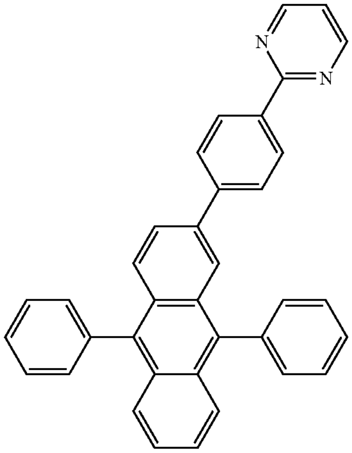
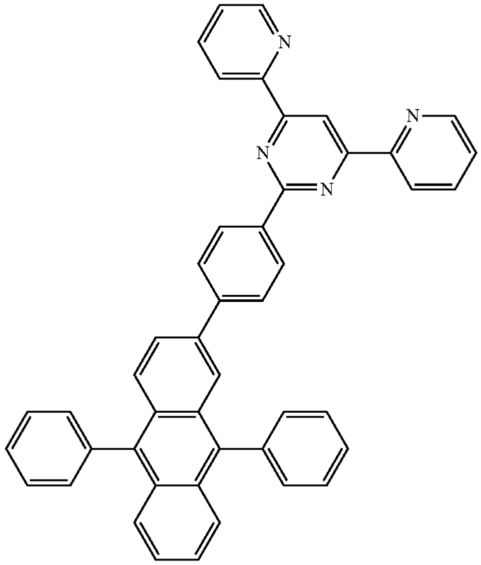

-continued
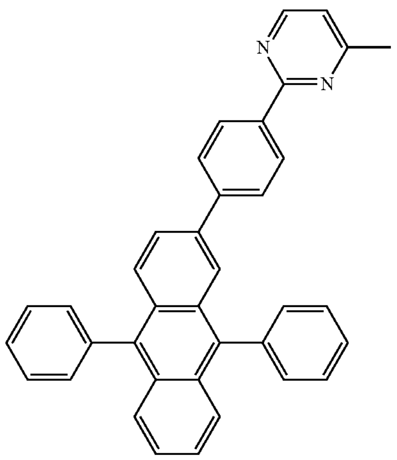
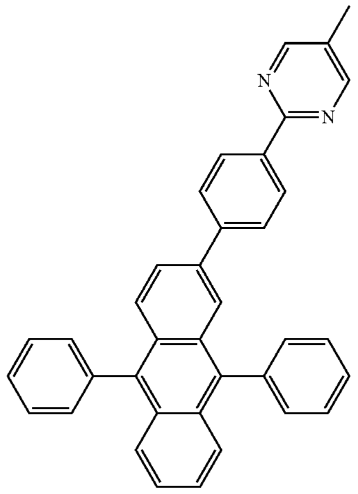
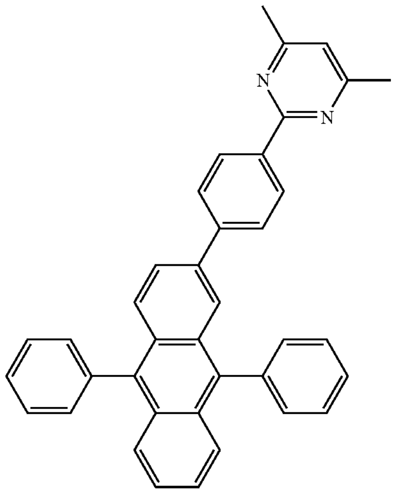
-continued
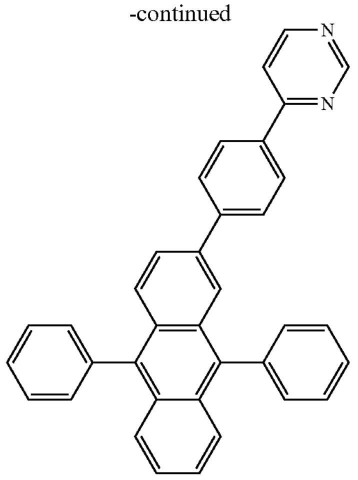
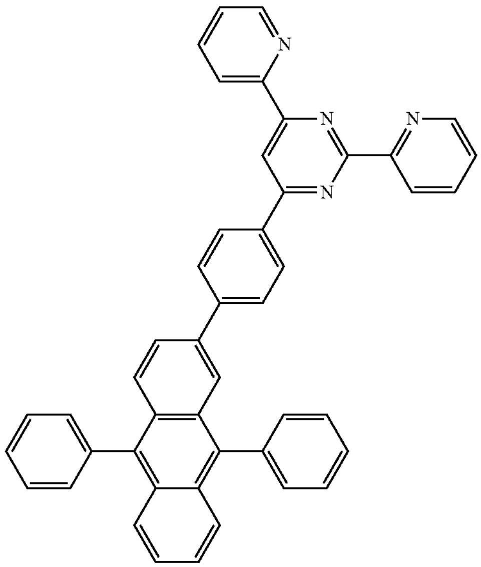
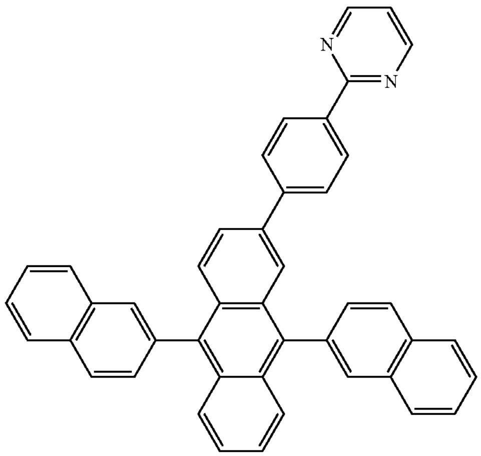

-continued
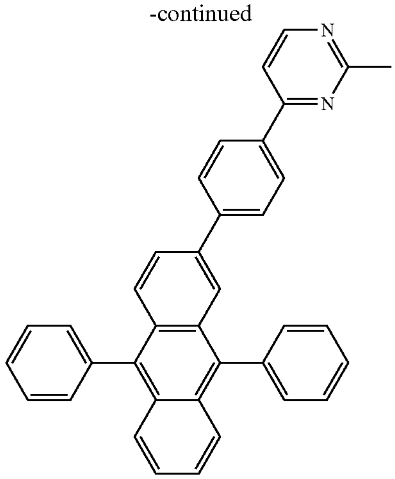
-continued
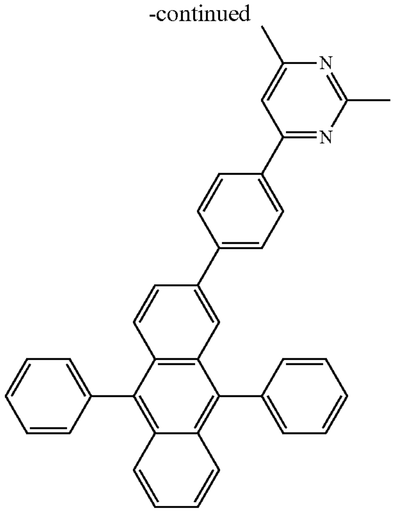
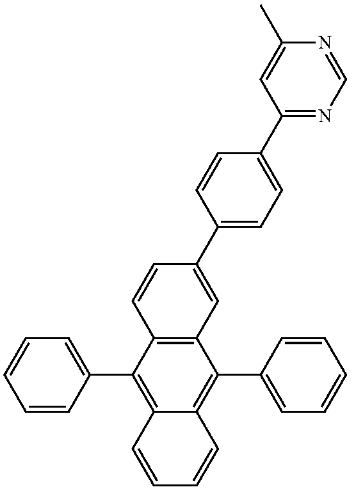
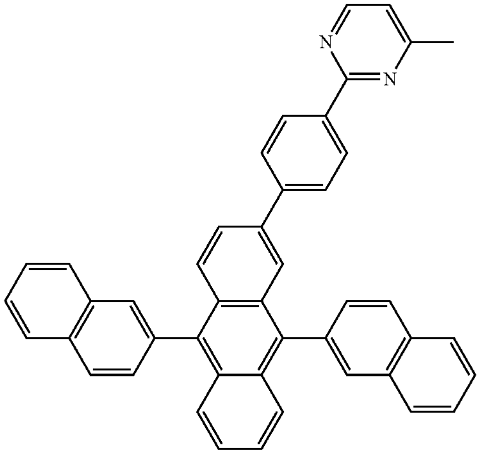
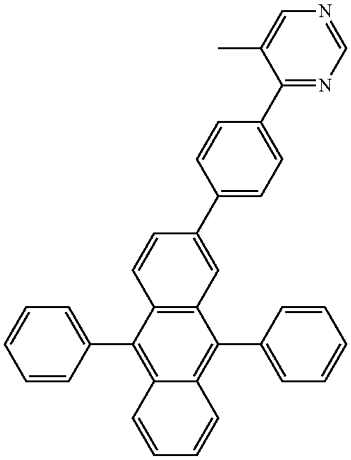
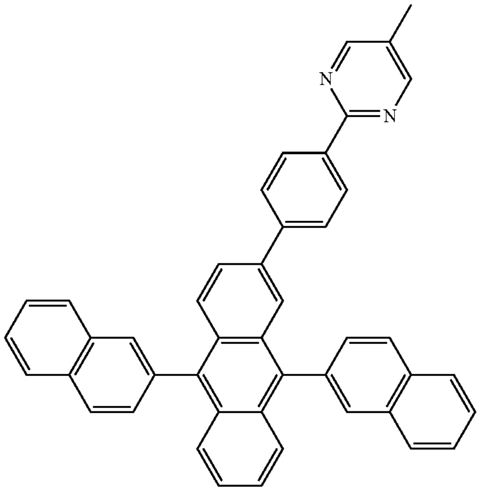

-continued
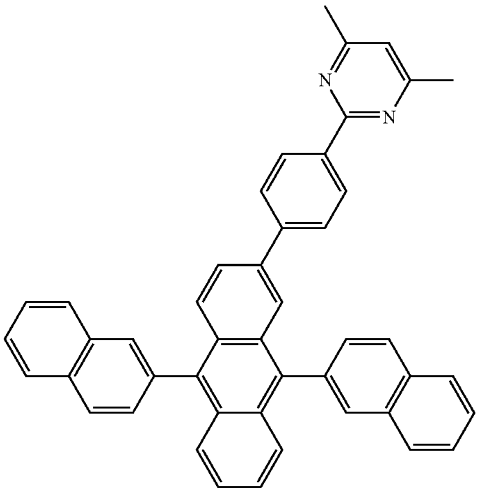
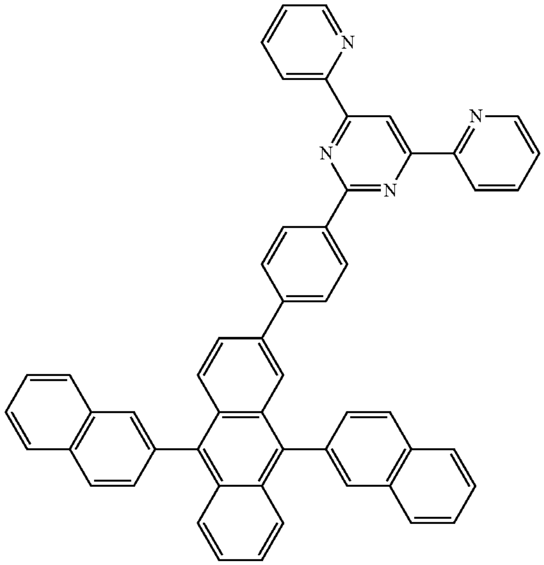
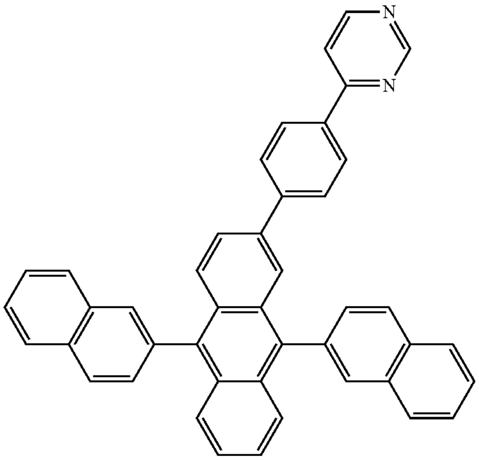
-continued
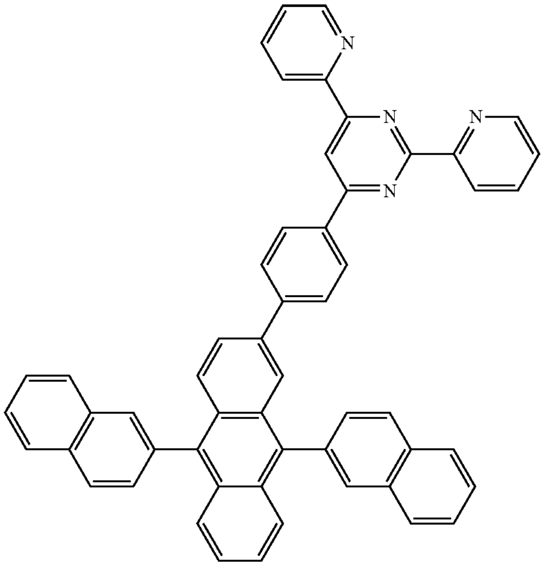
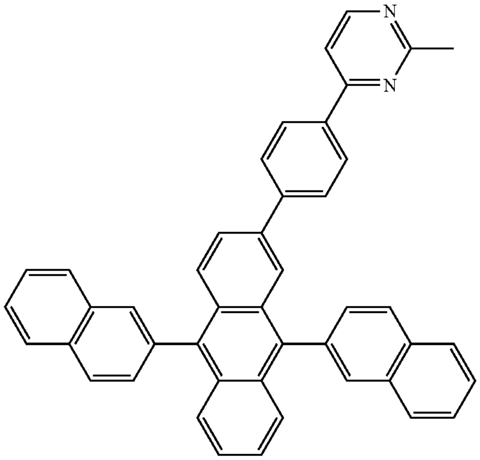
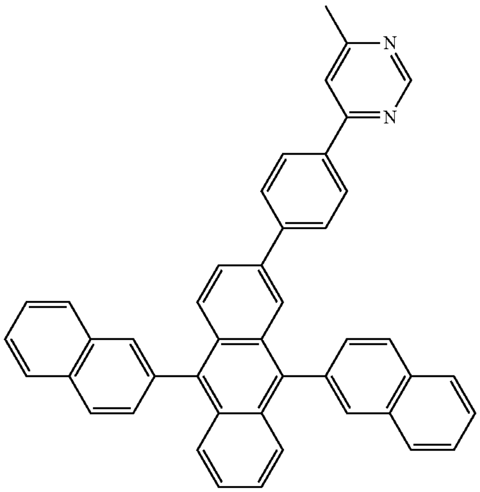

-continued
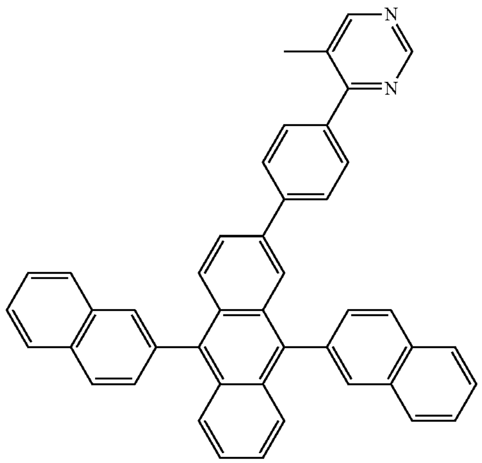
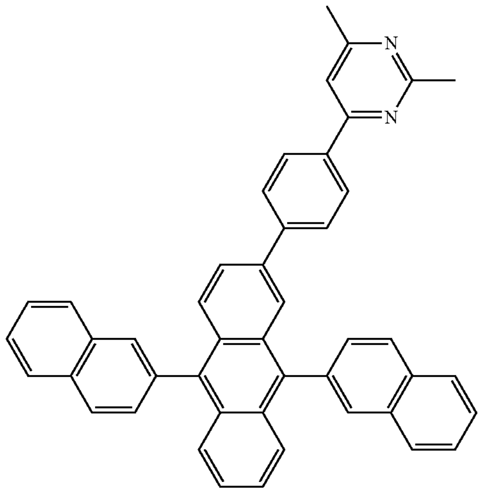
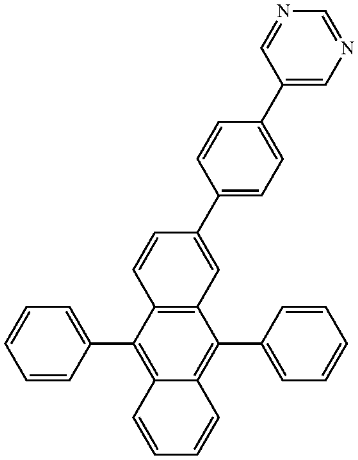
-continued
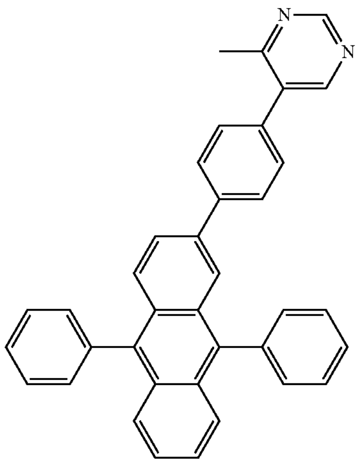
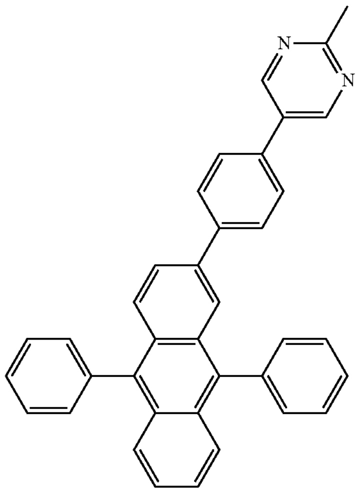
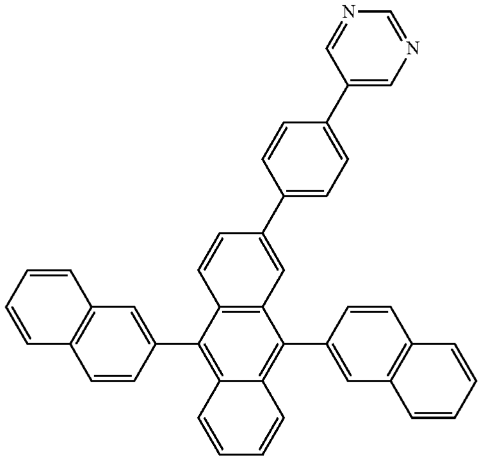

-continued
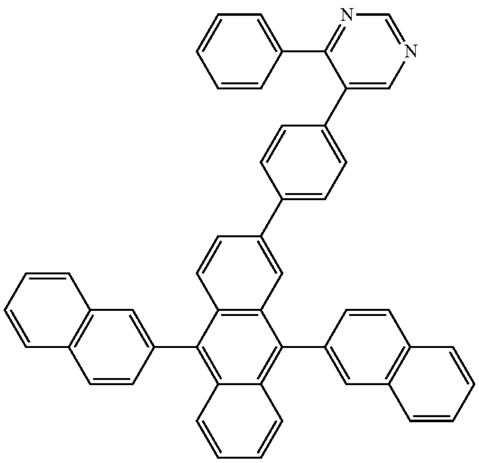
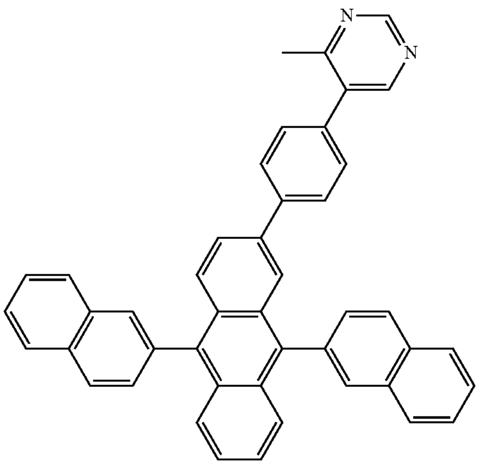
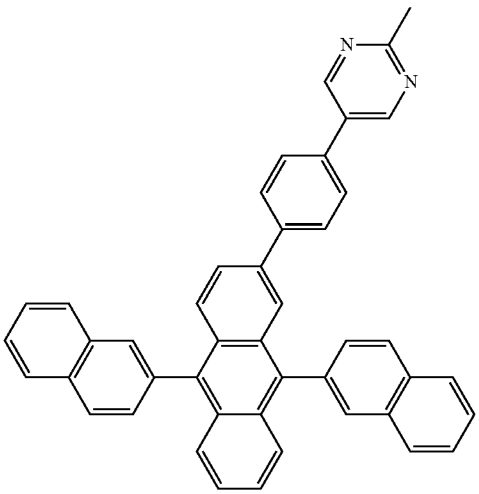
-continued
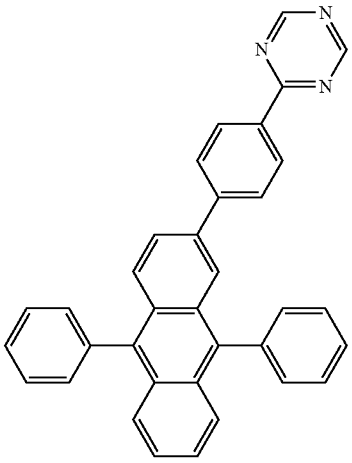
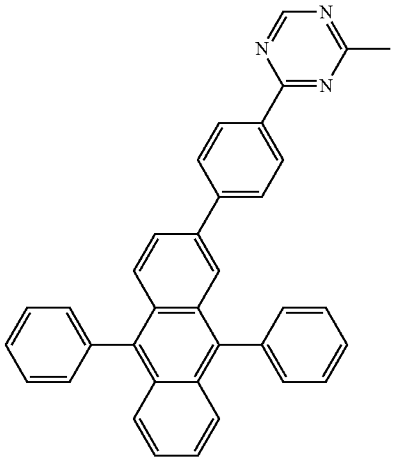
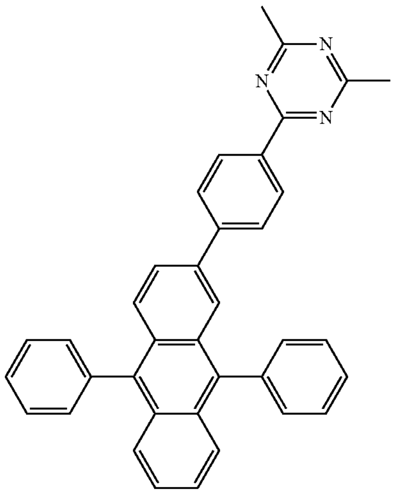

-continued
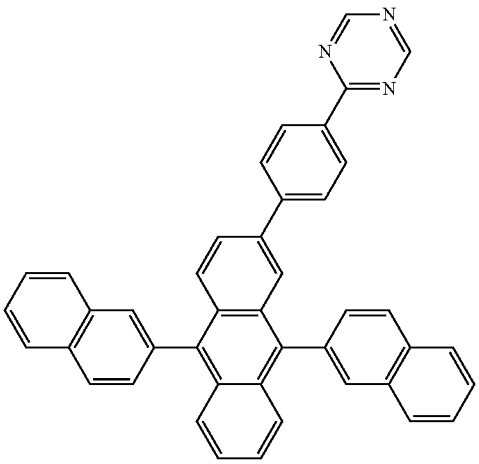
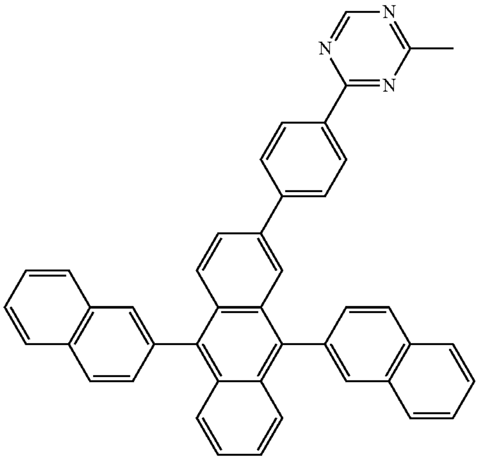
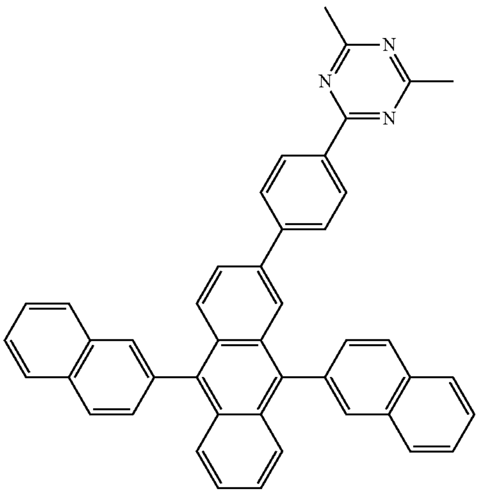
-continued
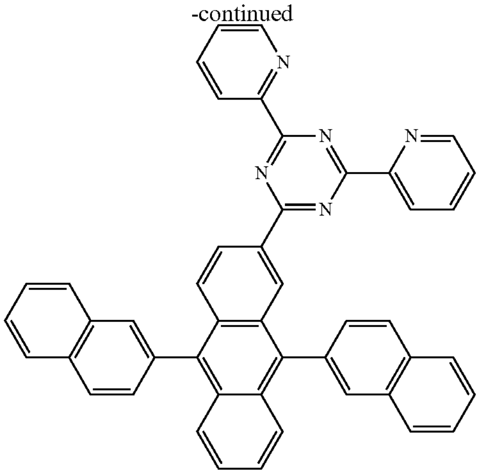
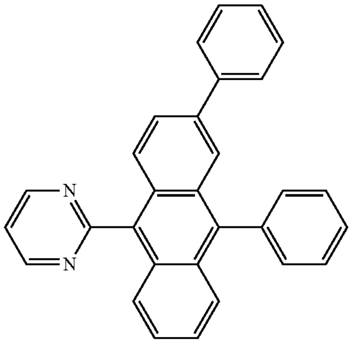
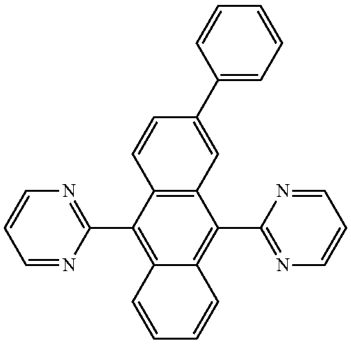
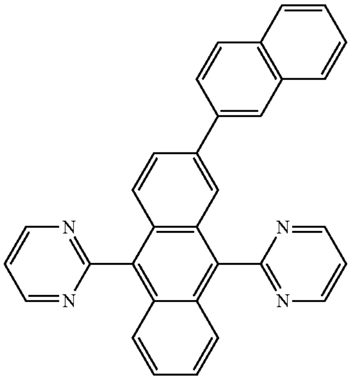

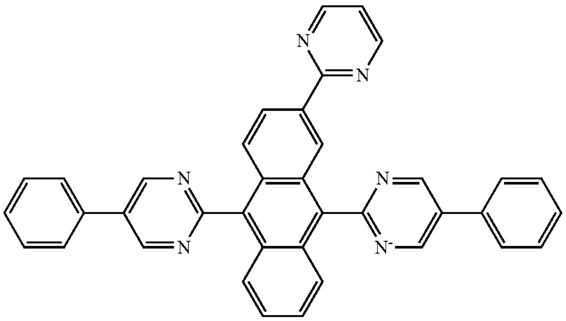
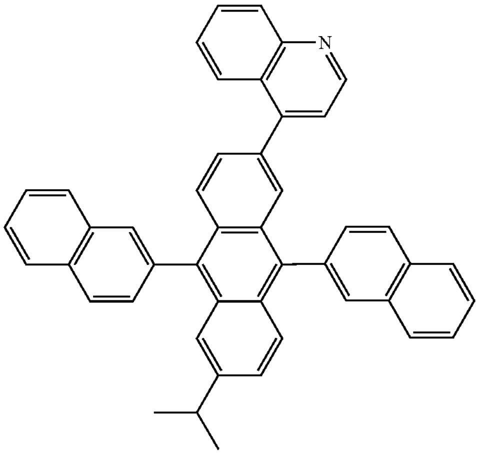
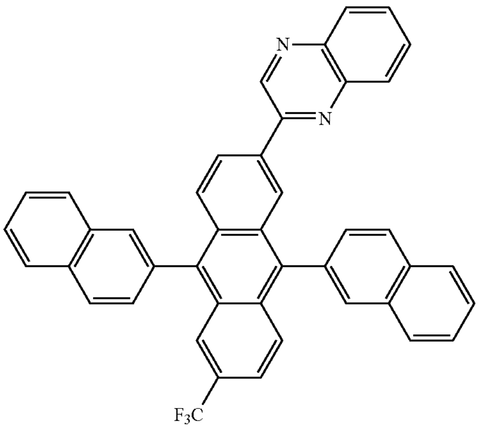
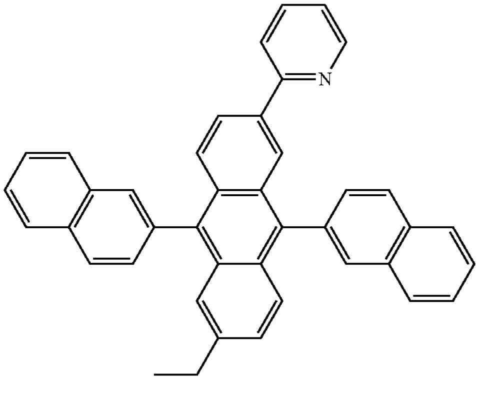
-continued
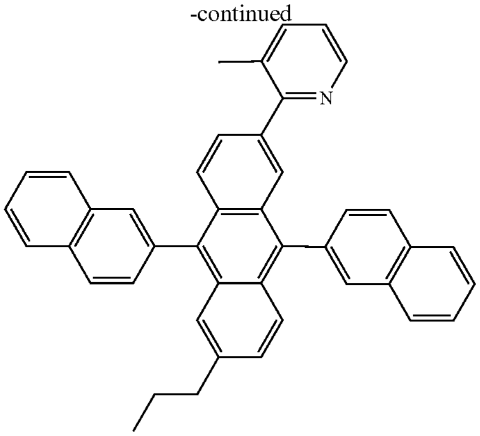
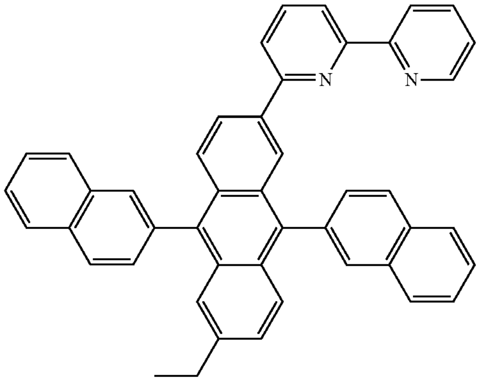
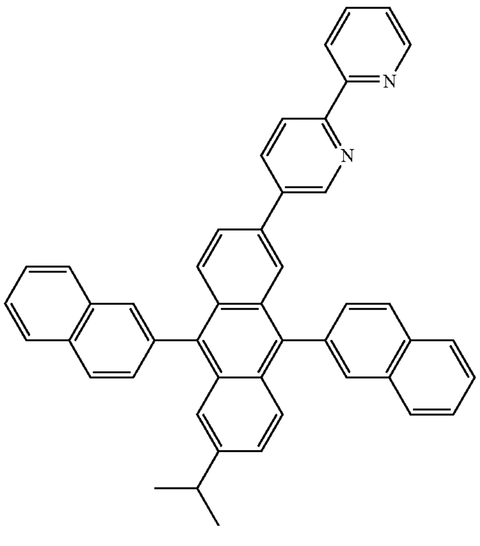

-continued
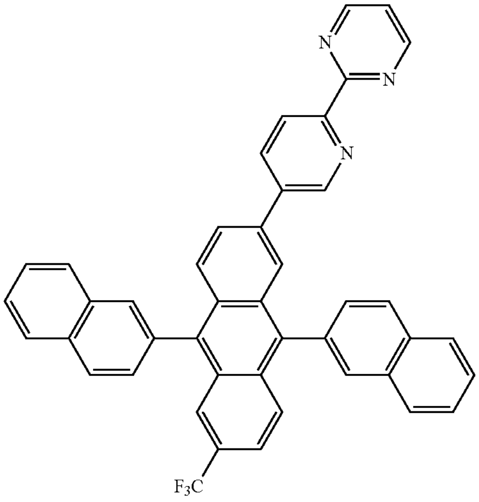
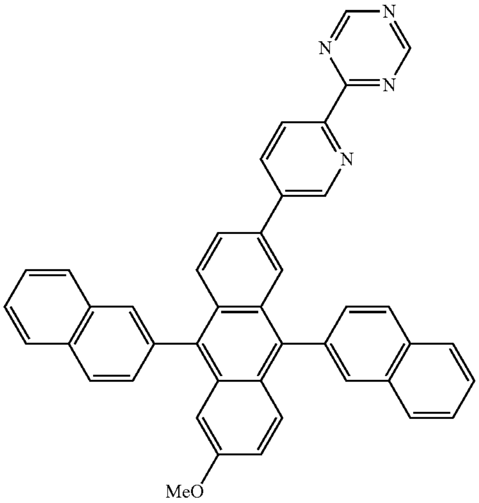
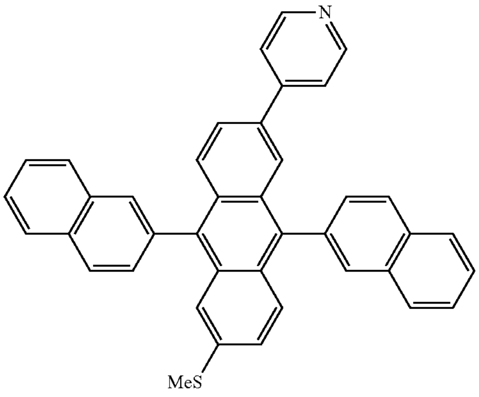
-continued
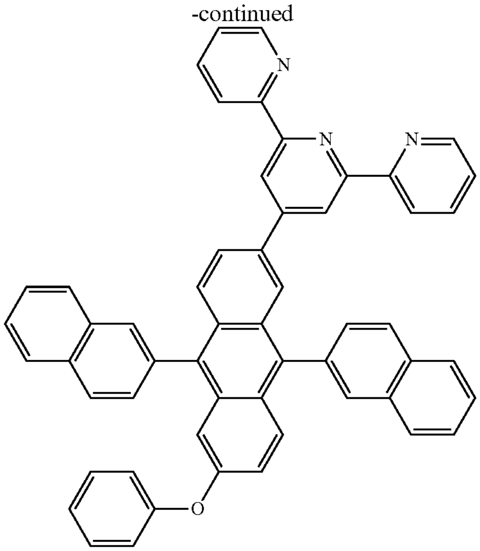
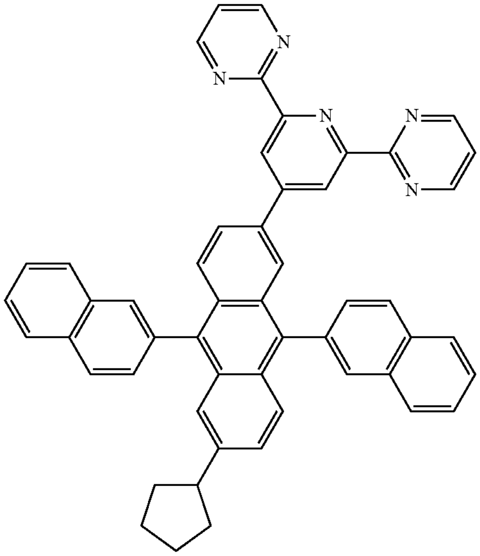
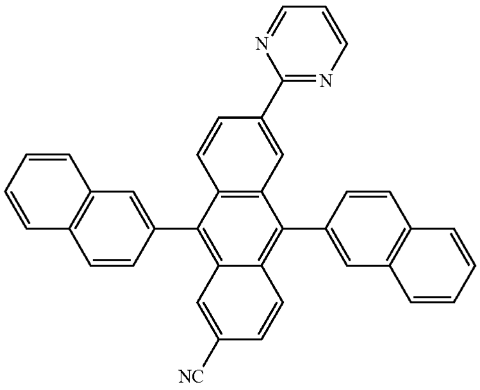

-continued
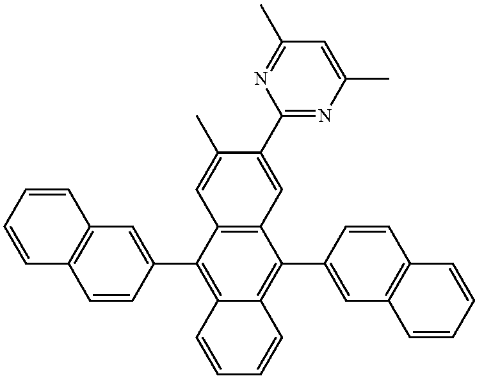
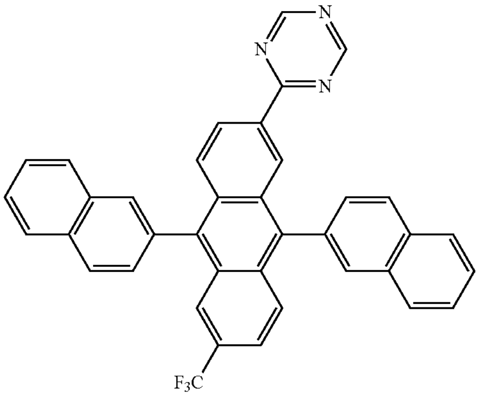
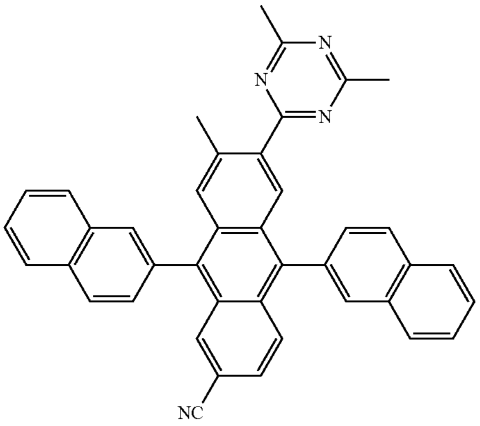
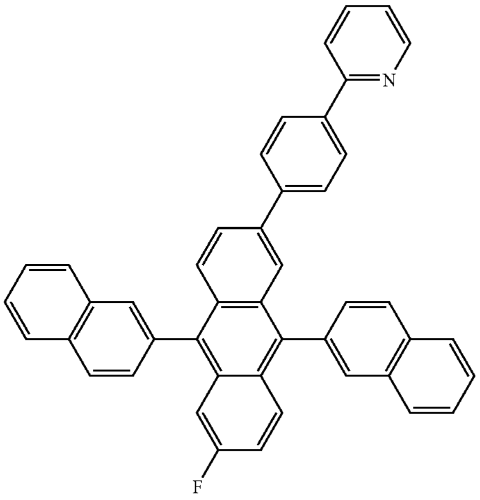
-continued
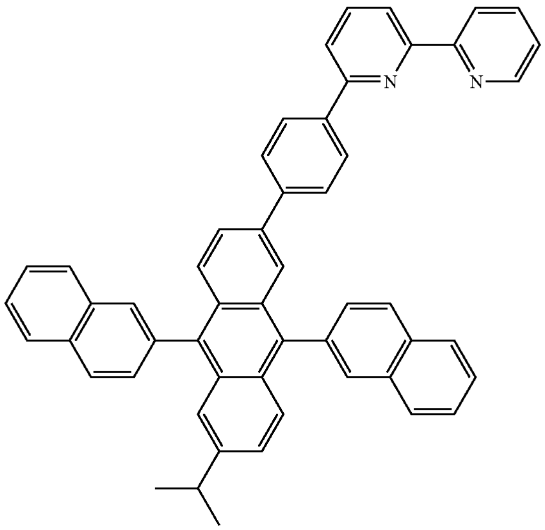
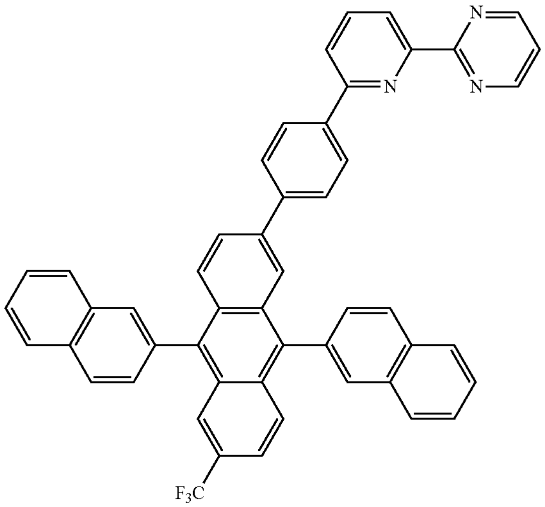
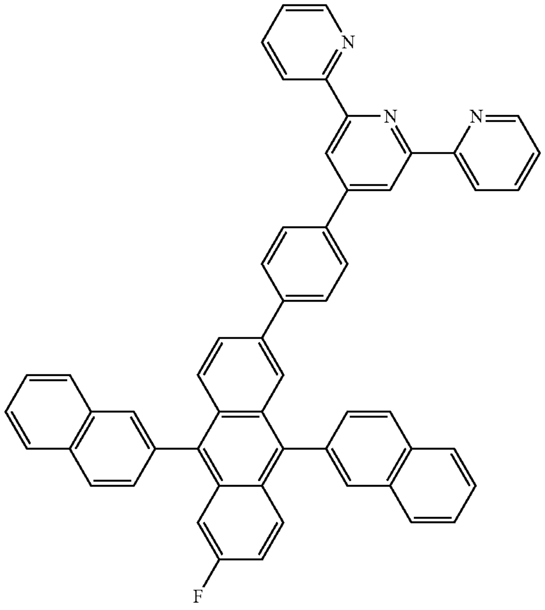

-continued
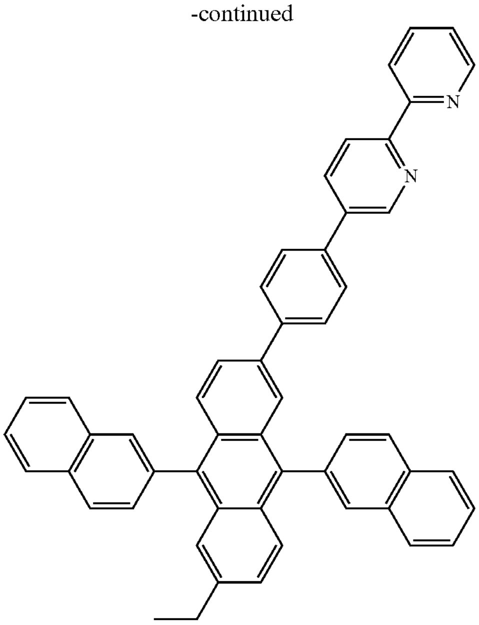
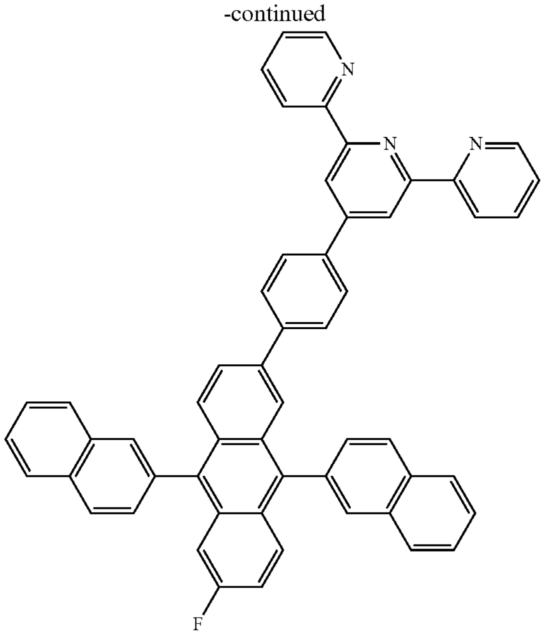
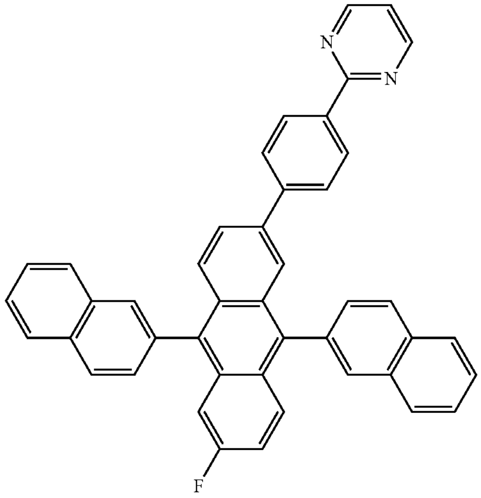
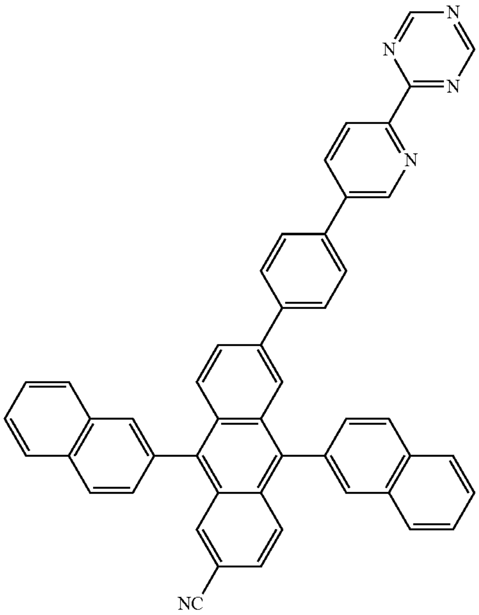
-continued
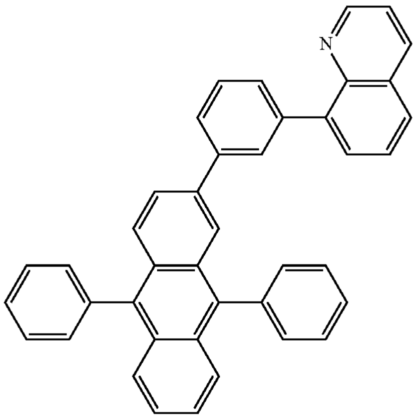

-continued
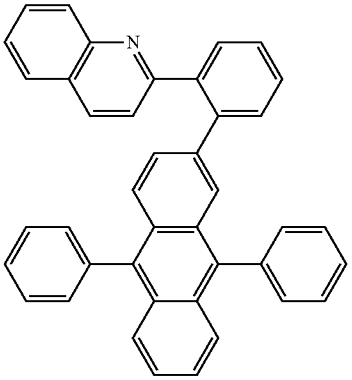
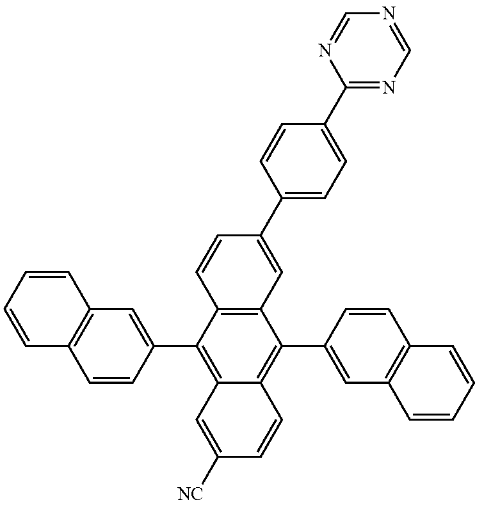
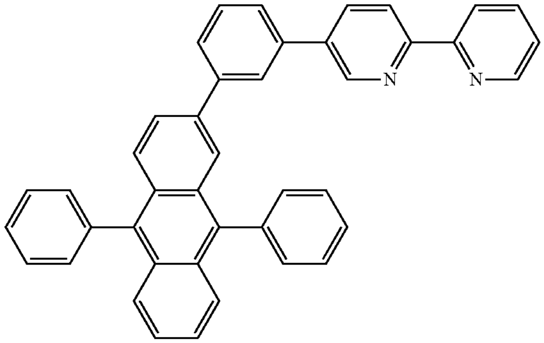
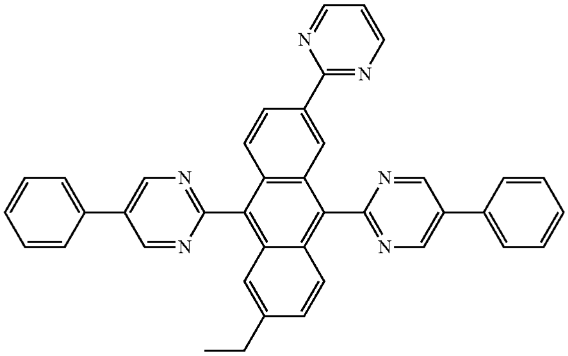
-continued
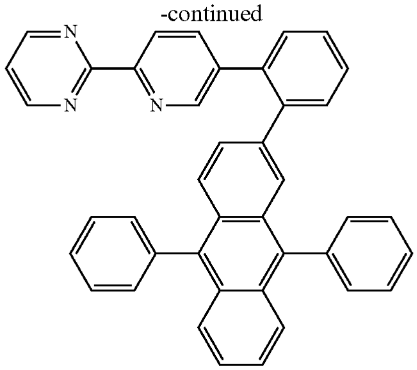
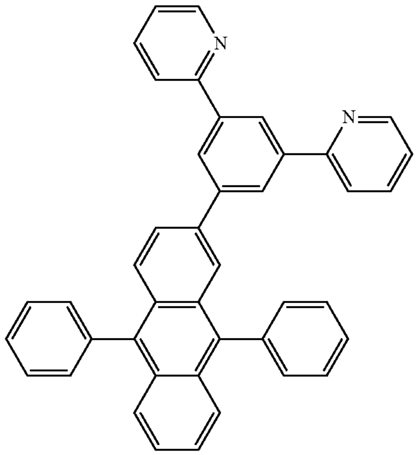
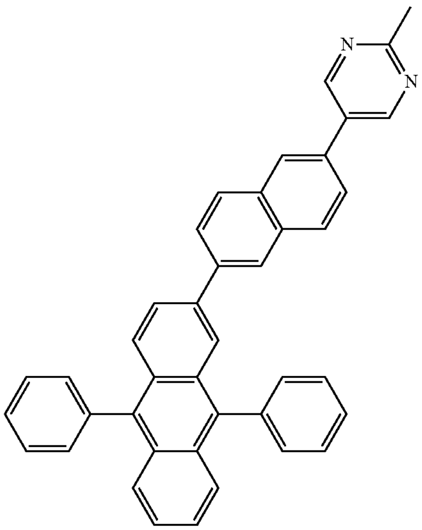

-continued
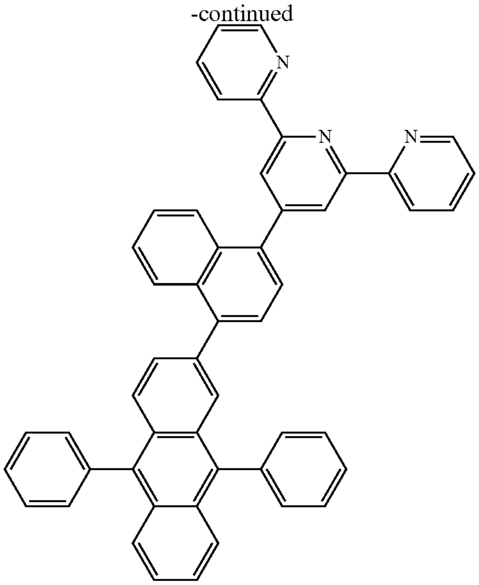
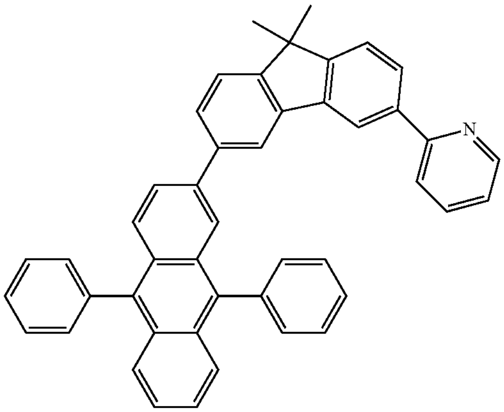
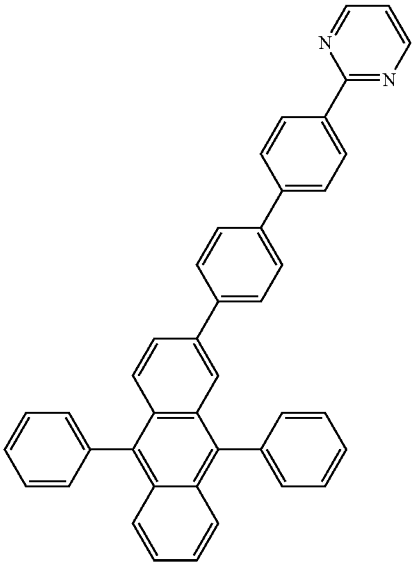
-continued
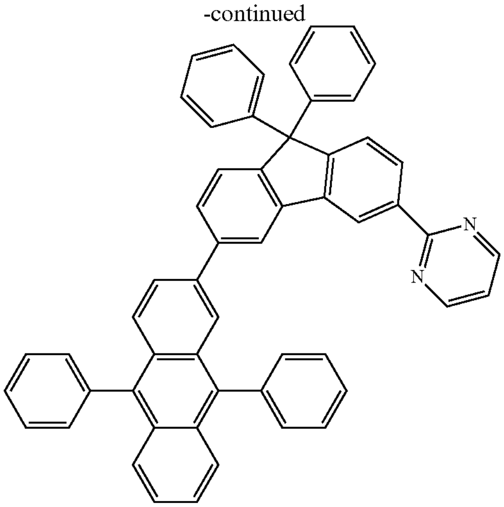
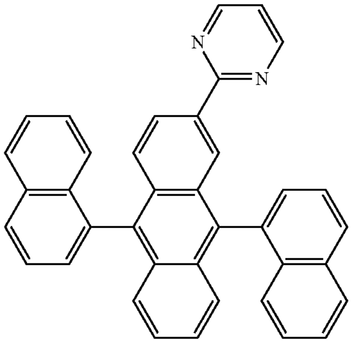
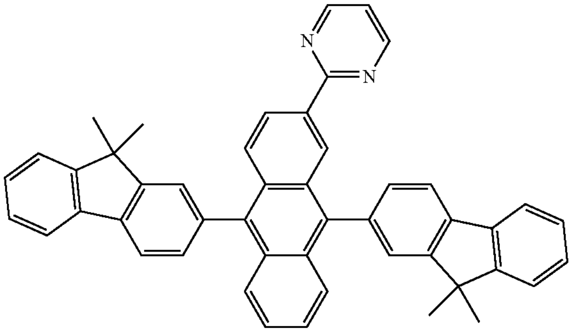
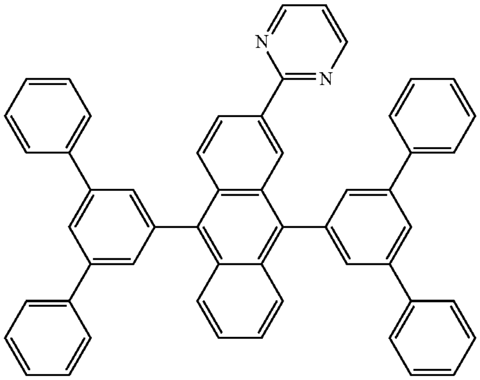

-continued
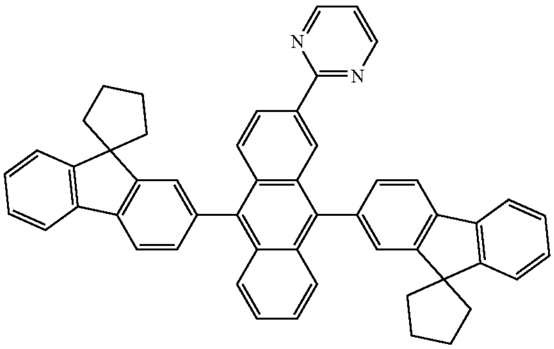
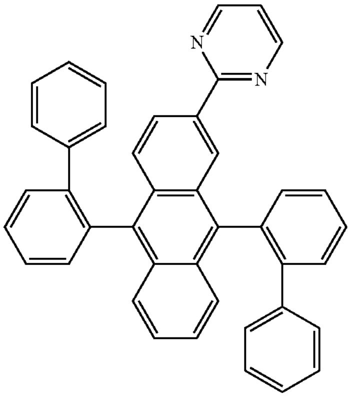
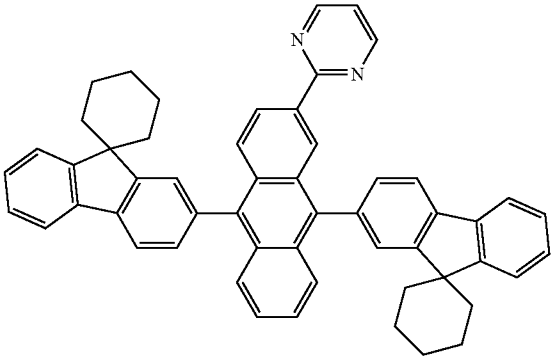
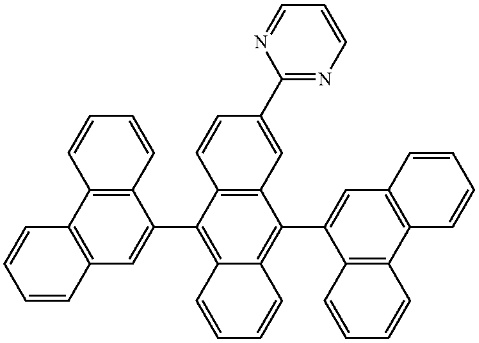
-continued
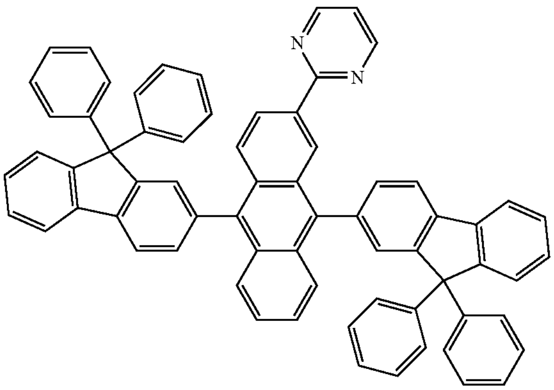
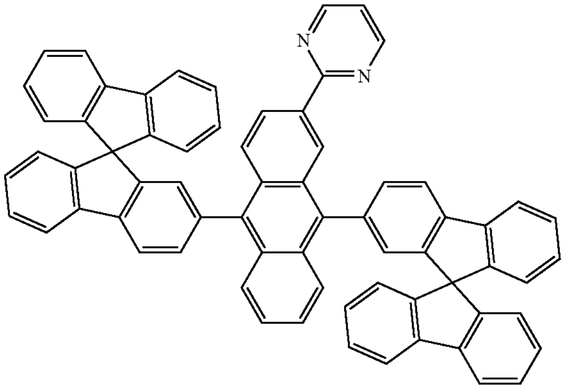
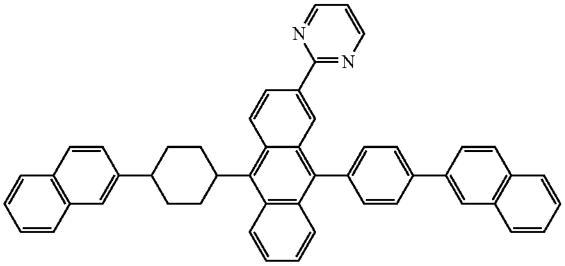
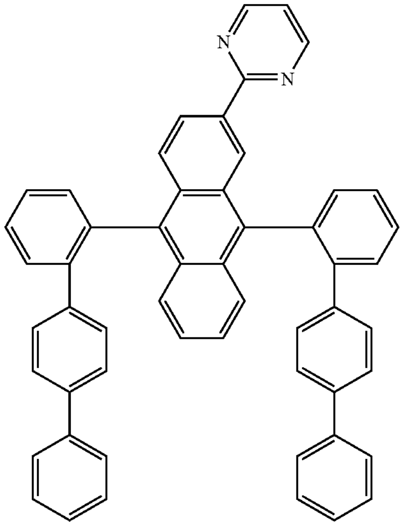

-continued
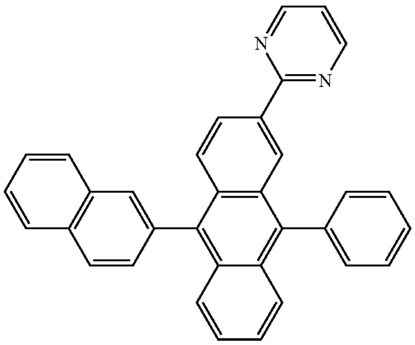
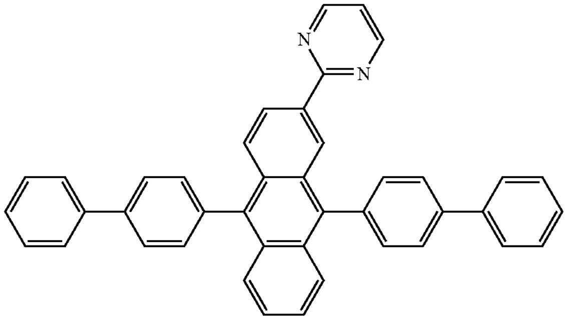
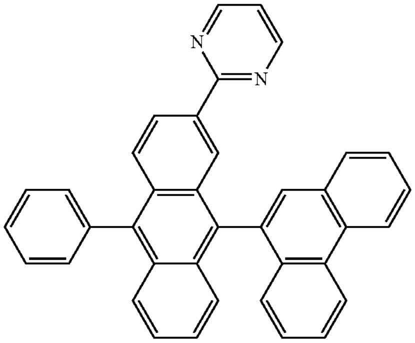
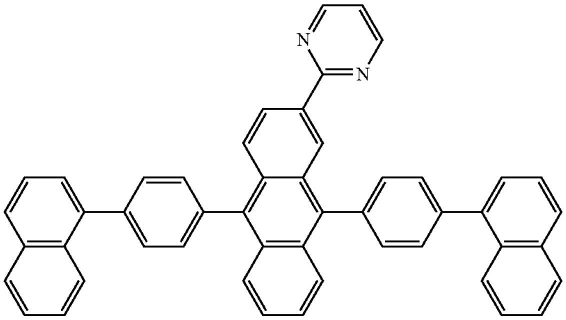
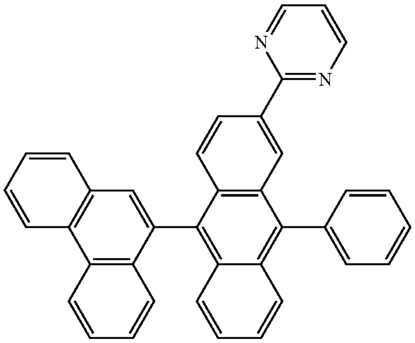
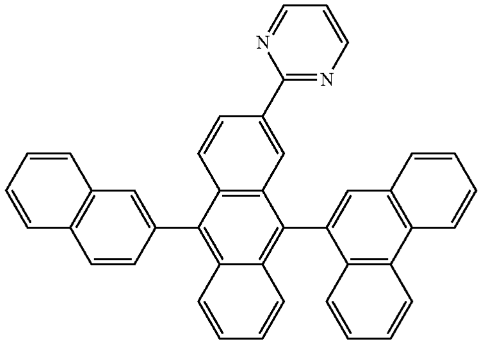
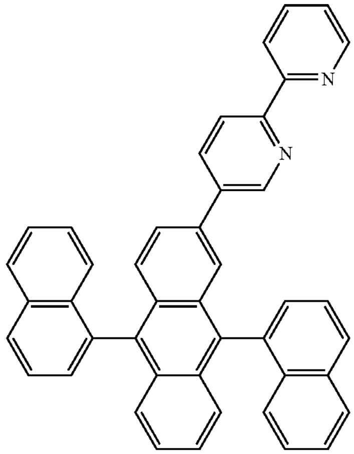
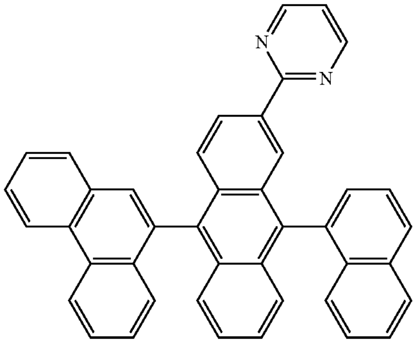
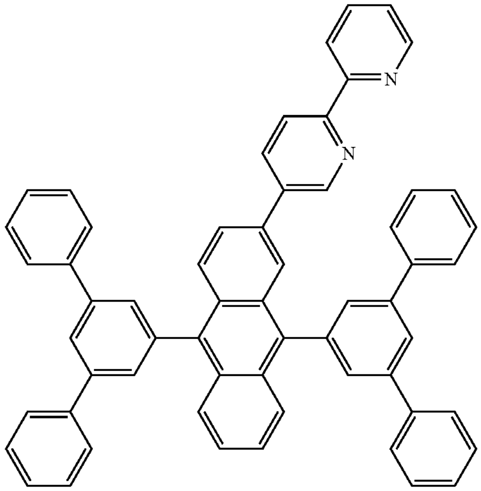

-continued
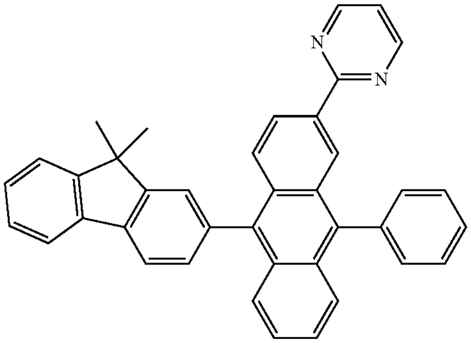
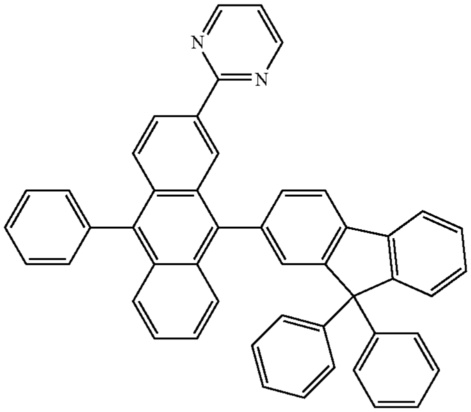
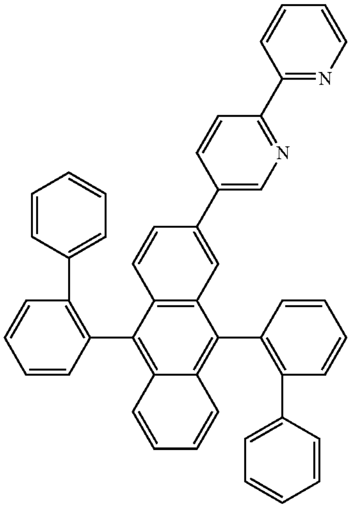
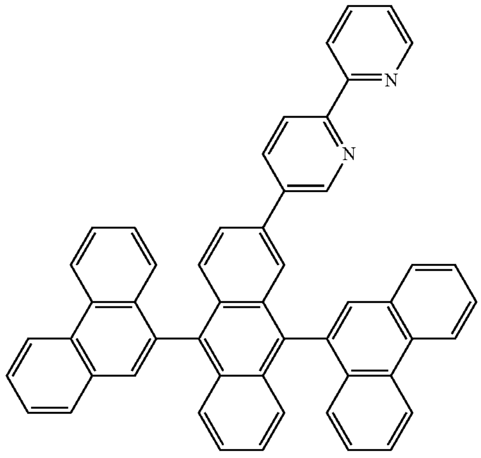
-continued
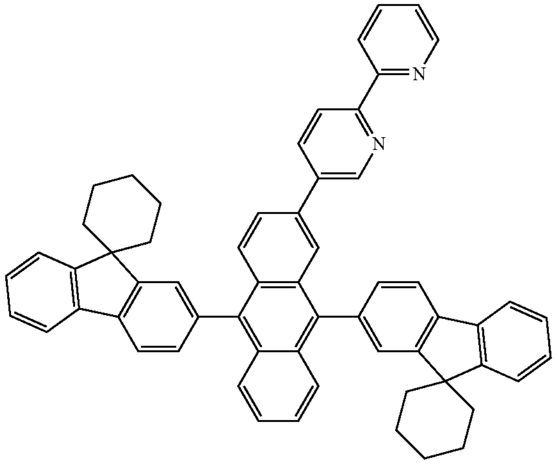
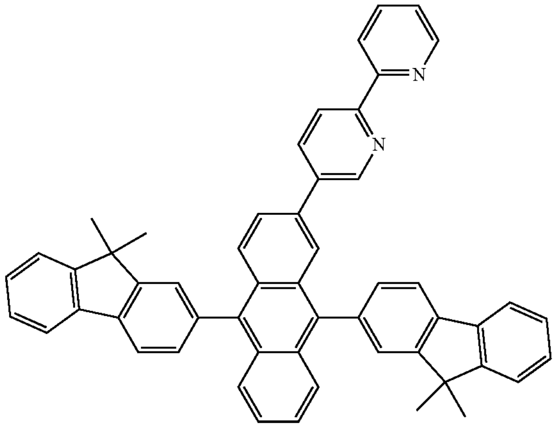
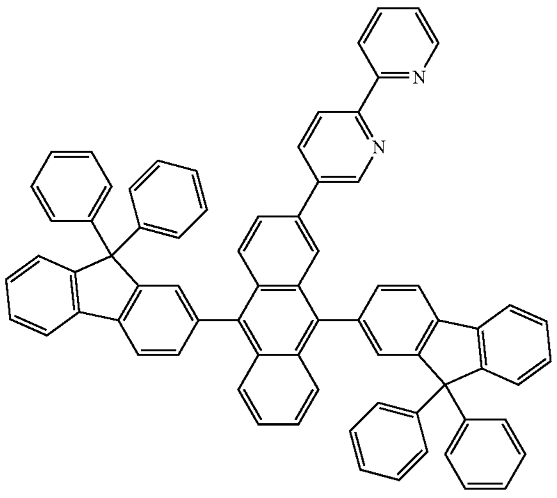

-continued
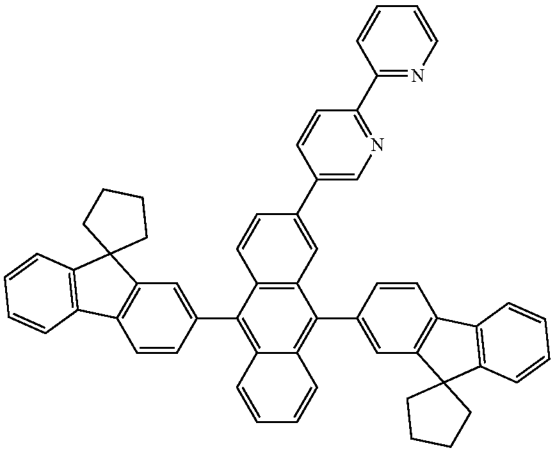
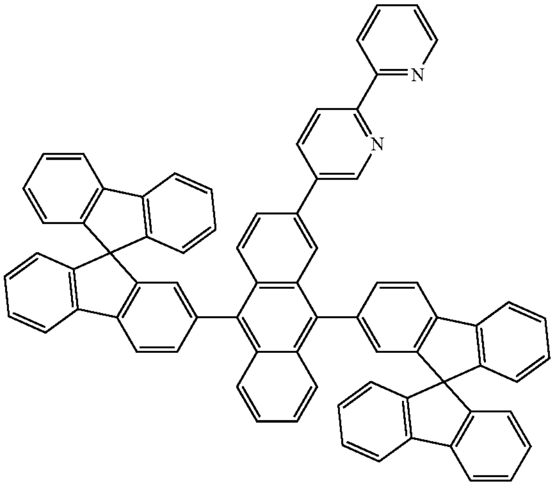
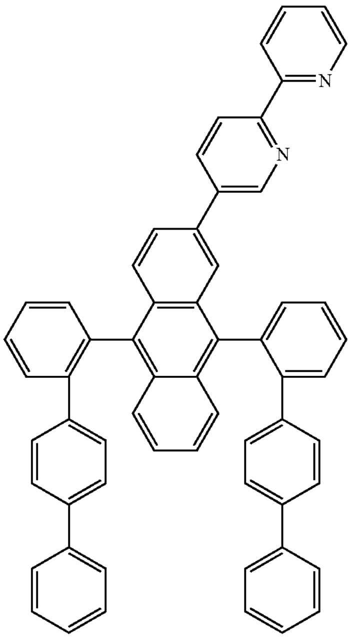
-continued
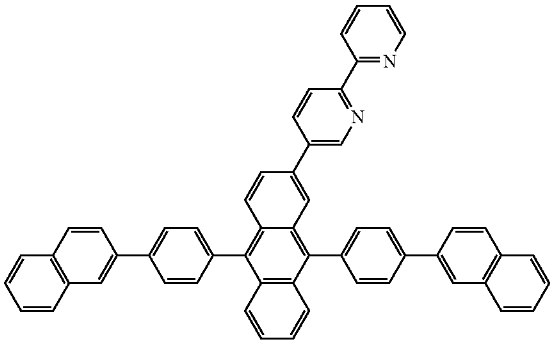
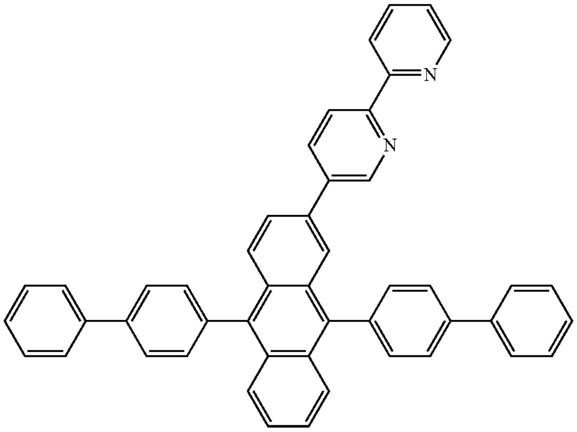
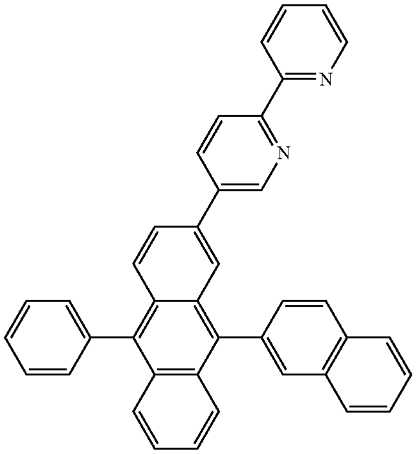
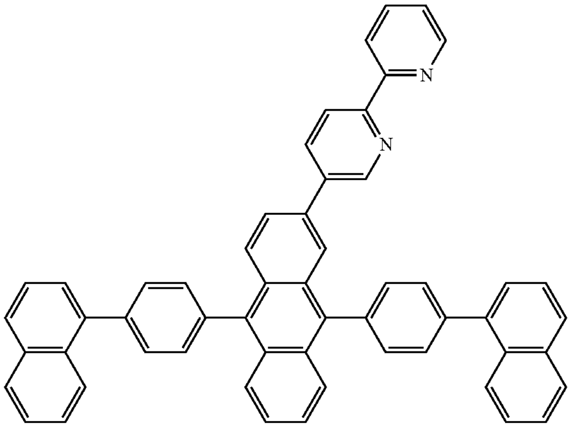

-continued
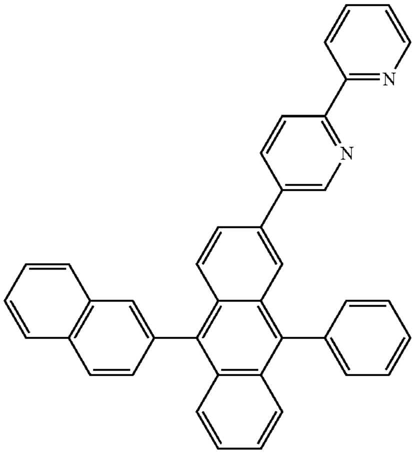
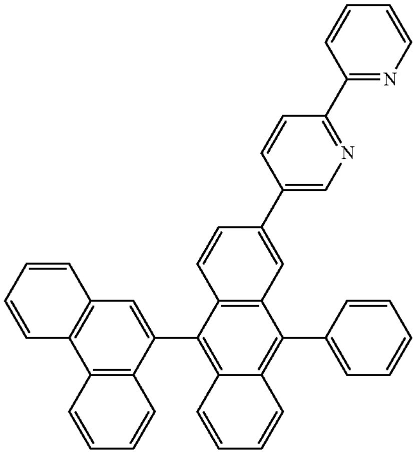
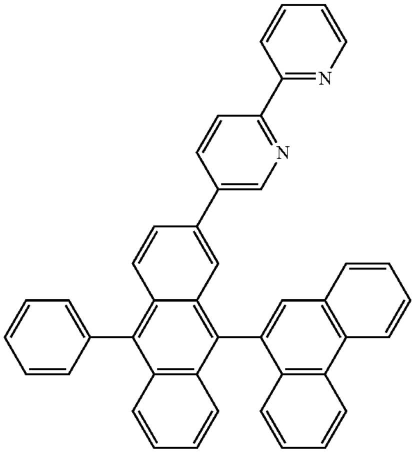
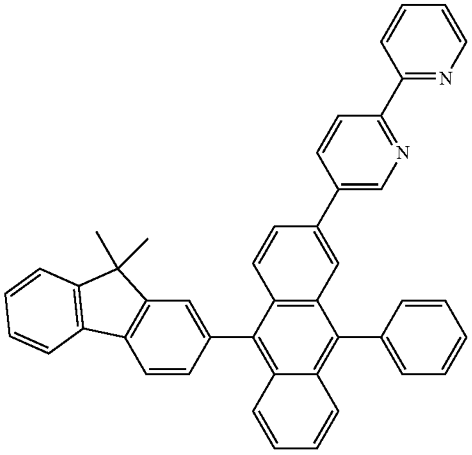
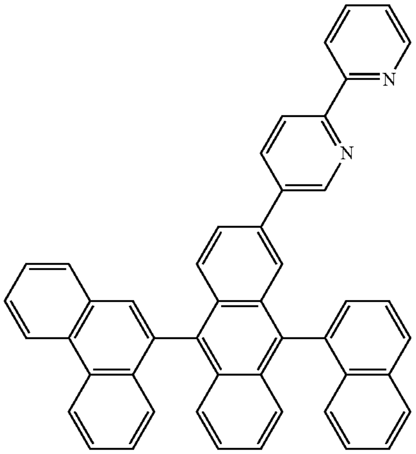
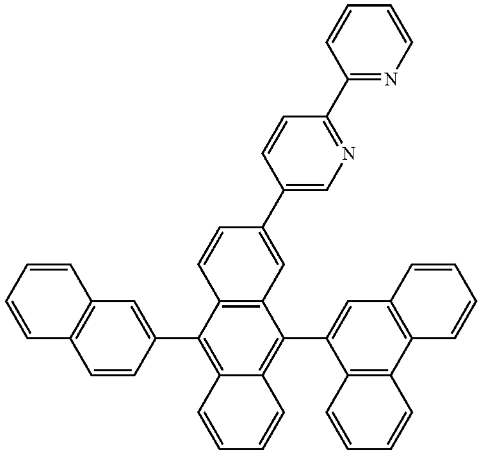
-continued -continued
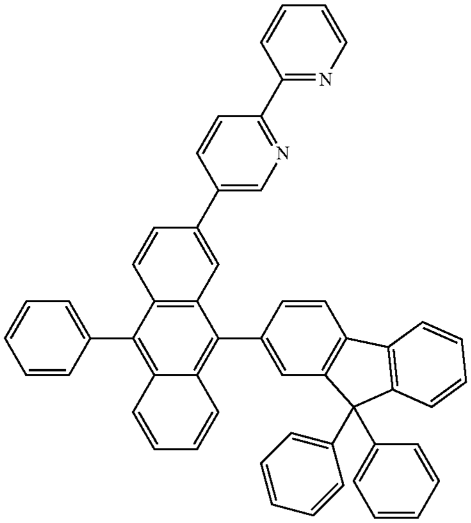
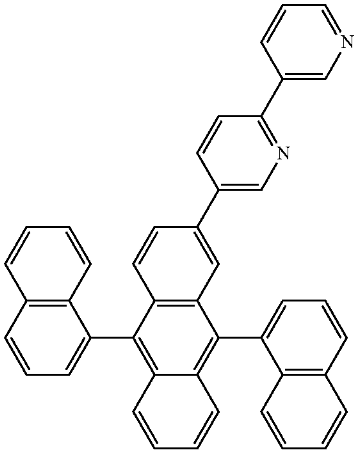
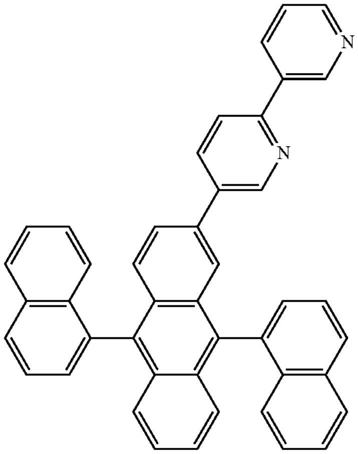
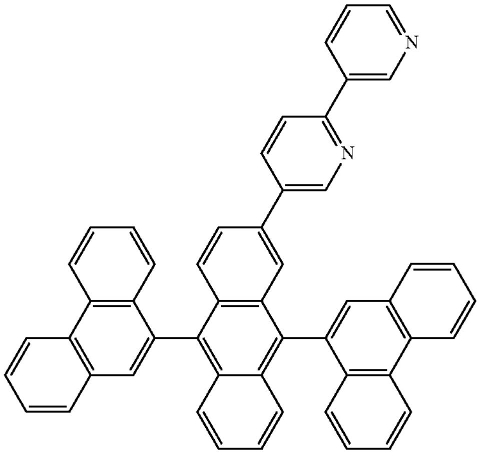
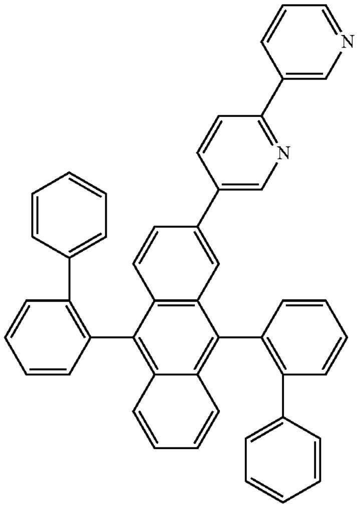
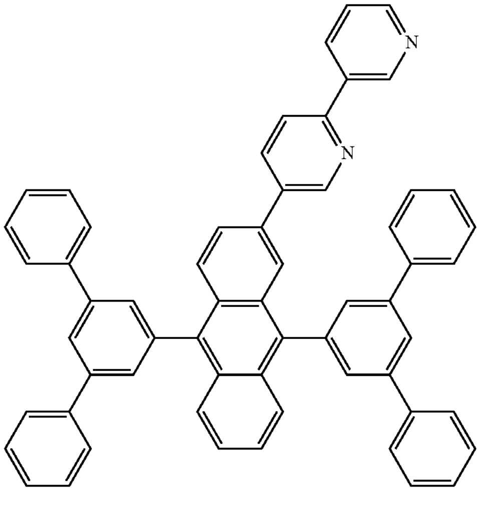
-continued -continued
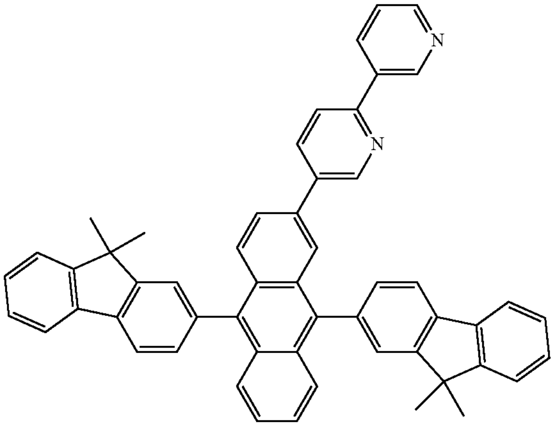
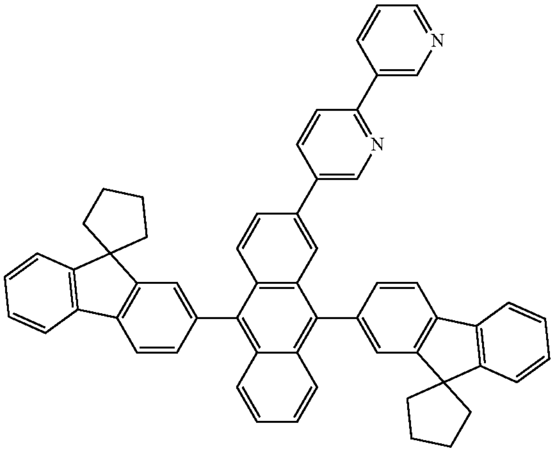
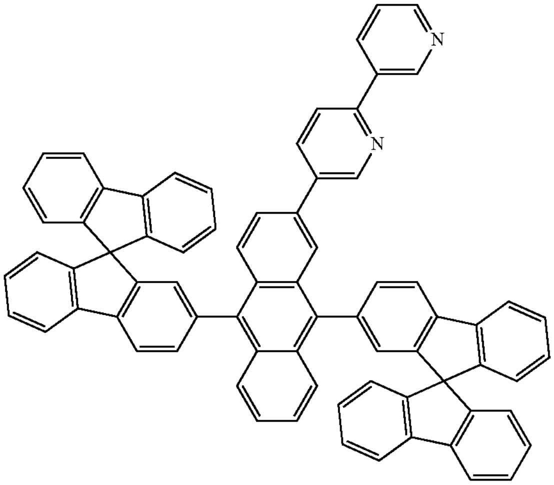
-continued
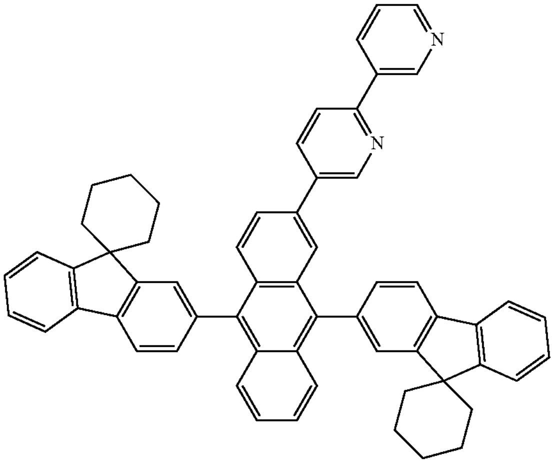
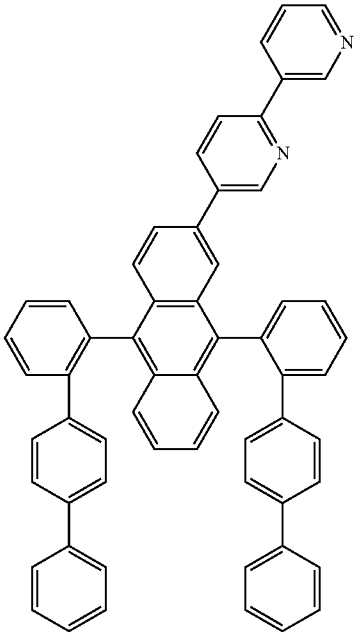
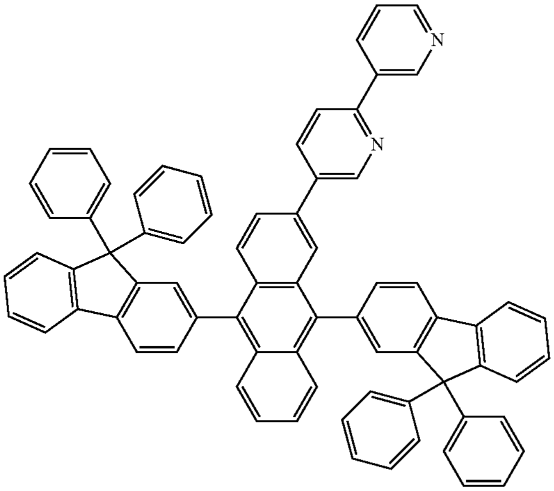

-continued
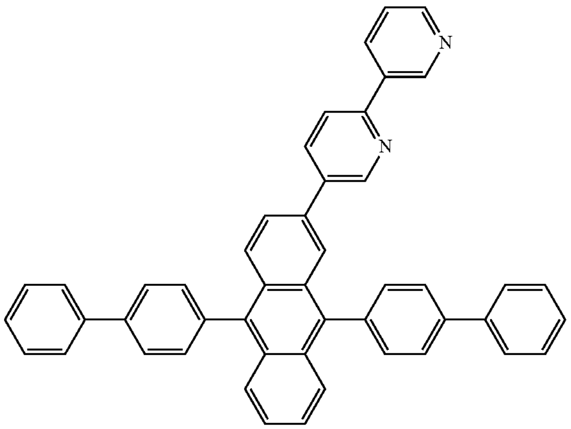
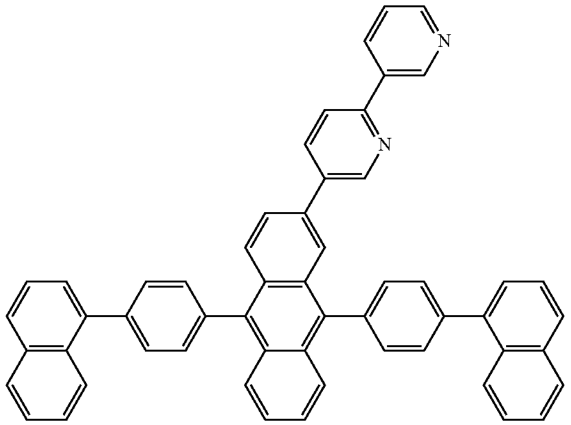
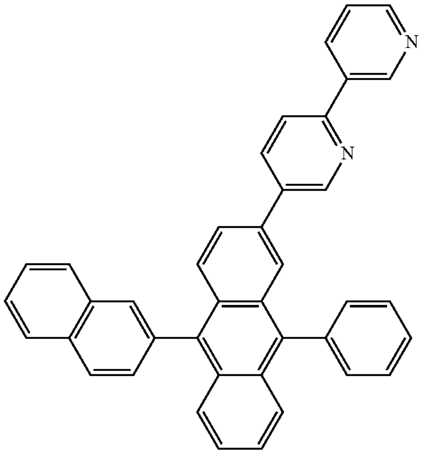
-continued
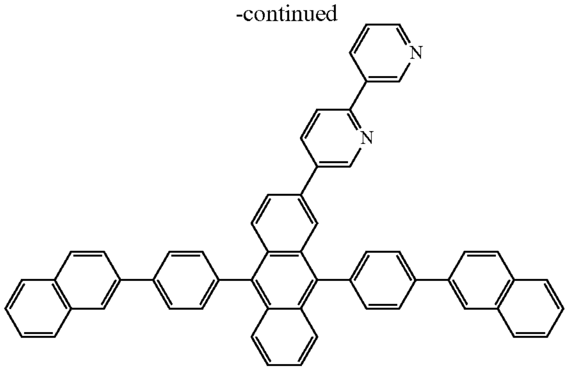
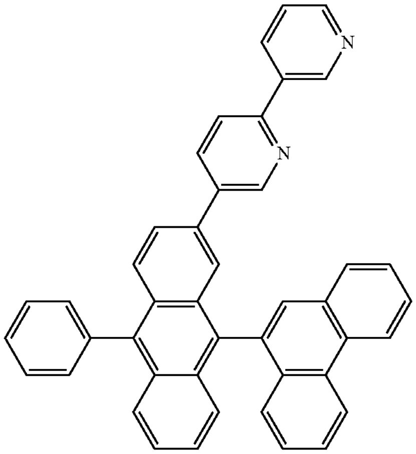
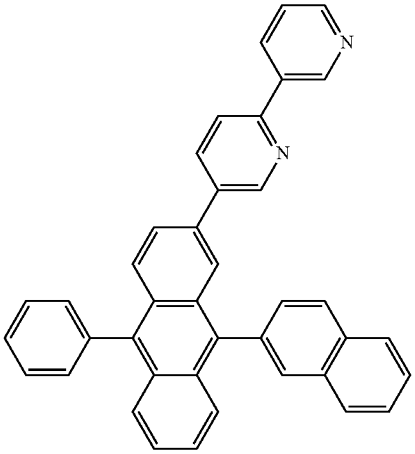
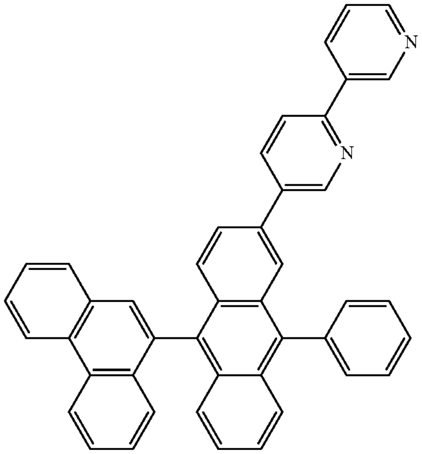

-continued
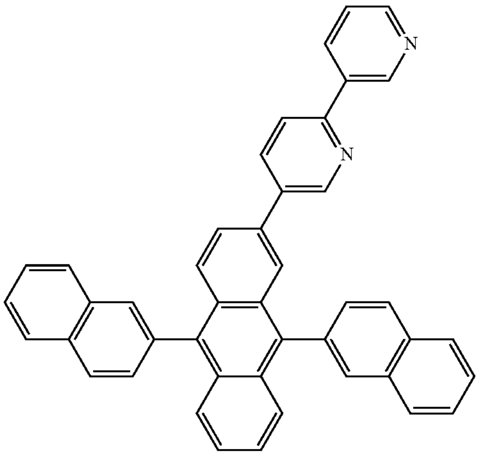
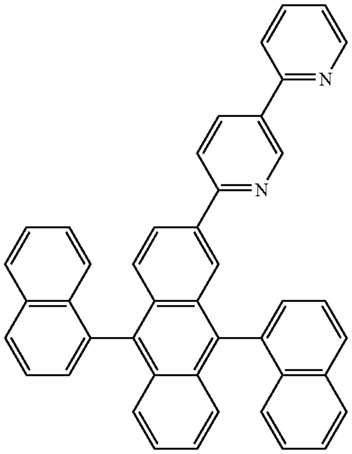
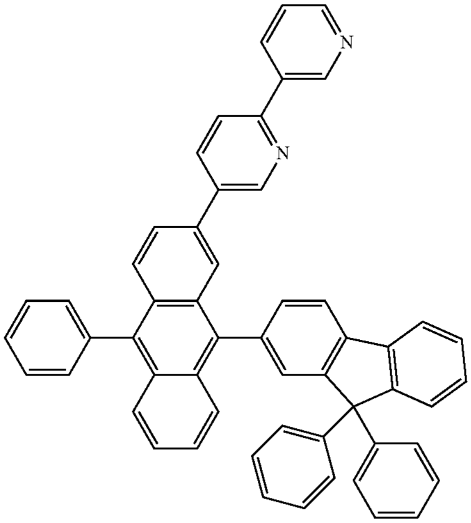
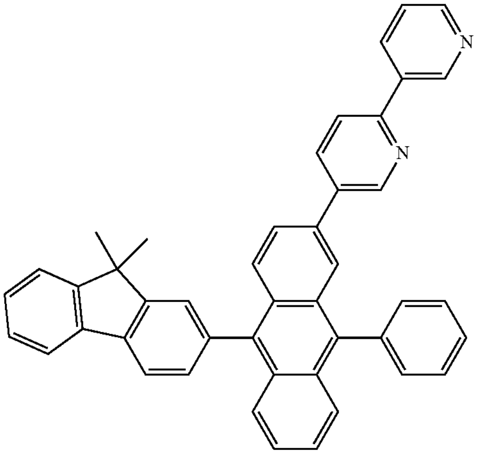
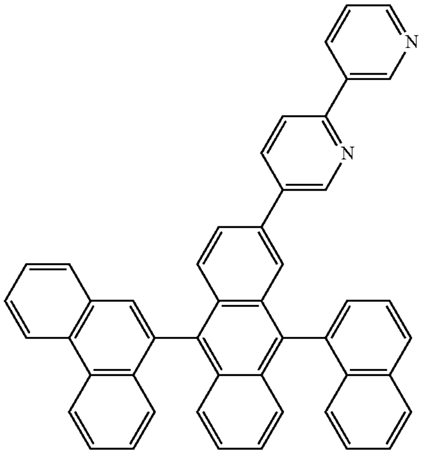
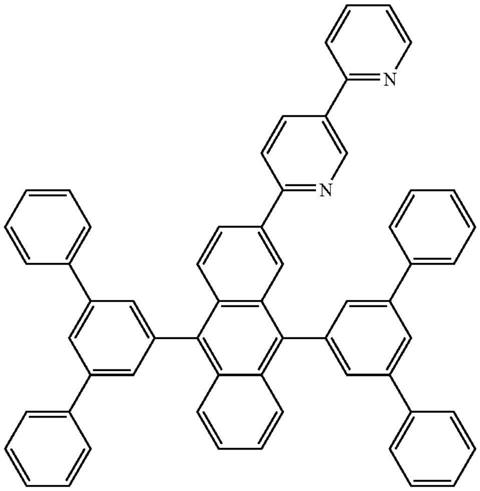

-continued
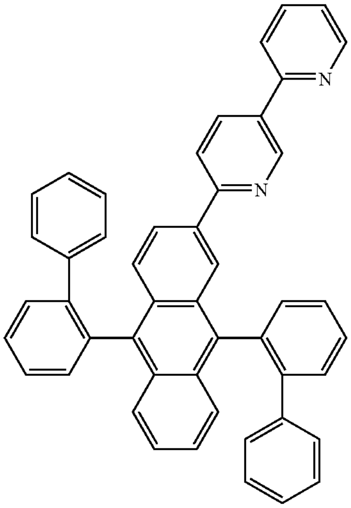
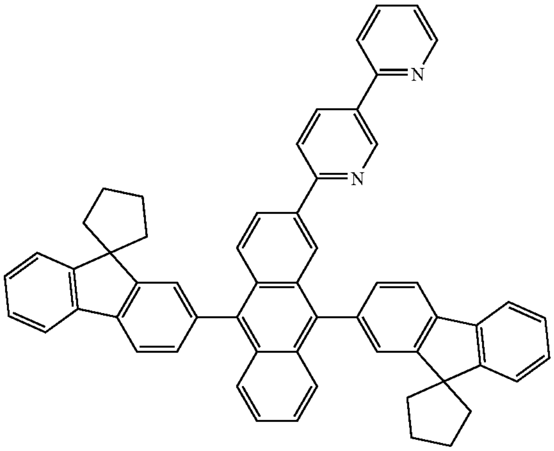
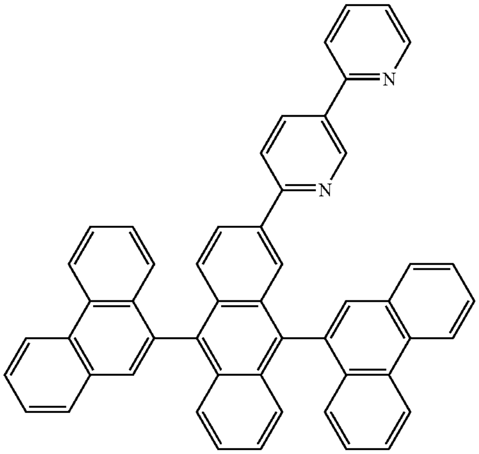
-continued
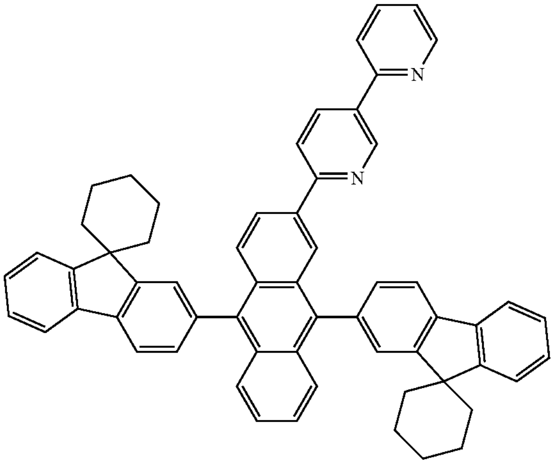
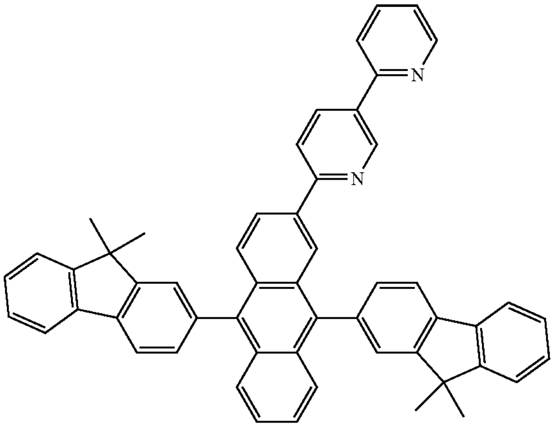
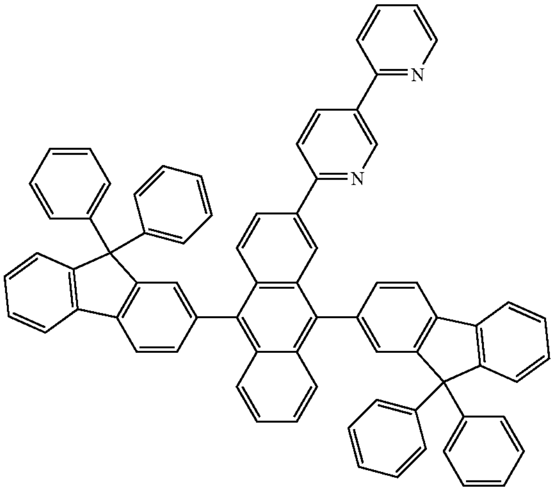

-continued
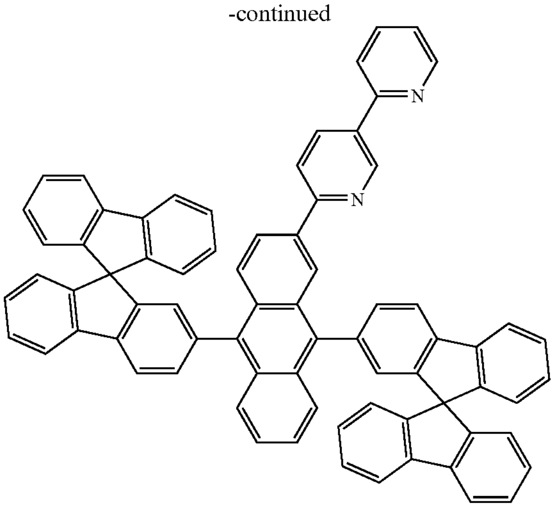
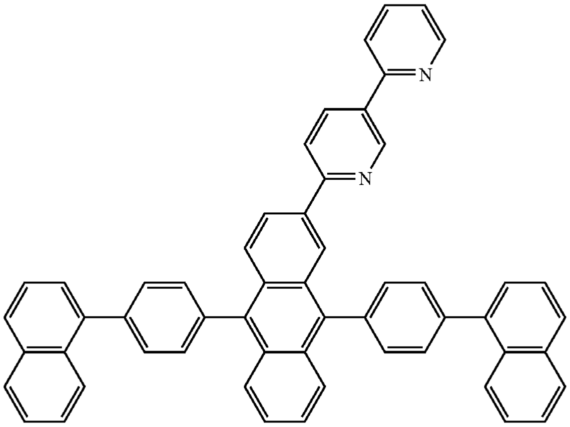
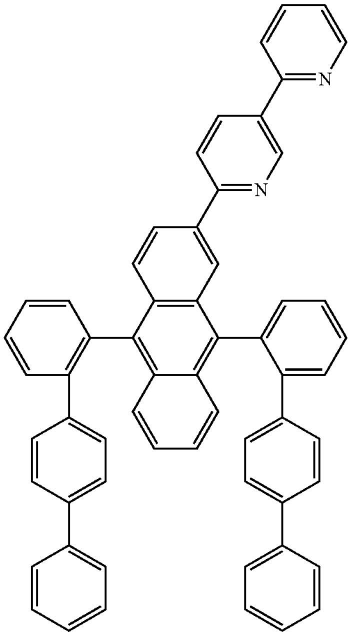
-continued
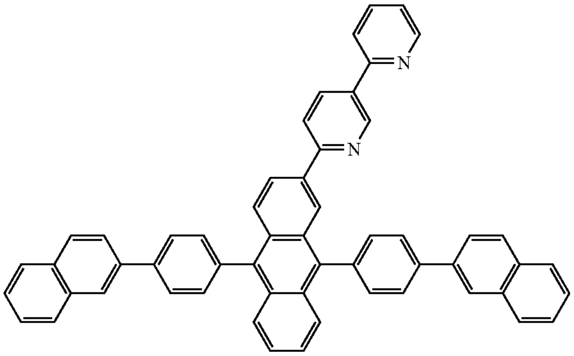
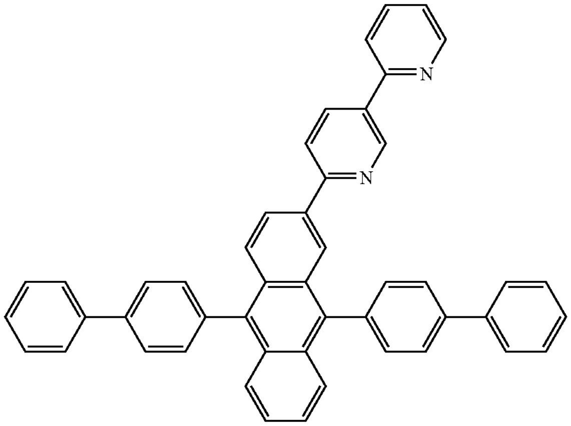
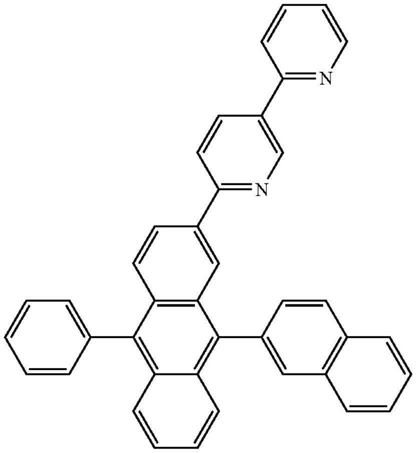
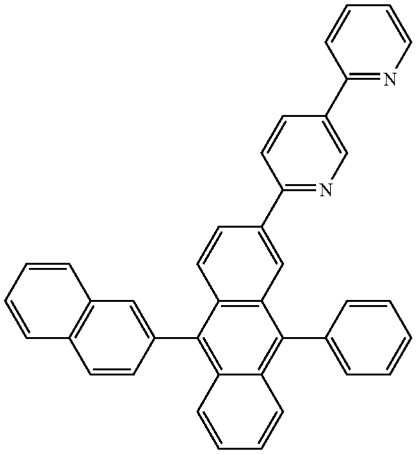

-continued
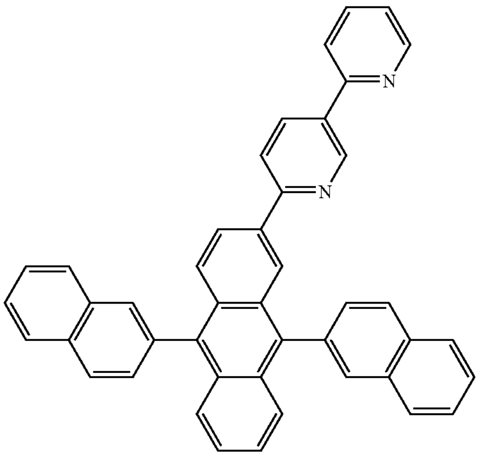
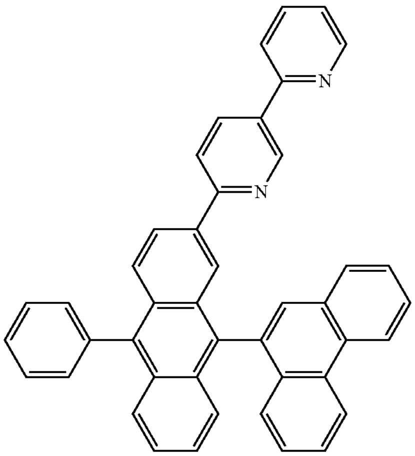
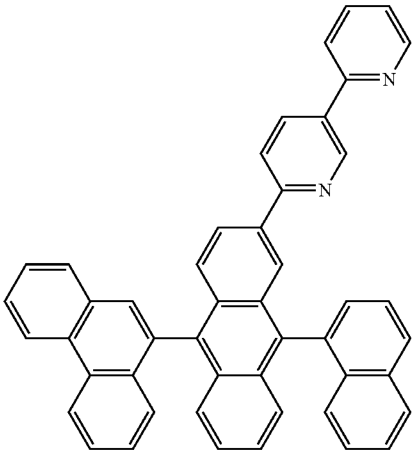
-continued
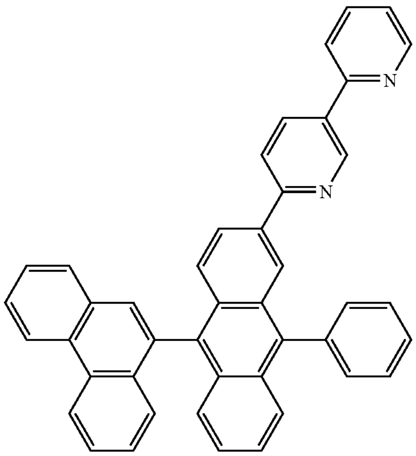
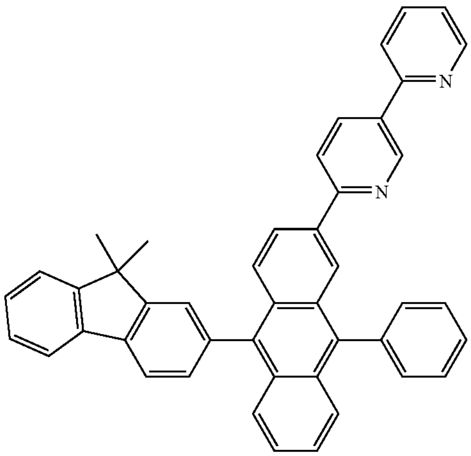
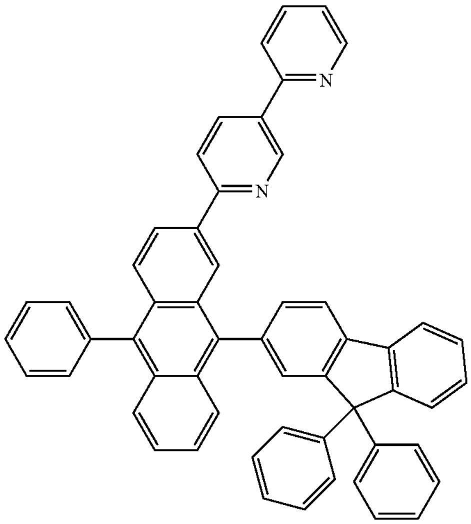

-continued
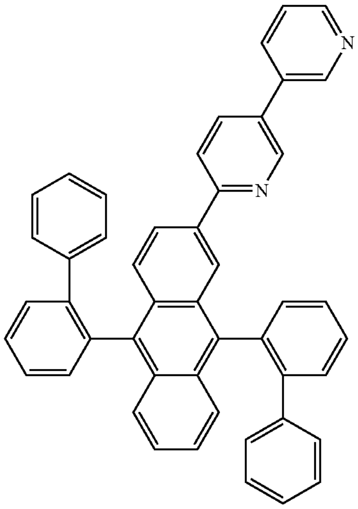
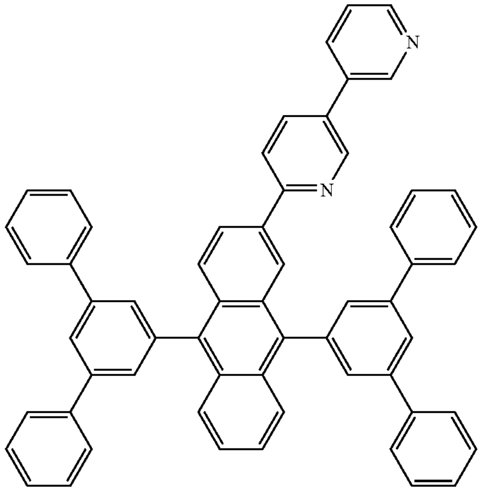
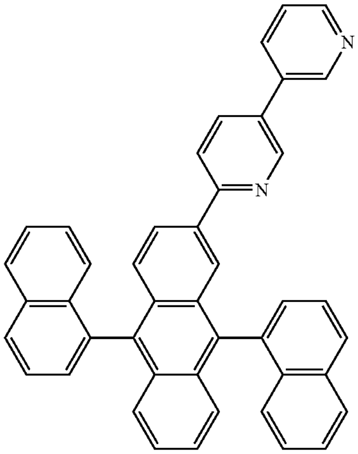
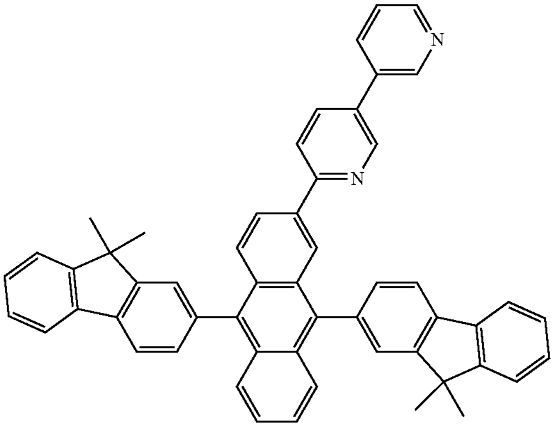
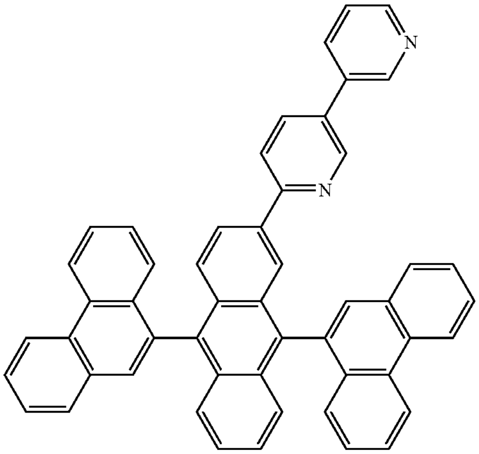
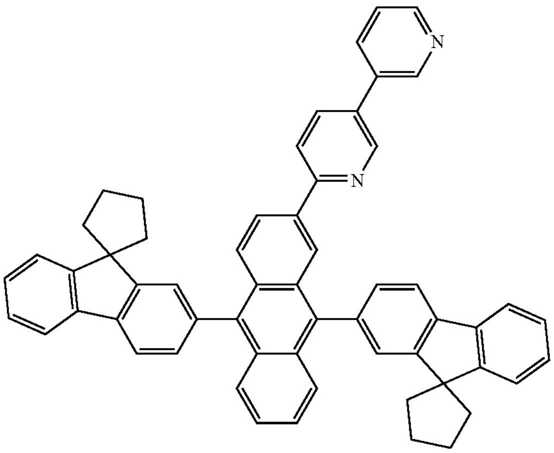
-continued -continued
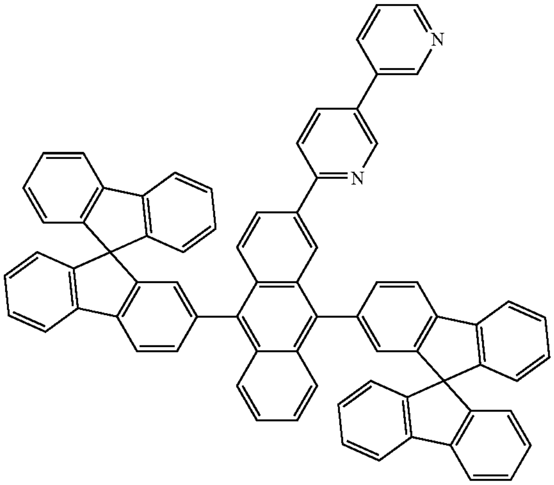
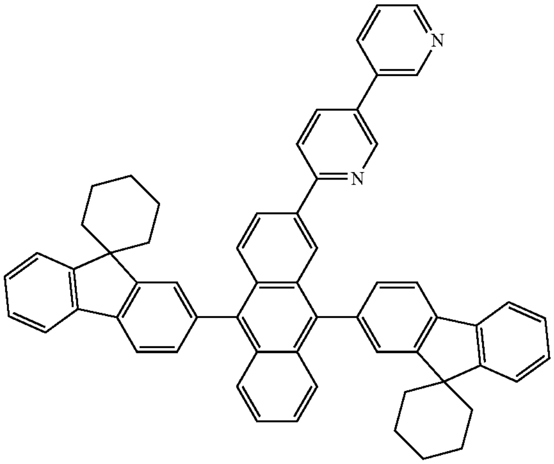
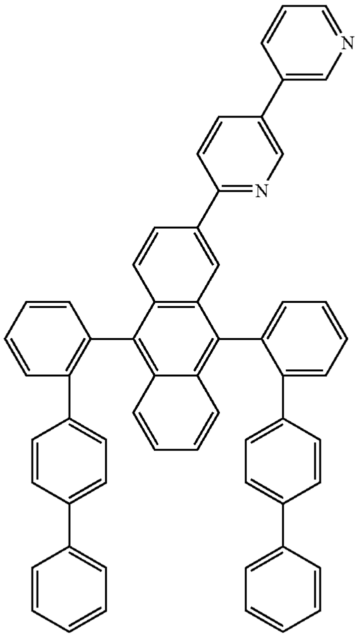
-continued
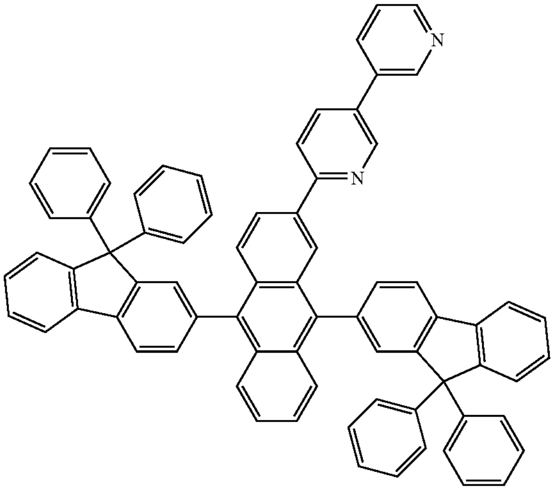
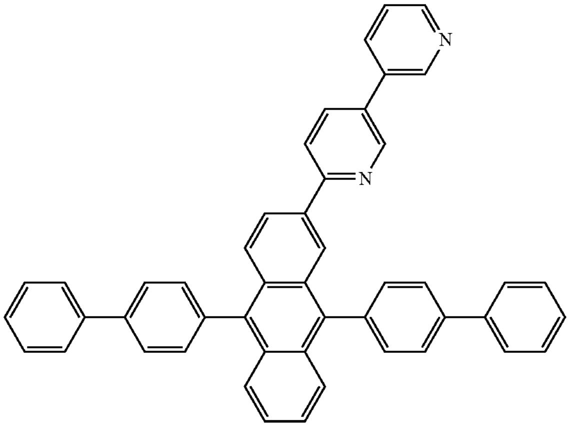
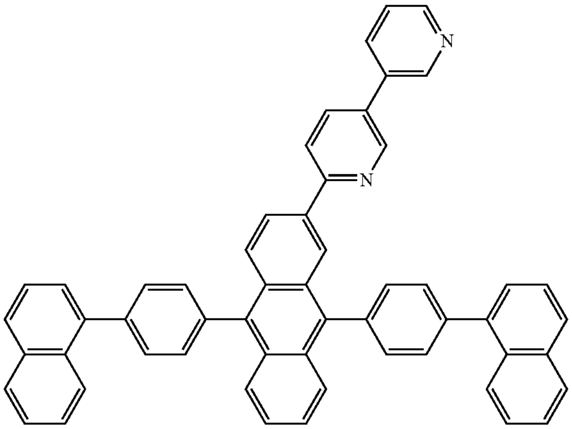

-continued
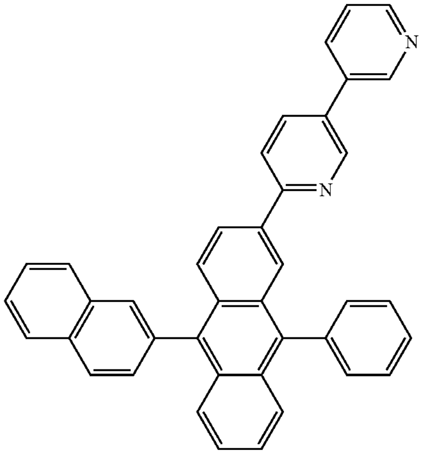
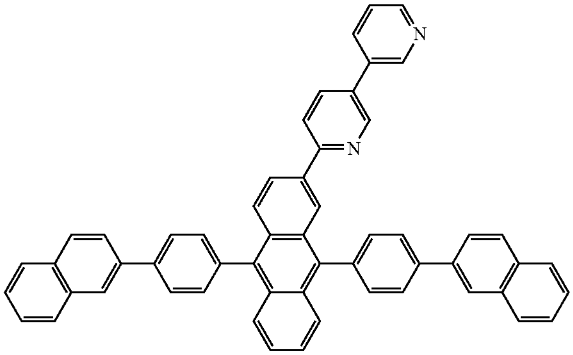
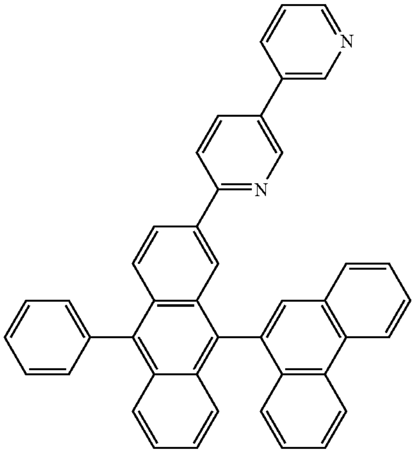
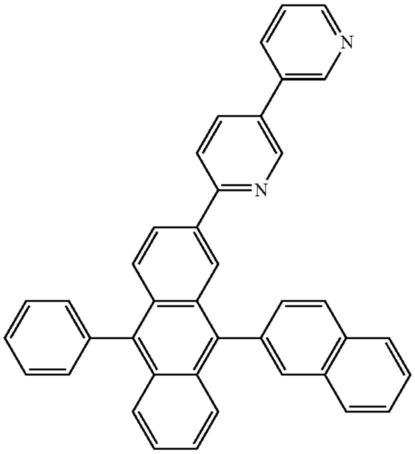
-continued
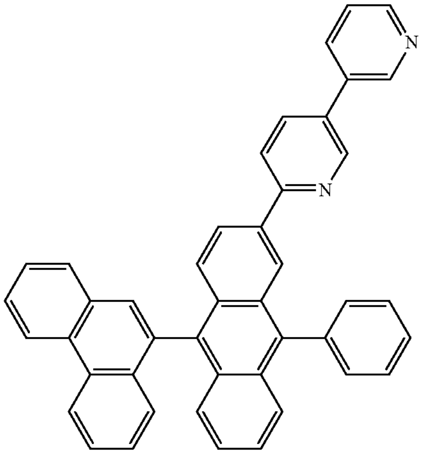
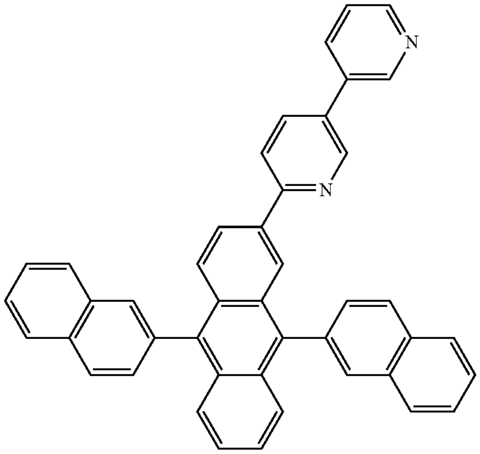
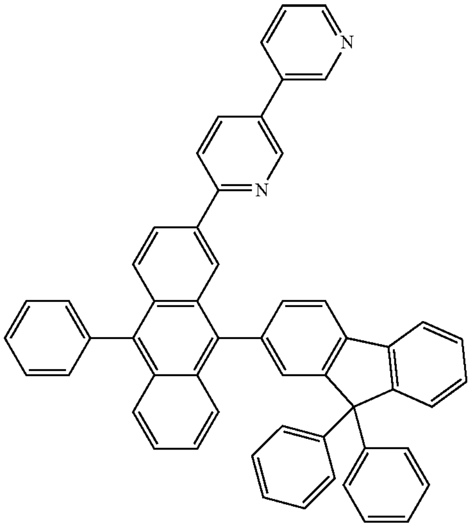

-continued
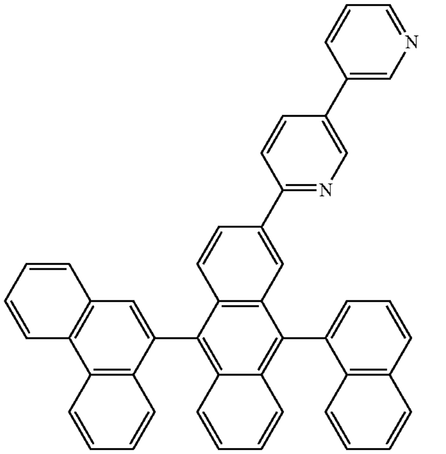
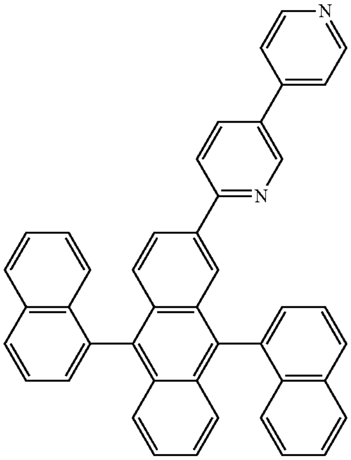
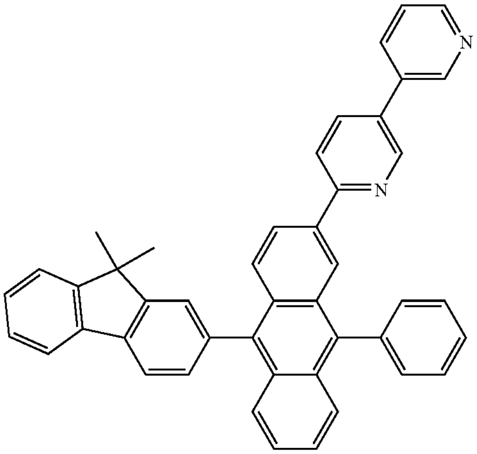
-continued
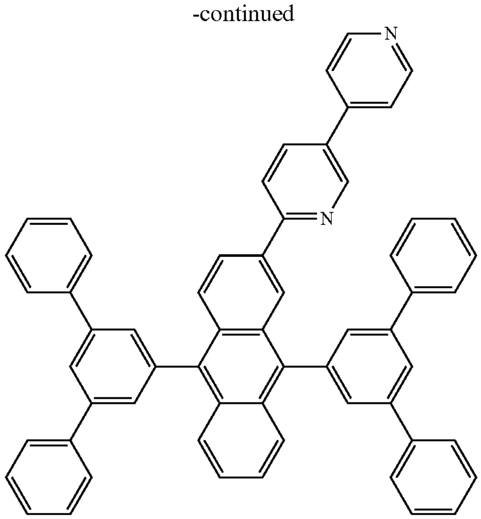
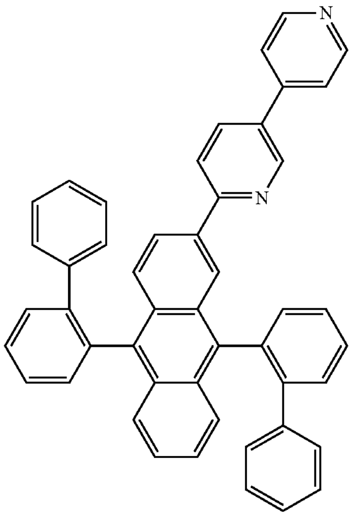
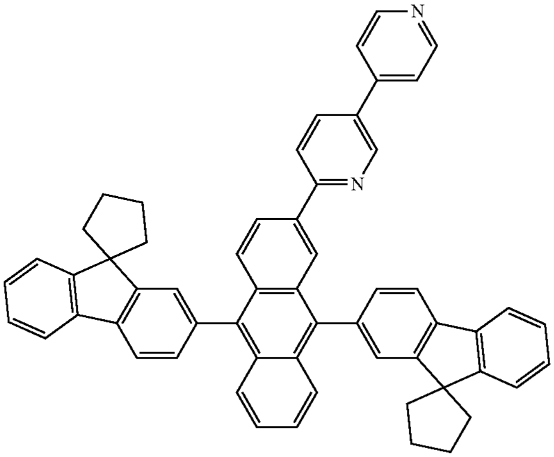

-continued
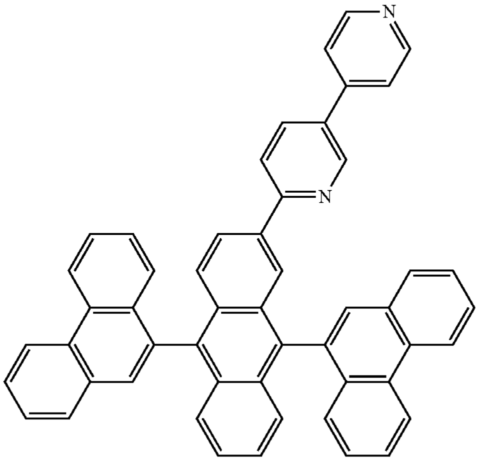
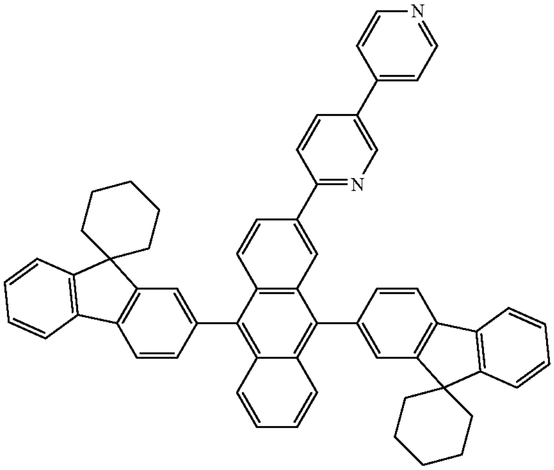
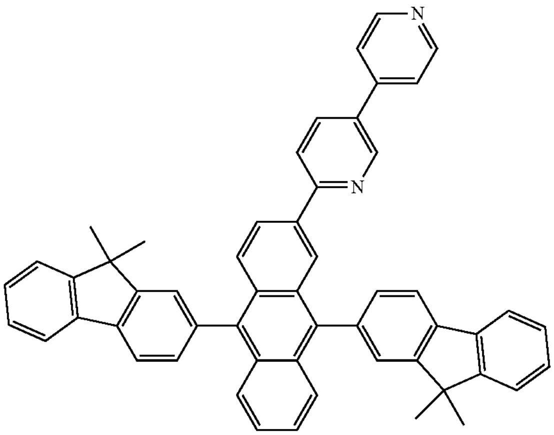
-continued
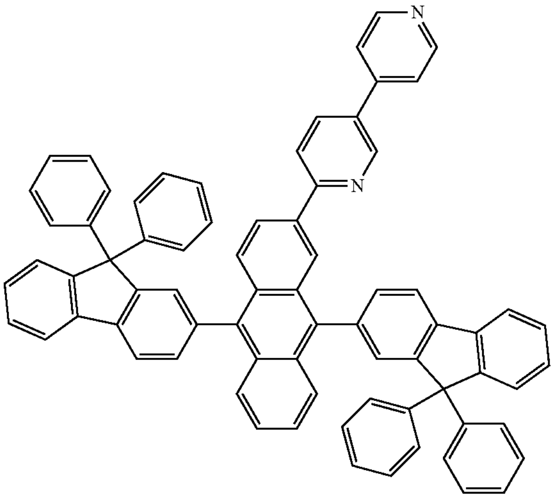
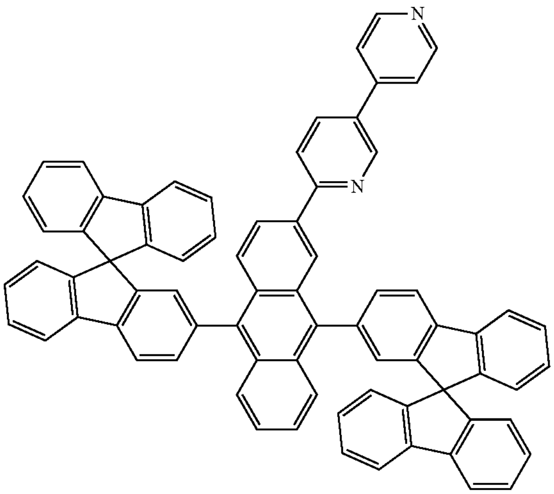
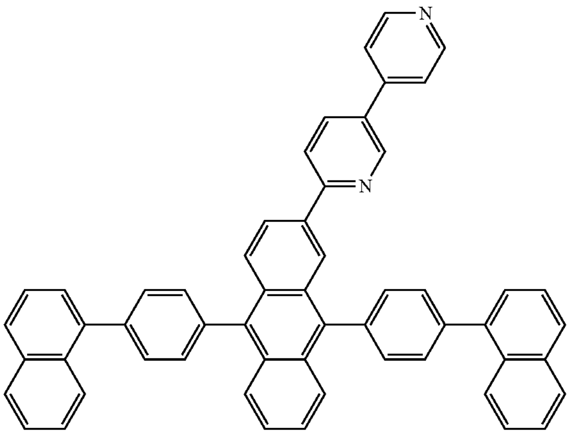

-continued
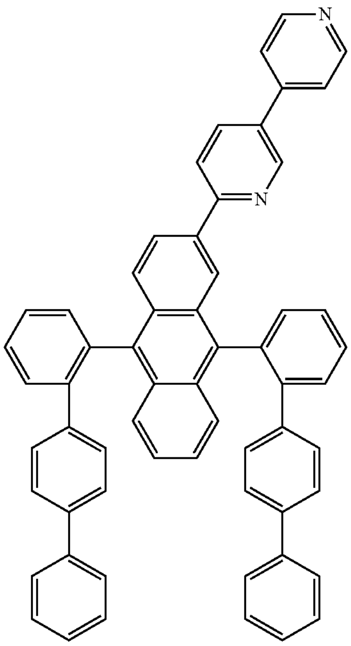
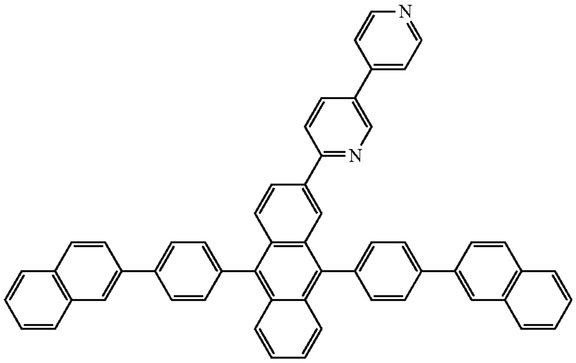
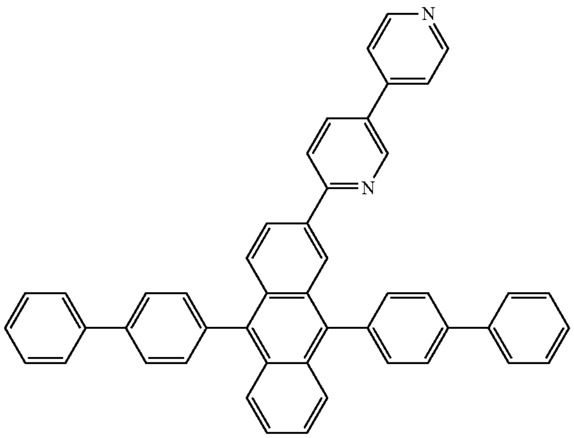
-continued
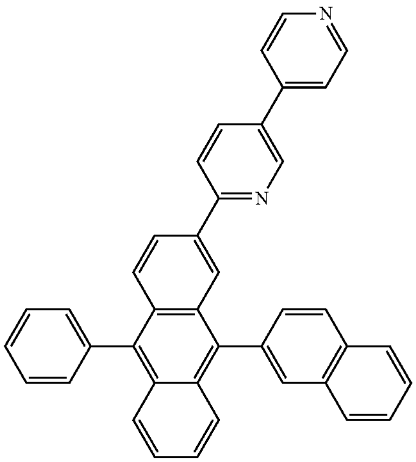
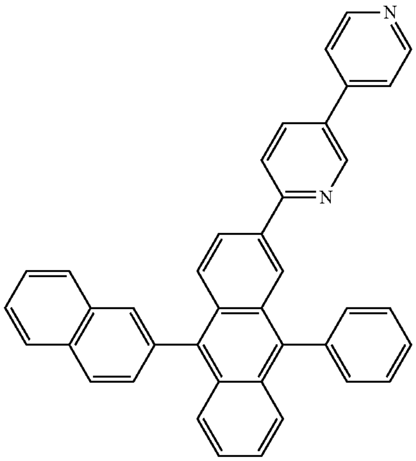
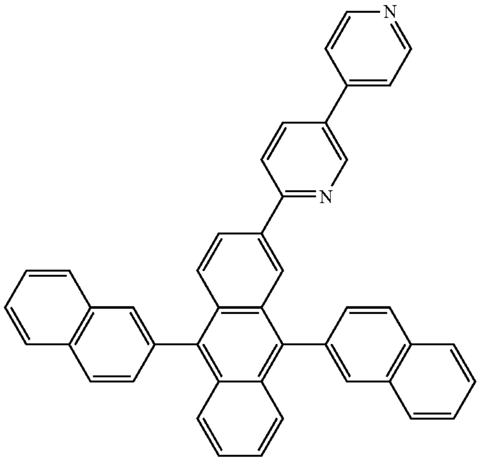

-continued
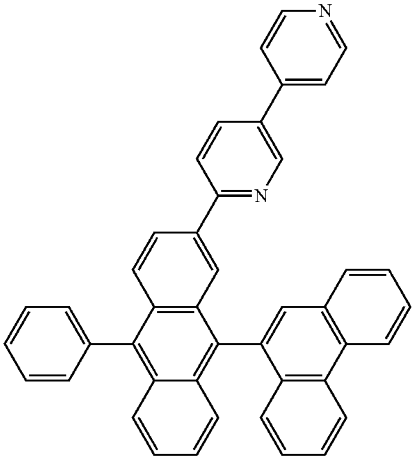
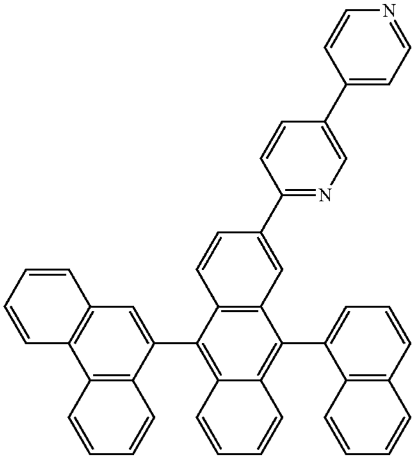
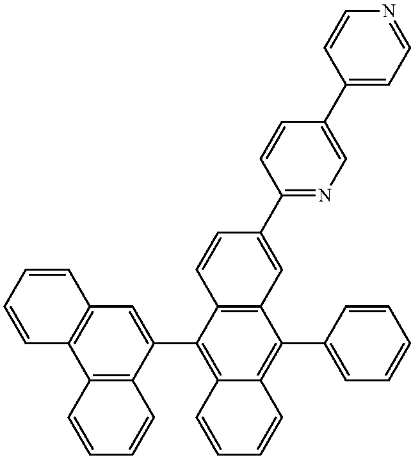
-continued
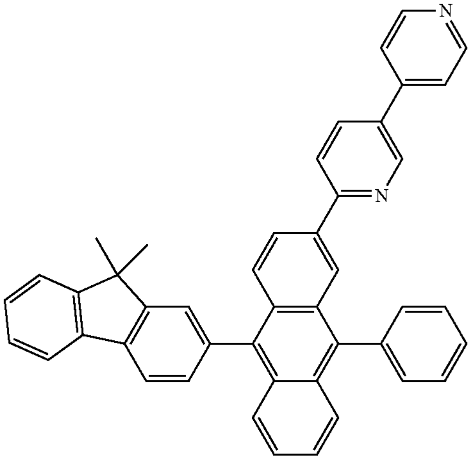
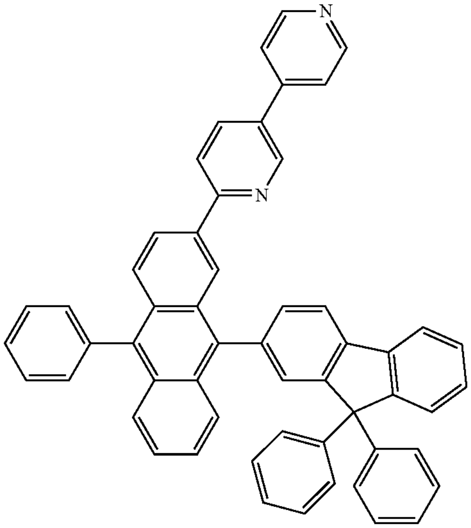
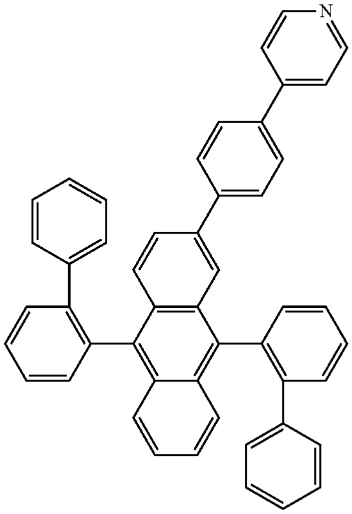

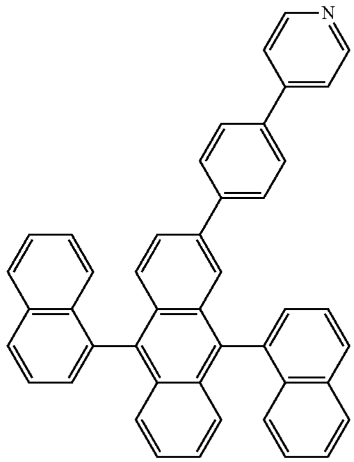
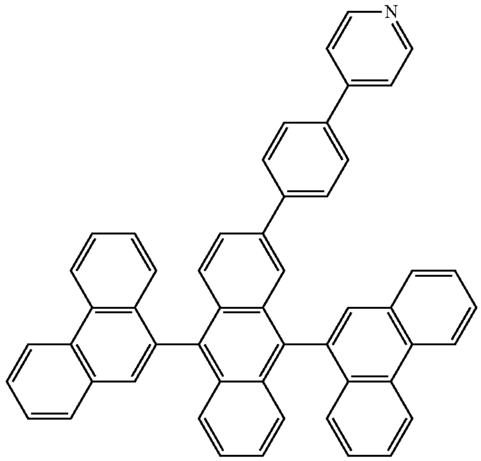
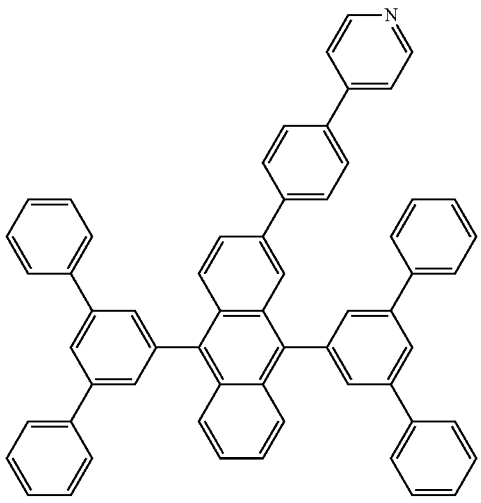
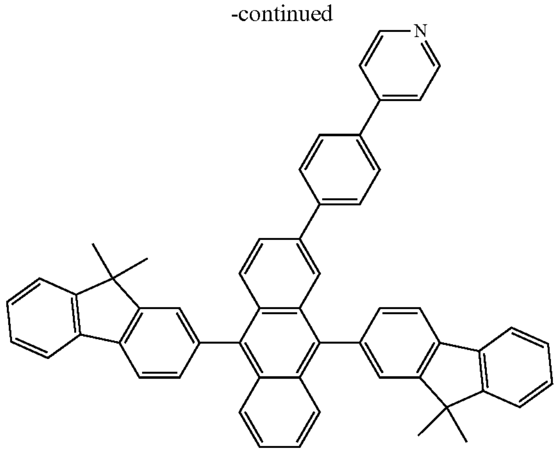
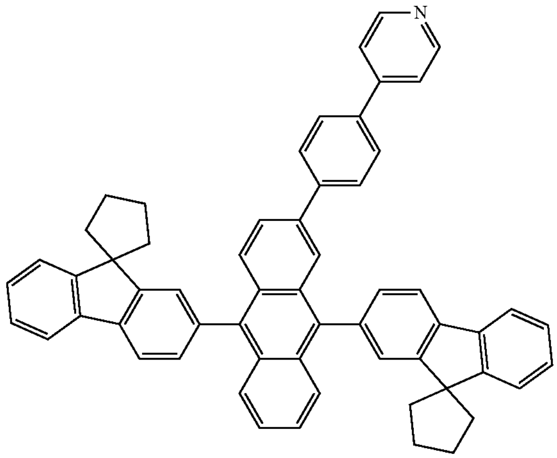
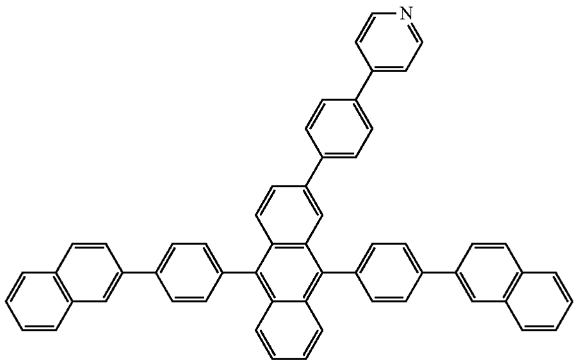

-continued
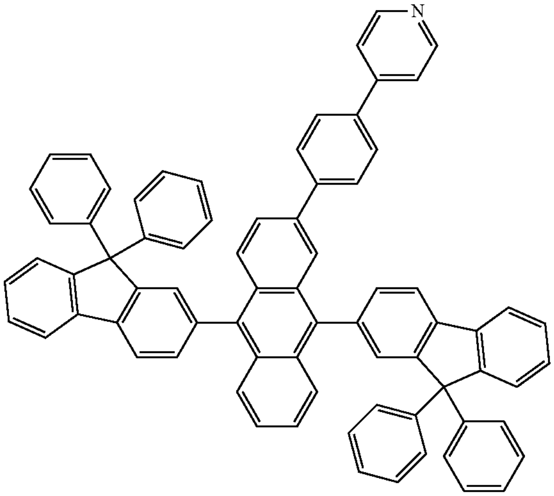
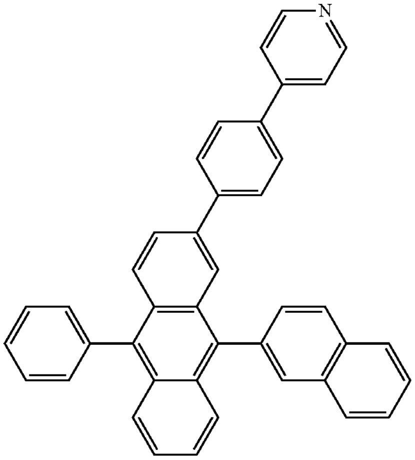
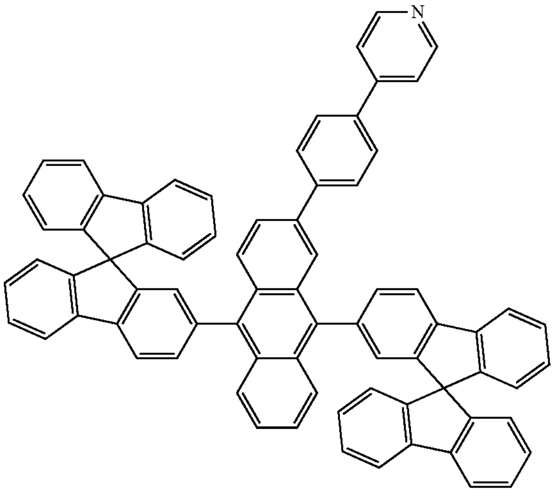
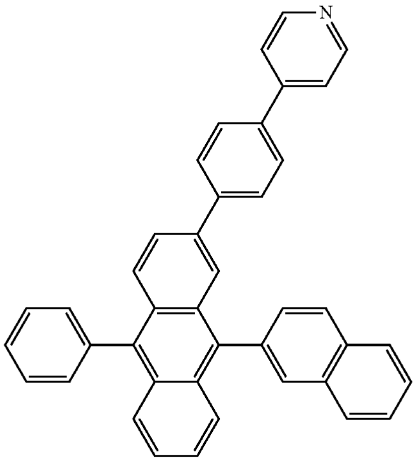
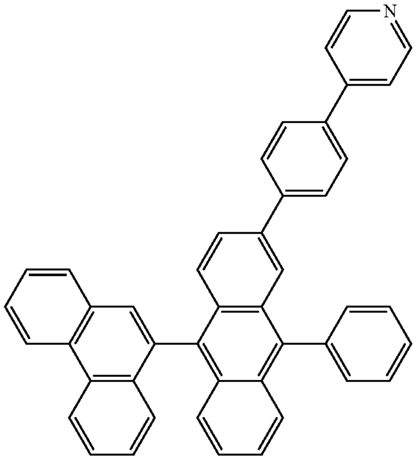
-continued
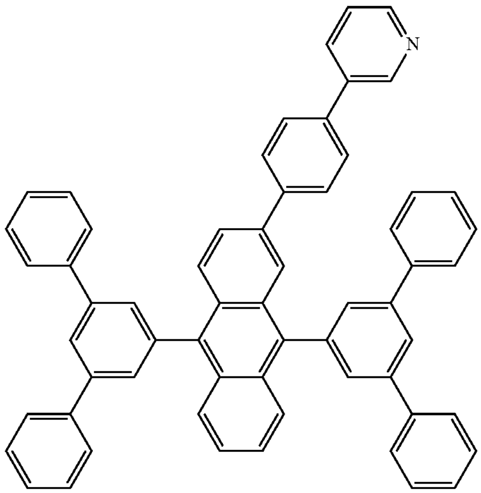

-continued
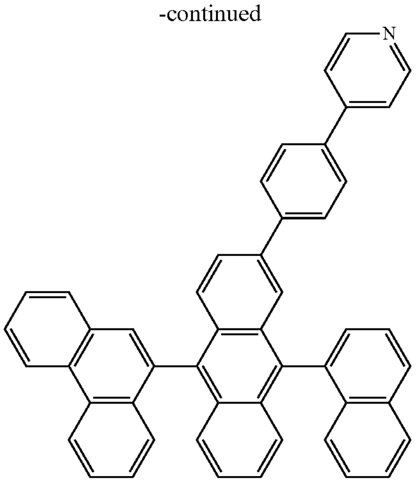
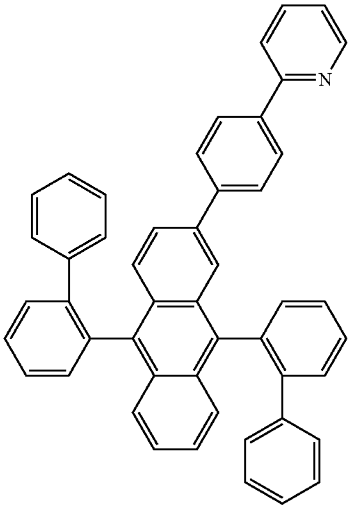
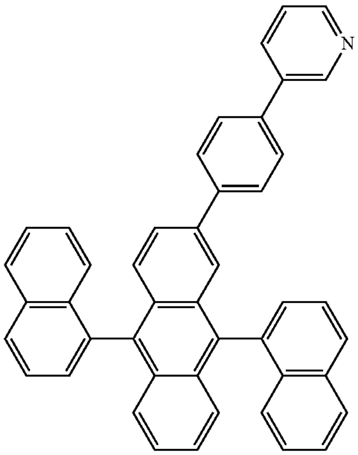
-continued
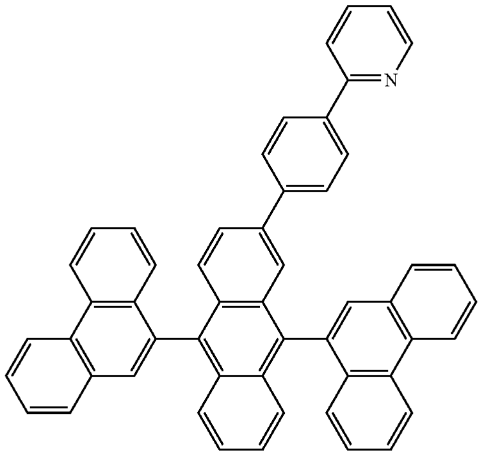
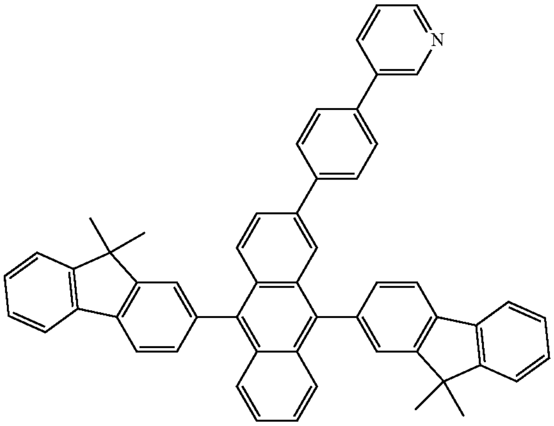
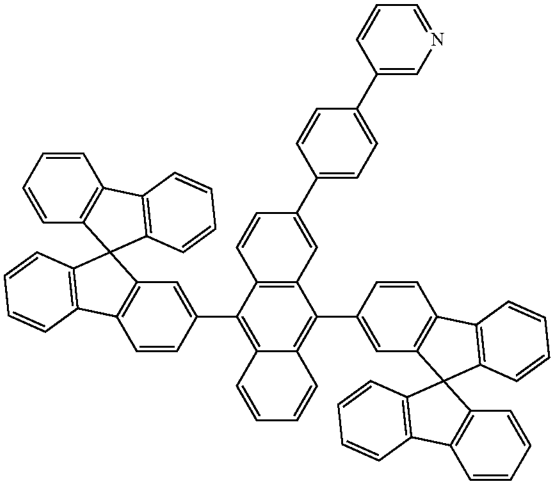

-continued
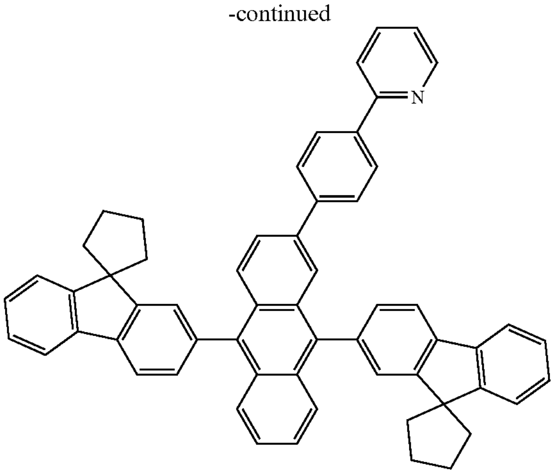
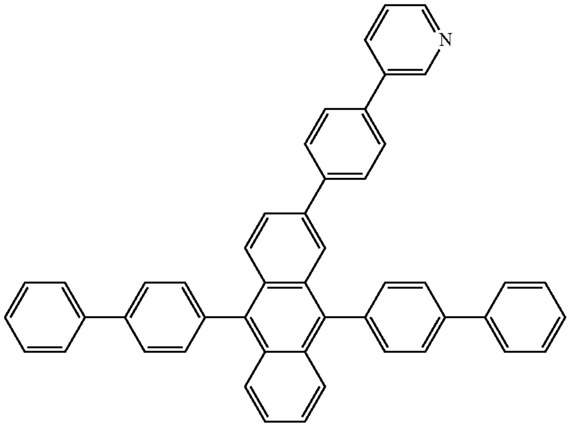
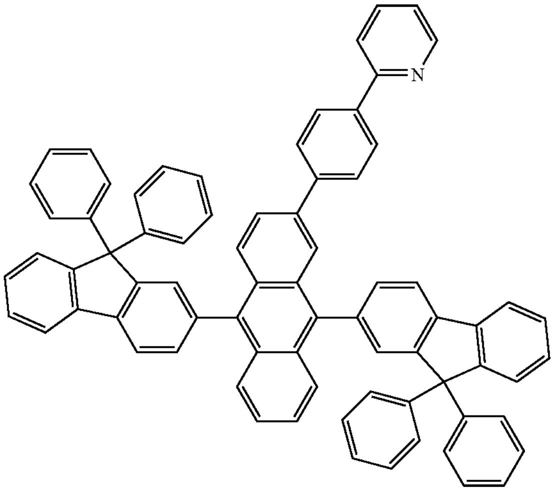
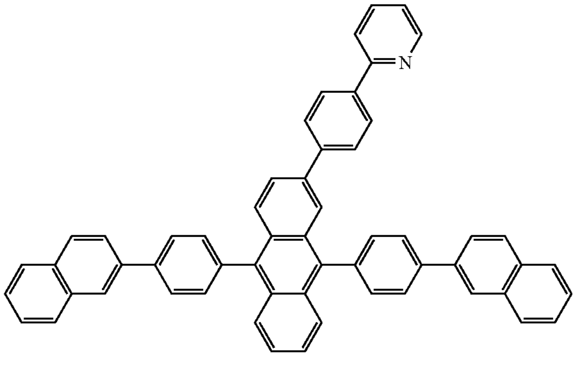
-continued
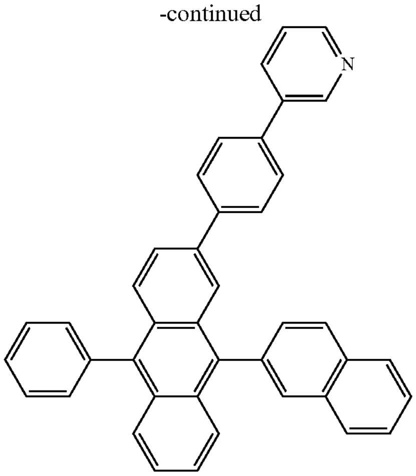
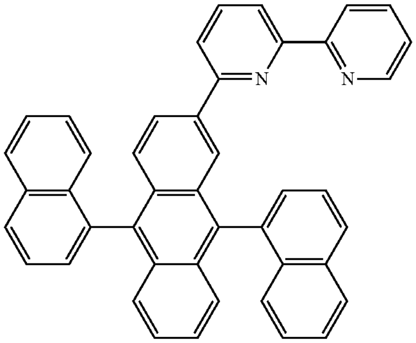
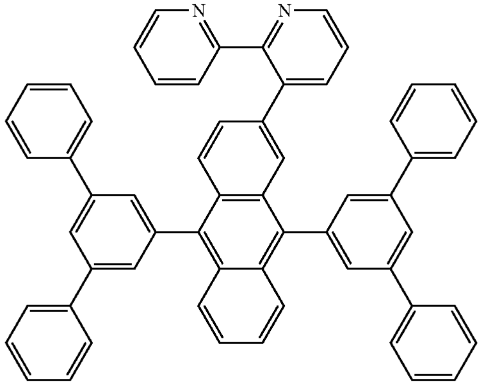
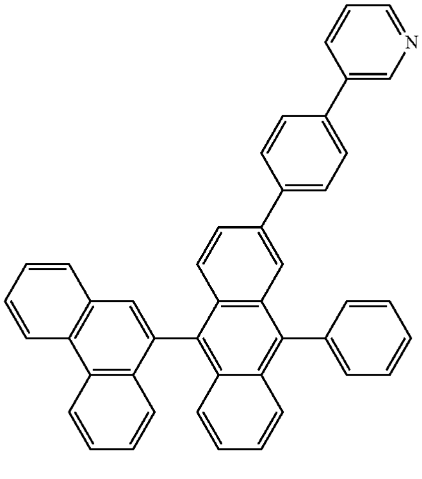

-continued
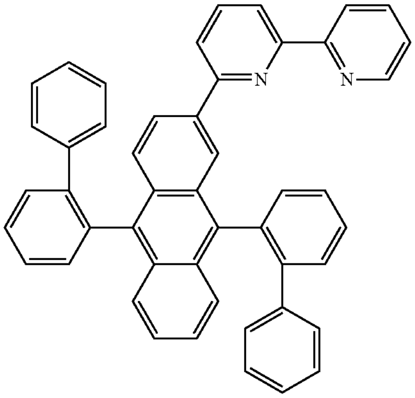
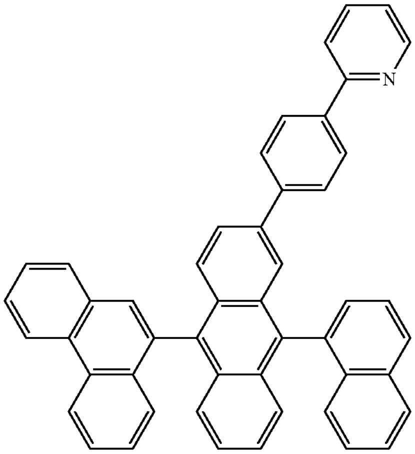
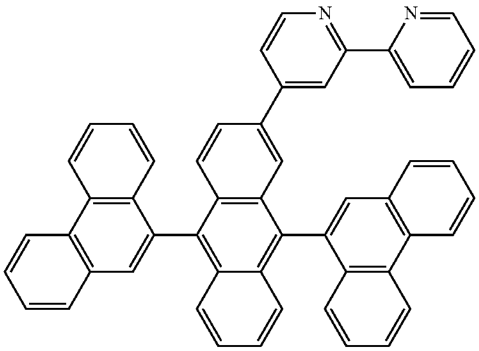
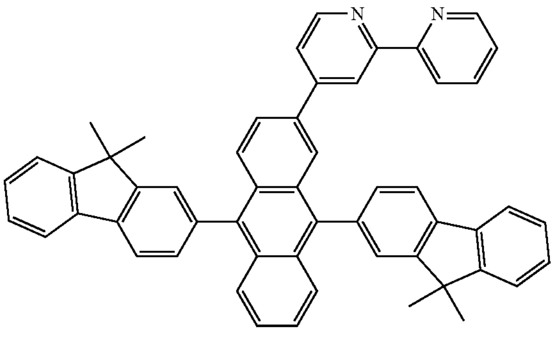
-continued
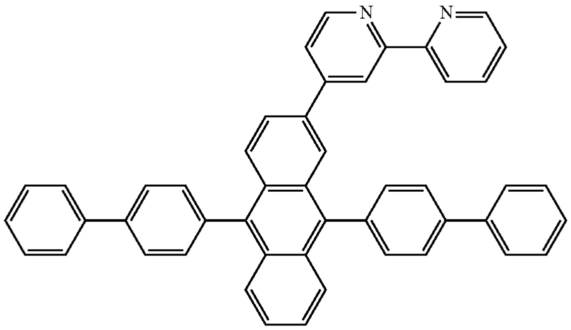
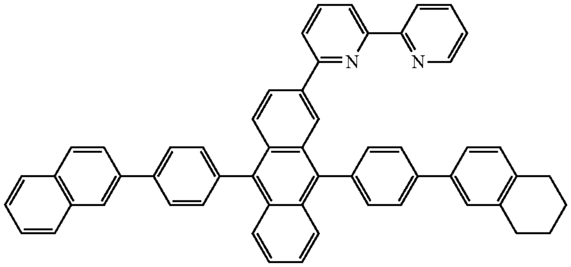
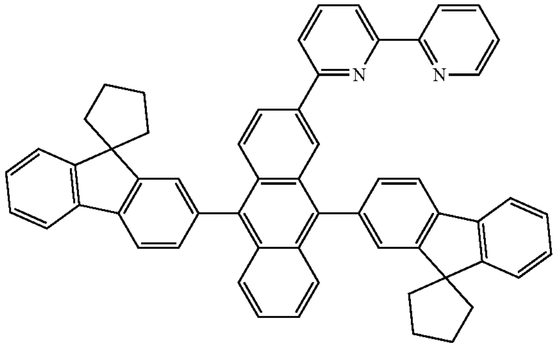
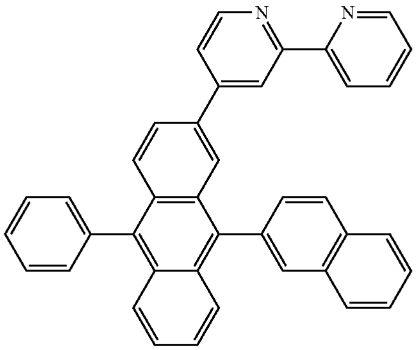
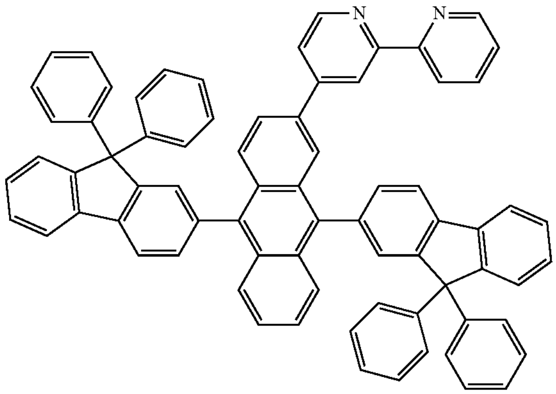

-continued
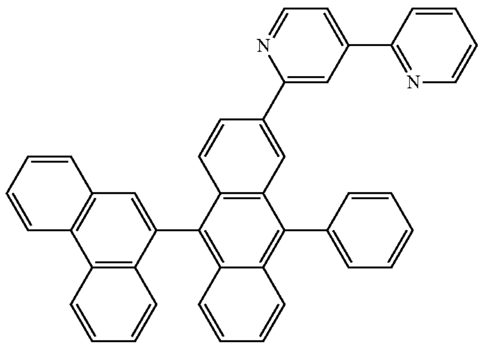
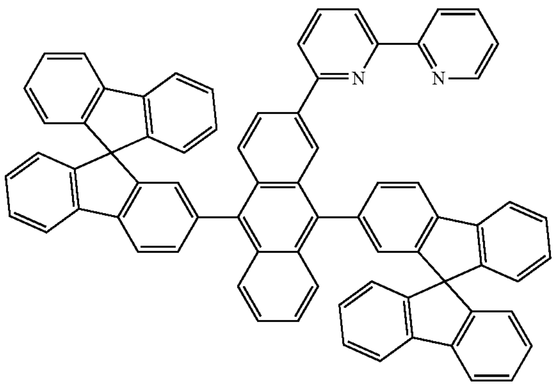
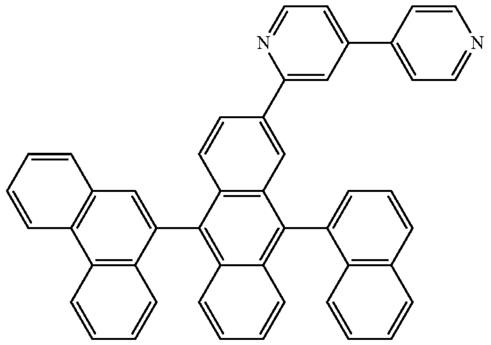
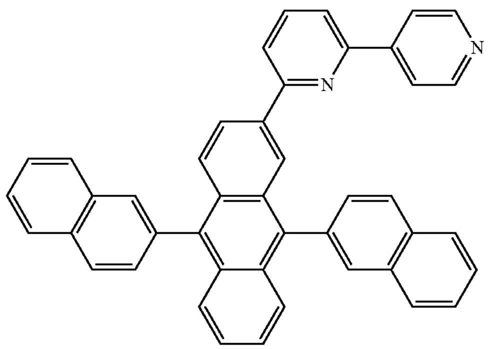
-continued
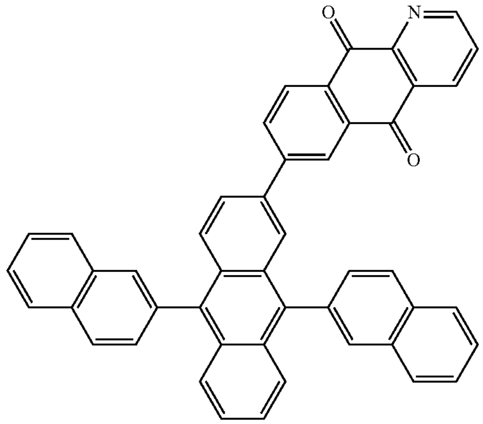
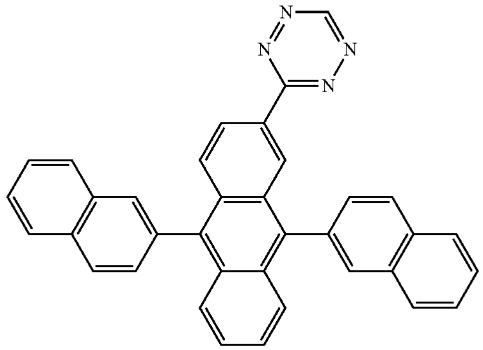
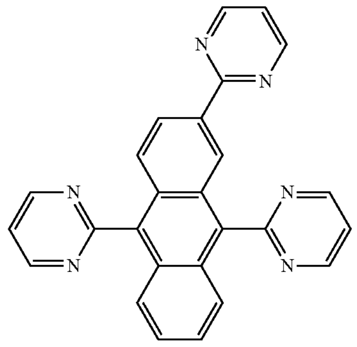
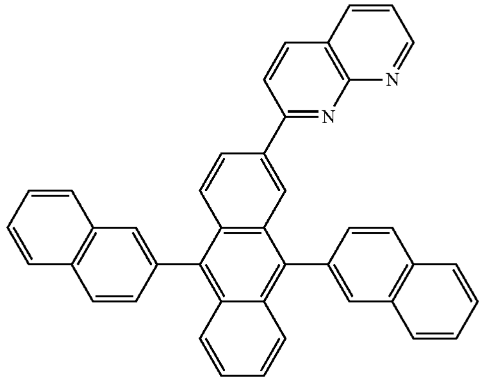

-continued
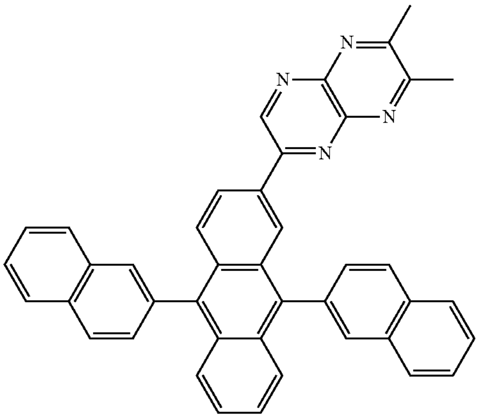
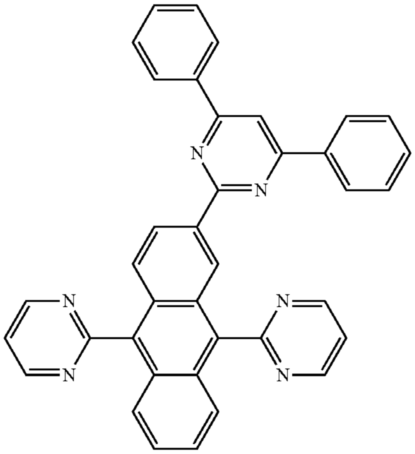
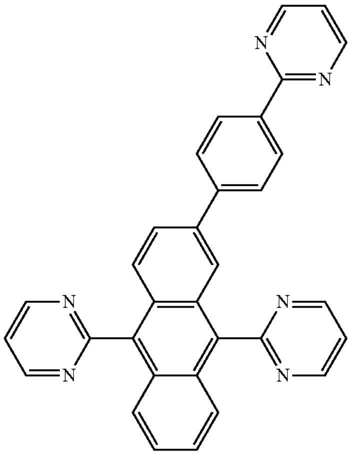
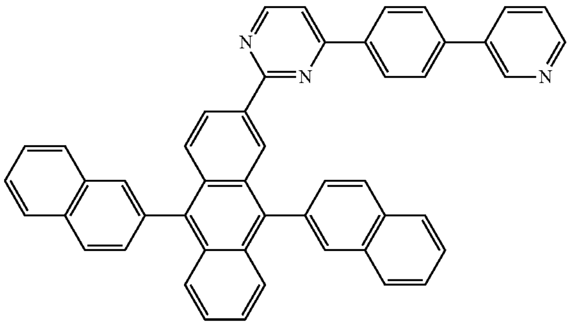
-continued
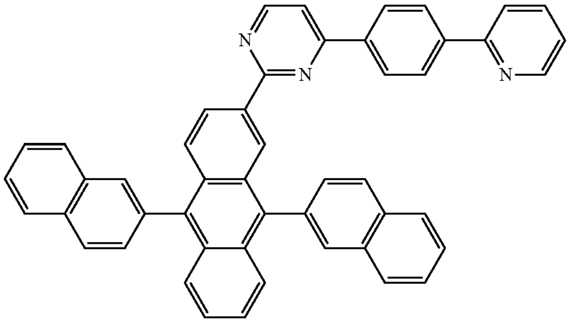
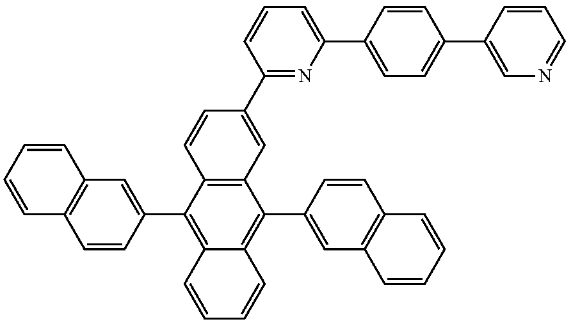
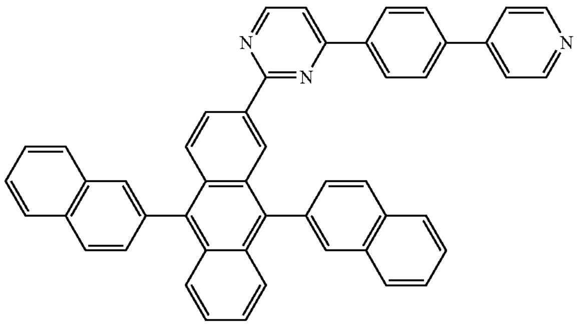
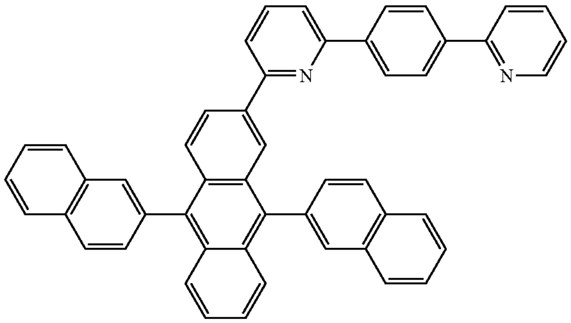
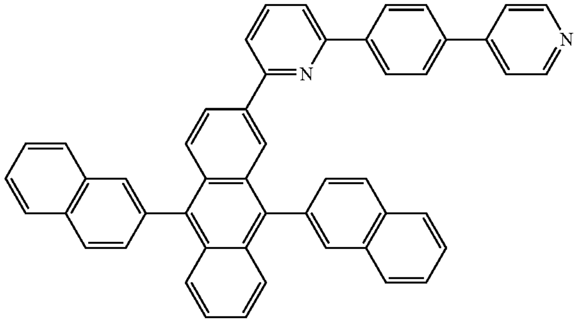

-continued
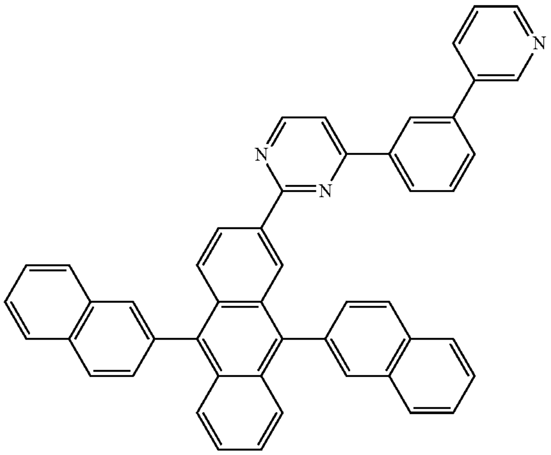
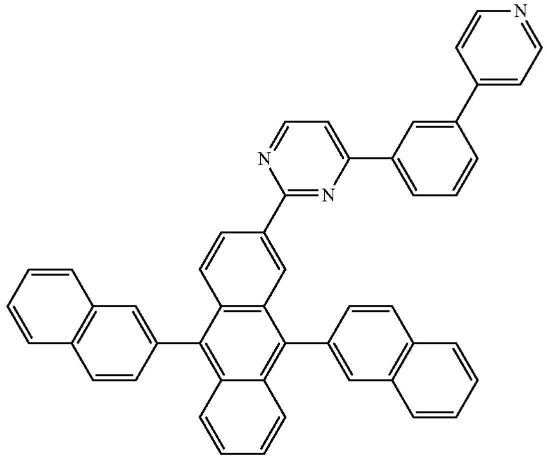
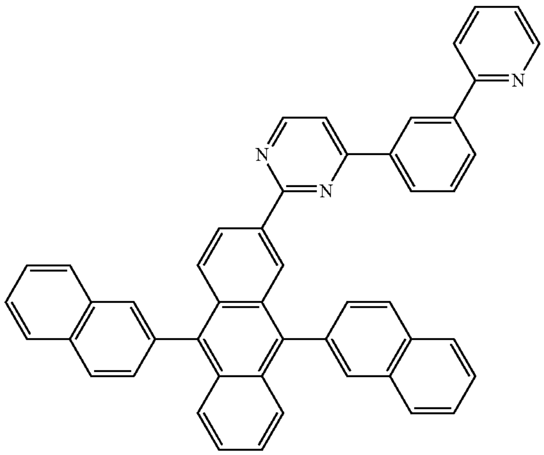
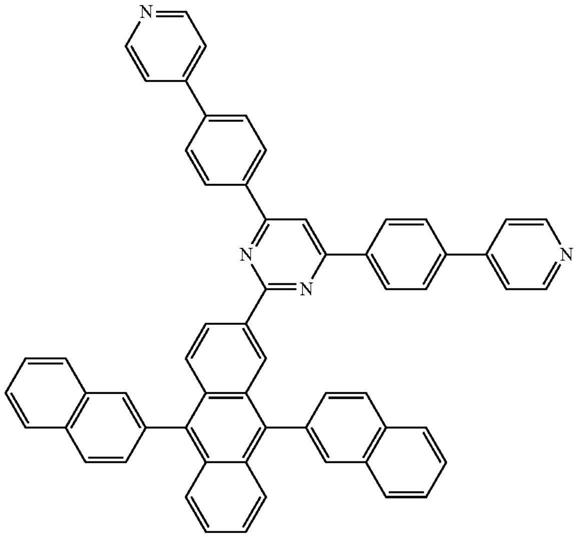
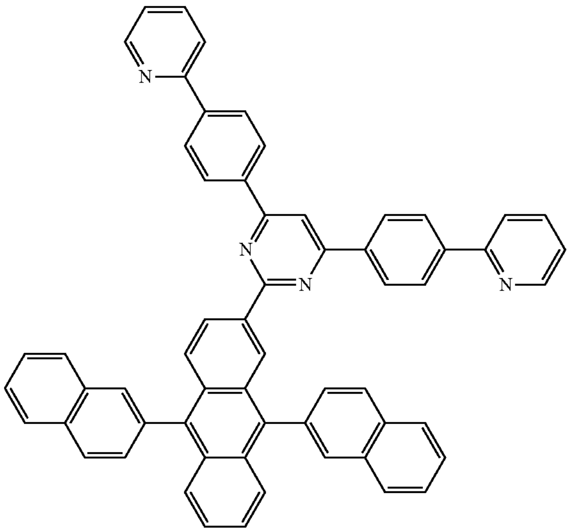
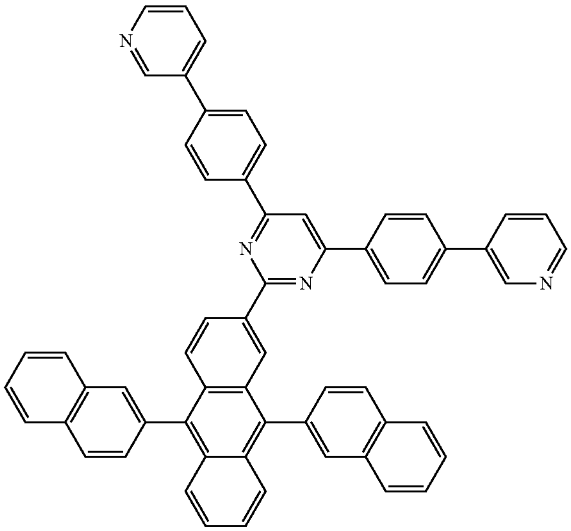
-continued -continued
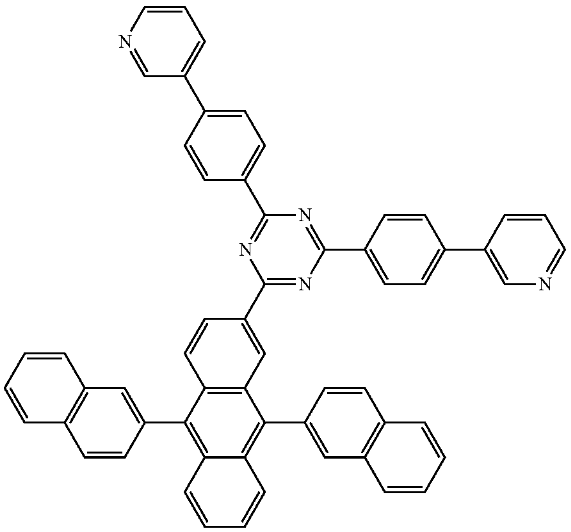
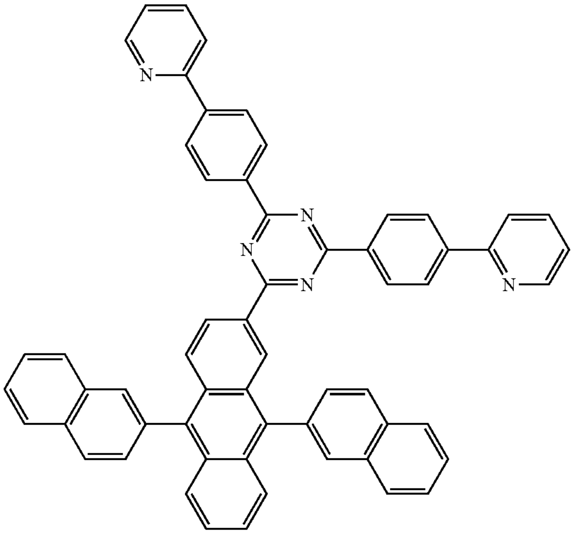
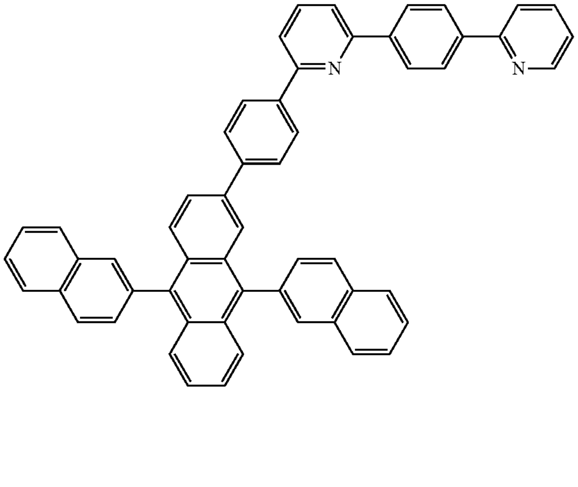
-continued
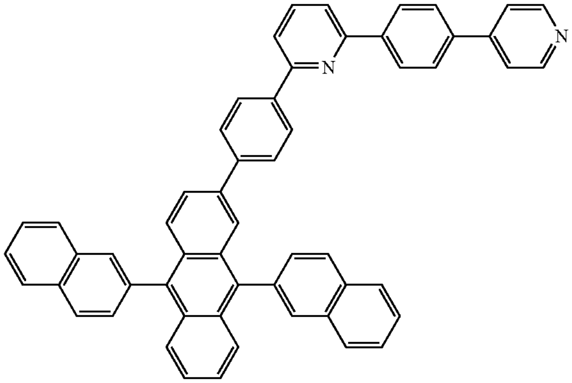
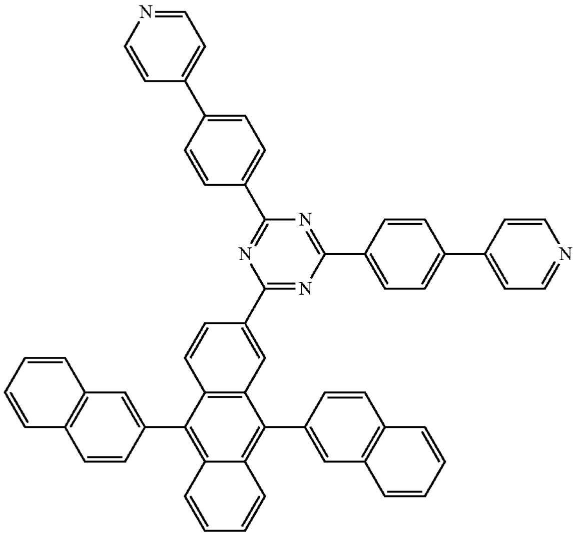
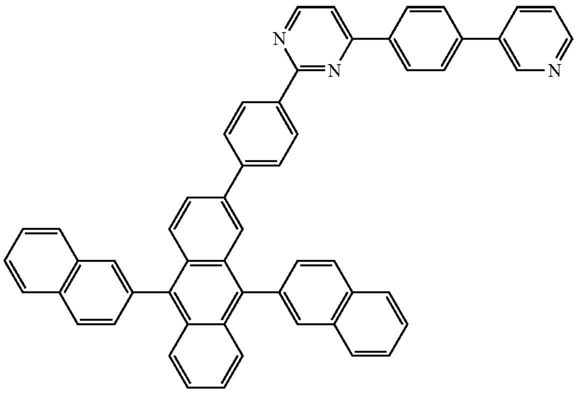
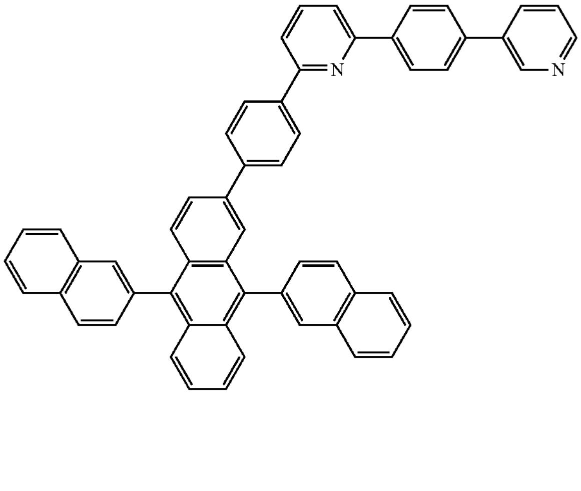

-continued
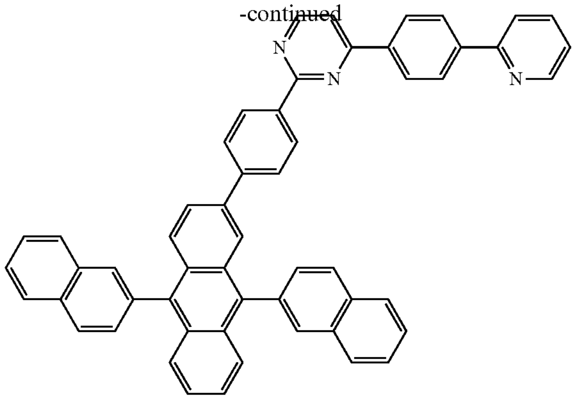
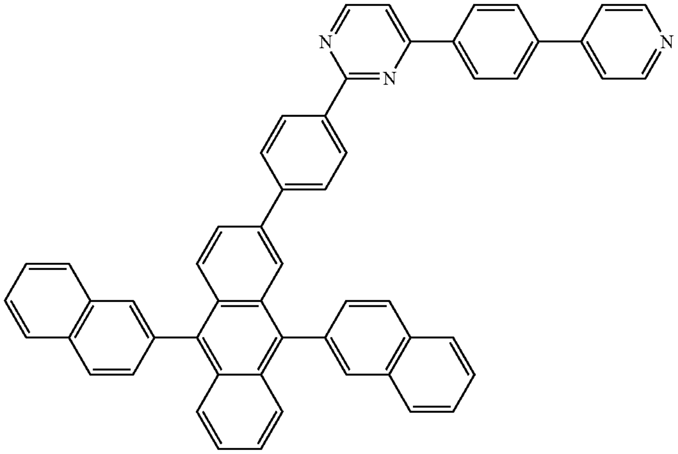
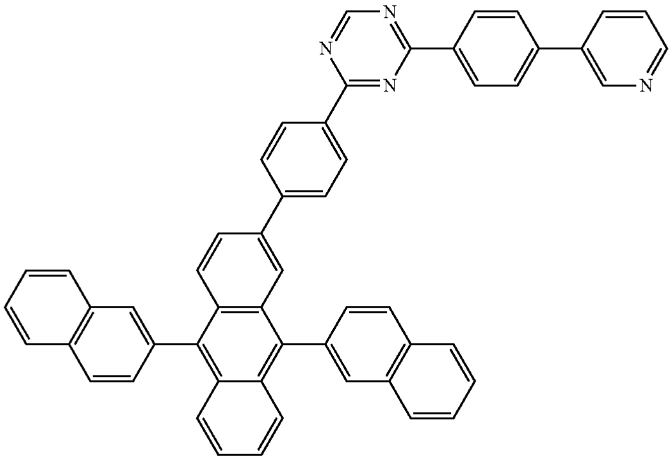

-continued
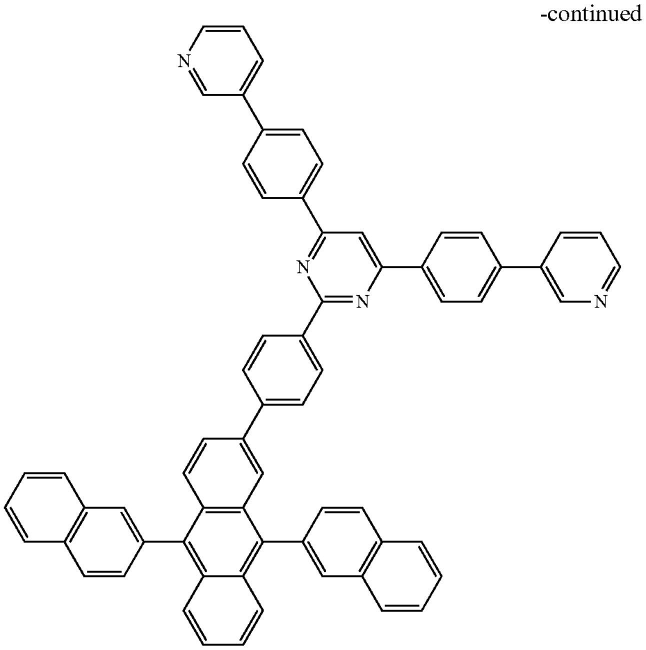
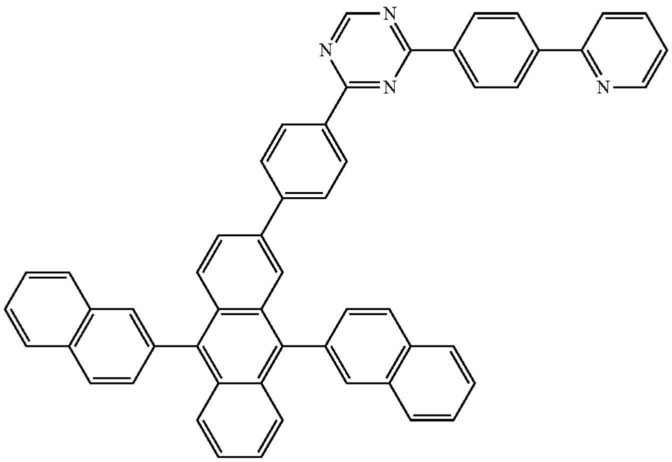
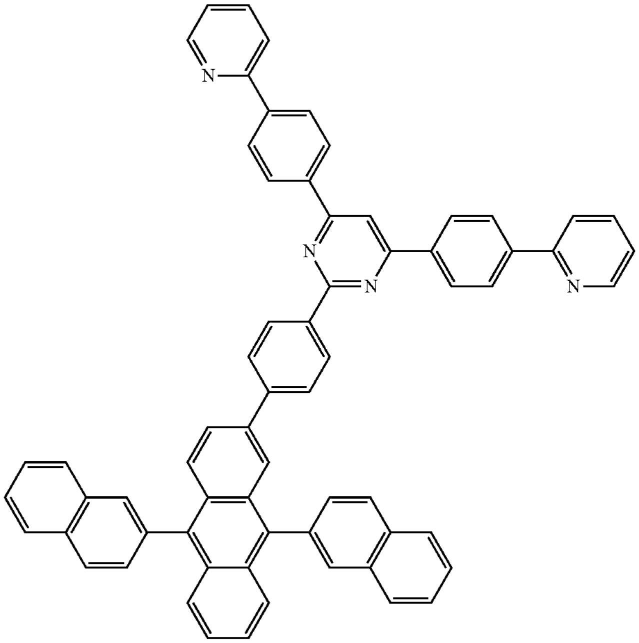

-continued
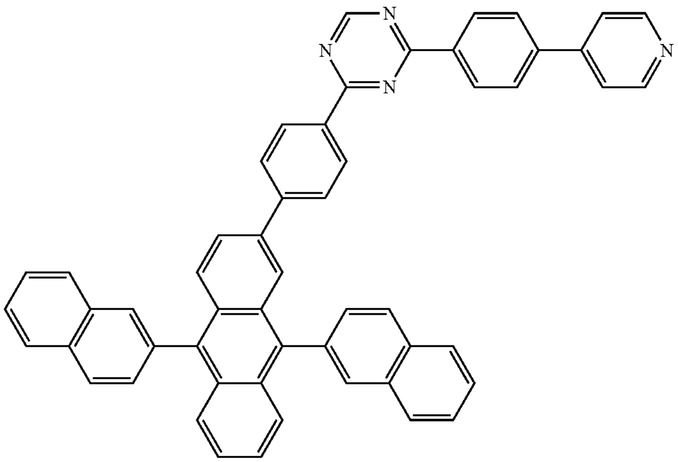
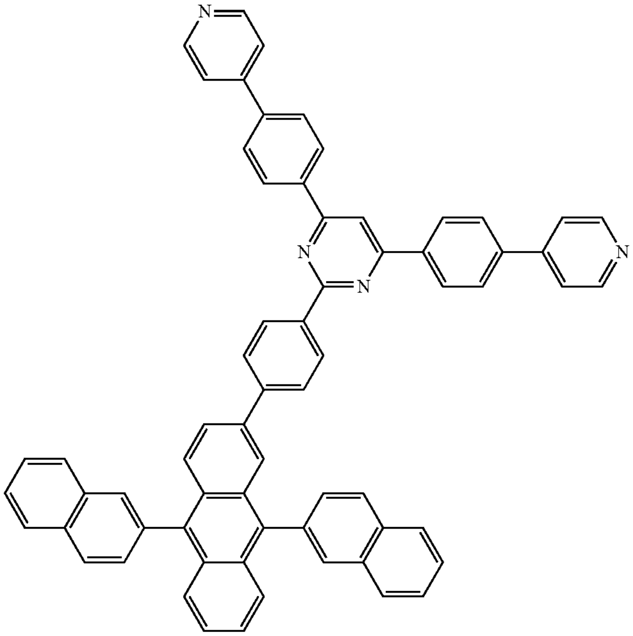
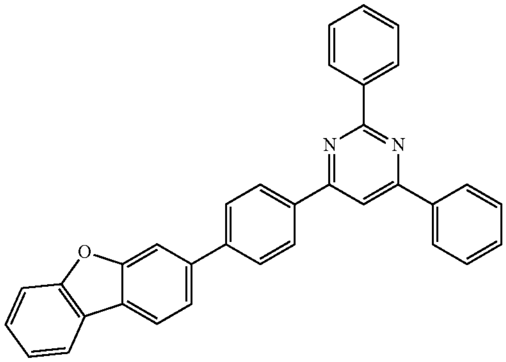
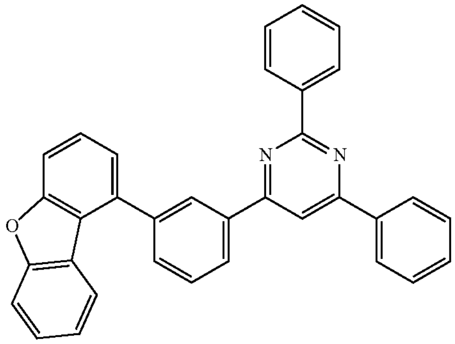
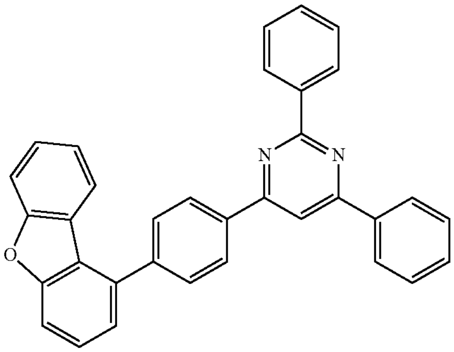

-continued
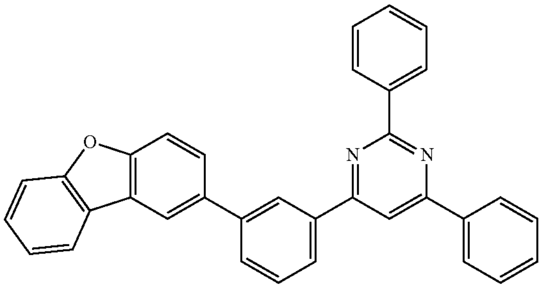
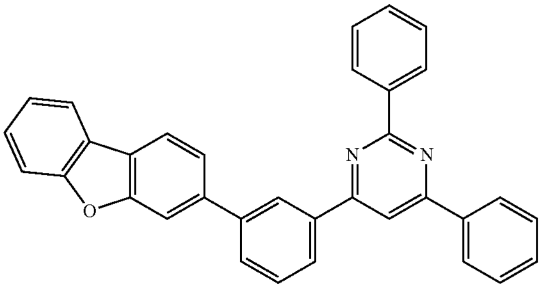
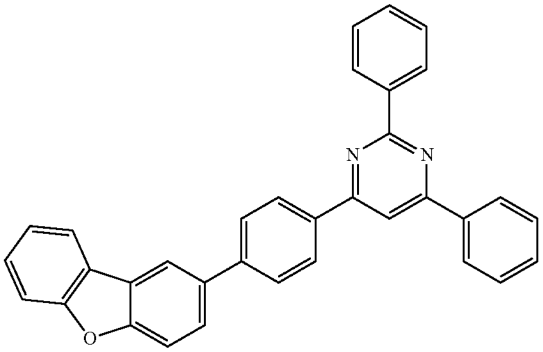
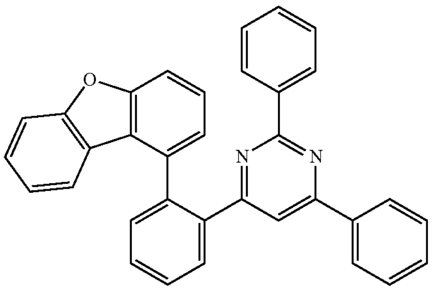
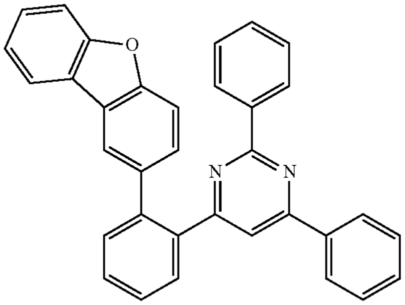
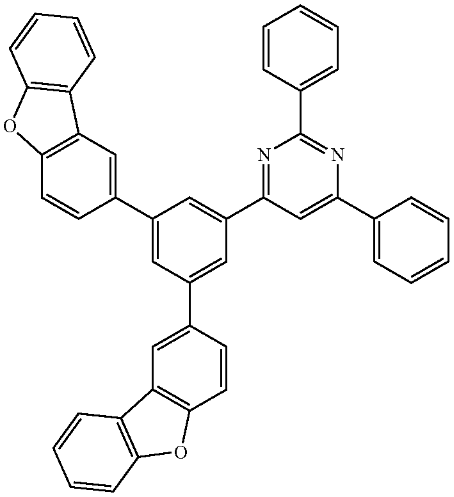
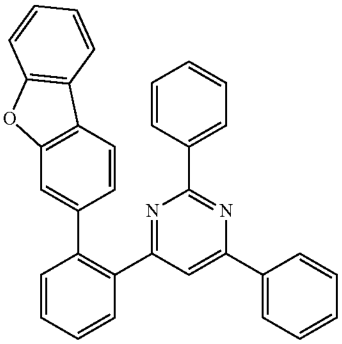
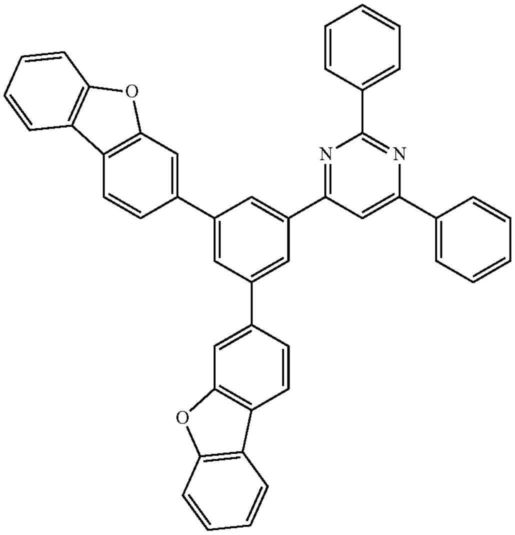

-continued
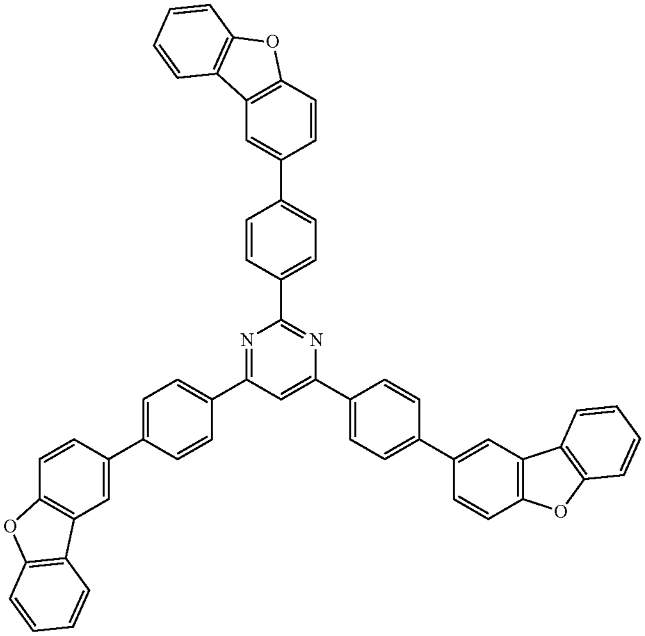
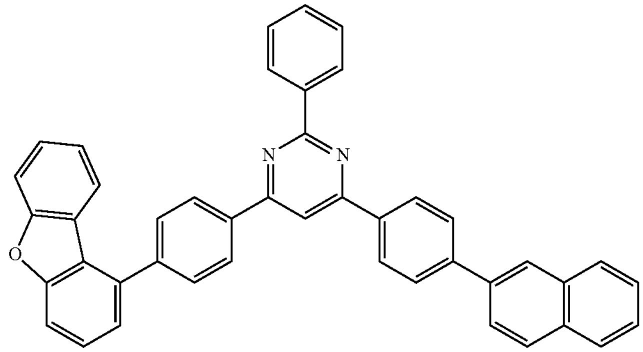
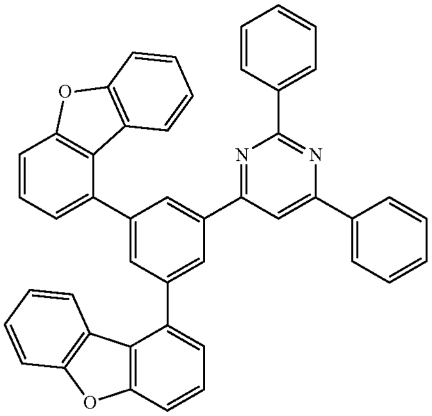
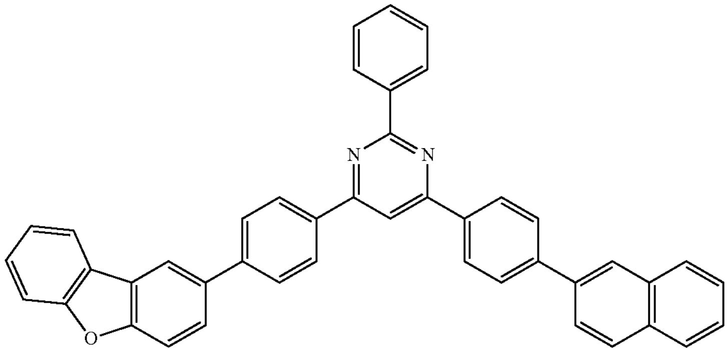

-continued
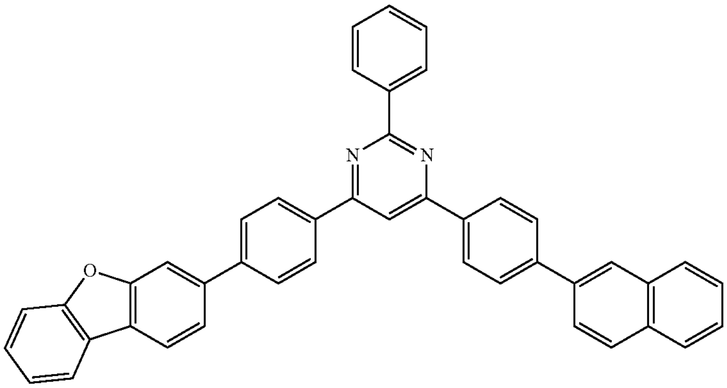
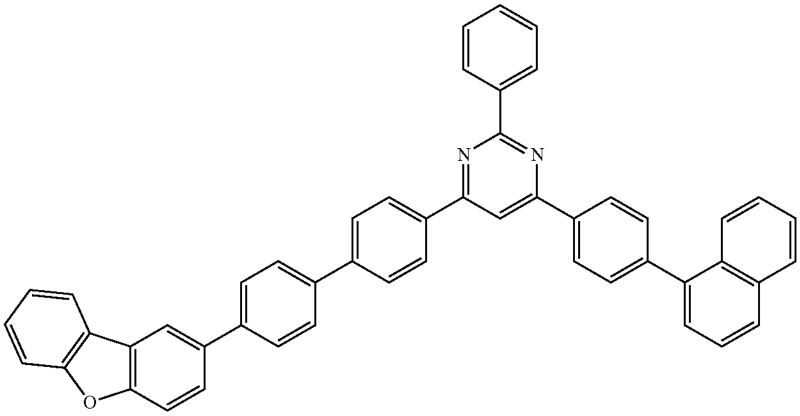
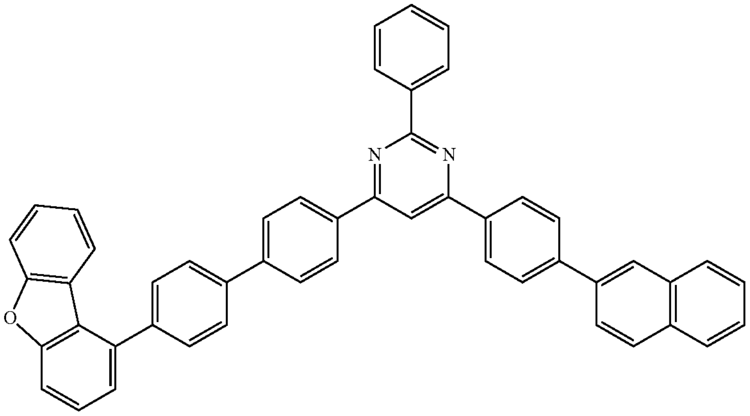
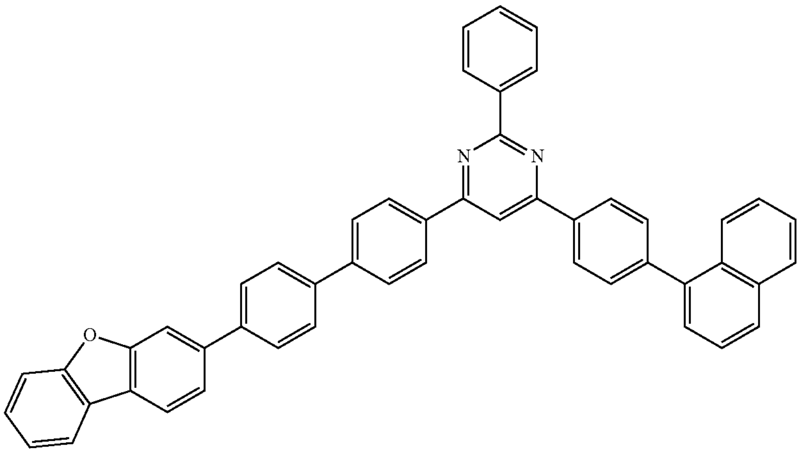

-continued
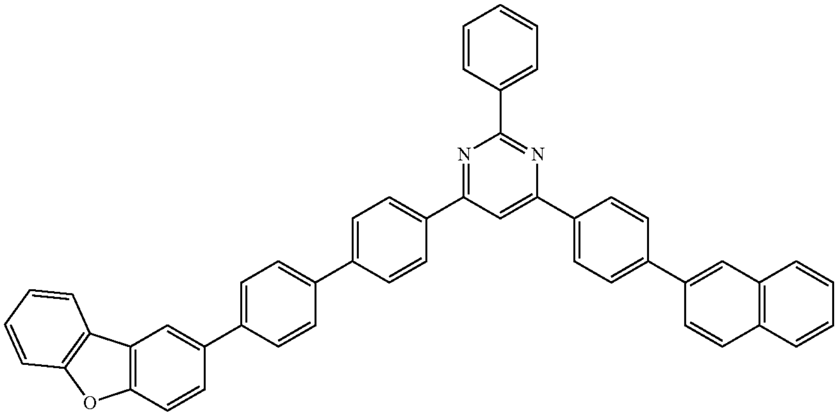
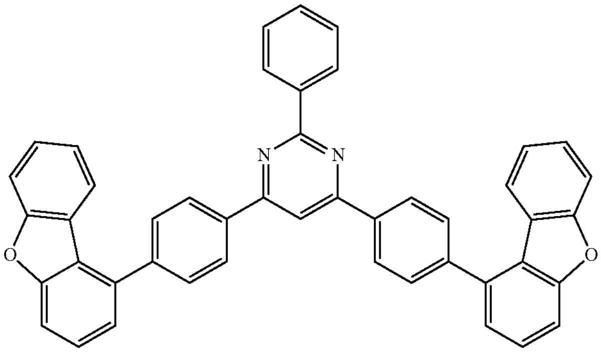
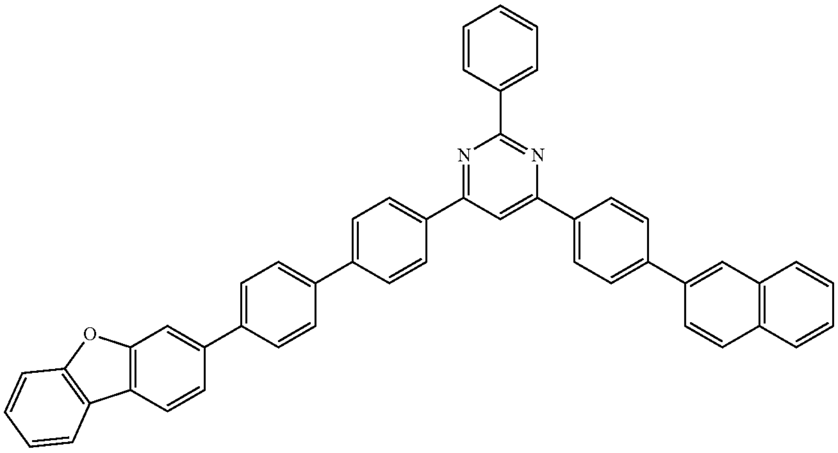
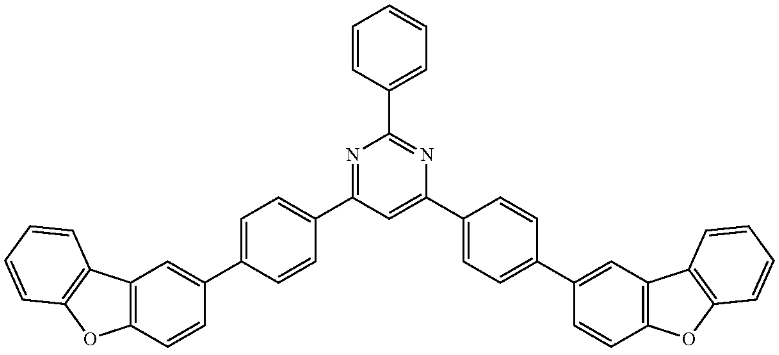

-continued
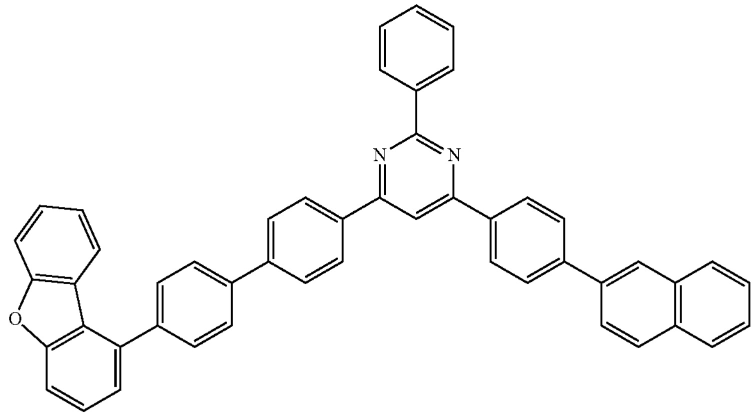
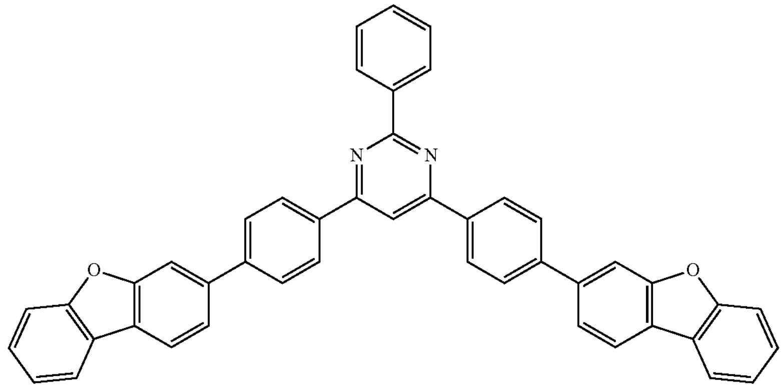
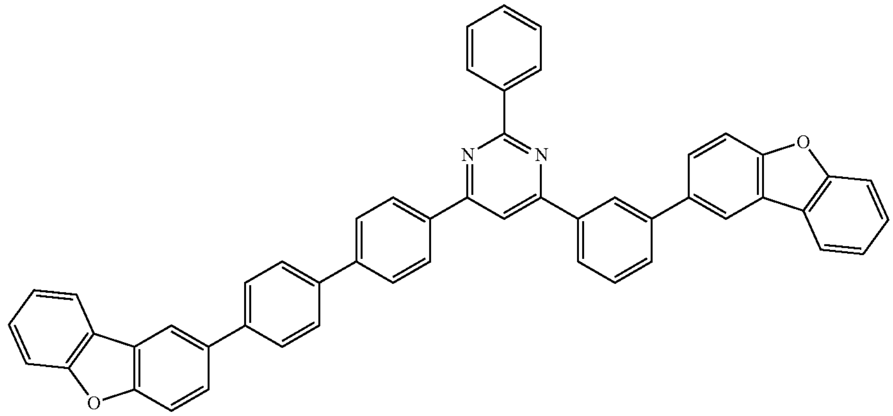
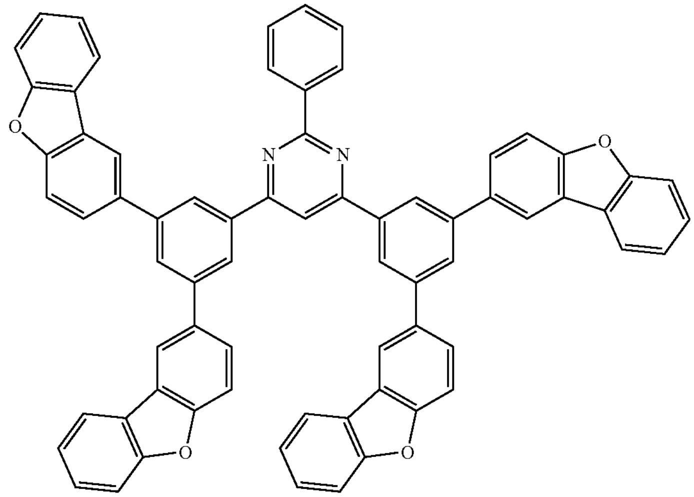

-continued
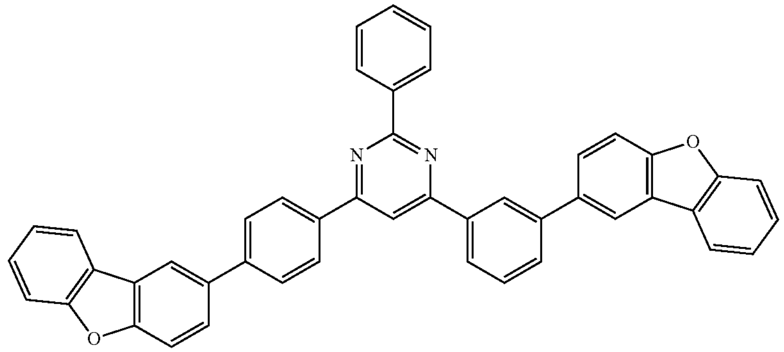
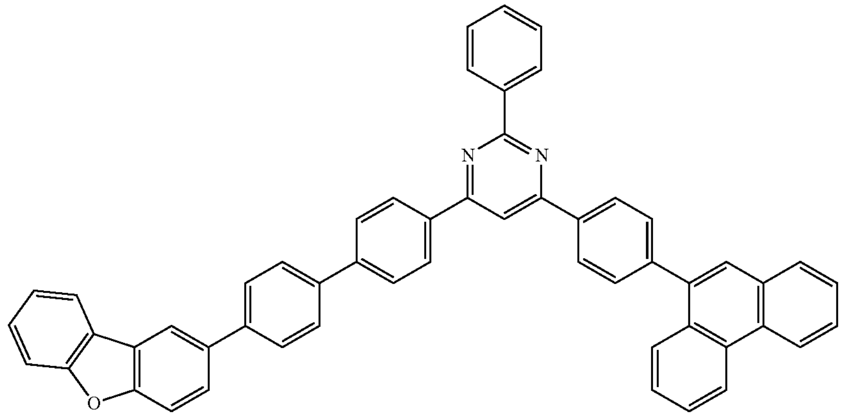
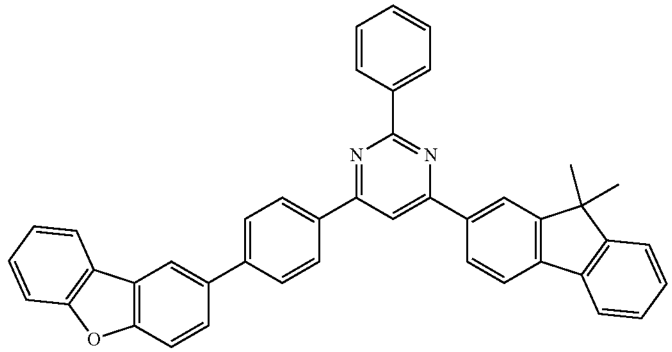
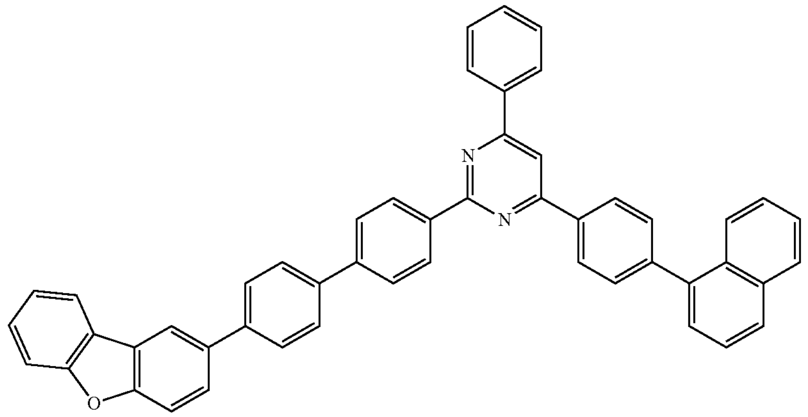

-continued
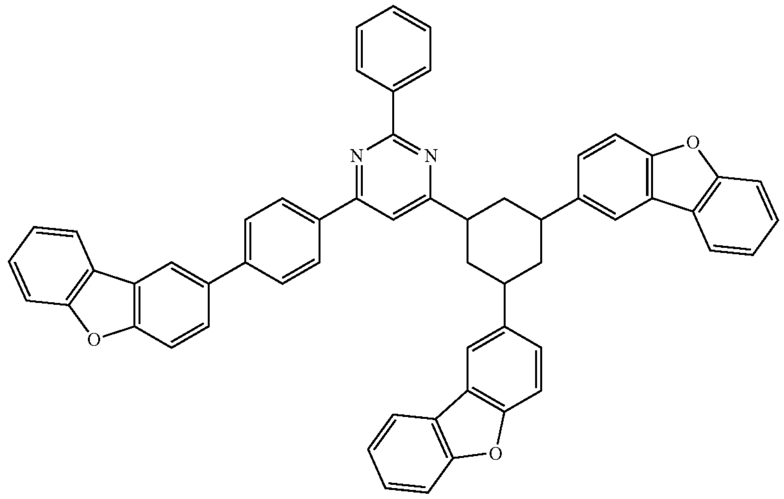
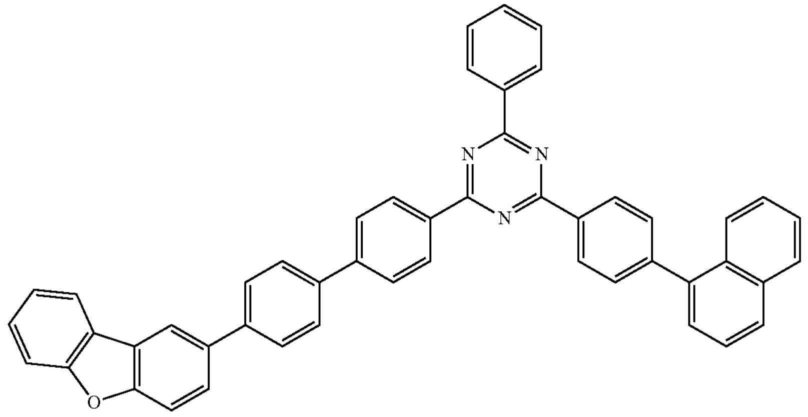
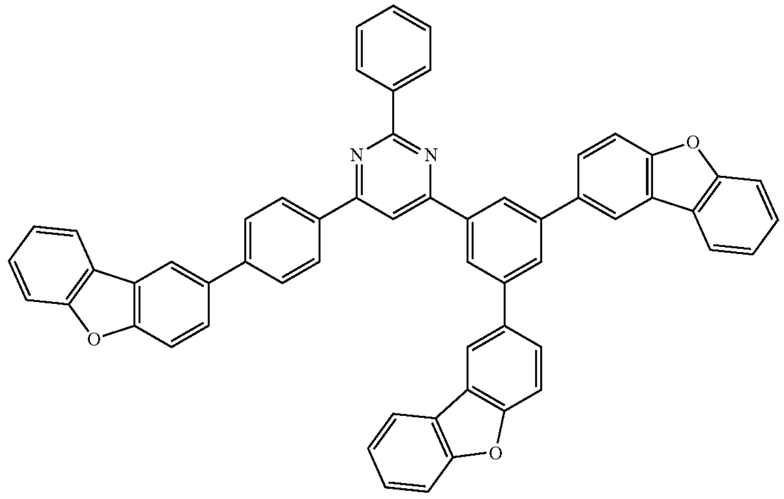

-continued
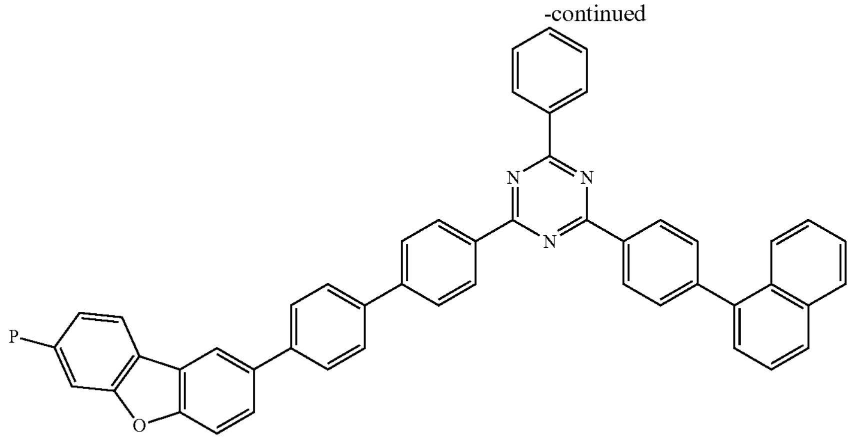
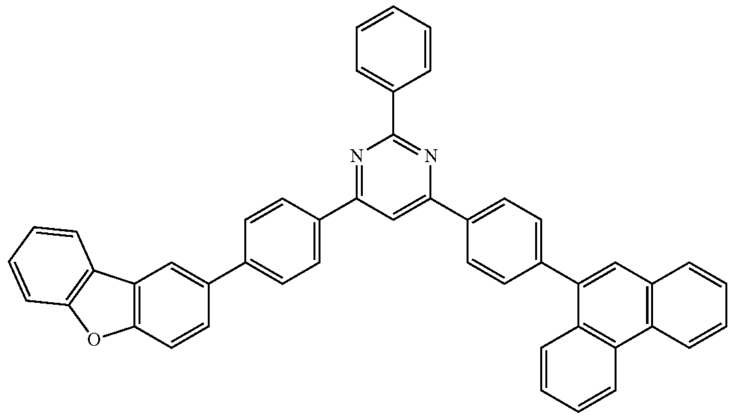
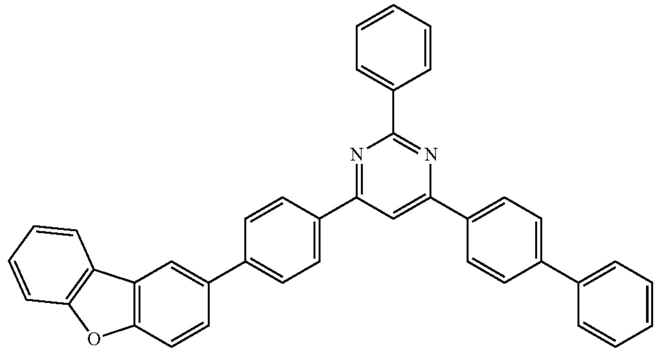
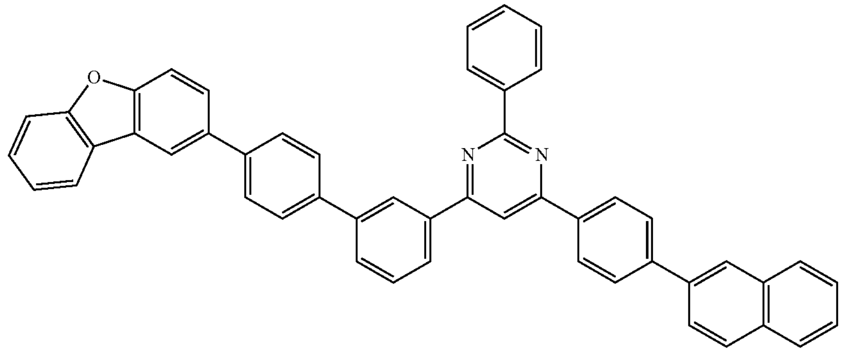

-continued
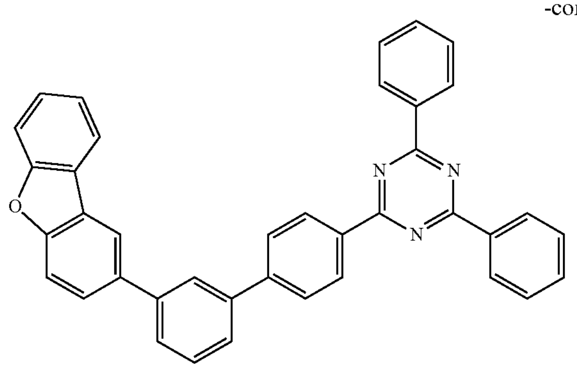
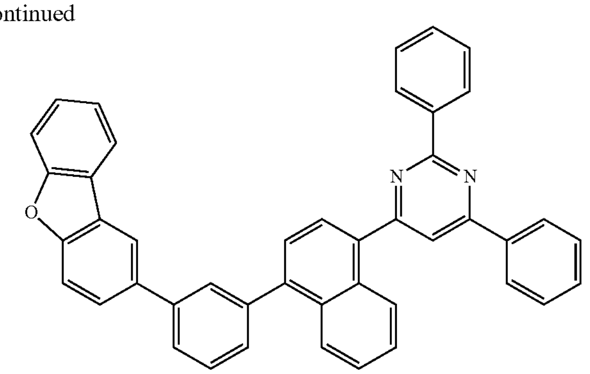
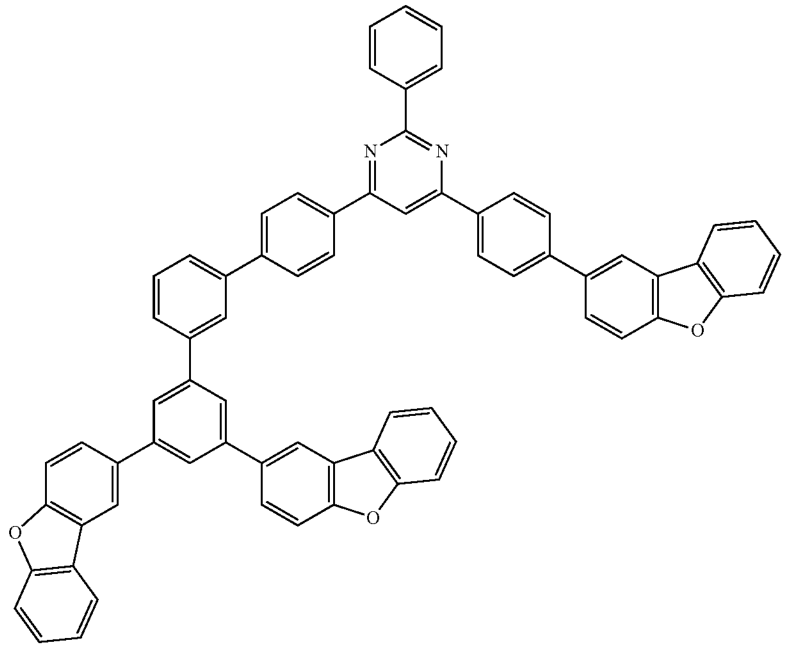
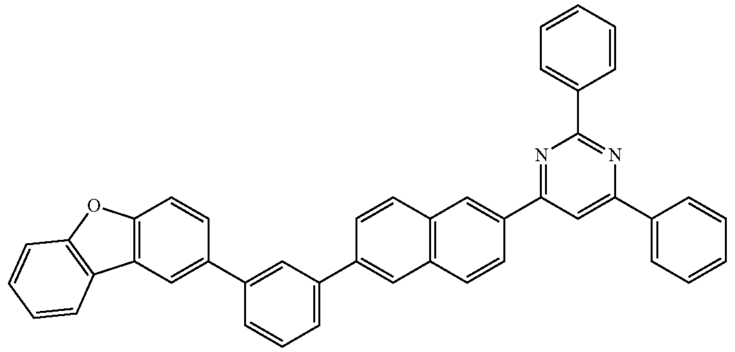

-continued
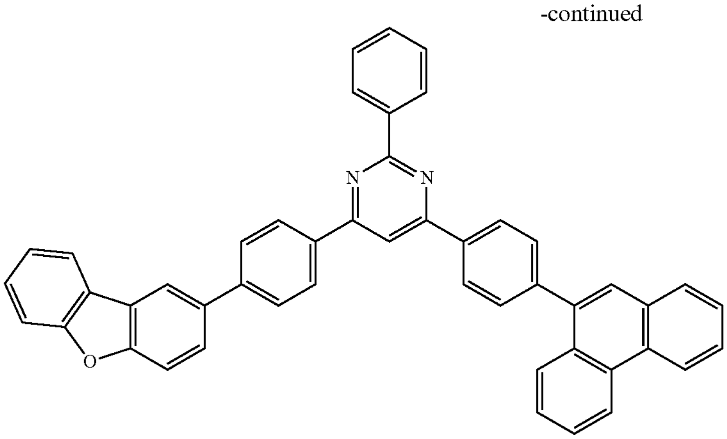
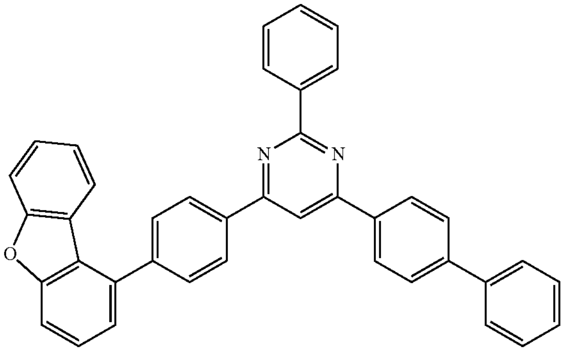
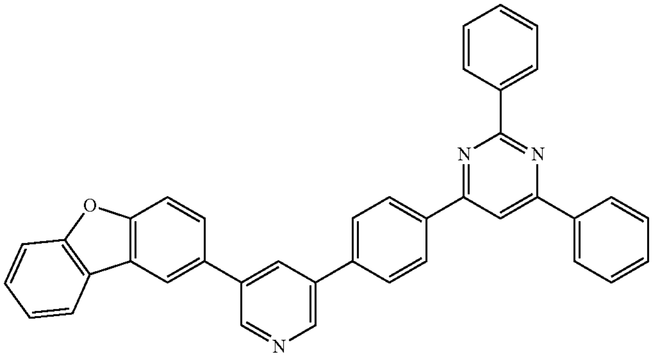
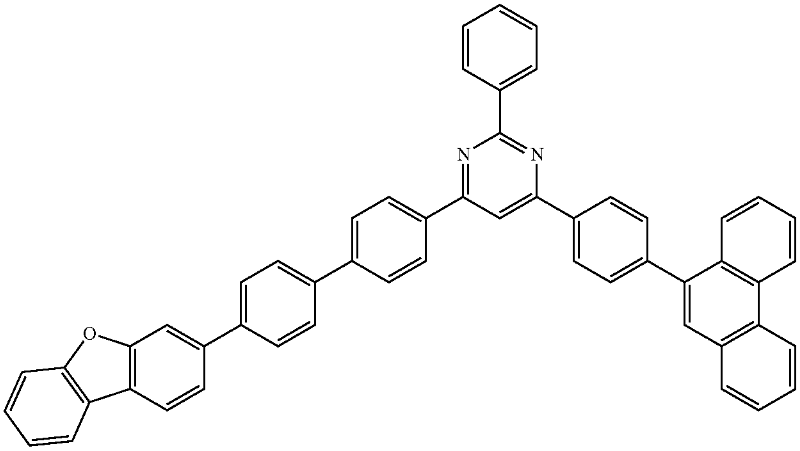

-continued
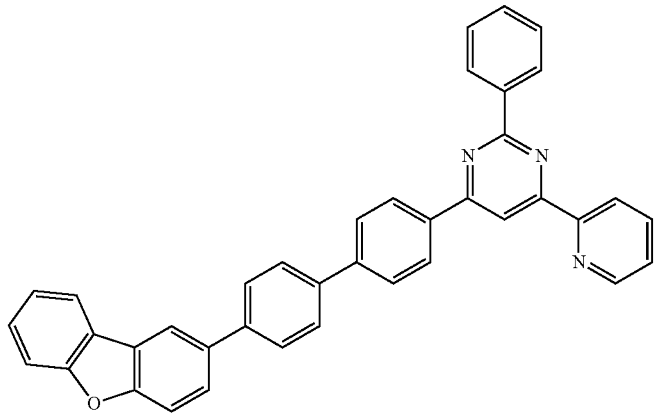
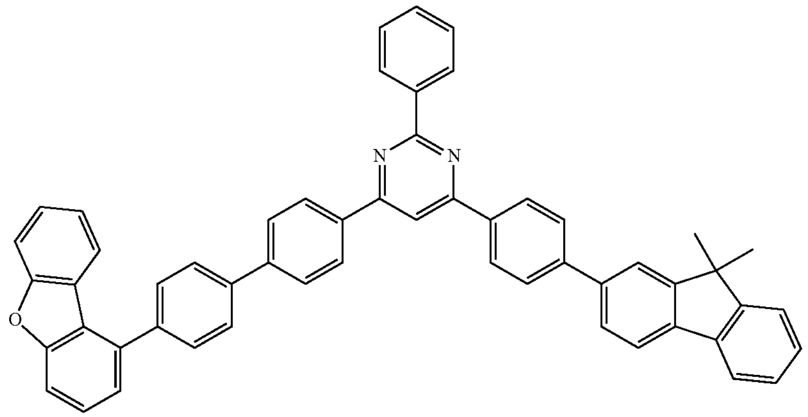
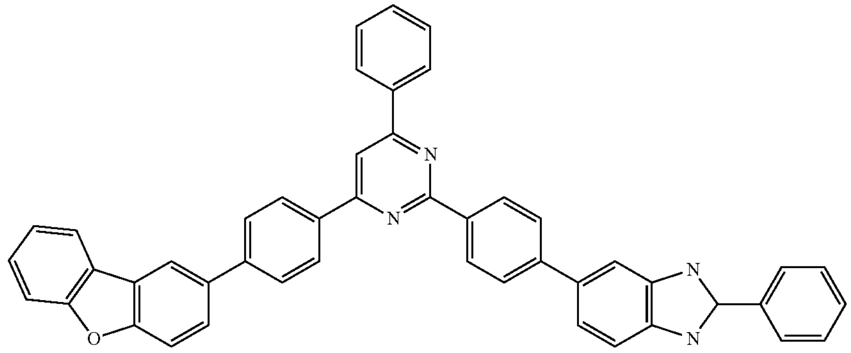
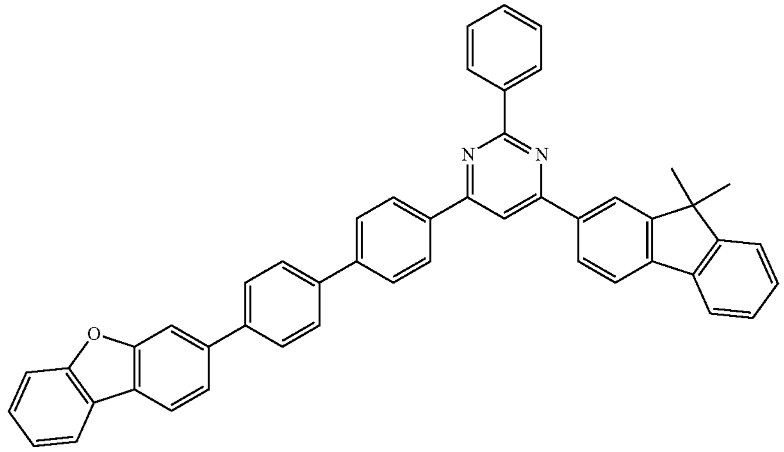

-continued
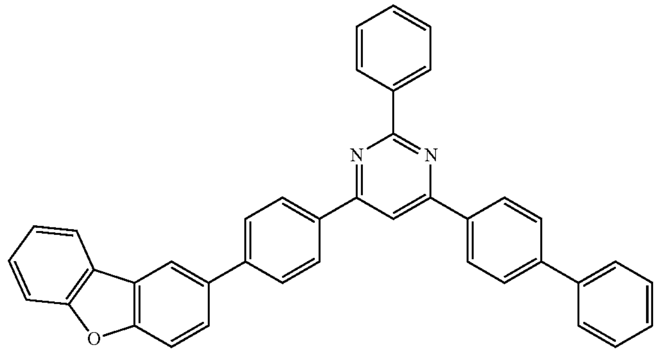
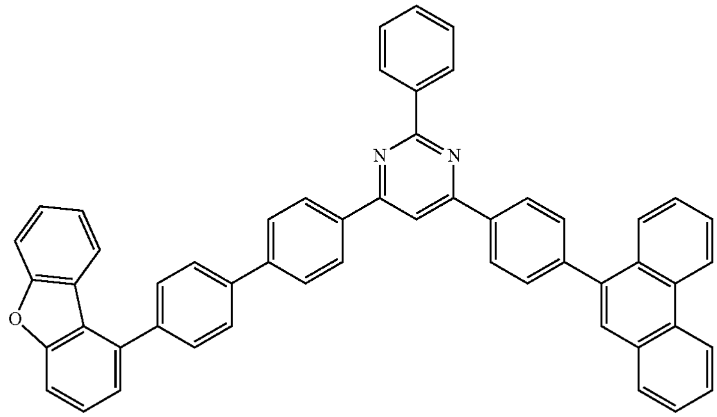
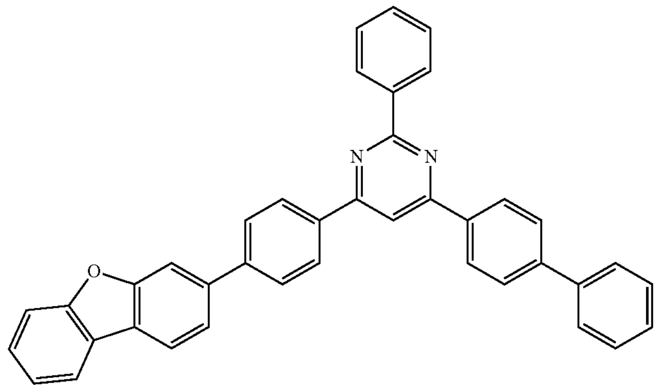
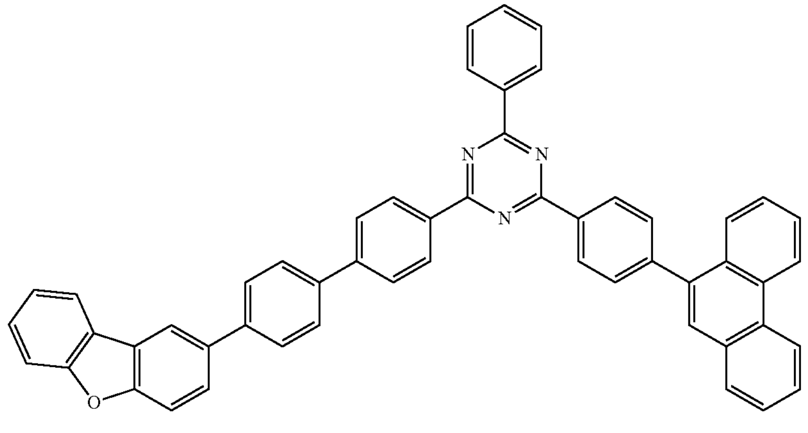

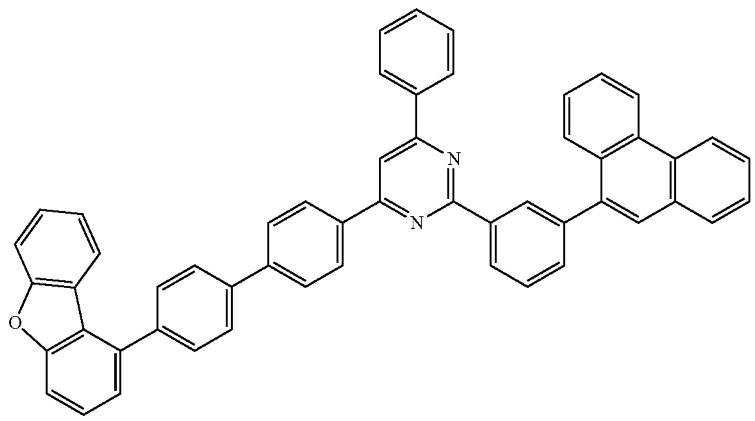
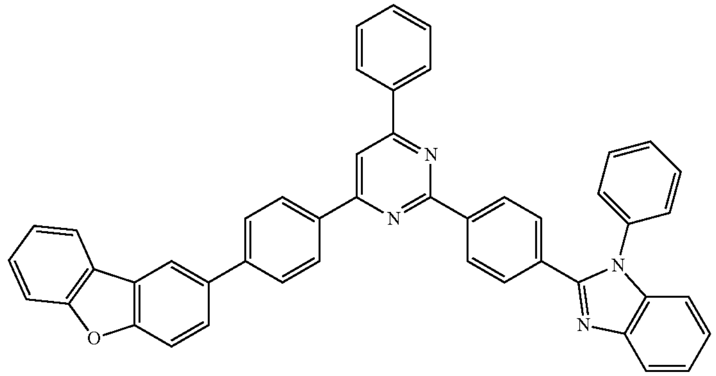
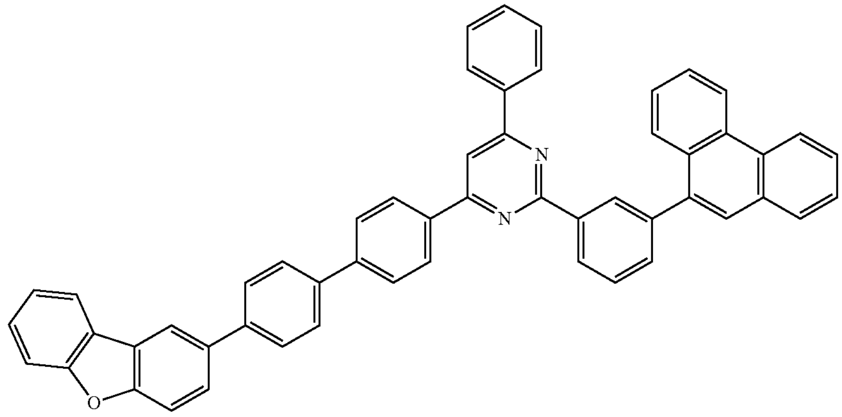
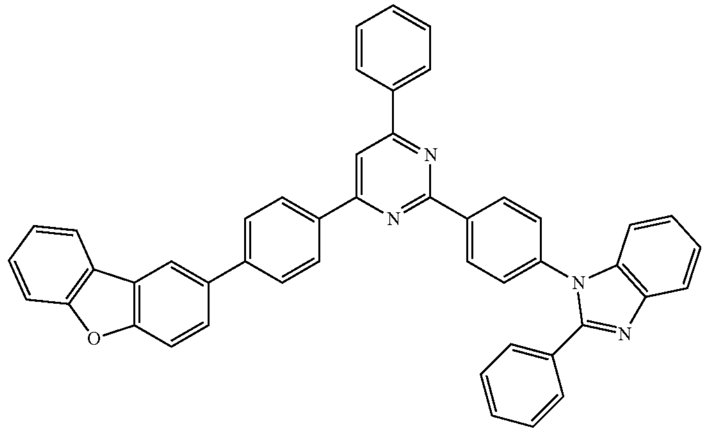

-continued
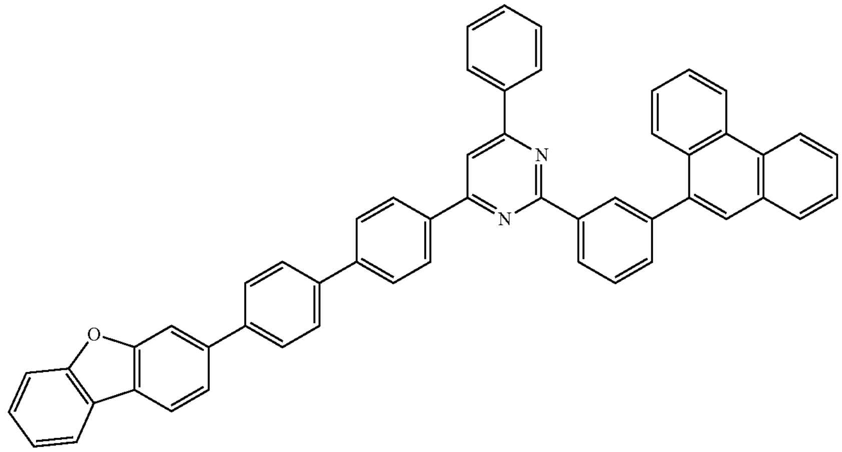
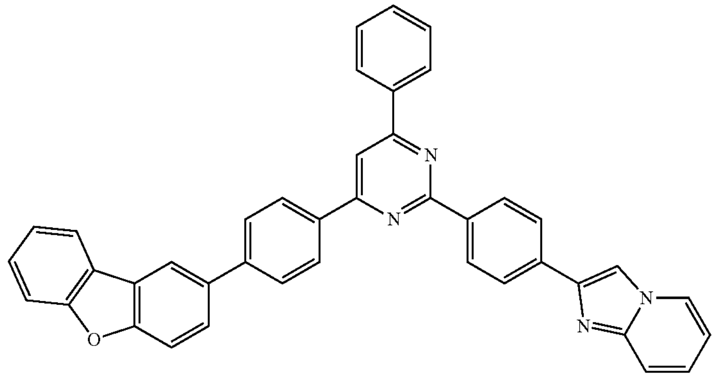
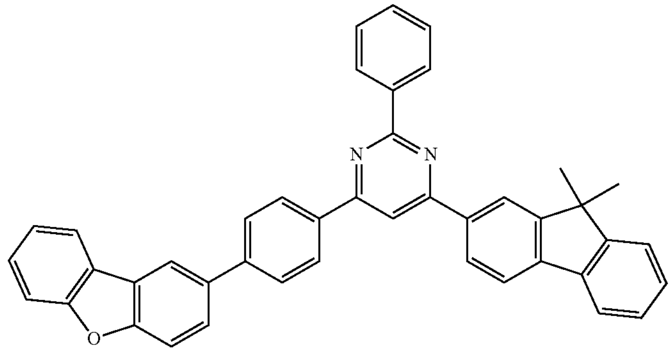
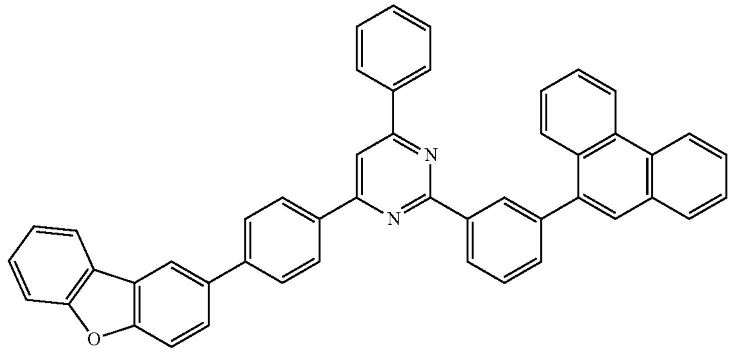

-continued
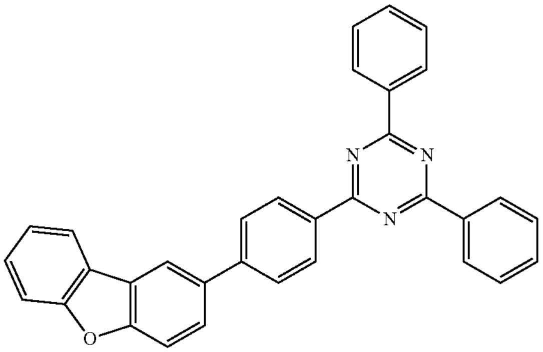
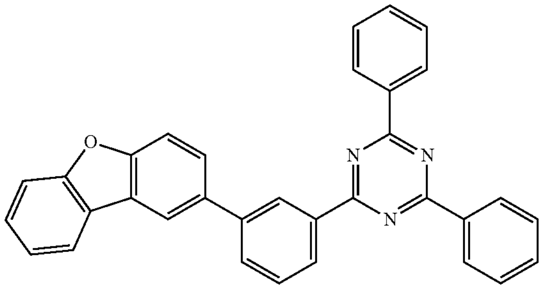
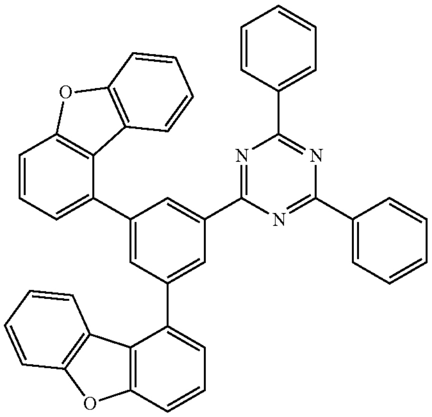
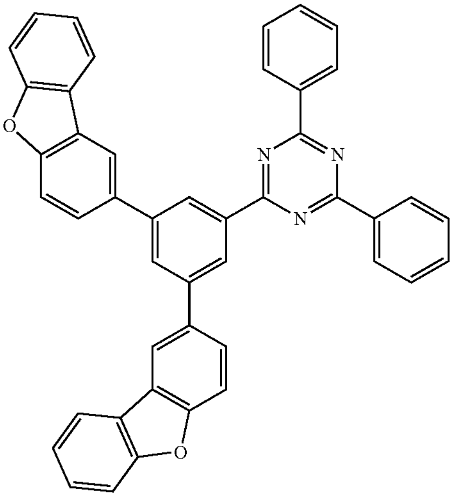
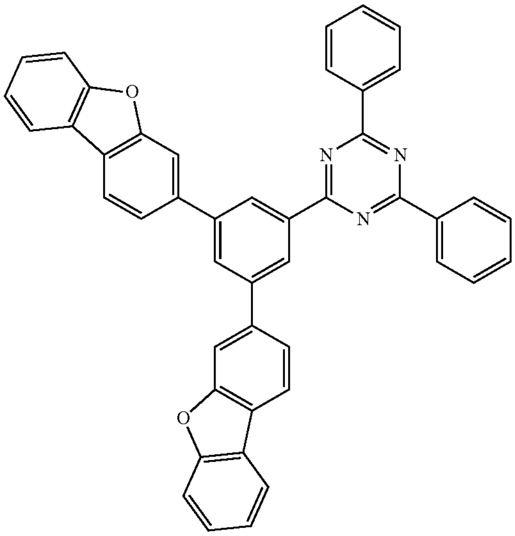

-continued
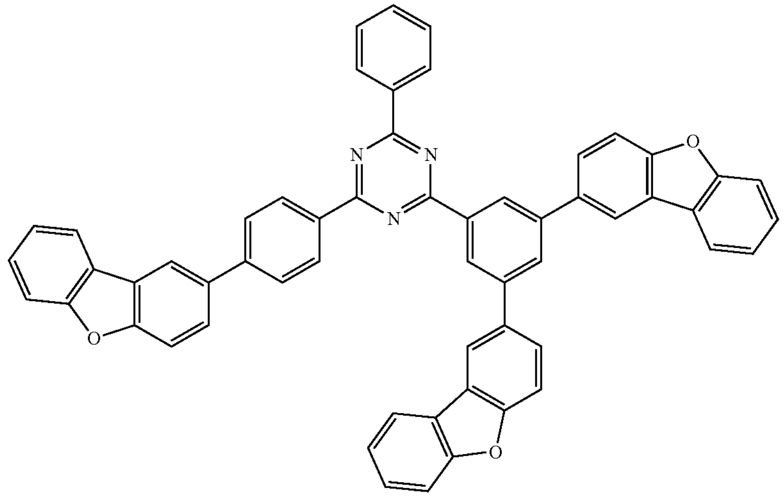
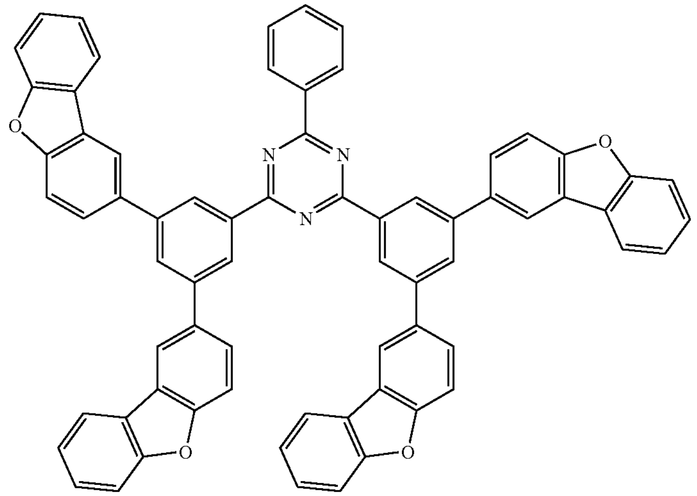
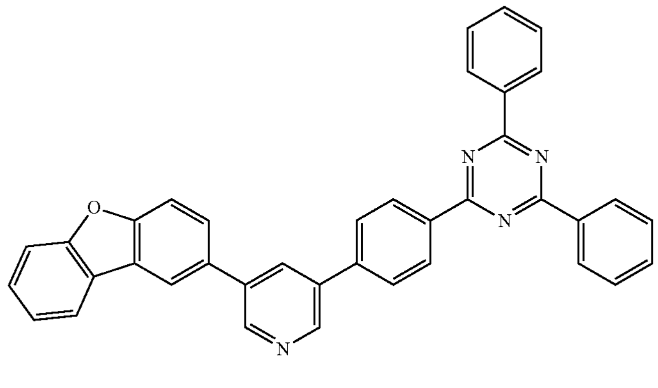

-continued
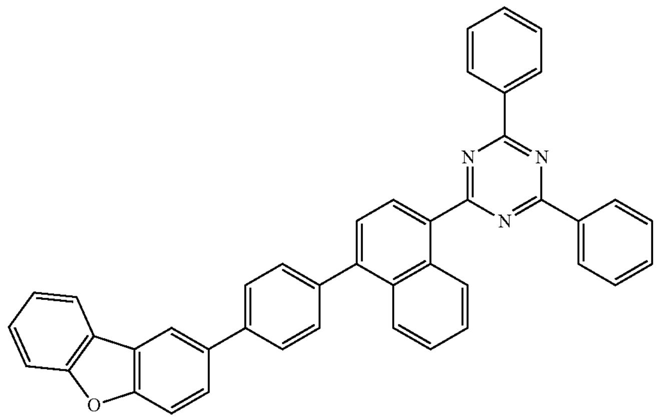
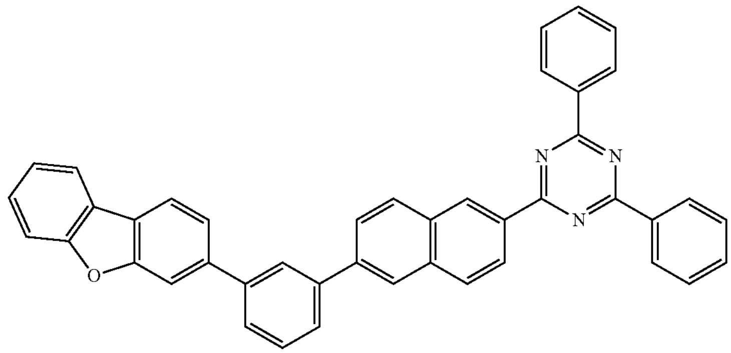
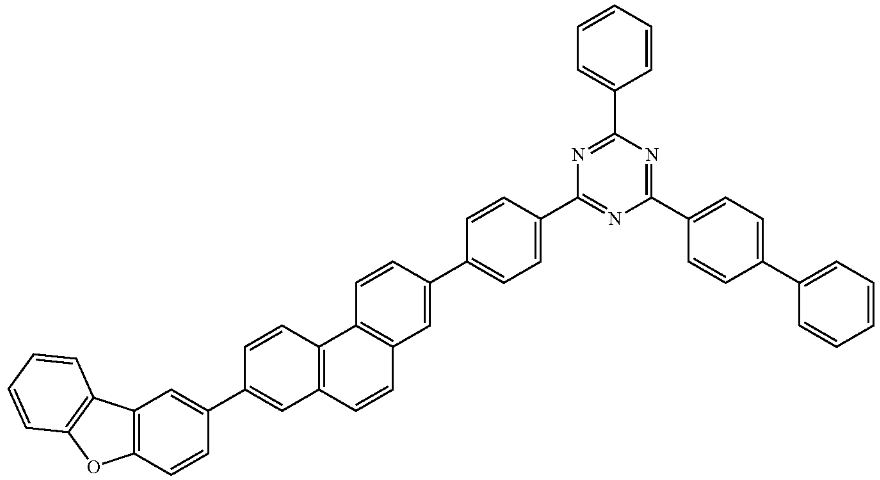
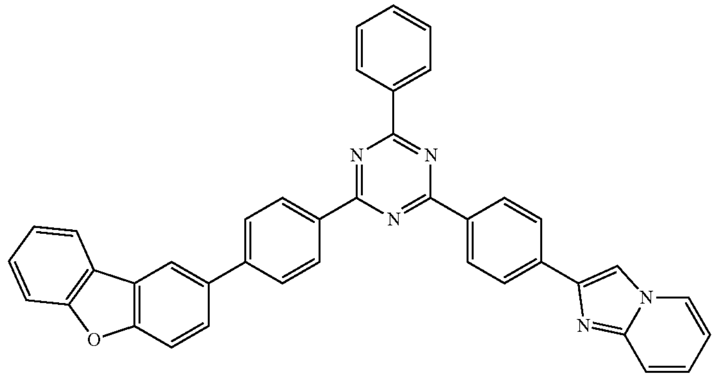

-continued
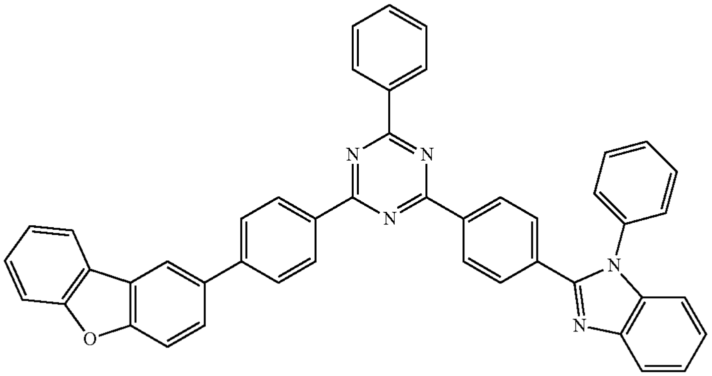
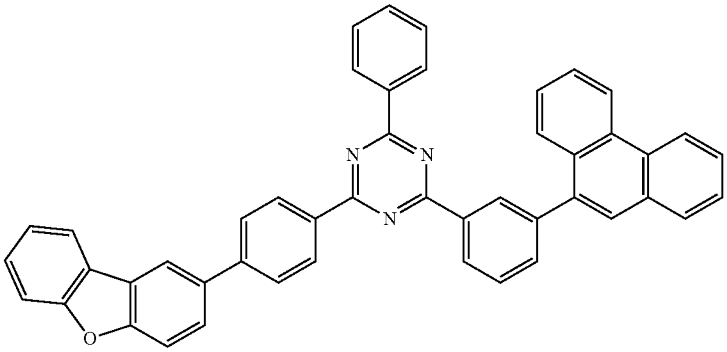
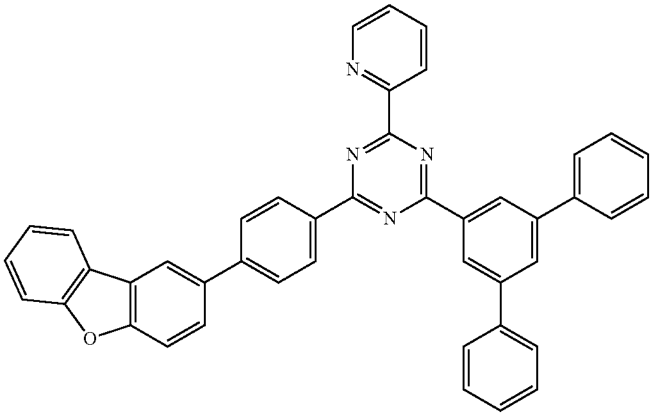
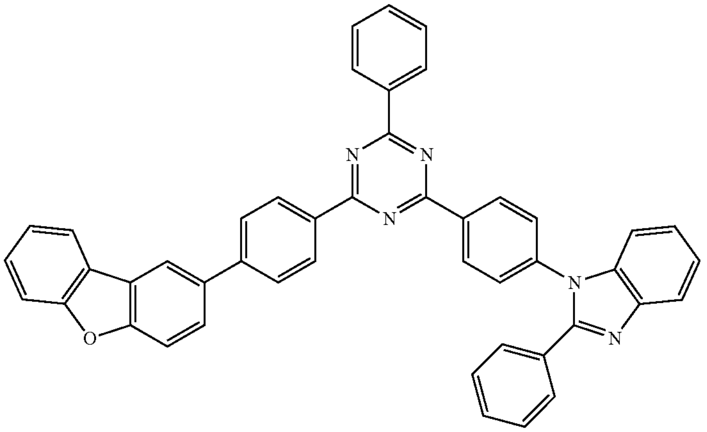

-continued
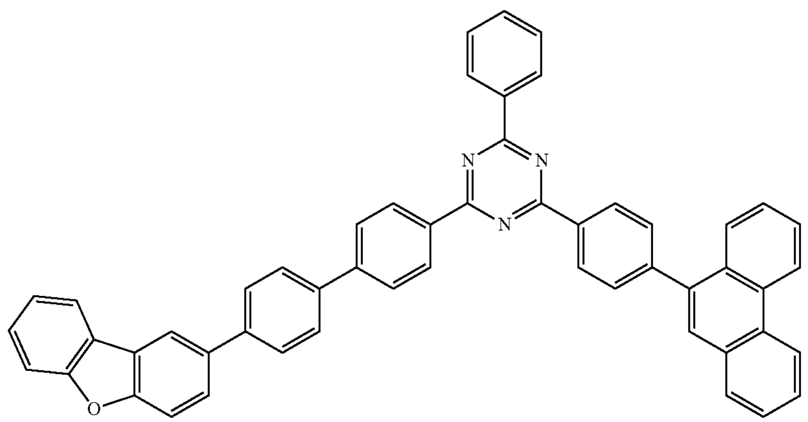
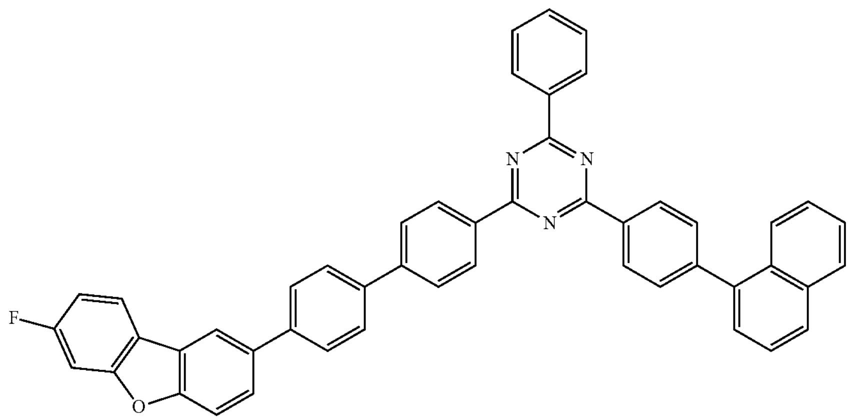
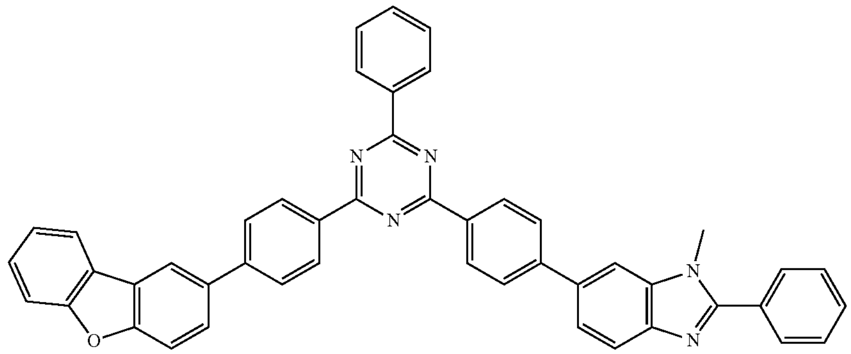
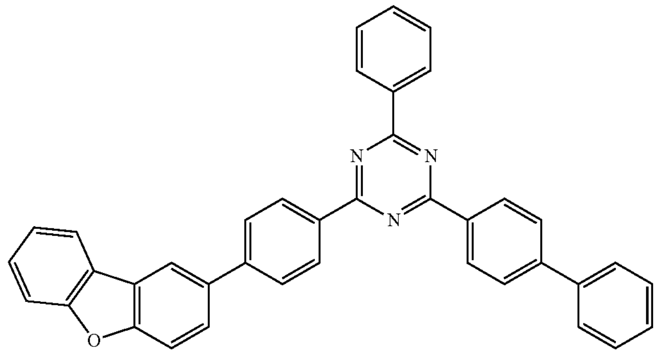

-continued
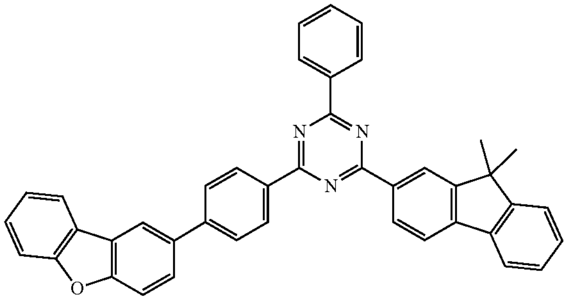
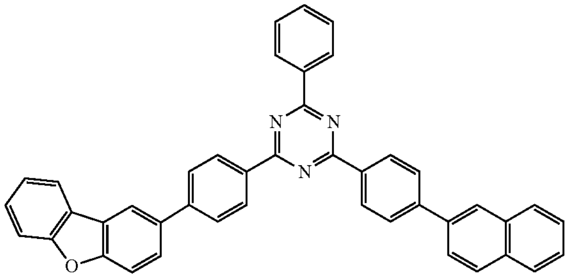
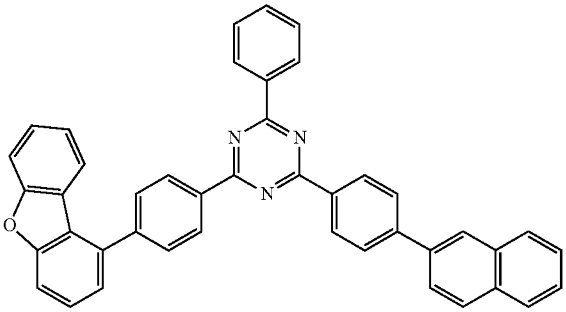
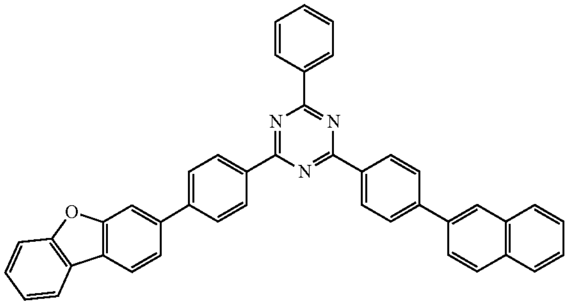
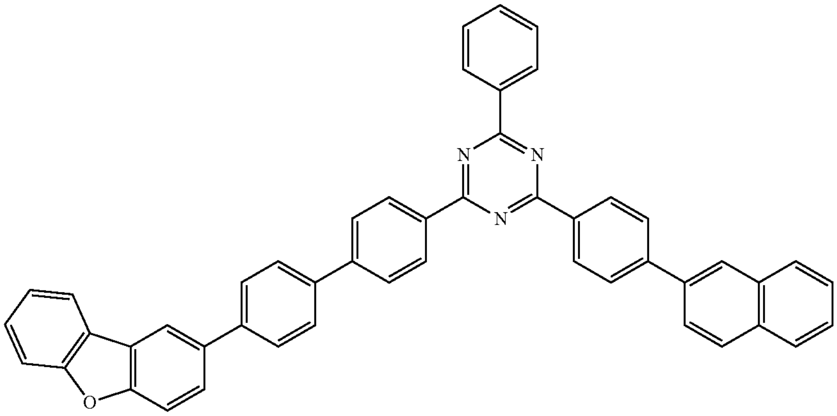
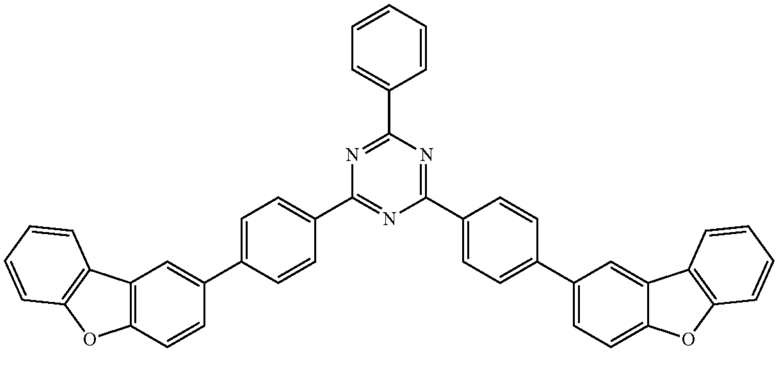

-continued
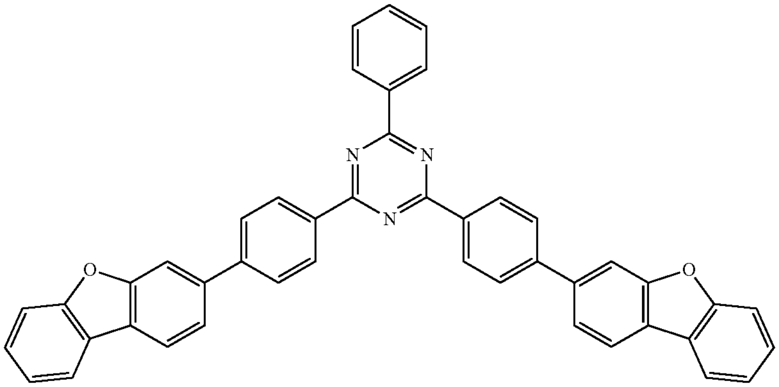
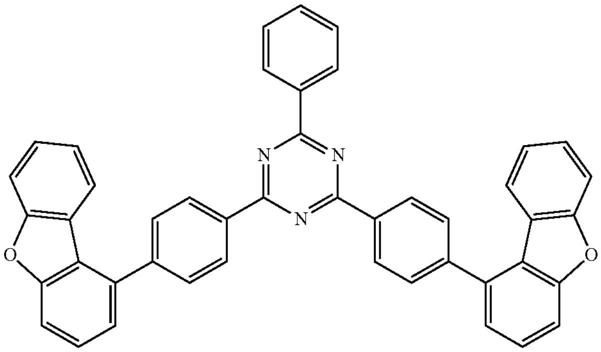
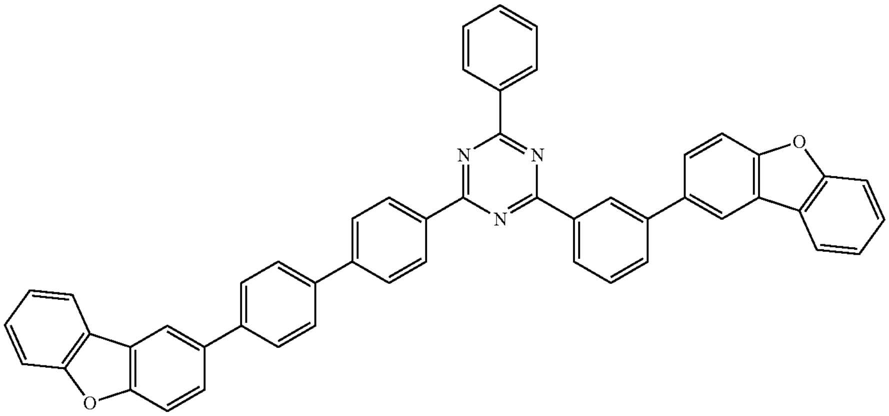
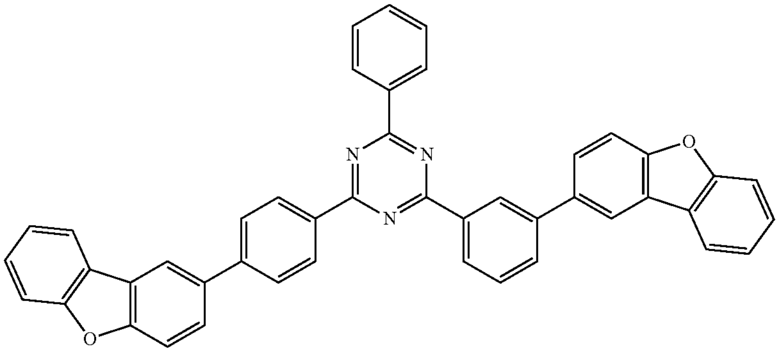

-continued
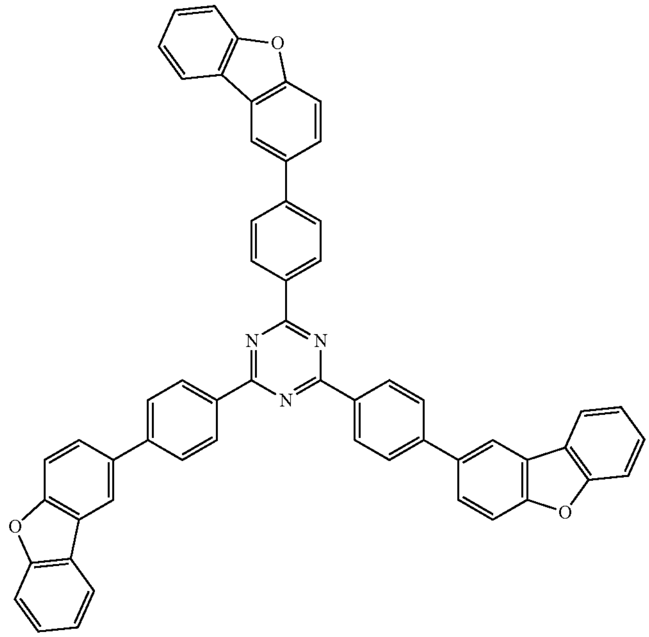
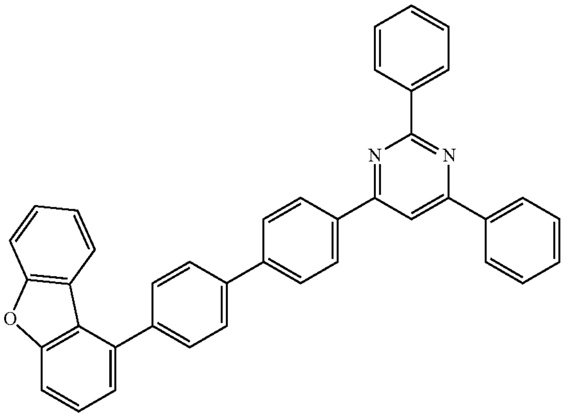
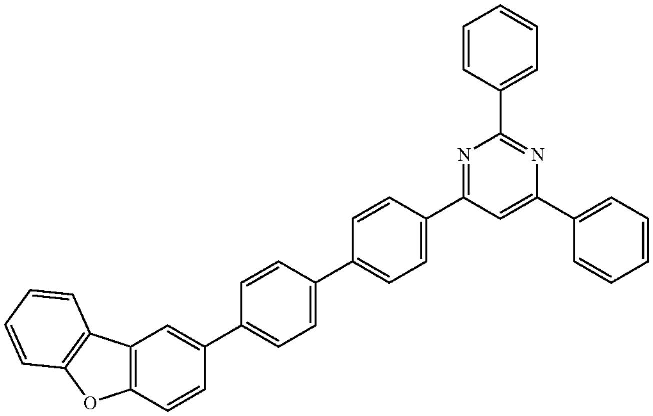

-continued
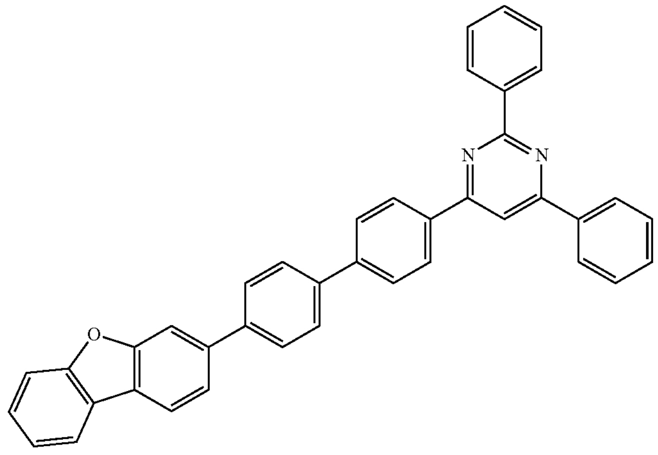
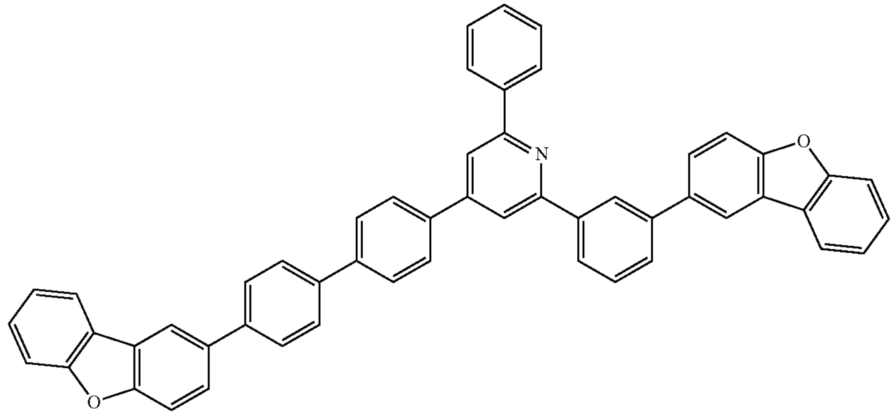
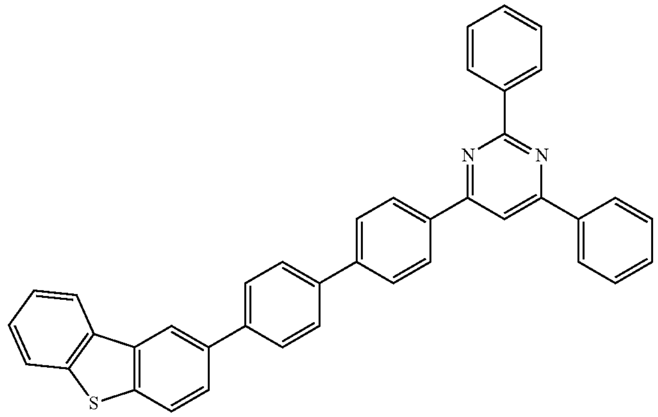
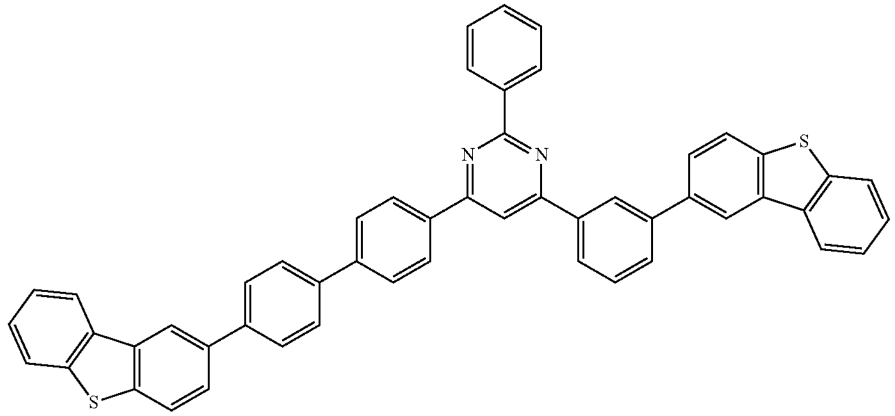

-continued
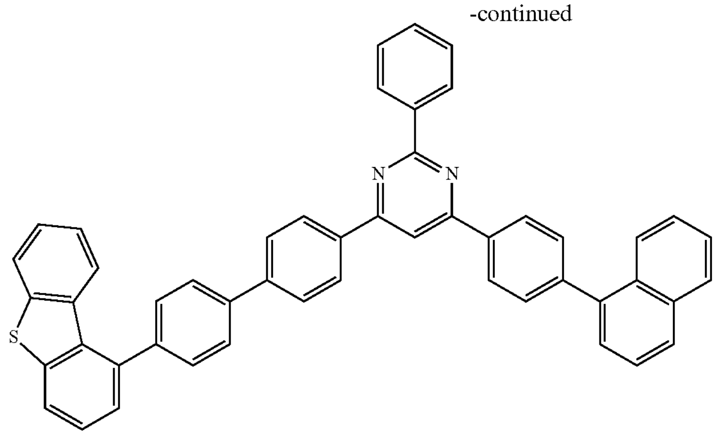
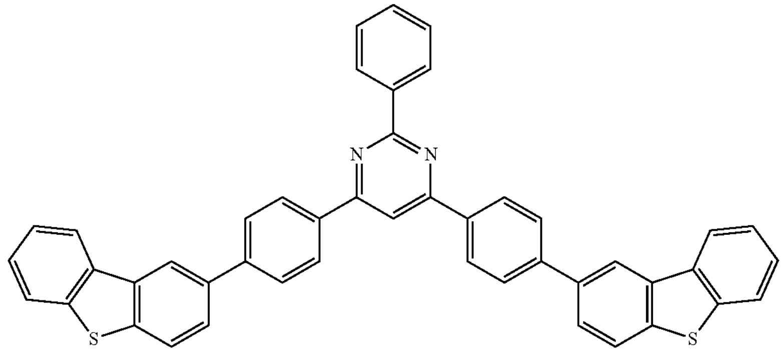
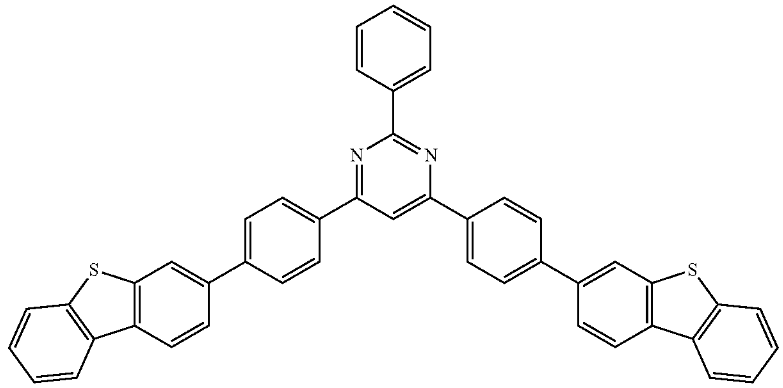
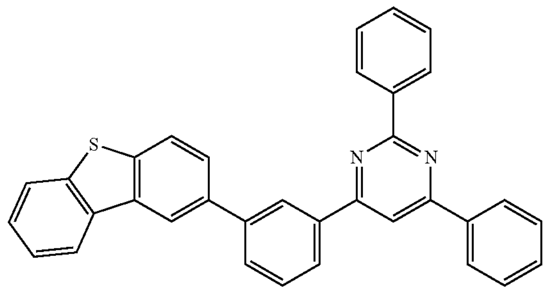

-continued
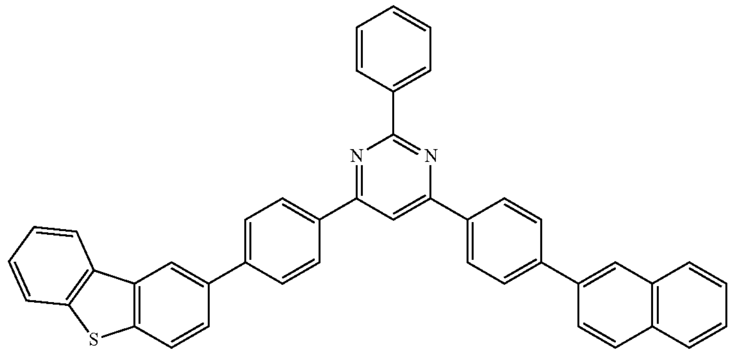
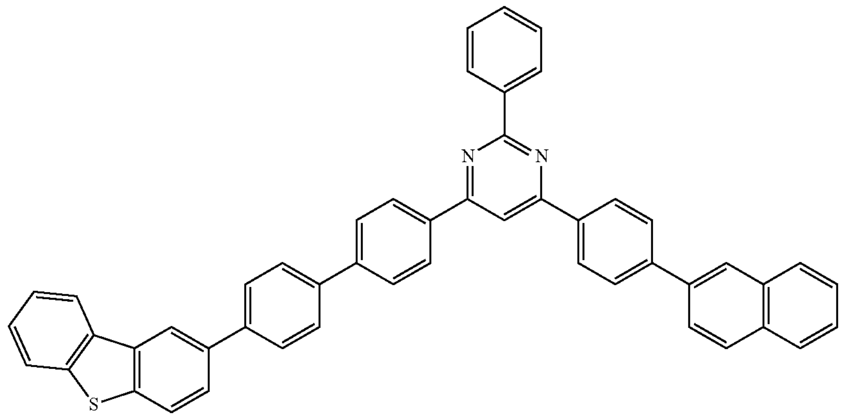
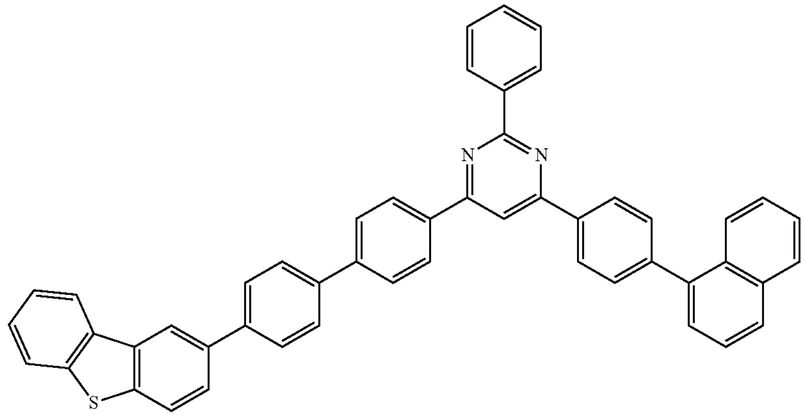
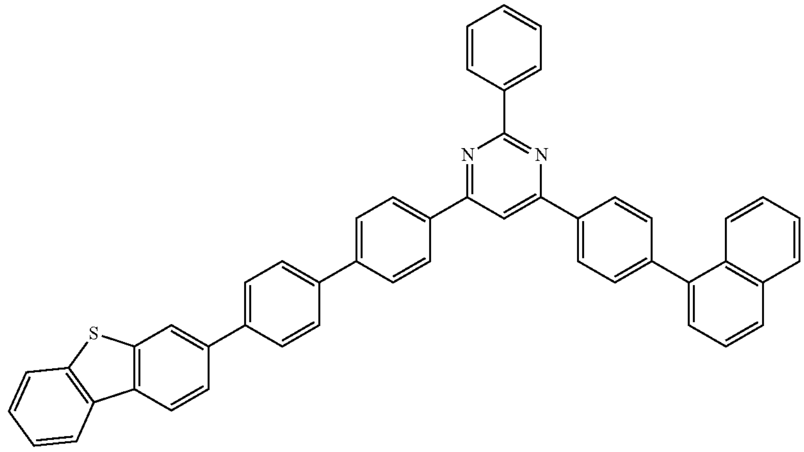

-continued
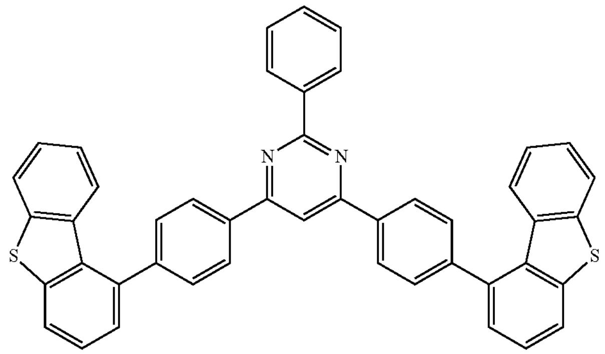
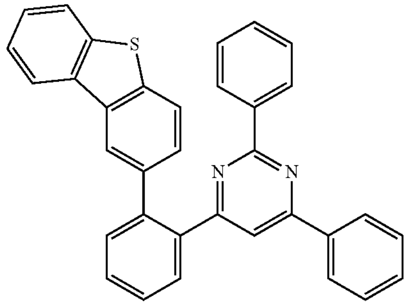
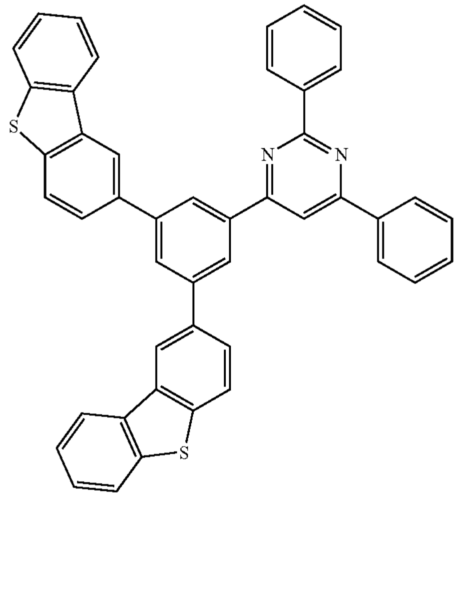

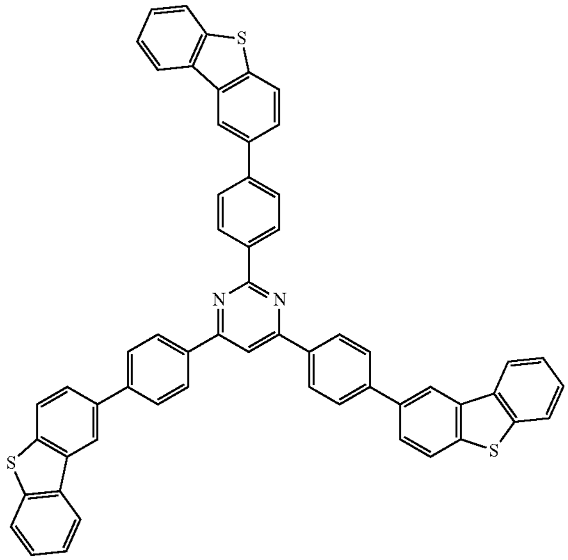
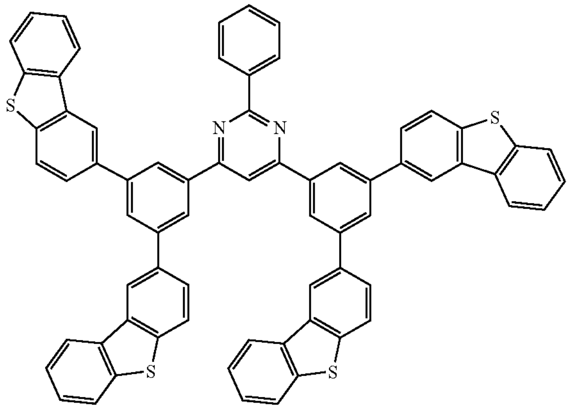
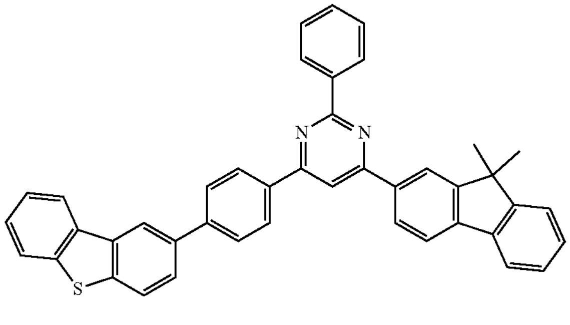

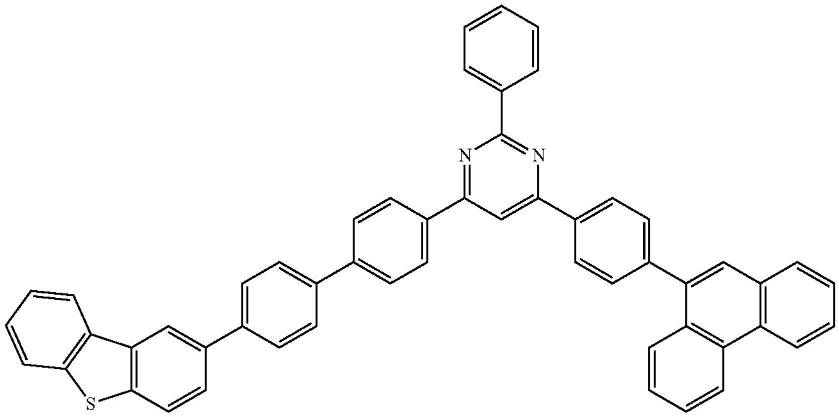
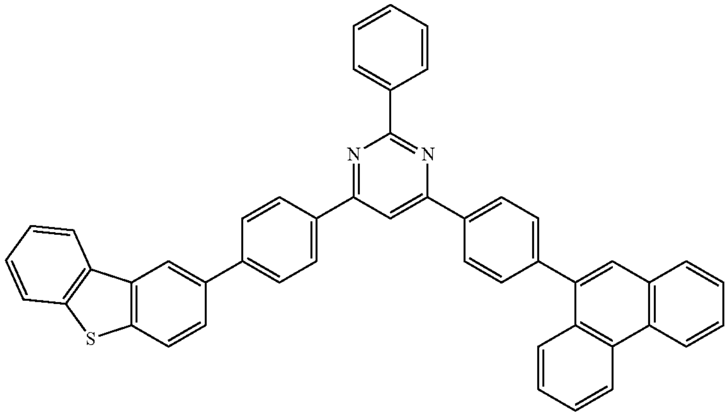
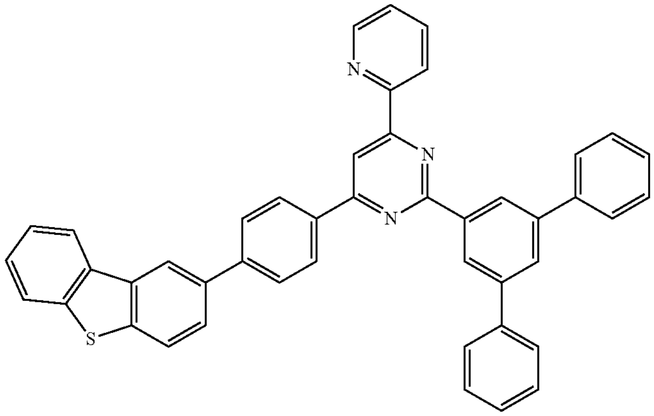
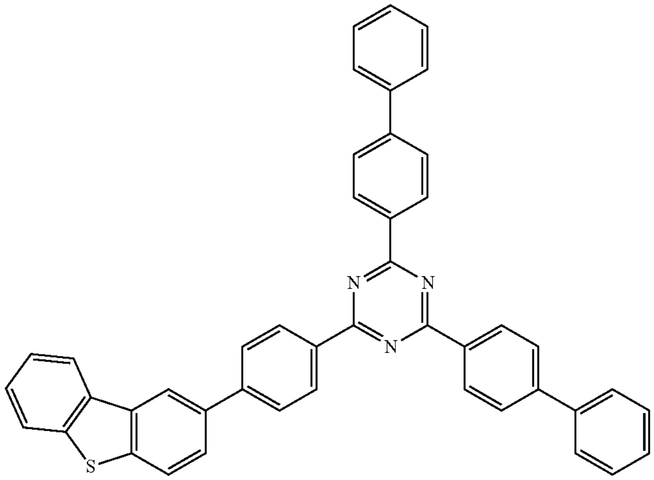

-continued
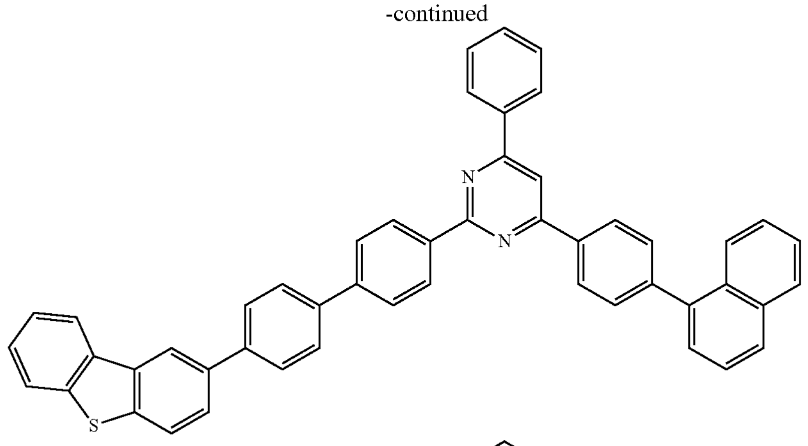
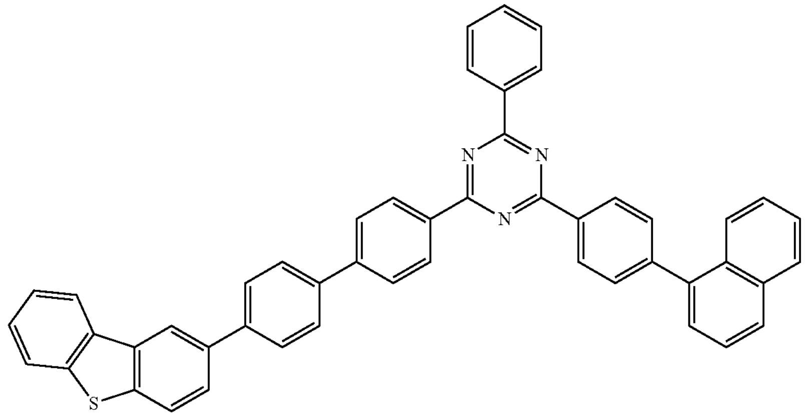
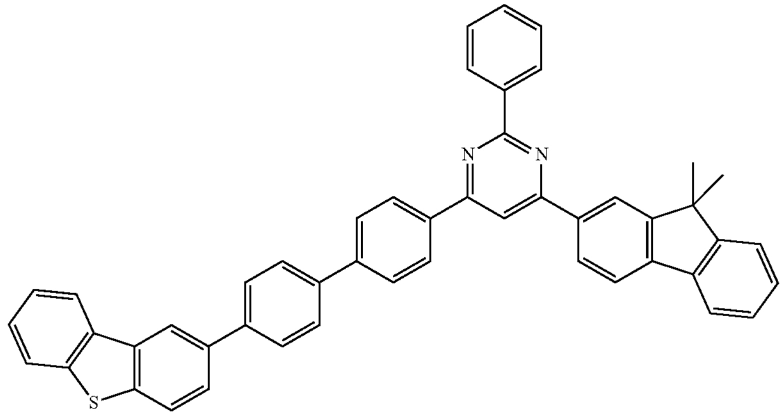
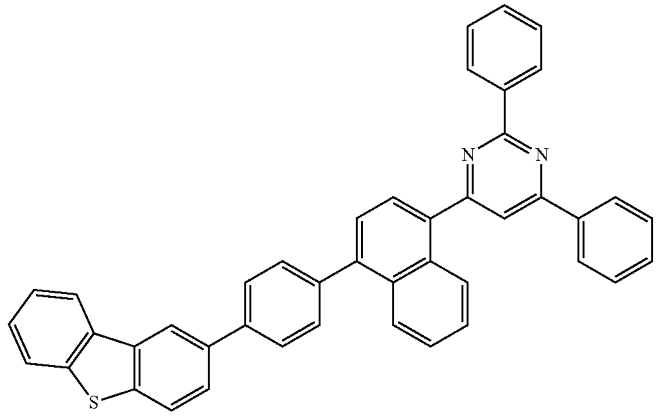

-continued
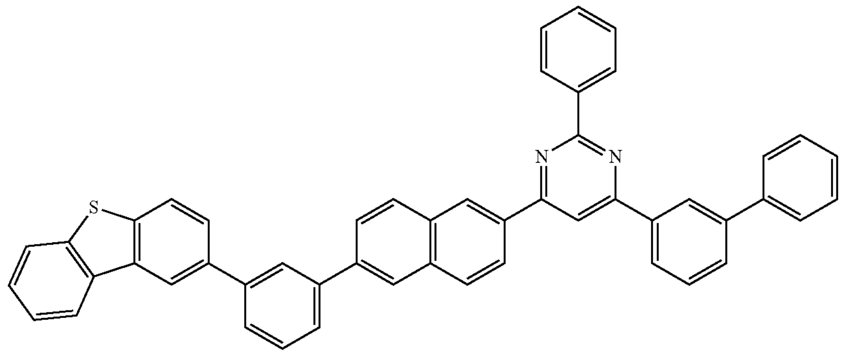
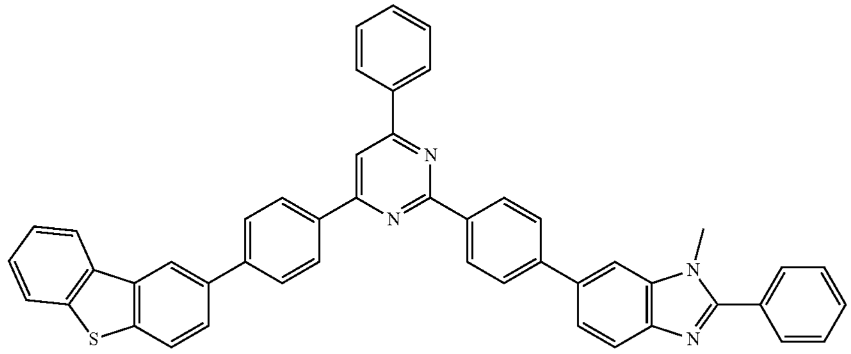
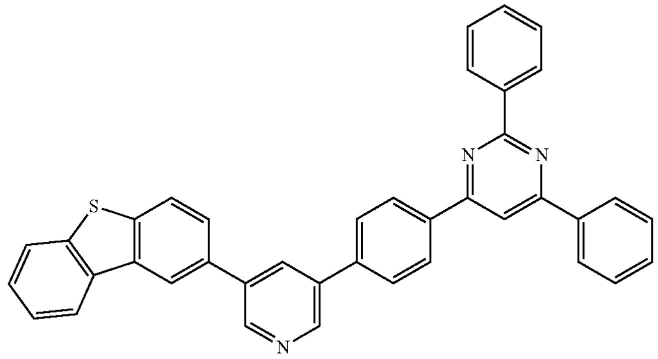
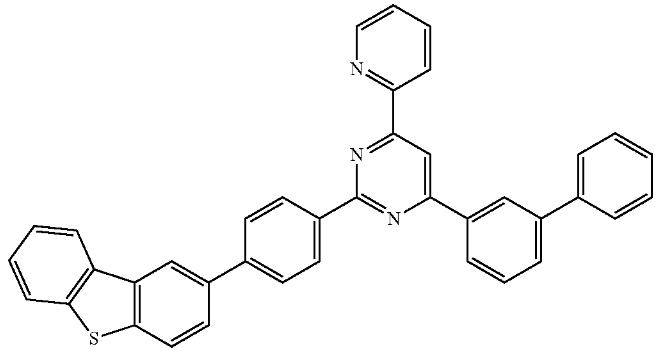

-continued
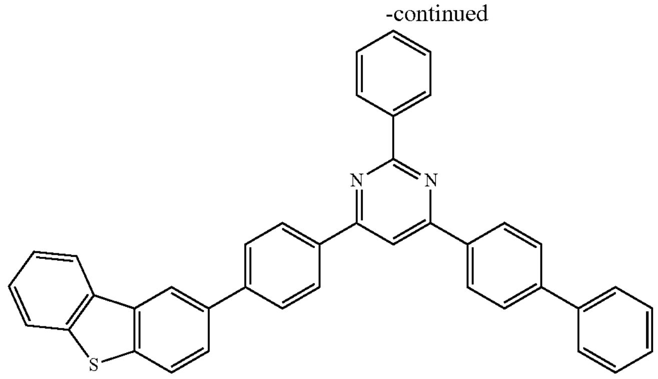
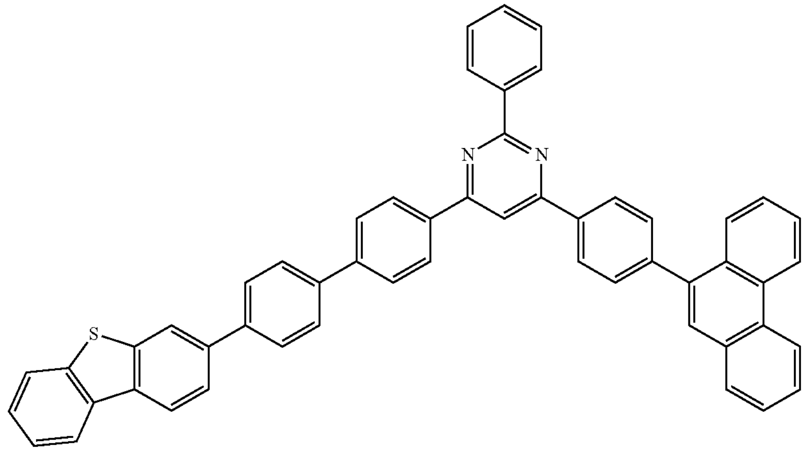
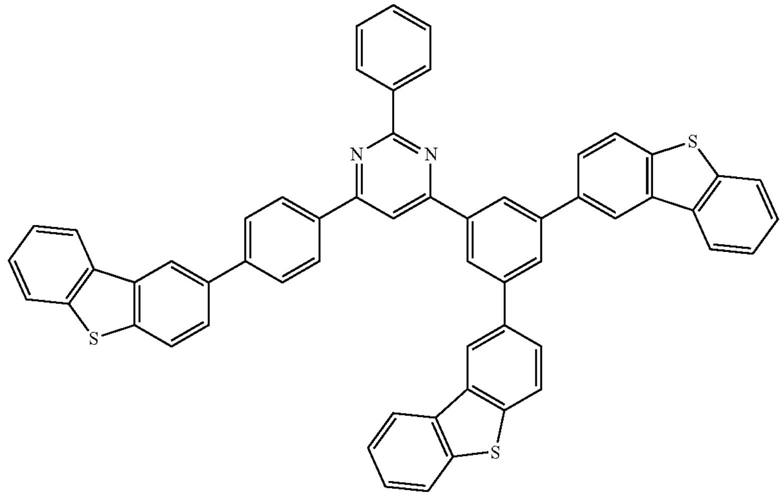
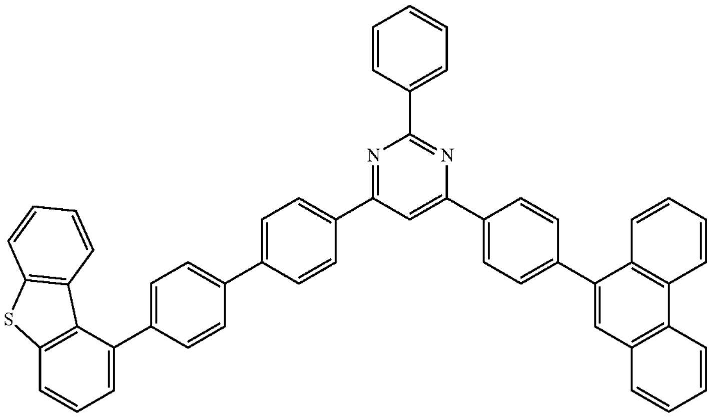

-continued
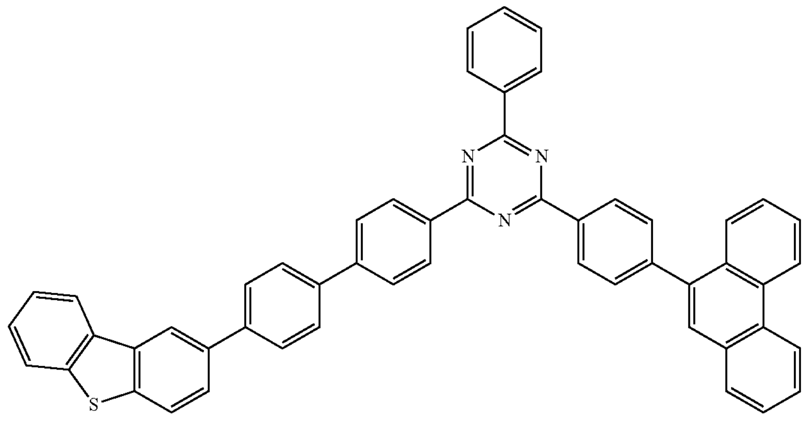
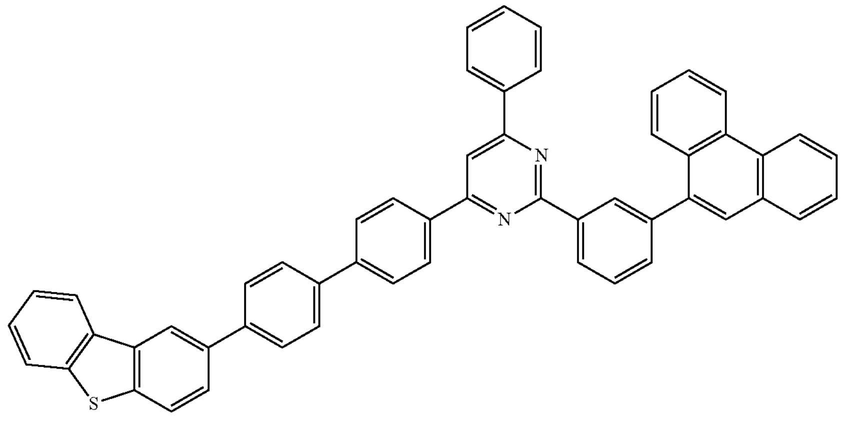
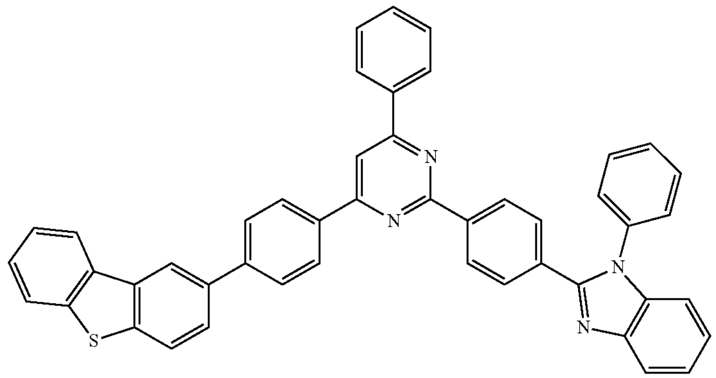
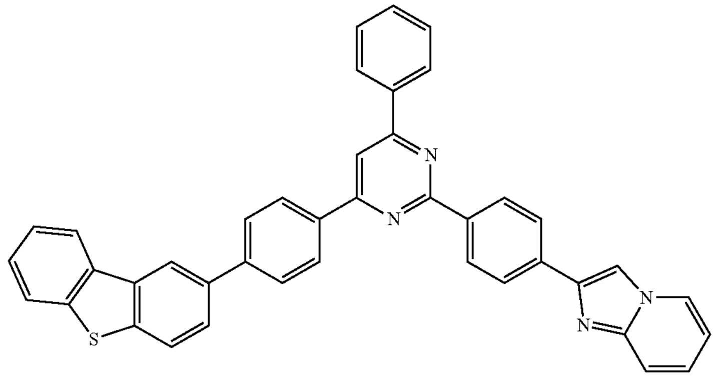

-continued
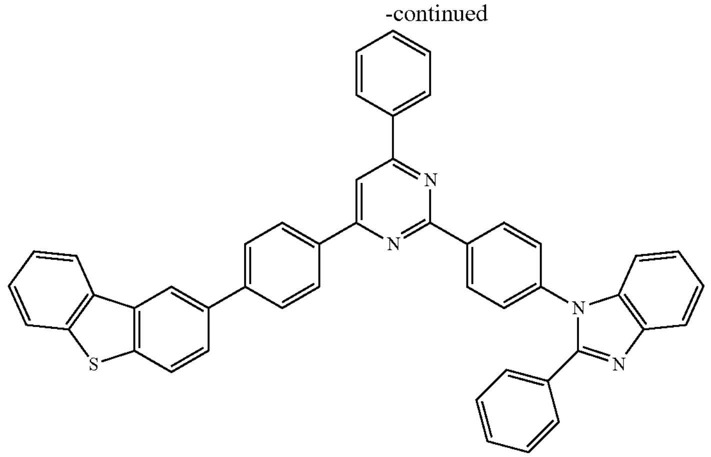
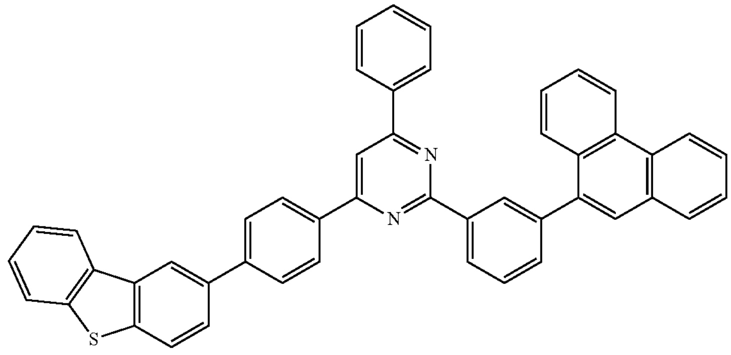
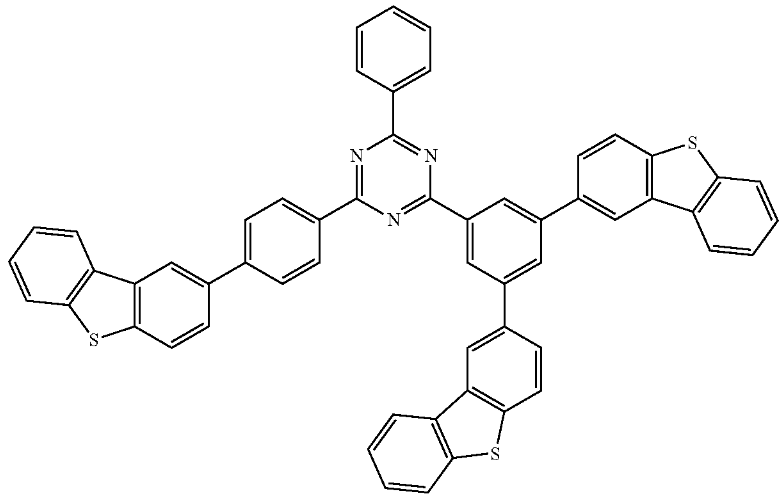

-continued
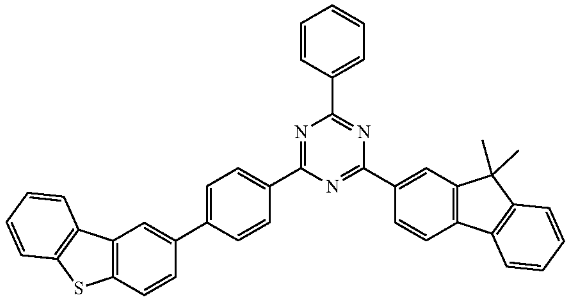
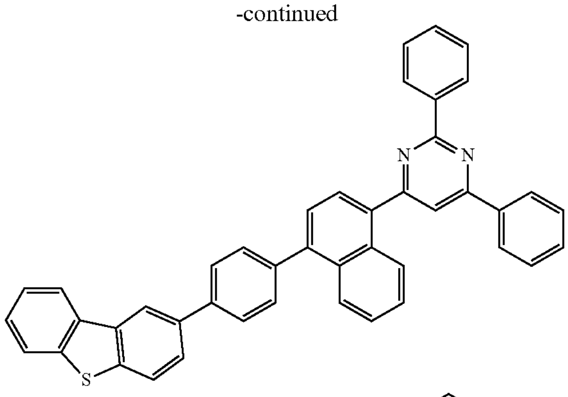
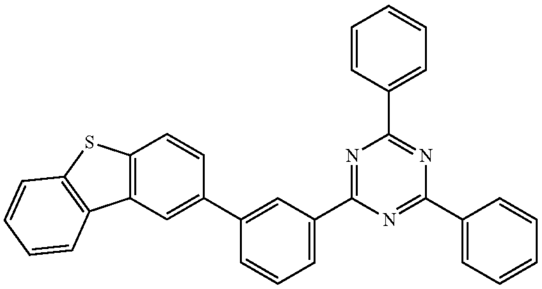
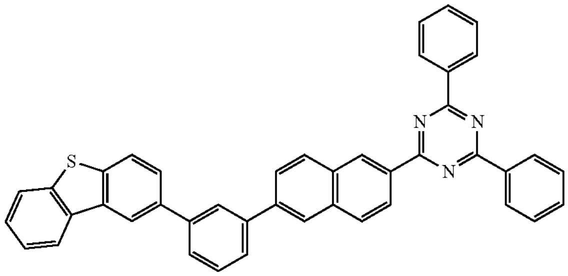
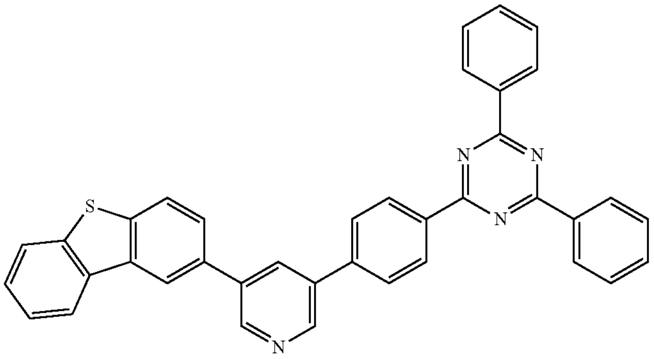
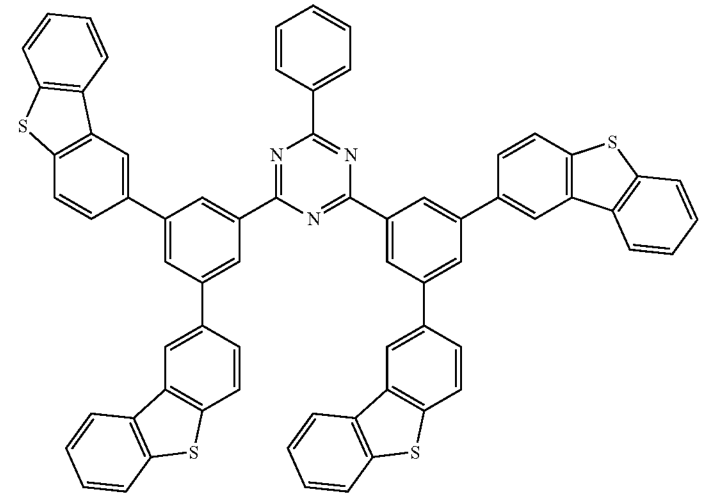
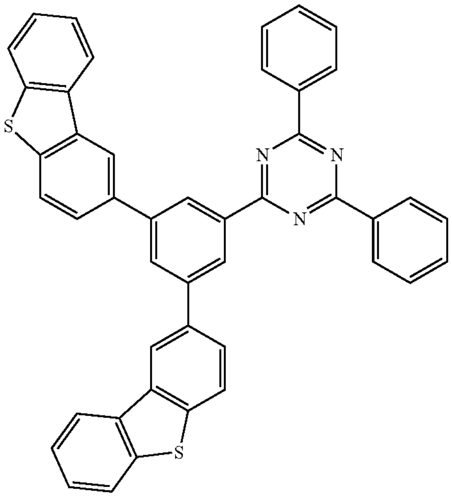 [SMILES: c1ccc(-c2cc(-c3cc(-c4ccc5sc6ccccc6c5c4)cc(-c4ccc5sc6ccccc6c5c4)c3)nc(-c3ccccc3)n2)cc1]

-continued
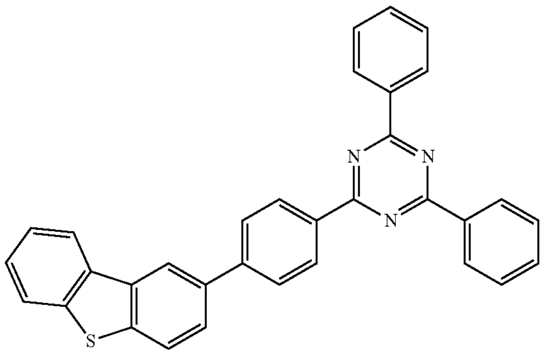
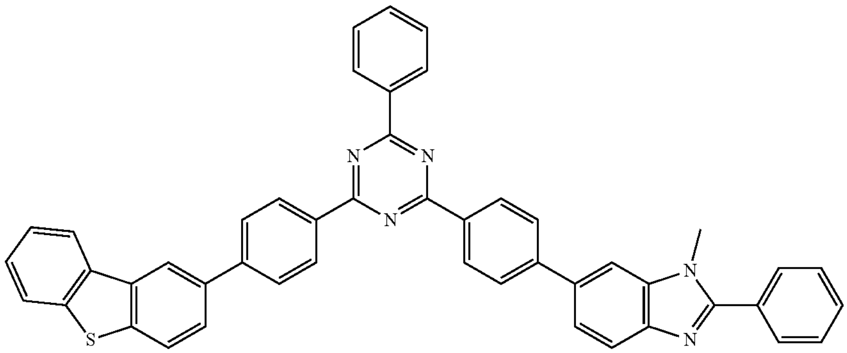
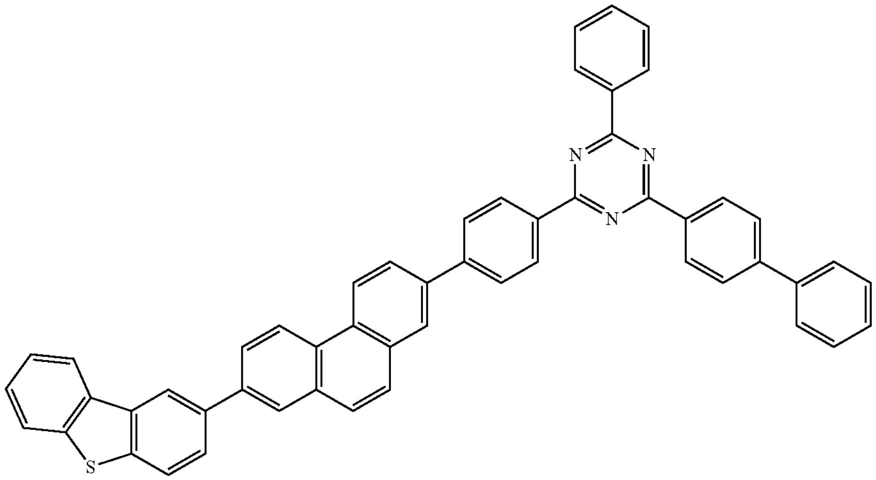
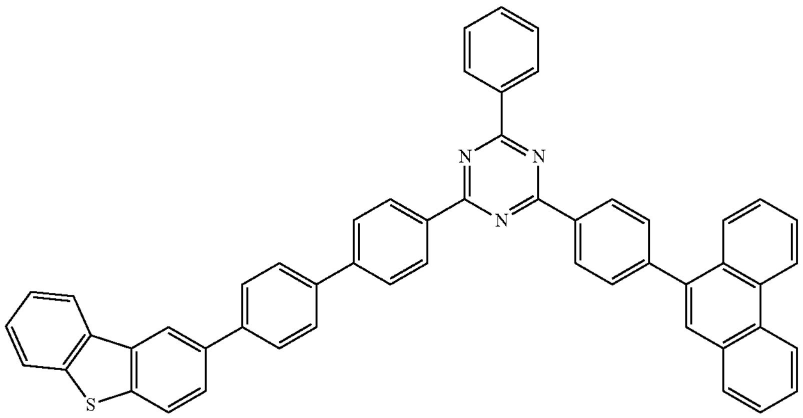

-continued
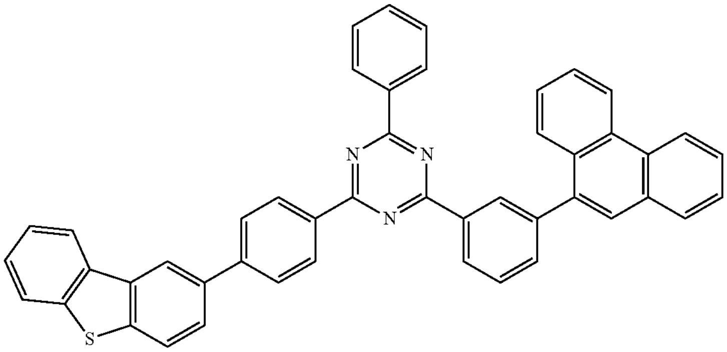
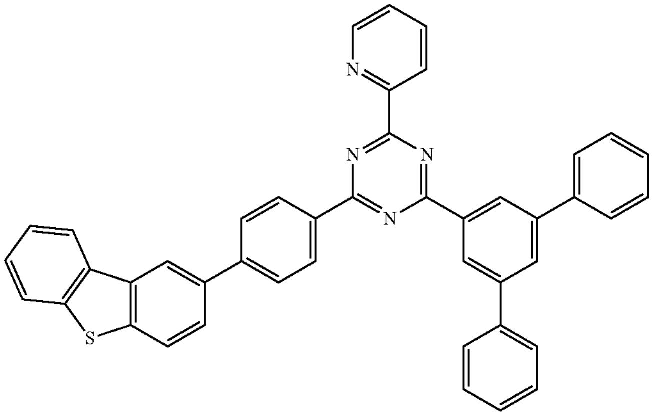
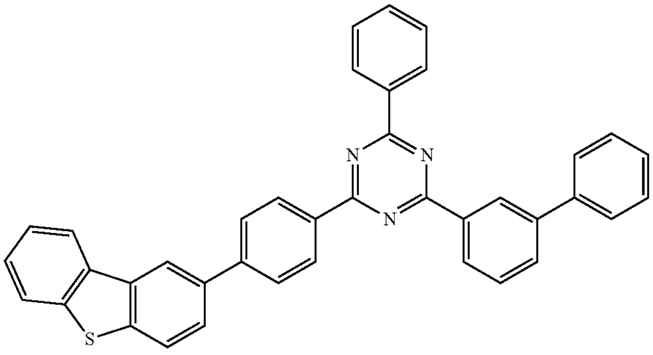
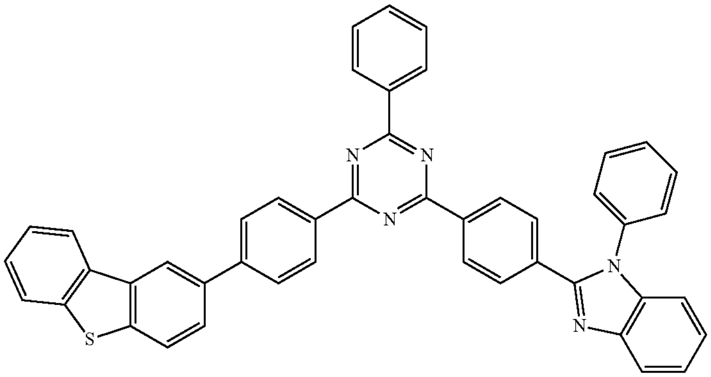

-continued
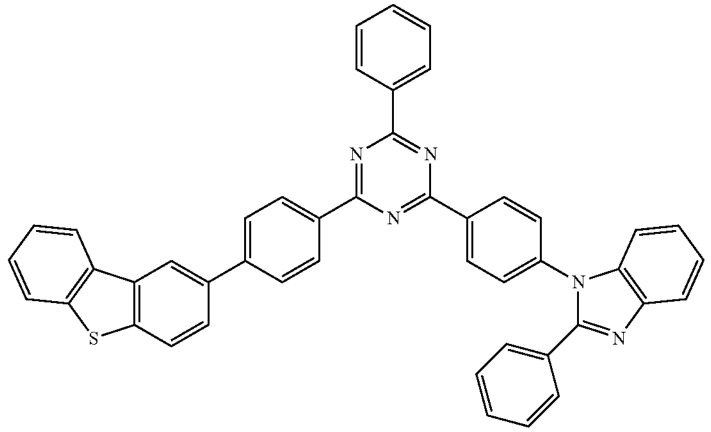
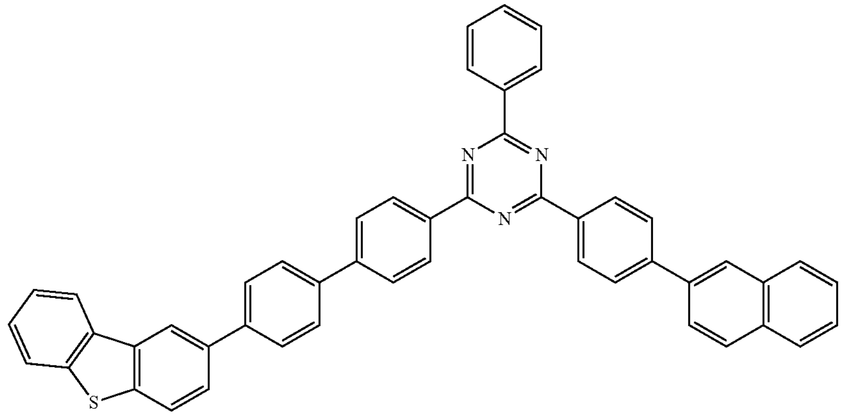
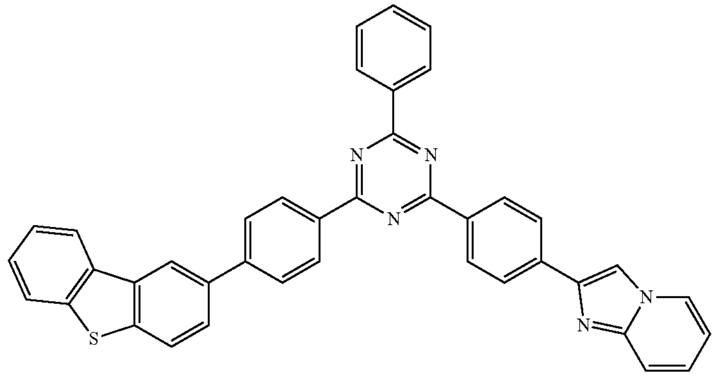
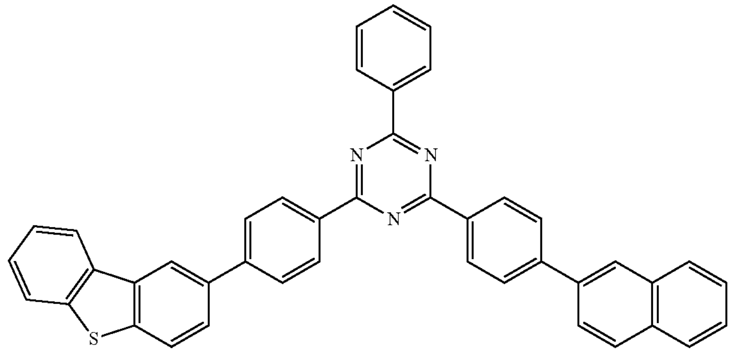

-continued
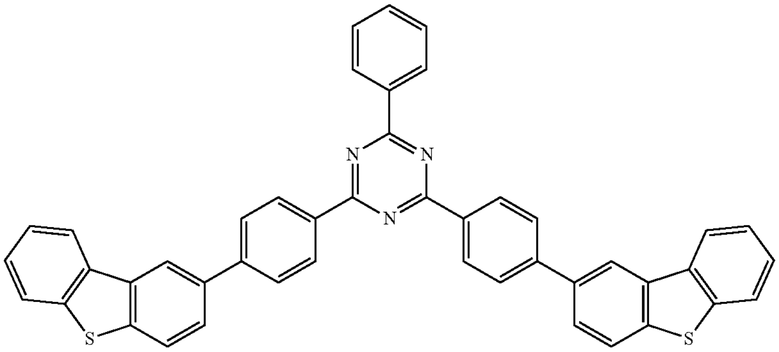
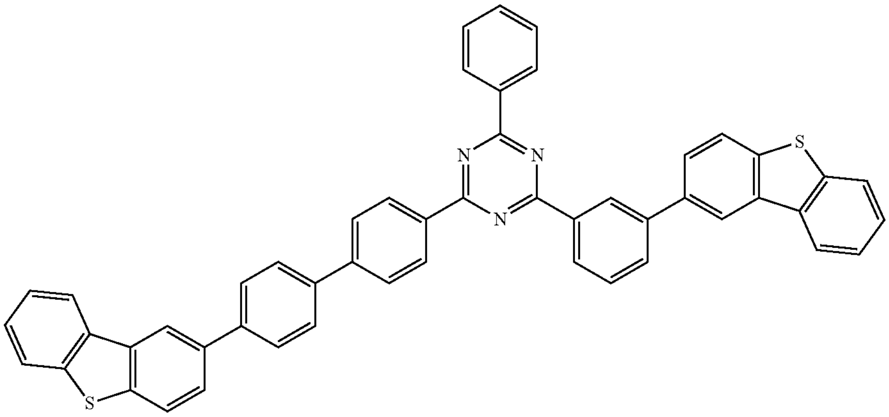
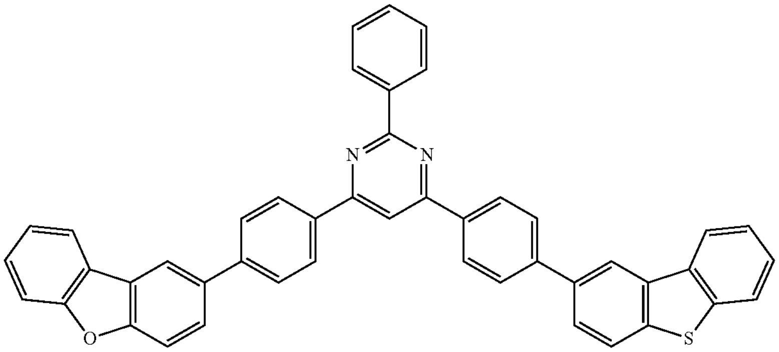
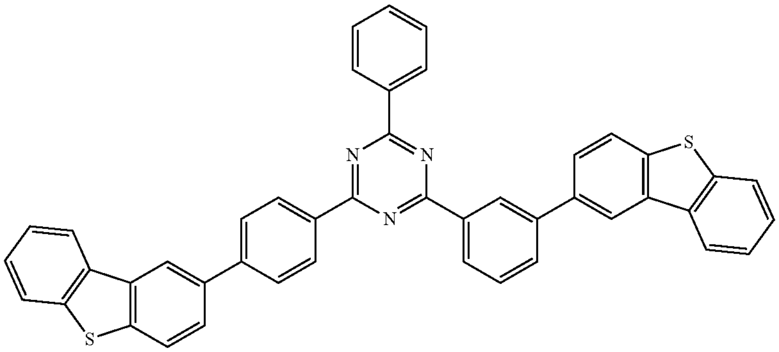

-continued
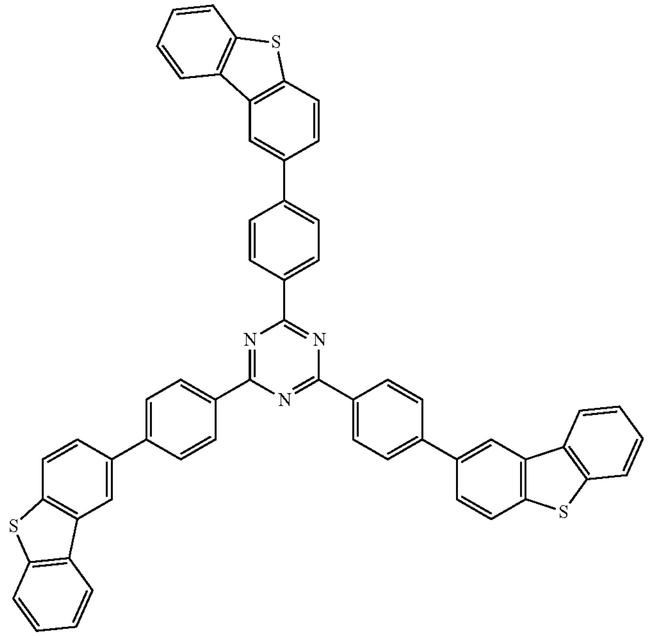
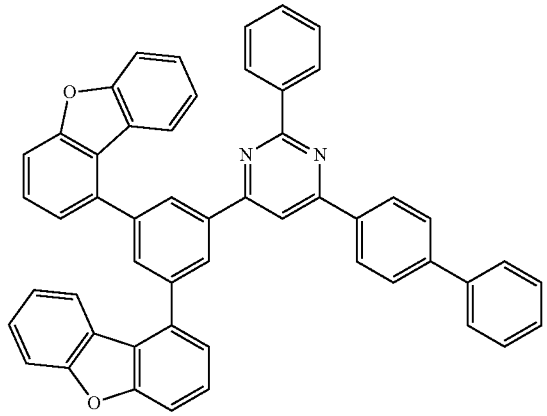
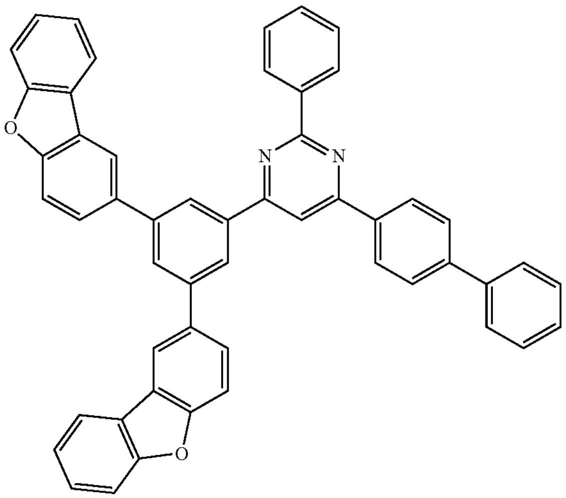
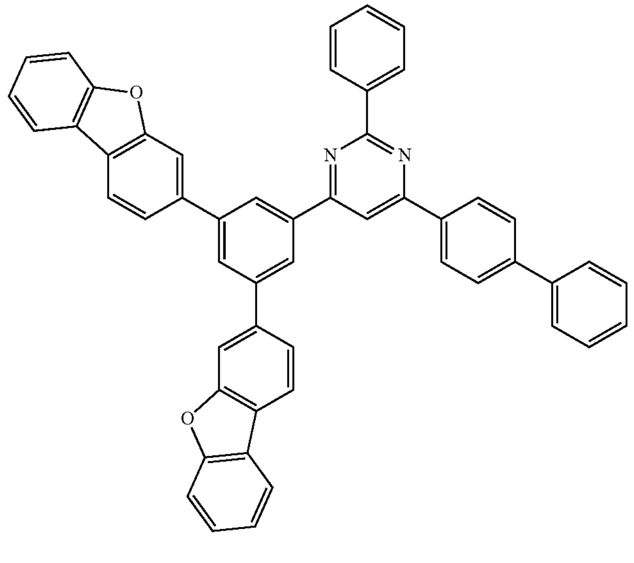
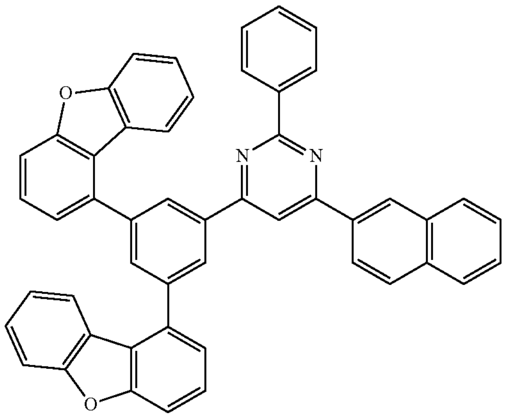

-continued
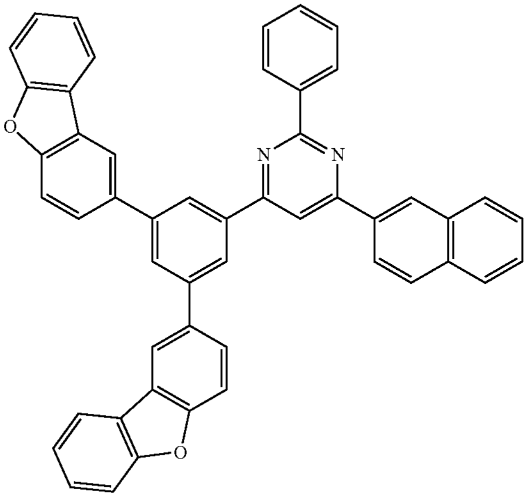
-continued
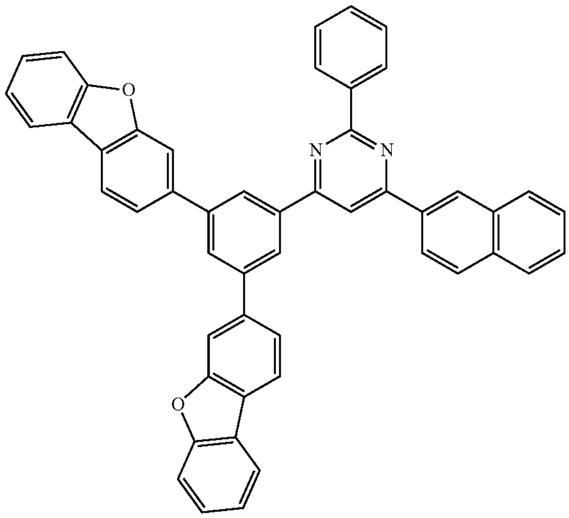
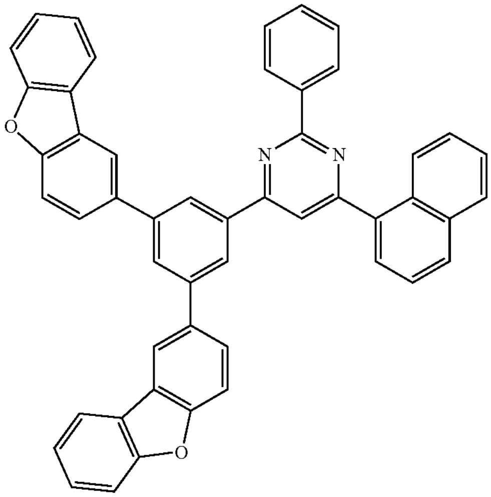
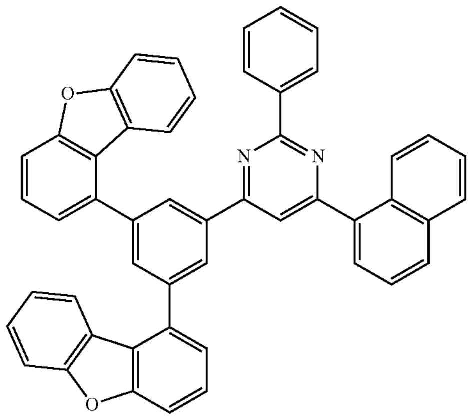
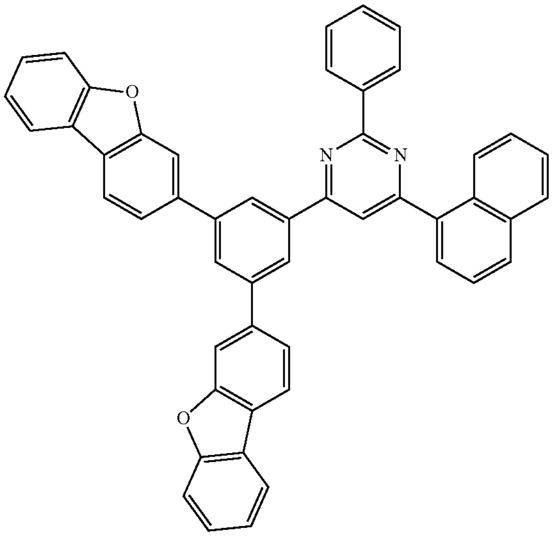

746
-continued
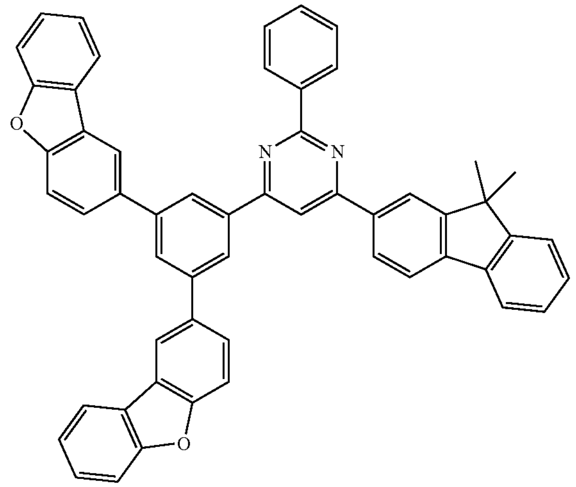
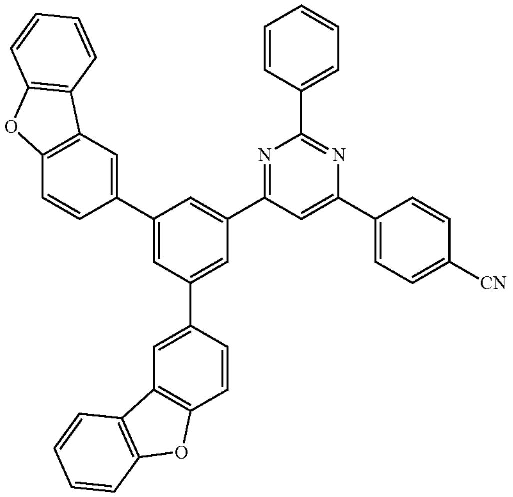
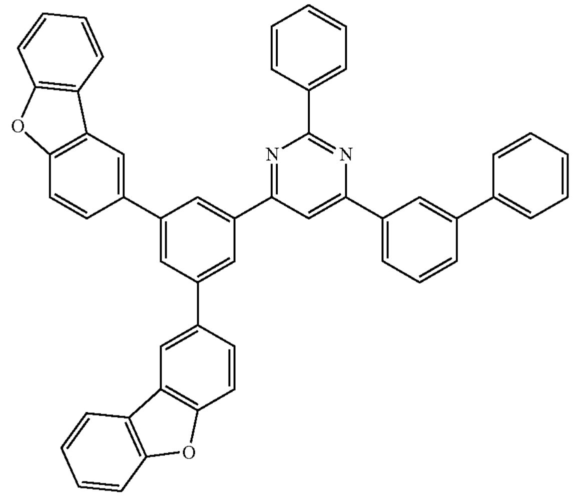
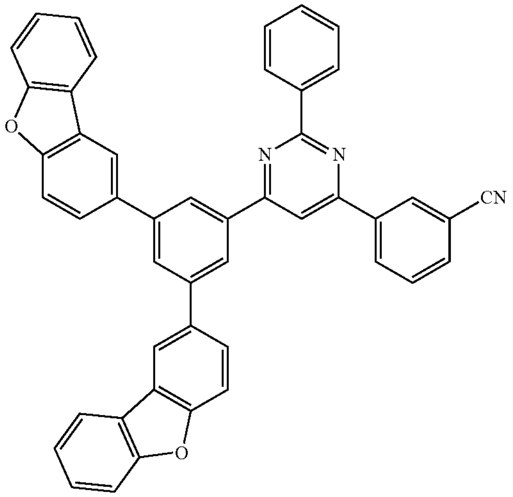
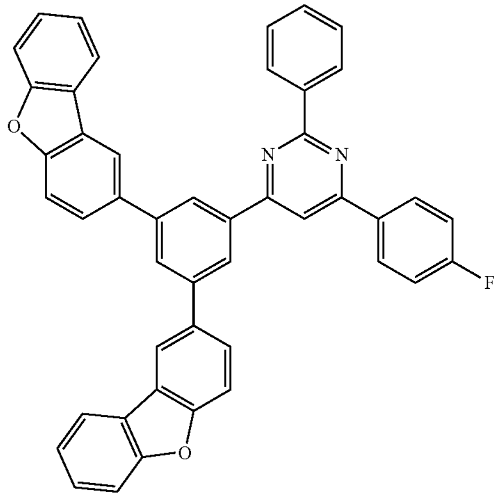
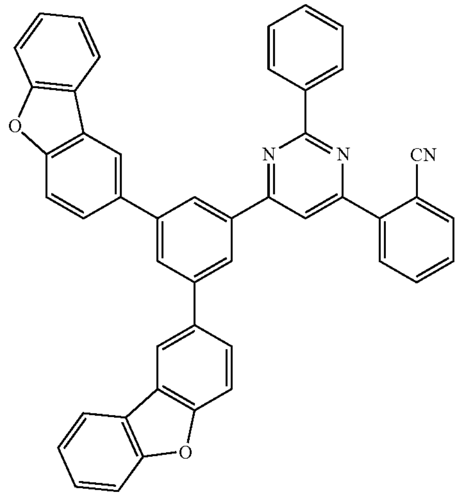

-continued
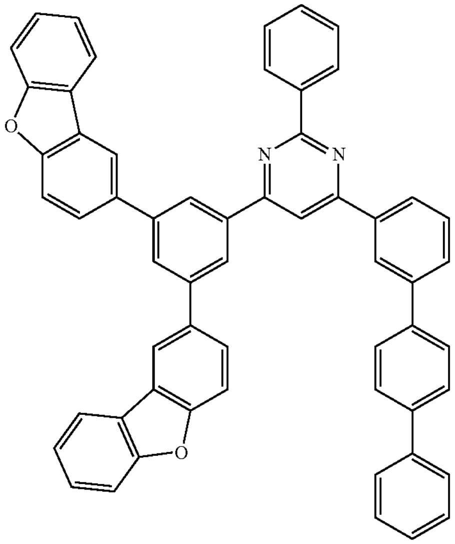
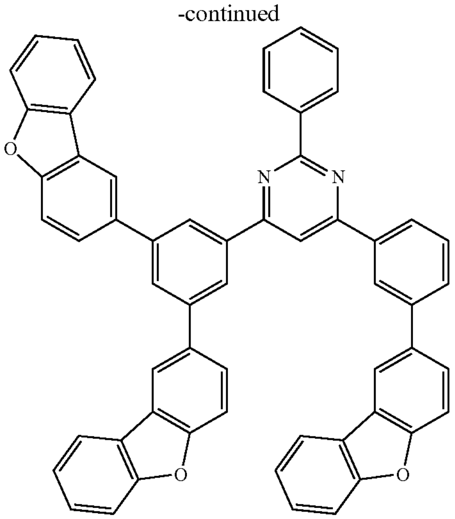
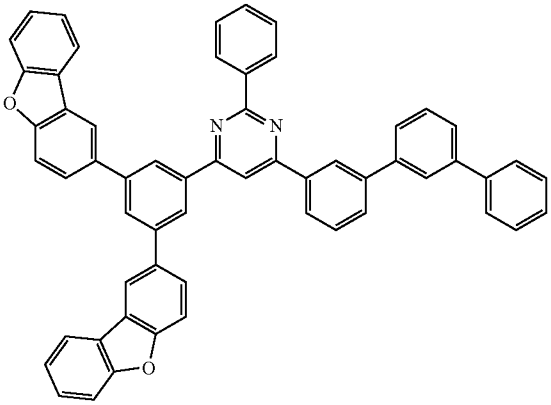
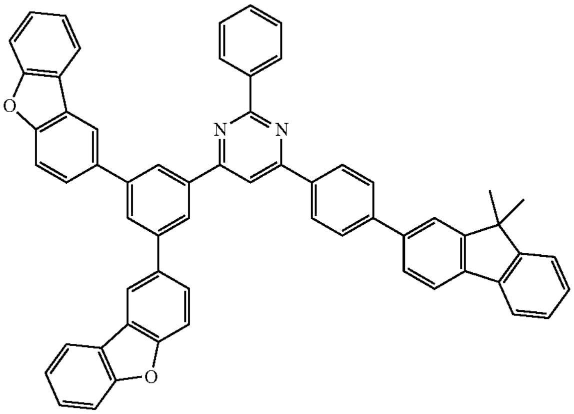
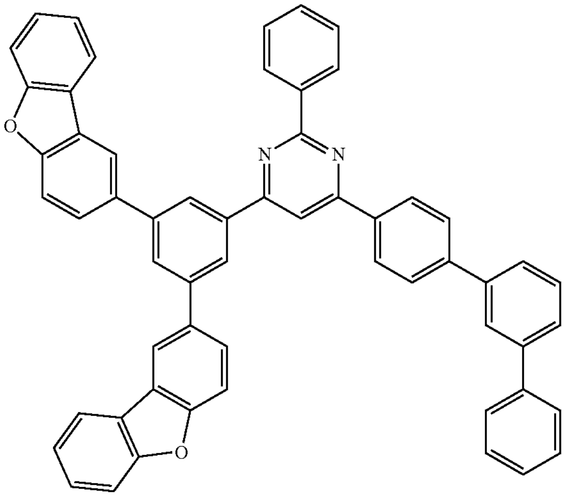
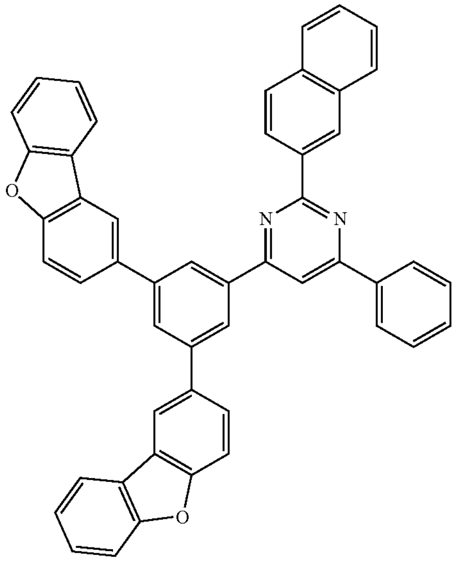
-continued -continued
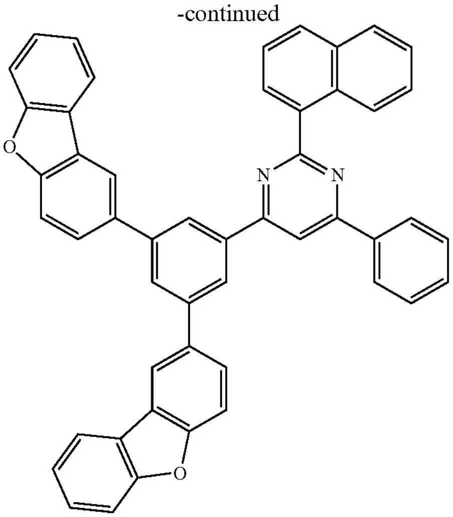
-continued
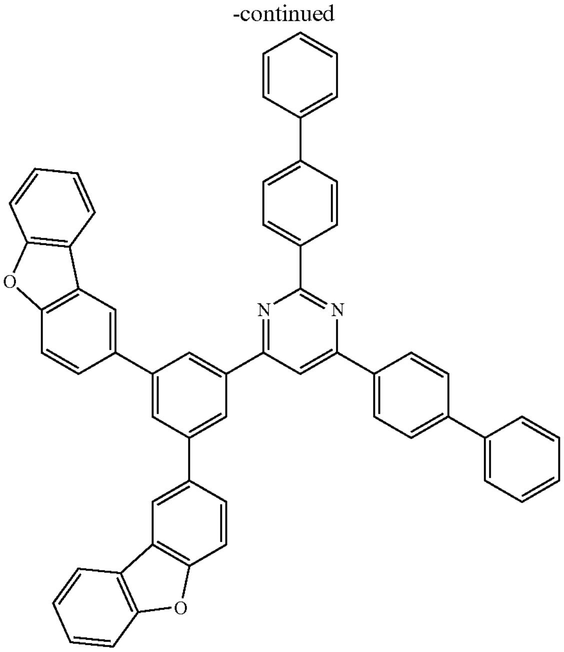
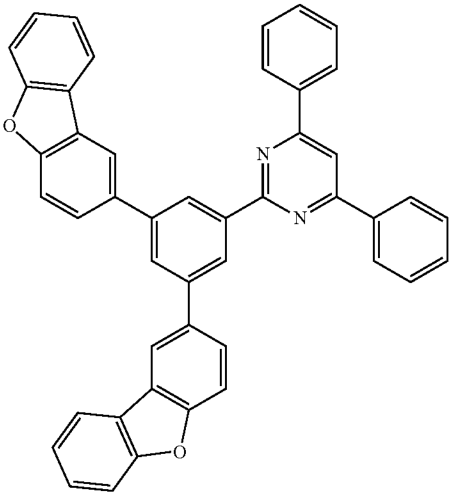
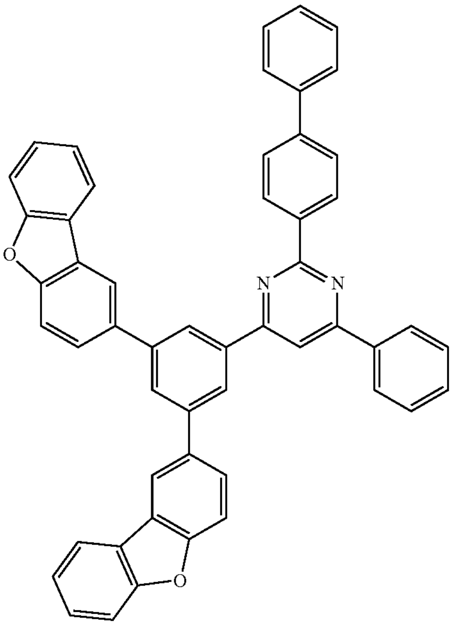
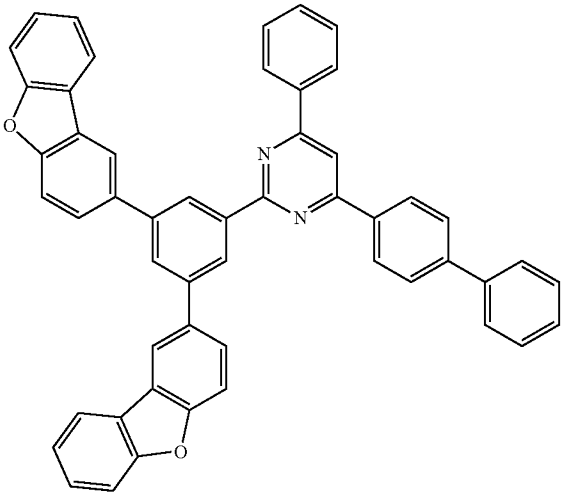

-continued
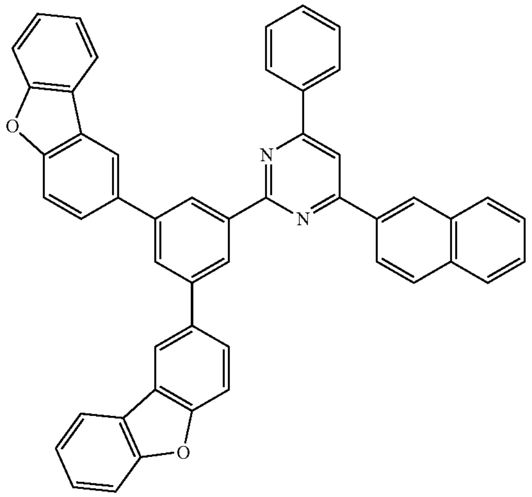
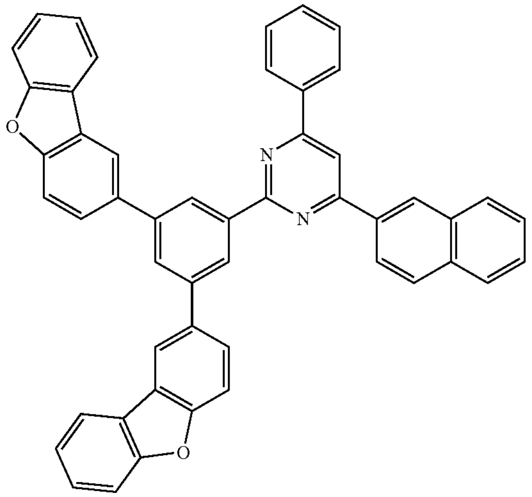
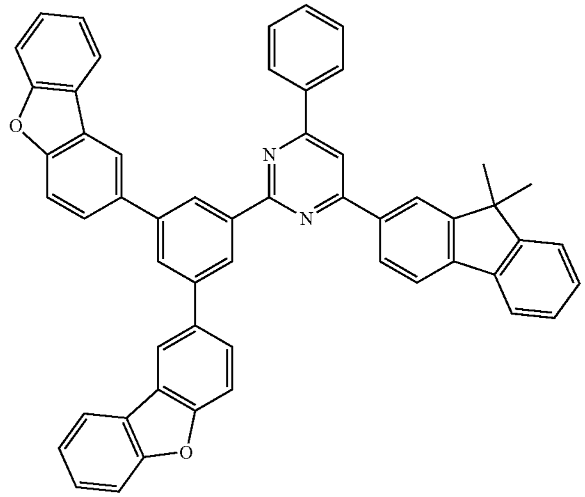
-continued
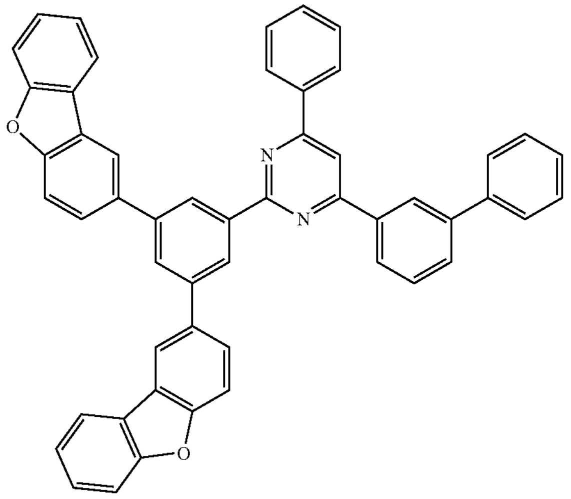
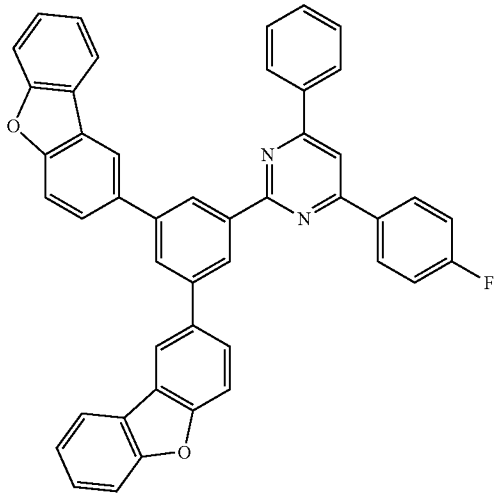
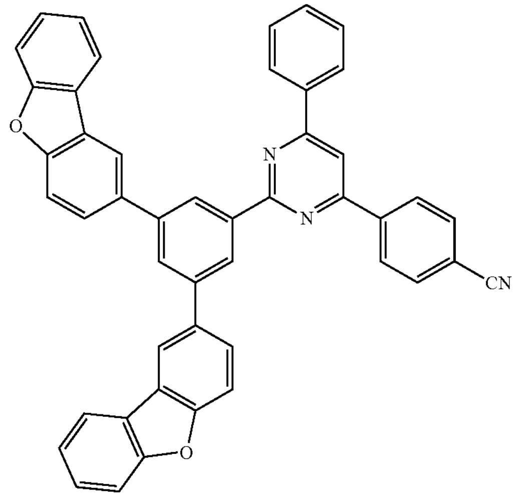

-continued
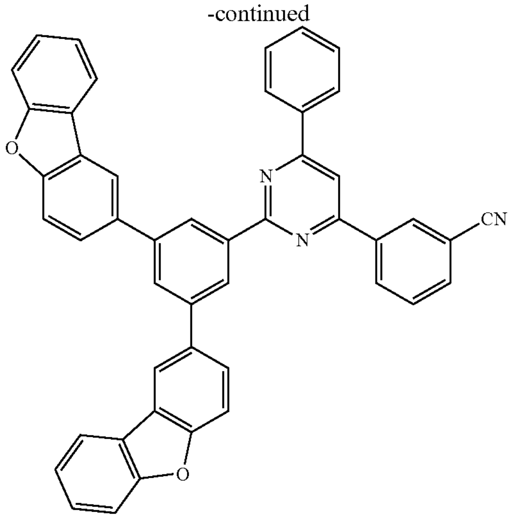
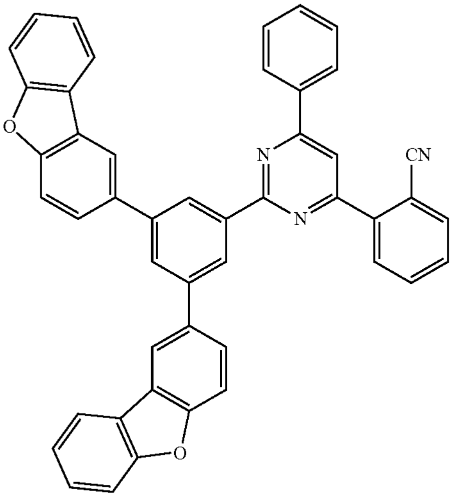
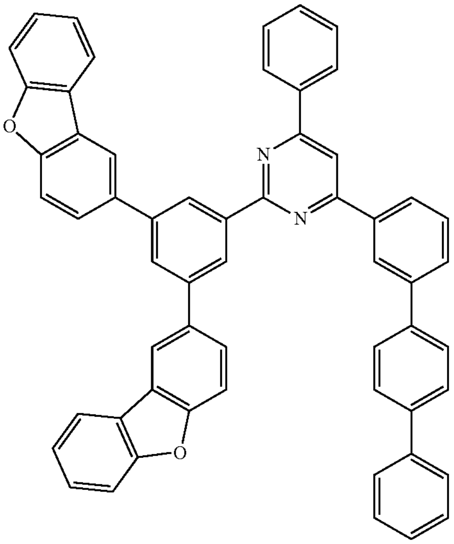 [SMILES: c1ccc(-c2ccc(-c3cccc(-c4cc(-c5ccccc5)nc(-c5cc(-c6ccc7oc8ccccc8c7c6)cc(-c6ccc7oc8ccccc8c7c6)c5)n4)c3)cc2)cc1]
-continued
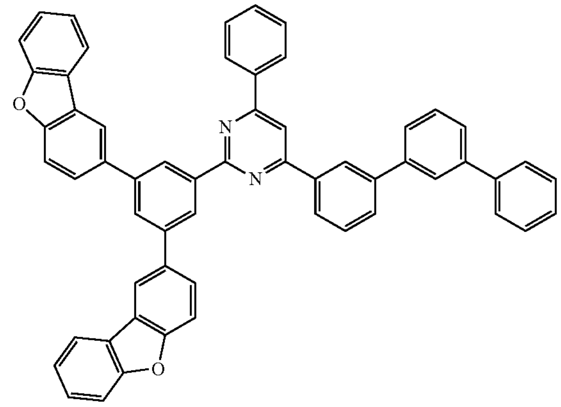
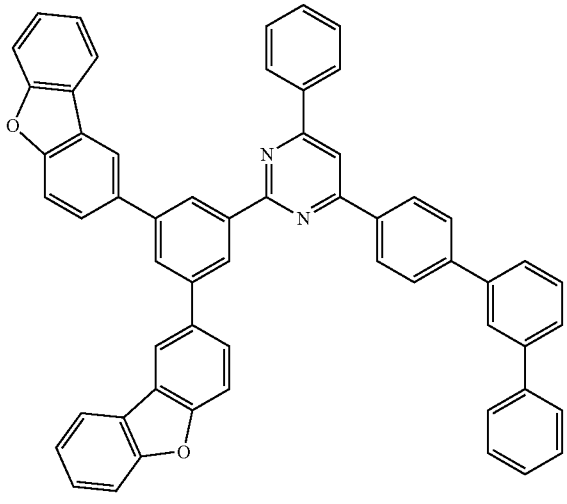
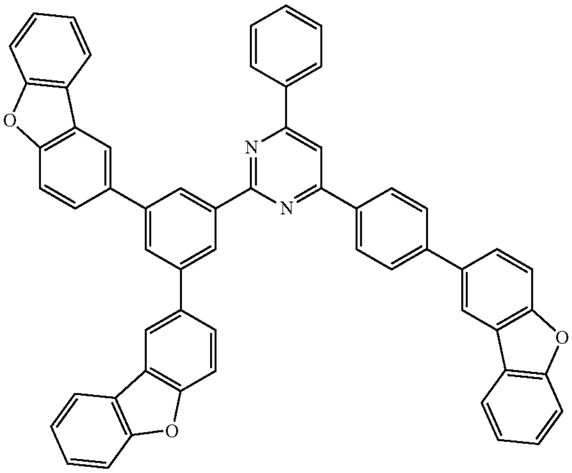

-continued
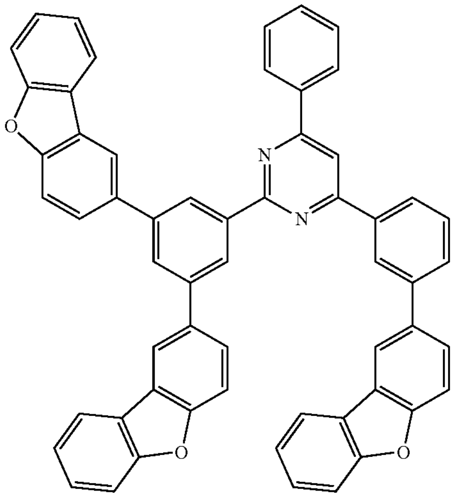
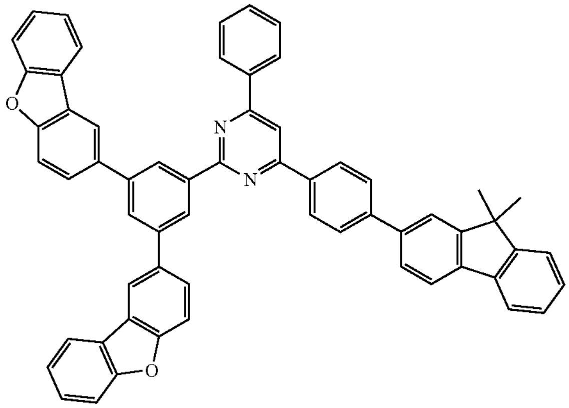
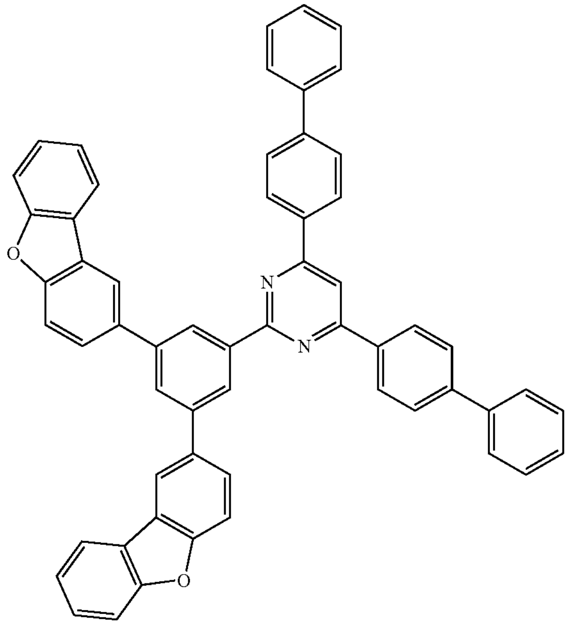
-continued
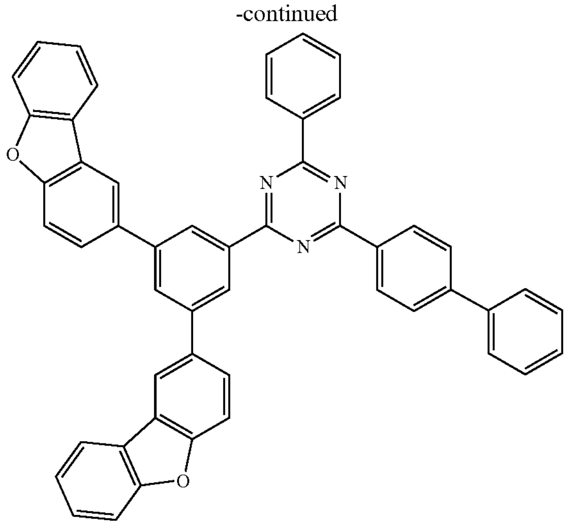
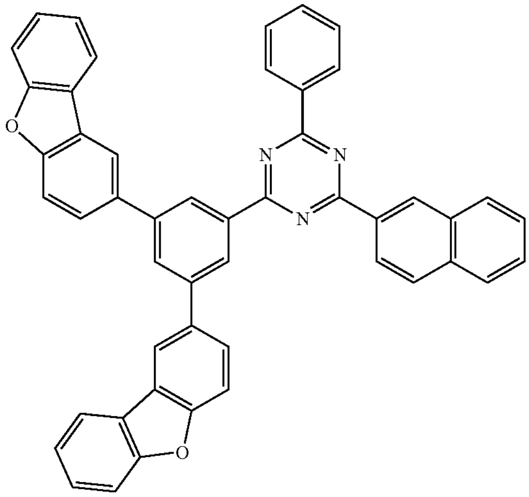

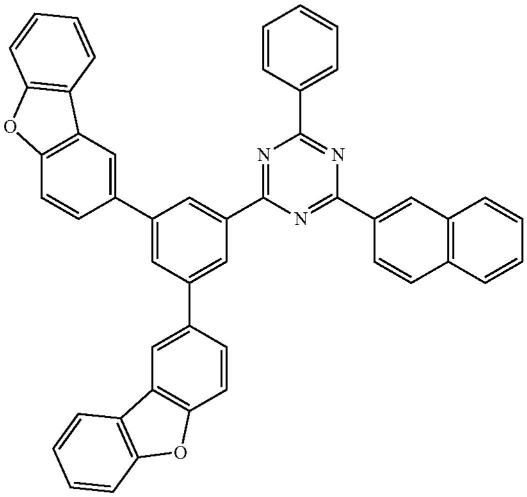
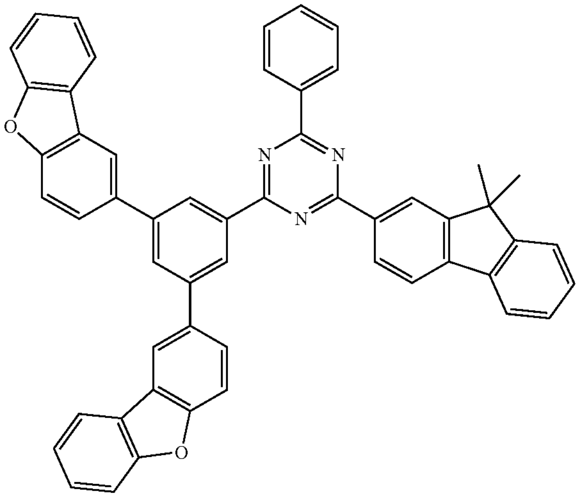
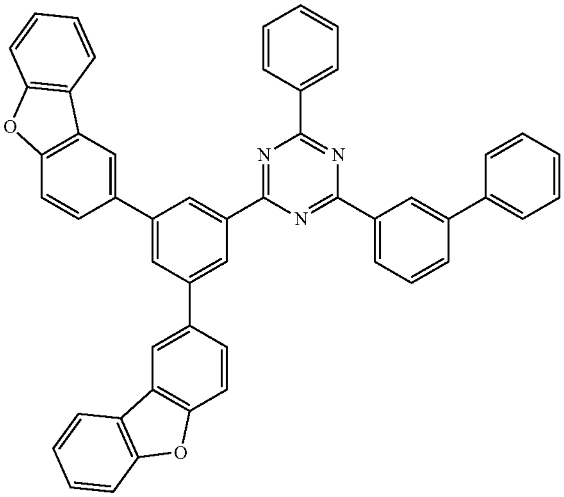
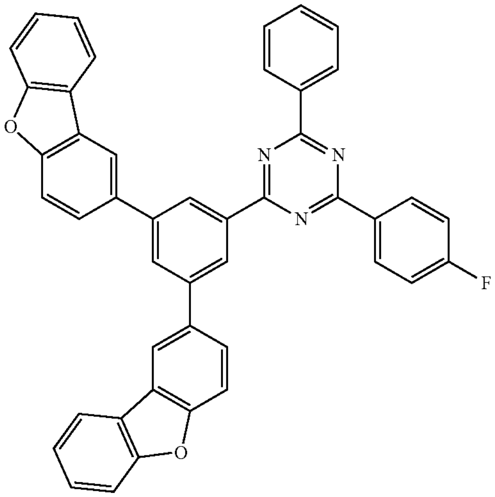
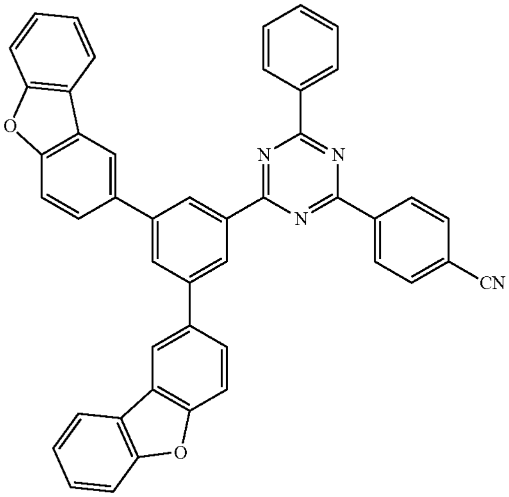
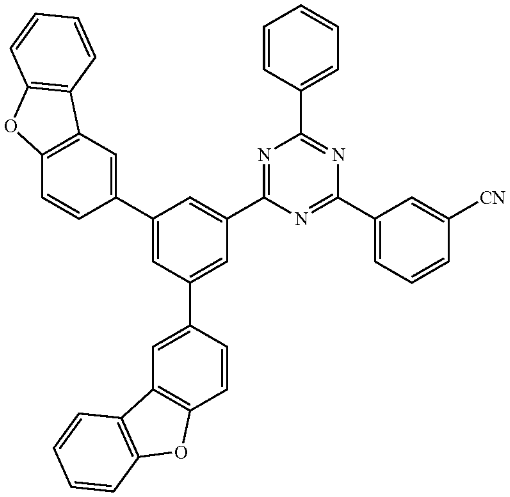

-continued
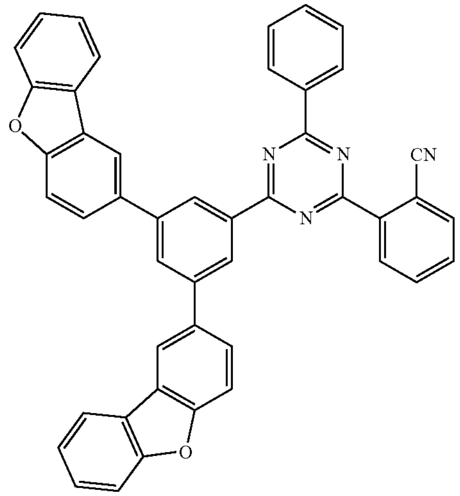
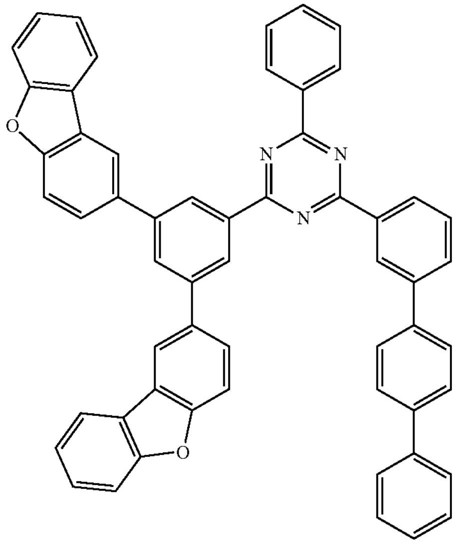
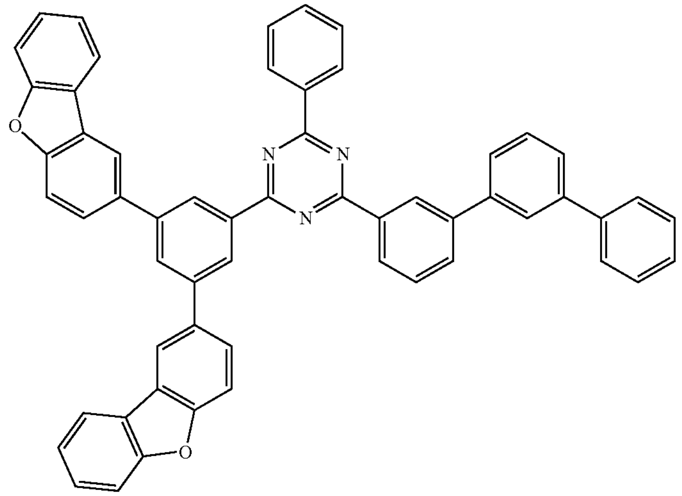
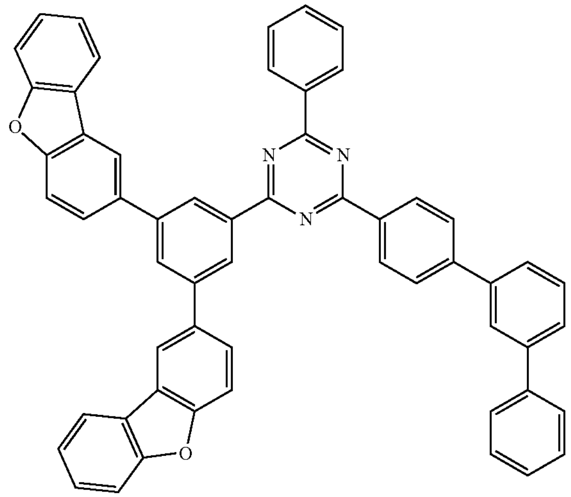
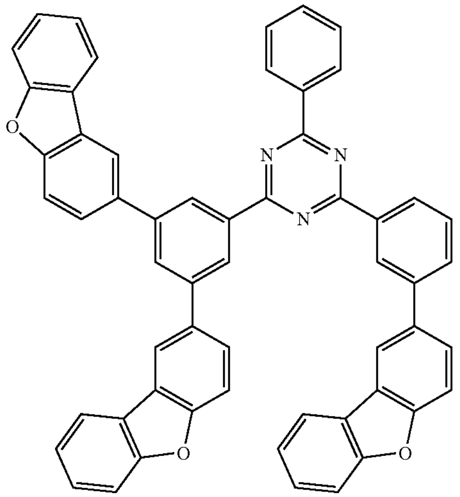 [SMILES: c1ccc(-c2cc(-c3cccc(-c4ccc5oc6ccccc6c5c4)c3)nc(-c3cc(-c4ccc5oc6ccccc6c5c4)cc(-c4ccc5oc6ccccc6c5c4)c3)n2)cc1]

-continued
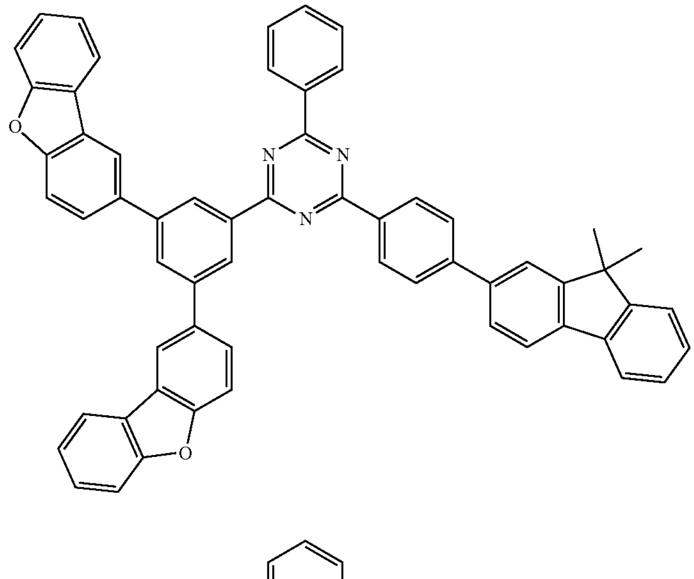
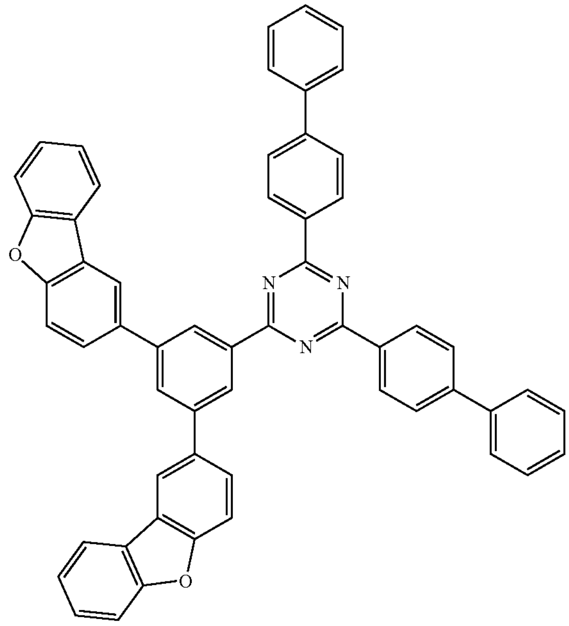
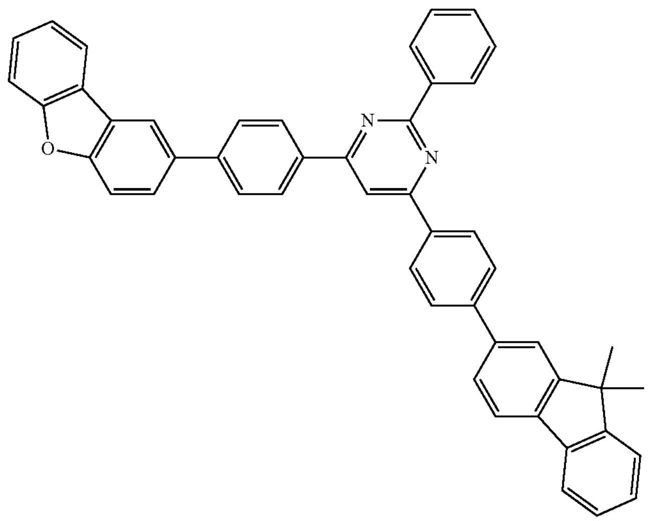

-continued
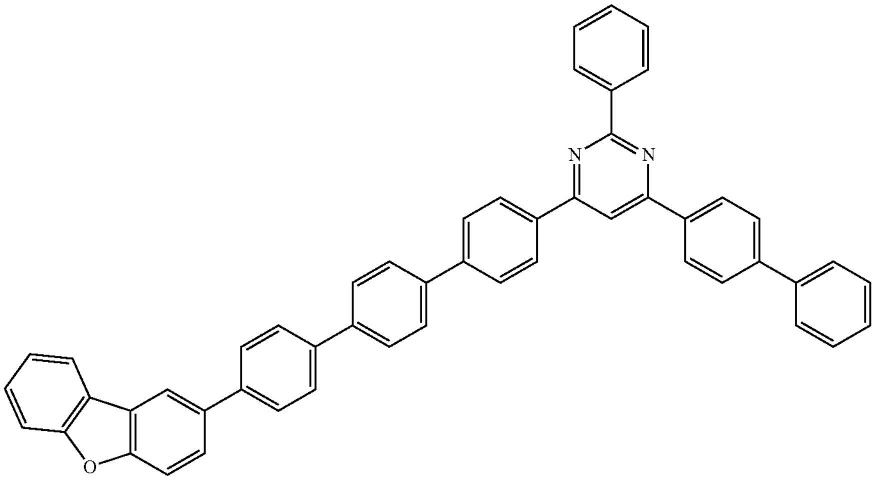
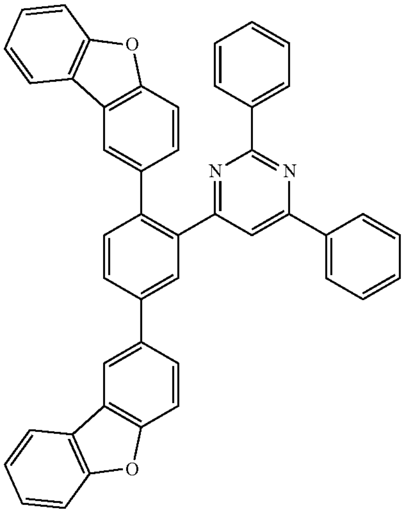
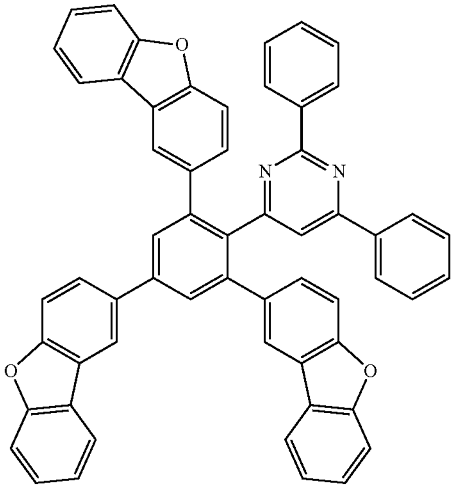
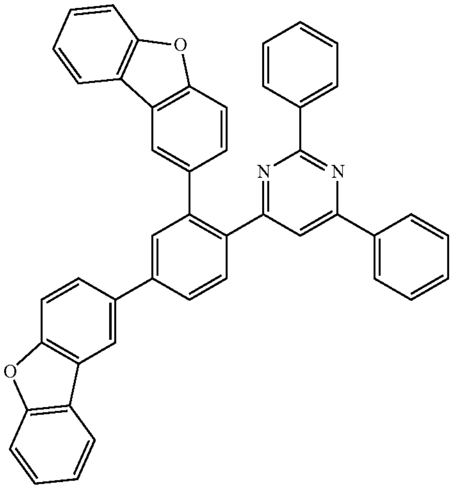
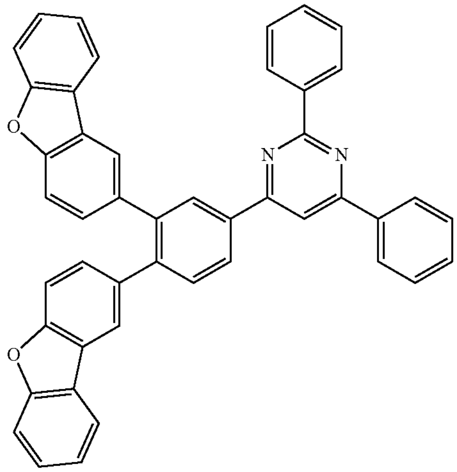

-continued
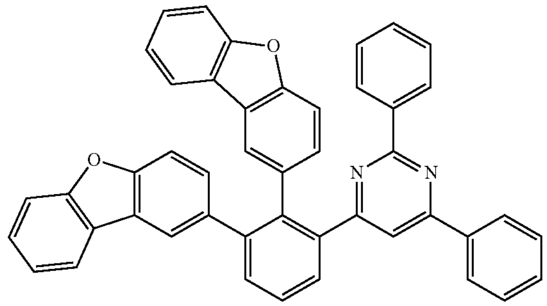
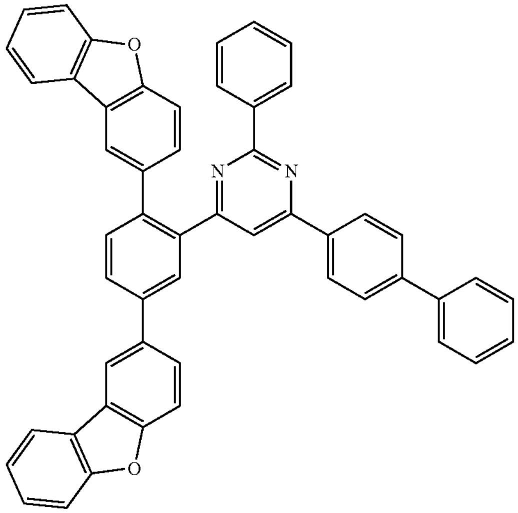
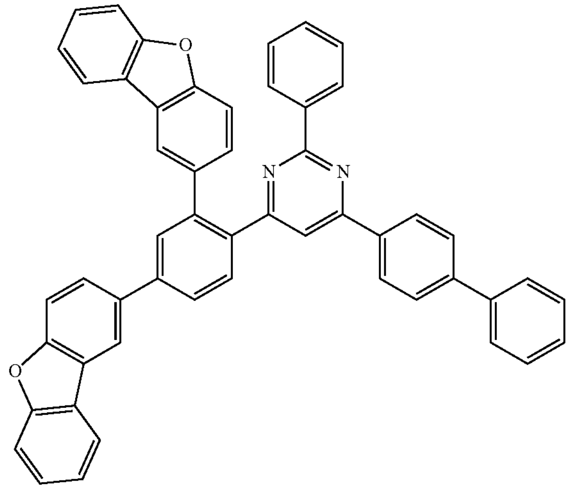
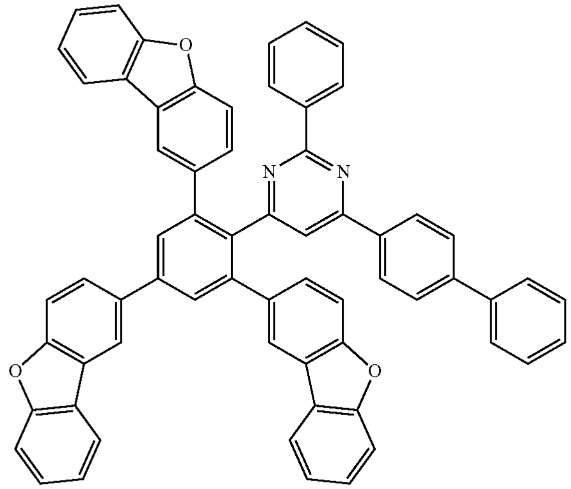
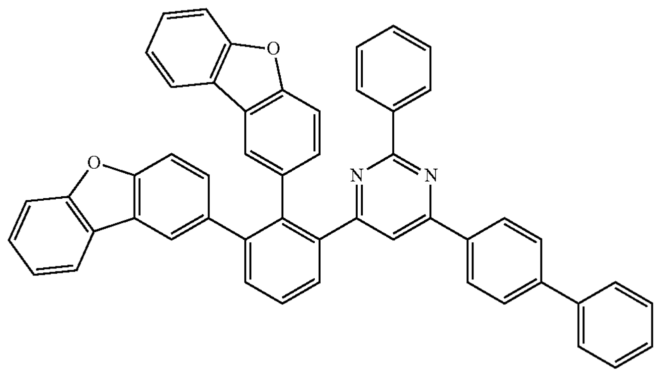

-continued
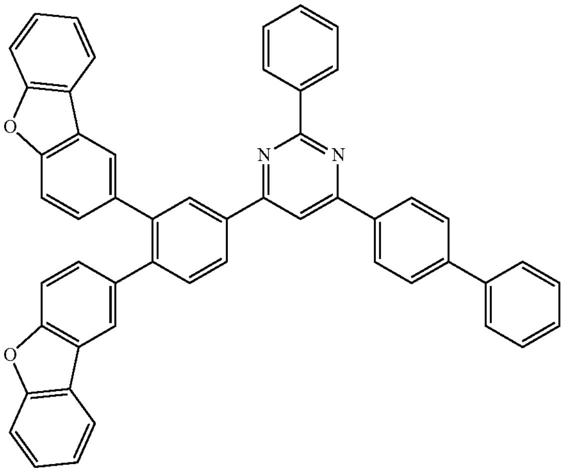
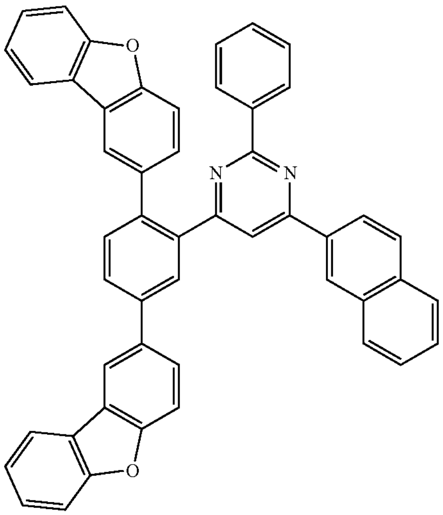
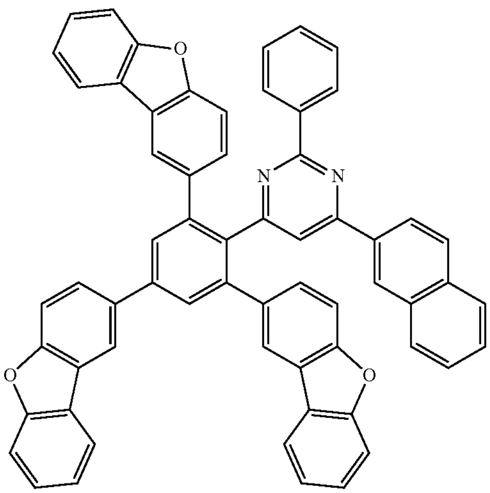
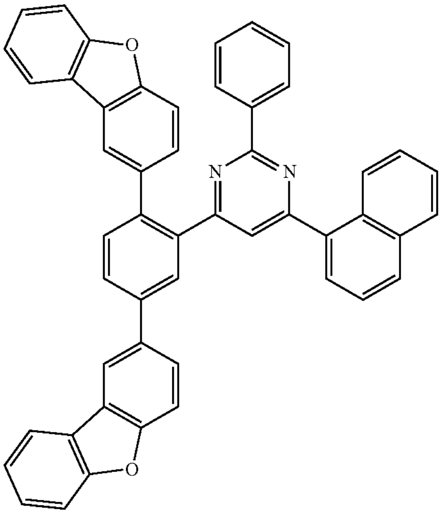

-continued
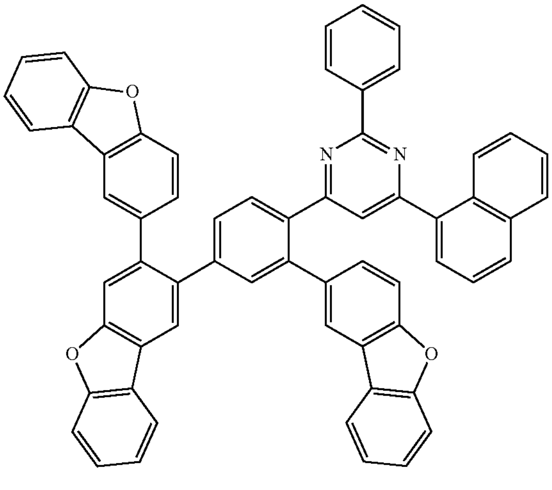
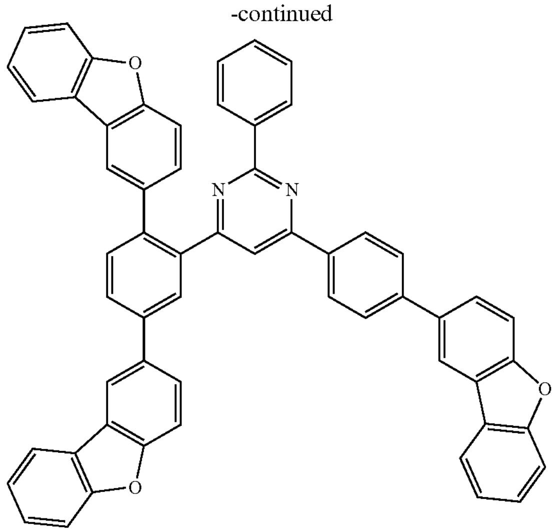
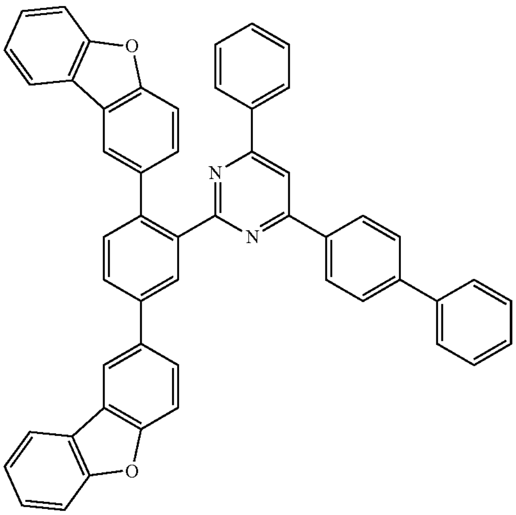
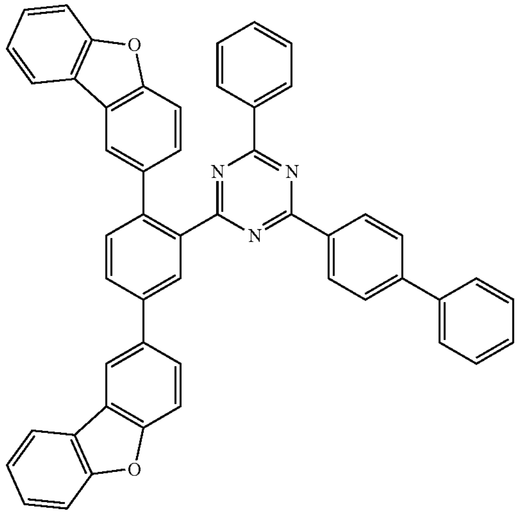
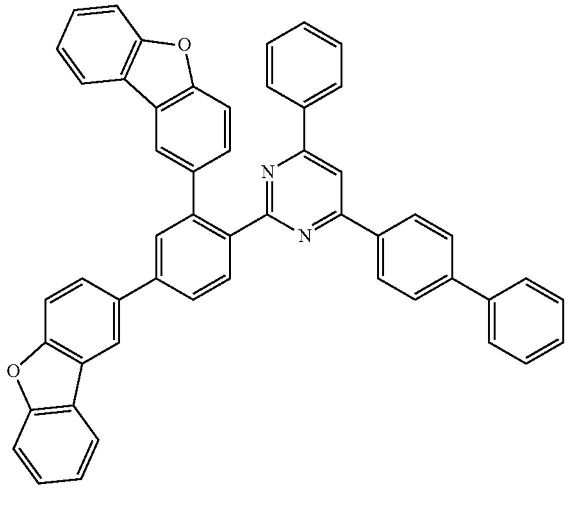
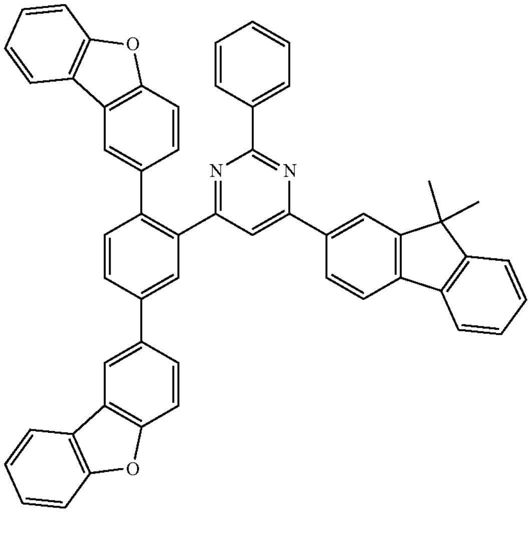

-continued
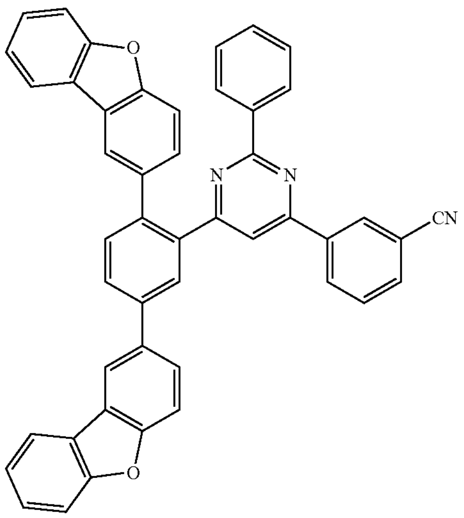
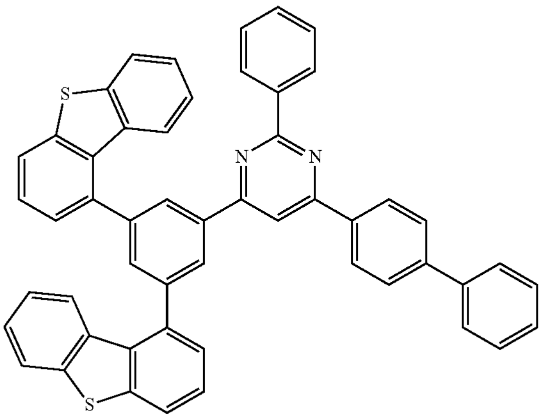
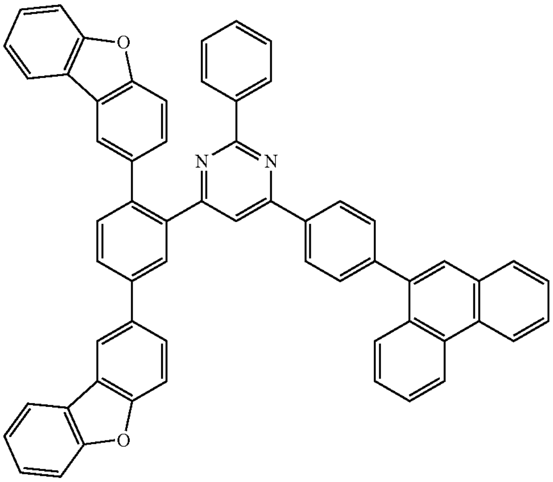
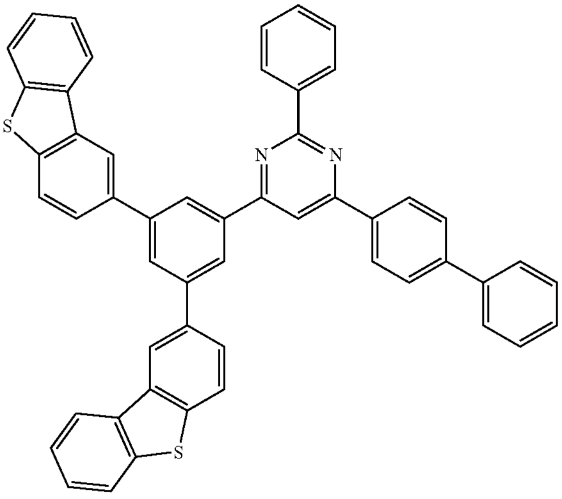
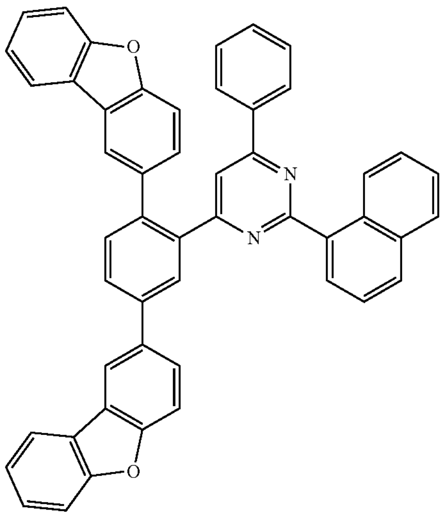
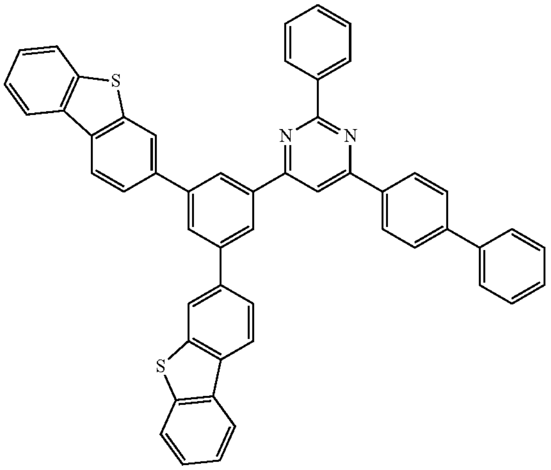

-continued
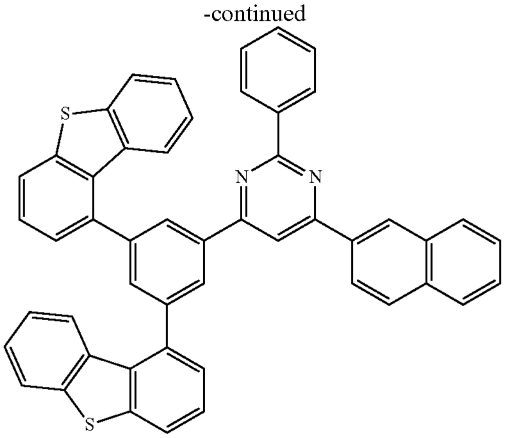
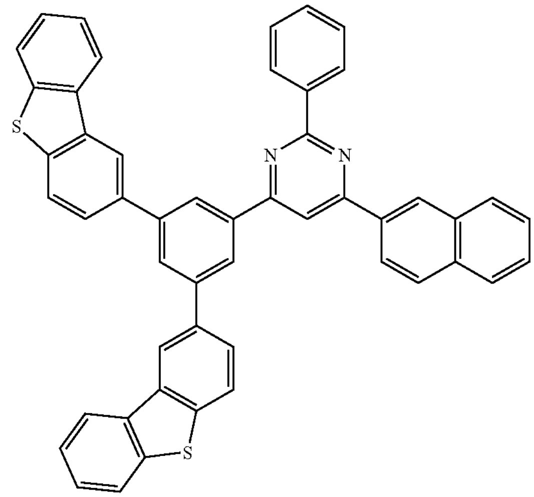
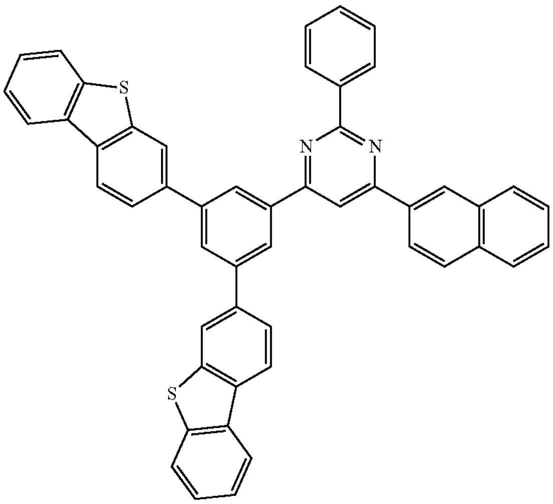
-continued
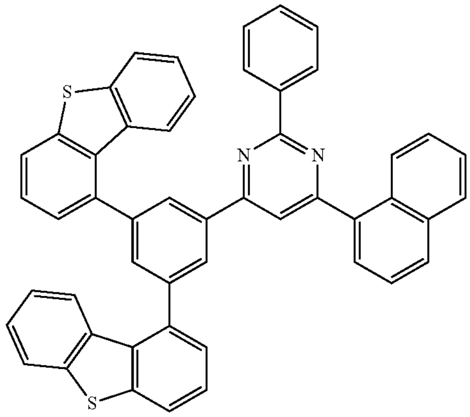
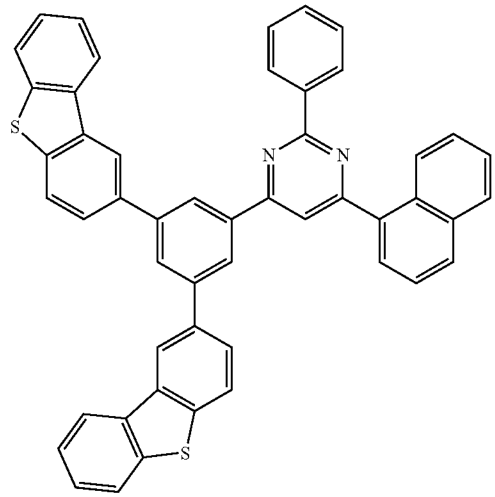
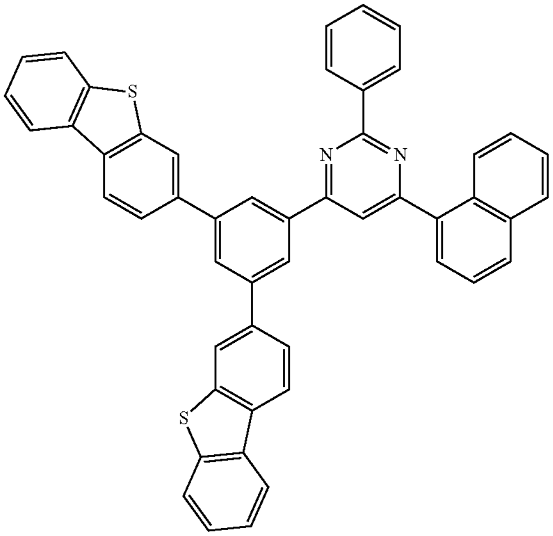

-continued
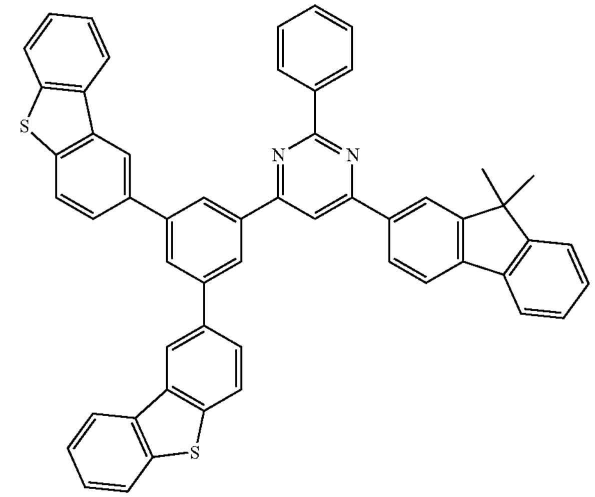
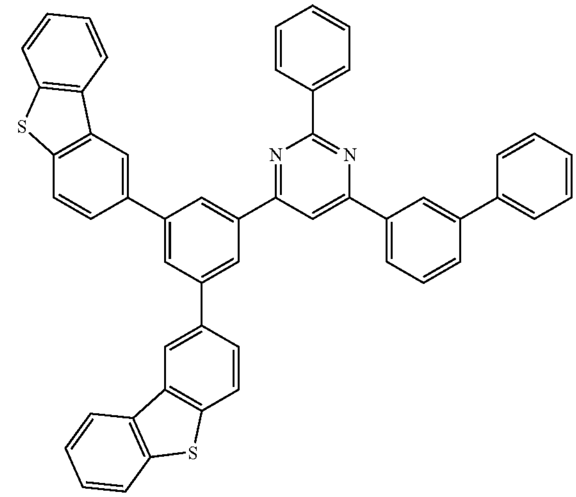
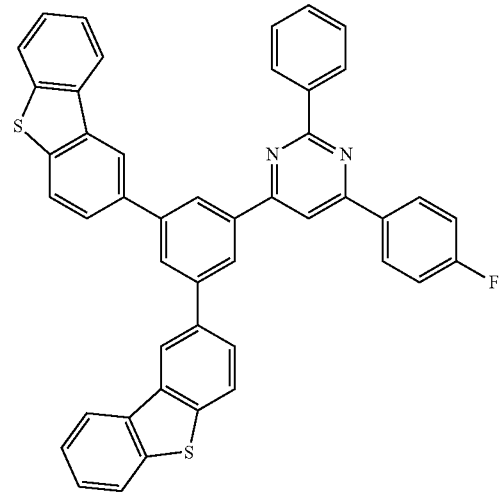
-continued
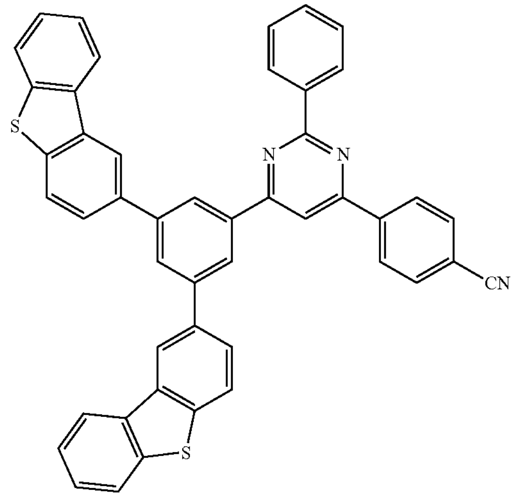
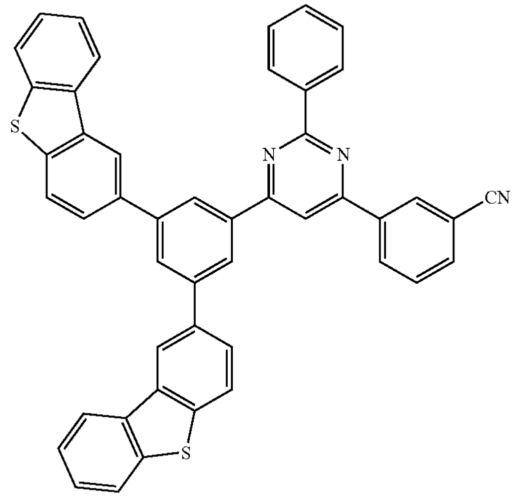
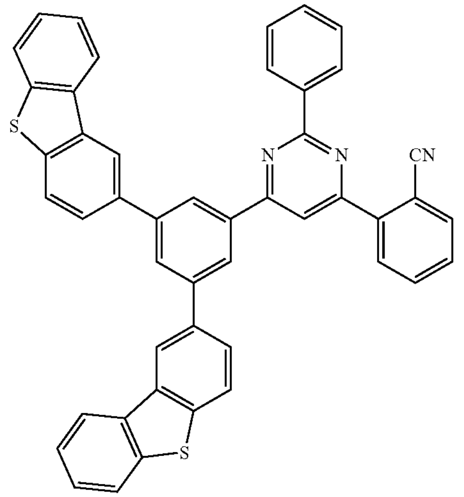

-continued
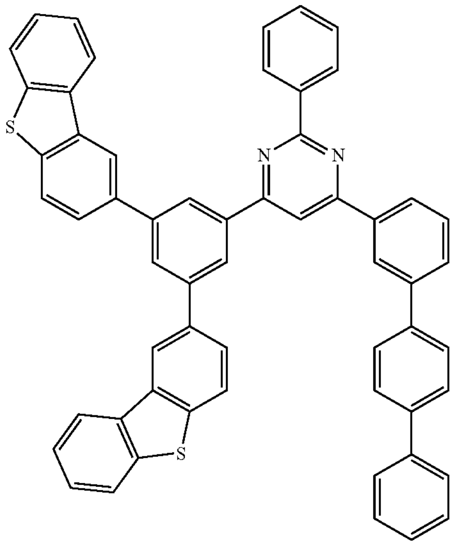
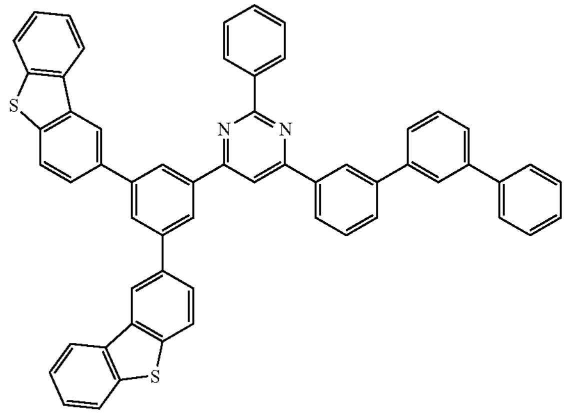
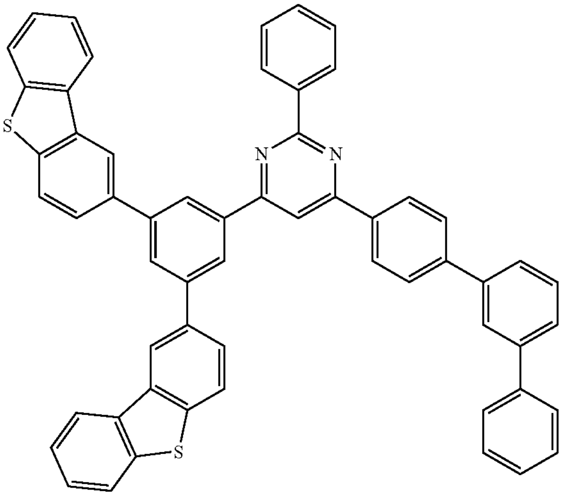
-continued
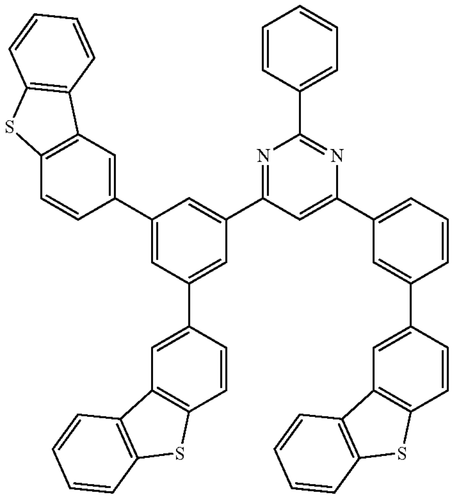
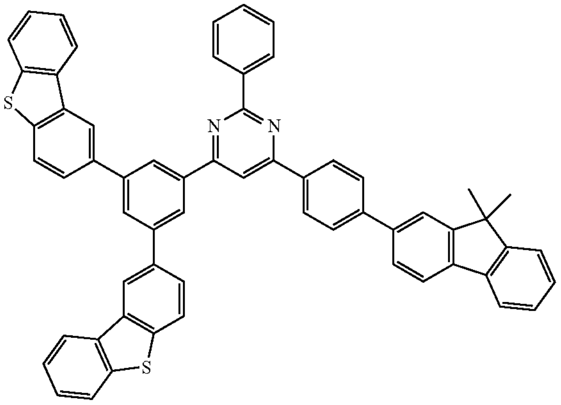
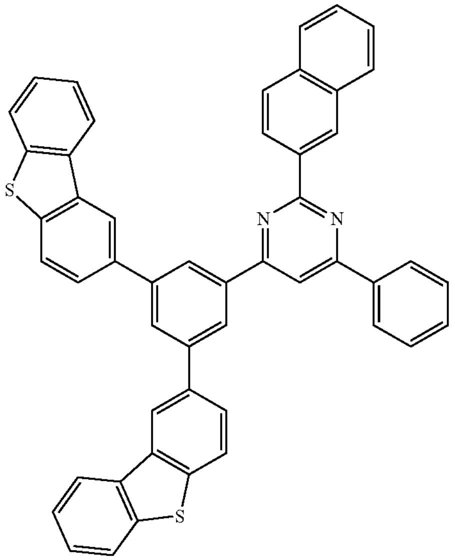

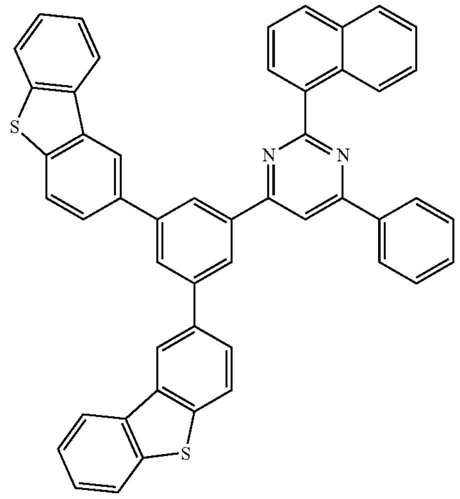
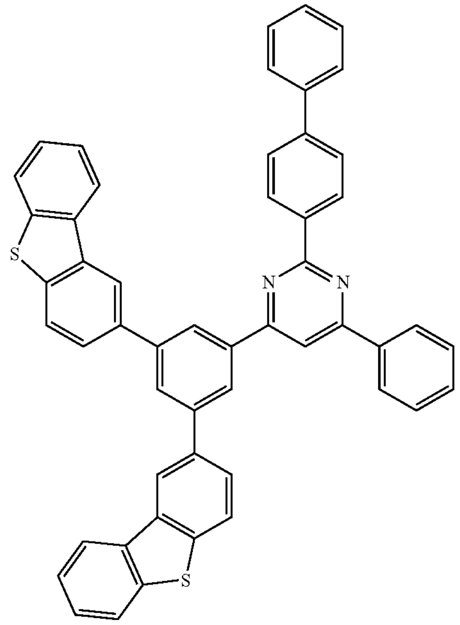
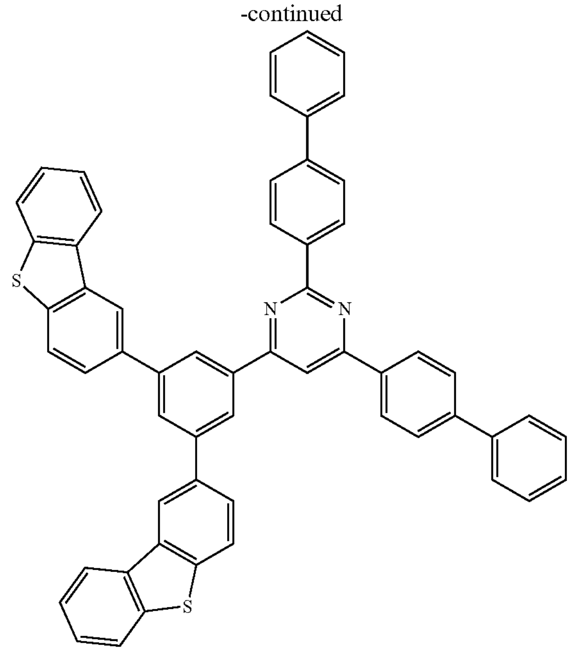
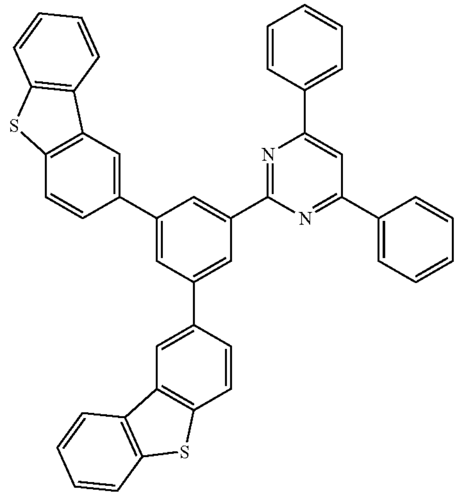
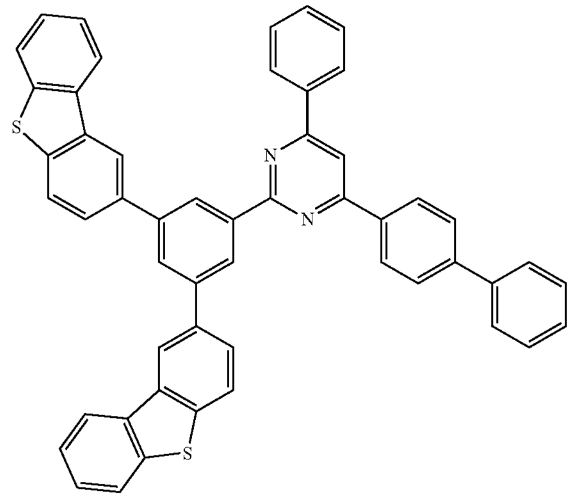

-continued
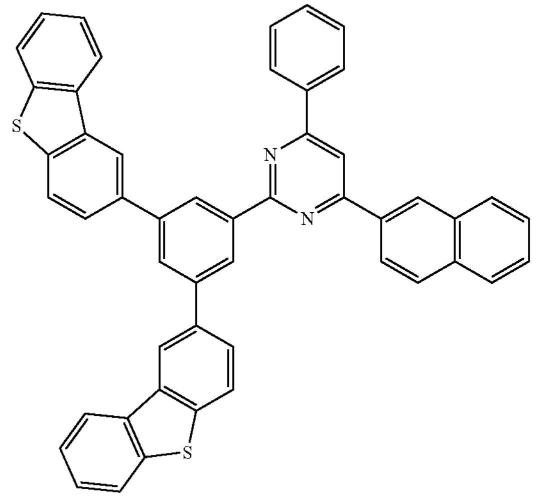
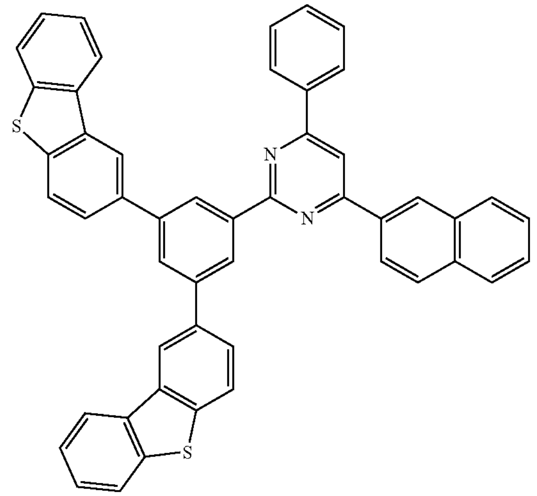
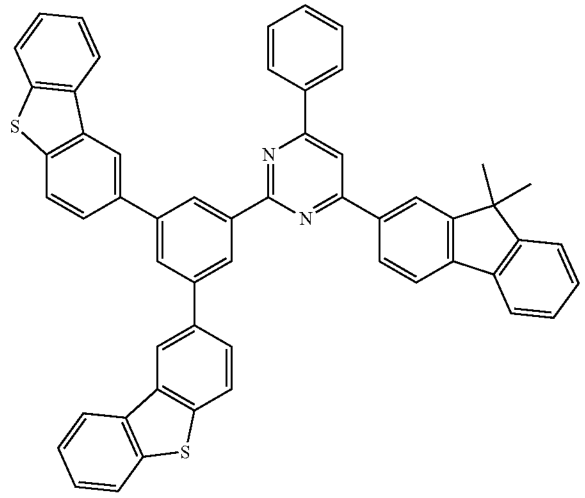
-continued
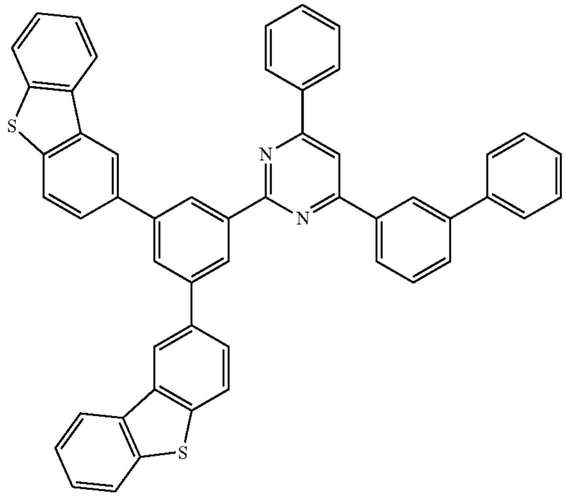
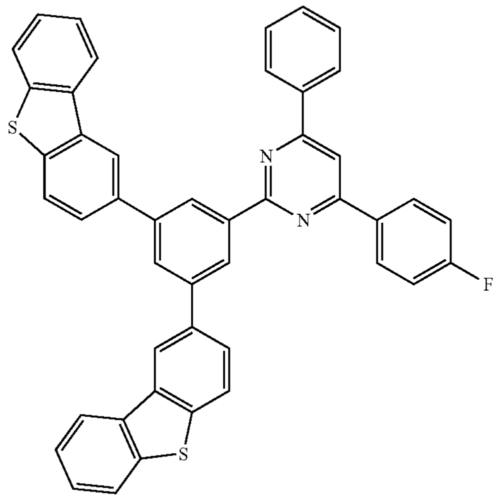
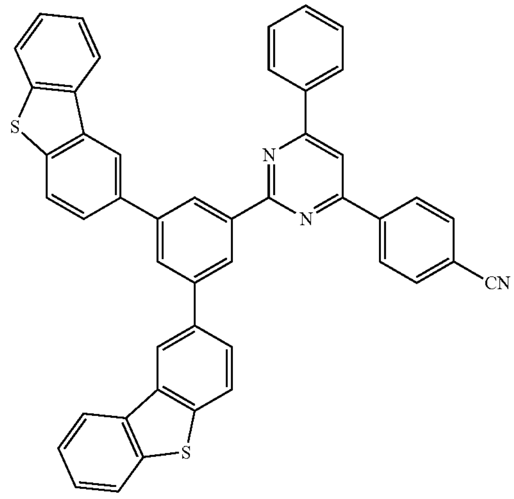

-continued
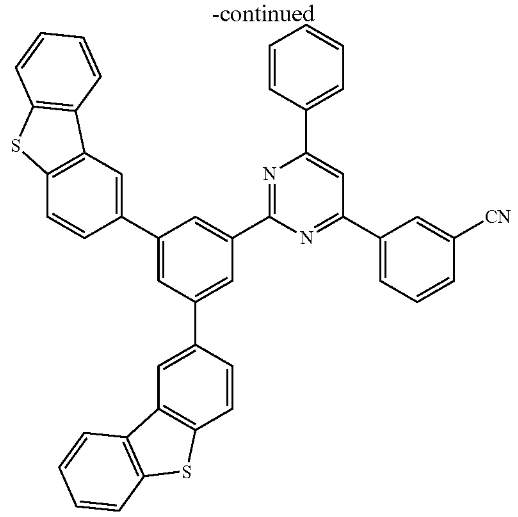
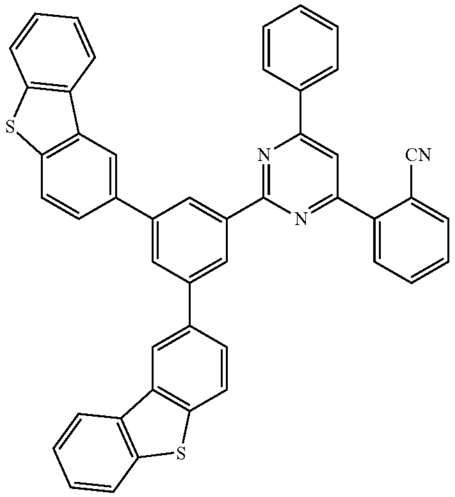
-continued
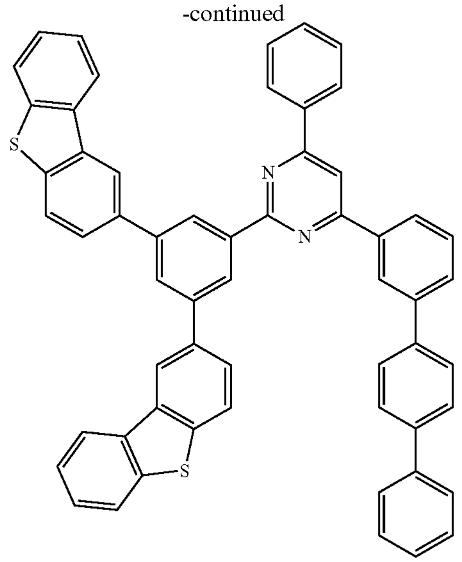
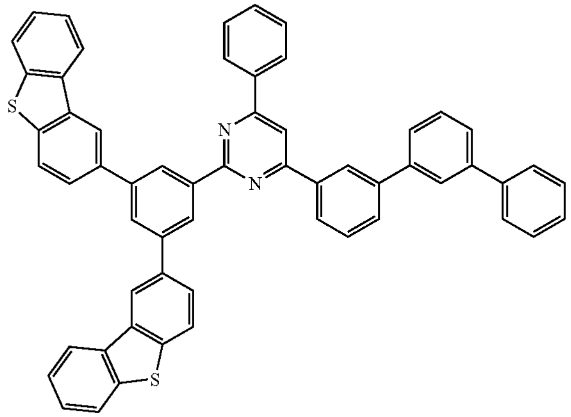
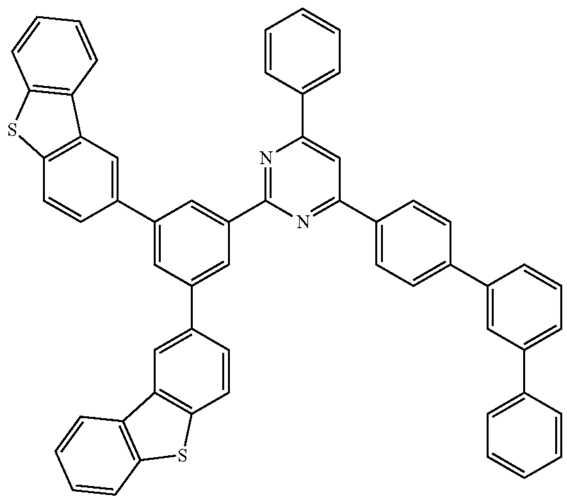
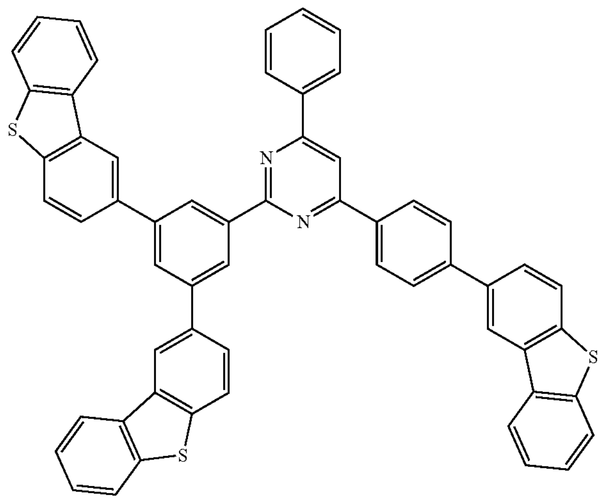

-continued
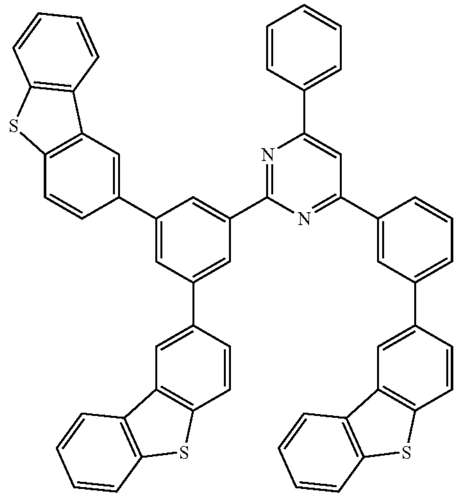
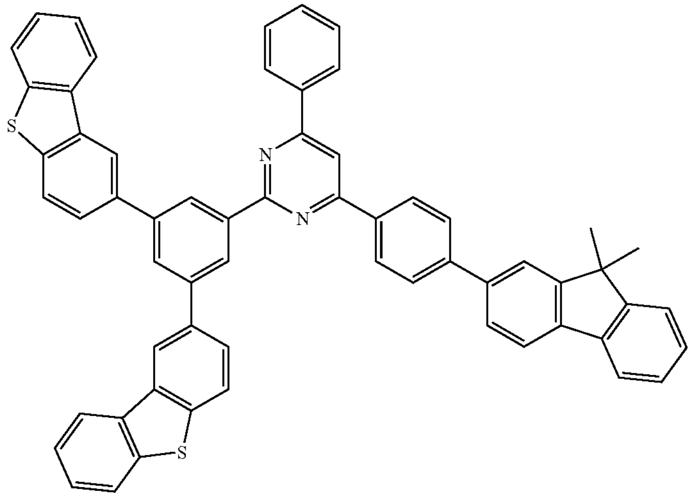
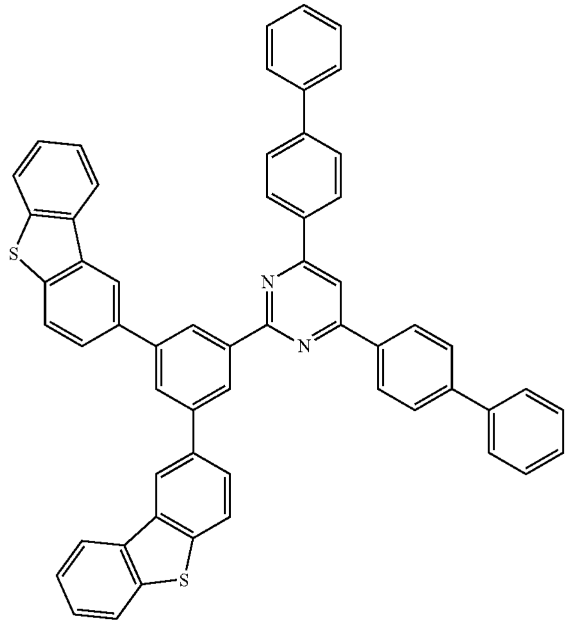
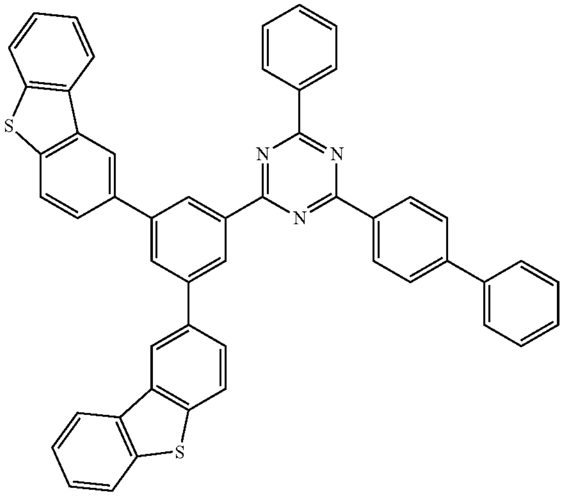
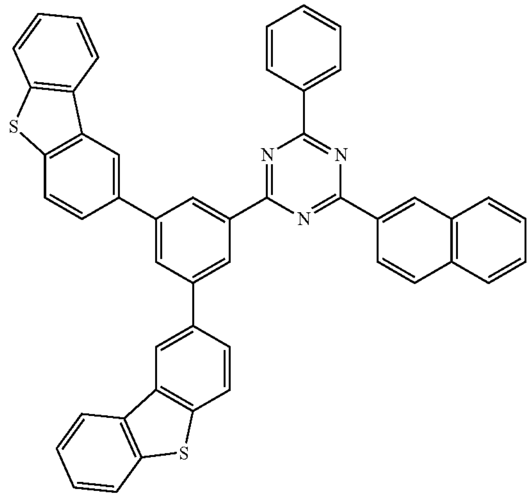
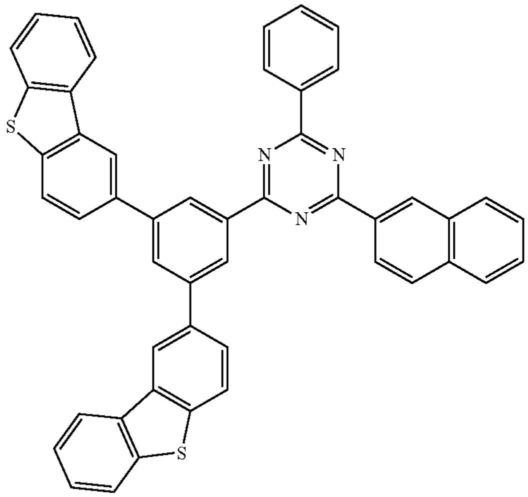

-continued
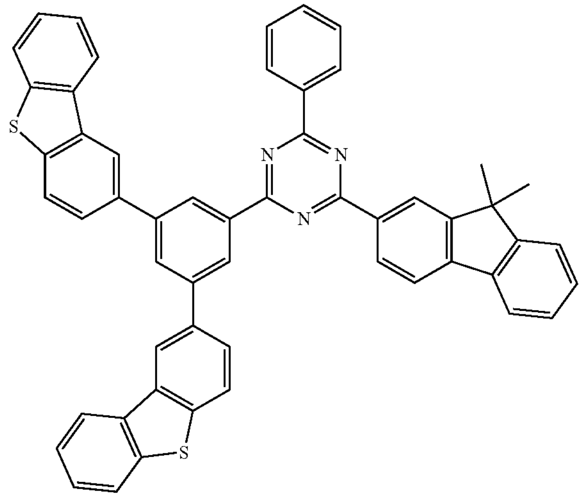
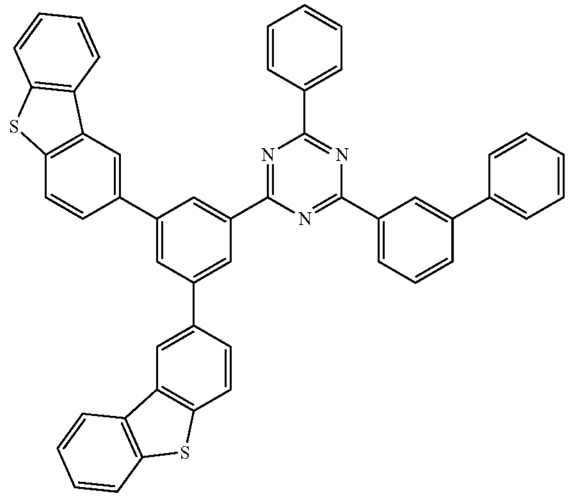
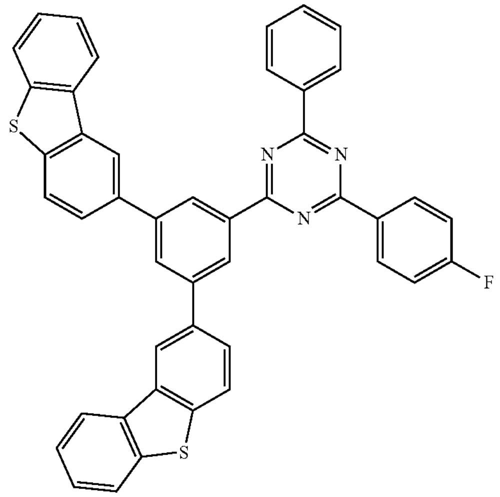
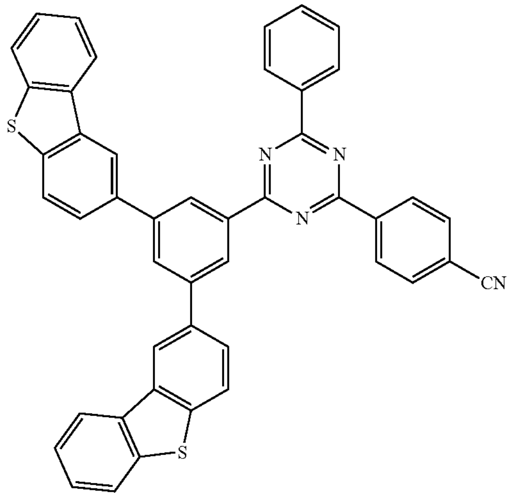
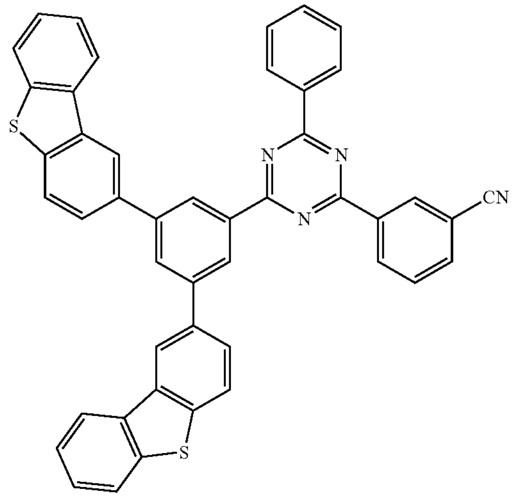
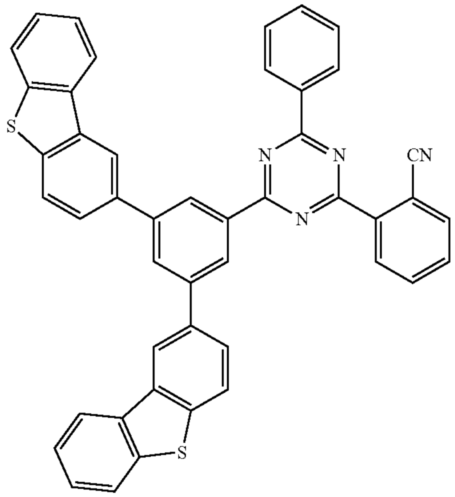

-continued
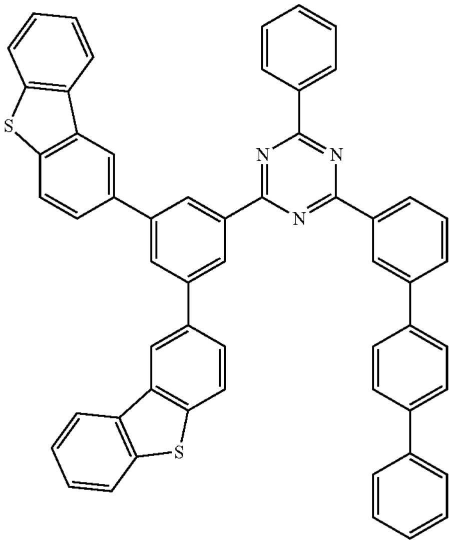
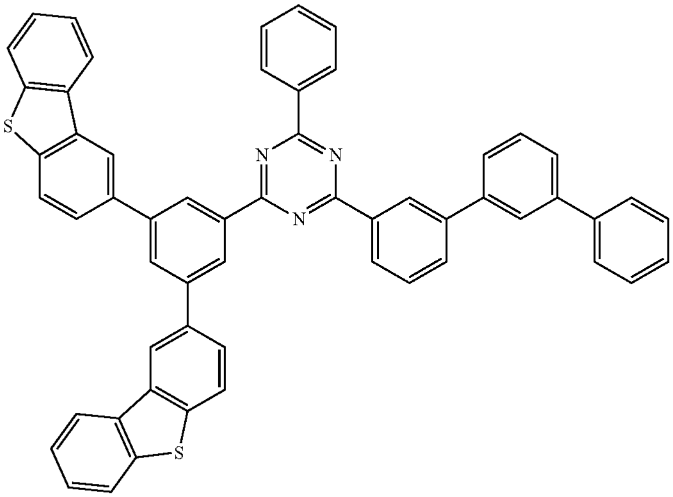
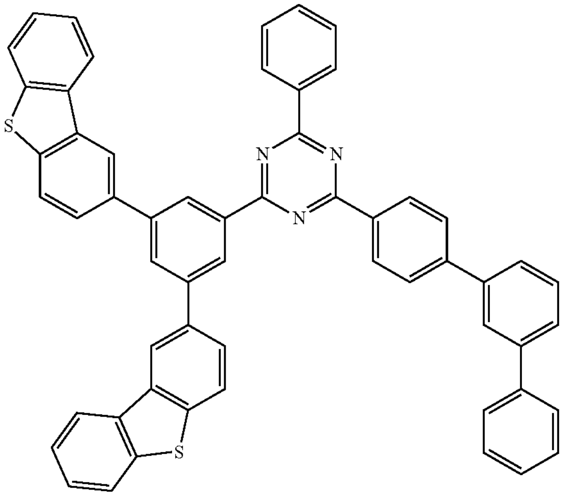
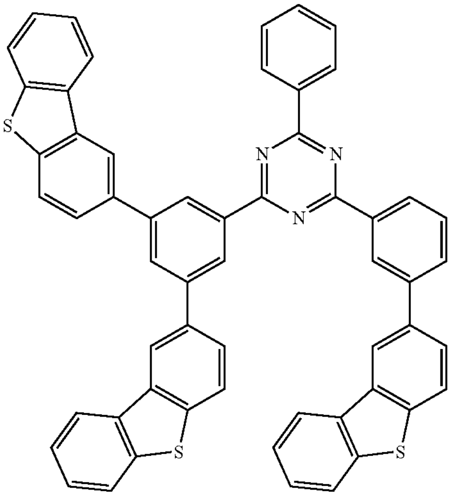
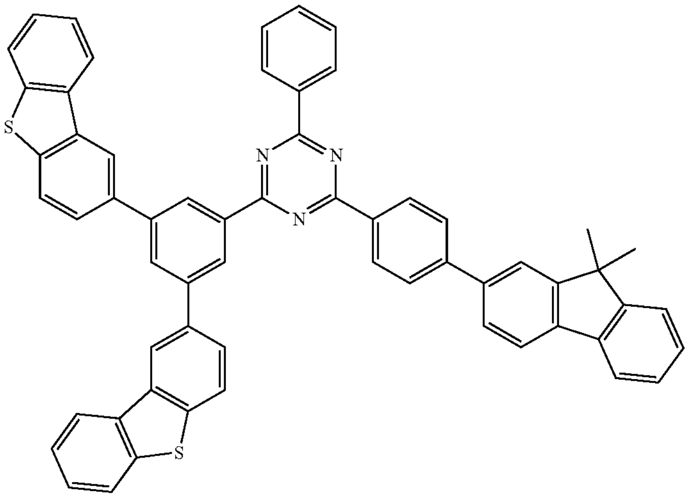

-continued
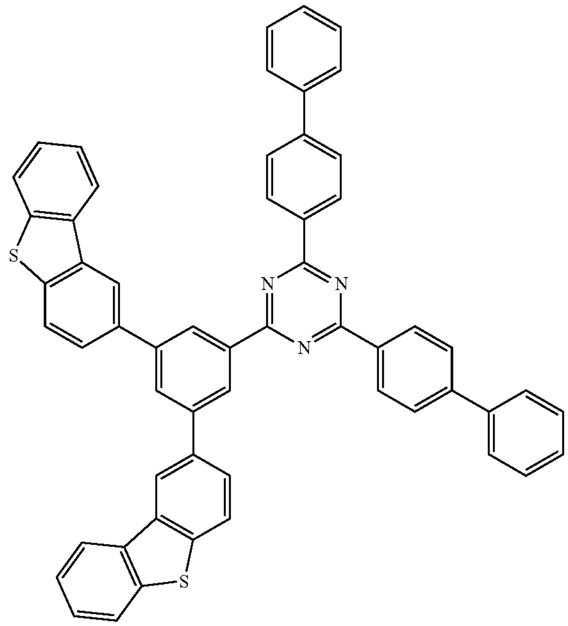
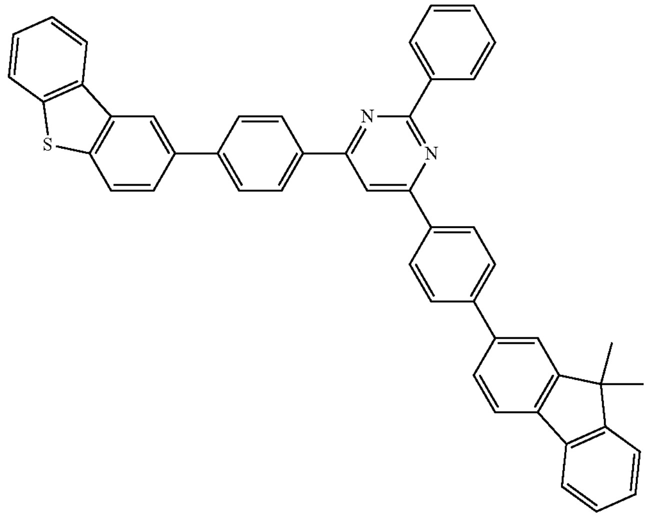
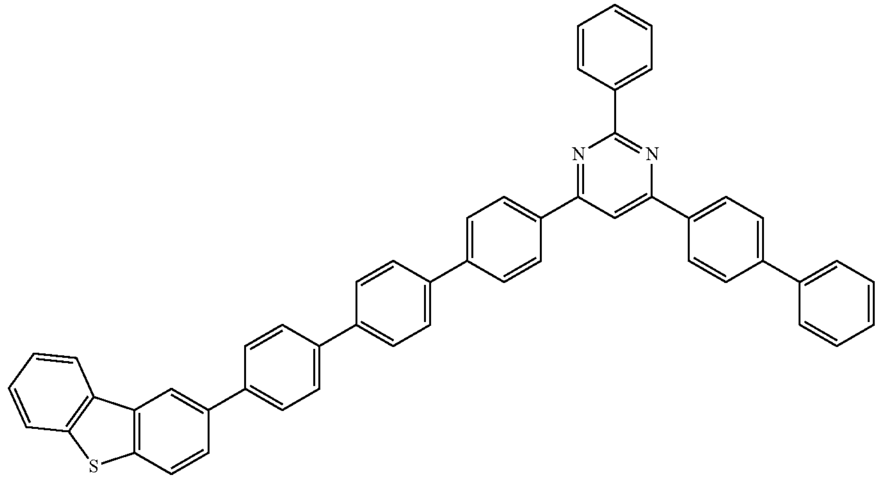

-continued
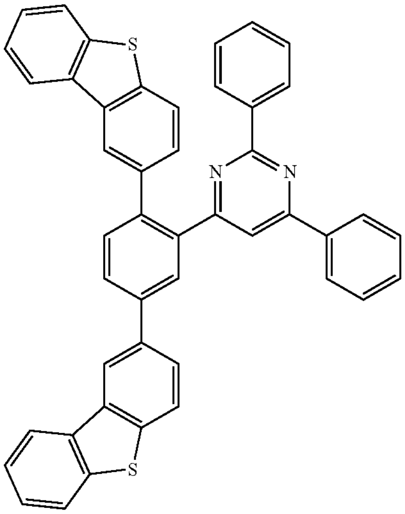
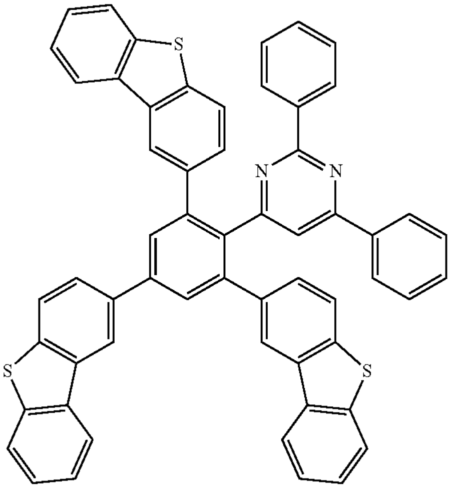
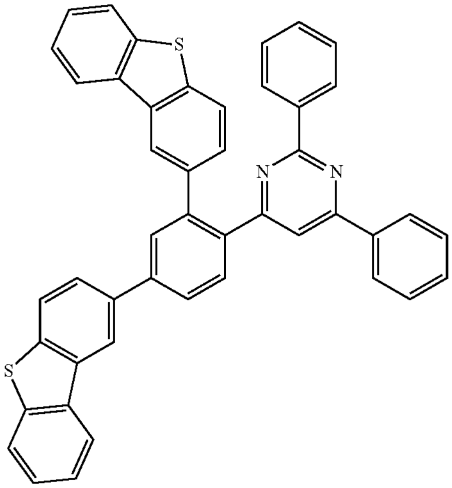
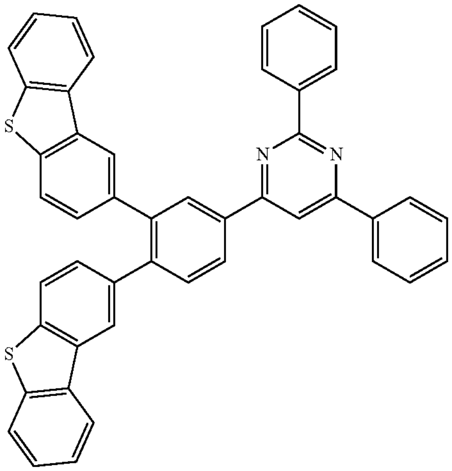
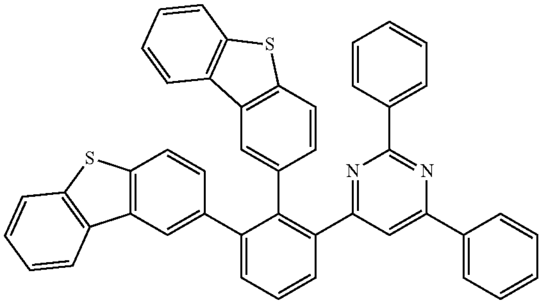
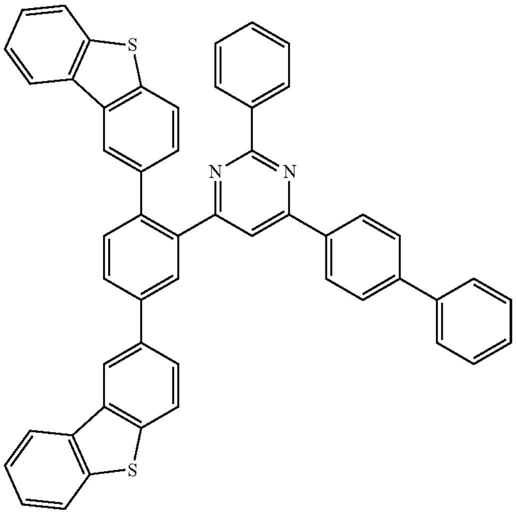

-continued
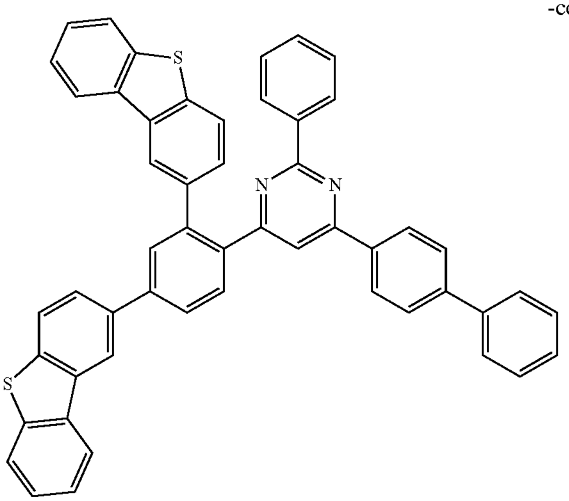
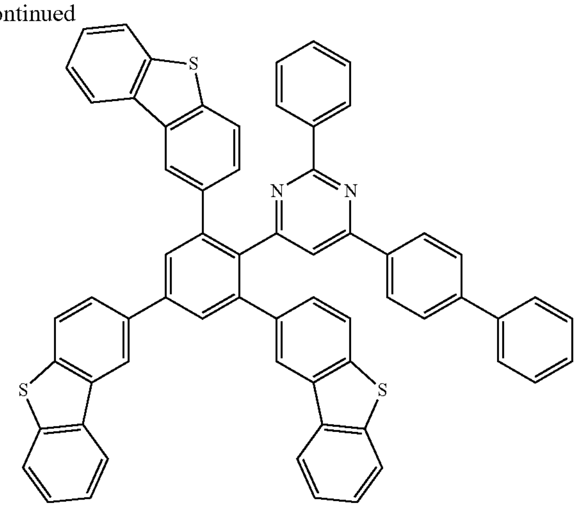
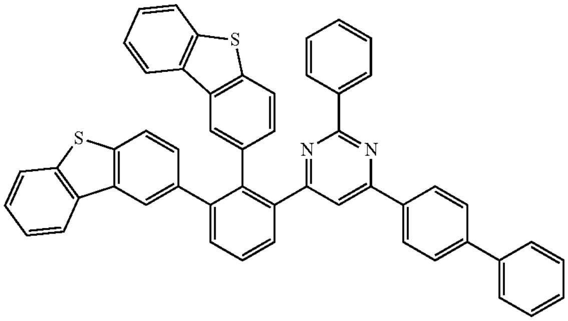
-continued
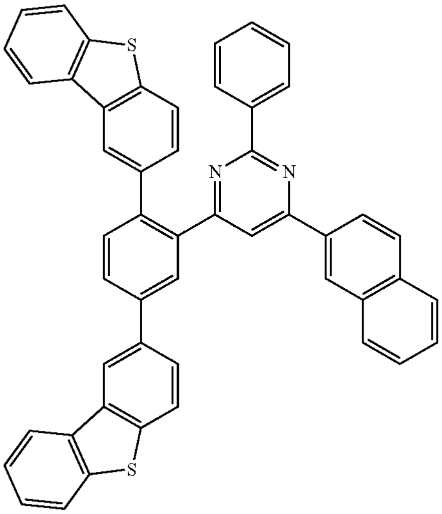
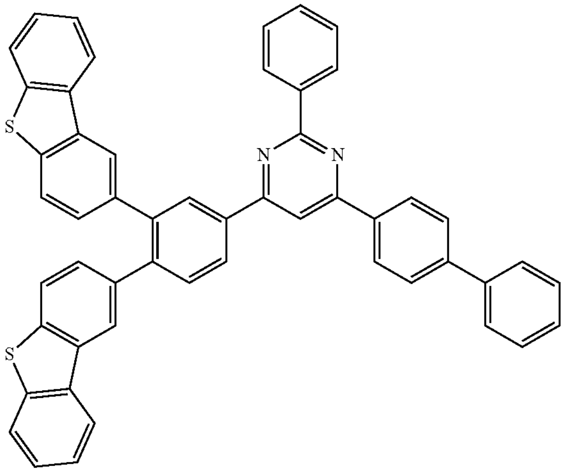
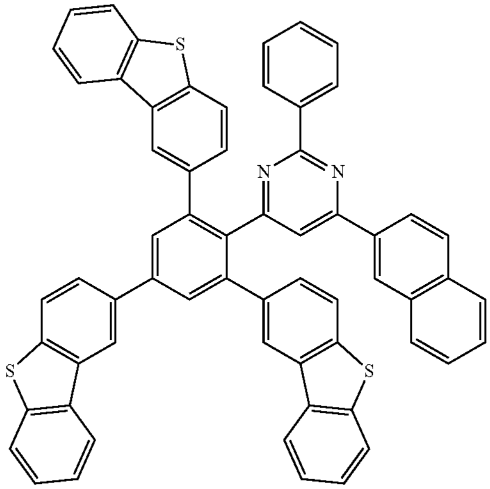

-continued
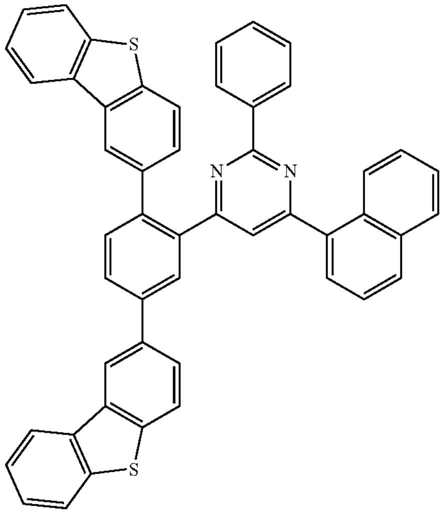
-continued
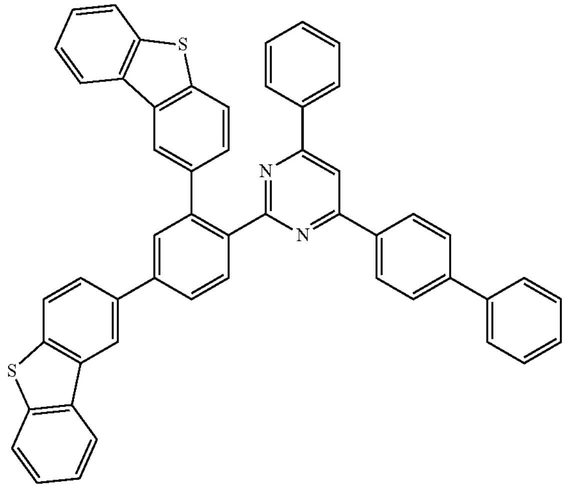
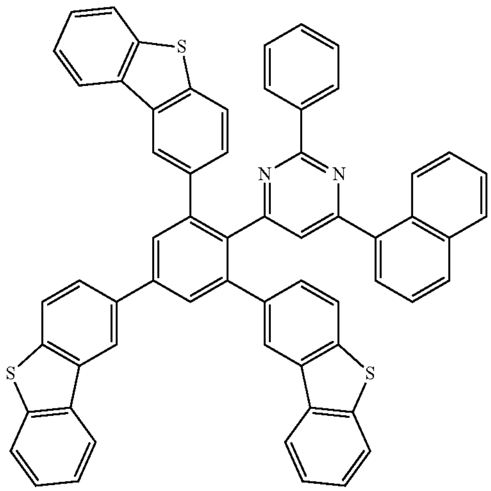
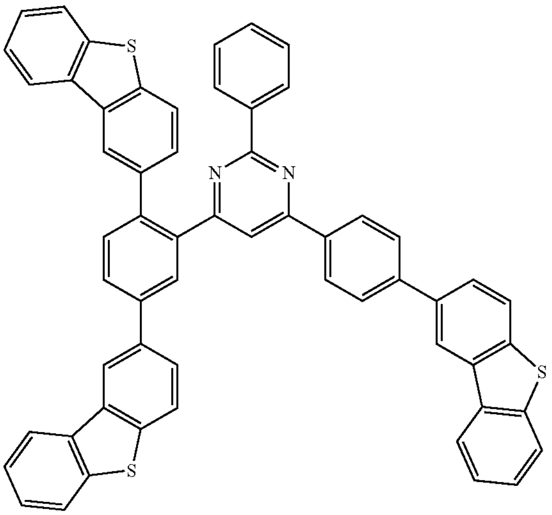
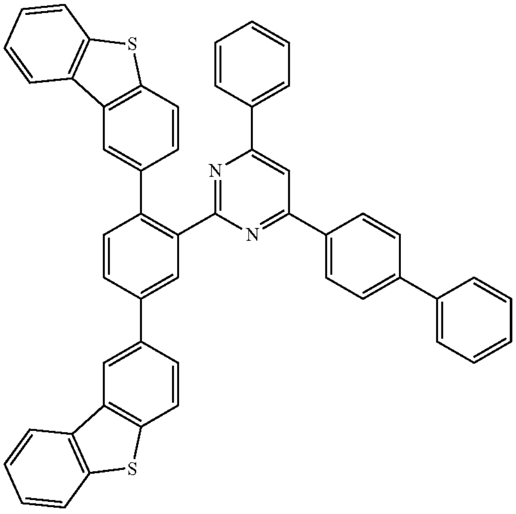
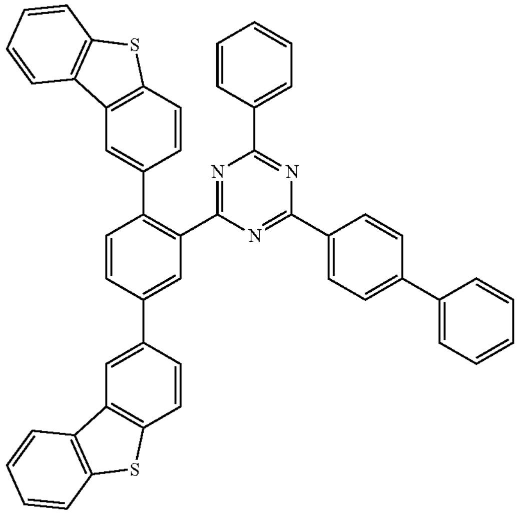

-continued
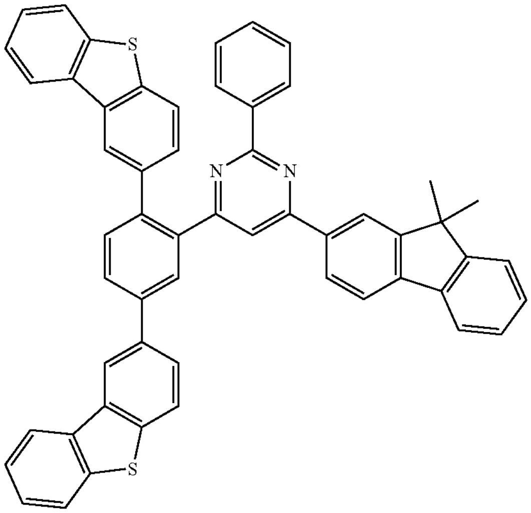
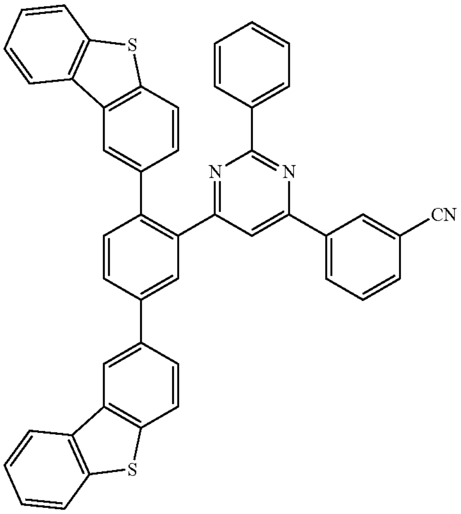
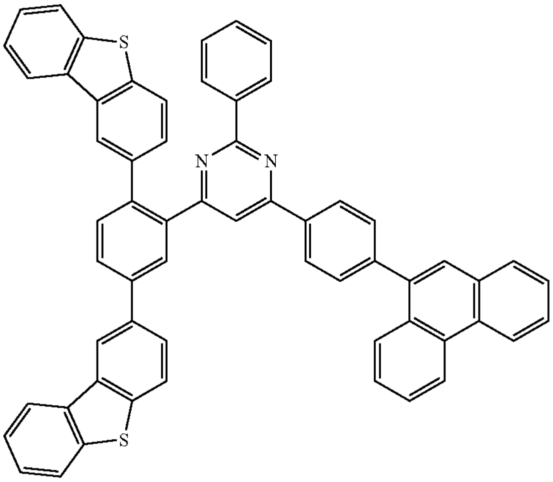
-continued
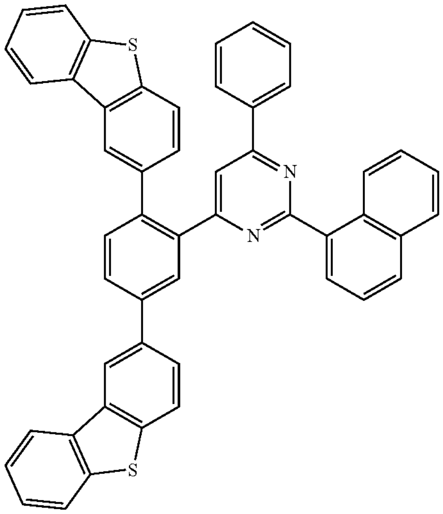
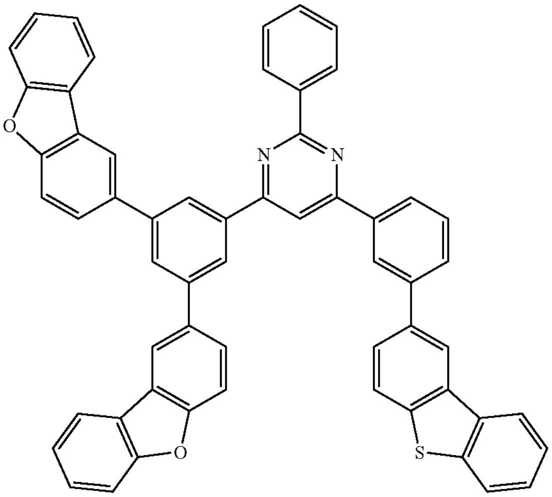
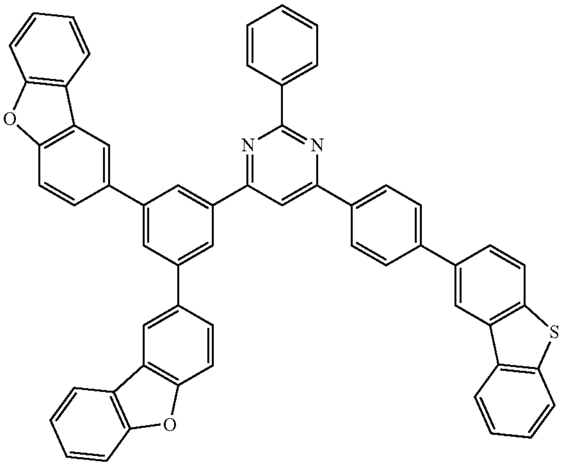

-continued
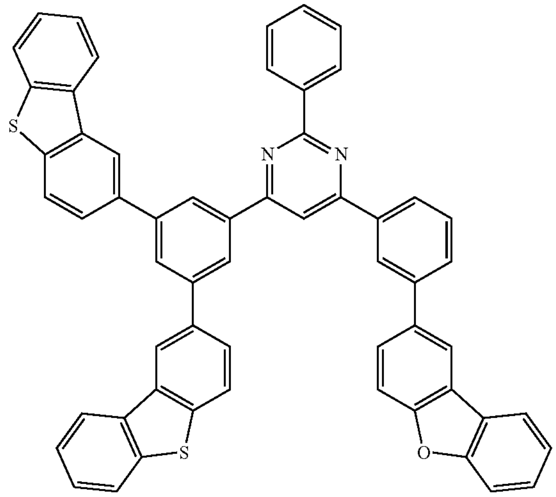
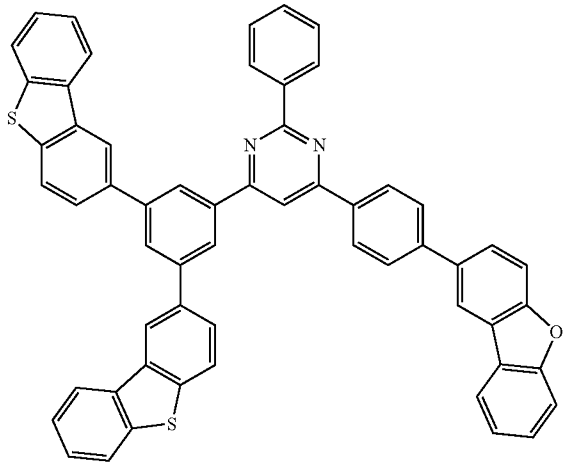
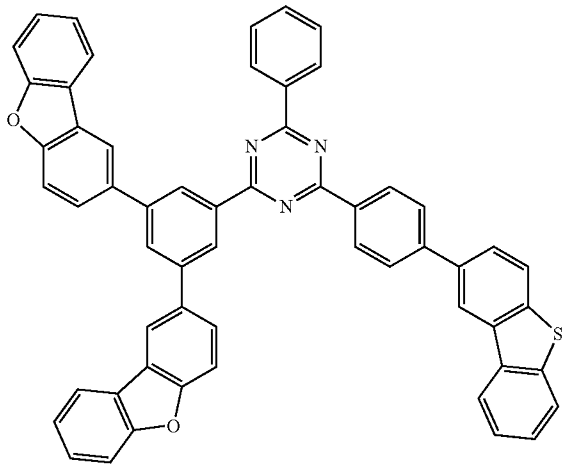
-continued
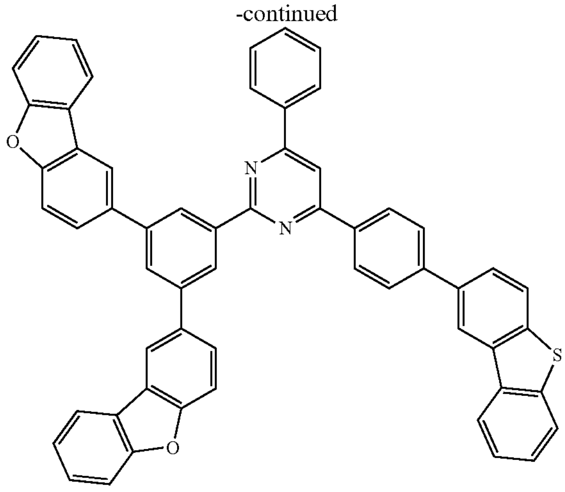
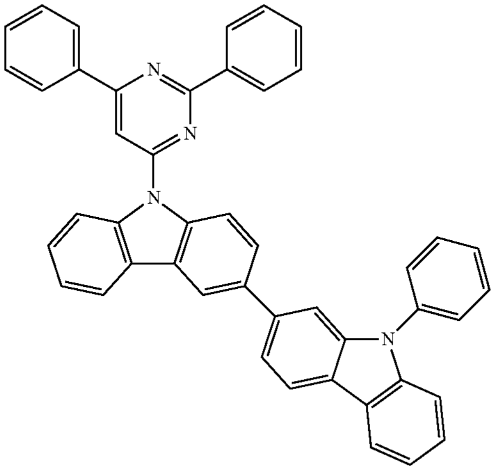
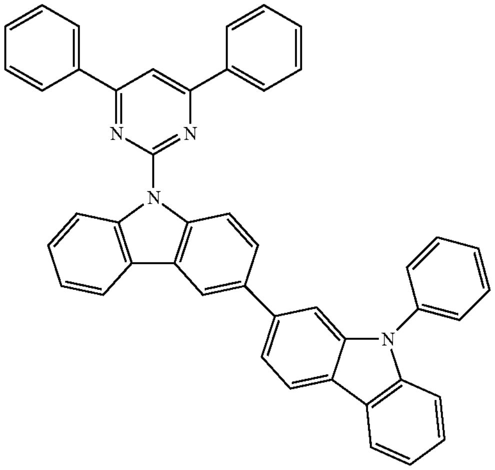

-continued
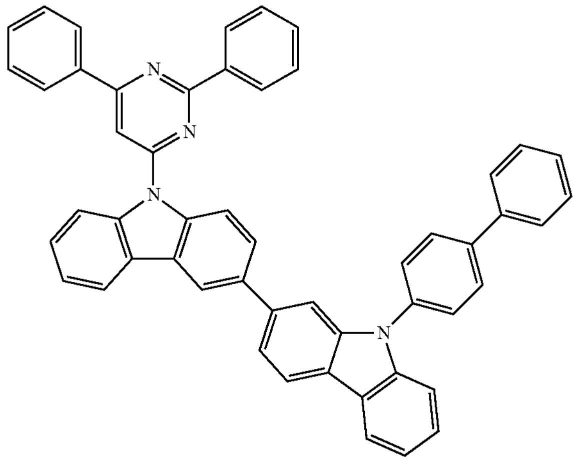
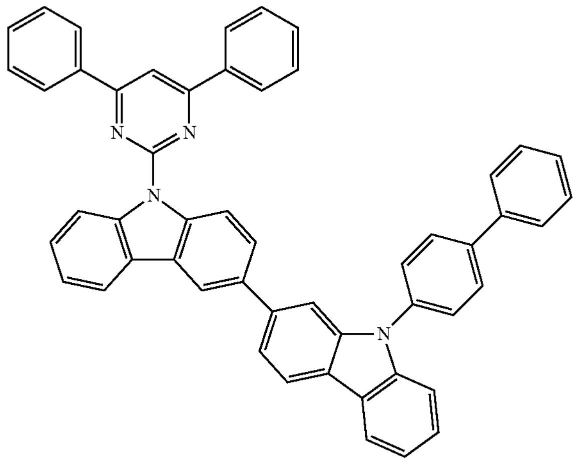
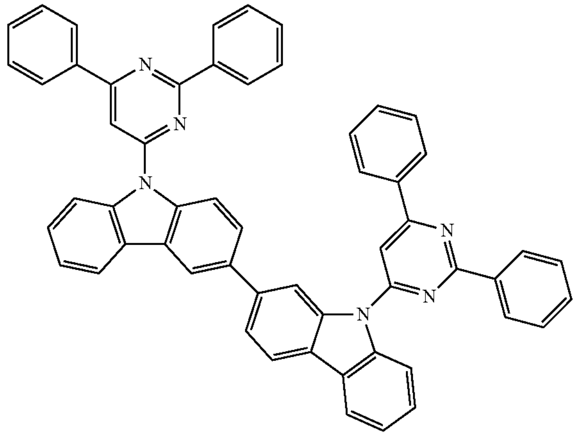
-continued
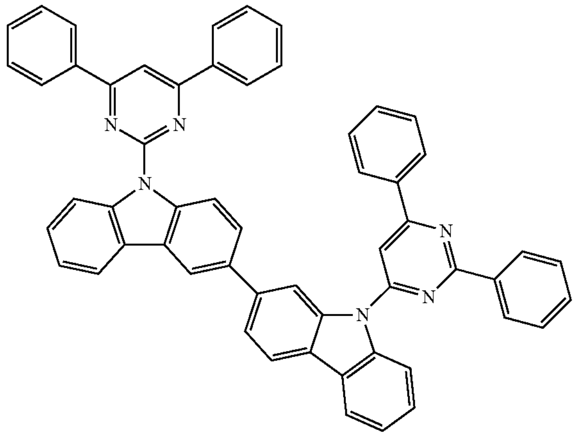
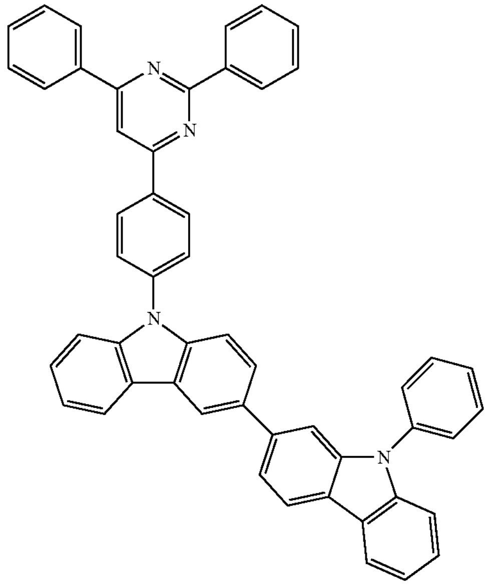
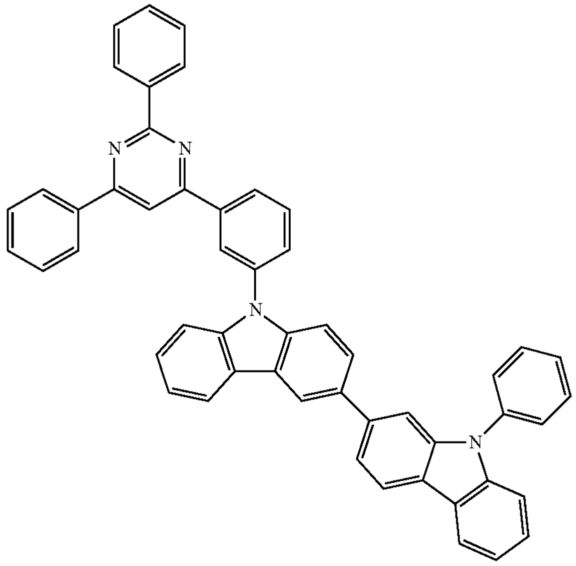

-continued
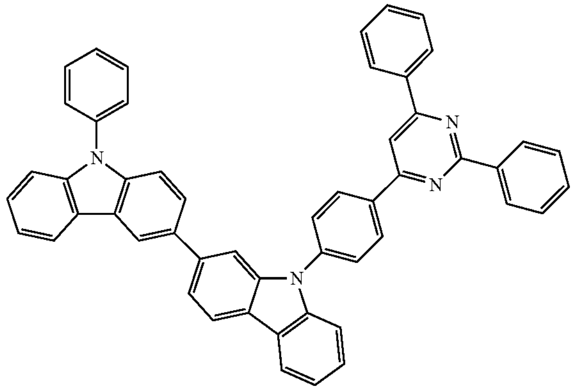
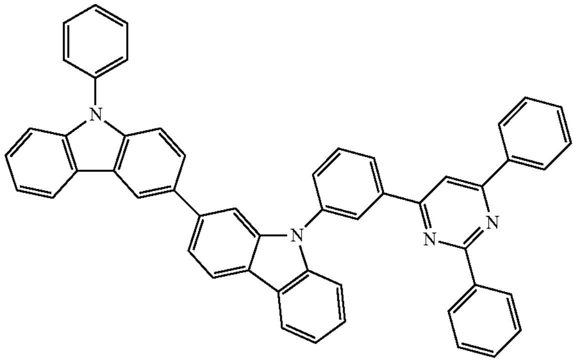 [SMILES: c1ccc(-c2cc(-c3cccc(-n4c5ccccc5c5ccc(-c6ccc7c(c6)c6ccccc6n7-c6ccccc6)cc54)c3)nc(-c3ccccc3)n2)cc1]
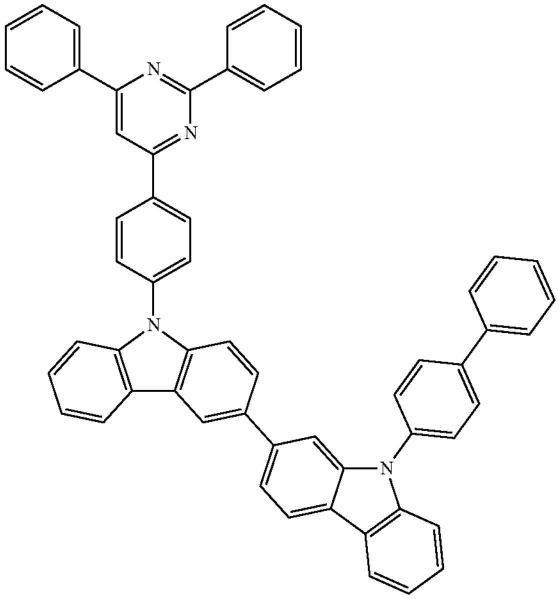
-continued
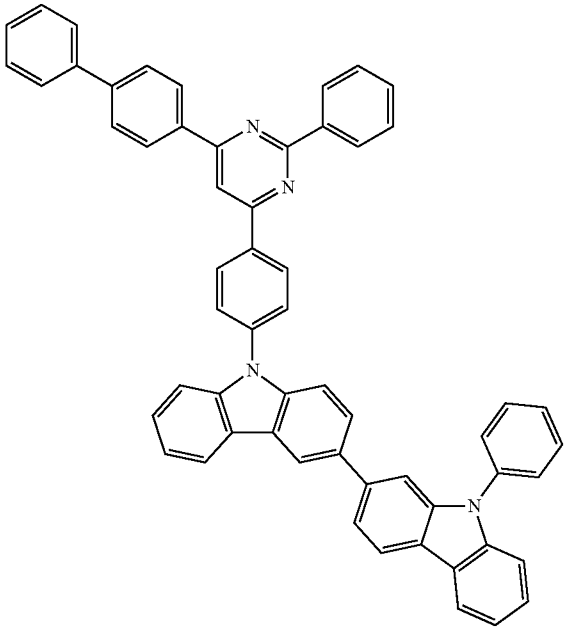
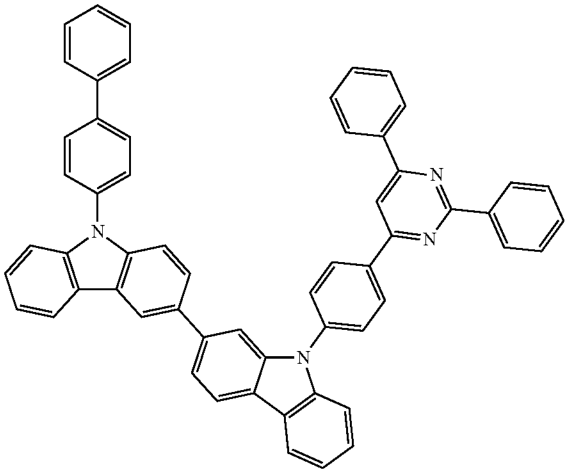
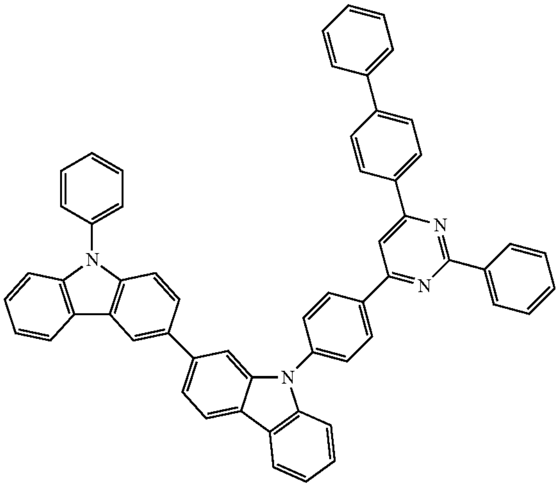

-continued
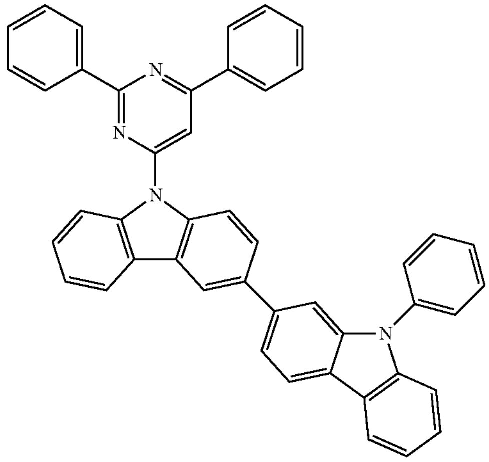
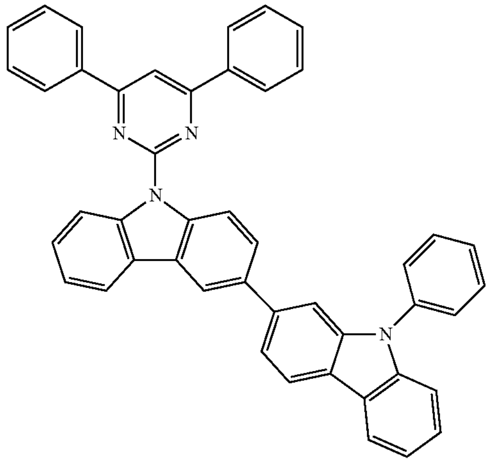
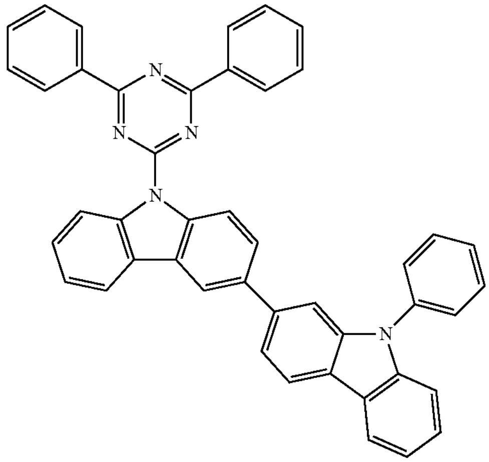
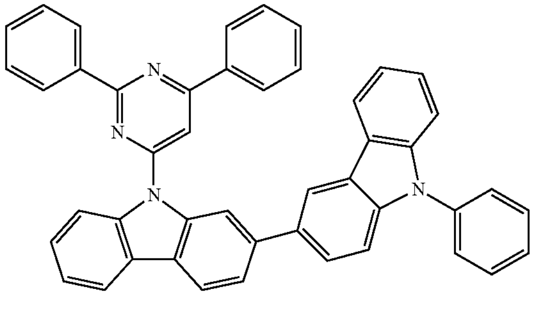
-continued
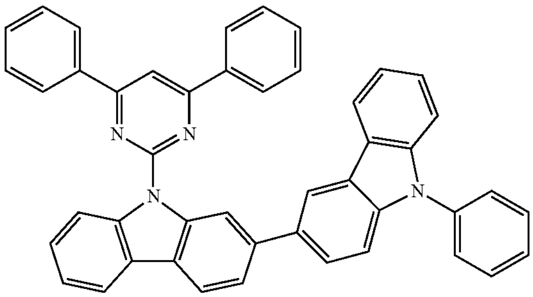
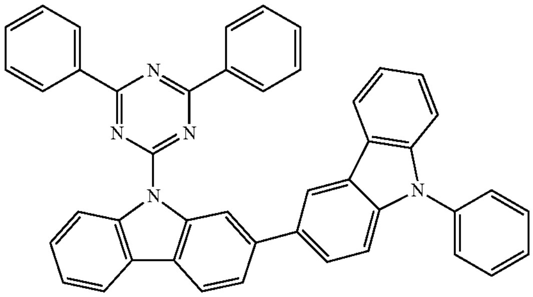
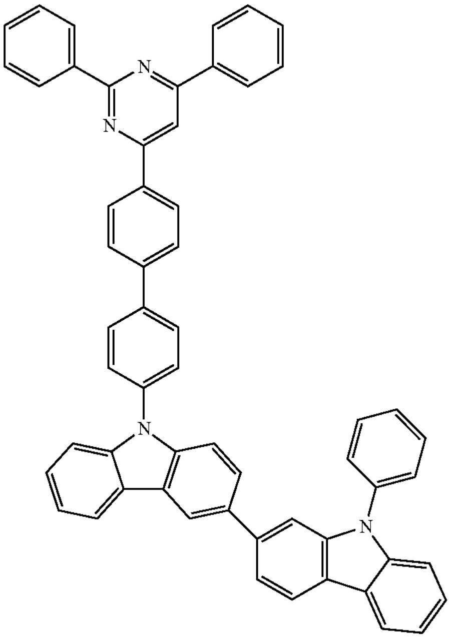

-continued
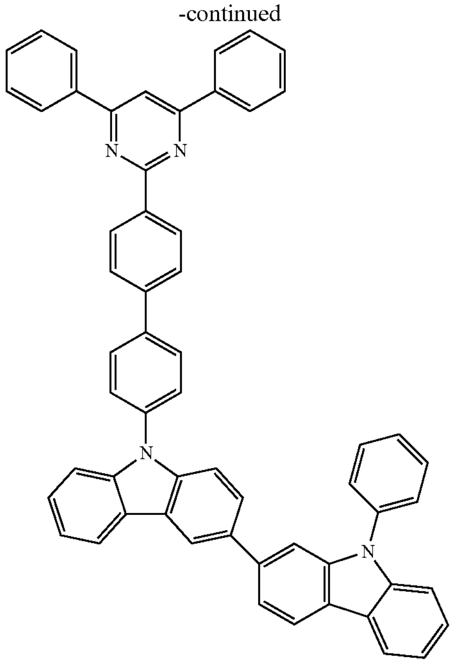
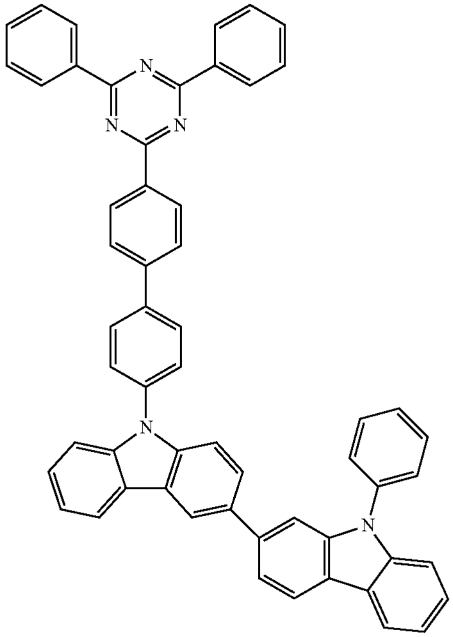
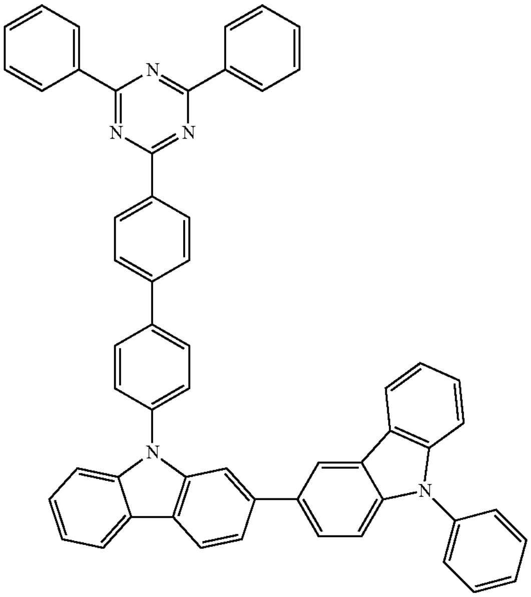
-continued
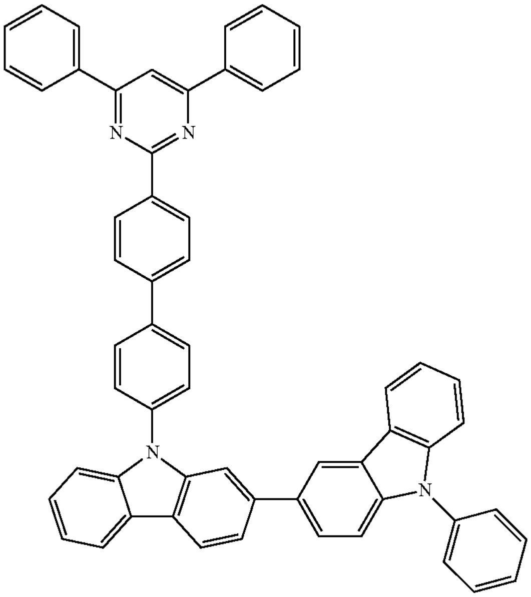

-continued
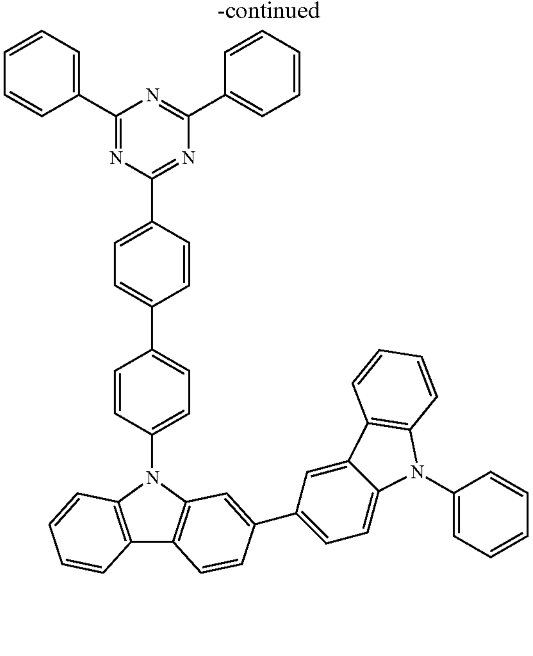
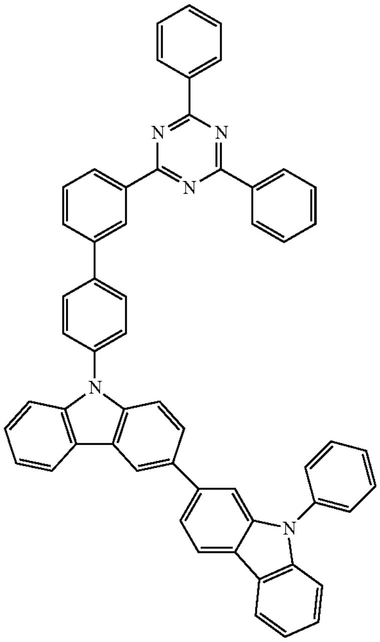
-continued
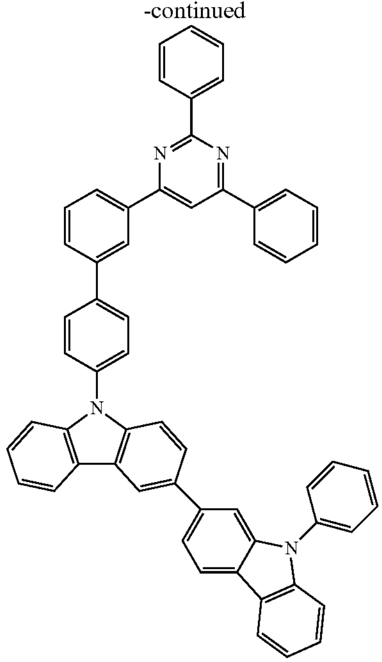
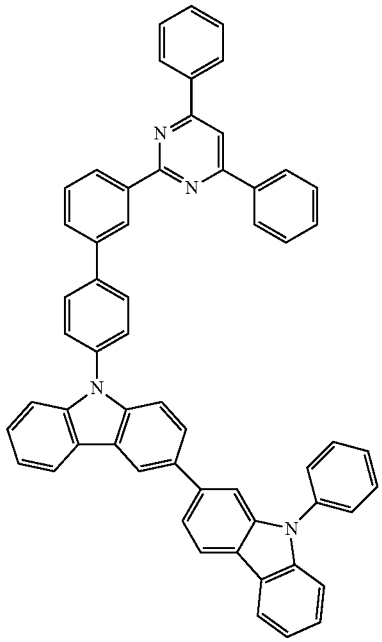

-continued
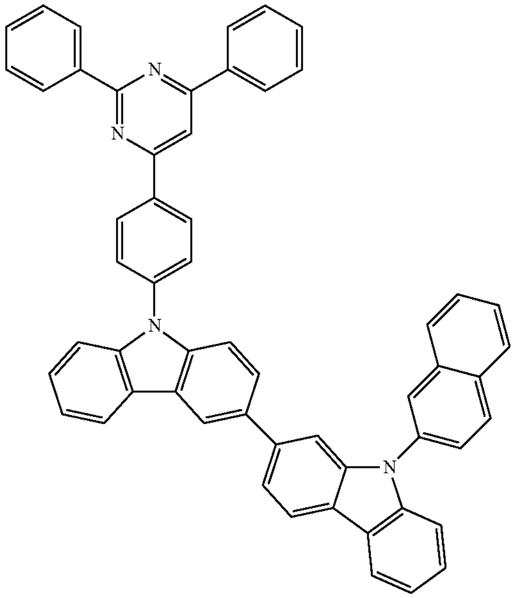
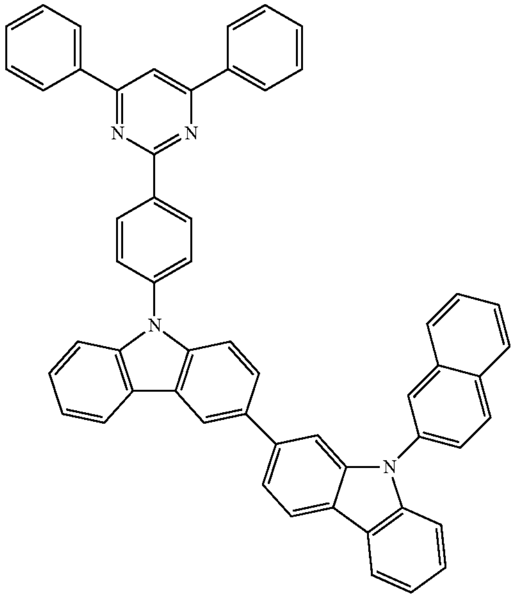
-continued
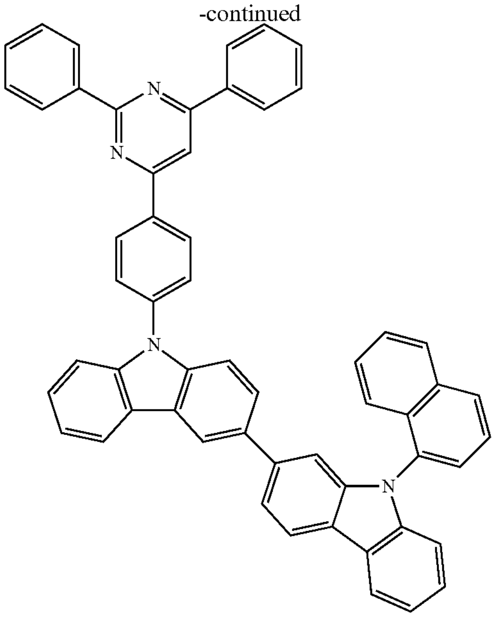
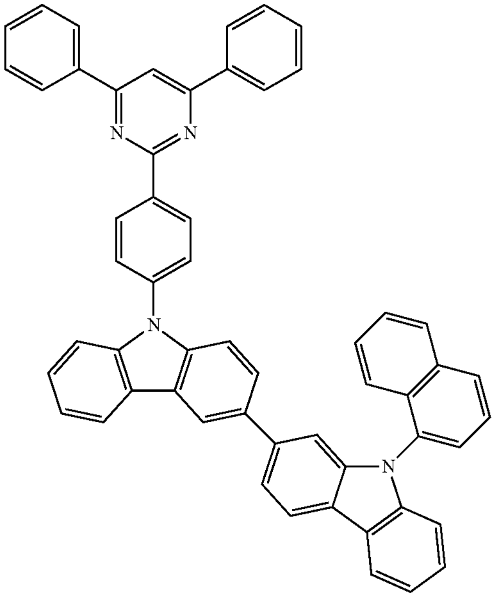

-continued
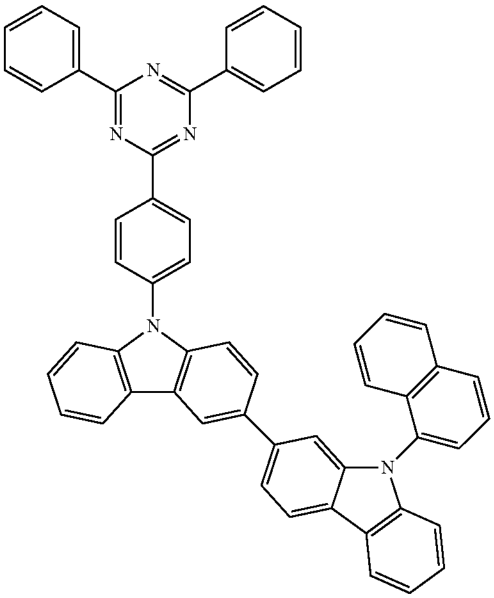
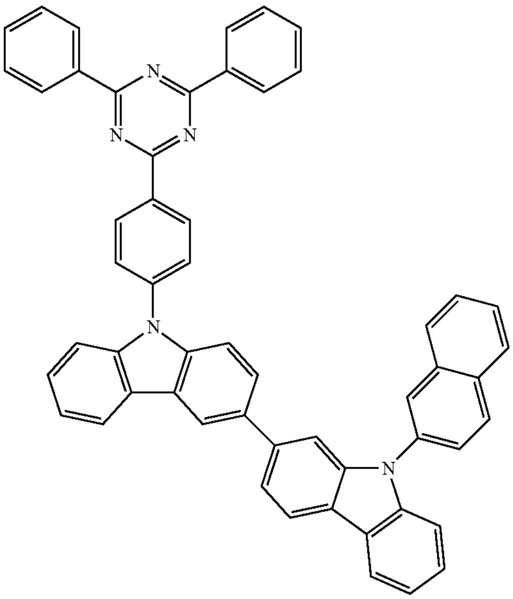
-continued
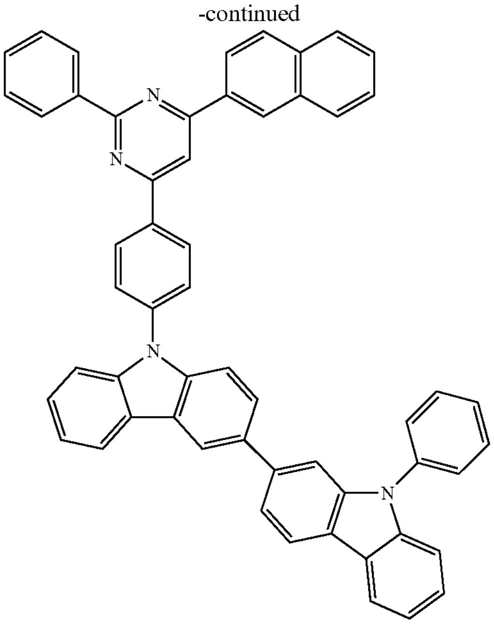
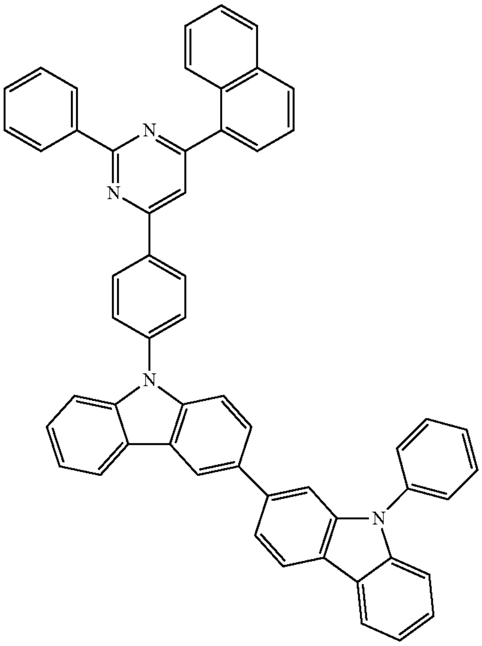

-continued
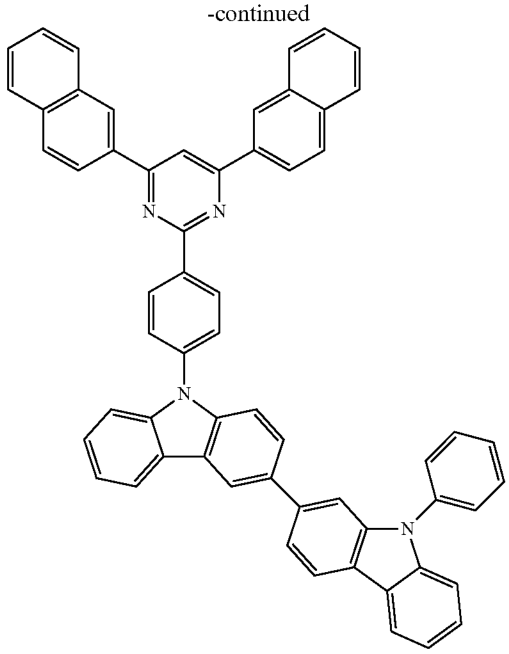
-continued
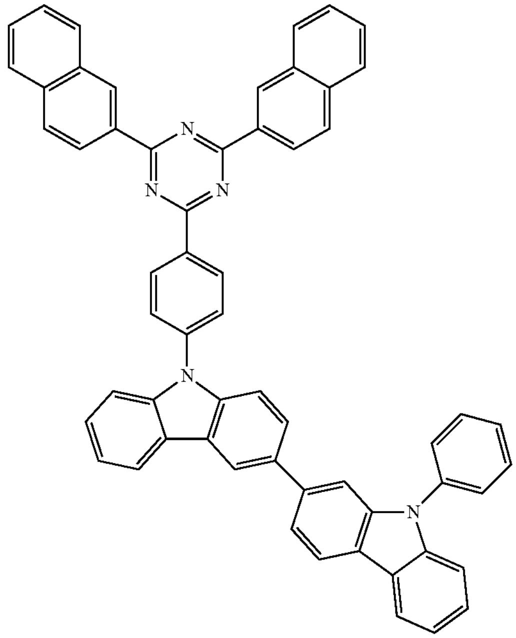 [SMILES: c1ccc(-n2c3ccccc3c3ccc(-c4ccc5c(c4)c4ccccc4n5-c4ccc(-c5nc(-c6ccc7ccccc7c6)nc(-c6ccc7ccccc7c6)n5)cc4)cc32)cc1]
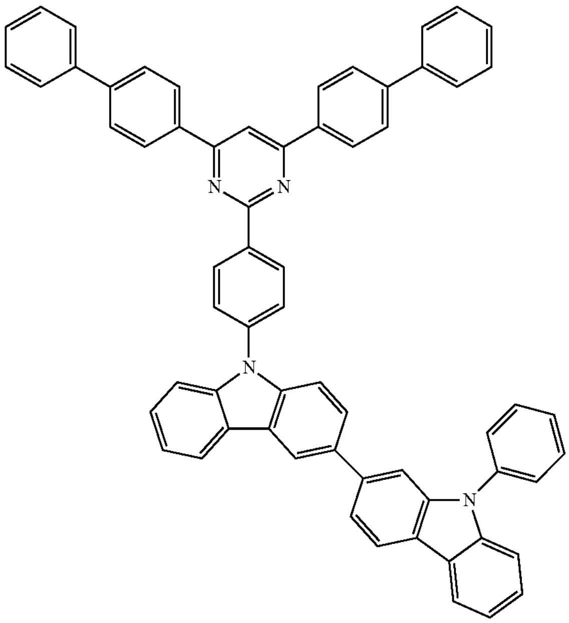
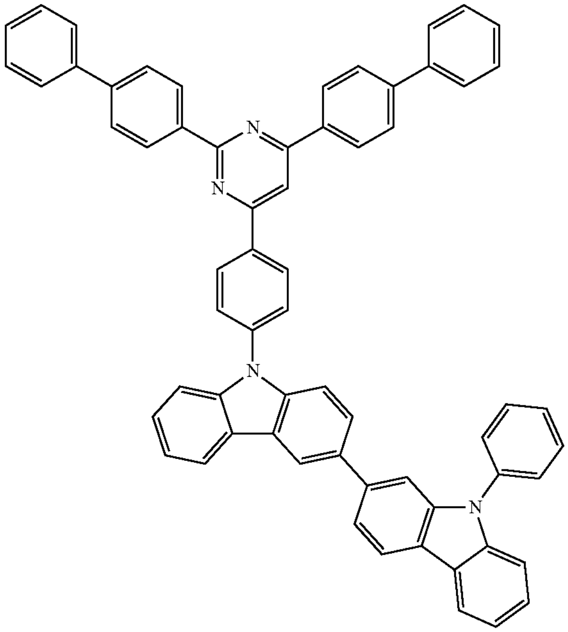

-continued
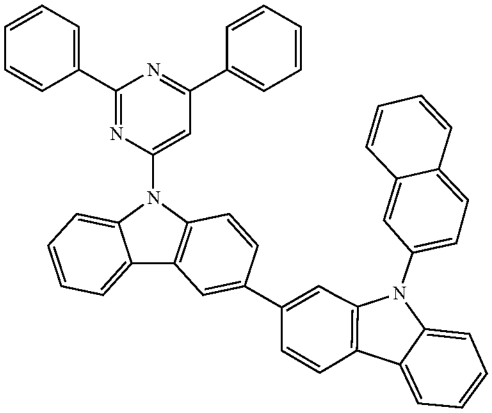
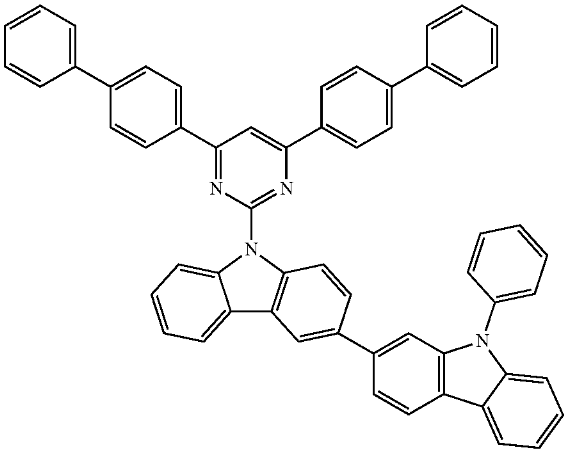
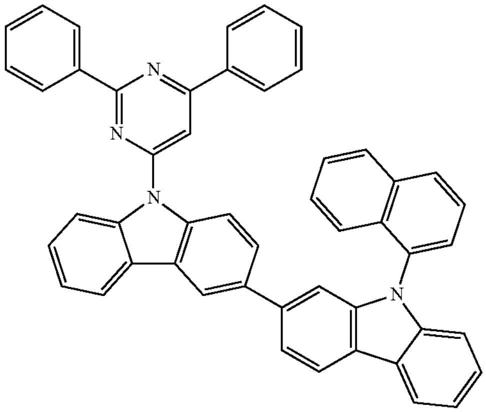
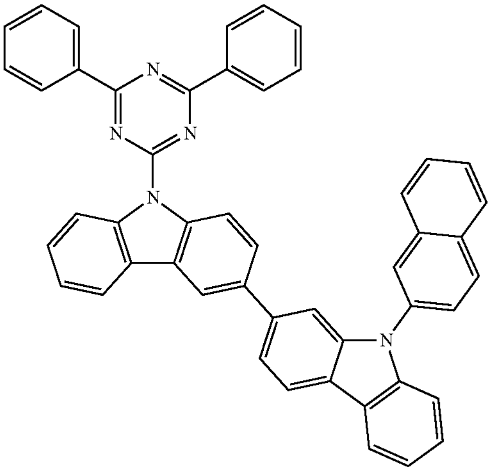
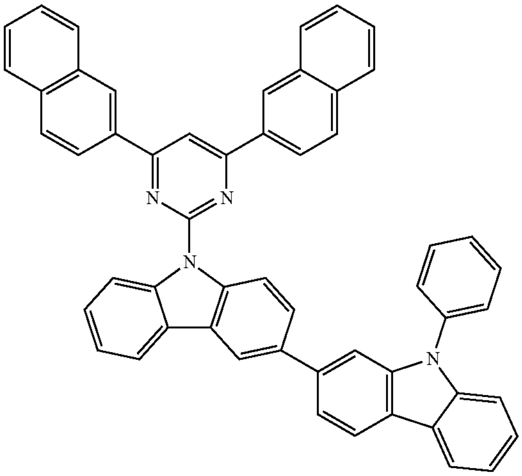
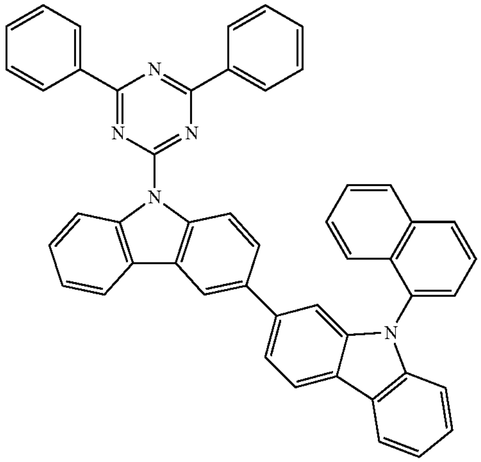
-continued -continued
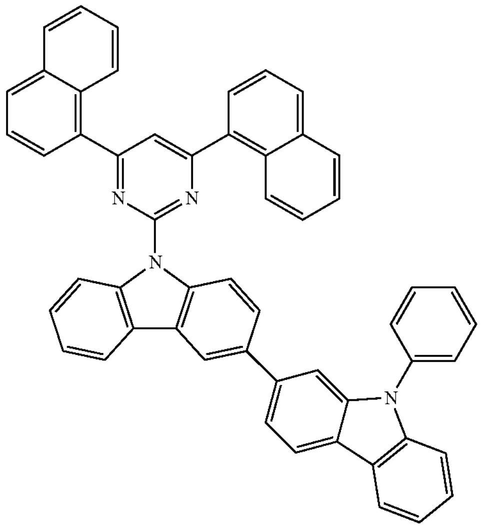
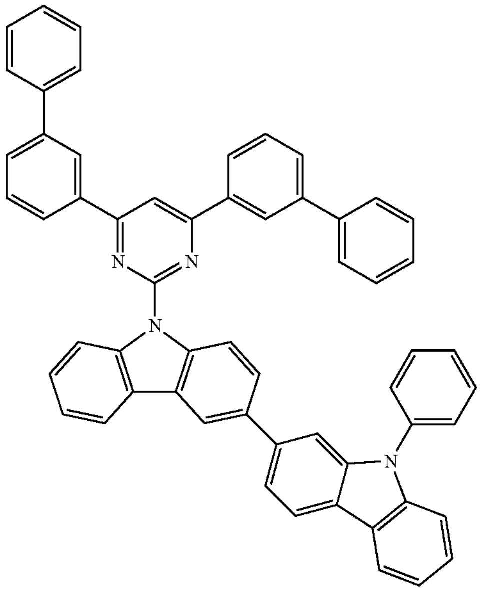
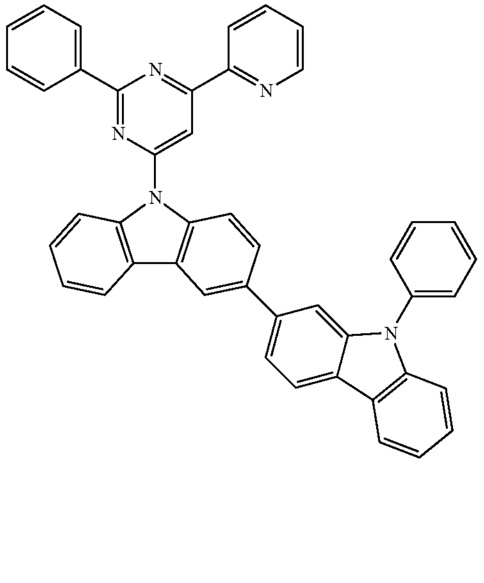
-continued
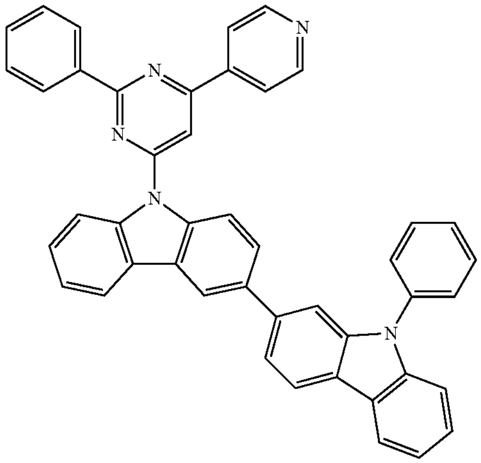
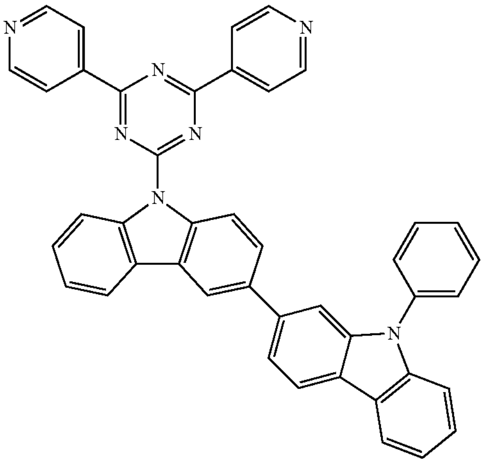
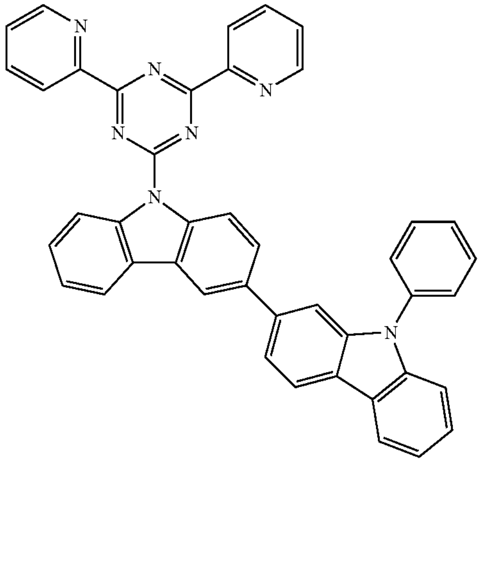

-continued
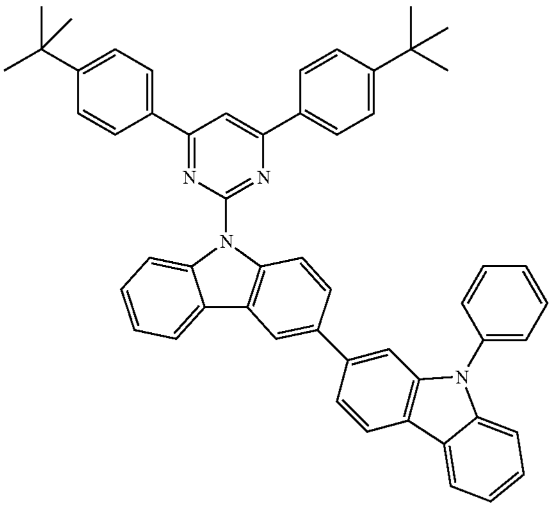
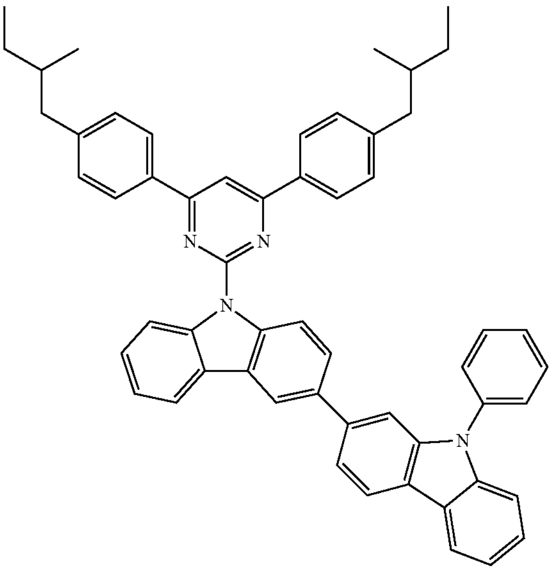
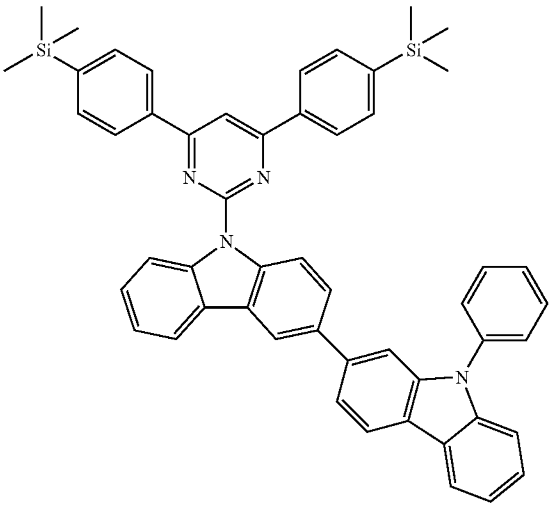
-continued
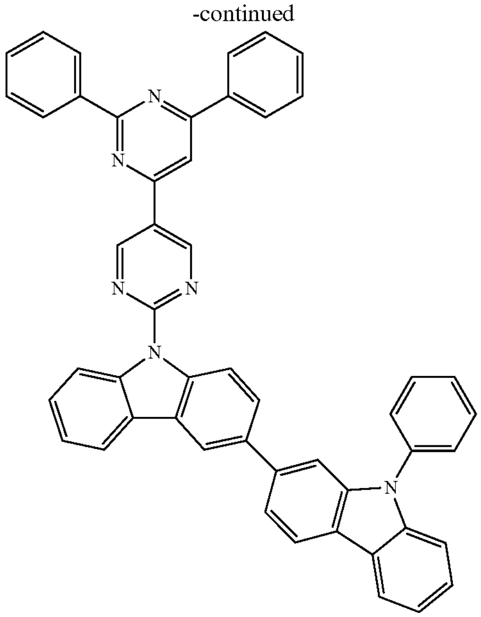
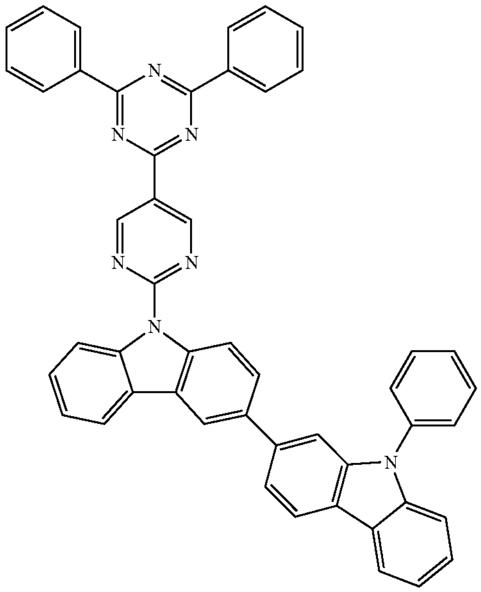

-continued
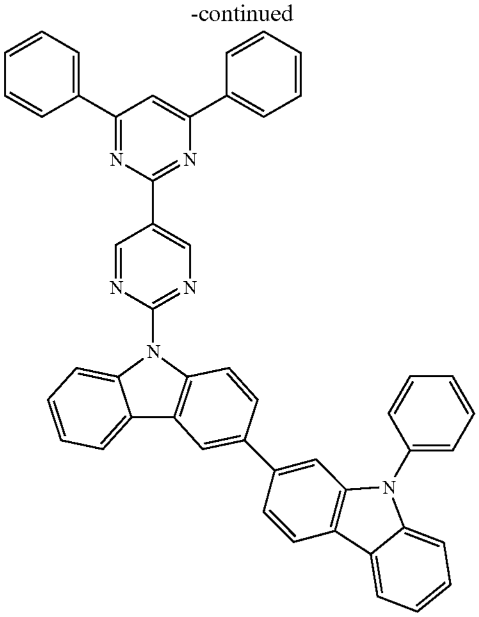
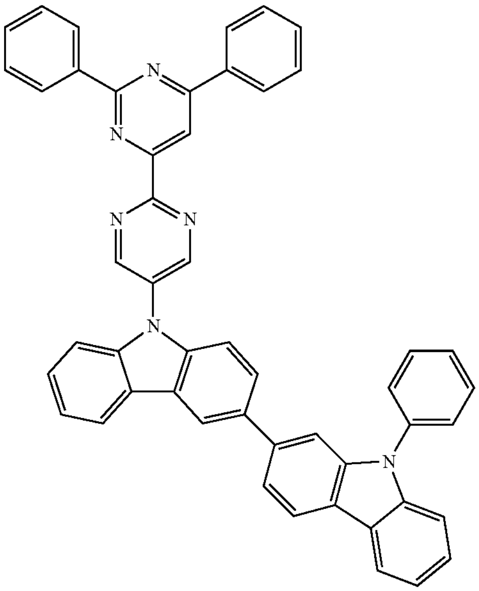
-continued
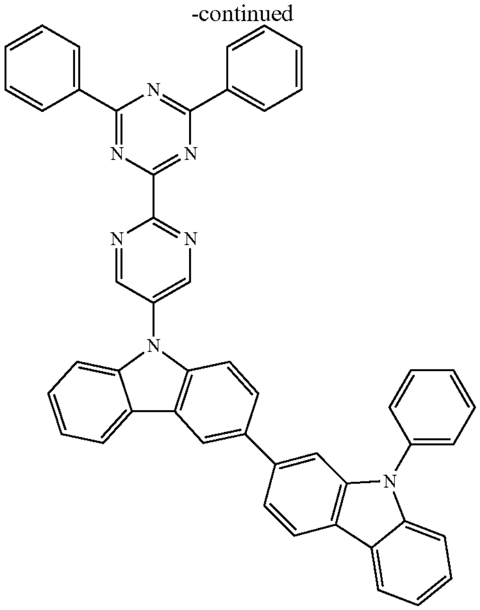
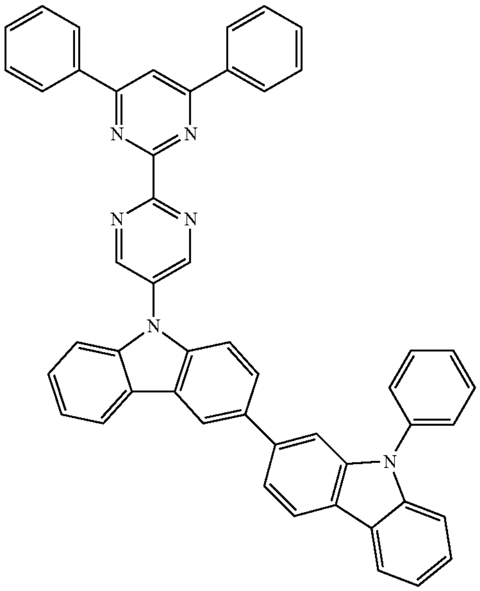
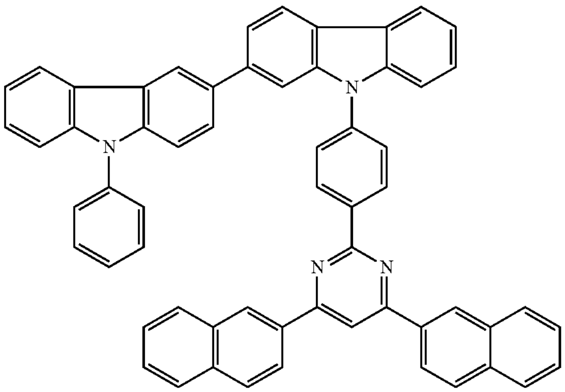

-continued
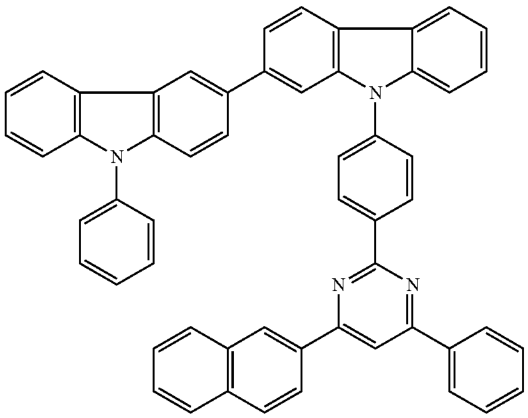
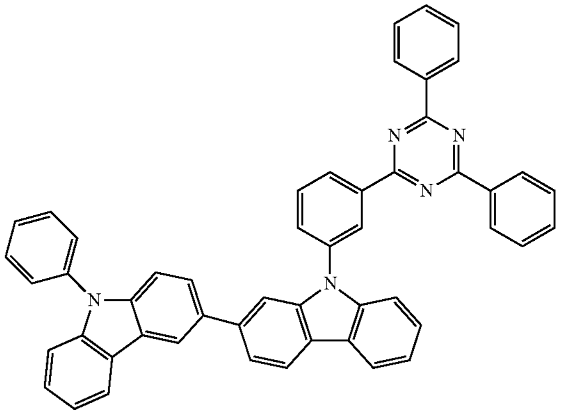
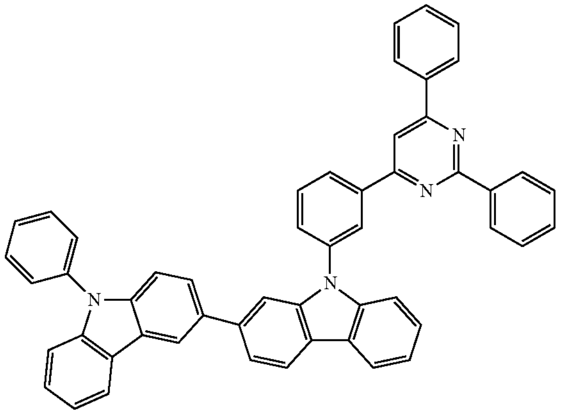
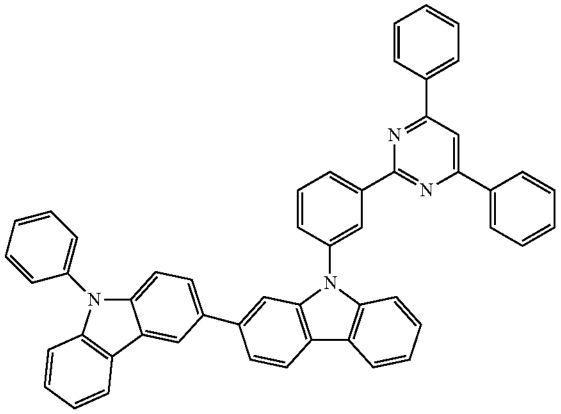
-continued
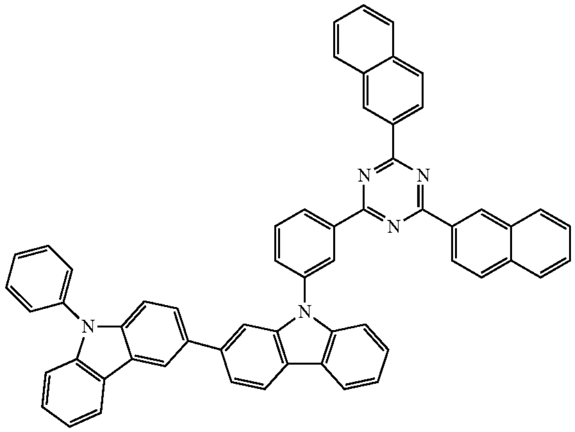
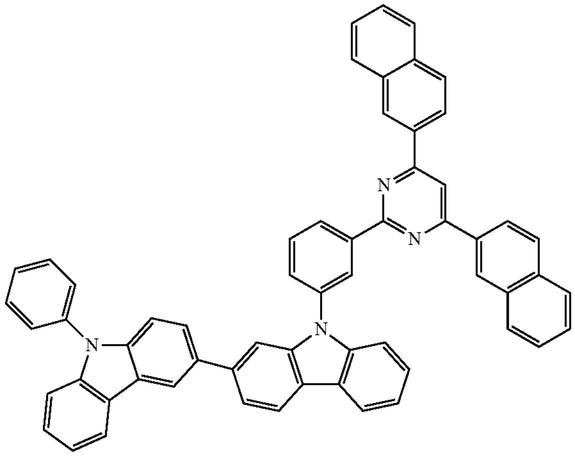
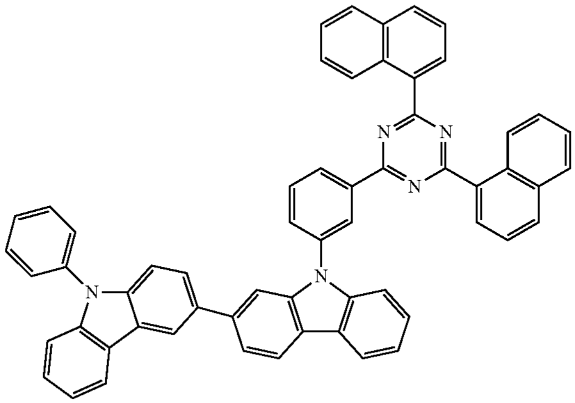

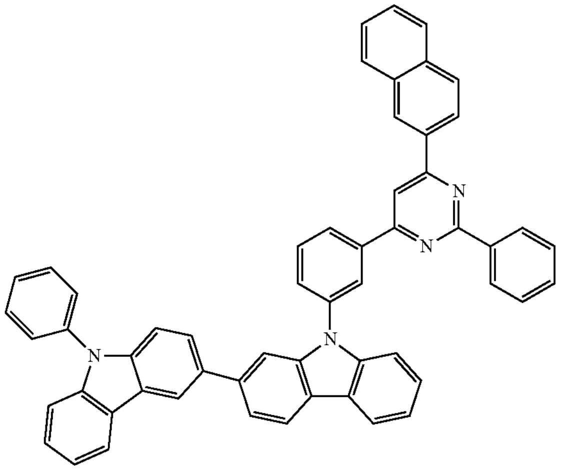
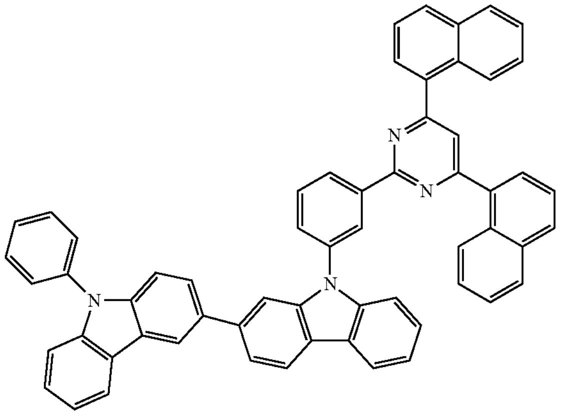
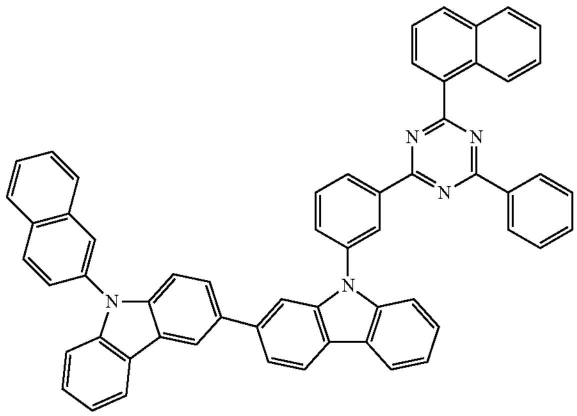
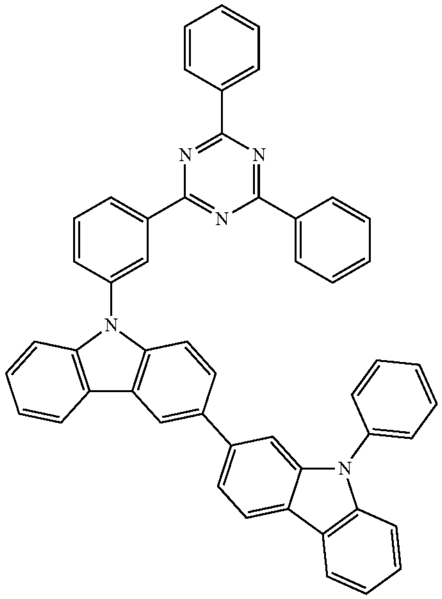
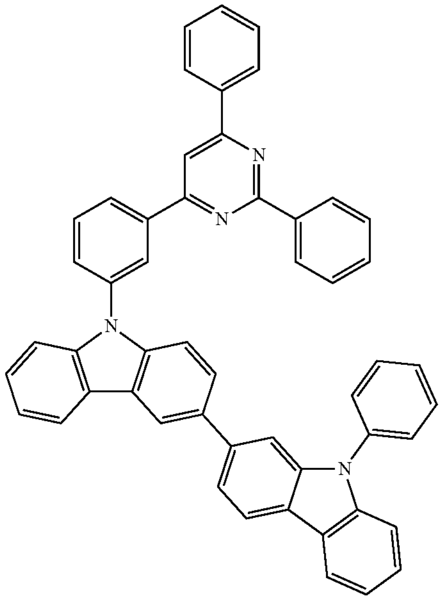
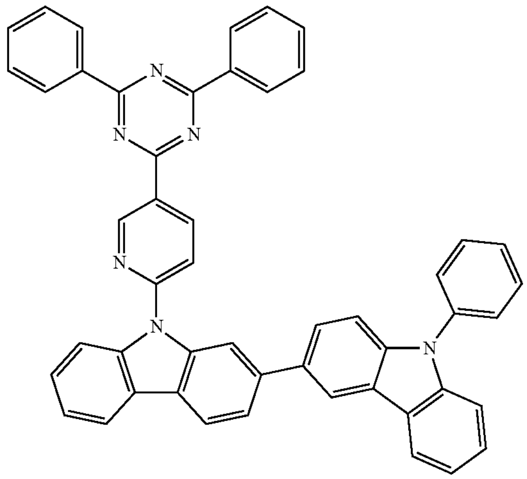

-continued
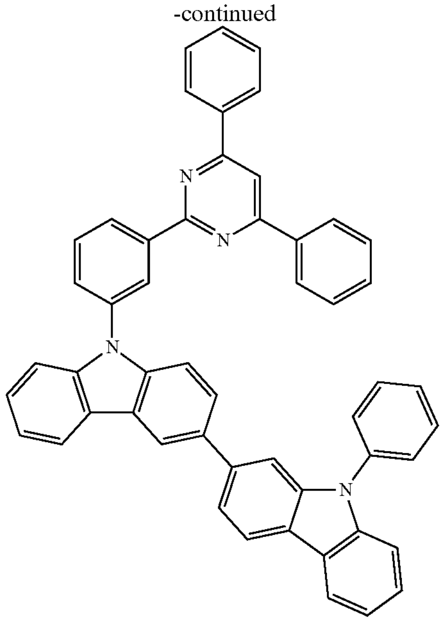
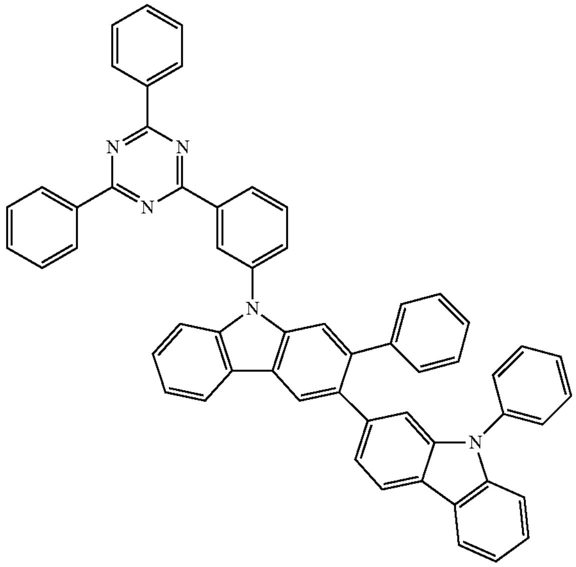
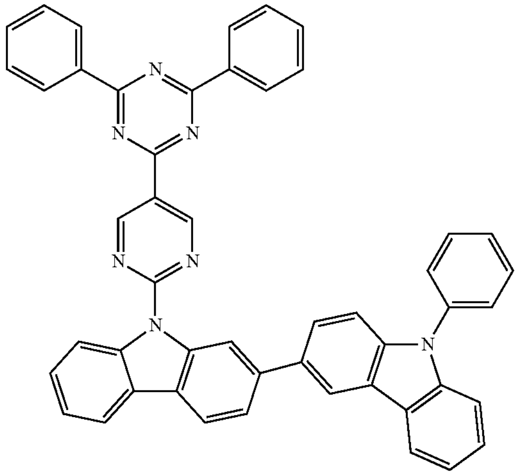
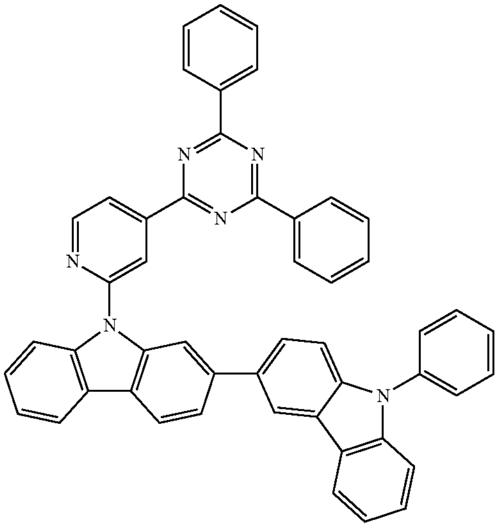
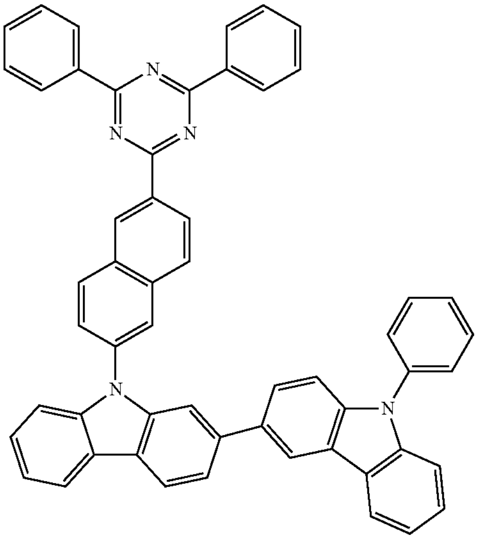

-continued
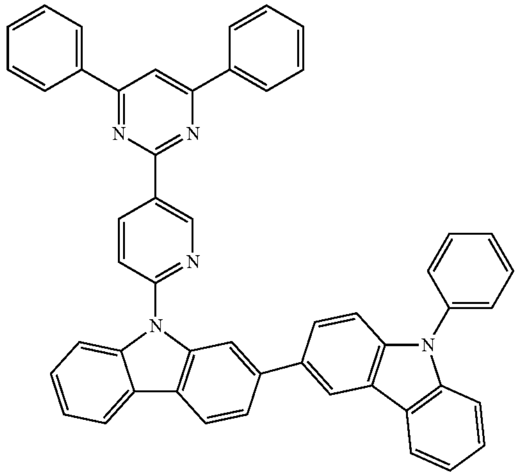
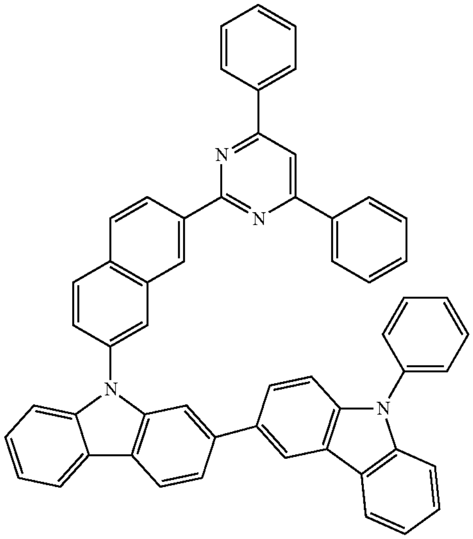
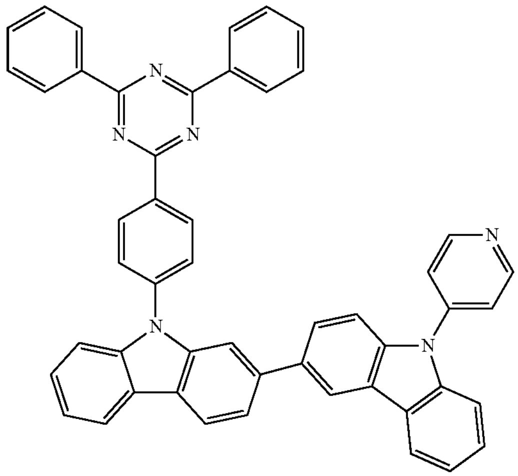
-continued
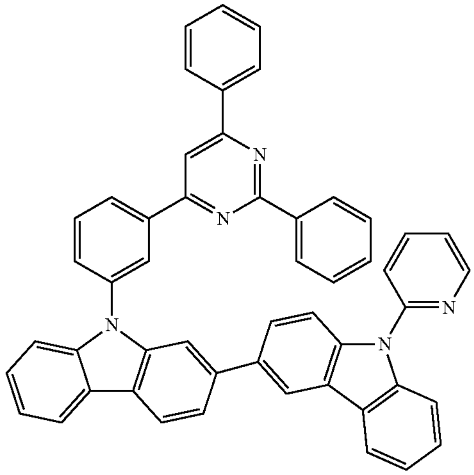
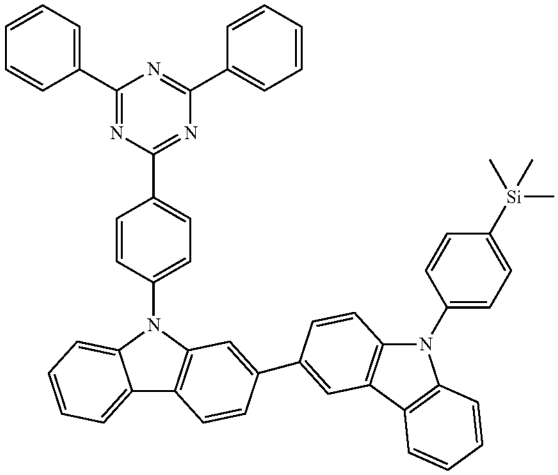
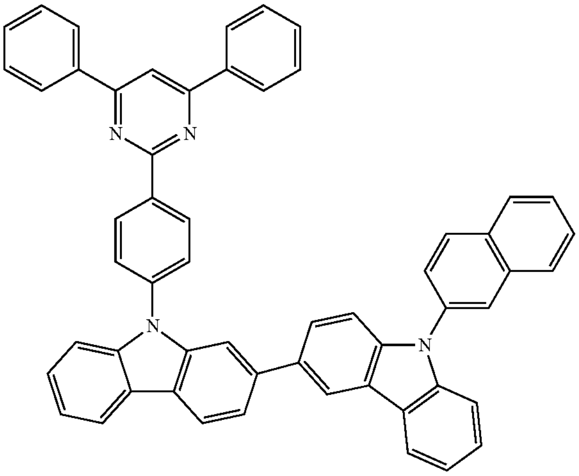

-continued
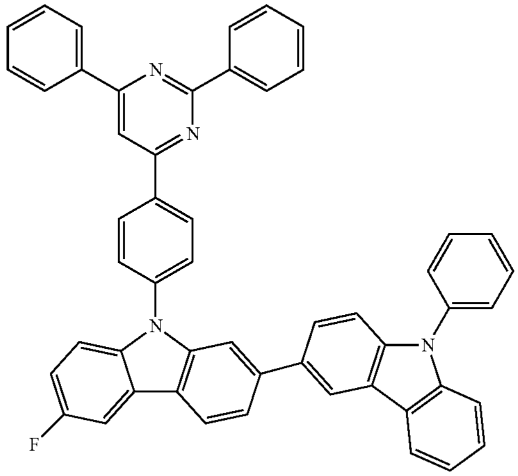
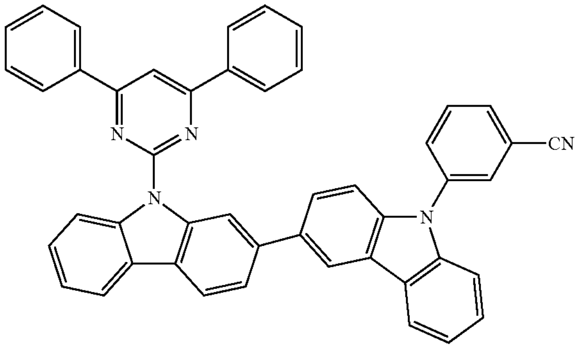
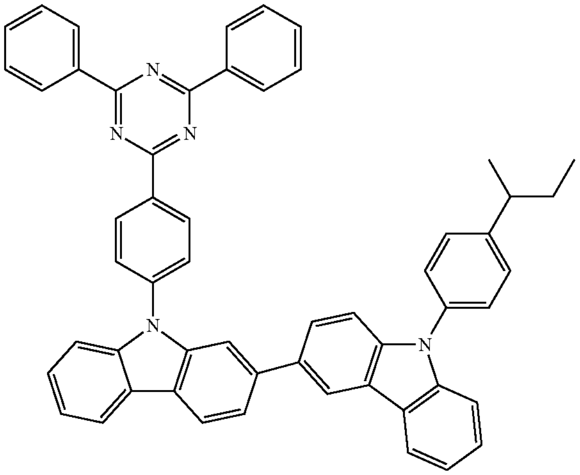
-continued
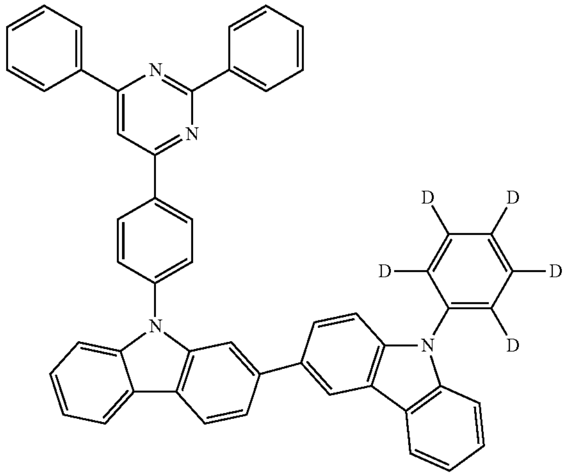
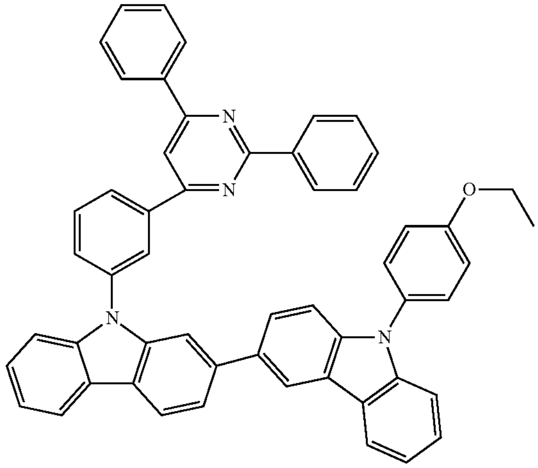
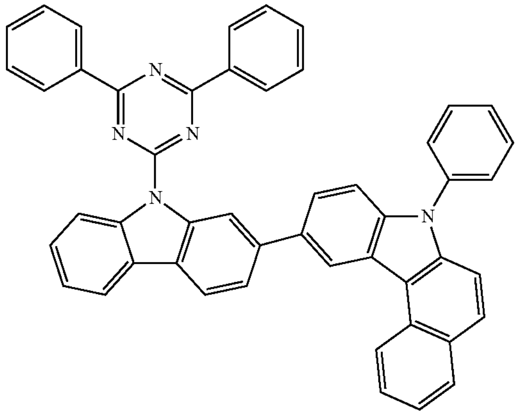
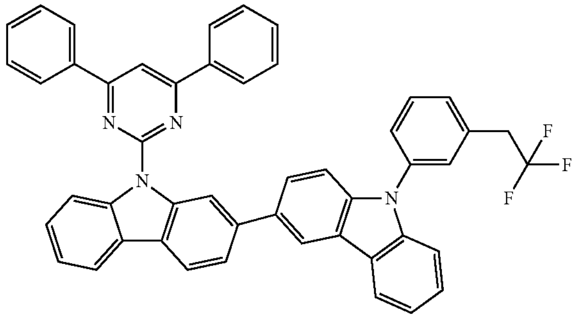

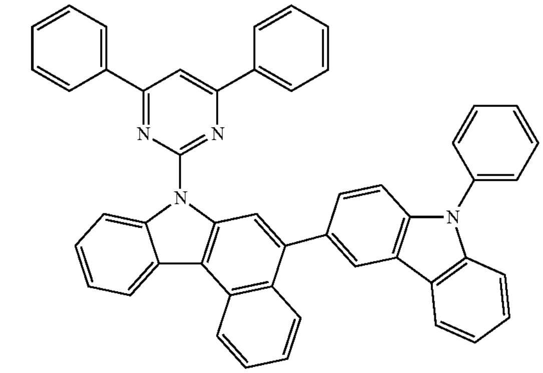
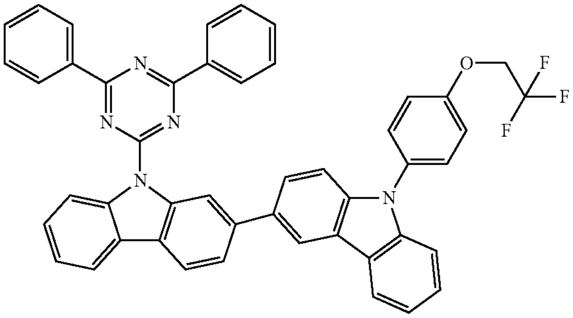
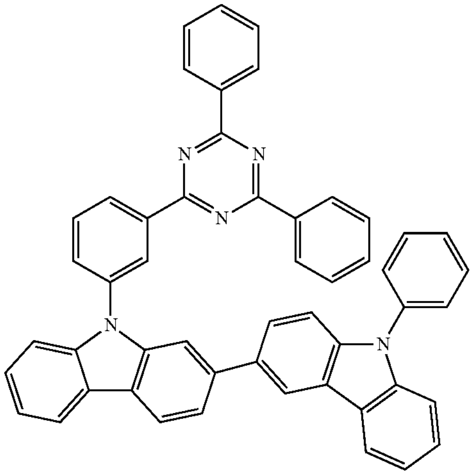
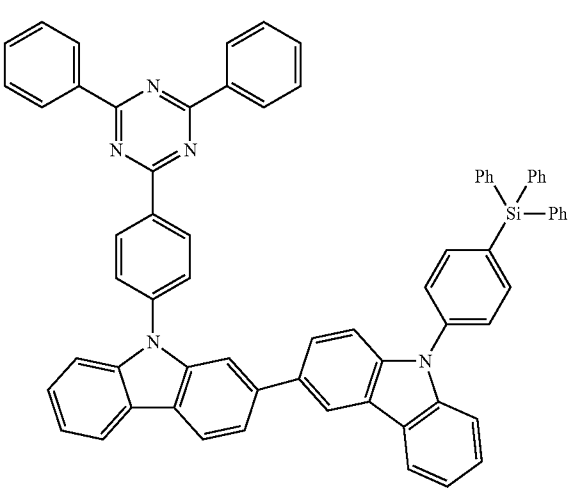
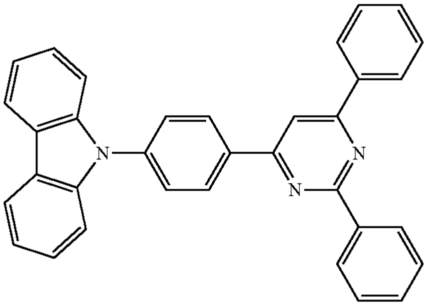
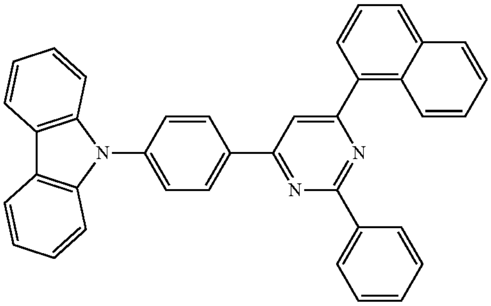
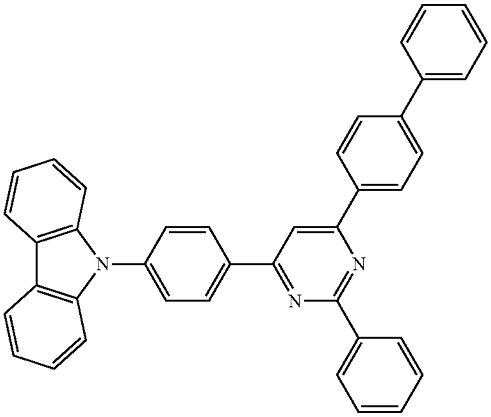
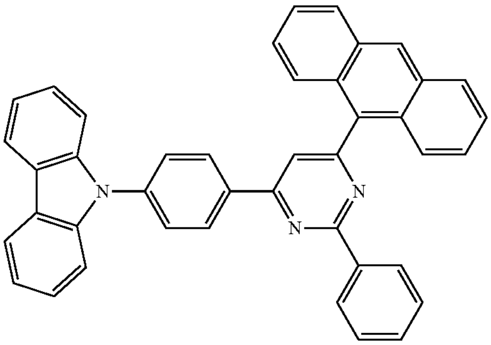
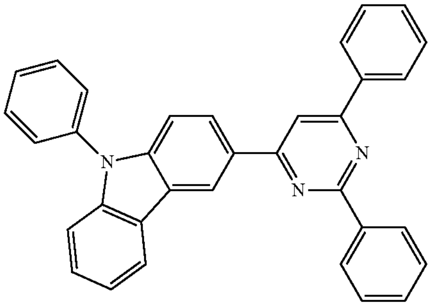

-continued
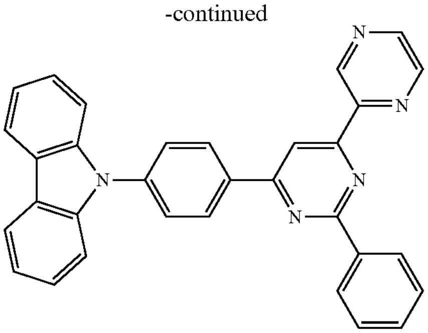
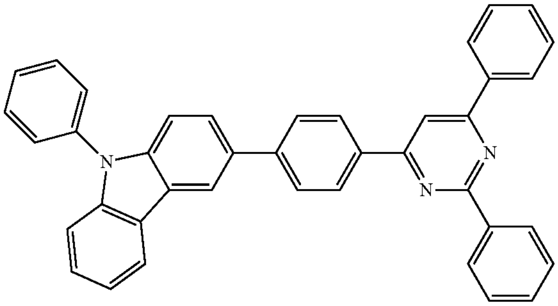
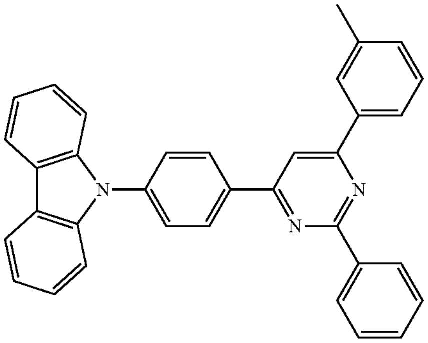
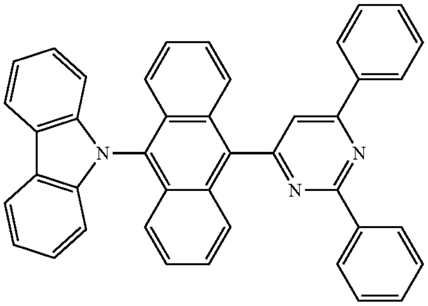
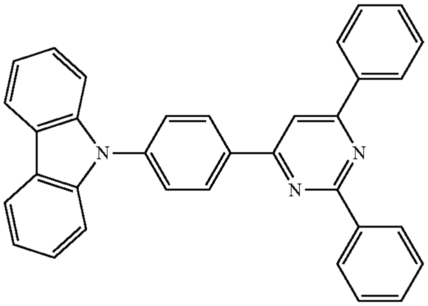
-continued
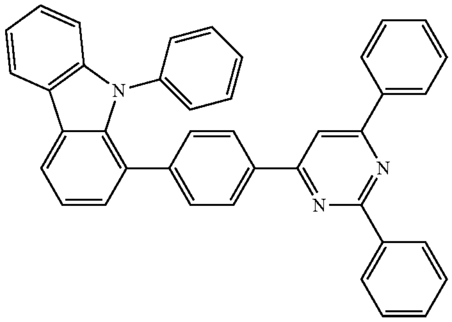
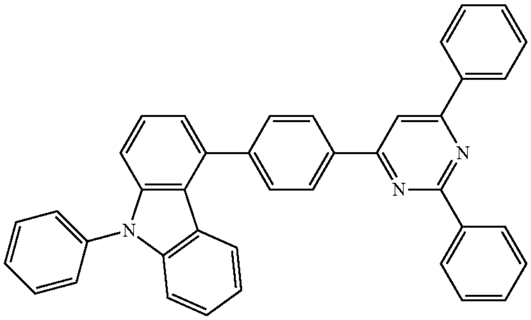
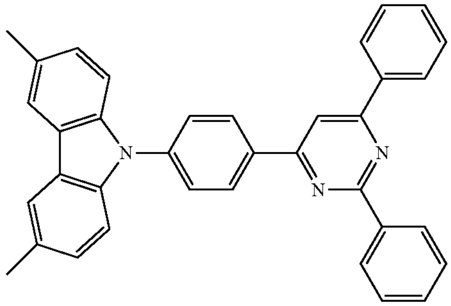
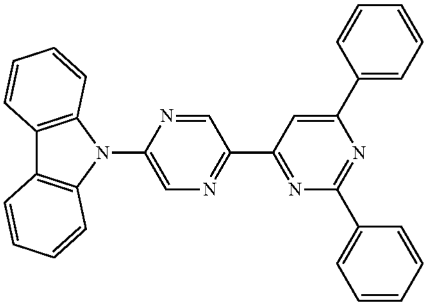
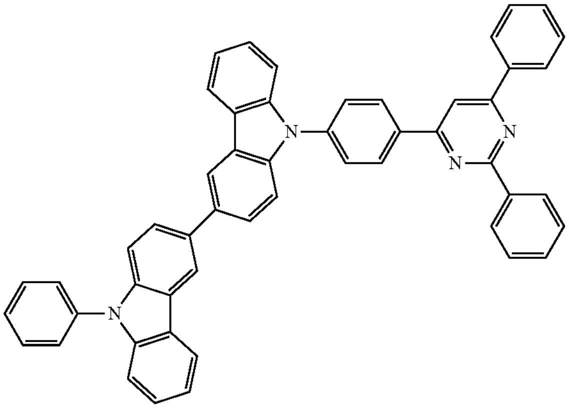

-continued
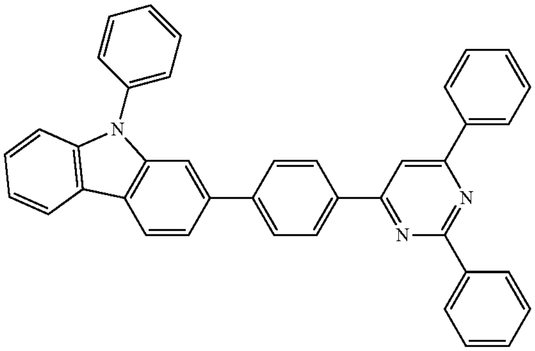
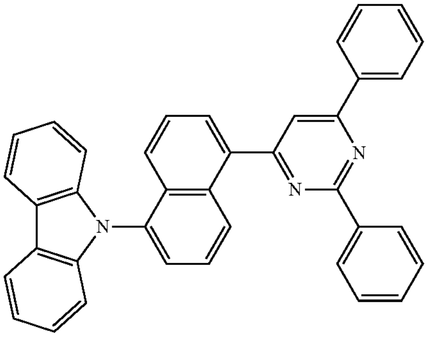
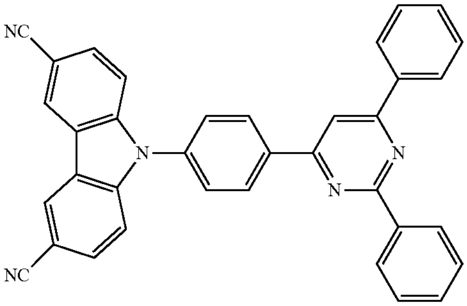
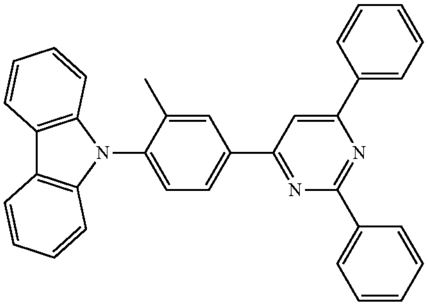
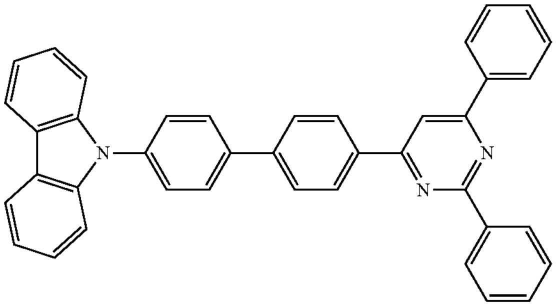
-continued
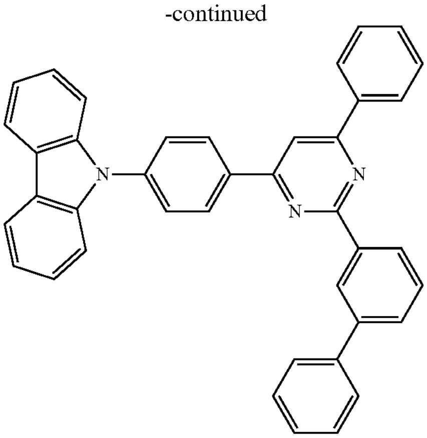
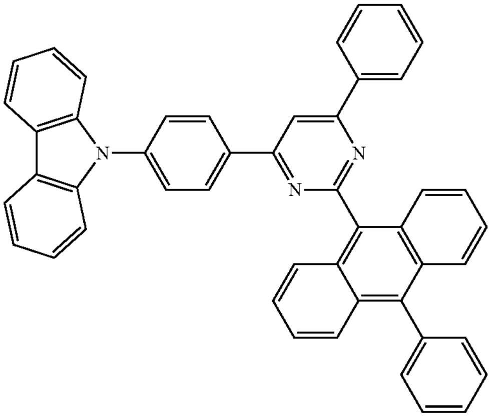
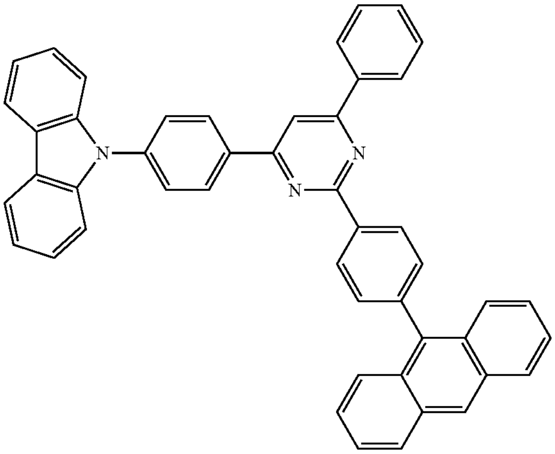

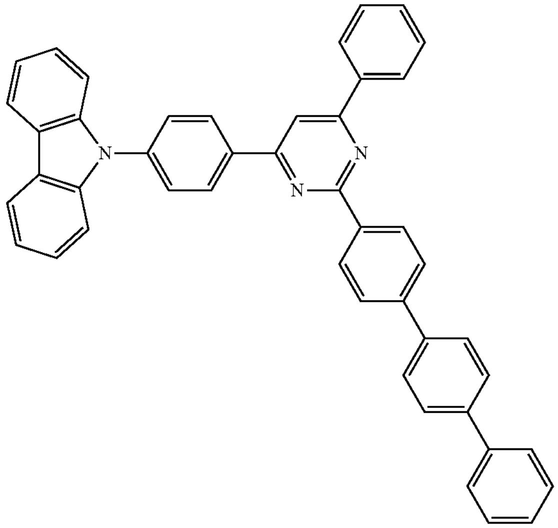
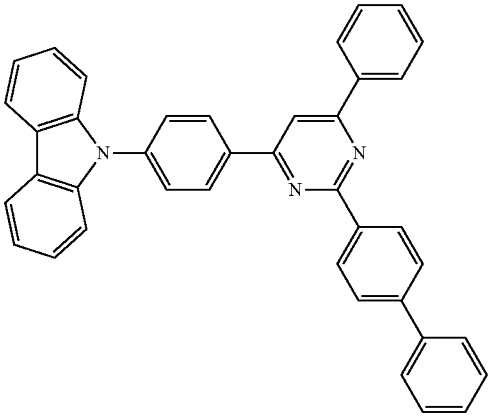
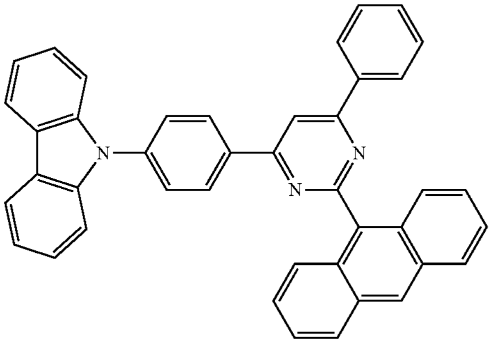
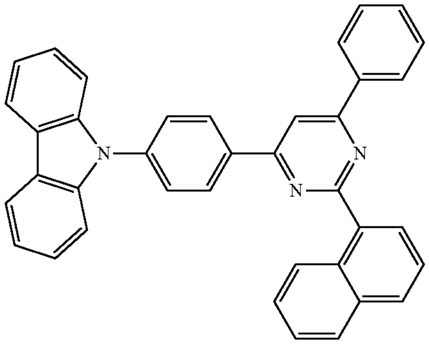
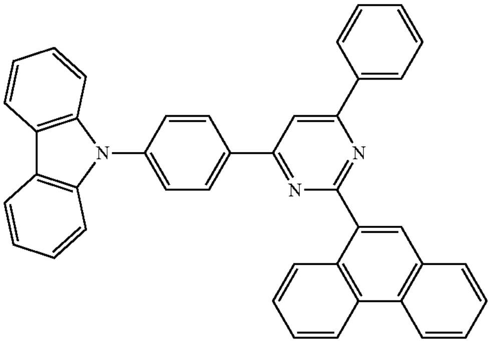
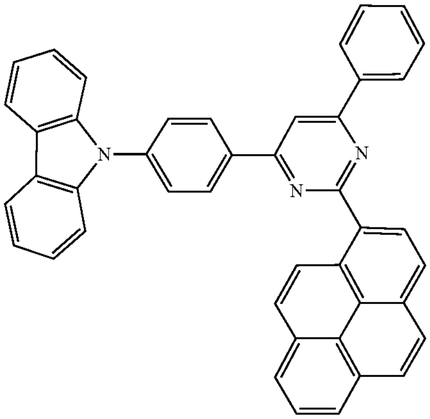
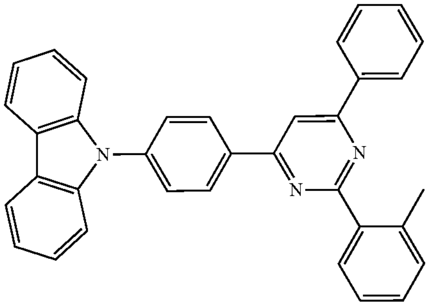
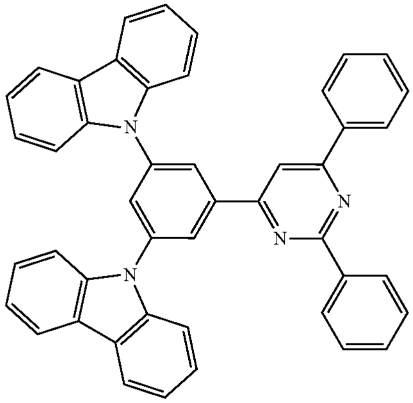

-continued
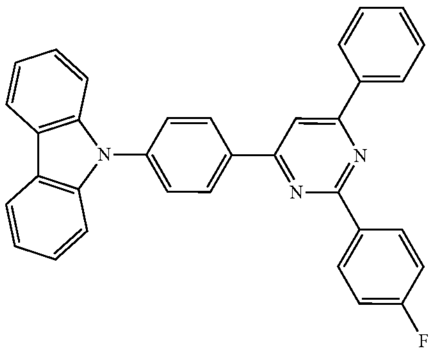
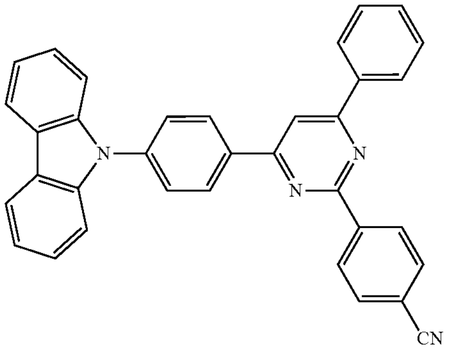
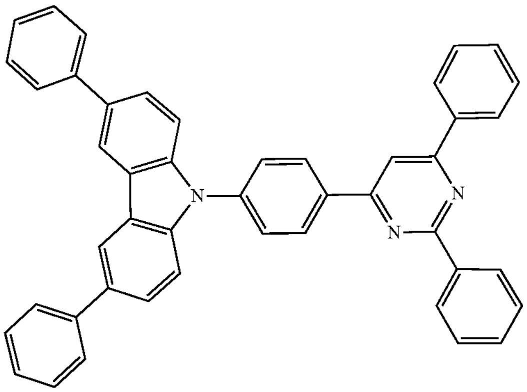
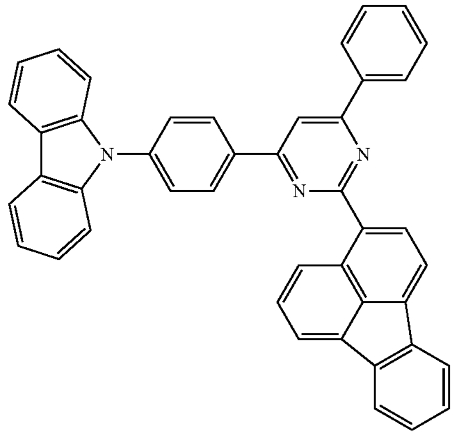
-continued
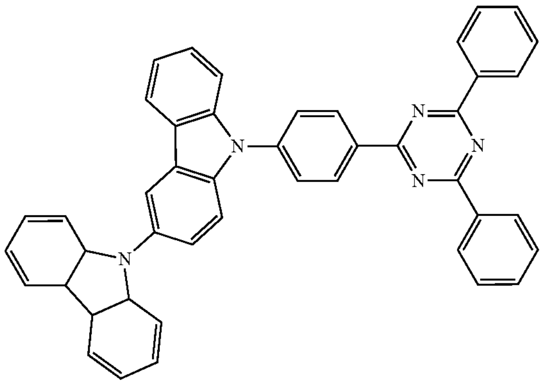
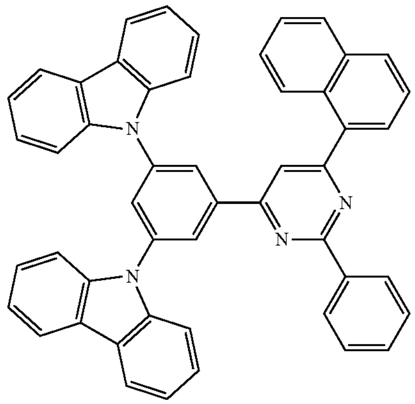
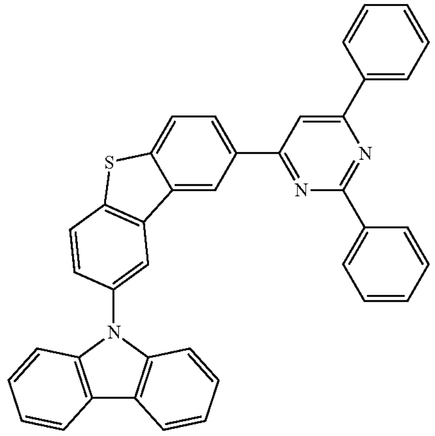
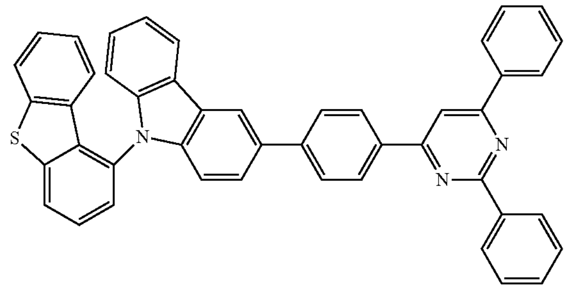

-continued
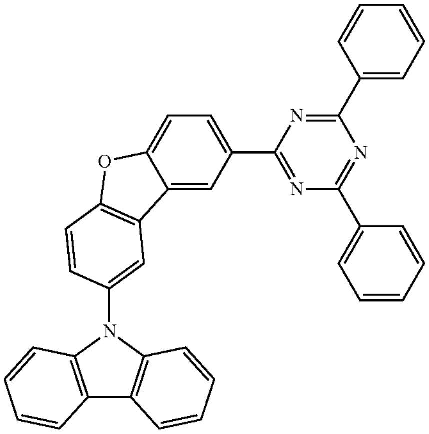
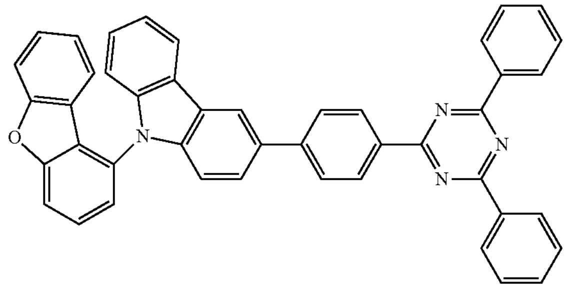
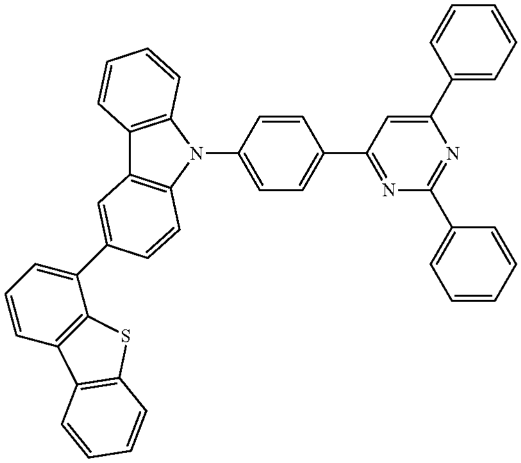
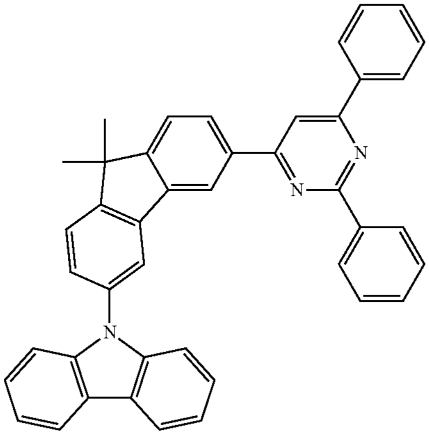
-continued
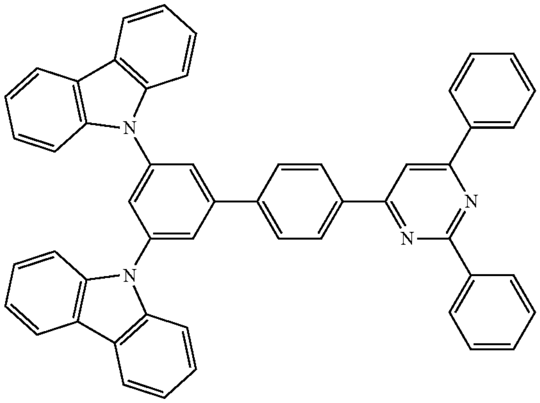
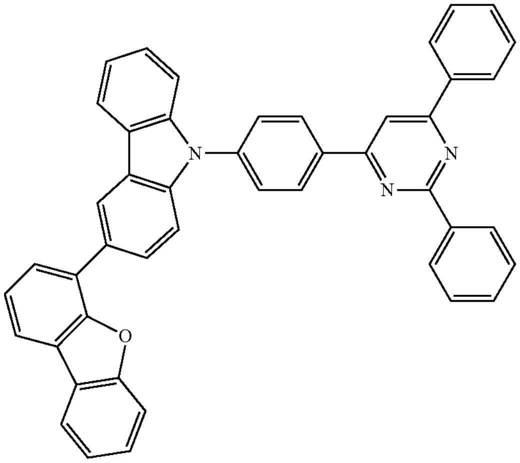
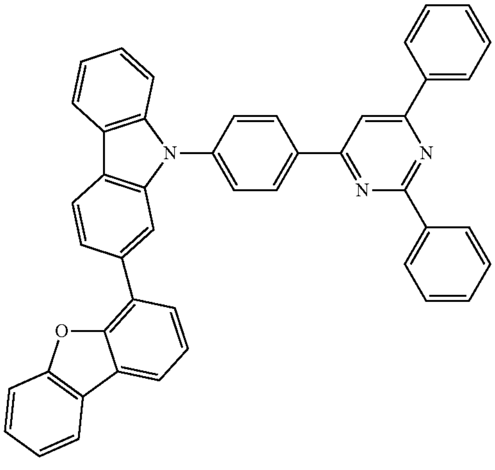

-continued
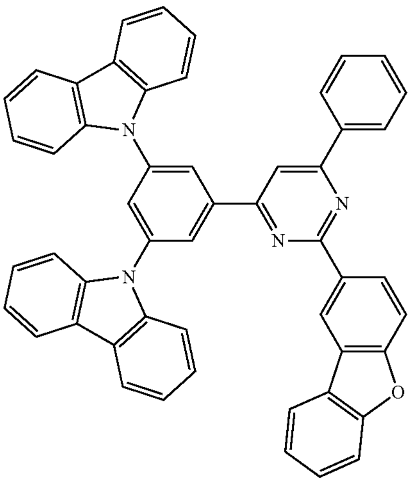
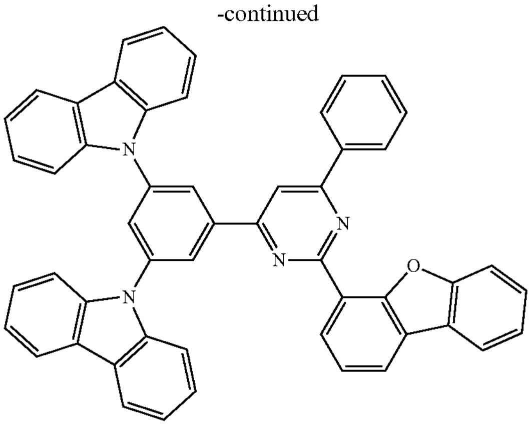
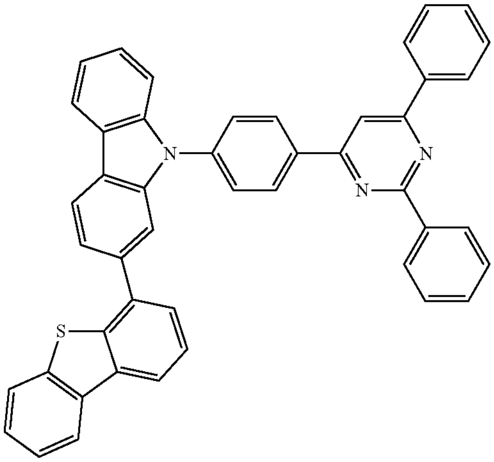
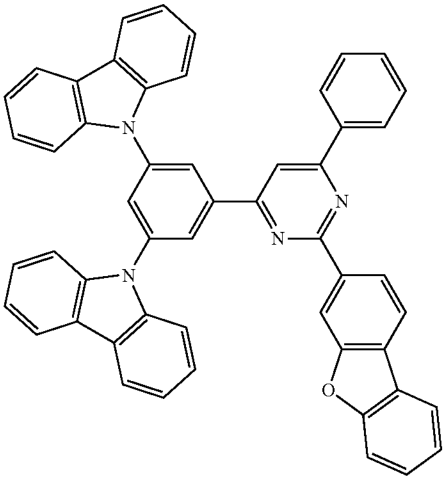
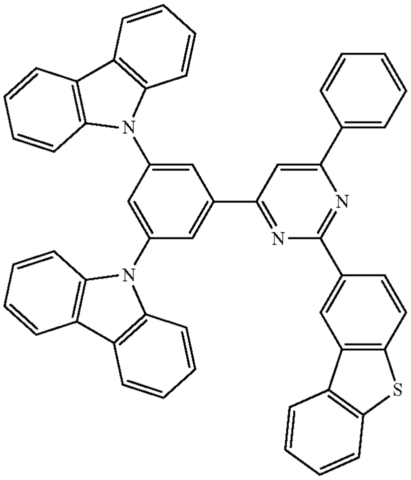
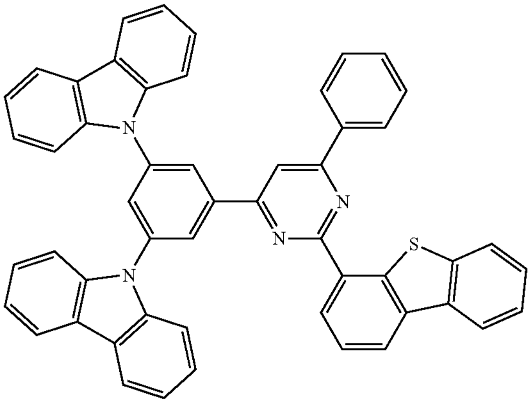
-continued

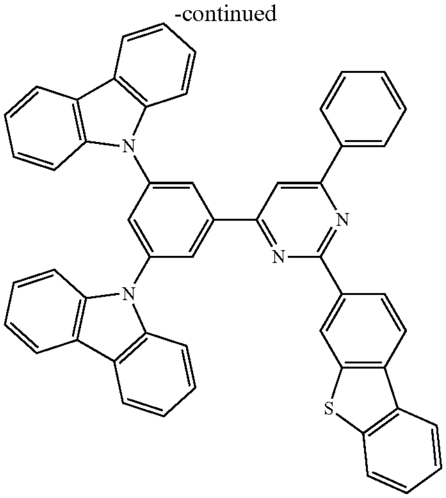
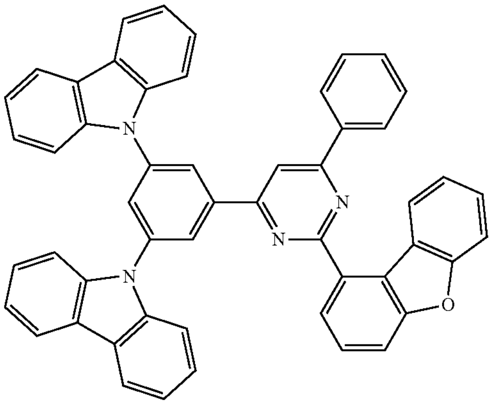
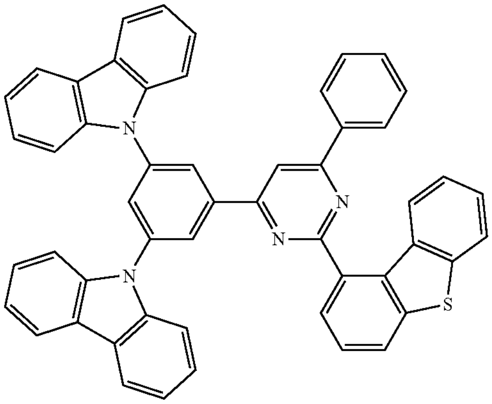
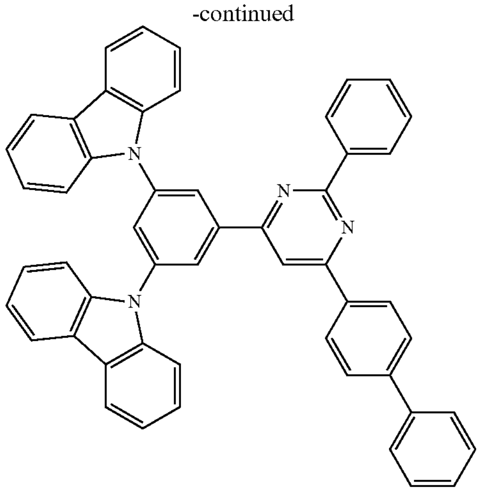
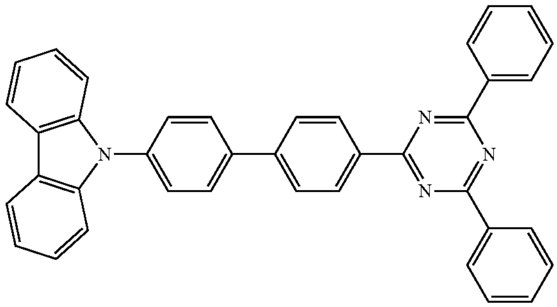
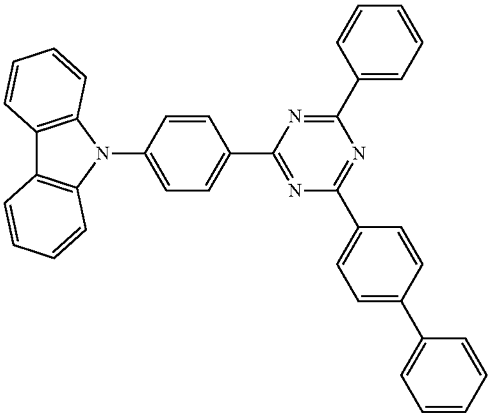
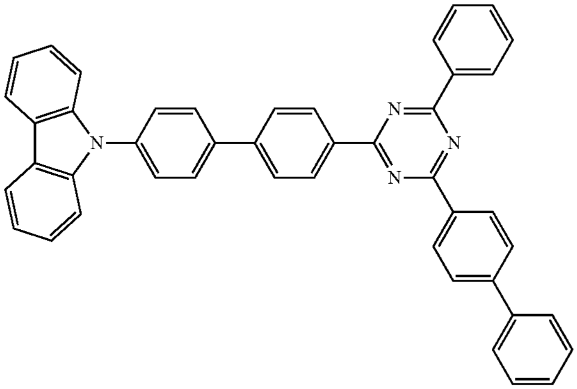

-continued
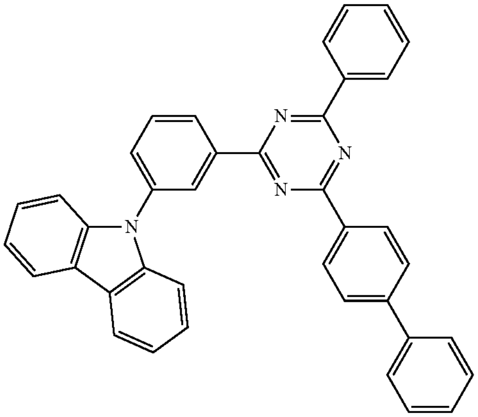
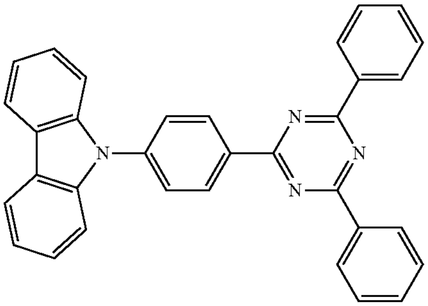
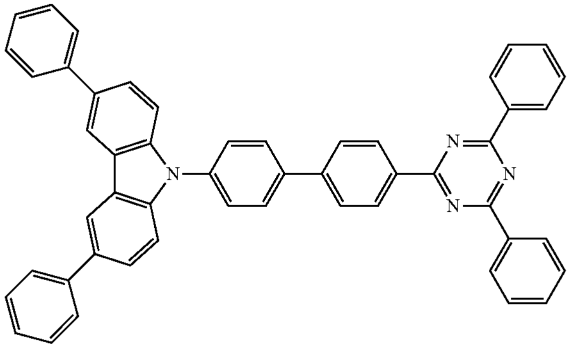
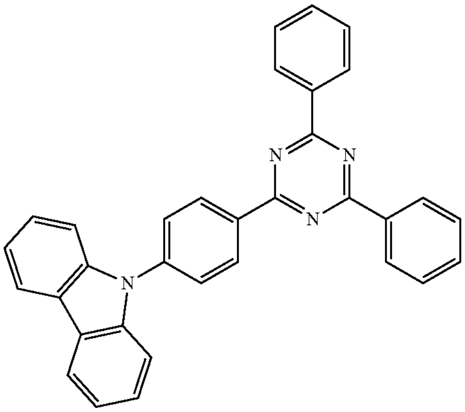
-continued
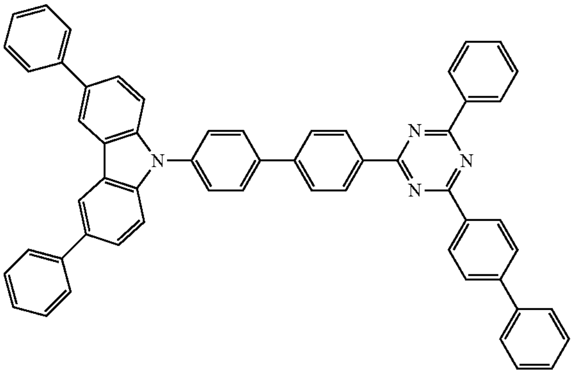
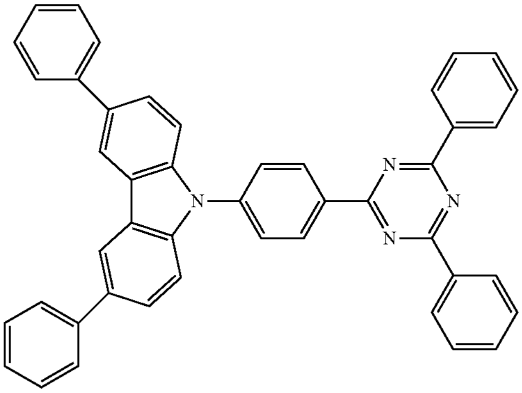
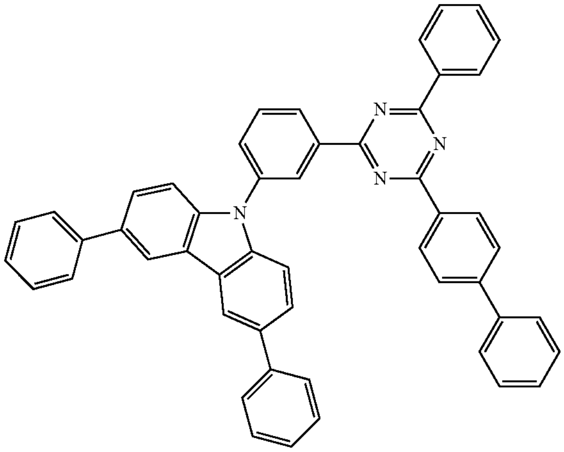
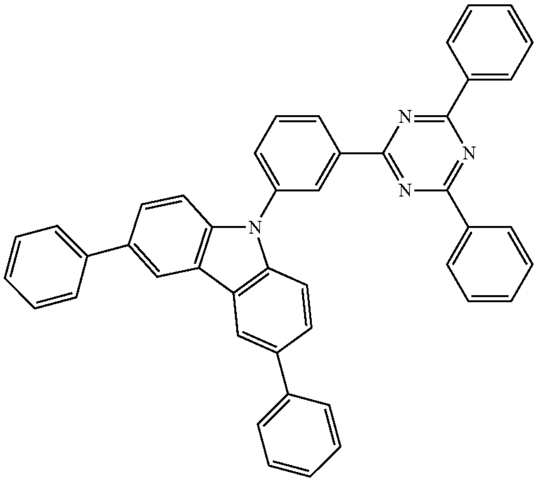

-continued
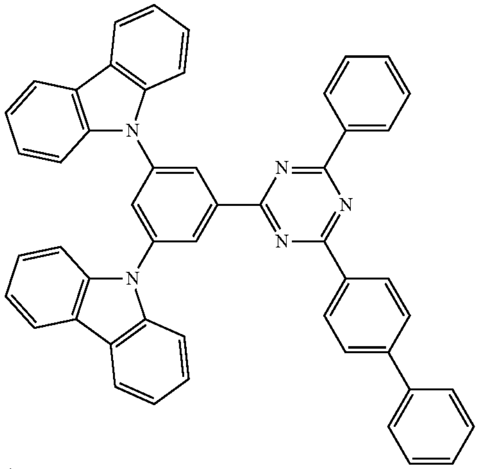
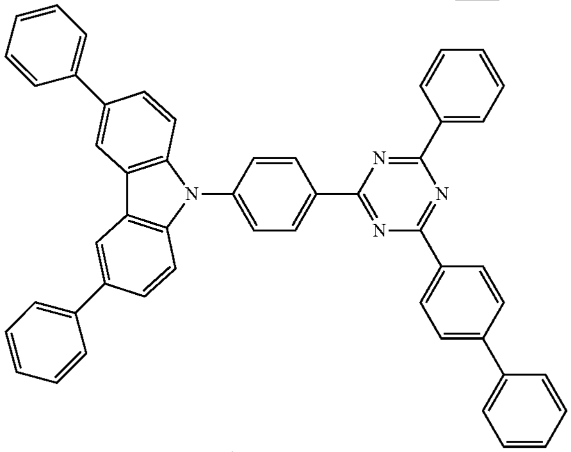
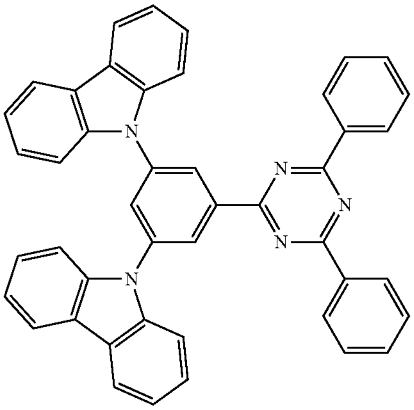
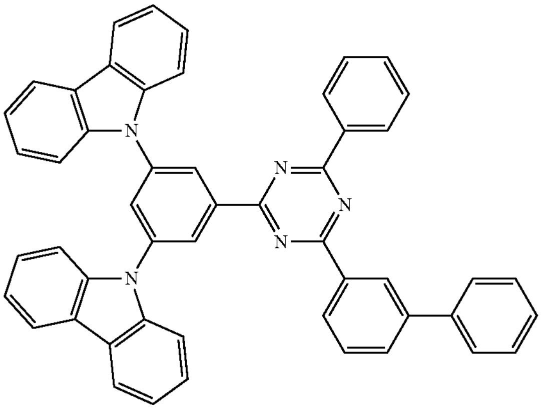
-continued
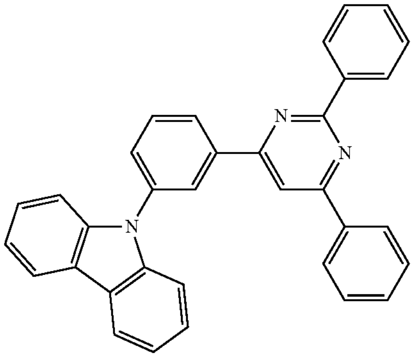
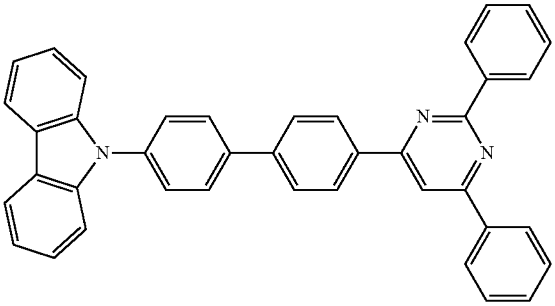
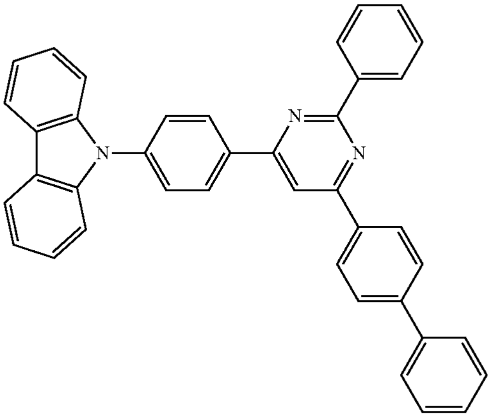
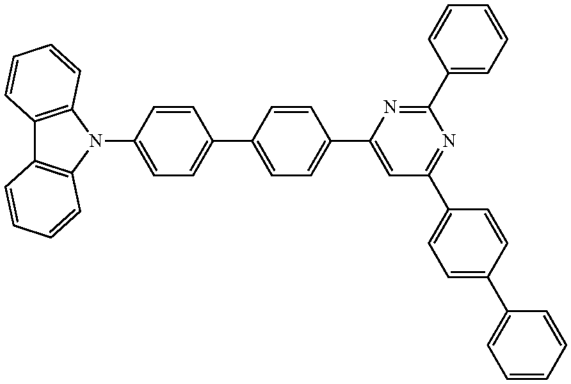

-continued
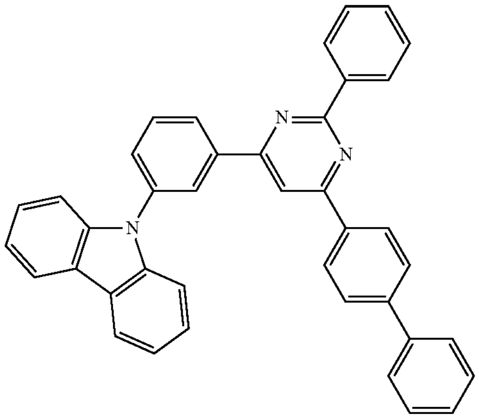
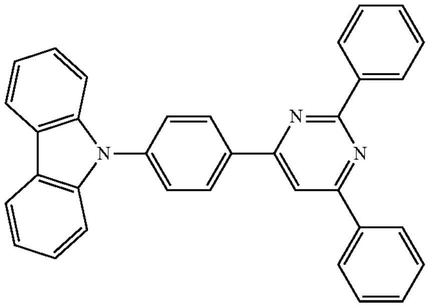
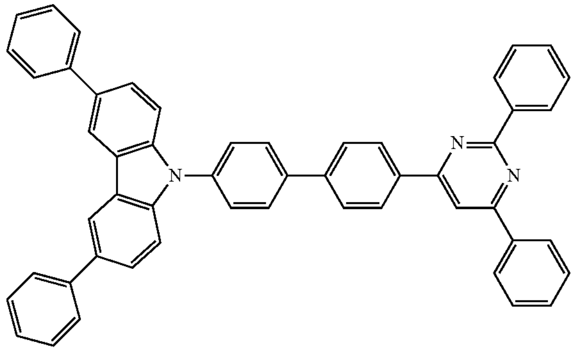
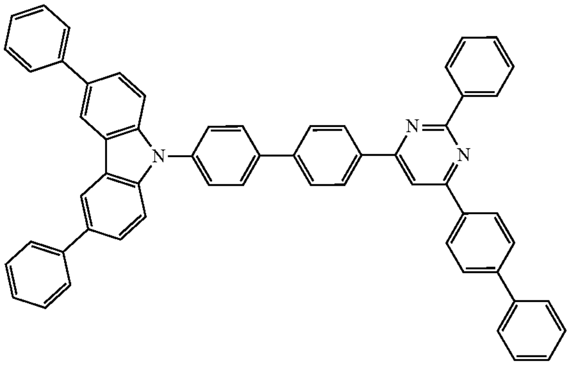
-continued
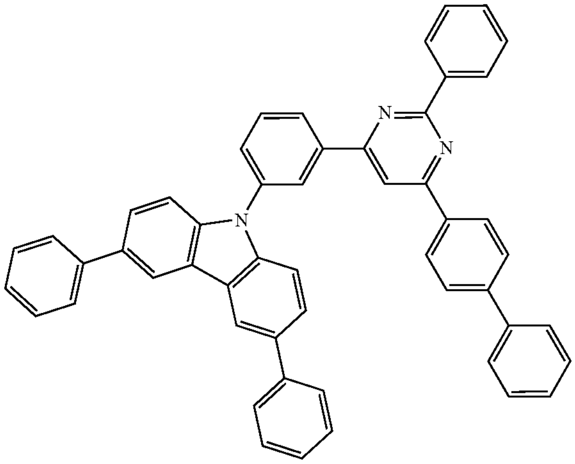
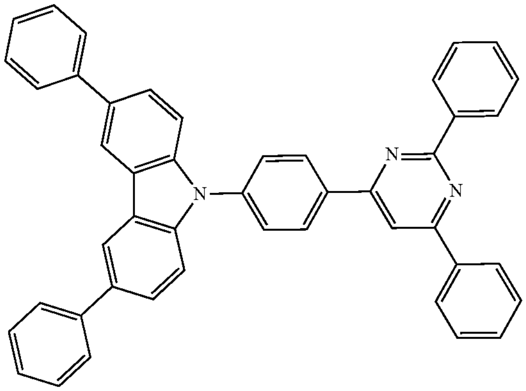
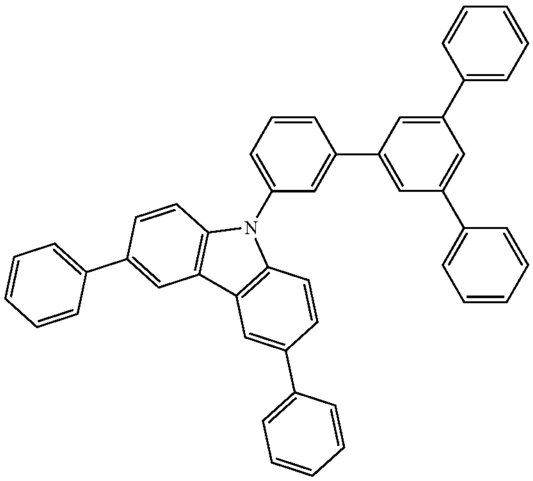

-continued
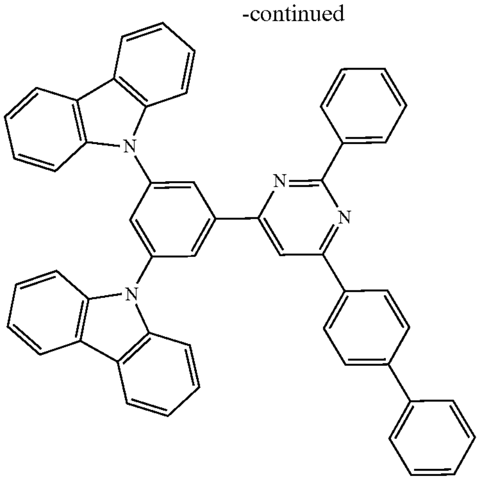
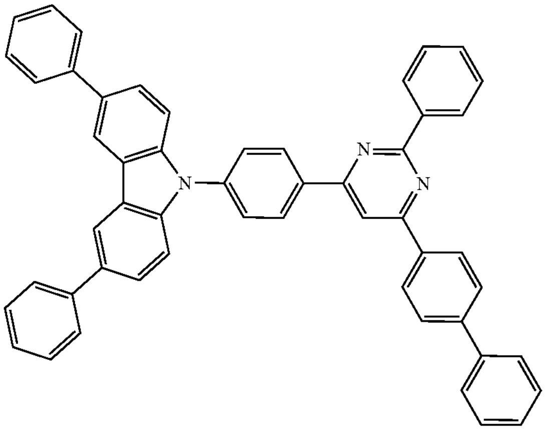
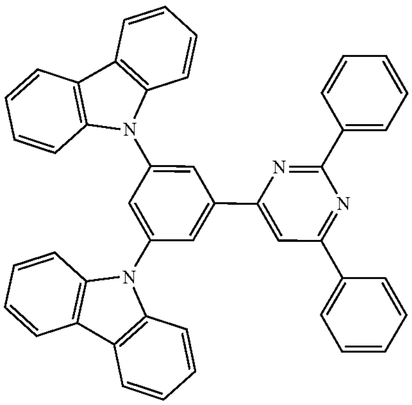
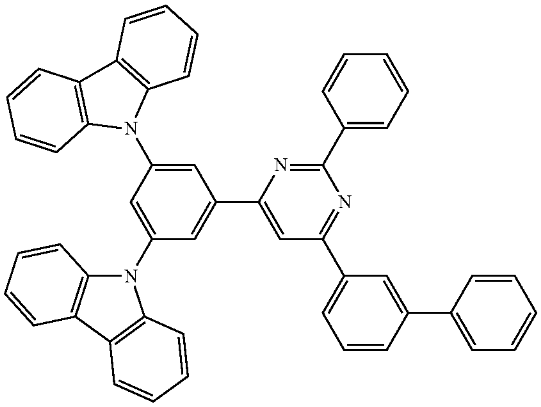
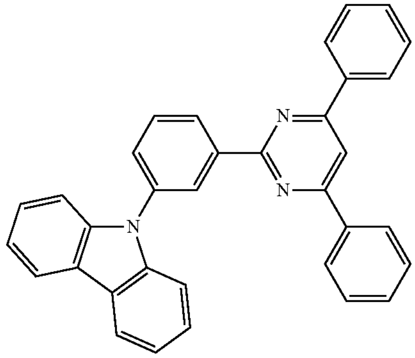
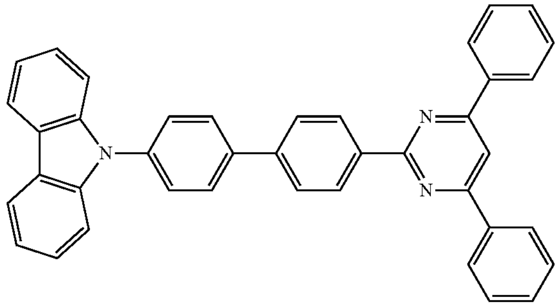
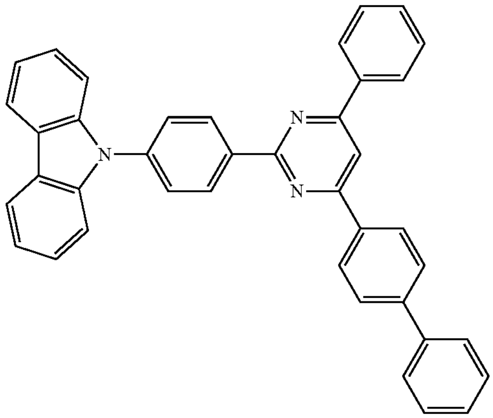

-continued
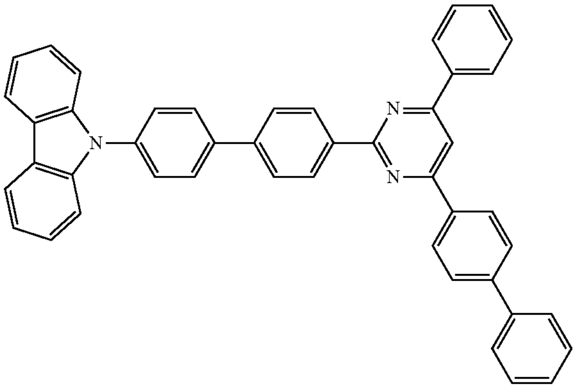
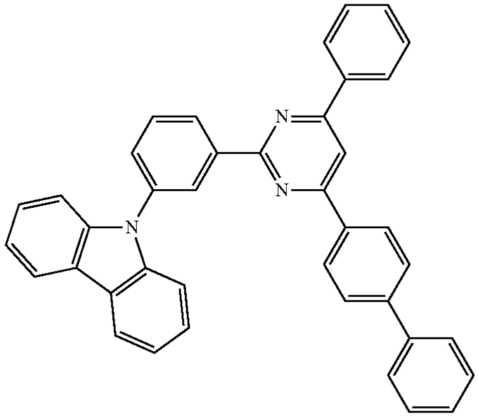
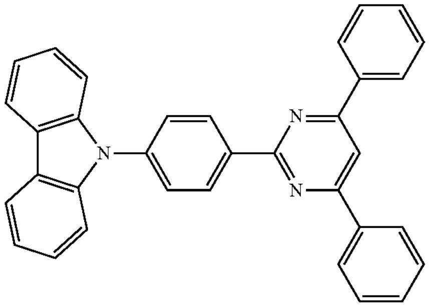
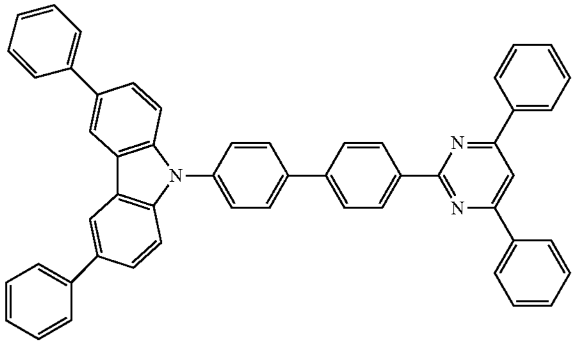
-continued
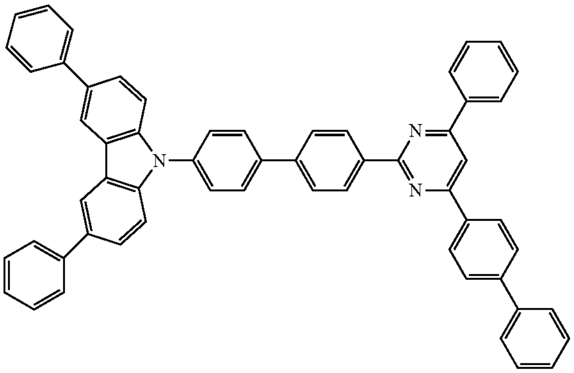
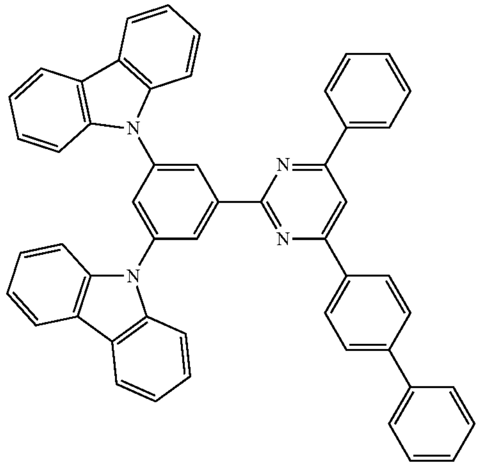
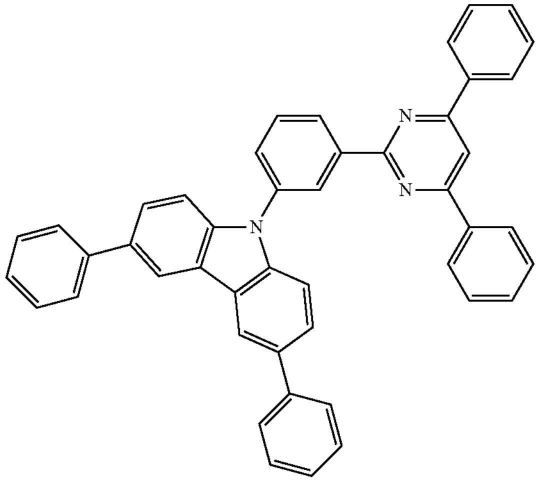
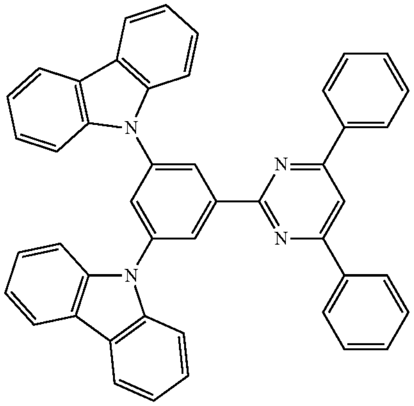

-continued
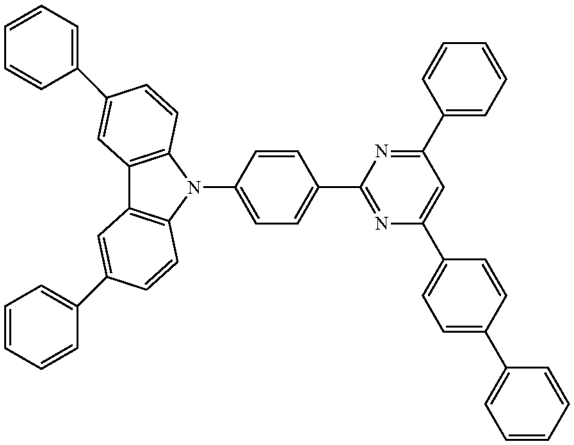
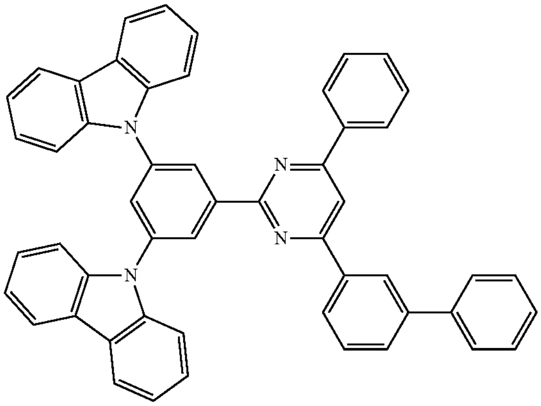
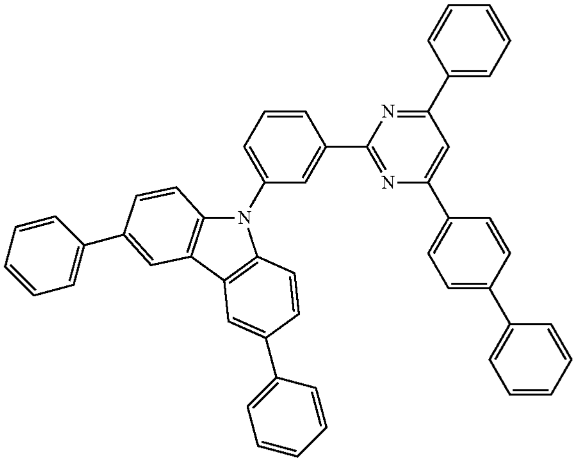
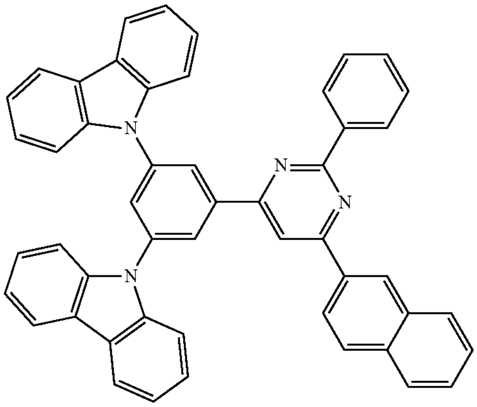
-continued
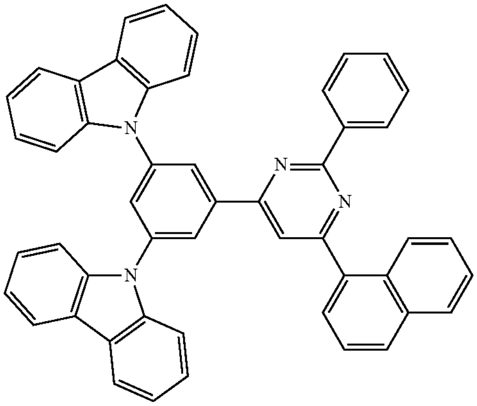
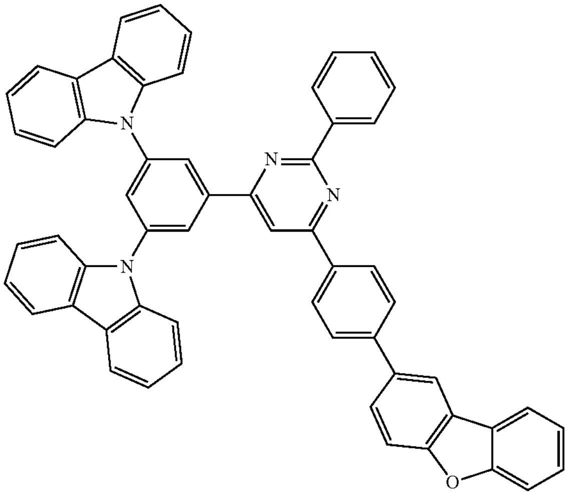
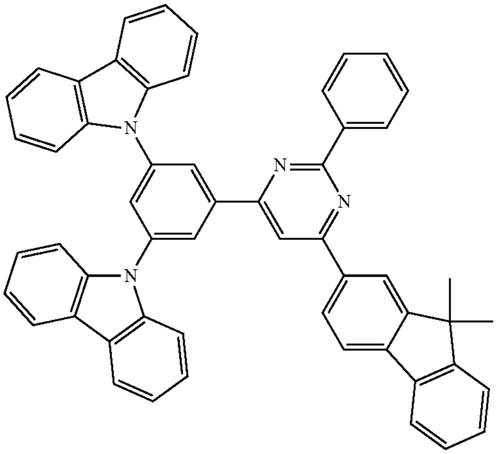

-continued
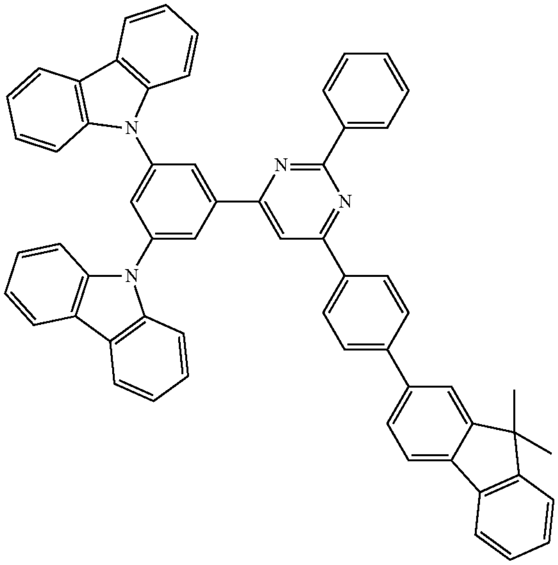
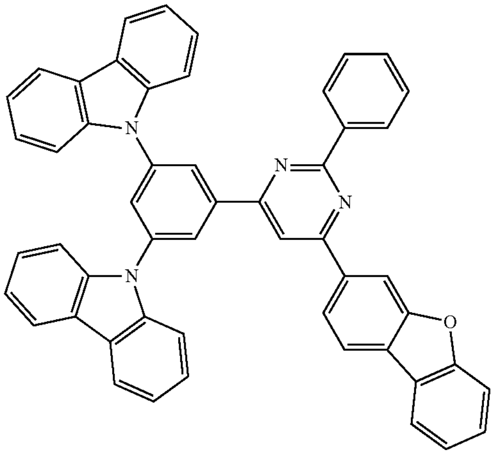
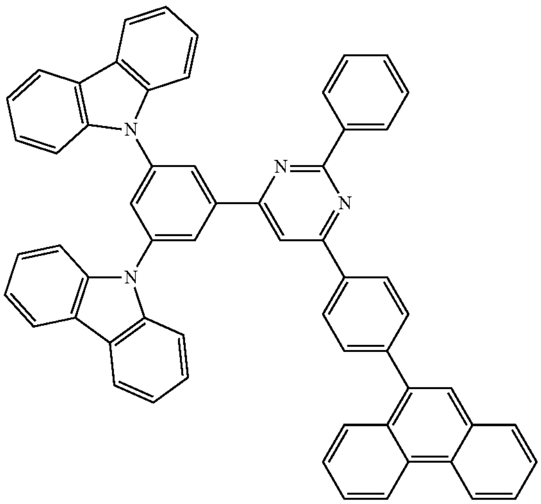
-continued
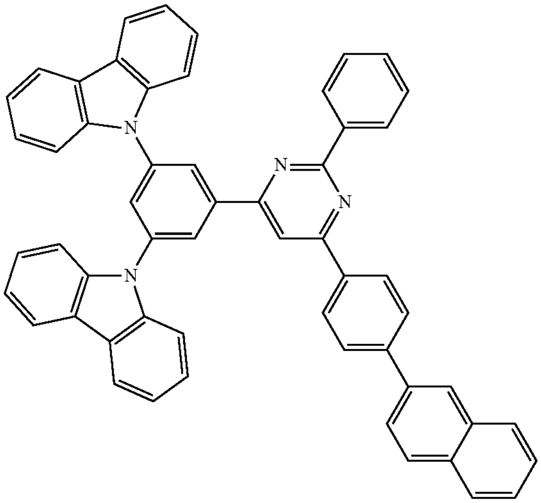
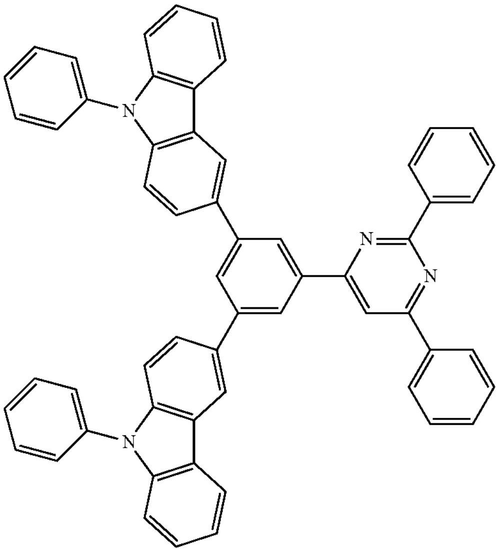
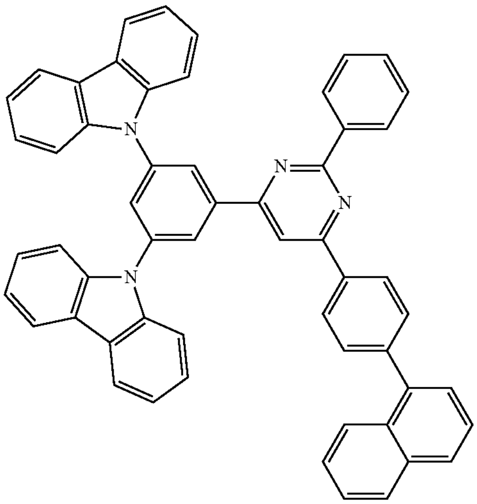

-continued
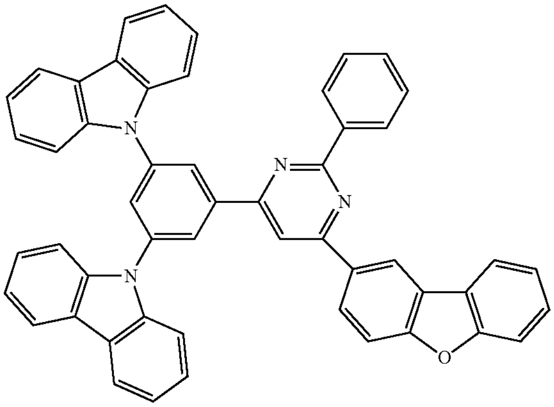
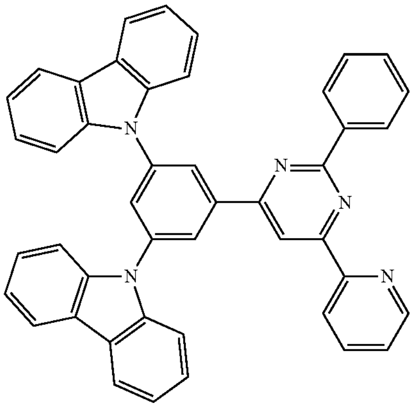
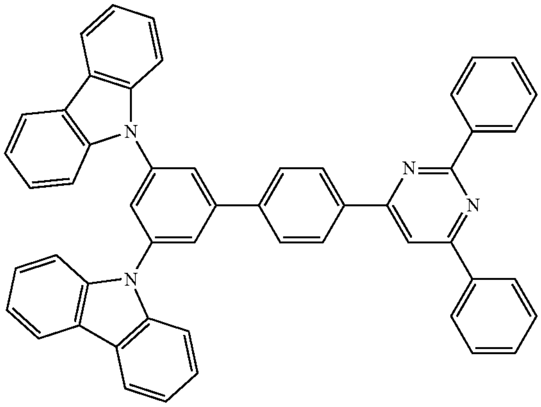
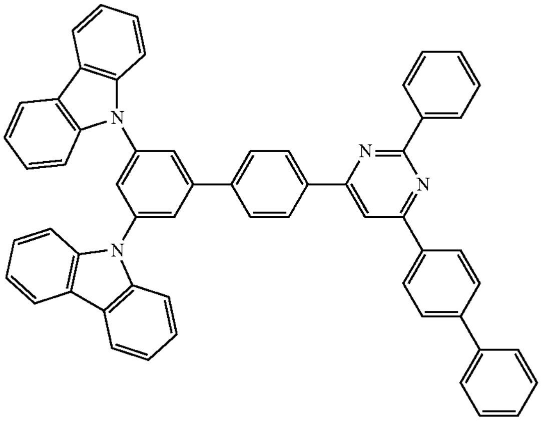
-continued
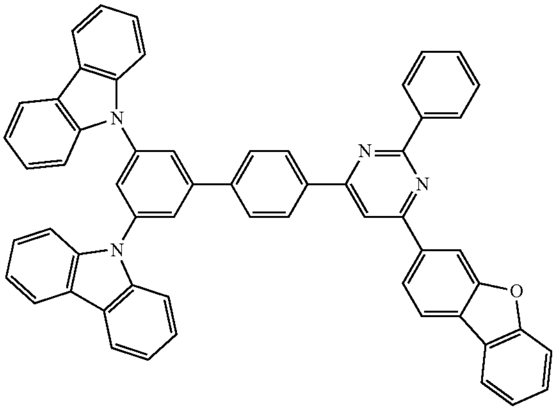
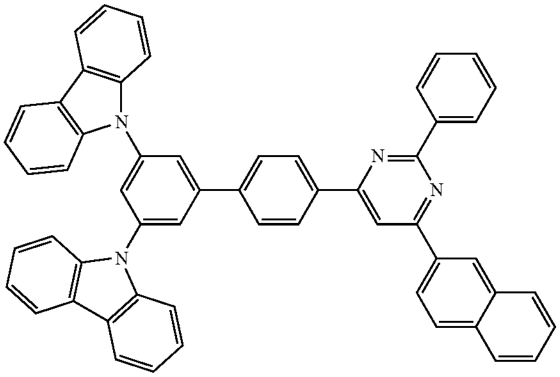
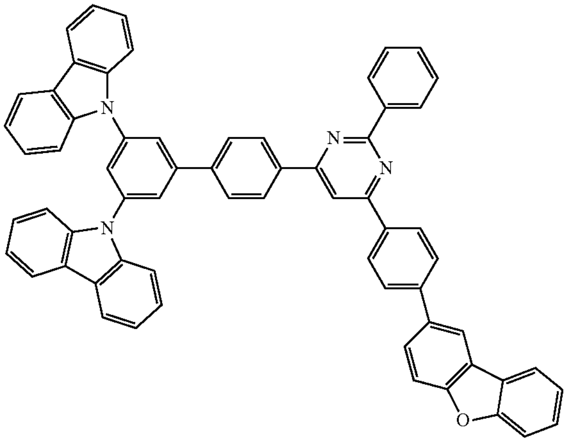
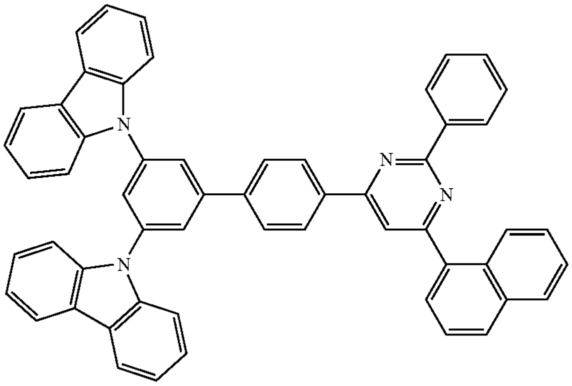

-continued
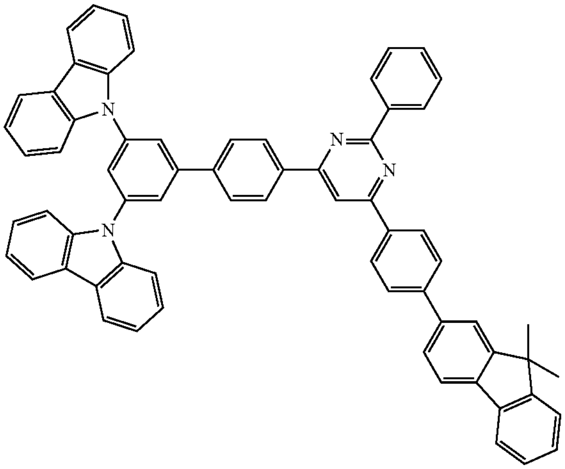
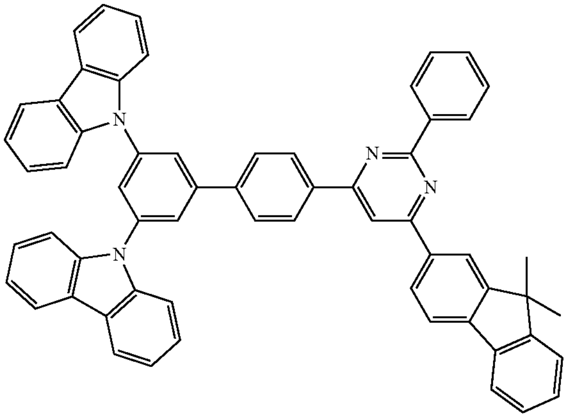
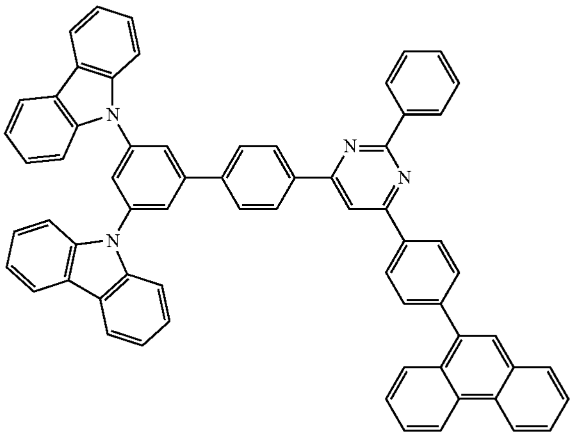
-continued
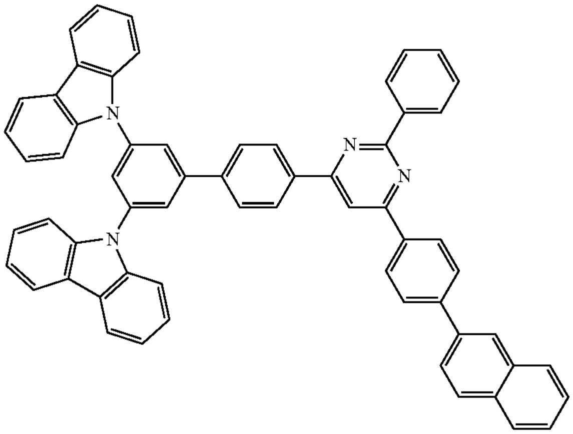
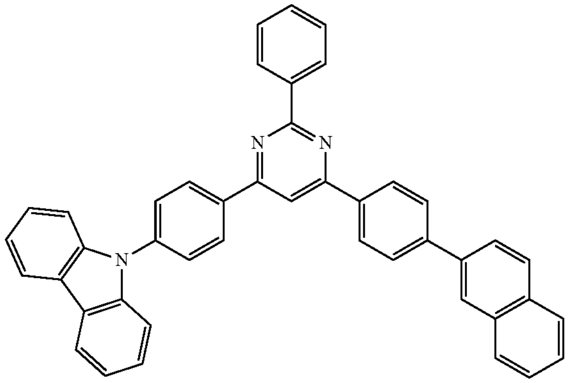
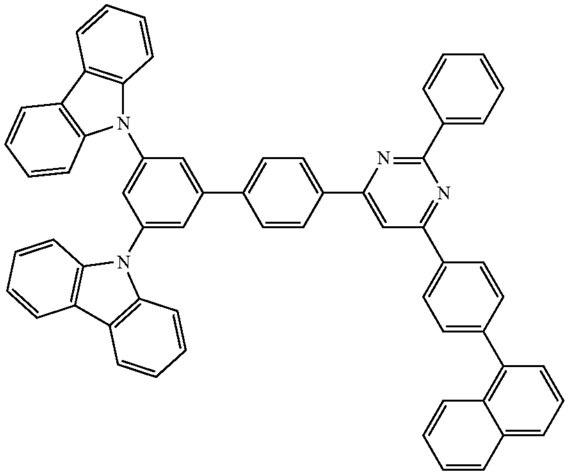
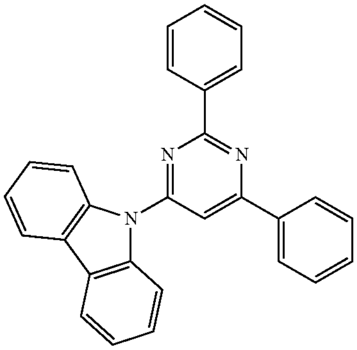

-continued
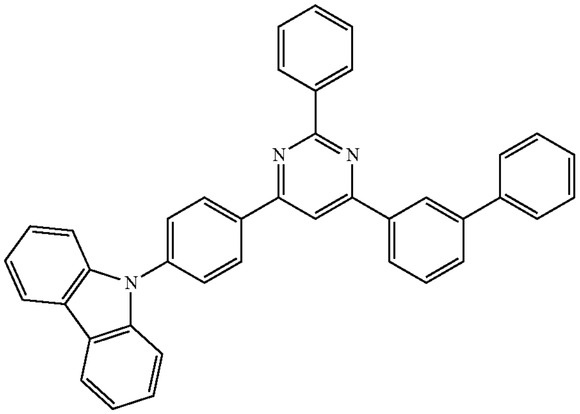
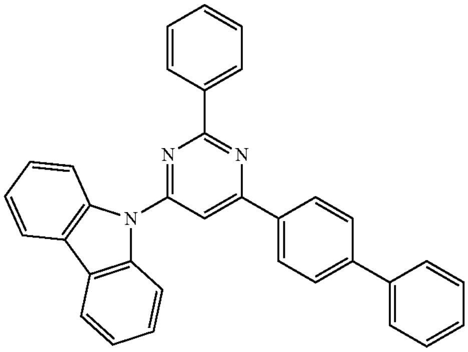
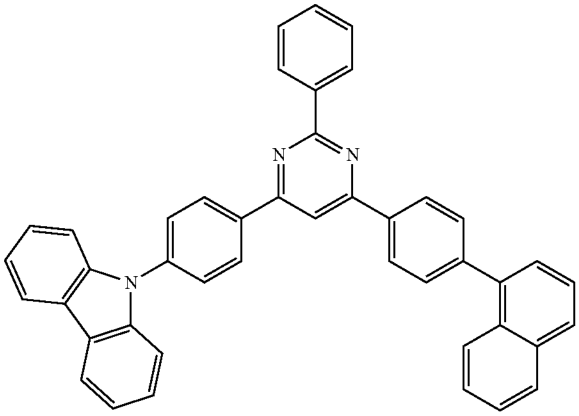
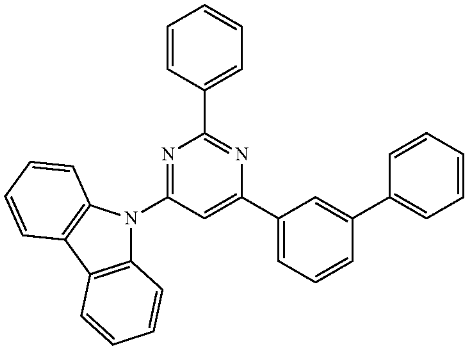
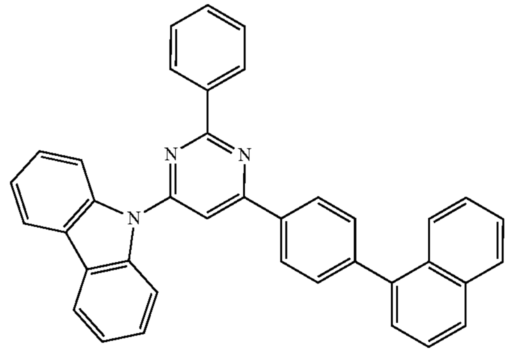
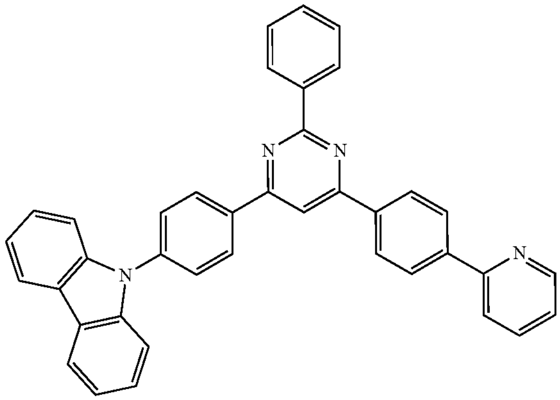
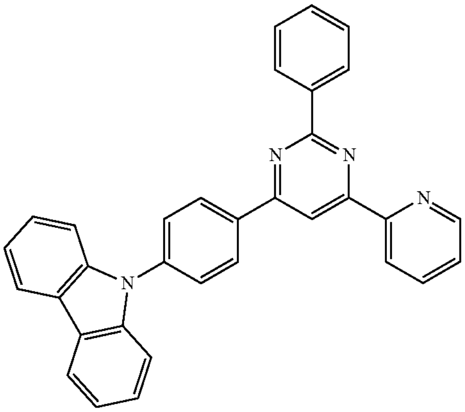
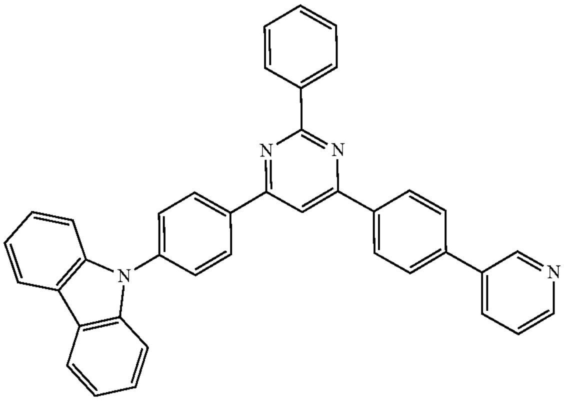

-continued
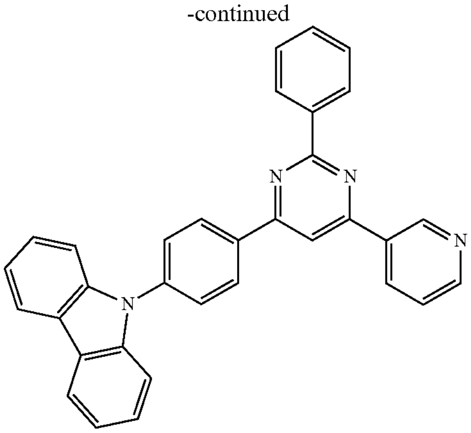
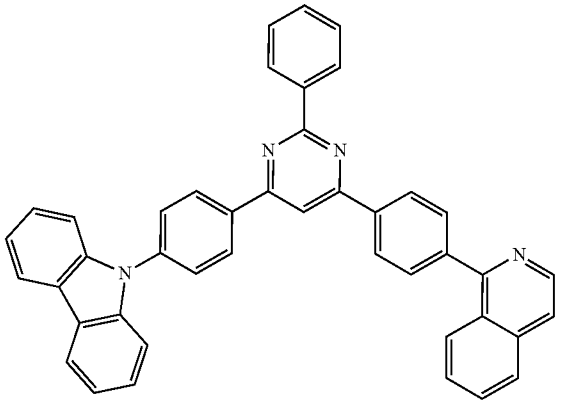
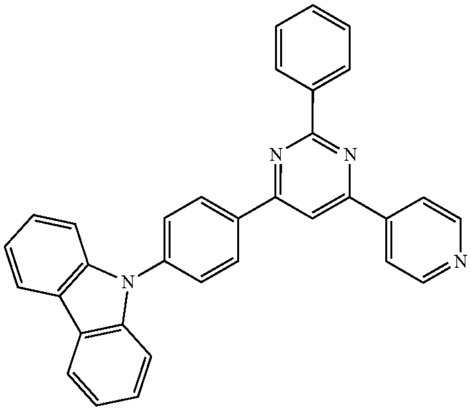
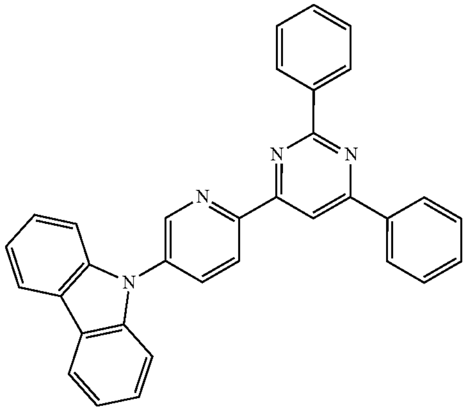
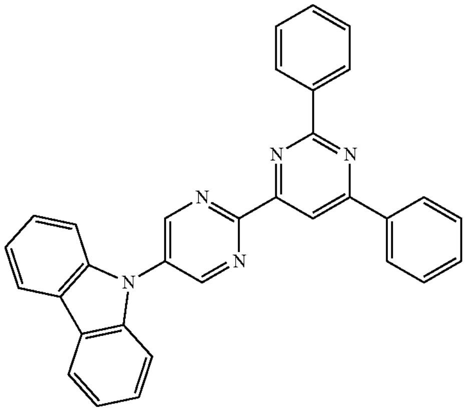
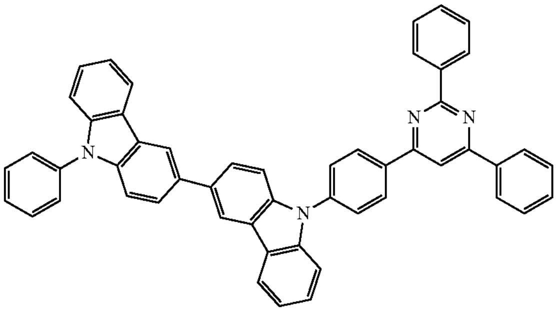
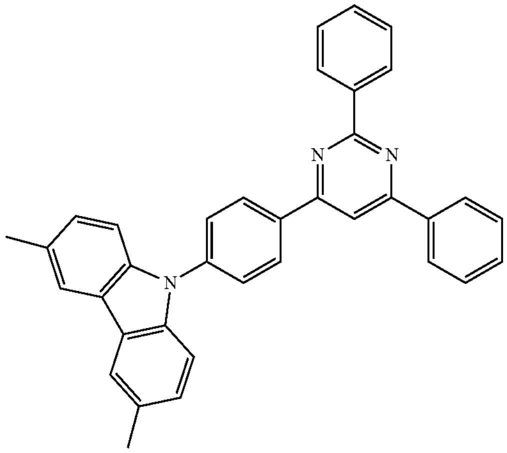
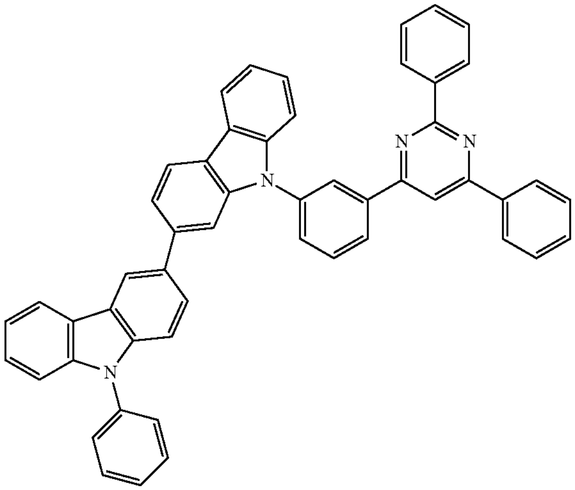

-continued
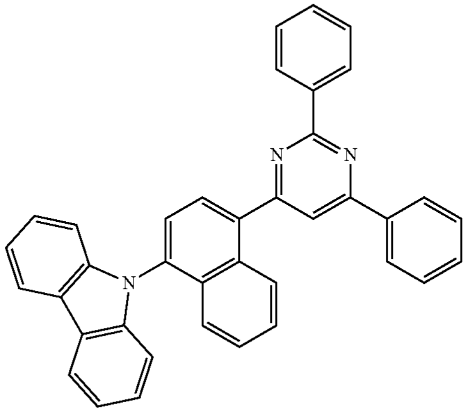
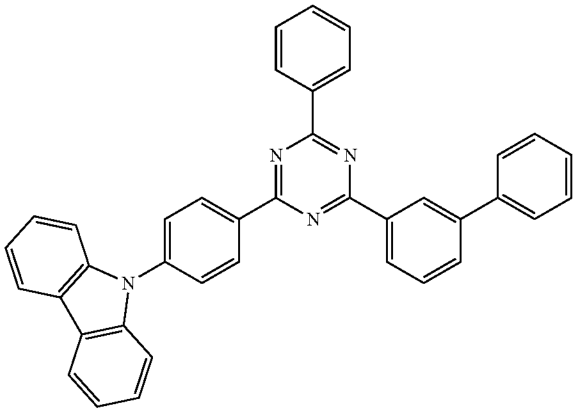
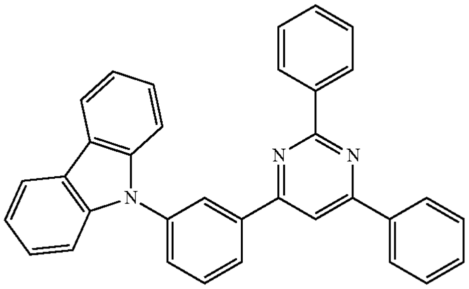
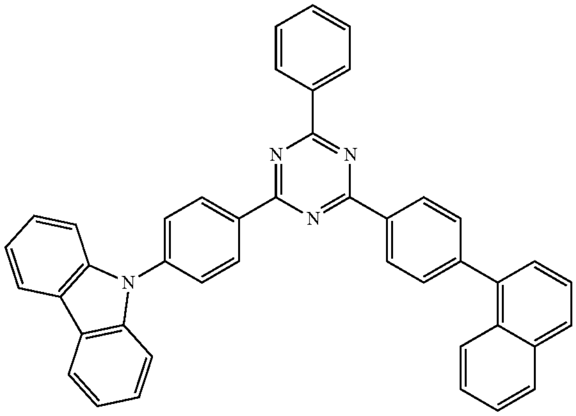
-continued
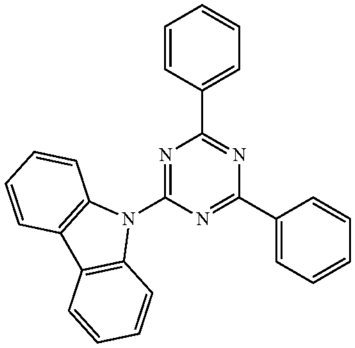
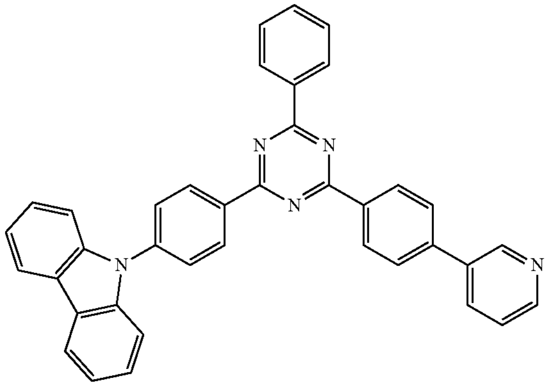
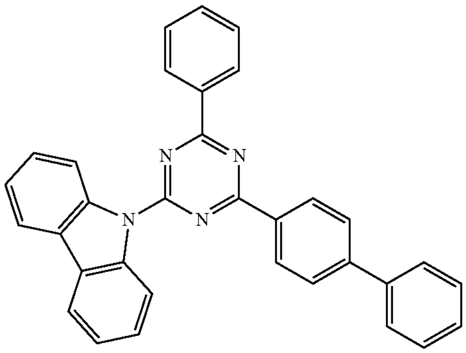
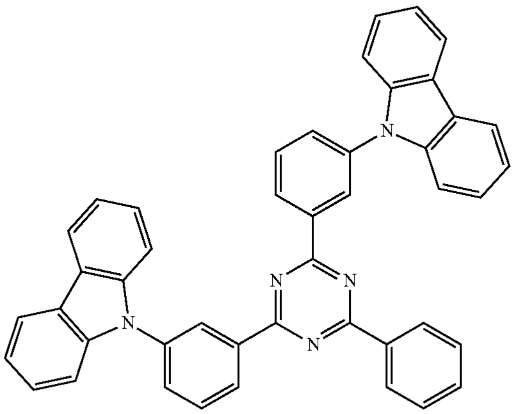

-continued
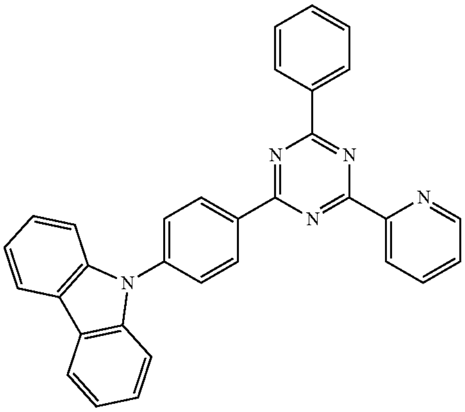
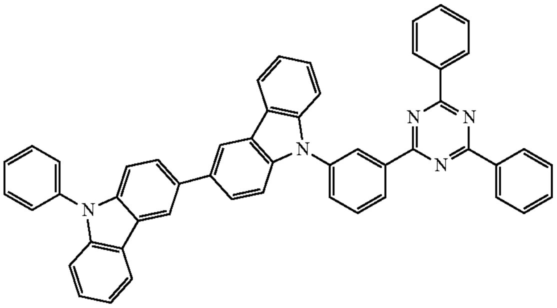
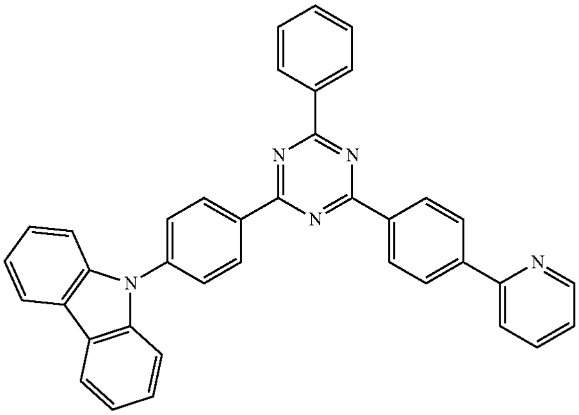
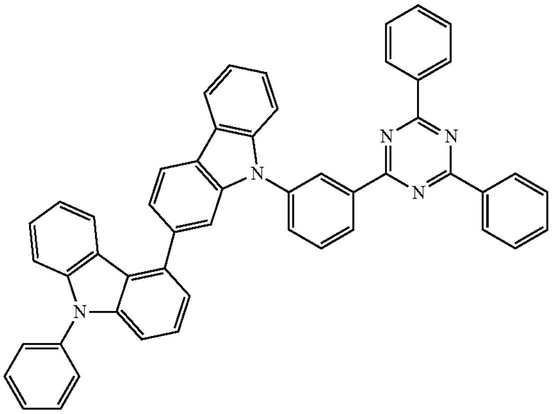
-continued
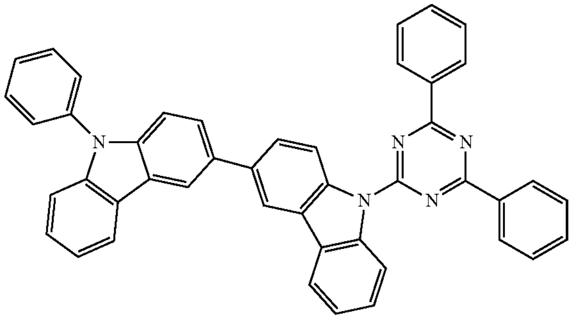
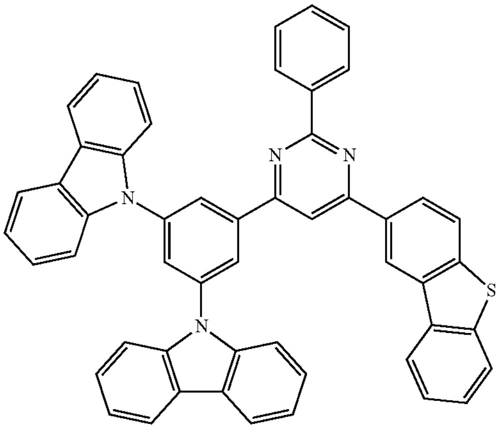
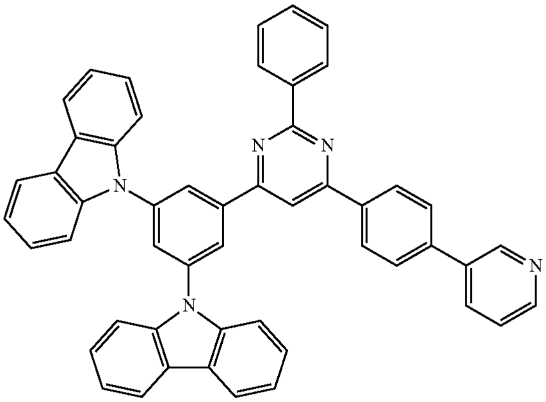
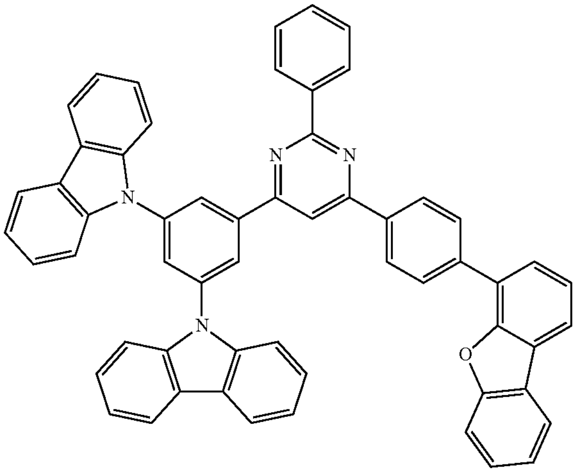

-continued

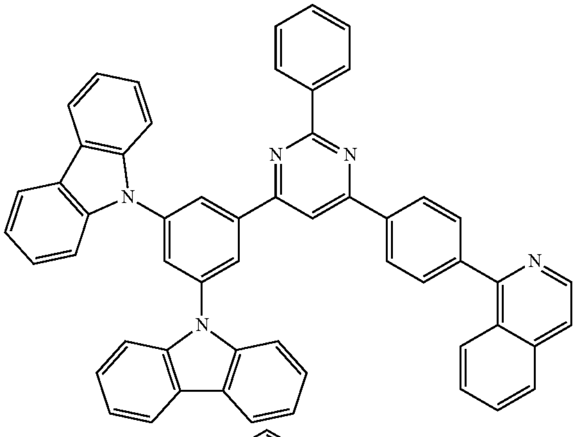

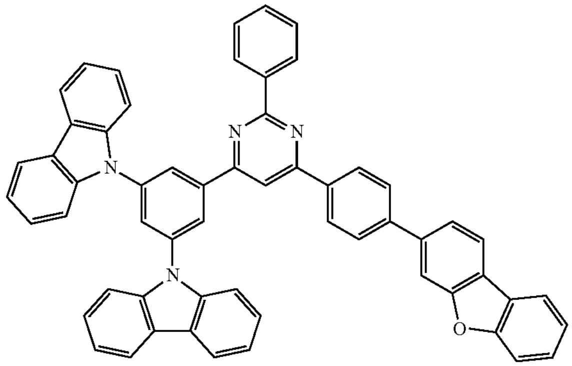

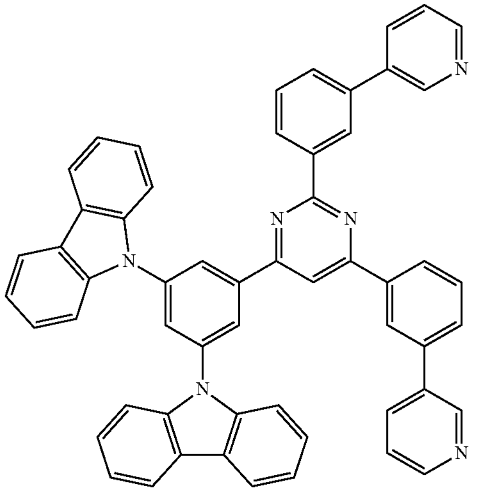

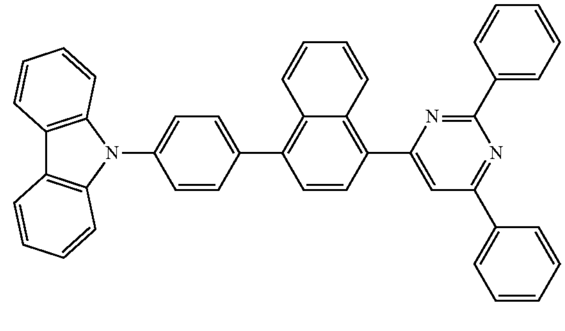

(Organic EL Device)

The organic EL device according to an aspect of the invention has a cathode, an anode, an emitting layer disposed between the cathode and the anode, and an electron-transporting zone disposed between the emitting layer and the cathode, wherein one layer in the electron-transporting zone (first layer) contains a first compound and a second compound.

In one embodiment of the organic EL device, one layer (first layer) in the electron-transporting zone contains a first compound and a second compound, the first compound is one or more selected from the group consisting of compounds represented by each of the formulas (1), (2), (3), and (4), and the second compound is one or more selected from the group consisting of compounds represented by each of the formulas (11), (12), and (13).

In one embodiment, in the organic EL device described above, the first compound is one or more selected from the group consisting of the compounds represented by each of the formulas (1), (2), (3), and (4), and the second compound is the compound represented by the formula (13).

In one embodiment, in the organic EL device described above, the first compound is one or more selected from the group consisting of compounds represented by each of the formulas (1-1), (2-1), (3-1), and (4-1), and the second compound is a compound represented by the formula (13-1).

In one embodiment, the organic EL device according to an aspect of the invention satisfies the following condition (A1).

$$1.0\times10^{-17}\leq\mu_2\times X_1 \quad \text{Condition (A1)}$$

wherein in the formula, $\mu_2$ represents a hole mobility ($cm^2/Vs$) of the first compound, and $X_1$ represents a mass ratio of the first compound in the first layer.

$\mu_2\times X_1$ is preferably $1.0\times10^{-14}$ or more.

In one embodiment, the organic EL device according to an aspect of the invention satisfies the following condition (A2).

$$\mu_2\times X_1\leq1.00\times10^{-6} \quad \text{Condition (A2)}$$

wherein in the formula, $\mu_2$ represents a hole mobility ($cm^2/Vs$) of the first compound, and $X_1$ represents a mass ratio of the first compound in the first layer.

$\mu_2\times X_1$ is preferably $1.0\times10^{-7}$ or less.

The proportion of the first compound in the first layer is not particularly limited, and is usually 5 to 70 mass %, preferably 5 to 60 mass % or 5 to 55 mass %. The ratio of the first compound in the first layer may be 10 to 60 mass % or 20 to 60 mass %.

As typical device configurations of the organic EL device, the structures obtained by stacking the following components on a substrate are exemplified.

(1) anode/emitting layer/electron-transporting zone/cathode (2) anode/hole-transporting zone/emitting layer/electron-transporting zone/cathode "/" indicates that the layers are stacked directly adjacent to each other.

The electron-transporting zone is usually composed of one or more layers selected from an electron-injecting layer and an electron-transporting layer. The hole-transporting zone is usually composed of one or more layers selected from a hole-injecting layer and a hole-transporting layer.

A schematic configuration of the organic EL device according to an aspect of the invention will be described with reference to FIG. 1.

The organic EL device 1 according to an aspect of the invention has a substrate 2, an anode 3, an emitting layer 5, a cathode 10, a hole-transporting zone 4 disposed between the anode 3 and the emitting layer 5, and an electron-transporting zone 6 disposed between the emitting layer 5 and the cathode 10.

Components which can be used in the organic EL device according to an aspect of the invention, materials for forming respective layers, other than the above-mentioned compounds, and the like, will be described below.

(Substrate)

A substrate is used as a support of an emitting device. As the substrate, glass, quartz, plastic or the like can be used, for example. Further, a flexible substrate may be used. The "flexible substrate" means a bendable (flexible) substrate, and specific examples thereof include a plastic substrate formed of polycarbonate, polyvinyl chloride, or the like.

(Anode)

For the anode formed on the substrate, metals, alloys, electrically conductive compounds, mixtures thereof, and the like, which have a large work function (specifically 4.0 eV or larger) are preferably used. Specific examples thereof include indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, and the like. In addition thereto, specific examples thereof include gold (Au), platinum (Pt), nitrides of metallic materials (for example, titanium nitride), and the like.

(Hole-Injecting Layer)

The hole-injecting layer is a layer containing a substance having a high hole-injecting property. As such substances having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, aromatic amine compounds, polymer compounds (oligomers, dendrimers, polymers, etc.), and the like can be given.

(Hole-Transporting Layer)

The hole-transporting layer is a layer containing a substance having a high hole-transporting property. For the hole-transporting layer, aromatic amine compounds, carbazole derivatives, anthracene derivatives, and the like can be used. Polymer compounds such as poly(N-vinylcarbazole) (abbreviation: PVK) and poly(4-vinyltriphenylamine) (abbreviation: PVTPA) can also be used. However, a substance other than the above-described substances may be used as long as the substance has a higher hole-transporting property in comparison with an electron-transporting property. It should be noted that the layer containing the substance having a high hole-transporting property may be composed of not only a single layer, but also layers in which two or more layers formed of the above-described substances are stacked.

(Guest (Dopant) Material of Emitting Layer)

The emitting layer is a layer containing a substance having a high emitting property, and various materials can be used for forming it. For example, as the substances having a high emitting property, fluorescent compounds which emit fluorescence or phosphorescent compounds which emit phosphorescence can be used. The fluorescent compounds are compound which can emit from a singlet excited state, and the phosphorescent compounds are compounds which can emit from a triplet excited state.

As blue fluorescent emitting materials which can be used for an emitting layer, pyrene derivatives, styrylamine derivatives, chrysene derivatives, fluoranthene derivatives, fluorene derivatives, diamine derivatives, triarylamine derivatives, and the like can be used. As green fluorescent emitting materials which can be used for an emitting layer, aromatic amine derivatives and the like can be used. As red fluorescent emitting materials which can be used for an emitting layer, tetracene derivatives, diamine derivatives and the like can be used.

As blue phosphorescent emitting materials which can be used for an emitting layer, metal complexes such as iridium complexes, osmium complexes, platinum complexes and the like are used. As green phosphorescent emitting materials which can be used for an emitting layer, iridium complexes and the like are used. As red phosphorescent emitting materials which can be used for an emitting layer, metal complexes such as iridium complexes, platinum complexes, terbium complexes, europium complexes and the like are used.

(Host Material for Emitting Layer)

The emitting layer may have a constitution in which the substance having a high emitting property (guest material) is dispersed in another substance (host material). As a substance for dispersing the substance having a high emitting property, a variety of substances can be used, and it is preferable to use a substance having a higher lowest unoccupied orbital level (LUMO level) and a lower highest occupied orbital level (HOMO level) than the substance having a high emitting property.

As a material (host material) for dispersing the substance having a high emitting property, 1) a metal complex such as an aluminum complex, a beryllium complex, a zinc complex or the like, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative, a chrysene derivative or the like, and 4) an aromatic amine compound such as a triarylamine derivative, a fused polycyclic aromatic amine derivative or the like are used.

(Electron-Transporting Layer)

An electron-transporting layer is a layer that contains a substance having a high electron-transporting property. For the electron-transporting layer, 1) metal complexes such as aluminum complexes, beryllium complexes, zinc complexes, and the like, 2) heteroaromatic complexes such as imidazole derivatives, benzimidazole derivatives, azine derivatives, carbazole derivatives, phenanthroline derivatives, and the like, and 3) polymer compounds can be used.

In an aspect of the invention, the electron-transporting layer may or may not contain the above-mentioned other materials in addition to the first compound and the second compound described above.

In one embodiment, the organic EL device has a first layer (also referred to as a "first electron-transporting layer" or a "hole barrier layer") and a second layer (also referred to as a "second electron-transporting layer") in this order from the emitting layer side in the electron-transporting zone, the first layer contains the above-mentioned first compound and the above-mentioned second compound, and no other layer is disposed between the emitting layer and the first layer. As the second layer, the above-described constitution of the electron-transporting layer can be applied.

(Electron-Injecting Layer)

An electron-injecting layer is a layer which contains a substance having a high electron-injecting property. For the electron-injecting layer, lithium (Li), ytterbium (Yb), lithium fluoride (LiF), cesium fluoride (CsF), calcium fluoride ($CaF_2$), metal complex compounds such as 8-hydroxyquinolinolato-lithium (Liq), alkali metals, alkaline earth metals or compounds thereof, such as lithium oxide ($LiO_x$) can be used.

(Cathode)

For the cathode, metals, alloys, electrically conductive compounds, mixtures thereof, and the like, which have a small work function (specifically, 3.8 eV or smaller) are preferably used. Specific examples of such cathode materials include elements belonging to Group 1 and Group 2 of the Periodic Table of the Elements, i.e., alkali metals such as lithium (Li), cesium (Cs) and the like, alkaline earth metals such as magnesium (Mg), calcium (Ca), strontium (Sr) and the like, and alloys containing these metals (e.g., MgAg and AlLi); rare earth metals such as europium (Eu), ytterbium (Yb) and the like, and alloys containing these metals.

The cathode is usually formed by a vacuum vapor deposition or a sputtering method. Further, in the case of using a silver paste or the like, a coating method, an inkjet method, or the like can be employed.

In the case where the electron-injecting layer is provided, the cathode can be formed of a substance selected from various electrically conductive materials such as aluminum, silver, ITO, graphene, indium oxide-tin oxide containing silicon or silicon oxide, and the like, regardless of the work function value.

In the organic EL device according to an aspect of the invention, the thickness of each layer is not particularly limited, but is generally preferable that the thickness be in the range of several nm to 1 μm in order to suppress defects such as pinholes, to suppress applied voltages to be low, and to increase luminous efficiency.

(Method for Fabricating Organic EL Device)

In the organic EL device according to an aspect of the invention, the method for forming the respective layers are not particularly limited. A conventionally-known methods for forming each layer such as a vacuum deposition process, a spin coating process and the like can be employed. Each layer such as the emitting layer can be formed by a known method such as a vacuum deposition process, a molecular beam deposition process (MBE process), or an application process such as a dipping process, a spin coating process, a casting process, a bar coating process, a roll coating process or the like, which uses a solution prepared by dissolving the material in a solvent.

In one embodiment, as a method of forming the first layer in the electron-transporting zone, a method may be employed in which the first compound and the second compound are simultaneously vapor-deposited from different vapor deposition sources to form a layer, or a method may be employed in which the first compound and the second compound are mixed in advance and then vapor-deposited from single vapor deposition source to form a layer. Specific examples of one embodiment of the latter method include a method in which a composition (powder) according to an aspect of the invention described later is used and vapor-deposited from single vapor deposition source to form a first layer.

The latter method has an advantage that the fabricating apparatus and the fabricating process can be simplified.

[Composition]

The composition according to an aspect of the invention contains one or more selected from the group consisting of compounds represented by each of the formulas (1), (2), (3), and (4) and one or more selected from the group consisting of compounds represented by each of the formulas (11), (12), and (13), and does not substantially contain a metal complex.

Specific aspects of one or more selected from the group consisting of the compounds represented by each of the formulas (1), (2), (3), and (4) are as described in the first compound of the organic EL device described above, and specific aspects of one or more selected from the group consisting of the compounds represented by each of the formulas (11), (12), and (13) are as described in the second compound of the organic EL device described above.

Provided that one or more selected from the group consisting of the compounds represented by each of the formulas (1), (2), (3), and (4) and one or more selected from the group consisting of the compounds represented by each of the formulas (11), (12), and (13) are different compounds.

In one embodiment, the above-mentioned composition contains one or more selected from the group consisting of the compounds represented by the formulas (1), (2), (3), and (4) and the compound represented by the formula (13), and does not substantially contain a metal complex.

In one embodiment, the above composition contains one or more selected from the group consisting of compounds represented by each of the formulas (1-1), (2-1), (3-1), and (4-1) and a compound represented by the formula (13-1), and does not substantially contain a metal complex.

The expression "does not substantially contain" a metal complex means that no metal complex is contained at all in the composition, or a metal complex is contained in the composition in a small amount within a range that it does not decrease the effect of the invention. For example, the case where a metal complex is contained in the composition as an inevitable impurity, is the state that the composition "does not substantially contain" a metal complex.

The content (total amount) of metal complexes in the composition according to an aspect of the invention is, for example, 1 mass % or less, 0.5 mass % or less, 0.1 mass % or less, or 0.01 mass % or less.

In addition, in one embodiment, the composition according to an aspect of the invention does not substantially contain a metal other than the metal complexes.

The expression "does not substantially contain" a metal means that no simple metal element or no metal compound is contained at all in the composition, or a simple metal element or a metal compound is contained in the composition in a small amount within a range that it does not impair the effect of the invention. For example, the case where a metal is contained in the composition as an inevitable impurity, is the state that the composition "does not substantially contain" a metal.

The content (total amount) of simple metal elements and metal compounds in the composition according to an aspect of the invention is, for example, 1 mass % or less, 0.5 mass % or less, 0.1 mass % or less, or 0.01 mass % or less.

In the composition according to an aspect of the invention, a blending ratio of one or more selected from the group consisting of the compounds represented by each of the formulas (1), (2), (3), and (4) and one or more selected from the group consisting of the compounds represented by each of the formulas (11), (12), and (13) is not particularly limited.

In one embodiment, the content ratio of the former in the total amount of the composition is usually 5 to 70 mass %, preferably 5 to 60 mass %, or 5 to 55 mass %. The content ratio of the former in the total amount of the composition may be 10 to 60 mass % or 20 to 60 mass %.

The form of the composition according to an aspect of the invention is not particularly limited, and examples thereof include a solid, a powder, a solution, a film (layer), and the like. The film (layer) includes, for example, an organic layer (e.g., an electron-transporting layer) constituting an organic EL device. When the form of the composition is a solid or a powder, the composition may be molded into a pellet form.

The composition according to an aspect of the invention can be applied to an organic EL device.

In the organic EL device (second organic EL device), one or more organic thin film layers including at least an emitting layer disposed between a cathode and an anode, and at least one layer of the organic thin film layers contains a composition according to an aspect of the invention. The organic EL device preferably has an electron-transporting zone between the emitting layer and the cathode, the electron-transporting zone has one or more organic thin film layers, and at least one layer of the organic thin film layers contains the composition according to an aspect of the invention. The at least one layer is preferably an electron-transporting layer.

A specific aspect of the second organic EL device is as described in the first organic EL device described above.

The composition according to an aspect of the invention may be in a powder form. The powder may be a form in which the first compound and the second compound are contained in single particle, or may be a mixture form of particles composed of the first compound and particles composed of the second compound.

The blending ratio of the first compound and the second compound is not particularly limited and is as described above for the composition.

As a method for producing the powder, a conventionally known method can be employed. For example, the first compound and the second compound may be pulverized and mixed using a mortar or the like; or the first compound and the second compound may be placed in a container or the like, heated in a chemically inert environment, and then cooled to an ambient temperature, and the obtained mixture may be pulverized by a mixer or the like to obtain a powder.

[Electronic Apparatus]

The electronic apparatus according to an aspect of the invention is equipped with the organic EL device according to an aspect of the invention.

Specific examples of the electronic apparatus include display components such as an organic EL panel module, and the like; display devices for a television, a cellular phone, a personal computer, and the like; and emitting devices such as a light, a vehicular lamp, and the like.

EXAMPLES

Hereinafter, Examples according to the invention will be described. The invention is not limited in any way by these Examples.

<Compounds>

The first compounds used for fabricating the organic EL devices of Examples are shown below.

Compound 1A

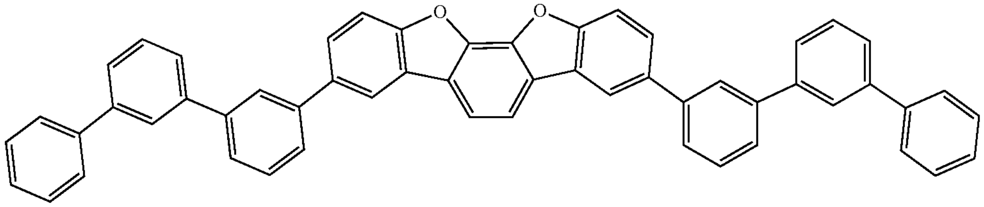

Compound 1B

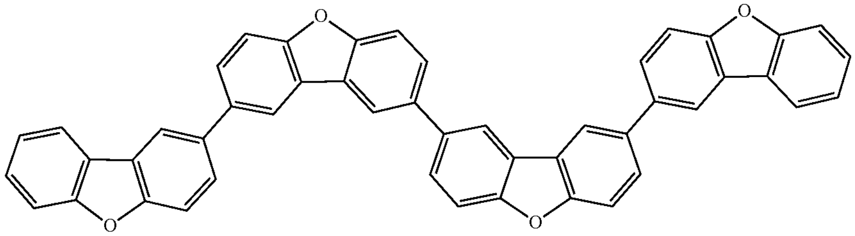

Compound 1C

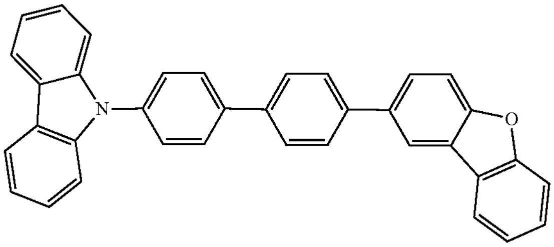

Compound 1D

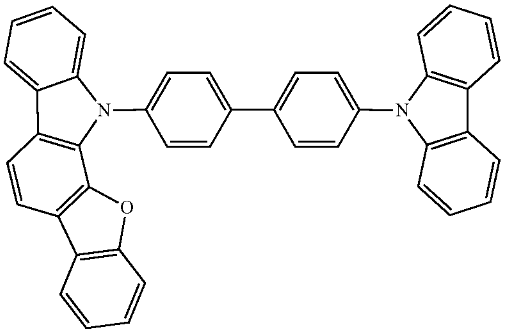

-continued
Compound 1E
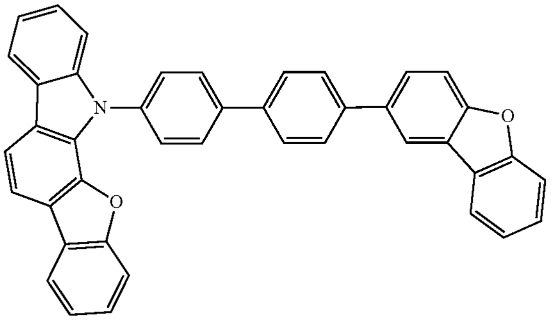
Compound 1F
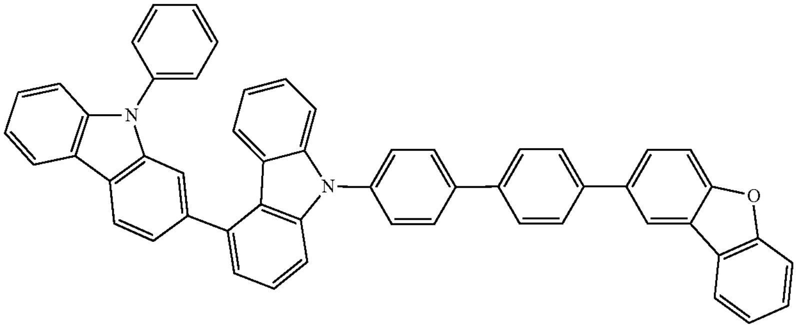
Compound 1G
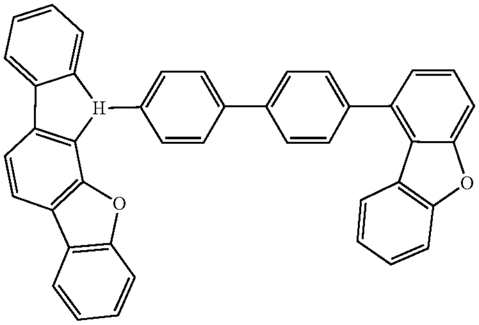
The second compounds used for fabricating the organic EL devices of Examples and Comparative Examples are shown below.
Compound 2A
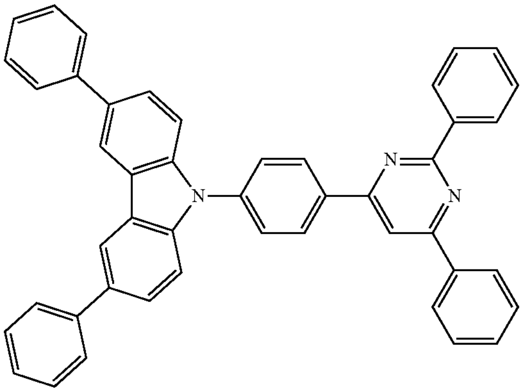
-continued
compound 2B
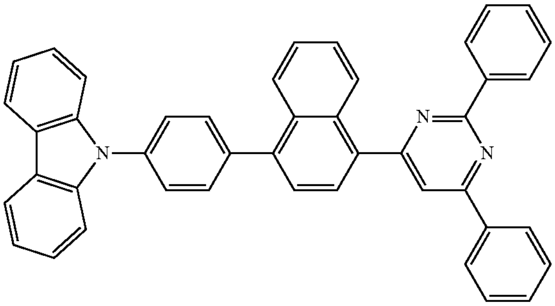
The structures of the other compounds used for fabricating the organic EL devices of Examples and Comparative Examples are shown below.

-continued

HT1

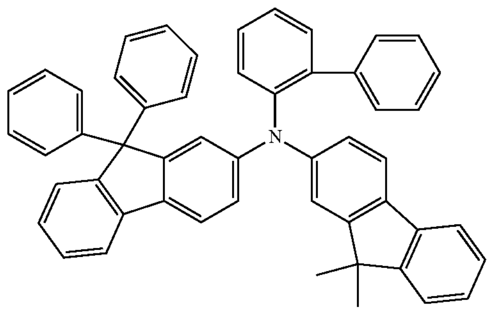

HI

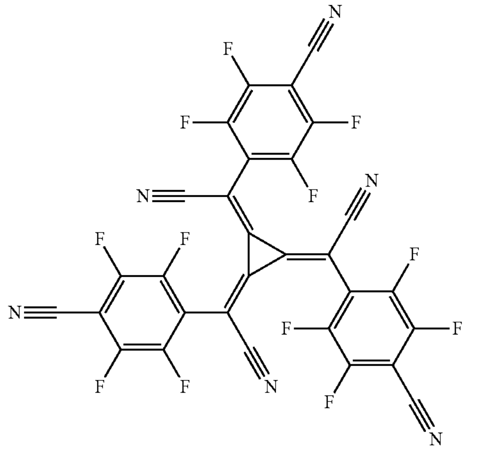

HT2

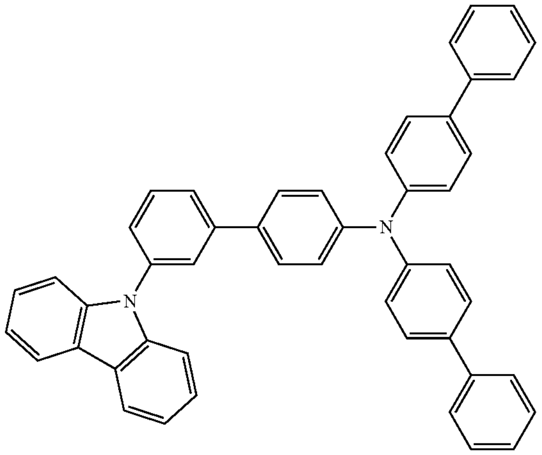

BH

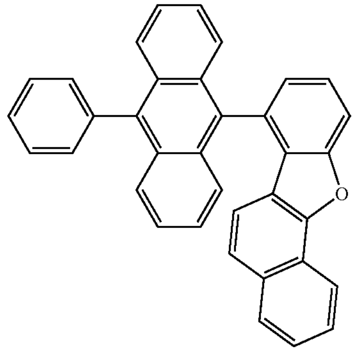

BD

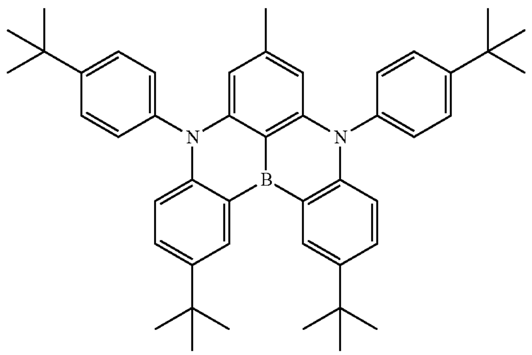

ET

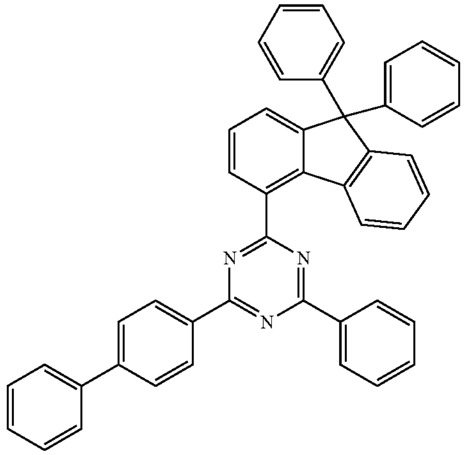

<Evaluation of Compound>

The ionization potential (Ip), the electron affinity (Af), the band gap (Eg), the triplet energy ($T_1$), the electron mobility $\mu_1$, and the hole mobility $\mu_2$ of the first compounds and the second compounds were evaluated by the following measuring methods. The results are shown in Table 1. In Table 1, "–" indicates that the measurement was not performed.

Ionization Potential (Ip)

The ionization potential was measured in air using a photoelectron spectrometer (manufactured by RIKEN KEIKI Co., Ltd., "AC-3"). Specifically, a compound to be measured was irradiated with light, and the quantity of electrons generated by charge-separation was measured.

Electron Affinity (Af)

The electron affinity was calculated by the following equation.

$$Af = -1.19 \times (Ere - Efc) - 4.78 \text{ eV}$$

Here, each symbol means the following.

Ere: First reduction potential (DPV, Negative scan)

Efc: First oxidation potential (DPV, Positive scan) of ferrocene, (ca.+0.55V vs Ag/AgCl)

The redox potential was measured by differential pulse voltammetry (DPV) using an electrochemical analyzer (CHI852D, manufactured by ALS Corporation).

N,N-dimethylformamide (DMF) was used as the solvent, and the sample concentration was set to be 1.0 mmol/L. Tetrabutylammonium hexafluorophosphate (TBHP) (100 mmol/L) was used as the supporting electrolyte. Glassy carbon and Pt were used as a working electrode and a counter electrode, respectively.

(Reference literatures) M. E. Thompson, et. al., Organic Electronics, 6 (2005), p. 11-20, Organic Electronics, 10 (2009), p. 515-520

Band Gap (Eg)

A 10 μmol/L toluene solution of a compound to be measured was prepared and placed in a quartz cell, and the absorption spectrum (vertical axis: absorption intensity, horizontal axis: wavelength) of this sample was measured at normal temperature (300 K). Drawing a tangent to the falling of the long wavelength side of the absorption spectrum, the wavelength value Δedge [nm] of the intersection of the tangent and the horizontal axis was substituted into the following conversion equation (F2) to calculate the band gap.

$$Eg[eV]=1239.85/\lambda edge \quad \text{Equation (F2)}$$

A spectrophotometer (device name: U3310) manufactured by Hitachi, Ltd. was used as an absorbance spectrum measuring device.

The tangent to the falling of the absorption spectrum of the long wavelength side is drawn as follows. The tangent at each point on the spectrum curve is supposed while moving on the spectrum curve in the long wavelength direction from the maximum value on the longest wavelength side among the maximum values of the absorption spectrum. The slope of this tangent repeatedly decreases and increases. Namely, the slope of this tangent decreases as the curve falls (i.e. as the value of the vertical axis decreases), and then, increases. The tangent drawn at the point where the slope has the minimum value on the longest wavelength side (excluding the point where the absorbance is 0.1 or less) shall be the tangent line to the falling on the long wavelength side of the absorption spectrum.

Note that a maximum point having an absorbance value of 0.2 or less is not included in the maximum value on the longest wavelength side described above.

Triplet Energy ($T_1$)

The triplet energy was measured as follows.

A compound to be measured was dissolved in EPA (diethyl ether:isopentane:ethanol=5:5:2 (volume ratio)) so as to have a concentration of 10 μmol/L, and this solution was placed in a quartz cell to serve as a measurement sample. The phosphorescence spectrum (vertical axis: phosphorescence emission intensity, horizontal axis: wavelength) was measured at a low temperature (77 [K]), a tangent was drawn to the rising on the short wavelength side of the phosphorescence spectrum, and the energy quantity calculated from the following conversion equation (F1) was taken as the triplet energy $T_1$ based on the wavelength value $\lambda_{edge}$ [nm] of the intersection point of the tangent line and the horizontal axis. Note that the triplet energy $T_1$ may have an error of about ±0.02 eV depending on the measuring condition.

$$T_1[eV]=1239.85/\lambda_{edge} \quad \text{Conversion equation (F1)}$$

The tangent to the rising on the short wavelength side of the phosphorescence spectrum is drawn as follows. The tangent at each point on the spectrum curve is supposed while moving on the spectrum curve in the long wavelength direction from the maximum value on the shortest wavelength side among the maximum values of the absorption spectrum. This tangent increases in slope as the curve rises, i.e. as the value of the vertical axis increases. The tangent drawn at the point where the value of this slope has the maximum value (i.e., the tangent at the inflection point) is defined as the tangent to the rising of the short wavelength side of the phosphorescence spectrum.

Incidentally, the maximum point having a peak intensity of 15% or lower of the maximum peak intensity of the spectrum is not included in the maximum value of the shortest wavelength side described above, and the tangent drawn at the point where the value of the slope has the maximum value and closest to the maximum value of the shortest wavelength side is defined as the tangent to the rising of the short wavelength side of the phosphorescence spectrum.

A main body of F-4500 spectrofluorometer manufactured by Hitachi High Technology Corporation can be used for measuring phosphorescence. Incidentally, the measuring instrument is not limited to the above, and measurement may be performed using a cooling apparatus and a low-temperature container, an excitation light source, and a light receiving device in combination.

Electron Mobility $\mu_1$

The electron mobility $\mu_1$ was measured by the following method using impedance spectroscopy.

The deposition was carried out on an Al substrate using a vacuum deposition apparatus, and the following single carrier device was fabricated. Numerical values in parentheses are film thicknesses (nm). Target is a compound to be measured.

Al(50)/Target(200)/ETB1(10)/LiF(1)/Al(50)

ETB1

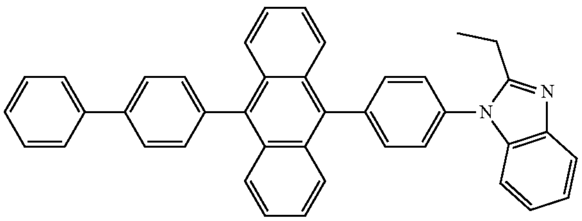

For the resulting single carrier device, DC voltage was applied with an AC voltage of 100 mV, and the AC current value (absolute value and phase) flowing at this time was measured. This measurement was carried out while changing the frequency of the AC voltage to calculate the complex impedance (Z) from the current value and the voltage value. At this time, the frequency dependence of the imaginary part (ImM) of the modulus M=iωZ (i: imaginary unit, ω: angular frequency) was obtained, and when the frequency at which the imaginary part of the modulus was maximized was defined as $f_{max}$ (Hz), the response time T (second) was calculated as $T=1/2/\pi/f_{max}$, and the field strength dependence of the mobility was determined using this value. The electron mobility at the square root $E^{1/2}=500[V^{1/2}/cm^{1/2}]$ of the electric field strength was defined as $\mu_1$.

The above-mentioned impedance measurement was performed using impedance analyzer SI1260 (manufactured by Toyo Corporation) as an impedance measuring apparatus.

Hole Mobility $\mu_2$

The hole mobility $\mu_2$ was measured using the hole mobility evaluating device fabricated in the following procedure.

A 25 mm×75 mm×1.1 mm-thick glass substrate with an ITO transparent electrode (anode) was subjected to ultrasonic cleaning in isopropyl alcohol for 5 minutes, followed by UV-ozone washing for 30 minutes. The thickness of the ITO film was 130 nm.

The glass substrate after being cleaned was mounted onto a substrate holder in a vacuum vapor deposition apparatus, and Compound HA-2 was deposited on a surface on the side on which the transparent electrode line was formed so as to cover the transparent electrode to form a hole-injecting layer having a thickness of 5 nm.

Compound HT-A was deposited on this formed film of the hole-injecting layer to form a hole-transporting layer having a thickness of 10 nm.

Subsequently, Compound Target as a measurement target of the hole mobility $\mu_2$ was deposited thereon to form a measurement target layer having a thickness of 200 nm.

Then, metal aluminum (Al) was deposited on the measurement target layer to form a metal cathode having a film thickness of 80 nm.

The device configuration of the hole mobility evaluating device is schematically shown as follows.

ITO(130)/HA-2(5)/HT-A(10)/Target(200)/Al(80)

Numerical values in parentheses indicate film thickness (nm).

HA-2

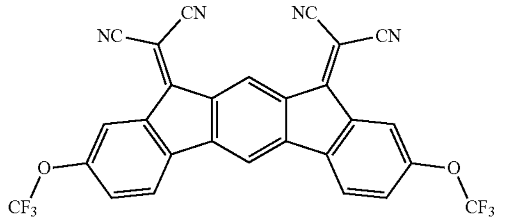

HT-A

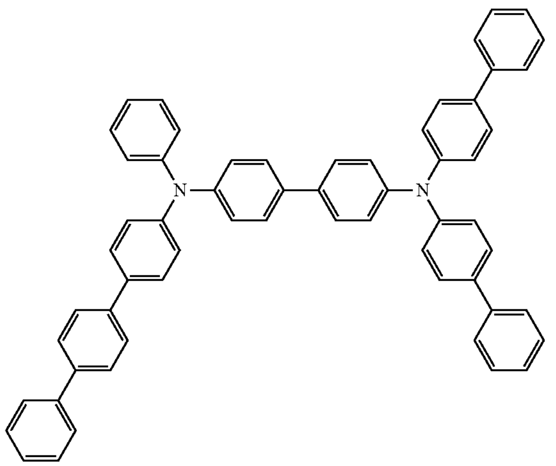

Subsequently, the hole mobility $\mu_2$ is measured by the following procedure using the mobility evaluating device fabricated by the above procedure.

The above-mentioned device for evaluating mobility was installed in the impedance measuring apparatus, and impedance measurement was carried out. Impedance measurement was performed by sweeping the measurement frequency from 1 Hz to 1 MHz. At that time, the device was applied a DC voltage V at the same time as the AC amplitude of 0.1 V. From the measured impedance Z, the modulus M was calculated using the relationship of the following equation (C1).

$$M=j\omega Z \qquad \text{Equation (C1)}$$

In the equation (C1), j is an imaginary unit whose square becomes −1, ω is the angular frequency [rad/s]. The electrical time constant τ of the device for evaluating the mobility was determined from the peak frequency fmax in a Bode plot with the imaginary part of the modulus M as the vertical axis and the frequency [Hz] as the horizontal axis by the following equation (C2).

$$\tau=1/(2\pi f\mathrm{max}) \qquad \text{Equation (C2)}$$

In the above equation (C2), π is a symbol representing the circumferential rate.

Using the above τ, the hole mobility μh was calculated from the relationship of the following equation (C3).

$$\mu h=d^2/(V_{\tau}) \qquad \text{Equation (C3)}$$

d in the above equation (C3) is the total film thickness of the organic thin film constituting the device, and as indicated in the above device configuration for evaluating the mobility, d=215 [nm].

The hole mobility in this specification is a value in the square root of the electric field strength $E^{1/2}$=500[$V^{1/2}$/$cm^{1/2}$. The square root of the electric field strength $E^{1/2}$ can be calculated from the relationship of the following equation (C4).

$$E^{1/2}=V^{1/2}/d^{1/2} \qquad \text{Equation (C4)}$$

In this Example, the impedance measurement was performed using the 1260 type of Solatron Co. as an impedance measuring device, together with the 1296 type dielectric constant measuring interface of Solatron Co. in order to make it high accurate.

TABLE 1

| | IP [eV] | Af [eV] | Eg [eV] | $T_1$ [eV] | Electron mobility $\mu_1$ [$cm^2$/Vs] | Hole mobility $\mu_2$ [$cm^2$/Vs] |
|---|---|---|---|---|---|---|
| Compound 1A | 6.17 | 1.58 | 3.64 | 2.81 | $2.3 \times 10^{-10}$ | $2.6 \times 10^{-8}$ |
| Compound 1B | 6.49 | 1.56 | 3.76 | 2.78 | $2.5 \times 10^{-11}$ | $2.4 \times 10^{-14}$ |
| Compound 1C | 6.09 | 1.54 | 3.5 | 2.54 | $2.5 \times 10^{-10}$ | $3.1 \times 10^{-10}$ |
| Compound 1D | 6.11 | 1.46 | 3.42 | 2.53 | $2.4 \times 10^{-10}$ | $3.0 \times 10^{-12}$ |
| Compound 1E | 6.01 | 1.54 | 3.41 | 2.52 | $2.4 \times 10^{-10}$ | $2.9 \times 10^{-10}$ |
| Compound 1F | 5.88 | 1.56 | 3.36 | 2.54 | $2.0 \times 10^{-10}$ | $2.4 \times 10^{-9}$ |
| Compound 1G | 6.06 | 1.69 | 3.42 | 2.52 | $2.4 \times 10^{-10}$ | $2.9 \times 10^{-11}$ |
| Compound 2A | 5.94 | 2.19 | 2.8 | 2.81 | $3.9 \times 10^{-5}$ | $2.4 \times 10^{-10}$ |
| Compound 2B | 6.17 | 2.2 | 3.29 | 2.48 | $1.71 \times 10^{-5}$ | — |

<Fabrication of Organic EL Device>

An organic EL device was fabricated as follows.

Example 1

A 25 mm×75 mm×1.1 mm-thick glass substrate with an ITO transparent electrode (anode) was subjected to ultrasonic cleaning in isopropyl alcohol for 5 minutes, followed by UV-ozone washing for 30 minutes. The thickness of the ITO film was 130 nm.

The glass substrate with transparent electrode after being cleaned was mounted onto a substrate holder in a vacuum vapor deposition apparatus, and Compound HT1 and Compound HI were co-deposited on a surface on the side on which the transparent electrode line was formed so as to cover the transparent electrode so that the proportion of Compound HI was 3 mass % to form a hole-injecting layer having a thickness of 10 nm.

Compound HT1 was deposited on the hole-injecting layer to form a first hole-transporting layer having a thickness of 80 nm.

Compound HT2 was deposited on the first hole-transporting layer to form a second hole-transporting layer having a thickness of 5 nm.

Compound BH (host material) and Compound BD (dopant material) were co-deposited on the second hole-transporting layer so that the proportion of Compound BD was 1 mass % to form an emitting layer having a thickness of 20 nm.

Compound 1A and Compound 2A were co-deposited on the emitting layer so that the proportion of Compound 1A was 30 mass % to form a first electron-transporting layer (hole barrier layer) having a thickness of 5 nm.

Compound ET and 8-hydroxyquinolinolato-lithium (Liq) were co-deposited on the first electron-transporting layer so that the proportion of Liq was 50 mass % to form a second electron-transporting layer having a thickness of 25 nm.

Then, metal ytterbium (Yb) was deposited on the second electron-transporting layer to form an electron-injecting layer having a thickness of 1 nm.

Metal aluminum (Al) was deposited on the electron-injecting layer to form a cathode having a thickness of 80 nm.

The device configuration of the organic EL device of Example 1 is schematically shown as follows.

ITO(130)/HT1:HI(10:3%)/HT1(80)/HT2(5)/BH:BD (20:1%)/Compound 2A:Compound 1A(5:30%)/ ET:Li*q*(25:50%)/Yb(1)/Al(80)

Numerical values in parentheses indicate a film thickness (unit: nm). In parentheses, the numerical values in percentage indicate the proportion (mass %) of the latter compound in the layer.

<Evaluation of Organic EL Device>

The fabricated organic EL devices were evaluated for external quantum efficiency and device lifetime as follows. Table 2 shows the relative values of the obtained external quantum efficiency and device lifetime when those of Comparative Example 1 was set to 100%, respectively. Further, the product of the external quantum efficiency (relative value) and the device lifetime (relative value) is shown in Table 2.

External Quantum Efficiency

Voltage was applied to the organic EL device so that the current density became 10 mA/cm$^2$, and the EL emission spectrum was measured by using Spectroradiometer CS-2000 (manufactured by KONICA MINOLTA, INC.). External quantum efficiency EQE (%) was calculated from the obtained spectral radiance spectrum.

Device Lifetime

For the resulting organic EL device, voltage was applied to the organic EL device to be 50 mA/cm$^p$ in current density at room temperature, and the time until the luminance reduced to 95% of the initial luminance (LT95 (unit: h)) was measured.

Further, the product of the hole mobility $\mu_2$ measured by <Evaluation of compound> and the mass ratio $X_1$ of the first compound in the first electron-transporting layer ($\mu_2$×1%) for each organic EL device fabricated is shown in Table 2.

TABLE 2

| | Composition of first electron-transporting layer Numerical values in parenthesis being proportion of the former in the layer (mass %) | EQE | Device lifetime | EQE × Device lifetime | $\mu_2 \times X_1$ |
|---|---|---|---|---|---|
| Example 1 | Compound 1A(30%) + Compound 2A | 101% | 189% | 191% | $7.8 \times 10^{-9}$ |
| Example 2 | Compound 1B(30%) + Compound 2A | 101% | 117% | 118% | $7.2 \times 10^{-15}$ |
| Example 3 | Compound 1C(30%) + Compound 2A | 104% | 120% | 125% | $9.3 \times 10^{-11}$ |
| Example 4 | Compound 1D(30%) + Compound 2A | 102% | 120% | 122% | $9.0 \times 10^{-13}$ |
| Example 5 | Compound 1E(30%) + Compound 2A | 103% | 134% | 138% | $8.7 \times 10^{-11}$ |
| Example 6 | Compound 1F(30%) + Compound 2A | 101% | 161% | 163% | $7.2 \times 10^{-10}$ |
| Example 7 | Compound 1G(30%) + Compound 2A | 102% | 129% | 132% | $8.7 \times 10^{-12}$ |
| Example 8 | Compound 1A(50%) + Compound 2A | 98% | 151% | 148% | $1.3 \times 10^{-8}$ |
| Example 9 | Compound 1B(50%) + Compound 2A | 99% | 231% | 229% | $1.2 \times 10^{-14}$ |
| Example 10 | Compound 1C(50%) + Compound 2A | 102% | 118% | 120% | $1.6 \times 10^{-10}$ |
| Example 11 | Compound 1D(50%) + Compound 2A | 103% | 130% | 134% | $1.5 \times 10^{-12}$ |
| Example 12 | Compound 1E(50%) + Compound 2A | 103% | 153% | 158% | $1.5 \times 10^{-10}$ |
| Example 13 | Compound 1F(50%) + Compound 2A | 91% | 222% | 202% | $1.2 \times 10^{-9}$ |
| Example 14 | Compound 1G(50%) + Compound 2A | 103% | 134% | 138% | $1.5 \times 10^{-11}$ |
| Comp. Ex. 1 | Compound 2A | 100% | 100% | 100% | — |

Examples 2 to 14

Organic EL devices were fabricated in the same manner as in Example 1, except that the configurations described in Table 2 were used in the formation of the first electron-transporting layer.

Comparative Example 1

An organic EL device was fabricated in the same manner as in Example 1, except that only Compound 2A was used in the formation of the first electron-transporting layer.

Examples 15 to 17

Organic EL devices were fabricated and evaluated in the same manner as in Example 1, except that the configurations described in Table 3 were used in the formation of the first electron-transporting layer. The results are shown in Table 3.

Comparative Example 2

An organic EL device was fabricated and evaluated in the same manner as in Example 1, except that only Compound 2B was used in in the formation of the first electron-transporting layer. The results are shown in Table 3.

TABLE 3

| | Composition of first electron-transporting layer Numerical values in parenthesis being proportion of the former in the layer (mass %) | EQE | Device lifetime | EQE × Device lifetime | $\mu_2 \times X_1$ |
|---|---|---|---|---|---|
| Example 15 | Compound 1D(10%) + Compound 2B | 100% | 118% | 118% | $3.0 \times 10^{-13}$ |
| Example 16 | Compound 1D(30%) + Compound 2B | 101% | 122% | 123% | $9.0 \times 10^{-13}$ |
| Example 17 | Compound 1E(30%) + Compound 2B | 101% | 115% | 116% | $8.7 \times 10^{-11}$ |
| Comp. Ex. 2 | Compound 2B | 100% | 100% | 100% | — |

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the specification of Japanese application(s) on the basis of which the present application claims Paris convention priority are incorporated herein by reference in its entirety.

The invention claimed is:

1. An electron-transporting layer for an organic electroluminescence device, wherein the electron-transporting layer comprises a composition comprising one or more selected from the group consisting of compounds represented by each of the following formulas (1), (2), (3), and (4) and one or more selected from the group consisting of compounds represented by each of the following formulas (11), (12), and (13), and comprising substantially no metal complex; and provided that the one or more selected from the group consisting of the compounds represented by each of the formulas (1), (2), (3), and (4) and the one or more selected from the group consisting of the compounds represented by each of the formulas (11), (12), and (13) are different compounds:

(1)

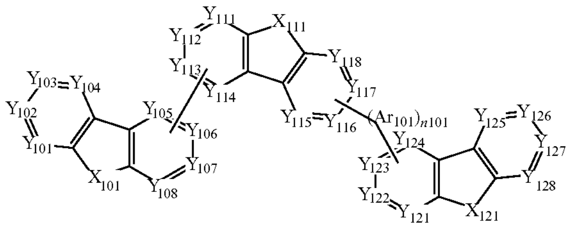

wherein in the formula (1), $X_{101}$, $X_{111}$, and $X_{121}$ are independently O or S;

$Ar_{101}$ is a substituted or unsubstituted arylene group including 6 to 30 ring carbon atoms, or a substituted or unsubstituted heteroarylene group including 5 to 30 ring atoms;

n101 is 0 or 1;

one of $Y_{105}$ to $Y_{108}$ and one of $Y_{111}$ to $Y_{114}$ are carbon atoms which are bonded with each other by a single bond;

when n101 is 0, one of $Y_{115}$ to $Y_{118}$ and one of $Y_{121}$ to $Y_{124}$ are carbon atoms which are bonded with each other by a single bond;

when n101 is 1, one of $Y_{115}$ to $Y_{118}$ and one of $Y_{121}$ to $Y_{124}$ are carbon atoms which are respectively bonded with $Ar_{101}$ by a single bond;

$Y_{101}$ to $Y_{104}$, $Y_{125}$ to $Y_{128}$, $Y_{105}$ to $Y_{108}$ which are not the carbon atom, $Y_{111}$ to $Y_{118}$ which are not the carbon atom, and $Y_{121}$ to $Y_{124}$ which are not the carbon atom are independently N or $CR_{131}$;

$R_{131}$ is a hydrogen atom or a substituent R;

when two or more $R_{131}$'s are present, the two or more $R_{131}$'s may be the same as or different from each other;

the substituent R is selected form the group consisting of a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$ (where $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; when two or more of each of $R_{901}$ to $R_{907}$ are present, the two or more of each of $R_{901}$ to $R_{907}$ are the same as or different from each other), a halogen atom, a cyano group, a nitro group, a substituted or unsubstituted aryl group including 6 to 50 ring carbon atoms, and a substituted or unsubstituted monovalent heterocyclic group including 5 to 50 ring atoms; and when two or more substituent R's are present, the two or more substituent R's may be the same as or different from each other;

(2)

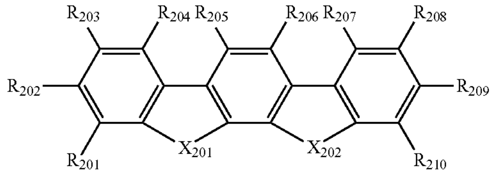

wherein in the formula (2), $X_{201}$ and $X_{202}$ are independently O or S;

at least one of $R_{201}$ to $R_{204}$ and $R_{207}$ to $R_{210}$ is a group represented by the following formula (2A);

$$-L_{201}-Ar_{201} \quad (2A)$$

wherein in the formula (2A), $L_{201}$ is a single bond, a substituted or unsubstituted arylene group including 6 to 50 ring carbon atoms, or a substituted or unsubstituted divalent heterocyclic group including 5 to 50 ring atoms;

$Ar_{201}$ is a substituted or unsubstituted aryl group including 6 to 50 ring carbon atoms, or a substituted or unsubstituted monovalent heterocyclic group including 5 to 50 ring atoms; and $R_{205}$ and $R_{206}$, and $R_{201}$ to $R_{204}$ and $R_{207}$ to $R_{210}$ which are not the group represented by the formulas (2A) are a hydrogen atom, a substituted or unsubstituted alkyl group including 1 to 50 carbon atoms, a substituted or unsubstituted aryl group including 6 to 50 ring carbon atoms, or a substituted or unsubstituted monovalent heterocyclic group including 5 to 50 ring atoms;

(3)

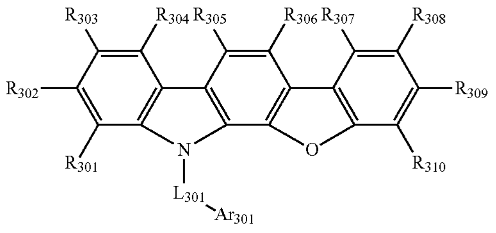

wherein in the formula (3), $R_{301}$ to $R_{310}$ are a hydrogen atom, a substituted or unsubstituted alkyl group including 1 to 50 carbon atoms, or a substituted or unsubstituted aryl group including 6 to 50 ring carbon atoms, $L_{301}$ is a single bond, a substituted or unsubstituted arylene group including 6 to 50 ring carbon atoms, or a substituted or unsubstituted divalent heterocyclic group including 5 to 50 ring atoms; and $Ar_{301}$ is a substituted or unsubstituted monovalent heterocyclic group including 5 to 50 ring atoms;

(4)

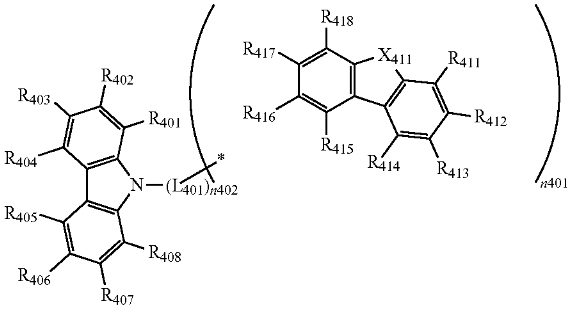

wherein in the formula (4), $R_{401}$ to $R_{408}$ is a hydrogen atom or a substituent R;

$L_{401}$ is a single bond, a substituted or unsubstituted aromatic hydrocarbon group including 6 to 50 ring carbon atoms, or a substituted or unsubstituted heterocyclic group including 5 to 50 ring atoms;

$X_{411}$ is O, S, or $NR_{419}$;

one of $R_{411}$ to $R_{418}$ is a single bond which bonds with $L_{401}$;

$R_{419}$, and $R_{411}$ to $R_{418}$ which are not a single bond which bonds with $L_{401}$ are independently a hydrogen atom or a substituent R;

n401 is an integer of 1 to 3;

when n401 is 2 or 3, the plurality of the structures in parentheses may be the same as or different from each other;

n402 is an integer of 1 to 3;

when n402 is 2 or 3, the two or more $L_{401}$'s may be the same as or different from each other; and the substituent R is as defined in the formula (1);

(11)

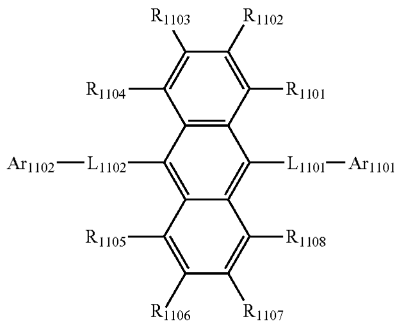

wherein in the formula (11), $R_{1101}$ to $R_{1108}$ are independently a hydrogen atom or a substituent R;

$L_{1101}$ and $L_{1102}$ are independently a single bond, a substituted or unsubstituted arylene group including 6 to 50 ring carbon atoms, or a substituted or unsubstituted divalent heterocyclic group including 5 to 50 ring atoms;

$Ar_{1101}$ is a substituted or unsubstituted monovalent nitrogen-containing heterocyclic group including 5 to 50 ring atoms;

$Ar_{1102}$ is a substituted or unsubstituted aryl group including 6 to 50 ring carbon atoms, or a substituted or unsubstituted monovalent heterocyclic group including 5 to 50 ring atoms; and the substituent R is as defined in the formula (1);

(12)

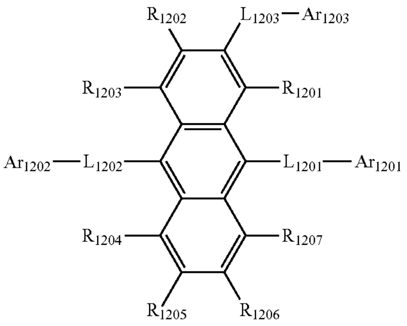

wherein in the formula (12), $R_{1201}$ to $R_{1207}$ are independently a hydrogen atom or a substituent R;

$L_{1201}$ to $L_{1203}$ are independently a single bond, a substituted or unsubstituted arylene group including 6 to 50 ring carbon atoms, or a substituted or unsubstituted divalent heterocyclic group including 5 to 50 ring atoms;

$Ar_{1201}$ and $Ar_{1202}$ are independently a substituted or unsubstituted aryl group including 6 to 50 ring carbon atoms, or a substituted or unsubstituted monovalent heterocyclic group including 5 to 50 ring atoms;

$Ar_{1203}$ is a substituted or unsubstituted monovalent nitrogen-containing heterocyclic group including 5 to 50 ring atoms; and the substituent R is as defined in the formula (1);

(13)

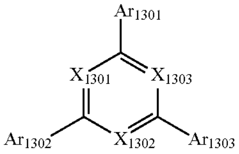

wherein in the formula (13), $X_{1301}$ to $X_{1303}$ are independently N or $CR_{1301}$, and at least two of $X_{1301}$ to $X_{1303}$ are N; $R_{1301}$ is a hydrogen atom or a substituent R;

$Ar_{1301}$ to $Ar_{1303}$ are independently a substituted or unsubstituted aryl group including 6 to 50 ring carbon atoms, or a group represented by the following formula (13A), and at least one of $Ar_{1301}$ to $Ar_{1303}$ is the group represented by the formula (13A); provided that none of $Ar_{1301}$ to $Ar_{1303}$ is a triphenylenyl group;

$$-(L_{13A})_{n13A}-Ar_{13A} \quad (13A)$$

wherein in the formula (13A), $L_{13A}$ is a single bond, a substituted or unsubstituted arylene group including 6 to 50 ring carbon atoms, or a substituted or unsubstituted divalent heterocyclic group including 5 to 50 ring atoms;

$Ar_{13A}$ is a substituted or unsubstituted monovalent heterocyclic group including 5 to 50 ring atoms;

n13A is an integer of 1 to 3; when two or more $L_{13}$A's are present, the two or more $L_{13}$A's may be the same as or different from each other;

when two or more groups represented by the formula (13A) are present, the two or more groups represented by the formula (13A) may be the same as or different from each other; and the substituent R is as defined in the formula (1).

2. The electron-transporting layer according to claim 1, wherein the compound represented by the formula (1) is a compound represented by the following formula (1-1):

(1-1)

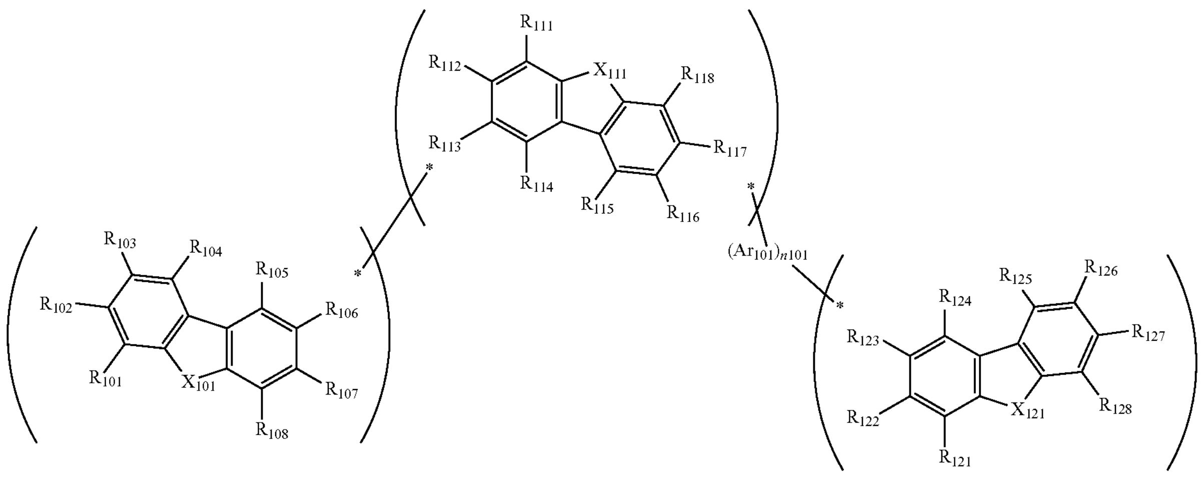

wherein in the formula (1-1), $X_{101}$, $X_{111}$, $X_{121}$, $Ar_{101}$, and n101 are as defined in the formula (1);

one of $R_{105}$ to $R_{108}$ and one of $R_{111}$ to $R_{114}$ are bonded with each other by a single bond;

when n101 is 0, one of $R_{115}$ to $R_{118}$ and one of $R_{121}$ to $R_{124}$ are bonded with each other by a single bond;

when n101 is 1, one of $R_{115}$ to $R_{118}$ and one of $R_{121}$ to $R_{124}$ are respectively bonded with $Ar_{101}$ by a single bond;

$R_{101}$ to $R_{104}$, $R_{125}$ to $R_{128}$, $R_{105}$ to $R_{108}$ which do not form a single bond, $R_{111}$ to $R_{118}$ which do not form a single bond, and $R_{121}$ to $R_{124}$ which do not form a single bond are independently a hydrogen atom or a substituent R; and the substituent R is as defined in the formula (1).

3. The electron-transporting layer according to claim 1, wherein the compound represented by the formula (1) is a compound represented by the following formula (1-2):

(1-2)

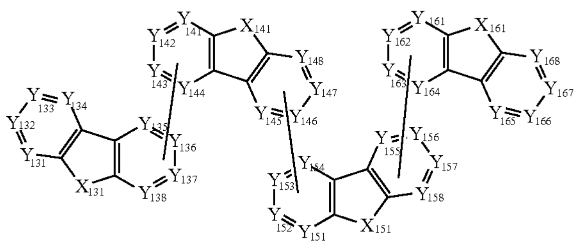

wherein in the formula (1-2), $X_{131}$, $X_{141}$, $X_{151}$, and $X_{161}$ are independently O or S;

one of $Y_{135}$ to $Y_{138}$ and one of $Y_{141}$ to $Y_{144}$ are carbon atoms which are bonded with each other by a single bond;

one of $Y_{145}$ to $Y_{148}$ and one of $Y_{151}$ to $Y_{154}$ are carbon atoms which are bonded with each other by a single bond;

one of $Y_{155}$ to $Y_{158}$ and one of $Y_{161}$ to $Y_{164}$ are carbon atoms which are bonded with each other by a single bond;

$Y_{131}$ to $Y_{134}$, $Y_{165}$ to $Y_{168}$, $Y_{135}$ to $Y_{138}$ which are not the carbon atom, $Y_{141}$ to Y 148 which are not the carbon atom, $Y_{151}$ to $Y_{158}$ which are not the carbon atom, and $Y_{161}$ to $Y_{164}$ which are not the carbon atom are independently N or $CR_{131}$;

$R_{131}$ is a hydrogen atom or a substituent R;

when two or more $R_{131}$'s are present, the two or more $R_{131}$'s may be the same as or different from each other; and the substituent R is as defined in the formula (1).

4. The electron-transporting layer according to claim 1, wherein the compound represented by the formula (1) is a compound represented by the following formula (1-11):

(1-11)

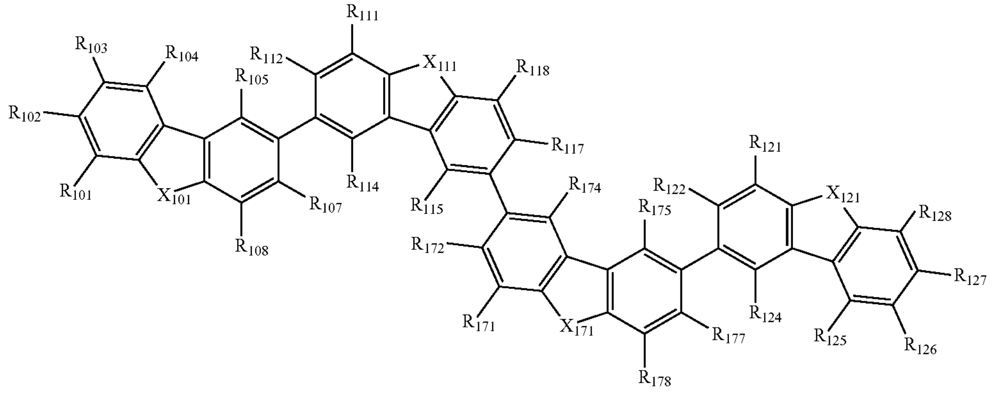

wherein in the formula (1-11), $X_{101}$, $X_{111}$, and $X_{121}$ are as defined in the formula (1);

$X_{171}$ is O or S;

$R_{101}$ to $R_{105}$, $R_{107}$ to $R_{108}$, $R_{111}$ to $R_{112}$, $R_{114}$ to $R_{115}$, $R_{117}$ to $R_{118}$, $R_{121}$ to $R_{122}$, $R_{124}$ to $R_{128}$, $R_{171}$ to $R_{172}$, $R_{174}$ to $R_{175}$ and $R_{177}$ to $R_{178}$ are independently a hydrogen atom or a substituent R; and the substituent R is as defined in the formula (1).

5. The electron-transporting layer according to claim 1, wherein in the formula (2), one of $R_{201}$ to $R_{204}$ is the group represented by the formula (2A), and one of $R_{207}$ to $R_{210}$ is the group represented by the formula (2A).

6. The electron-transporting layer according to claim 1, wherein in the formula (2A), $L_{201}$ is a single bond or a substituted or unsubstituted arylene group including 6 to 50 ring carbon atoms, and $Ar_{201}$ is a substituted or unsubstituted aryl group including 6 to 50 ring carbon atoms.

7. The electron-transporting layer according to claim 1, wherein the compound represented by the formula (2) is a compound represented by the following formula (2-1):

(2-1)

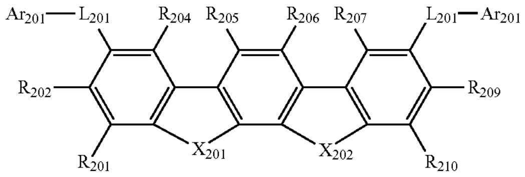

wherein in the formula (2-1), $X_{201}$, $X_{202}$, $L_{201}$, and $Ar_{201}$ are as defined in the formula (2); and $R_{201}$ to $R_{202}$, $R_{204}$ to $R_{207}$, and $R_{209}$ to $R_{210}$ are independently a hydrogen atom, a substituted or unsubstituted alkyl group including 1 to 50 carbon atoms, or a substituted or unsubstituted aryl group including 6 to 50 ring carbon atoms.

8. The electron-transporting layer according to claim 1, wherein the compound represented by the formula (2) is a compound represented by the following formula (2-11):

(2-11)

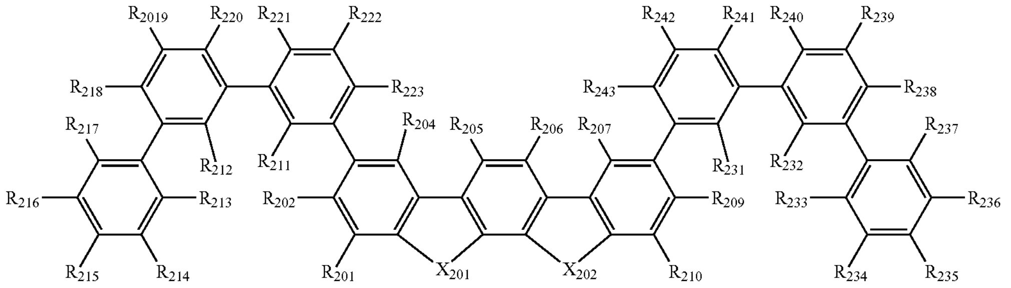

wherein in the formula (2-11), $X_{201}$ and $X_{202}$ are as defined in the formula (2); and $R_{201}$ to $R_{202}$, $R_{204}$ to $R_{207}$, $R_{209}$ to $R_{210}$, $R_{211}$ to $R_{223}$, and $R_{231}$ to $R_{243}$ are independently a hydrogen atom, a substituted or unsubstituted alkyl group including 1 to 50 carbon atoms, or a substituted or unsubstituted aryl group including 6 to 50 ring carbon atoms.

9. The electron-transporting layer according to claim 1, wherein in the formula (3), $L_{301}$ is a substituted or unsubstituted arylene group including 6 to 50 ring carbon atoms.

10. The electron-transporting layer according to claim 1, wherein the compound represented by the formula (3) is a compound represented by the following formula (3-1):

(3-1)

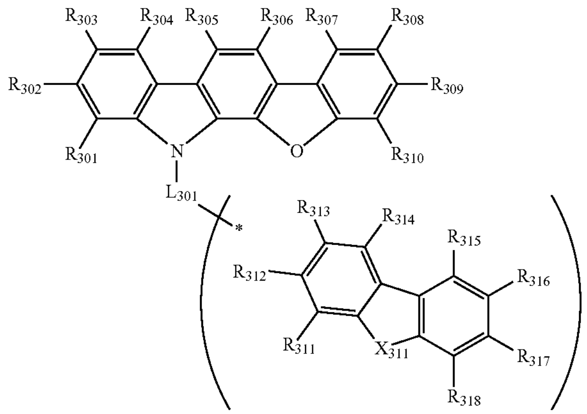

wherein in the formula (3-1), $R_{301}$ to $R_{310}$ and $L_{301}$ are as defined in the formula (3);

$X_{311}$ is O, S, or $NR_{319}$;

one of $R_{311}$ to $R_{319}$ is a single bond which bonds with $L_{301}$;

$R_{311}$ to $R_{319}$ which are not a single bond which bonds with $L_{301}$ are independently a hydrogen atom or a substituent R; and the substituent R is as defined in the formula (1).

11. The electron-transporting layer according to claim 1, wherein the compound represented by the formula (3) is a compound represented by the following formula (3-2):

(3-2)

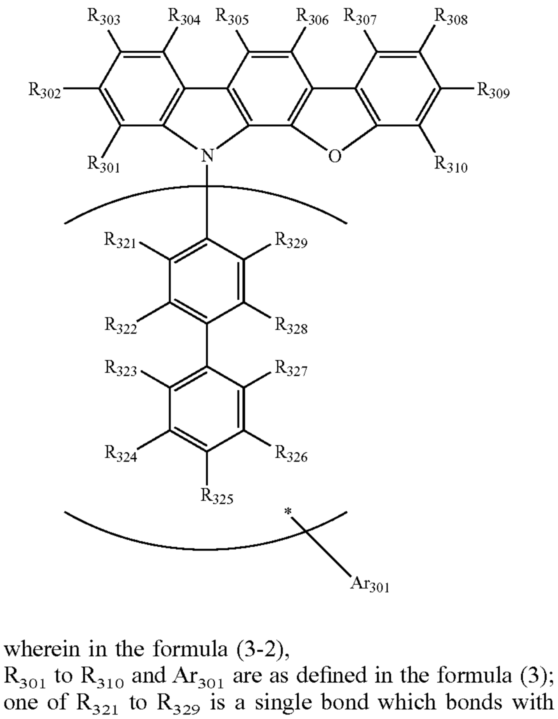

wherein in the formula (3-2), $R_{301}$ to $R_{310}$ and $Ar_{301}$ are as defined in the formula (3);

one of $R_{321}$ to $R_{329}$ is a single bond which bonds with $Ar_{301}$;

$R_{321}$ to $R_{329}$ which are not a single bond which bonds with $Ar_{301}$ are independently a hydrogen atom or a substituent R;

the substituent R is as defined in the formula (1).

12. The electron-transporting layer according to claim 1, wherein the compound represented by the formula (3) is a compound represented by the following formula (3-11):

(3-11)

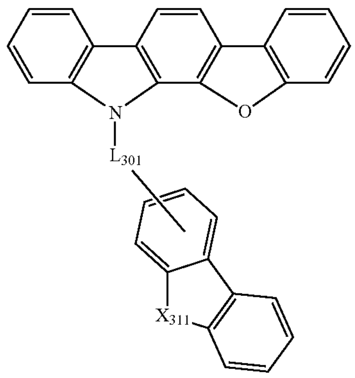

wherein in the formula (3-11), $L_{301}$ is as defined in the formula (3); $X_{311}$ is O, S, or $NR_{319}$; $R_{319}$ is a hydrogen atom or a substituent R; and the substituent R is as defined in the formula (1).

13. The electron-transporting layer according to claim 1, wherein in the formula (4), $X_{411}$ is O or S.

14. The electron-transporting layer according to claim 1, wherein in the formula (4), n401 is 1.

15. The electron-transporting layer according to claim 1, wherein in the formula (4), $L_{401}$ is a single bond or a substituted or unsubstituted arylene group including 6 to 50 ring carbon atoms.

16. The electron-transporting layer according to claim 1, wherein in the formula (4), at least one of $R_{401}$ to $R_{408}$ is the substituent R.

17. The electron-transporting layer according to claim 1, wherein in the formula (4), at least one of $R_{401}$ to $R_{408}$ is a substituted or unsubstituted monovalent heterocyclic group including 5 to 50 ring atoms.

18. The electron-transporting layer according to claim 1, wherein the compound represented by the formula (4) is a compound represented by the following formula (4-1):

(4-1)

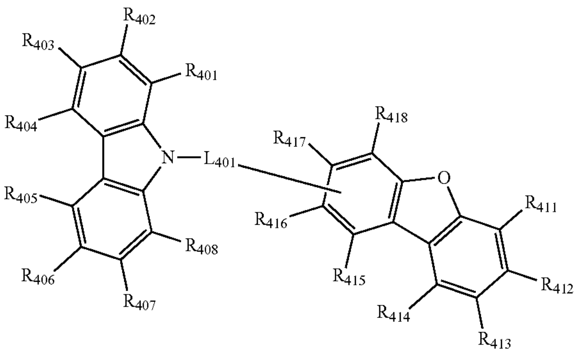

wherein in the formula (4-1), $R_{401}$ to $R_{408}$ and $L_{401}$ are as defined in the formula (4);

one of $R_{415}$ to $R_{418}$ is a single bond which bonds with $L_{401}$; $R_{411}$ to $R_{414}$, and $R_{415}$ to $R_{418}$ which are not a single bond which bonds with $L_{401}$ are independently a hydrogen atom or a substituent R; and the substituent R is as defined in the formula (1).

19. The electron-transporting layer according to claim 1, wherein the compound represented by the formula (4) is a compound represented by the following formula (4-11):

(4-11)

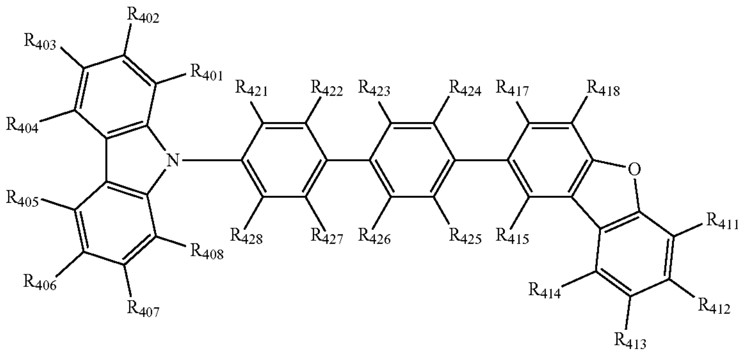

wherein in the formula (4-11), $R_{401}$ to $R_{408}$ is as defined in the formula (4);

$R_{411}$ to $R_{415}$, $R_{417}$ to $R_{418}$, and $R_{421}$ to $R_{428}$ are independently a hydrogen atom or a substituent R; and the substituent R is as defined in the formula (1).

20. The electron-transporting layer according to claim 1, wherein in the formula (13), one of $Ar_{1301}$ to $Ar_{1303}$ is the group represented by the formula (13A).

21. The electron-transporting layer according to claim 1, wherein in the formula (13), two of $Ar_{1301}$ to $Ar_{1303}$ are the groups represented by the formula (13A).

22. The electron-transporting layer according to claim 1, wherein in the formula (13), two of $X_{1301}$ to $X_{1303}$ are N.

23. The electron-transporting layer according to claim 1, wherein in the formula (13A), $L_{13A}$ is a single bond or a substituted or unsubstituted arylene group including 6 to 50 ring carbon atoms.

24. The electron-transporting layer according to claim 1, wherein the compound represented by the formula (13) is a compound represented by the following formula (13-1):

(13-1)

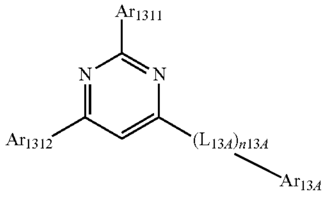

wherein in the formula (13-1), $L_{13A}$, $Ar_{13A}$, and n13A are as defined in the formula (13A); and $Ar_{1311}$ and $Ar_{1312}$ are independently a substituted or unsubstituted aryl group including 6 to 50 ring carbon atoms, or the group represented by the formula (13A).

25. The electron-transporting layer according to claim 24, wherein in the compound represented by the formula (13-1), $Ar_{1311}$ and $Ar_{1312}$ are independently a substituted or unsubstituted aryl group including 6 to 50 ring carbon atoms.

26. The electron-transporting layer according to claim 1, wherein the compound represented by the formula (13) is a compound represented by the following formula (13-2):

(13-2)

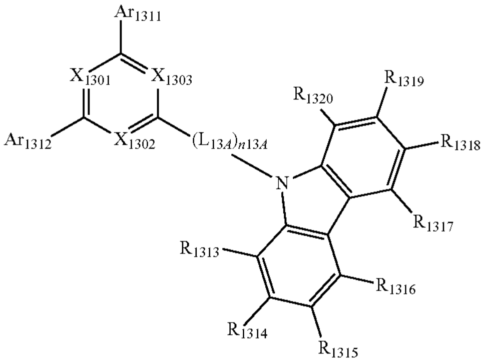

wherein in the formula (13-2), $X_{1301}$ to $X_{1303}$, $L_{13A}$, and n13A are as defined in the formula (13); $Ar_{1311}$ and $Ar_{1312}$ are independently a substituted or unsubstituted aryl group including 6 to 50 ring carbon atoms, or the group represented by the formula (13A); $R_{1313}$ to $R_{1320}$ are independently a hydrogen atom or a substituent R; and the substituent R is as defined in the formula (11).

27. The electron-transporting layer according to claim 26, wherein in the compound represented by the formula (13-2), $Ar_{1311}$ and $Ar_{1312}$ are independently a substituted or unsubstituted aryl group including 6 to 50 ring carbon atoms.

28. The electron-transporting layer according to claim 1, wherein the compound represented by the formula (13) is a compound represented by the following formula (13-11):

(13-11)
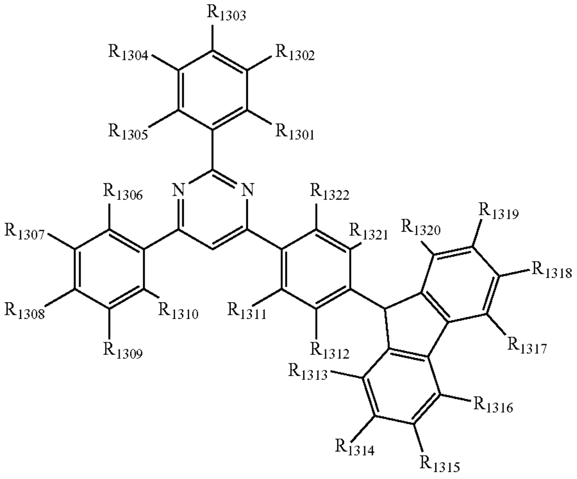
wherein in the formula (13-11), $R_{1301}$ to $R_{1322}$ are independently a hydrogen atom or a substituent R; and the substituent R is as defined in the formula (11).
29. An organic electroluminescence device comprising the electron-transporting layer according to claim 1.
* * * * *